United States Patent
Homburger et al.

(10) Patent No.: US 6,703,491 B1
(45) Date of Patent: Mar. 9, 2004

(54) DROSOPHILA SEQUENCES

(75) Inventors: Sheila Akiko Homburger, San Francisco, CA (US); Allen James Ebens, Jr., San Francisco, CA (US); Catherine Sue Erickson, San Francisco, CA (US); Helen Louise Francis-Lang, San Francisco, CA (US); Jonathan Scott Margolis, San Francisco, CA (US); Bindu Priya Reddy, San Francisco, CA (US); David Andrew Ruddy, San Francisco, CA (US); Andrew Roy Buchman, San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 09/270,767

(22) Filed: Mar. 17, 1999

(51) Int. Cl.$^7$ ............................ C07H 21/04; C12Q 1/68; C12N 1/21; C12N 15/63
(52) U.S. Cl. ........................ 536/23.1; 435/6; 435/252.3; 435/320.1
(58) Field of Search ............................... 435/6; 536/23.1

(56) References Cited

U.S. PATENT DOCUMENTS 5,776,762 A 7/1998 North et al.

OTHER PUBLICATIONS

Russell et al., "Structural Features can be Unconserved in Proteins with Similar Folds," Journal of Molecular Biology, 1994, vol. 244, pp. 332–350.*
Gerhold et al., "It's the genes! EST access to human genome content," BioEssays, 1996, vol. 18, No. 12, pp. 973–981.*
Wells et al., "The chemokine information source: identification and characterization of novel chemokines using the WorldWideWeb and Expressed Sequence Tag Databases," Journal of Leukocyte Biology, 1997, vol. 61, pp. 545–550.*
Sequence Homology Search.*
Iyer et al., "Quod erat demonstrandum? The mystery of experimental validation of apparently erroneous computational analyses of protein sequences," Genome Biology, 2001, vol. 2, No. 12, pp. 1–11.*
Bai and Satelle, 1995, "A $GABA_b$ Receptor on an Identified Insect Motor Neurone", J. Exp. Biol. 198:889–894.
Huang and Casida, 1996, "Characterization of [$^3$H]ethynyl-bicycloorthobenzoate ([$^3$H]EBOB) Binding and the Action of Insecticides on the γ–Aminobutyric Acid–Gated Chloride Channel in Cultured Cerebellar Granule Neurons", J. Pharmacol. Exp. Therapeutics 279:1191–1196.
Kaupmann et al., 1997, "Expression Cloning of $GABA_b$ Receptors Uncovers Similarity to Metabotropic Glutamate Receptors", Nature 386:239–246.
Kleyn et al., 1996, "Identification and Characterization of the Mouse Obesity Gene Tubby: a Member of a Novel Gene Family", Cell 85:281–290.

Latli et al., 1997, "Synthesis of a Novel [$^{125}$I]Neonicotinoid Photoaffinity Probe for the Drosophila Nicotinic Acetylcholine Receptor", Bioconjugate Chem. 8:7–14.
Narahashi et al., 1998, "Ion Channels as Targets for Insecticides", Neurotoxicology 19:581–590.
Noben–Trauth et al., 1996, "A Candidate Gene for the Mouse Mutation Tubby", Nature 380:534–538.
Wilson and Cryan, 1997, "Lufenuron, a Chitin–Synthesis Inhibitor, Interrupts Development of Drosophila melanogaster", J. Exp. Zool. 27:37–44.
www.ncbi.nih.gov (National Center for Biotechnology Information) Genbank Accession No. U73206 –Canis familiaris β2 Adrenergic Receptor (Dogβ2) Gene, Complete Cds; submitted Oct. 3, 1996.
www.ncbi.nih.gov (National Center for Biotechnology Information) Genbank Accession No. X94608—C. familiaris mRNA for β2–Adrenergic Receptor; submitted Dec. 29, 1995.
www.ncbi.nih.gov (National Center for Biotechnology Information) Genbank Accession No. J02960—Human β2–Adrenergic Receptor Gene, Complete Cds.
www.ncbi.nih.gov (National Center for Biotechnology Information) Genbank Accession No. Y13585—Cavia procellus mRNA for Serotonin Receptor 4, Long Splice Variant; submitted Jun. 3, 1997.
www.ncbi.nih.gov (National Center for Biotechnology Information) Genbank Accession No. U61264—Drosophila melanogaster Dopamine D1 Receptor DAMB mRNA, Complete Cds; submitted Jun. 18, 1996.

(List continued on next page.)

Primary Examiner—Kenneth R. Horlick
Assistant Examiner—Young Kim
(74) Attorney, Agent, or Firm—Pennie & Edmonds LLP

(57) ABSTRACT

The present invention relates to Drosophila genes and methods for their use. The invention provides nucleotide sequences of Drosophila genes, amino acid sequences of the encoded proteins, and derivatives (e.g., fragments) and analogs thereof. The invention further relates to fragments (and derivatives and analogs thereof) of proteins which comprise one or more domains of a Drosophila protein. Antibodies to Drosophila proteins, and derivatives and analogs thereof, are also provided. Also provided herein are vectors and host cells comprising such nucleic acids. Methods of production of a Drosophila protein (e.g., by recombinant means), and derivatives and analogs thereof, are provided. Chimeric polypeptide molecules comprising polypeptides of the invention fused to heterologous polypeptide sequences are provided. Methods to identify the biological function of a Drosophila gene are provided, including various methods for the functional modification (e.g., overexpression, underexpression, mutation, knock-out) of one gene, or of two or more genes simultaneously. Methods to identify a Drosophila gene which modifies the function of, and/or functions in a downstream pathway from, another gene are provided. The invention further provides for use of Drosophila proteins as media additives or pesticides.

18 Claims, 44 Drawing Sheets

OTHER PUBLICATIONS www.ncbi.nih.gov (National Center for Biotechnology Information) Genbank Accession No. AAC47161—Dopamine Receptor (*Drosophila melanogaster*); submitted Aug. 21, 1995.

www.ncbi.nih.gov (National Center for Biotechnology Information) Genbank Accession No. AI134060—GH11409.5' GH *Drosophila melanogaster* head pOT2 *Drosophila melanogaster* cDNA Clone GH11409 5' Similar to BcDNA:GH07312: FBan0006706 Located on: 3R 93F6–93F6: Apr. 10, 2001, mRNA Sequence; Entry Created Sep. 17, 1998; Last Updated Apr. 23, 2001.

www.ncbi.nih.gov (National Center for Biotechnology Information) Genbank Accession No. AI063197—GH02730.5' GH *Drosophila melanogaster* Head pOT2 *Drosophila melanogaster* cDNA Clone GH02730 5', mRNA Sequence; Entry Created Jul. 23, 1998; Last Updated Apr. 19, 2001.

www.ncbi.nih.gov (National Center for Biotechnology Information) Genbank Accession No. AI108469—GH07312.5' GH *Drosophila melanogaster* head pOT2 *Drosophila melanogaster* cDNA Clone GH07312 5', mRNA Sequence; Entry Created Aug. 26, 1998; Last Updated Apr. 19, 2001.

www.ncbi.nih.gov (National Center for Biotechnology Information) Genbank Accession No. AA567648—HL01578.5' HI *Drosophila melanogaster* head BlueScript *Drosophila melanogaster* cDNA Clone HL01578 5', mRNA Sequence; Entry Created Aug. 19, 1997; Last Updated Apr. 19, 2001.

www.ncbi.nih.gov (National Center for Biotechnology Information) Genbank Accession No. AF058795—*Rattus norvegicus* GABA–B Receptor gb2 mRNA, Complete Cds; submitted Apr. 9, 1998.

www.ncbi.nih.gov (National Center for Biotechnology Information) Genbank Accession No. AJ012188—*Homo sapiens* mRNA for GABA–B Receptor, Subunit 2; submitted Oct. 16, 1998.

www.ncbi.nih.gov (National Center for Biotechnology Information) Genbank Accession No. AF056085—*Homo sapiens* GABA–B Receptor mRNA, Complete Cds; submitted Mar. 27, 1998.

www.ncbi.nih.gov (National Center for Biotechnology Information) Genbank Accession No. AAC99345—Orphan G Protein–Coupled Receptor HG20 (Homo sapiens); submitted Jun. 3, 1998.

www.ncbi.nih.gov (National Center for Biotechnology Information) Genbank Accession No. AAD03336—GABA–B Receptor 2 (*Homo sapiens*); submitted Jun. 25, 1998; updated Jan. 6, 1999.

www.ncbi.nih.gov (National Center for Biotechnology Information) Genbank Accession No. AAD03338—GABA–B Receptor 2; GBR2 (*Rattus norvegicus*); submitted Nov. 25, 1998.

www.ncbi.nih.gov (National Center for Biotechnology Information) Genbank Accession No. AAD03335—GABA–B Receptor 2 (*Rattus norvegicus*); submitted Jun. 25, 1998.

www.ncbi.nih.gov (National Center for Biotechnology Information) Genbank Accession No. Z73167—*S. cerevisiae* Chromosome XII Reading Frame ORF YLL062c; submitted May 22, 1996.

www.ncbi.nih.gov (National Center for Biotechnology Information) Genbank Accession No. AAC63228—GABA–B Receptor (*Homo sapiens*); submitted Mar. 27, 1998.

www.ncbi.nih.gov (National Center for Biotechnology Information) Genbank Accession No. W48115—mc91h04.r1 Soares Mouse Embryo NbME13.5 14.5 Mus musculus cDNA Clone IMAGE:355927 5' Similar to SW:IF2G_$_G$Human P41091 Translational Initiation Factor $2\gamma$ Subunit, mRNA sequence; entry created May 24, 1996; last updated May 24, 1996.

www.ncbi.nih.gov (National Center for Biotechnology Information) Genbank Accession No. AAC63994—GABA–B Receptor gb2 (*Rattus norvegicus*); submitted Apr. 9, 1998.

www.ncbi.nih.gov (National Center for Biotechnology Information) Genbank Accession No. AL031765—*Drosophila melanogaster* Cosmid Clone 22E5;submitted Apr. 28, 1999.

www.ncbi.nih.gov (National Center for Biotechnology Information) Genbank Accession No. W44386—zc28c06.s1 Soares_Senescent_Fibroblasts_NbHSF *Homo sapiens* cDNA Clone IMAGE:323626 3', mRNA Sequence; entry created May 22, 1996; last updated Oct. 11, 1996.

www.ncbi.nih.gov (National Center for Biotechnology Information) Genbank Accession No. CAA47998—Zinc Finger Protein (*Saccharomyces cerevisiae*); submitted Oct. 22, 1992.

www.ncbi.nih.gov (National Center for Biotechnology Information) Genbank Accession No. S36794—$\beta$1—Adrenergic Receptor—Mouse.

www.ncbi.nih.gov (National Center for Biotechnology Information) Genbank Accession No. AAA02929—$\beta$1—Adrenergic Receptor—(*Mus musculus*).

www.ncbi.nih.gov (National Center for Biotechnology Information) Genbank Accession No. AAB71283—Similar to Chitin Synthases (*Caenorhabditis elegans*); submitted Sep. 22, 1997.

www.ncbi.nih.gov (National Center for Biotechnology Information) Genbank Accession No. CAA96688—Weak Similarity to Yeast Chitin Synthase; submitted May 5, 1996.

www.ncbi.nih.gov (National Center for Biotechnology Information) Genbank Accession No. CAA30172—Mature Acetylcholine Receptor $\alpha$–Like Subunit (*Drosophila melanogaster*).

www.ncbi.nih.gov (National Center for Biotechnology Information) Genbank Accession No. ACFFA1—Nicotinic Acetylcholine Receptor $\alpha$ 1 Chain Precursor—Fruit Fly (*Drosophila melanogaster*).

www.ncbi.nih.gov (National Center for Biotechnology Information) Genbank Accession No. CAA69328—Acid Sphingomyelinase–Like Phosphodiesterase (*Homo sapiens*); submitted Sep. 17, 1996.

www.ncbi.nih.gov (National Center for Biotechnology Information) Genbank Accession No. CAA69329—Acid Sphingomyelinase–Like Phosphodiesterase (*Mus musculus*); submitted Sep. 17, 1996.

www.ncbi.nih.gov (National Center for Biotechnology Information) Genbank Accession No. AAC91154—Sequence 27 from U.S. patent No. 5,776,762 (See Ref. AI).

www.ncbi.nih.gov (National Center for Biotechnology Information) Genbank Accession No. AAC91152—Sequence 7 from U.S. patent No. 5,776,762 (See Ref. AI).

* cited by examiner

```
                    10         20         30         40         50
          AGCATTGGCGGAGCAACTTGAATGAGCTGCGACTCAATTGGGCTGCGAAA
          TCGTAACCGCCTCGTTGAACTTACTCGACGCTGAGTTAACCCGACGCTTT 60             70             80
          TCGACGAG ATG TCA GGG GTT AAC GTG GCT GAC CTT CTG
          AGCTGCTC TAC AGT CCC CAA TTG CAC CGA CTG GAA GAC
                    M   S   G   V   N   V   A   D   L   L 90              100             110             120
          GCC ACG ACA ATG ACA TTA CCC ATA ACA GCC GCA GCA GGA
          CGG TGC TGT TAC TGT AAT GGG TAT TGT CGG CGT CGT CCT
           A   T   T   M   T   L   P   I   T   A   A   A   G

POSSIBLE N-GLYCOSYLATION SITE
                                                                |
           130             140             150             160  |
          GCA GCA ACA TCA CAA GCA GCA GCA ACA TCA GCC ACC AAC
          CGT CGT TGT AGT GTT CGT CGT CGT TGT AGT CGG TGG TTG
           A   A   T   S   Q   A   A   A   T   S   A   T   N 170             180             190             200
          GCC AGC CAC CTG CAA CCT GCA ACA TTA ACA GGC CAC ATT
          CGG TCG GTG GAC GTT GGA CGT TGT AAT TGT CCG GTG TAA
           A   S   H   L   Q   P   A   T   L   T   G   H   I 210             220             230             240
          TCC ACG ACA GCA GCA GCC AAA ACT ACG ACG ACG CCG ACG
          AGG TGC TGT CGT CGT CGG TTT TGA TGC TGC TGC GGC TGC
           S   T   T   A   A   A   K   T   T   T   T   P   T 250             260             270             280
          AGC AGT TTG CCT ATA ACA TCG CAA TTT GTG GAT GCC TCG
          TCG TCA AAC GGA TAT TGT AGC GTT AAA CAC CTA CGG AGC
           S   S   L   P   I   T   S   Q   F   V   D   A   S 290             300             310             320
          TTG ACT TCG CTA TCA TTA ACA GCC ACA TCG TCA GAT GCC
          AAC TGA AGC GAT AGT AAT TGT CGG TGT AGC AGT CTA CGG
           L   T   S   L   S   L   T   A   T   S   S   D   A 330             340             350             360
          TCC TAC TCC TCG CCC TTT TCA TCC TAC TTG TCG TCG GAT
          AGG ATG AGG AGC GGG AAA AGT AGG ATG AAC AGC AGC CTA
           S   Y   S   S   P   F   S   S   Y   L   S   S   D

POSSIBLE N-GLYCOSYLATION SITE
                                                                |
                   370             380             390          | 400
          TCC ACG TTT GAG CTC CTC TCG ACA GTC GGC CCA AAT ATA
          AGG TGC AAA CTC GAG GAG AGC TGT CAG CCG GGT TTA TAT
           S   T   F   E   L   L   S   T   V   G   P   N   I

POSSIBLE N-GLYCOSYLATION SITE
                    |
                    | 410             420             430
          ACG GCC AAT GGC AGT GAC ATT ACG GTG GAT AAC CAG GCG
          TGC CGG TTA CCG TCA CTG TAA TGC CAC CTA TTG GTC CGC
           T   A   N   G   S   D   I   T   V   D   N   Q   A
```

FIG. 1A

```
       440             450             460             470
    GAG CTG GAG GAG AGC TGG CTA GAT CTA TCG CTG CTG CTG
    CTC GAC CTC CTC TCG ACC GAT CTA GAT AGC GAC GAC GAC
     E   L   E   E   S   W   L   D   L   S   L   L   L
                                          TRANSMEMBRANE DOMAIN  1
                                                          |
       480             490             500             510
    CTC AAA GGA TTC ATC TTC TCG TCA ATT ATC CTG GCC GCT
    GAG TTT CCT AAG TAG AAG AGC AGT TAA TAG GAC CGG CGA
     L   K   G   F   I   F   S   S   I   I   L   A   A 520             530             540             550
    GTC CTC GGC AAT GCA TTG GTC ATC ATT TCA GTG CAG CGC
    CAG GAG CCG TTA CGT AAC CAG TAG TAA AGT CAC GTC GCG
     V   L   G   N   A   L   V   I   I   S   V   Q   R 560             570             580             590
    AAT CGA AAG CTG CGG GTG ATA ACC AAT TAC TTT GTT GTG
    TTA GCT TTC GAC GCC CAC TAT TGG TTA ATG AAA CAA CAC
     N   R   K   L   R   V   I   T   N   Y   F   V   V
TRANSMEMBRANE DOMAIN  2
             |
       600             610             620             630
    TCG CTG GCG ATG GCC GAC ATG CTG GTG GCC CTC TGT GCG
    AGC GAC CGC TAC CGG CTG TAC GAC CAC CGG GAG ACA CGC
     S   L   A   M   A   D   M   L   V   A   L   C   A 640             650             660             670
    ATG ACA TTC AAC GCC TCC GTG GAA CTG TCC GGC GGA AAG
    TAC TGT AAG TTG CGG AGG CAC CTT GAC AGG CCG CCT TTC
     M   T   F   N   A   S   V   E   L   S   G   G   K 680             690             700             710
    TGG ATG TTC GGA CCG TTC ATG TGC AAC GTG TAC AAC AGC
    ACC TAC AAG CCT GGC AAG TAC ACG TTG CAC ATG TTG TCG
     W   M   F   G   P   F   M   C   N   V   Y   N   S
                 TRANSMEMBRANE DOMAIN  3
                                 |
       720             730       |     740      .      750
    CTG GAT GTT TAC TTT TCC ACG GCC AGC ATA TTG CAC CTG
    GAC CTA CAA ATG AAA AGG TGC CGG TCG TAT AAC GTG GAC
     L   D   V   Y   F   S   T   A   S   I   L   H   L 760             770             780             790
    TGC TGC ATA TCA GTG GAC AGA TAC TAC GCC ATT GTG CGT
    ACG ACG TAT AGT CAC CTG TCT ATG ATG CGG TAA CAC GCA
     C   C   I   S   V   D   R   Y   Y   A   I   V   R 800             810             820
    CCA CTG GAG TAT CCA TTG AAT ATG ACA CAC AAA ACG GTC
    GGT GAC CTC ATA GGT AAC TTA TAC TGT GTG TTT TGC CAG
     P   L   E   Y   P   L   N   M   T   H   K   T   V
                  TRANSMEMBRANE DOMAIN  4
                              |
       830             840    |        850             860
    TGC TTC ATG CTC GCC AAT GTG TGG ATC CTG CCC GCC CTC
    ACG AAG TAC GAG CGG TTA CAC ACC TAG GAC GGG CGG GAG
     C   F   M   L   A   N   V   W   I   L   P   A   L
```

FIG. 1B

```
     870            880            890             900
ATA TCC TTC ACG CCC ATC TTT CTG GGC TGG TAC ACG ACG
TAT AGG AAG TGC GGG TAG AAA GAC CCG ACC ATG TGC TGC
 I   S   F   T   P   I   F   L   G   W   Y   T   T 910            920            930             940
GAG GAG CAC CTG CGG GAG ATT TCC CTG CAT CCG GAC CAG
CTC CTC GTG GAC GCC CTC TAA AGG GAC GTA GGC CTG GTC
 E   E   H   L   R   E   I   S   L   H   P   D   Q 950            960            970             980
TGC TCG TTT GTG GTC AAC AAG GCC TAC GCC CTC ATC TCC
ACG AGC AAA CAC CAG TTG TTC CGG ATG CGG GAG TAG AGG
 C   S   F   V   V   N   K   A   Y   A   L   I   S

TRANSMEMBRANE DOMAIN   5

990           |1000            1010            1020
AGT TCG GTG AGC TTC TGG ATA CCC GGC ATT GTG ATG CTG
TCA AGC CAC TCG AAG ACC TAT GGG CCG TAA CAC TAC GAC
 S   S   V   S   F   W   I   P   G   I   V   M   L 1030           1040           1050            1060
GTG ATG TAC TGG CGC ATC TTT AAG GAG GCG ATT CGT CAA
CAC TAC ATG ACC GCG TAG AAA TTC CTC CGC TAA GCA GTT
 V   M   Y   W   R   I   F   K   E   A   I   R   Q 1070           1080           1090            1100
CGC AAG GCC CTC AGC CGC ACC AGC TCC AAC ATC CTC CTT
GCG TTC CGG GAG TCG GCG TGG TCG AGG TTG TAG GAG GAA
 R   K   A   L   S   R   T   S   S   N   I   L   L 1110           1120           1130            1140
AAC AGC GTC CAC ATG GGC CAC ACC CAG CAG CCC ACC AGC
TTG TCG CAG GTG TAC CCG GTG TGG GTC GTC GGG TGG TCG
 N   S   V   H   M   G   H   T   Q   Q   P   T   S 1150           1160           1170            1180
CTG AGC TAT CTG CAT CCC AGT GAC TGT GAT CTG AAT GCC
GAC TCG ATA GAC GTA GGG TCA CTG ACA CTA GAC TTA CGG
 L   S   Y   L   H   P   S   D   C   D   L   N   A 1190           1200           1210
ACA TCC GCC CGG GAG GAA ACG CAC AGT GCG CTT AGT AAC
TGT AGG CGG GCC CTC CTT TGC GTG TCA CGC GAA TCA TTG
 T   S   A   R   E   E   T   H   S   A   L   S   N 1220           1230           1240            1250
    TTG GAG GAC ATG CTG CAG CCG GCC ACC GAC GAG GAC GAC
    AAC CTC CTG TAC GAC GTC GGC CGG TGG CTG CTC CTG CTG
     L   E   D   M   L   Q   P   A   T   D   E   D   D 1260           1270           1280            1290
    GAT AGG GAC GAG TGC GAT GAA CTG AGA GTG CCA TCG CCG
    CTA TCC CTG CTC ACG CTA CTT GAC TCT CAC GGT AGC GGC
     D   R   D   E   C   D   E   L   R   V   P   S   P 1300           1310           1320            1330
    CCG CCA CGC CGC CTC AGC CGC AGC AGC ATC GAT CTG AGG
    GGC GGT GCG GCG GAG TCG GCG TCG TCG TAG CTA GAC TCC
     P   P   R   R   L   S   R   S   S   I   D   L   R
```

FIG. 1C

```
      1340              1350              1360              1370
GAC TTG GAG CAG GAG CGG TAC GAG AAG GTC ACC CAC ACG
CTG AAC CTC GTC CTC GCC ATG CTC TTC CAG TGG GTG TGC
 D   L   E   Q   E   R   Y   E   K   V   T   H   T 1380              1390              1400              1410
GAC AGT GCT CCC TCG ATG ATG GCA CTG CAG CAA CAG CAG
CTG TCA CGA GGG AGC TAC TAC CGT GAC GTC GTT GTC GTC
 D   S   A   P   S   M   M   A   L   Q   Q   Q   Q 1420              1430              1440              1450
CCC TCC CAC AAT CAG TTG CAG CCA CCG GCG CCA GTG TTC
GGG AGG GTG TTA GTC AAC GTC GGT GGC CGC GGT CAC AAG
 P   S   H   N   Q   L   Q   P   P   A   P   V   F 1460              1470              1480              1490
AAT CCG CAG ATA TGG ACG GAG GGC AAG ATG ATC CCT TCG
TTA GGC GTC TAT ACC TGC CTC CCG TTC TAC TAG GGA AGC
 N   P   Q   I   W   T   E   G   K   M   I   P   S 1500              1510              1520              1530
AAG GAG CTC GAT AAG GAG CAT TCT CAT CCC AAT GGC CCG
TTC CTC GAG CTA TTC CTC GTA AGA GTA GGG TTA CCG GGC
 K   E   L   D   K   E   H   S   H   P   N   G   P 1540              1550              1560              1570
CAA CAG CAG CTC AGC CTG ACC AGC GGC AGT GGG AAC AGC
GTT GTC GTC GAG TCG GAC TGG TCG CCG TCA CCC TTG TCG
 Q   Q   Q   L   S   L   T   S   G   S   G   N   S 1580              1590              1600
GAA CCG GAA CCG GAG TCC ACT GCG TAC CGG GTC TTT GGT
CTT GGC CTT GGC CTC AGG TGA CGC ATG GCC CAG AAA CCA
 E   P   E   P   E   S   T   A   Y   R   V   F   G 1610              1620              1630              1640
 GGT CTC AAC AGC GAC GAG AGC GAG GGC AAC GAC CTG TAC
 CCA GAG TTG TCG CTG CTC TCG CTC CCG TTG CTG GAC ATG
  G   L   N   S   D   E   S   E   G   N   D   L   Y 1650              1660              1670              1680
 GAC ACC CAC CTG CCG CTG GCC GAG GAC AAC AAG GAG CTG
 CTG TGG GTG GAC GGC GAC CGG CTC CTG TTG TTC CTC GAC
  D   T   H   L   P   L   A   E   D   N   K   E   L 1690              1700              1710              1720
 AAG CGC CTG ATA GAG GAC AAC TAT CTG TAC TTT AAG CGC
 TTC GCG GAC TAT CTC CTG TTG ATA GAC ATG AAA TTC GCG
  K   R   L   I   E   D   N   Y   L   Y   F   K   R 1730              1740              1750              1760
 CAG ACG GGC GGC ACC ATT ATC AGT GGC CCA GGC GGA GGA
 GTC TGC CCG CCG TGG TAA TAG TCA CCG GGT CCG CCT CCT
  Q   T   G   G   T   I   I   S   G   P   G   G   G 1770              1780              1790              1800
 AAG TAC GCT GCC CTC AGT GAA ACG GAC TTC ATC CGG CTG
 TTC ATG CGA CGG GAG TCA CTT TGC CTG AAG TAG GCC GAC
  K   Y   A   A   L   S   E   T   D   F   I   R   L
```

FIG. 1D

```
      1810           1820           1830           1840
AAG GCG GGC GCA GCG GCC TGT GGG CGT AAG GCA TTC GCC
TTC CGC CCG CGT CGC CGG ACA CCC GCA TTC CGT AAG CGG
 K   A   G   A   A   A   C   G   R   K   A   F   A 1850           1860           1870           1880
TCC AGC GAT TCG GAG TTC CTG CGC ACC ATT AGT GAA TCG
AGG TCG CTA AGC CTC AAG GAC GCG TGG TAA TCA CTT AGC
 S   S   D   S   E   F   L   R   T   I   S   E   S 1890           1900           1910           1920
CGG GCG TTG CCG GAG CAG CCA GTG CCC GGG AAG GAG AAG
GCC CGC AAC GGC CTC GTC GGT CAC GGG CCC TTC CTC TTC
 R   A   L   P   E   Q   P   V   P   G   K   E   K 1930           1940           1950           1960
GGC TTC AAC ATT CTG TCC CTG CTG TCG AAG ACG AAA CGC
CCG AAG TTG TAA GAC AGG GAC GAC AGC TTC TGC TTT GCG
 G   F   N   I   L   S   L   L   S   K   T   K   R 1970           1980           1990
TCG AGC ACC GAG TGC TTT ACG CTG GAA AAG AAG CGA CAT
AGC TCG TGG CTC ACG AAA TGC GAC CTT TTC TTC GCT GTA
 S   S   T   E   C   F   T   L   E   K   K   R   H 2000           2010           2020           2030
CAG GCC AAC TCC GAG GGA TCC AGC TTC TTC CGG CGC TCC
GTC CGG TTG AGG CTC CCT AGG TCG AAG AAG GCC GCG AGG
 Q   A   N   S   E   G   S   S   F   F   R   R   S 2040           2050           2060           2070
CGG AAC CGG AAA TTG TCG CAC AGC TAC AAC GGA TGC GGT
GCC TTG GCC TTT AAC AGC GTG TCG ATG TTG CCT ACG CCA
 R   N   R   K   L   S   H   S   Y   N   G   C   G 2080           2090           2100           2110
GGC GGC AAG GAA CGC AAA CTT GAG AGA CGC CAG CGG CAG
CCG CCG TTC CTT GCG TTT GAA CTC TCT GCG GTC GCC GTC
 G   G   K   E   R   K   L   E   R   R   Q   R   Q 2120           2130           2140           2150
CAC AGC GAT ACG GAC TCC ACG CCC AAC AAG CCG GAC ATC
GTG TCG CTA TGC CTG AGG TGC GGG TTG TTC GGC CTG TAG
 H   S   D   T   D   S   T   P   N   K   P   D   I 2160           2170           2180           2190
CTG CTG GAC ATC AAT GTG CTC AGC GAG CAG AGT GGA GCC
GAC GAC CTG TAG TTA CAC GAG TCG CTC GTC TCA CCT CGG
 L   L   D   I   N   V   L   S   E   Q   S   G   A 2200           2210           2220           2230
AGT GTG ATC CAG CAG TTC AGC GAC GGG GTA CAG CTG ATT
TCA CAC TAG GTC GTC AAG TCG CTG CCC CAT GTC GAC TAA
 S   V   I   Q   Q   F   S   D   G   V   Q   L   I 2240           2250           2260           2270
GAC TTC AGT GAG CTG AAA ACA CCG CCC GAG AGG ATT CGG
CTG AAG TCA CTC GAC TTT TGT GGC GGG CTC TCC TAA GCC
 D   F   S   E   L   K   T   P   P   E   R   I   R
```

FIG. 1E

```
            2280             2290              2300             2310
      AGC GAC GAC GAG TTG GCG CAG CTG GCC GAT TGC TTT GGG
      TCG CTG CTG CTC AAC CGC GTC GAC CGG CTA ACG AAA CCC
       S   D   D   E   L   A   Q   L   A   D   C   F   G 2320             2330              2340             2350
      GAG TCG CCC CAG CAG CCG GCC ACG CCG CCA CCA TCG TTG
      CTC AGC GGG GTC GTC GGC CGG TGC GGC GGT GGT AGC AAC
       E   S   P   Q   Q   P   A   T   P   P   P   S   L 2360             2370             2380
      TCG CCG CCA GAA TTG CCA GAA CCG AGT GGC CTG CTC ATT
      AGC GGC GGT CTT AAC GGT CTT GGC TCA CCG GAC GAG TAA
       S   P   P   E   L   P   E   P   S   G   L   L   I 2390             2400             2410             2420
      GCC AGC AGC TCG GAA CTG GCC GAG ATC TTT CGC TCG CTG
      CGG TCG TCG AGC CTT GAC CGG CTC TAG AAA GCG AGC GAC
       A   S   S   S   E   L   A   E   I   F   R   S   L 2430             2440             2450             2460
      AGC TTT CCG CTG GGC CGA CCG GCT GGT GCT CCA CAG CGC
      TCG AAA GGC GAC CCG GCT GGC CGA CCA CGA GGT GTC GCG
       S   F   P   L   G   R   P   A   G   A   P   Q   R 2470             2480             2490             2500
      CTG AGC ACG CTC AGT GAC CAG GTG TGC GCC AAC TAT CTG
      GAC TCG TGC GAG TCA CTG GTC CAC ACG CGG TTG ATA GAC
       L   S   T   L   S   D   Q   V   C   A   N   Y   L 2510             2520             2530             2540
      ATG TCC CCA CCG AAC ACA CCG GCT CCG CCG GCC ATT TCC
      TAC AGG GGT GGC TTG TGT GGC CGA GGC GGC CGG TAA AGG
       M   S   P   P   N   T   P   A   P   P   A   I   S 2550             2560             2570             2580
      GTG CCG AAC GGA GGT GCC ATG GAC TCT TCC GCC TCT TCC
      CAC GGC TTG CCT CCA CGG TAC CTG AGA AGG CGG AGA AGG
       V   P   N   G   G   A   M   D   S   S   A   S   S 2590             2600             2610             2620
      AAC GCG CAG TCG GCG TCC ATC AAT GTG TAC TTC CTA TCG
      TTG CGC GTC AGC CGC AGG TAG TTA CAC ATG AAG GAT AGC
       N   A   Q   S   A   S   I   N   V   Y   F   L   S 2630             2640             2650             2660
      CCG CCG CCG CAT GCC GCC GCA CCT GGT TAT ACG CCC AGT
      GGC GGC GGC GTA CGG CGG CGT GGA CCA ATA TGC GGG TCA
       P   P   P   H   A   A   A   P   G   Y   T   P   S 2670             2680             2690             2700
      GAC ACA TCC ACT GTG TCC TTG GAT GTG GTG ACC AGC CTG
      CTG TGT AGG TGA CAC AGG AAC CTA CAC CAC TGG TCG GAC
       D   T   S   T   V   S   L   D   V   V   T   S   L 2710             2720             2730             2740
      CCT ATG CCC GTT CCA GTG CCG CAG CCA AAT CCC CAA ATG
      GGA TAC GGG CAA GGT CAC GGC GTC GGT TTA GGG GTT TAC
       P   M   P   V   P   V   P   Q   P   N   P   Q   M
```

FIG. 1F

```
              2750             2760            2770
     GCC TCA CAG TCC AAC ATA TCG CCC AAG CCG GAG ATC ATA
     CGG AGT GTC AGG TTG TAT AGC GGG TTC GGC CTC TAG TAT
      A   S   Q   S   N   I   S   P   K   P   E   I   I 2780            2790            2800            2810
  CTC GAT TCC ACG CTG TCG CCG GTT GAG GGA TGC GGC GAT
  GAG CTA AGG TGC GAC AGC GGC CAA CTC CCT ACG CCG CTA
   L   D   S   T   L   S   P   V   E   G   C   G   D 2820            2830            2840            2850
  GAG CAC CGG GAT GTC ACG TCG CCA CTG TTC AAG CGC AAA
  CTC GTG GCC CTA CAG TGC AGC GGT GAC AAG TTC GCG TTT
   E   H   R   D   V   T   S   P   L   F   K   R   K 2860            2870            2880            2890
  GAT AGC GCC GGC GAT GCG GAC GTG AGC GTT TCC GGC AAT
  CTA TCG CGG CCG CTA CGC CTG CAC TCG CAA AGG CCG TTA
   D   S   A   G   D   A   D   V   S   V   S   G   N 2900            2910            2920            2930
  GGA GGG GCT GGT GGC GTT GGA GGA GTG GGT GGC CGC CAA
  CCT CCC CGA CCA CCG CAA CCT CCT CAC CCA CCG GCG GTT
   G   G   A   G   G   V   G   G   V   G   G   R   Q 2940            2950            2960            2970
  GGC CGC TGC AGC ATC CTG GCA GGC TAC GAT GGC ATC CAA
  CCG GCG ACG TCG TAG GAC CGT CCG ATG CTA CCG TAG GTT
   G   R   C   S   I   L   A   G   Y   D   G   I   Q 2980            2990            3000            3010
   ACT GTG CGG AAG AGA CAG GCG TCC GTG GTG ACC TAC GAC
   TGA CAC GCC TTC TCT GTC CGC AGG CAC CAC TGG ATG CTG
    T   V   R   K   R   Q   A   S   V   V   T   Y   D 3020            3030            3040            3050
   GTG AAT GTC ATC AAC TTC TCG CAG GAG AAC AGC GAC AGT
   CAC TTA CAG TAG TTG AAG AGC GTC CTC TTG TCG CTG TCA
    V   N   V   I   N   F   S   Q   E   N   S   D   S 3060            3070            3080            3090
      CGC AGC TAC ATC CCG ATG GGC CGC GTT TCC ACC AGT TCC
      GCG TCG ATG TAG GGC TAC CCG GCG CAA AGG TGG TCA AGG
       R   S   Y   I   P   M   G   R   V   S   T   S   S 3100            3110            3120           3130
         GCA AGC GGT TCC GTG CGA CCG GCC AAA GGA TGG AAG GCC
         CGT TCG CCA AGG CAC GCT GGC CGG TTT CCT ACC TTC CGG
          A   S   G   S   V   R   P   A   K   G   W   K   A 3140            3150            3160
           GAA CAC AAG GCC GCC CGC ACC CTG GGC ATC ATC ATG GGC
           CTT GTG TTC CGG CGG GCG TGG GAC CCG TAG TAG TAC CCG
            E   H   K   A   A   R   T   L   G   I   I   M   G

TRANSMEMBRANE DOMAIN  6
 3170            3180            3190            3200
  GTC TTT CTG CTC TGC TGG CTG CCC TTC TTT CTG TGG TAT
  CAG AAA GAC GAG ACG ACC GAC GGG AAG AAA GAC ACC ATA
   V   F   L   L   C   W   L   P   F   F   L   W   Y
```

FIG. 1G

```
      3210          3220           3230          3240
     GTT ATC ACA TCG CTC TGC GGT CCG GCC TGC CCA TGT CCC
     CAA TAG TGT AGC GAG ACG CCA GGC CGG ACG GGT ACA GGG
      V   I   T   S   L   C   G   P   A   C   P   C   P 3250          3260           3270          3280
     GAT GTG CTC GTG GTG GTG TTA TTC TGG ATC GGT TAC TTC
     CTA CAC GAG CAC CAC CAC AAT AAG ACC TAG CCA ATG AAG
      D   V   L   V   V   V   L   F   W   I   G   Y   F

TRANSMEMBRANE DOMAIN  7
     |
     |3290          3300           3310          3320
     AAC TCC ACG CTA AAT CCG CTT ATA TAC GCC TAC TTT AAT
     TTG AGG TGC GAT TTA GGC GAA TAT ATG CGG ATG AAA TTA
      N   S   T   L   N   P   L   I   Y   A   Y   F   N 3330          3340           3350          3360
     CGC GAT TTT CGC GAG GCA TTC CGC AAT ACG CTG GAG TGT
     GCG CTA AAA GCG CTC CGT AAG GCG TTA TGC GAC CTC ACA
      R   D   F   R   E   A   F   R   N   T   L   E   C 3370          3380           3390          3400
     GTG CTG CCC TGT CTG GAG AAA CGA AAT CCG TAC AAC GCC
     CAC GAC GGG ACA GAC CTC TTT GCT TTA GGC ATG TTG CGG
      V   L   P   C   L   E   K   R   N   P   Y   N   A 3410          3420          3430          3440         3450
     TAC TAC GTC TAGACCGGATAGCGTCTGCATCCCGGCCACATTCCTGC
     ATG ATG CAG ATCTGGCCTATCGCAGACGTAGGGCCGGTGTAAGGACG
      Y   Y   V

3460
     TTCGTCCACCCTCGT
     AAGCAGGTGGGAGCA
```

FIG. 1H

```
         10         20         30         40         50
GACGGATCGGGAGATCTCCCGATCCCCTATGGTCGACTCTCAGTACAATC
CTGCCTAGCCCTCTAGAGGGCTAGGGGATACCAGCTGAGAGTCATGTTAG 60         70         80         90        100
TGCTCTGATGCCGCATAGTTAAGCCAGTATCTGCTCCCTGCTTGTGTGTT
ACGAGACTACGGCGTATCAATTCGGTCATAGACGAGGGACGAACACACAA 110        120        130        140        150
GGAGGTCGCTGAGTAGTGCGCGAGCAAAATTTAAGCTACAACAAGGCAAG
CCTCCAGCGACTCATCACGCGCTCGTTTTAAATTCGATGTTGTTCCGTTC 160        170        180        190        200
GCTTGACCGACAATTGCATGAAGAATCTGCTTAGGGTTAGGCGTTTTGCG
CGAACTGGCTGTTAACGTACTTCTTAGACGAATCCCAATCCGCAAAACGC 210        220        230        240        250
CTGCTTCGCGATGTACGGGCCAGATATACGCGTTGACATTGATTATTGAC
GACGAAGCGCTACATGCCCGGTCTATATGCGCAACTGTAACTAATAACTG 260        270        280        290        300
TAGTTATTAATAGTAATCAATTACGGGGTCATTAGTTCATAGCCCATATA
ATCAATAATTATCATTAGTTAATGCCCCAGTAATCAAGTATCGGGTATAT 310        320        330        340        350
TGGAGTTCCGCGTTACATAACTTACGGTAAATGGCCCGCCTGGCTGACCG
ACCTCAAGGCGCAATGTATTGAATGCCATTTACCGGGCGGACCGACTGGC 360        370        380        390        400
CCCAACGACCCCCGCCCATTGACGTCAATAATGACGTATGTTCCCATAGT
GGGTTGCTGGGGGCGGGTAACTGCAGTTATTACTGCATACAAGGGTATCA 410        420        430        440        450
AACGCCAATAGGGACTTTCCATTGACGTCAATGGGTGGACTATTTACGGT
TTGCGGTTATCCCTGAAAGGTAACTGCAGTTACCCACCTGATAAATGCCA 460        470        480        490        500
AAACTGCCCACTTGGCAGTACATCAAGTGTATCATATGCCAAGTACGCCC
TTTGACGGGTGAACCGTCATGTAGTTCACATAGTATACGGTTCATGCGGG 510        520        530        540        550
CCTATTGACGTCAATGACGGTAAATGGCCCGCCTGGCATTATGCCCAGTA
GGATAACTGCAGTTACTGCCATTTACCGGGCGGACCGTAATACGGGTCAT 560        570        580        590        600
CATGACCTTATGGGACTTTCCTACTTGGCAGTACATCTACGTATTAGTCA
GTACTGGAATACCCTGAAAGGATGAACCGTCATGTAGATGCATAATCAGT 610        620        630        640        650
TCGCTATTACCATGGTGATGCGGTTTTGGCAGTACATCAATGGGCGTGGA
AGCGATAATGGTACCACTACGCCAAAACCGTCATGTAGTTACCCGCACCT
```

FIG. 2A

```
                660       670       680       690       700
          TAGCGGTTTGACTCACGGGGATTTCCAAGTCTCCACCCCATTGACGTCAA
          ATCGCCAAACTGAGTGCCCCTAAAGGTTCAGAGGTGGGGTAACTGCAGTT 710       720       730       740       750
          TGGGAGTTTGTTTTGGCACCAAAATCAACGGGACTTTCCAAAATGTCGTA
          ACCCTCAAACAAAACCGTGGTTTTAGTTGCCCTGAAAGGTTTTACAGCAT 760       770       780       790       800
          ACAACTCCGCCCCATTGACGCAAATGGGCGGTAGGCGTGTACGGTGGGAG
          TGTTGAGGCGGGGTAACTGCGTTTACCCGCCATCCGCACATGCCACCCTC 810       820       830       840       850
          GTCTATATAAGCAGAGCTCTCTGGCTAACTAGAGAACCCACTGCTTACTG
          CAGATATATTCGTCTCGAGAGACCGATTGATCTCTTGGGTGACGAATGAC 860       870       880       890       900
          GCTTATCGAAATTAATACGACTCACTATAGGGAGACCCAAGCTGGCTAGC
          CGAATAGCTTTAATTATGCTGAGTGATATCCCTCTGGGTTCGACCGATCG 910       920       930       940       950
          GTTTAAACGGGCCCTCTAGACTCGAGCGGCCGCGTGAAATAAAGAGCCAG
          CAAATTTGCCCGGGAGATCTGAGCTCGCCGGCGCACTTTATTTCTCGGTC 960       970       980       990
          TTCTGGGACTAAGCAAGCTGCCCACGCGGTCAAC ATG TTC CGG CCA
          AAGACCCTGATTCGTTCGACGGGTGCGCCAGTTG TAC AAG GCC GGT
                                              M   F   R   P 1000           1010           1020           1030
          AGT TGG TTT CCA TTC GCC AGC CTG CTG TTC CTG CTC CTT
          TCA ACC AAA GGT AAG CGG TCG GAC GAC AAG GAC GAG GAA
           S   W   F   P   F   A   S   L   L   F   L   L   L 1040           1050           1060           1070
          TGG AGC ACC GCC TGT GGC AGG ACA GCC AAG AGA TCG GAC
          ACC TCG TGG CGG ACA CCG TCC TGT CGG TTC TCT AGC CTG
           W   S   T   A   C   G   R   T   A   K   R   S   D 1080           1090           1100           1110
          GTC TAC ATA GCG GGA TTC TTC CCG TAC GGG GAT GGC GTG
          CAG ATG TAT CGC CCT AAG AAG GGC ATG CCC CTA CCG CAC
           V   Y   I   A   G   F   F   P   Y   G   D   G   V 1120           1130           1140           1150
          GAA AAC TCC TAC ACC GGT CGG GGC GTT ATG CCC AGT GTA
          CTT TTG AGG ATG TGG CCA GCC CCG CAA TAC GGG TCA CAT
           E   N   S   Y   T   G   R   G   V   M   P   S   V
```

FIG. 2B

```
           1160           1170          1180           1190
     AAG CTC GCC TTG GGT CAC GTT AAT GAG CAT GGA AAG ATA
     TTC GAG CGG AAC CCA GTG CAA TTA CTC GTA CCT TTC TAT
      K   L   A   L   G   H   V   N   E   H   G   K   I 1200          1210          1220           1230
     CTG GCC AAC TAC AGG CTG CAC ATG TGG TGG AAC GAC ACT
     GAC CGG TTG ATG TCC GAC GTG TAC ACC ACC TTG CTG TGA
      L   A   N   Y   R   L   H   M   W   W   N   D   T 1240          1250          1260
     CAG TGC AAT GCT GCT GTG GGC GTA AAG TCC TTC TTC GAT
     GTC ACG TTA CGA CGA CAC CCG CAT TTC AGG AAG AAG CTA
      Q   C   N   A   A   V   G   V   K   S   F   F   D 1270           1280          1290          1300
     ATG ATG CAT TCG GGT CCC AAT AAA GTG ATG CTC TTC GGC
     TAC TAC GTA AGC CCA GGG TTA TTT CAC TAC GAG AAG CCG
      M   M   H   S   G   P   N   K   V   M   L   F   G 1310           1320          1330          1340
     GCT GCG TGC ACC CAT GTG ACC GAT CCC ATA GCC AAG GCC
     CGA CGC ACG TGG GTA CAC TGG CTA GGG TAT CGG TTC CGG
      A   A   C   T   H   V   T   D   P   I   A   K   A 1350          1360          1370          1380
     AGC AAG CAC TGG CAC CTC ACC CAG CTC AGC TAC GCG GAC
     TCG TTC GTG ACC GTG GAG TGG GTC GAG TCG ATG CGC CTG
      S   K   H   W   H   L   T   Q   L   S   Y   A   D 1390          1400          1410          1420
     ACC CAT CCC ATG TTC ACC AAG GAT GCG TTT CCG AAT TTC
     TGG GTA GGG TAC AAG TGG TTC CTA CGC AAA GGC TTA AAG
      T   H   P   M   F   T   K   D   A   F   P   N   F 1430          1440          1450          1460
     TTT CGC GTG GTA CCC TCG GAG AAT GCC TTT AAT GCG CCG
     AAA GCG CAC CAT GGG AGC CTC TTA CGG AAA TTA CGC GGC
      F   R   V   V   P   S   E   N   A   F   N   A   P 1470          1480          1490          1500
     CGA CTG GCC TTG CTG AAG GAG TTC AAT TGG ACC AGA GTG
     GCT GAC CGG AAC GAC TTC CTC AAG TTA ACC TGG TCT CAC
      R   L   A   L   L   K   E   F   N   W   T   R   V 1510          1520          1530          1540
     GGC ACT GTC TAC CAG AAT GAG CCA CGC TAT TCG CTG CCC
     CCG TGA CAG ATG GTC TTA CTC GGT GCG ATA AGC GAC GGG
      G   T   V   Y   Q   N   E   P   R   Y   S   L   P
```

FIG. 2C

```
              1550           1560           1570           1580
       CAC AAT CAC ATG GTG GCT GAC CTG GAT GCC ATG GAG GTC
       GTG TTA GTG TAC CAC CGA CTG GAC CTA CGG TAC CTC CAG
        H   N   H   M   V   A   D   L   D   A   M   E   V 1590           1600           1610           1620
       GAG GTG GTG GAA ACG CAG AGC TTC GTC AAC GAT GTG GCT
       CTC CAC CAC CTT TGC GTC TCG AAG CAG TTG CTA CAC CGA
        E   V   V   E   T   Q   S   F   V   N   D   V   A
                   1630           1640           1650
       GAA TCA TTG AAG AAA CTG CGC GAG AAG GAC GTG AGG ATC
       CTT AGT AAC TTC TTT GAC GCG CTC TTC CTG CAC TCC TAG
        E   S   L   K   K   L   R   E   K   D   V   R   I 1660           1670           1680           1690
   ATT CTG GGC AAC TTT AAC GAG CAC TTT GCA CGC AAG GCA
   TAA GAC CCG TTG AAA TTG CTC GTG AAA CGT GCG TTC CGT
    I   L   G   N   F   N   E   H   F   A   R   K   A 1700           1710           1720           1730
   TTC TGT GAG GCT TAT AAA TTG GAT ATG TAT GGC AGA GCC
   AAG ACA CTC CGA ATA TTT AAC CTA TAC ATA CCG TCT CGG
    F   C   E   A   Y   K   L   D   M   Y   G   R   A 1740           1750           1760           1770
   TAT CAA TGG CTG ATC ATG GCT ACC TAT TCC ACG GAT TGG
   ATA GTT ACC GAC TAG TAC CGA TGG ATA AGG TGC CTA ACC
    Y   Q   W   L   I   M   A   T   Y   S   T   D   W 1780           1790           1800           1810
   TGG AAT GTC ACG CAG GAC AGC GAG TGC AGT GTG GAG GAG
   ACC TTA CAG TGC GTC CTG TCG CTC ACG TCA CAC CTC CTC
    W   N   V   T   Q   D   S   E   C   S   V   E   E

TRANSMEMBRANE DOMAIN 1
              |
       1820           1830           1840           1850
       ATC GCT ACA GCC TTG GAA GGT GCC ATT CTA GTG GAT CTT
       TAG CGA TGT CGG AAC CTT CCA CGG TAA GAT CAC CTA GAA
        I   A   T   A   L   E   G   A   I   L   V   D 1860           1870           1880           1890
       TTG CCC TTG TCC ACC AGT GGT GAC ATC ACA GTG GCT GGC
       AAC GGG AAC AGG TGG TCA CCA CTG TAG TGT CAC CGA CCG
        L   P   L   S   T   S   G   D   I   T   V   A   G 1900           1910           1920           1930
       ATT ACT GCT GAT GAG TAT CTT GTG GAG TAC GAC AGA CTG
       TAA TGA CGA CTA CTC ATA GAA CAC CTC ATG CTG TCT GAC
        I   T   A   D   E   Y   L   V   E   Y   D   R   L
```

FIG. 2D

```
              1940           1950          1960           1970
         CGA GGC ACT GAA TAT TCC CGC TTT CAT GGC TAT ACC TAC
         GCT CCG TGA CTT ATA AGG GCG AAA GTA CCG ATA TGG ATG
          R   G   T   E   Y   S   R   F   H   G   Y   T   Y 1980           1990          2000           2010
         GAT GGT ATC TGG GCA GCT GCC CTG GCC ATT CAG TAT GTG
         CTA CCA TAG ACC CGT CGA CGG GAC CGG TAA GTC ATA CAC
          D   G   I   W   A   A   A   L   A   I   Q   Y   V 2020           2030          2040
         GCC GAA AAG CGA GAG GAT CTG CTA ACA CAT TTT GAT TAT
         CGG CTT TTC GCT CTC CTA GAC GAT TGT GTA AAA CTA ATA
          A   E   K   R   E   D   L   L   T   H   F   D   Y 2050           2060          2070           2080
         CGC GTG AAG GAC TGG GAG AGT GTC TTC CTT GAG GCT CTA
         GCG CAC TTC CTG ACC CTC TCA CAG AAG GAA CTC CGA GAT
          R   V   K   D   W   E   S   V   F   L   E   A   L 2090           2100          2110           2120
         CGT AAT ACA TCC TTC GAG GGT GTG ACG GGA CCC GTG CGT
         GCA TTA TGT AGG AAG CTC CCA CAC TGC CCT GGG CAC GCA
          R   N   T   S   F   E   G   V   T   G   P   V   R 2130           2140          2150           2160
         TTC TAC AAC AAC GAG CGC AAG GCC AAC ATC CTG ATC AAT
         AAG ATG TTG TTG CTC GCG TTC CGG TTG TAG GAC TAG TTA
          F   Y   N   N   E   R   K   A   N   I   L   I   N
     2170           2180          2190           2200
         CAG TTT CAG CTG GGA CAA ATG GAA AAG ATC GGG GAA TAC
         GTC AAA GTC GAC CCT GTT TAC CTT TTC TAG CCC CTT ATG
          Q   F   Q   L   G   Q   M   E   K   I   G   E   Y 2210           2220          2230           2240
         CAC TCA CAG AAG TCA CAC TTG GAT TTA AGC TTG GGA AAA
         GTG AGT GTC TTC AGT GTG AAC CTA AAT TCG AAC CCT TTT
          H   S   Q   K   S   H   L   D   L   S   L   G   K 2250           2260          2270           2280
         CCA GTC AAA TGG GTG GGG AAA ACT CCT CCC AAG GAT CGC
         GGT CAG TTT ACC CAC CCC TTT TGA GGA GGG TTC CTA GCG
          P   V   K   W   V   G   K   T   P   P   K   D   R
             2290           2300          2310           2320
         ACT TTG ATC TAC ATC GAG CAC AGT CAG GTC AAT CCA ACC
         TGA AAC TAG ATG TAG CTC GTG TCA GTC CAG TTA GGT TGG
          T   L   I   Y   I   E   H   S   Q   V   N   P   T
```

FIG. 2E

TRANSMEMBRANE DOMAIN 2

```
             2330              2340    |     2350              2360
      ATA TAT ATT GTA TCG GCT AGT GCT TCG GTC ATT GGA GTG
      TAT ATA TAA CAT AGC CGA TCA CGA AGC CAG TAA CCT CAC
       I   Y   I   V   S   A   S   A   S   V   I   G   V 2370              2380              2390        2400
      ATT ATT GCC ACA GTT TTT CTG GCC TTT AAC ATT AAG TAT
      TAA TAA CGG TGT CAA AAA GAC CGG AAA TTG TAA TTC ATA
       I   I   A   T   V   F   L   A   F   N   I   K   Y 2410              2420              2430
      CGC AAT CAA AGA TAC ATC AAG ATG TCC AGT CCC CAT TTG
      GCG TTA GTT TCT ATG TAG TTC TAC AGG TCA GGG GTA AAC
       R   N   Q   R   Y   I   K   M   S   S   P   H   L
```

TRANSMEMBRANE DOMAIN 3

```
 2440          2450              2460              2470
   AAC AAT CTG ATC ATT GTG GGC TGT ATG ATG ACC TAT TTG
   TTG TTA GAC TAG TAA CAC CCG ACA TAC TAC TGG ATA AAC
    N   N   L   I   I   V   G   C   M   M   T   Y   L 2480          2490              2500              2510
   AGC ATC ATT TTC CTG GGT CTC GAT ACC ACA TTA AGT AGT
   TCG TAG TAA AAG GAC CCA GAG CTA TGG TGT AAT TCA TCA
    S   I   I   F   L   G   L   D   T   T   L   S   S
 2520          2530              2540              2550
   GTG GCA GCT TTT CCC TAT ATC TGC ACA GCT CGA GCC TGG
   CAC CGT CGA AAA GGG ATA TAG ACG TGT CGA GCT CGG ACC
    V   A   A   F   P   Y   I   C   T   A   R   A   W 2560          2570              2580              2590
      ATC TTG ATG GCT GGA TTC AGT CTC AGT TTT GGA GCC ATG
      TAG AAC TAC CGA CCT AAG TCA GAG TCA AAA CCT CGG TAC
       I   L   M   A   G   F   S   L   S   F   G   A   M 2600          2610              2620              2630
      TTC TCG AAG ACG TGG CGG GTG CAT TCG ATA TTC ACC GAT
      AAG AGC TTC TGC ACC GCC CAC GTA AGC TAT AAG TGG CTA
       F   S   K   T   W   R   V   H   S   I   F   T   D 2640              2650              2660        2670
      CTG AAG CTC AAT AAG AAG GTG ATC AAG GAC TAT CAA TTG
      GAC TTC GAG TTA TTC TTC CAC TAG TTC CTG ATA GTT AAC
       L   K   L   N   K   K   V   I   K   D   Y   Q   L
```

FIG. 2F

TRANSMEMBRANE DOMAIN 4

```
      |
      |      2680            2690            2700            2710
      TTT ATG GTT GTG GGC GTG CTT TTG GCC ATT GAT ATA GCC
      AAA TAC CAA CAC CCG CAC GAA AAC CGG TAA CTA TAT CGG
       F   M   V   V   G   V   L   L   A   I   D   I   A
             2720            2730            2740            2750
      ATT ATA ACC ACC TGG CAG ATT GCC GAT CCC TTT TAC CGC
      TAA TAT TGG TGG ACC GTC TAA CGG CTA GGG AAA ATG GCG
       I   I   T   T   W   Q   I   A   D   P   F   Y   R 2760            2770            2780            2790
      GAA ACT AAA CAG TTG GAA CCC TTG CAT CAC GAG AAT ATT
      CTT TGA TTT GTC AAC CTT GGG AAC GTA GTG CTC TTA TAA
       E   T   K   Q   L   E   P   L   H   H   E   N   I 2800            2810            2820
      GAT GAT GTC TTG GTG ATC CCC GAA AAC GAG TAC TGC CAG
      CTA CTA CAG AAC CAC TAG GGG CTT TTG CTC ATG ACG GTC
       D   D   V   L   V   I   P   E   N   E   Y   C   Q
```

TRANSMEMBRANE DOMAIN 5

```
                                         |
2830            2840            2850            2860
  TCT GAG CAC ATG ACC ATA TTC GTT AGC ATT ATT TAT GCC
  AGA CTC GTG TAC TGG TAT AAG CAA TCG TAA TAA ATA CGG
   S   E   H   M   T   I   F   V   S   I   I   Y   A
2870            2880            2890            2900
  TAC AAG GGA CTG TTG TTG GTT TTT GGC GCC TTT TTG GCC
  ATG TTC CCT GAC AAC AAC CAA AAA CCG CGG AAA AAC CGG
   Y   K   G   L   L   V   F   G   A   F   L   A
2910            2920            2930            2940
  TGG GAA ACT CGA CAT GTT TCT ATA CCG GCT CTG AAC GAT
  ACC CTT TGA GCT GTA CAA AGA TAT GGC CGA GAC TTG CTA
   W   E   T   R   H   V   S   I   P   A   L   N   D
```

TRANSMEMBRANE DOMAIN 6

```
                                              |
   2950            2960            2970       |2980
   TCC AAG CAT ATT GGT TTC TCC GTT TAT AAC GTG TTC ATC
   AGG TTC GTA TAA CCA AAG AGG CAA ATA TTG CAC AAG TAG
    S   K   H   I   G   F   S   V   Y   N   V   F   I 2990            3000            3010            3020
   ACT TGT CTG GCC GGA GCG GCT ATA TCC CTG GTG CTA TCG
   TGA ACA GAC CGG CCT CGC CGA TAT AGG GAC CAC GAT AGC
    T   C   L   A   G   A   A   I   S   L   V   L   S
```

FIG. 2G

```
                    TRANSMEMBRANE DOMAIN 7
                            |
         3030           3040           3050           3060
    GAT CGA AAG GAT TTA GTT TTT GTC TTA CTC TCG TTT TTT
    CTA GCT TTC CTA AAT CAA AAA CAG AAT GAG AGC AAA AAA
     D   R   K   D   L   V   F   V   L   S   F   F 3070           3080           3090           3100
    ATC ATT TTT TGT ACG ACA GCC ACT TTG TGT TTG GTG TTC
    TAG TAA AAA ACA TGC TGT CGG TGA AAC ACA AAC CAC AAG
     I   I   F   C   T   T   A   T   L   C   L   V   F 3110           3120           3130           3140
    GTA CCG AAA TTG GTG GAG CTG AAG CGG AAT CCC CAG GGC
    CAT GGC TTT AAC CAC CTC GAC TTC GCC TTA GGG GTC CCG
     V   P   K   L   V   E   L   K   R   N   P   Q   G 3150           3160           3170           3180
    GTG GTG GAC AAA CGC GTT AGG GCC ACG TTG AGA CCC ATG
    CAC CAC CTG TTT GCG CAA TCC CGG TGC AAC TCT GGG TAC
     V   V   D   K   R   V   R   A   T   L   R   P   M 3190           3200           3210
    TCC AAA AAC GGA CGC CGG GAT TCC TCG GTG TGC GAA CTG
    AGG TTT TTG CCT GCG GCC CTA AGG AGC CAC ACG CTT GAC
     S   K   N   G   R   R   D   S   S   V   C   E   L 3220           3230           3240           3250
    GAG CAA CGA TTG CGA GAT GTA AAG AAC ACA AAC TGC CGA
    CTC GTT GCT AAC GCT CTA CAT TTC TTG TGT TTG ACG GCT
     E   Q   R   L   R   D   V   K   N   T   N   C   R 3260           3270           3280           3290
    TTC CGA AAG GCG CTG ATG GAG AAG GAG AAC GAG CTG CAG
    AAG GCT TTC CGC GAC TAC CTC TTC CTC TTG CTC GAC GTC
     F   R   K   A   L   M   E   K   E   N   E   L   Q 3300           3310           3320           3330
    GCC TTA ATC CGC AAG CTG GGA CCC GAG GCA CGC AAA TGG
    CGG AAT TAG GCG TTC GAC CCT GGG CTC CGT GCG TTT ACC
     A   L   I   R   K   L   G   P   E   A   R   K   W 3340           3350           3360           3370
    ATC GAT GGG GTG ACC TGC ACA GGT GGC TCC AAC GTC GGT
    TAG CTA CCC CAC TGG ACG TGT CCA CCG AGG TTG CAG CCA
     I   D   G   V   T   C   T   G   G   S   N   V   G 3380           3390           3400           3410
    AGC GAA CTG GAG CCC ATA CTG AAC GAT GAC ATT GTT AGG
    TCG CTT GAC CTC GGG TAT GAC TTG CTA CTG TAA CAA TCC
     S   E   L   E   P   I   L   N   D   D   I   V   R
```

FIG. 2H

```
       3420            3430            3440            3450
CTC TCA GCT CCA CCG GTG CGT CGA GAG ATG CCC AGC ACC
GAG AGT CGA GGT GGC CAC GCA GCT CTC TAC GGG TCG TGG
 L   S   A   P   P   V   R   R   E   M   P   S   T 3460            3470            3480            3490
ACA GTT ACC GAG ATG ACG TCC GTG GAT AGT GTG ACC TCG
TGT CAA TGG CTC TAC TGC AGG CAC CTA TCA CAC TGG AGC
 T   V   T   E   M   T   S   V   D   S   V   T   S
       3500            3510            3520            3530
ACT CAT GTG GAG ATG GAT AAC TCC TTT GTG TCG GTG CAG
TGA GTA CAC CTC TAC CTA TTG AGG AAA CAC AGC CAC GTC
 T   H   V   E   M   D   N   S   F   V   S   V   Q 3540            3550            3560            3570
TCT ACA GTG ATG GCG CCA TCG CTT CCT CCC AAA AAG AAA
AGA TGT CAC TAC CGC GGT AGC GAA GGA GGG TTT TTC TTT
 S   T   V   M   A   P   S   L   P   P   K   K   K
          3580            3590            3600
AAG CAA TCG ATT GTA GAG CAC CAC TCG CAT GCC CCT GCT
TTC GTT AGC TAA CAT CTC GTG GTG AGC GTA CGG GGA CGA
 K   Q   S   I   V   E   H   H   S   H   A   P   A 3610            3620            3630            3640
CCA ACT ATG ATG CAG CCC ATC CAG CAG CAA CTG CAG CAG
GGT TGA TAC TAC GTC GGG TAG GTC GTC GTT GAC GTC GTC
 P   T   M   M   Q   P   I   Q   Q   Q   L   Q   Q 3650            3660            3670            3680
CAC TTA CAG CAA CAT CAG CAG ATG CAG CAG CAG CAC CTG
GTG AAT GTC GTT GTA GTC GTC TAC GTC GTC GTC GTG GAC
 H   L   Q   Q   H   Q   Q   M   Q   Q   Q   H   L 3690            3700            3710            3720
CAG CAG CAG CAA CAC CAG CAG ATG CAA CAG CAA CAG CAG
GTC GTC GTC GTT GTG GTC GTC TAC GTT GTC GTT GTC GTC
 Q   Q   Q   Q   H   Q   Q   M   Q   Q   Q   Q   Q 3730            3740            3750            3760
CAG CAG CAG CAT CAT CAT CGC CAT CTG GAG AAG AGA AAC
GTC GTC GTC GTA GTA GTA GCG GTA GAC CTC TTC TCT TTG
 Q   Q   Q   H   H   H   R   H   L   E   K   R   N 3770            3780            3790            3800
TCG GTG TCC GCT CAG ACC GAT GAT AAT ATA GGC AGC ATC
AGC CAC AGG CGA GTC TGG CTA CTA TTA TAT CCG TCG TAG
 S   V   S   A   Q   T   D   D   N   I   G   S   I
     3810            3820            3830            3840
ACC AGT ACG GCG GGC AAG CGG AGC GGA GGA GAC TGC TCC
TGG TCA TGC CGC CCG TTC GCC TCG CCT CCT CTG ACG AGG
 T   S   T   A   G   K   R   S   G   G   D   C   S
```

FIG. 21

```
              3850            3860            3870            3880
       AGC ATG CGG GAG AGG CGT CAA TCG ACC GCC TCC AGG CAC
       TCG TAC GCC CTC TCC GCA GTT AGC TGG CGG AGG TCC GTG
        S   M   R   E   R   R   Q   S   T   A   S   R   H 3890            3900            3910            3920
       TAC GAC AGT GGC AGC CAG ACG CCC ACC GCC CGG CCA AAG
       ATG CTG TCA CCG TCG GTC TGC GGG TGG CGG GCC GGT TTC
        Y   D   S   G   S   Q   T   P   T   A   R   P   K 3930            3940            3950            3960
       TAC AGC AGC TCG CAC CGG AAC TCC TCC ACC AAC ATC TCC
       ATG TCG TCG AGC GTG GCC TTG AGG AGG TGG TTG TAG AGG
        Y   S   S   S   H   R   N   S   S   T   N   I   S 3970            3980            3990
       ACA TCG CAA TCG GAG TTG AGC AAC ATG TGT CCA CAC TCA
       TGT AGC GTT AGC CTC AAC TCG TTG TAC ACA GGT GTG AGT
        T   S   Q   S   E   L   S   N   M   C   P   H   S
       4000            4010            4020            4030
       AAG CCC AGT ACT CCG GCT GTG ATT AAG ACT CCC ACT GCC
       TTC GGG TCA TGA GGC CGA CAC TAA TTC TGA GGG TGA CGG
        K   P   S   T   P   A   V   I   K   T   P   T   A 4040            4050            4060            4070
       TCC GAC CAT CGC CGC ACC AGC ATG GGC TCC GCT CTG AAG
       AGG CTG GTA GCG GCG TGG TCG TAC CCG AGG CGA GAC TTC
        S   D   H   R   R   T   S   M   G   S   A   L   K 4080            4090            4100            4110
       TCC AAT TTC GTG GTT TCA CAG AGT GAC CTC TGG GAC ACG
       AGG TTA AAG CAC CAA AGT GTC TCA CTG GAG ACC CTG TGC
        S   N   F   V   V   S   Q   S   D   L   W   D   T 4120            4130            4140            4150
       CAC ACG CTG TCG CAC GCC AAG CAG CGC CAG TCG CCG CGG
       GTG TGC GAC AGC GTG CGG TTC GTC GCG GTC AGC GGC GCC
        H   T   L   S   H   A   K   Q   R   Q   S   P   R
       4160            4170            4180            4190
       AAC TAC GCC AGT CCG CAG CGC TGT GCG GAA CAT CAT GGC
       TTG ATG CGG TCA GGC GTC GCG ACA CGC CTT GTA GTA CCG
        N   Y   A   S   P   Q   R   C   A   E   H   H   G 4200            4210            4220            4230
       GGC CAC GGG ATG ACC TAT GAC CCG AAC ACC ACC TCG CCC
       CCG GTG CCC TAC TGG ATA CTG GGC TTG TGG TGG AGC GGG
        G   H   G   M   T   Y   D   P   N   T   T   S   P
```

FIG. 2J

```
       4240            4250            4260            4270
ATC CAG CGG TCC GTC TCC GAG AAG AAC CGC AAC AAA CAT
TAG GTC GCC AGG CAG AGG CTC TTC TTG GCG TTG TTT GTA
 I   Q   R   S   V   S   E   K   N   R   N   K   H 4280            4290            4300            4310
CGG CCA AAA CCG CAA AAG GGC ACC GTT TGC CAG AGC GAG
GCC GGT TTT GGC GTT TTC CCG TGG CAA ACG GTC TCG CTC
 R   P   K   P   Q   K   G   T   V   C   Q   S   E 4320            4330            4340            4350
ACG GAC AGC GAA CGG GAA CGA GAT CCG CCG CCC AAC AGT
TGC CTG TCG CTT GCC CTT GCT CTA GGC GGC GGG TTG TCA
 T   D   S   E   R   E   R   D   P   P   P   N   S 4360            4370            4380
CAG CCG TGC GTC CAG CCG CGT AAG GTC AGC CGG AGC TCT
GTC GGC ACG CAG GTC GGC GCA TTC CAG TCG GCC TCG AGA
 Q   P   C   V   Q   P   R   K   V   S   R   S   S 4390            4400            4410            4420
AAC ATC CAG CAC GCC GCC CAC CAC CAC AGT TCG CCC AAT
TTG TAG GTC GTG CGG CGG GTG GTG GTG TCA AGC GGG TTA
 N   I   Q   H   A   A   H   H   H   S   S   P   N 4430            4440            4450            4460
GTG GCG CCC GAT AAG CAG CGG AGC AGG CAG CGC GGC AAG
CAC CGC GGG CTA TTC GTC GCC TCG TCC GTC GCG CCG TTC
 V   A   P   D   K   Q   R   S   R   Q   R   G   K 4470            4480            4490            4500
CAG GAT AGC AGC ATC TAC GGC GCC AGC AGC GAG ACG GAA
GTC CTA TCG TCG TAG ATG CCG CGG TCG TCG CTC TGC CTT
 Q   D   S   S   I   Y   G   A   S   S   E   T   E 4510            4520            4530            4540
CTG CTC GAG GGC GAG ACG GCA ATT TTG CCC ATC TTC CGG
GAC GAG CTC CCG CTC TGC CGT TAA AAC GGG TAG AAG GCC
 L   L   E   G   E   T   A   I   L   P   I   F   R 4550            4560            4570            4580
AAA CTC CTC ACC GAG AAG AGT CCC AAC TAT CGG GGC CGC
TTT GAG GAG TGG CTC TTC TCA GGG TTG ATA GCC CCG GCG
 K   L   L   T   E   K   S   P   N   Y   R   G   R 4590            4600            4610            4620
AGT GCC GTG GGC CAG AGC TGT CCG AAT ATA TCC ATC AAA
TCA CGG CAC CCG GTC TCG ACA GGC TTA TAT AGG TAG TTT
 S   A   V   G   Q   S   C   P   N   I   S   I   K
```

FIG. 2K

```
              4630           4640           4650
        TGC GAT ATC GTC GAG TAC TTG TAG GCG
        ACG CTA TAG CAG CTC ATG AAC ATC CGC
         C   D   I   V   E   Y   L 4660      4670      4680      4690      4700
        GCGCGAGTCATATGCATTATGCCGTAGTTAAACTCCTATTGTTAGATCCA
        CGCGCTCAGTATACGTAATACGGCATCAATTTGAGGATAACAATCTAGGT 4710      4720      4730      4740      4750
        GTTGCAGTGTAAAGATTATCTTTGTTTTCTTTGGAGTTACGCATCTACAT
        CAACGTCACATTTCTAATAGAAACAAAAGAAACCTCAATGCGTAGATGTA 4760      4770      4780      4790      4800
        ACATACCCTGTGAAGCAGGACACACACCATTTAGTGAACTAGTAGCAATG
        TGTATGGGACACTTCGTCCTGTGTGTGGTAAATCACTTGATCATCGTTAC 4810      4820      4830      4840      4850
        ACATGAGATAGTTGGGAAATAAATTACAATTTAAAATAATCATAAAAAAA
        TGTACTCTATCAACCCTTTATTTAATGTTAAATTTTATTAGTATTTTTTT 4860      4870      4880      4890      4900
        AAAAAAAAAAAAAAAAAAAAAAAAAAAAAAAAAAAAAAAAAAAAAAAAA
        TTTTTTTTTTTTTTTTTTTTTTTTTTTTTTTTTTTTTTTTTTTTTTTTT 4910      4920      4930      4940      4950
        AAAAAAAAAAAAAAAAAAAAAAAAAAAAAAAAAAAAAACTCGAGGGGGG
        TTTTTTTTTTTTTTTTTTTTTTTTTTTTTTTTTTTTTTGAGCTCCCCCC 4960      4970      4980      4990      5000
        CCCGGTACCAAGCTTGGGCCCGAACAAAAACTCATCTCAGAAGAGGATCT
        GGGCCATGGTTCGAACCCGGGCTTGTTTTTGAGTAGAGTCTTCTCCTAGA 5010      5020      5030      5040      5050
        GAATAGCGCCGTCGACCATCATCATCATCATTGAGTTTAAACCGCTG
        CTTATCGCGGCAGCTGGTAGTAGTAGTAGTAGTAACTCAAATTTGGCGAC 5060      5070      5080      5090      5100
        ATCAGCCTCGACTGTGCCTTCTAGTTGCCAGCCATCTGTTGTTTGCCCCT
        TAGTCGGAGCTGACACGGAAGATCAACGGTCGGTAGACAACAAACGGGGA 5110      5120      5130      5140      5150
        CCCCCGTGCCTTCCTTGACCCTGGAAGGTGCCACTCCCACTGTCCTTTCC
        GGGGGCACGGAAGGAACTGGGACCTTCCACGGTGAGGGTGACAGGAAAGG 5160      5170      5180      5190      5200
        TAATAAAATGAGGAAATTGCATCGCATTGTCTGAGTAGGTGTCATTCTAT
        ATTATTTTACTCCTTTAACGTAGCGTAACAGACTCATCCACAGTAAGATA
```

FIG. 2L

```
         5210      5220      5230      5240      5250
     TCTGGGGGGTGGGGTGGGGCAGGACAGCAAGGGGGAGGATTGGGAAGACA
     AGACCCCCCACCCCACCCCGTCCTGTCGTTCCCCCTCCTAACCCTTCTGT 5260      5270      5280      5290      5300
     ATAGCAGGCATGCTGGGGATGCGGTGGGCTCTATGGCTTCTGAGGCGGAA
     TATCGTCCGTACGACCCCTACGCCACCCGAGATACCGAAGACTCCGCCTT 5310      5320      5330      5340      5350
     AGAACCAGCTGGGGCTCTAGGGGGTATCCCCACGCGCCCTGTAGCGGCGC
     TCTTGGTCGACCCCGAGATCCCCCATAGGGGTGCGCGGGACATCGCCGCG 5360      5370      5380      5390      5400
     ATTAAGCGCGGCGGGTGTGGTGGTTACGCGCAGCGTGACCGCTACACTTG
     TAATTCGCGCCGCCCACACCACCAATGCGCGTCGCACTGGCGATGTGAAC 5410      5420      5430      5440      5450
     CCAGCGCCCTAGCGCCCGCTCCTTTCGCTTTCTTCCCTTCCTTTCTCGCC
     GGTCGCGGGATCGCGGGCGAGGAAAGCGAAAGAAGGGAAGGAAAGAGCGG 5460      5470      5480      5490      5500
     ACGTTCGCCGGCTTTCCCCGTCAAGCTCTAAATCGGGGCATCCCTTTAGG
     TGCAAGCGGCCGAAAGGGGCAGTTCGAGATTTAGCCCCGTAGGGAAATCC 5510      5520      5530      5540      5550
     GTTCCGATTTAGTGCTTTACGGCACCTCGACCCCAAAAAACTTGATTAGG
     CAAGGCTAAATCACGAAATGCCGTGGAGCTGGGGTTTTTTGAACTAATCC 5560      5570      5580      5590      5600
     GTGATGGTTCACGTAGTGGGCCATCGCCCTGATAGACGGTTTTTCGCCCT
     CACTACCAAGTGCATCACCCGGTAGCGGGACTATCTGCCAAAAAGCGGGA 5610      5620      5630      5640      5650
     TTGACGTTGGAGTCCACGTTCTTTAATAGTGGACTCTTGTTCCAAACTGG
     AACTGCAACCTCAGGTGCAAGAAATTATCACCTGAGAACAAGGTTTGACC 5660      5670      5680      5690      5700
     AACAACACTCAACCCTATCTCGGTCTATTCTTTTGATTTATAAGGGATTT
     TTGTTGTGAGTTGGGATAGAGCCAGATAAGAAAACTAAATATTCCCTAAA 5710      5720      5730      5740      5750
     TGGGGATTTCGGCCTATTGGTTAAAAAATGAGCTGATTTAACAAAAATTT
     ACCCCTAAAGCCGGATAACCAATTTTTTACTCGACTAAATTGTTTTTAAA 5760      5770      5780      5790      5800
     AACGCGAATTAATTCTGTGGAATGTGTGTCAGTTAGGGTGTGGAAAGTCC
     TTGCGCTTAATTAAGACACCTTACACACAGTCAATCCCACACCTTTCAGG 5810      5820      5830      5840      5850
     CCAGGCTCCCCAGGCAGGCAGAAGTATGCAAAGCATGCATCTCAATTAGT
     GGTCCGAGGGGTCCGTCCGTCTTCATACGTTTCGTACGTAGAGTTAATCA
```

FIG. 2M

```
       5860      5870      5880      5890      5900
CAGCAACCAGGTGTGGAAAGTCCCCAGGCTCCCCAGCAGGCAGAAGTATG
GTCGTTGGTCCACACCTTTCAGGGGTCCGAGGGGTCGTCCGTCTTCATAC 5910      5920      5930      5940      5950
CAAAGCATGCATCTCAATTAGTCAGCAACCATAGTCCCGCCCCTAACTCC
GTTTCGTACGTAGAGTTAATCAGTCGTTGGTATCAGGGCGGGGATTGAGG 5960      5970      5980      5990      6000
GCCCATCCCGCCCCTAACTCCGCCCAGTTCCGCCCATTCTCCGCCCCATG
CGGGTAGGGCGGGGATTGAGGCGGGTCAAGGCGGGTAAGAGGCGGGGTAC 6010      6020      6030      6040      6050
GCTGACTAATTTTTTTTATTTATGCAGAGGCCGAGGCCGCCTCTGCCTCT
CGACTGATTAAAAAAAATAAATACGTCTCCGGCTCCGGCGGAGACGGAGA 6060      6070      6080      6090      6100
GAGCTATTCCAGAAGTAGTGAGGAGGCTTTTTTGGAGGCCTAGGCTTTTG
CTCGATAAGGTCTTCATCACTCCTCCGAAAAAACCTCCGGATCCGAAAAC 6110      6120      6130      6140      6150
CAAAAAGCTCCCGGGAGCTTGTATATCCATTTTCGGATCTGATCAAGAGA
GTTTTTCGAGGGCCCTCGAACATATAGGTAAAAGCCTAGACTAGTTCTCT 6160      6170      6180      6190      6200
CAGGATGAGGATCGTTTCGCATGATTGAACAAGATGGATTGCACGCAGGT
GTCCTACTCCTAGCAAAGCGTACTAACTTGTTCTACCTAACGTGCGTCCA 6210      6220      6230      6240      6250
TCTCCGGCCGCTTGGGTGGAGAGGCTATTCGGCTATGACTGGGCACAACA
AGAGGCCGGCGAACCCACCTCTCCGATAAGCCGATACTGACCCGTGTTGT 6260      6270      6280      6290      6300
GACAATCGGCTGCTCTGATGCCGCCGTGTTCCGGCTGTCAGCGCAGGGGC
CTGTTAGCCGACGAGACTACGGCGGCACAAGGCCGACAGTCGCGTCCCCG 6310      6320      6330      6340      6350
GCCCGGTTCTTTTTGTCAAGACCGACCTGTCCGGTGCCCTGAATGAACTG
CGGGCCAAGAAAAACAGTTCTGGCTGGACAGGCCACGGGACTTACTTGAC 6360      6370      6380      6390      6400
CAGGACGAGGCAGCGCGGCTATCGTGGCTGGCCACGACGGGCGTTCCTTG
GTCCTGCTCCGTCGCGCCGATAGCACCGACCGGTGCTGCCCGCAAGGAAC 6410      6420      6430      6440      6450
CGCAGCTGTGCTCGACGTTGTCACTGAAGCGGGAAGGGACTGGCTGCTAT
GCGTCGACACGAGCTGCAACAGTGACTTCGCCCTTCCCTGACCGACGATA
```

FIG. 2N

```
            6460       6470       6480       6490       6500
      TGGGCGAAGTGCCGGGGCAGGATCTCCTGTCATCTCACCTTGCTCCTGCC
      ACCCGCTTCACGGCCCCGTCCTAGAGGACAGTAGAGTGGAACGAGGACGG 6510       6520       6530       6540       6550
      GAGAAAGTATCCATCATGGCTGATGCAATGCGGCGGCTGCATACGCTTGA
      CTCTTTCATAGGTAGTACCGACTACGTTACGCCGCCGACGTATGCGAACT 6560       6570       6580       6590       6600
      TCCGGCTACCTGCCCATTCGACCACCAAGCGAAACATCGCATCGAGCGAG
      AGGCCGATGGACGGGTAAGCTGGTGGTTCGCTTTGTAGCGTAGCTCGCTC 6610       6620       6630       6640       6650
      CACGTACTCGGATGGAAGCCGGTCTTGTCGATCAGGATGATCTGGACGAA
      GTGCATGAGCCTACCTTCGGCCAGAACAGCTAGTCCTACTAGACCTGCTT 6660       6670       6680       6690       6700
      GAGCATCAGGGGCTCGCGCCAGCCGAACTGTTCGCCAGGCTCAAGGCGCG
      CTCGTAGTCCCCGAGCGCGGTCGGCTTGACAAGCGGTCCGAGTTCCGCGC 6710       6720       6730       6740       6750
      CATGCCCGACGGCGAGGATCTCGTCGTGACCCATGGCGATGCCTGCTTGC
      GTACGGGCTGCCGCTCCTAGAGCAGCACTGGGTACCGCTACGGACGAACG 6760       6770       6780       6790       6800
      CGAATATCATGGTGGAAAATGGCCGCTTTTCTGGATTCATCGACTGTGGC
      GCTTATAGTACCACCTTTTACCGGCGAAAAGACCTAAGTAGCTGACACCG 6810       6820       6830       6840       6850
      CGGCTGGGTGTGGCGGACCGCTATCAGGACATAGCGTTGGCTACCCGTGA
      GCCGACCCACACCGCCTGGCGATAGTCCTGTATCGCAACCGATGGGCACT 6860       6870       6880       6890       6900
      TATTGCTGAAGAGCTTGGCGGCGAATGGGCTGACCGCTTCCTCGTGCTTT
      ATAACGACTTCTCGAACCGCCGCTTACCCGACTGGCGAAGGAGCACGAAA 6910       6920       6930       6940       6950
      ACGGTATCGCCGCTCCCGATTCGCAGCGCATCGCCTTCTATCGCCTTCTT
      TGCCATAGCGGCGAGGGCTAAGCGTCGCGTAGCGGAAGATAGCGGAAGAA 6960       6970       6980       6990       7000
      GACGAGTTCTTCTGAGCGGGACTCTGGGGTTCGAAATGACCGACCAAGCG
      CTGCTCAAGAAGACTCGCCCTGAGACCCCAAGCTTTACTGGCTGGTTCGC 7010       7020       7030       7040       7050
      ACGCCCAACCTGCCATCACGAGATTTCGATTCCACCGCCGCCTTCTATGA
      TGCGGGTTGGACGGTAGTGCTCTAAAGCTAAGGTGGCGGCGGAAGATACT 7060       7070       7080       7090       7100
      AAGGTTGGGCTTCGGAATCGTTTTCCGGGACGCCGGCTGGATGATCCTCC
      TTCCAACCCGAAGCCTTAGCAAAAGGCCCTGCGGCCGACCTACTAGGAGG
```

FIG. 20

```
            7110       7120       7130       7140       7150
     AGCGCGGGGATCTCATGCTGGAGTTCTTCGCCCACCCCAACTTGTTTATT
     TCGCGCCCCTAGAGTACGACCTCAAGAAGCGGGTGGGGTTGAACAAATAA 7160       7170       7180       7190       7200
     GCAGCTTATAATGGTTACAAATAAAGCAATAGCATCACAAATTTCACAAA
     CGTCGAATATTACCAATGTTTATTTCGTTATCGTAGTGTTTAAAGTGTTT 7210       7220       7230       7240       7250
     TAAAGCATTTTTTTCACTGCATTCTAGTTGTGGTTTGTCCAAACTCATCA
     ATTTCGTAAAAAAAGTGACGTAAGATCAACACCAAACAGGTTTGAGTAGT 7260       7270       7280       7290       7300
     ATGTATCTTATCATGTCTGTATACCGTCGACCTCTAGCTAGAGCTTGGCG
     TACATAGAATAGTACAGACATATGGCAGCTGGAGATCGATCTCGAACCGC 7310       7320       7330       7340       7350
     TAATCATGGTCATAGCTGTTTCCTGTGTGAAATTGTTATCCGCTCACAAT
     ATTAGTACCAGTATCGACAAAGGACACACTTTAACAATAGGCGAGTGTTA 7360       7370       7380       7390       7400
     TCCACACAACATACGAGCCGGAAGCATAAAGTGTAAAGCCTGGGGTGCCT
     AGGTGTGTTGTATGCTCGGCCTTCGTATTTCACATTTCGGACCCCACGGA 7410       7420       7430       7440       7450
     AATGAGTGAGCTAACTCACATTAATTGCGTTGCGCTCACTGCCCGCTTTC
     TTACTCACTCGATTGAGTGTAATTAACGCAACGCGAGTGACGGGCGAAAG 7460       7470       7480       7490       7500
     CAGTCGGGAAACCTGTCGTGCCAGCTGCATTAATGAATCGGCCAACGCGC
     GTCAGCCCTTTGGACAGCACGGTCGACGTAATTACTTAGCCGGTTGCGCG 7510       7520       7530       7540       7550
     GGGGAGAGGCGGTTTGCGTATTGGGCGCTCTTCCGCTTCCTCGCTCACTG
     CCCCTCTCCGCCAAACGCATAACCCGCGAGAAGGCGAAGGAGCGAGTGAC 7560       7570       7580       7590       7600
     ACTCGCTGCGCTCGGTCGTTCGGCTGCGGCGAGCGGTATCAGCTCACTCA
     TGAGCGACGCGAGCCAGCAAGCCGACGCCGCTCGCCATAGTCGAGTGAGT 7610       7620       7630       7640       7650
     AAGGCGGTAATACGGTTATCCACAGAATCAGGGGATAACGCAGGAAAGAA
     TTCCGCCATTATGCCAATAGGTGTCTTAGTCCCCTATTGCGTCCTTTCTT 7660       7670       7680       7690       7700
     CATGTGAGCAAAAGGCCAGCAAAAGGCCAGGAACCGTAAAAAGGCCGCGT
     GTACACTCGTTTTCCGGTCGTTTTCCGGTCCTTGGCATTTTTCCGGCGCA 7710       7720       7730       7740       7750
     TGCTGGCGTTTTTCCATAGGCTCCGCCCCCCTGACGAGCATCACAAAAAT
     ACGACCGCAAAAAGGTATCCGAGGCGGGGGGACTGCTCGTAGTGTTTTTA
```

FIG. 2P

```
              7760       7770       7780       7790      7800
       CGACGCTCAAGTCAGAGGTGGCGAAACCCGACAGGACTATAAAGATACCA
       GCTGCGAGTTCAGTCTCCACCGCTTTGGGCTGTCCTGATATTTCTATGGT 7810       7820       7830       7840      7850
       GGCGTTTCCCCCTGGAAGCTCCCTCGTGCGCTCTCCTGTTCCGACCCTGC
       CCGCAAAGGGGGACCTTCGAGGGAGCACGCGAGAGGACAAGGCTGGGACG 7860       7870       7880       7890      7900
       CGCTTACCGGATACCTGTCCGCCTTTCTCCCTTCGGGAAGCGTGGCGCTT
       GCGAATGGCCTATGGACAGGCGGAAGAGGGAAGCCCTTCGCACCGCGAA 7910       7920       7930       7940      7950
       TCTCAATGCTCACGCTGTAGGTATCTCAGTTCGGTGTAGGTCGTTCGCTC
       AGAGTTACGAGTGCGACATCCATAGAGTCAAGCCACATCCAGCAAGCGAG 7960       7970       7980       7990      8000
       CAAGCTGGGCTGTGTGCACGAACCCCCCGTTCAGCCCGACCGCTGCGCCT
       GTTCGACCCGACACACGTGCTTGGGGGGCAAGTCGGGCTGGCGACGCGGA 8010       8020       8030       8040      8050
       TATCCGGTAACTATCGTCTTGAGTCCAACCCGGTAAGACACGACTTATCG
       ATAGGCCATTGATAGCAGAACTCAGGTTGGGCCATTCTGTGCTGAATAGC 8060       8070       8080       8090      8100
       CCACTGGCAGCAGCCACTGGTAACAGGATTAGCAGAGCGAGGTATGTAGG
       GGTGACCGTCGTCGGTGACCATTGTCCTAATCGTCTCGCTCCATACATCC 8110       8120       8130       8140      8150
       CGGTGCTACAGAGTTCTTGAAGTGGTGGCCTAACTACGGCTACACTAGAA
       GCCACGATGTCTCAAGAACTTCACCACCGGATTGATGCCGATGTGATCTT 8160       8170       8180       8190      8200
       GGACAGTATTTGGTATCTGCGCTCTGCTGAAGCCAGTTACCTTCGGAAAA
       CCTGTCATAAACCATAGACGCGAGACGACTTCGGTCAATGGAAGCCTTTT 8210       8220       8230       8240      8250
       AGAGTTGGTAGCTCTTGATCCGGCAAACAAACCACCGCTGGTAGCGGTGG
       TCTCAACCATCGAGAACTAGGCCGTTTGTTTGGTGGCGACCATCGCCACC 8260       8270       8280       8290      8300
       TTTTTTTGTTTGCAAGCAGCAGATTACGCGCAGAAAAAAAGGATCTCAAG
       AAAAAAACAAACGTTCGTCGTCTAATGCGCGTCTTTTTTTCCTAGAGTTC 8310       8320       8330       8340      8350
       AAGATCCTTTGATCTTTTCTACGGGGTCTGACGCTCAGTGGAACGAAAAC
       TTCTAGGAAACTAGAAAAGATGCCCCAGACTGCGAGTCACCTTGCTTTTG 8360       8370       8380       8390      8400
       TCACGTTAAGGGATTTTGGTCATGAGATTATCAAAAAGGATCTTCACCTA
       AGTGCAATTCCCTAAAACCAGTACTCTAATAGTTTTTCCTAGAAGTGGAT
```

FIG. 2Q

```
          8410      8420      8430      8440      8450
GATCCTTTTAAATTAAAAATGAAGTTTTAAATCAATCTAAAGTATATATG
CTAGGAAAATTTAATTTTTACTTCAAAATTTAGTTAGATTTCATATATAC 8460      8470      8480      8490      8500
AGTAAACTTGGTCTGACAGTTACCAATGCTTAATCAGTGAGGCACCTATC
TCATTTGAACCAGACTGTCAATGGTTACGAATTAGTCACTCCGTGGATAG 8510      8520      8530      8540      8550
TCAGCGATCTGTCTATTTCGTTCATCCATAGTTGCCTGACTCCCCGTCGT
AGTCGCTAGACAGATAAAGCAAGTAGGTATCAACGGACTGAGGGGCAGCA

-8560      8570      8580      8590      8600
GTAGATAACTACGATACGGGAGGGCTTACCATCTGGCCCCAGTGCTGCAA
CATCTATTGATGCTATGCCCTCCCGAATGGTAGACCGGGGTCACGACGTT 8610      8620      8630      8640      8650
TGATACCGCGAGACCCACGCTCACCGGCTCCAGATTTATCAGCAATAAAC
ACTATGGCGCTCTGGGTGCGAGTGGCCGAGGTCTAAATAGTCGTTATTTG 8660      8670      8680      8690      8700
CAGCCAGCCGGAAGGGCCGAGCGCAGAAGTGGTCCTGCAACTTTATCCGC
GTCGGTCGGCCTTCCCGGCTCGCGTCTTCACCAGGACGTTGAAATAGGCG 8710      8720      8730      8740      8750
CTCCATCCAGTCTATTAATTGTTGCCGGGAAGCTAGAGTAAGTAGTTCGC
GAGGTAGGTCAGATAATTAACAACGGCCCTTCGATCTCATTCATCAAGCG 8760      8770      8780      8790      8800
CAGTTAATAGTTTGCGCAACGTTGTTGCCATTGCTACAGGCATCGTGGTG
GTCAATTATCAAACGCGTTGCAACAACGGTAACGATGTCCGTAGCACCAC 8810      8820      8830      8840      8850
TCACGCTCGTCGTTTGGTATGGCTTCATTCAGCTCCGGTTCCCAACGATC
AGTGCGAGCAGCAAACCATACCGAAGTAAGTCGAGGCCAAGGGTTGCTAG 8860      8870      8880      8890      8900
AAGGCGAGTTACATGATCCCCCATGTTGTGCAAAAAAGCGGTTAGCTCCT
TTCCGCTCAATGTACTAGGGGGTACAACACGTTTTTTCGCCAATCGAGGA 8910      8920      8930      8940      8950
TCGGTCCTCCGATCGTTGTCAGAAGTAAGTTGGCCGCAGTGTTATCACTC
AGCCAGGAGGCTAGCAACAGTCTTCATTCAACCGGCGTCACAATAGTGAG 8960      8970      8980      8990      9000
ATGGTTATGGCAGCACTGCATAATTCTCTTACTGTCATGCCATCCGTAAG
TACCAATACCGTCGTGACGTATTAAGAGAATGACAGTACGGTAGGCATTC 9010      9020      9030      9040      9050
ATGCTTTTCTGTGACTGGTGAGTACTCAACCAAGTCATTCTGAGAATAGT
TACGAAAAGACACTGACCACTCATGAGTTGGTTCAGTAAGACTCTTATCA
```

FIG. 2R

```
           9060      9070      9080      9090      9100
GTATGCGGCGACCGAGTTGCTCTTGCCCGGCGTCAATACGGGATAATACC
CATACGCCGCTGGCTCAACGAGAACGGGCCGCAGTTATGCCCTATTATGG 9110      9120      9130      9140      9150
GCGCCACATAGCAGAACTTTAAAAGTGCTCATCATTGGAAAACGTTCTTC
CGCGGTGTATCGTCTTGAAATTTTCACGAGTAGTAACCTTTTGCAAGAAG 9160      9170      9180      9190      9200
GGGGCGAAAACTCTCAAGGATCTTACCGCTGTTGAGATCCAGTTCGATGT
CCCCGCTTTTGAGAGTTCCTAGAATGGCGACAACTCTAGGTCAAGCTACA 9210      9220      9230      9240      9250
AACCCACTCGTGCACCCAACTGATCTTCAGCATCTTTTACTTTCACCAGC
TTGGGTGAGCACGTGGGTTGACTAGAAGTCGTAGAAAATGAAAGTGGTCG 9260      9270      9280      9290      9300
GTTTCTGGGTGAGCAAAAACAGGAAGGCAAAATGCCGCAAAAAAGGGAAT
CAAAGACCCACTCGTTTTTGTCCTTCCGTTTTACGGCGTTTTTTCCCTTA 9310      9320      9330      9340      9350
AAGGGCGACACGGAAATGTTGAATACTCATACTCTTCCTTTTTCAATATT
TTCCCGCTGTGCCTTTACAACTTATGAGTATGAGAAGGAAAAAGTTATAA 9360      9370      9380      9390      9400
ATTGAAGCATTTATCAGGGTTATTGTCTCATGAGCGGATACATATTTGAA
TAACTTCGTAAATAGTCCCAATAACAGAGTACTCGCCTATGTATAAACTT 9410      9420      9430      9440      9450
TGTATTTAGAAAAATAAACAAATAGGGGTTCCGCGCACATTTCCCCGAAA
ACATAAATCTTTTTATTTGTTTATCCCCAAGGCGCGTGTAAAGGGGCTTT

9460
AGTGCCACCTGACGTC
TCACGGTGGACTGCAG
```

FIG. 2S

```
         10         20         30         40         50
GACGGATCGGGAGATCTCCCGATCCCCTATGGTCGACTCTCAGTACAATC
CTGCCTAGCCCTCTAGAGGGCTAGGGGATACCAGCTGAGAGTCATGTTAG 60         70         80         90        100
TGCTCTGATGCCGCATAGTTAAGCCAGTATCTGCTCCCTGCTTGTGTGTT
ACGAGACTACGGCGTATCAATTCGGTCATAGACGAGGGACGAACACACAA 110        120        130        140        150
GGAGGTCGCTGAGTAGTGCGCGAGCAAAATTTAAGCTACAACAAGGCAAG
CCTCCAGCGACTCATCACGCGCTCGTTTTAAATTCGATGTTGTTCCGTTC 160        170        180        190        200
GCTTGACCGACAATTGCATGAAGAATCTGCTTAGGGTTAGGCGTTTTGCG
CGAACTGGCTGTTAACGTACTTCTTAGACGAATCCCAATCCGCAAAACGC 210        220        230        240        250
CTGCTTCGCGATGTACGGGCCAGATATACGCGTTGACATTGATTATTGAC
GACGAAGCGCTACATGCCCGGTCTATATGCGCAACTGTAACTAATAACTG 260        270        280        290        300
TAGTTATTAATAGTAATCAATTACGGGGTCATTAGTTCATAGCCCATATA
ATCAATAATTATCATTAGTTAATGCCCCAGTAATCAAGTATCGGGTATAT 310        320        330        340        350
TGGAGTTCCGCGTTACATAACTTACGGTAAATGGCCCGCCTGGCTGACCG
ACCTCAAGGCGCAATGTATTGAATGCCATTTACCGGGCGGACCGACTGGC 360        370        380        390        400
CCCAACGACCCCCGCCCATTGACGTCAATAATGACGTATGTTCCCATAGT
GGGTTGCTGGGGGCGGGTAACTGCAGTTATTACTGCATACAAGGGTATCA 410        420        430        440        450
AACGCCAATAGGGACTTTCCATTGACGTCAATGGGTGGACTATTTACGGT
TTGCGGTTATCCCTGAAAGGTAACTGCAGTTACCCACCTGATAAATGCCA 460        470        480        490        500
AAACTGCCCACTTGGCAGTACATCAAGTGTATCATATGCCAAGTACGCCC
TTTGACGGGTGAACCGTCATGTAGTTCACATAGTATACGGTTCATGCGGG 510        520        530        540        550
CCTATTGACGTCAATGACGGTAAATGGCCCGCCTGGCATTATGCCCAGTA
GGATAACTGCAGTTACTGCCATTTACCGGGCGGACCGTAATACGGGTCAT 560        570        580        590        600
CATGACCTTATGGGACTTTCCTACTTGGCAGTACATCTACGTATTAGTCA
GTACTGGAATACCCTGAAAGGATGAACCGTCATGTAGATGCATAATCAGT 610        620        630        640        650
TCGCTATTACCATGGTGATGCGGTTTTGGCAGTACATCAATGGGCGTGGA
AGCGATAATGGTACCACTACGCCAAAACCGTCATGTAGTTACCCGCACCT 660        670        680        690        700
TAGCGGTTTGACTCACGGGGATTTCCAAGTCTCCACCCCATTGACGTCAA
ATCGCCAAACTGAGTGCCCCTAAAGGTTCAGAGGTGGGGTAACTGCAGTT 710        720        730        740        750
TGGGAGTTTGTTTTGGCACCAAAATCAACGGGACTTTCCAAAATGTCGTA
ACCCTCAAACAAAACCGTGGTTTTAGTTGCCCTGAAAGGTTTTACAGCAT
```

FIG. 3A

```
         760       770       780       790       800
ACAACTCCGCCCCATTGACGCAAATGGGCGGTAGGCGTGTACGGTGGGAG
TGTTGAGGCGGGGTAACTGCGTTTACCCGCCATCCGCACATGCCACCCTC 810       820       830       840       850
GTCTATATAAGCAGAGCTCTCTGGCTAACTAGAGAACCCACTGCTTACTG
CAGATATATTCGTCTCGAGAGACCGATTGATCTCTTGGGTGACGAATGAC 860       870       880       890       900
GCTTATCGAAATTAATACGACTCACTATAGGGAGACCCAAGCTGGCTAGC
CGAATAGCTTTAATTATGCTGAGTGATATCCCTCTGGGTTCGACCGATCG

>NotI
         910       920    |  930       940       950
GTTTAAACGGGCCCTCTAGACTCGAGCGGCCGCTCTATCAAGCTTACTTG
CAAATTTGCCCGGGAGATCTGAGCTCGCCGGCGAGATAGTTCGAATGAAC 960       970       980       990
ATTTCATAGTTCTAAAAGTCCGATTTTTTCTTTTTTATTCTAAAGC ATG
TAAAGTATCAAGATTTTCAGGCTAAAAAAGAAAAAATAAGATTTCG TAC
                                                 M
```

```
 1000          1010         1020         1030
 AGT GAT GAG ACA ACT ATT AGC CTG GAG GAC GGC TAT CCC
 TCA CTA CTC TGT TGA TAA TCG GAC CTC CTG CCG ATA GGG
  S   D   E   T   T   I   S   L   E   D   G   Y   P 1040          1050         1060         1070
 CCC CTG GAG GCG TTG ACA ACT ATG GTT CCC CCG GCG GAC
 GGG GAC CTC CGC AAC TGT TGA TAC CAA GGG GGC CGC CTG
  P   L   E   A   L   T   T   M   V   P   P   A   D

TRANSMEMBRANE DOMAIN 1
 1080          1090         1100    |    1110
 GCG ACT GGT TTT TCG CAG TCG CTT TTG ACA TTT GCC GCG
 CGC TGA CCA AAA AGC GTC AGC GAA AAC TGT AAA CGG CGC
  A   T   G   F   S   Q   S   L   L   T   F   A   A 1120          1130         1140         1150
 GTC ATG ACC TTT CTC ATA ATG ATC GTG GGC ATA TGC GGC
 CAG TAC TGG AAA GAG TAT TAC TAG CAC CCG TAT ACG CCG
  V   M   T   F   L   I   M   I   V   G   I   C   G 1160          1170         1180         1190
 AAC CTG TTG ACC GTA GTG GCC CTG CTG AAA TGT CCC AAG
 TTG GAC AAC TGG CAT CAC CGG GAC GAC TTT ACA GGG TTC
  N   L   L   T   V   V   A   L   L   K   C   P   K

TRANSMEMBRANE DOMAIN 2
                                    |
 1200          1210         1220         1230
 GTG CGC AAC GTG GCG GCT GCC TTT ATC ATC AGC CTC TGT
 CAC GCG TTG CAC CGC CGA CGG AAA TAG TAG TCG GAG ACA
  V   R   N   V   A   A   A   F   I   I   S   L   C 1240          1250         1260         1270
 ATT GCC GAC CTG CTC TTC TGC GCC CTG GTG CTG CCA TTC
 TAA CGG CTG GAC GAG AAG ACG CGG GAC CAC GAC GGT AAG
  I   A   D   L   L   F   C   A   L   V   L   P   F
```

FIG. 3B

```
      1280           1290           1300           1310
CAG GGT CTG CGG TTC GTC CAA GGA ACC TGG CGA CAT GGC
GTC CCA GAC GCC AAG CAG GTT CCT TGG ACC GCT GTA CCG
 Q   G   L   R   F   V   Q   G   T   W   R   H   G 1320           1330           1340           1350
CAG GTG CTG TGC CGC CTC ATT CCC TTT ATC CAA TAC GGA
GTC CAC GAC ACG GCG GAG TAA GGG AAA TAG GTT ATG CCT
 Q   V   L   C   R   L   I   P   F   I   Q   Y   G

TRANSMEMBRANE DOMAIN 3
                             |
         1360                |  1370           1380
AAC ATA GGG GTA TCC CTG TTG TGC ATC GCA ATG ATC ACG
TTG TAT CCC CAT AGG GAC AAC ACG TAG CGT TAC TAG TGC
 N   I   G   V   S   L   L   C   I   A   M   I   T 1390           1400           1410           1420
ATC AAT CGG TAT GTG ATG ATC ACA CAT CAC GGA CTT TAT
TAG TTA GCC ATA CAC TAC TAG TGT GTA GTG CCT GAA ATA
 I   N   R   Y   V   M   I   T   H   H   G   L   Y

TRANSMEMBRANE DOMAIN 4
                                             |
  1430           1440           1450          | 1460
GCC AGG ATC TAT AAA CGC CAC TGG ATT GCG GTA ATG ATC
CGG TCC TAG ATA TTT GCG GTG ACC TAA CGC CAT TAC TAG
 A   R   I   Y   K   R   H   W   I   A   V   M   I 1470           1480           1490           1500
GCC GCC TGC TGG CTG TTC TCC TAC GGC ATG CAG CTC CCG
CGG CGG ACG ACC GAC AAG AGG ATG CCG TAC GTC GAG GGC
 A   A   C   W   L   F   S   Y   G   M   Q   L   P 1510           1520           1530           1540
ACG CTT CTG GGA GAG TGG GGT CGC TTT GGC TAC GAC TCG
TGC GAA GAC CCT CTC ACC CCA GCG AAA CCG ATG CTG AGC
 T   L   L   G   E   W   G   R   F   G   Y   D   S 1550           1560           1570           1580
AGA TTA CAG ACC TGC TCC ATC ATG ACC GAC GAC CAT GGG
TCT AAT GTC TGG ACG AGG TAG TAC TGG CTG CTG GTA CCC
 R   L   Q   T   C   S   I   M   T   D   D   H   G

TRANSMEMBRANE DOMAIN 5
                                           |
    1590           1600          | 1610           1620
CAC AGC AGC AAG ACG ACG TTG TTT ATC ACC GCC TTC GTC
GTG TCG TCG TTC TGC TGC AAC AAA TAG TGG CGG AAG CAG
 H   S   S   K   T   T   L   F   I   T   A   F   V 1630           1640           1650           1660
ATC CCT TGC CTG GTT ATC ATT GCC TGC TAT GCC AAG ATC
TAG GGA ACG GAC CAA TAG TAA CGG ACG ATA CGG TTC TAG
 I   P   C   L   V   I   I   A   C   Y   A   K   I 1670           1680           1690           1700
TTC TGG GTG GTC CAC AAG TCG GAG CAG CGC TTG AAG CGC
AAG ACC CAC CAG GTG TTC AGC CTC GTC GCG AAC TTC GCG
 F   W   V   V   H   K   S   E   Q   R   L   K   R
```

FIG. 3C

```
         1710           1720           1730           1740
CAT GCC ACC AAA CAA AAC TCC ATA CCC AAC AAC CTC CGC
GTA CGG TGG TTT GTT TTG AGG TAT GGG TTG TTG GAG GCG
 H   A   T   K   Q   N   S   I   P   N   N   L   R 1750           1760           1770
CCC CTA GCC TCT ACA GGA TCA GGA GCC CTG CCC TCC GGC
GGG GAT CGG AGA TGT CCT AGT CCT CGG GAC GGG AGG CCG
 P   L   A   S   T   G   S   G   A   L   P   S   G 1780           1790           1800           1810
   GCG GAA TGC CAG CCA AGC AAC CGC GTC TCC TCG GAC AGC
   CGC CTT ACG GTC GGT TCG TTG GCG CAG AGG AGC CTG TCG
    A   E   C   Q   P   S   N   R   V   S   S   D   S 1820           1830           1840           1850
   AGC AGT AGC TTC TCC ATC GAT GTG CCG GAG ACA GCG CCC
   TCG TCA TCG AAG AGG TAG CTA CAC GGC CTC TGT CGC GGG
    S   S   S   F   S   I   D   V   P   E   T   A   P
1860           1870           1880           1890
   AGC GGC AAG CAG CAG CCA ACC CGA GTC AAG GAT CAG CGT
   TCG CCG TTC GTC GTC GGT TGG GCT CAG TTC CTA GTC GCA
    S   G   K   Q   Q   P   T   R   V   K   D   Q   R 1900           1910           1920           1930
   GAA GTA CGT GCC AAG CGA AAC GAG TGG CGC ATC ACT AAG
   CTT CAT GCA CGG TTC GCT TTG CTC ACC GCG TAG TGA TTC
    E   V   R   A   K   R   N   E   W   R   I   T   K

TRANSMEMBRANE DOMAIN 6
                |
    1940        |  1950           1960           1970
   ATG GTG CTG GCC ATC TTC CTG TCC TTC GTC GTC TGC TAC
   TAC CAC GAC CGG TAG AAG GAC AGG AAG CAG CAG ACG ATG
    M   V   L   A   I   F   L   S   F   V   V   C   Y 1980           1990           2000           2010
   TTG CCC ATC ACA ATT GTT AAG GTG GCC GAC AAG AAT GTG
   AAC GGG TAG TGT TAA CAA TTC CAC CGG CTG TTC TTA CAC
    L   P   I   T   I   V   K   V   A   D   K   N   V

TRANSMEMBRANE DOMAIN 7
                                                |
         2020           2030           2040     | 2050
   GAG CAC CCC AGC CTG CAC ATC TGC AGC TAT ATC CTG CTC
   CTC GTG GGG TCG GAC GTG TAG ACG TCG ATA TAG GAC GAG
    E   H   P   S   L   H   I   C   S   Y   I   L   L 2060           2070           2080           2090
   TAC CTG TCG GCT TGT ATT AAT CCG ATC ATC TAT GTC ATC
   ATG GAC AGC CGA ACA TAA TTA GGC TAG TAG ATA CAG TAG
    Y   L   S   A   C   I   N   P   I   I   Y   V   I 2100           2110           2120           2130
   ATG AAC AAG CAG TAC CGC AAG GCC TAC AAG ACG GTG GTT
   TAC TTG TTC GTC ATG GCG TTC CGG ATG TTC TGC CAC CAA
    M   N   K   Q   Y   R   K   A   Y   K   T   V   V 2140           2150           2160
   TTC TGT CAG CCC GCC CGT CTT CTG CTG CCC TTC GGG AAG
   AAG ACA GTC GGG CGG GCA GAA GAC GAC GGG AAG CCC TTC
    F   C   Q   P   A   R   L   L   L   P   F   G   K
```

FIG. 3D

```
      2170           2180          2190           2200
    ACC AAT GGC GCT AGC AGC GCA GCA GAA ATG GAA AGA TAC
    TGG TTA CCG CGA TCG TCG CGT CGT CTT TAC CTT TCT ATG
     T   N   G   A   S   S   A   A   E   M   E   R   Y 2210           2220          2230           2240
    CGG GTT GAG CAA CAA CCA CAG CCG CAC AAT CGT CTC CCA
    GCC CAA CTC GTT GTT GGT GTC GGC GTG TTA GCA GAG GGT
     R   V   E   Q   Q   P   Q   P   H   N   R   L   P 2250           2260          2270           2280
    GAT GTC GGG GGG AAC GGG AGC CGC ATC GGG AGC AGG GAC
    CTA CAG CCC CCC TTG CCC TCG GCG TAG CCC TCG TCC CTG
     D   V   G   G   N   G   S   R   I   G   S   R   D 2290           2300          2310           2320
    GGC AAC GGG AAC GGC AGC GGT GGC GGT GAT GCA GAC CCC
    CCG TTG CCC TTG CCG TCG CCA CCG CCA CTA CGT CTG GGG
     G   N   G   N   G   S   G   G   G   D   A   D   P 2330           2340          2350           2360
    ACC GGA GGT CCA ACA AGC CCA AGC CTT GGA GAT GGT GTC
    TGG CCT CCA GGT TGT TCG GGT TCG GAA CCT CTA CCA CAG
     T   G   G   P   T   S   P   S   L   G   D   G   V 2370           2380          2390           2400
    GCG GGG ACC GGA CCT AAT AAG CAA ATC GAA CCT CCC GCA
    CGC CCC TGG CCT GGA TTA TTC GTT TAG CTT GGA GGG CGT
     A   G   T   G   P   N   K   Q   I   E   P   P   A 2410           2420          2430           2440
    GCC GAA CGT TAC GCC TCC GCC ACC CTC GGT CCT CAC GGC
    CGG CTT GCA ATG CGG AGG CGG TGG GAG CCA GGA GTG CCG
     A   E   R   Y   A   S   A   T   L   G   P   H   G 2450           2460          2470           2480
    GAC ACC CAA CGG AAG CAA CAG CAA CAG CCT CAC CCT GCG
    CTG TGG GTT GCC TTC GTT GTC GTT GTC GGA GTG GGA CGC
     D   T   Q   R   K   Q   Q   Q   Q   P   H   P   A 2490           2500          2510           2520
    ACT GCC GCT CAA GAA GAA CAA TCA CTG CTA CAC CAA CAG
    TGA CGG CGA GTT CTT CTT GTT AGT GAC GAT GTG GTT GTC
     T   A   A   Q   E   E   Q   S   L   L   H   Q   Q 2530          2540          2550
            CGG CTT CAA CAG CAG CAC TCC CAG CCC CAG CAG CGG CTT
            GCC GAA GTT GTC GTC GTG AGG GTC GGG GTC GTC GCC GAA
             R   L   Q   Q   Q   H   S   Q   P   Q   Q   R   L 2560           2570          2580           2590
    GGG GAT CGG GAT CAG CAG CAG CTC CAT TTA CCG GCC CGG
    CCC CTA GCC CTA GTC GTC GTC GAG GTA AAT GGC CGG GCC
     G   D   R   D   Q   Q   Q   L   H   L   P   A   R 2600           2610          2620           2630
    AGT TGG CTC ACT GGG GAG CGG CTC CGC CTC GAT CCG TCG
    TCA ACC GAG TGA CCC CTC GCC GAG GCG GAG CTA GGC AGC
     S   W   L   T   G   E   R   L   R   L   D   P   S
```

FIG. 3E

```
       2640             2650              2660             2670
CAT AAC AAT GGT GGG GGA CGA CAT AAT ACT GGA GGA AGA
GTA TTG TTA CCA CCC CCT GCT GTA TTA TGA CCT CCT TCT
 H   N   N   G   G   G   R   H   N   T   G   G   R 2680             2690             2700              2710
GGA GCT GCC GCC CAC GCC TCC GGC GAC TTC TGC GCC GAC
CCT CGA CGG CGG GTG CGG AGG CCG CTG AAG ACG CGG CTG
 G   A   A   A   H   A   S   G   D   F   C   A   D 2720             2730              2740             2750
AAC GCC GGC ACC TCC CCC ACC CTC ATC CCC ACT GCA TCC
TTG CGG CCG TGG AGG GGG TGG GAG TAG GGG TGA CGT AGG
 N   A   G   T   S   P   T   L   I   P   T   A   S 2760             2770             2780              2790
GCT GTC CAC GGA CTC ATC AAC AAC AAC AAT CAG CGG CGG
CGA CAG GTG CCT GAG TAG TTG TTG TTG TTA GTC GCC GCC
 A   V   H   G   L   I   N   N   N   Q   R   R 2800             2810             2820              2830
AGC AGT GGT AGC GGG GAG CAG TGC ACC AAA GCC GGC GAC
TCG TCA CCA TCG CCC CTC GTC ACG TGG TTT CGG CCG CTG
 S   S   G   S   G   E   Q   C   T   K   A   G   D 2840             2850              2860             2870
GCC AAC GCC CCA CAT CTA CAT GAA TGT CGA CAG CCC GAA
CGG TTG CGG GGT GTA GAT GTA CTT ACA GCT GTC GGG CTT
 A   N   A   P   H   L   H   E   C   R   Q   P   E 2880             2890             2900
GAG AAA CCA ATA CTA CAT GGA TCG TAA TA
CTC TTT GGT TAT GAT GTA CCT AGC ATT AT
 E   K   P   I   L   H   G   S

>BamHI
             |
    2910     |    2920      2930      2940      2950
CAAATGCCGTGGATCCGAGCTCGGTACCAAGCTTGGGCCCGAACAAAAAC
GTTTACGGCACCTAGGCTCGAGCCATGGTTCGAACCCGGGCTTGTTTTTG 2960      2970      2980      2990      3000
TCATCTCAGAAGAGGATCTGAATAGCGCCGTCGACCATCATCATCATCAT
AGTAGAGTCTTCTCCTAGACTTATCGCGGCAGCTGGTAGTAGTAGTAGTA 3010      3020      3030      3040      3050
CATTGAGTTTAAACCGCTGATCAGCCTCGACTGTGCCTTCTAGTTGCCAG
GTAACTCAAATTTGGCGACTAGTCGGAGCTGACACGGAAGATCAACGGTC 3060      3070      3080      3090      3100
CCATCTGTTGTTTGCCCCTCCCCCGTGCCTTCCTTGACCCTGGAAGGTGC
GGTAGACAACAAACGGGGAGGGGGCACGGAAGGAACTGGGACCTTCCACG 3110      3120      3130      3140      3150
CACTCCCACTGTCCTTTCCTAATAAAATGAGGAAATTGCATCGCATTGTC
GTGAGGGTGACAGGAAAGGATTATTTTACTCCTTTAACGTAGCGTAACAG 3160      3170      3180      3190      3200
TGAGTAGGTGTCATTCTATTCTGGGGGGTGGGTGGGGCAGGACAGCAAG
ACTCATCCACAGTAAGATAAGACCCCCCACCCCACCCCGTCCTGTCGTTC
```

FIG. 3F

```
          3210       3220       3230       3240       3250
GGGGAGGATTGGGAAGACAATAGCAGGCATGCTGGGGATGCGGTGGGCTC
CCCCTCCTAACCCTTCTGTTATCGTCCGTACGACCCCTACGCCACCCGAG 3260       3270       3280       3290       3300
TATGGCTTCTGAGGCGGAAAGAACCAGCTGGGGCTCTAGGGGTATCCCC
ATACCGAAGACTCCGCCTTTCTTGGTCGACCCCGAGATCCCCCATAGGGG 3310       3320       3330       3340       3350
ACGCGCCCTGTAGCGGCGCATTAAGCGCGGCGGGTGTGGTGGTTACGCGC
TGCGCGGGACATCGCCGCGTAATTCGCGCCGCCCACACCACCAATGCGCG 3360       3370       3380       3390       3400
AGCGTGACCGCTACACTTGCCAGCGCCCTAGCGCCCGCTCCTTTCGCTTT
TCGCACTGGCGATGTGAACGGTCGCGGGATCGCGGGCGAGGAAAGCGAAA 3410       3420       3430       3440       3450
CTTCCCTTCCTTTCTCGCCACGTTCGCCGGCTTTCCCCGTCAAGCTCTAA
GAAGGGAAGGAAAGAGCGGTGCAAGCGGCCGAAAGGGGCAGTTCGAGATT 3460       3470       3480       3490       3500
ATCGGGGCATCCCTTTAGGGTTCCGATTTAGTGCTTTACGGCACCTCGAC
TAGCCCCGTAGGGAAATCCCAAGGCTAAATCACGAAATGCCGTGGAGCTG 3510       3520       3530       3540       3550
CCCAAAAAACTTGATTAGGGTGATGGTTCACGTAGTGGGCCATCGCCCTG
GGGTTTTTTGAACTAATCCCACTACCAAGTGCATCACCCGGTAGCGGGAC 3560       3570       3580       3590       3600
ATAGACGGTTTTTCGCCCTTTGACGTTGGAGTCCACGTTCTTTAATAGTG
TATCTGCCAAAAAGCGGGAAACTGCAACCTCAGGTGCAAGAAATTATCAC 3610       3620       3630       3640       3650
GACTCTTGTTCCAAACTGGAACAACACTCAACCCTATCTCGGTCTATTCT
CTGAGAACAAGGTTTGACCTTGTTGTGAGTTGGGATAGAGCCAGATAAGA 3660       3670       3680       3690       3700
TTTGATTTATAAGGGATTTTGGGGATTTCGGCCTATTGGTTAAAAAATGA
AAACTAAATATTCCCTAAAACCCCTAAAGCCGGATAACCAATTTTTTACT 3710       3720       3730       3740       3750
GCTGATTTAACAAAAATTTAACGCGAATTAATTCTGTGGAATGTGTGTCA
CGACTAAATTGTTTTTAAATTGCGCTTAATTAAGACACCTTACACACAGT 3760       3770       3780       3790       3800
GTTAGGGTGTGGAAAGTCCCCAGGCTCCCCAGGCAGGCAGAAGTATGCAA
CAATCCCACACCTTTCAGGGGTCCGAGGGGTCCGTCCGTCTTCATACGTT 3810       3820       3830       3840       3850
AGCATGCATCTCAATTAGTCAGCAACCAGGTGTGGAAAGTCCCCAGGCTC
TCGTACGTAGAGTTAATCAGTCGTTGGTCCACACCTTTCAGGGTCCGAG 3860       3870       3880       3890       3900
CCCAGCAGGCAGAAGTATGCAAAGCATGCATCTCAATTAGTCAGCAACCA
GGGTCGTCCGTCTTCATACGTTTCGTACGTAGAGTTAATCAGTCGTTGGT 3910       3920       3930       3940       3950
TAGTCCCGCCCCTAACTCCGCCCATCCCGCCCCTAACTCCGCCCAGTTCC
ATCAGGGCGGGGATTGAGGCGGGTAGGGCGGGGATTGAGGCGGGTCAAGG 3960       3970       3980       3990       4000
GCCCATTCTCCGCCCCATGGCTGACTAATTTTTTTTATTTATGCAGAGGC
CGGGTAAGAGGCGGGGTACCGACTGATTAAAAAAAATAAATACGTCTCCG
```

FIG. 3G

```
        4010      4020      4030      4040      4050
CGAGGCCGCCTCTGCCTCTGAGCTATTCCAGAAGTAGTGAGGAGGCTTTT
GCTCCGGCGGAGACGGAGACTCGATAAGGTCTTCATCACTCCTCCGAAAA 4060      4070      4080      4090      4100
TTGGAGGCCTAGGCTTTTGCAAAAAGCTCCCGGGAGCTTGTATATCCATT
AACCTCCGGATCCGAAAACGTTTTTCGAGGGCCCTCGAACATATAGGTAA 4110      4120      4130      4140      4150
TTCGGATCTGATCAAGAGACAGGATGAGGATCGTTTCGCATGATTGAACA
AAGCCTAGACTAGTTCTCTGTCCTACTCCTAGCAAAGCGTACTAACTTGT 4160      4170      4180      4190      4200
AGATGGATTGCACGCAGGTTCTCCGGCCGCTTGGGTGGAGAGGCTATTCG
TCTACCTAACGTGCGTCCAAGAGGCCGGCGAACCCACCTCTCCGATAAGC 4210      4220      4230      4240      4250
GCTATGACTGGGCACAACAGACAATCGGCTGCTCTGATGCCGCCGTGTTC
CGATACTGACCCGTGTTGTCTGTTAGCCGACGAGACTACGGCGGCACAAG 4260      4270      4280      4290      4300
CGGCTGTCAGCGCAGGGGCGCCCGGTTCTTTTTGTCAAGACCGACCTGTC
GCCGACAGTCGCGTCCCCGCGGGCCAAGAAAAACAGTTCTGGCTGGACAG 4310      4320      4330      4340      4350
CGGTGCCCTGAATGAACTGCAGGACGAGGCAGCGCGGCTATCGTGGCTGG
GCCACGGGACTTACTTGACGTCCTGCTCCGTCGCGCCGATAGCACCGACC 4360      4370      4380      4390      4400
CCACGACGGGCGTTCCTTGCGCAGCTGTGCTCGACGTTGTCACTGAAGCG
GGTGCTGCCCGCAAGGAACGCGTCGACACGAGCTGCAACAGTGACTTCGC 4410      4420      4430      4440      4450
GGAAGGGACTGGCTGCTATTGGGCGAAGTGCCGGGGCAGGATCTCCTGTC
CCTTCCCTGACCGACGATAACCCGCTTCACGGCCCCGTCCTAGAGGACAG 4460      4470      4480      4490      4500
ATCTCACCTTGCTCCTGCCGAGAAAGTATCCATCATGGCTGATGCAATGC
TAGAGTGGAACGAGGACGGCTCTTTCATAGGTAGTACCGACTACGTTACG 4510      4520      4530      4540      4550
GGCGGCTGCATACGCTTGATCCGGCTACCTGCCCATTCGACCACCAAGCG
CCGCCGACGTATGCGAACTAGGCCGATGGACGGGTAAGCTGGTGGTTCGC 4560      4570      4580      4590      4600
AAACATCGCATCGAGCGAGCACGTACTCGGATGGAAGCCGGTCTTGTCGA
TTTGTAGCGTAGCTCGCTCGTGCATGAGCCTACCTTCGGCCAGAACAGCT 4610      4620      4630      4640      4650
TCAGGATGATCTGGACGAAGAGCATCAGGGGCTCGCGCCAGCCGAACTGT
AGTCCTACTAGACCTGCTTCTCGTAGTCCCCGAGCGCGGTCGGCTTGACA 4660      4670      4680      4690      4700
TCGCCAGGCTCAAGGCGCGCATGCCCGACGGCGAGGATCTCGTCGTGACC
AGCGGTCCGAGTTCCGCGCGTACGGGCTGCCGCTCCTAGAGCAGCACTGG 4710      4720      4730      4740      4750
CATGGCGATGCCTGCTTGCCGAATATCATGGTGGAAAATGGCCGCTTTTC
GTACCGCTACGGACGAACGGCTTATAGTACCACCTTTTACCGGCGAAAAG 4760      4770      4780      4790      4800
TGGATTCATCGACTGTGGCCGGCTGGGTGTGGCGGACCGCTATCAGGACA
ACCTAAGTAGCTGACACCGGCCGACCCACACCGCCTGGCGATAGTCCTGT
```

FIG. 3H

```
          4810      4820      4830      4840      4850
TAGCGTTGGCTACCCGTGATATTGCTGAAGAGCTTGGCGGCGAATGGGCT
ATCGCAACCGATGGGCACTATAACGACTTCTCGAACCGCCGCTTACCCGA 4860      4870      4880      4890      4900
GACCGCTTCCTCGTGCTTTACGGTATCGCCGCTCCCGATTCGCAGCGCAT
CTGGCGAAGGAGCACGAAATGCCATAGCGGCGAGGGCTAAGCGTCGCGTA 4910      4920      4930      4940      4950
CGCCTTCTATCGCCTTCTTGACGAGTTCTTCTGAGCGGGACTCTGGGGTT
GCGGAAGATAGCGGAAGAACTGCTCAAGAAGACTCGCCCTGAGACCCCAA 4960      4970      4980      4990      5000
CGAAATGACCGACCAAGCGACGCCCAACCTGCCATCACGAGATTTCGATT
GCTTTACTGGCTGGTTCGCTGCGGGTTGGACGGTAGTGCTCTAAAGCTAA 5010      5020      5030      5040      5050
CCACCGCCGCCTTCTATGAAAGGTTGGGCTTCGGAATCGTTTTCCGGGAC
GGTGGCGGCGGAAGATACTTTCCAACCCGAAGCCTTAGCAAAAGGCCCTG 5060      5070      5080      5090      5100
GCCGGCTGGATGATCCTCCAGCGCGGGGATCTCATGCTGGAGTTCTTCGC
CGGCCGACCTACTAGGAGGTCGCGCCCCTAGAGTACGACCTCAAGAAGCG 5110      5120      5130      5140      5150
CCACCCCAACTTGTTTATTGCAGCTTATAATGGTTACAAATAAAGCAATA
GGTGGGGTTGAACAAATAACGTCGAATATTACCAATGTTTATTTCGTTAT 5160      5170      5180      5190      5200
GCATCACAAATTTCACAAATAAAGCATTTTTTTCACTGCATTCTAGTTGT
CGTAGTGTTTAAAGTGTTTATTTCGTAAAAAAAGTGACGTAAGATCAACA 5210      5220      5230      5240      5250
GGTTTGTCCAAACTCATCAATGTATCTTATCATGTCTGTATACCGTCGAC
CCAAACAGGTTTGAGTAGTTACATAGAATAGTACAGACATATGGCAGCTG 5260      5270      5280      5290      5300
CTCTAGCTAGAGCTTGGCGTAATCATGGTCATAGCTGTTTCCTGTGTGAA
GAGATCGATCTCGAACCGCATTAGTACCAGTATCGACAAAGGACACACTT 5310      5320      5330      5340      5350
ATTGTTATCCGCTCACAATTCCACACAACATACGAGCCGGAAGCATAAAG
TAACAATAGGCGAGTGTTAAGGTGTGTTGTATGCTCGGCCTTCGTATTTC 5360      5370      5380      5390      5400
TGTAAAGCCTGGGGTGCCTAATGAGTGAGCTAACTCACATTAATTGCGTT
ACATTTCGGACCCCACGGATTACTCACTCGATTGAGTGTAATTAACGCAA 5410      5420      5430      5440      5450
GCGCTCACTGCCCGCTTTCCAGTCGGGAAACCTGTCGTGCCAGCTGCATT
CGCGAGTGACGGGCGAAAGGTCAGCCCTTTGGACAGCACGGTCGACGTAA 5460      5470      5480      5490      5500
AATGAATCGGCCAACGCGCGGGGAGAGGCGGTTTGCGTATTGGGCGCTCT
TTACTTAGCCGGTTGCGCGCCCCTCTCCGCCAAACGCATAACCCGCGAGA 5510      5520      5530      5540      5550
TCCGCTTCCTCGCTCACTGACTCGCTGCGCTCGGTCGTTCGGCTGCGGCG
AGGCGAAGGAGCGAGTGACTGAGCGACGCGAGCCAGCAAGCCGACGCCGC 5560      5570      5580      5590      5600
AGCGGTATCAGCTCACTCAAAGGCGGTAATACGGTTATCCACAGAATCAG
TCGCCATAGTCGAGTGAGTTTCCGCCATTATGCCAATAGGTGTCTTAGTC
```

FIG. 31

```
          5610      5620      5630      5640      5650
GGGATAACGCAGGAAAGAACATGTGAGCAAAAGGCCAGCAAAAGGCCAGG
CCCTATTGCGTCCTTTCTTGTACACTCGTTTTCCGGTCGTTTTCCGGTCC 5660      5670      5680      5690      5700
AACCGTAAAAAGGCCGCGTTGCTGGCGTTTTTCCATAGGCTCCGCCCCCC
TTGGCATTTTTCCGGCGCAACGACCGCAAAAAGGTATCCGAGGCGGGGGG 5710      5720      5730      5740      5750
TGACGAGCATCACAAAAATCGACGCTCAAGTCAGAGGTGGCGAAACCCGA
ACTGCTCGTAGTGTTTTTAGCTGCGAGTTCAGTCTCCACCGCTTTGGGCT 5760      5770      5780      5790      5800
CAGGACTATAAAGATACCAGGCGTTTCCCCCTGGAAGCTCCCTCGTGCGC
GTCCTGATATTTCTATGGTCCGCAAAGGGGGACCTTCGAGGGAGCACGCG 5810      5820      5830      5840      5850
TCTCCTGTTCCGACCCTGCCGCTTACCGGATACCTGTCCGCCTTTCTCCC
AGAGGACAAGGCTGGGACGGCGAATGGCCTATGGACAGGCGGAAAGAGGG 5860      5870      5880      5890      5900
TTCGGGAAGCGTGGCGCTTTCTCAATGCTCACGCTGTAGGTATCTCAGTT
AAGCCCTTCGCACCGCGAAAGAGTTACGAGTGCGACATCCATAGAGTCAA 5910      5920      5930      5940      5950
CGGTGTAGGTCGTTCGCTCCAAGCTGGGCTGTGTGCACGAACCCCCCGTT
GCCACATCCAGCAAGCGAGGTTCGACCCGACACACGTGCTTGGGGGGCAA 5960      5970      5980      5990      6000
CAGCCCGACCGCTGCGCCTTATCCGGTAACTATCGTCTTGAGTCCAACCC
GTCGGGCTGGCGACGCGGAATAGGCCATTGATAGCAGAACTCAGGTTGGG 6010      6020      6030      6040      6050
GGTAAGACACGACTTATCGCCACTGGCAGCAGCCACTGGTAACAGGATTA
CCATTCTGTGCTGAATAGCGGTGACCGTCGTCGGTGACCATTGTCCTAAT 6060      6070      6080      6090      6100
GCAGAGCGAGGTATGTAGGCGGTGCTACAGAGTTCTTGAAGTGGTGGCCT
CGTCTCGCTCCATACATCCGCCACGATGTCTCAAGAACTTCACCACCGGA 6110      6120      6130      6140      6150
AACTACGGCTACACTAGAAGGACAGTATTTGGTATCTGCGCTCTGCTGAA
TTGATGCCGATGTGATCTTCCTGTCATAAACCATAGACGCGAGACGACTT 6160      6170      6180      6190      6200
GCCAGTTACCTTCGGAAAAAGAGTTGGTAGCTCTTGATCCGGCAAACAAA
CGGTCAATGGAAGCCTTTTTCTCAACCATCGAGAACTAGGCCGTTTGTTT 6210      6220      6230      6240      6250
CCACCGCTGGTAGCGGTGGTTTTTTTGTTTGCAAGCAGCAGATTACGCGC
GGTGGCGACCATCGCCACCAAAAAAACAAACGTTCGTCGTCTAATGCGCG 6260      6270      6280      6290      6300
AGAAAAAAAGGATCTCAAGAAGATCCTTTGATCTTTTCTACGGGTCTGA
TCTTTTTTTCCTAGAGTTCTTCTAGGAAACTAGAAAAGATGCCCCAGACT 6310      6320      6330      6340      6350
CGCTCAGTGGAACGAAAACTCACGTTAAGGGATTTTGGTCATGAGATTAT
GCGAGTCACCTTGCTTTTGAGTGCAATTCCCTAAAACCAGTACTCTAATA 6360      6370      6380      6390      6400
CAAAAAGGATCTTCACCTAGATCCTTTTAAATTAAAAATGAAGTTTTAAA
GTTTTTCCTAGAAGTGGATCTAGGAAAATTTAATTTTTACTTCAAAATTT
```

FIG. 3J

```
      6410      6420      6430      6440      6450
TCAATCTAAAGTATATATGAGTAAACTTGGTCTGACAGTTACCAATGCTT
AGTTAGATTTCATATATACTCATTTGAACCAGACTGTCAATGGTTACGAA 6460      6470      6480      6490      6500
AATCAGTGAGGCACCTATCTCAGCGATCTGTCTATTTCGTTCATCCATAG
TTAGTCACTCCGTGGATAGAGTCGCTAGACAGATAAAGCAAGTAGGTATC 6510      6520      6530      6540      6550
TTGCCTGACTCCCCGTCGTGTAGATAACTACGATACGGGAGGGCTTACCA
AACGGACTGAGGGGCAGCACATCTATTGATGCTATGCCCTCCCGAATGGT 6560      6570      6580      6590      6600
TCTGGCCCCAGTGCTGCAATGATACCGCGAGACCCACGCTCACCGGCTCC
AGACCGGGGTCACGACGTTACTATGGCGCTCTGGGTGCGAGTGGCCGAGG 6610      6620      6630      6640      6650
AGATTTATCAGCAATAAACCAGCCAGCCGGAAGGGCCGAGCGCAGAAGTG
TCTAAATAGTCGTTATTTGGTCGGTCGGCCTTCCCGGCTCGCGTCTTCAC 6660      6670      6680      6690      6700
GTCCTGCAACTTTATCCGCCTCCATCCAGTCTATTAATTGTTGCCGGGAA
CAGGACGTTGAAATAGGCGGAGGTAGGTCAGATAATTAACAACGGCCCTT 6710      6720      6730      6740      6750
GCTAGAGTAAGTAGTTCGCCAGTTAATAGTTTGCGCAACGTTGTTGCCAT
CGATCTCATTCATCAAGCGGTCAATTATCAAACGCGTTGCAACAACGGTA 6760      6770      6780      6790      6800
TGCTACAGGCATCGTGGTGTCACGCTCGTCGTTTGGTATGGCTTCATTCA
ACGATGTCCGTAGCACCACAGTGCGAGCAGCAAACCATACCGAAGTAAGT 6810      6820      6830      6840      6850
GCTCCGGTTCCCAACGATCAAGGCGAGTTACATGATCCCCCATGTTGTGC
CGAGGCCAAGGGTTGCTAGTTCCGCTCAATGTACTAGGGGGTACAACACG 6860      6870      6880      6890      6900
AAAAAAGCGGTTAGCTCCTTCGGTCCTCCGATCGTTGTCAGAAGTAAGTT
TTTTTTCGCCAATCGAGGAAGCCAGGAGGCTAGCAACAGTCTTCATTCAA 6910      6920      6930      6940      6950
GGCCGCAGTGTTATCACTCATGGTTATGGCAGCACTGCATAATTCTCTTA
CCGGCGTCACAATAGTGAGTACCAATACCGTCGTGACGTATTAAGAGAAT 6960      6970      6980      6990      7000
CTGTCATGCCATCCGTAAGATGCTTTTCTGTGACTGGTGAGTACTCAACC
GACAGTACGGTAGGCATTCTACGAAAAGACACTGACCACTCATGAGTTGG 7010      7020      7030      7040      7050
AAGTCATTCTGAGAATAGTGTATGCGGCGACCGAGTTGCTCTTGCCCGGC
TTCAGTAAGACTCTTATCACATACGCCGCTGGCTCAACGAGAACGGGCCG 7060      7070      7080      7090      7100
GTCAATACGGGATAATACCGCGCCACATAGCAGAACTTTAAAAGTGCTCA
CAGTTATGCCCTATTATGGCGCGGTGTATCGTCTTGAAATTTTCACGAGT 7110      7120      7130      7140      7150
TCATTGGAAAACGTTCTTCGGGGCGAAAACTCTCAAGGATCTTACCGCTG
AGTAACCTTTTGCAAGAAGCCCCGCTTTTGAGAGTTCCTAGAATGGCGAC 7160      7170      7180      7190      7200
TTGAGATCCAGTTCGATGTAACCCACTCGTGCACCCAACTGATCTTCAGC
AACTCTAGGTCAAGCTACATTGGGTGAGCACGTGGGTTGACTAGAAGTCG
```

FIG. 3K

```
          7210       7220       7230       7240       7250
ATCTTTTACTTTCACCAGCGTTTCTGGGTGAGCAAAAACAGGAAGGCAAA
TAGAAAATGAAAGTGGTCGCAAAGACCCACTCGTTTTTGTCCTTCCGTTT 7260       7270       7280       7290       7300
ATGCCGCAAAAAAGGGAATAAGGGCGACACGGAAATGTTGAATACTCATA
TACGGCGTTTTTTCCCTTATTCCCGCTGTGCCTTTACAACTTATGAGTAT 7310       7320       7330       7340       7350
CTCTTCCTTTTTCAATATTATTGAAGCATTTATCAGGGTTATTGTCTCAT
GAGAAGGAAAAAGTTATAATAACTTCGTAAATAGTCCCAATAACAGAGTA 7360       7370       7380       7390       7400
GAGCGGATACATATTTGAATGTATTTAGAAAAATAAACAAATAGGGGTTC
CTCGCCTATGTATAAACTTACATAAATCTTTTATTTGTTTATCCCCAAG 7410       7420       7430
CGCGCACATTTCCCCGAAAAGTGCCACCTGACGTC
GCGCGTGTAAAGGGGCTTTTCACGGTGGACTGCAG
```

FIG. 3L

```
                10                  20                  30
    ATG TTG TTG TGC GAC GGA CTT GGC CCG GAG CCA CCG CGG
    TAC AAC AAC ACG CTG CCT GAA CCG GGC CTC GGT GGC GCC
     M   L   L   C   D   G   L   G   P   E   P   P   R 40                  50                  60                  70
    CAA AGG CAT CGA AAT CGA ACC AGT GCC GCC AGG ATT AGA
    GTT TCC GTA GCT TTA GCT TGG TCA CGG CGG TCC TAA TCT
     Q   R   H   R   N   R   T   S   A   A   R   I   R 80                  90                  100                 110
    AAA AGA CCG AAA TGC TGC TGC GGC GAT GGC GGC AGC GGC
    TTT TCT GGC TTT ACG ACG ACG CCG CTA CCG CCG TCG CCG
     K   R   P   K   C   C   C   G   D   G   G   S   G 120                 130                 140                 150
    AAT CAG GCG GAG CAG CCC GGC GGG ATA GTT AGC AAC CCA
    TTA GTC CGC CTC GTC GGG CCG CCC TAT CAA TCG TTG GGT
     N   Q   A   E   Q   P   G   G   I   V   S   N   P 160                 170                 180                 190
    ATT AGT TAT GGC CAA AGT CTG ACA ACA TTG GCG CGG GTC
    TAA TCA ATA CCG GTT TCA GAC TGT TGT AAC CGC GCC CAG
     I   S   Y   G   Q   S   L   T   T   L   A   R   V 200                 210                 220                 230
    ACG GCG GCC GCA CTG ACC ACG GCG GCC ATG CTG CAC ACA
    TGC CGC CGG CGT GAC TGG TGC CGC CGG TAC GAC GTG TGT
     T   A   A   A   L   T   T   A   A   M   L   H   T
       240                 250                 260                 270
    ACG AAT GCC CTG GCT GCC ACC GGC TCA TCC AGC GCA TCC
    TGC TTA CGG GAC CGA CGG TGG CCG AGT AGG TCG CGT AGG
     T   N   A   L   A   A   T   G   S   S   S   A   S
           280                 290                 300                 310
    AAC TCT TCC ACC GGC GGA ATA GCA CTG CCG CTG GGC ACT
    TTG AGA AGG TGG CCG CCT TAT CGT GAC GGC GAC CCG TGA
     N   S   S   T   G   G   I   A   L   P   L   G   T 320                 330                 340                 350
    GCC ACA CCT GCC ACA CAC GAA CTG AAT GCC ACA CAG CCG
    CGG TGT GGA CGG TGT GTG CTT GAC TTA CGG TGT GTC GGC
     A   T   P   A   T   H   E   L   N   A   T   Q   P 360                 370                 380                 390
    TTT GGC GGC TCG GGT CTG AAC TTC AAC GAA AGC GGC GCA
    AAA CCG CCG AGC CCA GAC TTG AAG TTG CTT TCG CCG CGT
     F   G   G   S   G   L   N   F   N   E   S   G
```

FIG. 4A

```
                400               410              420
       GGA TTA AGT GAC CAT CAT CAT CAT CAA CAA CAC AAT CCC
       CCT AAT TCA CTG GTA GTA GTA GTA GTT GTT GTG TTA GGG
        G   L   S   D   H   H   H   H   Q   Q   H   N   P 430               440              450              460
       GAC GAG GAT TGG CTG GAC AAC ATC GTT TGG GTG TTC AAG
       CTG CTC CTA ACC GAC CTG TTG TAG CAA ACC CAC AAG TTC
        D   E   D   W   L   D   N   I   V   W   V   F   K

TRANSMEMBRANE DOMAIN 1
                             |
  470              480              490              500
       GCC TTT GTC ATG CTG CTC ATC ATC ATT GCG GCC ATC TGC
       CGG AAA CAG TAC GAC GAG TAG TAG TAA CGC CGG TAG ACG
        A   F   V   M   L   L   I   I   I   A   A   I   C 510              520              530              540
       GGC AAT CTG CTT GTT ATT ATT TCT GTG ATG CGT GTT AGA
       CCG TTA GAC GAA CAA TAA TAA AGA CAC TAC GCA CAA TCT
        G   N   L   L   V   I   I   S   V   M   R   V   R

TRANSMEMBRANE DOMAIN 2
                                             |
  550              560              570    |       580
       AAA TTA AGA GTT ATA ACG AAT TAC TTT GTA GTT TCC TTA
       TTT AAT TCT CAA TAT TGC TTA ATG AAA CAT CAA AGG AAT
        K   L   R   V   I   T   N   Y   F   V   V   S   L 590              600              610              620
       GCC ATG GCT GAT ATA ATG GTC GCT ATT ATG GCC ATG ACA
       CGG TAC CGA CTA TAT TAC CAG CGA TAA TAC CGG TAC TGT
        A   M   A   D   I   M   V   A   I   M   A   M   T 630              640              650              660
       TTT AAC TTT AGT GTG CAA GTA ACT GGG CGG TGG AAC TTC
       AAA TTG AAA TCA CAC GTT CAT TGA CCC GCC ACC TTG AAG
        F   N   F   S   V   Q   V   T   G   R   W   N   F

TRANSMEMBRANE DOMAIN 3
                             |
  670              680|             690              700
       AGC CCC TTC CTG TGC GAT TTG TGG AAC AGC CTC GAT GTC
       TCG GGG AAG GAC ACG CTA AAC ACC TTG TCG GAG CTA CAG
        S   P   F   L   C   D   L   W   N   S   L   D   V 710              720              730              740
       TAC TTC TCA ACA GCG AGT ATT TTG CAT TTA TGC TGC ATA
       ATG AAG AGT TGT CGC TCA TAA AAC GTA AAT ACG ACG TAT
        Y   F   S   T   A   S   I   L   H   L   C   C   I
```

FIG. 4B

```
                750              760              770              780
         TCT GTG GAT AGA TAC TAT GCT ATT GTT AAG CCC CTC AAG
         AGA CAC CTA TCT ATG ATA CGA TAA CAA TTC GGG GAG TTC
          S   V   D   R   Y   Y   A   I   V   K   P   L   K
                                          TRANSMEMBRANE DOMAIN 4
                                                      |
                790              800             | 810
         TAT CCG ATT AGC ATG ACG AAA CGC GTG GTC GGC ATT ATG
         ATA GGC TAA TCG TAC TGC TTT GCG CAC CAG CCG TAA TAC
          Y   P   I   S   M   T   K   R   V   V   G   I   M 820              830              840              850
      CTG CTA AAC ACA TGG ATA TCG CCG GCA CTG CTC TCC TTC
      GAC GAT TTG TGT ACC TAT AGC GGC CGT GAC GAG AGG AAG
       L   L   N   T   W   I   S   P   A   L   L   S   F 860              870              880              890
      TTG CCC ATC TTC ATC GGC TGG TAC ACC ACG CCG CAG CAC
      AAC GGG TAG AAG TAG CCG ACC ATG TGG TGC GGC GTC GTG
       L   P   I   F   I   G   W   Y   T   T   P   Q   H 900              910              920              930
      CAG CAG TTC GTC ATC CAG AAT CCG ACG CAG TGC TCG TTC
      GTC GTC AAG CAG TAG GTC TTA GGC TGC GTC ACG AGC AAG
       Q   Q   F   V   I   Q   N   P   T   Q   C   S   F

TRANSMEMBRANE DOMAIN 5
                                                                |
         940              950              960              970  |
         GTG GTG AAC AAG TAC TAC GCC GTC ATC TCG AGC TCC ATA
         CAC CAC TTG TTC ATG ATG CGG CAG TAG AGC TCG AGG TAT
          V   V   N   K   Y   Y   A   V   I   S   S   S   I 980              990             1000             1010
         TCG TTC TGG ATA CCC TGC ACC ATT ATG ATA TTC ACC TAC
         AGC AAG ACC TAT GGG ACG TGG TAA TAC TAT AAG TGG ATG
          S   F   W   I   P   C   T   I   M   I   F   T   Y
              1020             1030             1040             1050
         CTG GCC ATC TTC CGG GAA GCC AAT CGG CAG GAG AAG CAG
         GAC CGG TAG AAG GCC CTT CGG TTA GCC GTC CTC TTC GTC
          L   A   I   F   R   E   A   N   R   Q   E   K   Q 1060             1070             1080             1090
         CTG ATG ATG CGG CAC GGC AAT GCC ATG CTG ATG CAC CGA
         GAC TAC TAC GCC GTG CCG TTA CGG TAC GAC TAC GTG GCT
          L   M   M   R   H   G   N   A   M   L   M   H   R 1100             1110             1120             1130
         CCA TCC ATG CAG CCA TCA GGC GAG GCG CTG AGC GGA TCC
         GGT AGG TAC GTC GGT AGT CCG CTC CGC GAC TCG CCT AGG
          P   S   M   Q   P   S   G   E   A   L   S   G   S
```

FIG. 4C

```
            1140           1150           1160           1170
       GGG TCG TCG AAA ACA TTG ACG CTG CAC GAG GTC GAG CAG
       CCC AGC AGC TTT TGT AAC TGC GAC GTG CTC CAG CTC GTC
        G   S   S   K   T   L   T   L   H   E   V   E   Q 1180           1190           1200
       GAG CAC ACC CCC ACT AAG GAC AAG CAC TTA ATC AAA ATG
       CTC GTG TGG GGG TGA TTC CTG TTC GTG AAT TAG TTT TAC
        E   H   T   P   T   K   D   K   H   L   I   K   M

TRANSMEMBRANE DOMAIN 6
                                                  |
   1210           1220           1230           1240
   AAG CGG GAG CAC AAG GCC GCA CGC ACG CTG GGC ATC ATC
   TTC GCC CTC GTG TTC CGG CGT GCG TGC GAC CCG TAG TAG
    K   R   E   H   K   A   A   R   T   L   G   I   I 1250           1260           1270           1280
   ATG GGC ACC TTC ATC CTC TGC TGG CTG CCT TTC TTC CTG
   TAC CCG TGG AAG TAG GAG ACG ACC GAC GGA AAG AAG GAC
    M   G   T   F   I   L   C   W   L   P   F   F   L

TRANSMEMBRANE DOMAIN 7
                                                  |
       1290           1300           1310           1320
       TGG TAC ACA CTC TCC ATG ACC TGC GAG GAG TGC CAA GTG
       ACC ATG TGT GAG AGG TAC TGG ACG CTC CTC ACG GTT CAC
        W   Y   T   L   S   M   T   C   E   E   C   Q   V 1330           1340           1350           1360
       CCG GAC ATA GTC GTC TCA ATC CTC TTC TGG ATC GGG TAC
       GGC CTG TAT CAG CAG AGT TAG GAG AAG ACC TAG CCC ATG
        P   D   I   V   V   S   I   L   F   W   I   G   Y 1370           1380           1390           1400
       TTC AAC TCA ACG CTA AAC CCG CTG ATC TAC GCG TAC TTC
       AAG TTG AGT TGC GAT TTG GGC GAC TAG ATG CGC ATG AAG
        F   N   S   T   L   N   P   L   I   Y   A   Y   F 1410           1420           1430           1440
       AAC CGC GAC TTC CGG GAG GCG TTC CGC AAC ACG CTG CTC
       TTG GCG CTG AAG GCC CTC CGC AAG GCG TTG TGC GAC GAG
        N   R   D   F   R   E   A   F   R   N   T   L   L 1450           1460           1470           1480
       TGC CTG TTC TGC AAT TGG TGG AAG GAT CGC CAC CTG CCT
       ACG GAC AAG ACG TTA ACC ACC TTC CTA GCG GTG GAC GGA
        C   L   F   C   N   W   W   K   D   R   H   L   P
```

FIG. 4D

```
      1490           1500           1510           1520
CTG GAC ATC GAC ATC CGG CGC TCC AGC CTG CGC TAC GAC
GAC CTG TAG CTG TAG GCC GCG AGG TCG GAC GCG ATG CTG
 L   D   I   D   I   R   R   S   S   L   R   Y   D 1530           1540           1550           1560
CAG CGG GCG AAG AGC GTC TAC TCG GAG AGC TAC CTT AAC
GTC GCC CGC TTC TCG CAG ATG AGC CTC TCG ATG GAA TTG
 Q   R   A   K   S   V   Y   S   E   S   Y   L   N 1570           1580           1590
TCG ACA ACG CCC TCG CAT CGC CGC CAG TCT CAG ATG CAG
AGC TGT TGC GGG AGC GTA GCG GCG GTC AGA GTC TAC GTC
 S   T   T   P   S   H   R   R   Q   S   Q   M   Q 1600           1610           1620           1630
CAG CGG CTG GCG GCG GGC GGA TCC CGC CTG GGC GGA CAA
GTC GCC GAC CGC CGC CCG CCT AGG GCG GAC CCG CCT GTT
 Q   R   L   A   A   G   G   S   R   L   G   G   Q 1640           1650           1660           1670
TTG GCA GCT GCC GCC AAG GAT GGC AGG GAG TCG AAG GAT
AAC CGT CGA CGG CGG TTC CTA CCG TCC CTC AGC TTC CTA
 L   A   A   A   A   K   D   G   R   E   S   K   D 1680           1690           1700           1710
GCA AAG GAT ACG GGC AAG GAT GCG GGC AAG GGC AAA TCC
CGT TTC CTA TGC CCG TTC CTA CGC CCG TTC CCG TTT AGG
 A   K   D   T   G   K   D   A   G   K   G   K   S 1720           1730           1740           1750
AAT GTC GAT TGC TTG GCG GGC GAC GAT GTG CAG GAG ATC
TTA CAG CTA ACG AAC CGC CCG CTG CTA CAC GTC CTC TAG
 N   V   D   C   L   A   G   D   D   V   Q   E   I 1760           1770           1780           1790
CAG ATT GAA ATA CCC ATG GAG TAC ATC AAC AAA TGG AAC
GTC TAA CTT TAT GGG TAC CTC ATG TAG TTG TTT ACC TTG
 Q   I   E   I   P   M   E   Y   I   N   K   W   N 1800           1810           1820           1830
AAG AAC AAC AAT GCC GCC GCC TCG ACG GCC TCG AGT CAT
TTC TTG TTG TTA CGG CGG CGG AGC TGC CGG AGC TCA GTA
 K   N   N   N   A   A   A   S   T   A   S   S   H

GTG TAA
CAC ATT
 V
```

FIG. 4E

DROSOPHILA SEQUENCES

1. INTRODUCTION

The present invention relates to Drosophila genes and methods for their use. The invention provides nucleotide sequences of Drosophila genes, amino acid sequences of the encoded proteins, and derivatives (e.g., fragments) and analogs thereof. The invention further relates to fragments (and derivatives and analogs thereof) of proteins which comprise one or more domains of a Drosophila protein. Antibodies to Drosophila proteins, and derivatives and analogs thereof, are also provided. Also provided herein are vectors and host cells comprising such nucleic acids. Methods of production of a Drosophila protein (e.g., by recombinant means), and derivatives and analogs thereof, are provided. Chimeric polypeptide molecules comprising polypeptides of the invention fused to heterologous polypeptide sequences are provided. Methods to identify the biological function of a Drosophila gene are provided, including various methods for the functional modification (e.g., overexpression, underexpression, mutation, knock-out) of one gene, or of two or more genes simultaneously. Methods to identify a Drosophila gene which modifies the function of, and/or functions in a downstream pathway from, another gene are provided. The invention further provides for use of Drosophila proteins as media additives or pesticides.

2. BACKGROUND OF THE INVENTION

Citation of a reference herein shall not be construed as an admission that such reference is prior art to the present invention.

2.1. G-Protein Coupled Receptors

G-protein coupled receptors (GPCRs) form an extensive family of transmembrane regulatory proteins that elicit intracellular signals in nearly every physiological system of chordates and invertebrate organisms. As a consequence of relatively small ligand-binding sites and the wide range of physiological events which they regulate, GPCRs have established the precedent of being the largest class of drug targets in humans. As described below, the sequence conservation of GPCRs across vertebrate and invertebrate species suggests that novel receptors identified in invertebrate species could aid in identification of homologues in other species, and the application of the appropriate agonist or antagonist mammalian receptor drugs to invertebrate species could result in the identification of effective pesticide agents. GPCRs can be divided into five broad structural classes, A–E, based on amino acid sequence similarity and sequence motifs. The largest class is class A, which can, in turn, be divided into subgroups according to receptor sequence similarity and ligand characteristics. The categorization of these relationships is illustrated by the following examples:

Class A (rhodopsin-like) GPCRs include: biogenic amine receptors (e.g. α-adrenergic, β-adrenergic, dopamine, histamine, muscarinic acetylcholine, melatonin, 5-HT, octopamine and tyramine); peptidic ligand receptors (e.g., angiotensin, bombesin, chemokine, endothelin, galanin, hormone protein, F-met-leu-phe, melanocortin, N-formyl peptide, neuropeptide Y, neurokinin, opiate, tachykinin, vasopressin, oxytocin and somatostatin); rhodopsin receptors (e.g., vertebrate rhodopsin, arthropod rhodopsin, and olfactory receptors); prostanoid receptors (e.g., prostaglandin, prostacyclin, and thromboxane); nucleotide receptors (e.g., adenosine and purinoceptors); hormone-releasing GPCRs (e.g., gonadotropin-releasing hormone, thyrotropin-releasing hormone, growth hormone, and secretagogue GPCRs);

Class B (secretin like) GPCRs include calcitonin, calcitonin releasing factor, calcitonin gene-related peptide, gastrin, cholecystokinin, glucagon, growth hormone-releasing hormone, parathyroid hormone, vasoactive intestinal peptide, PACAP, diuretic hormone and secretin GPCRs;

Class C (metabotropic glutamate-like) GPCRs include metabotropic glutamate, metabotropic $GABA_B$, and extracellular calcium-sensing GPCRs;

Class D includes pheromone GPCRs; and

Class E includes cAMP-binding GPCRs.

Among their many functions, extensive study has revealed that GPCRs play a prominent role as receptors for neurotransmitters within the central and peripheral nervous systems, notably illustrated by the biogenic amine ligands such as norepinephrine (NE), octopamine (Oct), dopamine (DA), acetylcholine (ACh) and 5-hydroxytryptamine (5-HT). Several GPCRs for the biogenic amines have been identified in insects by pharmacological and molecular cloning approaches, including two octopamine/tyramine receptors from *Drosophila melanogaster* (Arakawa et al., 1990, Neuron 4, 343–354; Saudou et al., 1990, EMBO 9, 3611–3617; Han et al., 1990, J. Neurosci. 18, 3650–3658; see also Venter et al, U.S. Pat. Nos. 5,474,898 and 5,344,776) as well from other insect species such as moth, locus, and honey bee (von Nickisch-Rosenegk et al., 1996, Insect Biochem. Mol. Biol. 26: 817–827; Hiripi et al., 1994, Brain Res. 7, 119–126; Roeder et al., 1995, Prog. Brain Res. 106, 249–258; Evans, 1987, J. Exp. Biol. 129:239–250; Ebert et al., 1998, Insect Mol. Biol. 7, 151–162). Two putative Drosophila dopamine receptors, (Sugamori et al., 1995, FEBS Lett. 362, 131–138; Feng et al., 1996, J. Neurosci. 16, 3925–3933), two 5-HT receptors (Saudou et al., 1992, EMBO J. 11, 7–17), and one muscarinic acetylcholine receptor (Shapiro et al., 1989, Proc. Natl. Acad. Sci. U.S.A. 86, 9039–9043) have been identified and molecularly cloned, and are shown to be expressed in the nervous system. Glutamate and GABA are also CNS neurotransmitters involved in memory and mediation of pain sensation, and the metabotropic glutamate and GABA GPCRs form a structurally separate class of receptors (Class C). A Drosophila metabotropic glutamate receptor has been cloned and is expressed in the embryonic central nervous system (CNS) (Parmentier et al., 1996, J. Neurosci. 16, 6687–6694).

Other classes of GPCRs, such as rhodopsins and odorant receptors, are light and chemosensory receptors for the CNS and enable the senses of vision and odor. A number of rhodopsin genes have been identified and sequenced from *Drosophila melanogaster, virilis,* and *simulans* (Carulli et al., 1994, J. Mol. Evol. 38, 250–262), honey bee (Bellingham et al., 1997, Eur. J. Biochem. 243, 775–781; Townson et al., 1998, J. Neurosci. 18, 2412–2422), ant and tobacco hornworm (Chase et al., 1997, J. Exp. Biol. 200, 2469–2478; Popp et al., 1996, Invert. Neurosci. 1, 323–329). Related to actions within the nervous system, GPCRs regulate aspects of neuroendocrine secretion such as thyroid releasing hormone (TRH), thyroid stimulating hormone (TSH), growth hormone releasing hormone (GHRH), adrenocorticotropin (ACTH), and water balance via diuretic hormone or vasopressin. Extending to the regulation of cell growth and mammalian reproduction, GPCRs can couple to mitogenic pathways as illustrated by the bombesin and endothelin receptors, and can control ovulation, lactation and birth through the action of follicular stimulating hormone (FSH), luteinizing hormone (LH), and oxytocin.

Numerous neuropeptides have been identified from insects which perform similar overall roles to some of these mammalian peptides. However, the molecular characterization is incomplete with respect to the insect GPCRs which bind these analogous peptides; several may be homologous to mammalian receptors. A number of diuretic peptides, including an arginine vasopressin-like diuretic hormone, have been identified in locusts (Lehmberg et al., 1991, Biochem. Biophys. Res. Comm. 179, 1036–1041; Thompson et al., 1995, Peptides 16, 95–104; Schoofs et al., 1997, Peptides 18, 145–156; Proux et al., 1987, Biochem. Biophys. Res. Comm. 149, 180–186), while a diuretic hormone GPCR has been cloned from the house cricket and tobacco hornworm (Reagan, 1996, Insect Biochem. Mol. Biol. 26, 1–6; Reagan, 1994, Biol. Chem. 269, 9–12). A Drosophila GPCR with 50% identity to the transmembrane regions of rat TSH, FSH, and LH receptors has been cloned and sequenced (Hauser et al., 1997, J. Biol. Chem. 272, 1002–1010). Within the immune system, GPCRs can influence neutrophil chemotaxis through the action of chemokines, while modulation of digestion via gastric secretion and gut motility is regulated through GPCRs by the peptidic ligands gastrin and cholecystokinin (CCK). Insect GPCRs related to chemokine or CCK receptors have not been previously reported. However, leucosulfakin, proctolin, and FMRFamide peptides, which share sequence identity or functions similar to CCK/gastrin, have been isolated from several insect species (Nachman et al., 1986, Science 234, 71–73; Veenstra, 1989, Neuropeptides 14, 145–149; De Loof and Schoofs, 1990, Comp. Biochem. Physiol. [B] 95, 459–468; Starrat and Brown, 1975, Life Sci. 17, 1253–1256; O'Shea and Adams, 1981, Science 213, 567–569), including Drosophila (Nichols et al., 1988, J. Biol. Chem. 263, 12167–12170). These examples suggest a general structural conservation of certain GPCR subclasses across vertebrate and invertebrate species, and reinforce the notion that GPCRs play essential roles in the signaling and regulation of invertebrate physiology, such as for insects.

Gamma aminobutyric acid (GABA) is an important inhibitory neurotransmitter in both insects and vertebrates (Kuffler et al., 1965, Neurophysiol. 21, 589–601; Usherwood et al., 1965, Neurophysiol. 28, 497–519). In vertebrates, there are three broad families of GABA receptors found on both pre- and post-synaptic membranes. The $GABA_A$ and $GABA_C$ families are ionotropic receptors, i.e., ligand-gated ion channels which mediate fast inhibitory neurotransmission (Hevers et al., 1998, Mol. Neurobiol. 18:35–86; Bormann et al., 1995, Trends Neurosci. 18:515–519). Homologs of these ionotropic receptors are known in insects. For example, the receptor rdl belongs to the $GABA_A$ class, and is the target of cyclodiene pesticides such as Dieldrin (ffrench-Constant et al., 1993, Naure 363, 449–451).

The $GABA_B$ family of vertebrate receptors are entirely distinct from the $GABA_A$ and $GABA_C$ classes in structure and mechanism; they are seven transmembrane domain G-protein coupled receptors (GPCRs) which mediate slow, long-lasting inhibitory effects of GABA via G-mediated effects on the activity of adenylate cyclase, and potassium and calcium channels (for review, see Bowery, 1993, $GABA_B$ receptor pharmacology, Annu. Rev. Pharmacol. Toxicol. 33, 109–147; Kerr and Ong, 1995, $GABA_B$ receptors, Pharmacol. Ther. 67, 187–246). Initial cloning of the vertebrate $GABA_B$R1 receptor (Kaupmann et al., 1997, Nature 386, 239–246) suggested that additional subunits may be required to mediate the full physiologic response to GABA. Subsequent work has identified a second subunit, $GABA_B$R2, which physically associates with $GABA_B$R1 to form an unusual heteromeric GPCR that appears to mediate the complete physiologic effects of $GABA_B$ receptors (Kuner et al., 1999, Science 283, 74–77; Jones et al., 1999, Nature 396, 674–678; White et al., 1999, Nature 396, 679–682; and Kaupmann et al., 1999, Nature 396, 683–687).

Vertebrate $GABA_B$ receptors are activated specifically by baclofen and 3-aminopropylphosphonous acid (3-APPA) and are blocked by phaclofen, saclofen and CGP35348 (Bowery, 1993, $GABA_B$ receptor pharmacology, Annu. Rev. Pharmacol. Toxicol. 33, 109–147). However, baclofen is inactive in many invertebrate preparations, leading investigators to question if this receptor class existed in invertebrates (Sattelle et al., 1988, GABA receptors on the cell body membrane of an identified insect motor neuron, Proc. R. Soc. Lond. B 232, 445–456; Benson, 1989, A novel GABA receptor in the heart of a primitive arthropod, Exp. Biol. 147, 421–438 ). Furthermore, photoaffinity crosslinking studies with the ligand CGP71782, did not reveal the presence of $GABA_B$ receptors in invertebrates, though receptors from several vertebrate species were identified (Kaupmann et al., 1997, Nature 386, 239).

The biogenic amines form one of the largest subgroups of neurotransmitters, and regulate numerous physiological processes. (see Goodman and Gilman's: The pharmacological basis of therapeutics, ninth edition, p. 118–130, Hardman and Limbird, eds., McGraw-Hill, New York). One of the most widely characterized biogenic amine ligand and receptor systems are those of the catecholamines. These include the adrenergic system (α-adrenergic and β-adrenergic), which is central to autonomic functions such as sympathetic regulation of arteriole smooth muscle contraction and dilatation, and to regulation of heart contractility and conduction velocity. Epineprine and norepinephrine are the physiological adrenergic ligands; they signal their action through β- and α-adrenergic GPCRs. Another catecholamine is dopamine, which can also influence vascular smooth muscle contractility predominately through the action of receptors in the renal, coronary and mesenteric arteriole beds. In the CNS, dopamine plays a critical role in initiating voluntary motor movement through post-synapatic stimulation of the extrapyramidal motor system. Deficits in this pathway are most notable with the uncontrolled tremors observed in human Parkinson's disease. Octopamine is a related biogenic amine whose role in mammals is not clear, but which plays a significant role in invertebrates as a neurotransmitter and hormone (Evans, 1980, Adv. Insect Physiol. 15, 317–473), and acts similarly through a class of GPCRs closely related to the mammalian adrenergic receptors (Arakawa et al., 1990, Neuron 4, 343–354; Evans et al., 1993, Neurochem. Res. 18, 869–874).

In mammals, the actions of epinephrine and norepinephrine are mediated through three β-adrenergic receptors (β1, β2 and β3) and six α-adrenergic receptors (α1A, α1B, α1D, α2A, α2B and α2C) (see Kobilka, 1992, Annu. Rev. Neurosci. 15, 87–114; Insel, 1993, Exp. Gerontol. 28, 341–348; Hein et al.,1995, Neuropharmacology 34, 357–366). These seven transmembrane-spanning domain GPCRs are charcterized by a large intracellular loop connecting transmembrane domains five and six; this intracellular loop domain contributes to the interaction with specific heterotrimeric G-proteins which mediate downstream second messenger signaling events (Kobilka et al., 1988, Science 240, 1310–1316).

The β-adrenergic receptors can be distinguished pharmacologically from the α-adrenergic receptors by the use of subtype-specific agonists and antagonists (see Lefkowitz, 1979, Ann. Intern. Med. 91, 450–458; Frielle et al., 1989, Clin. Chem. 35, 721–725; Ruffolo et al., 1995, J. Med. Chem. 38, 3681–3716; and Kobilka et al., 1988, Science 240, 1310–1316). The intracellular effects of ligand-dependent activation of β-adrenergic receptors result principally from the intracellular increase in cAMP via adenylyl cyclases (see Lefkowitz, 1976, In: Properties of purified cholinergic and adrenergic receptors, pp.69–83; Strosberg, 1995, Obes. Res. 4, 501S–505S). Subtype diversity of α-adrenergic receptors is correlated to the intracellular signaling through multiple but specific effector pathways. These include $IP_3$ and $Ca^{+2}$ mobilization, diacylglycerol (α1A–D), activation of adenylyl cyclase, decreased cAMP, increased $K^+$ conductance, and decreased $Ca^{+2}$ conductance (α2A–C) (Kobilka, 1992, Annu. Rev. Neursci. 15:87–114; Hein et al., 1995, Neuropharmacology 34, 357–366).

Diversity also exists within dopamine GPCR signaling. Five dopamine receptor subtypes (D1–5) have been pharmacologically and molecularly characterized in mammals as being structurally similar to the adrenergic receptors. Subtype-specific agonists and antagonists are available for several of the dopamine receptors, notably for D1–3. The dopamine receptors couple to a similar intracellular signaling pathway as do the adrenergic receptors; D1 receptor elicts the activation of adenylyl cyclase while the D2 receptor is coupled to the decrease of cAMP, reduced $Ca^{+2}$ conductance and increased $K^+$ conductance. Although there have been reports of mammalian octopamine receptors with pharmacological properties distinct from adrenergic and dopamine receptors (Hicks et al., 1979, Brain Res. 157, 402–406), and octopamine exists in mammalian brain (see Axelrod et al., 1977, Nature 265, 501–504), these receptors have not been molecularly identified.

Catecholamine signaling in invertebrates has, to date, been demonstrated by the existence of dopamine-elicited physiology and GPCRs sharing similarity to mammalian GPCRs. Two dopamine GPCRs have been identified and cloned from Drosophila, (Sugamori et al., 1995, FEBS Lett. 362, 131–138; Feng et al., 1996, J. Neurosci. 16, 3925–3933), and share pharmacological and intracellular signaling characteristics of mammalian D1 and D2 receptors (Sugamori et al., 1995, FEBS Lett. 362, 131–138; Feng et al., 1996, 16, 3925–3933; Yellman et al., 1997, Proc. Natl. Acad. Sci. U.S.A. 94, 4131–4136; Reale et al., 1997, J. Neurosci. 17, 6545–6553; Torres et al., 1998, Synapse 29, 148–161). However, the pharmacological profile of the insect D1-like receptor is not totally consistent with the profile exhibited by the mammalian receptor (Sugamori, 1995, FEBS Lett. 362, 131–138). Epinephrine and norepinephrine have been identified in invertebrates and can elict invertebrate biological responses (see Murdock, 1971, Comp. Gen. Pharmacol. 7, 254–274 for review; Watson et al., 1993, J. Pharm. Biomed. Anal. 11–12, 1145–1149; Johnson et al., 1997, J. Comp. Physiol. [B] 167, 89–97; Park et al., 1998, Gen. Comp. Endocrinol. 110, 88–95). However, the physiological receptors which mediate the action of these catecholamines in invertebrates is not clear. The GPCRs most highly related to the adrenergic receptors in invertebrates are the three octopamine receptors identified in multiple insect species (OCT1–3). The insect octopamine receptors are pharmacologically similar to mammalian α-adrenergic receptors (Evans, 1981, J. Physiol. 318, 99–122; Evans, 1987, J. Exp. Biol. 129, 239–250; Venter et al., 1988, Biochem. Pharmacol. 38, 1197–1208; Nathanson, 1993, Pharmacol. Exp. Ther. 265, 509–515; see also Evans et al., 1993, Neurochem Res. 18, 869–874). However, there can be considerable cross-interaction of mammalian dopaminergic and adrenergic receptor agonists and antagonists with the invertebrate octopamine and related tyramine receptors, resulting in difficulties in assigning the specific signaling role for a given invertebrate biogenic amine receptor.

Accordingly, there exists a need in the art to determine the identity and role of GPCRs in invertebrates, including flies and other insects. Such determinations may lead to the development of powerful and specific pesticides, and further, may enhance understanding of mammalian, including human, physiologic functions of this important superfamily of receptor molecules. This invention provides novel fly GPCRs and methods for their use, as described in detail below.

Knowledge of the expressed and/or genomic sequences of an organism is a great aid to the use of that organism as a research tool in the study of genes and their function. Drosophila melanogaster is a model system that enables powerful genetic manipulations and studies not available in higher organisms, and thus knowledge of its expressed sequences is highly desired. The present invention also provides such nucleotide and protein sequences of D. melanogaster genes.

3. SUMMARY OF THE INVENTION

The present invention relates to full-length and partial nucleotide sequences. of D. melanogaster genes, including full-length fly GPCR genes, amino acid sequences of the encoded proteins, and derivatives (e.g., fragments) and analogs thereof. Nucleic acids capable of hybridizing to or complementary to the foregoing nucleotide sequences are also provided. The invention further relates to a method of identifying genes that are modified by, or that participate in signal transduction with, D. melanogaster GPCR genes. The invention still further relates to derivatives and analogs of D. melanogaster GPCR genes and proteins which are functionally active (e.g., "minigenes"), and to D. melanogaster protein fragments which are capable of displaying one or more known functional activities associated with a full-length (wild-type) GPCR protein. Such functional activities include but are not limited to antigenicity (ability to bind to, or to compete for binding with, an anti-peptide antibody), immunogenicity (ability to generate antibody), and ability to bind to (or to compete for binding with) a GPCR ligand. The invention further relates to a fragment (or a derivative or analog thereof) of a D. melanogaster GPCR protein which comprises one or more domains of the protein, such as a transmembrane domain, a ligand-binding domain, or a cytosolic domain (e.g., the intracellular loop domain between transmembrane domains five and six of the GPCR). Antibodies to D. melanogaster GPCR proteins, and derivatives and analogs thereof, are additionally provided. Methods of production of such proteins, derivatives and analogs, e.g., by recombinant means, are also provided. Methods to identify the biological function of a Drosophila GPCR gene are provided, including various methods for the functional modification (e.g., overexpression, underexpression, mutation, knock-out) of one gene, or of two or more genes simultaneously. Methods to identify a Drosophila gene which modifies the function of, and/or functions in an upstream or downstream pathway from, a D. melanogaster GPCR gene are provided. The invention further provides for use of Drosophila GPCR proteins, derivatives, fragments, or ligands thereof as media additives or pesticides.

This invention provides a method of detecting the effect of expression of a D. melanogaster GPCR gene which encodes a *D. melanogaster* GPCR protein comprising an amino acid sequence as set forth in FIG. 1 (SEQ ID NO:2), FIG. 2 (SEQ ID NO:4), FIG. 3 (SEQ ID NO:6), or FIG. 4 (SEQ ID NO:32,370), on a *D. melanogaster* signaling pathway, the method comprising: (a) mutating or abnormally expressing a wild-type *D. melanogaster* GPCR gene that encodes a protein comprising an amino acid sequence as set forth in FIG. 1 (SEQ ID NO:2), FIG. 2 (SEQ ID NO:4), FIG. 3 (SEQ ID NO:6), or FIG. 4 (SEQ ID NO:32,370), in a fly already having a mutation in a *D. melanogaster* signaling pathway that displays a phenotype-of-interest; and (b) detecting the effect of step (a) on the phenotype-of-interest, so as to detect the effect of expression of the *D. melanogaster* GPCR gene.

This invention provides a cell culture medium or medium supplement comprising: (a) a sterile liquid carrier; and (b) a protein encoded by a first nucleic acid which hybridizes under conditions selected from the group consisting of high stringency, moderate stringency and low stringency to a second nucleic acid, which second nucleic acid comprises a nucleotide sequence selected from the group consisting of SEQ ID NO:1, SEQ ID NO:3, SEQ ID NO:5 and SEQ ID NO:741. In another embodiment, the nucleotide sequence is selected from the group consisting SEQ ID NO:15,289 through SEQ ID NO:31,635.

The invention provides a purified *Drosophila melanogaster* G-protein coupled receptor ("GPCR") comprising or defined by the amino acid sequence set forth in SEQ ID NO:2, 4, 6 or 32,370, as well as purified derivatives thereof which are able to display one or more functional activities of a *Drosophila melanogaster* GPCR protein. In particular embodiments, the derivative is able to be bound by an antibody directed against a *Drosophila melanogaster* GPCR protein, or is a fragment.

The invention also provides a purified fragment of a *Drosophila melanogaster* GPCR, which fragment comprises a domain of the GPCR protein selected from the group consisting of the extracellular domain, the intracellular domain, a membrane spanning domain, and the ligand-binding domain. In a particular embodiment, the fragment comprises at least one membrane spanning domain.

The invention also provides a mature *Drosophila melanogaster* GPCR protein defined by an amino acid sequence of SEQ ID NO:2, 4, 6 or 32,370 from which the secretory signal peptide sequence has been removed.

The invention further provides a purified protein comprising at least 25 contiguous amino acids of the sequence set forth in any one of SEQ ID NO:2, 4, 6 or 32,370. In a specific embodiment, such protein is fused to a second protein that is not a GPCR protein. The invention further relates to a chimeric protein comprising a fragment of a *Drosophila melanogaster* GPCR protein consisting of at least 25 contiguous amino acids of the an amino acid sequence set forth in SEQ ID NO:2, 4, 6 or 32,370 fused to a second protein, in which the second protein is not the GPCR protein.

Also provided by the invention is an antibody which is capable of binding a *Drosophila melanogaster* GPCR protein and which does not bind a GPCR protein of another species.

The invention also provides an isolated nucleic acid comprising a nucleotide sequence selected from the group consisting of SEQ ID NO:1, 3, 5 or 741 or a coding region thereof. In a specific embodiment the nucleic acid is DNA. The invention further provides an isolated RNA comprising the sequence of SEQ ID NO:1, 3, 5 or 741 wherein T (thymidine) residues are substituted by U (uracil) residues. Nucleic acids comprising a nucleotide sequence complementary to the nucleotide sequence of the foregoing nucleic acids are also provided.

The invention further provides an isolated nucleic acid comprising at least 50 contiguous nucleotides of SEQ ID NO:1, 3, 5 or 741.

Recombinant vectors comprising the above-described nucleic acids are also provided, as are recombinant host cells containing such a vector or a recombinant form of the nucleic acid.

The invention also provides a method for producing a *Drosophila melanogaster* GPCR protein comprising growing a recombinant cell containing the above-described vectors such that the GPCR protein encoded by said nucleic acid is expressed by the cell, and recovering the expressed GPCR protein. Also provided is the product of such method, said product being purified.

The invention further relates to a pharmaceutical composition comprising a therapeutically effective amount of a molecule comprising a fragment of a GPCR protein, said fragment (i) lacking an intracellular domain and a transmembrane domain, and (ii) exhibiting a functional activity of said GPCR protein; and a pharmaceutically acceptable carrier.

Another pharmaceutical composition provided by the invention comprises a therapeutically effective amount of an antibody that binds to the extracellular domain of a GPCR protein; and a pharmaceutically acceptable carrier. Alternatively, or additionally, the pharmaceutical composition comprises a therapeutically effective amount of a molecule comprising a nucleic acid encoding a fragment of a GPCR protein and a pharmaceutically acceptable carrier, said fragment (i) lacking an intracellular domain and a transmembrane domain, and (ii) exhibiting a functional activity of said GPCR protein.

The invention provides a purified *Drosophila melanogaster* protein which is encoded by a first nucleic acid that is hybridizable under high, moderate or low stringency conditions to a second nucleic acid, said second nucleic acid defined by the nucleotide sequence as set forth in SEQ ID NO:1, 3, 5 or 741.

The invention provides an isolated nucleic acid comprising a nucleotide sequence which encodes an amino acid sequence set forth in SEQ ID NO:2, 4, 6 or 32,370.

The invention provides a non-human transgenic animal which contains a recombinant nucleotide sequence that is inserted into or replaces at least a portion of the genomic sequence corresponding to the nucleotide sequence set forth in SEQ ID NO:1, 3, 5 or 741.

The invention provides a method for identifying a molecule that binds to a protein, said protein comprising an amino acid sequence depicted in SEQ ID NO:2, 4, 6 or 32,370, comprising contacting one or more candidate molecules with said protein under conditions conducive to binding to said protein; and detecting any binding that occurs of said candidate molecules to said protein.

The invention provides a method for screening for a molecule that modulates directly or indirectly the formation of a complex of a protein comprising an amino acid sequence depicted in SEQ ID NO:2, 4, 6 or 32,370 and its respective ligand comprising measuring the level of said complex formed under conditions conducive to formation of the complex, and comparing the levels of said complex with the levels of said complex that are formed in the absence of said molecule, wherein a higher or lower level of said complex in the presence of said molecule indicates that the molecule modulates formation of said complex.

The invention provides a method for screening for a molecule that modulates directly or indirectly the activity of a protein comprising an amino acid sequence depicted in SEQ ID NO:4 comprising measuring the potassium conductance of a cell expressing said protein in the presence of a candidate molecule, and comparing the levels of potassium conductance with the levels of potassium conductance in the absence of said molecule, wherein a higher or lower level of potassium conductance in the presence of said molecule indicates that the molecule modulates the potassium conductance of a cell expressing said protein.

The invention further provides a purified *Drosophila melanogaster* chitin synthase comprising or defined by the amino acid sequence set forth in SEQ ID NO:42,135, as well as a purified derivative of the chitin synthase, which is able to display one or more functional activities of a *Drosophila melanogaster* chitin synthase. In a specific embodiment, the derivative is able to be bound by an antibody directed against a *Drosophila melanogaster* chitin synthase. In another specific embodiment, the derivative is a fragment. The invention also provides a purified fragment of a *Drosophila melanogaster* chitin synthase protein, which fragment comprises a domain of the protein selected from the group consisting of the extracellular domain, the intracellular domain, a membrane spanning domain, and the catalytic domain. In a specific embodiment, the fragment comprises at least one membrane spanning domain.

The invention also provides a mature *Drosophila melanogaster* chitin synthase protein defined by the amino acid sequence set forth in SEQ ID NO:42,135 from which the secretory signal peptide sequence has been removed. Also provided is a purified protein comprising at least 25 contiguous amino acids of the amino acid sequence set forth in SEQ ID NO:42,135; in a specific embodiment, such protein is fused to a second protein that is not a chitin synthase protein. The invention further relates to a chimeric protein comprising a fragment of a *Drosophila melanogaster* chitin synthase protein consisting of at least 25 contiguous amino acids of the amino acid sequence set forth in SEQ ID NO:42,135 fused to a second protein, in which the second protein is not the GPCR protein.

The invention further provides an antibody which is capable of binding a chitin synthase protein as described above, and which does not bind another *Drosophila melanogaster* chitin synthase protein.

Also provided is an isolated nucleic acid comprising the nucleotide sequence set forth in SEQ ID NO:10,540 or a coding region thereof. In a specific embodiment, the nucleic is DNA. The invention also relates to an isolated RNA comprising the sequence of SEQ ID NO:10,540 wherein T (thymidine) residues are substituted by U (uracil) residues. The invention further provides an isolated nucleic acid comprising a nucleotide sequence complementary to the nucleotide sequence of one of the above-described nucleic acids. The invention also provides an isolated nucleic acid comprising at least 50 contiguous nucleotides of SEQ ID NO:10,540. A recombinant vector comprising an above-described nucleic acid, and a recombinant host cell containing the vector, are also provided. The invention further relates to a recombinant host cell containing an above-described nucleic acid, said nucleic acid being recombinant. The invention provides a method for producing a *Drosophila melanogaster* chitin synthase protein comprising growing a recombinant cell containing the above-described vector such that the chitin synthase protein encoded by said nucleic acid is expressed by the cell, and recovering the expressed chitin synthase protein; the purified product of such method is also provided. The invention further provides a pharmaceutical composition comprising a therapeutically effective amount of a molecule comprising a fragment of the above-described chitin synthase protein, said fragment comprising the catalytic domain of the chitin synthase protein; and a pharmaceutically acceptable carrier. Also provided is a pharmaceutical composition comprising a therapeutically effective amount of an antibody that binds to the catalytic domain of the above-described chitin synthase protein; and a pharmaceutically acceptable carrier. The invention further provides a pharmaceutical composition comprising a therapeutically effective amount of a molecule comprising a nucleic acid encoding a fragment of the above-described chitin synthase protein and a pharmaceutically acceptable carrier, said fragment comprising the catalytic domain of the chitin synthase protein.

The invention provides a purified *Drosophila melanogaster* protein which is encoded by a first nucleic acid that is hybridizable under high, moderate or low stringency conditions to a second nucleic acid, said second nucleic acid defined by the nucleotide sequence set forth in SEQ ID NO:10,540.

The invention also provides an isolated nucleic acid comprising a nucleotide sequence which encodes the amino acid sequence set forth in SEQ ID NO:42,135.

The invention also provides a non-human transgenic animal which contains a recombinant nucleotide sequence that is inserted into or replaces at least a portion of the genomic sequence corresponding to the nucleotide sequence set forth in SEQ ID NO:10,540.

The invention also provides a method for identifying a molecule that binds to a protein, said protein comprising the amino acid sequence set forth in SEQ ID NO:42,135, comprising contacting one or more candidate molecules with said protein under conditions conducive to binding to said protein; and detecting any binding that occurs of said candidate molecules to said protein.

The invention also provides a method for screening for a molecule that modulates directly or indirectly the activity of a protein comprising the amino acid sequence depicted in SEQ ID NO:42,135 comprising measuring the chitin synthase activity of a cell expressing said protein in the presence of a candidate molecule, and comparing the levels of chitin synthase activity with the levels of chitin synthase activity in the absence of said molecule, wherein a higher or lower level of chitin synthase activity in the presence of said molecule indicates that the molecule modulates the chitin synthase activity of a cell expressing said protein.

The invention also provides a method for protecting a plant or animal against a pest comprising contacting the plant or animal with a pesticide formulation comprising (3-aminopropyl)methylphosphinic acid, and a carrier.

The invention also provides a purified protein comprising an amino acid sequence of any one amino acid sequence of SEQ ID NOS:31,636 to 46,852.

The invention also provides a purified protein comprising an amino acid sequence of any one amino acid sequence of SEQ ID NOS:46,853 to 62,485.

Also provided is a purified protein comprising an amino acid sequence of at least n contiguous amino acids of any one amino acid sequence of SEQ ID NOS:31,636 to 62,485, wherein for each respective SEQ ID NO, n is the number of amino acids listed in the column entitled "100% identity length" in Table 2. In particular embodiments, such purified protein comprises an amino acid sequence of least n+10 contiguous amino acids of any one amino acid sequence of SEQ ID NOS:31,636 to 62,485, wherein for each respective SEQ ID NO, n is the number of amino acids listed in the column entitled "100% identity length" in Table 2; or comprises an amino acid sequence of least n+50 contiguous amino acids of any one amino acid sequence of SEQ ID NOS:31,636 to 62,485, wherein for each respective SEQ ID NO, n is the number of amino acids listed in the column entitled "100% identity length" in Table 2.

The invention also provides a purified protein comprising an amino acid sequence having a BLAST score value of at least b when compared to any one amino acid sequence of SEQ ID NOS:31,636 to 62,485, wherein for each respective SEQ ID NO, b has a value greater than the BLAST score value listed in the column entitled "BLAST score" in Table 2 for each respective SEQ ID NO, and wherein the BLAST score is determined using the same algorithm as used to calculate the BLAST score value of Table 2. In specific embodiments, for each respective SEQ ID NO, b has a value 3% greater than the BLAST score value listed in the column entitled "BLAST score" in Table 2 for each respective SEQ ID NO; or for each respective SEQ ID NO, b has a value 10% greater than the BLAST score value listed in the column entitled "BLAST score" in Table 2 for each respective SEQ ID NO.

The invention provides a purified derivative of one of the above-described proteins, which derivative is able to display one or more functional activities of said protein. In a specific embodiment, such derivative is able to be bound by an antibody directed against said protein.

The invention provides a purified fragment of a protein, said protein defined by an amino acid sequence of any one of SEQ ID NOS:31,636 to 62,485, said fragment comprising one or more domains of the protein as set forth in the column entitled "PFam motifs" or the column entitled "Prosite motifs" for each respective SEQ ID NO in Table 2.

The invention provides a purified fragment of a protein, said fragment defined by an amino acid sequence of at least n contiguous amino acids of any one amino acid sequence of SEQ ID NOS:31,636 to 62,485, wherein for each respective SEQ ID NO, n is the number of amino acids listed in the column entitled "100% identity length" in Table 2. In specific embodiments, the above-described protein or fragment comprises a protein domain as set forth in the corresponding column entitled "PFam motifs" or the column entitled "Prosite motifs" for each respective SEQ ID NO in Table 2.

The invention provides a purified fragment of a protein, said fragment defined by an amino acid sequence of at least n+50 contiguous amino acids of any one amino acid sequence of SEQ ID NOS:31,636 to 62,485, wherein for each respective SEQ ID NO, n is the number of amino acids listed in the column entitled "100% identity length" in Table 2. In specific embodiments, such fragment comprises a protein domain as set forth in the corresponding column entitled "PFam motifs" or the column entitled "Prosite motifs" for each respective SEQ ID NO in Table 2.

The invention provides a purified fragment of a protein, said protein defined by an amino acid sequence having a BLAST score value of at least b when compared to any one amino acid sequence of SEQ ID NOS:31,636 to 62,485, wherein for each respective SEQ ID NO, b has a value greater than the BLAST score value listed in the column entitled "BLAST score" in Table 2 for each respective SEQ ID NO, said fragment comprising a domain of the protein as set forth in the column entitled "PFam motifs" or the column entitled "Prosite motifs" for each respective SEQ ID NO in Table 2, and wherein the BLAST score is determined using the same algorithm as used to calculate the BLAST score value of Table 2. In a specific embodiment, for each respective SEQ ID NO, b has a value 10% greater than the BLAST score value listed in the column entitled "BLAST score" in Table 2 for each respective SEQ ID NO.

The invention provides an isolated nucleic acid comprising a nucleotide sequence of any one nucleotide sequence of SEQ ID NOS:7 to 15,288 or a coding region thereof.

The invention provides an isolated nucleic acid comprising a nucleotide sequence of any one nucleotide sequence of SEQ ID NOS:15,289 to 31,635 or a coding region thereof.

The invention provides an isolated nucleic acid comprising a nucleotide sequence complementary to any one nucleotide sequence of SEQ ID NOS:7 to 31,635.

The invention provides an isolated RNA molecule comprising a coding region of any one of SEQ ID NOS:7 to 31,635, wherein T (thymidine) residues are replaced with U (uracil) residues.

The invention provides an isolated nucleic acid comprising a nucleotide sequence of at least n contiguous nucleotides of any one nucleotide sequence of SEQ ID NOS:7 to 31,635, or a nucleotide sequence reverse complementary thereto, wherein for each respective SEQ ID NO, n is the number of nucleotides listed in the column entitled "100% identity length" in Table 1. In specific embodiments, such nucleic acid comprises a nucleotide sequence comprising at least n+25 contiguous nucleotides of any one nucleotide sequence of SEQ ID NOS:7 to 31,635, or a nucleotide sequence reverse complementary thereto, wherein for each respective SEQ ID NO, n is the number of nucleotides listed in the column entitled "100% identity length" in Table 1; or comprises a nucleotide sequence comprising at least n+50 contiguous nucleotides of any one nucleotide sequence of SEQ ID NOS:7 to 31,635, or a nucleotide sequence reverse complementary thereto, wherein for each respective SEQ ID NO, n is the number of nucleotides listed in the column entitled "100% identity length" in Table 1.

The invention provides an isolated first nucleic acid capable of hybridizing to a second nucleic acid consisting of any one nucleotide sequence of SEQ ID NOS:7 to 31,635, or a nucleotide sequence reverse complementary thereto, under hybridization condition x, wherein for each respective SEQ ID NO, x is the hybridization condition listed in the corresponding column entitled "hybriz. conditions" in Table 1. In a specific embodiment, the first nucleic acid encodes a protein (i) comprising a protein domain of the deduced protein sequence for the respective SEQ ID NO, as set forth in Table 1; or (ii) capable of being bound by an antibody to a protein defined by the deduced protein sequence for the respective SEQ ID NO, as set forth in Table 1.

The invention provides an isolated nucleic acid comprising a nucleotide sequence having at least z % sequence identity with any contiguous 125 bases of any one nucleotide sequence of SEQ ID NOS:7 to 31,635, or a nucleotide sequence reverse complementary thereto, wherein for each respective SEQ ID NO, z has a value greater than the value listed in the column entitled "125 bp % identity" in Table 1, and wherein the % sequence identity is determined using the same algorithm as used to calculate the % sequence identity value of Table 1. In specific embodiments, such nucleic acid comprises a nucleotide sequence having at least z % sequence identity with any contiguous 125 bases of any nucleotide sequence of SEQ ID NOS:7 to 31,635, or a nucleotide sequence reverse complementary thereto, wherein for each respective SEQ ID NO, z has a value 3% greater than the value listed in the column entitled "125 bp % identity" in Table 1, and wherein the % sequence identity is determined using the same algorithm as used to calculate the % sequence identity value of Table 1; or comprises a nucleotide sequence having at least z % sequence identity with any contiguous 125 bases of any nucleotide sequence of SEQ ID NOS:7 to 31,635, or a nucleotide sequence reverse complementary thereto, wherein for each respective SEQ ID NO, z has a value 10% greater than the value listed in the column entitled "125 bp % identity" in Table 1, and wherein the % sequence identity is determined using the same algorithm as used to calculate the % sequence identity value of Table 1.

The invention provides an isolated nucleic acid comprising a nucleotide sequence having at least w % sequence identity with any contiguous 275 bases of any nucleotide sequence of SEQ ID NOS:7 to 31,635, or a nucleotide sequence complementary thereto, wherein for each respective SEQ ID NO, w has a value greater than the value listed in the column entitled "275 bp % identity" in Table 1, and wherein the % sequence identity is determined using the same algorithm as used to calculate the % sequence identity value of Table 1. In specific embodiments, such nucleic acid comprises a nucleotide sequence having at least w % sequence identity with any contiguous 275 bases of any nucleotide sequence of SEQ ID NOS:7 to 31,635, or a nucleotide sequence complementary thereto, wherein for each respective SEQ ID NO, w has a value 3% greater than the value listed in the column entitled "275 bp % identity" in Table 1, and wherein the % sequence identity is determined using the same algorithm as used to calculate the % sequence identity value of Table 1; or comprises a nucleotide sequence having at least w % sequence identity with any contiguous 275 bases of any nucleotide sequence of SEQ ID NOS:7 to 31,635, or a nucleotide sequence complementary thereto, wherein for each respective SEQ ID NO, w has a value 10% greater than the value listed in the column entitled "275 bp % identity" in Table 1, and wherein the % sequence identity is determined using the same algorithm as used to calculate the % sequence identity value of Table 1.

The invention provides an isolated nucleic acid comprising a nucleotide sequence having a BLAST score value of at least b when compared to any one nucleotide sequence of SEQ ID NOS:7 to 31,635, or a nucleotide sequence reverse complementary thereto, wherein for each respective SEQ ID NO, b has a value greater than the BLAST score value listed in the column entitled "BLAST score" in Table 1 for each respective SEQ ID NO, and wherein the BLAST score is determined using the same algorithm as used to calculate the BLAST score value of Table 1. In specific embodiments, for each respective SEQ ID NO, b has a value 3% greater than the BLAST score value listed in the column entitled "BLAST score" in Table 1 for each respective SEQ ID NO; or b has a value 10% greater than the BLAST score value listed in the column entitled "BLAST score" in Table 1 for each respective SEQ ID NO.

In specific embodiments, the above-described nucleic acids are DNA.

Isolated nucleic acids comprising a nucleotide sequence encoding an above-described protein are also provided.

The invention provides an isolated nucleic acid comprising a nucleotide sequence which is at least 65% similar over an at least 20 contiguous nucleotides to any one of the nucleotide sequences of SEQ ID NOS:7–31,635. The invention also provides an isolated nucleic acid comprising a nucleotide sequence which is at least 95% similar over an at least 20 contiguous nucleotides to any one of the nucleotide sequences of SEQ ID NOS:7–31,635. In specific embodiments, such nucleic acid encodes a protein comprising a domain of the protein encoded by any one of SEQ ID NOS:7–31,635 as set forth in the column entitled "PFAM motifs" or the column entitled "Prosite motifs" for each respective SEQ ID NO in Table 2.

Recombinant vectors comprising the above-described nucleic acids, and recombinant host cell containing such vectors or containing the nucleic acid in recombinant form are also provided. The invention also provides a method for producing a protein comprising growing a recombinant cell containing such a vector such that the protein encoded by said nucleic acid is expressed by the cell, and recovering the expressed protein. The purified product of such method is also provided.

The invention provides an antibody which is capable of binding an amino acid sequence of any one of SEQ ID NOS:46,853 to 62,485.

The invention provides a transgenic non-human animal which contains a recombinant nucleotide sequence that is inserted into or replaces at least a portion of the genomic sequence corresponding to the nucleotide sequence set forth in any one of SEQ ID NOS:7 to 31,635.

The invention provides a computer readable medium having recorded thereon the amino acid sequence of any one of SEQ ID NOS:31,636 to 62,485 or a nucleotide sequence of any one of SEQ ID NOS:7 to 31,635.

The invention provides a computer readable medium having recorded thereon amino acid sequences comprising SEQ ID NOS:31,636 to 46,852, respectively, or nucleotide sequences comprising SEQ ID NOS:7–15,288, respectively.

The invention provides a method for identifying a molecule that binds to a protein, said protein comprising an amino acid sequence of any one of SEQ ID NOS:31,636 to 62,485, comprising contacting one or more candidate molecules with said protein under conditions conducive to binding to said protein; and detecting any binding that occurs of said candidate molecules to said protein.

4. BRIEF DESCRIPTION OF THE DRAWINGS

FIGS. 1A–1H shows the nucleotide sequence (SEQ ID NO:1) of a cDNA and the derived amino acid sequence (SEQ ID NO:2) of a G-protein coupled receptor (GPCR), herein referred to as "GPCR-3". Locations of possible N-glycosylation sites of GPCR-3 and approximate starting locations of the transmembrane domains are indicated.

FIGS. 2A–2S shows the nucleotide sequence (SEQ ID NO:3) of a cDNA and the derived amino acid sequence (SEQ ID NO:4) of a GPCR which is a related to the gamma aminobutyric acid type B (GABA$_B$) family of receptors, and is herein referred to as "GPCR-2" or "GABA$_B$R-1" or just "GABA$_B$". The approximate location of a cleavable signal peptide (indicated by underlining) and the starting location of the transmembrane domains are indicated.

FIGS. 3A–3L shows the nucleotide sequence (SEQ ID NO:5) of a cDNA and the derived amino acid sequence (SEQ ID NO:6) of a GPCR which is a receptor for melatonin and is herein referred to as "GPCR-1" or "DOPAD2". The approximate starting locations of the transmembrane domains are indicated.

FIGS. 4A–4E shows the nucleotide sequence (SEQ ID NO:741) of a cDNA and the derived amino acid sequence (SEQ ID NO:32,370) of a G-protein coupled receptor (GPCR), herein referred to as "GPCR-4". Locations of possible N-glycosylation sites of GPCR-4 and approximate starting locations of the transmembrane domains are indicated.

5. DETAILED DESCRIPTION OF THE INVENTION

As described herein, the inventors developed a strategy to search for novel genes in the genome of the fruit fly *Drosophila melanogaster* by making and using an EST database. Further, certain aspects of Drosophila gene function can now be determined as described herein. The results have revealed, inter alia, a number of novel Drosophila G protein coupled receptors (GPCRs). The Drosophila GPCR proteins exhibit significant sequence diversity. These new GPCR genes in Drosophila provide useful tools for probing the function and regulation of their corresponding biological pathways. Systematic genetic analysis of signaling pathways involving GPCR proteins in Drosophila can be expected to lead to the discovery of new drug targets, therapeutic proteins, diagnostics and prognostics useful in the treatment of diseases and other clinical problems associated with the function of GPCRs in humans and other animals. Furthermore, analysis of these same pathways using Drosophila proteins as tools has utility for identification and validation of pesticide targets that are components of signaling pathways in invertebrate pests.

Use of Drosophila GPCR and other fly genes of the invention as disclosed herein has advantages over manipulation of known components of fly signaling pathways. First, use of GPCR-encoding Drosophila genes provides a superior approach for identifying factors that are upstream of the receptor in the signal transduction pathway. Specifically, the specific ligands that bind to the novel GPCRs of the invention can now be readily identified. Further, the discovery of multiple, different GPCRs provides a rational approach to separate components involved in responses to different, specific environmental or regulatory signals. This is less technically feasible with manipulation of downstream components of the pathway found in target tissues. Still further, the diversity of different GPCRs provides a means to identify potential new hormones and/or signal transduction systems that are structurally different from those that have been characterized to date, in either vertebrates or invertebrates. Yet still further, use of Drosophila as a system for analyzing the function and regulation of GPCR genes has great advantages over approaches in other organisms due to the ability to rapidly carry out large-scale, systematic genetic screens, as well as the ability to screen small molecules directly on whole organisms for possible therapeutic or pesticide use. Particularly, the fruit fly Drosophila is clearly the preferred genetic model organism for dissecting the function of novel proteins, and for validating potential pesticide targets, with respect to other insect pest species.

The present invention thus relates to proteins encoded by and nucleotide sequences of *D. melanogaster* genes including GPCR genes. The invention further relates to fragments and other derivatives and analogs of such proteins. Nucleic acids encoding such fragments or derivatives are also within the scope of the invention. Production of the foregoing proteins, e.g., by recombinant methods, is provided. The invention also relates to protein derivatives and analogs which are functionally active, i.e., which are capable of displaying one or more known functional activities associated with a full-length (wild-type) fly protein. Such functional activities may include but are not limited to antigenicity (ability to bind, or to compete for binding, to an anti-peptide antibody), immunogenicity (ability to generate antibody), and ability to bind (or compete for binding) to a ligand for a fly GPCR.

The invention further relates to fragments (and derivatives and analogs thereof) of a fly GPCR protein which comprise one or more domains of the fly protein.

Antibodies to a fly GPCR protein, its derivatives and analogs, are additionally provided.

Methods for genetic analysis of pathways involving GPCRs in Drosophila are provided. Such methods may yield results of importance to human disease. For example, systematic identification of participants in intracellular signaling by fly GPCRs may provide leads to the identification of drug targets, therapeutic proteins, diagnostics, or prognostics useful for treatment or management of resistance in disease.

In a specific aspect, the present invention further relates to expressed sequence tag (EST) library analysis for the identification of novel genes, especially invertebrate genes such as fly genes, and their encoded proteins. For example, the EST library analysis of the invention has revealed several full-length invertebrate G-protein coupled receptor (GPCR) proteins and the nucleotide sequences encoding them (see FIGS. 1–4). More specifically, the present invention relates to the complete cDNA and genomic sequences for invertebrate y-aminobutyric acid subtype B ($GABA_B$) receptors, a melatonin receptor, and orphan receptors with similarity to dopaminergic/adrenergic receptors. The complete cDNA sequences were isolated and determined following identification in the *Drosophila melanogaster* EST library of the invention, which was produced as the initial part of a discovery strategy for genes encoding novel proteins.

Identification and analysis of other GPCR EST sequences in the database of the invention indicated the presence of 13 additional novel invertebrate receptor homologues. Moreover, the determination of the existence of invertebrate $GABA_B$ receptors has enabled the discovery that a compound may have selective effects on insects. The compound, SKF97541, is of unremarkable importance in vertebrate $GABA_B$ receptor pharmacology (see Knight et al., 1996, The pharmacology of adenylyl cyclase modulation by $GABA_B$ receptors in rat brain slices, Neuropharmacology 35, 703–712; see for review Bowery, 1993, $GABA_B$ receptor pharmacology, Ann. Rev. Pharmacol. Toxicol. 33, 109–147). However, when the invertebrate $GABA_B$ receptors of the invention were discovered, the compound was selected for testing for effects on flies and, remarkably, was found to be toxic in vivo. The results set forth herein thus identify a candidate insecticide. Perhaps more importantly, the results demonstrate the feasibility of progression from analysis of the EST database of the invention to identification of novel full-length genes and gene families, further to prediction of gene function, and finally to validation of such prediction with positive experimental results. This powerful approach has tremendous practical benefits, not only for pesticide discovery and development, but also for the many other applications described herein. For example, in addition to pesticides targeted to the specific $GABA_B$, adrenergic, and melatonin receptors disclosed herein, the present invention further relates to protein expression and drug screening methods for the development of human drugs of therapeutic value.

The invention further provides a large number of novel Drosophila EST sequences, contigs comprising the EST sequences, deduced protein sequences of the contigs and the novel EST sequences, and derivatives thereof and antibodies thereto, and further methods of use of the foregoing, as described below. Many of the detailed embodiments disclosed herein are discussed with respect to GPCRs, but are also intended to apply to the sequences of Table 1 and Table 2 hereof, and their corresponding genes and proteins.

The invention is illustrated by way of examples set forth in Section 6 below which disclose, inter alia, the cloning and characterization of several novel *D. melanogaster* GPCR genes, and numerous other Drosophila nucleotide and protein sequences.

For clarity of disclosure, and not by way of limitation, the detailed description of the invention is divided into the subsections which follow.

5.1. Isolation of Drosophila Genes

The invention relates to nucleotide sequences of *D. melanogaster* nucleic acids. In specific embodiments, such nucleic acids comprise a cDNA sequence of a fly GPCR as set forth in SEQ ID NO:1, SEQ ID NO:3, SEQ ID NO:5 or SEQ ID NO:741, or nucleic acids encoding a fly GPCR protein (e.g., a protein having the sequence of SEQ ID NO:2, SEQ ID NO:4, SEQ ID NO:6 or SEQ ID NO:32,370). As used herein, a gene "corresponding" to a cDNA sequence shall be construed to mean the gene that encodes the RNA from which the cDNA is derived. The invention provides purified or isolated nucleic acids consisting of at least 8 nucleotides (i.e., a hybridizable portion) of an gene sequence; in other embodiments, such nucleic acids consist of at least 25 (continuous) nucleotides, 50 nucleotides, 100 nucleotides, 150 nucleotides, or 200 nucleotides of a sequence, or a full-length coding sequence. In another embodiment, the nucleic acids are smaller than 35, 200, 500, or 5,000 nucleotides in length. Nucleic acids can be single or double stranded. The invention also relates to nucleic acids hybridizable to or complementary to the foregoing sequences or their reverse complements. In specific aspects, nucleic acids are provided which comprise a sequence complementary to at least 10, 25, 50, 100, or 200 nucleotides or the entire coding region of a gene.

The invention further relates to certain genomic nucleotide sequences of *D. melanogaster*, GPCR nucleic acids. In specific embodiments, such nucleic acids comprise the genomic GPCR sequences or the coding regions thereof, or nucleic acids encoding a GPCR protein (e.g., a protein having the sequence of SEQ ID NO:2, SEQ ID NO:4, SEQ ID NO:6 or SEQ ID NO:32,370).

In the above or alternative embodiments, the nucleic acids of the invention consist of a nucleotide sequence of not more than 2, 5, 10, 15, or 20 kilobases.

5.1.1. Hybridization Conditions

In a specific embodiment, a nucleic acid which is hybridizable to a fly GPCR nucleic acid (e.g., having a sequence as set forth in SEQ ID NO:1, SEQ ID NO:3, SEQ ID NO:5, or SEQ ID NO:741 or to its reverse complement, or to a nucleic acid encoding a GPCR derivative, or to its reverse complement), under conditions of low stringency is provided. By way of example and not limitation, procedures using such conditions of low stringency are as follows (see also Shilo and Weinberg, 1981, Proc. Natl. Acad. Sci. U.S.A. 78, 6789–6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film. Other conditions of low stringency which may be used are well known in the art (e.g., as employed for cross-species hybridizations).

In another specific embodiment, a nucleic acid which is hybridizable to a fly GPCR nucleic acid, or its reverse complement, under conditions of high stringency is provided. By way of example and not limitation, procedures using such conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In another specific embodiment, a nucleic acid which is hybridizable to a fly GPCR nucleic acid, or its reverse complement, under conditions of moderate stringency is provided. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, © 1987–1997, Current Protocols, © 1994–1997 John Wiley and Sons, Inc.; see especially, Dyson, 1991, "Immobilization of nucleic acids and hybridization analysis," In: Essential Molecular Biology: A Practical Approach, Vol. 2, T. A. Brown, ed., pp. 111–156, IRL Press at Oxford University Press, Oxford, UK).

Nucleic acids encoding derivatives and analogs of fly GPCR proteins, and fly GPCR antisense nucleic acids are additionally provided. As is readily apparent, as used herein, a "nucleic acid encoding a fragment or portion of a GPCR protein" shall be construed as referring to a nucleic acid encoding only the recited fragment or portion of the protein and not the other contiguous portions of the protein as a continuous sequence.

Fragments of fly GPCR nucleic acids comprising regions conserved between (i.e., with similarity to) other GPCR nucleic acids, of the same or different species, are also provided. Nucleic acids encoding one or more GPCR domains are also provided.

In one embodiment, after hybridization, stringency conditions for washing are as follows. Each membrane is washed two times each for 30 minutes each at 45° C. in 40 mM sodium phosphate, pH 7.2, 5% SDS, 1 mM EDTA, 0.5% bovine serum albumin, followed by four washes each for 30 minutes in sodium phosphate, pH 7.2, 1 % SDS, 1 mM EDTA, and subsequently each membrane is treated differently as described below for low, medium, or high stringency hybridization conditions. For low stringency hybridization, membranes are not washed further. For medium stringency hybridization, membranes are additionally subjected to four washes each for 30 minutes in 40 mM sodium phosphate, pH 7.2, 1% SDS, 1 mM EDTA at 55° C. For high stringency hybridization, following the washes for low stringency, membranes are additionally subjected to four washes each for 30 minutes in 40 mM sodium phosphate, pH 7.2, 1% SDS, 1 mM EDTA at 55° C., followed by four washes each for 30 minutes in sodium phosphate, pH 7.2, 1% SDS, 1 mM EDTA at 65° C.

In another specific embodiment of the invention, a nucleic acid is provided which is hybridizable to a Drosophila nucleic acid having a sequence as set forth in any one of SEQ ID NOs:15,289–31,635, or to a reverse complement thereof, under conditions of low, medium or high stringency. Hybridization protocols of differing stringencies are well known in the art. The temperature and salt concentrations at which hybridizations are performed have a direct effect on the results that are obtained. To achieve "stringent" or "high stringency" conditions, a denaturing agent such as formamide is typically used during hybridization. Formamide is typically used at 25% to 50% (v/v) in a buffered diluent comprising 1× to 6×SSC (1×SSC is 150 mM NaCl and 15 mM sodium citrate; SSPE may be substituted for SSC, where 1×SSPE is 150 mM NaCl, 10 mM $NaH_2PO_4$, and 1.25 mM EDTA, pH7.4). The hybridization temperature is typically about 42° C. High stringency conditions also employ a wash buffer with low ionic strength, such as from about 0.1× to about 0.5×SSC, at relatively high temperature, typically greater than about 55° C. up to about 70° C. Moderately stringent conditions typically use 0% to 25% formamide in 1× to 6×SSC, and use reduced hybridization temperatures, usually in the range of about 27° C. to about 40° C. The wash buffer can have increased ionic strength, e.g. from about 0.6× to about 2×SSC, and is used at reduced temperatures, usually from about 45° C. to about 55° C. To achieve "non-stringent" or "low stringency" hybridization conditions, the hybridization buffer is the same as that used for moderately stringent or high stringency, but does not contain a denaturing agent. A reduced hybridization temperature is used, typically in the range of from about 25° C. to about 30° C. The wash buffer has increased ionic strength, usually from about 2× to about 6×SSC, and the wash temperature is in the range of from about 35° C. to about 47° C.

As mentioned above, the procedures for nucleic acid hybridizations are well-known in the art (see e.g., Ausubel et al., 1995, Current Protocols In Molecular Biology, Wiley Interscience Publishers; Sambrook et al., 1989, Molecular Cloning: A Laboratory Manual, Cold Spring Harbor Laboratory Press, New York; Shilo and Weinberg, 1981, *Proc. Natl. Acad. Sci. U.S.A.* 78, 6789–6792; and PCT Publication No. WO 99/01466, each of which is incorporated by reference herein in its entirety). In a specific embodiment of the invention, nucleic acids are provided that are capable of hybridizing to a nucleic acid consisting of a coding sequence encoding a polypeptide of any one of SEQ ID NOs:46,853 to 62,485, or the reverse complement thereof, under the hybridization conditions listed in Table 1 (column 7) for each of SEQ ID NOs:46,853 to 62,485. The "Hybridization Condition #" (column 1 of Table C) for conditions 1 through 10 as listed individually for each novel sequence in column 7 of Table 1, are explained in Table C. Hybridization buffers A through R and wash buffers A through L used for each hybridization condition # from 1 through 10 are listed in column 2 and column 4, respectively, of Table C. The SSC and formamide compositions of hybridization buffers A through R and wash buffers A through L are defined in Table A and Table B, respectively. Thus, for example, if hybridization condition #7 is listed as the preferred hybridization condition for a given SEQ ID NO in Table 1, then the conditions used for finding homologous nucleic acids preferably employ any of hybridization buffers A through M at a hybridization temperature of about 40° C., and any of wash buffers A through E at a wash temperature of approximately 55° C. Hybridization conditions 8 through 10, as listed in Table C and Table 1, are generally considered "high stringency" conditions; hybridization conditions 4 through 7 are generally considered "moderately stringent", and hybridization conditions 1 through 3 are considered "low- or non-stringent". Hybridization condition #1 is designed to isolate nucleic acids having at least about 50% sequence identity with the target nucleic acid (with % identity defined as described above). With each subsequent condition, the stringency is such that the isolated nucleic acid has a sequence identity of at least 5% greater than what would be isolated by using the next lower hybridization condition number. Thus, for example, hybridization condition #2 is designed to isolate nucleic acids having at least about 55% sequence identity with the target nucleic acid, and hybridization conditions #9 and #10 are designed to isolate nucleic acids having at least about 90% and 95% sequence identity, respectively, to the target nucleic acid.

In some situations, where it is desired to isolate more closely homologous nucleic acids, the preferred hybridization condition for isolating a nucleic acid similar to the sequence of a given SEQ ID NO, or its reverse complement, will be at least 1 hybridization condition # greater than the hybridization condition listed in column 7 of Table 1 (applicable for SEQ ID NOs having a hybridization condition that is less than 9 as listed in Table 1). Similarly, if isolation of nucleic acids having even higher sequence similarity is desired, then the preferred hybridization condition will be at least 2 greater than that listed in Table 1 (applicable for SEQ ID NOs having a hybridization condition that is less than 8 as listed in Table 1). Accordingly, the preferred hybridization condition is chosen to be increasingly greater where an increasingly greater level of sequence similarity is desired.

Preferably, each hybridizing nucleic acid has a length that is at least 30% of the length of the novel nucleic acid sequences described herein (i.e. any one of SEQ ID NOs:15, 289–31,635, or a reverse complement thereof) to which it hybridizes. More preferably, a hybridizing nucleic acid has a length that is at least 50%, still more preferably at least 70%, and most preferably at least 90% of the length of the nucleic acid sequence described herein to which it hybridizes.

In using Table C below, a practitioner of the invention will note that, where a letter is recited for a Hybridization Buffer or a Wash Buffer, it is also permissible to use any Hybridization Buffer or a Wash Buffer having a letter which appears earlier in the alphabet. For example, where Hybridization Buffer R is recited for use in Hybridization Condition #1 in Table C, the user will note that Hybridization Buffers A through Q may also be used. Where Hybridization Buffer G is recited for use in Hybridization Condition #10 in Table C, the user will note that Hybridization Buffers A through F may also be used. Likewise, where Wash Buffer L is recited for use in Hybridization Condition #1 in Table C, the user will note that Wash Buffers A through K may also be used. Where Wash Buffer B is recited for use in Hybridization Condition #10 in Table C, the user will note that Wash Buffers A through B may also be used.

TABLE A

| Hybridization Buffer | X SSC | % Formamide |
|---|---|---|
| A | 1 | 50 |
| B | 2 | 50 |
| C | 3 | 50 |
| D | 4 | 50 |
| E | 5 | 50 |
| F | 6 | 50 |
| G | 1 | 25 |
| H | 2 | 25 |
| I | 3 | 25 |
| J | 4 | 25 |
| K | 5 | 25 |
| L | 6 | 25 |
| M | 1 | 0 |
| N | 2 | 0 |
| O | 3 | 0 |
| P | 4 | 0 |
| Q | 5 | 0 |
| R | 6 | 0 |

TABLE B

| Wash Buffer | X SSC |
|---|---|
| A | 0.2 |
| B | 0.3 |
| C | 0.4 |
| D | 0.5 |
| E | 0.6 |
| F | 0.8 |
| G | 1 |
| H | 2 |
| I | 3 |
| J | 4 |
| K | 5 |
| L | 6 |

TABLE C

| Hybridization Condition # | Hybridization Buffer | Hybridization Temperature | Wash Buffer | Wash Temperature |
|---|---|---|---|---|
| 1 | R | 25° C. | L | 35° C. |
| 2 | R | 25° C. | L | 40° C. |
| 3 | R | 27° C. | L | 47° C. |
| 4 | R | 34° C. | H | 45° C. |
| 5 | R | 40° C. | F | 45° C. |
| 6 | O | 40° C. | E | 50° C. |
| 7 | M | 40° C. | E | 55° C. |
| 8 | L | 42° C. | D | 60° C. |
| 9 | H | 42° C. | C | 65° C. |
| 10 | G | 42° C. | B | 70° C. |

5.1.2. Cloning Procedures

Specific embodiments for the cloning of a fly gene (e.g. a fly GPCR gene) follow. For expression cloning (a technique well known in the art), an expression library is constructed by any method known in the art. For example, mRNA is isolated, and cDNA is made and ligated into an expression vector (e.g., a bacteriophage derivative) such that it is capable of being expressed by the host cell into which it is then introduced. Various screening assays can then be used to select for the expressed GPCR product. In one embodiment, anti-GPCR antibodies can be used for selection.

In another embodiment, polymerase chain reaction (PCR) is used to amplify the desired sequence in a genomic or cDNA library, prior to selection. Oligonucleotide primers representing known sequences can be used as primers in PCR. In a preferred aspect, the oligonucleotide primers represent at least part of conserved segments of strong similarity between GPCR genes of different species. The synthetic oligonucleotides may be utilized as primers to amplify sequences from a source (RNA or DNA), preferably a cDNA library, of potential interest. PCR can be carried out, e.g., by use of a Perkin-Elmer Cetus thermal cycler and Taq polymerase (e.g., Gene Amp™). The nucleic acid being amplified can include mRNA or cDNA or genomic DNA from any species. One may synthesize degenerate primers for amplifying homologs from other species in such PCR reactions.

It is also possible to vary the stringency of hybridization conditions used in priming the PCR reactions to allow for greater or lesser degrees of nucleotide sequence similarity between the known nucleotide sequences and a nucleic acid homolog (or ortholog) being isolated. For cross-species hybridization reactions, low stringency conditions are preferred. For same-species hybridization, moderately stringent conditions are preferred. After successful amplification of a segment of a GPCR homolog, that segment may be cloned and sequenced by standard techniques and utilized as a probe to isolate a complete cDNA or genomic clone. This, in turn, permits the determination of the gene's complete nucleotide sequence, the analysis of its expression, and the production of its protein product for functional analysis, as described below. In this fashion, additional genes encoding proteins and analogs may be identified.

In another embodiment, the organizational characteristics of fly genes may be used to identify clones containing novel members of a fly gene superfamily (e.g. a fly GPCR superfamily). For example, insulin-like genes in the silkworm insect *B. Mori* encode the bombyxin proteins and have been demonstrated to be organized in large multi-gene clusters (Kondo et al., 1996, J. Mol. Biol. 259:926–937). Identification and characterization of a genomic region surrounding a known GPCR gene could, therefore, be used to identify additional genes that encode GPCR proteins or analogs which are located within these clusters, using methods generally known in the art such as those described above.

The above-described methods are not meant to limit the following general description of methods by which clones of genes may be obtained.

Any eukaryotic cell potentially can serve as the nucleic acid source for molecular cloning of a GPCR gene. The nucleic acid sequences encoding proteins may be isolated from vertebrate, including mammalian, porcine, murine, bovine, feline, avian, equine, canine, and human, as well as additional primate sources; invertebrates, including insects (e.g., Drosophila), nematodes; and plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see e.g., Sambrook et al., 1989, Molecular Cloning, A Laboratory Manual, 2d Ed., Vol. I, II, Cold Spring Harbor Laboratory Press, Cold Spring Harbor, N.Y.; Glover, ed., 1985, DNA Cloning: A Practical Approach, MRL Press, Ltd., Oxford, U.K.). Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNase in the presence of manganese to fragment the DNA, or the DNA can be physically sheared (e.g., by sonication). The linear DNA fragments can then be separated according to size by standard techniques, including but not limited to agarose and polyacrylamide gel electrophoresis and column chromatography.

Once the DNA fragments are generated, identification of the specific DNA fragment containing the desired gene may be accomplished in a number of ways. For example, if a portion of a GPCR gene or its specific RNA or a fragment thereof is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial similarity to the probe will hybridize. It is also possible to identify the appropriate fragment by restriction enzyme digestion(s) and comparison of fragment sizes with those expected according to a known restriction map if such is available. Further selection can be carried out on the basis of the properties of the gene.

Alternatively, the presence of the desired gene may be detected by assays based on the physical, chemical, or immunological properties of its expressed product. For example, cDNA clones, or DNA clones which hybrid-select the proper mRNAs, can be selected and expressed to produce a protein that has, e.g., similar or identical electrophoretic migration, isoelectric focusing behavior, proteolytic digestion maps, hormonal activity, binding activity, or antigenic properties as known for an protein. Using an antibody to a known GPCR protein, other GPCR proteins may be identified by binding of the labeled antibody to expressed putative proteins, e.g., in an ELISA (enzyme-linked immunosorbent assay)-type procedure. Further, using a binding protein specific to a known GPCR protein, other GPCR proteins may be identified by binding to such a protein (see e.g., Clemmons, 1993, Mol. Reprod. Dev. 35:368–374; Loddick et al., 1998, Proc. Natl. Acad. Sci. U.S.A. 95:1894–1898).

A GPCR gene can also be identified by mRNA selection using nucleic acid hybridization followed by in vitro translation. In this procedure, fragments are used to isolate complementary mRNAs by hybridization. Such DNA fragments may represent available, purified GPCR DNA of another species (e.g., C. elegans, mouse, human). Immunoprecipitation analysis or functional assays (e.g., aggregation ability in vitro, binding to receptor, etc.) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against protein. A radiolabeled GPCR cDNA can be synthesized using the selected mRNA (from the adsorbed polysomes) as a template. The radiolabeled mRNA or cDNA may then be used as a probe to identify the GPCR DNA fragments from among other genomic DNA fragments.

Alternatives to isolating the GPCR genomic DNA include, but are not limited to, chemically synthesizing the gene sequence itself from a known sequence or making cDNA to the mRNA which encodes the GPCR protein. For example, RNA for cDNA cloning of the GPCR gene can be isolated from cells which express the gene.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Stratagene USA, La Jolla, Calif.). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and an gene may be modified by homopolymeric tailing. Recombinant molecules can be introduced into host cells via transformation, transfection, infection, electroporation, etc., so that many copies of the gene sequence are generated.

In an alternative method, the desired gene (e.g. a GPCR gene) may be identified and isolated after insertion into a suitable cloning vector in a "shot gun" approach. Enrichment for the desired gene, for example, by size fractionization, can be done before insertion into the cloning vector.

In an additional embodiment, the desired gene (e.g. a GPCR gene) may be identified and isolated after insertion into a suitable cloning vector using a strategy that combines a "shot gun" approach with a "directed sequencing" approach. Here, the entire DNA sequence of a specific region of the genome, such as a sequence tagged site (STS), can be obtained using clones that molecularly map in and around the region of interest.

In specific embodiments, transformation of host cells with recombinant DNA molecules that incorporate an isolated GPCR gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The GPCR sequences provided by the instant invention include those nucleotide sequences encoding substantially the same amino acid sequences as found in native proteins, and those encoded amino acid sequences with functionally equivalent amino acids, as well as those encoding other GPCR derivatives or analogs, as described below for GPCR derivatives and analogs.

5.2. Expression of *D. melanogaster* Genes

The nucleotide sequence coding for a fly protein (e.g., a GPCR protein) or a functionally-active analog or fragment or other derivative thereof (see Section 5.6), can be inserted into an appropriate expression vector, i.e., a vector which contains the necessary elements for the transcription and translation of the inserted protein-coding sequence. The necessary transcriptional and translational signals can also be supplied by the native gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In yet another embodiment, a fragment of an protein comprising one or more domains of the protein is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of a nucleic acid sequence encoding an protein or peptide fragment may be regulated by a second nucleic acid sequence so that the protein or peptide is expressed in a host transformed with the recombinant DNA molecule. For example, expression of an protein may be controlled by any promoter/ enhancer element known in the art. A promoter/enhancer may be homologous (i.e. native) or heterologous (i.e. not native). Promoters which may be used to control gene expression include, but are not limited to, the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), prokaryotic expression vectors such as the P-lactamase promoter (Villa-Kamaroff et al., 1978, Proc. Natl. Acad. Sci. U.S.A. 75:3727–3731), or the lac promoter (DeBoer et al., 1983, Proc. Natl. Acad. Sci. U.S.A. 80:21–25; Scientific American, 1980, 242:74–94), plant expression vectors comprising the nopaline synthetase promoter region (Herrera-Estrella et al., Nature 303:209–213), the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120), promoter elements from yeast or other fungi such as the Gal4-responsive promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); a gene control region which is active in pancreatic beta cells (Hanahan, 1985, Nature 315:115–122), an immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus. (Mason et al., 1986, Science 234:1372–1378).

In a specific embodiment, a vector is used that comprises a promoter operably linked to an gene nucleic acid, one or more origins of replication, and, optionally, one or more selectable markers (e.g., an antibiotic resistance gene).

In a specific embodiment, an expression construct is made by subcloning an coding sequence into the EcoRI restriction site of each of the three pGEX vectors (Glutathione S-Transferase expression vectors; Smith and Johnson, 1988, Gene 7:31–40). This allows for the expression of the protein product from the subclone in the correct reading frame.

In another specific embodiment, the promoter that is operably linked to the Drosophila GPCR gene is not the native Drosophila GPCR gene promoter (i.e., it is a heterologous promoter).

Expression vectors containing fly gene inserts can be identified by at least three general approaches: (a) nucleic acid hybridization; (b) presence or absence of "marker" gene functions; and (c) expression of inserted sequences. In the first approach, the presence of a fly gene inserted in an expression vector can be detected by nucleic acid hybridization using probes comprising sequences that are homologous to an inserted fly gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a fly gene in the vector. For example, if a fly GPCR gene is inserted within the marker gene sequence of the vector, recombinants containing the GPCR insert can be identified by the absence of the marker gene function. In the third approach, recombinant expression vectors can be identified by assaying the product expressed by the recombinant. Such assays can be based, for example, on the physical or functional properties of the fly protein in in vitro assay systems, e.g., binding with anti-GPCR protein antibody.

Once a particular recombinant DNA molecule is identified and isolated, several methods known in the art may be used to propagate it. Once a suitable host system and growth conditions are established, recombinant expression vectors can be propagated and prepared in quantity. As previously mentioned, expression vectors which can be used include any such vectors known in the art. Specific examples include but are not limited to the following or their derivatives: human or animal viruses such as vaccinia virus or adenovirus; insect viruses such as baculovirus; yeast vectors; bacteriophage vectors (e.g., lambda phage); and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered protein may be controlled. Furthermore, different host cells have characteristic and specific mechanisms for the translational and posttranslational processing and modification (e.g., glycosylation, phosphorylation of proteins). Appropriate cell lines or host systems can be chosen to ensure the desired modification and processing of the foreign protein expressed. For example, expression in a bacterial system can be used to produce a non-glycosylated core protein product. Expression in yeast will produce a glycosylated product. Expression in animal cells can be used to ensure "native" glycosylation of a heterologous protein. Furthermore, different vector/host expression systems may affect processing reactions to different extents.

In other specific embodiments, the fly protein (e.g., a fly GPCR protein), fragment, analog, or derivative may be expressed as a fusion, or chimeric protein product (comprising the protein, fragment, analog, or derivative joined via a peptide bond to a heterologous protein sequence, e.g., derived from a different protein). A chimeric protein may include fusion of the fly protein, fragment, analog, or derivative to a second protein or at least a portion thereof, wherein a portion is one (but preferably 3, 5, 10, 15, or 20) or more amino acids of said second protein. The second protein, or one or more amino acid portion thereof, may be from a different fly protein or may be from a protein that is not a fly protein. Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

5.3. Identification and Purification of Gene Products

In particular aspects, the invention provides amino acid sequences of fly proteins (e.g., a fly GPCR protein) and fragments and derivatives thereof which comprise an antigenic determinant (i.e., which can be recognized by an antibody) or which are otherwise functionally active, as well as nucleic acid sequences encoding the foregoing. "Functionally active" GPCR material as used herein refers to that material displaying one or more functional activities associated with a full-length (wild-type) protein, e.g., binding to a GPCR ligand (e.g., a hormone), antigenicity (e.g., binding to an anti-GPCR antibody), immunogenicity, etc.

In specific embodiments, the invention provides fragments of a fly protein (e.g., a fly GPCR protein) consisting of at least 10 amino acids, 20 amino acids, 50 amino acids, or of at least 75 amino acids. In other embodiments, the proteins comprise or consist essentially of a GPCR domain, such as a ligand-binding domain, one or more of the seven transmembrane spanning domains, or a cytosolic domain (e.g., the intracellular loop domain between transmembrane domains five and six of the GPCR), or any combination of the foregoing. Fragments, or proteins comprising fragments, lacking some or all of the foregoing regions of a protein are also provided. Nucleic acids encoding the foregoing are provided. In specific embodiments, the foregoing proteins or fragments are not more than 25, 50 or 100 contiguous amino acids.

Once a recombinant which expresses the gene sequence is identified, the gene product can be analyzed. This is achieved by assays based on the physical or functional properties of the product, including radioactive labeling of the product followed by analysis by gel electrophoresis, immunoassay, etc.

Once a fly protein (e.g., a fly GPCR) is identified, it may be isolated and purified by standard methods including chromatography (e.g., ion exchange, affinity, or sizing column chromatography), centrifugation, differential solubility, or by any other standard technique for the purification of proteins. The functional properties may be evaluated using any suitable assay (see Section 5.7).

Alternatively, once a fly protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller et al., 1984, Nature 310:105–111).

In another alternate embodiment, native proteins can be purified from natural sources, by standard methods such as those described above (e.g., immunoaffinity purification).

In a specific embodiment of the present invention, such proteins (whether produced by recombinant DNA techniques or by chemical synthetic methods or by purification of native proteins) include but are not limited to those containing, as a primary amino acid sequence, all or part of the amino acid sequence substantially as depicted in FIG. 1 through FIG. 4 (SEQ ID NO:2, SEQ ID NO:4, SEQ ID NO:6, or SEQ ID NO:741, respectively), as well as fragments and other derivatives, and analogs thereof, including proteins homologous thereto.

5.4. Structure of Drosophila Genes and Proteins

The structure of genes and proteins of the invention, including naturally occuring proteins, can be analyzed by various methods known in the art. Some examples of such methods are described below.

5.4.1. Genetic Analysis

The cloned DNA or cDNA corresponding to a fly gene (e.g., a fly GPCR gene) can be analyzed by methods including but not limited to Southern hybridization (Southern, 1975, J. Mol. Biol. 98:503–517), Northern hybridization (see e.g., Freeman et al., 1983, Proc. Natl. Acad. Sci. U.S.A. 80:4094–4098), restriction endonuclease mapping (Maniatis, 1982, Molecular Cloning, A Laboratory Manual, Cold Spring Harbor Laboratory Press, Cold Spring Harbor, N.Y.), and DNA sequence analysis. Accordingly, this invention provides nucleic acid probes recognizing a fly gene. For example, polymerase chain reaction (PCR; U.S. Pat. Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220) followed by Southern hybridization with a fly gene-specific probe can allow the detection of an gene in DNA from various cell types. Methods of amplification other than PCR are commonly known and can also be employed. In one embodiment, Southern hybridization can be used to determine the genetic linkage of a fly gene. Northern hybridization analysis can be used to determine the expression of a fly gene. Various cell types, at various states of development or activity can be tested for fly gene expression. The stringency of the hybridization conditions for both Southern and Northern hybridization can be manipulated to ensure detection of nucleic acids with the desired degree of relatedness to the specific fly gene probe used. Modifications of these methods and other methods commonly known in the art can be used.

Restriction endonuclease mapping can be used to roughly determine the genetic structure of a fly gene. Restriction maps derived by restriction endonuclease cleavage can be confirmed by DNA sequence analysis.

DNA sequence analysis can be performed by any techniques known in the art, including but not limited to the method of Maxam and Gilbert (1 980, Meth. Enzymol. 65:499–560), the Sanger dideoxy chain termination method (Sanger et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.).

5.4.2. Protein Analysis

The amino acid sequence of a fly protein (e.g. a fly GPCR) can be derived by deduction from the DNA sequence, or alternatively, by direct sequencing of the protein, e.g., with an automated amino acid sequencer.

A fly protein sequence can be further characterized by a hydrophilicity analysis (Hopp and Woods, 1981, Proc. Natl. Acad. Sci. U.S.A. 78:3824). A hydrophilicity profile can be used to identify the hydrophobic and hydrophilic regions of the fly protein and the corresponding regions of the gene sequence which encode such regions.

Structural prediction analysis (Chou and Fasman, 1974, Biochemistry 13:222) can also be performed to identify regions of a fly protein that form specific secondary structures.

Manipulation, translation, and secondary structure prediction, open reading frame prediction and plotting, as well as determination of sequence homologies, can also be accomplished using computer software programs available in the art.

Other methods of structural analysis can also be employed. These include but are not limited to X-ray crystallography (Engstom, 1974, Biochem. Exp. Biol. 11:7–13), nuclear magnetic resonance spectroscopy (Clore and Gonenborn, 1989, CRC Crit. Rev. Biochem. 24:479–564) and computer modeling (Fletterick and Zoller, 1986, Computer Graphics and Molecular Modeling, in *Current Communications in Molecular Biology*, Cold Spring Harbor Laboratory Press, Cold Spring Harbor, N.Y.).

5.5. Antibodies

According to the invention, a fly protein, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In another embodiment, antibodies to a domain (e.g., a GPCR ligand-binding, transmembrane, or cytosolic domain) of a fly protein are produced. In a specific embodiment, fragments of a fly protein identified as hydrophilic are used as immunogens for antibody production.

Various procedures known in the art may be used for the production of polyclonal antibodies to a fly protein or derivative or analog. In a particular embodiment, rabbit polyclonal antibodies to an epitope of a fly GPCR protein having the sequence of SEQ ID NO:2, SEQ ID NO:4, SEQ ID NO:6, or SEQ ID NO:32,370 (see also FIGS. 1–4), or a subsequence thereof, can be obtained. For the production of antibody, various host animals can be immunized by injection with the native protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For preparation of monoclonal antibodies directed to an protein sequence or analog thereof, any technique which provides for the production of antibody molecules by continuous cell lines in culture may be used. For example, the hybridoma technique originally developed by Kohler and Milstein, (Kohler and Milstein 1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (see e.g., PCT/US90/02545). According to the invention, human antibodies may be used and can be obtained by using human hybridomas (Cole et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for an protein together with genes from a human antibody molecule of appropriate biological activity can be used; such antibodies are within the scope of this invention. In another embodiment, "humanized" antibodies are provided in this invention (see U.S. Pat. No. 5,225,539).

According to the invention, techniques described for the production of single chain antibodies (U.S. Pat. No. 4,946,778) can be adapted to produce fly protein-specific single chain antibodies. An additional embodiment of the invention utilizes the techniques described for the construction of Fab' expression libraries (Huse et al., 1989, Science 246:1275–1281) to allow rapid and easy identification of monoclonal Fab fragments with the desired specificity for proteins, derivatives, or analogs.

Antibody fragments which contain the idiotype of the molecule can be generated by known techniques. For example, such fragments include but are not limited to, the $F(ab')_2$ fragment which can be produced by pepsin digestion of the antibody molecule, the Fab' fragments which can be generated by reducing the disulfide bridges of the $F(ab')_2$ fragment, the Fab fragments which can be generated by treating the antibody molecule with papain and a reducing agent, and Fv fragments.

In the production of antibodies, screening for the desired antibody can be accomplished by techniques known in the art (e.g., enzyme-linked immunosorbent assay or ELISA). For example, to select antibodies which recognize a specific domain of a protein, one may assay generated hybridomas for a product which binds to a fragment containing such domain. For selection of an antibody that specifically binds a first homolog but which does not specifically bind a different homolog, one can select on the basis of positive binding to the first homolog and a lack of binding to the second homolog.

Antibodies specific to a domain of an protein are also provided. Antibodies specific to an epitope of an protein are also provided.

The foregoing antibodies can be used in methods known in the art relating to the localization and activity of the protein sequences of the invention, e.g., for imaging these proteins, measuring levels thereof in appropriate physiological samples, in diagnostic methods, etc.

5.6. Proteins, Derivatives and Analogs

The invention further relates to fly proteins, derivatives (including but not limited to fragments), analogs, and molecules of fly proteins. As used herein, a molecule defined by a particular SEQ ID NO shall be construed to mean that the sequence of that molecule consists of that SEQ ID NO. A chimeric fly protein having one or more domains from one or more other fly or non-fly proteins is within the scope of the invention. Chimeric proteins are well known in the art (see e.g. Kobilka, 1992, Annu. Rev. Neurosci. 15, 87–114; Insel, 1993, Exp. Gerontol. 28, 341–348; Hein et al.,1995, Neuropharmacology. 34, 357–366 for discussion of and citations to chimeric GPCRs). Nucleic acids encoding fly protein derivatives and protein analogs are also provided. In one embodiment, the fly proteins are encoded by the nucleic acids described in Section 5.1 above. In particular aspects, the proteins, derivatives, or analogs are of fly GPCR proteins encoded by the nucleotide sequence of SEQ ID NO:1, SEQ ID NO:3, SEQ ID NO:5, or SEQ ID NO:741. In another embodiment, this invention provides one or more fragments (or derivatives or analogs thereof) of a fly chitin synthase 2 protein greater than or equal to 55 contiguous amino acids of SEQ ID NO:42,135.

Transmembrane domain proteins typically contain a hydrophobic domain near the 5' end of the expressed protein called a secretory signal peptide. This peptide is necessary for insertion of the protein into a membrane of the cell in which the protein is expressed. As the protein is inserted into a membrane, the secretory signal peptide is removed from the protein by enzymatic action of a signal peptidase resulting in the mature form of the protein. Thus, in one embodiment, the present invention is directed to a mature form of a protein comprising an amino acid sequence of SEQ ID NO:2, 4, 6, 32,370 or 42,135 from which the secretory signal peptide has been removed.

The production and use of derivatives and analogs related to a fly protein are within the scope of the present invention. In a specific embodiment, the derivative or analog is functionally active, i.e., capable of exhibiting one or more functional activities associated with a full-length, wild-type fly protein. As one example, such derivatives or analogs which have the desired immunogenicity or antigenicity can be used in immunoassays, for immunization, for inhibition of GPCR ligand activity, etc. As another example, such derivatives or analogs which have the desired binding activity can be used for binding to a GPCR gene product. As yet another example, such derivatives or analogs which have the desired binding activity can be used for binding to a binding protein specific for a known GPCR protein (see e.g., Clemmons, 1993, Mol. Reprod. Dev. 35:368–374; Loddick et al., 1998, Proc. Natl. Acad. Sci. U.S.A 95:1894–1898). Derivatives or analogs that retain, or alternatively lack or inhibit, a desired protein property-of-interest (e.g., binding to a fly protein binding partner), can be used as inducers, or inhibitors, respectively, of such property and its physiological correlates. A specific embodiment relates to a fly GPCR fragment that can be bound by an anti-GPCR antibody. Derivatives or analogs of a fly protein (e.g., a GPCR) can be tested for the desired activity by procedures known in the art, including but not limited to the assays described below.

In particular, GPCR derivatives can be made by altering GPCR sequences by substitutions, additions (e.g., insertions) or deletions that provide for functionally equivalent molecules. Due to the degeneracy of nucleotide coding sequences, other DNA sequences which encode substantially the same amino acid sequence as a GPCR gene may be used in the practice of the present invention. These include but are not limited to nucleotide sequences comprising all or portions of a GPCR gene which is altered by the substitution of different codons that encode a functionally equivalent amino acid residue within the sequence, thus producing a silent change. Likewise, the fly protein derivatives of the invention, including GPCR derivatives, include but are not limited to those containing, as a primary amino acid sequence, all or part of the amino acid sequence of a fly protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In a specific embodiment of the invention, proteins consisting of or comprising a fragment of a fly protein consisting of at least 10 (continuous) amino acids of the protein is provided. In other embodiments, the fragment consists of at least 20 or at least 50 amino acids of the fly protein. In specific embodiments, such fragments are not larger than 35, 100 or 200 amino acids. Derivatives or analogs of proteins include but are not limited to those molecules comprising regions that are substantially homologous to an protein or fragment thereof (e.g., in various embodiments, at least 60% or 70% or 80% or 90% or 95% identity over an amino acid sequence of identical size without any insertions or deletions or when compared to an aligned sequence in which the alignment is done by a computer similarity program known in the art) or whose encoding nucleic acid is capable of hybridizing to a coding gene sequence, under high stringency, moderate stringency, or low stringency conditions.

Specifically, by way of example computer programs for determining similarity may include but are not limited to TBLASTN, BLASTP, FASTA, TFASTA, and CLUSTALW (Pearson and Lipman, 1988, Proc. Natl. Acad. Sci. U.S.A. 85:2444–2448; Altschul et al., 1990, J. Mol. Biol. 215:403–410; Thompson et al., 1994, Nucleic Acids Res. 22:4673–4680; and Higgins et al., 1996, Methods Enzymol. 266:383–402).

Specifically, Basic Local Alignment Search Tool (BLAST) (www.ncbi.nlm.nih.gov) (Altschul et al., 1990, J. Mol. Biol. 215:403–410, "The BLAST Algorithm"; Altschul et al., 1997, Nucl. Acids Res. 25:3389–3402) is a heuristic search algorithm tailored to searching for sequence similarity which ascribes significance using the statistical methods of Karlin and Altschul (1990, Proc. Nat'l Acad. Sci. U.S.A., 87:2264–2268; 1993, Proc. Nat'l Acad. Sci. U.S.A. 90:5873–5877). Five specific BLAST programs are used to perform the following tasks: (1) the WU-BLASTP program compares an amino acid query sequence against a protein sequence database; (2) the WU-BLASTN program compares a nucleotide query sequence against a nucleotide sequence database; (3) the BLASTX program compares the six-frame conceptual translation products of a nucleotide query sequence (both strands) against a protein sequence database; (4) the TBLASTN program compares a protein query sequence against a nucleotide sequence database translated in all six reading frames (both strands); and (5) the TBLASTX program compares the six-frame translations of a nucleotide query sequence against the six-frame translations of a nucleotide sequence database.

Smith-Waterman (database: European Bioinformatics Institute wwwz.ebi.ac.uk/bic_sw/) (Smith-Waterman, 1981, J. Mol. Biol. 147:195–197) is a mathematically rigorous algorithm for sequence alignments.

FASTA (see Pearson et al., 1988, Proc. Nat'l Acad. Sci. U.S.A., 85:2444–2448) is a heuristic approximation to the Smith-Waterman algorithm. For a general discussion of the procedure and benefits of the BLAST, Smith-Waterman and FASTA algorithms see Nicholas et al., 1998, "A Tutorial on Searching Sequence Databases and Sequence Scoring Methods" (www.psc.edu) and references cited therein.

The derivatives and analogs of the invention can be produced by various methods known in the art. The manipulations which result in their production can occur at the gene or protein level. For example, a cloned gene sequence can be modified by any of numerous strategies known in the art (Sambrook et al., 1989, *Molecular Cloning, A Laboratory Manual*, 2d ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro. In the production of a modified gene encoding a derivative or analog of an protein, care should be taken to ensure that the modified gene remains within the same translational reading frame as the native protein, uninterrupted by translational stop signals, in the gene region where the desired protein activity is encoded.

Additionally, a fly nucleic acid sequence (e.g., a GPCR sequence) can be mutated in vitro or in vivo, to create and/or destroy translation, initiation, and/or termination sequences, or to create variations in coding regions and/or to form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson et al., 1978, J. Biol. Chem. 253:6551), use of TAB® linkers (Pharmacia), PCR with primers containing a mutation, etc.

Manipulations of a fly GPCR polypeptide sequence may also be made at the protein level. Included within the scope of the invention are GPCR protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH$_4$, acetylation, formylation, oxidation, reduction, metabolic synthesis in the presence of tunicamycin, etc. In addition, naturally occuring fly proteins are within the scope of the invention.

In addition, analogs and derivatives of a fly protein can be chemically synthesized. For example, a peptide corresponding to a portion of a GPCR protein which comprises the desired domain, or which mediates the desired activity in vitro, can be synthesized by use of a peptide synthesizer. Furthermore, if desired, non-classical amino acids or chemical amino acid analogs can be introduced as a substitution or addition into the sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alamine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, a GPCR protein derivative is a chimeric or fusion protein comprising a GPCR protein or fragment thereof (preferably consisting of at least a domain or motif of the GPCR protein, or at least 10 amino acids of the protein) joined at its amino- or carboxy-terminus via a peptide bond to an amino acid sequence of a different GPCR protein, fly or non-fly. In specific embodiments, the amino acid sequence of the different GPCR protein is at least 6, 10, 20 or 30 continuous amino acids of the different protein, or a portion of the different protein that is functionally active. In one embodiment, such a chimeric protein is produced by recombinant expression of a nucleic acid encoding the protein (comprising a GPCR-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of a GPCR gene fused to any heterologous protein-encoding sequences may be constructed. A specific embodiment relates to a chimeric protein comprising a fragment of a GPCR protein of at least six amino acids, or a fragment that displays one or more functional activities of the protein.

In another specific embodiment, the GPCR derivative is a molecule comprising a region of similarity with a GPCR protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region without any insertions or deletions or when compared to an aligned sequence of the second region that has been aligned by a computer similarity program known in the art. For example, a molecule can comprise one or more regions homologous to a GPCR transmembrane domain or a portion thereof.

In a specific embodiment, the invention relates to GPCR derivatives and analogs, in particular GPCR fragments and derivatives of such fragments, that comprise, or alternatively consist of, one or more domains of a GPCR protein, including but not limited to a GPCR ligand-binding domain and/or a GPCR transmembrane domain, and/or a cytosolic domain (e.g., the intracellular loop domain between transmembrane domains five and six of the GPCR).

A specific embodiment relates to molecules comprising specific fragments of a GPCR protein that are those fragments in the respective GPCR proteins of the invention most homologous to specific fragments of a human or mouse protein. A fragment comprising a domain of a GPCR homolog can be identified by protein analysis methods well known in the art.

In another specific embodiment, a molecule is provided that comprises one or more domains (or functional portion thereof) of a GPCR protein but that also lacks one or more domains (or functional portion thereof) of a GPCR protein. In particular examples, protein derivatives are provided that contain either a GPCR ligand-binding domain, transmembrane domain, or a cytosolic domain (e.g., the intracellular loop domain between transmembrane domains five and six of the GPCR). By way of another example, such a protein may retain such domains separated by a peptide spacer. Such spacer may be the same as or different from a native GPCR linker peptide. In another embodiment, a molecule is provided that comprises one or more domains (or functional portion(s) thereof) of a GPCR protein, and that has one or more mutant (e.g., due to deletion or point mutation) domains of a GPCR protein (e.g., such that the mutant domain has decreased function).

In other embodiments, derivatives of Drosophila proteins (and their encoding nucleic acids) are provided that display a particular % identity or similarity to the Drosophila protein or are encoded by a nucleic acid that hybridizes to the cDNA encoding the protein, and, optionally, comprises one or more domains of the protein and/or displays the antigenicity of the protein (i.e., can be immunospecifically bound by an antibody to the protein).

5.7. Generation of Mutant Phenotypes

The present invention provides for methods of creating genetically-engineered fruit flies and laboratory-generated mutant fruit flies, as described below.

5.7.1. Generation and Genetic Analysis of Drosophila with Altered GPCR Genes In a specific embodiment, genetically-engineered fruit flies are made that harbor one or more deletions or insertions in a fly GPCR gene or genes. In another embodiment, genetically-engineered fruit flies harbor interfering RNAs derived from such genes. In another embodiment, genetically-engineered fruit flies harbor one or more transgenes for mis-expression of wild-type or mutant forms of such genes. The invention provides for laboratory-generated mutant fruit flies which contain deletions, insertions, rearrangements, or point mutations in a fly gene or genes, such as a fly GPCR gene, or combinations thereof.

The present invention provides a method by which Drosophila strains with laboratory-generated alterations in GPCR genes may be used for the identification of GPCR and/or other genes that participate in particular biochemical and/or genetic pathways. In a specific embodiment, Drosophila strains with laboratory-generated alterations in one or more GPCR genes may be used for the identification of GPCR genes that participate in biochemical and/or genetic pathways that constitute possible pesticide targets, as judged by phenotypes such as non-viability, block of normal development, defective feeding, defective movement, or defective reproduction. That is, development of such a phenotype in a Drosophila containing an alteration in a Drosophila GPCR gene indicates that the gene is a potential pesticide target.

In another embodiment, Drosophila strains with laboratory-generated alterations relate to therapeutic applications associated with the superfamily hormones, such as metabolic control, growth regulation, differentiation, reproduction, and aging.

In another embodiment, Drosophila strains with laboratory-generated alterations relate to large-scale genetic modifier screens aimed at systematic identification of components of genetic and/or biochemical pathways that serve as novel drug targets, diagnostics, prognostics, therapeutic proteins, pesticide targets or protein pesticides.

The invention provides methods for creating and analyzing Drosophila strains having modified expression of genes, as described in the Sections below. In one embodiment, expression modification methods include any method known to one skilled in the art. Specific examples include but are not limited to chemical mutagenesis, transposon mutagenesis, antisense RNA interference, and transgene-mediated mis-expression. In the creation of transgenic animals, it is preferred that heterologous (i.e., non-native) promoters be used to drive transgene expression.

5.7.2. Generation of Loss-of-Function Mutation in GPCR Genes

The present invention provides methods of testing for preexisting mutations in a *D. melanogaster* GPCR gene. In a specific embodiment, the genomic sequence containing the entire cluster can be used to determine whether an existing mutant Drosophila line corresponds to a mutation in one or more of the GPCR genes. Specifically, but not by limitation, mutations in genes that map to the same genetic region as a GPCR gene cluster are of particular interest. For example, a large number of previously identified mutations have been mapped to certain genetic regions of certain clusters (see FlyBase: a Drosophila database, Flybase consortium, Harvard University). To ascertain whether any of such mutations are in a GPCR gene, a genomic fragment containing a Drosophila gene cluster and potential flanking regulatory regions can be subcloned into any appropriate Drosophila transformation vector, such as the Carnegie series of vectors (Rubin and Spradling, 1983, Nucleic Acids Res. 11:6341–6351), the pCaspeR series of vectors (Thummel et al., 1988, Gene 74:445–456), or the pW8 vector (Klemenz et al., 1987, Nucleic Acids Res. 15:3947–3959) and injected into flies along with an appropriate helper plasmid to supply transposase. Resulting transformants are crossed for complementation testing to an existing panel of Drosophila lines containing mutations that have been mapped to the appropriate genomic region as described above (see Greenspan, 1997, in *Fly pushing: The Theory and Practice of Drosophila Genetics*, Cold Spring Harbor Press, Plainview, N.Y., pp. 3–46). If a mutant line is discovered to be rescued by such a genomic fragment, as judged by complementation of the mutant phenotype, progressively smaller subclones or clones containing a single gene can be individually tested until the responsible locus is identified.

5.7.3. Generating Loss-of-Function Mutations by Mutagenesis

Further, the invention herein provides a method for generating loss-of-Function mutations in a *D. melanogaster* GPCR gene. Mutations can be generated by one of many mutagenesis methods known to investigators skilled in the art (Ashburner, 1989, In *Drosophila: A Laboratory Manual*, Cold Spring Harbor Laboratory Press, Cold Spring Harbor, N.Y., pp. 299–418.; "*Fly pushing: The Theory and Practice of Drosophila Genetics*" Cold Spring Harbor Press, Plainview, N.Y.). In a specific embodiment, the mutagens that can be used include but are not restricted to: transposons such as the P or hobo elements; chemical mutagens such as ethylmethane sulfonate (EMS), methylmethane sulfonate (MMS), N-ethyl-N-nitrosourea (ENU), triethylmelamine, diepoxyalkanes, ICR-170, or formaldehyde; and irradiation with X-rays, gamma rays, or ultraviolet radiation.

Mutagenesis by P elements, or marked P elements, is particularly appropriate for isolation of loss-of-Function mutations in Drosophila genes, such as fly GPCR genes, due to the precise molecular mapping of these genes, the small size of these targets, the availability and proximity of preexisting P element insertions for use as a localized transposon source, and the potential to knock out several of these genes by induction of a small deletion of the locus (Hamilton and Zinn, 1994, Methods in Cell Biology 44:81–94; Wolfner and Goldberg, 1994, Methods in Cell Biology 44:33–80; Clark et al., 1994, Proc. Natl. Acad. Sci. U.S.A. 91:719–722; Kaiser, 1990, Bioessays 12:297–301, In *Drosophila melanogaster: Practical Uses in Cell and Molecular Biology*, Goldstein and Fryberg, Eds., Academic Press, Inc., San Diego, Calif.). For the purposes of mutagenesis, modified P elements are typically used which contain one or more of the following elements: sequences encoding a dominant visible marker, usually a wild-type white+ or rosy+ eye color gene, to allow detection of animals containing the P element and to screen for transposition events (Rubin and Spradling, 1982, Science 218:348–353; Klemenz et al., 1987, Nucleic Acids Res. 15:3947–3959), bacterial plasmid sequences including a selectable marker such as ampicillin resistance to facilitate cloning of genomic sequences adjacent to the insertion site (Steller and Pirrotta, 1985, EMBO J. 4:167–171) and lacZ sequences fused to a weak general promoter to detect the presence of enhancers with a developmental expression pattern of interest (Bellen et al., 1989, Genes Dev. 3:1288–1300; Bier et al., 1989, Genes Dev. 3:1273–1287; Wilson et al., 1989, Genes Dev. 3:1301–1313). For examples of marked P elements useful for mutagenesis, see "FlyBase—A Drosophila Database", Nucleic Acids Res. 26:85–88 (see especially http://flybase.bio.indiana.edu).

A preferred method of transposon mutagenesis employs the "local hopping" method (Tower et al., 1993, Genetics 133:347–359). Briefly, an existing mutant Drosophila line containing a P element inserted into chromosomal bands near a gene-of-interest, such as 93E for $GABA_B$, or 87D for GPCR-3 or GPCR-4, is crossed to a Drosophila line expressing transposase in order to mobilize the transposon. Transposition of the P element, which contains a marker gene that typically affects eye color, is determined phenotypically on the basis of eye color change in the resulting progeny. Candidate insertion lines are selected for further analysis on the basis of close linkage of the new insertion to the initial insertion site, which can be determined by standard genetic mapping techniques such as high frequency cosegregation of markers. Each new P insertion line can be tested molecularly for transposition of the P element into the gene cluster by assays based on PCR amplification. For each reaction, one PCR primer is used that is homologous to sequences contained within the P element and a second primer is homologous to one of the individual genes, in either the coding region or flanking regions of the gene. Products of the PCR reactions are detected by agarose gel electrophoresis. The sizes of the resulting DNA fragments are used to map the site of P element insertion.

Alternatively, Southern blotting and restriction mapping using DNA probes derived from genomic DNA or cDNAs of the genes can be used to detect transposition events that rearrange the genomic DNA of the genes. P transposition events that map to the gene cluster can be assessed for phenotypic effects in heterozygous or homozygous mutant Drosophila, as described in detail below.

5.7.4. Generating Localized Deletions in the Gene Cluster

In another embodiment, Drosophila lines carrying P insertions in the gene cluster can be used to generate localized deletions in the gene cluster by previously described methods known in the art (Kaiser, 1990, Bioessays 12:297–301; Harnessing the power of Drosophila genetics, In *Drosophila melanogaster: Practical Uses in Cell and Molecular Biology*, Goldstein and Fryberg, Eds., Academic Press, Inc., San Diego, Calif.; Preston et al., 1996, Genetics 144, 1623–1638). This is particularly useful if no P elements transpositions are found that disrupt a particular gene of interest. In one method, flies containing P elements inserted into the gene cluster are exposed to a further round of transposase to induce excision of the element. Progeny in which the transposon has excised are typically identified by loss of the eye color marker associated with the transposable element. The resulting progeny will include flies with either precise or imprecise excision of the P element, where the imprecise excision events often result in deletion of genomic DNA neighboring the site of P insertion. In another method, male flies containing the P element of interest and heterozygous for genetic markers distal and proximal to the insertion are exposed to transposase. Selection of the appropriate class of recombinant progeny identifies animals with directed deletions or duplications on just one side of the transposon. Progeny from both of these methods can be screened by molecular techniques to identify deletion events that remove flanking genomic sequence. Such methods include, but are not limited to: (a) methods of detecting alterations in the genomic DNA based on PCR amplification with primers flanking the insertion site of the P element; (b) methods based on Southern blotting and restriction mapping using DNA probes derived from the P element, DNA probes derived from flanking genomic sequence in the region of the genes, or DNA probes derived from cDNAs of fly genes such as GPCR genes of the invention. Deletions generated in this manner that remove one or more GPCR loci can be assessed for phenotypic effects in heterozygous and homozygous mutant Drosophila as described below.

5.7.5. Generating Loss-of-Function Phenotypes Using Methods Based on RNA-Mediated Interference with Gene Expression The invention further provides a method for generating loss-of-Function phenotypes using methods based on RNA-mediated interference with gene expression. The function of the Drosophila GPCR genes identified herein may be characterized and/or determined by generating loss-of-Function phenotypes through such RNA-based methods.

In one embodiment, loss-of-Function phenotypes are generated by antisense RNA methods (Schubiger and Edgar, 1994, Methods in Cell Biology 44:697–713). One form of the antisense RNA method involves the injection of embryos with an antisense RNA that is partially homologous to the gene-of-interest (e.g., a fly GPCR gene). Another form of the antisense RNA method involves expression of an antisense RNA partially homologous to the gene-of-interest by operably joining a portion of the gene-of-interest in the antisense orientation to a powerful promoter that can drive the expression of large quantities of antisense RNA, either generally throughout the animal or in specific tissues. Examples of powerful promoters that can be used in this strategy of antisense RNA include heat shock gene promoters or promoters controlled by potent exogenous transcription factors, such as GAL4 and tTA, described in more detail in the following section. Antisense RNA-generated loss-of-Function phenotypes have been reported previously for several Drosophila genes including cactus, pecanex, and Kruppel (LaBonne et al., 1989, Dev. Biol. 136:1–16; Schuh and Jackle, 1989, Genome 31:422–425; Geisler et al., 1992, Cell 71:613–621).

In a second embodiment, loss-of-Function phenotypes are generated by co-suppression methods (Bingham, 1997, Cell 90:385–387; Smyth, 1997, Curr. Biol. 7:793–795; Que and Jorgensen, 1998, Dev. Genet. 22:100–109). Co-suppression is a phenomenon of reduced gene expression produced by expression or injection of a sense strand RNA corresponding to a partial segment of the gene-of-interest. Cosuppression effects have been employed extensively in plants to generate loss-of-Function phenotypes, and there is report of cosuppression in Drosophila where reduced expression of the Adh gene was induced from a white-Adh transgene (Pal-Bhadra et al., 1997, Cell 90:479–490).

In a third embodiment, loss-of-Function phenotypes may be generated by double-stranded RNA interference. This method is based on the interfering properties of double-stranded RNA derived from the coding regions of genes. Termed dsRNAi, this method has proven to be of great utility in genetic studies of the nematode *C. elegans* (see Fire et al., 1998, Nature 391:806–811) and more recently in Drosophila (see Misquitta et al., 1999, Proc. Natl. Acad. Sci. U.S.A. 96, 1451–1456; and Kennerdell et al., 1998, Cell 95, 1017–1026). In a preferred embodiment of this method, complementary sense and antisense RNAs derived from a substantial portion of a gene-of-interest, such as a GPCR gene, are synthesized in vitro. Phagemid DNA templates containing cDNA clones of the gene-of-interest are inserted between opposing promoters for T3 and T7 phage RNA polymerases. Alternatively, one can use PCR products amplified from coding regions of genes, where the primers used for the PCR reactions are modified by the addition of phage T3 and T7 promoters. The resulting sense and antisense RNAs are annealed in an injection buffer, and the double-stranded RNA injected or otherwise introduced into animals. Injected animals and/or their progeny are then inspected for phenotypes-of-interest.

5.7.6. Antisense Regulation of Gene Expression

The invention provides for antisense uses of *D. melanogaster* genes such as fly GPCR genes. In a specific embodiment, a fly GPCR protein function is inhibited by use of GPCR antisense nucleic acids. The present invention provides for use of nucleic acids of at least six nucleotides that are antisense to a gene or cDNA encoding an protein or a portion thereof. A fly GPCR "antisense" nucleic acid as used herein refers to a nucleic acid capable of hybridizing to a sequence-specific (i.e., non-poly $A^+$) portion of a GPCR RNA (preferably mRNA) by virtue of some sequence complementarily. Antisense nucleic acids may also be referred to as inverse (or reverse) complement nucleic acids. The antisense nucleic acid may be complementary to a coding and/or noncoding region of a GPCR mRNA. Such antisense nucleic acids have utility in inhibiting fly GPCR protein function. For example, such antisense nucleic acids may be useful as pesticides to eradicate parasites in plants, or in animals such as dogs, horses, and cattle.

The antisense nucleic acids of the invention can be oligonucleotides that are double-stranded or single-stranded, RNA or DNA, or a modification or derivative thereof, which can be directly administered to a cell, or which can be produced intracellularly by transcription of exogenous introduced sequences. In a preferred embodiment, the antisense nucleic acids of the invention are double-stranded RNA mentioned previously (see Fire et al., 1998, Nature 391:806–811).

The antisense nucleic acids of the invention are preferably oligonucleotides (ranging from 6 to about 50 nucleotides). In specific aspects, an oligonucleotide is at least 10 nucleotides, at least 15 nucleotides, at least 100 nucleotides, or at least 200 nucleotides in length. The oligonucleotide can be DNA or RNA or chimeric mixtures or derivatives or modified versions thereof (e.g., protein nucleic acid, or PNA), or single-stranded or double-stranded. The oligonucleotide can be modified at the base moiety, sugar moiety, or phosphate backbone. The oligonucleotide may include other appending groups such as peptides, or agents facilitating transport across the cell membrane (see e.g., Letsinger et al., 1989, Proc. Natl. Acad. Sci. U.S.A. 86:6553–6556; Lemaitre et al., 1987, Proc. Natl. Acad. Sci. U.S.A. 84:648–652; PCT Publication No. WO 88/09810, published Dec. 15, 1988) or the blood-brain barrier (see e.g., PCT Publication No. WO 89/10134, published Apr. 25, 1988), hybridization-triggered cleavage agents (see e.g., Krol et al., 1988, BioTechniques 6:958–976) or intercalating agents (see e.g., Zon, 1988, Pharm. Res. 5:539–549).

In a preferred aspect of the invention, a fly GPCR antisense oligonucleotide is provided as single-stranded DNA. In another preferred aspect, such an oligonucleotide comprises a sequence antisense to the sequence encoding a ligand-binding domain, a transmembrane domain, or a cytoplasmic domain of a fly GPCR protein (e.g., the intracellular loop domain between transmembrane domains five and six of the GPCR). The oligonucleotide may be modified at any position in its structure with substituents generally known in the art.

An antisense oligonucleotide such as a fly GPCR antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine. In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide may be conjugated to another molecule, e.g., a peptide, a hybridization-triggered cross-linking agent, a transport agent, a hybridization-triggered cleavage agent, etc.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (Stein et al., 1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

In a specific embodiment, a fly GPCR antisense oligonucleotide comprises catalytic RNA, or a ribozyme (see e.g., PCT Publication WO 90/11364, published Oct. 4, 1990; Sarver et al., 1990, Science 247:1222–1225). In another embodiment, the oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, a fly GPCR antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the fly GPCR antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the fly GPCR antisense RNA can be by any promoter known in the art. Such promoters can be inducible or constitutive. Such promoters include but are not limited to: the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a sequence-specific portion of an RNA transcript of an gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded GPCR antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a GPCR RNA it may contain and still form a stable duplex (or triplex, as the case may be). One skilled in the art can ascertain a tolerable degree of mismatch by use of standard procedures to determine, e.g., the melting point of the hybridized complex.

5.7.7. Generating Gain-of-Function Phenotypes by Ectopic Expression of Genes The current invention provides methods for generating gain-of-Function phenotypes by ectopic expression of fly genes such as GPCR genes. Ectopic expression, including mis-expression or overexpression, of wild type or altered Drosophila GPCR genes in transgenic animals is another useful method for the analysis of gene function (Brand et al., 1994, Methods in Cell Biology 44:635–654, Ectopic expression in Drosophila; Hay et al., 1997, Proc. Natl. Acad. Sci. U.S.A. 94:5195–5200). Such transgenic Drosophila may be created that contain gene fusions of the coding regions of genes (from either genomic DNA or cDNA) operably joined to a specific promoter and transcriptional enhancer whose regulation has preferably been well characterized, preferably heterologous promoters/enhancers that do not normally drive the expression of the GPCR genes. Examples of promoters/enhancers that can be used to drive such misexpression of GPCR genes include, but are not limited to, the heat shock promoters/enhancers from the hsp70 and hsp83 genes, useful for temperature induced expression; tissue specific promoters/enhancers such as the sevenless promoter/enhancer (Bowtell et al., 1988, Genes Dev. 2:620–634), the eyeless promoter/enhancer (Bowtell et al., 1991, Proc. Natl. Acad. Sci. U.S.A. 88:6853–6857), and glass-responsive promoters/enhancers (Quiring et al., 1994, Science 265:785–789) useful for expression in the eye; enhancers/promoters derived from the dpp or vetigal genes useful for expression in the wing (Staehling-Hampton et al., 1994, Cell Growth Differ. 5:585–593; Kim et al., 1996, Nature 382:133–138) and binary control systems employing exogenous DNA regulatory elements and exogenous transcriptional activator proteins, useful for testing the misexpression of genes in a wide variety of developmental stage-specific and tissue-specific patterns. Two examples of binary exogenous regulatory systems include the UAS/GAL4 system from yeast (Hay et al., 1997, Proc. Natl. Acad. Sci. U.S.A. 94:5195–5200; Ellis et al., 1993, Development 119:855–865) and the "Tet system" derived from *E. coli*, which are described below. It is readily apparent to those skilled in the art that additional binary systems can be used which are based on other sets of exogenous transcriptional activators and cognate DNA regulatory elements in a manner similar to that for the UAS/GAL4 system and the Tet system.

In a specific embodiment, the UAS/GAL4 system is used. This system is a well-established and powerful method of mis-expression in Drosophila which employs the $UAS_G$ upstream regulatory sequence for control of promoters by the yeast GAL4 transcriptional activator protein (Brand and Perrimon, 1993, Development 118:401–415). In this approach, transgenic Drosophila, termed "target" lines, are generated where the gene-of-interest (e.g., a fly GPCR gene) to be mis-expressed is operably fused to an appropriate promoter controlled by UASG. Other transgenic Drosophila strains, termed "driver" lines, are generated where the GAL4 coding region is operably fused to promoters/enhancers that direct the expression of the GAL4 activator protein in specific tissues, such as the eye, wing, nervous system, gut, or musculature. The gene-of-interest is not expressed in the so-called target lines for lack of a transcriptional activator to "drive" transcription from the promoter joined to the gene-of-interest. However, when the UAS-target line is crossed with a GAL4 driver line, mis-expression of the gene-of-interest is induced in resulting progeny in a specific pattern that is characteristic for that GAL4 line. The technical simplicity of this approach makes it possible to sample the effects of directed mis-expression of the gene-of-interest in a wide variety of tissues by generating one transgenic target line with the gene-of-interest, and crossing that target line with a panel of pre-existing driver lines. A very large number of specific GAL4 driver lines have been generated previously and are available for use with this system.

In a second embodiment, a related method of directed mis-expression in Drosophila uses a system adapted from a tetracycline-regulated operon from *E. coli*, referred to as the "Tet system". In this case, transgenic Drosophila driver lines are generated where the coding region for a tetracycline-controlled transcriptional activator (tTA) is operably fused to promoters/enhancers that direct the expression of tTA in a tissue-specific and/or developmental stage-specific manner. Also, transgenic Drosophila target lines are generated where the coding region for the gene-of-interest to be mis-expressed (e.g., a fly GPCR gene) is operably fused to a promoter that possesses a tTA-responsive regulatory element. Here again, mis-expression of the gene-of-interest can be induced in progeny from a cross of the target line with any driver line of interest; moreover, the use of the Tet system as a binary control mechanism allows for an additional level of tight control in the resulting progeny of this cross. When Drosophila food is supplemented with a sufficient amount of tetracycline, it completely blocks expression of the gene-of-interest in the resulting progeny. Expression of the gene-of-interest can be induced at will simply by removal of tetracycline from the food. Also, the level of expression of the gene-of-interest can be adjusted by varying the level of tetracycline in the food. Thus, the use of the Tet system as a binary control mechanism for mis-expression has the advantage of providing a means to control the amplitude and timing of mis-expression of the gene-of-interest, in addition to spatial control. Consequently, if a gene-of-interest (e.g., a fly GPCR gene) has lethal or deleterious effects when mis-expressed at an early stage in development, such as the embryonic or larval stages, the function of the gene-of-interest in the adult can still be assessed using the Tet system, by adding tetracycline to the food during early stages of development and removing tetracycline later so as to induce mis-expression only at the adult stage.

5.8. Aanalysis of Mutant Phenotypes

After isolation of flies carrying mutated or mis-expressed genes such as GPCR genes, or inhibitory RNAs, animals are carefully examined for phenotypes-of-interest. For the situations involving deletions, insertions, point mutations, or mis-expression of GPCR genes, fruit flies are generated that are homozygous and heterozygous for the altered genes.

Examples of specific phenotypes that may be investigated include but are not limited to: altered body shape, altered body size, lethality, sterility, reduced brood size, increased brood size, altered life span, defective locomotion, altered body plan, altered cell size, increased cell division, decreased cell division, altered feeding, slowed development, increased development, altered metabolism, (such as altered glycogen synthesis, storage, or degradation; altered lipid synthesis, storage or degradation; altered levels of carbohydrate in the hemolymph; and altered levels of lipid in the hemolymph), and altered morphogenesis of specific organs and tissues such as gonad, nervous system, fat body, hemocytes, peripheral sensory organs, bristles, imaginal discs, eye, wing, leg, antennae, gut, or musculature. For example, it is of particular interest to identify the ligand or ligands responsible for activating the GPCRs of the invention, or a non-Drosophila homologue thereof.

Methods for creation and analysis of transgenic Drosophila strains having modified expression of genes are well known to those skilled in the art (Brand et al., 1994, Methods in Cell Biology 44:635–654; Hay et al., 1997, Proc. Natl. Acad. Sci. U.S.A. 94:5195–5200). cDNAs or genomic regions encoding normal or mutant genes can be operably fused to a desired promoter, as described above, and the promoter-GPCR gene fusion inserted into any appropriate Drosophila transformation vector for the generation of transgenic flies. Typically, such transformation vectors are based on a well-characterized transposable elements, for example the P element (Rubin and Spradling, 1982, Science 218:348–53), the hobo element (Blackman et al., 1989, EMBO J. 8:211–217), mariner element (Lidholm et al., 1993, Genetics 134:859–868), the hermes element (O'Brochta et al., 1996, Genetics 142:907–914), Minos (Loukeris et al., 1995, Proc. Natl. Acad. Sci. U.S.A. 92:9485–9489), or the PiggyBac element (Handler et al., 1998, Proc. Natl. Acad. Sci. U.S.A. 95:7520–7525), where the terminal repeat sequences of the transposon that are required for transposition are incorporated into the transformation vector and arranged such that the terminal repeat sequences flank the transgene of interest (in this case a promoter-gene fusion) as well as a marker gene used to identify transgenic animals. Most often, marker genes are used that affect the eye color of Drosophila, such as derivatives of the Drosophila white or rosy genes; however, in principle, any gene can be used as a marker that causes a reliable and easily scored phenotypic change in transgenic animals, and examples of other marker genes used for transformation include the $Adh^+$ gene used as a selectable marker for the transformation of $Adh^-$ strains, Ddc+ gene used to transform $Ddc^{ts2}$ mutant strains, the lacZ gene of *E. coli*, and the $neomycin^R$ gene from the *E. coli* transposon Tn5. Plasmid constructs for introduction of the desired transgene are coinjected into Drosophila embryos having an appropriate genetic background, along with a helper plasmid that expresses the specific transposase need to mobilized the transgene into the genomic DNA. Animals arising from the injected embryos (G0 adults) are selected, or screened manually, for transgenic mosaic animals based on expression of the marker gene phenotype and are subsequently crossed to generate fully transgenic animals (G1 and subsequent generations) that will stably carry one or more copies of the transgene of interest. Such stable transgenic animals are inspected for mutant phenotypes, such as abnormal development, morphology, metabolism, growth, longevity, reproduction, viability, or behavior, in order to determine a function for the gene created by ectopic expression or overexpression of the gene, or by expression of mutant genes.

Generation of an overexpression/mis-expression phenotype is likely to result from either activation or inhibition of a receptor-linked signaling pathway. If such an overexpression/mis-expression phenotype is defined for a fly GPCR gene, clonal analysis can then be used to determine whether this phenotype is restricted to cells expressing the gene (i.e., whether the phenotype is cell autonomous or cell non-autonomous). Methods of mitotic recombination of chromosomes in heterozygous flies can be used to generate mitotic clones of genetically homozygous cells that are well known to those skilled in the art, which include the use of X-rays or preferably FLP/FRT mediated recombination (Xu and Harrison, 1994, Methods in Cell Biology 44:655–681; Greenspan, 1979, In *Fly Pushing: The Theory and Practice of Drosophila Genetics*. Plainview, N.Y., Cold Spring Harbor Laboratory Press, pp. 103–124). These mitotic recombination techniques result in patches of cells, mitotic clones, that contain two or no functional copies of the gene-of-interest. Production of the overexpression/mis-expression phenotype within cells in a clone having no copies of the gene-of-interest indicates that the effect is not cell autonomous, and is therefore likely to be the effect of a secreted molecule, as might be expected for molecules.

5.9. Identification of Compounds with Binding Capacity

This invention provides screening methodologies useful in the identification of proteins and other compounds which bind to, or otherwise directly interact with, the *D. melanogaster* genes and proteins of the invention, such as fly GPCR genes and proteins. Screening methodologies are well known in the art (see e.g., PCT International Publication No. WO 96/34099, published Oct. 31, 1996, which is incorporated by reference herein in its entirety). The proteins and compounds include endogenous cellular components which interact with the identified genes and proteins in vivo and which, therefore, may provide new targets for pharmaceutical and therapeutic interventions, as well as recombinant, synthetic, and otherwise exogenous compounds which may have binding capacity and, therefore, may be candidates for pharmaceutical agents. Thus, in one series of embodiments, cell lysates or tissue homogenates may be screened for proteins or other compounds which bind to one of the normal or mutant *D. melanogaster* GPCR genes and proteins.

Alternatively, any of a variety of exogenous compounds, both naturally occurring and/or synthetic (e.g., libraries of small molecules or peptides), may be screened for binding capacity.

As will be apparent to one of ordinary skill in the art, there are numerous other methods of screening individual proteins or other compounds, as well as large libraries of proteins or other compounds (e.g., phage display libraries) to identify molecules which bind to *D. melanogaster* GPCR proteins. All of these methods comprise the step of mixing a *D. melanogaster* GPCR protein or. fragment with test compounds, allowing time for any binding to occur, and assaying for any resultant bound complexes. All such methods are enabled by the present disclosure of substantially pure *D. melanogaster* GPCR proteins, substantially pure functional domain fragments, fusion proteins, antibodies, and methods of making and using the same.

5.9.1. Yeast Two-Hybrid with Drosophila Proteins

The present invention further provides methods of identifying or screening for proteins which interact with *D. melanogaster* GPCR proteins, or derivatives, fragments or analogs thereof. In specific embodiments, the method of identifying a molecule that binds to a ligand comprises (a) contacting the ligand with a plurality of molecules under conditions conducive to binding between the ligand and the molecules; and (b) identifying a molecule within the plurality that binds to the ligand. The ligand or protein in the method can either be a purified or non-purified form. Preferably, the method of identifying or screening is a yeast two-hybrid assay system or a variation thereof, as further described below. In this regard, the yeast two-hybrid method has been used to analyze IGF-1-receptor interactions (see Zhu and Kahn, 1997, Proc. Natl. Acad. Sci. U.S.A. 94:13063–13068). Derivatives (e.g., fragments) and analogs of a protein can also be assayed for binding to a binding partner by any method known in the art, for example, immunoprecipitation with an antibody that binds to the protein in a complex followed by analysis by size fractionation of the immunoprecipitated proteins (e.g., by denaturing or nondenaturing polyacrylamide gel electrophoresis), Western analysis, non-denaturing gel electrophoresis, etc.

One aspect of the present invention provides methods for assaying and screening fragments, derivatives and analogs of *D. melanogaster* GPCR proteins for interacting proteins. Derivatives, analogs and fragments of proteins that interact with a *D. melanogaster* GPCR protein are preferably identified by means of a yeast two hybrid assay system (Fields and Song, 1989, Nature 340:245–246; U.S. Pat. No. 5,283, 173). Because the interactions are screened for in yeast, the intermolecular protein interactions detected in this system occur under physiological conditions that mimic the conditions in eukaryotic cells, including vertebrates or invertebrates (Chien et al., 1991, Proc. Natl. Acad. Sci. U.S.A. 88:9578–9581). This feature facilitates identification of proteins capable of interaction with a *D. melanogaster* GPCR protein from species other than *D. melanogaster*.

Identification of interacting proteins by the improved yeast two-hybrid system is based upon the detection of expression of a reporter gene, the transcription of which is dependent upon the reconstitution of a transcriptional regulator by the interaction of two proteins, each fused to one half of the transcriptional regulator. The "bait" (e.g., *D. melanogaster* GPCR protein or derivative or analog thereof) and "prey" (proteins to be tested for ability to interact with the bait) proteins are expressed as fusion proteins to a DNA binding domain, and to a transcriptional regulatory domain, respectively, or vice versa. In various specific embodiments, the prey has a complexity of at least about 50, about 100, about 500, about 1,000, about 5,000, about 10,000, or about 50,000; or has a complexity in the range of about 25 to about 100,000, about 100 to about 100,000, about 50,000 to about 100,000, or about 100,000 to about 500,000. For example, the prey population can be one or more nucleic acids encoding mutants of a protein (e.g., as generated by site-directed mutagenesis or another method of making mutations in a nucleotide sequence). Preferably, the prey populations are proteins encoded by DNA, e.g., cDNA or genomic DNA or synthetically-generated DNA. For example, the populations can be expressed from chimeric genes comprising cDNA sequences from an un-characterized sample of a population of cDNA from mRNA.

One characteristic of the yeast two-hybrid system is that proteins examined in this system are expressed as cytoplasmic proteins, and therefore do not pass through the secretory pathway. The GPCR proteins of the present invention are integral membrane proteins. Other proteins, such as secreted protein hormones of the invention, normally undergo protein processing during trafficking leading to the removal of certain domains such as a pre-domain, a pro-domain, a prepro-domain, and/or a signal peptide. Therefore, expression of precursor forms of Drosophila secreted proteins in the yeast two-hybrid system does not lead to the removal of such domains. However, several methods are incorporated in the present invention to examine derivatives of secreted proteins that mimic processed forms of these proteins. By way of example, but not limitation, in one embodiment, a secreted protein that is examined in the yeast two-hybrid system is expressed as a modified form containing a prepropeptide but lacking a signal peptide (Zhu and Kahn, 1997, Proc. Natl . Acad. Sci. U.S.A. 94:13063–13068). In another embodiment, an integral membrane protein such a GPCR that is examined in the yeast two-hybrid system is expressed as a modified form containing individual intracellular or extracellular domains of the GPCR. For example, the cytoplasmic loop between TM5 and TM6 is of particular interest for use in a yeast two-hybrid screen.

In a specific embodiment, recombinant biological libraries expressing random peptides can be used as the source of prey nucleic acids.

In another embodiment, the invention provides methods of screening for inhibitors or enhancers of the protein interactants identified herein. Briefly, a protein-protein interaction assay can be carried out as described herein, except that it is done in the presence of one or more candidate molecules. An increase or decrease in reporter gene activity relative to that present when the one or more candidate molecules are absent indicates that the candidate molecule has an effect on the interacting pair. In a preferred method, inhibition of the interaction is selected for (i.e., inhibition of the interaction is necessary for the cells to survive), for example, where the interaction activates the URA3 gene, causing yeast to die in medium containing the chemical 5-fluoroorotic acid (Rothstein, 1983, Meth. Enzymol. 101:167–180). The identification of inhibitors of such interactions can also be accomplished, for example, but not by way of limitation, using competitive inhibitor assays, as described above.

5.9.2. Variations of Yeast Two-Hybrid Assays

In general, proteins of the bait and prey populations are provided as fusion (chimeric) proteins (preferably by recombinant expression of a chimeric coding sequence) comprising each protein contiguous to a pre-selected sequence. For one population, the pre-selected sequence is a DNA binding domain. The DNA binding domain can be any DNA binding domain, as long as it specifically recognizes a DNA sequence within a promoter. For example, the DNA binding domain is of a transcriptional activator or inhibitor. For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably do not detectably interact (so as to avoid false positives in the assay). The assay system further includes a reporter gene operably linked to a promoter that contains a binding site for the DNA binding domain of the transcriptional activator (or inhibitor).

Accordingly, in the present method of the invention, binding of a *D. melanogaster* GPCR fusion protein to a prey fusion protein leads to reconstitution of a transcriptional activator (or inhibitor) which activates (or inhibits) expression of the reporter gene. The activation (or inhibition) of transcription of the reporter gene occurs intracellularly, e.g., in prokaryotic or eukaryotic cells, preferably in cell culture.

The promoter that is operably linked to the reporter gene nucleotide sequence can be a native or non-native promoter of the nucleotide sequence, and the DNA binding site(s) that are recognized by the DNA binding domain portion of the fusion protein can be native to the promoter (if the promoter normally contains such binding site(s)) or non-native to the promoter. Thus, for example, one or more tandem copies (e.g., four or five copies) of the appropriate DNA binding site can be introduced upstream of the TATA box in the desired promoter (e.g., in the area of about position −100 to about −400). In a preferred aspect, four or five tandem copies of the 17 bp UAS (GAL4 DNA binding site) are introduced upstream of the TATA box in the desired promoter, which is upstream of the desired coding sequence for a selectable or detectable marker. In a preferred embodiment, the GAL1-10 promoter is operably fused to the desired nucleotide sequence; the GAL1-10 promoter already contains four binding sites for GAL4.

Alternatively, the transcriptional activation binding site of the desired gene(s) can be deleted and replaced with GAL4 binding sites (Bartel et al., 1993, BioTechniques 14:920–924; Chasman et al., 1989, Mol. Cell. Biol. 9:4746–4749). The reporter gene preferably contains the sequence encoding a detectable or selectable marker, the expression of which is regulated by the transcriptional activator, such that the marker is either turned on or off in the cell in response to the presence of a specific interaction. Preferably, the assay is carried out in the absence of background levels of the transcriptional activator (e.g., in a cell that is mutant or otherwise lacking in the transcriptional activator).

In one embodiment, more than one reporter gene is used to detect transcriptional activation, e.g., one reporter gene encoding a detectable marker and one or more reporter genes encoding different selectable markers. The detectable marker can be any molecule that can give rise to a detectable signal, e.g., a fluorescent protein or a protein that can be readily visualized or that is recognizable by a specific antibody. The selectable marker can be any protein molecule that confers the ability to grow under conditions that do not support the growth of cells not expressing the selectable marker, e.g., the selectable marker is an enzyme that provides an essential nutrient and the cell in which the interaction assay occurs is deficient in the enzyme and the selection medium lacks such nutrient. The reporter gene can either be under the control of the native promoter that naturally contains a binding site for the DNA binding protein, or under the control of a heterologous or synthetic promoter.

The activation domain and DNA binding domain used in the assay can be from a wide variety of transcriptional activator proteins, as long as these transcriptional activators have separable binding and transcriptional activation domains. For example, the GAL4 protein of *S. cerevisiae* (Ma et al., 1987, Cell 48:847–853), the GCN4 protein of *S. cerevisiae* (Hope and Struhl, 1986, Cell 46:885–894), the ARDI protein of *S. cerevisiae* (Thukral et al., 1989, Mol. Cell. Biol. 9:2360–2369), and the human estrogen receptor (Kumar et al., 1987, Cell 51:941–951), have separable DNA binding and activation domains. The DNA binding domain and activation domain that are employed in the fusion proteins need not be from the same transcriptional activator. In a specific embodiment, a GAL4 or LEXA DNA binding domain is employed. In another specific embodiment, a GAL4 or herpes simplex virus VP 16 (Triezenberg et al., 1988, Genes Dev. 2:730–742) activation domain is employed. In a specific embodiment, amino acids 1–147 of GAL4 (Ma et al., 1987, Cell 48:847–853; Ptashne et al., 1990, Nature 346:329–331) is the DNA binding domain, and amino acids 411–455 of VP16 (Triezenberg et al., 1988, Genes Dev. 2:730–742; Cress et al., 1991, Science 251:87–90) comprise the activation domain.

In a preferred embodiment, the yeast transcription factor GAL4 is reconstituted by protein-protein interaction and the host strain is mutant for GAL4. In another embodiment, the DNA-binding domain is Ace1N and/or the activation domain is Ace1, the DNA binding and activation domains of the Ace1 protein, respectively. Ace1 is a yeast protein that activates transcription from the CUP1 operon in the presence of divalent copper. CUP1 encodes metallothionein, which chelates copper, and the expression of CUP1 protein allows growth in the presence of copper, which is otherwise toxic to the host cells. The reporter gene can also be a CUP1-lacZ fusion that expresses the enzyme beta-galactosidase (detectable by routine chromogenic assay) upon binding of a reconstituted Ace1N transcriptional activator (see Chaudhuri et al., 1995, FEBS Lett. 357:221–226). In another specific embodiment, the DNA binding domain of the human estrogen receptor is used, with a reporter gene driven by one or three estrogen receptor response elements (Le Douarin et al., 1995, Nucl. Acids. Res. 23:876–878).

The DNA binding domain and the transcriptional activator/inhibitor domain each preferably has a nuclear localization signal (see Ylikomi et al., 1992, EMBO J. 11:3681–3694; Dingwall and Laskey, 1991, TIBS 16:479–481) functional in the cell in which the fusion proteins are to be expressed.

To facilitate isolation of the encoded proteins, the fusion constructs can further contain sequences encoding affinity tags such as glutathione-S-transferase or maltose-binding protein or an epitope of an available antibody, for affinity purification (e.g., binding to glutathione, maltose, or a particular antibody specific for the epitope, respectively) (Allen et al., 1995, TIBS 20:511–516). In another embodiment, the fusion constructs further comprise bacterial promoter sequences for recombinant production of the fusion protein in bacterial cells.

The host cell in which the interaction assay occurs can be any cell, prokaryotic or eukaryotic, in which transcription of the reporter gene can occur and be detected, including, but not limited to, mammalian (e.g., monkey, mouse, rat, human, bovine), chicken, bacterial, or insect cells, and is preferably a yeast cell. Expression constructs encoding and capable of expressing the binding domain fusion proteins, the transcriptional activation domain fusion proteins, and the reporter gene product(s) are provided within the host cell, by mating of cells containing the expression constructs, or by cell fusion, transformation, electroporation, microinjection, etc. In a specific embodiment in which the assay is carried out in mammalian cells (e.g., hamster cells, HeLa cells), the DNA binding domain is the GAL4 DNA binding domain, the activation domain is the herpes simplex virus VP16 transcriptional activation domain, and the reporter gene contains the desired coding sequence operably linked to a minimal promoter element from the adenovirus E1B gene driven by several GAL4 DNA binding sites (see Fearon et al., 1992, Proc. Natl. Acad. Sci. U.S.A. 89:7958–7962). The host cell used should not express an endogenous transcription factor that binds to the same DNA site as that recognized by the DNA binding domain fusion population. Also, preferably, the host cell is mutant or otherwise lacking in an endogenous, functional form of the reporter gene(s) used in the assay. Various vectors and host strains for expression of the two fusion protein populations in yeast are known and can be used (see e.g., U.S. Pat. No. 5,1468,614; Bartel et al., 1993, "Using the two-hybrid system to detect protein-protein interactions" In *Cellular Interactions in Development*, Hartley, ed., Practical Approach Series xviii, IRL Press at Oxford University Press, New York, N.Y., pp. 153–179; Fields and Stemglanz, 1994, Trends In Genetics 10:286–292). By way of example but not limitation, yeast strains or derivative strains made therefrom, which can be used are N105, N106, N1051, N1061, and YULH. Other exemplary strains that can be used in the assay of the invention also include, but are not limited to, the following:

Y190: MATa, ura3-52, his3-200, lys2-801, ade2-101, trp1-901, leu2-3,112, gal4α, gal80α, cyh$^r$2, LYS2::GAL1$_{UAS}$-HIS3$_{TATA}$HIS3, URA3::GAL1$_{UAS}$-GAL1$_{TATA}$-lacZ; Harper et al., 1993, Cell 75:805–816, available from Clontech, Palo Alto, Calif. Y190 contains HIS3 and lacZ reporter genes driven by GAL4 binding sites.

CG-1945: MATa, ura3-52, his3-200, lys2-801, ade2-101, trp1-901, leu2-3,112, gal4-542, gal80-538, cyh$^r$2, LYS2::GAL1$_{UAS}$-HIS3$_{TATA}$HIS3, URA3::GAL1$_{UAS17mers(x3)}$-CYC1$_{TATA}$-lacZ, available from Clontech, Palo Alto, Calif. CG-1945 contains HIS3 and lacZ reporter genes driven by GAL4 binding sites.

Y187: MAT-α, ura3-52, his3-200, ade2-101, trp1-901, leu2-3,112, gal4α, gal80α, URA3::GAL1$_{UAS}$-GAL1$_{TATA}$-lacZ, available from Clontech, Palo Alto, Calif. Y187 contains a lacZ reporter gene driven by GAL4 binding sites.

SFY526: MATa, ura3-52, his3-200, lys2-801, ade2-101, trp1-901, leu2-3,112, gal4-542, gal80-538, can$^r$, URA3::GAL1-lacZ, available from Clontech, Palo Alto, Calif. SFY526 contains HIS3 and lacZ reporter genes driven by GAL4 binding sites.

HF7c: MATa, ura3-52, his3-200, lys2-801, ade2-101, trp1-901, leu2-3,112, gal4-542, gal80-538, LYS2::GAL1-HIS3, URA3::GAL1$_{USA17MERS(x3)}$-CYC1-lacZ, available from Clontech, Palo Alto, Calif. HF7c contains HIS3 and lacZ reporter genes driven by GAL4 binding sites.

YRG-2: MATa, ura3-52, his3-200, lys2-801, ade2-101, trp1-901, leu2-3,112, gal4-542, gal80-538, LYS2::GAL1$_{UAS}$-GAL1$_{TATA}$-HIS3, URA3::GAL1$_{UAS17mers(x3)}$-CYC1-lacZ, available from Stratagene, La Jolla, Calif. YRG-2 contains HIS3 and lacZ reporter genes driven by GAL4 binding sites.

Many other strains commonly known and available in the art can be used.

If not already lacking in endogenous reporter gene activity, cells mutant in the reporter gene may be selected by known methods, or the cells can be made mutant in the target reporter gene by known gene-disruption methods prior to introducing the reporter gene (Rothstein, 1983, Meth. Enzymol. 101:202–211).

In a specific embodiment, plasmids encoding the different fusion protein populations can be introduced simultaneously into a single host cell (e.g., a haploid yeast cell) containing one or more reporter genes, by co-transformation, to conduct the assay for protein-protein interactions. Or, preferably, the two fusion protein populations are introduced into a single cell either by mating (e.g., for yeast cells) or cell fusions (e.g., of mammalian cells). In a mating type assay, conjugation of haploid yeast cells of opposite mating type that have been transformed with a binding domain fusion expression construct (preferably a plasmid) and an activation (or inhibitor) domain fusion expression construct (preferably a plasmid), respectively, will deliver both constructs into the same diploid cell. The mating type of a yeast strain may be manipulated by transformation with the HO gene (Herskowitz and Jensen, 1991, Meth. Enzymol. 194:132–146).

In a preferred embodiment, a yeast interaction mating assay is employed using two different types of host cells, strain-type a and alpha of the yeast *Saccharomyces cerevisiae*. The host cell preferably contains at least two reporter genes, each with one or more binding sites for the DNA-binding domain (e.g., of a transcriptional activator). The activator domain and DNA binding domain are each parts of chimeric proteins formed from the two respective populations of proteins. One strain of host cells, for example the a strain, contains fusions of the library of nucleotide sequences with the DNA-binding domain of a transcriptional activator, such as GAL4. The hybrid proteins expressed in this set of host cells are capable of recognizing the DNA-binding site in the promoter or enhancer region in the reporter gene construct. The second set of yeast host cells, for example, the alpha strain, contains nucleotide sequences encoding fusions of a library of DNA sequences fused to the activation domain of a transcriptional activator.

In a preferred embodiment, the fusion protein constructs are introduced into the host cell as a set of plasmids. These plasmids are preferably capable of autonomous replication in a host yeast cell and preferably can also be propagated in E. coli. The plasmid contains a promoter directing the transcription of the DNA binding or activation domain fusion genes, and a transcriptional termination signal. The plasmid also preferably contains a selectable marker gene, permitting selection of cells containing the plasmid. The plasmid can be single-copy or multi-copy. Single-copy yeast plasmids that have the yeast centromere may also be used to express the activation and DNA binding domain fusions (Elledge et al., 1988, Gene 70:303–312).

In another embodiment, the fusion constructs are introduced directly into the yeast chromosome via homologous recombination. The homologous recombination for these purposes is mediated through yeast sequences that are not essential for vegetative growth of yeast, e.g., the MER2, MER1, ZIPI, REC102, or ME14 gene.

Bacteriophage vectors can also be used to express the DNA binding domain and/or activation domain fusion proteins. Libraries can generally be prepared faster and more easily from bacteriophage vectors than from plasmid vectors.

In a specific embodiment, the present invention provides a method of detecting one or more protein-protein interactions comprising: (a) recombinantly expressing a D. melanogaster GPCR protein or a derivative or analog thereof in a first population of yeast cells being of a first mating type and comprising a first fusion protein containing the D. melanogaster GPCR sequence and a DNA binding domain, wherein said first population of yeast cells contains a first nucleotide sequence operably linked to a promoter driven by one or more DNA binding sites recognized by said DNA binding domain such that an interaction of said first fusion protein with a second fusion protein, said second fusion protein comprising a transcriptional activation domain, results in increased transcription of said first nucleotide sequence; (b) recombinantly expressing in a second population of yeast cells of a second mating type different from said first mating type, a plurality of said second fusion proteins, each second fusion protein comprising a sequence of a fragment, derivative or analog of a protein and an activation domain of a transcriptional activator, in which the activation domain is the same in each said second fusion protein; (c) mating said first population of yeast cells with said second population of yeast cells to form a third population of diploid yeast cells, wherein said third population of diploid yeast cells contains a second nucleotide sequence operably linked to a promoter driven by a DNA binding site recognized by said DNA binding domain such that an interaction of a first fusion protein with a second fusion protein results in increased transcription of said second nucleotide sequence, in which the first and second nucleotide sequences can be the same or different; and (d) detecting said increased transcription of said first and/or second nucleotide sequence, thereby detecting an interaction between a first fusion protein and a second fusion protein. In a preferred aspect, between step (a) and (b), a step is carried out of negatively selecting to eliminate those yeast cells in said first population which said increased transcription of said first nucleotide sequence occurs in the absence of said second fusion protein (see e.g. PCT International Publication No. WO97/47763, published Dec. 18, 1997, which is incorporated by reference herein in its entirety).

In a preferred embodiment, the bait D. melanogaster GPCR cytoplasmic domain sequence and the prey library of chimeric genes are combined by mating the two yeast strains on solid media, such that the resulting diploids contain both kinds of chimeric genes, i.e., the DNA-binding domain fusion and the activation domain fusion.

Preferred reporter genes include the URA3, HIS3 and/or the lacZ genes (see e.g., Rose and Botstein, 1983, Meth. Enzymol. 101:167–180) operably linked to GAL4 DNA-binding domain recognition elements. Other reporter genes include but are not limited to, Green Fluorescent Protein (GFP) (Cubitt et al., 1995, Trends Biochem. Sci. 20:448–455), luciferase, LEU2, LYS2, ADE2, TRP1, CAN1, CYH2, GUS, CUP1 or chloramphenicol acetyl transferase (CAT). Expression of the reporter genes can be detected by techniques known in the art (see e.g. PCT International Publication No. WO97/47763, published Dec. 18, 1997, which is incorporated by reference herein in its entirety).

In a specific embodiment, transcription of the reporter gene is detected by a linked replication assay. For example, as described by Vasavada et al., 1991, Proc. Natl. Acad. Sci. U.S.A. 88:10686–10690, expression of SV40 large T antigen is under the control of the E1B promoter responsive to GAL4 binding sites. The replication of a plasmid containing the SV40 origin of replication, indicates a protein-protein interaction. Alternatively, a polyoma virus replicon can be used (Vasavada et al., 1991, Proc. Natl. Acad. Sci. U.S.A. 88:10686–90).

In another embodiment, the expression of reporter genes that encode proteins can be detected by immunoassay, i.e., by detecting the immunospecific binding of an antibody to such protein, which antibody can be labeled, or incubated with a labeled binding partner to the antibody, to yield a detectable signal. Alam and Cook disclose non-limiting examples of detectable marker genes that can be operably linked to a transcriptional regulatory region responsive to a reconstituted transcriptional activator, and thus used as reporter genes (Alam and Cook, 1990, Anal. Biochem. 188:245–254).

The activation of reporter genes like URA3 or HIS3 enables the cells to grow in the absence of uracil or histidine, respectively, and hence serves as a selectable marker. Thus, after mating, the cells exhibiting protein-protein interactions are selected by the ability to grow in media lacking a nutritional component, such as uracil or histidine (see Le Douarin et al., 1995, Nucl. Acids Res. 23:876–878; Durfee et al., 1993, Genes Dev. 7:555–569; Pierrat et al., 1992, Gene 119:237–245; Wolcott et al., 1966, Biochem. Biophys. Acta 122:532–534). In other embodiments of the present invention, the activities of the reporter genes like GFP or lacZ are monitored by measuring a detectable signal (e.g., fluorescent or chromogenic, respectively) that results from the activation of these reporter genes. LacZ transcription, for example, can be monitored by incubation in the presence of a substrate, such as X-gal (5-bromo-4-chloro-3-indolyl-β-D-galactoside), of its encoded enzyme, β-galactosidase.

In a preferred embodiment of the present invention, false positives arising from transcriptional activation by the DNA binding domain fusion proteins in the absence of a transcriptional activator domain fusion protein are prevented or reduced by negative selection prior to exposure to the activation domain fusion population (see e.g. PCT International Publication No. WO97/47763, published Dec. 18, 1997, which is incorporated by reference herein in its entirety). By way of example, if such cell contains URA3 as a reporter gene, negative selection is carried out by incubating the cell in the presence of 5-fluoroorotic acid (5-FOA, which kills URA+ cells (Rothstein, 1983, Meth. Enzymol. 101:167–180). Hence, the metabolism of 5-FOA will lead to cell death of self-activating DNA-binding domain hybrids.

In a preferred aspect, negative selection involving a selectable marker as a reporter gene can be combined with the use of a toxic or growth inhibitory agent to allow a higher rate of processing than other methods. Negative selection can also be carried out on the activation domain fusion population prior to interaction with the DNA binding domain fusion population, by similar methods, either alone or in addition to negative selection of the DNA binding fusion population. Negative selection can be carried out on the recovered protein-protein complex by known methods (see e.g., Bartel et al., 1993, BioTechniques 14:920–924; PCT International Publication No. WO97/47763, published Dec. 18, 1997).

In a preferred embodiment of the invention, DNA sequences encoding pairs of interacting proteins are isolated by a method wherein either the DNA-binding domain hybrids or the activation domain hybrids are amplified, in separate respective reactions. Preferably, the amplification is carried out by polymerase chain reaction (PCR) (see U.S. Pat. Nos. 4,683,202; 4,683,195; and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220; Innis et al., 1990, *PCR Protocols*, Academic Press, Inc., San Diego, Calif.) using pairs of oligonucleotide primers specific for either the DNA-binding domain hybrids or the activation domain hybrids. Other amplification methods known in the art can be used, including but not limited to ligase chain reaction (see EP 320,308), use of Qβ replicase, or methods listed in Kricka et al., 1995, *Molecular Probing, Blotting, and Sequencing*, Academic Press, New York, Chapter 1 and Table IX.

The plasmids encoding the DNA-binding domain hybrid and the activation domain hybrid proteins can also be isolated and cloned by any of the methods well known in the art. For example, but not by way of limitation, if a shuttle (yeast to *E. coli*) vector is used to express the fusion proteins, the genes can be recovered by transforming the yeast DNA into *E. coli* and recovering the plasmids from *E. coli* (see e.g., Hoffman et al., 1987, Gene 57:267–272). Alternatively, the yeast vector can be isolated, and the insert encoding the fusion protein subcloned into a bacterial expression vector, for growth of the plasmid in *E. coli*.

5.10. Biochemical Assays Using Drosophila Proteins

The present invention provides biochemical assays using fly proteins of the invention. In one embodiment, Drosophila proteins such as GPCR proteins are useful for biochemical assays aimed at the identification and characterization of the ligand(s) which bind under physiologic conditions, or the identification of ligands for new GPCR receptors or other proteins that are discovered. The cDNAs encoding the GPCR proteins can be individually subcloned into any of a large variety of eukaryotic expression vectors permitting expression in insect and mammalian cells, described above. The resulting genetically engineered cell lines expressing GPCR proteins can be assayed for production and processing of the mature GPCR proteins, for example, with antibodies to Drosophila GPCR proteins and Western blotting assays or ELISA assays. For assays of specific receptor binding and functional activation of receptor proteins, one can employ genetically engineered cells over-expressing fly GPCRs. Such engineered cells may exhibit characteristics providing clues to determining specific GPCR functions. Further, partially-purified culture medium or extracts, or highly-purified Drosophila or other proteins can also be screened for functional activity when exposed to such engineered cells.

Specific protein binding of Drosophila GPCR proteins to Drosophila GPCR ligands can be assayed, for example, by following the procedures of Yamaguchi et al. (Yamaguchi et al., 1995, Biochemistry 34:4962–4968). Chinese hamster ovary cells, COS cells, or any other suitable cell line, can be transiently transfected or stably transformed with expression constructs that direct the production of a Drosophila GPCR. Direct binding of a Drosophila GPCR ligand to such recombinant receptor-expressing cells can be measured using, e.g., a labeled Drosophila ligand population. The label is typically a chemical or protein moiety covalently attached to the ligand population which permits the experimental monitoring and quantitation of any labeled ligand that binds to the Drosophila GPCR protein.

More specifically, a label attached to a ligand population to be screened for binding to a fly GPCR can be a radioactive substituent such as a $^{125}$I-moiety or a $^{32}$P-phosphate moiety, a fluorescent moiety, or a label which allows for indirect methods of detection such as a biotin-moiety for binding by avidin or streptavidin, an epitope-tag such as a Myc-tag or FLAG-tag, or a protein fusion domain which allows for direct or indirect enzymatic detection such as an alkaline phosphatase-fusion or Fc-fusion domain. Such labeled ligands can be used to test for direct and specific binding to fly GPCR-expressing cells by incubating the labeled proteins with the GPCR-expressing cells in serum-free medium, washing the cells with ice-cold phosphate-buffered saline to remove unbound protein, lysing the cells in buffer with an appropriate detergent, and measuring label in the lysates to determine the amount of bound protein. Alternatively, in place of whole cells, membrane fractions obtained from GPCR-expressing cells may also be used. Also, instead of a direct binding assay, a competition binding assay may be used. The specificity and affinity of binding of Drosophila GPCR proteins can be judged by comparison with other superfamily proteins tested in the same assay, for example, vertebrate GPCRs.

5.10.1. Identification of Additional Ligands or Other GPCR Binding Proteins The invention described herein provides methods wherein Drosophila GPCR proteins are used for the identification of novel GPCR ligands, other than Drosophila ligands, using biochemical methods well known to those skilled in the art for detecting specific protein-protein interactions (see e.g., Current Protocols In Protein Science, 1998, Coligan et al., eds., John Wiley & Sons, Inc., Somerset, N.J.). In particular, it is likely that some Drosophila GPCRs interact with ligand types that have not yet been identified in vertebrates, or with ligand types that are specific to invertebrates. The identification of either novel vertebrate ligand types or invertebrate-specific ligand types is of great interest with respect to human therapeutic applications, or pesticide applications, respectively. Assuming some Drosophila GPCRs do not exhibit specific protein binding to any known ligand in the binding assays described above, then the novel cognate ligands for these GPCRs can be investigated and identified as follows.

Labeled ligand populations can be used for binding assays in situ to identify ligands binding to fly GPCR receptors, for example, as described elsewhere (Gorczyca et al., 1993, J. Neurosci. 13:3692–3704; see also Formosa et al., 1991, Methods Enzymol. 208:24–45; Formosa et al., 1983, Proc. Natl. Acad. Sci. U.S.A. 80:2442–2446). Further, specific binding proteins can be identified by cross-linking radioactively-labeled or epitope-tagged GPCRs to specific binding proteins in lysates, followed by electrophoresis to identify and isolate the cross-linked protein species (Ransone, 1995, Methods Enzymol. 254:491–497). Still further, molecular cloning methods can be used to identify novel GPCR interacting proteins, e.g., by expression cloning using Drosophila cDNA expression libraries transfected into mammalian cells, expression cloning of specific binding proteins using Drosophila cDNA libraries expressed in *E. coli* (Cheng and Flanagan, 1994, Cell 79:157–168), and yeast two-hybrid methods (as described above) using a Drosophila GPCR fusion (such as a cytosolic domain fusion) as "bait" for screening activation-domain fusion libraries derived from Drosophila cDNA (Young and Davis, 1983, Science 222:778–782; Young and Davis, 1983, Proc. Natl. Acad. Sci. U.S.A. 80:1194–1198; Sikela and Hahn, 1987, Proc. Natl. Acad. Sci. U.S.A. 84:3038–3042; Takemoto et al., 1997, DNA Cell Biol. 16:797–799).

5.10.2. Assays of Drosophila Domains

Ligands that bind to domains of novel fly proteins of the invention identified herein, such as GPCR cytosolic domains (e.g., the intracellular loop domain between transmembrane domains five and six of a GPCR), transmembrane domains or ligand-binding domains, may also be identified, e.g., from screening of a cDNA expression library, synthetic combinatorial chemistry library, or a phage-displayed random peptide library. Such random peptide libraries have been extensively described elsewhere (see e.g., Kay et al., 1992, Gene 128, 59–65). A brief description of the preparation of a phage-displayed random peptide library follows. One such library is referred to as a TSAR library, for Totally Synthetic Affinity Reagent library. By cloning degenerate oligonucleotides of fixed length into bacteriophage vectors, recombinant libraries of random peptides can be generated which are expressed at the amino-terminus of the pill protein on the surface of M13 viral particles. From three to five copies of the pIII-fusion peptide is expressed on the surface of each particle. Phage display of such random peptides offers at least three conveniences: first, the expressed peptides are on the surface of the viral particles and accessible for interactions; second, the recombinant viral particles are stable (e.g., they can be frozen and/or exposed to pH extremes); and third, the viruses can be easily amplified. Consequently, such libraries can be screened by isolating viral particles that bind to targets, such as fly GPCRs. The isolates can be grown up overnight, and the displayed peptide sequence responsible for binding can be quickly deduced by DNA sequencing. Libraries such as these have approximately $>10^8$ different recombinants, and nucleotide sequencing of the inserts suggests that the expressed peptides are indeed random in amino acid sequence.

Accordingly, in another embodiment, this invention provides a method of identifying a compound (e.g., peptide) having a region that binds to a fly domain comprising: (a) providing a (preferably immobilized) target molecule comprising the fly domain; (b) incubating the target molecule with one or more candidate compounds (e.g., an aliquot taken from a random peptide library); (c) removing unbound compounds from the target molecule; and (d) recovering the compound bound to the target molecule. Optionally, the structure of the compound is then determined (e.g., by sequencing).

5.10.3. Assays of Drosophila Proteins

The functional activity of fly proteins, such as GPCRs or derivatives or analogs, can be assayed by various methods known to one skilled in the art.

For example, in one embodiment, where one is assaying for the ability to bind to or compete with a wild-type GPCR protein for binding to an anti-GPCR antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), western blots, precipitation reactions, agglutination assays (e.g., gel agglutination assays, hemagglutination assays), complement fixation assays, immunofluorescence assays, protein A assays, and immunoelectrophoresis assays, etc. In another embodiment, antibody binding is detected by detecting a label on the primary antibody. In yet another embodiment, the primary antibody is detected by detecting binding of a secondary antibody or reagent to the primary antibody. In a further embodiment, the secondary antibody is labeled. Many means are well known in the art for detecting binding in an immunoassay and are within the scope of the present invention. In another embodiment, where a GPCR-binding protein is identified, the binding can be assayed, e.g., by any means known in the art. In another embodiment, physiological correlates of protein binding to its substrates and/or receptors (e.g., signal transduction) can be assayed. Here, for example, downstream activation of various physiologic effectors by GPCRs of the invention may be assayed in vitro. Examples of such effectors include but are not limited to adenylyl cyclase and phospholipase C. Other examples are provided below.

In another embodiment, genetic studies can be done to determine the phenotypic effect of a GPCR gene mutant that is a derivative or analog of a wild-type GPCR gene. Other such methods will be readily apparent to the skilled artisan and are within the scope of the invention.

5.10.4. Other Functional Assays

Other functional assays of Drosophila GPCR proteins that go beyond ligand or interactor binding can be investigated using recombinant GPCR-expressing cells. Assayable functional activities may include but are not limited to stimulation of cell proliferation, stimulation of overall tyrosine kinase activity (as determined by immunoblotting cell extracts with an anti-phosphotyrosine antibody), stimulation of phosphorylation of specific substrate proteins such as ion channels or transcription factors (using, e.g., $^{32}$P-labeling and immunoprecipitation with antibodies that specifically recognize a substrate protein), and stimulation of other enzymatic activities linked to a signaling pathway of interest, including assays of the following activities: GTPase, adenylyl cyclase, potassium ion conductance, calcium ion conductance, and/or phospholipase C.

5.11. Identifying Signaling Pathways and Phenotypes

This invention provides animal models which may be used in the identification and characterization of *D. melanogaster* protein signaling pathways, and/or phenotypes associated with the mutation or abnormal expression of a *D. melanogaster* protein. In a specific embodiment, the protein is a GPCR. Methods of producing such animal models using novel genes and proteins are well known in the art (see e.g., PCT International Publication No. WO 96/34099, published Oct. 31, 1996, which is incorporated by reference herein in its entirety). Such models include but are not limited to the following embodiments.

First, animals are provided in which a normal *D. melanogaster* GPCR gene has been recombinantly introduced into the genome of the animal as an additional gene, under the regulation of either an exogenous or an endogenous promoter element, and as either a minigene or a large genomic fragment. Animals are also provided in which a normal gene has been recombinantly substituted for one or both copies of the animal's homologous gene by homologous recombination or gene targeting.

Second, animals are provided in which a mutant *D. melanogaster* GPCR gene has been recombinantly introduced into the genome of the animal as an additional gene, under the regulation of either an exogenous or an endogenous promoter element, and as either a minigene or a large genomic fragment. Animals are also provided in which a mutant gene has been recombinantly substituted for one or both copies of the animal's homologous gene by homologous recombination or gene targeting.

Third, animals are provided in which a mutant version of one of that animal's own genes (bearing, for example, a specific mutation corresponding to, or similar to, a pathogenic mutation of a GPCR gene from another species) has been recombinantly introduced into the genome of the animal as an additional gene, under the regulation of either an exogenous or an endogenous promoter element, and as either a minigene or a large genomic fragment.

Finally, equivalents of transgenic animals, including animals with mutated or inactivated genes, may be produced using chemical or x-ray mutagenesis. Using the isolated nucleic acids disclosed or otherwise enabled herein, one of ordinary skill may more rapidly screen the resulting offspring by, for example, direct sequencing, restriction fragment length polymorphism (RFLP) analysis, PCR, or hybridization analysis to detect mutants, or Southern blotting to demonstrate loss of an allele.

Such animal models may be used to identify a *D. melanogaster* GPCR protein signaling pathway by various methods. In one embodiment, this invention provides a method of identifying a *D. melanogaster* GPCR signaling pathway comprising: (a) disrupting a *D. melanogaster* GPCR gene; and (b) identifying the effect of the gene disrupted in step (a) in an assay selected from the group consisting of a developmental assay, an energy metabolism assay, a growth rate assay, and a reproductive capacity assay. Further specific assays may be performed to test for lethality, sterility, reduced brood size, increased brood size, altered life span, defective locomotion, altered body shape, altered body plan, altered body size, altered bristles, altered body weight, altered cell size, increased cell division, decreased cell division, altered feeding, slowed development, increased development, decreased metabolism (including but not limited to alterations in glycogen synthesis, storage, and/or degradation, alterations in lipid synthesis, storage and/or degradation, alterations in levels of carbohydrate in hemolymph, alterations in levels of lipid in hemolymph), alterations in morphogenesis (including but not limited to organs or tissues of the gonad, nervous system, fat body, hemacytes, peripheral sensory organs, imaginal discs, eye, wing, leg, antennae, bristle, gut or musculature). Such assays are well known in the art. In one embodiment, results of an assay may be compared to known mutant phenotypes to determine the signaling pathway involved. In another embodiment, a GPCR gene is disrupted using chemical mutagenesis. In another embodiment, a GPCR gene is disrupted using transposon mutagenesis. In a further embodiment, a GPCR gene is disrupted by radiation mutagenesis. Further, other novel fly genes identified using the methods and database of the invention may be subjected to such analysis.

Further, this invention provides a method of identifying a phenotype associated with mutation or abnormal expression of a *D. melanogaster* GPCR protein comprising identifying the effect of a mutated or abnormally expressed *D. melanogaster* GPCR gene in a *D. melanogaster* animal. In one embodiment, the effect is determined by an assay as set forth above.

In yet another embodiment, a GPCR gene is mutated or abnormally expressed using a technique selected from the group consisting of chemical mutagenesis, radiation mutagenesis, transposon mutagenesis, antisense and double-stranded RNA interference. Abnormal (i.e., ectopic) expression can be overexpression, underexpression (e.g., due to inactivation), expression at a developmental time different from wild-type animals, or expression in a cell type different from in wild-type animals.

5.11.1. Anaylsis of Genetic Interactions and Multiple Mutants

Yet another approach that may be used to probe the biological function of the genes identified herein is by using tests for genetic interactions with other genes that may participate in the same, related, interacting, or modifying genetic or biochemical pathways. In particular, since it is evident that there are multiple GPCR genes in the Drosophila genome, this raises the possibility of functional redundancy of one or more genes. Consequently, it is of interest to investigate the phenotypes of fruit flies containing mutations that eliminate the function of more than one GPCR gene. Such strains carrying mutations in multiple genes can be generated by cross breeding animals carrying the individual mutations, followed by selection of recombinant progeny that carry the desired multiple mutations.

One specific question is whether genetic analysis of interactions of GPCR genes with other well-characterized Drosophila genes and pathways identifies any novel interactions. Thus, double mutant fruit flies may be constructed that carry mutations in a GPCR gene and any other gene-of-interest.

It is of particular interest to test the interaction of the GPCR genes with other genes implicated in G-protein signaling, especially those that exhibit similarity to signaling components in vertebrates. For example, fruit flies carrying mutations in GPCR genes and a mutation in such genes as adenylyl cyclase, phospholipase C, or potassium channels would be of use in investigating the involvement of different GPCR genes in the signaling pathway where these genes participate. The database FlyBase (1998, "FlyBase—A Drosophila Database", Nucl. Acids Res. 26:85–88; see also flybase.bio.indiana.edu) can be consulted for a listing known fly genes that participate in G-protein coupled receptor pathways. Similarly, transgenic animals mis-expressing GPCR genes which further carry mutations in known GPCR signal transduction genes are of interest. Other genetic interactions may be tested based on the actual phenotypes observed for alterations of the GPCR genes alone.

5.11.2. Genetic Modifier Screens

The initial characterization of phenotypes created by mutations in single or multiple GPCR genes is expected to lead to the identification of Drosophila strains that exhibit mutant phenotypes suitable for large scale genetic modifier screens aimed at discovering other components of the same pathway. The procedures involved in typical genetic modifier screens to define other components of a genetic/biochemical pathway are well known to those skilled in the art and have been described elsewhere (Wolfner and Goldberg, 1994, Methods in Cell Biology 44:33–80; Karim et al., 1996, Genetics 143:315–329). Such genetic modifier screens are based on the identification of mutations in other genes that modify an initial mutant phenotype, by isolating either suppressor mutations that return the mutant phenotype toward normal, or enhancer mutations that make the initial mutant phenotype more severe.

5.11.3. Standard Genetic Modifier Screens

Genetic modifier screens can follow a variety of strategies, depending on the nature of the sensitizing mutation and the specific pathway affected. Most commonly, a dominant mutation is used as the sensitizer and females carrying this mutation are crossed to wild type males exposed to an effective mutagen, such as EMS, MMS, ENU, triethylamine, diepoxyalkanes, ICR-170, formaldehyde, X-rays, gamma rays, or ultraviolet radiation. The progeny are scored for rare mutations that result in an enhanced or suppressed version of the original mutant phenotype, indicating the presence of a second site modifier mutation. Any new mutations identified as modifiers (i.e. suppressors or enhancers) are candidates for genes that participate in the same pathway. Some sensitizer mutations allow both enhancer and suppressor mutations to be identified by alterations in a dispensable tissue, such as the eye. Others, such as inducible dominant lethals, only permit the recovery of suppressor mutations. The mutagenized animals are crossed to animals of the opposite sex that also carrying the mutant allele to be modified, and the resulting progeny are scored for rare events that result in a suppressed or enhanced version of the original mutant phenotype. In the case where the mutant allele being modified is genetically dominant, as is commonly the situation for ectopically expressed genes, wild type males are mutagenized and crossed to females carrying the mutant allele to be modified. Any new mutations identified as modifiers (i.e., suppressors or enhancers) are candidates for genes that participate in the same phenotype-generating pathway.

In a pilot-scale genetic modifier screen, 10,000 or fewer mutagenized progeny are inspected; in a moderate size screen, 10,000 to 50,000 mutagenized progeny are inspected; and in a large scale screen, over 50,000 mutagenized progeny are inspected. Progeny exhibiting either enhancement or suppression of the original phenotype are immediately crossed to adults containing balancer chromosomes and used as founders of a stable genetic line. In addition, progeny of the founder adult are retested under the original screening conditions to ensure stability and reproducibility of the phenotype. Additional secondary screens may be employed, as appropriate, to confirm the suitability of each new modifier mutant line for further analysis. For example, newly identified modifier mutations can be tested directly for interaction with other genes of interest known to be involved or implicated in signaling pathways of interest (e.g., hedgehog, patched, smoothened, frizzled, wingless, dunce, rutabaga, amnesiac, mutations in modifier genes obtained from different genetic screens of a signaling pathway of interest), using methods described above. Also, the new modifier mutations can be tested for interactions with genes in other pathways thought to be unrelated or distantly related, such as genes in the Notch signaling pathway. New modifier mutations that exhibit specific genetic interactions with other genes implicated in signaling, but not interactions with genes in unrelated pathways, are of particular interest. Additionally, strains can be generated that carry the new modifier mutations of interest in the absence of the original gene mutation (i.e. a strain wild type for the mutant allele being suppressed or enhanced) to determine whether the new modifier mutation exhibits an intrinsic phenotype, independent of the mutation in a GPCR gene or other novel gene of the invention, which might provide further clues as to the normal function of the new modifier gene.

Each newly-identified modifier mutation can be crossed to other modifier mutations identified in the same screen to place them into complementation groups, which typically correspond to individual genes (see Greenspan, 1997, In *Fly Pushing: The Theory and Practice of Drosophila Genetics*, Plainview, N.Y., Cold Spring Harbor Laboratory Press, pp. 23–46). Two modifier mutations are said to fall within the same complementation group if animals carrying both mutations in trans exhibit essentially the same phenotype as animals that are homozygous for each mutation individually.

5.11.4. Gain-of-Function Modifier Screens

Although the genetic modifier screens described above are quite powerful and sensitive, some genes that participate in a GPCR pathway may be missed in this approach, particularly if there is functional redundancy of those genes. This is because the vast majority of the mutations generated in the standard mutagenesis methods described above will be loss-of-Function mutations, whereas gain-of-Function mutations that could reveal genes with functional redundancy will be relatively rare. Another method of genetic screening in Drosophila has been developed that focuses specifically on systematic gain-of-Function genetic screens (Rorth, et al., 1998, Development 125:1049–1057). This method is based on a modular mis-expression system utilizing components of the GAL4/UAS system (which were defined above). In this case, a modified P element, termed an EP element, is genetically engineered to contain a GAL4-responsive UAS element and promoter, and this engineered transposon is used to randomly tag genes by insertional mutagenesis (similar to the method of P mutagenesis described above). Thousands of transgenic Drosophila strains, termed EP lines, can thus be generated each containing a specific UAS-tagged gene. This approach takes advantage of a well-recognized insertional preference of P elements, where it has been found that P elements have a strong tendency to insert at the 5'-ends of genes. Consequently, many of the genes that have been tagged by insertion of EP elements become operably fused to a GAL4-regulated promoter, and increased expression or mis-expression of the randomly tagged gene can be induced by crossing in a GAL4 driver gene (similar that described above).

Thus, systematic gain-of-Function genetic screens for modifiers of phenotypes induced by mutation or mis-expression of a GPCR gene can be performed as follows. A large battery of thousands of Drosophila EP lines can be crossed into a genetic background containing a mutant or mis-expressed GPCR gene, and further containing an appropriate GAL4 driver transgene. The progeny of this cross can be inspected for enhancement or suppression of the original phenotype induced by mutation/mis-expression of the GPCR gene. Progeny that exhibit an enhanced or suppressed phenotype can be crossed further to verify the reproducibility and specificity of this genetic interaction with the GPCR gene. EP insertions that demonstrate a specific genetic interaction with a mutant or mis-expressed GPCR gene, have therefore physically tagged a new gene that genetically interacts with the . The new modifier gene can be identified and sequenced using PCR or hybridization screening methods that allow the isolation of the genomic DNA adjacent to the position of the EP element insertion.

5.12. Assays for Changes in Gene Expression

This invention provides assays for detecting changes in the expression of the *D. melanogaster* genes and proteins. Assays for changes in gene expression are well known in the art (see e.g., PCT Publication No. WO 96/34099, published Oct. 31, 1996, which is incorporated by reference herein in its entirety). Such assays may be performed in vitro using transformed cell lines, immortalized cell lines, or recombinant cell lines, or in vivo using animal models.

In a specific embodiment, expression of a GPCR gene or protein is assayed. In particular, the assays may detect the presence of increased or decreased expression of a *D. melanogaster* GPCR gene or protein on the basis of increased or decreased mRNA expression (using, e.g., nucleic acid probes), increased or decreased levels of related protein products (using, e.g., the antibodies disclosed herein), or increased or decreased levels of expression of a marker gene (e.g., β-galactosidase or luciferase) operably linked to a 5' regulatory region in a recombinant construct.

In yet another series of embodiments, various expression analysis techniques may be used to identify genes which are differentially expressed between two conditions, such as a cell line or animal expressing a normal *D. melanogaster* GPCR gene compared to another cell line or animal expressing a mutant *D. melanogaster* GPCR gene. Such techniques comprise any expression analysis technique known to one skilled in the art, including but not limited to differential display, serial analysis of gene expression (SAGE), nucleic acid array technology, subtractive hybridization, proteome analysis and mass-spectrometry of two-dimensional protein gels. In a specific embodiment, nucleic acid array technology (i.e., gene chips) may be used to determine a global (i.e., genome-wide) gene expression pattern in a normal *D. melanogaster* animal for comparison with an animal having a mutation in one or more *D. melanogaster* genes.

To elaborate further, the various methods of gene expression profiling mentioned above can be used to identify other genes (or proteins) that may have a functional relation to (e.g., may participate in a signaling pathway with) a *D. melanogaster* GPCR gene. Gene identification of such other genes is made by detecting changes in their expression levels following mutation, i.e., insertion, deletion or substitution in, or overexpression, underexpression, mis-expression or knock-out, of a *D. melanogaster* GPCR gene, as described herein. Expression profiling methods thus provide a powerful approach for analyzing the effects of mutation in a *D. melanogaster* gene.

Methods of gene expression profiling are well-known in the art, as exemplified by the following references describing subtractive hybridization (Wang and Brown, 1991, Proc. Natl. Acad. Sci. U.S.A. 88:11505–11509), differential display (Liang and Pardee, 1992, Science 257:967–971), SAGE (Velculescu et al., 1995, Science 270:484–487), proteome analysis (Humphery-Smith et al., 1997, Electrophoresis 18:1217–1242; Dainese et al., 1997, Electrophoresis 18:432–442), and hybridization-based methods employing nucleic acid arrays (Heller et al., 1997, Proc. Natl. Acad. Sci. U.S.A. 94:2150–2155; Lashkari et al., 1997, Proc. Natl. Acad. Sci. U.S.A. 94:13057–13062; Wodicka et al., 1997, Nature Biotechnol. 15:1259–1267).

5.13. Gene Regulatory Elements

This invention provides methods for using gene regulatory DNA elements to identify tissues, cells, genes and factors that specifically control GPCR protein production. In one embodiment, regulatory DNA elements, such as enhancers/promoters, from Drosophila GPCR genes are useful for identifying and manipulating specific cells and tissues that synthesize a GPCR protein. Such cells and tissues are of considerable interest since they are likely to have an important regulatory function within the animal in sensing and controlling various aspects of cellular signaling. Analyzing components that are specific to cell signaling is likely to lead to an understanding of how to manipulate these regulatory processes, either for therapeutic applications or pesticide applications, as well as an understanding of how to diagnose dysfunction in these processes. Regulatory DNA elements derived from GPCR genes provide a means to mark and manipulate such cells, and further, identify regulatory genes and proteins, as described below.

5.13.1. Gene Fusions with Gene Regulatroy DNA Elements

In a specific embodiment, gene fusions with GPCR gene regulatory elements can be made. For compact genes that have relatively few and small intervening sequences, it is typical that the regulatory elements that control spatial and temporal expression patterns are found in the DNA immediately upstream of the coding region, often extending to the nearest neighboring gene. Regulatory regions can be used to construct gene fusions where the regulatory DNAs are operably fused to a coding region for a reporter protein whose expression is easily detected, and these constructs may be introduced as transgenes into Drosophila. An entire regulatory DNA region can be used, or the regulatory region can be divided into smaller segments to identify sub-elements that might be specific for controlling expression a given cell type or stage of development. Examples of reporter proteins that can be used for construction of these gene fusions include but are not limited to *E. coli* beta-galactosidase or green fluorescent protein (GFP), whose products can be detected readily in situ and which are useful for histological studies (O'Kane,and Gehring, 1987, Proc. Natl. Acad. Sci. U.S.A. 84:9123–9127; Chalfie et al., 1994, Science 263:802–805) and sorting of specific cells that express proteins (Cumberledge and Krasnow, 1994, Methods in Cell Biology 44:143–159); the cre or FLP recombinase proteins that can be used to control the presence and expression of other genes in the same cells through site-specific recombination (Golic and Lindquist, 1989, Cell 59:499–509; White et al., 1996, Science 271:805–807); toxic proteins such as the reaper, and cell death proteins which are useful to specifically ablate cells that normally express certain proteins in order to assess the physiological function of certain tissues (see Kingston, 1998, In *Current Protocols in Molecular Biology*. Ausubel et al., John Wiley & Sons, Inc. sections 12.0.3–12.10) or any other protein where it is desired to examine the function this particular protein specifically in cells that synthesize and secrete proteins (as described in the mis-expression analysis above).

Alternatively, a binary reporter system can be used, similar to that described above, where a GPCR regulatory element is operably fused to the coding region of an exogenous transcriptional activator protein, such as the GAL4 or tTA activators described above, to create a GPCR regulatory element "driver gene". For the other half of the binary system the exogenous activator controls a separate "target gene" containing a coding region of a reporter protein operably fused to a cognate regulatory element for the exogenous activator protein, such as UASG or a tTA-response element, respectively. An advantage of a binary system is that a single driver gene construct can be used to activate transcription from preconstructed target genes encoding different reporter proteins, each with its own uses as delineated above.

The regulatory element-reporter gene fusions described in the preceding paragraph are also useful for tests of genetic interactions, where the objective is to identify those genes that have a specific role in controlling the expression of GPCR genes, or promoting the growth and differentiation of the tissues that expresses a GPCR protein. Transgenic Drosophila carrying a GPCR regulatory element-reporter gene fusion can be crossed with another Drosophila strain carrying a mutation-of-interest and the resulting progeny examined. For example, the mutation-or-interest might be a modifier mutation arising from a genetic modifier screen as described in a preceding section. If no change of expression of the reporter gene in the resulting progeny is observed, this is indicative of a lack of involvement of the gene altered by the mutation-of-interest in controlling protein expression; by contrast, if a significant increase, decrease, loss, or mis-expression of the reporter protein in the resulting progeny is observed, this is indicative of a regulatory role for the gene altered by the mutation-of-interest in cells expressing the protein.

5.13.2. Protein-DNA Binding Assays

In yet another embodiment, GPCR gene regulatory DNA elements are used in protein-DNA binding assays to identify gene regulatory proteins that control the expression of GPCR genes. Such gene regulatory proteins can be detected using a variety of methods that probe specific protein-DNA interactions well known to those skilled in the art (see e.g., Kingston, 1998, In *Current Protocols in Molecular Biology*, Ausubel et al, John Wiley & Sons, Inc., sections 12.0.3–12.10) including in vivo footprinting assays based on protection of DNA sequences from chemical and enzymatic modification within living or permeabilized cells, in vitro footprinting assays based on protection of DNA sequences from chemical or enzymatic modification using protein extracts nitrocellulose filter-binding assays and gel electrophoresis mobility shift assays using radioactively labeled regulatory DNA elements mixed with protein extracts. In particular, it is of interest to identify those DNA binding proteins whose presence or absence is specific to GPCR protein expressing tissue, as judged by comparison of the DNA-binding assays described above using cells/extracts from a GPCR gene-expressing tissue versus other cells/extracts from tissues that do not express a certain GPCR gene or genes. For example, a DNA-binding activity that is specifically present in cells that normally express a GPCR protein might function as a transcriptional activator of the GPCR gene; conversely, a DNA-binding activity that is specifically absent in cells that normally express a GPCR protein might function as a transcriptional repressor of the GPCR gene. Having identified candidate GPCR gene regulatory proteins using the above DNA-binding assays, these regulatory proteins can themselves be purified using a combination of conventional and DNA-affinity purification techniques. In this case, the DNA-affinity resins/beads are generated by covalent attachment to the resin of a small synthetic double stranded oligonucleotide corresponding to the recognition site of the DNA binding activity, or a small DNA fragment corresponding to the recognition site of the DNA binding activity, or a DNA segment containing tandemly iterated versions of the recognition site of the DNA binding activity. Alternatively, molecular cloning strategies can be used to identify proteins that specifically bind GPCR gene regulatory DNA elements. For example, a Drosophila cDNA library in an *E. coli* expression vector, such as the lambda-gt11 vector, can be screened for Drosophila cDNAs that encode GPCR gene regulatory element DNA-binding activity by probing the library with a labeled DNA fragment, or synthetic oligonucleotide, derived from the gene regulatory DNA, preferably using a DNA region where specific protein binding has already been demonstrated with a protein-DNA binding assay described above (Singh et al., 1989, Biotechniques 7:252–261). Similarly, the yeast "one-hybrid" system can be used as another molecular cloning strategy (Li and Herskowitz, 1993, Science 262:1870–1874; Luo et al., 1996, Biotechniques 20:564–568; Vidal et al., 1996, Proc. Natl. Acad. Sci. U.S.A. 93:10315–10320). In this case, the gene regulatory DNA element is operably fused as an upstream activating sequence (UAS) to one, or typically more, yeast reporter genes such as the lacZ gene, the URA3 gene, the LEU2 gene, the HIS3 gene, or the LYS2 gene, and the reporter gene fusion construct(s) inserted into an appropriate yeast host strain. It is expected that in the engineered yeast host strain the reporter genes will not be transcriptionally active, for lack of a transcriptional activator protein to bind the UAS derived from the Drosophila GPCR gene regulatory DNA. The engineered yeast host strain can be transformed with a library of Drosophila cDNAs inserted in a yeast activation domain fusion protein expression vector, e.g. pGAD, where the coding regions of the Drosophila cDNA inserts are fused to a functional yeast activation domain coding segment, such as those derived from the GAL4 or VPI6 activators. Transformed yeast cells that acquire Drosophila cDNAs that encode proteins that bind the Drosophila GPCR gene regulatory element can be identified based on the concerted activation the reporter genes, either by genetic selection for prototrophy (e.g. LEU2, HIS3, or LYS2 reporters) or by screening with chromogenic substrates (lacZ reporter) by methods known in the art.

5.14. Use of Drosophila Protein as a Media Supplement for Growth and Maintenance of Insect Cells in Culture The present invention provides for the use of Drosophila GPCRs or fragments or derivatives thereof or ligands thereto as media additives. Such additives may modify growth, differentiation and/or maintenance of cells in culture. As signaling proteins, GPCRs may be useful to provide one or more of these functions.

Examples of known culture media that are commonly used to maintain Drosophila and other insect cell lines include Schneider's medium (Schneider, 1964, J. Exp. Zool. 156:91–103), D-22 (Echalier and Ohanessian, 1970, In Vitro 6:162–172), M3 (Shields and Sang, 1977, Drosophila Information Service 52:161), and commercially-available media such as HyQ-CCM3 (HyClone Laboratories, Inc., Logan, Utah), Sf-900 II (Life Technologies, Inc., Rockville, Md.), Grace's insect medium (Life Technologies, Inc., Rockville, Md.), IPL-41 insect medium (Life Technologies, Inc., Rockville, Md.), TC-100 insect medium (Life Technologies, Inc., Rockville, Md.), Ex-Cell 401 (JRH Biosciences, Lenexa, Kans.), and TMN-FH (PharMingen, San Diego, Calif.). However, not all insect cells can be propagated effectively in these available media. Furthermore, it is difficult and time consuming to wean cells onto serum-free media for large-scale protein production. Accordingly, a need exists for novel media additive capable of modifying growth, differentiation and/or maintenance of cells in culture.

In a specific embodiment, a fly GPCR protein or fragment (or ligand thereto) is used to facilitate the in vitro cultivation of Drosophila or other insect cells. Insect cell lines are widely used for basic research in cell and molecular biology. Also, Drosophila and other insect cell lines have application as a preferred system for developing cell-based assays for insecticide targets, particularly those that might be amenable to high-throughput screening methods (see U.S. Pat. Nos. 5,767,261; 5,487,986; 5,641,652; 5,593,862; 5,593,864; 5,550,049; 5,514,578).

In another embodiment, the Drosophila GPCR proteins are employed for the in vitro cultivation of Drosophila and other insect cell lines used as host cells for the economical production of recombinant proteins on laboratory, pilot, or commercial scales (Johansen et al., 1989, Genes Dev. 3:882–889; Culp et al., 1991, Biotechnology 9:173–177; Kirkpatrick et al., 1995, J. Biol. Chem. 270:19800–19805; Griffiths and Page, 1997, Methods Mol. Biol. 75:427–40; McCarroll and King, 1997, Curr. Opin. Biotechnol. 8:590–594; Merrington et al., 1997, Mol. Biotechnol. 8:283–297; Possee, 1997, Curr. Opin. Biotechnol. 8:569–572). Further, the Drosophila and other insect cell lines can be used as hosts for the large-scale growth in vitro of viruses or bacteria that can be used as commercial insect control agents (Zhou et al., 1998, Proc. R. Soc. Lond. B. Biol. Sci. 265:509–515; Miltenburger, 1980, Dev. Biol. Stand. 46:295–300; Miltenburger and Reimann, 1980, Dev. Biol. Stand. 46:217–22; Shuler, et al., 1990, Ann. N.Y. Acad. Sci. 589:399–422).

5.15. Pesticidal Uses of Drosophila Genes

In another embodiment of the invention, Drosophila genes may be used in controlling agriculturally important pest species. For example, the GPCR proteins disclosed herein, or analogs or derivatives thereof or ligands thereof or interactors thereto, may have activity in modifying the growth, feeding and/or reproduction of crop-damaging invertebrate pest species including insects, arachnids and acarids, molluscs, nematodes and other helminths. Such pest species include urban pests (e.g., cockroaches), agricultural crop pests (e.g., Colorado potato beetle, European corn borer), human and animal pests (e.g., mosquitoes, fleas, ticks, biting flies, parasitic nematodes, chiggers, mites), hygienic and esthetic pests (e.g., ants, clothes moths, flour beetles), home and garden pests (e.g., cockroaches, fleas, spiders), and pests posing a threat to the integrity of man-made structures including houses and marine piers (e.g., wood-boring pests such as termites, and marine pests such as snails and barnicles). In general, effective pesticides exert a disabling activity on the target pest, such as lethality, sterility, paralysis, blocked development, or cessation of feeding. Such pests may include but are not limited to egg, larval, juvenile and adult forms of dipterans (flies, mosquitos), lepidopterans (moths, caterpillars), coleopterans (beetles), hymenopterans (ants, wasps), homopterans (aphids, leafhoppers), hemipterans (lice), siphonapterans (fleas), isopterans (termites), blattarians (roaches), orthopterans (grasshoppers, locusts), arachnids (spiders, scorpions), and acarids (mites, ticks).

Tests for such activities can be carried out by any method known in the art. Pesticides comprising the nucleic acids of Drosophila GPCRs may be prepared in a suitable vector for delivery to a plant or animal. Such vectors include but are not limited to Agrobacterium tumefaciens Ti plasmid-based vectors for the generation of transgenic plants (Horsch et al., 1984, Science 233:496–489; Fraley et al., 1983, Proc. Natl. Acad. Sci. U.S.A. 80:4803) or recombinant cauliflower mosaic virus for the incoulation of plant cells or plants (Hohn et al., 1982, In Molecular Biology of Plant Tumors, Academic Press, New York, pp 549–560; Howell, U.S. Pat. No. 4,407,956); retrovirus-based vectors for the introduction of genes into vertebrate animals (Burns et al., 1993, Proc. Natl. Acad. Sci. U.S.A. 90:8033–8037); and vectors based on transposable elements such a P (Rubin and Spradling, 1982, Science 218:348–353), minos (Loukeris et al., 1995, Proc. Natl. Acad. Sci. U.S.A. 92:9485–9489), Hermes (O'Brochta et al., 1996, Genetics 142: 907–914), mariner (Coates et al., 1998, Proc. Natl. Acad. Sci. U.S.A. 95:3748–3751), or PiggyBac (Handler et al., 1998, Proc. Natl. Acad. Sci. U.S.A. 95:7520–7525) for.the introduction of genes into insects. For example, transgenic insects can be generated using a transgene comprising a GPCR gene operably fused to an appropriate inducible promoter. For example, a tTA-responsive promoter may be used (see above) in order to direct expression of the protein at an appropriate time in the life cycle of the insect. In this way, one may test efficacy as an insecticide in, for example, the larval phase of the life cycle (i.e., when feeding does the greatest damage to crops).

Further, recombinant or synthetic GPCR proteins, analogs, fragments, derivatives, ligands or interactors can be assayed for insecticidal activity by injection of solutions of proteins into the hemolymph of insect larvae (Blackburn et al., 1998, Appl. Environ. Microbiol. 64:3036–3041; Bowen and Ensign, 1998, Appl. Environ. Microbiol. 64:3029–3035). Still further, transgenic plants that express proteins can be tested for activity against insect pests (Estruch et al., 1997, Nat. Biotechnol. 15:137–141).

In a preferred embodiment, GPCR and other fly genes can be tested as insect control agents in the form of recombinant viruses that direct the expression of an gene in the target pest. Suitable recombinant virus systems for expression of proteins in infected insect cells include but are not limited to recombinant Semliki Forest virus (DiCiommo and Bremner, 1998, J. Biol. Chem. 273:18060–18066), recombinant sindbis virus (Higgs et al., 1995, Insect Mol. Biol. 4:97–103; Seabaugh et al., 1998, Virology 243:99–112), recombinant pantropic retrovirus (Matsubara et al., 1996, Proc. Natl. Acad. Sci. U.S.A. 93:6181–6185; Jordan et al., 1998, Insect Mol. Biol. 7:215–222), and most preferably recombinant baculovirus. Use of recombinant baculoviruses as a means to engineer expression of toxic proteins in insects, and as insect control agents, is well known in the art. This approach has a number of specific advantages including host specificity, environmental safety, the availability of easily manipulable vector systems, and the potential use of the recombinant virus directly as a pesticide without the need for purification or formulation of the protein (Cory and Bishop, 1997, Mol. Biotechnol. 7:303–313; U.S. Pat. Nos. 5,470,735; 5,352,451; 5,770,192; 5,759,809; 5,665,349; 5,554,592). Thus, recombinant baculoviruses that direct the expression of GPCR or other identified genes can be used for both testing the pesticidal activity of proteins under controlled laboratory conditions, and as insect control agents in the field. One disadvantage of wild type baculoviruses as insect control agents can be the amount of time between application of the virus and death of the target insect, typically one to two weeks. During this period, the insect larvae continue to feed and damage crops. Consequently, there is a need to develop improved baculovirus-derived insect control agents which result in a rapid cessation of feeding of infected target insects.

Mutational anaylsis of GPCR genes may also be used in connection with the control of agriculturally-important pests. In this regard, mutational analysis of genes encoding GPCRs in Drosophila provides a rational approach to determine the precise biological function of this class of proteins in invertebrates. Further, mutational analysis provides a means to validate potential pesticide targets that are constituents of these signaling pathways.

Drosophila GPCR genes, proteins, derivatives, fragments, analogs, and ligands and interactors thereof may be formulated with any carrier suitable for agricultural use, such as water, organic solvents and/or inorganic solvents. The pesticide composition may be in the form of a solid or liquid composition and may be prepared by fundamental formulation processes including but not limited to dissolving, mixing, milling, granulating, and dispersing.

The present invention encompasses compositions containing a Drosophila GPCR protein or gene in a mixture with agriculturally acceptable excipients known in the art, including but not limited to vehicles, carriers, binders, UV blockers, adhesives, hemecants, thickeners, dispersing agents, preservatives and insect attractants. Thus the compositions of the invention may, for example, be formulated as a solid comprising the active agent and a finely divided solid carrier. Alternatively, the active agent may be contained in liquid compositions including dispersions, emulsions and suspensions thereof. Any suitable final formulation may be used, including for example, granules, powder, bait pellets (a solid composition containing the active agent and an insect attractant or food substance), microcapsules, water dispersible granules, emulsions and emulsified concentrates.

Examples of adjuvant or carriers suitable for use with the present invention include but are not limited to water, organic solvent, inorganic solvent, talc, pyrophyllite, synthetic fine silica, attapugus clay, kieselguhr chalk, diatomaceous earth, lime, calcium carbonate, bontonite, fuller's earth, cottonseed hulls, wheat flour, soybean flour, pumice, tripoli, wood flour, walnut shell flour, redwood flour, and lignin.

The compositions of the present invention may also include conventional insecticidal agents and/or may be applied in conjunction with conventional insecticidal agents.

5.16. Uses of Drosophila EST Sequences

As described herein, the oligonucleotides comprising all or a portion of the nucleotide sequences having SEQ ID NOs listed in Table 1 can be used for a wide variety of purposes, e.g., mapping, double-stranded RNAi interference (described above), cloning of full-length genes, and in microarrays representing all or a portion (preferably, a majority) of the genes of Drosophila. A microarray, further described in section 5.17 below, is preferably used to detect or measure expression of the RNAs (or cDNAs derived therefrom) that hybridize to the oligonucleotides.

5.16.1. Use As Mapping Tools

Drosophila ESTs and sequence contigs derived from ESTs are useful as molecular markers to relate individual genes and proteins to the physical and genetic map of the genome of Drosophila melanogaster, and are particularly useful for assembly of a transcript map of the entire genome. Such transcript maps are important tools for rapidly identifying, mapping and characterizing mutant genes that arise from large scale genetic screens, such as those described herein. Drosophila ESTs can be connected to the physical map of the genome using a variety of methods known in the art. Individual ESTs can be mapped to specific cytogenetic locations by in situ hybridization of EST-derived DNA probes to Drosophila polytene chromosomes (Pardue, 1994, Meth. Cell Biol. 44: 333–351). Also, individual ESTs can be assigned to specific genomic locations by mapping each EST with respect to arrayed libraries of large insert genomic clones, such as cosmid, P1, BAC or YAC libraries, where the genomic clones have been assembled into contigs and have themselves been mapped to cytogenetic locations on polytene chromosomes (Kimmerly et al., 1996, Genome Research 6: 414–430; Rubin, 1996, Genome Research 6: 71–79). Mapping ESTs with respect to arrayed large-insert genomic libraries can be carried out using the EST DNA as a hybridization probe with filters containing spotted clones from the arrayed genomic library. Alternatively, the EST sequences can be used to design PCR primers for mapping to large-insert genomic clones using a so-called STS content approach (Kimmerly et al., 1996, Genome Research 6: 414–430). Because EST sequences are expected to be reasonably uniformly distributed throughout the euchromatic regions of the genome, these sequences also have utility for the identification of single nucleotide polymorphisms (SNPs) which can be employed as molecular markers for moderate and high resolution genetic mapping of genes (WO 98/38846). Specific SNP alleles in different Drosophila stocks, which can be used as markers for genetic mapping, can be identified using any of several different methods including direct DNA sequencing, denaturing gradient gel electrophoresis (Erlich, ed., 1992, PCR Technology, Principles and Applications for DNA Amplification, W H Freeman and Co., New York, Chapter 7), single-stranded conformation polymorphism analysis (Orita et al., 1989, Proc. Natl. Acad. Sci. U.S.A. 86, 1766–1770), and denaturing high pressure liquid chromatography.

5.16.2. Use for Full-Length Cloning and Proteomics

Drosophila ESTs and sequence contigs derived from ESTs are useful as tools for retrieval of full-length protein coding sequences, and for proteomics analysis.

Full-length Cloning

Full length cloning of genes based on the EST information can be accomplished using at least two different methods: (a) Rapid Amplification of cDNA Ends (RACE); and/or (b) hybridization of a nucleic acid comprising an EST to a library of full-length cDNA clones. RACE is a rapid, PCR-based technique for obtaining full-length cDNA clones when a partial cDNA sequence is available (Frohman et al., 1988, Proc. Natl. Acad. Sci. U.S.A. 85:8998–9002; Zhang et al., 1997, Meth. Mol. Biol. 69:61–87). First, PCR is used to amplify partial cDNAs from the the region between a single point in an mRNA transcript and its 3' or 5' end. For this procedure, a short internal stretch of sequence (such as an EST) must already be known from the mRNA of interest. From this sequence, gene-specific primers are chosen that are oriented in the direction of the missing sequence. Extension of the partial cDNAs from the unknown end of the message back to the known region is achieved using primers that anneal to the preexisting poly $A^+$ tail at the 3' end, or to an appended homopolymer oligonucleotide tail at the 5' end.

In one RACE variation, total RNA is first purified from cells of interest. Oligo-dT primers are then used to isolate the poly $A^+$mRNA from total RNA. This step enhances successful isolation of 3'RACE products. An RNA anchor oligo may also be attached to the 5' end of the mRNA. This step permits successful isolation of 5' RACE products. First and second strand cDNAs are then synthesized from mRNA, and RACE PCR reactions are carried out. Full-length cDNAs can then be generated by end-to-end amplification using 5' and 3' gene-specific primers, or by ligating the two fragments using a unique restriction site in the overlapping CDNA sequence. The resulting product can then be cloned and sequenced. In another RACE variation, first and second-strand cDNAs are synthesized from mRNA, and adaptors are ligated to the 5' end of the double-stranded cDNA population.

Another method of obtaining full-length cDNA clones from partial cDNA sequences such as ESTs is by hybridization of the partial cDNA clones, or PCR products amplified therefrom, to a library of full-length cDNA clones. (see e.g., Ausubel et al., 1999, In: Current Protocols in Molecular Biology, John Wiley & Sons, Inc., New York). Briefly, the library is first plated onto nutrient agar plates at a high enough density to allow separation of individual clones. Nitrocellulose or nylon membranes the exact size of the plate are then placed over the clones, marked, and then lifted. In this way, an accurate replica representation of the clones on a plate is made on the membrane which contacted the plate. The DNA from clone replicas on each membrane is denatured and fixed. Specific clones are then identified by hybridization to a labeled nucleic acid, such as an EST, representing the cDNA of interest. Positive clones are identified and isolated by aligning the original nutrient agar plate with the resulting autoradiograph from the hybridization to the labeled EST. Labeling of EST cDNA for hybridization can be accomplished by a variety of methods well known in the art. A preferred method is the Rediprime labeling system, available from Amersham (Amersham Pharmacia Biotech, U.S.A.). This system is based on random labeling and uses radioactive dCTP. Unincorporated nucleotides can be removed using, e.g., Clontech spin columns as per manufacturer's suggestions. Hybridizations may be carried out in a solution containing 5×SSC, 0.5%SDS, 5×Denhardt's and 0.2 mg/ml sonicated fish sperm DNA, at 65° C. Washes are carried out at 65° C. with a solution containing 0.1×SSC and 0.1%SDS, three times, for 20 minutes each.

Proteomics

The EST sequences of the invention provide novel sequences useful in proteomics analysis. Genome sequencing efforts provide a wealth of data on DNA and RNA sequences. Proteomics, the study of all the proteins of an organism, aims to supplement the gene sequence data with information on how the gene sequences predict their respective protein sequences, what proteins are made where, in what amounts, and under what conditions. Proteomics further aims to show how protein cascades inside cells change as a result of specific diseases, thereby identifying novel prospective drug targets. Proteomics still further aims to validate particular drug leads against identified prospective targets by providing information on how lead compounds interact with and affect proteome cascades (e.g., signal transduction pathways).

From a technological standpoint, the essence of proteomics analysis is protein characterization. As such, the oldest technique known for accomplishing this task is protein sequencing using Edman Degradation (Edman, 1950, Acta Chem. Scand. 4, 282–283; Wasinger et al., 1995, Electrophoresis 16, 1090–1094). Mass spectrometry (MS) methods have also been developed as alternatives to Edman sequencing. With this approach, proteins and peptides are first digested, either chemically or enzymatically, to produce a unique degradation pattern that can then be analyzed by MS (Henzel et al., 1993, Proc. Natl. Acad. Sci. U.S.A. 90, 5011–5015). Another essential and heavily-used technique for charaterization of protein expression patterns is 2-dimensional gel electrophoresis (2-DE). At high resolution, this powerful technique produces gels containing up to 10,000 distinct protein and peptide spots (Klose et al., 1995, Electrophoresis 16, 1034–1059).

Analysis of 2-DE and MS data is an integral part of the proteomics approach. Currently, 2-DE gel patterns are scanned into a computer and analyzed using algorithms that quantitate the different gel patterns that arise when a proteome complement of a cell is obtained under normal or altered states (Taylor et al., 1982, Clin. Chem. 28, 861–866). Computer algorithms are also used to analyze data from peptide mass fingerprints. One method relies on comparing the actual MS spectrum of a test sample to a database of predicted spectra (Yates et al., 1993, Anal. Biochem. 214, 397–408; Yates, 1998, J. Mass Spec. 33, 1–19).

5.17. Use of Drosophlia ESTs in Microarrays

As mentioned above, the oligonucleotides comprising all or a portion of the nucleotide sequences having SEQ ID NOs listed in Table 1 can be used in microarrays representing all or a portion (preferably, a majority) of the genes of Drosophila. A microarray, as stated above, is preferably used to detect or measure expression of the RNAs (or cDNAs derived therefrom) that hybridize to the oligonucleotides. In one embodiment, a microarray is used to detect or measure the expression of genes which function in any given pathway-of-interest (such as a GPCR pathway). In another embodiment, a microarray is used to detect or measure the expression of genes which function in a GPCR pathway (e.g., a fly $GABA_B$ pathway or a fly melatonin receptor pathway) or another pathway (e.g., a fly chitin synthase 2 pathway or a fly sphingomyelinase pathway).

The present invention further relates to methods for using proteins and nucleotide sequences of a Drosophila pathway gene as a drug target. The invention still further relates to pharmaceutical compositions comprising a pharmaceutically acceptable carrier and a fragment or other derivative or analog of such fly pathway proteins (e.g., a protein encoded by a gene in a GPCR-pathway) which may be used, e.g., as a pesticide target.

In one embodiment, expressed sequence tags (ESTs), or contigs comprising EST sequence, may be used to construct a microarray. For example, any number of EST cDNAs of interest, or fragments thereof, may be attached to a solid support to construct a microarray.

In a preferred embodiment, a microarray is constructed using DNA fragments of from 10 to 300, of from 15 to 150, of from 20 to 75, or of from 25 to 50 nucleotides in length.

5.17.1. Constructing a Microarray

In a preferred embodiment of the invention, an initial step in identifying expression of a gene or gene family, or quantitating same, is by the construction of a DNA microarray from any number of novel ESTs of the invention (SEQ ID NOs:15,289–31,635) or from any number of the contigs of the invention (SEQ ID NOs:7–15,288). In another preferred embodiment, a microarray of the invention comprises a surface with an ordered array of binding (e.g., hybridization) sites for products ranging from 2 to 20,000, from 5 to 15,000, from 10 to 10,000, from 20 to 5,000, from 50 to 2,500, from 100 to 1,000, or from 200 to 500 of the genes in the genome of Drosophila. In yet another embodiment, the microarray comprises at least a portion of at least 17 contiguous nucleotides of one or more novel ESTs of the invention (i.e., SEQ ID NOs:15,289–31,635). In another embodiment, a microarray is an array of less than 6.25 cm$^2$ in size. Microarrays may be employed, e.g., for analyzing the transcriptional status of a cell, i.e., as a measure of the genes in a genome that are and are not expressed, and if expressed, to what extent.

Microarrays can be made in a number of ways well known in the art, of which several are described below. However produced, microarrays share certain characteristics. The arrays are reproducible, allowing multiple copies of a given array to be produced and compared with one another. Preferably, the microarrays are small, usually smaller than 5 cm$^2$ and they are made from materials that are stable under binding (e.g., nucleic acid hybridization) conditions. Preferably, a given binding site or unique set of binding sites in the microarray will specifically bind (e.g., hybridize) to the product of a single gene in a cell (e.g., to a specific mRNA, or to a specific cDNA derived therefrom). However, in general, other related or similar sequences will cross hybridize to a given binding site. Although there may be more than one physical binding site per specific RNA or DNA, for the sake of clarity, the discussion below will assume that there is a single, completely complementary binding site.

The microarrays of the present invention include one or more test binding sites, each of which has a polynucleotide sequence that is complementary to a subsequence of RNA or DNA to be detected. Each binding site preferably has a different nucleic acid sequence. The position of each binding site on the solid surface is preferably known. In one embodiment, the microarray is a high density array, preferably having a density greater than about 60 different binding sites per cm$^2$. In another embodiment, the microarray is an array (i.e., a matrix) in which each position represents a discrete binding site for a product encoded by a gene (i.e., an mRNA or a cDNA derived therefrom), and in which binding sites are present for products of most or almost all of the genes in the organism's genome. For example, the binding site can be a DNA or DNA analogue to which a particular RNA can specifically hybridize. The DNA or DNA analogue can be, e.g., a synthetic oligomer, a full-length cDNA, a less-than-full-length cDNA, or a gene fragment. In a specific embodiment, a DNA microarray, or chip, is a microscopic array of DNA fragments or synthetic oligonucleotides, disposed in a defined pattern on a solid support, wherein they are amenable to analysis by standard hybridization methods (Schena, *BioEssays* 18, 427, 1996, which is incorporated herein by reference in its entirety).

In another specific embodiment, the DNA in a microarray is derived from genomic or cDNA libraries, from fully-sequenced clones, or from partially or fully sequenced cDNAs known as expressed sequence tags (ESTs). In a preferred embodiment, the DNA in a microarray is derived from one or more novel fly ESTs of the invention (SEQ ID NOs:15,289–31,365) or contigs comprising novel EST sequence (SEQ ID NOs:7–15,288). Methods for obtaining such DNA molecules are generally known in the art (see e.g., Ausbel et al., eds., 1994, Current Protocols in Molecular Biology, New York). In another embodiment, oligonucleotides may be synthesized by conventional methods, such as phosphoramidite-based synthesis. Oligonucleotides for microarrays may range in length from 10 to 300 bases, but are preferably from about 20 to about 50 bases in length, and most preferably about 25 bases in length (i.e. 25 mers). In a further embodiment, where the particular base in a given sequence is unknown or is polymorphic, a universal base, such as inosine or 5-nitroindole, may be substituted. Additionally, it is possible to vary the charge on the phosphate backbone of the oligonucleotide, for example, by thiolation or methylation, or even to use a peptide rather than a phosphate backbone (i.e., as for peptide nucleic acid or PNA).

Although in a preferred embodiment the microarray contains binding sites for products of almost all genes in the fly genome, such comprehensiveness is not necessarily required. A microarray may have binding sites corresponding to at least about 1% or less of the genes in the genome (e.g., as for a chip for detection of a family of related genes). Further, where most of the genome is to be represented on a chip, a microarray may have binding sites corresponding to about 50%, about 75%, about 90%, or about 99% of the genes in the genome. Preferably, the microarray has binding sites for genes relevant to the action of a drug of interest or for a collection of genes that participate in a biological pathway of interest. The number of genes in a genome can be estimated from the number of mRNAs expressed by the organism, or by extrapolation from a well characterized portion of the genome.

5.17.2. Preparing Binding Sites for Microarrays

As noted above, the "binding site" to which a particular polynucleotide molecule specifically hybridizes according to the invention is usually a complementary polynucleotide sequence. In one embodiment, the binding sites of the microarray are DNA or DNA "mimics" (e.g., derivatives and analogues such as PNA) corresponding to at least a portion of two or more genes in an organism's genome. In another embodiment, the binding sites of the microarray are complementary RNA or RNA mimics.

DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates and PNA.

DNA can be obtain, e.g., by PCR amplification of gene segments from genomic DNA, cDNA, or other cloned sequences. PCR primers are preferably chosen based on known sequences of the genes or cDNA that result in amplification of unique fragments (e.g, fragments that do not share more than 10 bases of contiguous identical sequence with any other fragment on the microarray). Computer programs that are well known in the art are useful in the design of primer with the required specificity and optimal amplification properties, such as Oligo version 5.0 (National Biosciences). PCR methods are well known in the art, and are described, for example, in Innis et al., eds., 1990, *PCR*

Protocols: A Guide to Methods and Applications, Academic Press, Inc., San Diego. It will be apparent to one skilled in the art that controlled robotic systems are useful for isolating and amplifying nucleic acids.

Another means for generating the polynucleotide binding sites of the microarray is by synthesis of synthetic polynucleotides or oligonucleotides, e.g., using N-phosphonate or phosphoramidite chemistries (Froehler et al., 1986, Nucl. Acid Res. 14, 5399–5407; McBrid et al., 1983, Tetrahedron Lett., 246–248). Synthetic sequences are typically between about 15 and about 500 bases in length, more typically between about 20 and about 60 bases. In another embodiment, synthetic nucleic acids may include non-natural bases, such as inosine. Another example of a suitable nucleic acid analogue is peptide nucleic acid (see e.g., Eghohn et al., 1993, Nature 363:566–568; U.S. Pat. No. 5,539,083).

In alternative embodiments, the hybridization sites (i.e., the binding sites) are made from plasmid or phage clones of genes, cDNAs (e.g., expressed sequence tags), or inserts or fragments derived therefrom (Nguyen et al., 1995, Genomics 29:207–209).

5.17.3. Attaching Binding Sites to a Solid Surface

Solid supports on which binding sites of microarrays may be immobilized are well-known in the art and include filter materials, such as nitrocellulose, cellulose acetate, nylon, and polyester, among others, as well as non-porous materials, such as glass, plastic (e.g., polypropylene), polyacrylamide, and silicon. In general, non-porous supports, and glass in particular, are preferred. The solid support may also be treated in such a way as to enhance binding of oligonucleotides thereto, or to reduce non-specific binding of unwanted substances thereto. For example, it is often desirable to treat a glass support with polylysine or silane to facilitate attachment of binding sites such as oligonucleotides to the glass. A preferred method for attaching binding sites such as nucleic acids to a surface is by printing on glass plates, as is described generally by Schena et al., 1995, Science 270:467–470. This method is especially useful for preparing microarrays of cDNA (See also, DeRisi et al., 1996, Nature Genetics 14:457–460; Shalon et al., 1996, Genome Res. 6:689–645; and Schena et al., 1995, Proc. Natl. Acad. Sci. U.S.A. 93:10539–11286).

Methods of immobilizing binding sites on the solid support may include direct touch, micropipetting (Yershov et al., 1996, Genetics 93: 4913), or the use of controlled electric fields to direct a given oligonucleotide to a specific spot in the array (U.S. Pat. No. 5,605,662 issued to Heller et al.). In a specific embodiment, DNA is typically immobilized at a density of from 100 to 10,000 oligonucleotides per $cm^2$ and preferably at a density of about 1000 oligonucleotides per $cm^2$.

In a preferred embodiment, binding sites (e.g., oligonucleotides) are synthesized directly on said support (Maskos et al., 1993, Nucl. Acids Res. 21, 2267; Fodor et al., 1991, Science 281, 767; Blanchard et al., 1996, Biosens. Bioelectron. 11, 687). Among methods of synthesizing oligonucleotides directly on a solid support, particularly preferred method are photolithography (see e.g., Fodor, supra., and McGall et al.,1996, Proc. Natl. Acad. Sci. U.S.A. 93: 13,555) and most preferred, piezoelectric printing (see e.g., Blanchard, supra).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Science 251:767–773; Pease et al., 1994, Proc. Natl. Acad. Sci. U.S.A. 91:5022–5026; Lockhart et al., 1996, Nature Biotechnology 14:1675; U.S. Pat. Nos. 5,578,832, 5,556,752 and 5,510,270) or other methods for rapid synthesis and deposition of defined oligonucleotides (Blanchard et al., Biosensors & Bioelectronics 11:687–690). When these methods are used, oligonucleotides (e.g., 20-mers) of known sequence are synthesized directly on a surface such as a derivatized glass slides. Usually, the array produced is redundant, with several oligonucleotide molecules per RNA.

Other methods for making microarrays, e.g., by masking (Maskos and Southern, 1992, Nuc. Acids. Res. 20:1679–1684), may also be used. In principle, any type of array, for example, dot blots on a nylon hybridization membrane (see Sambrook et al., supra) could be used. However, as will be recognized by those skilled in the art, very small arrays will frequently be preferred because, e.g., hybridization volumes will be smaller.

5.17.4. Hybridizing Target Polynucleotides to a Microarray

As described, supra, the polynucleotide molecules which may be analyzed by the present invention may be from any source, including naturally-occurring nucleic acid molecules, as well as synthetic nucleic acid molecules. In a preferred embodiment, the polynucleotide molecules analyzed by the invention comprise RNA, including, but not limited to, total cellular RNA, poly $A^+$ RNA, fractions thereof, or RNA transcribed from cDNA. In a specific embodiment, cellular RNA or DNAs from two cell populations (e.g., RNA of Drosophila untreated or treated with a specific drug) are analyzed by incubating both populations of RNAs with the microarray. In a specific embodiment, Drosophila are treated with an agent known or suspected to alter a pathway of interest. In yet another specific embodiment, Drosophila containing a deletion mutation is used to identify gene function. Methods for preparing total and poly $A^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation (Chirgwin et al., 1979, Biochemistry 18:5294–5299). Poly $A^+$ RNA is selected by selection with oligo-dT cellulose. Cells of interest include, but are by no means limited to, wild-type cells, drug-exposed wild-type cells, modified cells, diseased cells, and, in a particular embodiment, cancer cells.

In one embodiment, RNA can be fragmented by methods known in the art, e.g., by incubation with $ZnCl_2$, to generate fragments of RNA prior to analysis using a microarray. In another embodiment, isolated mRNA can be converted to antisense RNA synthesized by in vitro transcription of double-stranded cDNA in the presence of labeled dNTPs (Lockhart et al., 1996, Nature Biotechnology 14:1675).

5.17.5. Hybridization to Microarrays

Nucleic acid hybridization and wash conditions are chosen for microarrays so that the polynucleotide molecules to be analyzed "specifically bind" or "specifically hybridize" to the complementary polynucleotide sequences of the array, preferably to a specific array site, wherein its complementary DNA is located.

Arrays containing double-stranded DNA situated thereon are preferably subjected to denaturing conditions to render the DNA single-stranded prior to contacting with the target polynucleotide molecules. Arrays containing single-stranded binding site DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA or DNA) of binding site and target nucleic acids. General parameters for specific (i.e., stringent) hybridization conditions are described in Sambrook et al. (supra), and in Ausubel et al., 1987, *Current Protocols in Molecular Biology*, Greene Publishing and Wiley-Interscience, New York. When the CDNA microarrays of Schena et al. are used, typical hybridization conditions are hybridization in 5×SSC plus 0.2% SDS at 65° C. for four hours, followed by washes at 25° C. in high stringency wash buffer (0.1×SSC plus 0.2% SDS) (Shena et al., 1996, Proc. Natl. Acad. Sci. U.S.A. 93:10614). Useful hybridization conditions are also provided, e.g., in Tijessen, 1993, *Hybridization With Nucleic Acid Probes*, Elsevier Science Publishers B.V.; and in Kricka, 1992, *Nonisotopic DNA Probe Techniques*, Academic Press, San Diego.

In a another specific embodiment, use of a nucleic acid which is hybridizable to a fly GPCR nucleic acid (e.g., having a sequence or subsequence of at least 17 nucleotides as set forth in SEQ ID NO:1, SEQ ID NO:3, SEQ ID NO:5 or SEQ ID NO:741, or to its reverse complement) under conditions of low, moderate, or high stringency is provided. By way of example and not limitation, procedures using conditions of low stringency are as follows (see also Shilo and Weinberg, 1981, Proc. Natl. Acad. Sci. U.S.A. 78, 6789–6792). Arrays containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Arrays are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Arrays are blotted dry and visualized. If necessary, arrays are washed for a third time at 65–68° C. and re-visualized. Other conditions of low stringency which may be used are well known in the art (e.g., as employed for cross-species hybridizations).

In another specific embodiment, use of a nucleic acid which is hybridizable to a GPCR nucleic acid, or its reverse complement, under conditions of high stringency is provided. By way of example and not limitation, procedures using such conditions of high stringency are as follows. Prehybridization of arrays containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Arrays are hybridized for 48 h at 65° C. in prehybridization mixture containing 100 µg/ml denatured salmon sperm DNA and 5–20×10$^6$ cpm of $^{32}$P-labeled probe. Washing of arrays is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In another embodiment, after hybridization, stringency conditions are as follows. Each array is washed two times each for 30 minutes each at 45° C. in 40 mM sodium phosphate, pH 7,2, 5% SDS, 1 mM EDTA, 0.5% bovine serum albumin, followed by four washes each for 30 minutes in sodium phosphate, pH 7.2, 1% SDS, 1 mM EDTA, and subsequently each array is treated differently as described below for low, medium, or high stringency hybridization conditions. For low stringency hybridization, arrays are not washed further. For medium stringency hybridization, membranes are additionally subjected to four washes each for 30 minutes in 40 mM sodium phosphate, pH 7.2, 1% SDS, 1 mM EDTA at 55° C. For high stringency hybridization, following the washes for low stringency, membranes are additionally subjected to four washes each for 30 minutes in 40 mM sodium phosphate, pH 7.2, 1% SDS, 1 mM EDTA at 55° C., followed by four washes each for 30 minutes in sodium phosphate, pH 7.2, 1% SDS, 1 mM EDTA at 65° C.

Use of nucleic acids encoding derivatives and analogs of proteins in a signal transduction pathway of interest (e.g., a GPCR pathway) are additionally provided.

5.17.6. Signal Detection on Hybridized Microarrays

It will be appreciated that when cDNA complementary to the mRNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells or organisms (e.g. untreated and drug treated flies or fly parts) are hybridized to the binding sites of the microarray. In the case of drug responses, one cell is exposed to a drug and another cell of the same type is not exposed to the drug. The cDNA derived from each of the two cell types are differently labeled so that they can be distinguished. In one embodiment, for example, cDNA from a cell treated with a drug is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA is thereby detected.

In the example described above, the cDNA from the drug-treated cell will fluoresce green when the fluorophore is stimulated, and the cDNA from the untreated cell will fluoresce red. As a result, when the drug treatment has no effect, either directly or indirectly, on the relative abundance of a particular mRNA in a cell, the mRNA will be equally prevalent in both cells, and, upon reverse transcription, red-labeled and green-labeled cDNA will be equally prevalent. When hybridized to the microarray, the binding site(s) for that species of RNA will emit wavelength characteristic of both fluorophores. In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described (see e.g., Shena et al., 1995, *Science* 270, 467–470).

When fluorescently labeled probes are used, the fluorescence emissions at each site of a transcript array can be, preferably, detected by scanning confocal laser microscopy (see e.g., Fodor et al., 1993, Nature 364:555). In a specific embodiment, where the sample to be hybridized is a cDNA, labeling is accomplished by incorporating fluoresecently-labeled deoxynucleotide triphosphates (dNTPs), during in vitro reverse transcription. Fluorescently-labeled dNTPs are commercially available from sources such as Amersham and Perkin Elmer Cetus. Alternatively, cDNAs are labeled indirectly by incorporating biotinylated nucleotides during cDNA synthesis, followed by the addition of fluorescently-labeled avidin or streptavidin. Biotinylated dNTPS are available from Enzo (Farmingdale, N.Y.) and Boehringer Mannheim (Indianapolis, Ind.), while fluorescently labeled avidin and streptavidin are available from Becton Dickinson (Mountain View, Calif.) and Molecular Probes (Eugene, Oreg.). Methods of reverse transcription and labeling are well-known in the art and are described for example, in Ausbel et al., eds., 1994, Current Protocols in Molecular Biology, New York; DeRisi, 1997, Science 278:680; and Schena et al.,1996, Proc. Natl. Acad Sci. U.S.A. 93:10614.

Alternatively, a laser can be used that allows simultaneous specimen illumination at wavelengths specific to the two fluorophores and emissions from the two fluorophores can be analyzed simultaneously (see Shalon et al., 1996, Genome Res. 6:639–645).

In one embodiment, where the sample to be hybridized is mRNA, labeling is accomplished by incorporating fluoresecently-labeled ribonucleotides or biotinylated ribonucleotides during in vitro transcription, as described in Lockhart, D. J. et al., 1996, Nature Biotech. 14:1675.

Although it is preferred to use fluorescent labels, other labels may also be employed, such as radioisotopes, enzymes, and luminescent substances. Such methods are well-known in the art; (see e.g., Zhao et al.,1997, Gene 156:207).

To probe a DNA microarray, the labeled samples are first hybridized to the microarray such as under hybridization conditions as set forth above. After washing to remove unbound sample, the microarray is excited with specific wavelengths of light and scanned to detect fluorescence. Typically, two samples, each labeled with a different fluor, are hybridized simultaneously to permit differential expression measurements. When neither sample hybridizes to a given spot in the array, no fluorescence is detected. When only one sample hybridizes to a given spot, the color of the resulting fluorescence will correspond to that of the fluor used to label the hybridizing sample (e.g., green when the sample was labeled with fluorescein, or red when the sample was labeled with rhodamine). When both samples hybridize to the same spot, a combined color signal is produced (e.g., yellow if the samples were labeled with fluorescein and rhodamine). Then, by applying routine computer methods of pattern recognition and data analysis, it is possible to quantify differences in gene expression between the samples.

Signals are recorded and, in a preferred embodiment, analyzed by computer.

5.17.7. Database Implementations Systems

Any method known in the art may be used to search the database of the invention containing at least a portion of the sequences of the SEQ ID NOs set forth in Table 1 and Table 2. However, database searches of the invention are preferably executed on an automated system (e.g., a computer system). Accordingly, this invention provides a computer system comprising: (a) a computer-readable medium having computer-readable program code embodied thereon (e.g., all of or a portion of the FlyTag™ contig database, SEQ ID NOs:7–15,288, either alone or together with the sequences of the other SEQ ID NOs of the invention, on permanent or removable storage media such as a CD-ROM or floppy disk) useful for effecting one or more database searches or methods of the invention; and (b) a computer and associated software capable of searching the database.

For example, when searching the Drosophila sequence database of the invention (i.e. FlyTag™) for nucleotide or predicted protein sequences related to a known query sequence (e.g., a vertebrate dopamine receptor), one typically uses a computer program, such as the BLAST suite of programs, to carry out the query. This section describes exemplary computer systems, as well as methods and programs for operating such computer systems, which may be used to perform methods of the invention.

In certain embodiments, a search algorithm used to search the database of the invention may be programmed using mathematical software packages which allow symbolic entry of equations and high-level specification of processing, including the specific algorithms to be used. Such software packages are preferred since they free a user of the need to procedurally program individual equations or algorithms. Exemplary mathematical software packages which may be used include Matlab from Mathworks (Natick, Mass.), Mathematica from Wolfram Research (Champaign, Ill.), or S-Plus from Math Soft (Cambridge, Mass.). Alternative computer systems and software for implementing analytical search methods of the database of the invention will be readily apparent to one of skill in the art.

6. EXAMPLES

The following examples are provided merely as illustrative of various aspects of the invention and shall not be construed to limit the invention in any way.

Commercially available reagents referred to in the examples were used according to manufacturer's instructions unless otherwise indicated.

6.1. Database Construction

Preparation of cDNA Library

Tissue from mixed-stage embryos (0–20 hour), imaginal disks, and adult fly heads were collected and total RNA was prepared. Mitochondrial rRNA was removed from the total RNA by hybridization with biotinylated rRNA-specific oligonucleotides, and the resulting RNA was selected for polyadenylated mRNA. The resulting material was then used to construct a random-primed library. First strand cDNA synthesis was primed using a six nucleotide random primer. The first strand cDNA was then tailed with terminal transferase to add approximately 15 dGTP molecules. The second strand was synthesized using a primer which contained a NotI site followed by a 13 nucleotide C tail to hybridize to the G-tailed first strand cDNA. The double stranded cDNA was ligated with BstXI adaptors and digested with NotI. The cDNA was then sized on an agarose gel and the cDNA greater than 700 bp was purified. The cDNA was then ligated with NotI, BstXI-digested pCDNA-sk$^+$ vector (a derivative of pBluescript) and transformed into bacterial cells (XL1blue). The final complexity of the library was 6×10⁶ independent clones.

The cDNA library was normalized using a modification of the method described by Bonaldo and others (Bonaldo et al., 1996, Genome Research 6:791–806). Biotinylated driver was prepared from the cDNA by PCR amplification of the inserts and allowed to hybridize with single stranded plasmids of the same library. The resulting double stranded forms were removed using streptavidin magnetic beads, and the remaining single stranded plasmids were converted to double stranded molecules using Sequenase (United States Biochemical); the plasmid DNA was stored at −20° C. prior to transformation. Aliquots of the normalized plasmid library were transformed into bacteria (XL1blue or DH10B) and plated at moderate density. The colonies were picked and transferred using a Qbot robot into 384-well master plates containing bacterial growth media. The clones were allowed to grow for 24 hours at 37° C., then the master plates were frozen at −80° C. for storage. The total number of colonies picked for sequencing from the normalized library was 230,000. The master plates were used to inoculate media for growth and preparation of DNA for use as template in sequencing reactions. The sequencing reactions were primarily carried out with a primer that initiated at the 5' end of the cDNA inserts. However, a minor percentage of the clones were also sequenced from the 3' end. Clones were selected for 3' end sequencing based on either further biological interest or the selection of clones that could extend assemblies of contigs (see below). Sequencing reactions were carried out on ABI377s (Applied Biosystems) and used either ABI FS, dirhodamine or BigDye chemistires.

Analysis of sequences were done as follows: the traces generated by the automated sequencers were base-called using the program Phred (Gordon, 1998, Genome Res. 8:195–202), which also assigned quality values to each base. The resulting sequences were trimmed for quality bases using the quality scores; vector sequences were also removed. Each sequence was compared to all other known fly expressed sequence tag (EST) sequences using the specific BLAST program and parameters described in the explanation of Tables provided in section 6 below, and a filter to identify regions of near 100% identity. Sequences with potential overlap were then assembled into contigs using the program Phrap. The resulting assemblies were then compared to existing public databases, and similarity to known proteins was then used to direct translation of the consensus sequence. Where no BLAST similarity was available, the statistically most likely translation based on codon and hexanucleotide preference was used. The Pfam and Prosite collections of protein domains were used to identify motifs in the resulting translations.

6.2. Identification of *D. Melanogaster* GPCR Genes

In one embodiment, a mentioned above, the invention relates to novel GPCR nucleotide and deduced protein sequences. The novel sequences were initially identified by computer comparison of ESTs from cDNA libraries of Drosophila with known sequence databases. The sequences were then analyzed for a variety of uses, including as protein targets for the screening of novel pesticide drugs. For several of the GPCR ESTs identified herein, the complete cDNA sequence was also determined and confirmed by the predicted cDNA sequence of a genomic-derived gene sequence. Four unique Drosophila full-length gene sequences which were determined represent four GPCRs within three structural subclasses, i.e. metabotropic γ-aminobutyric acid subtype B receptors (GABA$_B$), a melatonin-like receptor, and an orphan receptor having greatest similarity to dopamine/adrenergic/octopamine receptors of the class A biogenic amine GPCR subgroup.

Accordingly, in one embodiment, the present invention relates to a product, a composition, or a method of use comprising a Drosophila GPCR cDNA and/or the protein encoded thereby which is highly related to vertebrate GABA$_B$ GPCRs. In this regard, it has recently been demonstrated by several groups that functional GABA$_B$ receptors exist as heterodimers of similar but distinct gene products. This is consistent with the finding here of at least three independent GABA$_B$ receptors in Drosophila. Thus, the active unit for successful drug screening for pesticide drugs or therapeutics for human disease may contain combinations of at least two of the GABA$_B$ receptor subunits of the invention.

In an attempt to discover members of the catecholamine/β-adrenergic receptor family in invertebrates, a sequence related to vertebrate β-adrenergic receptors has been identified from the Drosophila EST library of the invention, and the complete cDNA has been isolated. Although sequence analysis of the predicted protein suggests that it is not a clear member of either the dopamine receptor or adrenergic receptor subfamilies, it is nevertheless found to be most related to these two GPCR subgroups.

A summary of information follows which relates to GPCR-1, GPCR-2 and GPCR-3 predicted ligand-binding domains, signal sequence locations, and transmembrane domain locations.

GPCR-1 (Predicted DOPAD2 or Melatonin Receptor)

The ligand-binding domain for members of this family of receptors is part of the solvent-accessible surface of transmembrane (TM) domains 3, 5 and 7. The transmembrane domains of GPCR-1 are located at approximately amino acid residues 35–51, 74–90, 122–138, 153–169, 202–218, 315–331 and 350–366 (see SEQ ID NO:6 and FIG. 3).

GPCR-2 (Predicted GABA$_B$R-1)

The ligand-binding domain of this class of GPCRs resides in the N-terminal region of the protein, minus the signal peptide. The signal peptide is located at approximately amino acid residues 1–23 of SEQ ID NO:4. The transmembrane domains are located at approximately amino acid residues 278–294, 452–468, 488–504, 563–579, 621–637, 664–680 and 685–701 (see SEQ ID NO:4 and FIG. 2).

GPCR-3

The ligand-binding domain for this receptor is predicted to reside in parts of TM3, TM5 and TM7. The transmembrane domains are located at approximately amino acid residues 151–167, 180–196, 224–240, 261–277, 312–328, 1049–1065 and 1076–1092 (see SEQ ID NO:2 and FIG. 1).

6.2.1. Cloning GPCR-3

A re-sequenced EST clone, CK01.91B.D9, was used as primary starting material for isolation of the complete cDNA sequence for GPCR-3 and for the isolation of a P1 genomic clone encoding the GPCR-3 gene. The genomic clone was analyzed to determine the intron/exon structure of the GPCR-3 gene.

Isolation of a P1 Clone

The insert from clone CK01.91B.D9 was radioactively labeled and used as a probe to screen a Drosophila P1 library filter (Genome Systems, Inc.). The following clones showed positive hybridization signals: DS02125, DS04390, DS03124, DS04877, DS00309, DS06179, DS00214, DS06380, and DS03327.

Four of these clones, i.e. DS02125, DS04390, DS00214, and DS06179, mapped to a region of contig GstD1 spanning cytogenetic bands 87C2 to 87D13, and were chosen for further characterization. Each clone was streaked onto LB/Kanamycin plates and grown overnight at 37° C. The presence of EST sequences in single isolates from the streaks was confirmed by PCR using the following EST-specific primer pairs: ADR-FWD2/ADR-REV2; ADR-FWD3/ADR-REV; and ADR-FWD3/ADR-REV2. DS04390 mapped to the largest genomic region and was chosen for genomic sequencing.

Rapid Amplification of cDNA Ends (RACE)

The following components were used to carry out RACE for isolation of full-length GPCR-3. Poly A+ mRNA from Canton S strain Drosophila embryos (Clontech, lot#7070254) was used as a template and turned into RACE-ready cDNA using Clontech's Marathon cDNA amplification kit (cat#K1802-1), according to manufacturer's instructions. The resultant cDNA was diluted 1:100 and used as template for RACE reactions.

3' and 5' RACE reactions were performed by PCR, using manufacturer's suggestions under the following conditions. Primers were used at a final concentration of 0.2 µM.

Primary 3' RACE:

> Reaction A: Template: RACE-ready cDNA; Primers: ADR-REV2/AP1.
>
> Reaction B: Template: RACE-ready cDNA; Primers: ADR-REV/AP1.

Nested 3' RACE:

> Reaction C: Template: Reaction A product; Primers: ADRR-REV/AP2.
>
> Reaction D: Template: Reaction B product; Primers: ADR3'4/AP2.

All products were resolved on 1.5% agarose gels in kilobase (kb). Bands of approximately 1.4 kb and 1.8 kb were excised from reaction C; bands of approximately 0.9 kb, 1.2 kb, and 1.9 kb were excised form reaction D.

Primary 5' RACE:

> Template: RACE-ready cDNA; Primers: ADRR-FWD2/AP1.

Nested 5' RACE:

> Template: Primary 5' RACE product; Primers: ADR-REV/AP2.

Nested 5' RACE product was run on a 1.5% gel and the approximately 1.2 kb and 1.4 kb bands excised. All excised bands from 3' and 5' RACE reactions were gel-purified (Geneclean II kit, BIO 101) and cloned (PCR II-TOPO kit, Invitrogen), each according to manufacturer's instructions. Colonies were tested by PCR for presence of EST CK01.9B.D9 sequences. DNA was extracted from clones with positive PCR results (Zhou, 1990, Biotechniques 8, 172–173), digested to confirm presence of inserts, and sequenced. Sequences obtained were compared with the genomic sequence from P1 clone DS04390 and EST clone CK01.91B.D9 (Sequencher, Gene Codes Corporation). Primers were then designed using the RACE products to produce full-length CDNA clones by PCR. PCR reactions were carried out according to manufacturer's protocols (Boehringer Mannheim) using the following components.

> Reaction A: Template: RACE-ready cDNA; Primers: cDNA.O.F./cDNA.I.R.
>
> Reaction B: Template: RACE-ready cDNA; Primers: cDNA.I.F./cDNA.I.R.

Reactions were run on a gel and bands of 1.6 kb and 3.5 kb were excised from each reaction, gel-purified, and cloned (PCR II-TOPO kit, Invitrogen). DNA from positive clones was next run on gels, and clones of appropriate size (5.5 and 7.4 kb) were sequenced using several primers as follows: M13 Forward, M13 Reverse, 1350F, 1350R, 2050F, 2050R, 2500F, 2500R, 27REV, 28FWD, 1500R, 400F, 400R, ADR3'4, ADRR-REV, ADRR-FWD2, ADR5'2. All sequencing reactions were analyzed to assemble the contiguous, full-length nucleotide sequence of GPCR-3, the translation of which represents a functional 7-transmembrane domain protein.

The cloning of GPCR-3 (cDNA SEQ ID NO:1) just described was carried out using the following PCR primer sequences.

| | |
|---|---|
| adr3'3 GATCTGAATGCCACATCCGCCCG | (SEQ ID NO:62,486) |
| adr5'1 AGCCCAGAAAGATGGGCGTGAAGG | (SEQ ID NO:62,487) |
| adr5'2 TGGTCCGGATGCAGGGAAATCTCC | (SEQ ID NO:62,488) |
| adrR-Rev TTTCCCTGCATCCGGACCAGTGC | (SEQ ID NO:62,489) |
| adr3'4 GAGCTATCTGCATCCCAGTGACTG | (SEQ ID NO:62,490) |
| adrR-Fwd2 CAGTCACTGGGATGCAGATAGCTC | (SEQ ID NO:62,491) |
| adr-Rev2 TACACGACGGAGGAGCACCTG | (SEQ ID NO:62,492) |
| adr-Fwd3 GCCCATGTGGACGCTGTTAAGG | (SEQ ID NO:62,493) |
| 7B.Fwd TAATCCAAAGTTCTAGAATTCAGC | (SEQ ID NO:62,494) |
| 7C.Rev CAGCGTGTTCGAGGATATCGTGG | (SEQ ID NO:62,495) |
| 28.Fwd CTGAAGCGCCTGATAGAGGACAAC | (SEQ ID NO:62,496) |
| 27.Rev CGGCCTTGTGTTCGGCCTTCC | (SEQ ID NO:62,497) |
| 39.Fwd TGAAGCTAAGCAATACTCGATGTG | (SEQ ID NO:62,498) |
| 4D.Rev CATAACGTCAGCTACACAATTCTC | (SEQ ID NO:62,499) |
| 36.Rev CATTTGACAACATTTCACTTGAAG | (SEQ ID NO:62,500) |
| AdRcDNA.F GGAGCAACTTGAATGAGCTGCGAC | (SEQ ID NO:62,501) |
| AdR400F TAACCAGGCGGAGCTGGAGGAGAG | (SEQ ID NO:62,502) |
| AdR400R CTCTCCTCCAGCTCCGCCTGGTTA | (SEQ ID NO:62,503) |
| AdR1350F ATGTCCCGATGTGCTCGTGGTGG | (SEQ ID NO:62,504) |
| AdR1350R CCACCACGAGCACATCGGGACAT | (SEQ ID NO:62,505) |
| 5.1500R GTTGCGGGCCATTGGGATGAGAAT | (SEQ ID NO:62,506) |
| 5.2050F CAGCTACAACGGATGCGGTGGCGG | (SEQ ID NO:62,507) |

| | |
|---|---|
| 5.2050R CCGCCACCGCATCCGTTGTAGCTG | (SEQ ID NO:62,508) |
| 5.2500F CCGCCGGCCATTTCCGTGCCGAAC | (SEQ ID NO:62,509) |
| 5.2500R GTTCGGCACGGAAATGGCCGGCGG | (SEQ ID NO:62,510) |
| shrt.O.R GAACTTTGGATTAATGTGTATTTT | (SEQ ID NO:62,511) |
| shrt.I.R TTCATTTTGAACATCTTTGAAATG | (SEQ ID NO:62,512) |
| cDNA.I.R ACGAGGGTGGACGAAGCAGGAATG | (SEQ ID NO:62,513) |
| cDNA.O.F AGCATTGGCGGAGCAACTTGAATG | (SEQ ID NO:62,514) |
| cDNA.I.F ACTCAATTGGGCTGCGAAATCGAC | (SEQ ID NO:62,515) |
| M13 Forward GTTTTCCCAGTCACGA | (SEQ ID NO:62,516) |
| M13 Reverse CAGGAAACAGCTATGAC | (SEQ ID NO:62,517) |

The RACE primers used were those included with the Clontech Marathon kit referred to as AP1 and AP2.

The cytogenetic location of the GPCR-3 gene, like the GPCR-4 gene, is 87D.

6.2.2. Cloning GPCR-2

Cloning of GPCR-2 (cDNA SEQ ID NO:3)

Two completely sequenced ESTs (CK01.119B.H9 and CK01.59A.E6) from the cDNA library described in Section 6.1 and one partially sequenced Berkeley Drosophila Genome Project EST (BDGP EST HL01578) were found to form a sequence contig with highest predicted protein sequence similarity to rat $GABA_BR1$. The complete sequence of HL01578 was subsequently obtained by several rounds of "primer walking," i.e. sequencing and analysis followed by design of new primers for additional sequencing reactions into undetermined regions. The clone HL01578 was shown to contain a poly $A^+$ tail, indicating it was a full-length cDNA at the 3' end. However, comparison of the predicted protein coding regions between rat and fly sequences suggested the fly contig was incomplete at the 5' end. Consistent with this analysis, the fly open reading frame (ORF) was "open" at the 5' end (i.e., it did not contain an initiating methionine).

To facilitate determination of the missing 5' sequence, four drosophila P1 genomic DNA clones were identified by probing a filter of arrayed clones (Genome Systems) with a $^{32}P$-labeled probe consisting of a 1.6 kb XhoI fragment of HL01578. The probe was prepared using a RediPrime kit (Amersham) according to the manufacturer's instructions. The filter was pre-hybridized at 65° C. overnight in 30 ml of hybridization buffer (5×SSPE, 5×Denhardt's solution, 0.5% SDS, and 0.1 mg/ml herring sperm DNA). The following day, thirty million cpm of probe was added and the hybridization continued overnight. On the third day, the filter was washed twice for 10 minutes each with wash solution (0.1×SSC and 0.1% SDS) at 65° C. and exposed to film overnight at −70° C. with an intensifying screen. Four positive clones were recovered from frozen stocks by decoding the arrayed filter according to the manufacturer's instructions. Four additional clones were picked from frozen stocks based on their inclusion in the same genomic contig on the Berkeley Drosophila Genome Project internet site.

Together, these eight clones were retested by PCR amplification using primers derived from the cDNA sequence obtained above. PCR conditions were as follows: 35 cycles of 95° C. for thirty seconds, 60° C. for thirty seconds, and 72° C. for 120 seconds in a reaction containing the bacterial clone in 1×reaction buffer (Boehringer Mannheim Biochemical, BMB), 200 μM dNTPs, 1 μM primers, and 1 U of Expand thermostable polymerase (BMB). The 5' primer "$GABA_B$+240" ATTTTCCTGGGTCTCGATACC (nucleotides 1552–1572 of SEQ ID NO:3) and 3' primer "$GABA_B$-710" AATATGCTTGGAATCGTTCAG (nucleotides 2005–2025 of SEQ ID NO:3) yielded a product of approximately 550 nucleotides (nt). Four clones tested positive by this assay, and one clone (DS01103) was sequenced.

Twenty (20) kb of genomic sequence around the $GABA_BR1$ gene from P1 clone DS01103 was obtained, as well as a BLAST analysis of this region, and a predicted $GABA_BR1$ gene sequence determined. The comparison of this sequence to the Drosophila EST database identified a previously unrecognized EST (exs|297454|) which overlapped the predicted 5' UTR and initiating methionine.

To produce a full-length physical clone and a complete predicted peptide sequence, the putative $GABA_BR1$ ORF was PCR amplified in two separate pieces from a cDNA template. These two pieces were then joined together by PCR using primers in the 5' and 3' untranslated regions (UTRs) of the sequence. The resulting product (~4 kb) was subcloned into pcDNA 3.1 (−) myc-his A (Invitrogen). The inserts were re-sequenced in their entirety to verify correct sequence and assembly, and a predicted full-length peptide sequence was inferred.

The cytogenetic location of the GPCR-2 gene is 93F.

6.2.3. Cloning GPCR-1

Fly EST clone CK01.44B.E6 from the library described herein was chosen based on display of a high predicted amino acid sequence similarity to the human dopamine D2 receptor. Complete sequencing of this EST clone revealed an insert of approximately 576 nucleotides. Comparison of the predicted open reading frame (ORF) to vertebrate proteins suggested the EST clone was missing both 3' and 5' coding sequences.

Using the cDNA sequence of CK01.44B.E6, nested oligonucleotide primers were designed for both 3' and 5' RACE reactions and used to PCR amplify Drosophila cDNA prepared from embryo, larval, or adult RNA, or to amplify random-primed or oligo dT-primed embryonic cDNA libraries. For the 5' RACE reactions, the primers were as follows:

"dopa-30" AGGCAAGGGATGACGAAGGCGGTG (the portion of SEQ ID NO:5 encoding residues 1352–1375 of SEQ ID NO:6);

"dopa-70" CCAGAAGATCTTGGCATAGCAGGC (the portion of SEQ ID NO:5 encoding residues 1384–1409 of SEQ ID NO:6);

"dopa-90" CAAGCGCTGCTCCGACTTGTGGAC (the portion of SEQ ID NO:5 encoding residues 1413–1436 of SEQ ID NO:6);

and

"dopa-470" AATACAAGCCGACAGGTAGAGCAG (the portion of SEQ ID NO:5 encoding residues 1788–1811 of SEQ ID NO:6).

The initial reaction products obtained for 5' RACE were obtained only with "dopa-30" primers and were cloning artifacts. When subcloned and sequenced, these products were found to encode tropomyosin-related sequences. Conditions were varied to obtain products of ~1500 nucleotides from all 4 primer combinations. Final reaction conditions were: 1×reaction buffer and 2 U "Advantage" thermostable polymerase (ClonTech), 200 µM dNTPs (Pharmacia), 50 ng of dT-primed LD embryonic cDNA library, and 0.2 µM primers. The PCR cycling conditions were 35 cycles of 94° C. for 30 seconds and 68° C. for 180 seconds. The products were excised from an agarose gel, pooled, ligated into pCRIII (Invitrogen), and sequenced by primer walking. The sequence of these products overlapped the existing contig exactly and were found to extend the ORF to include a putative initiating methionine preceded by stop codons in all 3 frames and about 700 nucleotides of 5' untranslated region (UTR).

The initial reaction products for 3' RACE appeared very promising: three different gene-specific primers yielded appropriately sized fragments (each about 300 nucleotides) with two different anchor primers. Reaction conditions were as above; PCR cycling conditions were 35 cycles of 94° C. for 15 seconds and 68° C. for 30 seconds. The primers used were:

"dopa+450" CTATATCCTGCTCTACCTGTCGGC (the portion of SEQ ID NO:5 encoding residues 1781–1804 of SEQ ID NO:6);

"dopa+510" AGTACCGCAAGGCCTACAAGACGG (the portion of SEQ ID NO:5 encoding residues 1843–1866 of SEQ ID NO:6);

and

"dopa+550" CTTCTGCTGCCCTTCGGGAAGACC (the portion of SEQ ID NO:5 encoding residues 1890–1913 of SEQ ID NO:6).

The product generated by amplification with "dopa+510" and the M13 reverse anchor primer was excised from an agarose gel, purified using QiaQuick (Qiagen), ligated into pCRII T/A vector (Invitrogen), and sequenced using forward and reverse primers. The sequence obtained contiged perfectly with existing data, extending the ORF 230 nucleotides to the 3' without hitting a stop codon. Thus, three additional primers were designed for an additional round of 3' RACE:

"dopa+680" GGAGCAGGGACGGCAACGGGAACG (the portion of SEQ ID NO:5 encoding residues 2017–2040 of SEQ ID NO:6);

"dopa+730" ACCCCACCGGAGGTCCAACAAGCC (the portion of SEQ ID NO:5 encoding residues 2062–2085 of SEQ ID NO:6);

and

"dopa+760" AGATGGTGTCGCGGGACCGGACC (the portion of SEQ ID NO:5 encoding residues 2096–2119 of SEQ ID NO:6).

Using these primers with the reaction conditions above and 35 cycles of 94° C. for 30 seconds and 70° C. for 120 seconds, reaction products of ~1.6 kb were obtained. The product obtained using "dopa+680" and an M13 anchor primer was excised from an agarose gel, ligated into pCR2.1 (Invitrogen), and sequenced through several rounds of primer walking. This sequence was found to extend the ORF further to the 3' to include a stop codon, 3' untranslated sequences, and a poly A$^+$ tail, thus indicating the clone was complete at the 3' end. BLAST analysis of the completed predicted protein sequence indicated that the clone is most closely related to the human melatonin R1α protein.

6.2.4. Cloning GPCR-4

Cloning of GPCR-4 (cDNA, SEQ ID NO:741; Predicted Protein SEQ ID NO:32,370)

The GPCR-4 sequence was assembled from a computational gene prediction performed on a P1 clone of genomic DNA originally isolated and sequenced for determining the structure of GPCR-3. GPCR-4 was predicted by BLAST similarity to other GPCRs of the invention. The genomic sequence is not presented herein.

The cytogenetic location of the GPCR-4 gene, like the GPCR-3 gene, is 87D.

6.3. Other Full-length Genes

In a similar manner, the fly EST database of the invention has been analyzed to discover several other full-length genes that are either strong candidates for use as pesticide targets or are of interest for other reasons. Some of these full-length genes are briefly described below.

6.3.1. Chitin Synthase 2

The complete CDNA nucleotide sequence of chitin synthase 2 is set forth in SEQ ID NO:10,540, and the complete amino sequence is set forth in SEQ ID NO:42,135. This gene represents a strong pesticide target gene candidate due to the importance of chitin in the construction of the exoskeleton of insect pests. The catalytic domain of chitin synthase 2 is from amino residues 440 to 935 of SEQ ID NO:42,135. In one embodiment, this invention provides one or more fragments (or derivatives or analogs thereof) of a fly chitin synthase 2 protein greater than or equal to 55 contiguous amino acids of SEQ ID NO:42,135.

6.3.2. Nicotinic Acetylcholine Receptor Alpha Subunit

The complete cDNA nucleotide sequence of an alpha subunit of a fly nicotinic acetylcholine receptor (nAChR) is set forth in SEQ ID NO:13,473, and the complete amino sequence is set forth in SEQ ID NO:45,044. This gene represents a strong pesticide target gene candidate due to the importance of the nAChR in nervous system function of insect pests.

6.3.3. Sphingomyelinase

The complete cDNA nucleotide sequence of a fly sphingomyelinase (SMase) is set forth in SEQ ID NO:10,989, and the complete amino sequence is set forth in SEQ ID NO:42,580. This gene is of general interest due to the ubiquitous importance of lipid second messengers such as ceramide, and may also represent a pesticide target gene candidate. Methods for investigation of lipid second messengers have recently been reviewed (see Rubin and Laychock, eds., 1998, Lipid Second Messengers, In: Methods In Life Sciences: Methods In Signal Transduction Series, Eichberg, series ed., CRC Press, Boca Raton, pp. 1–176; see also, www.crcpress.com) and many volumes are available describing the SMase signal transduction pathway (see e.g., Bell, Hannun and Merrill, eds., 1993, Sphingolipids, Part A: Functions and breakdown products, Advances in Lipid Research 25, Academic Press, Inc., San Diego, pp. 1–327).

6.3.4. Fly Tubby Gene

The complete cDNA nucleotide sequence of a fly homolog of the mouse Tubby gene has been identified and is set forth in SEQ ID NO:13,498, and the complete amino sequence is set forth in SEQ ID NO:45,069. This gene is of interest for understanding the regulation of metabolism and weight gain.

6.4. Identification of a Candidate Pesticide GABA$_B$ Receptor Agonist SKF97541 Has Dramatic Effects on Drosophila A number of GABA$_B$ receptor agonists known to act on vertebrate receptors (e.g., baclofen) were tested for activity in Drosophila and gave negative results, suggesting that the insect receptors of the invention display novel pharmacology compared to vertebrate receptors. Indeed, one agonist of little importance in vertebrates, SKF97541, i.e. (3-aminopropyl)methylphosphinic acid, had dramatic effects in flies, as described below.

For adult fly assays, a 20 mg ml$^{-1}$ stock solution of SKF97541 (Tocris) in DMSO was diluted in water to the desired concentration. 30 μl aliquots of the stock were mixed with 120 μl of acetone and then used to coat the inside of scintillation vials. Control scintillation vials were coated with an equivalent amount of DMSO in acetone. Next, 12 male and 12 female w, iso 2, iso 3 (stock A5001) Drosophila melanogaster were put into the prepared scintillation vials. The top of each vial was immediately plugged with a cotton ball soaked in 1% sucrose solution. The time to reach severe paralysis of 100% of the flies was observed and recorded. Additionally, flies were left in the vials overnight, and the extent of toxic effects at given concentrations was observed and recorded the following morning. Severe paralysis was defined as inability to walk on a vial wall, staggering, falling onto the back, remaining on the bottom of a vial for a prolonged period, or death. In this assay, SKF97541 had obvious effects at concentrations equal or greater than 0.9 μg/cm$^2$ per coated vial. Shortly after exposure to SKF97541, flies become unable to fly or walk up the sides of a vial without falling onto the back. With prolonged exposure, flies remained at the bottom of a vial, eventually dying after overnight treatment.

Embryonic and larval assays of SKF97541 were also performed. The acute effects on larvae were assayed as follows. First, 40 μl of the desired concentration of SKF97541 in DMSO, or DMSO alone as a control, was applied to the surface of apple juice agar plates (surface area 18.25 cm$^2$) and allowed to dry. A spot of yeast paste was applied to the center of the plate, and 25 embryos, $1^{st}$, $2^{nd}$ or $3^{rd}$ instar larvae were added to each plate. Plates were observed after two hours and after overnight incubation, and larval behavior and mobility were recorded. "Immobile" larvae were defined as larvae unable to move towards food.

Exposure to SKF97541 caused mobility and feeding defects in $1^{st}$ and $2^{nd}$ instar larvae at concentrations greater than 1.6 μg/cm$^2$. Concentrations greater than 5.4 μg/cm$^2$ caused defects in $1^{st}$, $2^{nd}$ and $3^{rd}$ instars. Immobile larvae were able to recoil normally when touched with a brush on the head, body or tail, but were unable to crawl towards food, instead displaying a "lurching on the spot" phenotype.

Chronic effects of SKF97541 exposure were assayed as follows. Five female and two male Drosophila (A5001) were allowed to lay eggs for two days at 25° C. in vials containing approximately 8 ml of standard cornmeal-agar-molasses fly medium (surface area 5 cm$^2$). Flies were removed and 40 μl of defined concentrations of SKF97541 in DMSO, or DMSO alone, was applied to the food surface bearing the zero to 48 hr old embryos and larvae. The solution was allowed to soak into the surface, the vial was re-plugged with cotton wool, and fly development was allowed to proceed at 25° C. The vials containing developing larvae were observed and the effects on development were recorded compared to controls. The dramatic effects, described in detail in the next paragraph, were observed with decreasing penetrance when SKF97541 was applied at 100, 20 or 4 μg/cm$^2$, respectively, to vials of 48 hr egg lays.

After three days, corpses of $1^{st}$ instar larvae were visible in treated vials. Thin, $2^{nd}$ instar larvae were visible on the surface of the food displaying lurching mobility defects. After four days, the control vials contained $3^{rd}$ instar larvae burrowing into the food. By contrast, larvae in the treated vials appeared to be developmentally delayed; there were many thin larvae and no larvae burrowing in the food. Even larvae of normal size for $3^{rd}$ instars in the treated vials remained on the surface, lurching and sluggish. A few $2^{nd}/3^{rd}$ instar corpses were visible on the food surface at day four. After five days, wandering $3^{rd}$ instar larvae and pupae were visible on the walls of control vials. By contrast, treated vials did not have larvae on their walls, although some pupae were forming on the surface of the food. At eight days of treatment, adults were enclosing in control vials, but none emerged in the treated vials. Some pupae in the treated vials were visible on the surface of the food, but not on the walls of the vial. After ten days of treatment, some adults eventually enclosed from the pupae on the surface of the food of treated vials; all were female, and were two days developmentally delayed compared to controls.

GABA$_B$ Receptor GPCR-2 RNA in situ Hybridization on Embryos

An RNA GPCR-2 probe was synthesized from The Berkeley Drosophila Genome Project (BDGP) clone HL01578. This clone, which contains a 2.4 kb fragment corresponding to a portion of the GABA$_B$ receptor sequence, was used as a transcription template for T7 RNA polymerase. Antisense DIG-labeled RNA probes were synthesized using the Boehringer Mannheim Dig RNA Labeling Kit and T7 RNA polymerase according to the in situ hybridization protocol of BDGP genome project methods page. The in situ hybridization results indicate that GABA$_B$ (GPCR-2) is expressed in Drosophila embryos throughout the central nervous system in stages 11 through 17.

6.5. Explanation of Table 1

Column 1 of Table 1 provides the SEQ ID NOs for the nucleotide sequences of all contiguous sequence assemblies generated from novel Drosophila ESTs and publically-available sequences (SEQ ID NOs:7–15,288) ("Contig SEQ ID NO"). Column 2 of Table 1 provides the SEQ ID NOs for the nucleotide sequences of all novel portions of each contig listed in column 1 (SEQ ID NOs:15,289–31,365) ("novel DNA SEQ ID NOs"). This latter sequence information was generated by first building contigs using the EST library of the invention and public sequence information, and next eliminating all portions of each contig sequence contained within public databases using the BLAST algorithms defined below. Column 3 of Table 1 provides percentage identity values of each nucleotide sequence of column 2 with respect to the closest public sequence over a window size of 125 base pairs using the specific percent identity algorithm described below ("125 bp % identity"). In cases where the closest known sequence in the BLAST search exhibited less than 50% identity to the sequence of column 2, 50% is reported as a default floor value in column 3. In cases where the sequence in column 2 is less than 125 base pairs, the length of the window in base pairs used to determine the % identity is given in parentheses in column 3. Column 4 of Table 1 provides percentage identity values of each nucleotide sequence of column 2 with respect to the closest public sequence over a window size of 275 base pairs using the specific percent identity algorithm defined below ("275 bp % identity"). In cases where the closest known sequence in the BLAST search exhibited less than 50% identity to the sequence of column 2, 50% is reported as a default floor value in column 4. In cases where the sequence in column 2 is less than 275 base pairs, the length of the window in base pairs used to determine the % identity is given in parentheses in column 4. Column 5 of Table 1 provides the length of the longest contiguous stretch of nucleotides, plus one, which is 100% identical between any known sequence and the sequence of column 2 ("100% identity length"). This value thus can be thought of as a measure of the smallest novel or unique contiguous fragment of the sequence of column 2. Column 6 of Table 1 provides the BLAST score, computed using the specific algorithm defined below, of the closest public sequence compared to the sequence of column 2 ("Blast score"). Higher BLAST scores reflect greater similarity between the sequence of column 2 and the closest public sequence. Column 7 of Table 1 provides a condition as set forth in Table C for use in hybridization reactions to isolate sequences which are more related to the sequence of column 2 than is the nearest public sequence ("hybridiz conditions"). For each hybridization condition set forth in Table C, Table A sets forth hybridization buffer conditions and Table B sets forth wash buffer conditions. Column 8 of Table 1 provides the protein translations of the predicted coding regions of each nucleotide sequence in column 2 (SEQ ID NOs:46,853–62,485) ("encoded polypep. SEQ ID NO"). They are therefore believed to represent novel polypeptide sequences of the invention.

A public sequence database was assembled and used for all BLAST comparisons and was a combination of GenBank and the Berkeley Drosophila Genome Project database (BDGP) as they existed on or about Feb. 15, 1999.

Nucleic acids comprising or defined by any one of the SEQ ID NOs of Table 1, coding regions thereof, and derivatives, recombinant cells, transgenics, methods of production, etc., comprising or using same, as set forth in the subsections of section 5 herein are also provided.

"Percent (%) sequence identity" with respect to the amino acid sequences and nucleotide sequences disclosed in Table 1 and Table 2 was calculated as the percentage of amino residues (or nucleotides) in a candidate sequence that are identical with the amino acid residues (or nucleotides) in the sequence after aligning the sequences and introducing gaps, if necessary, to achieve the maximum percent sequence identity, and, for amino acid sequences, not considering any conservative substitutions as part of the sequence identity. "Percent (%) nucleotide sequence identity over a specified window size "W" with respect to the sequences disclosed herein was calculated as the percentage of nucleotide residues in any window of W base pairs (e.g., the window of 125 or 275 base pairs set forth in columns 3 and 4, respectively, of Table 1) in the candidate sequence that are identical with the nucleotides in the disclosed sequence, after aligning the sequences and introducing gaps, if necessary, to achieve the maximum percent sequence identity. A percent nucleic acid sequence identity value is determined by the number of matching identical residues divided by the window size W for which the percent identity is reported.

Unless otherwise indicated, the % identity values used in Table 1 and Table 2 mean those values that were generated by WU-BLAST-2a19, WU-BLASTP program (for % amino acid sequence identity) and WU-BLASTN program (for % nucleic acid sequence identity) (Altschul et al., 1997, Meth. Enzymol. 215, 403–410; http://blast.wustl.edu/blast/README.html). WU-BLAST-2a19 uses several search parameters, all of which were set to the default values. The HSP S and HSP S2 parameters are dynamic values and are established by the program itself, depending upon the composition of the particular sequence and composition of the particular database against which the sequence of interest is being searched. Values may be adjusted to increase sensitivity. A % sequence identity value is determined by the number of matching identical residues divided by the total number of residues of the "longer" sequence in the aligned region. The "longer" sequence is the one having the most actual residues in the aligned region (gaps introduced by WU-BLAST-2a19 to maximize the alignment score are ignored).

"Percent (%) amino acid sequence similarity" with respect to amino acid sequences was determined by doing the same calculation as for determining % amino acid sequence identity described above, but including conservative amino acid substitutions in additional to identical amino acids in the computation. Conservative amino acids are those that do not significantly affect the folding or activity of the protein. Conservative aromatic amino acids that may be substituted for each other are phenylalanine, tryptophan, and tyrosine. Conservative hydrophobic amino acids that may be substituted for each other are leucine, isoleucine and valine. Conservative polar amino acids that may be substituted for each other are glutamine and asparagine. Conservative basic amino acids that may be substituted for each other are arginine, lysine and histidine. Conservative acidic amino acids that may be substituted for each other are aspartic acid and glutamic acid. Finally, conservative small amino acids that may be substituted for each other are alanine, serine, threonine, methionine, and glycine.

6.6. Explanation of Table 2

For each contig nucleotide sequence (SEQ ID NOs:7–15, 288) listed in Table 2 (column 1), the corresponding SEQ ID NO of the amino acid sequence of any predicted polypeptide encoded thereby is also disclosed (column 2). For each of these amino acid sequences (SEQ ID NOs:31,636 to 46,852), BLAST, PFam, and Prosite information is further provided, as appropriate. Accordingly, the invention provides proteins comprising or defined by any one of these amino acid sequences, as well as derivatives thereof, antibodies thereto, nucleic acids encoding them, etc., as set forth in the subsections of section 5 hereinabove. Mature proteins in which precursor sequences (e.g., secretory signal peptide sequences) have also been removed are also provided.

The cell in Table 2 designated "Blast Description" (column 3 and sub-columns therein) discloses the top two database hits obtained using BLAST. BLAST (Basic Local Alignment Search Tool) is a set of similarity search programs designed to explore all of the available sequence databases. The scores assigned by WU-BLASTP in a protein search have a well-defined statistical interpretation designed to identify related proteins. WU-BLASTP uses a heuristic algorithm which seeks local as opposed to global alignments and is therefore able to detect relationships among sequences which share only isolated regions of similarity (Altschul et al., 1990, Id.; Altschul et al., 1997, Nucl. Acids Res. 25, 3389–3402). For each BLAST hit, a BLAST score is provided at the left margin of the "Blast Description" cell. The score was computed using the same WU-BLASTP program set to the same parameters as described above for ascertaining % amino acid sequence identity. Next to the BLAST score is a GenBank identifier number, followed by the description line in GenBank.

For each contig SEQ ID NO listed in Table 2 (column 1), one or more predicted protein subsequences are reported which were predicted to be novel from the BLAST search results ("Polypeptide subsequence SEQ ID NO"). For each Polypeptide subsequence SEQ ID NO listed, the associated parameters from the BLAST search are also reported ("100% identity length") ("100% similarity length") ("Blast score"). The values listed for 100% identity length, 100% similarity length, and Blast score were generated for these amino acid sequences in an analogous manner to the computations explained in Table 1 for nucleotide sequences.

In the "PFam motifs" cell (column 4), a PFam motif number may be provided, along with the beginning and ending amino acid residue numbers of the portion of the sequence where the PFam motif is located. A description for each PFam motif number is provided in Table 3. The PFam value was obtained by using PFam database version 3.2 (created by Sean Eddy et al., Washington University, St. Louis, Mo.). Using the HMMER software, version 2.0, PFam was searched using the "hmmpfam" program, version 2.1. All PFam search hits with an E score less than or equal to 0.5 were reported. PFam is described by Bateman et al. (1999, Nucl. Acids Res. 27, 260–262). The HMMER software is described by Eddy (1996, Curr. Opin. Struct. Biol. 6, 361–365; see also http://hmmer.wustl.edu). Briefly, PFam is a large collection of multiple sequence alignments of protein domains or conserved protein regions which represent evolutionarily conserved structure having implications for a protein's function. The HMMER software uses hidden Markov models (HMMs) (described by Durbin et al., 1998, Biological sequence analysis: probabilistic models of proteins and nucleic acids, Cambridge University Press) to find new members of a domain family.

In the "Prosite motifs" cell (column5), a Prosite motif number may be provided along with the beginning and ending amino acid residue numbers of the portion of the sequence where the Prosite motif is located. A description for each Prosite motif number is provided in Table 4. Prosite is described in Hoffmann et al. (1999, Nucl. Acids Res. 27, 215–219). Briefly, Prosite is a database of protein families and domains. It is based on the observation that, while there is a huge number of different proteins, most of them can be grouped, on the basis of similarities in their sequences, into a limited number of families. Proteins or protein domains belonging to a particular family generally share functional attributes and are derived from a common ancestor. It is apparent, when studying protein sequence families, that some regions have been better conserved than others during evolution. These regions are generally important for the function of a protein and/or for the maintenance of its three-dimensional structure. By analyzing the constant and variable properties of such groups of similar sequences, it is possible to derive a signature for a protein family or domain which distinguishes its members from all other unrelated proteins. Prosite contains signatures specific for about one thousand protein families or domains. Each Prosite signature is documented to provide background information on the structure and function of these proteins (available at http://expasy.hcuge.ch/sprot/prosite.html).

In one aspect of the present invention, a protein (including peptides and polypeptides) is provided having an amino acid sequence with a BLAST score of at least X compared with any one of SEQ ID NOs:46,853 to 62,485, wherein for each of these sequences, X is greater than the value shown in the "Blast score" cell of Table 2. Preferably the value of X is at least 1%, 2%, 5% or 10%, more preferably 20%, 30%, 40% or 50% greater than the value shown in the "Blast score" cell. In addition to having a BLAST score of at least X compared with one of the sequences of SEQ ID NOs:46,853 to 62,485, preferably the amino acid sequence of the protein includes the amino acid sequence of the PFam and/or Prosite motif, if any, listed in Table 2 for that sequence (i.e. one of SEQ ID NOs:46,853 to 62,485) or another example of that motif type. In an another embodiment, in addition to having a BLAST score of at least X with one of the sequences of SEQ ID NOs:46,853 to 62,485, preferably the protein has a biological activity of a GenBank protein, if any, listed in the "Blast description" cell for the related 'parent' protein (i.e. the protein defined by the sequence of any one of SEQ ID NOs:31,636–46,852 to which the protein motif subsequence of any one of SEQ ID NOs:46,853 to 62,485 is related). Alternatively, and/or additionally, the related protein displays the antigenicity of the protein defined by any one of SEQ ID NOs:46,853 to 62,485.

Another aspect of the invention is directed to a protein having an amino acid sequence of at least 60% sequence identity, at least 70% sequence identity, preferably at least 80% sequence identity, more preferably at least 90% sequence identity, and most preferably at least 95% sequence identity when compared with any one of SEQ ID NOs:46,853 to 62,485. In addition to sharing sequence identity with any one of SEQ ID NOs:46,853 to 62,485, preferably, the amino acid sequence of the protein includes the amino acid sequences of the PFam and/or Prosite motif, if any, listed in Table 2 for the sequence (i.e. one of SEQ ID NOs:46,853 to 62,485). or another example of that motif type. In an another embodiment, in addition to having an amino acid sequence sharing the above-mentioned sequence identity with any one of SEQ ID NOs:46,853 to 62,485, preferably the protein additionally has the biological activity of a Genbank protein, if any, listed in the "Blast description" cell for the related 'parent' protein, and/or has the antigenicity of the protein defined by any one of SEQ ID NOs:46, 853 to 62,485.

Yet another aspect of the invention is directed to a polypeptide having an amino acid sequence of at least 60% sequence similarity, at least 70% sequence similarity, preferably at least 80% sequence similarity, more preferably at least 90% sequence similarity, and most preferably at least 95% sequence similarity when compared with any one of SEQ ID NOs:46,853 to 62,485. In addition to sharing sequence similarity with any one of SEQ ID NOs:46,853 to 62,485, preferably, the amino acid sequence of the protein includes the amino acid sequences of the PFam and/or Prosite motif, if any, listed in Table 2 for the sequence (i.e. one of SEQ ID NOs:46,853 to 62,485). or another example of that motif type. In an another embodiment, in addition to having an amino acid sequence sharing the above-mentioned sequence similarity with any one of SEQ ID NOs:46,853 to 62,485, preferably the protein additionally has the biological activity of a Genbank protein, if any, listed in the "Blast description" cell for the related 'parent' protein, and/or has the antigenicity of the protein defined by any one of SEQ ID NOs:46,853 to 62,485.

6.7. Explanation of Tables 3 and 4

For each PFam entry listed in column one of Table 3 ("ID No.") and each Prosite entry listed in column one of Table 4 ("ID No."), a brief, one-line description obtained from the respective Pfam and Prosite databases is provided in column 2 of each of these tables ("Description"). This information further describes the motifs identified in Table 2 in the "PFam motifs" and "Prosite motifs" cells of Table 2 (columns 4 and 5, respectively).

The present invention is not to be limited in scope by the specific embodiments described herein. Indeed, various modifications of the invention in addition to those described herein will become apparent to those skilled in the art from the foregoing description and accompanying drawings and Sequence Listing containing, inter alia, an extensive fly EST database. Such modifications are intended to fall within the scope of the appended claims. The various references cited herein may include patent applications, patents, and other publications; the disclosure of each reference cited is hereby incorporated herein by reference in its entirety.

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7 | 15289 | 66.4 | 59.6 | 21 | 483 | #4 | 46853 |
| 8 | 15290 | 62.4 | 50.0 | 12 | 176 | #3 | 46854 |
| 9 | 15291 | 50.0 | 50.0 | 12 | 150 | #1 | 46855 |
| 10 | 15292 | 84.0 | 79.4 (155) | 30 | 461 | #7 | 46856 |
| 11 | 15293 | 72.8 | 66.9 | 18 | 593 | #5 | 46857 |
| 12 | 15294 | 79.2 | 76.0 | 17 | 1075 | #6 | 46858 |
| 13 | 15295 | 79.2 | 72.4 | 24 | 997 | #6 | 46859 |
| 14 | 15296 | 50.0 | 50.0 | 12 | 150 | #1 | 46860 |
| 15 | 15297 | 64.0 | 50.0 | 12 | 166 | #3 | 46861 |
| 16 | 15298 | 50.0 | 50.0 (270) | 12 | 150 | #1 | 46862 |
| 17 | 15299 | 69.6 | 64.4 | 15 | 438 | #4 | 46863 |
| 18 | 15300 | 67.2 | 58.3 (211) | 20 | 230 | #4 | 46864 |
| 19 | 15301 | 69.6 | 62.5 | 23 | 291 | #4 | 46865 |
| 20 | 15302 | 50.0 | 50.0 | 12 | 150 | #1 | 46866 |
| 21 | 15303 | 64.8 | 58.9 | 15 | 192 | #3 | 46867 |
| 22 | 15304 | 65.6 | 60.4 | 13 | 398 | #4 | 46868 |
| 23 | 15305 | 66.4 | 60.7 | 17 | 278 | #4 | 46869 |
| 24 | 15306 | 77.6 | 59.3 | 14 | 391 | #6 | 46870 |
| 25 | 15307 | 73.6 | 55.3 | 18 | 274 | #5 | 46871 |
| 26 | 15308 | 50.0 | 50.0 | 12 | 150 | #1 | 46872 |
| 27 | 15309 | 76.8 | 71.6 | 16 | 679 | #6 | 46873 |
| 28 | 15310 | 67.2 | 60.4 | 14 | 266 | #4 | 46874 |
| 29 | 15311 | 64.0 | 53.8 | 14 | 192 | #3 | 46875 |
| 30 | 15312 | 100.0 | 99.6 | 198 | 2426 | #10 | 46876 |
| 31 | 15313 | 66.4 | 56.0 | 13 | 205 | #4 | 46877 |
| 32 | 15314 | 74.4 | 62.9 | 23 | 366 | #5 | 46878 |
| 33 | 15315 | 63.2 | 58.9 | 16 | 237 | #3 | 46879 |
| 34 | 15316 | 90.4 | 69.1 | 30 | 589 | #9 | 46880 |
| 35 | 15317 | 64.0 | 56.0 | 14 | 240 | #3 | 46881 |
| 36 | 15318 | 87.2 | 63.6 | 36 | 711 | #8 | 46882 |
| 37 | 15319 | 88.0 | 85.1 | 30 | 1025 | #8 | 46883 |
| 38 | 15320 | 76.8 | 52.6 (249) | 18 | 398 | #6 | 46884 |
| 39 | 15321 | 68.8 | 61.8 | 22 | 303 | #4 | 46885 |
| 40 | 15322 | 71.2 | 68.4 | 13 | 682 | #5 | 46886 |
| 41 | 15323 | 68.8 | 65.8 | 21 | 506 | #4 | 46887 |
| 42 | 15324 | 50.0 | 50.0 | 12 | 150 | #1 | 46888 |
| 43 | 15325 | 77.6 | 68.0 | 20 | 647 | #6 | 46889 |
| 44 | 15326 | 67.2 | 60.0 | 18 | 321 | #4 | 46890 |
| 45 | 15327 | 71.2 | 59.6 | 32 | 279 | #5 | 46891 |
| 46 | 15328 | 63.2 | 50.0 | 16 | 166 | #3 | 46892 |
| 47 | 15329 | 50.0 | 50.0 | 12 | 150 | #1 | 46893 |
| 48 | 15330 | 60.8 | 52.3 (195) | 17 | 150 | #3 | 46894 |
| 49 | 15331 | 74.4 | 69.8 | 15 | 759 | #5 | 46895 |
| 50 | 15332 | 65.6 | 61.6 (216) | 16 | 272 | #4 | 46896 |
| 51 | 15333 | 74.4 | 61.5 | 21 | 373 | #5 | 46897 |
| 52 | 15334 | 68.0 | 60.0 | 18 | 226 | #4 | 46898 |
| 53 | 15335 | 79.2 | 72.0 | 18 | 1064 | #6 | 46899 |
| 54 | 15336 | 50.0 | 50.0 | 12 | 150 | #1 | 46900 |
| 55 | 15337 | 66.4 | 57.1 | 14 | 183 | #4 | 46901 |
| 56 | 15338 | 64.8 | 57.5 | 14 | 228 | #3 | 46902 |
| 57 | 15339 | 72.8 | 63.3 | 15 | 498 | #5 | 46903 |
| 58 | 15340 | 57.6 | 50.0 | 15 | 180 | #2 | 46904 |
| 59 | 15341 | 68.0 | 61.8 | 21 | 384 | #4 | 46905 |
| 60 | 15342 | 80.8 | 77.8 | 24 | 946 | #7 | 46906 |
| 61 | 15343 | 63.2 | 50.0 | 13 | 205 | #3 | 46907 |
| 62 | 15344 | 64.0 | 54.9 | 14 | 208 | #3 | 46908 |
| 63 | 15345 | 68.0 | 55.8 (274) | 21 | 234 | #4 | 46909 |
| 64 | 15346 | 70.4 | 58.5 | 13 | 483 | #5 | 46910 |
| 65 | 15347 | 70.4 | 65.8 | 21 | 669 | #5 | 46911 |
| 66 | 15348 | 65.6 | 61.1 | 15 | 446 | #4 | 46912 |
| 67 | 15349 | 68.0 | 63.3 | 18 | 712 | #4 | 46913 |
| 68 | 15350 | 50.0 | 50.0 | 12 | 150 | #1 | 46914 |
| 69 | 15351 | 85.6 | 82.9 | 26 | 992 | #8 | 46915 |
| 70 | 15352 | 79.2 | 60.4 | 33 | 618 | #6 | 46916 |
| 71 | 15353 | 66.4 | 61.5 | 14 | 367 | #4 | 46917 |
| 72 | 15354 | 64.8 | 54.2 | 16 | 197 | #3 | 46918 |
| 73 | 15355 | 50.0 | 50.0 | 12 | 150 | #1 | 46919 |
| 74 | 15356 | 50.0 | 50.0 | 12 | 150 | #1 | 46920 |
| 75 | 15357 | 62.4 | 50.0 | 15 | 223 | #3 | 46921 |
| 76 | 15358 | 61.6 | 57.1 | 15 | 208 | #3 | 46922 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
| --- | --- | --- | --- | --- | --- | --- | --- |
| 77 | 15359 | 50.0 | 50.0 | 12 | 150 | #1 | 46923 |
| 78 | 15360 | 68.0 | 59.6 | 18 | 249 | #4 | 46924 |
| 79 | 15361 | 75.2 | 63.6 | 36 | 353 | #6 | 46925 |
| 80 | 15362 | 72.0 | 66.9 | 16 | 612 | #5 | 46926 |
| 81 | 15363 | 72.0 | 64.4 | 14 | 453 | #5 | 46927 |
| 82 | 15364 | 72.8 | 69.5 | 26 | 827 | #5 | 46928 |
| 83 | 15365 | 50.0 | 50.0 | 12 | 150 | #1 | 46929 |
| 84 | 15366 | 79.2 | 66.4 (241) | 21 | 524 | #6 | 46930 |
| 85 | 15367 | 68.0 | 53.9 (245) | 17 | 360 | #4 | 46931 |
| 86 | 15368 | 76.0 | 65.5 | 15 | 445 | #6 | 46932 |
| 87 | 15369 | 68.0 | 61.1 | 19 | 408 | #4 | 46933 |
| 88 | 15370 | 64.0 | 50.0 | 12 | 174 | #3 | 46934 |
| 89 | 15371 | 65.6 | 50.0 (222) | 17 | 165 | #4 | 46935 |
| 90 | 15372 | 64.8 | 62.2 | 17 | 374 | #3 | 46936 |
| 91 | 15373 | 78.4 | 72.7 | 16 | 807 | #6 | 46937 |
| 92 | 15374 | 99.2 | 98.9 | 123 | 1935 | #10 | 46938 |
| 93 | 15375 | 50.0 | 50.0 | 12 | 150 | #1 | 46939 |
| 94 | 15376 | 80.0 | 73.5 | 18 | 1061 | #6 | 46940 |
| 95 | 15377 | 72.8 | 61.8 | 28 | 310 | #5 | 46941 |
| 96 | 15378 | 63.2 | 56.0 | 13 | 199 | #3 | 46942 |
| 97 | 15379 | 82.4 | 59.3 | 17 | 515 | #7 | 46943 |
| 98 | 15380 | 71.2 | 61.1 | 17 | 398 | #5 | 46944 |
| 99 | 15381 | 66.4 | 57.1 | 14 | 235 | #4 | 46945 |
| 100 | 15382 | 80.8 | 76.0 (208) | 24 | 590 | #7 | 46946 |
| 101 | 15383 | 76.8 | 60.3 (242) | 27 | 432 | #6 | 46947 |
| 102 | 15384 | 65.6 | 57.1 | 16 | 231 | #4 | 46948 |
| 103 | 15385 | 83.2 | 69.5 | 19 | 698 | #7 | 46949 |
| 104 | 15386 | 78.4 | 61.1 | 23 | 484 | #6 | 46950 |
| 105 | 15387 | 50.0 | 50.0 | 12 | 157 | #1 | 46951 |
| 106 | 15388 | 68.8 | 62.9 | 15 | 454 | #4 | 46952 |
| 107 | 15389 | 64.0 | 56.7 | 15 | 207 | #3 | 46953 |
| 108 | 15390 | 62.4 | 50.0 (234) | 17 | 158 | #3 | 46954 |
| 109 | 15391 | 77.6 | 73.5 | 29 | 787 | #6 | 46955 |
| 110 | 15392 | 74.4 | 64.0 | 15 | 436 | #5 | 46956 |
| 111 | 15393 | 50.0 | 50.0 | 12 | 150 | #1 | 46957 |
| 112 | 15394 | 70.4 | 57.5 | 20 | 269 | #5 | 46958 |
| 113 | 15395 | 72.8 | 66.9 | 15 | 509 | #5 | 46959 |
| 114 | 15396 | 74.4 | 68.4 | 18 | 531 | #5 | 46960 |
| 115 | 15397 | 64.0 | 51.3 | 12 | 202 | #3 | 46961 |
| 116 | 15398 | 64.8 | 50.0 | 15 | 204 | #3 | 46962 |
| 117 | 15399 | 68.0 | 62.2 | 12 | 379 | #4 | 46963 |
| 118 | 15400 | 72.8 | 65.8 | 25 | 868 | #5 | 46964 |
| 119 | 15401 | 66.4 | 61.1 | 15 | 342 | #4 | 46965 |
| 120 | 15402 | 64.0 | 61.1 | 12 | 544 | #3 | 46966 |
| 121 | 15403 | 61.6 | 56.7 | 13 | 214 | #3 | 46967 |
| 122 | 15404 | 66.4 | 59.6 | 19 | 295 | #4 | 46968 |
| 123 | 15405 | 50.0 | 50.0 | 12 | 150 | #1 | 46969 |
| 124 | 15406 | 75.2 | 68.0 | 18 | 576 | #6 | 46970 |
| 125 | 15407 | 70.4 | 61.1 | 23 | 349 | #5 | 46971 |
| 126 | 15408 | 69.6 | 63.6 | 18 | 371 | #4 | 46972 |
| 127 | 15409 | 77.6 | 56.4 | 15 | 542 | #6 | 46973 |
| 128 | 15410 | 50.0 | 50.0 | 12 | 150 | #1 | 46974 |
| 129 | 15411 | 50.0 | 50.0 | 12 | 150 | #1 | 46975 |
| 130 | 15412 | 79.2 | 69.1 | 21 | 797 | #6 | 46976 |
| 131 | 15413 | 74.4 | 68.0 | 19 | 556 | #5 | 46977 |
| 132 | 15414 | 67.2 | 55.6 | 16 | 303 | #4 | 46978 |
| 133 | 15415 | 68.0 | 53.5 | 13 | 379 | #4 | 46979 |
| 134 | 15416 | 73.6 | 63.6 | 21 | 396 | #5 | 46980 |
| 135 | 15417 | 80.8 | 71.3 | 24 | 685 | #7 | 46981 |
| 136 | 15418 | 60.8 | 55.3 | 13 | 219 | #3 | 46982 |
| 137 | 15419 | 78.4 | 69.5 | 15 | 573 | #6 | 46983 |
| 138 | 15420 | 63.2 | 50.0 | 13 | 219 | #3 | 46984 |
| 139 | 15421 | 64.0 | 50.0 | 13 | 178 | #3 | 46985 |
| 140 | 15422 | 72.8 | 67.6 | 20 | 538 | #5 | 46986 |
| 141 | 15423 | 71.2 | 66.2 | 16 | 620 | #5 | 46987 |
| 142 | 15424 | 50.0 | 50.0 | 12 | 150 | #1 | 46988 |
| 143 | 15425 | 99.2 | 97.8 | 87 | 2577 | #10 | 46989 |
| 144 | 15426 | 84.0 | 77.5 | 21 | 918 | #7 | 46990 |
| 145 | 15427 | 50.0 | 50.0 | 12 | 150 | #1 | 46991 |
| 146 | 15428 | 67.2 | 60.0 | 17 | 237 | #4 | 46992 |
| 147 | 15429 | 68.0 | 64.0 | 15 | 483 | #4 | 46993 |
| 148 | 15430 | 67.2 | 61.8 | 19 | 438 | #4 | 46994 |
| 149 | 15431 | 68.8 | 61.5 | 15 | 453 | #4 | 46995 |
| 150 | 15432 | 50.0 | 50.0 | 12 | 150 | #1 | 46996 |
| 151 | 15433 | 77.6 | 74.5 | 17 | 814 | #6 | 46997 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 152 | 15434 | 50.0 | 50.0 (272) | 12 | 150 | #1 | 46998 |
| 153 | 15435 | 64.8 | 60.4 | 15 | 362 | #3 | 46999 |
| 154 | 15436 | 67.2 | 56.4 | 15 | 199 | #4 | 47000 |
| 155 | 15437 | 75.2 | 59.6 | 16 | 310 | #6 | 47001 |
| 156 | 15438 | 80.8 | 73.1 | 21 | 875 | #7 | 47002 |
| 157 | 15439 | 68.8 | 61.1 | 16 | 276 | #4 | 47003 |
| 158 | 15440 | 81.6 | 76.4 | 27 | 1295 | #7 | 47004 |
| 159 | 15441 | 50.0 | 50.0 | 12 | 150 | #1 | 47005 |
| 160 | 15442 | 50.0 | 50.0 | 12 | 150 | #1 | 47006 |
| 161 | 15443 | 60.0 | 50.0 | 12 | 180 | #2 | 47007 |
| 162 | 15444 | 70.4 | 66.2 | 23 | 458 | #5 | 47008 |
| 163 | 15445 | 75.2 | 68.4 | 25 | 1353 | #6 | 47009 |
| 164 | 15446 | 92.8 | 86.9 | 42 | 1279 | #9 | 47010 |
| 165 | 15447 | 72.8 | 62.9 | 20 | 570 | #5 | 47011 |
| 166 | 15448 | 78.4 | 69.5 | 21 | 769 | #6 | 47012 |
| 167 | 15449 | 70.4 | 58.2 | 16 | 286 | #5 | 47013 |
| 168 | 15450 | 68.0 | 58.9 | 21 | 296 | #4 | 47014 |
| 169 | 15451 | 71.2 | 61.1 | 15 | 315 | #5 | 47015 |
| 170 | 15452 | 50.0 | 50.0 | 12 | 150 | #1 | 47016 |
| 171 | 15453 | 63.2 | 57.5 | 14 | 239 | #3 | 47017 |
| 172 | 15454 | 66.4 | 62.2 | 17 | 324 | #4 | 47018 |
| 173 | 15455 | 90.4 | 87.6 | 30 | 1260 | #9 | 47019 |
| 174 | 15456 | 71.2 | 61.5 | 13 | 389 | #5 | 47020 |
| 175 | 15457 | 50.0 | 50.0 | 12 | 150 | #1 | 47021 |
| 176 | 15458 | 64.0 | 58.2 | 12 | 221 | #3 | 47022 |
| 177 | 15459 | 50.0 | 50.0 | 12 | 150 | #1 | 47023 |
| 178 | 15460 | 74.4 | 70.5 | 21 | 1124 | #5 | 47024 |
| 179 | 15461 | 75.2 | 64.4 | 31 | 395 | #6 | 47025 |
| 180 | 15462 | 64.0 | 54.2 | 15 | 233 | #3 | 47026 |
| 181 | 15463 | 74.4 | 50.0 | 28 | 343 | #5 | 47027 |
| 182 | 15464 | 65.6 | 60.4 | 17 | 218 | #4 | 47028 |
| 183 | 15465 | 72.8 | 51.6 | 17 | 400 | #5 | 47029 |
| 184 | 15466 | 66.4 | 59.6 | 12 | 414 | #4 | 47030 |
| 185 | 15467 | 72.0 | 61.5 | 18 | 306 | #5 | 47031 |
| 186 | 15468 | 68.0 | 58.9 | 17 | 308 | #4 | 47032 |
| 187 | 15469 | 68.8 | 50.0 | 15 | 221 | #4 | 47033 |
| 188 | 15470 | 72.8 | 70.2 | 21 | 1019 | #5 | 47034 |
| 189 | 15471 | 69.6 | 63.3 | 20 | 393 | #4 | 47035 |
| 190 | 15472 | 68.8 | 61.8 | 21 | 363 | #4 | 47036 |
| 191 | 15473 | 63.2 | 50.0 | 14 | 167 | #3 | 47037 |
| 192 | 15474 | 50.0 | 50.0 | 12 | 150 | #1 | 47038 |
| 193 | 15475 | 66.4 | 57.5 | 15 | 222 | #4 | 47039 |
| 194 | 15476 | 61.6 | 50.0 | 15 | 167 | #3 | 47040 |
| 195 | 15477 | 68.0 | 58.5 | 21 | 242 | #4 | 47041 |
| 196 | 15478 | 64.8 | 50.0 | 13 | 171 | #3 | 47042 |
| 197 | 15479 | 50.0 | 50.0 | 12 | 150 | #1 | 47043 |
| 198 | 15480 | 64.8 | 50.0 | 12 | 236 | #3 | 47044 |
| 199 | 15481 | 84.8 | 80.7 | 27 | 937 | #7 | 47045 |
| 200 | 15482 | 66.4 | 59.3 | 14 | 283 | #4 | 47046 |
| 201 | 15483 | 64.8 | 50.2 | 12 | 214 | #3 | 47047 |
| 202 | 15484 | 60.8 | 55.6 | 13 | 187 | #3 | 47048 |
| 203 | 15485 | 87.2 | 75.6 | 22 | 1002 | #8 | 47049 |
| 204 | 15486 | 82.4 | 74.9 | 30 | 762 | #7 | 47050 |
| 205 | 15487 | 66.4 | 61.1 | 15 | 368 | #4 | 47051 |
| 206 | 15488 | 68.8 | 64.4 | 16 | 504 | #4 | 47052 |
| 207 | 15489 | 69.6 | 64.4 | 13 | 901 | #4 | 47053 |
| 208 | 15490 | 61.6 | 50.0 | 12 | 212 | #3 | 47054 |
| 209 | 15491 | 77.6 | 75.3 | 19 | 1160 | #6 | 47055 |
| 210 | 15492 | 64.8 | 50.0 | 16 | 208 | #3 | 47056 |
| 211 | 15493 | 63.2 | 50.0 | 19 | 371 | #3 | 47057 |
| 212 | 15494 | 84.8 | 71.3 | 22 | 802 | #7 | 47058 |
| 213 | 15495 | 78.4 | 67.3 | 15 | 527 | #6 | 47059 |
| 214 | 15496 | 76.8 | 71.6 | 21 | 1036 | #6 | 47060 |
| 215 | 15497 | 73.6 | 69.1 | 24 | 575 | #5 | 47061 |
| 216 | 15498 | 64.2 (120) | — | 18 | 216 | #3 | 47062 |
| 217 | 15499 | 71.2 | 59.3 | 18 | 307 | #5 | 47063 |
| 218 | 15500 | 64.0 | 57.8 | 13 | 180 | #3 | 47064 |
| 219 | 15501 | 64.8 | 60.0 | 12 | 510 | #3 | 47065 |
| 220 | 15502 | 61.6 | 57.1 | 13 | 187 | #3 | 47066 |
| 221 | 15503 | 68.0 | 63.6 | 16 | 448 | #4 | 47067 |
| 222 | 15504 | 74.4 | 61.5 | 21 | 396 | #5 | 47068 |
| 223 | 15505 | 64.0 | 50.0 | 14 | 193 | #3 | 47069 |
| 224 | 15506 | 70.4 | 61.1 | 18 | 266 | #5 | 47070 |
| 225 | 15507 | 63.2 | 60.6 (274) | 12 | 279 | #3 | 47071 |
| 226 | 15508 | 66.4 | 60.7 | 16 | 255 | #4 | 47072 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 227 | 15509 | 57.6 | 50.0 | 15 | 156 | #2 | 47073 |
| 228 | 15510 | 50.0 | 50.0 | 12 | 150 | #1 | 47074 |
| 229 | 15511 | 60.0 | 55.6 | 15 | 209 | #2 | 47075 |
| 230 | 15512 | 71.2 | 65.1 | 15 | 454 | #5 | 47076 |
| 231 | 15513 | 64.8 | 50.0 (255) | 15 | 175 | #3 | 47077 |
| 232 | 15514 | 67.2 | 62.2 | 17 | 367 | #4 | 47078 |
| 233 | 15515 | 50.0 | 50.0 | 12 | 150 | #1 | 47079 |
| 234 | 15516 | 61.6 | 50.0 | 14 | 160 | #3 | 47080 |
| 235 | 15517 | 67.2 | 63.3 | 15 | 729 | #4 | 47081 |
| 236 | 15518 | 73.6 | 61.5 | 35 | 324 | #5 | 47082 |
| 237 | 15519 | 64.8 | 50.0 | 15 | 213 | #3 | 47083 |
| 238 | 15520 | 64.0 | 56.3 (197) | 20 | 260 | #3 | 47084 |
| 239 | 15521 | 62.4 | 58.1 (179) | 21 | 171 | #3 | 47085 |
| 240 | 15522 | 62.4 | 56.0 | 13 | 200 | #3 | 47086 |
| 241 | 15523 | 66.4 | 59.6 | 15 | 384 | #4 | 47087 |
| 242 | 15524 | 66.4 | 52.8 (246) | 14 | 252 | #4 | 47088 |
| 243 | 15525 | 64.0 | 57.1 | 14 | 233 | #3 | 47089 |
| 244 | 15526 | 72.0 | 67.6 | 15 | 567 | #5 | 47090 |
| 245 | 15527 | 98.4 | 97.8 | 63 | 1783 | #10 | 47091 |
| 246 | 15528 | 77.6 | 71.6 | 18 | 758 | #6 | 47092 |
| 247 | 15529 | 69.6 | 61.1 | 20 | 390 | #4 | 47093 |
| 248 | 15530 | 72.8 | 67.6 | 28 | 634 | #5 | 47094 |
| 249 | 15531 | 50.0 | 50.0 | 12 | 150 | #1 | 47095 |
| 250 | 15532 | 77.6 | 71.6 | 23 | 678 | #6 | 47096 |
| 251 | 15533 | 50.0 | 50.0 | 12 | 150 | #1 | 47097 |
| 252 | 15534 | 53.6 | 50.0 | 14 | 165 | #1 | 47098 |
| 253 | 15535 | 58.4 | 50.0 | 12 | 167 | #2 | 47099 |
| 254 | 15536 | 88.0 | 69.8 | 33 | 651 | #8 | 47100 |
| 255 | 15537 | 69.6 | 66.2 | 24 | 652 | #4 | 47101 |
| 256 | 15538 | 59.2 | 55.6 | 12 | 190 | #2 | 47102 |
| 257 | 15539 | 70.4 | 68.0 | 19 | 677 | #5 | 47103 |
| 258 | 15540 | 50.0 | 50.0 | 12 | 150 | #1 | 47104 |
| 259 | 15541 | 67.2 | 59.3 | 20 | 290 | #4 | 47105 |
| 260 | 15542 | 72.0 | 66.5 | 16 | 615 | #5 | 47106 |
| 261 | 15543 | 58.4 | 50.0 | 14 | 172 | #2 | 47107 |
| 262 | 15544 | 82.4 | 70.5 | 30 | 708 | #7 | 47108 |
| 263 | 15545 | 84.0 | 79.6 | 27 | 2352 | #7 | 47109 |
| 264 | 15546 | 50.0 | 50.0 | 12 | 150 | #1 | 47110 |
| 265 | 15547 | 67.2 | 59.3 | 18 | 212 | #4 | 47111 |
| 266 | 15548 | 68.8 | 50.9 | 29 | 272 | #4 | 47112 |
| 267 | 15549 | 72.8 | 66.9 | 19 | 1010 | #5 | 47113 |
| 268 | 15550 | 83.2 | 78.9 | 21 | 904 | #7 | 47114 |
| 269 | 15551 | 66.4 | 60.4 | 18 | 247 | #4 | 47115 |
| 270 | 15552 | 66.4 | 58.2 | 13 | 206 | #4 | 47116 |
| 271 | 15553 | 65.6 | 50.0 | 14 | 260 | #4 | 47117 |
| 272 | 15554 | 50.0 (98) | — | 12 | 150 | #1 | 47118 |
| 273 | 15555 | 65.6 | 58.9 | 16 | 243 | #4 | 47119 |
| 274 | 15556 | 65.6 | 58.9 | 19 | 308 | #4 | 47120 |
| 275 | 15557 | 99.2 | 96.7 | 69 | 2000 | #10 | 47121 |
| 276 | 15558 | 63.2 | 59.6 | 15 | 323 | #3 | 47122 |
| 277 | 15559 | 75.2 | 65.1 | 17 | 441 | #6 | 47123 |
| 278 | 15560 | 98.4 | 96.0 | 96 | 1288 | #10 | 47124 |
| 279 | 15561 | 98.4 | 97.1 | 78 | 2589 | #10 | 47125 |
| 280 | 15562 | 63.2 | 58.9 | 13 | 206 | #3 | 47126 |
| 281 | 15563 | 50.0 | 50.0 | 12 | 150 | #1 | 47127 |
| 282 | 15564 | 50.0 | 50.0 | 12 | 150 | #1 | 47128 |
| 283 | 15565 | 55.2 | 54.8 (126) | 12 | 157 | #2 | 47129 |
| 284 | 15566 | 50.0 | 50.0 | 12 | 150 | #1 | 47130 |
| 285 | 15567 | 77.6 | 57.1 | 21 | 433 | #6 | 47131 |
| 286 | 15568 | 73.6 | 65.5 | 15 | 386 | #5 | 47132 |
| 287 | 15569 | 65.6 | 58.9 | 14 | 292 | #4 | 47133 |
| 288 | 15570 | 79.2 | 63.6 | 23 | 483 | #6 | 47134 |
| 289 | 15571 | 67.2 | 57.8 | 18 | 289 | #4 | 47135 |
| 290 | 15572 | 65.6 | 50.0 | 14 | 219 | #4 | 47136 |
| 291 | 15573 | 64.0 | 58.5 | 16 | 230 | #3 | 47137 |
| 292 | 15574 | 72.0 | 67.3 | 21 | 776 | #5 | 47138 |
| 293 | 15575 | 75.2 | 73.5 | 15 | 769 | #6 | 47139 |
| 294 | 15576 | 64.8 | 58.5 | 12 | 330 | #3 | 47140 |
| 295 | 15577 | 67.2 | 57.5 | 14 | 339 | #4 | 47141 |
| 296 | 15578 | 64.8 | 57.6 (210) | 17 | 153 | #3 | 47142 |
| 297 | 15579 | 64.0 | 62.5 (128) | 12 | 158 | #3 | 47143 |
| 298 | 15580 | 72.8 | 50.0 | 16 | 366 | #5 | 47144 |
| 299 | 15581 | 50.0 | 50.0 | 12 | 150 | #1 | 47145 |
| 300 | 15582 | 75.2 | 68.0 | 20 | 741 | #6 | 47146 |
| 301 | 15583 | 50.0 | 50.0 | 12 | 150 | #1 | 47147 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 302 | 15584 | 66.4 | 60.4 | 17 | 247 | #4 | 47148 |
| 303 | 15585 | 76.0 | 66.5 | 21 | 662 | #6 | 47149 |
| 304 | 15586 | 68.0 | 50.0 | 16 | 252 | #4 | 47150 |
| 305 | 15587 | 63.2 | 56.0 | 18 | 237 | #3 | 47151 |
| 306 | 15588 | 63.2 | 57.5 | 13 | 279 | #3 | 47152 |
| 307 | 15589 | 84.8 | 79.3 | 24 | 1183 | #7 | 47153 |
| 308 | 15590 | 62.4 | 50.0 | 14 | 150 | #3 | 47154 |
| 309 | 15591 | 50.0 | 50.0 | 12 | 150 | #1 | 47155 |
| 310 | 15592 | 100.0 | 97.5 | 154 | 1870 | #10 | 47156 |
| 311 | 15593 | 59.2 | 50.0 (193) | 15 | 150 | #2 | 47157 |
| 312 | 15594 | 50.0 | 50.0 | 12 | 150 | #1 | 47158 |
| 313 | 15595 | 65.6 | 57.8 | 23 | 238 | #4 | 47159 |
| 314 | 15596 | 84.8 | 77.8 | 26 | 1421 | #7 | 47160 |
| 315 | 15597 | 70.4 | 65.5 | 12 | 644 | #5 | 47161 |
| 316 | 15598 | 96.8 | 65.1 | 93 | 847 | #10 | 47162 |
| 317 | 15599 | 68.0 | 59.3 | 15 | 231 | #4 | 47163 |
| 318 | 15600 | 66.4 | 60.0 | 19 | 322 | #4 | 47164 |
| 319 | 15601 | 70.4 | 56.7 (187) | 19 | 298 | #5 | 47165 |
| 320 | 15602 | 69.6 | 66.2 | 15 | 518 | #4 | 47166 |
| 321 | 15603 | 50.0 | 50.0 | 13 | 155 | #1 | 47167 |
| 322 | 15604 | 72.8 | 65.8 | 12 | 428 | #5 | 47168 |
| 323 | 15605 | 61.6 | 57.8 | 13 | 185 | #3 | 47169 |
| 324 | 15606 | 72.8 | 67.3 | 22 | 560 | #5 | 47170 |
| 325 | 15607 | 86.4 | 77.1 | 21 | 910 | #8 | 47171 |
| 326 | 15608 | 75.2 | 60.7 | 20 | 418 | #6 | 47172 |
| 327 | 15609 | 81.8 (110) | — | 36 | 355 | #7 | 47173 |
| 328 | 15610 | 72.0 | 67.6 | 22 | 691 | #5 | 47174 |
| 329 | 15611 | 79.2 | 74.9 | 29 | 1082 | #6 | 47175 |
| 330 | 15612 | 84.0 | 74.1 (189) | 18 | 580 | #7 | 47176 |
| 331 | 15613 | 63.2 | 54.6 (273) | 14 | 201 | #3 | 47177 |
| 332 | 15614 | 50.0 | 50.0 | 12 | 150 | #1 | 47178 |
| 333 | 15615 | 65.6 | 57.4 (244) | 18 | 204 | #4 | 47179 |
| 334 | 15616 | 76.0 | 70.2 | 22 | 568 | #6 | 47180 |
| 335 | 15617 | 68.8 | 56.0 | 15 | 235 | #4 | 47181 |
| 336 | 15618 | 72.0 | 61.2 (273) | 15 | 411 | #5 | 47182 |
| 337 | 15619 | 56.1 (107) | — | 15 | 156 | #2 | 47183 |
| 338 | 15620 | 63.2 | 57.1 | 14 | 229 | #3 | 47184 |
| 339 | 15621 | 79.2 | 73.5 | 20 | 786 | #6 | 47185 |
| 340 | 15622 | 67.2 | 60.0 | 17 | 404 | #4 | 47186 |
| 341 | 15623 | 69.6 | 58.9 | 15 | 280 | #4 | 47187 |
| 342 | 15624 | 60.8 | 50.0 | 14 | 150 | #3 | 47188 |
| 343 | 15625 | 64.0 | 54.4 (272) | 13 | 217 | #3 | 47189 |
| 344 | 15626 | 58.4 | 50.0 | 12 | 164 | #2 | 47190 |
| 345 | 15627 | 50.0 | 50.0 | 12 | 150 | #1 | 47191 |
| 346 | 15628 | 66.4 | 59.3 | 19 | 203 | #4 | 47192 |
| 347 | 15629 | 76.8 | 74.2 | 18 | 862 | #6 | 47193 |
| 348 | 15630 | 50.0 | 50.0 | 12 | 150 | #1 | 47194 |
| 349 | 15631 | 75.2 | 67.3 | 27 | 773 | #6 | 47195 |
| 350 | 15632 | 77.6 | 71.3 | 19 | 734 | #6 | 47196 |
| 351 | 15633 | 50.0 | 50.0 | 19 | 158 | #1 | 47197 |
| 352 | 15634 | 61.6 | 57.5 | 13 | 206 | #3 | 47198 |
| 353 | 15635 | 64.0 | 60.4 | 14 | 257 | #3 | 47199 |
| 354 | 15636 | 79.2 | 70.5 | 22 | 1073 | #6 | 47200 |
| 355 | 15637 | 66.4 | 60.7 | 15 | 216 | #4 | 47201 |
| 356 | 15638 | 50.0 | 50.0 | 12 | 150 | #1 | 47202 |
| 357 | 15639 | 68.8 | 60.4 | 17 | 256 | #4 | 47203 |
| 358 | 15640 | 69.6 | 61.8 | 23 | 348 | #4 | 47204 |
| 359 | 15641 | 69.6 | 58.1 (260) | 13 | 291 | #4 | 47205 |
| 360 | 15642 | 68.8 | 59.6 | 16 | 265 | #4 | 47206 |
| 361 | 15643 | 63.2 | 58.2 | 12 | 233 | #3 | 47207 |
| 362 | 15644 | 50.0 | 50.0 | 19 | 150 | #1 | 47208 |
| 363 | 15645 | 50.0 | 50.0 | 12 | 150 | #1 | 47209 |
| 364 | 15646 | 76.0 | 70.9 | 15 | 844 | #6 | 47210 |
| 365 | 15647 | 81.6 | 73.8 | 22 | 1229 | #7 | 47211 |
| 366 | 15648 | 63.2 | 59.3 | 13 | 351 | #3 | 47212 |
| 367 | 15649 | 50.0 | 50.0 | 12 | 150 | #1 | 47213 |
| 368 | 15650 | 50.0 | 50.0 | 12 | 150 | #1 | 47214 |
| 369 | 15651 | 68.8 | 59.3 | 12 | 382 | #4 | 47215 |
| 370 | 15652 | 50.0 | 50.0 | 12 | 150 | #1 | 47216 |
| 371 | 15653 | 71.2 | 64.0 | 20 | 376 | #5 | 47217 |
| 372 | 15654 | 66.4 | 58.9 | 16 | 278 | #4 | 47218 |
| 373 | 15655 | 68.8 | 65.8 | 13 | 739 | #4 | 47219 |
| 374 | 15656 | 64.8 | 62.0 (184) | 20 | 221 | #3 | 47220 |
| 375 | 15657 | 72.0 | 66.5 | 21 | 486 | #5 | 47221 |
| 376 | 15658 | 75.2 | 64.0 | 18 | 539 | #6 | 47222 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 377 | 15659 | 72.8 | 65.1 | 30 | 937 | #5 | 47223 |
| 378 | 15660 | 60.0 | 55.3 | 15 | 194 | #2 | 47224 |
| 379 | 15661 | 67.2 | 64.4 | 13 | 530 | #4 | 47225 |
| 380 | 15662 | 75.2 | 66.5 | 14 | 599 | #6 | 47226 |
| 381 | 15663 | 56.0 | 50.0 | 13 | 154 | #2 | 47227 |
| 382 | 15664 | 75.2 | 64.0 | 21 | 516 | #6 | 47228 |
| 383 | 15665 | 65.6 | 58.2 | 13 | 241 | #4 | 47229 |
| 384 | 15666 | 50.0 | 50.0 | 12 | 150 | #1 | 47230 |
| 385 | 15667 | 70.4 | 61.1 | 19 | 344 | #5 | 47231 |
| 386 | 15668 | 84.0 | 77.1 | 29 | 1435 | #7 | 47232 |
| 387 | 15669 | 67.2 | 60.7 | 16 | 359 | #4 | 47233 |
| 388 | 15670 | 67.2 | 60.2 (231) | 17 | 261 | #4 | 47234 |
| 389 | 15671 | 72.8 | 65.1 | 12 | 642 | #5 | 47235 |
| 390 | 15672 | 64.8 | 62.2 | 13 | 386 | #3 | 47236 |
| 391 | 15673 | 65.6 | 60.4 | 17 | 267 | #4 | 47237 |
| 392 | 15674 | 63.3 (98) | — | 20 | 274 | #3 | 47238 |
| 393 | 15675 | 64.8 | 59.3 | 12 | 246 | #3 | 47239 |
| 394 | 15676 | 58.4 | 50.0 | 17 | 202 | #2 | 47240 |
| 395 | 15677 | 64.8 | 59.3 | 15 | 227 | #3 | 47241 |
| 396 | 15678 | 68.8 | 59.6 | 21 | 276 | #4 | 47242 |
| 397 | 15679 | 65.6 | 50.0 | 12 | 195 | #4 | 47243 |
| 398 | 15680 | 62.4 | 56.1 (148) | 16 | 150 | #3 | 47244 |
| 399 | 15681 | 73.6 | 61.8 | 24 | 310 | #5 | 47245 |
| 400 | 15682 | 71.2 | 61.8 | 26 | 279 | #5 | 47246 |
| 401 | 15683 | 74.4 | 68.0 | 16 | 618 | #5 | 47247 |
| 402 | 15684 | 63.2 | 57.1 | 13 | 214 | #3 | 47248 |
| 403 | 15685 | 59.2 | 55.3 | 12 | 239 | #2 | 47249 |
| 404 | 15686 | 50.0 | 50.0 | 12 | 150 | #1 | 47250 |
| 405 | 15687 | 72.8 | 64.0 | 16 | 389 | #5 | 47251 |
| 406 | 15688 | 79.2 | 73.1 | 19 | 705 | #6 | 47252 |
| 407 | 15689 | 61.6 | 50.0 (180) | 12 | 175 | #3 | 47253 |
| 408 | 15690 | 68.0 | 64.0 | 16 | 448 | #4 | 47254 |
| 409 | 15691 | 71.2 | 66.5 | 18 | 702 | #5 | 47255 |
| 410 | 15692 | 50.0 | 50.0 | 12 | 150 | #1 | 47256 |
| 411 | 15693 | 64.0 | 56.0 | 15 | 204 | #3 | 47257 |
| 412 | 15694 | 73.6 | 69.8 | 25 | 603 | #5 | 47258 |
| 413 | 15695 | 75.2 | 67.6 | 18 | 533 | #6 | 47259 |
| 414 | 15696 | 73.6 | 70.5 | 35 | 1187 | #5 | 47260 |
| 415 | 15697 | 50.0 | 50.0 | 12 | 150 | #1 | 47261 |
| 416 | 15698 | 64.8 | 50.0 (199) | 32 | 175 | #3 | 47262 |
| 417 | 15699 | 95.2 | 61.5 | 30 | 698 | #10 | 47263 |
| 418 | 15700 | 60.8 | 50.0 | 15 | 190 | #3 | 47264 |
| 419 | 15701 | 64.0 | 56.7 | 14 | 216 | #3 | 47265 |
| 420 | 15702 | 61.6 | 57.5 | 13 | 210 | #3 | 47266 |
| 421 | 15703 | 69.6 | 63.6 | 15 | 398 | #4 | 47267 |
| 422 | 15704 | 75.2 | 68.4 | 20 | 543 | #6 | 47268 |
| 423 | 15705 | 73.6 | 64.0 | 21 | 593 | #5 | 47269 |
| 424 | 15706 | 70.4 | 66.9 | 17 | 679 | #5 | 47270 |
| 425 | 15707 | 67.2 | 61.1 | 13 | 229 | #4 | 47271 |
| 426 | 15708 | 50.0 | 50.0 | 12 | 150 | #1 | 47272 |
| 427 | 15709 | 68.0 | 61.8 | 22 | 324 | #4 | 47273 |
| 428 | 15710 | 68.0 | 60.4 | 15 | 416 | #4 | 47274 |
| 429 | 15711 | 50.0 | 50.0 | 12 | 150 | #1 | 47275 |
| 430 | 15712 | 64.0 | 58.5 | 13 | 316 | #3 | 47276 |
| 431 | 15713 | 85.6 | 81.8 | 34 | 2529 | #8 | 47277 |
| 432 | 15714 | 63.2 | 56.4 | 14 | 270 | #3 | 47278 |
| 433 | 15715 | 50.0 | 50.0 | 12 | 150 | #1 | 47279 |
| 434 | 15716 | 66.4 | 56.4 | 15 | 224 | #4 | 47280 |
| 435 | 15717 | 50.0 | 50.0 (163) | 12 | 150 | #1 | 47281 |
| 436 | 15718 | 100.0 | 100.0 | 19 | 5097 | #10 | 47282 |
| 437 | 15719 | 62.4 | 56.4 | 17 | 193 | #3 | 47283 |
| 438 | 15720 | 50.0 | 50.0 | 12 | 150 | #1 | 47284 |
| 439 | 15721 | 50.0 | 50.0 (197) | 12 | 150 | #1 | 47285 |
| 440 | 15722 | 68.8 | 50.0 | 20 | 298 | #4 | 47286 |
| 441 | 15723 | 99.2 | 97.8 | 87 | 2269 | #10 | 47287 |
| 442 | 15724 | 62.4 | 50.0 | 13 | 170 | #3 | 47288 |
| 443 | 15725 | 50.0 | 50.0 | 12 | 150 | #1 | 47289 |
| 444 | 15726 | 59.2 | 57.5 | 18 | 254 | #2 | 47290 |
| 445 | 15727 | 62.4 | 50.0 | 12 | 205 | #3 | 47291 |
| 446 | 15728 | 72.0 | 62.9 | 17 | 408 | #5 | 47292 |
| 447 | 15729 | 50.0 | 50.0 | 12 | 150 | #1 | 47293 |
| 448 | 15730 | 75.2 | 67.6 | 45 | 900 | #6 | 47294 |
| 449 | 15731 | 76.0 | 68.0 | 18 | 1297 | #6 | 47295 |
| 450 | 15732 | 61.6 | 51.6 | 17 | 200 | #3 | 47296 |
| 451 | 15733 | 78.4 | 75.3 | 17 | 1056 | #6 | 47297 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 452 | 15734 | 69.6 | 63.3 | 18 | 431 | #4 | 47298 |
| 453 | 15735 | 66.4 | 62.2 | 19 | 239 | #4 | 47299 |
| 454 | 15736 | 62.4 | 55.6 | 12 | 224 | #3 | 47300 |
| 455 | 15737 | 76.0 | 69.1 | 18 | 604 | #6 | 47301 |
| 456 | 15738 | 66.4 | 61.8 | 17 | 305 | #4 | 47302 |
| 457 | 15739 | 66.4 | 61.1 | 17 | 272 | #4 | 47303 |
| 458 | 15740 | 68.0 | 60.0 | 16 | 270 | #4 | 47304 |
| 459 | 15741 | 72.8 | 65.1 | 12 | 527 | #5 | 47305 |
| 460 | 15742 | 50.0 | 50.0 | 12 | 150 | #1 | 47306 |
| 461 | 15743 | 71.2 | 65.8 | 20 | 472 | #5 | 47307 |
| 462 | 15744 | 67.2 | 64.0 | 24 | 419 | #4 | 47308 |
| 463 | 15745 | 79.2 | 69.8 | 17 | 601 | #6 | 47309 |
| 464 | 15746 | 66.4 | 60.0 | 17 | 257 | #4 | 47310 |
| 465 | 15747 | 69.6 | 59.3 | 14 | 393 | #4 | 47311 |
| 466 | 15748 | 70.4 | 60.7 | 20 | 264 | #5 | 47312 |
| 467 | 15749 | 72.8 | 66.2 | 18 | 462 | #5 | 47313 |
| 468 | 15750 | 50.0 | 50.0 | 12 | 150 | #1 | 47314 |
| 469 | 15751 | 64.8 | 58.9 | 16 | 242 | #3 | 47315 |
| 470 | 15752 | 67.2 | 62.9 | 14 | 411 | #4 | 47316 |
| 471 | 15753 | 71.2 | 64.4 | 27 | 466 | #5 | 47317 |
| 472 | 15754 | 65.6 | 60.7 | 15 | 218 | #4 | 47318 |
| 473 | 15755 | 66.4 | 60.7 | 13 | 278 | #4 | 47319 |
| 474 | 15756 | 68.0 | 64.7 | 12 | 393 | #4 | 47320 |
| 475 | 15757 | 68.0 | 58.2 | 18 | 259 | #4 | 47321 |
| 476 | 15758 | 80.8 | 69.7 (145) | 23 | 405 | #7 | 47322 |
| 477 | 15759 | 76.8 | 66.9 | 36 | 583 | #6 | 47323 |
| 478 | 15760 | 67.2 | 50.0 | 17 | 272 | #4 | 47324 |
| 479 | 15761 | 60.8 | 57.1 | 13 | 243 | #3 | 47325 |
| 480 | 15762 | 50.0 | 50.0 | 12 | 150 | #1 | 47326 |
| 481 | 15763 | 50.0 | 50.0 | 12 | 150 | #1 | 47327 |
| 482 | 15764 | 72.0 | 59.3 | 22 | 409 | #5 | 47328 |
| 483 | 15765 | 73.6 | 69.1 | 18 | 673 | #5 | 47329 |
| 484 | 15766 | 74.4 | 71.3 | 21 | 1067 | #5 | 47330 |
| 485 | 15767 | 99.2 | 97.8 | 87 | 2932 | #10 | 47331 |
| 486 | 15768 | 50.0 | 50.0 | 12 | 150 | #1 | 47332 |
| 487 | 15769 | 62.4 | 58.5 | 19 | 364 | #3 | 47333 |
| 488 | 15770 | 50.0 | 50.0 | 12 | 150 | #1 | 47334 |
| 489 | 15771 | 63.2 | 59.3 | 14 | 280 | #3 | 47335 |
| 490 | 15772 | 50.0 | 50.0 | 12 | 150 | #1 | 47336 |
| 491 | 15773 | 84.0 | 76.0 | 21 | 685 | #7 | 47337 |
| 492 | 15774 | 75.2 | 66.9 | 16 | 569 | #6 | 47338 |
| 493 | 15775 | 50.0 | 50.0 (209) | 12 | 150 | #1 | 47339 |
| 494 | 15776 | 68.8 | 61.1 | 22 | 346 | #4 | 47340 |
| 495 | 15777 | 64.0 | 58.5 | 16 | 186 | #3 | 47341 |
| 496 | 15778 | 72.8 | 68.7 | 15 | 705 | #5 | 47342 |
| 497 | 15779 | 64.0 | 59.6 | 16 | 249 | #3 | 47343 |
| 498 | 15780 | 62.4 | 60.0 | 15 | 335 | #3 | 47344 |
| 499 | 15781 | 68.0 | 51.3 | 18 | 250 | #4 | 47345 |
| 500 | 15782 | 72.0 | 65.8 | 14 | 491 | #5 | 47346 |
| 501 | 15783 | 62.4 | 50.0 | 13 | 195 | #3 | 47347 |
| 502 | 15784 | 64.8 | 50.0 | 12 | 165 | #3 | 47348 |
| 503 | 15785 | 68.8 | 63.6 | 15 | 401 | #4 | 47349 |
| 504 | 15786 | 76.0 | 74.2 | 24 | 1673 | #6 | 47350 |
| 505 | 15787 | 64.0 | 50.0 | 12 | 173 | #3 | 47351 |
| 506 | 15788 | 73.6 | 67.6 | 17 | 670 | #5 | 47352 |
| 507 | 15789 | 50.0 | 50.0 | 12 | 150 | #1 | 47353 |
| 508 | 15790 | 50.0 | 50.0 | 12 | 150 | #1 | 47354 |
| 509 | 15791 | 76.0 | 69.5 | 20 | 593 | #6 | 47355 |
| 510 | 15792 | 68.8 | 62.9 | 13 | 449 | #4 | 47356 |
| 511 | 15793 | 72.8 | 62.5 | 20 | 437 | #5 | 47357 |
| 512 | 15794 | 64.0 | 58.5 | 13 | 194 | #3 | 47358 |
| 513 | 15795 | 65.6 | 60.4 | 15 | 208 | #4 | 47359 |
| 514 | 15796 | 80.8 | 77.8 | 16 | 2752 | #7 | 47360 |
| 515 | 15797 | 65.6 | 60.4 | 17 | 421 | #4 | 47361 |
| 516 | 15798 | 74.4 | 66.9 | 27 | 592 | #5 | 47362 |
| 517 | 15799 | 50.0 | 50.0 | 12 | 150 | #1 | 47363 |
| 518 | 15800 | 71.2 | 50.0 | 17 | 293 | #5 | 47364 |
| 519 | 15801 | 63.2 | 58.9 | 16 | 224 | #3 | 47365 |
| 520 | 15802 | 63.2 | 57.8 | 14 | 262 | #3 | 47366 |
| 521 | 15803 | 72.0 | 61.1 | 26 | 405 | #5 | 47367 |
| 522 | 15804 | 97.6 | 80.0 | 62 | 1044 | #10 | 47368 |
| 523 | 15805 | 50.0 | 50.0 | 12 | 150 | #1 | 47369 |
| 524 | 15806 | 65.6 | 50.0 | 15 | 218 | #4 | 47370 |
| 525 | 15807 | 96.0 | 93.8 | 72 | 1944 | #10 | 47371 |
| 526 | 15808 | 80.0 | 59.6 | 25 | 492 | #6 | 47372 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 527 | 15809 | 68.8 | 65.5 | 16 | 507 | #4 | 47373 |
| 528 | 15810 | 67.2 | 60.4 | 17 | 253 | #4 | 47374 |
| 529 | 15811 | 63.2 | 57.5 | 12 | 276 | #3 | 47375 |
| 530 | 15812 | 100.0 | 99.3 | 184 | 1754 | #10 | 47376 |
| 531 | 15813 | 65.6 | 57.8 | 19 | 289 | #4 | 47377 |
| 532 | 15814 | 66.4 | 61.1 | 19 | 327 | #4 | 47378 |
| 533 | 15815 | 85.6 | 62.5 | 32 | 598 | #8 | 47379 |
| 534 | 15816 | 90.4 | 66.9 | 49 | 558 | #9 | 47380 |
| 535 | 15817 | 64.8 | 50.0 | 13 | 215 | #3 | 47381 |
| 536 | 15818 | 68.0 | 60.7 | 25 | 279 | #4 | 47382 |
| 537 | 15819 | 79.2 | 72.4 | 17 | 661 | #6 | 47383 |
| 538 | 15820 | 71.2 | 60.0 | 28 | 317 | #5 | 47384 |
| 539 | 15821 | 70.4 | 62.9 | 17 | 604 | #5 | 47385 |
| 540 | 15822 | 65.6 | 59.6 | 18 | 215 | #4 | 47386 |
| 541 | 15823 | 68.0 | 62.5 | 27 | 456 | #4 | 47387 |
| 542 | 15824 | 50.0 | 50.0 | 12 | 150 | #1 | 47388 |
| 543 | 15825 | 99.2 | 97.5 | 87 | 2104 | #10 | 47389 |
| 544 | 15826 | 64.0 | 57.8 (223) | 16 | 191 | #3 | 47390 |
| 545 | 15827 | 50.0 | 50.0 | 12 | 150 | #1 | 47391 |
| 546 | 15828 | 68.0 | 63.3 | 19 | 555 | #4 | 47392 |
| 547 | 15829 | 50.0 | 50.0 | 12 | 150 | #1 | 47393 |
| 548 | 15830 | 50.0 | 50.0 | 12 | 150 | #1 | 47394 |
| 549 | 15831 | 65.6 | 50.0 | 13 | 265 | #4 | 47395 |
| 550 | 15832 | 64.0 | 50.0 | 13 | 197 | #3 | 47396 |
| 551 | 15833 | 57.6 | 54.2 | 12 | 214 | #2 | 47397 |
| 552 | 15834 | 81.6 | 60.7 | 27 | 455 | #7 | 47398 |
| 553 | 15835 | 72.8 | 61.5 | 17 | 330 | #5 | 47399 |
| 554 | 15836 | 71.2 | 65.1 | 15 | 498 | #5 | 47400 |
| 555 | 15837 | 67.2 | 60.0 | 19 | 259 | #4 | 47401 |
| 556 | 15838 | 63.2 | 60.1 (158) | 15 | 155 | #3 | 47402 |
| 557 | 15839 | 72.8 | 70.9 | 12 | 981 | #5 | 47403 |
| 558 | 15840 | 50.0 | 50.0 | 12 | 150 | #1 | 47404 |
| 559 | 15841 | 78.4 | 76.0 | 20 | 740 | #6 | 47405 |
| 560 | 15842 | 82.4 | 80.0 | 27 | 1295 | #7 | 47406 |
| 561 | 15843 | 78.4 | 72.7 | 21 | 904 | #6 | 47407 |
| 562 | 15844 | 90.4 | 86.2 | 39 | 1577 | #9 | 47408 |
| 563 | 15845 | 68.8 | 57.8 | 15 | 356 | #4 | 47409 |
| 564 | 15846 | 63.2 | 60.4 | 14 | 286 | #3 | 47410 |
| 565 | 15847 | 74.4 | 66.9 | 18 | 673 | #5 | 47411 |
| 566 | 15848 | 50.0 | 50.0 | 12 | 150 | #1 | 47412 |
| 567 | 15849 | 70.4 | 62.9 | 31 | 409 | #5 | 47413 |
| 568 | 15850 | 71.2 | 63.3 | 18 | 489 | #5 | 47414 |
| 569 | 15851 | 67.2 | 56.4 | 19 | 228 | #4 | 47415 |
| 570 | 15852 | 52.8 | 50.0 | 14 | 154 | #1 | 47416 |
| 571 | 15853 | 50.0 | 50.0 | 12 | 150 | #1 | 47417 |
| 572 | 15854 | 66.4 | 61.1 | 13 | 218 | #4 | 47418 |
| 573 | 15855 | 50.0 | 50.0 | 12 | 188 | #1 | 47419 |
| 574 | 15856 | 97.6 | 91.3 | 49 | 1334 | #10 | 47420 |
| 575 | 15857 | 50.4 | 50.0 | 12 | 150 | #1 | 47421 |
| 576 | 15858 | 73.6 | 70.2 | 21 | 790 | #5 | 47422 |
| 577 | 15859 | 68.0 | 50.5 | 18 | 194 | #4 | 47423 |
| 578 | 15860 | 68.8 | 60.7 | 22 | 356 | #4 | 47424 |
| 579 | 15861 | 64.8 | 59.3 | 13 | 235 | #3 | 47425 |
| 580 | 15862 | 82.4 | 67.5 (231) | 17 | 506 | #7 | 47426 |
| 581 | 15863 | 68.8 | 63.6 | 17 | 519 | #4 | 47427 |
| 582 | 15864 | 68.0 | 57.0 (263) | 16 | 162 | #4 | 47428 |
| 583 | 15865 | 69.6 | 50.0 | 14 | 300 | #4 | 47429 |
| 584 | 15866 | 64.0 | 57.8 | 13 | 225 | #3 | 47430 |
| 585 | 15867 | 71.2 | 50.0 | 17 | 349 | #5 | 47431 |
| 586 | 15868 | 60.0 | 50.0 | 12 | 187 | #2 | 47432 |
| 587 | 15869 | 72.8 | 66.2 | 19 | 631 | #5 | 47433 |
| 588 | 15870 | 68.8 | 61.8 (173) | 12 | 261 | #4 | 47434 |
| 589 | 15871 | 70.4 | 60.7 | 16 | 286 | #5 | 47435 |
| 590 | 15872 | 62.5 (88) | — | 24 | 255 | #3 | 47436 |
| 591 | 15873 | 67.2 | 60.4 | 17 | 267 | #4 | 47437 |
| 592 | 15874 | 91.2 | 85.9 (206) | 27 | 773 | #9 | 47438 |
| 593 | 15875 | 71.2 | 65.8 | 19 | 409 | #5 | 47439 |
| 594 | 15876 | 66.4 | 60.3 (247) | 14 | 345 | #4 | 47440 |
| 595 | 15877 | 72.0 | 63.6 | 25 | 586 | #5 | 47441 |
| 596 | 15878 | 50.0 | 50.0 | 12 | 150 | #1 | 47442 |
| 597 | 15879 | 78.4 | 63.3 | 33 | 479 | #6 | 47443 |
| 598 | 15880 | 60.8 | 50.0 | 15 | 154 | #3 | 47444 |
| 599 | 15881 | 66.4 | 50.0 | 15 | 216 | #4 | 47445 |
| 600 | 15882 | 69.6 | 65.5 | 14 | 490 | #4 | 47446 |
| 601 | 15883 | 75.2 | 66.2 | 24 | 579 | #6 | 47447 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 602 | 15884 | 76.0 | 66.9 | 22 | 494 | #6 | 47448 |
| 603 | 15885 | 84.0 | 76.7 | 21 | 801 | #7 | 47449 |
| 604 | 15886 | 82.4 | 69.8 | 20 | 628 | #7 | 47450 |
| 605 | 15887 | 72.8 | 62.9 | 13 | 420 | #5 | 47451 |
| 606 | 15888 | 68.8 | 58.5 | 16 | 432 | #4 | 47452 |
| 607 | 15889 | 85.6 | 65.8 | 24 | 500 | #8 | 47453 |
| 608 | 15890 | 71.2 | 66.5 | 18 | 592 | #5 | 47454 |
| 609 | 15891 | 67.2 | 58.9 | 12 | 318 | #4 | 47455 |
| 610 | 15892 | 69.6 | 64.4 | 19 | 550 | #4 | 47456 |
| 611 | 15893 | 80.0 | 76.7 | 19 | 1067 | #6 | 47457 |
| 612 | 15894 | 64.8 | 50.9 | 12 | 252 | #3 | 47458 |
| 613 | 15895 | 68.0 | 57.8 | 24 | 356 | #4 | 47459 |
| 614 | 15896 | 73.6 | 61.1 | 29 | 297 | #5 | 47460 |
| 615 | 15897 | 62.4 | 50.9 | 14 | 209 | #3 | 47461 |
| 616 | 15898 | 71.2 | 52.5 (179) | 34 | 298 | #5 | 47462 |
| 617 | 15899 | 69.6 | 62.5 | 17 | 501 | #4 | 47463 |
| 618 | 15900 | 76.8 | 66.5 | 17 | 631 | #6 | 47464 |
| 619 | 15901 | 78.4 | 68.0 | 16 | 572 | #6 | 47465 |
| 620 | 15902 | 73.6 | 60.0 | 25 | 325 | #5 | 47466 |
| 621 | 15903 | 74.4 | 66.9 | 18 | 682 | #5 | 47467 |
| 622 | 15904 | 50.0 | 50.0 | 12 | 150 | #1 | 47468 |
| 623 | 15905 | 68.8 | 61.8 | 15 | 390 | #4 | 47469 |
| 624 | 15906 | 71.2 | 50.0 | 20 | 311 | #5 | 47470 |
| 625 | 15907 | 66.4 | 56.0 | 14 | 245 | #4 | 47471 |
| 626 | 15908 | 50.0 | 50.0 (271) | 12 | 150 | #1 | 47472 |
| 627 | 15909 | 75.2 | 71.6 | 19 | 1196 | #6 | 47473 |
| 628 | 15910 | 65.6 | 52.4 | 12 | 218 | #4 | 47474 |
| 629 | 15911 | 66.4 | 59.6 | 13 | 210 | #4 | 47475 |
| 630 | 15912 | 69.6 | 61.8 | 15 | 437 | #4 | 47476 |
| 631 | 15913 | 79.2 | 69.8 | 21 | 596 | #6 | 47477 |
| 632 | 15914 | 65.6 | 50.0 | 16 | 242 | #4 | 47478 |
| 633 | 15915 | 63.2 | 56.7 | 13 | 230 | #3 | 47479 |
| 634 | 15916 | 100.0 | 99.3 | 139 | 1859 | #10 | 47480 |
| 635 | 15917 | 77.6 | 71.3 | 25 | 768 | #6 | 47481 |
| 636 | 15918 | 67.2 | 50.0 | 13 | 237 | #4 | 47482 |
| 637 | 15919 | 66.4 | 61.1 | 14 | 342 | #4 | 47483 |
| 638 | 15920 | 50.0 | 50.0 | 12 | 150 | #1 | 47484 |
| 639 | 15921 | 71.2 | 50.0 | 16 | 247 | #5 | 47485 |
| 640 | 15922 | 61.6 | 56.0 | 15 | 222 | #3 | 47486 |
| 641 | 15923 | 79.2 | 75.3 | 16 | 845 | #6 | 47487 |
| 642 | 15924 | 66.4 | 60.0 | 16 | 325 | #4 | 47488 |
| 643 | 15925 | 50.0 | 50.0 | 12 | 150 | #1 | 47489 |
| 644 | 15926 | 63.2 | 58.9 | 14 | 205 | #3 | 47490 |
| 645 | 15927 | 50.0 | 50.0 | 12 | 150 | #1 | 47491 |
| 646 | 15928 | 66.4 | 59.6 | 17 | 238 | #4 | 47492 |
| 647 | 15929 | 50.0 | 50.0 | 12 | 150 | #1 | 47493 |
| 648 | 15930 | 78.4 | 63.6 | 29 | 353 | #6 | 47494 |
| 649 | 15931 | 72.8 | 66.2 | 23 | 596 | #5 | 47495 |
| 650 | 15932 | 77.6 | 74.9 | 24 | 823 | #6 | 47496 |
| 651 | 15933 | 69.6 | 51.6 | 19 | 314 | #4 | 47497 |
| 652 | 15934 | 50.0 | 50.0 | 12 | 150 | #1 | 47498 |
| 653 | 15935 | 71.2 | 61.1 | 24 | 329 | #5 | 47499 |
| 654 | 15936 | 75.2 | 68.4 | 14 | 562 | #6 | 47500 |
| 655 | 15937 | 64.0 | 50.0 | 13 | 214 | #3 | 47501 |
| 656 | 15938 | 74.4 | 50.9 | 23 | 428 | #5 | 47502 |
| 657 | 15939 | 68.8 | 60.4 | 15 | 305 | #4 | 47503 |
| 658 | 15940 | 64.0 | 50.0 (218) | 19 | 166 | #3 | 47504 |
| 659 | 15941 | 69.6 | 63.3 | 15 | 444 | #4 | 47505 |
| 660 | 15942 | 68.0 | 62.5 | 18 | 480 | #4 | 47506 |
| 661 | 15943 | 67.2 | 61.5 | 27 | 314 | #4 | 47507 |
| 662 | 15944 | 67.2 | 64.4 | 16 | 499 | #4 | 47508 |
| 663 | 15945 | 67.2 | 59.6 | 15 | 264 | #4 | 47509 |
| 664 | 15946 | 99.2 | 97.5 | 125 | 2344 | #10 | 47510 |
| 665 | 15947 | 66.4 | 55.3 | 16 | 230 | #4 | 47511 |
| 666 | 15948 | 68.8 | 61.1 | 20 | 420 | #4 | 47512 |
| 667 | 15949 | 69.6 | 60.0 | 14 | 246 | #4 | 47513 |
| 668 | 15950 | 70.4 | 63.6 | 16 | 493 | #5 | 47514 |
| 669 | 15951 | 50.0 | 50.0 | 12 | 150 | #1 | 47515 |
| 670 | 15952 | 64.8 | 57.1 | 12 | 278 | #3 | 47516 |
| 671 | 15953 | 87.2 | 81.1 (196) | 25 | 625 | #8 | 47517 |
| 672 | 15954 | 70.4 | 66.5 | 15 | 941 | #5 | 47518 |
| 673 | 15955 | 73.6 | 67.3 | 18 | 622 | #5 | 47519 |
| 674 | 15956 | 68.8 | 63.6 | 18 | 441 | #4 | 47520 |
| 675 | 15957 | 71.2 | 65.1 | 20 | 404 | #5 | 47521 |
| 676 | 15958 | 61.6 | 57.5 | 14 | 178 | #3 | 47522 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 677 | 15959 | 61.6 | 50.0 | 14 | 184 | #3 | 47523 |
| 678 | 15960 | 66.4 | 61.5 | 16 | 601 | #4 | 47524 |
| 679 | 15961 | 79.2 | 73.8 | 21 | 1205 | #6 | 47525 |
| 680 | 15962 | 63.2 | 58.2 | 15 | 273 | #3 | 47526 |
| 681 | 15963 | 69.6 | 62.9 | 15 | 538 | #4 | 47527 |
| 682 | 15964 | 72.8 | 66.2 | 16 | 701 | #5 | 47528 |
| 683 | 15965 | 71.2 | 64.0 | 20 | 547 | #5 | 47529 |
| 684 | 15966 | 67.2 | 56.0 | 15 | 232 | #4 | 47530 |
| 685 | 15967 | 66.4 | 50.0 | 14 | 191 | #4 | 47531 |
| 686 | 15968 | 64.0 | 59.1 (254) | 17 | 252 | #3 | 47532 |
| 687 | 15969 | 69.6 | 62.2 | 15 | 440 | #4 | 47533 |
| 688 | 15970 | 79.2 | 73.8 | 26 | 743 | #6 | 47534 |
| 689 | 15971 | 83.2 | 78.9 | 23 | 1321 | #7 | 47535 |
| 690 | 15972 | 83.2 | 78.2 | 27 | 835 | #7 | 47536 |
| 691 | 15973 | 76.8 | 71.6 | 18 | 641 | #6 | 47537 |
| 692 | 15974 | 61.6 | 57.8 | 13 | 189 | #3 | 47538 |
| 693 | 15975 | 65.6 | 58.9 | 15 | 217 | #4 | 47539 |
| 694 | 15976 | 78.4 | 69.5 | 25 | 708 | #6 | 47540 |
| 695 | 15977 | 70.4 | 60.4 | 26 | 399 | #5 | 47541 |
| 696 | 15978 | 76.0 | 69.5 | 20 | 610 | #6 | 47542 |
| 697 | 15979 | 50.0 | 50.0 | 12 | 150 | #1 | 47543 |
| 698 | 15980 | 50.0 | 50.0 | 12 | 150 | #1 | 47544 |
| 699 | 15981 | 100.0 | 99.6 | 230 | 3251 | #10 | 47545 |
| 700 | 15982 | 61.6 | 57.1 | 15 | 189 | #3 | 47546 |
| 701 | 15983 | 71.2 | 65.5 | 17 | 578 | #5 | 47547 |
| 702 | 15984 | 66.4 | 61.1 | 16 | 350 | #4 | 47548 |
| 703 | 15985 | 50.0 | 50.0 | 12 | 150 | #1 | 47549 |
| 704 | 15986 | 64.0 | 61.1 | 18 | 356 | #3 | 47550 |
| 705 | 15987 | 68.0 | 50.0 | 13 | 205 | #4 | 47551 |
| 706 | 15988 | 50.0 | 50.0 | 12 | 150 | #1 | 47552 |
| 707 | 15989 | 50.0 | 50.0 | 12 | 150 | #1 | 47553 |
| 708 | 15990 | 71.2 | 65.5 | 15 | 548 | #5 | 47554 |
| 709 | 15991 | 50.0 | 50.0 | 13 | 173 | #1 | 47555 |
| 710 | 15992 | 70.4 | 64.4 | 12 | 388 | #5 | 47556 |
| 711 | 15993 | 60.8 | 56.7 | 16 | 225 | #3 | 47557 |
| 712 | 15994 | 64.8 | 59.3 | 16 | 360 | #3 | 47558 |
| 713 | 15995 | 68.8 | 59.3 | 35 | 256 | #4 | 47559 |
| 714 | 15996 | 80.0 | 77.1 | 29 | 1948 | #6 | 47560 |
| 715 | 15997 | 64.0 | 59.3 | 12 | 293 | #3 | 47561 |
| 716 | 15998 | 63.2 | 56.3 (252) | 16 | 167 | #3 | 47562 |
| 717 | 15999 | 75.2 | 57.1 | 13 | 432 | #6 | 47563 |
| 718 | 16000 | 68.0 | 63.3 | 18 | 406 | #4 | 47564 |
| 719 | 16001 | 72.8 | 59.6 | 15 | 430 | #5 | 47565 |
| 720 | 16002 | 62.4 | 58.2 | 12 | 266 | #3 | 47566 |
| 721 | 16003 | 63.2 | 58.8 (257) | 18 | 217 | #3 | 47567 |
| 722 | 16004 | 50.0 | 50.0 | 12 | 150 | #1 | 47568 |
| 723 | 16005 | 64.8 | 60.0 | 20 | 259 | #3 | 47569 |
| 724 | 16006 | 73.6 | 65.5 | 28 | 714 | #5 | 47570 |
| 725 | 16007 | 67.2 | 50.0 | 14 | 208 | #4 | 47571 |
| 726 | 16008 | 60.8 | 58.2 | 13 | 219 | #3 | 47572 |
| 727 | 16009 | 99.2 | 97.8 | 87 | 7077 | #10 | 47573 |
| 728 | 16010 | 100.0 | 97.8 | 138 | 1986 | #10 | 47574 |
| 729 | 16011 | 64.8 | 59.6 | 16 | 333 | #3 | 47575 |
| 730 | 16012 | 67.2 | 59.6 | 12 | 344 | #4 | 47576 |
| 731 | 16013 | 70.4 | 60.0 | 19 | 292 | #5 | 47577 |
| 732 | 16014 | 71.2 | 63.3 | 16 | 441 | #5 | 47578 |
| 733 | 16015 | 73.6 | 68.0 | 20 | 548 | #5 | 47579 |
| 734 | 16016 | 50.0 | 50.0 | 12 | 150 | #1 | 47580 |
| 735 | 16017 | 76.8 | 68.0 | 20 | 527 | #6 | 47581 |
| 736 | 16018 | 66.4 | 50.0 | 12 | 217 | #4 | 47582 |
| 737 | 16019 | 50.0 | 50.0 | 12 | 156 | #1 | 47583 |
| 738 | 16020 | 66.4 | 61.7 (141) | 15 | 221 | #4 | 47584 |
| 739 | 16021 | 60.0 | 50.0 | 12 | 155 | #2 | 47585 |
| 740 | 16022 | 60.8 | 50.0 | 12 | 152 | #3 | 47586 |
| 741 | 16023 | 75.2 | 67.6 | 45 | 900 | #6 | 47587 |
| 742 | 16024 | 66.4 | 59.6 | 16 | 245 | #4 | 47588 |
| 743 | 16025 | 65.6 | 58.5 | 16 | 204 | #4 | 47589 |
| 744 | 16026 | 50.0 | 50.0 | 12 | 150 | #1 | 47590 |
| 745 | 16027 | 67.2 | 60.7 | 14 | 475 | #4 | 47591 |
| 746 | 16028 | 68.0 | 62.5 | 19 | 359 | #4 | 47592 |
| 747 | 16029 | 76.0 | 69.8 | 18 | 636 | #6 | 47593 |
| 748 | 16030 | 50.0 | 50.0 | 12 | 150 | #1 | 47594 |
| 749 | 16031 | 50.0 | 50.0 | 12 | 150 | #1 | 47595 |
| 750 | 16032 | 68.0 | 62.2 | 20 | 427 | #4 | 47596 |
| 751 | 16033 | 79.2 | 73.5 | 21 | 1059 | #6 | 47597 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 752 | 16034 | 66.4 | 61.5 | 23 | 397 | #4 | 47598 |
| 753 | 16035 | 64.0 | 50.0 | 14 | 187 | #3 | 47599 |
| 754 | 16036 | 60.0 | 50.0 | 13 | 156 | #2 | 47600 |
| 755 | 16037 | 60.0 | 50.0 | 13 | 167 | #2 | 47601 |
| 756 | 16038 | 69.6 | 62.2 | 20 | 411 | #4 | 47602 |
| 757 | 16039 | 70.4 | 61.1 (265) | 19 | 362 | #5 | 47603 |
| 758 | 16040 | 75.2 | 71.3 | 17 | 711 | #6 | 47604 |
| 759 | 16041 | 99.2 | 97.8 | 87 | 2285 | #10 | 47605 |
| 760 | 16042 | 61.6 | 54.5 | 13 | 180 | #3 | 47606 |
| 761 | 16043 | 74.4 | 61.5 | 26 | 368 | #5 | 47607 |
| 762 | 16044 | 64.0 | 55.8 (258) | 15 | 167 | #3 | 47608 |
| 763 | 16045 | 67.2 | 63.3 | 13 | 537 | #4 | 47609 |
| 764 | 16046 | 64.8 | 50.0 | 15 | 199 | #3 | 47610 |
| 765 | 16047 | 76.8 | 70.5 | 18 | 688 | #6 | 47611 |
| 766 | 16048 | 79.2 | 62.2 | 19 | 405 | #6 | 47612 |
| 767 | 16049 | 50.0 | 50.0 | 12 | 150 | #1 | 47613 |
| 768 | 16050 | 50.0 | 50.0 | 12 | 150 | #1 | 47614 |
| 769 | 16051 | 70.4 | 60.4 | 19 | 370 | #5 | 47615 |
| 770 | 16052 | 84.8 | 81.1 | 21 | 895 | #7 | 47616 |
| 771 | 16053 | 63.2 | 50.0 | 18 | 230 | #3 | 47617 |
| 772 | 16054 | 76.0 | 69.8 | 17 | 872 | #6 | 47618 |
| 773 | 16055 | 50.0 | 50.0 | 12 | 150 | #1 | 47619 |
| 774 | 16056 | 63.2 | 50.2 | 18 | 165 | #3 | 47620 |
| 775 | 16057 | 69.6 | 65.8 | 21 | 605 | #4 | 47621 |
| 776 | 16058 | 72.0 | 62.2 | 35 | 398 | #5 | 47622 |
| 777 | 16059 | 66.4 | 58.2 | 17 | 275 | #4 | 47623 |
| 778 | 16060 | 72.0 | 65.1 | 16 | 477 | #5 | 47624 |
| 779 | 16061 | 50.0 | 50.0 | 12 | 150 | #1 | 47625 |
| 780 | 16062 | 69.6 | 60.2 (211) | 21 | 347 | #4 | 47626 |
| 781 | 16063 | 50.0 | 50.0 | 12 | 150 | #1 | 47627 |
| 782 | 16064 | 50.0 | 50.0 | 12 | 150 | #1 | 47628 |
| 783 | 16065 | 72.8 | 65.5 | 25 | 729 | #5 | 47629 |
| 784 | 16066 | 68.8 | 62.5 | 21 | 309 | #4 | 47630 |
| 785 | 16067 | 63.2 | 50.0 (226) | 20 | 185 | #3 | 47631 |
| 786 | 16068 | 50.0 | 50.0 | 12 | 150 | #1 | 47632 |
| 787 | 16069 | 80.8 | 67.6 | 31 | 528 | #7 | 47633 |
| 788 | 16070 | 76.8 | 73.8 | 14 | 899 | #6 | 47634 |
| 789 | 16071 | 71.2 | 65.1 | 18 | 389 | #5 | 47635 |
| 790 | 16072 | 78.4 | 72.4 | 18 | 1083 | #6 | 47636 |
| 791 | 16073 | 60.8 | 57.8 | 12 | 179 | #3 | 47637 |
| 792 | 16074 | 50.0 | 50.0 | 12 | 150 | #1 | 47638 |
| 793 | 16075 | 66.4 | 58.9 | 24 | 228 | #4 | 47639 |
| 794 | 16076 | 50.0 | 50.0 | 12 | 150 | #1 | 47640 |
| 795 | 16077 | 85.6 | 62.9 | 30 | 507 | #8 | 47641 |
| 796 | 16078 | 80.8 | 73.1 | 15 | 1044 | #7 | 47642 |
| 797 | 16079 | 50.0 | 50.0 | 17 | 176 | #1 | 47643 |
| 798 | 16080 | 77.6 | 64.7 | 17 | 589 | #6 | 47644 |
| 799 | 16081 | 82.4 | 80.0 | 24 | 1346 | #7 | 47645 |
| 800 | 16082 | 66.4 | 60.4 | 15 | 338 | #4 | 47646 |
| 801 | 16083 | 66.4 | 60.4 | 16 | 386 | #4 | 47647 |
| 802 | 16084 | 65.6 | 63.3 | 15 | 436 | #4 | 47648 |
| 803 | 16085 | 50.0 | 50.0 | 12 | 150 | #1 | 47649 |
| 804 | 16086 | 64.8 | 60.7 | 12 | 361 | #3 | 47650 |
| 805 | 16087 | 50.0 | 50.0 | 12 | 150 | #1 | 47651 |
| 806 | 16088 | 73.6 | 58.5 | 18 | 344 | #5 | 47652 |
| 807 | 16089 | 64.8 | 59.3 | 21 | 305 | #3 | 47653 |
| 808 | 16090 | 72.8 | 64.4 | 18 | 471 | #5 | 47654 |
| 809 | 16091 | 79.2 | 77.1 | 20 | 1065 | #6 | 47655 |
| 810 | 16092 | 80.8 | 74.5 | 18 | 879 | #7 | 47656 |
| 811 | 16093 | 77.6 | 53.1 | 19 | 492 | #6 | 47657 |
| 812 | 16094 | 64.8 | 61.1 | 16 | 246 | #3 | 47658 |
| 813 | 16095 | 66.4 | 57.5 | 16 | 209 | #4 | 47659 |
| 814 | 16096 | 50.0 | 50.0 | 12 | 150 | #1 | 47660 |
| 815 | 16097 | 64.0 | 60.0 | 16 | 273 | #3 | 47661 |
| 816 | 16098 | 68.0 | 58.9 | 16 | 393 | #4 | 47662 |
| 817 | 16099 | 98.4 | 97.8 | 78 | 2091 | #10 | 47663 |
| 818 | 16100 | 77.6 | 56.7 | 18 | 456 | #6 | 47664 |
| 819 | 16101 | 100.0 | 100.0 | 372 | 2402 | #10 | 47665 |
| 820 | 16102 | 75.2 | 63.6 | 20 | 426 | #6 | 47666 |
| 821 | 16103 | 50.0 | 50.0 | 12 | 150 | #1 | 47667 |
| 822 | 16104 | 70.4 | 57.1 | 16 | 249 | #5 | 47668 |
| 823 | 16105 | 76.0 | 69.2 (211) | 21 | 504 | #6 | 47669 |
| 824 | 16106 | 64.0 | 59.3 | 16 | 232 | #3 | 47670 |
| 825 | 16107 | 68.0 | 64.0 | 16 | 454 | #4 | 47671 |
| 826 | 16108 | 68.8 | 59.3 | 21 | 248 | #4 | 47672 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 827 | 16109 | 63.2 | 57.8 | 12 | 298 | #3 | 47673 |
| 828 | 16110 | 74.4 | 63.6 | 12 | 457 | #5 | 47674 |
| 829 | 16111 | 77.6 | 69.8 | 15 | 808 | #6 | 47675 |
| 830 | 16112 | 76.8 | 69.8 | 18 | 833 | #6 | 47676 |
| 831 | 16113 | 50.0 | 50.0 | 12 | 150 | #1 | 47677 |
| 832 | 16114 | 65.6 | 59.3 | 30 | 333 | #4 | 47678 |
| 833 | 16115 | 64.8 | 60.0 | 16 | 221 | #3 | 47679 |
| 834 | 16116 | 68.0 | 58.5 | 27 | 216 | #4 | 47680 |
| 835 | 16117 | 50.0 | 50.0 | 12 | 150 | #1 | 47681 |
| 836 | 16118 | 73.6 | 67.6 | 18 | 701 | #5 | 47682 |
| 837 | 16119 | 69.6 | 61.8 | 22 | 382 | #4 | 47683 |
| 838 | 16120 | 76.8 | 72.0 | 29 | 829 | #6 | 47684 |
| 839 | 16121 | 66.4 | 60.0 | 16 | 238 | #4 | 47685 |
| 840 | 16122 | 50.0 | 50.0 | 14 | 153 | #1 | 47686 |
| 841 | 16123 | 64.8 | 60.7 | 13 | 372 | #3 | 47687 |
| 842 | 16124 | 50.0 | 50.0 | 12 | 150 | #1 | 47688 |
| 843 | 16125 | 61.6 | 58.5 | 12 | 201 | #3 | 47689 |
| 844 | 16126 | 89.6 | 86.2 | 27 | 1261 | #8 | 47690 |
| 845 | 16127 | 68.0 | 61.8 | 23 | 384 | #4 | 47691 |
| 846 | 16128 | 75.2 | 65.1 | 18 | 570 | #6 | 47692 |
| 847 | 16129 | 61.6 | 50.0 | 14 | 172 | #3 | 47693 |
| 848 | 16130 | 50.0 | 50.0 | 12 | 150 | #1 | 47694 |
| 849 | 16131 | 62.4 | 60.0 | 12 | 560 | #3 | 47695 |
| 850 | 16132 | 72.8 | 68.4 | 14 | 742 | #5 | 47696 |
| 851 | 16133 | 72.0 | 62.3 (167) | 15 | 308 | #5 | 47697 |
| 852 | 16134 | 74.4 | 64.0 | 21 | 516 | #5 | 47698 |
| 853 | 16135 | 50.0 | 50.0 | 12 | 150 | #1 | 47699 |
| 854 | 16136 | 66.4 | 59.6 | 22 | 236 | #4 | 47700 |
| 855 | 16137 | 62.4 | 50.0 | 18 | 188 | #3 | 47701 |
| 856 | 16138 | 71.2 | 65.5 | 18 | 455 | #5 | 47702 |
| 857 | 16139 | 50.0 | 50.0 | 12 | 150 | #1 | 47703 |
| 858 | 16140 | 63.2 | 50.9 | 18 | 226 | #3 | 47704 |
| 859 | 16141 | 65.6 | 56.4 | 14 | 197 | #4 | 47705 |
| 860 | 16142 | 80.8 | 77.5 | 20 | 862 | #7 | 47706 |
| 861 | 16143 | 72.0 | 66.2 | 19 | 566 | #5 | 47707 |
| 862 | 16144 | 62.4 | 58.9 | 14 | 195 | #3 | 47708 |
| 863 | 16145 | 50.0 | 50.0 | 12 | 150 | #1 | 47709 |
| 864 | 16146 | 68.0 | 64.0 | 18 | 540 | #4 | 47710 |
| 865 | 16147 | 50.0 | 50.0 | 12 | 150 | #1 | 47711 |
| 866 | 16148 | 50.0 | 50.0 | 12 | 150 | #1 | 47712 |
| 867 | 16149 | 50.0 | 50.0 | 12 | 150 | #1 | 47713 |
| 868 | 16150 | 65.6 | 60.4 | 18 | 237 | #4 | 47714 |
| 869 | 16151 | 67.2 | 60.7 | 16 | 216 | #4 | 47715 |
| 870 | 16152 | 64.0 | 50.0 | 15 | 181 | #3 | 47716 |
| 871 | 16153 | 83.2 | 73.1 | 26 | 805 | #7 | 47717 |
| 872 | 16154 | 60.0 | 50.0 (262) | 21 | 218 | #2 | 47718 |
| 873 | 16155 | 74.4 | 68.7 | 18 | 558 | #5 | 47719 |
| 874 | 16156 | 50.0 | 50.0 | 12 | 150 | #1 | 47720 |
| 875 | 16157 | 71.2 | 67.3 | 15 | 627 | #5 | 47721 |
| 876 | 16158 | 69.6 | 65.8 | 22 | 419 | #4 | 47722 |
| 877 | 16159 | 61.6 | 50.0 | 12 | 167 | #3 | 47723 |
| 878 | 16160 | 72.8 | 65.8 | 22 | 870 | #5 | 47724 |
| 879 | 16161 | 60.8 | 58.9 | 21 | 194 | #3 | 47725 |
| 880 | 16162 | 78.4 | 74.9 | 23 | 1125 | #6 | 47726 |
| 881 | 16163 | 50.0 | 50.0 | 12 | 150 | #1 | 47727 |
| 882 | 16164 | 69.6 | 63.3 | 28 | 464 | #4 | 47728 |
| 883 | 16165 | 67.2 | 59.6 | 19 | 259 | #4 | 47729 |
| 884 | 16166 | 68.8 | 58.9 | 14 | 292 | #4 | 47730 |
| 885 | 16167 | 65.6 | 50.0 | 16 | 214 | #4 | 47731 |
| 886 | 16168 | 69.6 | 61.1 | 21 | 282 | #4 | 47732 |
| 887 | 16169 | 62.4 | 50.0 | 12 | 187 | #3 | 47733 |
| 888 | 16170 | 83.2 | 79.3 | 21 | 1630 | #7 | 47734 |
| 889 | 16171 | 64.8 | 57.1 | 13 | 215 | #3 | 47735 |
| 890 | 16172 | 65.6 | 60.4 | 16 | 222 | #4 | 47736 |
| 891 | 16173 | 73.6 | 64.7 | 13 | 912 | #5 | 47737 |
| 892 | 16174 | 76.0 | 68.7 | 17 | 645 | #6 | 47738 |
| 893 | 16175 | 68.0 | 61.5 | 22 | 255 | #4 | 47739 |
| 894 | 16176 | 50.0 | 50.0 | 12 | 150 | #1 | 47740 |
| 895 | 16177 | 65.6 | 60.0 | 15 | 236 | #4 | 47741 |
| 896 | 16178 | 50.0 | 50.0 | 12 | 150 | #1 | 47742 |
| 897 | 16179 | 50.0 | 50.0 | 12 | 150 | #1 | 47743 |
| 898 | 16180 | 70.4 | 57.1 (266) | 16 | 362 | #5 | 47744 |
| 899 | 16181 | 71.2 | 66.9 | 14 | 556 | #5 | 47745 |
| 900 | 16182 | 50.0 | 50.0 | 12 | 150 | #1 | 47746 |
| 901 | 16183 | 66.4 | 50.0 | 12 | 197 | #4 | 47747 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 902 | 16184 | 67.2 | 64.0 | 17 | 367 | #4 | 47748 |
| 903 | 16185 | 68.0 | 61.5 | 13 | 399 | #4 | 47749 |
| 904 | 16186 | 70.4 | 50.0 | 22 | 382 | #5 | 47750 |
| 905 | 16187 | 59.2 | 50.0 | 15 | 157 | #2 | 47751 |
| 906 | 16188 | 92.0 | 67.6 (262) | 35 | 583 | #9 | 47752 |
| 907 | 16189 | 69.6 | 58.2 | 15 | 348 | #4 | 47753 |
| 908 | 16190 | 72.0 | 64.0 | 15 | 843 | #5 | 47754 |
| 909 | 16191 | 64.0 | 50.0 | 13 | 172 | #3 | 47755 |
| 910 | 16192 | 64.8 | 57.8 | 15 | 303 | #3 | 47756 |
| 911 | 16193 | 68.8 | 57.5 | 13 | 397 | #4 | 47757 |
| 912 | 16194 | 71.2 | 64.4 | 19 | 434 | #5 | 47758 |
| 913 | 16195 | 88.0 | 83.3 | 30 | 1237 | #8 | 47759 |
| 914 | 16196 | 91.2 | 65.1 (175) | 31 | 526 | #9 | 47760 |
| 915 | 16197 | 64.8 | 58.5 | 17 | 251 | #3 | 47761 |
| 916 | 16198 | 64.0 | 55.6 | 21 | 213 | #3 | 47762 |
| 917 | 16199 | 78.4 | 71.3 | 13 | 647 | #6 | 47763 |
| 918 | 16200 | 50.0 | 50.0 | 12 | 150 | #1 | 47764 |
| 919 | 16201 | 66.4 | 52.7 | 15 | 281 | #4 | 47765 |
| 920 | 16202 | 50.0 | 50.0 | 12 | 150 | #1 | 47766 |
| 921 | 16203 | 67.2 | 58.5 | 17 | 246 | #4 | 47767 |
| 922 | 16204 | 62.4 | 50.0 | 15 | 196 | #3 | 47768 |
| 923 | 16205 | 68.0 | 62.9 | 17 | 620 | #4 | 47769 |
| 924 | 16206 | 65.6 | 50.0 | 13 | 182 | #4 | 47770 |
| 925 | 16207 | 67.2 | 50.0 | 13 | 208 | #4 | 47771 |
| 926 | 16208 | 55.2 | 50.0 | 13 | 183 | #2 | 47772 |
| 927 | 16209 | 68.0 | 60.0 | 23 | 266 | #4 | 47773 |
| 928 | 16210 | 64.8 | 62.9 | 13 | 516 | #3 | 47774 |
| 929 | 16211 | 61.6 | 56.7 | 12 | 184 | #3 | 47775 |
| 930 | 16212 | 76.0 | 71.3 | 17 | 881 | #6 | 47776 |
| 931 | 16213 | 65.6 | 50.0 (256) | 16 | 172 | #4 | 47777 |
| 932 | 16214 | 50.0 | 50.0 | 12 | 150 | #1 | 47778 |
| 933 | 16215 | 66.4 | 61.1 | 17 | 285 | #4 | 47779 |
| 934 | 16216 | 50.0 | 50.0 | 12 | 150 | #1 | 47780 |
| 935 | 16217 | 68.8 | 61.1 | 19 | 262 | #4 | 47781 |
| 936 | 16218 | 83.2 | 81.1 | 28 | 1794 | #7 | 47782 |
| 937 | 16219 | 79.2 | 71.6 | 21 | 701 | #6 | 47783 |
| 938 | 16220 | 67.2 | 64.0 | 15 | 590 | #4 | 47784 |
| 939 | 16221 | 76.8 | 70.5 | 16 | 612 | #6 | 47785 |
| 940 | 16222 | 69.6 | 60.0 | 21 | 225 | #4 | 47786 |
| 941 | 16223 | 72.0 | 63.3 | 20 | 327 | #5 | 47787 |
| 942 | 16224 | 66.4 | 60.7 | 15 | 276 | #4 | 47788 |
| 943 | 16225 | 61.6 | 56.0 | 15 | 242 | #3 | 47789 |
| 944 | 16226 | 64.0 | 58.9 | 18 | 248 | #3 | 47790 |
| 945 | 16227 | 65.6 | 59.3 | 15 | 250 | #4 | 47791 |
| 946 | 16228 | 68.8 | 58.2 | 16 | 236 | #4 | 47792 |
| 947 | 16229 | 76.8 | 74.7 (174) | 19 | 474 | #6 | 47793 |
| 948 | 16230 | 72.8 | 67.6 | 18 | 516 | #5 | 47794 |
| 949 | 16231 | 50.0 | 50.0 | 12 | 196 | #1 | 47795 |
| 950 | 16232 | 64.8 | 50.0 | 14 | 181 | #3 | 47796 |
| 951 | 16233 | 84.0 | 73.1 | 19 | 1031 | #7 | 47797 |
| 952 | 16234 | 50.0 | 50.0 | 12 | 150 | #1 | 47798 |
| 953 | 16235 | 72.0 | 64.4 | 14 | 494 | #5 | 47799 |
| 954 | 16236 | 73.6 | 59.3 | 16 | 329 | #5 | 47800 |
| 955 | 16237 | 65.6 | 61.8 | 16 | 394 | #4 | 47801 |
| 956 | 16238 | 66.4 | 61.5 | 17 | 257 | #4 | 47802 |
| 957 | 16239 | 66.4 | 56.7 | 16 | 286 | #4 | 47803 |
| 958 | 16240 | 65.6 | 57.8 | 14 | 229 | #4 | 47804 |
| 959 | 16241 | 57.6 | 50.0 (202) | 14 | 224 | #2 | 47805 |
| 960 | 16242 | 63.2 | 58.5 | 13 | 348 | #3 | 47806 |
| 961 | 16243 | 50.0 | 50.0 | 12 | 150 | #1 | 47807 |
| 962 | 16244 | 60.8 | 57.8 | 20 | 229 | #3 | 47808 |
| 963 | 16245 | 72.8 | 58.9 | 15 | 369 | #5 | 47809 |
| 964 | 16246 | 68.8 | 58.5 | 38 | 262 | #4 | 47810 |
| 965 | 16247 | 60.0 | 58.9 | 12 | 160 | #2 | 47811 |
| 966 | 16248 | 71.2 | 60.7 (272) | 19 | 350 | #5 | 47812 |
| 967 | 16249 | 66.4 | 60.0 | 15 | 357 | #4 | 47813 |
| 968 | 16250 | 50.0 | 50.0 | 12 | 150 | #1 | 47814 |
| 969 | 16251 | 72.0 | 56.4 | 13 | 312 | #5 | 47815 |
| 970 | 16252 | 64.0 | 58.5 | 14 | 217 | #3 | 47816 |
| 971 | 16253 | 98.4 | 97.1 | 78 | 1853 | #10 | 47817 |
| 972 | 16254 | 69.6 | 51.3 | 16 | 285 | #4 | 47818 |
| 973 | 16255 | 64.8 | 50.0 | 12 | 241 | #3 | 47819 |
| 974 | 16256 | 64.0 | 58.5 | 15 | 306 | #3 | 47820 |
| 975 | 16257 | 61.6 | 58.2 | 12 | 220 | #3 | 47821 |
| 976 | 16258 | 67.2 | 53.1 | 12 | 216 | #4 | 47822 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 977 | 16259 | 63.2 | 53.1 (258) | 17 | 187 | #3 | 47823 |
| 978 | 16260 | 50.0 | 50.0 | 12 | 150 | #1 | 47824 |
| 979 | 16261 | 71.2 | 60.0 | 28 | 317 | #5 | 47825 |
| 980 | 16262 | 76.8 | 70.5 | 21 | 706 | #6 | 47826 |
| 981 | 16263 | 80.0 | 72.4 | 22 | 1208 | #6 | 47827 |
| 982 | 16264 | 66.4 | 60.4 | 18 | 281 | #4 | 47828 |
| 983 | 16265 | 61.6 | 50.0 | 13 | 164 | #3 | 47829 |
| 984 | 16266 | 68.0 | 62.2 | 16 | 318 | #4 | 47830 |
| 985 | 16267 | 63.2 | 52.0 | 13 | 181 | #3 | 47831 |
| 986 | 16268 | 50.0 | 50.0 | 12 | 150 | #1 | 47832 |
| 987 | 16269 | 71.2 | 65.7 (251) | 26 | 414 | #5 | 47833 |
| 988 | 16270 | 60.8 | 50.0 | 12 | 187 | #3 | 47834 |
| 989 | 16271 | 72.0 | 63.3 | 22 | 511 | #5 | 47835 |
| 990 | 16272 | 72.0 | 63.3 | 19 | 529 | #5 | 47836 |
| 991 | 16273 | 65.6 | 58.4 (262) | 20 | 259 | #4 | 47837 |
| 992 | 16274 | 67.2 | 50.0 | 16 | 186 | #4 | 47838 |
| 993 | 16275 | 50.0 | 50.0 | 12 | 150 | #1 | 47839 |
| 994 | 16276 | 68.0 | 60.4 | 19 | 258 | #4 | 47840 |
| 995 | 16277 | 68.0 | 62.9 | 28 | 596 | #4 | 47841 |
| 996 | 16278 | 50.0 | 50.0 | 12 | 150 | #1 | 47842 |
| 997 | 16279 | 66.4 | 50.0 | 12 | 211 | #4 | 47843 |
| 998 | 16280 | 50.0 | 50.0 | 12 | 150 | #1 | 47844 |
| 999 | 16281 | 67.2 | 64.0 | 15 | 663 | #4 | 47845 |
| 1000 | 16282 | 66.4 | 60.0 | 15 | 295 | #4 | 47846 |
| 1001 | 16283 | 86.4 | 82.5 | 28 | 1358 | #8 | 47847 |
| 1002 | 16284 | 73.6 | 68.0 | 23 | 646 | #5 | 47848 |
| 1003 | 16285 | 76.8 | 68.0 | 18 | 552 | #6 | 47849 |
| 1004 | 16286 | 93.6 | 78.5 | 26 | 928 | #9 | 47850 |
| 1005 | 16287 | 66.4 | 59.6 | 15 | 253 | #4 | 47851 |
| 1006 | 16288 | 64.0 | 56.7 | 16 | 219 | #3 | 47852 |
| 1007 | 16289 | 68.8 | 63.3 | 14 | 558 | #4 | 47853 |
| 1008 | 16290 | 80.8 | 67.6 | 21 | 652 | #7 | 47854 |
| 1009 | 16291 | 63.2 | 50.0 | 15 | 217 | #3 | 47855 |
| 1010 | 16292 | 68.8 | 63.3 | 15 | 501 | #4 | 47856 |
| 1011 | 16293 | 70.4 | 59.6 | 17 | 476 | #5 | 47857 |
| 1012 | 16294 | 71.2 | 65.5 | 21 | 545 | #5 | 47858 |
| 1013 | 16295 | 79.2 | 73.1 | 27 | 730 | #6 | 47859 |
| 1014 | 16296 | 70.4 | 63.6 | 14 | 445 | #5 | 47860 |
| 1015 | 16297 | 74.4 | 72.0 | 15 | 712 | #5 | 47861 |
| 1016 | 16298 | 73.6 | 66.5 | 18 | 792 | #5 | 47862 |
| 1017 | 16299 | 50.0 | 50.0 | 12 | 150 | #1 | 47863 |
| 1018 | 16300 | 50.0 | 50.0 | 12 | 150 | #1 | 47864 |
| 1019 | 16301 | 66.4 | 61.5 | 17 | 341 | #4 | 47865 |
| 1020 | 16302 | 64.8 | 60.4 | 13 | 285 | #3 | 47866 |
| 1021 | 16303 | 59.2 | 58.2 | 13 | 277 | #2 | 47867 |
| 1022 | 16304 | 68.0 | 63.3 | 20 | 308 | #4 | 47868 |
| 1023 | 16305 | 69.6 | 64.0 | 17 | 461 | #4 | 47869 |
| 1024 | 16306 | 69.6 | 58.2 | 14 | 339 | #4 | 47870 |
| 1025 | 16307 | 71.2 | 63.6 | 21 | 405 | #5 | 47871 |
| 1026 | 16308 | 50.0 | 50.0 | 12 | 150 | #1 | 47872 |
| 1027 | 16309 | 64.8 | 57.5 (268) | 19 | 189 | #3 | 47873 |
| 1028 | 16310 | 72.0 | 62.5 | 16 | 430 | #5 | 47874 |
| 1029 | 16311 | 64.8 | 53.5 | 13 | 242 | #3 | 47875 |
| 1030 | 16312 | 65.6 | 50.0 | 13 | 221 | #4 | 47876 |
| 1031 | 16313 | 50.0 | 50.0 | 12 | 150 | #1 | 47877 |
| 1032 | 16314 | 68.8 | 61.8 | 25 | 437 | #4 | 47878 |
| 1033 | 16315 | 50.0 | 50.0 | 12 | 150 | #1 | 47879 |
| 1034 | 16316 | 50.0 | 50.0 | 19 | 153 | #1 | 47880 |
| 1035 | 16317 | 68.8 | 65.1 | 29 | 733 | #4 | 47881 |
| 1036 | 16318 | 71.2 | 61.1 | 17 | 280 | #5 | 47882 |
| 1037 | 16319 | 63.2 | 57.5 | 17 | 212 | #3 | 47883 |
| 1038 | 16320 | 84.8 | 83.3 | 23 | 2299 | #7 | 47884 |
| 1039 | 16321 | 73.6 | 67.6 | 15 | 525 | #5 | 47885 |
| 1040 | 16322 | 100.0 | 99.3 | 212 | 2706 | #10 | 47886 |
| 1041 | 16323 | 81.6 | 59.6 | 26 | 401 | #7 | 47887 |
| 1042 | 16324 | 68.0 | 56.4 | 17 | 423 | #4 | 47888 |
| 1043 | 16325 | 86.4 | 82.9 | 25 | 1147 | #8 | 47889 |
| 1044 | 16326 | 68.0 | 58.2 | 16 | 234 | #4 | 47890 |
| 1045 | 16327 | 50.0 | 50.0 | 12 | 150 | #1 | 47891 |
| 1046 | 16328 | 75.2 | 72.7 | 18 | 1387 | #6 | 47892 |
| 1047 | 16329 | 63.2 | 50.0 | 15 | 192 | #3 | 47893 |
| 1048 | 16330 | 50.0 | 50.0 | 12 | 150 | #1 | 47894 |
| 1049 | 16331 | 50.0 | 50.0 | 12 | 150 | #1 | 47895 |
| 1050 | 16332 | 77.6 | 68.0 | 16 | 1030 | #6 | 47896 |
| 1051 | 16333 | 80.0 | 76.0 | 23 | 1035 | #6 | 47897 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1052 | 16334 | 75.2 | 72.0 | 19 | 721 | #6 | 47898 |
| 1053 | 16335 | 68.0 | 50.0 | 13 | 395 | #4 | 47899 |
| 1054 | 16336 | 63.2 | 50.0 | 12 | 189 | #3 | 47900 |
| 1055 | 16337 | 83.2 | 80.7 | 28 | 1703 | #7 | 47901 |
| 1056 | 16338 | 82.4 | 74.5 | 12 | 949 | #7 | 47902 |
| 1057 | 16339 | 75.2 | 68.0 | 24 | 1312 | #6 | 47903 |
| 1058 | 16340 | 84.0 | 79.6 | 24 | 2222 | #7 | 47904 |
| 1059 | 16341 | 81.6 | 78.5 | 25 | 1275 | #7 | 47905 |
| 1060 | 16342 | 66.4 | 59.3 | 18 | 235 | #4 | 47906 |
| 1061 | 16343 | 68.0 | 58.2 | 16 | 320 | #4 | 47907 |
| 1062 | 16344 | 65.6 | 58.5 | 13 | 307 | #4 | 47908 |
| 1063 | 16345 | 68.0 | 63.6 | 19 | 549 | #4 | 47909 |
| 1064 | 16346 | 50.0 | 50.0 | 12 | 150 | #1 | 47910 |
| 1065 | 16347 | 70.4 | 62.5 | 18 | 407 | #5 | 47911 |
| 1066 | 16348 | 63.2 | 50.0 | 15 | 252 | #3 | 47912 |
| 1067 | 16349 | 76.8 | 68.0 | 15 | 607 | #6 | 47913 |
| 1068 | 16350 | 64.8 | 50.0 | 12 | 225 | #3 | 47914 |
| 1069 | 16351 | 65.6 | 50.0 | 12 | 154 | #4 | 47915 |
| 1070 | 16352 | 71.2 | 67.6 | 15 | 556 | #5 | 47916 |
| 1071 | 16353 | 69.6 | 63.3 | 27 | 486 | #4 | 47917 |
| 1072 | 16354 | 100.0 | 99.6 | 174 | 6493 | #10 | 47918 |
| 1073 | 16355 | 65.6 | 58.2 | 16 | 208 | #4 | 47919 |
| 1074 | 16356 | 50.0 | 50.0 | 12 | 150 | #1 | 47920 |
| 1075 | 16357 | 67.2 | 58.5 | 17 | 226 | #4 | 47921 |
| 1076 | 16358 | 50.0 | 50.0 | 12 | 150 | #1 | 47922 |
| 1077 | 16359 | 64.8 | 56.2 (274) | 14 | 194 | #3 | 47923 |
| 1078 | 16360 | 63.2 | 50.0 | 13 | 183 | #3 | 47924 |
| 1079 | 16361 | 68.0 | 59.6 | 15 | 235 | #4 | 47925 |
| 1080 | 16362 | 61.6 | 57.1 | 13 | 235 | #3 | 47926 |
| 1081 | 16363 | 72.0 | 69.5 | 16 | 821 | #5 | 47927 |
| 1082 | 16364 | 81.6 | 57.5 | 32 | 409 | #7 | 47928 |
| 1083 | 16365 | 62.4 | 50.0 | 12 | 203 | #3 | 47929 |
| 1084 | 16366 | 50.0 | 50.0 | 12 | 150 | #1 | 47930 |
| 1085 | 16367 | 69.6 | 57.5 | 20 | 260 | #4 | 47931 |
| 1086 | 16368 | 50.0 | 50.0 | 12 | 150 | #1 | 47932 |
| 1087 | 16369 | 77.6 | 67.3 | 13 | 537 | #6 | 47933 |
| 1088 | 16370 | 66.4 | 60.0 | 19 | 259 | #4 | 47934 |
| 1089 | 16371 | 65.6 | 60.4 | 18 | 371 | #4 | 47935 |
| 1090 | 16372 | 73.6 | 66.5 (257) | 14 | 461 | #5 | 47936 |
| 1091 | 16373 | 63.2 | 55.3 | 17 | 185 | #3 | 47937 |
| 1092 | 16374 | 65.6 | 52.0 | 15 | 216 | #4 | 47938 |
| 1093 | 16375 | 68.8 | 64.7 | 18 | 518 | #4 | 47939 |
| 1094 | 16376 | 62.4 | 58.2 | 16 | 218 | #3 | 47940 |
| 1095 | 16377 | 66.4 | 60.4 | 15 | 316 | #4 | 47941 |
| 1096 | 16378 | 70.4 | 64.4 | 17 | 891 | #5 | 47942 |
| 1097 | 16379 | 50.0 | 50.0 | 12 | 150 | #1 | 47943 |
| 1098 | 16380 | 64.0 | 62.2 | 12 | 507 | #3 | 47944 |
| 1099 | 16381 | 66.4 | 59.3 | 17 | 255 | #4 | 47945 |
| 1100 | 16382 | 72.0 | 64.4 | 13 | 451 | #5 | 47946 |
| 1101 | 16383 | 50.0 | 50.0 | 12 | 150 | #1 | 47947 |
| 1102 | 16384 | 50.0 | 50.0 (260) | 12 | 150 | #1 | 47948 |
| 1103 | 16385 | 76.8 | 70.9 | 27 | 629 | #6 | 47949 |
| 1104 | 16386 | 69.6 | 57.5 | 16 | 274 | #4 | 47950 |
| 1105 | 16387 | 67.2 | 61.1 | 22 | 291 | #4 | 47951 |
| 1106 | 16388 | 69.6 | 61.1 | 17 | 304 | #4 | 47952 |
| 1107 | 16389 | 72.0 | 67.7 (150) | 22 | 352 | #5 | 47953 |
| 1108 | 16390 | 72.0 | 65.1 | 21 | 597 | #5 | 47954 |
| 1109 | 16391 | 66.4 | 60.4 | 14 | 511 | #4 | 47955 |
| 1110 | 16392 | 64.8 | 55.7 (201) | 15 | 214 | #3 | 47956 |
| 1111 | 16393 | 64.8 | 60.0 | 15 | 285 | #3 | 47957 |
| 1112 | 16394 | 62.4 | 58.2 | 14 | 201 | #3 | 47958 |
| 1113 | 16395 | 65.6 | 60.7 | 14 | 237 | #4 | 47959 |
| 1114 | 16396 | 68.8 | 63.3 | 20 | 461 | #4 | 47960 |
| 1115 | 16397 | 50.0 | 50.0 | 12 | 150 | #1 | 47961 |
| 1116 | 16398 | 68.0 | 58.9 | 14 | 374 | #4 | 47962 |
| 1117 | 16399 | 74.4 | 66.9 | 18 | 691 | #5 | 47963 |
| 1118 | 16400 | 64.0 | 58.9 | 14 | 220 | #3 | 47964 |
| 1119 | 16401 | 67.2 | 61.5 | 15 | 244 | #4 | 47965 |
| 1120 | 16402 | 72.8 | 65.5 | 16 | 895 | #5 | 47966 |
| 1121 | 16403 | 67.2 | 61.8 | 19 | 615 | #4 | 47967 |
| 1122 | 16404 | 68.0 | 62.9 | 12 | 440 | #4 | 47968 |
| 1123 | 16405 | 56.8 | 50.0 | 12 | 161 | #2 | 47969 |
| 1124 | 16406 | 68.8 | 63.3 | 19 | 370 | #4 | 47970 |
| 1125 | 16407 | 75.2 | 70.2 | 12 | 632 | #6 | 47971 |
| 1126 | 16408 | 50.0 | 50.0 | 12 | 150 | #1 | 47972 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1127 | 16409 | 66.4 | 61.8 | 14 | 461 | #4 | 47973 |
| 1128 | 16410 | 61.6 | 57.1 | 18 | 184 | #3 | 47974 |
| 1129 | 16411 | 64.8 | 60.0 | 15 | 225 | #3 | 47975 |
| 1130 | 16412 | 64.8 | 50.0 | 12 | 200 | #3 | 47976 |
| 1131 | 16413 | 68.0 | 62.5 | 13 | 555 | #4 | 47977 |
| 1132 | 16414 | 73.6 | 67.6 | 21 | 882 | #5 | 47978 |
| 1133 | 16415 | 68.0 | 61.1 | 22 | 313 | #4 | 47979 |
| 1134 | 16416 | 76.8 | 73.5 | 12 | 859 | #6 | 47980 |
| 1135 | 16417 | 64.8 | 52.7 | 16 | 223 | #3 | 47981 |
| 1136 | 16418 | 100.0 | 72.7 | 199 | 992 | #10 | 47982 |
| 1137 | 16419 | 50.0 | 50.0 | 12 | 150 | #1 | 47983 |
| 1138 | 16420 | 65.6 | 58.9 | 14 | 273 | #4 | 47984 |
| 1139 | 16421 | 63.2 | 58.5 | 12 | 209 | #3 | 47985 |
| 1140 | 16422 | 62.4 | 59.3 | 13 | 194 | #3 | 47986 |
| 1141 | 16423 | 68.8 | 60.0 | 17 | 225 | #4 | 47987 |
| 1142 | 16424 | 66.4 | 50.0 | 16 | 241 | #4 | 47988 |
| 1143 | 16425 | 68.8 | 61.5 | 18 | 257 | #4 | 47989 |
| 1144 | 16426 | 50.0 | 50.0 | 12 | 150 | #1 | 47990 |
| 1145 | 16427 | 68.8 | 64.0 | 19 | 314 | #4 | 47991 |
| 1146 | 16428 | 71.2 | 62.7 (236) | 17 | 374 | #5 | 47992 |
| 1147 | 16429 | 50.0 | 50.0 | 12 | 150 | #1 | 47993 |
| 1148 | 16430 | 64.0 | 50.0 | 12 | 196 | #3 | 47994 |
| 1149 | 16431 | 68.0 | 57.8 | 21 | 216 | #4 | 47995 |
| 1150 | 16432 | 61.6 | 50.0 | 14 | 184 | #3 | 47996 |
| 1151 | 16433 | 76.0 | 65.5 | 30 | 394 | #6 | 47997 |
| 1152 | 16434 | 68.0 | 62.5 | 19 | 379 | #4 | 47998 |
| 1153 | 16435 | 85.6 | 82.2 | 24 | 924 | #8 | 47999 |
| 1154 | 16436 | 50.4 | 50.0 | 14 | 199 | #1 | 48000 |
| 1155 | 16437 | 50.0 | 50.0 | 12 | 150 | #1 | 48001 |
| 1156 | 16438 | 50.0 | 50.0 | 12 | 150 | #1 | 48002 |
| 1157 | 16439 | 60.0 | 55.3 | 13 | 220 | #2 | 48003 |
| 1158 | 16440 | 65.6 | 58.2 | 19 | 233 | #4 | 48004 |
| 1159 | 16441 | 81.9(116) | — | 21 | 419 | #7 | 48005 |
| 1160 | 16442 | 78.4 | 62.9 | 25 | 493 | #6 | 48006 |
| 1161 | 16443 | 62.4 | 59.3 | 12 | 259 | #3 | 48007 |
| 1162 | 16444 | 77.6 | 74.2 | 20 | 854 | #6 | 48008 |
| 1163 | 16445 | 65.6 | 50.0 | 16 | 199 | #4 | 48009 |
| 1164 | 16446 | 50.0 | 50.0 | 12 | 150 | #1 | 48010 |
| 1165 | 16447 | 50.0 | 50.0 | 12 | 150 | #1 | 48011 |
| 1166 | 16448 | 66.4 | 50.0 | 16 | 179 | #4 | 48012 |
| 1167 | 16449 | 59.2 | 50.0(185) | 20 | 164 | #2 | 48013 |
| 1168 | 16450 | 70.4 | 55.6(261) | 21 | 285 | #5 | 48014 |
| 1169 | 16451 | 74.4 | 54.5 | 27 | 319 | #5 | 48015 |
| 1170 | 16452 | 64.0 | 51.6 | 12 | 254 | #3 | 48016 |
| 1171 | 16453 | 68.0 | 58.5 | 24 | 278 | #4 | 48017 |
| 1172 | 16454 | 66.4 | 57.8 | 13 | 201 | #4 | 48018 |
| 1173 | 16455 | 78.4 | 69.5 | 24 | 621 | #6 | 48019 |
| 1174 | 16456 | 64.0 | 50.0 | 15 | 190 | #3 | 48020 |
| 1175 | 16457 | 69.6 | 53.8 | 12 | 354 | #4 | 48021 |
| 1176 | 16458 | 63.2 | 58.9 | 15 | 348 | #3 | 48022 |
| 1177 | 16459 | 64.8 | 59.3 | 15 | 220 | #3 | 48023 |
| 1178 | 16460 | 68.8 | 61.1 | 21 | 309 | #4 | 48024 |
| 1179 | 16461 | 68.0 | 62.2 | 12 | 381 | #4 | 48025 |
| 1180 | 16462 | 59.0 | 50.0 | 12 | 150 | #1 | 48026 |
| 1181 | 16463 | 50.0 | 50.0 | 12 | 150 | #1 | 48027 |
| 1182 | 16464 | 50.0 | 50.0 | 12 | 150 | #1 | 48028 |
| 1183 | 16465 | 51.2 | 50.0 | 14 | 180 | #1 | 48029 |
| 1184 | 16466 | 50.0 | 50.0 | 12 | 150 | #1 | 48030 |
| 1185 | 16467 | 50.4 | 50.0 | 12 | 150 | #1 | 48031 |
| 1186 | 16468 | 62.4 | 57.8 | 21 | 184 | #3 | 48032 |
| 1187 | 16469 | 69.6 | 63.6 | 25 | 349 | #4 | 48033 |
| 1188 | 16470 | 84.0 | 79.3 | 26 | 1137 | #7 | 48034 |
| 1189 | 16471 | 68.0 | 50.0 | 13 | 199 | #4 | 48035 |
| 1190 | 16472 | 67.2 | 60.7 | 19 | 272 | #4 | 48036 |
| 1191 | 16473 | 75.2 | 57.8 | 15 | 391 | #6 | 48037 |
| 1192 | 16474 | 68.8 | 63.3 | 14 | 423 | #4 | 48038 |
| 1193 | 16475 | 50.0 | 50.0 | 15 | 150 | #1 | 48039 |
| 1194 | 16476 | 72.8 | 68.7 | 13 | 1026 | #5 | 48040 |
| 1195 | 16477 | 76.8 | 68.7 | 16 | 761 | #6 | 48041 |
| 1196 | 16478 | 78.4 | 61.9(252) | 15 | 462 | #6 | 48042 |
| 1197 | 16479 | 50.0 | 50.0 | 12 | 150 | #1 | 48043 |
| 1198 | 16480 | 68.0 | 58.9 | 21 | 262 | #4 | 48044 |
| 1199 | 16481 | 60.8 | 50.0 | 25 | 166 | #3 | 48045 |
| 1200 | 16482 | 61.6 | 56.4 | 12 | 196 | #3 | 48046 |
| 1201 | 16483 | 92.0 | 88.0 | 33 | 1574 | #9 | 48047 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1202 | 16484 | 64.0 | 58.9 | 15 | 241 | #3 | 48048 |
| 1203 | 16485 | 69.6 | 63.9(263) | 17 | 358 | #4 | 48049 |
| 1204 | 16486 | 66.4 | 58.5 | 15 | 207 | #4 | 48050 |
| 1205 | 16487 | 55.2 | 50.0 | 12 | 169 | #2 | 48051 |
| 1206 | 16488 | 68.0 | 58.5 | 16 | 248 | #4 | 48052 |
| 1207 | 16489 | 50.0 | 50.0 | 12 | 150 | #1 | 48053 |
| 1208 | 16490 | 73.6 | 66.9 | 12 | 544 | #5 | 48054 |
| 1209 | 16491 | 63.2 | 56.4(264) | 18 | 169 | #3 | 48055 |
| 1210 | 16492 | 71.2 | 60.0 | 23 | 273 | #5 | 48056 |
| 1211 | 16493 | 50.0 | 50.0 | 12 | 150 | #1 | 48057 |
| 1212 | 16494 | 79.2 | 70.5 | 19 | 788 | #6 | 48058 |
| 1213 | 16495 | 54.4 | 50.0 | 13 | 154 | #1 | 48059 |
| 1214 | 16496 | 64.8 | 61.8 | 16 | 387 | #3 | 48060 |
| 1215 | 16497 | 68.0 | 60.4 | 19 | 318 | #4 | 48061 |
| 1216 | 16498 | 68.8 | 59.3 | 18 | 351 | #4 | 48062 |
| 1217 | 16499 | 76.8 | 69.1 | 25 | 696 | #6 | 48063 |
| 1218 | 16500 | 67.2 | 59.3 | 17 | 418 | #4 | 48064 |
| 1219 | 16501 | 50.0 | 50.0 | 12 | 150 | #1 | 48065 |
| 1220 | 16502 | 70.4 | 62.2 | 25 | 342 | #5 | 48066 |
| 1221 | 16503 | 68.0 | 61.8 | 21 | 370 | #4 | 48067 |
| 1222 | 16504 | 62.4 | 57.1 | 14 | 204 | #3 | 48068 |
| 1223 | 16505 | 68.0 | 61.1 | 18 | 304 | #4 | 48069 |
| 1224 | 16506 | 64.8 | 58.2 | 17 | 214 | #3 | 48070 |
| 1225 | 16507 | 76.0 | 69.8 | 22 | 618 | #6 | 48071 |
| 1226 | 16508 | 66.4 | 50.0 | 12 | 258 | #4 | 48072 |
| 1227 | 16509 | 72.0 | 54.2 | 13 | 332 | #5 | 48073 |
| 1228 | 16510 | 79.2 | 70.2 | 21 | 787 | #6 | 48074 |
| 1229 | 16511 | 64.0 | 50.0 | 12 | 181 | #3 | 48075 |
| 1230 | 16512 | 50.0 | 50.0 | 12 | 150 | #1 | 48076 |
| 1231 | 16513 | 50.0 | 50.0 | 12 | 150 | #1 | 48077 |
| 1232 | 16514 | 65.6 | 59.3 | 14 | 365 | #4 | 48078 |
| 1233 | 16515 | 50.0 | 50.0 | 12 | 150 | #1 | 48079 |
| 1234 | 16516 | 50.0 | 50.0 | 12 | 150 | #1 | 48080 |
| 1235 | 16517 | 78.4 | 73.1 | 24 | 1128 | #6 | 48081 |
| 1236 | 16518 | 61.6 | 53.1 | 15 | 174 | #3 | 48082 |
| 1237 | 16519 | 62.4 | 57.1 | 17 | 277 | #3 | 48083 |
| 1238 | 16520 | 66.4 | 50.2 | 15 | 200 | #4 | 48084 |
| 1239 | 16521 | 64.0 | 50.0(249) | 25 | 368 | #3 | 48085 |
| 1240 | 16522 | 65.6 | 50.0 | 16 | 221 | #4 | 48086 |
| 1241 | 16523 | 50.0 | 50.0 | 12 | 150 | #1 | 48087 |
| 1242 | 16524 | 50.0 | 50.0 | 12 | 150 | #1 | 48088 |
| 1243 | 16525 | 66.4 | 62.9 | 17 | 375 | #4 | 48089 |
| 1244 | 16526 | 66.4 | 59.3 | 15 | 233 | #4 | 48090 |
| 1245 | 16527 | 87.2 | 73.1 | 21 | 785 | #8 | 48091 |
| 1246 | 16528 | 68.0 | 56.4 | 21 | 272 | #4 | 48092 |
| 1247 | 16529 | 50.0 | 50.0 | 12 | 150 | #1 | 48093 |
| 1248 | 16530 | 68.8 | 66.9 | 14 | 911 | #4 | 48094 |
| 1249 | 16531 | 60.0 | 50.0 | 15 | 157 | #2 | 48095 |
| 1250 | 16532 | 66.4 | 57.8 | 21 | 211 | #4 | 48096 |
| 1251 | 16533 | 73.6 | 57.6(255) | 21 | 433 | #5 | 48097 |
| 1252 | 16534 | 61.6 | 50.0 | 14 | 166 | #3 | 48098 |
| 1253 | 16535 | 70.4 | 62.5 | 15 | 458 | #5 | 48099 |
| 1254 | 16536 | 74.4 | 64.4 | 24 | 580 | #5 | 48100 |
| 1255 | 16537 | 68.0 | 61.1 | 17 | 411 | #4 | 48101 |
| 1256 | 16538 | 68.8 | 59.3 | 12 | 295 | #4 | 48102 |
| 1257 | 16539 | 73.6 | 68.0 | 24 | 824 | #5 | 48103 |
| 1258 | 16540 | 65.6 | 50.0 | 12 | 173 | #4 | 48104 |
| 1259 | 16541 | 71.2 | 63.3 | 17 | 414 | #5 | 48105 |
| 1260 | 16542 | 65.6 | 50.0 | 16 | 232 | #4 | 48106 |
| 1261 | 16543 | 60.0 | 57.1 | 12 | 197 | #2 | 48107 |
| 1262 | 16544 | 65.6 | 50.0 | 40 | 295 | #4 | 48108 |
| 1263 | 16545 | 76.0 | 69.5 | 18 | 768 | #6 | 48109 |
| 1264 | 16546 | 64.0 | 52.7 | 15 | 270 | #3 | 48110 |
| 1265 | 16547 | 74.4 | 67.6 | 15 | 834 | #5 | 48111 |
| 1266 | 16548 | 72.0 | 67.3 | 15 | 699 | #5 | 48112 |
| 1267 | 16549 | 76.0 | 68.4 | 15 | 834 | #6 | 48113 |
| 1268 | 16550 | 78.4 | 74.2 | 21 | 1366 | #6 | 48114 |
| 1269 | 16551 | 73.6 | 71.6 | 30 | 679 | #5 | 48115 |
| 1270 | 16552 | 72.8 | 62.5 | 22 | 394 | #5 | 48116 |
| 1271 | 16553 | 68.8 | 62.2 | 20 | 275 | #4 | 48117 |
| 1272 | 16554 | 66.4 | 62.5 | 12 | 394 | #4 | 48118 |
| 1273 | 16555 | 84.0 | 74.5 | 16 | 832 | #7 | 48119 |
| 1274 | 16556 | 69.6 | 60.7 | 19 | 322 | #4 | 48120 |
| 1275 | 16557 | 66.4 | 60.4 | 18 | 275 | #4 | 48121 |
| 1276 | 16558 | 71.2 | 62.2 | 18 | 474 | #5 | 48122 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1277 | 16559 | 70.4 | 64.0 | 15 | 485 | #5 | 48123 |
| 1278 | 16560 | 72.0 | 63.3 | 30 | 319 | #5 | 48124 |
| 1279 | 16561 | 70.4 | 62.9 | 20 | 359 | #5 | 48125 |
| 1280 | 16562 | 63.2 | 58.5 | 14 | 216 | #3 | 48126 |
| 1281 | 16563 | 69.6 | 65.1 | 18 | 760 | #4 | 48127 |
| 1282 | 16564 | 77.6 | 72.7 | 19 | 1083 | #6 | 48128 |
| 1283 | 16565 | 53.6 | 50.0 | 15 | 177 | #1 | 48129 |
| 1284 | 16566 | 88.8 | 83.3 | 33 | 3691 | #8 | 48130 |
| 1285 | 16567 | 60.0 | 57.8 | 13 | 185 | #2 | 48131 |
| 1286 | 16568 | 64.8 | 54.9 | 14 | 274 | #3 | 48132 |
| 1287 | 16569 | 67.2 | 60.4 | 17 | 411 | #4 | 48133 |
| 1288 | 16570 | 69.6 | 53.1 | 16 | 270 | #4 | 48134 |
| 1289 | 16571 | 60.8 | 58.2 | 13 | 233 | #3 | 48135 |
| 1290 | 16572 | 50.0 | 50.0 | 12 | 150 | #1 | 48136 |
| 1291 | 16573 | 72.0 | 60.7 | 21 | 455 | #5 | 48137 |
| 1292 | 16574 | 73.6 | 67.3 | 36 | 719 | #5 | 48138 |
| 1293 | 16575 | 75.2 | 66.5 | 14 | 730 | #6 | 48139 |
| 1294 | 16576 | 60.8 | 59.6 | 12 | 195 | #3 | 48140 |
| 1295 | 16577 | 64.8 | 56.0 | 34 | 234 | #3 | 48141 |
| 1296 | 16578 | 72.8 | 69.1 | 12 | 607 | #5 | 48142 |
| 1297 | 16579 | 67.2 | 61.5 | 15 | 395 | #4 | 48143 |
| 1298 | 16580 | 73.6 | 68.0 | 21 | 1172 | #5 | 48144 |
| 1299 | 16581 | 50.0 | 50.0 | 15 | 184 | #1 | 48145 |
| 1300 | 16582 | 81.6 | 64.0 | 22 | 487 | #7 | 48146 |
| 1301 | 16583 | 67.2 | 60.4 | 24 | 260 | #4 | 48147 |
| 1302 | 16584 | 57.6 | 50.0 | 12 | 150 | #2 | 48148 |
| 1303 | 16585 | 72.0 | 65.1 | 12 | 656 | #5 | 48149 |
| 1304 | 16586 | 70.4 | 53.3(225) | 18 | 275 | #5 | 48150 |
| 1305 | 16587 | 72.0 | 66.5 | 19 | 386 | #5 | 48151 |
| 1306 | 16588 | 70.4 | 62.5 | 15 | 315 | #5 | 48152 |
| 1307 | 16589 | 71.2 | 58.2 | 14 | 442 | #5 | 48153 |
| 1308 | 16590 | 85.6 | 81.1 | 24 | 2137 | #8 | 48154 |
| 1309 | 16591 | 50.0 | 50.0 | 12 | 150 | #1 | 48155 |
| 1310 | 16592 | 76.8 | 68.4 | 19 | 690 | #6 | 48156 |
| 1311 | 16593 | 65.6 | 60.0 | 16 | 238 | #4 | 48157 |
| 1312 | 16594 | 61.6 | 50.0 | 12 | 165 | #3 | 48158 |
| 1313 | 16595 | 75.2 | 60.0 | 14 | 415 | #6 | 48159 |
| 1314 | 16596 | 75.2 | 64.7 | 24 | 383 | #6 | 48160 |
| 1315 | 16597 | 67.2 | 61.5 | 18 | 386 | #4 | 48161 |
| 1316 | 16598 | 65.6 | 58.9 | 15 | 210 | #4 | 48162 |
| 1317 | 16599 | 60.8 | 50.0(254) | 16 | 179 | #3 | 48163 |
| 1318 | 16600 | 78.4 | 70.5 | 18 | 664 | #6 | 48164 |
| 1319 | 16601 | 65.6 | 57.8 | 17 | 221 | #4 | 48165 |
| 1320 | 16602 | 71.2 | 65.5 | 27 | 447 | #5 | 48166 |
| 1321 | 16603 | 68.8 | 64.0 | 14 | 409 | #4 | 48167 |
| 1322 | 16604 | 70.4 | 65.1 | 15 | 508 | #5 | 48168 |
| 1323 | 16605 | 67.2 | 59.3 | 12 | 330 | #4 | 48169 |
| 1324 | 16606 | 79.2 | 73.8 | 19 | 1217 | #6 | 48170 |
| 1325 | 16607 | 76.0 | 68.7 | 21 | 763 | #6 | 48171 |
| 1326 | 16608 | 69.6 | 66.2 | 15 | 637 | #4 | 48172 |
| 1327 | 16609 | 72.8 | 68.0 | 14 | 634 | #5 | 48173 |
| 1328 | 16610 | 85.6 | 77.1 | 26 | 1032 | #8 | 48174 |
| 1329 | 16611 | 64.0 | 56.4 | 12 | 203 | #3 | 48175 |
| 1330 | 16612 | 64.0 | 53.0(230) | 15 | 208 | #3 | 48176 |
| 1331 | 16613 | 68.0 | 61.5 | 16 | 383 | #4 | 48177 |
| 1332 | 16614 | 72.8 | 64.7 | 22 | 505 | #5 | 48178 |
| 1333 | 16615 | 67.2 | 58.2 | 17 | 296 | #4 | 48179 |
| 1334 | 16616 | 50.0 | 50.0 | 12 | 150 | #1 | 48180 |
| 1335 | 16617 | 68.0 | 50.9 | 12 | 280 | #4 | 48181 |
| 1336 | 16618 | 68.0 | 60.4 | 20 | 389 | #4 | 48182 |
| 1337 | 16619 | 50.0 | 50.0 | 12 | 150 | #1 | 48183 |
| 1338 | 16620 | 72.8 | 65.5 | 18 | 665 | #5 | 48184 |
| 1339 | 16621 | 81.6 | 76.7 | 30 | 893 | #7 | 48185 |
| 1340 | 16622 | 68.0 | 60.4 | 38 | 273 | #4 | 48186 |
| 1341 | 16623 | 66.4 | 59.6 | 17 | 296 | #4 | 48187 |
| 1342 | 16624 | 64.0 | 58.2 | 12 | 193 | #3 | 48188 |
| 1343 | 16625 | 64.0 | 50.0 | 19 | 194 | #3 | 48189 |
| 1344 | 16626 | 68.8 | 59.6 | 19 | 374 | #4 | 48190 |
| 1345 | 16627 | 60.0 | 57.8 | 16 | 199 | #2 | 48191 |
| 1346 | 16628 | 69.6 | 59.6 | 18 | 302 | #4 | 48192 |
| 1347 | 16629 | 50.0 | 50.0 | 12 | 150 | #1 | 48193 |
| 1348 | 16630 | 67.2 | 57.5 | 14 | 246 | #4 | 48194 |
| 1349 | 16631 | 50.0 | 50.0 | 12 | 150 | #1 | 48195 |
| 1350 | 16632 | 74.4 | 64.7 | 17 | 750 | #5 | 48196 |
| 1351 | 16633 | 67.2 | 60.4 | 12 | 402 | #4 | 48197 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1352 | 16634 | 66.4 | 62.9 | 12 | 411 | #4 | 48198 |
| 1353 | 16635 | 60.8 | 50.0 | 13 | 150 | #3 | 48199 |
| 1354 | 16636 | 76.8 | 74.2 | 18 | 886 | #6 | 48200 |
| 1355 | 16637 | 68.8 | 61.1 | 16 | 339 | #4 | 48201 |
| 1356 | 16638 | 50.0 | 50.0 | 12 | 150 | #1 | 48202 |
| 1357 | 16639 | 63.2 | 57.5 | 16 | 205 | #3 | 48203 |
| 1358 | 16640 | 65.6 | 60.0 | 16 | 290 | #4 | 48204 |
| 1359 | 16641 | 82.4 | 66.5 | 18 | 491 | #7 | 48205 |
| 1360 | 16642 | 75.2 | 70.5 | 27 | 859 | #6 | 48206 |
| 1361 | 16643 | 62.4 | 50.0 | 13 | 188 | #3 | 48207 |
| 1362 | 16644 | 50.0 | 50.0 | 12 | 150 | #1 | 48208 |
| 1363 | 16645 | 69.6 | 64.0 | 19 | 598 | #4 | 48209 |
| 1364 | 16646 | 77.6 | 70.5 | 20 | 737 | #6 | 48210 |
| 1365 | 16647 | 76.8 | 73.1 | 25 | 714 | #6 | 48211 |
| 1366 | 16648 | 77.6 | 73.8 | 22 | 949 | #6 | 48212 |
| 1367 | 16649 | 67.2 | 50.0 | 14 | 284 | #4 | 48213 |
| 1368 | 16650 | 76.8 | 66.5 | 28 | 655 | #6 | 48214 |
| 1369 | 16651 | 91.2 | 86.5 | 36 | 1128 | #9 | 48215 |
| 1370 | 16652 | 64.0 | 50.0 | 12 | 191 | #3 | 48216 |
| 1371 | 16653 | 99.2 | 97.8 | 87 | 2772 | #10 | 48217 |
| 1372 | 16654 | 64.8 | 55.0(238) | 18 | 167 | #3 | 48218 |
| 1373 | 16655 | 98.4 | 96.4 | 96 | 1698 | #10 | 48219 |
| 1374 | 16656 | 68.8 | 61.5 | 17 | 313 | #4 | 48220 |
| 1375 | 16657 | 100.0 | 99.6 | 197 | 2138 | #10 | 48221 |
| 1376 | 16658 | 68.0 | 56.4 | 25 | 255 | #4 | 48222 |
| 1377 | 16659 | 50.0 | 50.0 | 12 | 150 | #1 | 48223 |
| 1378 | 16660 | 50.0 | 50.0 | 12 | 150 | #1 | 48224 |
| 1379 | 16661 | 71.2 | 66.5 | 19 | 996 | #5 | 48225 |
| 1380 | 16662 | 93.6 | 89.8 | 38 | 1146 | #9 | 48226 |
| 1381 | 16663 | 67.2 | 57.5 | 13 | 221 | #4 | 48227 |
| 1382 | 16664 | 64.8 | 57.1 | 13 | 211 | #3 | 48228 |
| 1383 | 16665 | 91.2 | 85.1 | 27 | 1035 | #9 | 48229 |
| 1384 | 16666 | 68.8 | 61.5 | 28 | 306 | #4 | 48230 |
| 1385 | 16667 | 60.0 | 52.7 | 16 | 187 | #2 | 48231 |
| 1386 | 16668 | 68.8 | 61.8 | 20 | 400 | #4 | 48232 |
| 1387 | 16669 | 76.0 | 61.8(228) | 23 | 336 | #6 | 48233 |
| 1388 | 16670 | 68.8 | 56.7 | 12 | 319 | #4 | 48234 |
| 1389 | 16671 | 62.4 | 50.0 | 12 | 183 | #3 | 48235 |
| 1390 | 16672 | 77.6 | 69.5 | 19 | 842 | #6 | 48236 |
| 1391 | 16673 | 70.4 | 67.6 | 18 | 823 | #5 | 48237 |
| 1392 | 16674 | 95.2 | 92.1(203) | 45 | 869 | #10 | 48238 |
| 1393 | 16675 | 50.0 | 50.0 | 12 | 150 | #1 | 48239 |
| 1394 | 16676 | 63.2 | 56.4 | 17 | 207 | #3 | 48240 |
| 1395 | 16677 | 66.4 | 57.5 | 14 | 368 | #4 | 48241 |
| 1396 | 16678 | 70.4 | 63.3 | 20 | 329 | #5 | 48242 |
| 1397 | 16679 | 73.6 | 50.0(263) | 23 | 378 | #5 | 48243 |
| 1398 | 16680 | 50.0 | 50.0 | 12 | 150 | #1 | 48244 |
| 1399 | 16681 | 64.0 | 59.6 | 21 | 333 | #3 | 48245 |
| 1400 | 16682 | 68.0 | 58.2 | 16 | 246 | #4 | 48246 |
| 1401 | 16683 | 60.0 | 56.7 | 14 | 313 | #2 | 48247 |
| 1402 | 16684 | 50.0 | 50.0 | 12 | 150 | #1 | 48248 |
| 1403 | 16685 | 75.2 | 67.6 | 16 | 703 | #6 | 48249 |
| 1404 | 16686 | 68.8 | 61.5 | 38 | 280 | #4 | 48250 |
| 1405 | 16687 | 50.0 | 50.0 | 12 | 150 | #1 | 48251 |
| 1406 | 16688 | 50.0 | 50.0 | 12 | 150 | #1 | 48252 |
| 1407 | 16689 | 85.6 | 80.0 | 28 | 1056 | #8 | 48253 |
| 1408 | 16690 | 50.0 | 50.0 | 12 | 150 | #1 | 48254 |
| 1409 | 16691 | 73.6 | 63.3 | 31 | 451 | #5 | 48255 |
| 1410 | 16692 | 77.6 | 60.0 | 18 | 499 | #6 | 48256 |
| 1411 | 16693 | 68.8 | 61.8 | 17 | 264 | #4 | 48257 |
| 1412 | 16694 | 78.4 | 74.9 | 16 | 893 | #6 | 48258 |
| 1413 | 16695 | 72.0 | 65.1 | 30 | 520 | #5 | 48259 |
| 1414 | 16696 | 75.2 | 63.3 | 16 | 542 | #6 | 48260 |
| 1415 | 16697 | 80.0 | 76.7 | 23 | 1208 | #6 | 48261 |
| 1416 | 16698 | 66.4 | 50.0(220) | 14 | 236 | #4 | 48262 |
| 1417 | 16699 | 67.2 | 58.5 | 18 | 237 | #4 | 48263 |
| 1418 | 16700 | 76.0 | 69.1 | 16 | 621 | #6 | 48264 |
| 1419 | 16701 | 66.4 | 59.3 | 20 | 260 | #4 | 48265 |
| 1420 | 16702 | 74.4 | 66.9 | 19 | 789 | #5 | 48266 |
| 1421 | 16703 | 65.6 | 50.5 | 15 | 186 | #4 | 48267 |
| 1422 | 16704 | 64.0 | 58.5 | 18 | 252 | #3 | 48268 |
| 1423 | 16705 | 63.2 | 57.1 | 13 | 176 | #3 | 48269 |
| 1424 | 16706 | 70.4 | 63.3 | 25 | 655 | #5 | 48270 |
| 1425 | 16707 | 80.0 | 58.5 | 15 | 478 | #6 | 48271 |
| 1426 | 16708 | 68.8 | 62.5 | 13 | 472 | #4 | 48272 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1427 | 16709 | 68.0 | 53.8 | 18 | 346 | #4 | 48273 |
| 1428 | 16710 | 69.6 | 57.3(260) | 23 | 279 | #4 | 48274 |
| 1429 | 16711 | 68.8 | 50.0 | 17 | 332 | #4 | 48275 |
| 1430 | 16712 | 69.6 | 64.4 | 17 | 669 | #4 | 48276 |
| 1431 | 16713 | 66.4 | 50.0 | 14 | 187 | #4 | 48277 |
| 1432 | 16714 | 70.4 | 61.1 | 20 | 351 | #5 | 48278 |
| 1433 | 16715 | 68.8 | 64.4 | 16 | 469 | #4 | 48279 |
| 1434 | 16716 | 76.0 | 73.5 | 21 | 928 | #6 | 48280 |
| 1435 | 16717 | 69.6 | 66.5 | 15 | 475 | #4 | 48281 |
| 1436 | 16718 | 80.8 | 61.1 | 19 | 452 | #7 | 48282 |
| 1437 | 16719 | 72.8 | 66.9 | 14 | 502 | #5 | 48283 |
| 1438 | 16720 | 50.0 | 50.0 | 12 | 150 | #1 | 48284 |
| 1439 | 16721 | 50.0 | 50.0 | 12 | 150 | #1 | 48285 |
| 1440 | 16722 | 69.6 | 62.2 | 13 | 421 | #4 | 48286 |
| 1441 | 16723 | 70.4 | 50.0 | 12 | 323 | #5 | 48287 |
| 1442 | 16724 | 68.0 | 62.2 | 13 | 357 | #4 | 48288 |
| 1443 | 16725 | 76.8 | 68.4 | 18 | 601 | #6 | 48289 |
| 1444 | 16726 | 50.0 | 50.0 | 12 | 150 | #1 | 48290 |
| 1445 | 16727 | 64.8 | 58.9 | 19 | 252 | #3 | 48291 |
| 1446 | 16728 | 76.8 | 71.3 | 20 | 795 | #6 | 48292 |
| 1447 | 16729 | 99.2 | 97.8 | 87 | 2504 | #10 | 48293 |
| 1448 | 16730 | 64.8 | 50.0 | 16 | 186 | #3 | 48294 |
| 1449 | 16731 | 67.2 | 57.8 | 33 | 307 | #4 | 48295 |
| 1450 | 16732 | 50.0 | 50.0 | 14 | 151 | #1 | 48296 |
| 1451 | 16733 | 68.0 | 60.4 | 20 | 290 | #4 | 48297 |
| 1452 | 16734 | 70.4 | 65.1 | 14 | 440 | #5 | 48298 |
| 1453 | 16735 | 80.8 | 77.5 | 18 | 1077 | #7 | 48299 |
| 1454 | 16736 | 50.0 | 50.0 | 12 | 150 | #1 | 48300 |
| 1455 | 16737 | 67.2 | 59.3 | 14 | 343 | #4 | 48301 |
| 1456 | 16738 | 76.8 | 72.4 | 20 | 1378 | #6 | 48302 |
| 1457 | 16739 | 63.2 | 57.1 | 13 | 191 | #3 | 48303 |
| 1458 | 16740 | 68.0 | 58.5 | 19 | 281 | #4 | 48304 |
| 1459 | 16741 | 76.8 | 69.5 | 17 | 1566 | #6 | 48305 |
| 1460 | 16742 | 50.0 | 50.0 | 12 | 150 | #1 | 48306 |
| 1461 | 16743 | 71.2 | 64.7 | 16 | 484 | #5 | 48307 |
| 1462 | 16744 | 68.0 | 50.0 | 15 | 236 | #4 | 48308 |
| 1463 | 16745 | 75.2 | 65.1 | 15 | 497 | #6 | 48309 |
| 1464 | 16746 | 64.0 | 59.3 | 13 | 411 | #3 | 48310 |
| 1465 | 16747 | 70.4 | 52.7 | 13 | 433 | #5 | 48311 |
| 1466 | 16748 | 72.8 | 67.3 | 34 | 606 | #5 | 48312 |
| 1467 | 16749 | 64.8 | 60.0 | 15 | 334 | #3 | 48313 |
| 1468 | 16750 | 50.0 | 50.0 | 12 | 150 | #1 | 48314 |
| 1469 | 16751 | 64.8 | 59.3 | 15 | 246 | #3 | 48315 |
| 1470 | 16752 | 50.0 | 50.0 | 12 | 150 | #1 | 48316 |
| 1471 | 16753 | 57.6 | 50.0(207) | 14 | 150 | #2 | 48317 |
| 1472 | 16754 | 73.6 | 70.5 | 19 | 769 | #5 | 48318 |
| 1473 | 16755 | 65.6 | 60.7 | 18 | 397 | #4 | 48319 |
| 1474 | 16756 | 64.0 | 60.4 | 13 | 344 | #3 | 48320 |
| 1475 | 16757 | 66.4 | 61.8 | 16 | 377 | #4 | 48321 |
| 1476 | 16758 | 63.2 | 57.8 | 13 | 224 | #3 | 48322 |
| 1477 | 16759 | 73.6 | 69.5 | 17 | 686 | #5 | 48323 |
| 1478 | 16760 | 64.8 | 59.3 | 17 | 276 | #3 | 48324 |
| 1479 | 16761 | 64.8 | 58.9 | 17 | 185 | #3 | 48325 |
| 1480 | 16762 | 74.4 | 66.5 | 19 | 567 | #5 | 48326 |
| 1481 | 16763 | 61.6 | 55.6 | 13 | 227 | #3 | 48327 |
| 1482 | 16764 | 70.4 | 60.4 | 15 | 291 | #5 | 48328 |
| 1483 | 16765 | 70.4 | 61.8 | 15 | 375 | #5 | 48329 |
| 1484 | 16766 | 72.0 | 50.0 | 12 | 328 | #5 | 48330 |
| 1485 | 16767 | 60.0 | 52.4(164) | 14 | 154 | #2 | 48331 |
| 1486 | 16768 | 72.0 | 66.9 | 22 | 627 | #5 | 48332 |
| 1487 | 16769 | 78.4 | 76.4 | 15 | 1238 | #6 | 48333 |
| 1488 | 16770 | 84.8 | 74.2 | 25 | 918 | #7 | 48334 |
| 1489 | 16771 | 65.6 | 52.7 | 13 | 245 | #4 | 48335 |
| 1490 | 16772 | 76.8 | 69.5 | 15 | 569 | #6 | 48336 |
| 1491 | 16773 | 68.0 | 60.4 | 15 | 308 | #4 | 48337 |
| 1492 | 16774 | 50.0 | 50.0 | 12 | 150 | #1 | 48338 |
| 1493 | 16775 | 77.6 | 72.4 | 20 | 677 | #6 | 48339 |
| 1494 | 16776 | 50.0 | 50.0 | 12 | 150 | #1 | 48340 |
| 1495 | 16777 | 50.0 | 50.0 | 12 | 150 | #1 | 48341 |
| 1496 | 16778 | 71.2 | 65.5 | 26 | 727 | #5 | 48342 |
| 1497 | 16779 | 80.0 | 55.3 | 21 | 431 | #6 | 48343 |
| 1498 | 16780 | 64.0 | 58.5 | 12 | 207 | #3 | 48344 |
| 1499 | 16781 | 71.2 | 65.5 | 19 | 696 | #5 | 48345 |
| 1500 | 16782 | 61.6 | 50.0 | 12 | 158 | #3 | 48346 |
| 1501 | 16783 | 68.0 | 62.2 | 16 | 337 | #4 | 48347 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1502 | 16784 | 71.2 | 58.9 | 20 | 396 | #5 | 48348 |
| 1503 | 16785 | 50.0 | 50.0 | 12 | 150 | #1 | 48349 |
| 1504 | 16786 | 63.2 | 50.0 | 13 | 187 | #3 | 48350 |
| 1505 | 16787 | 63.2 | 58.5 | 14 | 213 | #3 | 48351 |
| 1506 | 16788 | 50.0 | 50.0 | 12 | 150 | #1 | 48352 |
| 1507 | 16789 | 66.4 | 50.0 | 13 | 211 | #4 | 48353 |
| 1508 | 16790 | 91.2 | 87.3 | 33 | 1683 | #9 | 48354 |
| 1509 | 16791 | 60.0 | 56.7 | 12 | 192 | #2 | 48355 |
| 1510 | 16792 | 64.0 | 50.5 | 34 | 195 | #3 | 48356 |
| 1511 | 16793 | 69.6 | 59.3 | 15 | 309 | #4 | 48357 |
| 1512 | 16794 | 71.2 | 61.1 | 30 | 506 | #5 | 48358 |
| 1513 | 16795 | 81.6 | 74.5 | 25 | 1035 | #7 | 48359 |
| 1514 | 16796 | 63.2 | 57.1 | 14 | 204 | #3 | 48360 |
| 1515 | 16797 | 76.0 | 74.5 | 21 | 1266 | #6 | 48361 |
| 1516 | 16798 | 65.6 | 50.0 | 12 | 247 | #4 | 48362 |
| 1517 | 16799 | 77.6 | 64.7 | 17 | 518 | #6 | 48363 |
| 1518 | 16800 | 63.2 | 50.0 | 19 | 184 | #3 | 48364 |
| 1519 | 16801 | 88.8 | 88.2(161) | 29 | 628 | #8 | 48365 |
| 1520 | 16802 | 63.2 | 56.4 | 15 | 189 | #3 | 48366 |
| 1521 | 16803 | 77.6 | 69.5 | 33 | 640 | #6 | 48367 |
| 1522 | 16804 | 76.0 | 71.3 | 15 | 769 | #6 | 48368 |
| 1523 | 16805 | 60.8 | 57.8 | 12 | 237 | #3 | 48369 |
| 1524 | 16806 | 80.0 | 74.5 | 20 | 1609 | #6 | 48370 |
| 1525 | 16807 | 75.2 | 74.5(247) | 23 | 645 | #6 | 48371 |
| 1526 | 16808 | 65.6 | 57.8 | 21 | 227 | #4 | 48372 |
| 1527 | 16809 | 70.4 | 62.2 | 19 | 384 | #5 | 48373 |
| 1528 | 16810 | 50.0 | 50.0 | 12 | 150 | #1 | 48374 |
| 1529 | 16811 | 53.6 | 50.0 | 13 | 173 | #1 | 48375 |
| 1530 | 16812 | 88.8 | 83.9(255) | 24 | 900 | #8 | 48376 |
| 1531 | 16813 | 77.6 | 70.5 | 19 | 662 | #6 | 48377 |
| 1532 | 16814 | 71.2 | 65.8 | 18 | 624 | #5 | 48378 |
| 1533 | 16815 | 52.0 | 50.0 | 12 | 150 | #1 | 48379 |
| 1534 | 16816 | 78.4 | 67.6 | 20 | 609 | #6 | 48380 |
| 1535 | 16817 | 62.4 | 50.0 | 12 | 171 | #3 | 48381 |
| 1536 | 16818 | 67.2 | 62.2 | 14 | 374 | #4 | 48382 |
| 1537 | 16819 | 75.2 | 64.4 | 18 | 585 | #6 | 48383 |
| 1538 | 16820 | 80.0 | 73.5 | 24 | 1015 | #6 | 48384 |
| 1539 | 16821 | 79.2 | 72.7 | 21 | 1177 | #6 | 48385 |
| 1540 | 16822 | 79.2 | 66.9 | 29 | 642 | #6 | 48386 |
| 1541 | 16823 | 69.6 | 62.5 | 20 | 413 | #4 | 48387 |
| 1542 | 16824 | 76.8 | 69.5 | 18 | 568 | #6 | 48388 |
| 1543 | 16825 | 62.4 | 57.8 | 15 | 226 | #3 | 48389 |
| 1544 | 16826 | 77.6 | 70.9 | 18 | 1208 | #6 | 48390 |
| 1545 | 16827 | 68.8 | 56.4 | 18 | 247 | #4 | 48391 |
| 1546 | 16828 | 64.8 | 60.7 | 12 | 366 | #3 | 48392 |
| 1547 | 16829 | 63.2 | 57.1 | 17 | 297 | #3 | 48393 |
| 1548 | 16830 | 62.4 | 50.0 | 14 | 182 | #3 | 48394 |
| 1549 | 16831 | 70.4 | 62.5 | 19 | 359 | #5 | 48395 |
| 1550 | 16832 | 64.8 | 61.1 | 15 | 364 | #3 | 48396 |
| 1551 | 16833 | 50.0 | 50.0 | 12 | 150 | #1 | 48397 |
| 1552 | 16834 | 50.0 | 50.0 | 12 | 150 | #1 | 48398 |
| 1553 | 16835 | 64.8 | 58.5 | 16 | 313 | #3 | 48399 |
| 1554 | 16836 | 50.0 | 50.0 | 12 | 150 | #1 | 48400 |
| 1555 | 16837 | 68.0 | 60.4 | 16 | 308 | #4 | 48401 |
| 1556 | 16838 | 50.0 | 50.0 | 12 | 150 | #1 | 48402 |
| 1557 | 16839 | 64.0 | 57.8 | 15 | 212 | #3 | 48403 |
| 1558 | 16840 | 72.0 | 65.1 | 15 | 505 | #5 | 48404 |
| 1559 | 16841 | 68.0 | 59.6 | 16 | 223 | #4 | 48405 |
| 1560 | 16842 | 89.6 | 84.5(161) | 20 | 612 | #8 | 48406 |
| 1561 | 16843 | 75.2 | 71.3 | 17 | 852 | #6 | 48407 |
| 1562 | 16844 | 67.2 | 53.5 | 17 | 210 | #4 | 48408 |
| 1563 | 16845 | 68.8 | 63.3 | 18 | 493 | #4 | 48409 |
| 1564 | 16846 | 50.0 | 50.0 | 12 | 150 | #1 | 48410 |
| 1565 | 16847 | 68.8 | 63.6 | 24 | 397 | #4 | 48411 |
| 1566 | 16848 | 50.0 | 50.0 | 12 | 150 | #1 | 48412 |
| 1567 | 16849 | 67.2 | 64.0 | 13 | 451 | #4 | 48413 |
| 1568 | 16850 | 50.0 | 50.0 | 12 | 150 | #1 | 48414 |
| 1569 | 16851 | 71.2 | 65.5 | 24 | 555 | #5 | 48415 |
| 1570 | 16852 | 69.6 | 62.9 | 17 | 410 | #4 | 48416 |
| 1571 | 16853 | 63.2 | 57.1 | 15 | 259 | #3 | 48417 |
| 1572 | 16854 | 70.4 | 65.5 | 15 | 489 | #5 | 48418 |
| 1573 | 16855 | 72.8 | 67.3 | 17 | 932 | #5 | 48419 |
| 1574 | 16856 | 70.3(74) | — | 16 | 172 | #5 | 48420 |
| 1575 | 16857 | 96.0 | 90.7(161) | 43 | 698 | #10 | 48421 |
| 1576 | 16858 | 50.0 | 50.0(260) | 14 | 160 | #1 | 48422 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1577 | 16859 | 64.0 | 58.5 | 18 | 271 | #3 | 48423 |
| 1578 | 16860 | 84.8 | 77.8 | 28 | 1073 | #7 | 48424 |
| 1579 | 16861 | 59.2 | 50.0 | 14 | 167 | #2 | 48425 |
| 1580 | 16862 | 68.0 | 58.5 | 25 | 263 | #4 | 48426 |
| 1581 | 16863 | 66.4 | 58.2 | 15 | 277 | #4 | 48427 |
| 1582 | 16864 | 76.8 | 71.6 | 27 | 1213 | #6 | 48428 |
| 1583 | 16865 | 60.8 | 50.0 | 14 | 174 | #3 | 48429 |
| 1584 | 16866 | 72.0 | 68.4 | 23 | 487 | #5 | 48430 |
| 1585 | 16867 | 98.4 | 97.8 | 98 | 2290 | #10 | 48431 |
| 1586 | 16868 | 73.6 | 65.5 | 18 | 788 | #5 | 48432 |
| 1587 | 16869 | 64.8 | 50.0 | 27 | 208 | #3 | 48433 |
| 1588 | 16870 | 78.4 | 71.3 | 20 | 799 | #6 | 48434 |
| 1589 | 16871 | 99.2 | 97.8 | 87 | 2093 | #10 | 48435 |
| 1590 | 16872 | 74.4 | 64.4 | 16 | 505 | #5 | 48436 |
| 1591 | 16873 | 50.0 | 50.0 | 12 | 150 | #1 | 48437 |
| 1592 | 16874 | 72.0 | 65.8 | 14 | 564 | #5 | 48438 |
| 1593 | 16875 | 68.8 | 62.9 | 21 | 471 | #4 | 48439 |
| 1594 | 16876 | 64.8 | 58.5 | 14 | 211 | #3 | 48440 |
| 1595 | 16877 | 76.0 | 62.5 | 16 | 411 | #6 | 48441 |
| 1596 | 16878 | 77.6 | 71.3 | 13 | 593 | #6 | 48442 |
| 1597 | 16879 | 96.8 | 95.6 | 55 | 1641 | #10 | 48443 |
| 1598 | 16880 | 80.0 | 72.4 | 17 | 1660 | #6 | 48444 |
| 1599 | 16881 | 67.2 | 60.0 | 16 | 235 | #4 | 48445 |
| 1600 | 16882 | 58.4 | 50.0 | 14 | 158 | #2 | 48446 |
| 1601 | 16883 | 69.6 | 60.4 | 19 | 313 | #4 | 48447 |
| 1602 | 16884 | 68.0 | 60.5(256) | 20 | 271 | #4 | 48448 |
| 1603 | 16885 | 83.2 | 80.7 | 18 | 1032 | #7 | 48449 |
| 1604 | 16886 | 73.6 | 63.6 | 12 | 418 | #5 | 48450 |
| 1605 | 16887 | 76.8 | 74.5 | 21 | 1074 | #6 | 48451 |
| 1606 | 16888 | 64.0 | 50.0 | 21 | 218 | #3 | 48452 |
| 1607 | 16889 | 66.4 | 57.8 | 15 | 248 | #4 | 48453 |
| 1608 | 16890 | 50.0 | 50.0 | 12 | 150 | #1 | 48454 |
| 1609 | 16891 | 60.8 | 50.0 | 16 | 155 | #3 | 48455 |
| 1610 | 16892 | 50.0 | 50.0 | 12 | 150 | #1 | 48456 |
| 1611 | 16893 | 72.8 | 58.9 | 18 | 336 | #5 | 48457 |
| 1612 | 16894 | 59.2 | 50.0 | 12 | 159 | #2 | 48458 |
| 1613 | 16895 | 93.6 | 87.6 | 30 | 1254 | #9 | 48459 |
| 1614 | 16896 | 80.0 | 61.5 | 18 | 475 | #6 | 48460 |
| 1615 | 16897 | 88.0 | 65.8 | 23 | 771 | #8 | 48461 |
| 1616 | 16898 | 64.0 | 58.5 | 18 | 205 | #3 | 48462 |
| 1617 | 16899 | 50.0 | 50.0 | 12 | 150 | #1 | 48463 |
| 1618 | 16900 | 100.0 | 100.0 | 12 | 4029 | #10 | 48464 |
| 1619 | 16901 | 66.4 | 58.5 | 16 | 315 | #4 | 48465 |
| 1620 | 16902 | 79.2 | 66.2 | 27 | 497 | #6 | 48466 |
| 1621 | 16903 | 69.6 | 64.4 | 21 | 683 | #4 | 48467 |
| 1622 | 16904 | 60.8 | 50.5 | 13 | 177 | #3 | 48468 |
| 1623 | 16905 | 63.2 | 58.5 | 14 | 230 | #3 | 48469 |
| 1624 | 16906 | 61.6 | 57.8 | 12 | 199 | #3 | 48470 |
| 1625 | 16907 | 65.6 | 58.2 | 18 | 216 | #4 | 48471 |
| 1626 | 16908 | 50.0 | 50.0 | 12 | 150 | #1 | 48472 |
| 1627 | 16909 | 50.0 | 50.0 | 12 | 150 | #1 | 48473 |
| 1628 | 16910 | 63.2 | 50.0 | 14 | 154 | #3 | 48474 |
| 1629 | 16911 | 72.0 | 62.9 | 25 | 657 | #5 | 48475 |
| 1630 | 16912 | 65.6 | 56.7(238) | 26 | 282 | #4 | 48476 |
| 1631 | 16913 | 50.0 | 50.0 | 12 | 150 | #1 | 48477 |
| 1632 | 16914 | 62.4 | 57.8 | 18 | 203 | #3 | 48478 |
| 1633 | 16915 | 70.4 | 65.5 | 33 | 573 | #5 | 48479 |
| 1634 | 16916 | 79.2 | 69.8 | 18 | 690 | #6 | 48480 |
| 1635 | 16917 | 70.4 | 65.5 | 18 | 574 | #5 | 48481 |
| 1636 | 16918 | 50.0 | 50.0 | 12 | 150 | #1 | 48482 |
| 1637 | 16919 | 63.2 | 57.8 | 16 | 188 | #3 | 48483 |
| 1638 | 16920 | 67.2 | 65.1 | 17 | 412 | #4 | 48484 |
| 1639 | 16921 | 64.0 | 57.1 | 12 | 203 | #3 | 48485 |
| 1640 | 16922 | 70.4 | 60.4 | 16 | 372 | #5 | 48486 |
| 1641 | 16923 | 55.2 | 50.0 | 12 | 195 | #2 | 48487 |
| 1642 | 16924 | 64.8 | 59.6 | 14 | 234 | #3 | 48488 |
| 1643 | 16925 | 79.2 | 75.3 | 20 | 836 | #6 | 48489 |
| 1644 | 16926 | 70.4 | 68.0 | 16 | 514 | #5 | 48490 |
| 1645 | 16927 | 64.0 | 60.0 | 13 | 305 | #3 | 48491 |
| 1646 | 16928 | 68.8 | 69.6 | 16 | 293 | #4 | 48492 |
| 1647 | 16929 | 65.6 | 53.1 | 12 | 252 | #4 | 48493 |
| 1648 | 16930 | 70.4 | 61.8 | 21 | 429 | #5 | 48494 |
| 1649 | 16931 | 56.0 | 52.2(134) | 12 | 158 | #2 | 48495 |
| 1650 | 16932 | 78.4 | 65.5 | 19 | 548 | #6 | 48496 |
| 1651 | 16933 | 50.0 | 50.0 | 12 | 150 | #1 | 48497 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1652 | 16934 | 90.4 | 78.9 | 34 | 906 | #9 | 48498 |
| 1653 | 16935 | 83.2 | 76.4 | 21 | 833 | #7 | 48499 |
| 1654 | 16936 | 68.8 | 64.7 | 14 | 690 | #4 | 48500 |
| 1655 | 16937 | 65.6 | 60.4 | 17 | 259 | #4 | 48501 |
| 1656 | 16938 | 60.0 | 57.1 | 18 | 270 | #2 | 48502 |
| 1657 | 16939 | 50.0 | 50.0 | 12 | 150 | #1 | 48503 |
| 1658 | 16940 | 98.4 | 97.1 | 61 | 2144 | #10 | 48504 |
| 1659 | 16941 | 76.0 | 64.7 | 26 | 519 | #6 | 48505 |
| 1660 | 16942 | 50.0 | 50.0 | 12 | 150 | #1 | 48506 |
| 1661 | 16943 | 77.6 | 72.4 | 31 | 674 | #6 | 48507 |
| 1662 | 16944 | 76.8 | 74.5 | 24 | 1489 | #6 | 48508 |
| 1663 | 16945 | 50.0 | 50.0 | 15 | 156 | #1 | 48509 |
| 1664 | 16946 | 50.0 | 50.0 | 12 | 150 | #1 | 48510 |
| 1665 | 16947 | 66.4 | 62.2 | 15 | 390 | #4 | 48511 |
| 1666 | 16948 | 63.2 | 60.7 | 13 | 319 | #3 | 48512 |
| 1667 | 16949 | 73.6 | 64.4 | 28 | 516 | #5 | 48513 |
| 1668 | 16950 | 64.0 | 58.5 | 14 | 221 | #3 | 48514 |
| 1669 | 16951 | 68.8 | 64.4 | 17 | 618 | #4 | 48515 |
| 1670 | 16952 | 67.2 | 60.4 | 19 | 306 | #4 | 48516 |
| 1671 | 16953 | 50.0 | 50.0 | 12 | 150 | #1 | 48517 |
| 1672 | 16954 | 63.2 | 50.0 | 12 | 225 | #3 | 48518 |
| 1673 | 16955 | 50.0 | 50.0 | 12 | 150 | #1 | 48519 |
| 1674 | 16956 | 50.0 | 50.0 | 12 | 150 | #1 | 48520 |
| 1675 | 16957 | 72.0 | 65.8 | 18 | 531 | #5 | 48521 |
| 1676 | 16958 | 79.2 | 73.1 | 15 | 944 | #6 | 48522 |
| 1677 | 16959 | 50.0 | 50.0 | 12 | 150 | #1 | 48523 |
| 1678 | 16960 | 50.0 | 50.0(160) | 16 | 154 | #1 | 48524 |
| 1679 | 16961 | 74.4 | 66.5 | 19 | 863 | #5 | 48525 |
| 1680 | 16962 | 72.0 | 66.5 | 19 | 481 | #5 | 48526 |
| 1681 | 16963 | 75.2 | 69.5 | 16 | 675 | #6 | 48527 |
| 1682 | 16964 | 71.2 | 50.2 | 21 | 348 | #5 | 48528 |
| 1683 | 16965 | 50.0 | 50.0 | 12 | 150 | #1 | 48529 |
| 1684 | 16966 | 50.0 | 50.0 | 12 | 150 | #1 | 48530 |
| 1685 | 16967 | 74.4 | 65.5 | 21 | 609 | #5 | 48531 |
| 1686 | 16968 | 63.2 | 57.1 | 12 | 233 | #3 | 48532 |
| 1687 | 16969 | 68.8 | 60.0 | 40 | 321 | #4 | 48533 |
| 1688 | 16970 | 76.8 | 72.7 | 19 | 1238 | #6 | 48534 |
| 1689 | 16971 | 70.4 | 65.5 | 18 | 498 | #5 | 48535 |
| 1690 | 16972 | 64.8 | 58.9 | 18 | 261 | #3 | 48536 |
| 1691 | 16973 | 79.2 | 73.5 | 23 | 783 | #6 | 48537 |
| 1692 | 16974 | 62.4 | 56.0 | 16 | 195 | #3 | 48538 |
| 1693 | 16975 | 63.2 | 50.0 | 13 | 248 | #3 | 48539 |
| 1694 | 16976 | 73.6 | 67.3 | 16 | 735 | #5 | 48540 |
| 1695 | 16977 | 66.4 | 54.9 | 15 | 248 | #4 | 48541 |
| 1696 | 16978 | 50.0 | 50.0 | 12 | 150 | #1 | 48542 |
| 1697 | 16979 | 68.0 | 62.2 | 22 | 492 | #4 | 48543 |
| 1698 | 16980 | 64.8 | 61.5 | 14 | 301 | #3 | 48544 |
| 1699 | 16981 | 80.0 | 65.1 | 24 | 517 | #6 | 48545 |
| 1700 | 16982 | 66.4 | 50.0 | 16 | 212 | #4 | 48546 |
| 1701 | 16983 | 79.2 | 77.1 | 18 | 958 | #6 | 48547 |
| 1702 | 16984 | 66.4 | 55.3 | 14 | 332 | #4 | 48548 |
| 1703 | 16985 | 50.0 | 50.0 | 12 | 150 | #1 | 48549 |
| 1704 | 16986 | 67.2 | 50.0 | 16 | 296 | #4 | 48550 |
| 1705 | 16987 | 79.2 | 71.3 | 23 | 626 | #6 | 48551 |
| 1706 | 16988 | 65.6 | 50.5 | 12 | 223 | #4 | 48552 |
| 1707 | 16989 | 50.0 | 50.0 | 12 | 150 | #1 | 48553 |
| 1708 | 16990 | 50.0 | 50.0 | 12 | 150 | #1 | 48554 |
| 1709 | 16991 | 64.8 | 53.5 | 15 | 179 | #3 | 48555 |
| 1710 | 16992 | 69.6 | 62.5 | 21 | 472 | #4 | 48556 |
| 1711 | 16993 | 67.2 | 56.4 | 12 | 316 | #4 | 48557 |
| 1712 | 16994 | 78.4 | 69.8 | 16 | 593 | #6 | 48558 |
| 1713 | 16995 | 69.6 | 58.9 | 15 | 299 | #4 | 48559 |
| 1714 | 16996 | 50.0 | 50.0 | 12 | 150 | #1 | 48560 |
| 1715 | 16997 | 71.2 | 60.0 | 13 | 384 | #5 | 48561 |
| 1716 | 16998 | 79.2 | 73.5 | 19 | 895 | #6 | 48562 |
| 1717 | 16999 | 82.4 | 79.6 | 23 | 1360 | #7 | 48563 |
| 1718 | 17000 | 69.6 | 61.8 | 17 | 522 | #4 | 48564 |
| 1719 | 17001 | 72.8 | 65.8 | 23 | 627 | #5 | 48565 |
| 1720 | 17002 | 64.0 | 58.5 | 17 | 200 | #3 | 48566 |
| 1721 | 17003 | 71.2 | 63.6 | 22 | 459 | #5 | 48567 |
| 1722 | 17004 | 74.4 | 69.5 | 17 | 803 | #5 | 48568 |
| 1723 | 17005 | 64.8 | 57.1 | 12 | 364 | #3 | 48569 |
| 1724 | 17006 | 50.0 | 50.0 | 12 | 150 | #1 | 48570 |
| 1725 | 17007 | 66.4 | 61.1 | 12 | 489 | #4 | 48571 |
| 1726 | 17008 | 77.6 | 70.9 | 18 | 747 | #6 | 48572 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1727 | 17009 | 60.0 | 57.5 | 14 | 169 | #2 | 48573 |
| 1728 | 17010 | 76.8 | 72.4 | 22 | 1050 | #6 | 48574 |
| 1729 | 17011 | 62.4 | 57.5 | 14 | 249 | #3 | 48575 |
| 1730 | 17012 | 74.4 | 66.5 | 15 | 634 | #5 | 48576 |
| 1731 | 17013 | 69.6 | 60.0 | 24 | 265 | #4 | 48577 |
| 1732 | 17014 | 70.4 | 62.2 | 15 | 432 | #5 | 48578 |
| 1733 | 17015 | 65.6 | 61.8 | 15 | 317 | #4 | 48579 |
| 1734 | 17016 | 70.4 | 62.2 | 23 | 349 | #5 | 48580 |
| 1735 | 17017 | 64.8 | 58.9 | 15 | 266 | #3 | 48581 |
| 1736 | 17018 | 76.0 | 70.9 | 15 | 750 | #6 | 48582 |
| 1737 | 17019 | 62.4 | 57.5 | 14 | 188 | #3 | 48583 |
| 1738 | 17020 | 64.0 | 58.2 | 13 | 202 | #3 | 48584 |
| 1739 | 17021 | 65.6 | 57.1 | 17 | 323 | #4 | 48585 |
| 1740 | 17022 | 68.8 | 63.3 | 19 | 343 | #4 | 48586 |
| 1741 | 17023 | 50.0 | 50.0 | 12 | 150 | #1 | 48587 |
| 1742 | 17024 | 63.2 | 50.0 | 12 | 297 | #3 | 48588 |
| 1743 | 17025 | 65.6 | 59.6 | 13 | 244 | #4 | 48589 |
| 1744 | 17026 | 65.6 | 55.3 | 17 | 195 | #4 | 48590 |
| 1745 | 17027 | 73.6 | 66.9 | 17 | 542 | #5 | 48591 |
| 1746 | 17028 | 50.0 | 50.0 | 12 | 150 | #1 | 48592 |
| 1747 | 17029 | 100.0 | 100.0 | 279 | 2478 | #10 | 48593 |
| 1748 | 17030 | 86.4 | 83.6 | 24 | 1024 | #8 | 48594 |
| 1749 | 17031 | 71.2 | 62.5 | 21 | 380 | #5 | 48595 |
| 1750 | 17032 | 63.2 | 58.9 | 12 | 213 | #3 | 48596 |
| 1751 | 17033 | 65.6 | 60.4 | 12 | 347 | #4 | 48597 |
| 1752 | 17034 | 66.4 | 62.2 | 19 | 239 | #4 | 48598 |
| 1753 | 17035 | 65.6 | 65.0(137) | 19 | 231 | #4 | 48599 |
| 1754 | 17036 | 68.0 | 65.1 | 13 | 671 | #4 | 48600 |
| 1755 | 17037 | 50.0 | 50.0 | 12 | 150 | #1 | 48601 |
| 1756 | 17038 | 85.6 | 81.1 | 25 | 1779 | #8 | 48602 |
| 1757 | 17039 | 72.0 | 68.4 | 16 | 697 | #5 | 48603 |
| 1758 | 17040 | 73.6 | 63.3 | 22 | 482 | #5 | 48604 |
| 1759 | 17041 | 62.4 | 50.0 | 12 | 182 | #3 | 48605 |
| 1760 | 17042 | 80.8 | 60.0 | 17 | 499 | #7 | 48606 |
| 1761 | 17043 | 76.0 | 71.3 | 22 | 740 | #6 | 48607 |
| 1762 | 17044 | 84.8 | 60.0 | 24 | 653 | #7 | 48608 |
| 1763 | 17045 | 50.0 | 50.0 | 12 | 150 | #1 | 48609 |
| 1764 | 17046 | 50.0 | 50.0 | 12 | 150 | #1 | 48610 |
| 1765 | 17047 | 69.6 | 59.6 | 15 | 240 | #4 | 48611 |
| 1766 | 17048 | 70.4 | 64.0 | 16 | 495 | #5 | 48612 |
| 1767 | 17049 | 86.4 | 81.3(225) | 30 | 749 | #8 | 48613 |
| 1768 | 17050 | 62.4 | 50.0 | 18 | 191 | #3 | 48614 |
| 1769 | 17051 | 80.8 | 74.5 | 24 | 719 | #7 | 48615 |
| 1770 | 17052 | 50.0 | 50.0 | 12 | 150 | #1 | 48616 |
| 1771 | 17053 | 74.4 | 69.5 | 16 | 734 | #5 | 48617 |
| 1772 | 17054 | 50.0 | 50.0 | 12 | 150 | #1 | 48618 |
| 1773 | 17055 | 61.6 | 50.0 | 17 | 252 | #3 | 48619 |
| 1774 | 17056 | 64.0 | 57.1(163) | 18 | 178 | #3 | 48620 |
| 1775 | 17057 | 82.4 | 71.3 | 19 | 702 | #7 | 48621 |
| 1776 | 17058 | 67.2 | 60.7 | 20 | 334 | #4 | 48622 |
| 1777 | 17059 | 50.0 | 50.0 | 12 | 150 | #1 | 48623 |
| 1778 | 17060 | 62.4 | 57.5 | 14 | 212 | #3 | 48624 |
| 1779 | 17061 | 79.2 | 74.2 | 22 | 745 | #6 | 48625 |
| 1780 | 17062 | 66.4 | 60.7 | 17 | 312 | #4 | 48626 |
| 1781 | 17063 | 74.4 | 67.3 | 15 | 820 | #5 | 48627 |
| 1782 | 17064 | 50.0 | 50.0 | 13 | 150 | #1 | 48628 |
| 1783 | 17065 | 65.6 | 50.9 | 14 | 188 | #4 | 48629 |
| 1784 | 17066 | 63.2 | 58.2 | 15 | 236 | #3 | 48630 |
| 1785 | 17067 | 50.0 | 50.0 | 12 | 150 | #1 | 48631 |
| 1786 | 17068 | 69.6 | 64.0 | 20 | 463 | #4 | 48632 |
| 1787 | 17069 | 69.6 | 59.3 | 15 | 253 | #4 | 48633 |
| 1788 | 17070 | 72.8 | 66.9 | 15 | 784 | #5 | 48634 |
| 1789 | 17071 | 50.0 | 50.0 | 12 | 150 | #1 | 48635 |
| 1790 | 17072 | 57.6 | 50.0 | 14 | 186 | #2 | 48636 |
| 1791 | 17073 | 50.0 | 50.0 | 12 | 150 | #1 | 48637 |
| 1792 | 17074 | 50.0 | 50.0 | 12 | 150 | #1 | 48638 |
| 1793 | 17075 | 50.0 | 50.0 | 12 | 150 | #1 | 48639 |
| 1794 | 17076 | 64.0 | 60.4 | 12 | 329 | #3 | 48640 |
| 1795 | 17077 | 50.0 | 50.0 | 12 | 150 | #1 | 48641 |
| 1796 | 17078 | 79.2 | 75.6 | 21 | 1178 | #6 | 48642 |
| 1797 | 17079 | 63.2 | 57.8 | 15 | 223 | #3 | 48643 |
| 1798 | 17080 | 70.4 | 62.9 | 20 | 325 | #5 | 48644 |
| 1799 | 17081 | 64.8 | 55.6 | 17 | 189 | #3 | 48645 |
| 1800 | 17082 | 68.8 | 61.5 | 18 | 354 | #4 | 48646 |
| 1801 | 17083 | 70.4 | 62.5 | 19 | 398 | #5 | 48647 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1802 | 17084 | 63.2 | 58.2 | 15 | 254 | #3 | 48648 |
| 1803 | 17085 | 72.8 | 66.5 | 18 | 544 | #5 | 48649 |
| 1804 | 17086 | 50.0 | 50.0 | 12 | 150 | #1 | 48650 |
| 1805 | 17087 | 77.6 | 72.0 | 17 | 716 | #6 | 48651 |
| 1806 | 17088 | 64.8 | 58.5 | 19 | 217 | #3 | 48652 |
| 1807 | 17089 | 65.6 | 60.7 | 16 | 315 | #4 | 48653 |
| 1808 | 17090 | 68.8 | 60.0 | 16 | 282 | #4 | 48654 |
| 1809 | 17091 | 69.6 | 64.0 | 22 | 437 | #4 | 48655 |
| 1810 | 17092 | 71.2 | 66.5 | 18 | 580 | #5 | 48656 |
| 1811 | 17093 | 50.0 | 50.0 | 12 | 150 | #1 | 48657 |
| 1812 | 17094 | 71.2 | 50.2 | 18 | 335 | #5 | 48658 |
| 1813 | 17095 | 66.4 | 62.2 | 14 | 357 | #4 | 48659 |
| 1814 | 17096 | 70.4 | 50.0 | 13 | 307 | #5 | 48660 |
| 1815 | 17097 | 71.2 | 66.2 | 21 | 680 | #5 | 48661 |
| 1816 | 17098 | 67.2 | 59.3 | 16 | 288 | #4 | 48662 |
| 1817 | 17099 | 74.4 | 68.6(220) | 16 | 426 | #5 | 48663 |
| 1818 | 17100 | 69.6 | 58.9 | 18 | 324 | #4 | 48664 |
| 1819 | 17101 | 68.8 | 59.6 | 17 | 304 | #4 | 48665 |
| 1820 | 17102 | 81.6 | 76.4 | 21 | 972 | #7 | 48666 |
| 1821 | 17103 | 62.4 | 56.4 | 13 | 227 | #3 | 48667 |
| 1822 | 17104 | 65.6 | 58.5 | 13 | 304 | #4 | 48668 |
| 1823 | 17105 | 64.0 | 59.6 | 16 | 260 | #3 | 48669 |
| 1824 | 17106 | 76.8 | 59.3 | 21 | 534 | #6 | 48670 |
| 1825 | 17107 | 52.8 | 50.0 | 13 | 156 | #1 | 48671 |
| 1826 | 17108 | 64.0 | 58.2 | 12 | 272 | #3 | 48672 |
| 1827 | 17109 | 65.6 | 61.8 | 15 | 422 | #4 | 48673 |
| 1828 | 17110 | 67.2 | 60.7 | 21 | 244 | #4 | 48674 |
| 1829 | 17111 | 64.8 | 58.5 | 17 | 309 | #3 | 48675 |
| 1830 | 17112 | 64.8 | 57.8 | 18 | 202 | #3 | 48676 |
| 1831 | 17113 | 74.4 | 61.1 | 16 | 393 | #5 | 48677 |
| 1832 | 17114 | 60.0 | 54.9 | 12 | 245 | #2 | 48678 |
| 1833 | 17115 | 50.0 | 50.0 | 12 | 150 | #1 | 48679 |
| 1834 | 17116 | 62.4 | 54.9 | 15 | 205 | #3 | 48680 |
| 1835 | 17117 | 61.6 | 50.0 | 12 | 150 | #3 | 48681 |
| 1836 | 17118 | 61.6 | 57.8 | 13 | 196 | #3 | 48682 |
| 1837 | 17119 | 68.8 | 65.8 | 20 | 464 | #4 | 48683 |
| 1838 | 17120 | 81.6 | 50.0 | 20 | 418 | #7 | 48684 |
| 1839 | 17121 | 68.0 | 60.4 | 23 | 271 | #4 | 48685 |
| 1840 | 17122 | 65.6 | 50.0 | 13 | 190 | #4 | 48686 |
| 1841 | 17123 | 66.4 | 50.0 | 12 | 220 | #4 | 48687 |
| 1842 | 17124 | 66.4 | 59.3 | 13 | 328 | #4 | 48688 |
| 1843 | 17125 | 72.8 | 70.2 | 17 | 683 | #5 | 48689 |
| 1844 | 17126 | 65.6 | 58.2 | 19 | 221 | #4 | 48690 |
| 1845 | 17127 | 70.4 | 60.0 | 17 | 296 | #5 | 48691 |
| 1846 | 17128 | 75.2 | 74.8(159) | 15 | 398 | #6 | 48692 |
| 1847 | 17129 | 85.6 | 82.2 | 27 | 1301 | #8 | 48693 |
| 1848 | 17130 | 69.6 | 62.9 | 16 | 442 | #4 | 48694 |
| 1849 | 17131 | 74.4 | 69.5 | 24 | 708 | #5 | 48695 |
| 1850 | 17132 | 65.6 | 59.6 | 15 | 272 | #4 | 48696 |
| 1851 | 17133 | 67.2 | 63.3 | 21 | 314 | #4 | 48697 |
| 1852 | 17134 | 72.0 | 66.5 | 15 | 624 | #5 | 48698 |
| 1853 | 17135 | 84.0 | 80.7 | 25 | 930 | #7 | 48699 |
| 1854 | 17136 | 75.2 | 64.7 | 18 | 454 | #6 | 48700 |
| 1855 | 17137 | 61.6 | 50.0 | 13 | 189 | #3 | 48701 |
| 1856 | 17138 | 63.2 | 60.0 | 15 | 207 | #3 | 48702 |
| 1857 | 17139 | 63.2 | 52.7 | 12 | 194 | #3 | 48703 |
| 1858 | 17140 | 50.0 | 50.0 | 12 | 150 | #1 | 48704 |
| 1859 | 17141 | 86.4 | 65.1 | 18 | 609 | #8 | 48705 |
| 1860 | 17142 | 69.6 | 61.8 | 15 | 359 | #4 | 48706 |
| 1861 | 17143 | 70.4 | 61.5 | 21 | 343 | #5 | 48707 |
| 1862 | 17144 | 63.2 | 58.9 | 21 | 221 | #3 | 48708 |
| 1863 | 17145 | 50.0 | 50.0 | 12 | 150 | #1 | 48709 |
| 1864 | 17146 | 68.8 | 65.1 | 16 | 555 | #4 | 48710 |
| 1865 | 17147 | 74.4 | 69.8 | 15 | 624 | #5 | 48711 |
| 1866 | 17148 | 74.4 | 70.9 | 18 | 625 | #5 | 48712 |
| 1867 | 17149 | 84.8 | 80.0 | 16 | 1907 | #7 | 48713 |
| 1868 | 17150 | 84.8 | 74.9 | 30 | 1165 | #7 | 48714 |
| 1869 | 17151 | 63.2 | 50.0 | 13 | 182 | #3 | 48715 |
| 1870 | 17152 | 61.6 | 58.5 | 17 | 209 | #3 | 48716 |
| 1871 | 17153 | 50.0 | 50.0 | 12 | 150 | #1 | 48717 |
| 1872 | 17154 | 62.4 | 50.5 | 12 | 199 | #3 | 48718 |
| 1873 | 17155 | 65.6 | 59.6 | 15 | 288 | #4 | 48719 |
| 1874 | 17156 | 80.0 | 76.0 | 22 | 815 | #6 | 48720 |
| 1875 | 17157 | 64.0 | 50.0 | 14 | 239 | #3 | 48721 |
| 1876 | 17158 | 50.0 | 50.0 | 12 | 150 | #1 | 48722 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1877 | 17159 | 90.4 | 82.5 | 24 | 1715 | #9 | 48723 |
| 1878 | 17160 | 70.4 | 65.8 | 18 | 556 | #5 | 48724 |
| 1879 | 17161 | 71.2 | 65.1 | 17 | 492 | #5 | 48725 |
| 1880 | 17162 | 74.4 | 68.4 | 21 | 668 | #5 | 48726 |
| 1881 | 17163 | 69.6 | 64.0 | 17 | 408 | #4 | 48727 |
| 1882 | 17164 | 78.4 | 71.6 | 29 | 816 | #6 | 48728 |
| 1883 | 17165 | 88.0 | 60.7 | 23 | 565 | #8 | 48729 |
| 1884 | 17166 | 68.8 | 66.2(210) | 17 | 406 | #4 | 48730 |
| 1885 | 17167 | 67.2 | 62.9 | 18 | 613 | #4 | 48731 |
| 1886 | 17168 | 50.0 | 50.0 | 12 | 150 | #1 | 48732 |
| 1887 | 17169 | 50.0 | 50.0 | 12 | 150 | #1 | 48733 |
| 1888 | 17170 | 61.6 | 50.0 | 12 | 184 | #3 | 48734 |
| 1889 | 17171 | 68.8 | 64.0 | 19 | 422 | #4 | 48735 |
| 1890 | 17172 | 73.6 | 68.0 | 17 | 721 | #5 | 48736 |
| 1891 | 17173 | 71.2 | 66.2 | 19 | 453 | #5 | 48737 |
| 1892 | 17174 | 59.2 | 56.4 | 12 | 223 | #2 | 48738 |
| 1893 | 17175 | 65.6 | 59.3 | 12 | 296 | #4 | 48739 |
| 1894 | 17176 | 68.0 | 65.8 | 19 | 648 | #4 | 48740 |
| 1895 | 17177 | 67.2 | 50.9 | 13 | 233 | #4 | 48741 |
| 1896 | 17178 | 74.4 | 68.4 | 22 | 581 | #5 | 48742 |
| 1897 | 17179 | 74.4 | 62.2 | 15 | 347 | #5 | 48743 |
| 1898 | 17180 | 70.4 | 50.0 | 15 | 341 | #5 | 48744 |
| 1899 | 17181 | 76.8 | 67.3 | 19 | 574 | #6 | 48745 |
| 1900 | 17182 | 60.0 | 50.0 | 12 | 158 | #2 | 48746 |
| 1901 | 17183 | 77.6 | 75.6 | 24 | 860 | #6 | 48747 |
| 1902 | 17184 | 55.2 | 50.0 | 13 | 181 | #2 | 48748 |
| 1903 | 17185 | 50.0 | 50.0 | 12 | 150 | #1 | 48749 |
| 1904 | 17186 | 68.0 | 60.7 | 21 | 258 | #4 | 48750 |
| 1905 | 17187 | 69.6 | 53.1 | 15 | 318 | #4 | 48751 |
| 1906 | 17188 | 65.6 | 61.5(182) | 13 | 264 | #4 | 48752 |
| 1907 | 17189 | 98.4 | 97.5 | 87 | 2119 | #10 | 48753 |
| 1908 | 17190 | 63.2 | 58.2 | 13 | 336 | #3 | 48754 |
| 1909 | 17191 | 50.0 | 50.0 | 12 | 150 | #1 | 48755 |
| 1910 | 17192 | 64.0 | 57.5 | 21 | 278 | #3 | 48756 |
| 1911 | 17193 | 57.6 | 50.0 | 12 | 150 | #2 | 48757 |
| 1912 | 17194 | 67.2 | 61.1 | 20 | 331 | #4 | 48758 |
| 1913 | 17195 | 64.8 | 55.6 | 15 | 263 | #3 | 48759 |
| 1914 | 17196 | 50.0 | 50.0 | 12 | 150 | #1 | 48760 |
| 1915 | 17197 | 64.8 | 59.6 | 19 | 274 | #3 | 48761 |
| 1916 | 17198 | 50.0 | 50.0 | 12 | 150 | #1 | 48762 |
| 1917 | 17199 | 50.0 | 50.0 | 12 | 150 | #1 | 48763 |
| 1918 | 17200 | 62.4 | 58.2 | 13 | 207 | #3 | 48764 |
| 1919 | 17201 | 64.8 | 50.0 | 17 | 249 | #3 | 48765 |
| 1920 | 17202 | 69.6 | 67.1(252) | 15 | 454 | #4 | 48766 |
| 1921 | 17203 | 50.0 | 50.0 | 12 | 150 | #1 | 48767 |
| 1922 | 17204 | 50.0 | 50.0 | 12 | 150 | #1 | 48768 |
| 1923 | 17205 | 68.8 | 66.2 | 12 | 652 | #4 | 48769 |
| 1924 | 17206 | 75.2 | 62.9 | 21 | 399 | #6 | 48770 |
| 1925 | 17207 | 82.4 | 61.8 | 17 | 588 | #7 | 48771 |
| 1926 | 17208 | 64.8 | 58.5 | 14 | 305 | #3 | 48772 |
| 1927 | 17209 | 90.4 | 80.2(167) | 31 | 511 | #9 | 48773 |
| 1928 | 17210 | 73.6 | 64.4 | 21 | 470 | #5 | 48774 |
| 1929 | 17211 | 70.4 | 65.7(143) | 18 | 298 | #5 | 48775 |
| 1930 | 17212 | 79.2 | 76.0 | 23 | 940 | #6 | 48776 |
| 1931 | 17213 | 72.8 | 64.0 | 22 | 407 | #5 | 48777 |
| 1932 | 17214 | 72.0 | 64.4 | 20 | 339 | #5 | 48778 |
| 1933 | 17215 | 68.0 | 63.6 | 15 | 421 | #4 | 48779 |
| 1934 | 17216 | 64.0 | 62.7(158) | 13 | 246 | #3 | 48780 |
| 1935 | 17217 | 63.2 | 58.2 | 14 | 192 | #3 | 48781 |
| 1936 | 17218 | 75.2 | 55.6 | 16 | 455 | #6 | 48782 |
| 1937 | 17219 | 77.5(120) | — | 17 | 357 | #6 | 48783 |
| 1938 | 17220 | 50.0 | 50.0 | 12 | 150 | #1 | 48784 |
| 1939 | 17221 | 50.0 | 50.0 | 16 | 158 | #1 | 48785 |
| 1940 | 17222 | 76.8 | 70.5 | 16 | 1420 | #6 | 48786 |
| 1941 | 17223 | 72.0 | 65.5 | 17 | 583 | #5 | 48787 |
| 1942 | 17224 | 50.0 | 50.0 | 12 | 150 | #1 | 48788 |
| 1943 | 17225 | 69.6 | 66.5 | 15 | 475 | #4 | 48789 |
| 1944 | 17226 | 53.6 | 50.0(136) | 17 | 150 | #1 | 48790 |
| 1945 | 17227 | 81.6 | 73.5 | 18 | 1076 | #7 | 48791 |
| 1946 | 17228 | 71.2 | 66.2 | 27 | 752 | #5 | 48792 |
| 1947 | 17229 | 50.0 | 50.0 | 12 | 150 | #1 | 48793 |
| 1948 | 17230 | 65.6 | 60.4 | 14 | 272 | #4 | 48794 |
| 1949 | 17231 | 72.8 | 64.0 | 22 | 428 | #5 | 48795 |
| 1950 | 17232 | 90.4 | 85.1 | 24 | 1002 | #9 | 48796 |
| 1951 | 17233 | 70.4 | 64.7 | 15 | 477 | #5 | 48797 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 1952 | 17234 | 75.2 | 69.5 | 19 | 991 | #6 | 48798 |
| 1953 | 17235 | 68.8 | 63.6 | 15 | 379 | #4 | 48799 |
| 1954 | 17236 | 64.0 | 60.7(252) | 18 | 211 | #3 | 48800 |
| 1955 | 17237 | 69.6 | 62.9 | 17 | 302 | #4 | 48801 |
| 1956 | 17238 | 67.2 | 62.2 | 19 | 379 | #4 | 48802 |
| 1957 | 17239 | 50.0 | 50.0 | 12 | 150 | #1 | 48803 |
| 1958 | 17240 | 61.6 | 50.0 | 15 | 157 | #3 | 48804 |
| 1959 | 17241 | 66.4 | 50.0 | 17 | 240 | #4 | 48805 |
| 1960 | 17242 | 80.0 | 76.3(215) | 27 | 591 | #6 | 48806 |
| 1961 | 17243 | 63.2 | 51.8(166) | 15 | 153 | #3 | 48807 |
| 1962 | 17244 | 70.4 | 68.0 | 20 | 1336 | #5 | 48808 |
| 1963 | 17245 | 60.0 | 50.0 | 31 | 183 | #2 | 48809 |
| 1964 | 17246 | 64.8 | 58.5 | 15 | 245 | #3 | 48810 |
| 1965 | 17247 | 64.8 | 59.6 | 15 | 218 | #3 | 48811 |
| 1966 | 17248 | 71.2 | 59.6 | 18 | 500 | #5 | 48812 |
| 1967 | 17249 | 66.4 | 58.9 | 18 | 326 | #4 | 48813 |
| 1968 | 17250 | 57.6 | 54.9 | 12 | 189 | #2 | 48814 |
| 1969 | 17251 | 60.8 | 50.0(209) | 12 | 157 | #3 | 48815 |
| 1970 | 17252 | 60.0 | 58.2 | 18 | 197 | #2 | 48816 |
| 1971 | 17253 | 87.2 | 80.1(226) | 21 | 789 | #8 | 48817 |
| 1972 | 17254 | 61.6 | 55.3 | 14 | 227 | #3 | 48818 |
| 1973 | 17255 | 72.8 | 67.3 | 16 | 675 | #5 | 48819 |
| 1974 | 17256 | 83.2 | 78.9 | 22 | 1715 | #7 | 48820 |
| 1975 | 17257 | 84.0 | 65.1 | 24 | 478 | #7 | 48821 |
| 1976 | 17258 | 84.8 | 60.7 | 17 | 662 | #7 | 48822 |
| 1977 | 17259 | 62.4 | 57.8(251) | 14 | 170 | #3 | 48823 |
| 1978 | 17260 | 72.8 | 66.2 | 18 | 486 | #5 | 48824 |
| 1979 | 17261 | 68.0 | 65.5 | 12 | 449 | #4 | 48825 |
| 1980 | 17262 | 50.0 | 50.0 | 12 | 150 | #1 | 48826 |
| 1981 | 17263 | 75.2 | 53.5 | 18 | 379 | #6 | 48827 |
| 1982 | 17264 | 75.2 | 50.0 | 16 | 370 | #6 | 48828 |
| 1983 | 17265 | 64.0 | 60.7 | 16 | 438 | #3 | 48829 |
| 1984 | 17266 | 66.4 | 54.9 | 15 | 214 | #4 | 48830 |
| 1985 | 17267 | 65.6 | 61.5 | 16 | 256 | #4 | 48831 |
| 1986 | 17268 | 50.0 | 50.0 | 12 | 150 | #1 | 48832 |
| 1987 | 17269 | 82.4 | 72.4 | 30 | 689 | #7 | 48833 |
| 1988 | 17270 | 64.0 | 59.3 | 18 | 251 | #3 | 48834 |
| 1989 | 17271 | 50.0 | 50.0 | 12 | 150 | #1 | 48835 |
| 1990 | 17272 | 67.2 | 61.1 | 18 | 312 | #4 | 48836 |
| 1991 | 17273 | 86.4 | 82.2 | 33 | 2027 | #8 | 48837 |
| 1992 | 17274 | 75.2 | 68.0 | 27 | 638 | #6 | 48838 |
| 1993 | 17275 | 75.2 | 70.9 | 19 | 711 | #6 | 48839 |
| 1994 | 17276 | 68.0 | 59.7(236) | 22 | 199 | #4 | 48840 |
| 1995 | 17277 | 68.0 | 65.1 | 17 | 716 | #4 | 48841 |
| 1996 | 17278 | 72.8 | 68.4 | 16 | 766 | #5 | 48842 |
| 1997 | 17279 | 70.4 | 66.2 | 18 | 860 | #5 | 48843 |
| 1998 | 17280 | 68.0 | 53.5 | 20 | 261 | #4 | 48844 |
| 1999 | 17281 | 72.8 | 65.5 | 16 | 607 | #5 | 48845 |
| 2000 | 17282 | 50.0 | 50.0 | 12 | 150 | #1 | 48846 |
| 2001 | 17283 | 68.8 | 66.5 | 18 | 821 | #4 | 48847 |
| 2002 | 17284 | 79.2 | 67.3 | 23 | 491 | #6 | 48848 |
| 2003 | 17285 | 55.2 | 50.0 | 38 | 311 | #2 | 48849 |
| 2004 | 17286 | 62.4 | 59.6 | 12 | 209 | #3 | 48850 |
| 2005 | 17287 | 75.2 | 69.5 | 23 | 634 | #6 | 48851 |
| 2006 | 17288 | 72.8 | 66.2 | 18 | 828 | #5 | 48852 |
| 2007 | 17289 | 50.0 | 50.0 | 12 | 150 | #1 | 48853 |
| 2008 | 17290 | 62.4 | 58.2 | 12 | 211 | #3 | 48854 |
| 2009 | 17291 | 63.2 | 57.5 | 16 | 203 | #3 | 48855 |
| 2010 | 17292 | 58.4 | 50.0(241) | 14 | 167 | #2 | 48856 |
| 2011 | 17293 | 60.8 | 50.0 | 13 | 226 | #3 | 48857 |
| 2012 | 17294 | 66.4 | 58.9 | 15 | 241 | #4 | 48858 |
| 2013 | 17295 | 66.4 | 58.5 | 16 | 215 | #4 | 48859 |
| 2014 | 17296 | 66.4 | 60.4 | 21 | 233 | #4 | 48860 |
| 2015 | 17297 | 62.4 | 53.8 | 16 | 164 | #3 | 48861 |
| 2016 | 17298 | 69.6 | 64.0 | 18 | 335 | #4 | 48862 |
| 2017 | 17299 | 63.2 | 60.0 | 12 | 226 | #3 | 48863 |
| 2018 | 17300 | 64.0 | 61.5 | 14 | 380 | #3 | 48864 |
| 2019 | 17301 | 62.4 | 57.1 | 13 | 216 | #3 | 48865 |
| 2020 | 17302 | 67.2 | 60.0 | 18 | 251 | #4 | 48866 |
| 2021 | 17303 | 74.4 | 60.4 | 18 | 388 | #5 | 48867 |
| 2022 | 17304 | 77.6 | 68.0 | 24 | 844 | #6 | 48868 |
| 2023 | 17305 | 50.0 | 50.0 | 12 | 150 | #1 | 48869 |
| 2024 | 17306 | 68.0 | 62.9 | 18 | 407 | #4 | 48870 |
| 2025 | 17307 | 85.6 | 82.2(185) | 27 | 636 | #8 | 48871 |
| 2026 | 17308 | 51.2 | 50.0 | 13 | 150 | #1 | 48872 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2027 | 17309 | 76.0 | 66.5 | 18 | 548 | #6 | 48873 |
| 2028 | 17310 | 73.6 | 72.0 | 39 | 862 | #5 | 48874 |
| 2029 | 17311 | 50.0 | 50.0 | 12 | 150 | #1 | 48875 |
| 2030 | 17312 | 83.2 | 76.4 | 19 | 898 | #7 | 48876 |
| 2031 | 17313 | 75.2 | 67.6 | 24 | 587 | #6 | 48877 |
| 2032 | 17314 | 72.0 | 66.9 | 15 | 601 | #5 | 48878 |
| 2033 | 17315 | 62.4 | 50.0 | 12 | 181 | #3 | 48879 |
| 2034 | 17316 | 72.0 | 50.0 | 12 | 337 | #5 | 48880 |
| 2035 | 17317 | 71.2 | 62.2 | 23 | 379 | #5 | 48881 |
| 2036 | 17318 | 65.6 | 50.0 | 13 | 190 | #4 | 48882 |
| 2037 | 17319 | 66.4 | 60.0 | 17 | 318 | #4 | 48883 |
| 2038 | 17320 | 66.4 | 61.5 | 23 | 259 | #4 | 48884 |
| 2039 | 17321 | 50.0 | 50.0 | 12 | 150 | #1 | 48885 |
| 2040 | 17322 | 50.0 | 50.0 | 12 | 150 | #1 | 48886 |
| 2041 | 17323 | 100.0 | 99.3 | 157 | 1893 | #10 | 48887 |
| 2042 | 17324 | 72.0 | 68.0 | 15 | 636 | #5 | 48888 |
| 2043 | 17325 | 50.0 | 50.0 | 12 | 150 | #1 | 48889 |
| 2044 | 17326 | 50.0 | 50.0 | 12 | 150 | #1 | 48890 |
| 2045 | 17327 | 63.2 | 58.2 | 12 | 211 | #3 | 48891 |
| 2046 | 17328 | 73.6 | 72.5(149) | 24 | 351 | #5 | 48892 |
| 2047 | 17329 | 62.4 | 50.0 | 15 | 180 | #3 | 48893 |
| 2048 | 17330 | 60.8 | 58.2 | 12 | 295 | #3 | 48894 |
| 2049 | 17331 | 76.8 | 74.5 | 15 | 1011 | #6 | 48895 |
| 2050 | 17332 | 71.2 | 67.3 | 13 | 636 | #5 | 48896 |
| 2051 | 17333 | 50.0 | 50.0 | 12 | 150 | #1 | 48897 |
| 2052 | 17334 | 67.2 | 59.6 | 16 | 237 | #4 | 48898 |
| 2053 | 17335 | 63.2 | 50.0 | 15 | 198 | #3 | 48899 |
| 2054 | 17336 | 67.2 | 62.2 | 20 | 291 | #4 | 48900 |
| 2055 | 17337 | 75.2 | 75.4(175) | 17 | 488 | #6 | 48901 |
| 2056 | 17338 | 63.2 | 54.5 | 14 | 194 | #3 | 48902 |
| 2057 | 17339 | 71.2 | 64.7 | 19 | 438 | #5 | 48903 |
| 2058 | 17340 | 72.8 | 60.4 | 20 | 327 | #5 | 48904 |
| 2059 | 17341 | 68.8 | 60.0 | 20 | 337 | #4 | 48905 |
| 2060 | 17342 | 68.8 | 57.5 | 15 | 259 | #4 | 48906 |
| 2061 | 17343 | 50.0 | 50.0 | 12 | 150 | #1 | 48907 |
| 2062 | 17344 | 75.2 | 65.1(261) | 19 | 526 | #6 | 48908 |
| 2063 | 17345 | 68.8 | 61.5 | 16 | 695 | #4 | 48909 |
| 2064 | 17346 | 50.0 | 50.0 | 12 | 150 | #1 | 48910 |
| 2065 | 17347 | 50.0 | 50.0 | 12 | 150 | #1 | 48911 |
| 2066 | 17348 | 64.0 | 50.0 | 12 | 188 | #3 | 48912 |
| 2067 | 17349 | 62.4 | 52.0 | 12 | 187 | #3 | 48913 |
| 2068 | 17350 | 63.2 | 50.0 | 36 | 195 | #3 | 48914 |
| 2069 | 17351 | 60.8 | 58.2 | 15 | 219 | #3 | 48915 |
| 2070 | 17352 | 50.0 | 50.0 | 12 | 150 | #1 | 48916 |
| 2071 | 17353 | 50.0 | 50.0 | 12 | 150 | #1 | 48917 |
| 2072 | 17354 | 61.6 | 59.3 | 12 | 318 | #3 | 48918 |
| 2073 | 17355 | 70.4 | 50.0(233) | 25 | 296 | #5 | 48919 |
| 2074 | 17356 | 72.0 | 62.9 | 16 | 425 | #5 | 48920 |
| 2075 | 17357 | 84.0 | 65.8 | 30 | 463 | #7 | 48921 |
| 2076 | 17358 | 76.0 | 62.9 | 18 | 418 | #6 | 48922 |
| 2077 | 17359 | 80.0 | 70.9 | 13 | 772 | #6 | 48923 |
| 2078 | 17360 | 50.0 | 50.0 | 12 | 150 | #1 | 48924 |
| 2079 | 17361 | 76.8 | 73.1 | 17 | 1183 | #6 | 48925 |
| 2080 | 17362 | 70.4 | 65.8 | 23 | 713 | #5 | 48926 |
| 2081 | 17363 | 64.8 | 50.0 | 13 | 253 | #3 | 48927 |
| 2082 | 17364 | 63.2 | 57.8 | 14 | 195 | #3 | 48928 |
| 2083 | 17365 | 50.0 | 50.0 | 12 | 150 | #1 | 48929 |
| 2084 | 17366 | 50.0 | 50.0 | 12 | 150 | #1 | 48930 |
| 2085 | 17367 | 50.0 | 50.0 | 12 | 150 | #1 | 48931 |
| 2086 | 17368 | 50.0 | 50.0 | 17 | 151 | #1 | 48932 |
| 2087 | 17369 | 50.0 | 50.0 | 12 | 150 | #1 | 48933 |
| 2088 | 17370 | 74.4 | 62.5 | 26 | 523 | #5 | 48934 |
| 2089 | 17371 | 71.2 | 65.8 | 18 | 1181 | #5 | 48935 |
| 2090 | 17372 | 67.2 | 50.0 | 16 | 233 | #4 | 48936 |
| 2091 | 17373 | 50.0 | 50.0 | 12 | 150 | #1 | 48937 |
| 2092 | 17374 | 62.4 | 50.0 | 12 | 205 | #3 | 48938 |
| 2093 | 17375 | 64.8 | 57.8(223) | 15 | 167 | #3 | 48939 |
| 2094 | 17376 | 67.2 | 59.3 | 15 | 234 | #4 | 48940 |
| 2095 | 17377 | 73.6 | 59.9(252) | 18 | 417 | #5 | 48941 |
| 2096 | 17378 | 69.6 | 54.9 | 16 | 270 | #4 | 48942 |
| 2097 | 17379 | 64.0 | 50.0(194) | 18 | 312 | #3 | 48943 |
| 2098 | 17380 | 50.0 | 50.0 | 12 | 150 | #1 | 48944 |
| 2099 | 17381 | 62.4 | 57.1 | 12 | 173 | #3 | 48945 |
| 2100 | 17382 | 67.2 | 59.3 | 17 | 242 | #4 | 48946 |
| 2101 | 17383 | 76.0 | 64.7 | 16 | 607 | #6 | 48947 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2102 | 17384 | 50.0 | 50.0 | 12 | 150 | #1 | 48948 |
| 2103 | 17385 | 81.6 | 77.5 | 23 | 1881 | #7 | 48949 |
| 2104 | 17386 | 76.8 | 68.7 | 23 | 870 | #6 | 48950 |
| 2105 | 17387 | 61.6 | 57.5 | 14 | 231 | #3 | 48951 |
| 2106 | 17388 | 63.2 | 57.8 | 14 | 215 | #3 | 48952 |
| 2107 | 17389 | 68.0 | 61.8 | 19 | 376 | #4 | 48953 |
| 2108 | 17390 | 50.0 | 50.0 | 12 | 150 | #1 | 48954 |
| 2109 | 17391 | 74.4 | 68.0 | 18 | 623 | #5 | 48955 |
| 2110 | 17392 | 50.0 | 50.0 | 12 | 150 | #1 | 48956 |
| 2111 | 17393 | 80.0 | 74.5 | 24 | 873 | #6 | 48957 |
| 2112 | 17394 | 81.6 | 77.5 | 27 | 1207 | #7 | 48958 |
| 2113 | 17395 | 62.4 | 57.8 | 18 | 203 | #3 | 48959 |
| 2114 | 17396 | 68.8 | 62.9 | 21 | 385 | #4 | 48960 |
| 2115 | 17397 | 79.2 | 71.3 | 32 | 727 | #6 | 48961 |
| 2116 | 17398 | 69.6 | 65.1 | 15 | 434 | #4 | 48962 |
| 2117 | 17399 | 65.6 | 50.0 | 18 | 189 | #4 | 48963 |
| 2118 | 17400 | 71.2 | 61.5 | 21 | 442 | #5 | 48964 |
| 2119 | 17401 | 67.2 | 60.4 | 21 | 288 | #4 | 48965 |
| 2120 | 17402 | 81.6 | 74.5 | 24 | 1038 | #7 | 48966 |
| 2121 | 17403 | 50.0 | 50.0 | 12 | 150 | #1 | 48967 |
| 2122 | 17404 | 50.0 | 50.0 | 12 | 150 | #1 | 48968 |
| 2123 | 17405 | 50.0 | 50.0 | 12 | 150 | #1 | 48969 |
| 2124 | 17406 | 72.8 | 65.8 | 21 | 602 | #5 | 48970 |
| 2125 | 17407 | 55.2 | 50.0 | 13 | 193 | #2 | 48971 |
| 2126 | 17408 | 78.4 | 73.5 | 21 | 959 | #6 | 48972 |
| 2127 | 17409 | 67.2 | 58.9 | 15 | 229 | #4 | 48973 |
| 2128 | 17410 | 64.0 | 50.0 | 13 | 205 | #3 | 48974 |
| 2129 | 17411 | 68.0 | 60.7 | 28 | 336 | #4 | 48975 |
| 2130 | 17412 | 65.6 | 60.0 | 15 | 304 | #4 | 48976 |
| 2131 | 17413 | 72.8 | 66.9 | 17 | 459 | #5 | 48977 |
| 2132 | 17414 | 77.6 | 72.7 | 18 | 854 | #6 | 48978 |
| 2133 | 17415 | 72.8 | 66.9 | 20 | 973 | #5 | 48979 |
| 2134 | 17416 | 50.0 | 50.0 | 12 | 150 | #1 | 48980 |
| 2135 | 17417 | 75.2 | 55.3 | 18 | 408 | #6 | 48981 |
| 2136 | 17418 | 64.8 | 50.0 | 12 | 167 | #3 | 48982 |
| 2137 | 17419 | 71.2 | 64.0 | 21 | 550 | #5 | 48983 |
| 2138 | 17420 | 62.4 | 58.5 | 13 | 257 | #3 | 48984 |
| 2139 | 17421 | 72.0 | 64.7 | 18 | 393 | #5 | 48985 |
| 2140 | 17422 | 73.6 | 69.1 | 21 | 845 | #5 | 48986 |
| 2141 | 17423 | 66.4 | 58.2 | 18 | 246 | #4 | 48987 |
| 2142 | 17424 | 64.0 | 51.3 | 14 | 183 | #3 | 48988 |
| 2143 | 17425 | 71.2 | 61.8 | 16 | 432 | #5 | 48989 |
| 2144 | 17426 | 60.8 | 55.6 | 14 | 274 | #3 | 48990 |
| 2145 | 17427 | 78.4 | 71.6 | 29 | 673 | #6 | 48991 |
| 2146 | 17428 | 75.2 | 50.0 | 20 | 367 | #6 | 48992 |
| 2147 | 17429 | 72.0 | 68.0 | 20 | 778 | #5 | 48993 |
| 2148 | 17430 | 68.8 | 57.5 | 17 | 283 | #4 | 48994 |
| 2149 | 17431 | 78.4 | 76.7 | 16 | 778 | #6 | 48995 |
| 2150 | 17432 | 69.6 | 64.0 | 18 | 524 | #4 | 48996 |
| 2151 | 17433 | 66.4 | 61.1 | 13 | 405 | #4 | 48997 |
| 2152 | 17434 | 50.0 | 50.0 | 12 | 150 | #1 | 48998 |
| 2153 | 17435 | 50.0 | 50.0 | 12 | 150 | #1 | 48999 |
| 2154 | 17436 | 50.0 | 50.0 | 12 | 150 | #1 | 49000 |
| 2155 | 17437 | 76.0 | 75.4 (138) | 20 | 354 | #6 | 49001 |
| 2156 | 17438 | 50.0 | 50.0 | 12 | 150 | #1 | 49002 |
| 2157 | 17439 | 72.8 | 63.3 | 16 | 779 | #5 | 49003 |
| 2158 | 17440 | 57.6 | 56.0 | 13 | 251 | #2 | 49004 |
| 2159 | 17441 | 50.0 | 50.0 | 12 | 150 | #1 | 49005 |
| 2160 | 17442 | 68.8 | 59.6 | 19 | 229 | #4 | 49006 |
| 2161 | 17443 | 67.2 | 55.3 | 18 | 227 | #4 | 49007 |
| 2162 | 17444 | 76.8 | 70.5 | 21 | 896 | #6 | 49008 |
| 2163 | 17445 | 50.0 | 50.0 | 12 | 150 | #1 | 49009 |
| 2164 | 17446 | 64.8 | 55.3 | 15 | 210 | #3 | 49010 |
| 2165 | 17447 | 76.0 | 55.3 | 19 | 430 | #6 | 49011 |
| 2166 | 17448 | 64.0 | 50.9 | 13 | 192 | #3 | 49012 |
| 2167 | 17449 | 62.4 | 50.0 | 14 | 150 | #3 | 49013 |
| 2168 | 17450 | 73.6 | 58.5 | 15 | 428 | #5 | 49014 |
| 2169 | 17451 | 72.8 | 65.5 | 14 | 534 | #5 | 49015 |
| 2170 | 17452 | 69.6 | 62.9 | 18 | 541 | #4 | 49016 |
| 2171 | 17453 | 50.0 | 50.0 | 12 | 150 | #1 | 49017 |
| 2172 | 17454 | 62.4 | 50.0 | 12 | 178 | #3 | 49018 |
| 2173 | 17455 | 62.4 | 50.0 | 13 | 202 | #3 | 49019 |
| 2174 | 17456 | 74.4 | 67.6 | 18 | 849 | #5 | 49020 |
| 2175 | 17457 | 79.2 | 75.3 | 17 | 891 | #6 | 49021 |
| 2176 | 17458 | 67.2 | 59.6 | 19 | 408 | #4 | 49022 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2177 | 17459 | 50.0 | 50.0 | 12 | 150 | #1 | 49023 |
| 2178 | 17460 | 66.4 | 60.7 | 17 | 251 | #4 | 49024 |
| 2179 | 17461 | 72.0 | 68.0 | 25 | 672 | #5 | 49025 |
| 2180 | 17462 | 60.0 | 57.1 | 15 | 180 | #2 | 49026 |
| 2181 | 17463 | 50.0 | 50.0 | 12 | 150 | #1 | 49027 |
| 2182 | 17464 | 71.2 | 52.0 | 21 | 337 | #5 | 49028 |
| 2183 | 17465 | 79.2 | 75.6 | 27 | 741 | #6 | 49029 |
| 2184 | 17466 | 72.8 | 66.9 | 18 | 503 | #5 | 49030 |
| 2185 | 17467 | 50.0 | 50.0 | 12 | 150 | #1 | 49031 |
| 2186 | 17468 | 61.6 | 50.0 | 12 | 155 | #3 | 49032 |
| 2187 | 17469 | 64.0 | 59.6 | 15 | 252 | #3 | 49033 |
| 2188 | 17470 | 73.6 | 68.0 | 17 | 594 | #5 | 49034 |
| 2189 | 17471 | 69.6 | 61.8 | 21 | 279 | #4 | 49035 |
| 2190 | 17472 | 67.2 | 65.1 | 14 | 499 | #4 | 49036 |
| 2191 | 17473 | 69.6 | 62.9 | 20 | 332 | #4 | 49037 |
| 2192 | 17474 | 72.8 | 67.3 | 16 | 551 | #5 | 49038 |
| 2193 | 17475 | 67.2 | 61.5 | 23 | 382 | #4 | 49039 |
| 2194 | 17476 | 69.6 | 50.0 | 14 | 376 | #4 | 49040 |
| 2195 | 17477 | 79.2 | 74.9 | 29 | 1082 | #6 | 49041 |
| 2196 | 17478 | 80.0 | 70.2 | 16 | 726 | #6 | 49042 |
| 2197 | 17479 | 78.4 | 73.1 | 18 | 850 | #6 | 49043 |
| 2198 | 17480 | 64.8 | 50.0 | 14 | 155 | #3 | 49044 |
| 2199 | 17481 | 64.8 | 52.0 | 13 | 319 | #3 | 49045 |
| 2200 | 17482 | 50.0 | 50.0 | 12 | 150 | #1 | 49046 |
| 2201 | 17483 | 64.0 | 59.3 | 13 | 208 | #3 | 49047 |
| 2202 | 17484 | 64.8 | 58.2 | 18 | 337 | #3 | 49048 |
| 2203 | 17485 | 54.4 | 50.0 | 39 | 190 | #1 | 49049 |
| 2204 | 17486 | 92.0 | 70.2 | 27 | 851 | #9 | 49050 |
| 2205 | 17487 | 65.6 | 58.5 | 15 | 296 | #4 | 49051 |
| 2206 | 17488 | 63.2 | 55.2 (212) | 18 | 245 | #3 | 49052 |
| 2207 | 17489 | 68.8 | 59.7 (216) | 24 | 301 | #4 | 49053 |
| 2208 | 17490 | 80.8 | 70.2 | 20 | 709 | #7 | 49054 |
| 2209 | 17491 | 68.8 | 53.5 | 18 | 292 | #4 | 49055 |
| 2210 | 17492 | 68.0 | 66.5 | 18 | 605 | #4 | 49056 |
| 2211 | 17493 | 69.6 | 61.8 | 22 | 434 | #4 | 49057 |
| 2212 | 17494 | 83.2 | 69.1 | 27 | 579 | #7 | 49058 |
| 2213 | 17495 | 65.6 | 60.4 | 15 | 209 | #4 | 49059 |
| 2214 | 17496 | 68.0 | 61.8 | 15 | 463 | #4 | 49060 |
| 2215 | 17497 | 71.2 | 62.9 | 32 | 332 | #5 | 49061 |
| 2216 | 17498 | 63.2 | 53.8 | 12 | 257 | #3 | 49062 |
| 2217 | 17499 | 50.0 | 50.0 | 12 | 150 | #1 | 49063 |
| 2218 | 17500 | 73.6 | 68.4 | 16 | 1175 | #5 | 49064 |
| 2219 | 17501 | 78.4 | 72.4 | 19 | 1129 | #6 | 49065 |
| 2220 | 17502 | 78.4 | 72.4 | 20 | 1201 | #6 | 49066 |
| 2221 | 17503 | 72.4 (98) | — | 13 | 228 | #5 | 49067 |
| 2222 | 17504 | 60.8 | 50.0 | 12 | 197 | #3 | 49068 |
| 2223 | 17505 | 77.6 | 57.5 | 24 | 400 | #6 | 49069 |
| 2224 | 17506 | 64.0 | 58.2 | 15 | 238 | #3 | 49070 |
| 2225 | 17507 | 65.6 | 61.5 | 14 | 347 | #4 | 49071 |
| 2226 | 17508 | 71.2 | 66.5 | 23 | 775 | #5 | 49072 |
| 2227 | 17509 | 78.4 | 74.5 | 22 | 1138 | #6 | 49073 |
| 2228 | 17510 | 67.2 | 61.5 | 13 | 663 | #4 | 49074 |
| 2229 | 17511 | 65.6 | 60.7 | 20 | 476 | #4 | 49075 |
| 2230 | 17512 | 61.6 | 58.2 | 12 | 306 | #3 | 49076 |
| 2231 | 17513 | 71.2 | 63.3 | 17 | 427 | #5 | 49077 |
| 2232 | 17514 | 64.0 | 50.0 | 16 | 217 | #3 | 49078 |
| 2233 | 17515 | 64.8 | 50.0 | 15 | 224 | #3 | 49079 |
| 2234 | 17516 | 75.2 | 66.2 | 20 | 530 | #6 | 49080 |
| 2235 | 17517 | 88.0 | 66.2 | 24 | 604 | #8 | 49081 |
| 2236 | 17518 | 55.2 | 54.8 (126) | 12 | 157 | #2 | 49082 |
| 2237 | 17519 | 60.0 | 55.3 | 14 | 190 | #2 | 49083 |
| 2238 | 17520 | 50.0 | 50.0 | 12 | 150 | #1 | 49084 |
| 2239 | 17521 | 83.2 | 77.1 | 18 | 832 | #7 | 49085 |
| 2240 | 17522 | 74.4 | 67.6 | 14 | 857 | #5 | 49086 |
| 2241 | 17523 | 72.8 | 61.5 | 28 | 331 | #5 | 49087 |
| 2242 | 17524 | 72.8 | 68.0 | 22 | 870 | #5 | 49088 |
| 2243 | 17525 | 72.8 | 50.0 | 13 | 324 | #5 | 49089 |
| 2244 | 17526 | 76.8 | 62.2 | 18 | 466 | #6 | 49090 |
| 2245 | 17527 | 64.0 | 50.0 (261) | 18 | 170 | #3 | 49091 |
| 2246 | 17528 | 50.0 | 50.0 | 12 | 150 | #1 | 49092 |
| 2247 | 17529 | 73.6 | 66.2 | 29 | 451 | #5 | 49093 |
| 2248 | 17530 | 62.4 | 50.0 | 13 | 236 | #3 | 49094 |
| 2249 | 17531 | 68.0 | 63.6 | 16 | 399 | #4 | 49095 |
| 2250 | 17532 | 73.6 | 64.7 | 22 | 481 | #5 | 49096 |
| 2251 | 17533 | 68.0 | 60.4 | 18 | 318 | #4 | 49097 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2252 | 17534 | 64.8 | 57.8 | 15 | 334 | #3 | 49098 |
| 2253 | 17535 | 69.6 | 60.4 | 15 | 429 | #4 | 49099 |
| 2254 | 17536 | 74.4 | 67.6 | 19 | 576 | #5 | 49100 |
| 2255 | 17537 | 50.0 | 50.0 | 12 | 150 | #1 | 49101 |
| 2256 | 17538 | 76.0 | 70.2 | 25 | 878 | #6 | 49102 |
| 2257 | 17539 | 60.0 | 56.7 | 12 | 200 | #2 | 49103 |
| 2258 | 17540 | 80.8 | 76.7 | 16 | 1396 | #7 | 49104 |
| 2259 | 17541 | 84.8 | 71.6 | 30 | 812 | #7 | 49105 |
| 2260 | 17542 | 78.4 | 76.4 | 22 | 904 | #6 | 49106 |
| 2261 | 17543 | 71.2 | 64.0 (267) | 16 | 455 | #5 | 49107 |
| 2262 | 17544 | 67.2 | 61.1 | 18 | 336 | #4 | 49108 |
| 2263 | 17545 | 88.8 | 73.5 | 29 | 842 | #8 | 49109 |
| 2264 | 17546 | 61.6 | 59.3 | 14 | 192 | #3 | 49110 |
| 2265 | 17547 | 50.0 | 50.0 | 12 | 150 | #1 | 49111 |
| 2266 | 17548 | 74.4 | 65.1 | 22 | 646 | #5 | 49112 |
| 2267 | 17549 | 72.8 | 67.3 | 21 | 917 | #5 | 49113 |
| 2268 | 17550 | 75.2 | 71.3 | 20 | 585 | #6 | 49114 |
| 2269 | 17551 | 50.0 | 50.0 | 12 | 150 | #1 | 49115 |
| 2270 | 17552 | 50.0 | 50.0 | 12 | 150 | #1 | 49116 |
| 2271 | 17553 | 63.2 | 58.5 | 13 | 227 | #3 | 49117 |
| 2272 | 17554 | 75.2 | 69.8 | 14 | 757 | #6 | 49118 |
| 2273 | 17555 | 50.0 | 50.0 | 12 | 150 | #1 | 49119 |
| 2274 | 17556 | 73.6 | 70.5 | 19 | 793 | #5 | 49120 |
| 2275 | 17557 | 63.2 | 56.7 | 13 | 210 | #3 | 49121 |
| 2276 | 17558 | 65.6 | 58.5 | 16 | 208 | #4 | 49122 |
| 2277 | 17559 | 77.6 | 74.2 | 14 | 727 | #6 | 49123 |
| 2278 | 17560 | 50.0 | 50.0 | 12 | 150 | #1 | 49124 |
| 2279 | 17561 | 65.6 | 60.4 | 19 | 367 | #4 | 49125 |
| 2280 | 17562 | 66.4 | 58.5 | 19 | 227 | #4 | 49126 |
| 2281 | 17563 | 68.8 | 60.4 | 18 | 308 | #4 | 49127 |
| 2282 | 17564 | 67.2 | 58.5 | 14 | 247 | #4 | 49128 |
| 2283 | 17565 | 67.2 | 50.0 | 13 | 329 | #4 | 49129 |
| 2284 | 17566 | 89.6 | 84.7 | 19 | 1005 | #8 | 49130 |
| 2285 | 17567 | 76.0 | 68.4 | 15 | 501 | #6 | 49131 |
| 2286 | 17568 | 50.0 | 50.0 | 12 | 150 | #1 | 49132 |
| 2287 | 17569 | 62.4 | 56.7 | 13 | 287 | #3 | 49133 |
| 2288 | 17570 | 68.0 | 54.5 (266) | 17 | 244 | #4 | 49134 |
| 2289 | 17571 | 79.2 | 76.0 | 27 | 1196 | #6 | 49135 |
| 2290 | 17572 | 62.4 | 50.0 | 17 | 153 | #3 | 49136 |
| 2291 | 17573 | 70.4 | 68.4 | 17 | 649 | #5 | 49137 |
| 2292 | 17574 | 67.2 | 60.0 | 20 | 251 | #4 | 49138 |
| 2293 | 17575 | 76.8 | 74.2 | 18 | 1015 | #6 | 49139 |
| 2294 | 17576 | 76.8 | 71.3 | 20 | 1166 | #6 | 49140 |
| 2295 | 17577 | 66.4 | 59.6 | 16 | 290 | #4 | 49141 |
| 2296 | 17578 | 67.2 | 60.7 | 13 | 351 | #4 | 49142 |
| 2297 | 17579 | 98.4 | 97.1 | 57 | 1847 | #10 | 49143 |
| 2298 | 17580 | 56.8 | 50.0 | 13 | 153 | #2 | 49144 |
| 2299 | 17581 | 66.4 | 55.6 | 14 | 229 | #4 | 49145 |
| 2300 | 17582 | 65.6 | 58.5 | 19 | 229 | #4 | 49146 |
| 2301 | 17583 | 64.0 | 57.1 | 14 | 233 | #3 | 49147 |
| 2302 | 17584 | 65.6 | 57.1 | 28 | 221 | #4 | 49148 |
| 2303 | 17585 | 74.4 | 66.9 | 15 | 796 | #5 | 49149 |
| 2304 | 17586 | 89.6 | 74.2 | 21 | 762 | #8 | 49150 |
| 2305 | 17587 | 62.4 | 50.0 | 12 | 174 | #3 | 49151 |
| 2306 | 17588 | 50.0 | 50.0 | 12 | 150 | #1 | 49152 |
| 2307 | 17589 | 50.0 | 50.0 | 12 | 150 | #1 | 49153 |
| 2308 | 17590 | 68.8 | 63.6 | 13 | 502 | #4 | 49154 |
| 2309 | 17591 | 77.6 | 70.2 | 17 | 627 | #6 | 49155 |
| 2310 | 17592 | 75.2 | 52.4 | 17 | 354 | #6 | 49156 |
| 2311 | 17593 | 64.8 | 60.4 | 17 | 263 | #3 | 49157 |
| 2312 | 17594 | 67.2 | 61.8 | 15 | 551 | #4 | 49158 |
| 2313 | 17595 | 72.0 | 68.0 | 22 | 656 | #5 | 49159 |
| 2314 | 17596 | 50.0 | 50.0 | 12 | 150 | #1 | 49160 |
| 2315 | 17597 | 100.0 | 98.9 | 160 | 3445 | #10 | 49161 |
| 2316 | 17598 | 66.4 | 59.3 | 20 | 234 | #4 | 49162 |
| 2317 | 17599 | 64.0 | 50.0 | 14 | 193 | #3 | 49163 |
| 2318 | 17600 | 72.8 | 64.4 | 17 | 1066 | #5 | 49164 |
| 2319 | 17601 | 81.6 | 67.6 | 29 | 520 | #7 | 49165 |
| 2320 | 17602 | 50.0 | 50.0 (198) | 12 | 150 | #1 | 49166 |
| 2321 | 17603 | 68.8 | 60.4 | 20 | 273 | #4 | 49167 |
| 2322 | 17604 | 50.0 | 50.0 | 12 | 150 | #1 | 49168 |
| 2323 | 17605 | 69.6 | 61.8 | 22 | 301 | #4 | 49169 |
| 2324 | 17606 | 50.0 | 50.0 | 13 | 150 | #1 | 49170 |
| 2325 | 17607 | 64.8 | 56.7 | 17 | 189 | #3 | 49171 |
| 2326 | 17608 | 68.0 | 60.2 (231) | 20 | 210 | #4 | 49172 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2327 | 17609 | 61.6 | 50.0 (257) | 14 | 174 | #3 | 49173 |
| 2328 | 17610 | 50.0 | 50.0 | 12 | 150 | #1 | 49174 |
| 2329 | 17611 | 68.8 | 59.6 | 29 | 260 | #4 | 49175 |
| 2330 | 17612 | 50.0 | 50.0 | 12 | 150 | #1 | 49176 |
| 2331 | 17613 | 77.6 | 67.3 | 31 | 630 | #6 | 49177 |
| 2332 | 17614 | 50.0 | 50.0 | 12 | 150 | #1 | 49178 |
| 2333 | 17615 | 75.2 | 64.0 | 36 | 459 | #6 | 49179 |
| 2334 | 17616 | 66.4 | 60.0 | 22 | 224 | #4 | 49180 |
| 2335 | 17617 | 64.0 | 58.9 | 15 | 234 | #3 | 49181 |
| 2336 | 17618 | 63.2 | 52.0 | 14 | 198 | #3 | 49182 |
| 2337 | 17619 | 71.2 | 60.7 | 25 | 298 | #5 | 49183 |
| 2338 | 17620 | 81.6 | 59.6 | 26 | 484 | #7 | 49184 |
| 2339 | 17621 | 50.0 (76) | — | 12 | 150 | #1 | 49185 |
| 2340 | 17622 | 64.8 | 50.0 | 12 | 191 | #3 | 49186 |
| 2341 | 17623 | 63.2 | 58.2 | 12 | 198 | #3 | 49187 |
| 2342 | 17624 | 64.0 | 50.0 | 16 | 186 | #3 | 49188 |
| 2343 | 17625 | 65.6 | 61.8 (170) | 15 | 169 | #4 | 49189 |
| 2344 | 17626 | 65.6 | 58.9 | 15 | 197 | #4 | 49190 |
| 2345 | 17627 | 70.4 | 61.1 | 17 | 257 | #5 | 49191 |
| 2346 | 17628 | 64.0 | 59.3 | 16 | 236 | #3 | 49192 |
| 2347 | 17629 | 72.0 | 62.2 | 27 | 310 | #5 | 49193 |
| 2348 | 17630 | 68.0 | 60.0 | 19 | 249 | #4 | 49194 |
| 2349 | 17631 | 66.4 | 54.9 | 17 | 209 | #4 | 49195 |
| 2350 | 17632 | 66.4 | 58.3 (264) | 19 | 195 | #4 | 49196 |
| 2351 | 17633 | 74.4 | 68.7 | 13 | 548 | #5 | 49197 |
| 2352 | 17634 | 67.2 | 57.5 | 17 | 208 | #4 | 49198 |
| 2353 | 17635 | 50.0 | 50.0 | 12 | 150 | #1 | 49199 |
| 2354 | 17636 | 67.2 | 58.5 | 19 | 235 | #4 | 49200 |
| 2355 | 17637 | 71.2 | 62.5 | 21 | 301 | #5 | 49201 |
| 2356 | 17638 | 54.4 | 50.0 | 15 | 150 | #1 | 49202 |
| 2357 | 17639 | 75.8 (66) | — | 40 | 195 | #6 | 49203 |
| 2358 | 17640 | 64.8 | 50.0 (247) | 17 | 191 | #3 | 49204 |
| 2359 | 17641 | 66.4 | 61.1 | 20 | 253 | #4 | 49205 |
| 2360 | 17642 | 68.8 | 57.8 | 18 | 223 | #4 | 49206 |
| 2361 | 17643 | 68.0 | 61.0 (228) | 20 | 204 | #4 | 49207 |
| 2362 | 17644 | 64.8 | 50.0 | 19 | 189 | #3 | 49208 |
| 2363 | 17645 | 56.0 | 50.0 | 15 | 156 | #2 | 49209 |
| 2364 | 17646 | 73.6 | 71.3 | 15 | 900 | #5 | — |
| 2365 | 17647 | 59.2 | 50.0 (150) | 14 | 150 | #2 | 49210 |
| 2366 | 17648 | 68.0 | 61.5 | 20 | 333 | #4 | 49211 |
| 2367 | 17649 | 64.0 | 50.0 (227) | 15 | 159 | #3 | 49212 |
| 2368 | 17650 | 62.4 | 50.0 | 12 | 192 | #3 | 49213 |
| 2369 | 17651 | 68.0 | 58.5 | 14 | 219 | #4 | 49214 |
| 2370 | 17652 | 66.4 | 58.5 | 19 | 254 | #4 | 49215 |
| 2371 | 17653 | 50.0 (120) | — | 12 | 150 | #1 | 49216 |
| 2372 | 17654 | 64.8 | 54.4 (204) | 21 | 182 | #3 | 49217 |
| 2373 | 17655 | 67.2 | 61.5 | 20 | 282 | #4 | 49218 |
| 2374 | 17656 | 64.8 | 50.0 (247) | 17 | 191 | #3 | 49219 |
| 2375 | 17657 | 71.2 | 63.6 | 20 | 600 | #5 | 49220 |
| 2376 | 17658 | 68.8 | 58.9 | 19 | 272 | #4 | 49221 |
| 2377 | 17659 | 73.6 | 64.0 | 31 | 512 | #5 | 49222 |
| 2378 | 17660 | 68.0 | 63.6 (151) | 18 | 196 | #4 | 49223 |
| 2379 | 17661 | 50.0 (98) | — | 12 | 150 | #1 | 49224 |
| 2380 | 17662 | 64.0 | 50.0 | 16 | 168 | #3 | 49225 |
| 2381 | 17663 | 73.6 (72) | — | 17 | 163 | #5 | 49226 |
| 2382 | 17664 | 64.8 | 60.3 (174) | 19 | 170 | #3 | 49227 |
| 2383 | 17665 | 71.2 | 64.0 | 21 | 333 | #5 | 49228 |
| 2384 | 17666 | 51.6 (95) | — | 12 | 150 | #1 | 49229 |
| 2385 | 17667 | 68.0 | 61.1 | 16 | 291 | #4 | 49230 |
| 2386 | 17668 | 66.4 | 59.6 | 18 | 292 | #4 | 49231 |
| 2387 | 17669 | 63.3 (120) | — | 22 | 192 | #3 | 49232 |
| 2388 | 17670 | 71.2 | 60.7 | 23 | 310 | #5 | 49233 |
| 2389 | 17671 | 63.2 | 62.0 (166) | 18 | 172 | #3 | 49234 |
| 2390 | 17672 | 65.6 | 50.0 | 12 | 209 | #4 | 49235 |
| 2391 | 17673 | 72.8 | 60.7 | 36 | 267 | #5 | 49236 |
| 2392 | 17674 | 64.8 | 53.5 | 16 | 219 | #3 | 49237 |
| 2393 | 17675 | 65.6 | 58.2 | 13 | 209 | #4 | 49238 |
| 2394 | 17676 | 66.4 | 50.0 | 16 | 223 | #4 | 49239 |
| 2395 | 17677 | 69.6 | 60.4 | 21 | 248 | #4 | 49240 |
| 2396 | 17678 | 65.6 | 50.0 (239) | 16 | 154 | #4 | 49241 |
| 2397 | 17679 | 66.4 | 59.3 | 16 | 228 | #4 | 49242 |
| 2398 | 17680 | 63.2 | 54.9 | 23 | 179 | #3 | 49243 |
| 2399 | 17681 | 50.0 | 50.0 | 12 | 150 | #1 | 49244 |
| 2400 | 17682 | 50.0 | 50.0 | 14 | 166 | #1 | 49245 |
| 2401 | 17683 | 65.6 | 60.0 | 18 | 235 | #4 | 49246 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2402 | 17684 | 71.2 | 63.9 (238) | 28 | 322 | #5 | 49247 |
| 2403 | 17685 | 70.4 | 61.8 | 20 | 260 | #5 | 49248 |
| 2404 | 17686 | 69.6 | 63.6 | 18 | 385 | #4 | 49249 |
| 2405 | 17687 | 69.6 | 61.5 | 18 | 293 | #4 | 49250 |
| 2406 | 17688 | 50.0 | 50.0 | 12 | 150 | #1 | 49251 |
| 2407 | 17689 | 74.4 | 61.8 | 29 | 341 | #5 | 49252 |
| 2408 | 17690 | 68.8 | 60.7 | 25 | 296 | #4 | 49253 |
| 2409 | 17691 | 50.0 | 50.0 | 12 | 150 | #1 | 49254 |
| 2410 | 17692 | 89.4 (104) | — | 19 | 421 | #8 | 49255 |
| 2411 | 17693 | 62.4 | 50.0 | 15 | 213 | #3 | 49256 |
| 2412 | 17694 | 64.0 | 58.9 (190) | 20 | 180 | #3 | 49257 |
| 2413 | 17695 | 66.4 | 60.7 | 20 | 281 | #4 | 49258 |
| 2414 | 17696 | 63.2 | 50.0 (263) | 14 | 166 | #3 | 49259 |
| 2415 | 17697 | 68.8 | 59.6 | 24 | 284 | #4 | 49260 |
| 2416 | 17698 | 74.4 | 64.7 | 26 | 858 | #5 | 49261 |
| 2417 | 17699 | 68.8 | 59.6 | 16 | 237 | #4 | 49262 |
| 2418 | 17700 | 88.0 | 63.6 | 38 | 572 | #8 | 49263 |
| 2419 | 17701 | 89.9 (99) | — | 22 | 399 | #8 | 49264 |
| 2420 | 17702 | 80.8 | 66.5 | 27 | 445 | #7 | 49265 |
| 2421 | 17703 | 67.2 | 50.0 | 15 | 213 | #4 | 49266 |
| 2422 | 17704 | 70.4 | 61.1 | 30 | 329 | #5 | 49267 |
| 2423 | 17705 | 64.0 | 51.3 | 18 | 196 | #3 | 49268 |
| 2424 | 17706 | 72.8 | 64.4 | 26 | 458 | #5 | 49269 |
| 2425 | 17707 | 68.0 | 61.1 | 19 | 256 | #4 | 49270 |
| 2426 | 17708 | 55.2 | 50.0 | 12 | 151 | #2 | 49271 |
| 2427 | 17709 | 50.0 | 50.0 (162) | 14 | 155 | #1 | 49272 |
| 2428 | 17710 | 64.0 | 58.2 | 15 | 196 | #3 | 49273 |
| 2429 | 17711 | 84.0 | 66.9 | 40 | 504 | #7 | 49274 |
| 2430 | 17712 | 66.4 | 50.0 | 22 | 179 | #4 | 49275 |
| 2431 | 17713 | 50.0 | 50.0 | 16 | 150 | #1 | 49276 |
| 2432 | 17714 | 75.8 (66) | — | 24 | 164 | #6 | 49277 |
| 2433 | 17715 | 74.4 | 63.6 | 25 | 412 | #5 | 49278 |
| 2434 | 17716 | 50.0 | 50.0 (194) | 15 | 150 | #1 | 49279 |
| 2435 | 17717 | 69.6 | 61.5 | 20 | 455 | #4 | 49280 |
| 2436 | 17718 | 76.8 | 63.6 | 41 | 484 | #6 | 49281 |
| 2437 | 17719 | 68.8 | 61.8 | 20 | 326 | #4 | 49282 |
| 2438 | 17720 | 67.2 | 60.0 | 20 | 241 | #4 | 49283 |
| 2439 | 17721 | 79.2 | 59.3 | 18 | 377 | #6 | 49284 |
| 2440 | 17722 | 68.0 | 58.9 | 17 | 217 | #4 | 49285 |
| 2441 | 17723 | 69.6 | 60.7 | 20 | 274 | #4 | 49286 |
| 2442 | 17724 | 50.0 | 50.0 (144) | 14 | 150 | #1 | 49287 |
| 2443 | 17725 | 65.6 | 57.8 | 19 | 258 | #4 | 49288 |
| 2444 | 17726 | 65.6 | 60.0 | 17 | 264 | #4 | 49289 |
| 2445 | 17727 | 61.6 | 56.7 | 14 | 210 | #3 | 49290 |
| 2446 | 17728 | 68.8 | 56.7 | 15 | 238 | #4 | 49291 |
| 2447 | 17729 | 68.0 | 59.6 | 18 | 266 | #4 | 49292 |
| 2448 | 17730 | 68.8 | 59.6 | 19 | 228 | #4 | 49293 |
| 2449 | 17731 | 66.4 | 63.3 | 13 | 536 | #4 | 49294 |
| 2450 | 17732 | 68.0 | 60.7 | 19 | 251 | #4 | 49295 |
| 2451 | 17733 | 64.8 | 50.0 | 16 | 164 | #3 | 49296 |
| 2452 | 17734 | 59.2 | 53.8 (247) | 14 | 152 | #2 | 49297 |
| 2453 | 17735 | 64.0 | 50.0 (221) | 16 | 163 | #3 | 49298 |
| 2454 | 17736 | 61.6 | 50.0 | 13 | 154 | #3 | 49299 |
| 2455 | 17737 | 50.0 | 50.0 (169) | 14 | 150 | #1 | 49300 |
| 2456 | 17738 | 66.4 | 61.1 | 20 | 297 | #4 | 49301 |
| 2457 | 17739 | 68.8 | 61.5 | 18 | 260 | #4 | 49302 |
| 2458 | 17740 | 68.0 | 60.7 | 19 | 258 | #4 | 49303 |
| 2459 | 17741 | 68.0 | 61.5 | 18 | 402 | #4 | 49304 |
| 2460 | 17742 | 62.4 | 52.0 | 15 | 195 | #3 | 49305 |
| 2461 | 17743 | 85.7 (105) | — | 20 | 386 | #8 | 49306 |
| 2462 | 17744 | 67.2 | 58.9 | 18 | 225 | #4 | 49307 |
| 2463 | 17745 | 66.4 | 58.5 | 18 | 238 | #4 | 49308 |
| 2464 | 17746 | 67.2 | 59.3 | 17 | 225 | #4 | 49309 |
| 2465 | 17747 | 67.2 | 59.3 | 23 | 248 | #4 | 49310 |
| 2466 | 17748 | 63.2 | 50.0 | 14 | 211 | #3 | 49311 |
| 2467 | 17749 | 69.6 | 60.7 | 18 | 257 | #4 | 49312 |
| 2468 | 17750 | 66.4 | 59.6 | 18 | 261 | #4 | 49313 |
| 2469 | 17751 | 64.8 | 58.2 | 16 | 235 | #3 | 49314 |
| 2470 | 17752 | 50.0 | 50.0 (183) | 14 | 150 | #1 | 49315 |
| 2471 | 17753 | 72.8 | 62.5 | 20 | 351 | #5 | 49316 |
| 2472 | 17754 | 62.4 | 50.0 | 14 | 198 | #3 | 49317 |
| 2473 | 17755 | 70.4 | 61.5 | 16 | 238 | #5 | 49318 |
| 2474 | 17756 | 70.4 | 61.8 | 22 | 287 | #5 | 49319 |
| 2475 | 17757 | 50.0 | 50.0 | 12 | 150 | #1 | 49320 |
| 2476 | 17758 | 64.0 | 56.7 | 19 | 257 | #3 | — |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2477 | 17759 | 71.2 | 61.1 | 23 | 301 | #5 | 49321 |
| 2478 | 17760 | 67.2 | 58.9 | 20 | 206 | #4 | 49322 |
| 2479 | 17761 | 70.4 | 60.7 | 32 | 272 | #5 | 49323 |
| 2480 | 17762 | 68.8 | 60.7 | 18 | 246 | #4 | 49324 |
| 2481 | 17763 | 74.4 | 67.3 | 26 | 755 | #5 | 49325 |
| 2482 | 17764 | 68.0 | 60.4 | 20 | 270 | #4 | 49326 |
| 2483 | 17765 | 50.0 | 50.0 | 12 | 150 | #1 | 49327 |
| 2484 | 17766 | 66.4 | 60.0 | 18 | 241 | #4 | 49328 |
| 2485 | 17767 | 50.0 | 50.0 | 12 | 150 | #1 | 49329 |
| 2486 | 17768 | 69.6 | 60.0 | 24 | 268 | #4 | 49330 |
| 2487 | 17769 | 70.4 | 63.6 | 22 | 391 | #5 | 49331 |
| 2488 | 17770 | 68.0 | 59.6 | 18 | 257 | #4 | 49332 |
| 2489 | 17771 | 72.0 | 60.0 | 22 | 281 | #5 | 49333 |
| 2490 | 17772 | 62.4 | 57.0 (158) | 15 | 152 | #3 | 49334 |
| 2491 | 17773 | 67.2 | 60.4 | 23 | 326 | #4 | 49335 |
| 2492 | 17774 | 64.0 | 55.6 (216) | 16 | 169 | #3 | 49336 |
| 2493 | 17775 | 67.2 | 61.8 | 29 | 354 | #4 | 49337 |
| 2494 | 17776 | 50.0 | 50.0 | 13 | 165 | #1 | 49338 |
| 2495 | 17777 | 67.2 | 56.7 | 18 | 220 | #4 | 49339 |
| 2496 | 17778 | 69.6 | 61.8 | 21 | 288 | #4 | 49340 |
| 2497 | 17779 | 66.4 | 60.0 | 15 | 241 | #4 | 49341 |
| 2498 | 17780 | 68.0 | 59.3 | 19 | 255 | #4 | 49342 |
| 2499 | 17781 | 66.4 | 59.6 | 21 | 238 | #4 | 49343 |
| 2500 | 17782 | 72.0 | 62.5 | 23 | 415 | #5 | 49344 |
| 2501 | 17783 | 72.8 | 64.0 | 22 | 598 | #5 | 49345 |
| 2502 | 17784 | 69.6 | 62.2 | 33 | 266 | #4 | 49346 |
| 2503 | 17785 | 64.8 | 57.5 | 18 | 208 | #3 | 49347 |
| 2504 | 17786 | 67.2 | 50.0 | 17 | 225 | #4 | 49348 |
| 2505 | 17787 | 50.0 | 50.0 | 12 | 150 | #1 | 49349 |
| 2506 | 17788 | 66.4 | 59.6 | 19 | 231 | #4 | 49350 |
| 2507 | 17789 | 50.0 | 50.0 | 12 | 150 | #1 | 49351 |
| 2508 | 17790 | 67.2 | 53.2 (222) | 21 | 218 | #4 | 49352 |
| 2509 | 17791 | 50.0 | 50.0 (141) | 12 | 150 | #1 | 49353 |
| 2510 | 17792 | 64.8 | 59.3 | 21 | 242 | #3 | 49354 |
| 2511 | 17793 | 50.0 | 50.0 | 12 | 150 | #1 | 49355 |
| 2512 | 17794 | 75.2 | 57.1 | 21 | 319 | #6 | 49356 |
| 2513 | 17795 | 50.0 | 50.0 | 12 | 150 | #1 | 49357 |
| 2514 | 17796 | 71.2 | 63.3 | 21 | 425 | #5 | 49358 |
| 2515 | 17797 | 61.6 | 50.0 | 14 | 158 | #3 | 49359 |
| 2516 | 17798 | 66.4 | 57.5 | 15 | 212 | #4 | 49360 |
| 2517 | 17799 | 67.2 | 59.6 | 19 | 244 | #4 | 49361 |
| 2518 | 17800 | 66.4 | 62.5 (168) | 18 | 197 | #4 | 49362 |
| 2519 | 17801 | 67.2 | 61.1 | 23 | 277 | #4 | 49363 |
| 2520 | 17802 | 68.0 | 58.9 | 14 | 207 | #4 | 49364 |
| 2521 | 17803 | 63.2 | 57.8 | 21 | 201 | #3 | 49365 |
| 2522 | 17804 | 65.6 | 50.0 | 12 | 193 | #4 | 49366 |
| 2523 | 17805 | 65.6 | 50.0 | 12 | 195 | #4 | 49367 |
| 2524 | 17806 | 65.6 | 58.9 | 28 | 223 | #4 | 49368 |
| 2525 | 17807 | 61.6 | 61.2 (134) | 16 | 154 | #3 | 49369 |
| 2526 | 17808 | 57.6 | 50.0 | 15 | 180 | #2 | 49370 |
| 2527 | 17809 | 52.8 | 50.0 | 14 | 150 | #1 | 49371 |
| 2528 | 17810 | 56.0 | 50.0 | 13 | 152 | #2 | 49372 |
| 2529 | 17811 | 64.0 | 54.8 (272) | 18 | 175 | #3 | 49373 |
| 2530 | 17812 | 50.0 | 50.0 | 12 | 150 | #1 | 49374 |
| 2531 | 17813 | 65.6 | 61.5 (200) | 20 | 202 | #4 | 49375 |
| 2532 | 17814 | 68.8 | 62.5 | 20 | 469 | #4 | 49376 |
| 2533 | 17815 | 67.2 | 60.4 | 22 | 266 | #4 | 49377 |
| 2534 | 17816 | 66.4 | 58.9 | 20 | 261 | #4 | 49378 |
| 2535 | 17817 | 63.2 | 58.2 | 13 | 212 | #3 | 49379 |
| 2536 | 17818 | 70.4 | 65.1 | 26 | 469 | #5 | 49380 |
| 2537 | 17819 | 69.6 | 62.9 | 21 | 458 | #4 | 49381 |
| 2538 | 17820 | 68.8 | 62.5 | 24 | 313 | #4 | 49382 |
| 2539 | 17821 | 64.0 | 56.0 | 13 | 170 | #3 | 49383 |
| 2540 | 17822 | 62.4 | 50.0 | 13 | 165 | #3 | 49384 |
| 2541 | 17823 | 64.8 | 57.4 (197) | 22 | 171 | #3 | 49385 |
| 2542 | 17824 | 65.6 | 58.2 (237) | 17 | 177 | #4 | 49386 |
| 2543 | 17825 | 69.6 | 61.8 | 20 | 288 | #4 | 49387 |
| 2544 | 17826 | 70.4 | 63.3 | 28 | 307 | #5 | 49388 |
| 2545 | 17827 | 69.6 | 59.6 | 27 | 278 | #4 | 49389 |
| 2546 | 17828 | 50.0 | 50.0 | 12 | 150 | #1 | 49390 |
| 2547 | 17829 | 67.2 | 62.2 | 16 | 305 | #4 | 49391 |
| 2548 | 17830 | 67.2 | 54.0 (252) | 29 | 236 | #4 | 49392 |
| 2549 | 17831 | 68.8 | 60.7 | 20 | 265 | #4 | 49393 |
| 2550 | 17832 | 70.4 | 62.5 | 32 | 355 | #5 | 49394 |
| 2551 | 17833 | 64.8 | 58.9 | 17 | 229 | #3 | 49395 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2552 | 17834 | 69.6 | 59.3 | 21 | 255 | #4 | 49396 |
| 2553 | 17835 | 70.4 | 50.9 | 25 | 287 | #5 | 49397 |
| 2554 | 17836 | 50.0 | 50.0 | 14 | 150 | #1 | 49398 |
| 2555 | 17837 | 72.0 | 57.8 (218) | 17 | 289 | #5 | 49399 |
| 2556 | 17838 | 61.6 | 51.7 (178) | 17 | 150 | #3 | 49400 |
| 2557 | 17839 | 67.2 | 60.7 | 18 | 262 | #4 | 49401 |
| 2558 | 17840 | 66.4 | 60.0 | 18 | 256 | #4 | 49402 |
| 2559 | 17841 | 68.0 | 63.6 | 20 | 291 | #4 | 49403 |
| 2560 | 17842 | 64.8 | 50.0 (212) | 19 | 167 | #3 | 49404 |
| 2561 | 17843 | 68.0 | 62.5 | 19 | 330 | #4 | 49405 |
| 2562 | 17844 | 50.0 | 50.0 | 12 | 150 | #1 | 49406 |
| 2563 | 17845 | 64.8 | 60.4 | 19 | 224 | #3 | 49407 |
| 2564 | 17846 | 50.0 (75) | — | 12 | 150 | #1 | 49408 |
| 2565 | 17847 | 65.6 | 52.4 | 16 | 204 | #4 | 49409 |
| 2566 | 17848 | 69.6 | 61.1 | 18 | 309 | #4 | 49410 |
| 2567 | 17849 | 71.2 | 60.4 | 22 | 319 | #5 | 49411 |
| 2568 | 17850 | 66.4 | 60.0 | 23 | 205 | #4 | 49412 |
| 2569 | 17851 | 68.0 | 60.0 | 20 | 283 | #4 | 49413 |
| 2570 | 17852 | 60.8 | 50.0 | 13 | 150 | #3 | 49414 |
| 2571 | 17853 | 64.0 | 62.5 (136) | 20 | 165 | #3 | 49415 |
| 2572 | 17854 | 65.6 | 50.0 | 13 | 192 | #4 | 49416 |
| 2573 | 17855 | 67.2 | 57.2 (236) | 19 | 207 | #4 | 49417 |
| 2574 | 17856 | 83.2 (95) | — | 27 | 335 | #7 | 49418 |
| 2575 | 17857 | 77.6 | 71.6 | 23 | 1481 | #6 | 49419 |
| 2576 | 17858 | 68.0 | 57.8 | 14 | 217 | #4 | 49420 |
| 2577 | 17859 | 68.8 | 58.9 | 17 | 228 | #4 | 49421 |
| 2578 | 17860 | 50.0 | 50.0 | 12 | 150 | #1 | 49422 |
| 2579 | 17861 | 68.0 | 62.5 | 23 | 313 | #4 | 49423 |
| 2580 | 17862 | 63.2 | 50.0 | 32 | 262 | #3 | 49424 |
| 2581 | 17863 | 67.2 | 50.0 | 13 | 194 | #4 | 49425 |
| 2582 | 17864 | 62.4 | 57.8 | 14 | 223 | #3 | 49426 |
| 2583 | 17865 | 68.0 | 59.6 | 24 | 238 | #4 | 49427 |
| 2584 | 17866 | 68.0 | 60.4 | 17 | 250 | #4 | 49428 |
| 2585 | 17867 | 68.0 | 62.9 | 23 | 341 | #4 | 49429 |
| 2586 | 17868 | 72.8 | 67.3 | 31 | 1109 | #5 | 49430 |
| 2587 | 17869 | 50.0 | 50.0 | 12 | 150 | #1 | 49431 |
| 2588 | 17870 | 64.0 | 59.6 | 16 | 203 | #3 | 49432 |
| 2589 | 17871 | 66.4 | 54.9 | 17 | 213 | #4 | 49433 |
| 2590 | 17872 | 68.0 | 57.8 | 18 | 215 | #4 | 49434 |
| 2591 | 17873 | 70.4 | 61.5 | 23 | 373 | #5 | 49435 |
| 2592 | 17874 | 50.0 | 50.0 | 12 | 150 | #1 | 49436 |
| 2593 | 17875 | 68.8 | 63.3 | 21 | 458 | #4 | 49437 |
| 2594 | 17876 | 50.0 | 50.0 | 12 | 150 | #1 | 49438 |
| 2595 | 17877 | 73.6 | 68.0 | 24 | 603 | #5 | 49439 |
| 2596 | 17878 | 67.2 | 59.9 (257) | 19 | 250 | #4 | 49440 |
| 2597 | 17879 | 70.4 | 64.0 | 21 | 375 | #5 | 49441 |
| 2598 | 17880 | 64.0 | 50.0 | 13 | 222 | #3 | 49442 |
| 2599 | 17881 | 50.0 (77) | — | 35 | 173 | #1 | 49443 |
| 2600 | 17882 | 60.8 | 56.0 | 13 | 186 | #3 | 49444 |
| 2601 | 17883 | 61.6 | 57.1 | 14 | 183 | #3 | 49445 |
| 2602 | 17884 | 64.8 | 50.0 | 14 | 206 | #3 | 49446 |
| 2603 | 17885 | 68.0 | 61.1 | 18 | 281 | #4 | 49447 |
| 2604 | 17886 | 68.8 | 62.5 | 20 | 345 | #4 | 49448 |
| 2605 | 17887 | 64.8 | 60.0 | 14 | 251 | #3 | 49449 |
| 2606 | 17888 | 80.8 | 69.1 | 27 | 511 | #7 | 49450 |
| 2607 | 17889 | 66.4 | 53.1 | 15 | 205 | #4 | 49451 |
| 2608 | 17890 | 66.4 | 50.6 (180) | 17 | 187 | #4 | 49452 |
| 2609 | 17891 | 50.0 | 50.0 | 12 | 150 | #1 | 49453 |
| 2610 | 17892 | 68.0 | 58.9 | 22 | 236 | #4 | 49454 |
| 2611 | 17893 | 50.0 | 50.0 | 12 | 150 | #1 | 49455 |
| 2612 | 17894 | 65.6 | 60.0 | 18 | 290 | #4 | 49456 |
| 2613 | 17895 | 63.2 | 50.0 (262) | 19 | 155 | #3 | 49457 |
| 2614 | 17896 | 70.4 | 62.9 | 20 | 388 | #5 | 49458 |
| 2615 | 17897 | 59.2 | 50.0 (151) | 13 | 150 | #2 | 49459 |
| 2616 | 17898 | 66.4 | 50.5 | 17 | 213 | #4 | 49460 |
| 2617 | 17899 | 71.2 | 61.5 | 21 | 291 | #5 | 49461 |
| 2618 | 17900 | 67.2 | 60.7 | 20 | 298 | #4 | 49462 |
| 2619 | 17901 | 68.0 | 61.5 | 21 | 335 | #4 | 49463 |
| 2620 | 17902 | 60.8 | 50.0 (192) | 15 | 159 | #3 | 49464 |
| 2621 | 17903 | 50.0 | 50.0 | 12 | 150 | #1 | 49465 |
| 2622 | 17904 | 73.6 | 54.2 (192) | 33 | 329 | #5 | 49466 |
| 2623 | 17905 | 67.2 | 61.1 | 21 | 331 | #4 | 49467 |
| 2624 | 17906 | 65.6 | 58.9 | 18 | 197 | #4 | 49468 |
| 2625 | 17907 | 68.8 | 64.0 | 23 | 460 | #4 | 49469 |
| 2626 | 17908 | 50.0 | 50.0 | 12 | 150 | #1 | 49470 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2627 | 17909 | 65.6 | 58.2 | 17 | 221 | #4 | 49471 |
| 2628 | 17910 | 62.4 | 57.5 | 12 | 190 | #3 | 49472 |
| 2629 | 17911 | 66.4 | 50.0 (242) | 15 | 184 | #4 | 49473 |
| 2630 | 17912 | 76.8 | 64.7 | 19 | 766 | #6 | 49474 |
| 2631 | 17913 | 61.6 | 57.8 | 13 | 210 | #3 | 49475 |
| 2632 | 17914 | 72.8 | 61.8 | 27 | 385 | #5 | 49476 |
| 2633 | 17915 | 63.2 | 61.7 (128) | 16 | 157 | #3 | 49477 |
| 2634 | 17916 | 68.0 | 61.8 | 19 | 290 | #4 | 49478 |
| 2635 | 17917 | 69.6 | 61.1 | 21 | 347 | #4 | 49479 |
| 2636 | 17918 | 50.0 | 50.0 | 12 | 150 | #1 | 49480 |
| 2637 | 17919 | 65.6 | 61.3 (168) | 12 | 151 | #4 | 49481 |
| 2638 | 17920 | 70.4 | 61.5 | 20 | 286 | #5 | 49482 |
| 2639 | 17921 | 50.0 | 50.0 | 12 | 150 | #1 | 49483 |
| 2640 | 17922 | 61.6 | 55.6 | 30 | 200 | #3 | 49484 |
| 2641 | 17923 | 50.0 | 50.0 | 12 | 150 | #1 | 49485 |
| 2642 | 17924 | 64.8 | 59.6 | 17 | 259 | #3 | 49486 |
| 2643 | 17925 | 69.6 | 60.7 | 20 | 317 | #4 | 49487 |
| 2644 | 17926 | 69.6 | 62.9 | 24 | 320 | #4 | 49488 |
| 2645 | 17927 | 75.3 (81) | — | 17 | 269 | #6 | 49489 |
| 2646 | 17928 | 69.6 | 61.5 | 22 | 280 | #4 | 49490 |
| 2647 | 17929 | 70.4 | 61.8 | 18 | 290 | #5 | 49491 |
| 2648 | 17930 | 67.2 | 56.4 | 17 | 245 | #4 | 49492 |
| 2649 | 17931 | 64.8 | 60.0 | 18 | 217 | #3 | 49493 |
| 2650 | 17932 | 98.4 | 96.0 | 82 | 1319 | #10 | 49494 |
| 2651 | 17933 | 70.4 | 61.1 | 26 | 316 | #5 | 49495 |
| 2652 | 17934 | 64.8 | 57.1 | 16 | 209 | #3 | 49496 |
| 2653 | 17935 | 73.6 | 63.3 | 33 | 431 | #5 | 49497 |
| 2654 | 17936 | 66.4 | 61.1 | 16 | 218 | #4 | 49498 |
| 2655 | 17937 | 66.4 | 59.6 | 22 | 242 | #4 | 49499 |
| 2656 | 17938 | 66.4 | 58.2 | 15 | 202 | #4 | 49500 |
| 2657 | 17939 | 64.0 | 59.6 | 12 | 226 | #3 | 49501 |
| 2658 | 17940 | 61.6 | 56.5 (138) | 12 | 150 | #3 | 49502 |
| 2659 | 17941 | 69.6 | 61.1 | 27 | 269 | #4 | 49503 |
| 2660 | 17942 | 68.8 | 61.8 | 22 | 316 | #4 | 49504 |
| 2661 | 17943 | 63.2 | 52.7 (150) | 13 | 151 | #3 | 49505 |
| 2662 | 17944 | 64.8 | 50.0 | 12 | 177 | #3 | 49506 |
| 2663 | 17945 | 50.0 | 50.0 | 12 | 150 | #1 | 49507 |
| 2664 | 17946 | 50.0 | 50.0 | 12 | 150 | #1 | 49508 |
| 2665 | 17947 | 64.0 | 50.0 | 13 | 165 | #3 | 49509 |
| 2666 | 17948 | 50.0 (106) | — | 12 | 150 | #1 | 49510 |
| 2667 | 17949 | 65.6 | 58.2 | 19 | 222 | #4 | 49511 |
| 2668 | 17950 | 68.8 | 62.5 | 19 | 556 | #4 | 49512 |
| 2669 | 17951 | 69.6 | 59.6 | 20 | 268 | #4 | 49513 |
| 2670 | 17952 | 71.2 | 62.9 | 28 | 424 | #5 | 49514 |
| 2671 | 17953 | 80.8 | 67.6 | 19 | 462 | #7 | 49515 |
| 2672 | 17954 | 67.2 | 59.3 | 22 | 221 | #4 | 49516 |
| 2673 | 17955 | 64.0 | 50.0 (230) | 16 | 170 | #3 | 49517 |
| 2674 | 17956 | 64.8 | 56.6 (173) | 17 | 194 | #3 | 49518 |
| 2675 | 17957 | 60.8 | 58.2 | 16 | 179 | #3 | 49519 |
| 2676 | 17958 | 50.0 | 50.0 | 12 | 150 | #1 | 49520 |
| 2677 | 17959 | 78.4 | 68.4 | 23 | 542 | #6 | 49521 |
| 2678 | 17960 | 68.0 | 60.4 | 18 | 265 | #4 | 49522 |
| 2679 | 17961 | 67.2 | 61.5 | 19 | 341 | #4 | 49523 |
| 2680 | 17962 | 72.0 | 65.1 | 28 | 501 | #5 | 49524 |
| 2681 | 17963 | 65.6 | 57.1 | 20 | 207 | #4 | 49525 |
| 2682 | 17964 | 68.0 | 61.1 | 21 | 354 | #4 | 49526 |
| 2683 | 17965 | 73.6 | 63.6 | 32 | 360 | #5 | 49527 |
| 2684 | 17966 | 68.8 | 60.7 | 18 | 274 | #4 | 49528 |
| 2685 | 17967 | 50.0 | 50.0 | 12 | 150 | #1 | 49529 |
| 2686 | 17968 | 59.2 | 53.9 (191) | 18 | 161 | #2 | 49530 |
| 2687 | 17969 | 67.2 | 50.0 | 27 | 206 | #4 | 49531 |
| 2688 | 17970 | 69.6 | 63.3 | 25 | 332 | #4 | 49532 |
| 2689 | 17971 | 65.6 | 60.0 | 16 | 276 | #4 | 49533 |
| 2690 | 17972 | 68.0 | 60.4 | 18 | 230 | #4 | 49534 |
| 2691 | 17973 | 68.0 | 58.9 | 21 | 250 | #4 | 49535 |
| 2692 | 17974 | 70.4 | 60.7 | 21 | 327 | #5 | 49536 |
| 2693 | 17975 | 73.6 | 64.5 (155) | 18 | 346 | #5 | 49537 |
| 2694 | 17976 | 50.0 | 50.0 | 12 | 150 | #1 | 49538 |
| 2695 | 17977 | 68.0 | 60.7 | 38 | 243 | #4 | 49539 |
| 2696 | 17978 | 69.6 | 62.2 | 23 | 314 | #4 | 49540 |
| 2697 | 17979 | 60.0 | 50.0 (194) | 14 | 157 | #2 | 49541 |
| 2698 | 17980 | 68.8 | 61.5 | 21 | 315 | #4 | 49542 |
| 2699 | 17981 | 72.0 | 60.4 | 31 | 262 | #5 | 49543 |
| 2700 | 17982 | 60.8 | 50.0 | 13 | 173 | #3 | 49544 |
| 2701 | 17983 | 67.2 | 61.8 | 23 | 387 | #4 | 49545 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2702 | 17984 | 58.4 | 55.6 (270) | 13 | 154 | #2 | 49546 |
| 2703 | 17985 | 63.2 | 50.0 | 13 | 188 | #3 | 49547 |
| 2704 | 17986 | 62.4 | 50.0 (265) | 19 | 176 | #3 | 49548 |
| 2705 | 17987 | 74.4 | 63.3 | 28 | 451 | #5 | 49549 |
| 2706 | 17988 | 66.4 | 60.4 | 22 | 237 | #4 | 49550 |
| 2707 | 17989 | 50.0 | 50.0 | 30 | 262 | #1 | 49551 |
| 2708 | 17990 | 64.8 | 58.5 | 20 | 222 | #3 | 49552 |
| 2709 | 17991 | 67.2 | 61.1 | 15 | 306 | #4 | 49553 |
| 2710 | 17992 | 84.0 | 72.7 | 34 | 691 | #7 | 49554 |
| 2711 | 17993 | 70.4 | 63.3 | 26 | 381 | #5 | 49555 |
| 2712 | 17994 | 72.0 | 62.2 | 20 | 327 | #5 | 49556 |
| 2713 | 17995 | 60.6 (99) | — | 12 | 150 | #3 | 49557 |
| 2714 | 17996 | 50.0 | 50.0 | 12 | 150 | #1 | 49558 |
| 2715 | 17997 | 62.4 | 50.2 | 14 | 203 | #3 | 49559 |
| 2716 | 17998 | 62.4 | 50.0 (227) | 13 | 167 | #3 | 49560 |
| 2717 | 17999 | 72.0 | 64.7 | 22 | 471 | #5 | 49561 |
| 2718 | 18000 | 66.4 | 59.3 | 20 | 246 | #4 | 49562 |
| 2719 | 18001 | 64.0 | 50.0 | 15 | 178 | #3 | 49563 |
| 2720 | 18002 | 59.2 | 50.0 | 13 | 164 | #2 | 49564 |
| 2721 | 18003 | 74.4 | 69.9 (209) | 28 | 435 | #5 | 49565 |
| 2722 | 18004 | 60.0 | 57.1 | 13 | 211 | #2 | 49566 |
| 2723 | 18005 | 50.0 | 50.0 | 12 | 150 | #1 | 49567 |
| 2724 | 18006 | 63.2 | 56.0 | 15 | 219 | #3 | 49568 |
| 2725 | 18007 | 68.8 | 60.4 | 20 | 250 | #4 | 49569 |
| 2726 | 18008 | 68.0 | 62.2 | 20 | 264 | #4 | 49570 |
| 2727 | 18009 | 68.0 | 62.2 | 20 | 315 | #4 | 49571 |
| 2728 | 18010 | 59.2 | 50.0 (216) | 12 | 150 | #2 | 49572 |
| 2729 | 18011 | 68.0 | 56.0 | 17 | 214 | #4 | 49573 |
| 2730 | 18012 | 69.6 | 68.7 (150) | 24 | 254 | #4 | 49574 |
| 2731 | 18013 | 72.8 | 62.5 | 40 | 397 | #5 | 49575 |
| 2732 | 18014 | 68.8 | 62.5 | 23 | 305 | #4 | 49576 |
| 2733 | 18015 | 69.6 | 62.2 | 23 | 287 | #4 | 49577 |
| 2734 | 18016 | 50.0 | 50.0 | 12 | 150 | #1 | 49578 |
| 2735 | 18017 | 64.0 | 63.4 (153) | 17 | 185 | #3 | 49579 |
| 2736 | 18018 | 68.0 | 56.7 | 17 | 197 | #4 | 49580 |
| 2737 | 18019 | 64.0 | 58.5 | 15 | 205 | #3 | 49581 |
| 2738 | 18020 | 70.4 | 59.6 | 19 | 243 | #5 | 49582 |
| 2739 | 18021 | 67.2 | 50.0 | 14 | 223 | #4 | 49583 |
| 2740 | 18022 | 70.4 | 62.9 | 20 | 313 | #5 | 49584 |
| 2741 | 18023 | 66.4 | 51.6 | 15 | 185 | #4 | 49585 |
| 2742 | 18024 | 59.2 | 50.0 (168) | 17 | 163 | #2 | 49586 |
| 2743 | 18025 | 80.0 | 62.9 | 30 | 492 | #6 | 49587 |
| 2744 | 18026 | 62.4 | 50.0 | 15 | 160 | #3 | 49588 |
| 2745 | 18027 | 58.4 | 55.6 | 15 | 183 | #2 | 49589 |
| 2746 | 18028 | 71.2 | 62.2 | 22 | 461 | #5 | 49590 |
| 2747 | 18029 | 65.6 | 59.3 | 16 | 259 | #4 | 49591 |
| 2748 | 18030 | 67.2 | 50.0 | 22 | 216 | #4 | 49592 |
| 2749 | 18031 | 68.8 | 59.3 | 24 | 268 | #4 | 49593 |
| 2750 | 18032 | 68.8 | 62.9 | 23 | 352 | #4 | 49594 |
| 2751 | 18033 | 67.2 | 50.0 | 19 | 210 | #4 | 49595 |
| 2752 | 18034 | 64.8 | 59.3 | 17 | 247 | #3 | 49596 |
| 2753 | 18035 | 50.0 | 50.0 | 12 | 150 | #1 | 49597 |
| 2754 | 18036 | 61.6 | 54.7 (150) | 14 | 150 | #3 | 49598 |
| 2755 | 18037 | 72.8 | 63.3 | 34 | 357 | #5 | 49599 |
| 2756 | 18038 | 69.6 | 61.5 | 29 | 297 | #4 | 49600 |
| 2757 | 18039 | 63.2 | 59.6 | 15 | 239 | #3 | 49601 |
| 2758 | 18040 | 70.4 | 64.4 | 20 | 443 | #5 | 49602 |
| 2759 | 18041 | 68.8 | 62.9 | 19 | 382 | #4 | 49603 |
| 2760 | 18042 | 72.8 | 61.1 | 24 | 301 | #5 | 49604 |
| 2761 | 18043 | 68.8 | 60.7 | 19 | 294 | #4 | 49605 |
| 2762 | 18044 | 67.2 | 57.0 (256) | 22 | 215 | #4 | 49606 |
| 2763 | 18045 | 65.6 | 59.3 | 14 | 215 | #4 | 49607 |
| 2764 | 18046 | 50.0 | 50.0 | 12 | 150 | #1 | 49608 |
| 2765 | 18047 | 50.0 | 50.0 | 15 | 150 | #1 | 49609 |
| 2766 | 18048 | 67.2 | 60.4 | 23 | 280 | #4 | 49610 |
| 2767 | 18049 | 69.6 | 59.6 | 19 | 259 | #4 | 49611 |
| 2768 | 18050 | 69.6 | 62.5 | 20 | 313 | #4 | 49612 |
| 2769 | 18051 | 68.8 | 60.7 | 17 | 305 | #4 | 49613 |
| 2770 | 18052 | 61.6 | 50.0 (244) | 13 | 150 | #3 | 49614 |
| 2771 | 18053 | 64.0 | 50.0 | 14 | 195 | #3 | 49615 |
| 2772 | 18054 | 64.8 | 50.0 | 14 | 196 | #3 | 49616 |
| 2773 | 18055 | 68.8 | 65.7 (181) | 26 | 238 | #4 | 49617 |
| 2774 | 18056 | 63.2 | 50.0 (212) | 16 | 158 | #3 | 49618 |
| 2775 | 18057 | 71.2 | 58.2 | 18 | 232 | #5 | 49619 |
| 2776 | 18058 | 71.2 | 64.7 | 20 | 486 | #5 | 49620 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2777 | 18059 | 83.3 (72) | — | 35 | 256 | #7 | 49621 |
| 2778 | 18060 | 65.6 | 59.6 | 17 | 236 | #4 | 49622 |
| 2779 | 18061 | 64.0 | 60.0 | 16 | 218 | #3 | 49623 |
| 2780 | 18062 | 63.2 | 50.0 (176) | 15 | 150 | #3 | 49624 |
| 2781 | 18063 | 70.4 | 60.7 | 36 | 229 | #5 | 49625 |
| 2782 | 18064 | 71.2 | 62.2 | 23 | 318 | #5 | 49626 |
| 2783 | 18065 | 65.6 | 51.3 | 16 | 211 | #4 | 49627 |
| 2784 | 18066 | 50.0 | 50.0 | 12 | 150 | #1 | 49628 |
| 2785 | 18067 | 50.0 | 50.0 | 12 | 150 | #1 | 49629 |
| 2786 | 18068 | 66.4 | 60.0 | 18 | 308 | #4 | 49630 |
| 2787 | 18069 | 65.6 | 60.0 | 18 | 265 | #4 | 49631 |
| 2788 | 18070 | 50.0 | 50.0 | 12 | 150 | #1 | 49632 |
| 2789 | 18071 | 62.4 | 57.5 (273) | 14 | 169 | #3 | 49633 |
| 2790 | 18072 | 67.2 | 56.7 | 16 | 239 | #4 | 49634 |
| 2791 | 18073 | 68.8 | 62.9 | 21 | 409 | #4 | 49635 |
| 2792 | 18074 | 70.4 | 61.8 | 24 | 360 | #5 | 49636 |
| 2793 | 18075 | 63.2 | 53.8 (171) | 15 | 171 | #3 | 49637 |
| 2794 | 18076 | 67.2 | 60.0 | 25 | 294 | #4 | 49638 |
| 2795 | 18077 | 50.0 (112) | — | 12 | 150 | #1 | 49639 |
| 2796 | 18078 | 64.0 | 57.5 | 19 | 208 | #3 | 49640 |
| 2797 | 18079 | 63.2 | 58.5 | 18 | 215 | #3 | 49641 |
| 2798 | 18080 | 67.2 | 58.5 | 18 | 207 | #4 | 49642 |
| 2799 | 18081 | 72.8 | 63.6 | 26 | 356 | #5 | 49643 |
| 2800 | 18082 | 68.0 | 60.9 (248) | 18 | 247 | #4 | 49644 |
| 2801 | 18083 | 59.2 | 57.5 | 13 | 176 | #2 | 49645 |
| 2802 | 18084 | 64.0 | 54.5 | 13 | 198 | #3 | 49646 |
| 2803 | 18085 | 65.6 | 59.6 | 17 | 254 | #4 | 49647 |
| 2804 | 18086 | 68.8 | 61.1 | 19 | 283 | #4 | 49648 |
| 2805 | 18087 | 79.2 | 64.0 | 21 | 469 | #6 | 49649 |
| 2806 | 18088 | 70.4 | 63.3 | 21 | 393 | #5 | 49650 |
| 2807 | 18089 | 65.6 | 59.3 | 19 | 235 | #4 | 49651 |
| 2808 | 18090 | 50.0 | 50.0 | 12 | 150 | #1 | 49652 |
| 2809 | 18091 | 68.8 | 63.6 | 26 | 555 | #4 | 49653 |
| 2810 | 18092 | 50.0 | 50.0 | 12 | 150 | #1 | 49654 |
| 2811 | 18093 | 84.0 | 65.5 | 27 | 556 | #7 | 49655 |
| 2812 | 18094 | 71.2 | 62.9 | 29 | 378 | #5 | 49656 |
| 2813 | 18095 | 72.8 | 64.4 | 28 | 379 | #5 | 49657 |
| 2814 | 18096 | 67.2 | 56.7 | 23 | 238 | #4 | 49658 |
| 2815 | 18097 | 68.8 | 60.7 | 14 | 234 | #4 | 49659 |
| 2816 | 18098 | 71.2 | 62.2 | 21 | 262 | #5 | 49660 |
| 2817 | 18099 | 66.4 | 59.3 | 16 | 235 | #4 | 49661 |
| 2818 | 18100 | 50.0 | 50.0 | 12 | 150 | #1 | 49662 |
| 2819 | 18101 | 68.8 | 59.3 | 26 | 251 | #4 | 49663 |
| 2820 | 18102 | 68.0 | 60.0 | 18 | 263 | #4 | 49664 |
| 2821 | 18103 | 50.0 | 50.0 | 12 | 150 | #1 | 49665 |
| 2822 | 18104 | 65.6 | 50.0 (271) | 13 | 184 | #4 | 49666 |
| 2823 | 18105 | 69.6 | 61.8 | 25 | 285 | #4 | 49667 |
| 2824 | 18106 | 70.4 | 62.2 | 21 | 335 | #5 | 49668 |
| 2825 | 18107 | 61.6 | 57.8 | 19 | 186 | #3 | 49669 |
| 2826 | 18108 | 60.8 | 50.0 | 12 | 157 | #3 | 49670 |
| 2827 | 18109 | 68.8 | 62.2 | 18 | 294 | #4 | 49671 |
| 2828 | 18110 | 67.2 | 60.4 | 18 | 255 | #4 | 49672 |
| 2829 | 18111 | 71.2 | 63.6 | 25 | 609 | #5 | 49673 |
| 2830 | 18112 | 76.0 | 65.5 | 26 | 447 | #6 | 49674 |
| 2831 | 18113 | 69.6 | 58.9 | 24 | 282 | #4 | 49675 |
| 2832 | 18114 | 64.8 | 59.7 (191) | 24 | 202 | #3 | 49676 |
| 2833 | 18115 | 66.4 | 57.4 (242) | 20 | 196 | #4 | 49677 |
| 2834 | 18116 | 68.0 | 60.4 | 18 | 248 | #4 | 49678 |
| 2835 | 18117 | 68.0 | 62.2 | 18 | 304 | #4 | 49679 |
| 2836 | 18118 | 76.0 | 71.0 (169) | 21 | 358 | #6 | 49680 |
| 2837 | 18119 | 60.8 | 56.0 | 16 | 187 | #3 | 49681 |
| 2838 | 18120 | 58.4 | 50.0 | 12 | 153 | #2 | 49682 |
| 2839 | 18121 | 73.6 | 63.6 | 40 | 341 | #5 | 49683 |
| 2840 | 18122 | 50.0 (89) | — | 12 | 150 | #1 | 49684 |
| 2841 | 18123 | 64.8 | 57.1 | 12 | 210 | #3 | 49685 |
| 2842 | 18124 | 64.0 | 52.7 | 18 | 200 | #3 | 49686 |
| 2843 | 18125 | 50.0 | 50.0 (252) | 12 | 150 | #1 | 49687 |
| 2844 | 18126 | 50.0 | 50.0 | 12 | 150 | #1 | 49688 |
| 2845 | 18127 | 68.8 | 61.5 | 19 | 390 | #4 | 49689 |
| 2846 | 18128 | 50.0 | 50.0 | 12 | 150 | #1 | 49690 |
| 2847 | 18129 | 61.6 | 52.1 (261) | 18 | 170 | #3 | 49691 |
| 2848 | 18130 | 80.8 | 75.3 | 23 | 1135 | #7 | 49692 |
| 2849 | 18131 | 65.6 | 59.3 | 17 | 218 | #4 | 49693 |
| 2850 | 18132 | 65.6 | 50.0 | 27 | 215 | #4 | 49694 |
| 2851 | 18133 | 67.2 | 57.8 | 16 | 241 | #4 | 49695 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2852 | 18134 | 69.6 | 61.5 | 23 | 310 | #4 | 49696 |
| 2853 | 18135 | 63.2 | 50.0 | 15 | 193 | #3 | 49697 |
| 2854 | 18136 | 64.8 | 50.0 | 13 | 204 | #3 | 49698 |
| 2855 | 18137 | 50.0 | 50.0 | 12 | 150 | #1 | 49699 |
| 2856 | 18138 | 66.4 | 60.0 | 17 | 316 | #4 | 49700 |
| 2857 | 18139 | 64.0 | 58.5 | 15 | 206 | #3 | 49701 |
| 2858 | 18140 | 66.4 | 59.3 | 16 | 218 | #4 | 49702 |
| 2859 | 18141 | 68.0 | 59.6 | 18 | 255 | #4 | 49703 |
| 2860 | 18142 | 66.4 | 50.0 | 14 | 234 | #4 | 49704 |
| 2861 | 18143 | 68.0 | 57.8 | 17 | 220 | #4 | 49705 |
| 2862 | 18144 | 61.6 | 50.0 | 12 | 205 | #3 | 49706 |
| 2863 | 18145 | 56.7 (97) | — | 25 | 150 | #2 | 49707 |
| 2864 | 18146 | 68.0 | 63.3 | 20 | 393 | #4 | 49708 |
| 2865 | 18147 | 64.8 | 60.7 | 19 | 270 | #3 | 49709 |
| 2866 | 18148 | 64.0 | 62.0 (129) | 31 | 172 | #3 | 49710 |
| 2867 | 18149 | 62.4 | 50.0 | 15 | 177 | #3 | 49711 |
| 2868 | 18150 | 54.4 | 50.0 | 12 | 150 | #1 | 49712 |
| 2869 | 18151 | 64.0 | 58.2 | 14 | 199 | #3 | 49713 |
| 2870 | 18152 | 65.6 | 50.0 | 15 | 191 | #4 | 49714 |
| 2871 | 18153 | 69.6 | 62.2 | 19 | 288 | #4 | 49715 |
| 2872 | 18154 | 62.4 | 50.0 | 12 | 185 | #3 | 49716 |
| 2873 | 18155 | 50.0 | 50.0 | 12 | 150 | #1 | 49717 |
| 2874 | 18156 | 66.4 | 53.5 (230) | 20 | 191 | #4 | 49718 |
| 2875 | 18157 | 60.8 | 52.2 (182) | 15 | 153 | #3 | 49719 |
| 2876 | 18158 | 66.4 | 59.6 | 22 | 219 | #4 | 49720 |
| 2877 | 18159 | 78.4 | 65.5 | 20 | 484 | #6 | 49721 |
| 2878 | 18160 | 65.6 | 50.0 | 18 | 215 | #4 | 49722 |
| 2879 | 18161 | 72.8 | 62.9 | 27 | 392 | #5 | 49723 |
| 2880 | 18162 | 70.4 | 61.7 (256) | 19 | 249 | #5 | 49724 |
| 2881 | 18163 | 70.4 | 62.5 | 22 | 447 | #5 | 49725 |
| 2882 | 18164 | 59.2 | 50.0 | 12 | 156 | #2 | 49726 |
| 2883 | 18165 | 64.8 | 59.7 (196) | 16 | 173 | #3 | 49727 |
| 2884 | 18166 | 67.2 | 61.1 | 18 | 276 | #4 | 49728 |
| 2885 | 18167 | 57.6 | 50.0 | 38 | 191 | #2 | 49729 |
| 2886 | 18168 | 72.0 | 60.0 | 23 | 268 | #5 | 49730 |
| 2887 | 18169 | 50.0 | 50.0 | 12 | 150 | #1 | 49731 |
| 2888 | 18170 | 62.4 | 59.3 | 13 | 217 | #3 | 49732 |
| 2889 | 18171 | 68.8 | 62.5 | 20 | 437 | #4 | 49733 |
| 2890 | 18172 | 68.8 | 60.0 | 39 | 266 | #4 | 49734 |
| 2891 | 18173 | 65.6 | 60.7 | 18 | 279 | #4 | 49735 |
| 2892 | 18174 | 62.4 | 56.9 (195) | 14 | 157 | #3 | 49736 |
| 2893 | 18175 | 64.8 | 55.4 (233) | 21 | 179 | #3 | 49737 |
| 2894 | 18176 | 68.8 | 62.2 | 20 | 332 | #4 | 49738 |
| 2895 | 18177 | 64.8 | 53.0 (198) | 18 | 179 | #3 | 49739 |
| 2896 | 18178 | 68.0 | 60.0 | 17 | 287 | #4 | 49740 |
| 2897 | 18179 | 69.6 | 59.3 | 23 | 357 | #4 | 49741 |
| 2898 | 18180 | 63.2 | 56.7 | 17 | 191 | #3 | 49742 |
| 2899 | 18181 | 68.8 | 62.5 | 21 | 394 | #4 | 49743 |
| 2900 | 18182 | 68.0 | 58.5 | 17 | 254 | #4 | 49744 |
| 2901 | 18183 | 63.2 | 61.5 (179) | 18 | 188 | #3 | 49745 |
| 2902 | 18184 | 68.0 | 60.0 | 15 | 242 | #4 | 49746 |
| 2903 | 18185 | 64.0 | 59.9 (202) | 16 | 172 | #3 | 49747 |
| 2904 | 18186 | 68.0 | 61.8 | 19 | 346 | #4 | 49748 |
| 2905 | 18187 | 67.2 | 61.1 | 19 | 304 | #4 | 49749 |
| 2906 | 18188 | 50.0 | 50.0 (144) | 12 | 150 | #1 | 49750 |
| 2907 | 18189 | 65.6 | 53.7 (255) | 20 | 195 | #4 | 49751 |
| 2908 | 18190 | 66.4 | 59.6 | 24 | 247 | #4 | 49752 |
| 2909 | 18191 | 69.6 | 62.5 | 21 | 324 | #4 | 49753 |
| 2910 | 18192 | 68.0 | 59.3 | 25 | 230 | #4 | 49754 |
| 2911 | 18193 | 68.0 | 62.2 | 22 | 307 | #4 | 49755 |
| 2912 | 18194 | 69.6 | 60.7 | 24 | 260 | #4 | 49756 |
| 2913 | 18195 | 68.0 | 59.6 | 19 | 257 | #4 | 49757 |
| 2914 | 18196 | 68.8 | 61.8 | 19 | 281 | #4 | 49758 |
| 2915 | 18197 | 68.0 | 62.5 | 22 | 392 | #4 | 49759 |
| 2916 | 18198 | 64.8 | 57.2 (152) | 18 | 182 | #3 | 49760 |
| 2917 | 18199 | 72.8 | 62.2 | 28 | 328 | #5 | 49761 |
| 2918 | 18200 | 52.8 | 50.0 | 12 | 150 | #1 | 49762 |
| 2919 | 18201 | 68.0 | 59.6 | 25 | 264 | #4 | 49763 |
| 2920 | 18202 | 69.6 | 60.7 | 20 | 299 | #4 | 49764 |
| 2921 | 18203 | 65.6 | 57.5 | 18 | 190 | #4 | 49765 |
| 2922 | 18204 | 50.0 | 50.0 | 12 | 150 | #1 | 49766 |
| 2923 | 18205 | 69.6 | 61.8 | 36 | 305 | #4 | 49767 |
| 2924 | 18206 | 62.4 | 50.0 (213) | 28 | 160 | #3 | 49768 |
| 2925 | 18207 | 64.0 | 57.5 | 13 | 201 | #3 | 49769 |
| 2926 | 18208 | 50.0 | 50.0 (154) | 14 | 150 | #1 | 49770 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 2927 | 18209 | 59.2 | 50.0 | 12 | 150 | #2 | 49771 |
| 2928 | 18210 | 65.6 | 58.6 (237) | 20 | 199 | #4 | 49772 |
| 2929 | 18211 | 72.0 | 64.4 | 27 | 746 | #5 | 49773 |
| 2930 | 18212 | 66.4 | 58.5 | 16 | 217 | #4 | 49774 |
| 2931 | 18213 | 50.0 | 50.0 | 12 | 150 | #1 | 49775 |
| 2932 | 18214 | 68.0 | 59.3 | 16 | 248 | #4 | 49776 |
| 2933 | 18215 | 50.0 | 50.0 | 12 | 150 | #1 | 49777 |
| 2934 | 18216 | 50.0 | 50.0 | 12 | 150 | #1 | 49778 |
| 2935 | 18217 | 89.6 | 67.3 | 32 | 807 | #8 | 49779 |
| 2936 | 18218 | 68.0 | 61.5 | 31 | 279 | #4 | 49780 |
| 2937 | 18219 | 69.6 | 60.4 | 20 | 298 | #4 | 49781 |
| 2938 | 18220 | 50.0 | 50.0 | 12 | 150 | #1 | 49782 |
| 2939 | 18221 | 73.9 (69) | — | 32 | 183 | #5 | 49783 |
| 2940 | 18222 | 66.4 | 61.3 (186) | 21 | 194 | #4 | 49784 |
| 2941 | 18223 | 61.6 | 50.0 | 14 | 189 | #3 | 49785 |
| 2942 | 18224 | 50.0 (86) | — | 12 | 150 | #1 | 49786 |
| 2943 | 18225 | 72.8 | 62.2 | 24 | 307 | #5 | 49787 |
| 2944 | 18226 | 63.2 | 56.0 | 17 | 204 | #3 | 49788 |
| 2945 | 18227 | 64.8 | 60.0 | 19 | 223 | #3 | 49789 |
| 2946 | 18228 | 67.2 | 50.0 | 15 | 218 | #4 | 49790 |
| 2947 | 18229 | 66.4 | 58.5 | 18 | 221 | #4 | 49791 |
| 2948 | 18230 | 66.4 | 55.6 | 19 | 209 | #4 | 49792 |
| 2949 | 18231 | 71.2 | 63.6 | 24 | 414 | #5 | 49793 |
| 2950 | 18232 | 66.4 | 60.7 (211) | 25 | 219 | #4 | 49794 |
| 2951 | 18233 | 67.2 | 57.8 | 14 | 222 | #4 | 49795 |
| 2952 | 18234 | 68.0 | 60.7 | 18 | 219 | #4 | 49796 |
| 2953 | 18235 | 64.0 | 50.9 | 15 | 182 | #3 | 49797 |
| 2954 | 18236 | 72.8 | 66.2 | 21 | 447 | #5 | 49798 |
| 2955 | 18237 | 69.6 | 58.9 | 35 | 265 | #4 | 49799 |
| 2956 | 18238 | 59.2 | 51.6 | 12 | 176 | #2 | 49800 |
| 2957 | 18239 | 50.0 | 50.0 (260) | 12 | 150 | #1 | 49801 |
| 2958 | 18240 | 50.0 | 50.0 | 12 | 150 | #1 | 49802 |
| 2959 | 18241 | 76.0 | 64.7 | 27 | 435 | #6 | 49803 |
| 2960 | 18242 | 67.2 | 59.6 | 19 | 293 | #4 | 49804 |
| 2961 | 18243 | 66.7 (96) | — | 16 | 153 | #4 | 49805 |
| 2962 | 18244 | 60.0 | 50.0 (164) | 13 | 150 | #2 | 49806 |
| 2963 | 18245 | 65.6 | 55.1 (176) | 18 | 193 | #4 | 49807 |
| 2964 | 18246 | 69.6 | 62.9 | 23 | 322 | #4 | 49808 |
| 2965 | 18247 | 65.6 | 62.0 (158) | 21 | 214 | #4 | 49809 |
| 2966 | 18248 | 58.3 (108) | — | 17 | 166 | #2 | 49810 |
| 2967 | 18249 | 64.0 | 50.0 | 13 | 171 | #3 | 49811 |
| 2968 | 18250 | 50.0 | 50.0 | 12 | 150 | #1 | 49812 |
| 2969 | 18251 | 68.0 | 50.0 | 20 | 186 | #4 | 49813 |
| 2970 | 18252 | 71.2 | 60.0 | 30 | 267 | #5 | 49814 |
| 2971 | 18253 | 65.6 | 58.9 | 20 | 242 | #4 | 49815 |
| 2972 | 18254 | 64.0 | 60.0 | 20 | 274 | #3 | 49816 |
| 2973 | 18255 | 64.0 | 58.0 (174) | 19 | 190 | #3 | 49817 |
| 2974 | 18256 | 76.8 | 58.9 | 22 | 425 | #6 | 49818 |
| 2975 | 18257 | 66.4 | 58.3 (211) | 18 | 213 | #4 | 49819 |
| 2976 | 18258 | 68.0 | 60.4 | 21 | 276 | #4 | 49820 |
| 2977 | 18259 | 64.0 | 57.8 | 29 | 260 | #3 | 49821 |
| 2978 | 18260 | 67.2 | 57.1 | 24 | 245 | #4 | 49822 |
| 2979 | 18261 | 50.0 | 50.0 | 12 | 150 | #1 | 49823 |
| 2980 | 18262 | 69.6 | 60.7 | 24 | 272 | #4 | 49824 |
| 2981 | 18263 | 66.4 | 59.6 | 19 | 219 | #4 | 49825 |
| 2982 | 18264 | 50.0 | 50.0 | 12 | 150 | #1 | 49826 |
| 2983 | 18265 | 63.2 | 50.0 | 13 | 188 | #3 | 49827 |
| 2984 | 18266 | 67.2 | 58.9 | 17 | 237 | #4 | 49828 |
| 2985 | 18267 | 67.2 | 55.6 | 19 | 215 | #4 | 49829 |
| 2986 | 18268 | 69.6 | 60.0 | 26 | 242 | #4 | 49830 |
| 2987 | 18269 | 83.2 | 78.1 (242) | 20 | 745 | #7 | 49831 |
| 2988 | 18270 | 66.4 | 59.6 | 18 | 244 | #4 | 49832 |
| 2989 | 18271 | 50.0 | 50.0 | 12 | 150 | #1 | 49833 |
| 2990 | 18272 | 70.4 | 62.2 | 20 | 303 | #5 | 49834 |
| 2991 | 18273 | 63.2 | 58.9 | 13 | 211 | #3 | 49835 |
| 2992 | 18274 | 67.2 | 57.1 | 17 | 206 | #4 | 49836 |
| 2993 | 18275 | 72.0 | 62.9 | 28 | 475 | #5 | 49837 |
| 2994 | 18276 | 71.2 | 62.5 | 34 | 330 | #5 | 49838 |
| 2995 | 18277 | 70.4 | 63.3 | 22 | 402 | #5 | 49839 |
| 2996 | 18278 | 68.8 | 63.6 (195) | 24 | 257 | #4 | 49840 |
| 2997 | 18279 | 65.6 | 59.3 | 17 | 214 | #4 | 49841 |
| 2998 | 18280 | 70.4 | 63.3 | 13 | 362 | #5 | 49842 |
| 2999 | 18281 | 61.6 | 58.2 | 12 | 180 | #3 | 49843 |
| 3000 | 18282 | 62.4 | 58.2 | 12 | 201 | #3 | 49844 |
| 3001 | 18283 | 68.0 | 62.2 | 18 | 255 | #4 | 49845 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3002 | 18284 | 76.0 | 62.2 | 21 | 312 | #6 | 49846 |
| 3003 | 18285 | 88.0 | 87.5 (136) | 26 | 522 | #8 | 49847 |
| 3004 | 18286 | 50.0 | 50.0 | 12 | 150 | #1 | 49848 |
| 3005 | 18287 | 63.2 | 50.0 | 13 | 173 | #3 | 49849 |
| 3006 | 18288 | 50.0 | 50.0 | 12 | 150 | #1 | 49850 |
| 3007 | 18289 | 65.6 | 58.2 | 22 | 207 | #4 | 49851 |
| 3008 | 18290 | 67.2 | 57.8 | 19 | 194 | #4 | 49852 |
| 3009 | 18291 | 50.0 | 50.0 | 12 | 150 | #1 | 49853 |
| 3010 | 18292 | 60.8 | 57.1 | 15 | 187 | #3 | 49854 |
| 3011 | 18293 | 68.0 | 60.4 | 27 | 250 | #4 | 49855 |
| 3012 | 18294 | 70.4 | 62.9 | 21 | 499 | #5 | 49856 |
| 3013 | 18295 | 63.2 | 50.0 | 13 | 192 | #3 | 49857 |
| 3014 | 18296 | 66.4 | 58.2 | 20 | 223 | #4 | 49858 |
| 3015 | 18297 | 67.2 | 61.8 | 17 | 254 | #4 | 49859 |
| 3016 | 18298 | 67.2 | 60.7 | 17 | 286 | #4 | 49860 |
| 3017 | 18299 | 64.0 | 60.0 | 16 | 235 | #3 | 49861 |
| 3018 | 18300 | 71.2 | 63.6 | 25 | 612 | #5 | 49862 |
| 3019 | 18301 | 50.0 | 50.0 (158) | 12 | 150 | #1 | 49863 |
| 3020 | 18302 | 64.8 | 59.5 (158) | 17 | 177 | #3 | 49864 |
| 3021 | 18303 | 67.2 | 57.8 | 16 | 241 | #4 | 49865 |
| 3022 | 18304 | 62.4 | 50.0 | 15 | 193 | #3 | 49866 |
| 3023 | 18305 | 74.4 | 65.8 | 30 | 527 | #5 | 49867 |
| 3024 | 18306 | 68.8 | 60.0 | 22 | 272 | #4 | 49868 |
| 3025 | 18307 | 63.2 | 50.0 | 17 | 182 | #3 | 49869 |
| 3026 | 18308 | 71.2 | 62.5 | 29 | 368 | #5 | 49870 |
| 3027 | 18309 | 79.2 | 67.6 | 26 | 490 | #6 | — |
| 3028 | 18310 | 72.0 | 62.5 | 22 | 325 | #5 | 49871 |
| 3029 | 18311 | 68.0 | 60.4 | 19 | 276 | #4 | 49872 |
| 3030 | 18312 | 72.0 | 54.9 | 30 | 305 | #5 | 49873 |
| 3031 | 18313 | 61.6 | 50.0 | 14 | 177 | #3 | 49874 |
| 3032 | 18314 | 64.0 | 50.0 | 13 | 157 | #3 | 49875 |
| 3033 | 18315 | 61.6 | 54.0 (161) | 15 | 160 | #3 | 49876 |
| 3034 | 18316 | 64.0 | 59.3 | 19 | 216 | #3 | 49877 |
| 3035 | 18317 | 67.2 | 58.9 | 19 | 262 | #4 | 49878 |
| 3036 | 18318 | 72.8 | 65.1 | 24 | 560 | #5 | 49879 |
| 3037 | 18319 | 73.6 | 61.5 | 25 | 352 | #5 | 49880 |
| 3038 | 18320 | 62.4 | 58.2 | 15 | 210 | #3 | 49881 |
| 3039 | 18321 | 68.8 | 50.0 | 18 | 248 | #4 | 49882 |
| 3040 | 18322 | 63.2 | 62.8 (129) | 17 | 164 | #3 | 49883 |
| 3041 | 18323 | 72.8 | 64.0 | 25 | 397 | #5 | 49884 |
| 3042 | 18324 | 64.0 | 63.0 (127) | 16 | 159 | #3 | 49885 |
| 3043 | 18325 | 72.0 | 61.1 | 30 | 320 | #5 | 49886 |
| 3044 | 18326 | 59.2 | 50.0 | 20 | 184 | #2 | 49887 |
| 3045 | 18327 | 63.2 | 50.0 | 15 | 174 | #3 | 49888 |
| 3046 | 18328 | 50.0 | 50.0 | 12 | 150 | #1 | 49889 |
| 3047 | 18329 | 68.0 | 61.1 | 25 | 281 | #4 | 49890 |
| 3048 | 18330 | 70.4 | 62.2 | 30 | 359 | #5 | 49891 |
| 3049 | 18331 | 69.6 | 60.4 | 23 | 269 | #4 | 49892 |
| 3050 | 18332 | 50.0 | 50.0 (258) | 12 | 150 | #1 | 49893 |
| 3051 | 18333 | 67.2 | 57.5 (261) | 19 | 203 | #4 | 49894 |
| 3052 | 18334 | 65.6 | 58.4 (166) | 15 | 189 | #4 | 49895 |
| 3053 | 18335 | 63.2 | 50.0 | 18 | 156 | #3 | 49896 |
| 3054 | 18336 | 50.0 | 50.0 | 12 | 150 | #1 | 49897 |
| 3055 | 18337 | 50.0 | 50.0 | 12 | 150 | #1 | 49898 |
| 3056 | 18338 | 50.0 | 50.0 | 12 | 150 | #1 | 49899 |
| 3057 | 18339 | 67.2 | 53.8 | 16 | 202 | #4 | 49900 |
| 3058 | 18340 | 67.2 | 61.5 | 18 | 283 | #4 | 49901 |
| 3059 | 18341 | 68.8 | 60.7 | 20 | 251 | #4 | 49902 |
| 3060 | 18342 | 69.6 | 63.3 | 24 | 314 | #4 | 49903 |
| 3061 | 18343 | 66.4 | 61.5 | 18 | 246 | #4 | 49904 |
| 3062 | 18344 | 67.2 | 60.4 | 23 | 244 | #4 | 49905 |
| 3063 | 18345 | 68.0 | 61.8 | 18 | 400 | #4 | 49906 |
| 3064 | 18346 | 65.6 | 53.1 | 15 | 223 | #4 | 49907 |
| 3065 | 18347 | 63.2 | 56.3 (190) | 25 | 176 | #3 | 49908 |
| 3066 | 18348 | 66.4 | 58.9 | 22 | 248 | #4 | 49909 |
| 3067 | 18349 | 62.4 | 50.2 | 17 | 184 | #3 | 49910 |
| 3068 | 18350 | 64.0 | 58.5 | 17 | 229 | #3 | 49911 |
| 3069 | 18351 | 65.6 | 59.6 | 16 | 225 | #4 | 49912 |
| 3070 | 18352 | 62.4 | 50.9 (169) | 19 | 160 | #3 | 49913 |
| 3071 | 18353 | 67.2 | 58.9 | 17 | 223 | #4 | 49914 |
| 3072 | 18354 | 50.0 (71) | — | 12 | 150 | #1 | 49915 |
| 3073 | 18355 | 67.2 | 56.4 | 14 | 203 | #4 | 49916 |
| 3074 | 18356 | 64.0 | 58.2 | 26 | 218 | #3 | 49917 |
| 3075 | 18357 | 59.2 | 56.4 | 14 | 197 | #2 | 49918 |
| 3076 | 18358 | 69.6 | 65.0 (177) | 24 | 241 | #4 | 49919 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3077 | 18359 | 50.0 | 50.0 | 12 | 150 | #1 | 49920 |
| 3078 | 18360 | 50.0 (75) | — | 12 | 150 | #1 | 49921 |
| 3079 | 18361 | 65.6 | 57.1 | 13 | 325 | #4 | 49922 |
| 3080 | 18362 | 68.8 | 63.3 | 24 | 362 | #4 | 49923 |
| 3081 | 18363 | 59.2 | 57.5 | 15 | 175 | #2 | 49924 |
| 3082 | 18364 | 71.2 | 61.1 | 23 | 325 | #5 | 49925 |
| 3083 | 18365 | 67.2 | 61.1 | 20 | 338 | #4 | 49926 |
| 3084 | 18366 | 65.6 | 59.3 | 14 | 221 | #4 | 49927 |
| 3085 | 18367 | 67.2 | 59.6 | 22 | 229 | #4 | 49928 |
| 3086 | 18368 | 64.0 | 58.9 | 15 | 212 | #3 | 49929 |
| 3087 | 18369 | 65.6 | 58.2 | 16 | 221 | #4 | 49930 |
| 3088 | 18370 | 67.2 | 58.5 | 19 | 210 | #4 | 49931 |
| 3089 | 18371 | 67.2 | 55.6 | 14 | 171 | #4 | 49932 |
| 3090 | 18372 | 50.0 | 50.0 | 12 | 150 | #1 | 49933 |
| 3091 | 18373 | 69.6 | 61.8 | 22 | 571 | #4 | 49934 |
| 3092 | 18374 | 68.0 | 61.1 | 24 | 350 | #4 | 49935 |
| 3093 | 18375 | 66.4 | 61.8 | 20 | 315 | #4 | 49936 |
| 3094 | 18376 | 69.6 | 54.2 | 21 | 228 | #4 | 49937 |
| 3095 | 18377 | 64.8 | 51.6 | 14 | 192 | #3 | 49938 |
| 3096 | 18378 | 97.6 | 72.2 (252) | 60 | 878 | #10 | 49939 |
| 3097 | 18379 | 69.6 | 62.9 (205) | 25 | 239 | #4 | 49940 |
| 3098 | 18380 | 64.8 | 50.0 (234) | 16 | 169 | #3 | 49941 |
| 3099 | 18381 | 77.6 | 61.1 | 30 | 391 | #6 | 49942 |
| 3100 | 18382 | 50.0 | 50.0 | 12 | 150 | #1 | 49943 |
| 3101 | 18383 | 68.8 | 60.7 | 19 | 276 | #4 | 49944 |
| 3102 | 18384 | 69.6 | 63.6 | 32 | 411 | #4 | 49945 |
| 3103 | 18385 | 63.2 | 50.0 | 16 | 196 | #3 | 49946 |
| 3104 | 18386 | 66.4 | 59.5 (257) | 17 | 185 | #4 | 49947 |
| 3105 | 18387 | 66.4 | 60.7 | 24 | 242 | #4 | 49948 |
| 3106 | 18388 | 64.0 | 50.0 | 38 | 187 | #3 | 49949 |
| 3107 | 18389 | 80.0 | 75.6 | 32 | 665 | #6 | 49950 |
| 3108 | 18390 | 64.8 | 61.7 (133) | 14 | 168 | #3 | 49951 |
| 3109 | 18391 | 50.0 (72) | — | 12 | 150 | #1 | — |
| 3110 | 18392 | 76.0 | 64.7 | 28 | 436 | #6 | 49952 |
| 3111 | 18393 | 50.0 | 50.0 | 12 | 150 | #1 | 49953 |
| 3112 | 18394 | 50.0 (99) | — | 12 | 150 | #1 | 49954 |
| 3113 | 18395 | 64.0 | 58.5 | 17 | 197 | #3 | 49955 |
| 3114 | 18396 | 50.0 | 50.0 | 12 | 150 | #1 | 49956 |
| 3115 | 18397 | 50.0 | 50.0 | 12 | 150 | #1 | 49957 |
| 3116 | 18398 | 63.2 | 58.2 | 13 | 192 | #3 | 49958 |
| 3117 | 18399 | 80.8 | 59.6 | 18 | 462 | #7 | 49959 |
| 3118 | 18400 | 71.2 | 62.5 | 21 | 309 | #5 | 49960 |
| 3119 | 18401 | 65.6 | 57.8 | 16 | 200 | #4 | 49961 |
| 3120 | 18402 | 62.4 | 50.0 | 12 | 165 | #3 | 49962 |
| 3121 | 18403 | 64.0 | 57.1 | 14 | 185 | #3 | 49963 |
| 3122 | 18404 | 50.0 | 50.0 | 12 | 150 | #1 | 49964 |
| 3123 | 18405 | 50.0 | 50.0 | 12 | 150 | #1 | 49965 |
| 3124 | 18406 | 76.0 | 66.5 | 25 | 458 | #6 | 49966 |
| 3125 | 18407 | 68.0 | 62.2 | 20 | 336 | #4 | 49967 |
| 3126 | 18408 | 70.4 | 63.6 | 22 | 457 | #5 | 49968 |
| 3127 | 18409 | 50.0 | 50.0 | 12 | 150 | #1 | 49969 |
| 3128 | 18410 | 66.3 (92) | — | 31 | 169 | #4 | 49970 |
| 3129 | 18411 | 50.0 | 50.0 | 13 | 155 | #1 | 49971 |
| 3130 | 18412 | 67.2 | 58.3 (254) | 18 | 218 | #4 | 49972 |
| 3131 | 18413 | 65.6 | 59.8 (189) | 20 | 182 | #4 | 49973 |
| 3132 | 18414 | 64.8 | 58.5 | 17 | 224 | #3 | 49974 |
| 3133 | 18415 | 61.6 | 61.1 (167) | 14 | 156 | #3 | 49975 |
| 3134 | 18416 | 68.8 | 60.7 | 20 | 312 | #4 | 49976 |
| 3135 | 18417 | 73.6 | 62.5 | 22 | 428 | #5 | 49977 |
| 3136 | 18418 | 50.0 | 50.0 | 12 | 150 | #1 | 49978 |
| 3137 | 18419 | 63.2 | 58.9 | 14 | 203 | #3 | 49979 |
| 3138 | 18420 | 72.8 | 65.5 | 27 | 503 | #5 | 49980 |
| 3139 | 18421 | 66.4 | 58.5 | 15 | 229 | #4 | 49981 |
| 3140 | 18422 | 50.0 | 50.0 | 12 | 150 | #1 | 49982 |
| 3141 | 18423 | 70.4 (81) | — | 21 | 181 | #5 | 49983 |
| 3142 | 18424 | 65.6 | 57.5 | 20 | 236 | #4 | 49984 |
| 3143 | 18425 | 63.2 | 52.7 | 12 | 221 | #3 | 49985 |
| 3144 | 18426 | 74.4 | 66.2 | 38 | 550 | #5 | 49986 |
| 3145 | 18427 | 68.8 | 61.8 | 20 | 321 | #4 | 49987 |
| 3146 | 18428 | 67.2 | 61.1 | 24 | 303 | #4 | 49988 |
| 3147 | 18429 | 70.4 | 64.0 | 22 | 368 | #5 | 49989 |
| 3148 | 18430 | 68.0 | 59.3 | 20 | 263 | #4 | 49990 |
| 3149 | 18431 | 64.8 | 50.0 (255) | 16 | 195 | #3 | 49991 |
| 3150 | 18432 | 63.2 | 50.0 | 13 | 169 | #3 | 49992 |
| 3151 | 18433 | 70.4 | 62.9 | 20 | 491 | #5 | 49993 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3152 | 18434 | 68.8 | 60.0 | 18 | 274 | #4 | 49994 |
| 3153 | 18435 | 50.0 (120) | — | 12 | 150 | #1 | 49995 |
| 3154 | 18436 | 66.4 | 54.9 (266) | 19 | 209 | #4 | 49996 |
| 3155 | 18437 | 61.6 | 57.8 | 12 | 203 | #3 | 49997 |
| 3156 | 18438 | 84.0 | 75.6 | 29 | 698 | #7 | 49998 |
| 3157 | 18439 | 86.4 | 61.1 | 33 | 504 | #8 | 49999 |
| 3158 | 18440 | 64.0 | 50.0 | 15 | 177 | #3 | 50000 |
| 3159 | 18441 | 50.0 | 50.0 | 12 | 150 | #1 | 50001 |
| 3160 | 18442 | 85.6 | 77.8 | 32 | 885 | #8 | 50002 |
| 3161 | 18443 | 66.4 | 53.1 | 15 | 245 | #4 | 50003 |
| 3162 | 18444 | 72.0 | 62.9 | 23 | 348 | #5 | 50004 |
| 3163 | 18445 | 65.6 | 52.6 (249) | 19 | 193 | #4 | 50005 |
| 3164 | 18446 | 66.4 | 60.0 | 19 | 237 | #4 | 50006 |
| 3165 | 18447 | 63.2 | 50.0 | 12 | 193 | #3 | 50007 |
| 3166 | 18448 | 50.0 | 50.0 | 12 | 150 | #1 | 50008 |
| 3167 | 18449 | 65.6 | 60.4 | 13 | 215 | #4 | 50009 |
| 3168 | 18450 | 62.4 | 50.0 | 14 | 210 | #3 | 50010 |
| 3169 | 18451 | 68.0 | 59.6 | 19 | 267 | #4 | 50011 |
| 3170 | 18452 | 69.6 | 62.2 | 18 | 289 | #4 | 50012 |
| 3171 | 18453 | 50.0 | 50.0 | 12 | 150 | #1 | 50013 |
| 3172 | 18454 | 67.2 | 61.5 | 21 | 327 | #4 | 50014 |
| 3173 | 18455 | 64.0 | 58.9 | 18 | 217 | #3 | 50015 |
| 3174 | 18456 | 60.0 | 57.5 | 12 | 221 | #2 | 50016 |
| 3175 | 18457 | 72.8 | 66.5 | 13 | 586 | #5 | 50017 |
| 3176 | 18458 | 50.0 | 50.0 | 12 | 150 | #1 | 50018 |
| 3177 | 18459 | 60.0 | 56.4 | 12 | 189 | #2 | 50019 |
| 3178 | 18460 | 70.4 | 62.7 (249) | 23 | 287 | #5 | 50020 |
| 3179 | 18461 | 68.8 | 60.4 | 21 | 236 | #4 | 50021 |
| 3180 | 18462 | 62.4 | 58.9 | 13 | 251 | #3 | 50022 |
| 3181 | 18463 | 63.2 | 50.0 (226) | 18 | 150 | #3 | 50023 |
| 3182 | 18464 | 68.0 | 61.1 | 21 | 310 | #4 | 50024 |
| 3183 | 18465 | 64.0 | 55.2 (252) | 18 | 164 | #3 | 50025 |
| 3184 | 18466 | 65.6 | 60.4 | 19 | 242 | #4 | 50026 |
| 3185 | 18467 | 78.4 | 61.8 | 25 | 387 | #6 | 50027 |
| 3186 | 18468 | 50.0 | 50.0 | 12 | 150 | #1 | 50028 |
| 3187 | 18469 | 65.6 | 58.9 | 16 | 249 | #4 | 50029 |
| 3188 | 18470 | 65.6 | 50.0 (241) | 14 | 170 | #4 | 50030 |
| 3189 | 18471 | 66.4 | 58.9 | 17 | 227 | #4 | 50031 |
| 3190 | 18472 | 68.0 | 59.6 | 19 | 233 | #4 | 50032 |
| 3191 | 18473 | 67.2 | 58.9 | 20 | 242 | #4 | 50033 |
| 3192 | 18474 | 69.6 | 60.0 | 16 | 211 | #4 | 50034 |
| 3193 | 18475 | 65.6 | 58.2 | 19 | 218 | #4 | 50035 |
| 3194 | 18476 | 66.4 | 50.0 | 24 | 252 | #4 | 50036 |
| 3195 | 18477 | 64.8 | 57.8 | 18 | 214 | #3 | 50037 |
| 3196 | 18478 | 65.6 | 62.7 (153) | 19 | 180 | #4 | 50038 |
| 3197 | 18479 | 69.6 | 61.8 | 13 | 347 | #4 | 50039 |
| 3198 | 18480 | 60.8 | 50.0 | 14 | 150 | #3 | 50040 |
| 3199 | 18481 | 68.8 | 62.2 | 20 | 399 | #4 | 50041 |
| 3200 | 18482 | 66.4 | 52.4 | 15 | 215 | #4 | 50042 |
| 3201 | 18483 | 61.6 | 58.8 (165) | 13 | 150 | #3 | 50043 |
| 3202 | 18484 | 69.6 | 62.5 | 20 | 406 | #4 | 50044 |
| 3203 | 18485 | 72.0 | 66.9 | 16 | 575 | #5 | 50045 |
| 3204 | 18486 | 71.2 | 64.0 | 19 | 339 | #5 | 50046 |
| 3205 | 18487 | 54.4 | 50.0 (232) | 14 | 150 | #1 | 50047 |
| 3206 | 18488 | 64.8 | 59.3 | 16 | 214 | #3 | 50048 |
| 3207 | 18489 | 68.8 | 62.5 | 24 | 383 | #4 | 50049 |
| 3208 | 18490 | 50.0 | 50.0 | 12 | 150 | #1 | 50050 |
| 3209 | 18491 | 63.2 | 58.2 | 12 | 207 | #3 | 50051 |
| 3210 | 18492 | 67.2 | 59.3 | 19 | 252 | #4 | 50052 |
| 3211 | 18493 | 64.0 | 58.2 | 14 | 216 | #3 | 50053 |
| 3212 | 18494 | 50.0 | 50.0 | 12 | 150 | #1 | 50054 |
| 3213 | 18495 | 71.2 | 64.0 | 28 | 490 | #5 | 50055 |
| 3214 | 18496 | 72.8 | 66.9 | 24 | 497 | #5 | 50056 |
| 3215 | 18497 | 67.2 | 60.4 | 18 | 281 | #4 | 50057 |
| 3216 | 18498 | 72.0 | 64.7 | 20 | 360 | #5 | 50058 |
| 3217 | 18499 | 65.6 | 58.5 | 21 | 227 | #4 | 50059 |
| 3218 | 18500 | 64.0 | 52.0 (175) | 19 | 168 | #3 | 50060 |
| 3219 | 18501 | 65.6 | 50.0 | 19 | 197 | #4 | 50061 |
| 3220 | 18502 | 50.0 | 50.0 | 12 | 150 | #1 | 50062 |
| 3221 | 18503 | 60.8 | 60.2 (128) | 20 | 158 | #3 | 50063 |
| 3222 | 18504 | 68.8 | 53.1 | 27 | 247 | #4 | 50064 |
| 3223 | 18505 | 70.4 | 61.8 | 27 | 280 | #5 | 59965 |
| 3224 | 18506 | 50.0 | 50.0 | 12 | 150 | #1 | 50066 |
| 3225 | 18507 | 50.0 | 50.0 | 12 | 150 | #1 | 50067 |
| 3226 | 18508 | 50.0 | 50.0 | 12 | 150 | #1 | 50068 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3227 | 18509 | 50.0 | 50.0 | 12 | 150 | #1 | 50069 |
| 3228 | 18510 | 64.0 | 50.0 | 13 | 185 | #3 | 50070 |
| 3229 | 18511 | 67.2 | 57.8 | 17 | 243 | #4 | 50071 |
| 3230 | 18512 | 60.6 (104) | — | 20 | 179 | #3 | 50072 |
| 3231 | 18513 | 66.4 | 50.0 | 12 | 236 | #4 | 50073 |
| 3232 | 18514 | 50.0 | 50.0 | 12 | 150 | #1 | 50074 |
| 3233 | 18515 | 50.0 | 50.0 | 12 | 150 | #1 | 50075 |
| 3234 | 18516 | 66.4 | 50.2 | 17 | 190 | #4 | 50076 |
| 3235 | 18517 | 50.0 | 50.0 | 12 | 150 | #1 | 50077 |
| 3236 | 18518 | 63.2 | 63.2 (125) | 14 | 162 | #3 | 50078 |
| 3237 | 18519 | 65.6 | 50.0 | 14 | 214 | #4 | 50079 |
| 3238 | 18520 | 65.6 | 59.3 | 15 | 277 | #4 | 50080 |
| 3239 | 18521 | 67.2 | 61.5 | 21 | 327 | #4 | 50081 |
| 3240 | 18522 | 50.0 | 50.0 | 12 | 150 | #1 | 50082 |
| 3241 | 18523 | 68.0 | 61.5 | 20 | 334 | #4 | 50083 |
| 3242 | 18524 | 70.4 | 50.0 | 12 | 327 | #5 | 50084 |
| 3243 | 18525 | 68.0 | 53.7 (175) | 25 | 199 | #4 | 50089 |
| 3244 | 18526 | 68.0 | 61.1 | 38 | 255 | #4 | 50086 |
| 3245 | 18527 | 60.8 | 50.0 (175) | 15 | 172 | #3 | 50087 |
| 3246 | 18528 | 71.2 | 61.8 | 28 | 384 | #5 | 50088 |
| 3247 | 18529 | 68.0 | 60.7 | 16 | 407 | #4 | 50089 |
| 3248 | 18530 | 68.8 | 61.1 | 20 | 392 | #4 | 50090 |
| 3249 | 18531 | 68.8 | 62.5 | 20 | 320 | #4 | 50091 |
| 3250 | 18532 | 71.2 | 62.4 (215) | 24 | 274 | #5 | 50092 |
| 3251 | 18533 | 75.2 | 62.9 | 32 | 341 | #6 | 50093 |
| 3252 | 18534 | 63.2 | 50.0 | 16 | 197 | #3 | 50094 |
| 3253 | 18535 | 64.8 | 60.4 | 17 | 221 | #3 | 50095 |
| 3254 | 18536 | 50.0 | 50.0 | 12 | 150 | #1 | 50096 |
| 3255 | 18537 | 73.6 | 66.2 | 36 | 501 | #5 | 50097 |
| 3256 | 18538 | 67.2 | 61.5 | 19 | 303 | #4 | 50098 |
| 3257 | 18539 | 69.6 | 62.5 | 23 | 379 | #4 | 50099 |
| 3258 | 18540 | 72.8 | 66.5 | 23 | 616 | #5 | 50100 |
| 3259 | 18541 | 84.0 | 79.3 | 25 | 854 | #7 | 50111 |
| 3260 | 18542 | 66.4 | 60.4 | 17 | 266 | #4 | 50102 |
| 3261 | 18543 | 71.2 | 63.6 | 20 | 516 | #5 | 50103 |
| 3262 | 18544 | 50.0 | 50.0 | 12 | 150 | #1 | 50104 |
| 3263 | 18545 | 50.0 (119) | — | 18 | 151 | #1 | 50105 |
| 3264 | 18546 | 66.4 | 59.6 | 17 | 244 | #4 | 50106 |
| 3265 | 18547 | 64.0 | 50.0 | 16 | 206 | #3 | 50107 |
| 3266 | 18548 | 67.2 | 57.5 | 14 | 229 | #4 | 50108 |
| 3267 | 18549 | 52.0 | 50.0 | 12 | 151 | #1 | 50109 |
| 3268 | 18550 | 69.6 | 62.5 | 16 | 235 | #4 | 50110 |
| 3269 | 18551 | 67.2 | 52.0 | 22 | 214 | #4 | 50111 |
| 3270 | 18552 | 68.0 | 60.0 | 17 | 276 | #4 | 50112 |
| 3271 | 18553 | 64.0 | 51.3 | 14 | 173 | #3 | 50113 |
| 3272 | 18554 | 68.0 | 57.5 | 16 | 213 | #4 | 50114 |
| 3273 | 18555 | 69.6 | 62.2 | 20 | 290 | #4 | 50115 |
| 3274 | 18556 | 67.2 | 60.7 | 19 | 239 | #4 | 50116 |
| 3275 | 18557 | 68.0 | 54.6 (218) | 14 | 189 | #4 | 50117 |
| 3276 | 18558 | 71.2 | 60.4 (260) | 28 | 255 | #5 | 50118 |
| 3277 | 18559 | 62.4 | 50.0 | 14 | 187 | #3 | 50119 |
| 3278 | 18560 | 66.4 | 58.5 | 15 | 219 | #4 | 50120 |
| 3279 | 18561 | 64.8 | 60.2 (181) | 17 | 188 | #3 | 50121 |
| 3280 | 18562 | 74.4 | 64.0 | 26 | 412 | #5 | 50122 |
| 3281 | 18563 | 66.4 | 59.6 | 17 | 240 | #4 | 50123 |
| 3282 | 18564 | 50.0 | 50.0 | 12 | 150 | #1 | 50124 |
| 3283 | 18565 | 73.6 | 64.4 | 28 | 462 | #5 | 50125 |
| 3284 | 18566 | 64.0 | 50.0 | 12 | 193 | #3 | 50126 |
| 3285 | 18567 | 67.2 | 62.4 (165) | 28 | 207 | #4 | 50127 |
| 3286 | 18568 | 71.2 | 65.5 | 14 | 576 | #5 | 50128 |
| 3287 | 18569 | 63.6 (88) | — | 18 | 195 | #3 | 50129 |
| 3288 | 18570 | 81.6 | 73.8 | 31 | 719 | #7 | 50130 |
| 3289 | 18571 | 50.0 | 50.0 | 12 | 150 | #1 | 50131 |
| 3290 | 18572 | 88.8 | 66.9 | 20 | 722 | #8 | 50132 |
| 3291 | 18573 | 69.6 | 61.5 | 23 | 420 | #4 | 50133 |
| 3292 | 18574 | 71.2 | 63.3 | 28 | 568 | #5 | 50134 |
| 3293 | 18575 | 68.5 (89) | — | 17 | 161 | #4 | 50135 |
| 3294 | 18576 | 63.2 | 57.8 | 13 | 233 | #3 | 50136 |
| 3295 | 18577 | 67.2 | 59.3 | 18 | 228 | #4 | 50137 |
| 3296 | 18578 | 50.0 | 50.0 | 12 | 150 | #1 | 50138 |
| 3297 | 18579 | 50.4 | 50.0 (252) | 12 | 153 | #1 | 50139 |
| 3298 | 18580 | 70.4 | 63.6 | 27 | 536 | #5 | 50140 |
| 3299 | 18581 | 68.8 | 61.1 | 24 | 439 | #4 | 50141 |
| 3300 | 18582 | 71.2 | 50.0 | 31 | 279 | #5 | 50142 |
| 3301 | 18583 | 71.2 | 62.5 | 22 | 381 | #5 | 50143 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3302 | 18584 | 50.0 (120) | — | 12 | 150 | #1 | 50144 |
| 3303 | 18585 | 65.6 | 60.0 | 19 | 223 | #4 | 50145 |
| 3304 | 18586 | 50.0 | 50.0 | 12 | 150 | #1 | 50146 |
| 3305 | 18587 | 69.6 | 63.3 | 19 | 349 | #4 | 50147 |
| 3306 | 18588 | 65.6 | 50.0 | 14 | 213 | #4 | 50148 |
| 3307 | 18589 | 50.0 | 50.0 | 12 | 150 | #1 | 50149 |
| 3308 | 18590 | 70.4 | 61.5 | 32 | 330 | #5 | 50150 |
| 3309 | 18591 | 90.4 | 73.8 | 33 | 760 | #9 | 50151 |
| 3310 | 18592 | 67.1 (82) | — | 16 | 150 | #4 | 50152 |
| 3311 | 18593 | 80.0 | 64.4 | 36 | 447 | #6 | 50153 |
| 3312 | 18594 | 64.0 | 56.7 | 14 | 224 | #3 | 50154 |
| 3313 | 18595 | 70.4 | 63.3 | 20 | 627 | #5 | 50155 |
| 3314 | 18596 | 69.6 | 61.8 | 18 | 352 | #4 | 50156 |
| 3315 | 18597 | 68.0 | 60.7 | 15 | 277 | #4 | 50157 |
| 3316 | 18598 | 67.2 | 59.6 (213) | 20 | 199 | #4 | 50158 |
| 3317 | 18599 | 68.0 | 61.8 | 26 | 342 | #4 | 50159 |
| 3318 | 18600 | 66.4 | 57.5 | 23 | 206 | #4 | 50160 |
| 3319 | 18601 | 66.4 | 58.9 | 15 | 255 | #4 | 50161 |
| 3320 | 18602 | 70.4 | 61.5 | 24 | 377 | #5 | 50162 |
| 3321 | 18603 | 68.0 | 60.7 | 23 | 262 | #4 | 50163 |
| 3322 | 18604 | 50.0 (102) | — | 12 | 150 | #1 | 50164 |
| 3323 | 18605 | 61.6 | 56.7 | 18 | 204 | #3 | 50165 |
| 3324 | 18606 | 62.4 | 54.3 (208) | 16 | 155 | #3 | 50166 |
| 3325 | 18607 | 72.8 | 64.0 | 28 | 376 | #5 | 50167 |
| 3326 | 18608 | 50.0 | 50.0 | 12 | 150 | #1 | 50168 |
| 3327 | 18609 | 86.6 (112) | — | 35 | 425 | #8 | 50169 |
| 3328 | 18610 | 50.0 | 50.0 | 12 | 150 | #1 | 50170 |
| 3329 | 18611 | 68.8 | 61.5 (221) | 36 | 232 | #4 | 50171 |
| 3330 | 18612 | 72.8 | 63.3 | 23 | 502 | #5 | 50172 |
| 3331 | 18613 | 70.4 | 61.5 | 24 | 277 | #5 | 50173 |
| 3332 | 18614 | 65.6 | 51.6 | 15 | 218 | #4 | 50174 |
| 3333 | 18615 | 66.4 | 55.6 | 18 | 219 | #4 | 50175 |
| 3334 | 18616 | 72.8 | 65.1 | 26 | 405 | #5 | 50176 |
| 3335 | 18617 | 69.6 | 63.3 | 22 | 350 | #4 | 50177 |
| 3336 | 18618 | 67.2 | 60.0 | 16 | 231 | #4 | 50178 |
| 3337 | 18619 | 81.0 (79) | — | 12 | 268 | #7 | 50179 |
| 3338 | 18620 | 62.4 | 50.0 (174) | 14 | 156 | #3 | 50180 |
| 3339 | 18621 | 64.8 | 57.5 | 15 | 204 | #3 | 50181 |
| 3340 | 18622 | 67.2 | 60.0 | 20 | 255 | #4 | 50182 |
| 3341 | 18623 | 68.8 | 61.5 | 32 | 319 | #4 | 50183 |
| 3342 | 18624 | 64.8 | 59.3 | 17 | 221 | #3 | 50184 |
| 3343 | 18625 | 60.8 | 56.4 | 12 | 194 | #3 | 50185 |
| 3344 | 18626 | 68.0 | 61.8 | 27 | 328 | #4 | 50186 |
| 3345 | 18627 | 68.8 | 61.8 | 21 | 293 | #4 | 50187 |
| 3346 | 18628 | 63.2 | 58.2 | 18 | 183 | #3 | 50188 |
| 3347 | 18629 | 50.0 | 50.0 | 12 | 150 | #1 | 50189 |
| 3348 | 18630 | 66.4 | 58.9 | 17 | 218 | #4 | 50190 |
| 3349 | 18631 | 63.2 | 59.6 | 12 | 222 | #3 | 50191 |
| 3350 | 18632 | 76.0 | 64.0 | 36 | 391 | #6 | 50192 |
| 3351 | 18633 | 69.9 (73) | — | 17 | 150 | #4 | 50193 |
| 3352 | 18634 | 61.6 | 60.7 (150) | 13 | 150 | #3 | 50194 |
| 3353 | 18635 | 50.0 | 50.0 | 12 | 150 | #1 | 50195 |
| 3354 | 18636 | 70.4 | 61.5 | 19 | 270 | #5 | 50196 |
| 3355 | 18637 | 62.4 | 50.0 (266) | 12 | 156 | #3 | 50197 |
| 3356 | 18638 | 61.6 | 50.0 | 13 | 186 | #3 | 50198 |
| 3357 | 18639 | 63.2 | 50.0 | 15 | 172 | #3 | 50199 |
| 3358 | 18640 | 71.2 | 63.3 | 20 | 310 | #5 | 50200 |
| 3359 | 18641 | 64.0 | 50.0 | 15 | 189 | #3 | 50201 |
| 3360 | 18642 | 68.8 | 58.9 | 24 | 265 | #4 | 50202 |
| 3361 | 18643 | 62.4 | 54.9 | 12 | 217 | #3 | 50203 |
| 3362 | 18644 | 67.2 | 59.6 | 17 | 243 | #4 | 50204 |
| 3363 | 18645 | 66.4 | 60.4 | 18 | 254 | #4 | 50205 |
| 3364 | 18646 | 76.8 | 62.2 | 29 | 365 | #6 | 50206 |
| 3365 | 18647 | 50.0 | 50.0 | 12 | 150 | #1 | 50207 |
| 3366 | 18648 | 65.6 | 60.9 (169) | 20 | 184 | #4 | 50208 |
| 3367 | 18649 | 70.4 | 59.6 | 22 | 287 | #5 | 50209 |
| 3368 | 18650 | 65.6 | 57.8 | 20 | 211 | #4 | 50210 |
| 3369 | 18651 | 65.6 | 50.0 | 15 | 200 | #4 | 50211 |
| 3370 | 18652 | 60.0 | 50.0 (246) | 12 | 150 | #2 | 50212 |
| 3371 | 18653 | 66.4 | 60.7 | 18 | 334 | #4 | 50213 |
| 3372 | 18654 | 70.4 | 60.7 | 21 | 302 | #5 | 50214 |
| 3373 | 18655 | 64.0 | 50.0 | 16 | 190 | #3 | 50215 |
| 3374 | 18656 | 72.0 | 62.5 | 21 | 383 | #5 | 50216 |
| 3375 | 18657 | 67.2 | 60.4 | 17 | 275 | #4 | 50217 |
| 3376 | 18658 | 65.6 | 58.1 (246) | 16 | 209 | #4 | 50218 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3377 | 18659 | 65.6 | 50.0 | 18 | 204 | #4 | 50219 |
| 3378 | 18660 | 69.6 | 62.2 | 26 | 301 | #4 | 50220 |
| 3379 | 18661 | 50.0 | 50.0 | 35 | 170 | #1 | 50221 |
| 3380 | 18662 | 72.8 | 64.0 | 33 | 460 | #5 | 50222 |
| 3381 | 18663 | 72.8 | 59.6 | 28 | 287 | #5 | 50223 |
| 3382 | 18664 | 71.2 | 62.9 | 21 | 361 | #5 | 50224 |
| 3383 | 18665 | 60.8 | 58.5 | 15 | 272 | #3 | 50225 |
| 3384 | 18666 | 68.0 | 59.3 | 18 | 284 | #4 | 50226 |
| 3385 | 18667 | 72.0 | 60.0 | 31 | 275 | #5 | 50227 |
| 3386 | 18668 | 64.0 | 50.0 (173) | 16 | 166 | #3 | 50228 |
| 3387 | 18669 | 64.0 | 57.5 | 15 | 222 | #3 | 50229 |
| 3388 | 18670 | 50.0 (117) | — | 12 | 150 | #1 | 50230 |
| 3389 | 18671 | 60.0 | 50.0 (173) | 13 | 151 | #2 | 50231 |
| 3390 | 18672 | 61.6 | 56.7 | 12 | 185 | #3 | 50232 |
| 3391 | 18673 | 64.0 | 58.5 | 13 | 190 | #3 | 50233 |
| 3392 | 18674 | 64.8 | 50.0 | 15 | 180 | #3 | 50234 |
| 3393 | 18675 | 64.8 | 60.0 | 19 | 249 | #3 | 50235 |
| 3394 | 18676 | 50.0 | 50.0 | 12 | 150 | #1 | 50236 |
| 3395 | 18677 | 50.0 | 50.0 | 12 | 150 | #1 | 50237 |
| 3396 | 18678 | 61.6 | 51.6 | 16 | 192 | #3 | 50238 |
| 3397 | 18679 | 68.8 | 61.5 | 17 | 274 | #4 | 50239 |
| 3398 | 18680 | 66.4 | 60.4 | 18 | 236 | #4 | 50240 |
| 3399 | 18681 | 68.0 | 61.1 | 18 | 289 | #4 | 50241 |
| 3400 | 18682 | 50.0 | 50.0 | 12 | 150 | #1 | 50242 |
| 3401 | 18683 | 65.6 | 56.7 | 14 | 199 | #4 | 50243 |
| 3402 | 18684 | 67.2 | 53.5 | 16 | 214 | #4 | 50244 |
| 3403 | 18685 | 72.0 | 58.9 | 26 | 295 | #5 | 50245 |
| 3404 | 18686 | 71.2 | 63.3 | 25 | 556 | #5 | 50246 |
| 3405 | 18687 | 73.6 | 60.7 | 24 | 297 | #5 | 50247 |
| 3406 | 18688 | 65.6 | 57.5 | 17 | 245 | #4 | 50248 |
| 3407 | 18689 | 62.4 | 53.1 | 13 | 200 | #3 | 50249 |
| 3408 | 18690 | 68.8 | 61.5 | 16 | 310 | #4 | 50250 |
| 3409 | 18691 | 64.8 | 59.6 | 16 | 297 | #3 | 50251 |
| 3410 | 18692 | 70.4 | 61.1 | 30 | 279 | #5 | 50252 |
| 3411 | 18693 | 98.4 | 96.7 | 80 | 1385 | #10 | 50253 |
| 3412 | 18694 | 67.2 | 61.1 | 26 | 302 | #4 | 50254 |
| 3413 | 18695 | 64.0 | 56.4 (179) | 17 | 167 | #3 | 50255 |
| 3414 | 18696 | 68.8 | 55.8 (249) | 22 | 217 | #4 | 50256 |
| 3415 | 18697 | 74.4 | 61.1 | 22 | 318 | #5 | 50257 |
| 3416 | 18698 | 69.6 | 62.5 | 33 | 487 | #4 | 50258 |
| 3417 | 18699 | 67.2 | 50.0 | 17 | 197 | #4 | 50259 |
| 3418 | 18700 | 64.8 | 58.5 (171) | 21 | 157 | #3 | 50260 |
| 3419 | 18701 | 69.6 | 61.1 | 20 | 364 | #4 | 50261 |
| 3420 | 18702 | 70.4 | 61.5 | 25 | 370 | #5 | 50262 |
| 3421 | 18703 | 69.6 | 62.9 | 20 | 312 | #4 | 50263 |
| 3422 | 18704 | 74.4 | 64.4 | 18 | 404 | #5 | 50264 |
| 3423 | 18705 | 68.0 | 61.1 | 20 | 409 | #4 | 50265 |
| 3424 | 18706 | 66.4 | 60.4 | 15 | 273 | #4 | 50266 |
| 3425 | 18707 | 65.6 | 58.5 | 18 | 266 | #4 | 50267 |
| 3426 | 18708 | 68.0 | 61.5 | 19 | 310 | #4 | 50268 |
| 3427 | 18709 | 64.8 | 56.4 | 17 | 212 | #3 | 50269 |
| 3428 | 18710 | 64.8 | 50.0 (252) | 18 | 166 | #3 | 50270 |
| 3429 | 18711 | 64.8 | 57.1 | 19 | 219 | #3 | 50271 |
| 3430 | 18712 | 50.0 | 50.0 | 12 | 150 | #1 | 50272 |
| 3431 | 18713 | 70.4 | 60.7 | 19 | 293 | #5 | 50273 |
| 3432 | 18714 | 66.4 | 59.3 | 20 | 219 | #4 | 50274 |
| 3433 | 18715 | 66.4 | 60.7 | 19 | 235 | #4 | 50275 |
| 3434 | 18716 | 65.6 | 50.0 (261) | 19 | 183 | #4 | 50276 |
| 3435 | 18717 | 68.0 | 62.2 | 21 | 408 | #4 | 50277 |
| 3436 | 18718 | 85.6 | 78.2 | 26 | 801 | #8 | 50278 |
| 3437 | 18719 | 69.6 | 61.8 | 20 | 324 | #4 | 50279 |
| 3438 | 18720 | 69.6 | 62.9 | 24 | 326 | #4 | 50280 |
| 3439 | 18721 | 65.6 | 50.0 | 15 | 189 | #4 | 50281 |
| 3440 | 18722 | 60.0 | 50.0 (169) | 13 | 150 | #2 | 50282 |
| 3441 | 18723 | 66.4 | 61.5 | 19 | 276 | #4 | 50283 |
| 3442 | 18724 | 68.8 | 58.9 | 22 | 253 | #4 | 50284 |
| 3443 | 18725 | 64.8 | 53.6 (207) | 20 | 175 | #3 | 50285 |
| 3444 | 18726 | 50.0 | 50.0 | 12 | 150 | #1 | 50286 |
| 3445 | 18727 | 50.0 | 50.0 | 17 | 158 | #1 | 50287 |
| 3446 | 18728 | 69.6 | 61.8 | 22 | 281 | #4 | 50288 |
| 3447 | 18729 | 50.0 | 50.0 | 12 | 150 | #1 | 50289 |
| 3448 | 18730 | 63.2 | 60.4 | 13 | 217 | #3 | 50290 |
| 3449 | 18731 | 68.0 | 59.6 | 18 | 272 | #4 | 50291 |
| 3450 | 18732 | 65.6 | 57.5 | 14 | 214 | #4 | 50292 |
| 3451 | 18733 | 69.6 | 57.8 | 26 | 222 | #4 | 50293 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3452 | 18734 | 61.6 | 59.6 | 16 | 228 | #3 | 50294 |
| 3453 | 18735 | 64.8 | 60.0 | 15 | 233 | #3 | 50295 |
| 3454 | 18736 | 64.8 | 50.0 | 12 | 169 | #3 | 50296 |
| 3455 | 18737 | 63.2 | 60.4 | 14 | 296 | #3 | 50297 |
| 3456 | 18738 | 50.0 | 50.0 | 12 | 150 | #1 | 50298 |
| 3457 | 18739 | 68.0 | 58.5 | 23 | 238 | #4 | 50299 |
| 3458 | 18740 | 50.0 | 50.0 | 12 | 150 | #1 | 50300 |
| 3459 | 18741 | 62.4 | 59.1 (154) | 30 | 163 | #3 | 50301 |
| 3460 | 18742 | 70.4 | 61.5 | 22 | 276 | #5 | 50302 |
| 3461 | 18743 | 63.2 | 51.6 | 19 | 344 | #3 | 50303 |
| 3462 | 18744 | 63.2 | 58.2 | 15 | 233 | #3 | 50304 |
| 3463 | 18745 | 68.0 | 61.5 | 20 | 283 | #4 | 50305 |
| 3464 | 18746 | 64.8 | 58.9 | 23 | 336 | #3 | 50306 |
| 3465 | 18747 | 64.8 | 60.0 | 14 | 299 | #3 | 50307 |
| 3466 | 18748 | 65.6 | 61.6 (211) | 22 | 177 | #4 | 50308 |
| 3467 | 18749 | 63.2 | 58.5 | 14 | 224 | #3 | 50309 |
| 3468 | 18750 | 65.6 | 59.3 | 15 | 226 | #4 | 50310 |
| 3469 | 18751 | 69.6 | 61.8 | 23 | 382 | #4 | 50311 |
| 3470 | 18752 | 67.2 | 60.0 | 18 | 260 | #4 | 50312 |
| 3471 | 18753 | 70.4 | 62.9 | 23 | 368 | #5 | 50313 |
| 3472 | 18754 | 75.7 (74) | — | 23 | 204 | #6 | 50314 |
| 3473 | 18755 | 68.0 | 62.2 | 21 | 301 | #4 | 50315 |
| 3474 | 18756 | 58.8 (119) | — | 17 | 298 | #2 | 50316 |
| 3475 | 18757 | 72.0 | 64.0 | 25 | 467 | #5 | 50317 |
| 3476 | 18758 | 50.0 | 50.0 | 12 | 150 | #1 | 50318 |
| 3477 | 18759 | 68.8 | 61.1 | 19 | 277 | #4 | 50319 |
| 3478 | 18760 | 50.0 | 50.0 | 12 | 150 | #1 | 50320 |
| 3479 | 18761 | 68.0 | 58.2 | 17 | 217 | #4 | 50321 |
| 3480 | 18762 | 65.6 | 52.5 (261) | 16 | 181 | #4 | 50322 |
| 3481 | 18763 | 69.6 | 61.1 | 19 | 265 | #4 | 50323 |
| 3482 | 18764 | 64.8 | 53.1 | 15 | 168 | #3 | 50324 |
| 3483 | 18765 | 68.0 | 61.5 | 20 | 262 | #4 | 50325 |
| 3484 | 18766 | 62.4 | 53.6 (179) | 20 | 180 | #3 | 50326 |
| 3485 | 18767 | 71.2 | 61.5 | 21 | 290 | #5 | 50327 |
| 3486 | 18768 | 64.8 | 50.0 | 16 | 201 | #3 | 50328 |
| 3487 | 18769 | 65.6 | 60.7 | 16 | 239 | #4 | 50329 |
| 3488 | 18770 | 52.7 (112) | — | 12 | 150 | #1 | 50330 |
| 3489 | 18771 | 62.4 | 52.4 | 17 | 182 | #3 | 50331 |
| 3490 | 18772 | 69.6 | 64.0 | 21 | 504 | #4 | 50332 |
| 3491 | 18773 | 72.0 | 61.8 | 30 | 300 | #5 | 50333 |
| 3492 | 18774 | 68.0 | 59.3 | 18 | 286 | #4 | 50334 |
| 3493 | 18775 | 68.8 | 61.8 | 23 | 323 | #4 | 50335 |
| 3494 | 18776 | 60.0 | 50.0 (183) | 17 | 150 | #2 | 50336 |
| 3495 | 18777 | 68.0 | 58.9 | 18 | 218 | #4 | 50337 |
| 3496 | 18778 | 52.0 | 50.0 (157) | 15 | 150 | #1 | 50338 |
| 3497 | 18779 | 64.0 | 50.0 | 14 | 187 | #3 | 50339 |
| 3498 | 18780 | 50.0 | 50.0 | 12 | 150 | #1 | 50340 |
| 3499 | 18781 | 50.0 | 50.0 | 12 | 150 | #1 | 50341 |
| 3500 | 18782 | 64.0 | 50.0 (255) | 19 | 181 | #3 | 50342 |
| 3501 | 18783 | 64.8 | 55.3 (266) | 18 | 175 | #3 | 50343 |
| 3502 | 18784 | 67.2 | 62.5 | 22 | 359 | #4 | 50344 |
| 3503 | 18785 | 71.2 | 60.4 | 20 | 309 | #5 | 50345 |
| 3504 | 18786 | 67.2 | 62.2 | 18 | 307 | #4 | 50346 |
| 3505 | 18787 | 65.6 | 60.0 (205) | 19 | 183 | #4 | 50347 |
| 3506 | 18788 | 64.0 | 58.2 | 15 | 226 | #3 | 50348 |
| 3507 | 18789 | 61.6 | 61.8 (178) | 18 | 150 | #3 | 50349 |
| 3508 | 18790 | 64.0 | 59.6 | 18 | 229 | #3 | 50350 |
| 3509 | 18791 | 50.0 | 50.0 | 12 | 150 | #1 | 50351 |
| 3510 | 18792 | 68.8 | 64.0 | 19 | 360 | #4 | 50352 |
| 3511 | 18793 | 72.0 | 63.3 | 31 | 406 | #5 | 50353 |
| 3512 | 18794 | 65.6 | 50.0 (272) | 18 | 181 | #4 | 50354 |
| 3513 | 18795 | 71.2 | 64.0 | 20 | 514 | #5 | 50355 |
| 3514 | 18796 | 65.6 | 58.9 | 16 | 225 | #4 | 50356 |
| 3515 | 18797 | 62.4 | 50.0 | 13 | 164 | #3 | 50357 |
| 3516 | 18798 | 64.0 | 60.7 | 15 | 221 | #3 | 50358 |
| 3517 | 18799 | 66.4 | 58.9 | 15 | 233 | #4 | 50359 |
| 3518 | 18800 | 70.4 | 62.9 | 23 | 401 | #5 | 50360 |
| 3519 | 18801 | 64.8 | 52.9 (153) | 16 | 157 | #3 | 50361 |
| 3520 | 18802 | 65.6 | 50.0 | 14 | 208 | #4 | 50362 |
| 3521 | 18803 | 64.8 | 50.0 (206) | 14 | 152 | #3 | 50363 |
| 3522 | 18804 | 65.6 | 50.0 (261) | 16 | 196 | #4 | 50364 |
| 3523 | 18805 | 73.6 | 66.9 | 39 | 474 | #5 | 50365 |
| 3524 | 18806 | 72.8 | 62.5 | 25 | 460 | #5 | 50366 |
| 3525 | 18807 | 67.2 | 50.0 | 12 | 188 | #4 | 50367 |
| 3526 | 18808 | 64.0 | 54.6 (174) | 17 | 183 | #3 | 50368 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3527 | 18809 | 65.6 | 60.9 (184) | 29 | 203 | #4 | 50369 |
| 3528 | 18810 | 66.4 | 57.1 (161) | 19 | 186 | #4 | 50370 |
| 3529 | 18811 | 63.2 | 50.0 | 12 | 183 | #3 | 50371 |
| 3530 | 18812 | 50.0 | 50.0 | 12 | 150 | #1 | 50372 |
| 3531 | 18813 | 50.0 | 50.0 | 12 | 150 | #1 | 50373 |
| 3532 | 18814 | 62.4 | 51.0 (208) | 17 | 156 | #3 | 50374 |
| 3533 | 18815 | 64.0 | 56.9 (211) | 16 | 170 | #3 | 50375 |
| 3534 | 18816 | 68.0 | 68.0 (128) | 21 | 207 | #4 | 50376 |
| 3535 | 18817 | 50.0 | 50.0 | 12 | 150 | #1 | 50377 |
| 3536 | 18818 | 70.4 | 63.3 | 22 | 515 | #5 | 50378 |
| 3537 | 18819 | 61.6 | 50.0 | 12 | 158 | #3 | 50379 |
| 3538 | 18820 | 50.0 (72) | — | 12 | 150 | #1 | 50380 |
| 3539 | 18821 | 68.0 | 58.2 | 14 | 192 | #4 | 50381 |
| 3540 | 18822 | 50.0 | 50.0 | 12 | 150 | #1 | 50382 |
| 3541 | 18823 | 62.4 | 59.2 (169) | 16 | 160 | #3 | 50383 |
| 3542 | 18824 | 50.0 (94) | — | 12 | 150 | #1 | 50384 |
| 3543 | 18825 | 64.8 | 60.7 | 14 | 229 | #3 | 50385 |
| 3544 | 18826 | 71.2 | 64.0 | 21 | 350 | #5 | 50386 |
| 3545 | 18827 | 56.5 (124) | — | 14 | 150 | #2 | 50387 |
| 3546 | 18828 | 50.0 | 50.0 | 12 | 150 | #1 | 50388 |
| 3547 | 18829 | 68.0 | 58.5 | 16 | 267 | #4 | 50389 |
| 3548 | 18830 | 74.4 | 65.1 | 29 | 437 | #5 | 50390 |
| 3549 | 18831 | 68.0 | 60.4 | 22 | 279 | #4 | 50391 |
| 3550 | 18832 | 60.0 | 50.0 | 14 | 177 | #2 | 50392 |
| 3551 | 18833 | 72.0 | 61.1 | 25 | 339 | #5 | 50393 |
| 3552 | 18834 | 71.2 | 64.7 | 26 | 557 | #5 | 50394 |
| 3553 | 18835 | 50.0 | 50.0 | 12 | 150 | #1 | 50395 |
| 3554 | 18836 | 72.0 | 63.3 | 29 | 383 | #5 | 50396 |
| 3555 | 18837 | 68.0 | 61.3 (248) | 25 | 226 | #4 | 50397 |
| 3556 | 18838 | 72.8 | 58.2 | 28 | 276 | #5 | 50398 |
| 3557 | 18839 | 69.6 | 62.2 | 21 | 310 | #4 | 50399 |
| 3558 | 18840 | 69.6 | 61.1 | 22 | 256 | #4 | 50400 |
| 3559 | 18841 | 69.6 | 59.6 | 24 | 255 | #4 | 50401 |
| 3560 | 18842 | 67.2 | 56.0 | 15 | 220 | #4 | 50402 |
| 3561 | 18843 | 64.8 | 59.6 | 16 | 220 | #3 | 50403 |
| 3562 | 18844 | 72.8 | 64.4 | 25 | 509 | #5 | 50404 |
| 3563 | 18845 | 68.8 | 63.3 | 23 | 421 | #4 | 50405 |
| 3564 | 18846 | 53.6 | 50.0 | 23 | 211 | #1 | 50406 |
| 3565 | 18847 | 64.8 | 57.8 | 14 | 209 | #3 | 50407 |
| 3566 | 18848 | 69.6 | 61.5 | 18 | 297 | #4 | 50408 |
| 3567 | 18849 | 71.2 | 60.7 | 23 | 272 | #5 | 50409 |
| 3568 | 18850 | 68.0 | 61.5 | 22 | 276 | #4 | 50410 |
| 3569 | 18851 | 68.8 | 61.8 | 19 | 285 | #4 | 50411 |
| 3570 | 18852 | 58.4 | 60.0 (140) | 13 | 150 | #2 | 50412 |
| 3571 | 18853 | 64.8 | 57.1 | 18 | 220 | #3 | 50413 |
| 3572 | 18854 | 67.2 | 59.3 | 16 | 213 | #4 | 50414 |
| 3573 | 18855 | 50.0 | 50.0 | 12 | 150 | #1 | 50415 |
| 3574 | 18856 | 62.4 | 57.8 | 13 | 185 | #3 | 50416 |
| 3575 | 18857 | 67.2 | 61.1 | 20 | 336 | #4 | 50417 |
| 3576 | 18858 | 76.8 | 63.3 | 26 | 374 | #6 | 50418 |
| 3577 | 18859 | 63.2 | 50.0 (176) | 19 | 161 | #3 | 50419 |
| 3578 | 18860 | 65.6 | 61.1 | 17 | 265 | #4 | 50420 |
| 3579 | 18861 | 50.0 | 50.0 | 12 | 150 | #1 | 50421 |
| 3580 | 18862 | 72.0 | 60.4 | 22 | 295 | #5 | 50422 |
| 3581 | 18863 | 69.6 | 59.6 | 18 | 263 | #4 | 50423 |
| 3582 | 18864 | 65.6 | 59.6 | 16 | 257 | #4 | 50424 |
| 3583 | 18865 | 65.6 | 54.8 (177) | 16 | 173 | #4 | 50425 |
| 3584 | 18866 | 58.4 | 57.0 (128) | 13 | 150 | #2 | 50426 |
| 3585 | 18867 | 59.2 | 50.0 | 15 | 168 | #2 | 50427 |
| 3586 | 18868 | 69.6 | 59.6 | 21 | 240 | #4 | 50428 |
| 3587 | 18869 | 66.4 | 50.2 | 16 | 192 | #4 | 50429 |
| 3588 | 18870 | 61.6 | 50.0 | 21 | 193 | #3 | 50430 |
| 3589 | 18871 | 63.2 | 53.8 | 14 | 192 | #3 | 50431 |
| 3590 | 18872 | 69.6 | 62.9 | 20 | 543 | #4 | 50432 |
| 3591 | 18873 | 71.2 | 60.0 | 19 | 245 | #5 | 50433 |
| 3592 | 18874 | 50.0 | 50.0 | 12 | 150 | #1 | 50434 |
| 3593 | 18875 | 70.4 | 61.8 | 23 | 406 | #5 | 50435 |
| 3594 | 18876 | 50.0 | 50.0 | 12 | 150 | #1 | 50436 |
| 3595 | 18877 | 50.0 | 50.0 | 12 | 150 | #1 | 50437 |
| 3596 | 18878 | 62.4 | 50.0 | 12 | 183 | #3 | 50438 |
| 3597 | 18879 | 50.0 | 50.0 | 12 | 150 | #1 | 50439 |
| 3598 | 18880 | 61.6 | 59.3 | 14 | 213 | #3 | 50440 |
| 3599 | 18881 | 50.0 | 50.0 | 12 | 150 | #1 | 50441 |
| 3600 | 18882 | 67.2 | 63.3 | 18 | 311 | #4 | 50442 |
| 3601 | 18883 | 71.2 | 61.8 | 30 | 316 | #5 | 50443 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3602 | 18884 | 67.2 | 59.6 | 27 | 239 | #4 | 50444 |
| 3603 | 18885 | 68.8 | 62.9 | 21 | 385 | #4 | 50445 |
| 3604 | 18886 | 81.6 | 75.4 (195) | 25 | 464 | #7 | 50446 |
| 3605 | 18887 | 50.0 | 50.0 | 12 | 150 | #1 | 50447 |
| 3606 | 18888 | 67.2 | 60.7 | 18 | 309 | #4 | 50448 |
| 3607 | 18889 | 68.0 | 63.3 | 20 | 302 | #4 | 50449 |
| 3608 | 18890 | 67.2 | 59.3 | 23 | 211 | #4 | 50450 |
| 3609 | 18891 | 68.8 | 61.1 | 24 | 508 | #4 | 50451 |
| 3610 | 18892 | 86.4 | 84.7 | 25 | 1177 | #8 | 50452 |
| 3611 | 18893 | 69.6 | 61.5 | 30 | 404 | #4 | 50453 |
| 3612 | 18894 | 64.0 | 54.9 | 12 | 237 | #3 | 50454 |
| 3613 | 18895 | 64.0 | 50.0 | 14 | 164 | #3 | 50455 |
| 3614 | 18896 | 68.8 | 61.5 | 23 | 269 | #4 | 50456 |
| 3615 | 18897 | 67.2 | 60.0 | 14 | 219 | #4 | 50457 |
| 3616 | 18898 | 67.2 | 60.7 | 19 | 280 | #4 | 50458 |
| 3617 | 18899 | 70.4 | 61.8 | 18 | 286 | #5 | 50459 |
| 3618 | 18900 | 69.6 | 63.3 | 22 | 362 | #4 | 50460 |
| 3619 | 18901 | 68.0 | 59.6 | 17 | 271 | #4 | 50461 |
| 3620 | 18902 | 66.4 | 50.0 | 12 | 175 | #4 | 50462 |
| 3621 | 18903 | 65.6 | 58.9 | 16 | 220 | #4 | 50463 |
| 3622 | 18904 | 66.4 | 54.9 | 14 | 191 | #4 | 50464 |
| 3623 | 18905 | 66.4 | 58.2 | 22 | 211 | #4 | 50465 |
| 3624 | 18906 | 64.0 | 50.0 | 18 | 194 | #3 | 50466 |
| 3625 | 18907 | 68.0 | 60.4 | 20 | 285 | #4 | 50467 |
| 3626 | 18908 | 65.6 | 60.0 | 13 | 266 | #4 | 50468 |
| 3627 | 18909 | 64.0 | 56.4 | 12 | 175 | #3 | 50469 |
| 3628 | 18910 | 69.6 | 62.2 | 22 | 339 | #4 | 50470 |
| 3629 | 18911 | 50.0 | 50.0 | 12 | 150 | #1 | 50471 |
| 3630 | 18912 | 63.2 | 50.0 | 12 | 202 | #3 | 50472 |
| 3631 | 18913 | 50.0 | 50.0 | 12 | 150 | #1 | 50473 |
| 3632 | 18914 | 50.0 | 50.0 | 12 | 150 | #1 | 50474 |
| 3633 | 18915 | 70.4 | 61.8 | 20 | 275 | #5 | 50475 |
| 3634 | 18916 | 69.6 | 64.7 | 20 | 339 | #4 | 50476 |
| 3635 | 18917 | 64.5 (121) | — | 17 | 156 | #3 | 50477 |
| 3636 | 18918 | 72.0 | 62.9 | 22 | 355 | #5 | 50478 |
| 3637 | 18919 | 71.2 | 62.9 | 22 | 335 | #5 | 50479 |
| 3638 | 18920 | 64.0 | 57.1 | 16 | 203 | #3 | 50480 |
| 3639 | 18921 | 68.0 | 60.3 (224) | 27 | 220 | #4 | 50481 |
| 3640 | 18922 | 66.4 | 55.8 (242) | 26 | 188 | #4 | 50482 |
| 3641 | 18923 | 68.8 | 62.9 | 17 | 268 | #4 | 50483 |
| 3642 | 18924 | 61.6 | 50.0 | 17 | 176 | #3 | 50484 |
| 3643 | 18925 | 67.2 | 50.2 | 19 | 224 | #4 | 50485 |
| 3644 | 18926 | 71.2 | 62.9 | 34 | 335 | #5 | 50486 |
| 3645 | 18927 | 67.2 | 61.1 | 18 | 281 | #4 | 50487 |
| 3646 | 18928 | 70.4 | 64.0 | 24 | 360 | #5 | 50488 |
| 3647 | 18929 | 64.8 | 54.3 (151) | 17 | 168 | #3 | 50489 |
| 3648 | 18930 | 69.6 | 62.2 | 20 | 312 | #4 | 50490 |
| 3649 | 18931 | 71.2 | 64.4 | 20 | 428 | #5 | 50491 |
| 3650 | 18932 | 72.0 | 62.9 | 25 | 312 | #5 | 50492 |
| 3651 | 18933 | 66.4 | 58.2 | 22 | 228 | #4 | 50493 |
| 3652 | 18934 | 65.6 | 50.0 | 17 | 210 | #4 | 50494 |
| 3653 | 18935 | 68.8 | 59.3 | 18 | 223 | #4 | 50495 |
| 3654 | 18936 | 61.6 | 51.9 (208) | 15 | 152 | #3 | 50496 |
| 3655 | 18937 | 50.0 | 50.0 (223) | 12 | 150 | #1 | 50497 |
| 3656 | 18938 | 50.0 | 50.0 | 12 | 150 | #1 | 50498 |
| 3657 | 18939 | 50.0 | 50.0 | 12 | 150 | #1 | 50499 |
| 3658 | 18940 | 71.2 | 60.4 | 23 | 284 | #5 | 50500 |
| 3659 | 18941 | 68.8 | 62.5 | 18 | 322 | #4 | 50501 |
| 3660 | 18942 | 64.0 | 50.0 | 17 | 192 | #3 | 50502 |
| 3661 | 18943 | 68.8 | 61.5 | 19 | 337 | #4 | 50503 |
| 3662 | 18944 | 68.0 | 61.5 | 20 | 246 | #4 | 50504 |
| 3663 | 18945 | 68.0 | 61.8 | 21 | 265 | #4 | 50505 |
| 3664 | 18946 | 68.0 | 61.1 | 18 | 288 | #4 | 50506 |
| 3665 | 18947 | 74.4 | 63.6 | 37 | 433 | #5 | 50507 |
| 3666 | 18948 | 66.4 | 61.1 | 20 | 291 | #4 | 50508 |
| 3667 | 18949 | 68.8 | 61.8 | 24 | 328 | #4 | 50509 |
| 3668 | 18950 | 50.0 | 50.0 | 12 | 150 | #1 | 50510 |
| 3669 | 18951 | 68.0 | 60.4 | 27 | 243 | #4 | 50511 |
| 3670 | 18952 | 70.4 | 59.6 | 25 | 422 | #5 | 50512 |
| 3671 | 18953 | 68.8 | 61.8 | 25 | 333 | #4 | 50513 |
| 3672 | 18954 | 52.8 | 50.0 | 12 | 150 | #1 | 50514 |
| 3673 | 18955 | 65.6 | 58.5 | 15 | 233 | #4 | 50515 |
| 3674 | 18956 | 67.2 | 61.1 | 18 | 316 | #4 | 50516 |
| 3675 | 18957 | 50.0 | 50.0 | 12 | 150 | #1 | 50517 |
| 3676 | 18958 | 50.0 | 50.0 | 12 | 150 | #1 | 50518 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3677 | 18959 | 75.2 | 65.1 | 24 | 470 | #6 | 50519 |
| 3678 | 18960 | 66.4 | 60.0 | 26 | 264 | #4 | 50520 |
| 3679 | 18961 | 71.2 | 63.3 | 16 | 416 | #5 | 50521 |
| 3680 | 18962 | 67.2 | 60.0 | 19 | 241 | #4 | 50522 |
| 3681 | 18963 | 50.0 | 50.0 | 12 | 150 | #1 | 50523 |
| 3682 | 18964 | 50.0 | 50.0 | 12 | 150 | #1 | 50524 |
| 3683 | 18965 | 66.4 | 59.2 (152) | 16 | 161 | #4 | 50525 |
| 3684 | 18966 | 62.4 | 58.3 (252) | 14 | 165 | #3 | 50526 |
| 3685 | 18967 | 63.2 | 51.6 | 14 | 182 | #3 | 50527 |
| 3686 | 18968 | 65.6 | 50.0 (258) | 16 | 150 | #4 | 50528 |
| 3687 | 18969 | 67.2 | 64.6 (147) | 27 | 199 | #4 | 50529 |
| 3688 | 18970 | 67.2 | 59.3 | 19 | 218 | #4 | 50530 |
| 3689 | 18971 | 74.4 | 65.8 | 21 | 608 | #5 | 50531 |
| 3690 | 18972 | 50.0 | 50.0 | 12 | 150 | #1 | 50532 |
| 3691 | 18973 | 72.8 | 61.8 | 19 | 269 | #5 | 50533 |
| 3692 | 18974 | 66.4 | 59.3 | 21 | 269 | #4 | 50534 |
| 3693 | 18975 | 60.8 | 58.9 | 12 | 196 | #3 | 50535 |
| 3694 | 18976 | 64.8 | 59.3 | 16 | 224 | #3 | 50536 |
| 3695 | 18977 | 68.0 | 61.1 | 19 | 373 | #4 | 50537 |
| 3696 | 18978 | 64.0 | 50.0 (269) | 12 | 178 | #3 | 50538 |
| 3697 | 18979 | 67.2 | 61.5 | 20 | 270 | #4 | 50539 |
| 3698 | 18980 | 72.0 | 63.3 | 20 | 572 | #5 | 50540 |
| 3699 | 18981 | 67.2 | 60.7 | 17 | 305 | #4 | 50541 |
| 3700 | 18982 | 67.2 | 53.5 | 17 | 199 | #4 | 50542 |
| 3701 | 18983 | 69.6 | 62.2 | 39 | 318 | #4 | 50543 |
| 3702 | 18984 | 72.0 | 65.1 | 25 | 338 | #5 | 50544 |
| 3703 | 18985 | 64.0 | 50.0 (238) | 26 | 173 | #3 | 50545 |
| 3704 | 18986 | 66.4 | 59.6 (267) | 22 | 212 | #4 | 50546 |
| 3705 | 18987 | 50.0 | 50.0 | 12 | 150 | #1 | 50547 |
| 3706 | 18988 | 70.4 | 64.4 | 24 | 384 | #5 | 50548 |
| 3707 | 18989 | 67.4 (95) | — | 16 | 160 | #4 | 50549 |
| 3708 | 18990 | 50.0 | 50.0 | 12 | 150 | #1 | 50550 |
| 3709 | 18991 | 81.6 | 77.5 | 27 | 804 | #7 | 50551 |
| 3710 | 18992 | 50.0 | 50.0 | 12 | 150 | #1 | 50552 |
| 3711 | 18993 | 65.6 | 60.4 | 22 | 224 | #4 | 50553 |
| 3712 | 18994 | 50.0 | 50.0 | 12 | 150 | #1 | 50554 |
| 3713 | 18995 | 68.8 | 61.5 | 23 | 249 | #4 | 50555 |
| 3714 | 18996 | 68.0 | 61.1 | 20 | 281 | #4 | 50556 |
| 3715 | 18997 | 66.4 | 60.4 | 19 | 224 | #4 | 50557 |
| 3716 | 18998 | 61.3 (62) | — | 25 | 167 | #3 | — |
| 3717 | 18999 | 68.0 | 63.4 (191) | 24 | 218 | #4 | 50558 |
| 3718 | 19000 | 69.6 | 61.5 | 21 | 298 | #4 | 50559 |
| 3719 | 19001 | 64.0 | 50.0 | 13 | 178 | #3 | 50560 |
| 3720 | 19002 | 64.0 | 50.0 (241) | 17 | 161 | #3 | 50561 |
| 3721 | 19003 | 63.2 | 58.9 | 21 | 217 | #3 | 50562 |
| 3722 | 19004 | 68.0 | 61.1 | 17 | 251 | #4 | 50563 |
| 3723 | 19005 | 70.4 | 62.9 | 20 | 354 | #5 | 50564 |
| 3724 | 19006 | 69.6 | 59.6 | 21 | 244 | #4 | 50565 |
| 3725 | 19007 | 68.0 | 57.8 | 21 | 221 | #4 | 50566 |
| 3726 | 19008 | 66.4 | 55.4 (240) | 21 | 191 | #4 | 50567 |
| 3727 | 19009 | 52.0 | 50.0 | 16 | 159 | #1 | 50568 |
| 3728 | 19010 | 63.2 | 57.5 | 16 | 216 | #3 | 50569 |
| 3729 | 19011 | 66.4 | 58.9 | 17 | 240 | #4 | 50570 |
| 3730 | 19012 | 60.8 | 50.0 (270) | 14 | 155 | #3 | 50571 |
| 3731 | 19013 | 68.8 | 61.1 | 20 | 301 | #4 | 50572 |
| 3732 | 19014 | 68.0 | 59.3 | 17 | 219 | #4 | 50573 |
| 3733 | 19015 | 62.4 | 56.4 | 15 | 200 | #3 | 50574 |
| 3734 | 19016 | 50.0 (73) | — | 12 | 150 | #1 | 50575 |
| 3735 | 19017 | 62.4 | 57.5 | 13 | 193 | #3 | 50576 |
| 3736 | 19018 | 67.2 | 61.1 | 18 | 288 | #4 | 50577 |
| 3737 | 19019 | 71.2 | 61.8 | 22 | 331 | #5 | 50578 |
| 3738 | 19020 | 68.0 | 50.5 | 16 | 207 | #4 | 50579 |
| 3739 | 19021 | 61.6 | 57.1 | 12 | 177 | #3 | 50580 |
| 3740 | 19022 | 67.2 | 65.5 (139) | 22 | 199 | #4 | 50581 |
| 3741 | 19023 | 71.2 | 63.3 | 22 | 351 | #5 | 50582 |
| 3742 | 19024 | 72.0 | 61.1 | 23 | 308 | #5 | 50583 |
| 3743 | 19025 | 65.6 | 50.0 | 39 | 386 | #4 | 50584 |
| 3744 | 19026 | 78.4 | 67.6 | 40 | 506 | #6 | 50585 |
| 3745 | 19027 | 74.4 | 57.8 | 14 | 497 | #5 | 50586 |
| 3746 | 19028 | 50.0 | 50.0 | 12 | 150 | #1 | 50587 |
| 3747 | 19029 | 50.0 (75) | — | 12 | 150 | #1 | 50588 |
| 3748 | 19030 | 68.0 | 50.0 | 14 | 198 | #4 | 50589 |
| 3749 | 19031 | 68.0 | 52.7 | 29 | 227 | #4 | 50590 |
| 3750 | 19032 | 70.4 | 63.6 | 28 | 391 | #5 | 50591 |
| 3751 | 19033 | 67.2 | 61.2 (147) | 15 | 154 | #4 | 50592 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3752 | 19034 | 71.2 | 58.5 | 14 | 285 | #5 | 50593 |
| 3753 | 19035 | 67.8 (121) | — | 16 | 168 | #4 | 50594 |
| 3754 | 19036 | 63.2 | 58.2 | 18 | 243 | #3 | 50595 |
| 3755 | 19037 | 68.8 | 61.5 | 20 | 313 | #4 | 50596 |
| 3756 | 19038 | 65.6 | 58.5 | 12 | 191 | #4 | 50597 |
| 3757 | 19039 | 67.2 | 60.0 | 14 | 220 | #4 | 50598 |
| 3758 | 19040 | 66.4 | 54.2 | 22 | 197 | #4 | 50599 |
| 3759 | 19041 | 66.4 | 59.6 | 15 | 235 | #4 | 50600 |
| 3760 | 19042 | 50.0 (113) | — | 12 | 150 | #1 | 50601 |
| 3761 | 19043 | 67.2 | 57.8 | 29 | 234 | #4 | 50602 |
| 3762 | 19044 | 70.4 | 62.9 | 24 | 518 | #5 | 50603 |
| 3763 | 19045 | 60.0 | 50.9 (218) | 13 | 150 | #2 | 50604 |
| 3764 | 19046 | 65.6 | 58.9 | 21 | 221 | #4 | 50605 |
| 3765 | 19047 | 97.6 | 96.4 | 60 | 1364 | #10 | 50606 |
| 3766 | 19048 | 71.2 | 61.5 | 24 | 348 | #5 | 50607 |
| 3767 | 19049 | 73.6 | 62.9 | 22 | 611 | #5 | 50608 |
| 3768 | 19050 | 50.0 (118) | — | 12 | 150 | #1 | 50609 |
| 3769 | 19051 | 66.4 | 59.3 | 17 | 238 | #4 | 50610 |
| 3770 | 19052 | 72.0 | 62.9 | 25 | 360 | #5 | 50611 |
| 3771 | 19053 | 63.2 | 57.8 | 14 | 197 | #3 | 50612 |
| 3772 | 19054 | 56.8 | 50.0 | 16 | 169 | #2 | 50613 |
| 3773 | 19055 | 68.0 | 58.9 | 25 | 233 | #4 | 50614 |
| 3774 | 19056 | 69.6 | 62.5 | 22 | 331 | #4 | 50615 |
| 3775 | 19057 | 81.6 | 56.7 | 21 | 452 | #7 | 50616 |
| 3776 | 19058 | 69.6 | 61.1 | 22 | 290 | #4 | 50617 |
| 3777 | 19059 | 66.4 | 59.3 | 18 | 237 | #4 | 50618 |
| 3778 | 19060 | 55.7 (88) | — | 12 | 150 | #2 | 50619 |
| 3779 | 19061 | 72.8 | 64.7 | 29 | 381 | #5 | 50620 |
| 3780 | 19062 | 69.6 | 60.0 | 18 | 234 | #4 | 50621 |
| 3781 | 19063 | 50.0 | 50.0 | 12 | 150 | #1 | 50622 |
| 3782 | 19064 | 80.0 | 69.8 | 29 | 530 | #6 | 50623 |
| 3783 | 19065 | 68.0 | 50.0 | 15 | 215 | #4 | 50624 |
| 3784 | 19066 | 68.8 | 57.1 | 31 | 223 | #4 | 50625 |
| 3785 | 19067 | 66.4 | 51.6 (213) | 20 | 183 | #4 | 50626 |
| 3786 | 19068 | 68.8 | 61.8 | 23 | 336 | #4 | 50627 |
| 3787 | 19069 | 66.4 | 56.7 | 18 | 200 | #4 | 50628 |
| 3788 | 19070 | 68.0 | 59.6 | 19 | 236 | #4 | 50629 |
| 3789 | 19071 | 54.4 | 50.0 | 12 | 150 | #1 | 50630 |
| 3790 | 19072 | 69.6 | 58.5 | 19 | 219 | #4 | 50631 |
| 3791 | 19073 | 50.0 | 50.0 | 12 | 150 | #1 | 50632 |
| 3792 | 19074 | 74.4 | 66.2 | 23 | 389 | #5 | 50633 |
| 3793 | 19075 | 50.0 | 50.0 | 12 | 150 | #1 | 50634 |
| 3794 | 19076 | 63.2 | 50.0 (187) | 17 | 250 | #3 | 50635 |
| 3795 | 19077 | 50.0 | 50.0 | 12 | 150 | #1 | 50636 |
| 3796 | 19078 | 68.0 | 61.8 | 18 | 314 | #4 | 50637 |
| 3797 | 19079 | 77.6 | 69.5 | 27 | 576 | #6 | 50638 |
| 3798 | 19080 | 69.6 | 61.1 | 20 | 290 | #4 | 50639 |
| 3799 | 19081 | 68.0 | 61.5 | 23 | 373 | #4 | 50640 |
| 3800 | 19082 | 69.6 | 61.8 | 20 | 302 | #4 | 50641 |
| 3801 | 19083 | 66.4 | 57.8 | 19 | 246 | #4 | 50642 |
| 3802 | 19084 | 62.4 | 52.0 | 12 | 207 | #3 | 50643 |
| 3803 | 19085 | 69.6 | 62.5 | 21 | 301 | #4 | 50644 |
| 3804 | 19086 | 66.4 | 61.2 (260) | 20 | 240 | #4 | 50645 |
| 3805 | 19087 | 70.4 | 62.9 | 21 | 339 | #5 | 50646 |
| 3806 | 19088 | 64.0 | 58.9 | 14 | 204 | #3 | 50647 |
| 3807 | 19089 | 71.2 | 58.9 | 20 | 292 | #5 | 50648 |
| 3808 | 19090 | 50.0 | 50.0 | 12 | 150 | #1 | 50649 |
| 3809 | 19091 | 65.6 | 59.6 | 17 | 226 | #4 | 50650 |
| 3810 | 19092 | 65.6 | 50.0 | 21 | 193 | #4 | 50651 |
| 3811 | 19093 | 67.2 | 59.6 | 18 | 307 | #4 | 50652 |
| 3812 | 19094 | 66.4 | 50.0 | 13 | 205 | #4 | 50653 |
| 3813 | 19095 | 64.0 | 58.2 | 16 | 235 | #3 | 50654 |
| 3814 | 19096 | 65.6 | 50.0 | 15 | 199 | #4 | 50655 |
| 3815 | 19097 | 69.6 | 58.5 | 19 | 222 | #4 | 50656 |
| 3816 | 19098 | 64.0 | 56.7 | 13 | 207 | #3 | 50657 |
| 3817 | 19099 | 67.2 | 54.7 (245) | 18 | 207 | #4 | 50658 |
| 3818 | 19100 | 69.6 | 60.4 | 23 | 268 | #4 | 50659 |
| 3819 | 19101 | 60.0 | 52.0 | 13 | 183 | #2 | 50660 |
| 3820 | 19102 | 71.2 (66) | — | 30 | 170 | #5 | 50661 |
| 3821 | 19103 | 65.6 | 59.6 | 14 | 223 | #4 | 50662 |
| 3822 | 19104 | 68.0 | 62.5 | 20 | 351 | #4 | 50663 |
| 3823 | 19105 | 69.6 | 61.8 | 26 | 311 | #4 | 50664 |
| 3824 | 19106 | 50.0 | 50.0 | 12 | 150 | #1 | 50665 |
| 3825 | 19107 | 60.8 | 50.0 (171) | 13 | 150 | #3 | 50666 |
| 3826 | 19108 | 72.0 | 61.8 | 25 | 353 | #5 | 50667 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3827 | 19109 | 56.0 | 50.0 | 17 | 176 | #2 | 50668 |
| 3828 | 19110 | 64.8 | 51.0 (261) | 18 | 182 | #3 | 50669 |
| 3829 | 19111 | 62.4 | 56.4 | 14 | 175 | #3 | 50670 |
| 3830 | 19112 | 66.4 | 54.5 | 19 | 210 | #4 | 50671 |
| 3831 | 19113 | 68.0 | 62.5 | 20 | 426 | #4 | 50672 |
| 3832 | 19114 | 69.6 | 61.8 | 17 | 280 | #4 | 50673 |
| 3833 | 19115 | 74.4 | 61.1 | 34 | 351 | #5 | 50674 |
| 3834 | 19116 | 84.4 (90) | — | 21 | 320 | #7 | 50675 |
| 3835 | 19117 | 50.0 | 50.0 | 12 | 150 | #1 | 50676 |
| 3836 | 19118 | 61.6 | 55.7 (192) | 14 | 153 | #3 | 50677 |
| 3837 | 19119 | 65.6 | 58.9 | 14 | 210 | #4 | 50678 |
| 3838 | 19120 | 68.8 | 59.6 | 33 | 243 | #4 | 50679 |
| 3839 | 19121 | 62.4 | 53.1 | 15 | 172 | #3 | 50680 |
| 3840 | 19122 | 76.0 | 63.3 | 25 | 334 | #6 | 50681 |
| 3841 | 19123 | 67.2 | 60.0 | 17 | 226 | #4 | 50682 |
| 3842 | 19124 | 50.0 | 50.0 | 12 | 150 | #1 | 50683 |
| 3843 | 19125 | 50.0 (69) | — | 12 | 150 | #1 | 50684 |
| 3844 | 19126 | 71.2 | 65.1 | 23 | 420 | #5 | 50685 |
| 3845 | 19127 | 66.4 | 60.4 | 17 | 266 | #4 | 50686 |
| 3846 | 19128 | 69.6 | 58.2 | 20 | 229 | #4 | 50687 |
| 3847 | 19129 | 53.6 | 50.0 (155) | 16 | 150 | #1 | 50688 |
| 3848 | 19130 | 66.4 | 59.6 | 16 | 207 | #4 | 50689 |
| 3849 | 19131 | 50.0 | 50.0 | 12 | 150 | #1 | 50690 |
| 3850 | 19132 | 72.0 | 62.9 | 28 | 348 | #5 | 50691 |
| 3851 | 19133 | 66.4 | 59.3 | 16 | 242 | #4 | 50692 |
| 3852 | 19134 | 63.2 | 50.0 (191) | 15 | 154 | #3 | 50693 |
| 3853 | 19135 | 69.6 | 61.5 | 14 | 396 | #4 | 50694 |
| 3854 | 19136 | 66.4 | 59.3 | 16 | 283 | #4 | 50695 |
| 3855 | 19137 | 67.2 | 61.5 | 21 | 273 | #4 | 50696 |
| 3856 | 19138 | 60.0 | 54.2 | 13 | 187 | #2 | 50697 |
| 3857 | 19139 | 70.4 | 60.7 | 22 | 293 | #5 | 50698 |
| 3858 | 19140 | 64.8 | 50.0 | 15 | 170 | #3 | 50699 |
| 3859 | 19141 | 60.0 | 50.0 (151) | 16 | 150 | #2 | 50700 |
| 3860 | 19142 | 50.0 | 50.0 | 12 | 150 | #1 | 50701 |
| 3861 | 19143 | 62.4 | 50.0 | 14 | 150 | #3 | 50702 |
| 3862 | 19144 | 71.2 | 62.9 | 25 | 395 | #5 | 50703 |
| 3863 | 19145 | 64.0 | 55.6 | 16 | 239 | #3 | 50704 |
| 3864 | 19146 | 69.6 | 61.1 | 19 | 279 | #4 | 50705 |
| 3865 | 19147 | 71.2 | 57.5 (259) | 33 | 223 | #5 | 50706 |
| 3866 | 19148 | 65.6 | 50.0 (218) | 20 | 170 | #4 | 50707 |
| 3867 | 19149 | 61.6 | 50.0 | 13 | 173 | #3 | 50708 |
| 3868 | 19150 | 72.8 | 60.0 | 20 | 269 | #5 | 50709 |
| 3869 | 19151 | 80.0 | 66.5 | 37 | 512 | #6 | 50710 |
| 3870 | 19152 | 62.4 | 50.0 | 14 | 150 | #3 | 50711 |
| 3871 | 19153 | 64.8 | 62.2 (148) | 18 | 170 | #3 | 50712 |
| 3872 | 19154 | 69.6 | 62.2 | 20 | 320 | #4 | 50713 |
| 3873 | 19155 | 64.8 | 58.9 | 17 | 200 | #3 | 50714 |
| 3874 | 19156 | 68.0 | 65.4 (159) | 24 | 250 | #4 | 50715 |
| 3875 | 19157 | 72.0 | 56.7 | 22 | 357 | #5 | 50716 |
| 3876 | 19158 | 69.6 | 60.7 | 20 | 267 | #4 | 50717 |
| 3877 | 19159 | 68.8 | 60.7 | 21 | 269 | #4 | 50718 |
| 3878 | 19160 | 69.6 | 61.5 | 21 | 325 | #4 | 50719 |
| 3879 | 19161 | 68.0 | 60.1 (233) | 19 | 239 | #4 | 50720 |
| 3880 | 19162 | 68.8 | 62.5 | 23 | 381 | #4 | 50721 |
| 3881 | 19163 | 50.0 (108) | — | 12 | 150 | #1 | 50722 |
| 3882 | 19164 | 69.6 | 61.5 | 24 | 314 | #4 | 50723 |
| 3883 | 19165 | 61.6 | 58.2 | 16 | 217 | #3 | 50724 |
| 3884 | 19166 | 63.2 | 50.0 | 14 | 206 | #3 | 50725 |
| 3885 | 19167 | 67.2 | 62.2 | 21 | 448 | #4 | 50726 |
| 3886 | 19168 | 67.2 | 60.7 | 14 | 253 | #4 | 50727 |
| 3887 | 19169 | 64.8 | 56.4 | 13 | 178 | #3 | 50728 |
| 3888 | 19170 | 65.6 | 59.6 | 17 | 275 | #4 | 50729 |
| 3889 | 19171 | 69.6 | 60.4 | 19 | 263 | #4 | 50730 |
| 3890 | 19172 | 70.4 | 59.6 | 15 | 247 | #5 | 50731 |
| 3891 | 19173 | 50.0 | 50.0 | 12 | 150 | #1 | 50732 |
| 3892 | 19174 | 70.4 | 57.5 | 17 | 237 | #5 | 50733 |
| 3893 | 19175 | 50.0 | 50.0 | 12 | 150 | #1 | 50734 |
| 3894 | 19176 | 50.0 | 50.0 | 12 | 150 | #1 | 50735 |
| 3895 | 19177 | 68.8 | 60.7 | 19 | 322 | #4 | 50736 |
| 3896 | 19178 | 59.2 | 50.0 | 15 | 150 | #2 | 50737 |
| 3897 | 19179 | 68.0 | 61.8 | 16 | 313 | #4 | 50738 |
| 3898 | 19180 | 50.0 | 50.0 | 12 | 150 | #1 | 50739 |
| 3899 | 19181 | 50.0 | 50.0 | 12 | 150 | #1 | 50740 |
| 3900 | 19182 | 65.6 | 59.2 (213) | 19 | 208 | #4 | 50741 |
| 3901 | 19183 | 50.0 | 50.0 | 12 | 150 | #1 | 50742 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3902 | 19184 | 64.0 | 57.5 | 13 | 190 | #3 | 50743 |
| 3903 | 19185 | 76.0 | 62.9 | 32 | 333 | #6 | 50744 |
| 3904 | 19186 | 63.2 | 59.6 | 17 | 217 | #3 | 50745 |
| 3905 | 19187 | 68.0 | 62.2 (217) | 24 | 266 | #4 | 50746 |
| 3906 | 19188 | 70.4 | 61.1 | 18 | 279 | #5 | 50747 |
| 3907 | 19189 | 62.4 | 50.0 (226) | 22 | 164 | #3 | 50748 |
| 3908 | 19190 | 66.4 | 60.4 | 18 | 251 | #4 | 50749 |
| 3909 | 19191 | 67.2 | 58.9 | 27 | 244 | #4 | 50750 |
| 3910 | 19192 | 50.0 | 50.0 | 12 | 150 | #1 | 50751 |
| 3911 | 19193 | 64.8 | 59.3 | 19 | 223 | #3 | 50752 |
| 3912 | 19194 | 68.8 | 60.4 | 19 | 291 | #4 | 50753 |
| 3913 | 19195 | 68.0 | 61.8 | 20 | 341 | #4 | 50754 |
| 3914 | 19196 | 70.4 | 64.0 | 22 | 469 | #5 | 50755 |
| 3915 | 19197 | 82.4 | 60.7 | 32 | 482 | #7 | 50756 |
| 3916 | 19198 | 65.6 | 50.0 (210) | 20 | 182 | #4 | 50757 |
| 3917 | 19199 | 69.6 | 62.2 | 25 | 386 | #4 | 50758 |
| 3918 | 19200 | 62.4 | 57.8 | 14 | 203 | #3 | 50759 |
| 3919 | 19201 | 64.0 | 50.0 | 16 | 166 | #3 | 50760 |
| 3920 | 19202 | 69.6 | 59.3 | 25 | 254 | #4 | 50761 |
| 3921 | 19203 | 62.4 | 56.0 | 13 | 184 | #3 | 50762 |
| 3922 | 19204 | 63.2 | 50.0 (228) | 16 | 182 | #3 | 50763 |
| 3923 | 19205 | 64.0 | 58.5 | 19 | 219 | #4 | 50764 |
| 3924 | 19206 | 69.6 | 60.4 | 22 | 238 | #4 | 50765 |
| 3925 | 19207 | 73.6 | 66.2 | 25 | 540 | #5 | 50766 |
| 3926 | 19208 | 67.2 | 60.4 | 20 | 302 | #4 | 50767 |
| 3927 | 19209 | 68.0 | 58.5 | 22 | 317 | #4 | 50768 |
| 3928 | 19210 | 68.0 | 63.0 (162) | 22 | 216 | #4 | 50769 |
| 3929 | 19211 | 50.0 | 50.0 | 12 | 150 | #1 | 50770 |
| 3930 | 19212 | 81.6 | 75.6 | 20 | 1260 | #7 | 50771 |
| 3931 | 19213 | 62.4 (117) | — | 16 | 157 | #3 | 50772 |
| 3932 | 19214 | 80.0 | 67.6 | 39 | 643 | #6 | 50773 |
| 3933 | 19215 | 57.6 | 50.0 | 15 | 169 | #2 | 50774 |
| 3934 | 19216 | 64.8 | 50.0 | 15 | 185 | #3 | 50775 |
| 3935 | 19217 | 69.6 | 62.2 | 25 | 294 | #4 | 50776 |
| 3936 | 19218 | 50.0 (94) | — | 12 | 150 | #1 | 50777 |
| 3937 | 19219 | 65.6 | 58.2 | 20 | 192 | #4 | 50778 |
| 3938 | 19220 | 69.6 | 60.4 | 21 | 264 | #4 | 50779 |
| 3939 | 19221 | 66.4 | 59.3 | 12 | 218 | #4 | 50780 |
| 3940 | 19222 | 67.2 | 58.9 | 18 | 217 | #4 | 50781 |
| 3941 | 19223 | 67.2 | 60.4 | 20 | 255 | #4 | 50782 |
| 3942 | 19224 | 69.6 | 56.7 | 30 | 241 | #4 | 50783 |
| 3943 | 19225 | 73.6 | 68.4 | 23 | 625 | #5 | 50784 |
| 3944 | 19226 | 68.8 | 60.0 | 23 | 286 | #4 | 50785 |
| 3945 | 19227 | 67.2 | 59.6 | 18 | 237 | #4 | 50786 |
| 3946 | 19228 | 50.0 | 50.0 | 15 | 153 | #1 | 50787 |
| 3947 | 19229 | 64.8 | 56.0 | 14 | 186 | #3 | 50788 |
| 3948 | 19230 | 69.6 | 61.5 | 18 | 240 | #4 | 50789 |
| 3949 | 19231 | 50.0 | 50.0 | 12 | 150 | #1 | 50790 |
| 3950 | 19232 | 50.0 | 50.0 | 12 | 150 | #1 | 50791 |
| 3951 | 19233 | 67.2 | 61.1 | 20 | 341 | #4 | 50792 |
| 3952 | 19234 | 68.0 | 60.7 | 18 | 268 | #4 | 50793 |
| 3953 | 19235 | 72.8 | 65.5 (235) | 23 | 356 | #5 | 50794 |
| 3954 | 19236 | 50.0 | 50.0 | 12 | 150 | #1 | 50795 |
| 3955 | 19237 | 72.0 | 61.1 | 32 | 296 | #5 | 50796 |
| 3956 | 19238 | 65.6 | 60.0 | 20 | 239 | #4 | 50797 |
| 3957 | 19239 | 50.0 | 50.0 (152) | 12 | 150 | #1 | 50798 |
| 3958 | 19240 | 50.0 | 50.0 | 12 | 150 | #1 | 50799 |
| 3959 | 19241 | 69.6 | 60.7 | 24 | 276 | #4 | 50800 |
| 3960 | 19242 | 50.0 | 50.0 | 12 | 150 | #1 | 50801 |
| 3961 | 19243 | 50.0 | 50.0 | 12 | 150 | #1 | 50802 |
| 3962 | 19244 | 68.0 | 58.5 | 29 | 243 | #4 | 50803 |
| 3963 | 19245 | 77.6 | 75.0 (168) | 16 | 444 | #6 | 50804 |
| 3964 | 19246 | 50.0 | 50.0 | 12 | 150 | #1 | 50805 |
| 3965 | 19247 | 73.6 | 61.5 | 32 | 289 | #5 | 50806 |
| 3966 | 19248 | 66.4 | 60.4 | 22 | 236 | #4 | 50807 |
| 3967 | 19249 | 68.0 | 60.0 | 21 | 251 | #4 | 50808 |
| 3968 | 19250 | 72.0 | 63.6 | 25 | 374 | #5 | 50809 |
| 3969 | 19251 | 63.2 | 58.8 (221) | 17 | 167 | #3 | 50810 |
| 3970 | 19252 | 50.0 | 50.0 | 12 | 150 | #1 | 50811 |
| 3971 | 19253 | 66.4 | 55.3 | 16 | 224 | #4 | 50812 |
| 3972 | 19254 | 68.8 | 63.3 | 27 | 465 | #4 | 50813 |
| 3973 | 19255 | 67.2 | 60.4 | 19 | 239 | #4 | 50814 |
| 3974 | 19256 | 69.6 | 62.5 | 21 | 453 | #4 | 50815 |
| 3975 | 19257 | 67.2 | 60.4 | 18 | 226 | #4 | 50816 |
| 3976 | 19258 | 69.6 | 62.5 | 28 | 321 | #4 | 50817 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 3977 | 19259 | 66.7 (75) | — | 14 | 150 | #4 | 50818 |
| 3978 | 19260 | 50.0 | 50.0 | 20 | 159 | #1 | 50819 |
| 3979 | 19261 | 65.6 | 60.7 | 16 | 216 | #4 | 50820 |
| 3980 | 19262 | 71.2 | 62.5 | 20 | 315 | #5 | 50821 |
| 3981 | 19263 | 68.8 | 61.8 | 19 | 377 | #4 | 50822 |
| 3982 | 19264 | 50.0 | 50.0 | 12 | 150 | #1 | 50823 |
| 3983 | 19265 | 64.8 | 50.0 (219) | 16 | 164 | #3 | 50824 |
| 3984 | 19266 | 66.4 | 60.0 | 16 | 269 | #4 | 50825 |
| 3985 | 19267 | 72.0 | 62.9 | 27 | 353 | #5 | 50826 |
| 3986 | 19268 | 84.0 | 66.9 | 30 | 474 | #7 | 50827 |
| 3987 | 19269 | 64.0 | 58.9 | 15 | 226 | #3 | 50828 |
| 3988 | 19270 | 63.2 | 50.0 (249) | 12 | 171 | #3 | 50829 |
| 3989 | 19271 | 67.2 | 62.2 | 19 | 352 | #4 | 50830 |
| 3990 | 19272 | 58.4 | 50.0 | 14 | 166 | #2 | 50831 |
| 3991 | 19273 | 64.0 | 50.9 | 15 | 184 | #3 | 50832 |
| 3992 | 19274 | 73.6 | 66.5 | 22 | 417 | #5 | 50833 |
| 3993 | 19275 | 68.0 | 61.1 | 20 | 288 | #4 | 50834 |
| 3994 | 19276 | 50.0 | 50.0 | 12 | 150 | #1 | 50835 |
| 3995 | 19277 | 76.8 | 63.6 | 28 | 342 | #6 | 50836 |
| 3996 | 19278 | 62.4 | 54.2 (166) | 23 | 169 | #3 | 50837 |
| 3997 | 19279 | 64.0 | 61.7 (180) | 17 | 172 | #3 | 50838 |
| 3998 | 19280 | 72.0 | 66.2 | 24 | 597 | #5 | 50839 |
| 3999 | 19281 | 65.6 | 55.3 | 15 | 202 | #4 | 50840 |
| 4000 | 19282 | 66.4 | 60.4 | 18 | 413 | #4 | 50841 |
| 4001 | 19283 | 63.2 | 58.5 | 15 | 287 | #3 | 50842 |
| 4002 | 19284 | 70.4 | 60.7 | 22 | 322 | #5 | 50843 |
| 4003 | 19285 | 66.4 | 60.0 | 16 | 246 | #4 | 50844 |
| 4004 | 19286 | 65.6 | 59.3 | 15 | 237 | #4 | 50845 |
| 4005 | 19287 | 69.3 (75) | — | 26 | 193 | #4 | — |
| 4006 | 19288 | 67.2 | 61.8 | 19 | 350 | #4 | 50846 |
| 4007 | 19289 | 50.0 | 50.0 | 12 | 150 | #1 | 50847 |
| 4008 | 19290 | 98.4 | 95.6 | 82 | 1283 | #10 | 50848 |
| 4009 | 19291 | 50.0 | 50.0 | 12 | 150 | #1 | 50849 |
| 4010 | 19292 | 68.0 | 57.5 | 27 | 222 | #4 | 50850 |
| 4011 | 19293 | 67.2 | 58.4 (274) | 17 | 208 | #4 | 50851 |
| 4012 | 19294 | 73.6 | 58.5 | 24 | 317 | #5 | 50852 |
| 4013 | 19295 | 68.0 | 59.3 | 18 | 229 | #4 | 50853 |
| 4014 | 19296 | 66.4 | 59.6 | 16 | 257 | #4 | 50854 |
| 4015 | 19297 | 64.8 | 59.3 | 12 | 248 | #3 | 50855 |
| 4016 | 19298 | 67.2 | 50.0 | 13 | 273 | #4 | 50856 |
| 4017 | 19299 | 66.4 | 59.3 | 16 | 210 | #4 | 50857 |
| 4018 | 19300 | 82.4 | 69.8 | 30 | 626 | #7 | 50858 |
| 4019 | 19301 | 50.0 | 50.0 | 12 | 150 | #1 | 50859 |
| 4020 | 19302 | 63.2 | 50.0 | 17 | 188 | #3 | 50860 |
| 4021 | 19303 | 75.2 | 69.5 | 32 | 727 | #6 | 50861 |
| 4022 | 19304 | 72.8 | 63.3 | 20 | 378 | #5 | 50862 |
| 4023 | 19305 | 65.6 | 62.0 (171) | 16 | 162 | #4 | 50863 |
| 4024 | 19306 | 64.8 | 53.1 | 17 | 192 | #3 | 50864 |
| 4025 | 19307 | 50.0 | 50.0 | 12 | 150 | #1 | 50865 |
| 4026 | 19308 | 64.8 | 52.7 | 15 | 216 | #3 | 50866 |
| 4027 | 19309 | 50.0 (111) | — | 12 | 150 | #1 | 50867 |
| 4028 | 19310 | 68.8 | 60.4 | 22 | 260 | #4 | 50868 |
| 4029 | 19311 | 64.8 | 59.6 | 18 | 248 | #3 | 50869 |
| 4030 | 19312 | 65.6 | 58.9 | 20 | 211 | #4 | 50870 |
| 4031 | 19313 | 69.6 | 58.5 | 34 | 257 | #4 | 50871 |
| 4032 | 19314 | 69.6 | 62.9 | 21 | 336 | #4 | 50872 |
| 4033 | 19315 | 68.0 | 59.3 | 21 | 243 | #4 | 50873 |
| 4034 | 19316 | 50.0 | 50.0 | 12 | 150 | #1 | 50874 |
| 4035 | 19317 | 63.2 | 59.3 | 13 | 237 | #3 | 50875 |
| 4036 | 19318 | 64.0 | 50.0 | 14 | 182 | #3 | 50876 |
| 4037 | 19319 | 50.0 | 50.0 | 12 | 150 | #1 | 50877 |
| 4038 | 19320 | 66.4 | 60.7 | 17 | 243 | #4 | 50878 |
| 4039 | 19321 | 64.0 | 56.7 (238) | 16 | 184 | #3 | 50879 |
| 4040 | 19322 | 69.6 | 60.0 | 20 | 274 | #4 | 50880 |
| 4041 | 19323 | 50.0 (69) | — | 27 | 150 | #1 | 50881 |
| 4042 | 19324 | 50.0 | 50.0 (126) | 13 | 153 | #1 | 50882 |
| 4043 | 19325 | 72.8 | 59.6 | 25 | 278 | #5 | 50883 |
| 4044 | 19326 | 67.2 | 57.8 | 22 | 245 | #4 | 50884 |
| 4045 | 19327 | 66.4 | 50.0 | 12 | 194 | #4 | 50885 |
| 4046 | 19328 | 50.0 | 50.0 | 12 | 150 | #1 | 50886 |
| 4047 | 19329 | 75.2 | 65.1 | 28 | 354 | #6 | 50887 |
| 4048 | 19330 | 50.0 | 50.0 | 12 | 150 | #1 | 50888 |
| 4049 | 19331 | 68.0 | 58.9 (214) | 16 | 233 | #4 | 50889 |
| 4050 | 19332 | 68.0 | 60.4 | 20 | 248 | #4 | 50890 |
| 4051 | 19333 | 68.0 | 61.1 | 18 | 247 | #4 | 50891 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 4052 | 19334 | 63.5 (115) | — | 12 | 167 | #3 | 50892 |
| 4053 | 19335 | 56.0 (100) | — | 13 | 164 | #2 | 50893 |
| 4054 | 19336 | 70.4 | 62.9 | 24 | 451 | #5 | 50894 |
| 4055 | 19337 | 50.0 | 50.0 | 12 | 150 | #1 | 50895 |
| 4056 | 19338 | 68.0 | 60.7 | 22 | 321 | #4 | 50896 |
| 4057 | 19339 | 71.2 | 62.5 | 20 | 369 | #5 | 50897 |
| 4058 | 19340 | 69.6 | 64.7 | 19 | 465 | #4 | 50898 |
| 4059 | 19341 | 68.0 | 62.9 | 19 | 313 | #4 | 50899 |
| 4060 | 19342 | 78.4 | 60.0 | 28 | 433 | #6 | 50890 |
| 4061 | 19343 | 71.2 | 61.1 | 34 | 266 | #5 | 50901 |
| 4062 | 19344 | 73.6 | 65.5 | 22 | 440 | #5 | 50902 |
| 4063 | 19345 | 50.0 | 50.0 | 12 | 150 | #1 | 50903 |
| 4064 | 19346 | 77.5 (80) | — | 22 | 238 | #6 | 50904 |
| 4065 | 19347 | 50.0 (101) | — | 12 | 150 | #1 | 50905 |
| 4066 | 19348 | 68.8 | 59.6 | 19 | 240 | #4 | 50906 |
| 4067 | 19349 | 72.0 | 62.2 | 21 | 308 | #5 | 50907 |
| 4068 | 19350 | 50.0 | 50.0 | 12 | 150 | #1 | 50908 |
| 4069 | 19351 | 71.2 | 62.5 | 30 | 430 | #5 | 50909 |
| 4070 | 19352 | 68.8 | 61.5 | 22 | 454 | #4 | 50910 |
| 4071 | 19353 | 69.6 | 60.7 | 20 | 265 | #4 | 50911 |
| 4072 | 19354 | 65.6 | 58.2 | 18 | 197 | #4 | 50912 |
| 4073 | 19355 | 50.0 | 50.0 | 12 | 150 | #1 | 50913 |
| 4074 | 19356 | 50.0 (87) | — | 12 | 150 | #1 | 50914 |
| 4075 | 19357 | 66.4 | 59.9 (269) | 18 | 245 | #4 | 50915 |
| 4076 | 19358 | 50.0 | 50.0 | 12 | 150 | #1 | 50916 |
| 4077 | 19359 | 50.0 | 50.0 | 12 | 150 | #1 | 50917 |
| 4078 | 19360 | 66.4 | 60.7 | 17 | 254 | #4 | 50918 |
| 4079 | 19361 | 66.4 | 60.0 | 18 | 308 | #4 | 50919 |
| 4080 | 19362 | 50.0 | 50.0 | 12 | 150 | #1 | 50920 |
| 4081 | 19363 | 50.0 | 50.0 (137) | 12 | 150 | #1 | 50921 |
| 4082 | 19364 | 77.6 | 64.4 | 32 | 606 | #6 | 50922 |
| 4083 | 19365 | 63.2 | 50.0 | 15 | 206 | #3 | 50923 |
| 4084 | 19366 | 67.2 | 59.3 | 20 | 207 | #4 | 50924 |
| 4085 | 19367 | 68.0 | 59.3 | 17 | 223 | #4 | 50925 |
| 4086 | 19368 | 50.0 | 50.0 | 14 | 165 | #1 | 50926 |
| 4087 | 19369 | 66.4 | 61.1 | 16 | 248 | #4 | 50927 |
| 4088 | 19370 | 65.6 | 60.0 | 15 | 235 | #4 | 50928 |
| 4089 | 19371 | 72.8 | 63.6 | 38 | 426 | #5 | 50929 |
| 4090 | 19372 | 64.8 | 55.7 (271) | 17 | 192 | #3 | 50930 |
| 4091 | 19373 | 72.8 | 57.8 | 35 | 331 | #5 | 50931 |
| 4092 | 19374 | 68.8 | 50.0 | 16 | 212 | #4 | 50932 |
| 4093 | 19375 | 50.0 | 50.0 | 12 | 150 | #1 | 50933 |
| 4094 | 19376 | 64.8 | 50.0 | 17 | 175 | #3 | 50934 |
| 4095 | 19377 | 64.8 | 58.2 | 12 | 212 | #3 | 50935 |
| 4096 | 19378 | 65.6 | 58.2 | 18 | 227 | #4 | 50936 |
| 4097 | 19379 | 72.0 | 60.4 | 35 | 285 | #5 | 50937 |
| 4098 | 19380 | 63.2 | 59.3 | 15 | 242 | #3 | 50938 |
| 4099 | 19381 | 63.2 | 50.0 | 21 | 169 | #3 | 50939 |
| 4100 | 19382 | 64.8 | 59.6 (235) | 16 | 182 | #3 | 50940 |
| 4101 | 19383 | 61.6 | 59.3 | 13 | 237 | #3 | 50941 |
| 4102 | 19384 | 50.0 | 50.0 | 12 | 150 | #1 | 50942 |
| 4103 | 19385 | 50.0 | 50.0 | 12 | 150 | #1 | 50943 |
| 4104 | 19386 | 50.0 | 50.0 | 12 | 150 | #1 | 50944 |
| 4105 | 19387 | 68.0 | 59.3 | 23 | 248 | #4 | 50945 |
| 4106 | 19388 | 62.4 | 53.7 (177) | 17 | 216 | #3 | 50946 |
| 4107 | 19389 | 67.2 | 50.0 (211) | 17 | 270 | #4 | 50947 |
| 4108 | 19390 | 68.8 | 62.5 | 18 | 274 | #4 | 50948 |
| 4109 | 19391 | 50.0 | 50.0 | 12 | 150 | #1 | 50949 |
| 4110 | 19392 | 59.2 | 50.0 | 12 | 204 | #2 | 50950 |
| 4111 | 19393 | 75.2 | 63.3 | 35 | 337 | #6 | 50951 |
| 4112 | 19394 | 71.2 | 64.7 | 21 | 431 | #5 | 50952 |
| 4113 | 19395 | 50.0 | 50.0 | 12 | 150 | #1 | 50953 |
| 4114 | 19396 | 68.0 | 58.2 | 22 | 242 | #4 | 50954 |
| 4115 | 19397 | 68.8 | 61.8 | 22 | 304 | #4 | 50955 |
| 4116 | 19398 | 50.0 | 50.0 | 12 | 150 | #1 | 50956 |
| 4117 | 19399 | 50.0 | 50.0 (230) | 12 | 150 | #1 | 50957 |
| 4118 | 19400 | 66.4 | 57.5 | 24 | 227 | #4 | 50958 |
| 4119 | 19401 | 64.8 | 58.5 | 18 | 228 | #3 | 50959 |
| 4120 | 19402 | 61.6 | 50.0 | 15 | 166 | #3 | 50960 |
| 4121 | 19403 | 67.2 | 60.4 | 20 | 297 | #4 | 50961 |
| 4122 | 19404 | 68.8 | 61.8 | 21 | 263 | #4 | 50962 |
| 4123 | 19405 | 66.4 | 60.7 | 18 | 254 | #4 | 50963 |
| 4124 | 19406 | 69.6 | 62.5 | 29 | 351 | #4 | 50964 |
| 4125 | 19407 | 69.6 | 61.8 | 22 | 327 | #4 | 50965 |
| 4126 | 19408 | 67.2 | 57.1 | 18 | 207 | #4 | 50966 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 4127 | 19409 | 68.8 | 60.0 | 20 | 270 | #4 | 50967 |
| 4128 | 19410 | 74.4 | 57.8 | 20 | 372 | #5 | 50968 |
| 4129 | 19411 | 67.2 | 60.4 | 18 | 235 | #4 | 50969 |
| 4130 | 19412 | 50.0 | 50.0 | 12 | 150 | #1 | 50970 |
| 4131 | 19413 | 64.8 | 57.1 | 18 | 175 | #3 | 50971 |
| 4132 | 19414 | 65.6 | 58.5 | 17 | 223 | #4 | 50972 |
| 4133 | 19415 | 65.6 | 59.3 | 15 | 219 | #4 | 50973 |
| 4134 | 19416 | 68.8 | 58.5 | 18 | 214 | #4 | 50974 |
| 4135 | 19417 | 67.2 | 61.8 | 21 | 283 | #4 | 50975 |
| 4136 | 19418 | 63.2 | 50.0 (263) | 15 | 172 | #3 | 50976 |
| 4137 | 19419 | 72.8 | 60.7 | 25 | 320 | #5 | 50977 |
| 4138 | 19420 | 72.0 | 64.4 | 26 | 386 | #5 | 50978 |
| 4139 | 19421 | 68.8 | 61.1 | 17 | 282 | #4 | 50979 |
| 4140 | 19422 | 68.0 | 62.5 | 19 | 290 | #4 | 50980 |
| 4141 | 19423 | 63.2 | 50.0 | 19 | 177 | #3 | 50981 |
| 4142 | 19424 | 72.0 | 59.6 | 21 | 258 | #5 | 50982 |
| 4143 | 19425 | 60.8 | 57.8 | 12 | 195 | #3 | 50983 |
| 4144 | 19426 | 72.0 | 61.5 | 25 | 432 | #5 | 50984 |
| 4145 | 19427 | 81.6 | 72.4 | 23 | 648 | #7 | 50985 |
| 4146 | 19428 | 74.4 | 64.0 | 34 | 389 | #5 | 50986 |
| 4147 | 19429 | 66.4 | 60.0 | 15 | 265 | #4 | 50987 |
| 4148 | 19430 | 86.4 (66) | — | 24 | 213 | #8 | — |
| 4149 | 19431 | 66.4 | 58.9 | 17 | 217 | #4 | 50988 |
| 4150 | 19432 | 50.0 (102) | — | 12 | 150 | #1 | 50989 |
| 4151 | 19433 | 64.8 | 51.3 | 17 | 199 | #3 | 50990 |
| 4152 | 19434 | 65.6 | 60.0 | 18 | 333 | #4 | 50991 |
| 4153 | 19435 | 64.8 | 53.1 (207) | 17 | 192 | #3 | 50992 |
| 4154 | 19436 | 61.6 | 53.8 | 14 | 178 | #3 | 50993 |
| 4155 | 19437 | 63.2 | 50.0 | 13 | 163 | #3 | 50994 |
| 4156 | 19438 | 62.4 | 50.0 | 16 | 215 | #3 | 50995 |
| 4157 | 19439 | 70.4 | 61.1 | 23 | 257 | #5 | 50996 |
| 4158 | 19440 | 50.0 | 50.0 | 12 | 150 | #1 | 50997 |
| 4159 | 19441 | 50.0 (68) | — | 12 | 150 | #1 | 50998 |
| 4160 | 19442 | 67.2 | 61.5 | 21 | 300 | #4 | 50999 |
| 4161 | 19443 | 68.0 | 59.6 | 17 | 230 | #4 | 51000 |
| 4162 | 19444 | 69.6 | 61.8 | 24 | 353 | #4 | 51001 |
| 4163 | 19445 | 68.8 | 61.8 | 21 | 338 | #4 | 51002 |
| 4164 | 19446 | 50.0 | 50.0 | 12 | 150 | #1 | 51003 |
| 4165 | 19447 | 68.8 | 60.0 | 21 | 268 | #4 | 51004 |
| 4166 | 19448 | 68.0 | 58.2 | 26 | 204 | #4 | 51005 |
| 4167 | 19449 | 68.0 | 57.5 | 23 | 220 | #4 | 51006 |
| 4168 | 19450 | 66.4 | 59.6 | 17 | 248 | #4 | 51007 |
| 4169 | 19451 | 67.2 | 50.0 | 12 | 190 | #4 | 51008 |
| 4170 | 19452 | 62.4 | 50.0 | 15 | 160 | #3 | 51009 |
| 4171 | 19453 | 65.6 | 58.1 (253) | 18 | 198 | #4 | 51010 |
| 4172 | 19454 | 50.0 | 50.0 (188) | 14 | 150 | #1 | 51011 |
| 4173 | 19455 | 72.0 | 60.7 | 23 | 323 | #5 | 51012 |
| 4174 | 19456 | 64.8 | 57.1 | 14 | 272 | #3 | 51013 |
| 4175 | 19457 | 77.6 | 65.8 | 35 | 429 | #6 | 51014 |
| 4176 | 19458 | 64.0 | 60.0 | 13 | 257 | #3 | 51015 |
| 4177 | 19459 | 71.2 | 62.2 | 30 | 277 | #5 | 51016 |
| 4178 | 19460 | 66.4 | 56.7 | 18 | 207 | #4 | 51017 |
| 4179 | 19461 | 60.0 | 51.6 | 14 | 184 | #2 | 51018 |
| 4180 | 19462 | 62.4 | 50.0 | 17 | 188 | #3 | 51019 |
| 4181 | 19463 | 67.2 | 63.4 (213) | 21 | 222 | #4 | 51020 |
| 4182 | 19464 | 64.0 | 50.0 (216) | 16 | 177 | #3 | 51021 |
| 4183 | 19465 | 69.6 | 63.3 | 28 | 314 | #4 | 51022 |
| 4184 | 19466 | 69.6 | 62.9 | 19 | 401 | #4 | 51023 |
| 4185 | 19467 | 67.2 | 61.5 | 20 | 285 | #4 | 51024 |
| 4186 | 19468 | 64.8 | 58.5 | 18 | 262 | #3 | 51025 |
| 4187 | 19469 | 54.4 | 50.0 | 14 | 190 | #1 | 51026 |
| 4188 | 19470 | 65.6 | 60.4 | 33 | 266 | #4 | 51027 |
| 4189 | 19471 | 70.4 | 61.1 | 39 | 238 | #5 | 51028 |
| 4190 | 19472 | 53.6 | 50.0 | 12 | 167 | #1 | 51029 |
| 4191 | 19473 | 65.6 | 58.9 | 16 | 220 | #4 | 51030 |
| 4192 | 19474 | 64.0 | 57.5 | 15 | 185 | #3 | 51031 |
| 4193 | 19475 | 63.2 | 60.4 | 14 | 199 | #3 | 51032 |
| 4194 | 19476 | 50.0 (96) | — | 12 | 150 | #1 | 51033 |
| 4195 | 19477 | 67.2 | 57.5 | 22 | 248 | #4 | 51034 |
| 4196 | 19478 | 64.0 | 53.1 | 15 | 202 | #3 | 51035 |
| 4197 | 19479 | 71.2 | 60.4 | 22 | 292 | #5 | 51036 |
| 4198 | 19480 | 50.0 | 50.0 | 12 | 150 | #1 | 51037 |
| 4199 | 19481 | 69.6 | 61.8 | 23 | 305 | #4 | 51038 |
| 4200 | 19482 | 64.8 | 59.6 | 16 | 225 | #3 | 51039 |
| 4201 | 19483 | 50.0 | 50.0 | 12 | 150 | #1 | 51040 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 4202 | 19484 | 50.0 | 50.0 | 12 | 150 | #1 | 51041 |
| 4203 | 19485 | 68.0 | 60.7 | 20 | 271 | #4 | 51042 |
| 4204 | 19486 | 50.0 | 50.0 | 12 | 150 | #1 | 51043 |
| 4205 | 19487 | 63.2 | 61.1 | 17 | 201 | #3 | 51044 |
| 4206 | 19488 | 66.4 | 59.3 | 19 | 225 | #4 | 51045 |
| 4207 | 19489 | 59.2 | 57.8 | 14 | 200 | #2 | 51046 |
| 4208 | 19490 | 76.0 | 66.2 | 25 | 506 | #6 | 51047 |
| 4209 | 19491 | 69.6 | 62.9 | 21 | 621 | #4 | 51048 |
| 4210 | 19492 | 61.6 | 50.0 (270) | 16 | 150 | #3 | 51049 |
| 4211 | 19493 | 68.0 | 61.1 | 21 | 254 | #4 | 51050 |
| 4212 | 19494 | 80.0 | 59.3 | 23 | 404 | #6 | 51051 |
| 4213 | 19495 | 67.2 | 58.3 (247) | 23 | 214 | #4 | 51052 |
| 4214 | 19496 | 70.4 | 62.2 | 25 | 366 | #5 | 51053 |
| 4215 | 19497 | 68.8 | 61.5 | 19 | 282 | #4 | 51054 |
| 4216 | 19498 | 63.2 | 52.4 | 13 | 186 | #3 | 51055 |
| 4217 | 19499 | 65.6 | 57.8 | 13 | 277 | #4 | 51056 |
| 4218 | 19500 | 81.6 | 66.2 | 38 | 457 | #7 | 51057 |
| 4219 | 19501 | 66.4 | 58.2 | 23 | 220 | #4 | 51058 |
| 4220 | 19502 | 64.0 | 50.0 | 18 | 185 | #3 | 51059 |
| 4221 | 19503 | 68.0 | 61.1 | 21 | 252 | #4 | 51060 |
| 4222 | 19504 | 50.0 | 50.0 | 12 | 151 | #1 | 51061 |
| 4223 | 19505 | 61.6 | 56.0 | 20 | 204 | #3 | 51062 |
| 4224 | 19506 | 65.6 | 50.0 | 12 | 180 | #4 | 51063 |
| 4225 | 19507 | 65.6 | 50.0 | 15 | 198 | #4 | 51064 |
| 4226 | 19508 | 70.4 | 63.6 | 29 | 368 | #5 | 51065 |
| 4227 | 19509 | 58.4 | 50.0 (187) | 13 | 150 | #2 | 51066 |
| 4228 | 19510 | 60.8 | 50.0 (211) | 12 | 150 | #3 | 51067 |
| 4229 | 19511 | 70.4 | 61.8 | 24 | 314 | #5 | 51068 |
| 4230 | 19512 | 50.0 | 50.0 | 12 | 150 | #1 | 51069 |
| 4231 | 19513 | 67.2 | 57.1 | 18 | 210 | #4 | 51070 |
| 4232 | 19514 | 64.8 | 58.2 | 16 | 207 | #3 | 51071 |
| 4233 | 19515 | 62.6 (123) | — | 13 | 162 | #3 | 51072 |
| 4234 | 19516 | 67.2 | 61.8 | 17 | 273 | #4 | 51073 |
| 4235 | 19517 | 81.6 | 65.5 | 21 | 676 | #7 | 51074 |
| 4236 | 19518 | 66.4 | 50.0 | 13 | 234 | #4 | 51075 |
| 4237 | 19519 | 65.6 | 58.2 | 17 | 224 | #4 | 51076 |
| 4238 | 19520 | 64.0 | 58.5 | 13 | 213 | #3 | 51077 |
| 4239 | 19521 | 64.8 | 50.0 | 13 | 187 | #3 | 51078 |
| 4240 | 19522 | 70.4 | 62.2 | 20 | 347 | #5 | 51079 |
| 4241 | 19523 | 72.0 | 58.9 | 38 | 274 | #5 | 51080 |
| 4242 | 19524 | 69.6 | 59.3 | 25 | 237 | #4 | 51081 |
| 4243 | 19525 | 71.2 | 60.0 | 26 | 264 | #5 | 51082 |
| 4244 | 19526 | 68.0 | 62.2 | 19 | 320 | #4 | 51083 |
| 4245 | 19527 | 68.0 | 61.5 | 20 | 286 | #4 | 51084 |
| 4246 | 19528 | 50.0 (81) | — | 13 | 150 | #1 | 51085 |
| 4247 | 19529 | 68.0 | 58.9 | 16 | 196 | #4 | 51086 |
| 4248 | 19530 | 63.2 | 50.0 | 13 | 174 | #3 | 51087 |
| 4249 | 19531 | 68.0 | 60.7 | 19 | 387 | #4 | 51088 |
| 4250 | 19532 | 67.2 | 59.3 | 21 | 277 | #4 | 51089 |
| 4251 | 19533 | 50.0 (68) | — | 12 | 150 | #1 | 51090 |
| 4252 | 19534 | 65.6 | 50.0 | 14 | 198 | #4 | 51091 |
| 4253 | 19535 | 50.0 | 50.0 | 12 | 150 | #1 | 51092 |
| 4254 | 19536 | 65.6 | 60.0 | 15 | 209 | #4 | 51093 |
| 4255 | 19537 | 68.8 | 63.7 (182) | 20 | 224 | #4 | 51094 |
| 4256 | 19538 | 66.4 | 57.5 | 20 | 205 | #4 | 51095 |
| 4257 | 19539 | 50.0 | 50.0 | 12 | 150 | #1 | 51096 |
| 4258 | 19540 | 67.2 | 58.5 | 18 | 218 | #4 | 51097 |
| 4259 | 19541 | 67.2 | 66.2 (130) | 18 | 203 | #4 | 51098 |
| 4260 | 19542 | 50.0 | 50.0 | 17 | 188 | #1 | 51099 |
| 4261 | 19543 | 69.6 | 61.5 | 19 | 324 | #4 | 51100 |
| 4262 | 19544 | 66.4 | 57.3 (255) | 17 | 200 | #4 | 51101 |
| 4263 | 19545 | 86.4 | 84.0 | 27 | 1187 | #8 | 51102 |
| 4264 | 19546 | 67.2 | 59.3 | 16 | 224 | #4 | 51103 |
| 4265 | 19547 | 72.8 | 61.8 | 19 | 433 | #5 | 51104 |
| 4266 | 19548 | 65.6 | 59.3 | 17 | 253 | #4 | 51105 |
| 4267 | 19549 | 69.6 | 62.2 | 18 | 296 | #4 | 51106 |
| 4268 | 19550 | 65.6 | 50.0 | 13 | 199 | #4 | 51107 |
| 4269 | 19551 | 61.6 | 59.3 | 15 | 203 | #3 | 51108 |
| 4270 | 19552 | 69.6 | 61.1 | 27 | 319 | #4 | 51109 |
| 4271 | 19553 | 61.6 | 50.0 | 12 | 166 | #3 | 51110 |
| 4272 | 19554 | 64.8 | 56.7 | 15 | 195 | #3 | 51111 |
| 4273 | 19555 | 50.0 (68) | — | 12 | 150 | #1 | 51112 |
| 4274 | 19556 | 66.4 | 50.0 (260) | 23 | 185 | #4 | 51113 |
| 4275 | 19557 | 68.8 | 62.2 | 18 | 281 | #4 | 51114 |
| 4276 | 19558 | 68.8 | 59.6 | 19 | 260 | #4 | 51115 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 4277 | 19559 | 68.8 | 61.8 | 18 | 228 | #4 | 51116 |
| 4278 | 19560 | 75.2 | 74.8 (135) | 21 | 313 | #6 | 51117 |
| 4279 | 19561 | 67.2 | 59.6 | 24 | 214 | #4 | 51118 |
| 4280 | 19562 | 68.0 | 62.9 | 18 | 355 | #4 | 51119 |
| 4281 | 19563 | 66.4 | 52.1 (261) | 18 | 215 | #4 | 51120 |
| 4282 | 19564 | 61.6 | 55.6 (153) | 13 | 160 | #3 | 51121 |
| 4283 | 19565 | 66.4 | 60.4 | 20 | 243 | #4 | 51122 |
| 4284 | 19566 | 68.8 | 57.1 | 20 | 277 | #4 | 51123 |
| 4285 | 19567 | 67.2 | 61.5 | 18 | 258 | #4 | 51124 |
| 4286 | 19568 | 70.4 | 64.0 | 24 | 761 | #5 | 51125 |
| 4287 | 19569 | 64.8 | 50.0 | 22 | 164 | #3 | 51126 |
| 4288 | 19570 | 68.0 | 62.2 | 21 | 390 | #4 | 51127 |
| 4289 | 19571 | 70.4 | 64.7 | 31 | 341 | #5 | 51128 |
| 4290 | 19572 | 66.4 | 57.5 | 13 | 203 | #4 | 51129 |
| 4291 | 19573 | 70.4 | 66.8 (187) | 23 | 289 | #5 | 51130 |
| 4292 | 19574 | 64.8 | 50.0 | 17 | 186 | #3 | 51131 |
| 4293 | 19575 | 50.0 | 50.0 | 12 | 150 | #1 | 51132 |
| 4294 | 19576 | 50.0 | 50.0 | 12 | 150 | #1 | 51133 |
| 4295 | 19577 | 50.0 | 50.0 | 12 | 150 | #1 | 51134 |
| 4296 | 19578 | 68.0 | 62.2 | 18 | 259 | #4 | 51135 |
| 4297 | 19579 | 50.0 | 50.0 | 12 | 150 | #1 | 51136 |
| 4298 | 19580 | 65.6 | 50.0 | 13 | 187 | #4 | 51137 |
| 4299 | 19581 | 69.6 | 67.5 (157) | 24 | 262 | #4 | 51138 |
| 4300 | 19582 | 68.0 | 61.1 | 18 | 307 | #4 | 51139 |
| 4301 | 19583 | 50.0 | 50.0 | 12 | 150 | #1 | 51140 |
| 4302 | 19584 | 64.8 | 58.2 | 15 | 234 | #3 | 51141 |
| 4303 | 19585 | 68.8 | 62.5 | 21 | 327 | #4 | 51142 |
| 4304 | 19586 | 85.4 (89) | — | 23 | 356 | #8 | 51143 |
| 4305 | 19587 | 67.2 | 61.5 | 20 | 268 | #4 | 51144 |
| 4306 | 19588 | 70.4 | 65.5 | 21 | 501 | #5 | 51145 |
| 4307 | 19589 | 61.6 | 58.0 (162) | 13 | 177 | #3 | 51146 |
| 4308 | 19590 | 68.3 (123) | — | 29 | 225 | #4 | 51147 |
| 4309 | 19591 | 72.0 | 64.4 | 25 | 576 | #5 | 51148 |
| 4310 | 19592 | 64.8 | 50.5 | 17 | 217 | #3 | 51149 |
| 4311 | 19593 | 68.0 | 61.1 | 23 | 281 | #4 | 51150 |
| 4312 | 19594 | 65.6 | 58.2 | 17 | 205 | #4 | 51151 |
| 4313 | 19595 | 50.0 | 50.0 | 12 | 150 | #1 | 51152 |
| 4314 | 19596 | 50.0 | 50.0 | 12 | 150 | #1 | 51153 |
| 4315 | 19597 | 56.0 | 50.0 (159) | 31 | 166 | #2 | 51154 |
| 4316 | 19598 | 68.0 | 61.1 | 18 | 310 | #4 | 51155 |
| 4317 | 19599 | 83.0 (112) | — | 17 | 417 | #7 | 51156 |
| 4318 | 19600 | 68.8 | 60.0 | 21 | 232 | #4 | 51157 |
| 4319 | 19601 | 69.6 | 58.9 | 22 | 254 | #4 | 51158 |
| 4320 | 19602 | 66.4 | 60.0 | 15 | 211 | #4 | 51159 |
| 4321 | 19603 | 62.4 | 56.0 | 18 | 200 | #3 | 51160 |
| 4322 | 19604 | 50.0 (83) | — | 12 | 150 | #1 | — |
| 4323 | 19605 | 74.4 | 66.9 | 37 | 535 | #5 | 51161 |
| 4324 | 19606 | 50.0 | 50.0 | 12 | 150 | #1 | 51162 |
| 4325 | 19607 | 50.0 | 50.0 | 12 | 150 | #1 | 51163 |
| 4326 | 19608 | 60.0 | 54.9 | 13 | 193 | #2 | 51164 |
| 4327 | 19609 | 65.6 | 50.0 | 12 | 183 | #4 | 51165 |
| 4328 | 19610 | 72.8 | 64.4 | 21 | 389 | #5 | 51166 |
| 4329 | 19611 | 65.6 | 58.0 (231) | 24 | 211 | #4 | 51167 |
| 4330 | 19612 | 50.0 | 50.0 | 12 | 150 | #1 | 51168 |
| 4331 | 19613 | 50.0 | 50.0 | 12 | 150 | #1 | 51169 |
| 4332 | 19614 | 70.4 | 61.8 | 20 | 397 | #5 | 51170 |
| 4333 | 19615 | 73.6 | 65.5 | 25 | 404 | #5 | 51171 |
| 4334 | 19616 | 50.0 | 50.0 | 12 | 150 | #1 | 51172 |
| 4335 | 19617 | 69.6 | 63.3 | 20 | 439 | #4 | 51173 |
| 4336 | 19618 | 63.2 | 53.8 | 15 | 176 | #3 | 51174 |
| 4337 | 19619 | 50.0 | 50.0 | 12 | 150 | #1 | 51175 |
| 4338 | 19620 | 70.4 | 60.7 | 25 | 280 | #5 | 51176 |
| 4339 | 19621 | 66.4 | 56.7 | 18 | 214 | #4 | 51177 |
| 4340 | 19622 | 64.8 | 50.0 | 13 | 198 | #3 | 51178 |
| 4341 | 19623 | 63.2 | 50.0 (204) | 13 | 150 | #3 | 51179 |
| 4342 | 19624 | 66.4 | 63.8 (152) | 17 | 185 | #4 | 51180 |
| 4343 | 19625 | 68.0 | 61.1 | 21 | 265 | #4 | 51181 |
| 4344 | 19626 | 50.0 | 50.0 | 12 | 150 | #1 | 51182 |
| 4345 | 19627 | 68.8 | 68.9 (132) | 29 | 210 | #4 | 51183 |
| 4346 | 19628 | 65.6 | 55.3 (228) | 13 | 159 | #4 | 51184 |
| 4347 | 19629 | 64.8 | 58.5 | 17 | 227 | #3 | 51185 |
| 4348 | 19630 | 73.6 | 65.1 | 26 | 468 | #5 | 51186 |
| 4349 | 19631 | 64.8 | 60.9 (151) | 17 | 215 | #3 | 51187 |
| 4350 | 19632 | 68.0 | 65.8 (155) | 24 | 219 | #4 | 51188 |
| 4351 | 19633 | 68.0 | 60.4 | 20 | 285 | #4 | 51189 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 4352 | 19634 | 50.0 | 50.0 | 12 | 150 | #1 | 51190 |
| 4353 | 19635 | 65.6 | 56.9 (274) | 16 | 191 | #4 | 51191 |
| 4354 | 19636 | 73.6 | 63.3 | 22 | 343 | #5 | 51192 |
| 4355 | 19637 | 61.6 | 57.8 | 12 | 205 | #3 | 51193 |
| 4356 | 19638 | 63.2 | 50.0 | 13 | 156 | #3 | 51194 |
| 4357 | 19639 | 55.2 | 53.9 (128) | 16 | 157 | #2 | 51195 |
| 4358 | 19640 | 88.8 | 80.7 | 37 | 933 | #8 | 51196 |
| 4359 | 19641 | 66.4 | 58.9 | 16 | 273 | #4 | 51197 |
| 4360 | 19642 | 68.0 | 61.5 | 25 | 262 | #4 | 51198 |
| 4361 | 19643 | 67.2 | 61.5 | 21 | 379 | #4 | 51199 |
| 4362 | 19644 | 68.8 | 58.5 | 14 | 204 | #4 | 51200 |
| 4363 | 19645 | 75.2 | 69.5 | 19 | 481 | #6 | 51201 |
| 4364 | 19646 | 50.0 | 50.0 | 12 | 150 | #1 | 51202 |
| 4365 | 19647 | 68.0 | 62.2 | 18 | 307 | #4 | 51203 |
| 4366 | 19648 | 56.8 | 50.0 (195) | 14 | 150 | #2 | 51204 |
| 4367 | 19649 | 60.8 | 58.2 | 12 | 195 | #3 | 51205 |
| 4368 | 19650 | 50.0 | 50.0 (160) | 12 | 150 | #1 | 51206 |
| 4369 | 19651 | 78.4 | 61.1 | 36 | 386 | #6 | 51207 |
| 4370 | 19652 | 50.0 | 50.0 (183) | 12 | 150 | #1 | 51208 |
| 4371 | 19653 | 63.2 | 50.0 | 18 | 180 | #3 | 51209 |
| 4372 | 19654 | 65.6 | 59.6 | 15 | 198 | #4 | 51210 |
| 4373 | 19655 | 69.6 | 60.4 | 35 | 251 | #4 | 51211 |
| 4374 | 19656 | 66.4 | 61.1 | 16 | 256 | #4 | 51212 |
| 4375 | 19657 | 68.0 | 59.6 | 19 | 243 | #4 | 51213 |
| 4376 | 19658 | 75.2 | 63.3 | 27 | 506 | #6 | 51214 |
| 4377 | 19659 | 74.4 | 63.3 | 15 | 481 | #5 | 51215 |
| 4378 | 19660 | 64.8 | 56.8 (222) | 17 | 190 | #3 | 51216 |
| 4379 | 19661 | 50.0 | 50.0 | 12 | 150 | #1 | 51217 |
| 4380 | 19662 | 86.8 (68) | — | 20 | 263 | #8 | — |
| 4381 | 19663 | 65.6 | 60.0 | 18 | 243 | #4 | 51218 |
| 4382 | 19664 | 70.4 | 63.3 | 60 | 415 | #5 | 51219 |
| 4383 | 19665 | 64.0 | 60.0 | 14 | 219 | #3 | 51220 |
| 4384 | 19666 | 63.2 | 58.5 | 17 | 189 | #3 | 51221 |
| 4385 | 19667 | 68.0 | 60.4 | 20 | 257 | #4 | 51222 |
| 4386 | 19668 | 65.6 | 60.4 | 17 | 228 | #4 | 51223 |
| 4387 | 19669 | 64.8 | 50.0 (253) | 16 | 159 | #3 | 51224 |
| 4388 | 19670 | 63.2 | 58.2 | 17 | 209 | #3 | 51225 |
| 4389 | 19671 | 67.2 | 56.4 | 19 | 235 | #4 | 51226 |
| 4390 | 19672 | 70.4 | 55.3 | 16 | 375 | #5 | 51227 |
| 4391 | 19673 | 50.0 | 50.0 | 12 | 150 | #1 | 51228 |
| 4392 | 19674 | 80.0 | 67.3 | 21 | 510 | #6 | 51229 |
| 4393 | 19675 | 67.2 | 58.9 | 15 | 234 | #4 | 51230 |
| 4394 | 19676 | 66.4 | 50.0 | 16 | 174 | #4 | 51231 |
| 4395 | 19677 | 75.2 | 64.7 | 25 | 424 | #6 | 51232 |
| 4396 | 19678 | 60.8 | 56.7 | 17 | 194 | #3 | 51233 |
| 4397 | 19679 | 68.8 | 58.5 | 15 | 225 | #4 | 51234 |
| 4398 | 19680 | 62.4 | 50.0 | 16 | 169 | #3 | 51235 |
| 4399 | 19681 | 65.6 | 59.6 | 17 | 219 | #4 | 51236 |
| 4400 | 19682 | 65.6 | 60.0 | 16 | 272 | #4 | 51237 |
| 4401 | 19683 | 66.4 | 60.4 | 23 | 277 | #4 | 51238 |
| 4402 | 19684 | 67.2 | 55.6 (243) | 19 | 208 | #4 | 51239 |
| 4403 | 19685 | 70.4 | 61.8 | 22 | 339 | #5 | 51240 |
| 4404 | 19686 | 50.0 | 50.0 (138) | 12 | 150 | #1 | 51241 |
| 4405 | 19687 | 68.0 | 61.1 | 18 | 270 | #4 | 51242 |
| 4406 | 19688 | 70.4 | 59.6 | 30 | 293 | #5 | 51243 |
| 4407 | 19689 | 50.0 | 50.0 | 12 | 150 | #1 | 51244 |
| 4408 | 19690 | 61.6 | 56.4 | 12 | 194 | #3 | 51245 |
| 4409 | 19691 | 78.4 | 73.1 | 16 | 772 | #6 | 51246 |
| 4410 | 19692 | 80.0 | 63.6 | 26 | 384 | #6 | 51247 |
| 4411 | 19693 | 68.0 | 61.1 | 19 | 247 | #4 | 51248 |
| 4412 | 19694 | 68.8 | 61.1 | 24 | 303 | #4 | 51249 |
| 4413 | 19695 | 63.2 | 57.8 | 12 | 203 | #3 | 51250 |
| 4414 | 19696 | 70.4 | 63.1 (222) | 20 | 231 | #5 | 51251 |
| 4415 | 19697 | 63.2 | 53.9 (154) | 14 | 164 | #3 | 51252 |
| 4416 | 19698 | 65.6 | 60.0 | 21 | 238 | #4 | 51253 |
| 4417 | 19699 | 67.2 | 50.0 | 24 | 196 | #4 | 51254 |
| 4418 | 19700 | 68.0 | 62.2 | 18 | 491 | #4 | 51255 |
| 4419 | 19701 | 66.4 | 58.5 | 18 | 221 | #4 | 51256 |
| 4420 | 19702 | 70.4 | 61.1 | 28 | 340 | #5 | 51257 |
| 4421 | 19703 | 62.4 | 53.1 | 14 | 190 | #3 | 51258 |
| 4422 | 19704 | 64.8 | 50.0 (245) | 16 | 167 | #3 | 51259 |
| 4423 | 19705 | 67.2 | 60.7 | 18 | 270 | #4 | 51260 |
| 4424 | 19706 | 67.2 | 63.5 (181) | 22 | 225 | #4 | 51261 |
| 4425 | 19707 | 64.0 | 57.3 (267) | 17 | 203 | #3 | 51262 |
| 4426 | 19708 | 100.0 | 100.0 | 313 | 1585 | #10 | 51263 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 4427 | 19709 | 68.8 | 59.6 | 17 | 234 | #4 | 51264 |
| 4428 | 19710 | 68.0 | 60.0 | 22 | 262 | #4 | 51265 |
| 4429 | 19711 | 63.2 | 57.8 | 16 | 194 | #3 | 51266 |
| 4430 | 19712 | 65.6 | 60.7 | 18 | 259 | #4 | 51267 |
| 4431 | 19713 | 70.4 | 63.0 (238) | 20 | 272 | #5 | 51268 |
| 4432 | 19714 | 63.2 | 55.8 (242) | 19 | 167 | #3 | 51269 |
| 4433 | 19715 | 66.4 | 57.1 | 18 | 215 | #4 | 51270 |
| 4434 | 19716 | 50.0 | 50.0 | 12 | 150 | #1 | 51271 |
| 4435 | 19717 | 52.5 (101) | — | 12 | 150 | #1 | 51272 |
| 4436 | 19718 | 64.8 | 51.6 | 13 | 254 | #3 | 51273 |
| 4437 | 19719 | 68.0 | 54.5 (220) | 23 | 234 | #4 | 51274 |
| 4438 | 19720 | 69.6 | 62.5 | 27 | 349 | #4 | 51275 |
| 4439 | 19721 | 69.6 | 60.7 | 24 | 289 | #4 | 51276 |
| 4440 | 19722 | 60.0 | 50.0 | 12 | 174 | #2 | 51277 |
| 4441 | 19723 | 66.4 | 57.1 | 18 | 225 | #4 | 51278 |
| 4442 | 19724 | 71.2 (66) | — | 16 | 160 | #5 | 51279 |
| 4443 | 19725 | 62.4 | 50.0 | 13 | 156 | #3 | 51280 |
| 4444 | 19726 | 68.0 | 59.3 | 21 | 265 | #4 | 51281 |
| 4445 | 19727 | 68.0 | 57.8 | 22 | 222 | #4 | 51282 |
| 4446 | 19728 | 72.0 | 62.5 | 20 | 302 | #5 | 51283 |
| 4447 | 19729 | 50.0 | 50.0 | 12 | 150 | #1 | 51284 |
| 4448 | 19730 | 68.8 | 60.7 | 27 | 252 | #4 | 51285 |
| 4449 | 19731 | 68.8 | 62.2 | 22 | 285 | #4 | 51286 |
| 4450 | 19732 | 59.2 | 55.3 | 12 | 178 | #2 | 51287 |
| 4451 | 19733 | 71.2 | 61.8 | 18 | 280 | #5 | 51288 |
| 4452 | 19734 | 73.6 | 64.7 | 30 | 392 | #5 | 51289 |
| 4453 | 19735 | 70.4 | 57.1 | 24 | 268 | #5 | 51290 |
| 4454 | 19736 | 71.2 | 61.5 | 20 | 302 | #5 | 51291 |
| 4455 | 19737 | 72.8 | 67.3 | 25 | 712 | #5 | 51292 |
| 4456 | 19738 | 72.0 | 65.1 | 21 | 505 | #5 | 51293 |
| 4457 | 19739 | 50.0 | 50.0 | 12 | 150 | #1 | 51294 |
| 4458 | 19740 | 68.8 | 62.5 | 20 | 385 | #4 | 51295 |
| 4459 | 19741 | 50.0 (82) | — | 12 | 150 | #1 | 51296 |
| 4460 | 19742 | 76.8 | 62.5 | 30 | 390 | #6 | 51297 |
| 4461 | 19743 | 64.8 | 57.5 | 17 | 225 | #3 | 51298 |
| 4462 | 19744 | 80.8 | 68.4 | 32 | 505 | #7 | 51299 |
| 4463 | 19745 | 63.2 | 51.9 (185) | 13 | 172 | #3 | 51300 |
| 4464 | 19746 | 80.0 | 69.8 | 27 | 765 | #6 | 51301 |
| 4465 | 19747 | 64.8 | 59.3 | 17 | 208 | #3 | 51302 |
| 4466 | 19748 | 68.0 | 63.3 | 19 | 335 | #4 | 51303 |
| 4467 | 19749 | 61.6 | 50.0 | 22 | 195 | #3 | 51304 |
| 4468 | 19750 | 65.6 | 55.3 (188) | 18 | 206 | #4 | 51305 |
| 4469 | 19751 | 50.0 | 50.0 | 12 | 150 | #1 | 51306 |
| 4470 | 19752 | 50.0 | 50.0 | 12 | 150 | #1 | 51307 |
| 4471 | 19753 | 61.6 | 57.5 | 16 | 318 | #3 | 51308 |
| 4472 | 19754 | 81.6 | 72.4 | 20 | 615 | #7 | 51309 |
| 4473 | 19755 | 61.6 | 50.0 | 15 | 155 | #3 | 51310 |
| 4474 | 19756 | 62.4 | 50.0 (174) | 12 | 152 | #3 | 51311 |
| 4475 | 19757 | 67.2 | 61.1 | 19 | 290 | #4 | 51312 |
| 4476 | 19758 | 68.8 | 58.5 | 19 | 306 | #4 | 51313 |
| 4477 | 19759 | 59.5 (84) | — | 15 | 150 | #2 | 51314 |
| 4478 | 19760 | 69.6 | 59.6 | 22 | 214 | #4 | 51315 |
| 4479 | 19761 | 68.8 | 58.2 | 18 | 224 | #4 | 51316 |
| 4480 | 19762 | 68.8 | 59.6 | 25 | 254 | #4 | 51317 |
| 4481 | 19763 | 50.0 | 50.0 | 12 | 150 | #1 | 51318 |
| 4482 | 19764 | 67.2 | 59.3 | 18 | 250 | #4 | 51319 |
| 4483 | 19765 | 91.2 | 67.3 | 31 | 813 | #9 | 51320 |
| 4484 | 19766 | 70.4 | 61.8 | 19 | 404 | #5 | 51321 |
| 4485 | 19767 | 70.4 | 60.7 | 22 | 277 | #5 | 51322 |
| 4486 | 19768 | 63.2 | 50.0 | 12 | 178 | #3 | 51323 |
| 4487 | 19769 | 68.8 | 66.9 (160) | 27 | 264 | #4 | 51324 |
| 4488 | 19770 | 65.6 | 50.0 (230) | 18 | 160 | #4 | 51325 |
| 4489 | 19771 | 70.4 | 63.3 | 21 | 315 | #5 | 51326 |
| 4490 | 19772 | 70.4 | 62.5 | 23 | 521 | #5 | 51327 |
| 4491 | 19773 | 67.2 | 60.7 | 21 | 309 | #4 | 51328 |
| 4492 | 19774 | 64.0 | 50.0 | 15 | 177 | #3 | 51329 |
| 4493 | 19775 | 66.4 | 56.4 | 31 | 239 | #4 | 51330 |
| 4494 | 19776 | 68.0 | 61.5 | 25 | 281 | #4 | 51331 |
| 4495 | 19777 | 72.8 | 58.9 | 29 | 276 | #5 | 51332 |
| 4496 | 19778 | 74.4 | 66.2 | 27 | 451 | #5 | 51333 |
| 4497 | 19779 | 50.0 | 50.0 | 12 | 150 | #1 | 51334 |
| 4498 | 19780 | 68.0 | 50.0 | 14 | 195 | #4 | 51335 |
| 4499 | 19781 | 71.2 | 63.6 | 20 | 324 | #5 | 51336 |
| 4500 | 19782 | 50.0 | 50.0 | 12 | 150 | #1 | 51337 |
| 4501 | 19783 | 68.0 | 61.5 | 20 | 328 | #4 | 51338 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 4502 | 19784 | 66.4 | 59.3 (243) | 21 | 210 | #4 | 51339 |
| 4503 | 19785 | 64.8 | 54.5 | 15 | 212 | #3 | 51340 |
| 4504 | 19786 | 60.8 | 50.0 | 15 | 186 | #3 | 51341 |
| 4505 | 19787 | 68.0 | 61.8 | 19 | 298 | #4 | 51342 |
| 4506 | 19788 | 50.0 | 50.0 | 12 | 150 | #1 | 51343 |
| 4507 | 19789 | 63.2 | 57.9 (252) | 14 | 194 | #3 | 51344 |
| 4508 | 19790 | 50.0 | 50.0 | 12 | 150 | #1 | 51345 |
| 4509 | 19791 | 67.2 | 60.4 | 22 | 243 | #4 | 51346 |
| 4510 | 19792 | 72.8 | 62.5 | 22 | 374 | #5 | 51347 |
| 4511 | 19793 | 50.0 | 50.0 | 12 | 150 | #1 | 51348 |
| 4512 | 19794 | 68.8 | 60.0 | 26 | 236 | #4 | 51349 |
| 4513 | 19795 | 50.0 | 50.0 | 12 | 167 | #1 | 51350 |
| 4514 | 19796 | 73.6 | 64.0 | 21 | 437 | #5 | 51351 |
| 4515 | 19797 | 68.0 | 56.7 | 22 | 269 | #4 | 51352 |
| 4516 | 19798 | 70.4 | 61.5 | 21 | 278 | #5 | 51353 |
| 4517 | 19799 | 62.4 | 54.4 (147) | 14 | 153 | #3 | 51354 |
| 4518 | 19800 | 69.6 | 62.5 | 19 | 300 | #4 | 51355 |
| 4519 | 19801 | 67.2 | 58.5 | 35 | 230 | #4 | 51356 |
| 4520 | 19802 | 65.6 | 59.9 (227) | 27 | 206 | #4 | 51357 |
| 4521 | 19803 | 64.0 | 57.8 | 16 | 207 | #3 | 51358 |
| 4522 | 19804 | 74.4 | 61.8 | 24 | 379 | #5 | 51359 |
| 4523 | 19805 | 70.4 | 60.0 | 26 | 313 | #5 | 51360 |
| 4524 | 19806 | 69.6 | 63.3 | 25 | 430 | #4 | 51361 |
| 4525 | 19807 | 68.0 | 58.5 | 18 | 207 | #4 | 51362 |
| 4526 | 19808 | 61.6 | 57.5 | 12 | 182 | #3 | 51363 |
| 4527 | 19809 | 68.8 | 52.2 (201) | 19 | 204 | #4 | 51364 |
| 4528 | 19810 | 68.0 | 60.4 | 22 | 278 | #4 | 51365 |
| 4529 | 19811 | 50.0 | 50.0 | 12 | 150 | #1 | 51366 |
| 4530 | 19812 | 71.2 | 64.0 | 19 | 438 | #5 | 51367 |
| 4531 | 19813 | 70.4 | 62.9 | 23 | 360 | #5 | 51368 |
| 4532 | 19814 | 70.4 | 62.2 | 20 | 327 | #5 | 51369 |
| 4533 | 19815 | 50.0 | 50.0 | 12 | 150 | #1 | 51370 |
| 4534 | 19816 | 68.0 | 57.8 | 15 | 254 | #4 | 51371 |
| 4535 | 19817 | 70.4 | 50.0 | 18 | 231 | #5 | 51372 |
| 4536 | 19818 | 68.0 | 61.1 | 20 | 308 | #4 | 51373 |
| 4537 | 19819 | 64.0 | 50.0 | 13 | 151 | #3 | 51374 |
| 4538 | 19820 | 68.0 | 60.4 | 27 | 245 | #4 | 51375 |
| 4539 | 19821 | 50.0 | 50.0 (144) | 12 | 150 | #1 | 51376 |
| 4540 | 19822 | 64.8 | 50.0 (212) | 29 | 150 | #3 | 51377 |
| 4541 | 19823 | 50.0 | 50.0 | 13 | 150 | #1 | 51378 |
| 4542 | 19824 | 50.0 | 50.0 | 12 | 150 | #1 | 51379 |
| 4543 | 19825 | 94.2 (69) | — | 17 | 309 | #9 | 51380 |
| 4544 | 19826 | 70.4 | 61.1 | 18 | 340 | #5 | 51381 |
| 4545 | 19827 | 65.6 | 60.4 | 16 | 266 | #4 | 51382 |
| 4546 | 19828 | 50.0 | 50.0 | 12 | 150 | #1 | 51383 |
| 4547 | 19829 | 65.6 | 60.4 | 19 | 238 | #4 | 51384 |
| 4548 | 19830 | 68.8 | 60.0 | 18 | 285 | #4 | 51385 |
| 4549 | 19831 | 71.2 | 68.7 (150) | 26 | 233 | #5 | 51386 |
| 4550 | 19832 | 64.0 | 50.0 | 14 | 172 | #3 | 51387 |
| 4551 | 19833 | 72.0 | 63.6 | 21 | 436 | #5 | 51388 |
| 4552 | 19834 | 62.4 | 50.0 | 12 | 160 | #3 | 51389 |
| 4553 | 19835 | 64.8 | 60.4 | 16 | 250 | #3 | 51390 |
| 4554 | 19836 | 68.0 | 60.7 | 20 | 253 | #4 | 51391 |
| 4555 | 19837 | 67.2 | 50.0 (249) | 16 | 175 | #4 | 51392 |
| 4556 | 19838 | 59.2 | 50.0 | 15 | 182 | #2 | 51393 |
| 4557 | 19839 | 70.4 | 61.8 | 21 | 336 | #5 | 51394 |
| 4558 | 19840 | 68.8 | 61.1 | 20 | 430 | #4 | 51395 |
| 4559 | 19841 | 97.6 | 96.0 | 60 | 1355 | #10 | 51396 |
| 4560 | 19842 | 65.7 (99) | — | 29 | 195 | #4 | 51397 |
| 4561 | 19843 | 63.2 | 56.7 | 15 | 205 | #3 | 51398 |
| 4562 | 19844 | 65.6 | 60.4 | 31 | 323 | #4 | 51399 |
| 4563 | 19845 | 50.0 | 50.0 | 12 | 150 | #1 | 51400 |
| 4564 | 19846 | 67.2 | 57.5 | 21 | 188 | #4 | 51401 |
| 4565 | 19847 | 87.6 (97) | — | 24 | 385 | #8 | 51402 |
| 4566 | 19848 | 60.0 | 50.0 | 12 | 152 | #2 | 51403 |
| 4567 | 19849 | 68.0 | 61.1 | 20 | 447 | #4 | 51404 |
| 4568 | 19850 | 50.0 | 50.0 | 12 | 150 | #1 | 51405 |
| 4569 | 19851 | 69.6 | 62.5 | 22 | 368 | #4 | 51406 |
| 4570 | 19852 | 74.4 | 66.7 (204) | 23 | 306 | #5 | 51407 |
| 4571 | 19853 | 64.8 | 59.3 | 18 | 210 | #3 | 51408 |
| 4572 | 19854 | 68.8 | 57.1 | 21 | 228 | #4 | 51409 |
| 4573 | 19855 | 68.8 | 61.9 (189) | 19 | 247 | #4 | 51410 |
| 4574 | 19856 | 63.2 | 57.5 | 19 | 203 | #3 | 51411 |
| 4575 | 19857 | 71.2 | 63.6 | 26 | 418 | #5 | 51412 |
| 4576 | 19858 | 68.0 | 58.9 | 18 | 217 | #4 | 51413 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 4577 | 19859 | 70.4 | 58.5 | 19 | 251 | #5 | 51414 |
| 4578 | 19860 | 68.8 | 60.0 | 22 | 226 | #4 | 51415 |
| 4579 | 19861 | 72.0 | 62.2 | 23 | 349 | #5 | 51416 |
| 4580 | 19862 | 64.8 | 50.4 (252) | 16 | 162 | #3 | 51417 |
| 4581 | 19863 | 65.6 | 50.0 | 13 | 206 | #4 | 51418 |
| 4582 | 19864 | 50.0 | 50.0 | 12 | 150 | #1 | 51419 |
| 4583 | 19865 | 64.8 | 61.4 (153) | 18 | 185 | #3 | 51420 |
| 4584 | 19866 | 67.2 | 61.5 | 26 | 347 | #4 | 51421 |
| 4585 | 19867 | 50.0 | 50.0 | 12 | 150 | #1 | 51422 |
| 4586 | 19868 | 50.0 | 50.0 | 12 | 150 | #1 | 51423 |
| 4587 | 19869 | 67.2 | 58.9 | 28 | 231 | #4 | 51424 |
| 4588 | 19870 | 63.2 | 56.4 | 18 | 219 | #3 | 51425 |
| 4589 | 19871 | 74.4 | 74.1 (135) | 12 | 353 | #5 | 51426 |
| 4590 | 19872 | 69.6 | 62.2 | 18 | 360 | #4 | 51427 |
| 4591 | 19873 | 67.2 | 59.6 | 17 | 244 | #4 | 51428 |
| 4592 | 19874 | 96.8 | 85.5 (248) | 47 | 1024 | #10 | 51429 |
| 4593 | 19875 | 70.4 | 61.1 | 22 | 273 | #5 | 51430 |
| 4594 | 19876 | 68.0 | 61.1 | 18 | 318 | #4 | 51431 |
| 4595 | 19877 | 60.8 | 50.0 (221) | 15 | 173 | #3 | 51432 |
| 4596 | 19878 | 50.0 | 50.0 | 12 | 150 | #1 | 51433 |
| 4597 | 19879 | 70.4 | 59.3 | 23 | 255 | #5 | 51434 |
| 4598 | 19880 | 72.0 | 64.7 | 21 | 413 | #5 | 51435 |
| 4599 | 19881 | 52.8 | 50.0 | 13 | 150 | #1 | 51436 |
| 4600 | 19882 | 57.6 | 50.0 | 12 | 186 | #2 | 51437 |
| 4601 | 19883 | 68.0 | 62.2 | 22 | 377 | #4 | 51438 |
| 4602 | 19884 | 67.2 | 60.7 | 17 | 227 | #4 | 51439 |
| 4603 | 19885 | 68.8 | 60.4 | 20 | 264 | #4 | 51440 |
| 4604 | 19886 | 67.2 | 61.8 | 19 | 397 | #4 | 51441 |
| 4605 | 19887 | 75.2 | 64.4 | 29 | 554 | #6 | 51442 |
| 4606 | 19888 | 63.2 | 51.5 (196) | 13 | 153 | #3 | 51443 |
| 4607 | 19889 | 64.0 | 59.6 | 16 | 229 | #3 | 51444 |
| 4608 | 19890 | 66.4 | 62.4 (181) | 24 | 213 | #4 | 51445 |
| 4609 | 19891 | 65.6 | 57.1 | 23 | 200 | #4 | 51446 |
| 4610 | 19892 | 75.2 | 57.1 | 13 | 434 | #6 | 51447 |
| 4611 | 19893 | 50.0 | 50.0 | 12 | 150 | #1 | 51448 |
| 4612 | 19894 | 60.8 | 50.0 | 13 | 159 | #3 | 51449 |
| 4613 | 19895 | 57.6 | 50.0 | 12 | 185 | #2 | 51450 |
| 4614 | 19896 | 74.4 | 65.5 | 26 | 587 | #5 | 51451 |
| 4615 | 19897 | 68.8 | 60.0 | 24 | 271 | #4 | 51452 |
| 4616 | 19898 | 68.0 | 58.7 (235) | 22 | 217 | #4 | 51453 |
| 4617 | 19899 | 64.8 | 56.0 | 16 | 202 | #3 | 51454 |
| 4618 | 19900 | 50.0 | 50.0 (136) | 17 | 260 | #1 | 51455 |
| 4619 | 19901 | 64.8 | 60.0 | 17 | 257 | #3 | 51456 |
| 4620 | 19902 | 50.0 | 50.0 (210) | 12 | 150 | #1 | 51457 |
| 4621 | 19903 | 66.4 | 59.6 | 20 | 255 | #4 | 51458 |
| 4622 | 19904 | 71.2 | 61.5 | 28 | 322 | #5 | 51459 |
| 4623 | 19905 | 66.4 | 59.3 | 17 | 227 | #4 | 51460 |
| 4624 | 19906 | 66.4 | 60.7 | 17 | 221 | #4 | 51461 |
| 4625 | 19907 | 50.0 | 50.0 | 12 | 150 | #1 | 51462 |
| 4626 | 19908 | 68.8 | 65.8 | 23 | 375 | #4 | 51463 |
| 4627 | 19909 | 72.8 | 68.0 | 19 | 592 | #5 | 51464 |
| 4628 | 19910 | 66.4 | 53.8 (173) | 14 | 165 | #4 | 51465 |
| 4629 | 19911 | 67.2 | 60.4 | 19 | 296 | #4 | 51466 |
| 4630 | 19912 | 72.8 | 63.6 | 23 | 488 | #5 | 51467 |
| 4631 | 19913 | 58.4 | 50.0 (272) | 13 | 165 | #2 | 51468 |
| 4632 | 19914 | 50.0 | 50.0 | 12 | 150 | #1 | 51469 |
| 4633 | 19915 | 68.8 | 60.4 | 26 | 319 | #4 | 51470 |
| 4634 | 19916 | 67.2 | 61.1 | 16 | 255 | #4 | 51471 |
| 4635 | 19917 | 66.4 | 59.3 | 15 | 215 | #4 | 51472 |
| 4636 | 19918 | 69.6 | 62.5 | 26 | 387 | #4 | 51473 |
| 4637 | 19919 | 64.8 | 57.5 | 15 | 235 | #3 | 51474 |
| 4638 | 19920 | 68.8 | 61.8 | 20 | 332 | #4 | 51475 |
| 4639 | 19921 | 67.2 | 62.0 (213) | 32 | 206 | #4 | 51476 |
| 4640 | 19922 | 50.0 (99) | — | 12 | 150 | #1 | 51477 |
| 4641 | 19923 | 68.0 | 50.0 | 17 | 192 | #4 | 51478 |
| 4642 | 19924 | 64.0 | 55.6 (257) | 16 | 175 | #3 | 51479 |
| 4645 | 19925 | 67.2 | 60.7 | 20 | 469 | #4 | 51480 |
| 4645 | 19926 | 84.0 | 79.5 (132) | 24 | 493 | #7 | 51481 |
| 4645 | 19927 | 65.6 | 60.0 | 21 | 257 | #4 | 51482 |
| 4646 | 19928 | 65.6 | 58.9 | 15 | 228 | #4 | 51483 |
| 4647 | 19929 | 72.0 | 57.7 (260) | 33 | 289 | #5 | 51484 |
| 4648 | 19930 | 64.0 | 50.0 | 13 | 180 | #3 | 51485 |
| 4649 | 19931 | 68.0 | 60.0 | 35 | 241 | #4 | 51486 |
| 4650 | 19932 | 68.8 | 60.7 | 23 | 288 | #4 | 51487 |
| 4651 | 19933 | 64.8 | 60.0 | 19 | 241 | #3 | 51488 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 4652 | 19934 | 78.4 | 65.5 | 34 | 412 | #6 | 51489 |
| 4653 | 19935 | 62.4 | 57.9 (171) | 22 | 166 | #3 | 51490 |
| 4654 | 19936 | 67.2 | 61.8 | 27 | 274 | #4 | 51491 |
| 4655 | 19937 | 61.6 | 59.3 | 15 | 211 | #3 | 51492 |
| 4656 | 19938 | 68.0 | 60.7 | 18 | 296 | #4 | 51493 |
| 4657 | 19939 | 50.0 | 50.0 | 12 | 150 | #1 | 51494 |
| 4658 | 19940 | 68.8 | 58.9 | 25 | 239 | #4 | 51495 |
| 4659 | 19941 | 68.0 | 62.5 | 19 | 254 | #4 | 51496 |
| 4660 | 19942 | 73.6 | 61.8 | 31 | 333 | #5 | 51497 |
| 4661 | 19943 | 66.4 | 55.3 | 16 | 199 | #4 | 51498 |
| 4662 | 19944 | 50.0 | 50.0 | 12 | 150 | #1 | 51499 |
| 4663 | 19945 | 50.0 | 50.0 | 12 | 150 | #1 | 51500 |
| 4664 | 19946 | 69.6 | 63.3 | 23 | 356 | #4 | 51501 |
| 4665 | 19947 | 68.0 | 60.4 | 18 | 266 | #4 | 51502 |
| 4666 | 19948 | 64.0 | 58.9 | 13 | 197 | #3 | 51503 |
| 4667 | 19949 | 65.3 (95) | — | 14 | 158 | #4 | 51504 |
| 4668 | 19950 | 65.6 | 50.0 | 15 | 184 | #4 | 51505 |
| 4669 | 19951 | 65.6 | 57.6 (236) | 20 | 192 | #4 | 51506 |
| 4670 | 19952 | 65.6 | 60.7 | 18 | 253 | #4 | 51507 |
| 4671 | 19953 | 72.8 | 64.7 | 20 | 401 | #5 | 51508 |
| 4672 | 19954 | 64.8 | 51.6 | 14 | 204 | #3 | 51509 |
| 4673 | 19955 | 64.8 | 57.8 | 17 | 201 | #3 | 51510 |
| 4674 | 19956 | 80.0 | 65.5 | 21 | 448 | #6 | 51511 |
| 4675 | 19957 | 68.0 | 58.9 | 24 | 249 | #4 | 51512 |
| 4676 | 19958 | 68.0 | 58.5 | 16 | 226 | #4 | 51513 |
| 4677 | 19959 | 75.2 | 53.8 | 15 | 323 | #6 | 51514 |
| 4678 | 19960 | 70.4 | 61.5 | 20 | 367 | #5 | 51515 |
| 4679 | 19961 | 63.2 | 58.5 | 13 | 246 | #3 | 51516 |
| 4680 | 19962 | 70.4 | 58.9 | 20 | 228 | #5 | 51517 |
| 4681 | 19963 | 79.0 (81) | — | 37 | 256 | #6 | 51518 |
| 4682 | 19964 | 62.4 | 60.0 | 13 | 207 | #3 | 51519 |
| 4683 | 19965 | 62.4 | 61.9 (147) | 17 | 181 | #3 | 51520 |
| 4684 | 19966 | 68.8 | 62.2 | 23 | 404 | #4 | 51521 |
| 4685 | 19967 | 69.6 | 62.5 | 21 | 450 | #4 | 51522 |
| 4686 | 19968 | 53.6 | 50.0 (194) | 13 | 150 | #1 | 51523 |
| 4687 | 19969 | 70.4 | 63.3 | 20 | 427 | #5 | 51524 |
| 4688 | 19970 | 70.4 | 61.8 | 23 | 328 | #5 | 51525 |
| 4689 | 19971 | 65.6 | 57.5 | 13 | 223 | #4 | 51526 |
| 4690 | 19972 | 66.4 | 59.6 | 17 | 210 | #4 | 51527 |
| 4691 | 19973 | 69.6 | 59.3 | 25 | 222 | #4 | 51528 |
| 4692 | 19974 | 66.4 | 59.6 | 18 | 251 | #4 | 51529 |
| 4693 | 19975 | 65.6 | 60.0 | 20 | 216 | #4 | 51530 |
| 4694 | 19976 | 68.0 | 62.5 | 18 | 277 | #4 | 51531 |
| 4695 | 19977 | 68.8 | 61.8 | 19 | 492 | #4 | 51532 |
| 4696 | 19978 | 62.4 | 52.8 (193) | 12 | 150 | #3 | 51533 |
| 4697 | 19979 | 67.2 | 61.1 | 20 | 292 | #4 | 51534 |
| 4698 | 19980 | 64.8 | 59.3 | 15 | 212 | #3 | 51535 |
| 4699 | 19981 | 62.4 | 54.7 (150) | 14 | 162 | #3 | 51536 |
| 4700 | 19982 | 65.6 | 50.0 (246) | 15 | 173 | #4 | 51537 |
| 4701 | 19983 | 50.0 | 50.0 | 12 | 150 | #1 | 51538 |
| 4702 | 19984 | 50.0 | 50.0 | 12 | 150 | #1 | 51539 |
| 4703 | 19985 | 66.4 | 60.7 | 16 | 225 | #4 | 51540 |
| 4704 | 19986 | 75.2 | 64.4 | 25 | 417 | #6 | 51541 |
| 4705 | 19987 | 50.0 | 50.0 | 12 | 150 | #1 | 51542 |
| 4706 | 19988 | 66.4 | 55.4 (213) | 18 | 160 | #4 | 51543 |
| 4707 | 19989 | 61.6 | 51.7 (149) | 15 | 151 | #3 | 51544 |
| 4708 | 19990 | 68.0 | 61.1 | 22 | 367 | #4 | 51545 |
| 4709 | 19991 | 71.2 | 67.3 (165) | 24 | 265 | #5 | 51546 |
| 4710 | 19992 | 64.0 | 57.9 (233) | 14 | 174 | #3 | 51547 |
| 4711 | 19993 | 67.2 | 58.2 | 16 | 233 | #4 | 51548 |
| 4712 | 19994 | 66.4 | 60.4 | 18 | 230 | #4 | 51549 |
| 4713 | 19995 | 60.8 | 50.0 (201) | 14 | 159 | #3 | 51550 |
| 4714 | 19996 | 73.6 | 64.4 | 27 | 443 | #5 | 51551 |
| 4715 | 19997 | 50.0 | 50.0 | 12 | 150 | #1 | 51552 |
| 4716 | 19998 | 64.8 | 57.1 | 15 | 211 | #3 | 51553 |
| 4717 | 19999 | 68.8 | 62.2 | 20 | 360 | #4 | 51554 |
| 4718 | 20000 | 57.6 | 56.7 | 13 | 187 | #2 | 51555 |
| 4719 | 20001 | 61.6 | 50.0 | 14 | 168 | #3 | 51556 |
| 4720 | 20002 | 50.0 | 50.0 | 12 | 150 | #1 | 51557 |
| 4721 | 20003 | 65.3 (101) | — | 18 | 213 | #4 | 51558 |
| 4722 | 20004 | 62.4 | 50.0 | 18 | 161 | #3 | 51559 |
| 4723 | 20005 | 50.0 | 50.0 | 12 | 150 | #1 | 51560 |
| 4724 | 20006 | 66.4 | 58.4 (245) | 19 | 193 | #4 | 51561 |
| 4725 | 20007 | 50.0 | 50.0 | 12 | 150 | #1 | 51562 |
| 4726 | 20008 | 68.8 | 61.4 (220) | 22 | 233 | #4 | 51563 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
| --- | --- | --- | --- | --- | --- | --- | --- |
| 4727 | 20009 | 50.0 | 50.0 | 12 | 150 | #1 | 51564 |
| 4728 | 20010 | 60.0 | 50.0 (256) | 16 | 171 | #2 | 51565 |
| 4729 | 20011 | 71.2 | 64.0 | 29 | 370 | #5 | 51566 |
| 4730 | 20012 | 70.4 | 62.2 | 24 | 278 | #5 | 51567 |
| 4731 | 20013 | 60.0 | 55.6 | 12 | 185 | #2 | 51568 |
| 4732 | 20014 | 67.2 | 58.2 | 18 | 195 | #4 | 51569 |
| 4733 | 20015 | 68.0 | 61.5 | 20 | 254 | #4 | 51570 |
| 4734 | 20016 | 70.4 | 61.8 | 23 | 279 | #5 | 51571 |
| 4735 | 20017 | 50.0 | 50.0 | 12 | 150 | #1 | 51572 |
| 4736 | 20018 | 69.6 | 62.5 | 20 | 396 | #4 | 51573 |
| 4737 | 20019 | 75.2 | 61.8 | 26 | 336 | #6 | 51574 |
| 4738 | 20020 | 66.4 | 55.6 | 15 | 239 | #4 | 51575 |
| 4739 | 20021 | 68.0 | 57.8 | 13 | 245 | #4 | 51576 |
| 4740 | 20022 | 64.0 | 59.3 | 15 | 233 | #3 | 51577 |
| 4741 | 20023 | 50.0 (123) | — | 12 | 150 | #1 | 51578 |
| 4742 | 20024 | 69.6 | 63.3 | 19 | 406 | #4 | 51579 |
| 4743 | 20025 | 67.2 | 50.0 | 18 | 197 | #4 | 51580 |
| 4744 | 20026 | 50.0 | 50.0 (229) | 12 | 150 | #1 | 51581 |
| 4745 | 20027 | 71.2 | 63.6 | 30 | 351 | #5 | 51582 |
| 4746 | 20028 | 65.6 | 53.5 (215) | 17 | 182 | #4 | 51583 |
| 4747 | 20029 | 79.2 | 67.6 | 24 | 457 | #6 | 51584 |
| 4748 | 20030 | 67.2 | 57.8 | 23 | 237 | #4 | 51585 |
| 4749 | 20031 | 61.6 | 50.0 | 15 | 175 | #3 | 51586 |
| 4750 | 20032 | 96.8 | 87.0 (246) | 53 | 1042 | #10 | 51587 |
| 4751 | 20033 | 65.6 | 50.0 | 18 | 224 | #4 | 51588 |
| 4752 | 20034 | 50.0 | 50.0 | 12 | 150 | #1 | 51589 |
| 4753 | 20035 | 64.8 | 52.9 (259) | 18 | 185 | #3 | 51590 |
| 4754 | 20036 | 50.0 | 50.0 | 12 | 150 | #1 | 51591 |
| 4755 | 20037 | 64.8 | 58.9 | 17 | 229 | #3 | 51592 |
| 4756 | 20038 | 72.8 | 64.0 | 27 | 322 | #5 | 51593 |
| 4757 | 20039 | 62.4 | 50.0 | 20 | 165 | #3 | 51594 |
| 4758 | 20040 | 71.2 | 60.0 | 20 | 254 | #5 | 51595 |
| 4759 | 20041 | 50.0 | 50.0 | 12 | 150 | #1 | 51596 |
| 4760 | 20042 | 63.2 | 63.7 (135) | 18 | 168 | #3 | 51597 |
| 4761 | 20043 | 64.8 | 54.4 (182) | 15 | 191 | #3 | 51598 |
| 4762 | 20044 | 71.2 | 63.6 | 23 | 590 | #5 | 51599 |
| 4763 | 20045 | 64.0 | 50.0 (269) | 16 | 187 | #3 | 51600 |
| 4764 | 20046 | 70.4 | 60.0 | 19 | 268 | #5 | 51601 |
| 4765 | 20047 | 50.0 | 50.0 | 12 | 150 | #1 | 51602 |
| 4766 | 20048 | 67.2 | 62.5 | 21 | 289 | #4 | 51603 |
| 4767 | 20049 | 68.8 | 60.7 | 19 | 255 | #4 | 51604 |
| 4768 | 20050 | 60.8 | 50.0 | 12 | 159 | #3 | 51605 |
| 4769 | 20051 | 65.6 | 58.9 | 18 | 211 | #4 | 51606 |
| 4770 | 20052 | 69.6 | 62.9 | 19 | 325 | #4 | 51607 |
| 4771 | 20053 | 50.0 | 50.0 | 12 | 150 | #1 | 51608 |
| 4772 | 20054 | 60.8 | 50.0 | 14 | 187 | #3 | 51609 |
| 4773 | 20055 | 50.0 | 50.0 | 12 | 150 | #1 | 51610 |
| 4774 | 20056 | 65.6 | 50.4 (238) | 20 | 182 | #4 | 51611 |
| 4775 | 20057 | 64.8 | 50.0 | 13 | 176 | #3 | 51612 |
| 4776 | 20058 | 60.0 | 50.0 | 15 | 209 | #2 | 51613 |
| 4777 | 20059 | 67.2 | 61.1 | 20 | 329 | #4 | 51614 |
| 4778 | 20060 | 65.6 | 52.4 | 13 | 208 | #4 | 51615 |
| 4779 | 20061 | 68.0 | 62.2 | 20 | 331 | #4 | 51616 |
| 4780 | 20062 | 69.6 | 61.1 | 22 | 278 | #4 | 51617 |
| 4781 | 20063 | 79.2 | 76.4 (195) | 23 | 554 | #6 | 51618 |
| 4782 | 20064 | 66.4 | 60.4 | 14 | 206 | #4 | 51619 |
| 4783 | 20065 | 64.0 | 50.0 (274) | 15 | 166 | #3 | 51620 |
| 4784 | 20066 | 60.8 | 57.1 | 12 | 190 | #3 | 51621 |
| 4785 | 20067 | 68.0 | 60.7 | 16 | 270 | #4 | 51622 |
| 4786 | 20068 | 71.2 | 60.4 | 25 | 298 | #5 | 51623 |
| 4787 | 20069 | 50.0 | 50.0 | 12 | 150 | #1 | 51624 |
| 4788 | 20070 | 64.8 | 61.1 | 17 | 279 | #3 | 51625 |
| 4789 | 20071 | 63.2 | 50.0 | 12 | 209 | #3 | 51626 |
| 4790 | 20072 | 68.0 | 59.6 | 20 | 273 | #4 | 51627 |
| 4791 | 20073 | 68.8 | 54.5 | 20 | 220 | #4 | 51628 |
| 4792 | 20074 | 59.2 | 50.0 (201) | 19 | 152 | #2 | 51629 |
| 4793 | 20075 | 50.0 | 50.0 | 12 | 150 | #1 | 51630 |
| 4794 | 20076 | 71.2 | 60.0 | 21 | 272 | #5 | 51631 |
| 4795 | 20077 | 62.4 | 50.0 | 13 | 183 | #3 | 51632 |
| 4796 | 20078 | 63.2 | 59.6 | 17 | 270 | #3 | 51633 |
| 4797 | 20079 | 68.8 | 61.8 | 25 | 311 | #4 | 51634 |
| 4798 | 20080 | 66.4 | 58.2 | 12 | 190 | #4 | 51635 |
| 4799 | 20081 | 67.2 | 58.6 (263) | 21 | 218 | #4 | 51636 |
| 4800 | 20082 | 72.8 | 62.2 | 21 | 435 | #5 | 51637 |
| 4801 | 20083 | 67.2 | 50.5 (273) | 16 | 216 | #4 | 51638 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 4802 | 20084 | 76.8 | 67.3 | 37 | 458 | #6 | 51639 |
| 4803 | 20085 | 63.2 | 57.9 (171) | 17 | 177 | #3 | 51640 |
| 4804 | 20086 | 68.0 | 60.7 | 18 | 279 | #4 | 51641 |
| 4805 | 20087 | 64.8 | 50.0 | 14 | 198 | #3 | 51642 |
| 4806 | 20088 | 63.2 | 50.0 | 12 | 176 | #3 | 51643 |
| 4807 | 20089 | 72.0 | 62.9 | 25 | 310 | #5 | 51644 |
| 4808 | 20090 | 66.4 | 60.7 | 20 | 292 | #4 | 51645 |
| 4809 | 20091 | 67.2 | 60.7 | 18 | 247 | #4 | 51646 |
| 4810 | 20092 | 64.8 | 54.6 (251) | 19 | 210 | #3 | 51647 |
| 4811 | 20093 | 63.2 | 50.0 | 13 | 166 | #3 | 51648 |
| 4812 | 20094 | 69.6 | 60.4 | 18 | 285 | #4 | 51649 |
| 4813 | 20095 | 67.2 | 50.0 | 13 | 218 | #4 | 51650 |
| 4814 | 20096 | 64.8 | 52.0 | 13 | 173 | #3 | 51651 |
| 4815 | 20097 | 69.6 | 64.0 | 21 | 388 | #4 | 51652 |
| 4816 | 20098 | 68.8 | 61.1 | 21 | 290 | #4 | 51653 |
| 4817 | 20099 | 76.0 | 62.5 | 28 | 360 | #6 | 51654 |
| 4818 | 20100 | 66.4 | 58.5 | 15 | 231 | #4 | 51655 |
| 4819 | 20101 | 59.2 | 52.8 (163) | 13 | 150 | #2 | 51656 |
| 4820 | 20102 | 70.4 | 61.8 | 22 | 311 | #5 | 51657 |
| 4821 | 20103 | 63.1 (103) | — | 38 | 297 | #3 | 51658 |
| 4822 | 20104 | 71.2 | 61.1 | 21 | 337 | #5 | 51659 |
| 4823 | 20105 | 73.0 (89) | — | 21 | 216 | #5 | 51660 |
| 4824 | 20106 | 70.4 | 61.5 | 23 | 330 | #5 | 51661 |
| 4825 | 20107 | 63.2 | 59.6 | 18 | 231 | #3 | 51662 |
| 4826 | 20108 | 61.6 | 50.0 (178) | 16 | 174 | #3 | 51663 |
| 4827 | 20109 | 61.6 | 58.8 (187) | 14 | 165 | #3 | 51664 |
| 4828 | 20110 | 69.6 | 61.5 | 17 | 274 | #4 | 51665 |
| 4829 | 20111 | 68.0 | 58.2 | 19 | 252 | #4 | 51666 |
| 4830 | 20112 | 61.6 | 50.0 | 19 | 193 | #3 | 51667 |
| 4831 | 20113 | 64.8 | 58.9 | 39 | 227 | #3 | 51668 |
| 4832 | 20114 | 68.8 | 62.2 | 20 | 288 | #4 | 51669 |
| 4833 | 20115 | 66.4 | 60.0 | 16 | 268 | #4 | 51670 |
| 4834 | 20116 | 50.0 | 50.0 | 12 | 150 | #1 | 51671 |
| 4835 | 20117 | 66.4 | 60.4 | 28 | 252 | #4 | 51672 |
| 4836 | 20118 | 68.0 | 59.6 | 20 | 253 | #4 | 51673 |
| 4837 | 20119 | 68.8 | 61.1 | 20 | 279 | #4 | 51674 |
| 4838 | 20120 | 70.4 | 60.4 | 24 | 261 | #5 | 51675 |
| 4839 | 20121 | 71.2 | 62.5 | 24 | 314 | #5 | 51676 |
| 4840 | 20122 | 69.6 | 64.2 (229) | 22 | 276 | #4 | 51677 |
| 4841 | 20123 | 69.6 | 60.7 | 23 | 339 | #4 | 51678 |
| 4842 | 20124 | 65.6 | 60.0 | 18 | 271 | #4 | 51679 |
| 4843 | 20125 | 50.0 (90) | — | 12 | 150 | #1 | 51680 |
| 4844 | 20126 | 68.0 | 50.0 | 13 | 199 | #4 | 51681 |
| 4845 | 20127 | 71.2 | 62.2 | 28 | 326 | #5 | 51682 |
| 4846 | 20128 | 68.0 | 61.8 | 24 | 356 | #4 | 51683 |
| 4847 | 20129 | 63.8 (105) | — | 29 | 196 | #3 | 51684 |
| 4848 | 20130 | 64.8 | 59.3 | 17 | 229 | #3 | 51685 |
| 4849 | 20131 | 50.0 | 50.0 | 12 | 150 | #1 | 51686 |
| 4850 | 20132 | 50.0 | 50.0 | 12 | 150 | #1 | 51687 |
| 4851 | 20133 | 72.0 | 63.6 | 20 | 452 | #5 | 51688 |
| 4852 | 20134 | 67.2 | 60.0 | 19 | 246 | #4 | 51689 |
| 4853 | 20135 | 65.6 | 59.6 | 16 | 195 | #4 | 51690 |
| 4854 | 20136 | 71.2 | 63.3 | 20 | 326 | #5 | 51691 |
| 4855 | 20137 | 65.6 | 50.0 | 19 | 176 | #4 | 51692 |
| 4856 | 20138 | 67.2 | 59.6 | 24 | 232 | #4 | 51693 |
| 4857 | 20139 | 69.6 | 61.5 | 19 | 283 | #4 | 51694 |
| 4858 | 20140 | 71.2 | 60.0 | 30 | 280 | #5 | 51695 |
| 4859 | 20141 | 65.6 | 59.6 | 15 | 216 | #4 | 51696 |
| 4860 | 20142 | 78.4 | 76.4 | 28 | 931 | #6 | 51697 |
| 4861 | 20143 | 50.0 | 50.0 | 12 | 150 | #1 | 51698 |
| 4862 | 20144 | 63.2 | 59.3 | 16 | 218 | #3 | 51699 |
| 4863 | 20145 | 64.8 | 50.0 | 13 | 196 | #3 | 51700 |
| 4864 | 20146 | 50.0 | 50.0 | 12 | 150 | #1 | 51701 |
| 4865 | 20147 | 52.0 | 50.0 | 16 | 171 | #1 | 51702 |
| 4866 | 20148 | 64.4 (90) | — | 24 | 184 | #3 | 51703 |
| 4867 | 20149 | 60.8 | 58.2 | 22 | 236 | #3 | 51704 |
| 4868 | 20150 | 77.6 | 66.2 | 34 | 402 | #6 | 51705 |
| 4869 | 20151 | 62.4 | 50.0 (179) | 17 | 179 | #3 | 51706 |
| 4870 | 20152 | 68.0 | 60.7 | 21 | 351 | #4 | 51707 |
| 4871 | 20153 | 64.0 | 50.0 | 12 | 191 | #3 | 51708 |
| 4872 | 20154 | 64.0 | 54.2 | 16 | 197 | #3 | 51709 |
| 4873 | 20155 | 70.4 | 60.0 | 19 | 256 | #5 | 51710 |
| 4874 | 20156 | 50.0 | 50.0 | 12 | 150 | #1 | 51711 |
| 4875 | 20157 | 62.4 | 58.9 | 13 | 201 | #3 | 51712 |
| 4876 | 20158 | 66.4 | 59.6 | 15 | 217 | #4 | 51713 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 4877 | 20159 | 70.4 | 62.9 | 23 | 377 | #5 | 51714 |
| 4878 | 20160 | 63.2 | 50.0 | 20 | 160 | #3 | 51715 |
| 4879 | 20161 | 65.6 | 58.9 | 18 | 245 | #4 | 51716 |
| 4880 | 20162 | 69.6 | 61.1 | 18 | 343 | #4 | 51717 |
| 4881 | 20163 | 69.6 | 59.6 | 21 | 240 | #4 | 51718 |
| 4882 | 20164 | 63.2 | 50.0 | 16 | 167 | #3 | 51719 |
| 4883 | 20165 | 66.4 | 60.0 | 18 | 253 | #4 | 51720 |
| 4884 | 20166 | 68.8 | 62.2 | 27 | 371 | #4 | 51721 |
| 4885 | 20167 | 63.2 | 50.0 | 14 | 179 | #3 | 51722 |
| 4886 | 20168 | 68.0 | 60.0 | 18 | 242 | #4 | 51723 |
| 4887 | 20169 | 70.4 | 61.5 | 24 | 279 | #5 | 51724 |
| 4888 | 20170 | 63.2 | 50.0 | 14 | 169 | #3 | 51725 |
| 4889 | 20171 | 68.8 | 60.7 | 19 | 245 | #4 | 51726 |
| 4890 | 20172 | 65.8 (76) | — | 16 | 152 | #4 | 51727 |
| 4891 | 20173 | 72.0 | 65.8 | 22 | 446 | #5 | 51728 |
| 4892 | 20174 | 56.8 | 50.0 | 16 | 159 | #2 | 51729 |
| 4893 | 20175 | 76.0 | 66.5 | 28 | 572 | #6 | 51730 |
| 4894 | 20176 | 71.2 | 62.2 | 31 | 385 | #5 | 51731 |
| 4895 | 20177 | 61.6 | 50.0 (262) | 14 | 152 | #3 | 51732 |
| 4896 | 20178 | 73.6 | 66.9 | 21 | 555 | #5 | 51733 |
| 4897 | 20179 | 50.0 (82) | — | 34 | 165 | #1 | 51734 |
| 4898 | 20180 | 70.4 | 63.3 | 24 | 435 | #5 | 51735 |
| 4899 | 20181 | 71.2 | 62.9 | 21 | 371 | #5 | 51736 |
| 4900 | 20182 | 67.2 | 61.2 (260) | 21 | 264 | #4 | 51737 |
| 4901 | 20183 | 70.4 | 60.7 | 35 | 288 | #5 | 51738 |
| 4902 | 20184 | 50.0 | 50.0 | 12 | 150 | #1 | 51739 |
| 4903 | 20185 | 64.0 | 58.5 | 16 | 199 | #3 | 51740 |
| 4904 | 20186 | 50.0 | 50.0 | 12 | 150 | #1 | 51741 |
| 4905 | 20187 | 69.6 | 62.9 | 18 | 320 | #4 | 51742 |
| 4906 | 20188 | 50.0 | 50.0 | 12 | 150 | #1 | 51743 |
| 4907 | 20189 | 74.4 | 64.4 | 30 | 422 | #5 | 51744 |
| 4908 | 20190 | 63.2 | 57.5 | 14 | 208 | #3 | 51745 |
| 4909 | 20191 | 68.8 | 60.0 | 18 | 244 | #4 | 51746 |
| 4910 | 20192 | 70.9 (79) | — | 25 | 164 | #5 | 51747 |
| 4911 | 20193 | 60.8 | 59.3 | 19 | 188 | #3 | 51748 |
| 4912 | 20194 | 68.8 | 61.1 | 31 | 282 | #4 | 51749 |
| 4913 | 20195 | 75.2 | 61.5 | 24 | 310 | #6 | 51750 |
| 4914 | 20196 | 68.0 | 61.8 | 26 | 260 | #4 | 51751 |
| 4915 | 20197 | 67.2 | 59.6 | 20 | 303 | #4 | 51752 |
| 4916 | 20198 | 64.8 | 59.8 (224) | 17 | 291 | #3 | 51753 |
| 4917 | 20199 | 70.4 | 62.9 | 20 | 318 | #5 | 51754 |
| 4918 | 20200 | 62.6 (91) | — | 16 | 154 | #3 | 51755 |
| 4919 | 20201 | 74.4 | 69.8 | 19 | 679 | #5 | 51756 |
| 4920 | 20202 | 64.0 | 50.0 | 18 | 168 | #3 | 51757 |
| 4921 | 20203 | 65.6 | 58.6 (198) | 19 | 176 | #4 | 51758 |
| 4922 | 20204 | 72.8 | 59.3 | 30 | 253 | #5 | 51759 |
| 4923 | 20205 | 68.8 | 64.4 | 22 | 439 | #4 | 51760 |
| 4924 | 20206 | 71.2 | 62.2 | 22 | 413 | #5 | 51761 |
| 4925 | 20207 | 62.4 | 60.0 | 14 | 194 | #3 | 51762 |
| 4926 | 20208 | 68.0 | 62.5 | 20 | 306 | #4 | 51763 |
| 4927 | 20209 | 86.4 | 72.7 | 32 | 603 | #8 | 51764 |
| 4928 | 20210 | 50.0 | 50.0 | 12 | 150 | #1 | 51765 |
| 4929 | 20211 | 68.0 | 61.1 | 21 | 269 | #4 | 51766 |
| 4930 | 20212 | 68.8 | 61.1 | 20 | 240 | #4 | 51767 |
| 4931 | 20213 | 69.6 | 60.4 | 24 | 246 | #4 | 51768 |
| 4932 | 20214 | 67.2 | 61.5 | 22 | 293 | #4 | 51769 |
| 4933 | 20215 | 50.0 | 50.0 | 12 | 150 | #1 | 51770 |
| 4934 | 20216 | 68.8 | 63.3 | 21 | 388 | #4 | 51771 |
| 4935 | 20217 | 50.0 | 50.0 | 12 | 150 | #1 | 51772 |
| 4936 | 20218 | 64.0 | 50.0 | 13 | 183 | #3 | 51773 |
| 4937 | 20219 | 71.2 | 61.1 | 30 | 506 | #5 | 51774 |
| 4938 | 20220 | 72.0 | 62.9 | 22 | 362 | #5 | 51775 |
| 4939 | 20221 | 62.4 | 57.1 | 27 | 185 | #3 | 51776 |
| 4940 | 20222 | 60.0 | 50.0 | 12 | 150 | #2 | 51777 |
| 4941 | 20223 | 77.1 (70) | — | 32 | 210 | #6 | 51778 |
| 4942 | 20224 | 80.0 | 66.2 | 31 | 507 | #6 | 51779 |
| 4943 | 20225 | 50.0 | 50.0 | 12 | 150 | #1 | 51780 |
| 4944 | 20226 | 67.2 | 58.2 (268) | 17 | 222 | #4 | 51781 |
| 4945 | 20227 | 70.4 | 64.0 | 20 | 376 | #5 | 51782 |
| 4946 | 20228 | 73.6 | 62.5 | 20 | 328 | #5 | 51783 |
| 4947 | 20229 | 50.0 | 50.0 | 12 | 150 | #1 | 51784 |
| 4948 | 20230 | 50.0 | 50.0 | 12 | 150 | #1 | 51785 |
| 4949 | 20231 | 88.4 (69) | — | 18 | 273 | #8 | 51786 |
| 4950 | 20232 | 67.2 | 58.5 (236) | 20 | 194 | #4 | 51787 |
| 4951 | 20233 | 50.0 | 50.0 | 12 | 150 | #1 | 51788 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 4952 | 20234 | 65.6 | 58.5 | 17 | 243 | #4 | 51789 |
| 4953 | 20235 | 50.0 | 50.0 | 12 | 150 | #1 | 51790 |
| 4954 | 20236 | 71.2 | 62.9 | 27 | 401 | #5 | 51791 |
| 4955 | 20237 | 64.8 | 50.0 | 16 | 221 | #3 | 51792 |
| 4956 | 20238 | 62.4 | 50.0 | 15 | 171 | #3 | 51793 |
| 4957 | 20239 | 50.0 | 50.0 | 12 | 150 | #1 | 51794 |
| 4958 | 20240 | 56.0 | 50.0 (160) | 14 | 150 | #2 | 51795 |
| 4959 | 20241 | 66.4 | 61.1 | 21 | 301 | #4 | 51796 |
| 4960 | 20242 | 66.4 (116) | — | 18 | 187 | #4 | 51797 |
| 4961 | 20243 | 50.0 | 50.0 | 12 | 150 | #1 | 51798 |
| 4962 | 20244 | 50.0 (82) | — | 12 | 150 | #1 | 51799 |
| 4963 | 20245 | 70.4 | 62.9 | 21 | 384 | #5 | 51800 |
| 4964 | 20246 | 65.6 | 59.3 | 21 | 226 | #4 | 51801 |
| 4965 | 20247 | 72.0 | 64.4 | 31 | 477 | #5 | 51802 |
| 4966 | 20248 | 65.6 | 59.6 | 17 | 228 | #4 | 51803 |
| 4967 | 20249 | 69.6 | 60.4 | 20 | 320 | #4 | 51804 |
| 4968 | 20250 | 60.0 | 50.0 | 16 | 189 | #2 | 51805 |
| 4969 | 20251 | 50.0 | 50.0 | 12 | 150 | #1 | 51806 |
| 4970 | 20252 | 72.0 | 63.3 | 27 | 348 | #5 | 51807 |
| 4971 | 20253 | 67.2 | 58.2 | 26 | 259 | #4 | 51808 |
| 4972 | 20254 | 68.0 | 59.6 | 18 | 276 | #4 | 51809 |
| 4973 | 20255 | 67.2 | 58.2 | 19 | 213 | #4 | 51810 |
| 4974 | 20256 | 69.9 (93) | — | 23 | 289 | #4 | 51811 |
| 4975 | 20257 | 68.0 | 62.5 | 20 | 381 | #4 | 51812 |
| 4976 | 20258 | 72.8 | 62.5 | 25 | 316 | #5 | 51813 |
| 4977 | 20259 | 74.4 | 65.8 | 29 | 445 | #5 | 51814 |
| 4978 | 20260 | 70.4 | 62.5 | 19 | 309 | #5 | 51815 |
| 4979 | 20261 | 64.8 | 57.5 | 14 | 215 | #3 | 51816 |
| 4980 | 20262 | 77.6 | 68.0 | 21 | 533 | #6 | 51817 |
| 4981 | 20263 | 66.4 | 56.7 | 18 | 200 | #4 | 51818 |
| 4982 | 20264 | 70.4 | 64.4 | 19 | 397 | #5 | 51819 |
| 4983 | 20265 | 68.8 | 62.2 | 27 | 374 | #4 | 51820 |
| 4984 | 20266 | 63.2 | 50.0 | 14 | 189 | #3 | 51821 |
| 4985 | 20267 | 68.8 | 61.5 | 24 | 292 | #4 | 51822 |
| 4986 | 20268 | 50.0 | 50.0 | 12 | 150 | #1 | 51823 |
| 4987 | 20269 | 62.4 | 58.2 | 16 | 186 | #3 | 51824 |
| 4988 | 20270 | 68.0 | 60.7 | 15 | 274 | #4 | 51825 |
| 4989 | 20271 | 68.8 | 60.4 | 16 | 242 | #4 | 51826 |
| 4990 | 20272 | 64.0 | 50.0 | 13 | 219 | #3 | 51827 |
| 4991 | 20273 | 72.0 | 64.0 | 28 | 355 | #5 | 51828 |
| 4992 | 20274 | 64.8 | 57.9 (209) | 23 | 178 | #3 | 51829 |
| 4993 | 20275 | 64.8 | 58.9 | 17 | 226 | #3 | 51830 |
| 4994 | 20276 | 69.6 | 61.5 | 19 | 355 | #4 | 51831 |
| 4995 | 20277 | 63.2 | 60.8 (130) | 15 | 151 | #3 | 51832 |
| 4996 | 20278 | 72.0 | 61.5 | 20 | 267 | #5 | 51833 |
| 4997 | 20279 | 73.6 | 66.5 | 22 | 562 | #5 | 51834 |
| 4998 | 20280 | 68.8 | 62.5 | 20 | 407 | #4 | 51835 |
| 4999 | 20281 | 66.4 | 60.4 | 18 | 217 | #4 | 51836 |
| 5000 | 20282 | 56.0 | 50.0 (144) | 16 | 172 | #2 | 51837 |
| 5001 | 20283 | 50.0 | 50.0 | 12 | 150 | #1 | 51838 |
| 5002 | 20284 | 63.2 | 57.8 | 13 | 188 | #3 | 51839 |
| 5003 | 20285 | 65.6 | 55.6 | 21 | 224 | #4 | 51840 |
| 5004 | 20286 | 68.8 | 57.1 | 28 | 228 | #4 | 51841 |
| 5005 | 20287 | 67.2 | 60.4 | 19 | 228 | #4 | 51842 |
| 5006 | 20288 | 64.8 | 58.9 | 16 | 221 | #3 | 51843 |
| 5007 | 20289 | 69.6 | 64.7 | 21 | 366 | #4 | 51844 |
| 5008 | 20290 | 62.4 | 52.7 | 15 | 228 | #3 | 51845 |
| 5009 | 20291 | 63.2 | 54.9 (195) | 18 | 180 | #3 | 51846 |
| 5010 | 20292 | 66.4 | 60.0 | 20 | 255 | #4 | 51847 |
| 5011 | 20293 | 68.8 | 61.8 | 21 | 282 | #4 | 51848 |
| 5012 | 20294 | 64.8 | 58.5 | 26 | 215 | #3 | 51849 |
| 5013 | 20295 | 65.6 | 59.6 | 19 | 245 | #4 | 51850 |
| 5014 | 20296 | 68.8 | 59.6 | 18 | 257 | #4 | 51851 |
| 5015 | 20297 | 63.2 | 50.0 | 12 | 199 | #3 | 51852 |
| 5016 | 20298 | 62.4 | 58.5 | 15 | 207 | #3 | 51853 |
| 5017 | 20299 | 60.6 (99) | — | 14 | 150 | #3 | 51854 |
| 5018 | 20300 | 63.8 (116) | — | 15 | 150 | #3 | 51855 |
| 5019 | 20301 | 53.6 | 50.0 | 13 | 171 | #1 | 51856 |
| 5020 | 20302 | 50.0 | 50.0 | 12 | 150 | #1 | 51857 |
| 5021 | 20303 | 65.6 | 60.0 | 20 | 229 | #4 | 51858 |
| 5022 | 20304 | 50.0 | 50.0 | 12 | 150 | #1 | 51859 |
| 5023 | 20305 | 60.0 | 56.4 (156) | 16 | 150 | #2 | 51860 |
| 5024 | 20306 | 65.6 | 59.6 | 17 | 242 | #4 | 51861 |
| 5025 | 20307 | 71.2 | 64.7 | 34 | 332 | #5 | 51862 |
| 5026 | 20308 | 63.2 | 59.3 | 14 | 241 | #3 | 51863 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5027 | 20309 | 68.0 | 57.8 | 22 | 241 | #4 | 51864 |
| 5028 | 20300 | 60.8 | 50.0 | 13 | 183 | #3 | 51865 |
| 5029 | 20301 | 68.8 | 61.1 | 19 | 277 | #4 | 51866 |
| 5030 | 20302 | 60.0 | 50.0 | 13 | 157 | #2 | 51867 |
| 5031 | 20303 | 67.2 | 60.4 | 17 | 210 | #4 | 51868 |
| 5032 | 20304 | 66.4 | 57.1 | 15 | 211 | #4 | 51869 |
| 5033 | 20305 | 66.4 | 63.3 | 18 | 393 | #4 | 51870 |
| 5034 | 20306 | 70.4 | 61.8 | 21 | 293 | #5 | 51871 |
| 5035 | 20307 | 68.0 | 57.5 | 14 | 235 | #4 | 51872 |
| 5036 | 20308 | 66.4 | 61.8 | 21 | 278 | #4 | 51873 |
| 5037 | 20309 | 64.8 | 54.2 | 15 | 235 | #3 | 51874 |
| 5038 | 20320 | 50.0 | 50.0 | 12 | 150 | #1 | 51875 |
| 5039 | 20321 | 50.0 | 50.0 | 19 | 174 | #1 | 51876 |
| 5040 | 20322 | 64.8 | 50.0 | 15 | 185 | #3 | 51877 |
| 5041 | 20323 | 67.2 | 61.6 (216) | 26 | 217 | #4 | 51878 |
| 5042 | 20324 | 77.1 (96) | — | 16 | 274 | #6 | 51879 |
| 5043 | 20325 | 50.0 | 50.0 | 12 | 150 | #1 | 51880 |
| 5044 | 20326 | 64.0 | 59.6 | 17 | 233 | #3 | 51881 |
| 5045 | 20327 | 69.6 | 60.7 | 35 | 314 | #4 | 51882 |
| 5046 | 20328 | 68.8 | 67.2 (137) | 24 | 231 | #4 | 51883 |
| 5047 | 20329 | 66.4 | 60.4 | 21 | 312 | #4 | 51884 |
| 5048 | 20330 | 51.2 | 50.0 | 12 | 150 | #1 | 51885 |
| 5049 | 20331 | 67.2 | 58.9 | 17 | 218 | #4 | 51886 |
| 5050 | 20332 | 66.4 | 59.3 | 18 | 239 | #4 | 51887 |
| 5051 | 20333 | 50.0 (115) | — | 12 | 150 | #1 | 51888 |
| 5052 | 20334 | 66.4 | 58.2 | 18 | 232 | #4 | 51889 |
| 5053 | 20335 | 68.8 | 63.6 | 19 | 331 | #4 | 51890 |
| 5054 | 20336 | 65.6 | 58.2 | 16 | 187 | #4 | 51891 |
| 5055 | 20337 | 50.0 (99) | — | 34 | 165 | #1 | 51892 |
| 5056 | 20338 | 50.0 | 50.0 | 12 | 150 | #1 | 51893 |
| 5057 | 20339 | 50.0 | 50.0 | 12 | 150 | #1 | 51894 |
| 5058 | 20340 | 68.8 | 58.9 | 20 | 247 | #4 | 51895 |
| 5059 | 20341 | 68.8 | 61.8 | 26 | 277 | #4 | 51896 |
| 5060 | 20342 | 65.6 | 57.1 | 13 | 271 | #4 | 51897 |
| 5061 | 20343 | 84.8 | 81.1 | 22 | 1326 | #7 | 51898 |
| 5062 | 20344 | 64.0 | 50.0 | 14 | 197 | #3 | 51899 |
| 5063 | 20345 | 68.0 | 60.4 | 19 | 283 | #4 | 51900 |
| 5064 | 20346 | 68.8 | 64.0 | 19 | 420 | #4 | 51901 |
| 5065 | 20347 | 68.0 | 60.0 | 18 | 286 | #4 | 51902 |
| 5066 | 20348 | 71.2 | 63.3 | 22 | 481 | #5 | 51903 |
| 5067 | 20349 | 50.0 | 50.0 | 12 | 150 | #1 | 51904 |
| 5068 | 20350 | 65.6 | 60.4 | 13 | 231 | #4 | 51905 |
| 5069 | 20351 | 50.0 | 50.0 | 12 | 150 | #1 | 51906 |
| 5070 | 20352 | 50.0 | 50.0 | 12 | 150 | #1 | 51907 |
| 5071 | 20353 | 68.8 | 61.1 | 23 | 270 | #4 | 51908 |
| 5072 | 20354 | 70.4 | 68.0 (147) | 24 | 262 | #5 | 51909 |
| 5073 | 20355 | 72.0 | 62.9 | 20 | 433 | #5 | 51910 |
| 5074 | 20356 | 84.0 | 79.3 | 34 | 840 | #7 | 51911 |
| 5075 | 20357 | 64.0 | 50.0 (244) | 20 | 169 | #3 | 51912 |
| 5076 | 20358 | 66.4 | 59.3 | 14 | 238 | #4 | 51913 |
| 5077 | 20359 | 68.0 | 60.4 | 17 | 267 | #4 | 51914 |
| 5078 | 20360 | 50.0 | 50.0 | 12 | 150 | #1 | 51915 |
| 5079 | 20361 | 70.4 | 62.9 | 20 | 317 | #5 | 51916 |
| 5080 | 20362 | 66.7 (93) | — | 14 | 150 | #4 | 51917 |
| 5081 | 20363 | 63.2 | 50.0 | 12 | 179 | #3 | 51918 |
| 5082 | 20364 | 67.2 | 60.4 | 20 | 317 | #4 | 51919 |
| 5083 | 20365 | 64.8 | 57.1 | 18 | 204 | #3 | 51920 |
| 5084 | 20366 | 67.2 | 60.4 | 18 | 253 | #4 | 51921 |
| 5085 | 20367 | 50.0 | 50.0 | 12 | 150 | #1 | 51922 |
| 5086 | 20368 | 50.0 | 50.0 | 12 | 150 | #1 | 51923 |
| 5087 | 20369 | 68.8 | 62.9 | 26 | 443 | #4 | 51924 |
| 5088 | 20370 | 67.2 | 56.4 | 19 | 221 | #4 | 51925 |
| 5089 | 20371 | 61.6 | 51.3 | 14 | 209 | #3 | 51926 |
| 5090 | 20372 | 63.2 | 52.4 | 14 | 189 | #3 | 51927 |
| 5091 | 20373 | 64.8 | 58.9 | 15 | 238 | #3 | 51928 |
| 5092 | 20374 | 63.2 | 50.0 | 20 | 181 | #3 | 51929 |
| 5093 | 20375 | 68.0 | 58.9 | 18 | 224 | #4 | 51930 |
| 5094 | 20376 | 62.4 | 58.5 | 19 | 197 | #3 | 51931 |
| 5095 | 20377 | 72.8 | 63.3 | 24 | 310 | #5 | 51932 |
| 5096 | 20378 | 68.0 | 58.9 | 15 | 222 | #4 | 51933 |
| 5097 | 20379 | 50.0 | 50.0 | 12 | 150 | #1 | 51934 |
| 5098 | 20380 | 70.4 | 59.3 | 21 | 263 | #5 | 51935 |
| 5099 | 20381 | 68.0 | 58.2 | 21 | 232 | #4 | 51936 |
| 5100 | 20382 | 70.4 | 62.9 | 20 | 353 | #5 | 51937 |
| 5101 | 20383 | 66.4 | 61.5 | 16 | 235 | #4 | 51938 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5102 | 20384 | 68.8 | 63.6 | 24 | 630 | #4 | 51939 |
| 5103 | 20385 | 50.0 | 50.0 | 12 | 150 | #1 | 51940 |
| 5104 | 20386 | 77.6 | 65.8 | 42 | 402 | #6 | 51941 |
| 5105 | 20387 | 50.0 | 50.0 | 12 | 150 | #1 | 51942 |
| 5106 | 20388 | 62.4 | 58.2 | 14 | 183 | #3 | 51943 |
| 5107 | 20389 | 72.0 | 64.0 | 23 | 452 | #5 | 51944 |
| 5108 | 20390 | 64.0 | 57.8 | 13 | 182 | #3 | 51945 |
| 5109 | 20391 | 64.0 | 58.5 | 17 | 228 | #3 | 51946 |
| 5110 | 20392 | 69.6 | 63.6 | 25 | 701 | #4 | 51947 |
| 5111 | 20393 | 60.0 | 50.0 | 14 | 181 | #2 | 51948 |
| 5112 | 20394 | 64.8 | 57.8 | 16 | 186 | #3 | 51949 |
| 5113 | 20395 | 58.4 | 50.0 | 18 | 150 | #2 | 51950 |
| 5114 | 20396 | 67.2 | 59.6 | 15 | 230 | #4 | 51951 |
| 5115 | 20397 | 71.2 | 62.9 | 21 | 398 | #5 | 51952 |
| 5116 | 20398 | 50.0 | 50.0 | 12 | 150 | #1 | 51953 |
| 5117 | 20399 | 63.2 | 50.0 | 12 | 191 | #3 | 51954 |
| 5118 | 20400 | 50.0 | 50.0 | 12 | 150 | #1 | 51955 |
| 5119 | 20401 | 67.2 | 60.7 | 19 | 258 | #4 | 51956 |
| 5120 | 20402 | 71.2 | 61.8 | 20 | 255 | #5 | 51957 |
| 5121 | 20403 | 66.4 | 58.9 | 16 | 218 | #4 | 51958 |
| 5122 | 20404 | 696 | 60.7 | 19 | 367 | #4 | 51959 |
| 5123 | 20405 | 67.2 | 60.7 | 30 | 304 | #4 | 51960 |
| 5124 | 20406 | 69.6 | 60.4 | 18 | 307 | #4 | 51961 |
| 5125 | 20407 | 68.0 | 60.7 | 21 | 273 | #4 | 51962 |
| 5126 | 20408 | 50.0 | 50.0 | 12 | 150 | #1 | 51963 |
| 5127 | 20409 | 71.2 | 61.8 | 24 | 300 | #5 | 51964 |
| 5128 | 20410 | 64.8 | 50.0 | 14 | 206 | #3 | 51965 |
| 5129 | 20411 | 72.0 | 63.6 | 18 | 362 | #5 | 51966 |
| 5130 | 20412 | 61.6 | 57.1 | 13 | 193 | #3 | 51967 |
| 5131 | 20413 | 68.8 | 59.6 | 17 | 263 | #4 | 51968 |
| 5132 | 20414 | 99.2 | 97.2 (253) | 118 | 1200 | #10 | 51969 |
| 5133 | 20415 | 61.6 | 58.0 (150) | 17 | 150 | #3 | 51970 |
| 5134 | 20416 | 69.6 | 59.3 | 27 | 250 | #4 | 51971 |
| 5135 | 20417 | 64.8 | 57.1 | 16 | 201 | #3 | 51972 |
| 5136 | 20418 | 69.6 | 62.2 | 20 | 444 | #4 | 51973 |
| 5137 | 20419 | 63.2 | 57.8 | 16 | 274 | #3 | 51974 |
| 5138 | 20420 | 71.2 | 60.4 | 19 | 261 | #5 | 51975 |
| 5139 | 20421 | 68.8 | 59.3 | 22 | 256 | #4 | 51976 |
| 5140 | 20422 | 90.4 | 72.4 | 41 | 671 | #9 | 51977 |
| 5141 | 20423 | 50.0 (113) | — | 12 | 150 | #1 | 51978 |
| 5142 | 20424 | 64.0 | 50.0 (207) | 13 | 166 | #3 | 51979 |
| 5143 | 20425 | 68.8 | 61.1 | 23 | 274 | #4 | 51980 |
| 5144 | 20426 | 68.0 | 61.1 | 20 | 319 | #4 | 51981 |
| 5145 | 20427 | 50.0 | 50.0 | 12 | 150 | #1 | 51982 |
| 5146 | 20428 | 69.6 | 59.6 | 19 | 284 | #4 | 51983 |
| 5147 | 20429 | 76.0 | 60.4 | 18 | 299 | #6 | 51984 |
| 5148 | 20430 | 70.4 | 61.1 | 27 | 293 | #5 | 51985 |
| 5149 | 20431 | 64.8 | 57.5 | 17 | 231 | #3 | 51986 |
| 5150 | 20432 | 68.0 | 55.1 (254) | 19 | 213 | #4 | 51987 |
| 5151 | 20433 | 72.8 | 64.4 | 23 | 322 | #5 | 51988 |
| 5152 | 20434 | 69.6 | 62.5 | 21 | 349 | #4 | 51989 |
| 5153 | 20435 | 50.0 (92) | — | 12 | 150 | #1 | 51990 |
| 5154 | 20436 | 68.8 | 62.2 | 27 | 349 | #4 | 51991 |
| 5155 | 20437 | 68.0 | 60.0 | 18 | 254 | #4 | 51992 |
| 5156 | 20438 | 72.8 | 63.6 | 25 | 384 | #5 | 51993 |
| 5157 | 20439 | 63.2 | 56.0 | 13 | 198 | #3 | 51994 |
| 5158 | 20440 | 67.2 | 59.6 | 17 | 245 | #4 | 51995 |
| 5159 | 20441 | 68.8 | 60.4 | 26 | 280 | #4 | 51996 |
| 5160 | 20442 | 50.0 | 50.0 | 12 | 150 | #1 | 51997 |
| 5161 | 20443 | 70.4 | 61.8 | 19 | 276 | #5 | 51998 |
| 5162 | 20444 | 64.8 | 58.1 (222) | 19 | 183 | #3 | 51999 |
| 5163 | 20445 | 68.8 | 58.5 | 26 | 218 | #4 | 52000 |
| 5164 | 20446 | 69.6 | 64.4 | 19 | 326 | #4 | 52001 |
| 5165 | 20447 | 69.6 | 67.7 (133) | 27 | 210 | #4 | 52002 |
| 5166 | 20448 | 71.2 | 63.3 | 28 | 479 | #5 | 52003 |
| 5167 | 20449 | 64.0 | 50.0 | 12 | 188 | #3 | 52004 |
| 5168 | 20450 | 50.0 (102) | — | 12 | 150 | #1 | 52005 |
| 5169 | 20451 | 50.0 | 50.0 | 12 | 150 | #1 | 52006 |
| 5170 | 20452 | 50.0 | 50.0 | 12 | 150 | #1 | 52007 |
| 5171 | 20453 | 50.0 | 50.0 | 12 | 150 | #1 | 52008 |
| 5172 | 20454 | 68.0 | 58.2 | 18 | 210 | #4 | 52009 |
| 5173 | 20455 | 68.8 | 63.6 | 20 | 381 | #4 | 52010 |
| 5174 | 20456 | 75.2 | 64.4 | 34 | 452 | #6 | 52011 |
| 5175 | 20457 | 70.4 | 59.3 | 26 | 264 | #5 | 52012 |
| 5176 | 20458 | 78.4 | 61.8 | 30 | 429 | #6 | 52013 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5177 | 20459 | 61.6 | 50.0 | 12 | 150 | #3 | 52014 |
| 5178 | 20460 | 74.4 | 63.6 | 28 | 501 | #5 | 52015 |
| 5179 | 20461 | 72.8 | 64.7 | 22 | 436 | #5 | 52016 |
| 5180 | 20462 | 50.0 | 50.0 | 12 | 150 | #1 | 52017 |
| 5181 | 20463 | 61.6 | 57.5 | 15 | 235 | #3 | 52018 |
| 5182 | 20464 | 50.0 | 50.0 | 12 | 150 | #1 | 52019 |
| 5183 | 20465 | 64.8 | 52.7 | 12 | 197 | #3 | 52020 |
| 5184 | 20466 | 77.6 | 50.5 | 16 | 433 | #6 | 52021 |
| 5185 | 20467 | 50.0 | 50.0 | 12 | 150 | #1 | 52022 |
| 5186 | 20468 | 69.6 | 62.5 | 26 | 536 | #4 | 52023 |
| 5187 | 20469 | 50.0 | 50.0 | 12 | 150 | #1 | 52024 |
| 5188 | 20470 | 73.6 | 62.5 | 37 | 452 | #5 | 52025 |
| 5189 | 20471 | 92.8 | 68.7 | 28 | 831 | #9 | 52026 |
| 5190 | 20472 | 50.0 | 50.0 | 12 | 150 | #1 | 52027 |
| 5191 | 20473 | 84.8 | 81.3 (150) | 16 | 484 | #7 | 52028 |
| 5192 | 20474 | 64.0 | 59.6 | 14 | 245 | #3 | 52029 |
| 5193 | 20475 | 60.8 | 56.3 (135) | 16 | 150 | #3 | 52030 |
| 5194 | 20476 | 66.4 | 59.7 (233) | 19 | 213 | #4 | 52031 |
| 5195 | 20477 | 68.0 | 61.5 | 20 | 290 | #4 | 52032 |
| 5196 | 20478 | 65.6 | 59.6 | 15 | 232 | #4 | 52033 |
| 5197 | 20479 | 68.0 | 60.7 | 17 | 303 | #4 | 52034 |
| 5198 | 20480 | 74.2 (120) | — | 26 | 273 | #5 | 52035 |
| 5199 | 20481 | 72.0 | 63.3 | 31 | 359 | #5 | 52036 |
| 5200 | 20482 | 64.0 | 53.5 | 13 | 233 | #3 | 52037 |
| 5201 | 20483 | 64.8 | 50.0 | 12 | 161 | #3 | 52038 |
| 5202 | 20484 | 70.4 | 59.0 (271) | 23 | 297 | #5 | 52039 |
| 5203 | 20485 | 66.4 | 62.2 | 19 | 387 | #4 | 52040 |
| 5204 | 20486 | 66.4 | 50.0 | 15 | 192 | #4 | 52041 |
| 5205 | 20487 | 72.8 | 64.7 | 22 | 662 | #5 | 52042 |
| 5206 | 20488 | 64.8 | 50.0 (187) | 12 | 158 | #3 | 52043 |
| 5207 | 20489 | 67.2 | 61.5 | 20 | 302 | #4 | 52044 |
| 5208 | 20490 | 68.0 | 61.8 | 19 | 329 | #4 | 52045 |
| 5209 | 20491 | 62.4 | 50.0 | 13 | 192 | #3 | 52046 |
| 5210 | 20492 | 68.8 | 58.9 | 24 | 258 | #4 | 52047 |
| 5211 | 20493 | 64.8 | 57.5 | 15 | 196 | #3 | 52048 |
| 5212 | 20494 | 72.0 | 60.4 | 28 | 336 | #5 | 52049 |
| 5213 | 20495 | 66.4 | 57.8 | 13 | 191 | #4 | 52050 |
| 5214 | 20496 | 66.4 | 60.4 | 20 | 245 | #4 | 52051 |
| 5215 | 20497 | 68.0 | 60.0 | 20 | 279 | #4 | 52052 |
| 5216 | 20498 | 62.4 | 50.9 | 17 | 196 | #3 | 52053 |
| 5217 | 20499 | 64.8 | 60.4 | 16 | 237 | #3 | 52054 |
| 5218 | 20500 | 68.0 | 58.5 | 23 | 256 | #4 | 52055 |
| 5219 | 20501 | 70.4 | 60.4 | 22 | 258 | #5 | 52056 |
| 5220 | 20502 | 67.2 | 58.5 | 16 | 215 | #4 | 52057 |
| 5221 | 20503 | 72.8 | 62.5 | 29 | 391 | #5 | 52058 |
| 5222 | 20504 | 66.4 | 60.0 | 17 | 272 | #4 | 52059 |
| 5223 | 20505 | 50.0 | 50.0 | 12 | 150 | #1 | 52060 |
| 5224 | 20506 | 64.8 | 57.5 | 17 | 204 | #3 | 52061 |
| 5225 | 20507 | 88.8 | 84.7 | 23 | 1759 | #8 | 52062 |
| 5226 | 20508 | 63.2 | 56.4 | 17 | 212 | #3 | 52063 |
| 5227 | 20509 | 71.2 | 63.3 | 21 | 293 | #5 | 52064 |
| 5228 | 20510 | 50.0 | 50.0 | 12 | 150 | #1 | 52065 |
| 5229 | 20511 | 68.0 | 60.0 | 20 | 238 | #4 | 52066 |
| 5230 | 20512 | 50.0 | 50.0 | 12 | 150 | #1 | 52067 |
| 5231 | 20513 | 66.4 | 50.0 | 20 | 222 | #4 | 52068 |
| 5232 | 20514 | 50.0 | 50.0 | 12 | 150 | #1 | 52069 |
| 5233 | 20515 | 71.2 | 63.6 | 23 | 490 | #5 | 52070 |
| 5234 | 20516 | 76.0 | 70.9 | 24 | 751 | #6 | 52071 |
| 5235 | 20517 | 70.4 | 60.4 | 19 | 317 | #5 | 52072 |
| 5236 | 20518 | 67.2 | 57.5 | 17 | 186 | #4 | 52073 |
| 5237 | 20519 | 77.6 | 64.0 | 15 | 341 | #6 | 52074 |
| 5238 | 20520 | 50.0 (98) | — | 12 | 150 | #1 | 52075 |
| 5239 | 20521 | 68.8 | 61.1 | 30 | 284 | #4 | 52076 |
| 5240 | 20522 | 68.0 | 58.9 | 16 | 205 | #4 | 52077 |
| 5241 | 20523 | 50.0 (69) | — | 12 | 150 | #1 | 52078 |
| 5242 | 20524 | 68.8 | 60.0 | 23 | 264 | #4 | 52079 |
| 5243 | 20525 | 84.8 | 72.7 | 24 | 613 | #7 | 52080 |
| 5244 | 20526 | 67.2 | 60.7 | 18 | 282 | #4 | 52081 |
| 5245 | 20527 | 60.0 | 50.0 | 12 | 151 | #2 | 52082 |
| 5246 | 20528 | 71.2 | 62.9 | 26 | 549 | #5 | 52083 |
| 5247 | 20529 | 69.6 | 64.7 | 22 | 398 | #4 | 52084 |
| 5248 | 20530 | 71.2 | 61.8 | 23 | 378 | #5 | 52085 |
| 5249 | 20531 | 72.8 | 62.5 | 23 | 458 | #5 | 52086 |
| 5250 | 20532 | 68.8 | 58.9 | 20 | 249 | #4 | 52087 |
| 5251 | 20533 | 66.4 | 52.9 (263) | 21 | 283 | #4 | 52088 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5252 | 20534 | 70.4 | 61.5 | 26 | 335 | #5 | 52089 |
| 5253 | 20535 | 65.6 | 58.5 | 18 | 231 | #4 | 52090 |
| 5254 | 20536 | 66.4 | 59.6 | 18 | 236 | #4 | 52091 |
| 5255 | 20537 | 71.2 | 62.5 | 26 | 316 | #5 | 52092 |
| 5256 | 20538 | 66.4 | 58.5 | 15 | 209 | #4 | 52093 |
| 5257 | 20539 | 50.0 | 50.0 | 12 | 150 | #1 | 52094 |
| 5258 | 20540 | 65.6 | 58.9 | 14 | 216 | #4 | 52095 |
| 5259 | 20541 | 68.8 | 60.4 | 19 | 329 | #4 | 52096 |
| 5260 | 20542 | 50.0 (76) | — | 12 | 150 | #1 | 52097 |
| 5261 | 20543 | 64.6 (79) | — | 12 | 153 | #3 | 52098 |
| 5262 | 20544 | 67.2 | 59.6 | 15 | 218 | #4 | 52099 |
| 5263 | 20545 | 69.6 | 62.9 | 19 | 325 | #4 | 52100 |
| 5264 | 20546 | 71.2 | 62.2 | 23 | 383 | #5 | 52101 |
| 5265 | 20547 | 50.0 | 50.0 (150) | 12 | 150 | #1 | 52102 |
| 5266 | 20548 | 64.8 | 61.5 | 17 | 230 | #3 | 52103 |
| 5267 | 20549 | 68.0 | 60.4 | 20 | 294 | #4 | 52104 |
| 5268 | 20550 | 64.8 | 58.2 | 18 | 235 | #3 | 52105 |
| 5269 | 20551 | 68.8 | 61.1 | 22 | 315 | #4 | 52106 |
| 5270 | 20552 | 72.8 | 64.0 | 21 | 490 | #5 | 52107 |
| 5271 | 20553 | 68.8 | 57.1 | 24 | 274 | #4 | 52108 |
| 5272 | 20554 | 50.0 | 50.0 | 12 | 150 | #1 | 52109 |
| 5273 | 20555 | 68.0 | 59.3 | 20 | 247 | #4 | 52110 |
| 5274 | 20556 | 64.8 | 57.1 | 15 | 201 | #3 | 52111 |
| 5275 | 20557 | 64.8 | 50.0 | 15 | 199 | #3 | 52112 |
| 5276 | 20558 | 62.4 | 50.0 (225) | 15 | 159 | #3 | 52113 |
| 5277 | 20559 | 64.8 | 58.9 | 17 | 232 | #3 | 52114 |
| 5278 | 20560 | 50.0 | 50.0 | 12 | 150 | #1 | 52115 |
| 5279 | 20561 | 65.6 | 61.1 | 17 | 289 | #4 | 52116 |
| 5280 | 20562 | 70.4 | 60.0 | 24 | 241 | #5 | 52117 |
| 5281 | 20563 | 68.8 | 60.7 | 15 | 243 | #4 | 52118 |
| 5282 | 20564 | 50.0 | 50.0 | 12 | 150 | #1 | 52119 |
| 5283 | 20565 | 64.0 | 50.0 | 37 | 197 | #3 | 52120 |
| 5284 | 20566 | 70.4 | 60.7 | 19 | 370 | #5 | 52121 |
| 5285 | 20567 | 68.0 | 62.5 | 23 | 307 | #4 | 52122 |
| 5286 | 20568 | 67.2 | 60.0 | 16 | 244 | #4 | 52123 |
| 5287 | 20569 | 51.2 | 50.0 (254) | 12 | 158 | #1 | 52124 |
| 5288 | 20570 | 69.6 | 59.6 | 29 | 233 | #4 | 52125 |
| 5289 | 20571 | 72.8 | 66.5 | 21 | 440 | #5 | 52126 |
| 5290 | 20572 | 69.6 | 58.5 | 21 | 278 | #4 | 52127 |
| 5291 | 20573 | 69.5 (82) | — | 12 | 179 | #4 | 52128 |
| 5292 | 20574 | 60.8 | 56.7 (233) | 12 | 163 | #3 | 52129 |
| 5293 | 20575 | 65.6 | 58.5 | 14 | 198 | #4 | 52130 |
| 5294 | 20576 | 60.8 | 55.3 (170) | 12 | 156 | #3 | 52131 |
| 5295 | 20577 | 64.8 | 59.6 | 15 | 272 | #3 | 52132 |
| 5296 | 20578 | 50.0 | 50.0 (246) | 12 | 150 | #1 | 52133 |
| 5297 | 20579 | 62.4 | 50.0 | 12 | 183 | #3 | 52134 |
| 5298 | 20580 | 68.8 | 50.0 | 27 | 227 | #4 | 52135 |
| 5299 | 20581 | 50.0 | 50.0 | 12 | 150 | #1 | 52136 |
| 5300 | 20582 | 91.2 | 84.7 | 27 | 1218 | #9 | 52137 |
| 5301 | 20583 | 66.4 | 58.9 | 15 | 231 | #4 | 52138 |
| 5302 | 20584 | 64.0 | 59.3 | 12 | 190 | #3 | 52139 |
| 5303 | 20585 | 69.9 (113) | — | 21 | 208 | #4 | 52140 |
| 5304 | 20586 | 69.6 | 61.8 | 20 | 365 | #4 | 52141 |
| 5305 | 20587 | 64.0 | 53.1 (211) | 17 | 166 | #3 | 52142 |
| 5306 | 20588 | 64.8 | 58.5 | 16 | 234 | #3 | 52143 |
| 5307 | 20589 | 50.0 | 50.0 | 12 | 150 | #1 | 52144 |
| 5308 | 20590 | 69.6 | 60.0 | 19 | 243 | #4 | 52145 |
| 5309 | 20591 | 67.2 | 60.4 | 18 | 249 | #4 | 52146 |
| 5310 | 20592 | 64.8 | 57.1 | 18 | 212 | #3 | 52147 |
| 5311 | 20593 | 63.2 | 50.0 | 15 | 185 | #3 | 52148 |
| 5312 | 20594 | 60.9 (92) | — | 28 | 200 | #3 | 52149 |
| 5313 | 20595 | 74.4 | 61.8 | 26 | 324 | #5 | 52150 |
| 5314 | 20596 | 70.4 | 66.0 (156) | 29 | 254 | #5 | 52151 |
| 5315 | 20597 | 66.3 (86) | — | 27 | 269 | #4 | — |
| 5316 | 20598 | 64.8 | 50.2 | 29 | 192 | #3 | 52152 |
| 5317 | 20599 | 50.0 | 50.0 (125) | 12 | 150 | #1 | 52153 |
| 5318 | 20600 | 76.0 | 67.6 | 24 | 417 | #6 | 52154 |
| 5319 | 20601 | 68.8 | 61.8 | 22 | 465 | #4 | 52155 |
| 5320 | 20602 | 50.0 (82) | — | 12 | 150 | #1 | 52156 |
| 5321 | 20603 | 68.0 | 52.7 | 19 | 232 | #4 | 52157 |
| 5322 | 20604 | 66.4 | 60.0 | 17 | 227 | #4 | 52158 |
| 5323 | 20605 | 52.8 | 50.0 (152) | 12 | 160 | #1 | 52159 |
| 5324 | 20606 | 64.0 | 50.0 | 17 | 197 | #3 | 52160 |
| 5325 | 20607 | 67.2 | 59.6 | 25 | 240 | #4 | 52161 |
| 5326 | 20608 | 72.0 | 63.3 | 23 | 385 | #5 | 52162 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5327 | 20609 | 66.4 | 55.6 | 13 | 197 | #4 | 52163 |
| 5328 | 20610 | 50.0 | 50.0 | 12 | 150 | #1 | 52164 |
| 5329 | 20611 | 71.2 | 62.5 | 27 | 572 | #5 | 52165 |
| 5330 | 20612 | 65.5 | 50.0 | 16 | 198 | #4 | 52166 |
| 5331 | 20613 | 72.0 | 64.4 | 23 | 384 | #5 | 52167 |
| 5332 | 20614 | 50.0 | 50.0 | 12 | 150 | #1 | 52168 |
| 5333 | 20615 | 67.2 | 58.5 | 19 | 230 | #4 | 52169 |
| 5334 | 20616 | 84.0 | 67.3 | 27 | 545 | #7 | 52170 |
| 5335 | 20617 | 62.4 | 53.5 | 14 | 169 | #3 | 52171 |
| 5336 | 20618 | 66.4 | 60.4 | 18 | 276 | #4 | 52172 |
| 5337 | 20619 | 50.0 | 50.0 | 12 | 150 | #1 | 52173 |
| 5338 | 20620 | 72.0 | 63.6 | 28 | 432 | #5 | 52174 |
| 5339 | 20621 | 65.6 | 52.0 | 15 | 205 | #4 | 52175 |
| 5340 | 20622 | 68.8 | 62.9 | 21 | 368 | #4 | 52176 |
| 5341 | 20623 | 64.0 | 52.4 | 12 | 178 | #3 | 52177 |
| 5342 | 20624 | 72.0 | 59.3 | 23 | 286 | #5 | 52178 |
| 5343 | 20625 | 50.0 | 50.0 | 12 | 150 | #1 | 52179 |
| 5344 | 20626 | 65.5 | 60.6 (180) | 17 | 201 | #4 | 52180 |
| 5345 | 20627 | 64.8 | 50.0 (272) | 17 | 200 | #3 | 52181 |
| 5346 | 20628 | 67.2 | 56.7 | 22 | 221 | #4 | 52182 |
| 5347 | 20629 | 50.0 | 50.0 | 12 | 150 | #1 | 52183 |
| 5348 | 20630 | 65.6 | 60.4 | 21 | 226 | #4 | 52184 |
| 5349 | 20631 | 68.8 | 62.2 | 21 | 458 | #4 | 52185 |
| 5350 | 20632 | 68.8 | 60.0 | 17 | 244 | #4 | 52186 |
| 5351 | 20633 | 64.0 | 55.6 | 13 | 202 | #3 | 52187 |
| 5352 | 20634 | 64.0 | 59.3 | 13 | 239 | #3 | 52188 |
| 5353 | 20635 | 78.4 | 61.5 | 32 | 409 | #6 | 52189 |
| 5354 | 20636 | 65.6 | 59.6 | 19 | 276 | #4 | 52190 |
| 5355 | 20637 | 59.2 | 50.0 | 37 | 202 | #2 | 52191 |
| 5356 | 20638 | 70.4 | 62.5 | 27 | 427 | #5 | 52192 |
| 5357 | 20639 | 50.0 | 50.0 | 12 | 150 | #1 | 52193 |
| 5358 | 20640 | 68.0 | 62.5 | 18 | 319 | #4 | 52194 |
| 5359 | 20641 | 71.2 | 63.6 | 20 | 388 | #5 | 52195 |
| 5360 | 20642 | 50.0 | 50.0 | 12 | 150 | #1 | 52196 |
| 5361 | 20643 | 97.6 | 96.0 | 60 | 1355 | #10 | 52197 |
| 5362 | 20644 | 67.2 | 50.0 | 16 | 190 | #4 | 52198 |
| 5363 | 20645 | 63.2 | 50.0 | 13 | 182 | #3 | 52199 |
| 5364 | 20646 | 52.5 (99) | — | 14 | 150 | #1 | 52200 |
| 5365 | 20647 | 67.2 | 58.2 | 17 | 204 | #4 | 52201 |
| 5366 | 20648 | 69.6 | 56.7 | 20 | 317 | #4 | 52202 |
| 5367 | 20649 | 63.2 | 51.0 (255) | 18 | 170 | #3 | 52203 |
| 5368 | 20650 | 50.0 | 50.0 | 12 | 150 | #1 | 52204 |
| 5369 | 20651 | 69.6 | 60.7 | 21 | 263 | #4 | 52205 |
| 5370 | 20652 | 64.8 | 57.5 | 14 | 225 | #3 | 52206 |
| 5371 | 20653 | 66.4 | 60.4 | 18 | 401 | #4 | 52207 |
| 5372 | 20654 | 64.8 | 59.6 | 13 | 212 | #3 | 52208 |
| 5373 | 20655 | 60.8 | 57.9 (183) | 13 | 150 | #3 | 52209 |
| 5374 | 20656 | 68.0 | 60.4 | 25 | 244 | #4 | 52210 |
| 5375 | 20657 | 62.4 | 58.2 (158) | 17 | 162 | #3 | 52211 |
| 5376 | 20658 | 65.6 | 50.0 | 17 | 201 | #4 | 52212 |
| 5377 | 20659 | 50.0 | 50.0 (259) | 12 | 150 | #1 | 52213 |
| 5378 | 20660 | 67.2 | 58.5 | 16 | 215 | #4 | 52214 |
| 5379 | 20661 | 68.0 | 57.5 | 15 | 214 | #4 | 52215 |
| 5380 | 20662 | 73.6 | 66.5 | 15 | 552 | #5 | 52216 |
| 5381 | 20663 | 69.6 | 61.1 | 21 | 280 | #4 | 52217 |
| 5382 | 20664 | 57.9 (76) | — | 12 | 150 | #2 | 52218 |
| 5383 | 20665 | 68.0 | 60.0 | 29 | 264 | #4 | 52219 |
| 5384 | 20666 | 68.0 | 60.4 | 23 | 326 | #4 | 52220 |
| 5385 | 20667 | 75.2 | 63.3 | 32 | 343 | #6 | 52221 |
| 5386 | 20668 | 63.2 | 50.0 | 13 | 171 | #3 | 52222 |
| 5387 | 20669 | 50.0 | 50.0 | 12 | 150 | #1 | 52223 |
| 5388 | 20670 | 67.2 | 58.5 | 23 | 220 | #4 | 52224 |
| 5389 | 20671 | 65.6 | 58.2 | 14 | 207 | #4 | 52225 |
| 5390 | 20672 | 64.8 | 50.0 | 12 | 219 | #3 | 52226 |
| 5391 | 20673 | 64.8 | 59.0 (266) | 24 | 195 | #3 | 52227 |
| 5392 | 20674 | 69.6 | 63.3 | 22 | 678 | #4 | 52228 |
| 5393 | 20675 | 68.8 | 60.0 | 19 | 243 | #4 | 52229 |
| 5394 | 20676 | 50.0 | 50.0 | 12 | 150 | #1 | 52230 |
| 5395 | 20677 | 70.4 | 60.4 | 20 | 265 | #5 | 52231 |
| 5396 | 20678 | 66.4 | 50.0 | 13 | 257 | #4 | 52232 |
| 5397 | 20679 | 50.0 | 50.0 | 12 | 150 | #1 | 52233 |
| 5398 | 20680 | 64.0 | 57.5 | 16 | 202 | #3 | 52234 |
| 5399 | 20681 | 50.0 | 50.0 | 12 | 150 | #1 | 52235 |
| 5400 | 20682 | 65.5 | 57.5 | 15 | 200 | #4 | 52236 |
| 5401 | 20683 | 70.4 | 58.5 | 16 | 262 | #5 | 52237 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5402 | 20684 | 66.4 | 60.0 | 19 | 273 | #4 | 52238 |
| 5403 | 20685 | 66.4 | 60.4 | 20 | 329 | #4 | 52239 |
| 5404 | 20686 | 50.0 | 50.0 (137) | 12 | 150 | #1 | 52240 |
| 5405 | 20687 | 70.4 | 62.9 | 24 | 333 | #5 | 52241 |
| 5406 | 20688 | 50.0 | 50.0 | 12 | 150 | #1 | 52242 |
| 5407 | 20689 | 68.8 | 63.3 | 20 | 466 | #4 | 52243 |
| 5408 | 20690 | 63.2 | 50.0 (197) | 16 | 185 | #3 | 52244 |
| 5409 | 20691 | 69.9 | 62.9 | 20 | 339 | #4 | 52245 |
| 5410 | 20692 | 64.0 | 58.0 (219) | 17 | 169 | #3 | 52246 |
| 5411 | 20693 | 66.4 | 59.3 | 15 | 219 | #4 | 52247 |
| 5412 | 20694 | 50.0 | 50.0 | 15 | 154 | #1 | 52248 |
| 5413 | 20695 | 64.0 | 56.0 | 15 | 198 | #3 | 52249 |
| 5414 | 20696 | 67.2 | 61.1 | 18 | 286 | #4 | 52250 |
| 5415 | 20697 | 68.8 | 60.0 | 19 | 277 | #4 | 52251 |
| 5416 | 20698 | 67.2 | 59.6 | 25 | 236 | #4 | 52252 |
| 5417 | 20699 | 69.6 | 60.7 | 20 | 286 | #4 | 52253 |
| 5418 | 20700 | 71.2 | 59.2 (196) | 18 | 254 | #5 | 52254 |
| 5419 | 20701 | 72.0 | 59.3 | 25 | 279 | #5 | 52255 |
| 5420 | 20702 | 64.8 | 57.1 | 16 | 201 | #3 | 52256 |
| 5421 | 20703 | 64.0 | 58.5 | 14 | 203 | #3 | 52257 |
| 5422 | 20704 | 67.2 | 57.1 | 27 | 218 | #4 | 52258 |
| 5423 | 20705 | 64.8 | 59.3 | 15 | 235 | #3 | 52259 |
| 5424 | 20706 | 64.8 | 58.9 | 17 | 218 | #3 | 52260 |
| 5425 | 20707 | 72.0 | 65.1 | 23 | 461 | #5 | 52261 |
| 5426 | 20708 | 54.4 | 50.0 (156) | 14 | 174 | #1 | 52262 |
| 5427 | 20709 | 61.6 | 50.0 | 19 | 150 | #3 | 52263 |
| 5428 | 20710 | 67.2 | 61.5 | 19 | 278 | #4 | 52264 |
| 5429 | 20711 | 63.2 | 57.8 | 13 | 227 | #3 | 52265 |
| 5430 | 20712 | 68.0 | 62.5 | 21 | 343 | #4 | 52266 |
| 5431 | 20713 | 70.4 | 62.9 | 21 | 407 | #5 | 52267 |
| 5432 | 20714 | 69.6 | 58.5 | 18 | 254 | #4 | 52268 |
| 5433 | 20715 | 64.0 | 50.0 | 12 | 160 | #3 | 52269 |
| 5434 | 20716 | 78.4 | 66.2 | 47 | 470 | #6 | 52270 |
| 5435 | 20717 | 50.0 | 50.0 | 12 | 150 | #1 | 52271 |
| 5436 | 20718 | 50.0 | 50.0 | 12 | 150 | #1 | 52272 |
| 5437 | 20719 | 50.0 | 50.0 | 12 | 150 | #1 | 52273 |
| 5438 | 20720 | 50.0 (110) | — | 20 | 150 | #1 | 52274 |
| 5439 | 20721 | 68.0 | 61.2 (219) | 20 | 240 | #4 | 52275 |
| 5440 | 20722 | 71.2 | 60.7 | 17 | 268 | #5 | 52276 |
| 5441 | 20723 | 60.8 | 57.1 | 15 | 196 | #3 | 52277 |
| 5442 | 20724 | 50.0 (76) | — | 12 | 150 | #1 | — |
| 5443 | 20725 | 64.0 | 53.1 | 16 | 199 | #3 | 52278 |
| 5444 | 20726 | 68.8 | 63.3 | 21 | 664 | #4 | 52279 |
| 5445 | 20727 | 69.6 | 61.1 | 19 | 256 | #4 | 52280 |
| 5446 | 20728 | 64.8 | 58.5 | 16 | 254 | #3 | 52281 |
| 5447 | 20729 | 64.8 | 58.5 | 14 | 229 | #3 | 52282 |
| 5448 | 20730 | 63.2 | 50.2 | 14 | 184 | #3 | 52283 |
| 5449 | 20731 | 63.2 | 53.5 | 14 | 193 | #3 | 52284 |
| 5450 | 20732 | 50.0 | 50.0 | 12 | 150 | #1 | 52285 |
| 5451 | 20733 | 61.6 | 60.3 (151) | 18 | 172 | #3 | 52286 |
| 5452 | 20734 | 70.4 | 63.3 | 20 | 337 | #5 | 52287 |
| 5453 | 20735 | 66.4 | 58.2 | 18 | 205 | #4 | 52288 |
| 5454 | 20736 | 50.0 | 50.0 | 12 | 150 | #1 | 52289 |
| 5455 | 20737 | 68.8 | 62.5 | 19 | 399 | #4 | 52290 |
| 5456 | 20738 | 68.0 | 61.5 | 17 | 252 | #4 | 52291 |
| 5457 | 20739 | 63.2 | 57.1 | 13 | 200 | #3 | 52292 |
| 5458 | 20740 | 65.6 | 50.0 | 12 | 177 | #4 | 52293 |
| 5459 | 20741 | 50.0 | 50.0 | 12 | 150 | #1 | 52294 |
| 5460 | 20742 | 64.8 | 59.9 (137) | 15 | 174 | #3 | 52295 |
| 5461 | 20743 | 67.2 | 53.5 | 17 | 225 | #4 | 52296 |
| 5462 | 20744 | 72.0 | 63.6 | 30 | 410 | #5 | 52297 |
| 5463 | 20745 | 65.6 | 59.6 | 16 | 232 | #4 | 52298 |
| 5464 | 20746 | 62.4 | 53.1 (147) | 12 | 166 | #3 | 52299 |
| 5465 | 20747 | 69.6 | 63.3 | 27 | 440 | #4 | 52300 |
| 5466 | 20748 | 65.6 | 50.0 | 15 | 192 | #4 | 52301 |
| 5467 | 20749 | 64.0 | 52.4 | 16 | 220 | #3 | 52302 |
| 5468 | 20750 | 77.6 | 66.2 | 28 | 465 | #6 | 52303 |
| 5469 | 20751 | 70.4 | 64.0 | 19 | 490 | #5 | 52304 |
| 5470 | 20752 | 68.8 | 62.5 | 19 | 303 | #4 | 52305 |
| 5471 | 20753 | 50.0 | 50.0 | 12 | 150 | #1 | 52306 |
| 5472 | 20754 | 50.0 | 50.0 | 12 | 150 | #1 | 52307 |
| 5473 | 20755 | 69.6 | 63.3 | 20 | 355 | #4 | 52308 |
| 5474 | 20756 | 75.2 | 65.8 | 25 | 561 | #6 | 52309 |
| 5475 | 20757 | 50.0 | 50.0 | 14 | 158 | #1 | 52310 |
| 5476 | 20758 | 68.8 | 61.1 | 27 | 306 | #4 | 52311 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5477 | 20759 | 67.2 | 60.4 | 19 | 252 | #4 | 52312 |
| 5478 | 20760 | 68.0 | 61.5 | 24 | 297 | #4 | 52313 |
| 5479 | 20761 | 65.6 | 57.5 | 17 | 230 | #4 | 52314 |
| 5480 | 20762 | 50.0 | 50.0 | 12 | 150 | #1 | 52315 |
| 5481 | 20763 | 74.4 | 58.9 | 19 | 340 | #5 | 52316 |
| 5482 | 20764 | 50.0 | 50.0 (133) | 12 | 150 | #1 | 52317 |
| 5483 | 20765 | 68.0 | 63.3 | 24 | 614 | #4 | 52318 |
| 5484 | 20766 | 60.8 | 50.0 (263) | 14 | 153 | #3 | 52319 |
| 5485 | 20767 | 71.2 | 63.6 | 19 | 285 | #5 | 52320 |
| 5486 | 20768 | 69.6 | 61.1 | 22 | 268 | #4 | 52321 |
| 5487 | 20769 | 60.8 | 50.0 (165) | 12 | 158 | #3 | 52322 |
| 5488 | 20770 | 66.4 | 58.7 (254) | 18 | 196 | #4 | 52323 |
| 5489 | 20771 | 68.0 | 59.6 | 18 | 252 | #4 | 52324 |
| 5490 | 20772 | 50.0 | 50.0 | 12 | 150 | #1 | 52325 |
| 5491 | 20773 | 68.8 | 61.5 | 19 | 324 | #4 | 52326 |
| 5492 | 20774 | 70.4 | 62.5 | 24 | 345 | #5 | 52327 |
| 5493 | 20775 | 69.6 | 64.7 | 21 | 443 | #4 | 52328 |
| 5494 | 20776 | 65.6 | 54.7 (192) | 22 | 160 | #4 | 52329 |
| 5495 | 20777 | 55.1 (98) | — | 34 | 200 | #2 | 52330 |
| 5496 | 20778 | 64.8 | 50.0 | 15 | 187 | #3 | — |
| 5497 | 20779 | 64.0 | 56.7 | 16 | 212 | #3 | 52331 |
| 5498 | 20780 | 50.0 | 50.0 | 12 | 150 | #1 | 52332 |
| 5499 | 20781 | 69.6 | 61.5 | 29 | 311 | #4 | 52333 |
| 5500 | 20782 | 64.0 | 50.0 (170) | 12 | 166 | #3 | 52334 |
| 5501 | 20783 | 70.5 (78) | — | 23 | 181 | #5 | 52335 |
| 5502 | 20784 | 68.0 | 61.1 | 18 | 420 | #4 | 52336 |
| 5503 | 20785 | 71.2 | 61.8 | 24 | 335 | #5 | 52337 |
| 5504 | 20786 | 76.0 | 66.2 | 33 | 437 | #6 | 52338 |
| 5505 | 20787 | 76.0 | 68.4 | 24 | 566 | #6 | 52339 |
| 5506 | 20788 | 50.0 | 50.0 | 12 | 150 | #1 | 52340 |
| 5507 | 20789 | 67.2 | 60.0 | 18 | 311 | #4 | 52341 |
| 5508 | 20790 | 68.8 | 56.4 | 16 | 221 | #4 | 52342 |
| 5509 | 20791 | 68.8 | 61.8 | 19 | 345 | #4 | 52343 |
| 5510 | 20792 | 72.8 | 61.8 | 35 | 351 | #5 | 52344 |
| 5511 | 20793 | 68.0 | 58.5 | 27 | 224 | #4 | 52345 |
| 5512 | 20794 | 71.2 | 60.7 | 34 | 278 | #5 | 52346 |
| 5513 | 20795 | 50.0 (82) | — | 12 | 150 | #1 | 52347 |
| 5514 | 20796 | 63.2 | 56.0 | 12 | 314 | #3 | 52348 |
| 5515 | 20797 | 64.8 | 50.0 (233) | 16 | 174 | #3 | 52349 |
| 5516 | 20798 | 68.8 | 57.5 | 20 | 215 | #4 | 52350 |
| 5517 | 20799 | 72.0 | 64.0 | 26 | 430 | #5 | 52351 |
| 5518 | 20800 | 65.6 | 57.5 | 16 | 221 | #4 | 52352 |
| 5519 | 20801 | 85.6 | 76.4 | 26 | 818 | #8 | 52353 |
| 5520 | 20802 | 68.0 | 53.5 | 24 | 226 | #4 | 52354 |
| 5521 | 20803 | 69.6 | 61.1 | 20 | 313 | #4 | 52355 |
| 5522 | 20804 | 63.2 | 56.0 | 12 | 175 | #3 | 52356 |
| 5523 | 20805 | 84.8 | 66.9 | 30 | 569 | #7 | 52357 |
| 5524 | 20806 | 68.8 | 61.5 | 21 | 338 | #4 | 52358 |
| 5525 | 20807 | 89.5 (86) | — | 32 | 359 | #8 | 52359 |
| 5526 | 20808 | 64.8 | 50.0 | 13 | 190 | #3 | 52360 |
| 5527 | 20809 | 66.4 | 50.0 | 14 | 190 | #4 | 52361 |
| 5528 | 20810 | 65.6 | 50.0 | 16 | 184 | #4 | 52362 |
| 5529 | 20811 | 64.8 | 58.9 | 14 | 210 | #3 | 52363 |
| 5530 | 20812 | 75.2 | 50.0 (262) | 13 | 370 | #6 | 52364 |
| 5531 | 20813 | 67.2 | 60.4 | 21 | 327 | #4 | 52365 |
| 5532 | 20814 | 68.0 | 61.5 | 20 | 258 | #4 | 52366 |
| 5533 | 20815 | 50.0 | 50.0 | 12 | 150 | #1 | 52367 |
| 5534 | 20816 | 50.0 | 50.0 | 12 | 150 | #1 | 52368 |
| 5535 | 20817 | 65.6 | 57.8 | 14 | 220 | #4 | 52369 |
| 5536 | 20818 | 70.4 | 61.8 | 23 | 283 | #5 | 52370 |
| 5537 | 20819 | 64.8 | 63.0 (154) | 17 | 171 | #3 | 52371 |
| 5538 | 20820 | 68.8 | 62.2 | 20 | 288 | #4 | 52372 |
| 5539 | 20821 | 66.4 | 54.0 (261) | 19 | 189 | #4 | 52373 |
| 5540 | 20822 | 63.2 | 58.2 | 15 | 197 | #3 | 52374 |
| 5541 | 20823 | 67.2 | 58.5 | 18 | 239 | #4 | 52375 |
| 5542 | 20824 | 64.8 | 56.7 | 16 | 200 | #3 | 52376 |
| 5543 | 20825 | 76.0 | 64.7 | 33 | 384 | #6 | 52377 |
| 5544 | 20826 | 66.4 | 59.6 | 17 | 269 | #4 | 52378 |
| 5545 | 20827 | 72.0 | 63.3 | 25 | 408 | #5 | — |
| 5546 | 20828 | 64.8 | 50.0 | 14 | 189 | #3 | 52379 |
| 5547 | 20829 | 78.4 | 68.7 | 26 | 524 | #6 | 52380 |
| 5548 | 20830 | 78.4 | 74.9 | 22 | 613 | #6 | 52381 |
| 5549 | 20831 | 64.8 | 50.0 | 17 | 216 | #3 | 52382 |
| 5550 | 20832 | 69.6 | 61.8 | 21 | 315 | #4 | 52383 |
| 5551 | 20833 | 64.0 | 50.0 | 13 | 190 | #3 | 52384 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5552 | 20834 | 66.4 | 58.2 | 15 | 232 | #4 | 52385 |
| 5553 | 20835 | 66.4 | 50.0 | 12 | 185 | #4 | 52386 |
| 5554 | 20836 | 67.2 | 60.0 | 17 | 251 | #4 | 52387 |
| 5555 | 20837 | 63.2 | 50.0 (198) | 14 | 150 | #3 | 52388 |
| 5556 | 20838 | 69.6 | 61.8 | 17 | 251 | #4 | 52389 |
| 5557 | 20839 | 71.2 | 60.7 | 30 | 273 | #5 | 52390 |
| 5558 | 20840 | 68.0 | 62.2 | 19 | 330 | #4 | 52391 |
| 5559 | 20841 | 68.0 | 61.1 | 24 | 231 | #4 | 52392 |
| 5560 | 20842 | 63.2 | 50.0 | 12 | 166 | #3 | 52393 |
| 5561 | 20843 | 66.4 | 50.0 | 25 | 219 | #4 | 52394 |
| 5562 | 20844 | 64.8 | 50.0 (241) | 19 | 174 | #3 | 52395 |
| 5563 | 20845 | 68.0 | 61.1 | 26 | 328 | #4 | 52396 |
| 5564 | 20846 | 50.0 | 50.0 | 14 | 150 | #1 | 52397 |
| 5565 | 20847 | 65.6 | 58.2 | 16 | 204 | #4 | 52398 |
| 5566 | 20848 | 59.2 | 50.0 | 12 | 162 | #2 | 52399 |
| 5567 | 20849 | 63.2 | 58.5 | 13 | 192 | #3 | 52400 |
| 5568 | 20850 | 50.0 | 50.0 | 12 | 150 | #1 | 52401 |
| 5569 | 20851 | 67.2 | 60.4 | 17 | 261 | #4 | 52402 |
| 5570 | 20852 | 100.0 | 100.0 | 20 | 3786 | #10 | 52403 |
| 5571 | 20853 | 64.8 | 52.2 (247) | 18 | 174 | #3 | 52404 |
| 5572 | 20854 | 64.0 | 50.0 | 12 | 181 | #3 | 52405 |
| 5573 | 20855 | 66.4 | 54.9 | 14 | 187 | #4 | 52406 |
| 5574 | 20856 | 70.4 | 62.5 | 22 | 367 | #5 | 52407 |
| 5575 | 20857 | 50.0 | 50.0 | 12 | 150 | #1 | 52408 |
| 5576 | 20858 | 64.8 | 57.8 | 15 | 221 | #3 | 52409 |
| 5577 | 20859 | 72.8 | 62.9 | 21 | 357 | #5 | 52410 |
| 5578 | 20860 | 50.0 (87) | — | 12 | 150 | #1 | 52411 |
| 5579 | 20861 | 70.4 | 62.5 | 26 | 364 | #5 | 52412 |
| 5580 | 20862 | 73.6 | 61.8 | 30 | 299 | #5 | 52413 |
| 5581 | 20863 | 76.0 | 63.6 | 25 | 516 | #6 | 52414 |
| 5582 | 20864 | 74.4 | 63.6 | 30 | 380 | #5 | 52415 |
| 5583 | 20865 | 65.6 | 57.8 | 18 | 209 | #4 | 52416 |
| 5584 | 20866 | 66.4 | 50.0 | 14 | 189 | #4 | 52417 |
| 5585 | 20867 | 50.0 | 50.0 | 12 | 150 | #1 | 52418 |
| 5586 | 20868 | 71.2 | 62.9 | 23 | 294 | #5 | 52419 |
| 5587 | 20869 | 66.4 | 60.7 | 23 | 273 | #4 | 52420 |
| 5588 | 20870 | 62.4 | 56.4 | 13 | 191 | #3 | 52421 |
| 5589 | 20871 | 69.6 | 62.9 | 24 | 317 | #4 | 52422 |
| 5590 | 20872 | 70.4 | 64.7 | 26 | 535 | #5 | 52423 |
| 5591 | 20873 | 72.8 | 59.3 | 22 | 284 | #5 | 52424 |
| 5592 | 20874 | 74.6 (67) | — | 19 | 162 | #5 | 52425 |
| 5593 | 20875 | 66.4 | 61.5 | 15 | 261 | #4 | 52426 |
| 5594 | 20876 | 68.8 | 58.9 | 17 | 262 | #4 | 52427 |
| 5595 | 20877 | 62.4 | 55.6 | 12 | 191 | #3 | 52428 |
| 5596 | 20878 | 65.6 | 50.0 | 13 | 202 | #4 | 52429 |
| 5597 | 20879 | 62.4 | 50.0 (233) | 13 | 155 | #3 | 52430 |
| 5598 | 20880 | 66.4 | 60.4 | 20 | 249 | #4 | 52431 |
| 5599 | 20881 | 69.6 | 61.5 | 19 | 271 | #4 | 52432 |
| 5600 | 20882 | 67.2 | 61.9 (194) | 22 | 229 | #4 | 52433 |
| 5601 | 20883 | 69.6 | 60.4 | 20 | 268 | #4 | 52434 |
| 5602 | 20884 | 68.0 | 61.3 (225) | 22 | 229 | #4 | 52435 |
| 5603 | 20885 | 70.4 | 61.5 | 24 | 261 | #5 | 52436 |
| 5604 | 20886 | 60.8 | 50.0 (251) | 14 | 168 | #3 | 52437 |
| 5605 | 20887 | 68.0 | 61.5 | 23 | 399 | #4 | 52438 |
| 5606 | 20888 | 61.6 | 50.0 (257) | 15 | 158 | #3 | 52439 |
| 5607 | 20889 | 88.8 | 58.8 (262) | 24 | 504 | #8 | 52440 |
| 5608 | 20890 | 68.0 | 62.5 | 20 | 341 | #4 | 52441 |
| 5609 | 20891 | 72.0 | 62.5 | 31 | 527 | #5 | 52442 |
| 5610 | 20892 | 50.0 | 50.0 | 12 | 150 | #1 | 52443 |
| 5611 | 20893 | 64.8 | 60.7 | 15 | 229 | #3 | 52444 |
| 5612 | 20894 | 65.6 | 62.5 (160) | 18 | 182 | #4 | 52445 |
| 5613 | 20895 | 71.2 | 61.8 | 31 | 349 | #5 | 52446 |
| 5614 | 20896 | 50.0 | 50.0 | 12 | 150 | #1 | 52447 |
| 5615 | 20897 | 50.0 | 50.0 | 12 | 150 | #1 | 52448 |
| 5616 | 20898 | 68.0 | 61.1 | 20 | 227 | #4 | 52449 |
| 5617 | 20899 | 62.4 | 50.0 | 12 | 183 | #3 | 52450 |
| 5618 | 20900 | 69.6 | 60.4 | 21 | 257 | #4 | 52451 |
| 5619 | 20901 | 68.0 | 52.4 | 17 | 226 | #4 | 52452 |
| 5620 | 20902 | 65.6 | 61.8 (157) | 19 | 193 | #4 | 52453 |
| 5621 | 20903 | 69.6 | 61.8 | 20 | 378 | #4 | 52454 |
| 5622 | 20904 | 76.0 | 64.4 | 25 | 443 | #6 | 52455 |
| 5623 | 20905 | 65.6 | 58.5 | 18 | 220 | #4 | 52456 |
| 5624 | 20906 | 68.8 | 57.1 | 15 | 223 | #4 | 52457 |
| 5625 | 20907 | 65.7 (102) | — | 16 | 159 | #4 | 52458 |
| 5626 | 20908 | 67.2 | 60.4 | 18 | 295 | #4 | 52459 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5627 | 20909 | 68.0 | 59.3 (150) | 14 | 173 | #4 | 52460 |
| 5628 | 20910 | 71.6 (81) | — | 19 | 166 | #5 | 52461 |
| 5629 | 20911 | 65.6 | 50.0 | 13 | 172 | #4 | 52462 |
| 5630 | 20912 | 65.6 | 59.3 | 13 | 222 | #4 | 52463 |
| 5631 | 20913 | 69.6 | 63.1 (236) | 23 | 252 | #4 | 52464 |
| 5632 | 20914 | 70.4 | 62.5 | 25 | 525 | #5 | 52465 |
| 5633 | 20915 | 75.2 | 61.1 | 20 | 342 | #6 | 52466 |
| 5634 | 20916 | 70.4 | 62.9 | 22 | 380 | #5 | 52467 |
| 5635 | 20917 | 68.8 | 60.0 | 17 | 331 | #4 | 52468 |
| 5636 | 20918 | 63.2 | 50.0 | 18 | 180 | #3 | 52469 |
| 5637 | 20919 | 62.4 | 58.2 | 15 | 218 | #3 | 52470 |
| 5638 | 20920 | 71.2 | 63.6 | 21 | 525 | #5 | 52471 |
| 5639 | 20921 | 50.0 | 50.0 | 12 | 150 | #1 | 52472 |
| 5640 | 20922 | 67.2 | 60.0 | 16 | 286 | #4 | 52473 |
| 5641 | 20923 | 69.6 | 61.1 | 21 | 274 | #4 | 52474 |
| 5642 | 20924 | 69.6 | 60.0 | 26 | 286 | #4 | 52475 |
| 5643 | 20925 | 64.8 | 60.4 | 16 | 238 | #3 | 52476 |
| 5644 | 20926 | 71.2 | 59.3 | 24 | 253 | #5 | 52477 |
| 5645 | 20927 | 65.6 | 57.1 | 16 | 228 | #4 | 52478 |
| 5646 | 20928 | 65.6 | 50.0 | 12 | 201 | #4 | 52479 |
| 5647 | 20929 | 66.4 | 58.2 | 16 | 211 | #4 | 52480 |
| 5648 | 20930 | 69.6 | 60.7 | 25 | 269 | #4 | 52481 |
| 5649 | 20931 | 65.6 | 59.6 | 25 | 218 | #4 | 52482 |
| 5650 | 20932 | 50.0 | 50.0 | 12 | 150 | #1 | 52483 |
| 5651 | 20933 | 72.8 | 66.2 | 24 | 520 | #5 | 52484 |
| 5652 | 20934 | 68.0 | 61.5 | 21 | 497 | #4 | 52485 |
| 5653 | 20935 | 50.0 | 50.0 | 12 | 150 | #1 | 52486 |
| 5654 | 20936 | 67.1 (76) | — | 33 | 162 | #4 | 52487 |
| 5655 | 20937 | 69.6 | 64.4 (208) | 19 | 282 | #4 | 52488 |
| 5656 | 20938 | 73.6 | 61.2 (250) | 28 | 308 | #5 | 52489 |
| 5657 | 20939 | 68.0 | 61.5 | 19 | 260 | #4 | 52490 |
| 5658 | 20940 | 56.1 (66) | — | 14 | 150 | #2 | 52491 |
| 5659 | 20941 | 65.6 | 59.3 | 20 | 350 | #4 | 52492 |
| 5660 | 20942 | 67.2 | 58.9 | 18 | 224 | #4 | 52493 |
| 5661 | 20943 | 50.0 | 50.0 | 12 | 150 | #1 | 52494 |
| 5662 | 20944 | 50.0 | 50.0 | 12 | 150 | #1 | 52495 |
| 5663 | 20945 | 73.6 | 62.5 | 38 | 340 | #5 | 52496 |
| 5664 | 20946 | 70.4 | 62.5 | 21 | 332 | #5 | 52497 |
| 5665 | 20947 | 69.6 | 59.3 | 26 | 270 | #4 | 52498 |
| 5666 | 20948 | 50.0 | 50.0 | 12 | 150 | #1 | 52499 |
| 5667 | 20949 | 68.8 | 66.7 (129) | 22 | 200 | #4 | 52500 |
| 5668 | 20950 | 68.0 | 61.1 | 20 | 298 | #4 | 52501 |
| 5669 | 20951 | 69.6 | 61.8 | 23 | 309 | #4 | 52502 |
| 5670 | 20952 | 66.4 | 60.7 | 23 | 279 | #4 | 52503 |
| 5671 | 20953 | 69.6 | 61.8 | 19 | 267 | #4 | 52504 |
| 5672 | 20954 | 68.8 | 59.6 | 19 | 238 | #4 | 52505 |
| 5673 | 20955 | 67.2 | 61.5 | 22 | 314 | #4 | 52506 |
| 5674 | 20956 | 72.0 | 61.8 | 27 | 369 | #5 | 52507 |
| 5675 | 20957 | 72.0 | 62.5 | 21 | 364 | #5 | 52508 |
| 5676 | 20958 | 68.8 | 61.1 | 19 | 289 | #4 | 52509 |
| 5677 | 20959 | 62.4 | 50.0 | 12 | 170 | #3 | 52510 |
| 5678 | 20960 | 61.6 | 50.0 (236) | 14 | 153 | #3 | 52511 |
| 5679 | 20961 | 68.8 | 62.9 | 21 | 530 | #4 | 52512 |
| 5680 | 20962 | 67.2 | 57.5 | 16 | 216 | #4 | 52513 |
| 5681 | 20963 | 69.6 | 62.5 | 20 | 384 | #4 | 52514 |
| 5682 | 20964 | 59.2 | 50.0 | 12 | 173 | #2 | 52515 |
| 5683 | 20965 | 66.4 | 54.5 | 13 | 242 | #4 | 52516 |
| 5684 | 20966 | 64.8 | 50.0 | 18 | 172 | #3 | 52517 |
| 5685 | 20967 | 64.0 | 58.5 | 18 | 183 | #3 | 52518 |
| 5686 | 20968 | 69.6 | 60.0 | 21 | 245 | #4 | 52519 |
| 5687 | 20969 | 77.6 | 65.8 | 29 | 449 | #6 | 52520 |
| 5688 | 20970 | 64.0 | 56.8 (273) | 14 | 183 | #3 | 52521 |
| 5689 | 20971 | 69.6 | 56.0 | 24 | 355 | #4 | 52522 |
| 5690 | 20972 | 71.2 | 62.9 | 21 | 610 | #5 | 52523 |
| 5691 | 20973 | 73.6 | 62.2 | 26 | 355 | #5 | 52524 |
| 5692 | 20974 | 65.6 | 58.9 | 18 | 201 | #4 | 52525 |
| 5693 | 20975 | 64.0 | 50.0 (211) | 18 | 160 | #3 | 52526 |
| 5694 | 20976 | 64.0 | 50.0 (171) | 15 | 184 | #3 | 52527 |
| 5695 | 20977 | 70.4 | 60.4 | 27 | 267 | #5 | 52528 |
| 5696 | 20978 | 50.0 | 50.0 | 12 | 150 | #1 | 52529 |
| 5697 | 20979 | 72.0 | 64.7 | 25 | 536 | #5 | 52530 |
| 5698 | 20980 | 66.4 | 56.4 | 34 | 223 | #4 | 52531 |
| 5699 | 20981 | 65.6 | 57.5 | 16 | 199 | #4 | 52532 |
| 5700 | 20982 | 53.6 | 50.0 (139) | 13 | 150 | #1 | 52533 |
| 5701 | 20983 | 56.8 | 50.0 | 19 | 153 | #2 | 52534 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5702 | 20984 | 68.8 (93) | — | 21 | 186 | #4 | 52535 |
| 5703 | 20985 | 68.8 | 60.7 | 20 | 300 | #4 | 52536 |
| 5704 | 20986 | 69.6 | 60.0 | 18 | 274 | #4 | 52537 |
| 5705 | 20987 | 67.2 | 56.4 | 19 | 198 | #4 | 52538 |
| 5706 | 20988 | 60.0 | 50.0 (252) | 16 | 150 | #2 | 52539 |
| 5707 | 20989 | 72.0 | 63.6 | 28 | 347 | #5 | 52540 |
| 5708 | 20990 | 64.8 | 55.6 | 18 | 192 | #3 | 52541 |
| 5709 | 20991 | 63.2 | 50.0 (222) | 18 | 170 | #3 | 52542 |
| 5710 | 20992 | 62.4 | 50.0 | 13 | 190 | #3 | 52543 |
| 5711 | 20993 | 68.8 | 60.4 | 19 | 276 | #4 | 52544 |
| 5712 | 20994 | 61.6 | 50.0 | 12 | 161 | #3 | 52545 |
| 5713 | 20995 | 65.6 | 57.8 | 16 | 219 | #4 | 52546 |
| 5714 | 20996 | 72.0 | 61.8 | 20 | 286 | #5 | 52547 |
| 5715 | 20997 | 63.2 | 50.0 (260) | 19 | 176 | #3 | 52548 |
| 5716 | 20998 | 70.4 | 60.4 | 23 | 277 | #5 | 52549 |
| 5717 | 20999 | 68.0 | 62.2 | 18 | 273 | #4 | 52550 |
| 5718 | 21000 | 64.8 | 50.0 | 13 | 214 | #3 | 52551 |
| 5719 | 21001 | 68.0 | 61.8 | 21 | 428 | #4 | 52552 |
| 5720 | 21002 | 67.2 | 58.2 | 16 | 196 | #4 | 52553 |
| 5721 | 21003 | 50.0 | 50.0 (152) | 12 | 150 | #1 | 52554 |
| 5722 | 21004 | 68.8 | 62.2 | 25 | 288 | #4 | 52555 |
| 5723 | 21005 | 61.6 | 50.0 | 13 | 169 | #3 | 52556 |
| 5724 | 21006 | 70.4 | 62.5 | 20 | 308 | #5 | 52557 |
| 5725 | 21007 | 64.0 | 56.6 (258) | 14 | 165 | #3 | 52558 |
| 5726 | 21008 | 68.8 | 60.4 | 19 | 244 | #4 | 52559 |
| 5727 | 21009 | 72.0 | 65.8 | 19 | 412 | #5 | 52560 |
| 5728 | 21010 | 64.8 | 50.0 (234) | 16 | 193 | #3 | 52561 |
| 5729 | 21011 | 63.2 | 50.5 | 19 | 189 | #3 | 52562 |
| 5730 | 21012 | 68.0 | 60.6 (216) | 24 | 238 | #4 | 52563 |
| 5731 | 21013 | 69.6 | 62.2 | 27 | 324 | #4 | 52564 |
| 5732 | 21014 | 63.2 | 50.0 | 13 | 191 | #3 | 52565 |
| 5733 | 21015 | 50.0 | 50.0 | 12 | 150 | #1 | 52566 |
| 5734 | 21016 | 68.0 | 57.5 | 18 | 226 | #4 | 52567 |
| 5735 | 21017 | 50.0 | 50.0 | 12 | 150 | #1 | 52568 |
| 5736 | 21018 | 69.6 | 63.4 (224) | 22 | 292 | #4 | 52569 |
| 5737 | 21019 | 68.0 | 57.2 (201) | 29 | 203 | #4 | 52570 |
| 5738 | 21020 | 62.4 | 56.0 | 17 | 192 | #3 | 52571 |
| 5739 | 21021 | 67.8 (115) | — | 19 | 205 | #4 | 52572 |
| 5740 | 21022 | 71.2 | 62.9 | 25 | 303 | #5 | 52573 |
| 5741 | 21023 | 59.2 | 57.8 | 14 | 238 | #2 | 52574 |
| 5742 | 21024 | 50.0 | 50.0 (145) | 12 | 150 | #1 | 52575 |
| 5743 | 21025 | 70.4 | 63.3 | 22 | 345 | #5 | 52576 |
| 5744 | 21026 | 68.8 | 60.7 | 19 | 321 | #4 | 52577 |
| 5745 | 21027 | 74.4 | 62.5 | 28 | 342 | #5 | 52578 |
| 5746 | 21028 | 68.0 | 62.9 | 19 | 298 | #4 | 52579 |
| 5747 | 21029 | 50.0 | 50.0 | 12 | 150 | #1 | 52580 |
| 5748 | 21030 | 72.8 | 59.3 | 18 | 288 | #5 | 52581 |
| 5749 | 21031 | 56.8 | 52.0 | 12 | 159 | #2 | 52582 |
| 5750 | 21032 | 59.2 | 50.0 (268) | 13 | 158 | #2 | 52583 |
| 5751 | 21033 | 54.4 | 50.0 | 12 | 150 | #1 | 52584 |
| 5752 | 21034 | 69.6 | 58.1 (270) | 24 | 265 | #4 | 52585 |
| 5753 | 21035 | 64.8 | 58.2 | 18 | 195 | #3 | 52586 |
| 5754 | 21036 | 50.0 | 50.0 (171) | 12 | 150 | #1 | 52587 |
| 5755 | 21037 | 50.0 | 50.0 | 12 | 150 | #1 | 52588 |
| 5756 | 21038 | 72.8 | 64.0 | 30 | 750 | #5 | 52589 |
| 5757 | 21039 | 68.0 | 62.5 | 21 | 316 | #4 | 52590 |
| 5758 | 21040 | 64.8 | 57.1 | 14 | 209 | #3 | 52591 |
| 5759 | 21041 | 79.2 | 71.3 | 21 | 608 | #6 | 52592 |
| 5760 | 21042 | 68.0 | 60.0 | 16 | 230 | #4 | 52593 |
| 5761 | 21043 | 64.0 | 56.3 (142) | 15 | 176 | #3 | 52594 |
| 5762 | 21044 | 69.6 | 58.5 | 17 | 220 | #4 | 52595 |
| 5763 | 21045 | 50.0 | 50.0 | 12 | 171 | #1 | 52596 |
| 5764 | 21046 | 64.8 | 56.4 | 17 | 241 | #3 | 52597 |
| 5765 | 21047 | 70.4 | 61.5 | 20 | 305 | #5 | 52598 |
| 5766 | 21048 | 72.0 | 61.5 | 22 | 315 | #5 | 52599 |
| 5767 | 21049 | 61.6 | 50.0 (267) | 13 | 159 | #3 | 52600 |
| 5768 | 21050 | 50.0 | 50.0 (153) | 12 | 150 | #1 | 52601 |
| 5769 | 21051 | 68.8 | 62.9 | 20 | 346 | #4 | 52602 |
| 5770 | 21052 | 65.6 | 59.3 (214) | 21 | 192 | #4 | 52603 |
| 5771 | 21053 | 64.8 | 55.6 | 16 | 198 | #3 | 52604 |
| 5772 | 21054 | 50.0 | 50.0 | 12 | 150 | #1 | 52605 |
| 5773 | 21055 | 65.6 | 59.3 | 17 | 239 | #4 | 52606 |
| 5774 | 21056 | 87.2 | 83.6 | 20 | 1029 | #8 | 52607 |
| 5775 | 21057 | 70.4 | 65.0 (180) | 28 | 246 | #5 | 52608 |
| 5776 | 21058 | 69.6 | 60.7 | 25 | 303 | #4 | 52609 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5777 | 21059 | 72.0 | 60.7 | 41 | 390 | #5 | 52610 |
| 5778 | 21060 | 68.0 | 60.4 | 19 | 269 | #4 | 52611 |
| 5779 | 21061 | 68.0 | 61.1 | 20 | 240 | #4 | 52612 |
| 5780 | 21062 | 67.2 | 60.4 | 21 | 262 | #4 | 52613 |
| 5781 | 21063 | 63.2 | 55.4 (168) | 17 | 176 | #3 | 52614 |
| 5782 | 21064 | 64.6 (96) | — | 13 | 150 | #3 | 52615 |
| 5783 | 21065 | 50.0 | 50.0 | 12 | 150 | #1 | 52616 |
| 5784 | 21066 | 64.0 | 58.5 | 14 | 195 | #3 | 52617 |
| 5785 | 21067 | 50.0 | 50.0 | 12 | 150 | #1 | 52618 |
| 5786 | 21068 | 64.0 | 57.8 | 12 | 199 | #3 | 52619 |
| 5787 | 21069 | 65.6 | 62.8 (164) | 16 | 182 | #4 | 52620 |
| 5788 | 21070 | 67.2 | 61.8 | 21 | 319 | #4 | 52621 |
| 5789 | 21071 | 72.0 | 64.7 | 20 | 398 | #5 | 52622 |
| 5790 | 21072 | 50.0 | 50.0 | 12 | 150 | #1 | 52623 |
| 5791 | 21073 | 68.0 | 61.5 | 21 | 306 | #4 | 52624 |
| 5792 | 21074 | 65.8 (76) | — | 13 | 150 | #4 | 52625 |
| 5793 | 21075 | 64.2 (95) | — | 15 | 150 | #3 | 52626 |
| 5794 | 21076 | 66.4 | 59.6 | 18 | 229 | #4 | 52627 |
| 5795 | 21077 | 66.4 | 59.6 | 18 | 268 | #4 | 52628 |
| 5796 | 21078 | 62.4 | 50.0 | 13 | 173 | #3 | 52629 |
| 5797 | 21079 | 76.8 | 73.1 | 15 | 770 | #6 | 52630 |
| 5798 | 21080 | 58.8 (114) | — | 13 | 150 | #2 | 52631 |
| 5799 | 21081 | 68.8 | 59.3 | 26 | 208 | #4 | 52632 |
| 5800 | 21082 | 72.0 | 61.7 (264) | 22 | 295 | #5 | 52633 |
| 5801 | 21083 | 64.0 | 50.5 (214) | 18 | 180 | #3 | 52634 |
| 5802 | 21084 | 63.2 | 57.8 | 18 | 199 | #3 | 52635 |
| 5803 | 21085 | 74.4 | 61.5 | 34 | 310 | #5 | 52636 |
| 5804 | 21086 | 69.6 | 61.5 | 19 | 276 | #4 | 52637 |
| 5805 | 21087 | 71.2 | 61.8 | 20 | 254 | #5 | 52638 |
| 5806 | 21088 | 64.0 | 50.0 | 13 | 183 | #3 | 52639 |
| 5807 | 21089 | 54.4 | 50.0 | 13 | 150 | #1 | 52640 |
| 5808 | 21090 | 50.0 | 50.0 (141) | 12 | 150 | #1 | 52641 |
| 5809 | 21091 | 68.0 | 61.5 | 22 | 343 | #4 | 52642 |
| 5810 | 21092 | 63.2 | 50.0 | 13 | 178 | #3 | 52643 |
| 5811 | 21093 | 68.8 | 61.5 | 27 | 292 | #4 | 52644 |
| 5812 | 21094 | 63.2 | 50.0 | 15 | 189 | #3 | 52645 |
| 5813 | 21095 | 67.2 | 62.2 | 24 | 354 | #4 | 52646 |
| 5814 | 21096 | 77.6 | 67.6 | 28 | 1733 | #6 | 52647 |
| 5815 | 21097 | 61.6 | 50.0 | 14 | 154 | #3 | 52648 |
| 5816 | 21098 | 72.8 | 62.2 | 34 | 340 | #5 | 52649 |
| 5817 | 21099 | 64.8 | 50.0 | 15 | 201 | #3 | 52650 |
| 5818 | 21100 | 68.0 | 61.5 | 24 | 328 | #4 | 52651 |
| 5819 | 21101 | 72.5 (80) | — | 27 | 166 | #5 | 52652 |
| 5820 | 21102 | 72.0 | 65.1 | 30 | 507 | #5 | 52653 |
| 5821 | 21103 | 59.2 | 50.0 (150) | 16 | 156 | #2 | 52654 |
| 5822 | 21104 | 68.8 | 63.3 | 33 | 506 | #4 | 52655 |
| 5823 | 21105 | 71.2 | 65.8 | 21 | 405 | #5 | 52656 |
| 5824 | 21106 | 66.4 | 58.2 | 18 | 231 | #4 | 52657 |
| 5825 | 21107 | 62.4 | 59.3 | 16 | 200 | #3 | 52658 |
| 5826 | 21108 | 62.4 | 50.0 | 14 | 222 | #3 | 52659 |
| 5827 | 21109 | 68.0 | 60.0 | 20 | 238 | #4 | 52660 |
| 5828 | 21110 | 67.2 | 61.5 | 20 | 278 | #4 | 52661 |
| 5829 | 21111 | 72.8 | 63.3 | 24 | 439 | #5 | 52662 |
| 5830 | 21112 | 50.0 | 50.0 | 12 | 150 | #1 | 52663 |
| 5831 | 21113 | 50.0 | 50.0 (151) | 12 | 150 | #1 | 52664 |
| 5832 | 21114 | 69.6 | 60.7 | 13 | 323 | #4 | 52665 |
| 5833 | 21115 | 50.0 (89) | — | 12 | 150 | #1 | 52666 |
| 5834 | 21116 | 76.0 | 64.4 | 22 | 382 | #6 | 52667 |
| 5835 | 21117 | 60.8 | 56.7 | 13 | 200 | #3 | 52668 |
| 5836 | 21118 | 50.0 | 50.0 | 12 | 150 | #1 | 52669 |
| 5837 | 21119 | 70.4 | 61.5 | 33 | 273 | #5 | 52670 |
| 5838 | 21120 | 64.0 | 50.0 | 14 | 165 | #3 | 52671 |
| 5839 | 21121 | 65.6 | 58.9 (265) | 21 | 220 | #4 | 52672 |
| 5840 | 21122 | 66.4 | 50.0 | 20 | 195 | #4 | 52673 |
| 5841 | 21123 | 68.8 | 58.2 | 17 | 222 | #4 | 52674 |
| 5842 | 21124 | 63.2 | 51.8 (199) | 15 | 150 | #3 | 52675 |
| 5843 | 21125 | 66.4 | 50.0 | 20 | 209 | #4 | 52676 |
| 5844 | 21126 | 68.8 | 59.6 | 25 | 238 | #4 | 52677 |
| 5845 | 21127 | 74.4 | 62.2 | 25 | 352 | #5 | 52678 |
| 5846 | 21128 | 70.4 | 64.7 | 21 | 357 | #5 | — |
| 5847 | 21129 | 64.8 | 54.5 (255) | 19 | 177 | #3 | 52679 |
| 5848 | 21130 | 68.0 | 60.7 | 21 | 305 | #4 | 52680 |
| 5849 | 21131 | 68.8 | 60.7 | 19 | 262 | #4 | 52681 |
| 5850 | 21132 | 68.0 | 61.5 | 25 | 329 | #4 | 52682 |
| 5851 | 21133 | 66.4 | 61.5 | 21 | 249 | #4 | 52683 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5852 | 21134 | 72.0 | 65.1 | 27 | 420 | #5 | 52684 |
| 5853 | 21135 | 50.0 | 50.0 (140) | 12 | 150 | #1 | 52685 |
| 5854 | 21136 | 70.4 | 62.9 | 31 | 388 | #5 | 52686 |
| 5855 | 21137 | 69.6 | 62.9 | 24 | 325 | #4 | 52687 |
| 5856 | 21138 | 64.8 | 61.5 | 19 | 271 | #3 | 52688 |
| 5857 | 21139 | 65.6 | 59.1 (164) | 13 | 162 | #4 | 52689 |
| 5858 | 21140 | 64.8 | 59.1 (247) | 16 | 163 | #3 | 52690 |
| 5859 | 21141 | 72.0 | 61.8 | 21 | 320 | #5 | 52691 |
| 5860 | 21142 | 71.2 | 61.5 | 19 | 281 | #5 | 52692 |
| 5861 | 21143 | 67.2 | 58.9 | 17 | 256 | #4 | 52693 |
| 5862 | 21144 | 68.0 | 60.7 | 21 | 315 | #4 | 52694 |
| 5863 | 21145 | 64.8 | 59.3 | 15 | 211 | #3 | 52695 |
| 5864 | 21146 | 64.8 | 57.8 | 15 | 203 | #3 | 52696 |
| 5865 | 21147 | 65.6 | 51.3 (265) | 16 | 189 | #4 | 52697 |
| 5866 | 21148 | 70.4 | 64.4 | 22 | 568 | #5 | 52698 |
| 5867 | 21149 | 68.8 | 59.6 | 20 | 268 | #4 | 52699 |
| 5868 | 21150 | 55.2 | 50.0 (222) | 12 | 159 | #2 | 52700 |
| 5869 | 21151 | 50.0 | 50.0 | 12 | 150 | #1 | 52701 |
| 5870 | 21152 | 71.2 | 61.5 | 18 | 354 | #5 | 52702 |
| 5871 | 21153 | 59.2 | 57.1 | 13 | 193 | #2 | 52703 |
| 5872 | 21154 | 70.4 | 60.4 | 29 | 268 | #5 | 52704 |
| 5873 | 21155 | 67.2 | 63.5 (230) | 19 | 227 | #4 | 52705 |
| 5874 | 21156 | 65.6 | 57.5 | 18 | 206 | #4 | 52706 |
| 5875 | 21157 | 68.8 | 62.9 | 23 | 318 | #4 | 52707 |
| 5876 | 21158 | 60.0 | 50.0 (167) | 17 | 150 | #2 | 52708 |
| 5877 | 21159 | 68.8 | 61.8 | 20 | 337 | #4 | 52709 |
| 5878 | 21160 | 68.8 | 62.2 | 22 | 324 | #4 | 52710 |
| 5879 | 21161 | 64.0 | 55.1 (225) | 18 | 160 | #3 | 52711 |
| 5880 | 21162 | 72.8 | 62.9 | 37 | 319 | #5 | 52712 |
| 5881 | 21163 | 61.6 | 57.1 (154) | 12 | 150 | #3 | 52713 |
| 5882 | 21164 | 62.4 | 57.5 | 17 | 215 | #3 | 52714 |
| 5883 | 21165 | 50.0 | 50.0 | 13 | 150 | #1 | 52715 |
| 5884 | 21166 | 64.8 | 50.0 (256) | 20 | 196 | #3 | 52716 |
| 5885 | 21167 | 64.0 | 50.0 | 15 | 174 | #3 | 52717 |
| 5886 | 21168 | 67.2 | 61.1 | 28 | 309 | #4 | 52718 |
| 5887 | 21169 | 66.4 | 50.0 | 13 | 191 | #4 | 52719 |
| 5888 | 21170 | 64.8 | 50.0 | 14 | 209 | #3 | 52720 |
| 5889 | 21171 | 69.6 | 57.5 | 17 | 234 | #4 | 52721 |
| 5890 | 21172 | 71.2 | 60.7 | 22 | 303 | #5 | 52722 |
| 5891 | 21173 | 60.8 | 50.0 | 13 | 167 | #3 | 52723 |
| 5892 | 21174 | 66.4 | 60.7 | 14 | 285 | #4 | 52724 |
| 5893 | 21175 | 66.4 | 59.6 | 16 | 238 | #4 | 52725 |
| 5894 | 21176 | 50.0 | 50.0 | 12 | 150 | #1 | 52726 |
| 5895 | 21177 | 62.4 | 60.5 (172) | 16 | 176 | #3 | 52727 |
| 5896 | 21178 | 72.8 | 61.8 | 27 | 341 | #5 | 52728 |
| 5897 | 21179 | 66.4 | 60.4 | 20 | 313 | #4 | 52729 |
| 5898 | 21180 | 64.8 | 60.4 | 17 | 259 | #3 | 52730 |
| 5899 | 21181 | 70.4 | 61.8 | 24 | 315 | #5 | 52731 |
| 5900 | 21182 | 76.8 | 65.1 | 30 | 463 | #6 | 52732 |
| 5901 | 21183 | 65.6 | 59.6 | 17 | 257 | #4 | 52733 |
| 5902 | 21184 | 74.4 | 65.8 | 23 | 485 | #5 | 52734 |
| 5903 | 21185 | 65.6 | 62.2 | 13 | 396 | #4 | 52735 |
| 5904 | 21186 | 61.6 | 50.0 | 12 | 190 | #3 | 52736 |
| 5905 | 21187 | 68.0 | 60.4 | 22 | 338 | #4 | 52737 |
| 5906 | 21188 | 67.2 | 60.0 | 24 | 235 | #4 | 52738 |
| 5907 | 21189 | 67.2 | 58.5 | 24 | 240 | #4 | 52739 |
| 5908 | 21190 | 67.2 | 61.1 | 16 | 258 | #4 | 52740 |
| 5909 | 21191 | 68.8 | 61.1 | 19 | 353 | #4 | 52741 |
| 5910 | 21192 | 66.4 | 50.0 | 15 | 188 | #4 | 52742 |
| 5911 | 21193 | 64.8 | 60.4 | 17 | 240 | #3 | 52743 |
| 5912 | 21194 | 66.4 | 56.8 (183) | 23 | 180 | #4 | 52744 |
| 5913 | 21195 | 80.8 | 70.5 | 20 | 549 | #7 | 52745 |
| 5914 | 21196 | 60.9 (87) | — | 12 | 150 | #3 | 52746 |
| 5915 | 21197 | 68.0 | 60.7 | 20 | 278 | #4 | 52747 |
| 5916 | 21198 | 72.0 | 70.6 (136) | 15 | 324 | #5 | 52748 |
| 5917 | 21199 | 67.2 | 58.2 | 23 | 237 | #4 | 52749 |
| 5918 | 21200 | 50.0 | 50.0 | 12 | 150 | #1 | 52750 |
| 5919 | 21201 | 65.6 | 50.0 | 21 | 196 | #4 | 52751 |
| 5920 | 21202 | 50.0 | 50.0 | 12 | 150 | #1 | 52752 |
| 5921 | 21203 | 66.4 | 60.0 | 14 | 243 | #4 | 52753 |
| 5922 | 21204 | 62.4 | 50.0 (254) | 39 | 207 | #3 | 52754 |
| 5923 | 21205 | 68.8 | 59.9 (212) | 20 | 201 | #4 | 52755 |
| 5924 | 21206 | 69.6 | 61.5 | 19 | 286 | #4 | 52756 |
| 5925 | 21207 | 66.4 | 60.0 | 18 | 274 | #4 | 52757 |
| 5926 | 21208 | 50.0 | 50.0 | 12 | 150 | #1 | 52758 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 5927 | 21209 | 50.0 (78) | — | 12 | 150 | #1 | 52759 |
| 5928 | 21210 | 69.6 | 60.4 | 20 | 255 | #4 | 52760 |
| 5929 | 21211 | 68.0 | 61.1 | 27 | 285 | #4 | 52761 |
| 5930 | 21212 | 70.4 | 61.1 | 20 | 279 | #5 | 52762 |
| 5931 | 21213 | 68.8 | 61.8 | 17 | 307 | #4 | 52763 |
| 5932 | 21214 | 68.0 | 59.3 | 19 | 260 | #4 | 52764 |
| 5933 | 21215 | 68.8 | 62.9 | 20 | 475 | #4 | 52765 |
| 5934 | 21216 | 64.8 | 58.9 | 15 | 221 | #3 | 52766 |
| 5935 | 21217 | 67.2 | 60.4 | 22 | 236 | #4 | 52767 |
| 5936 | 21218 | 50.0 (111) | — | 12 | 150 | #1 | 52768 |
| 5937 | 21219 | 70.4 | 63.6 | 30 | 548 | #5 | 52769 |
| 5938 | 21220 | 71.2 | 62.5 | 19 | 368 | #5 | 52770 |
| 5939 | 21221 | 85.7 (84) | — | 22 | 306 | #8 | 52771 |
| 5940 | 21222 | 64.8 | 50.0 (258) | 15 | 166 | #3 | 52772 |
| 5941 | 21223 | 72.0 | 62.9 | 21 | 511 | #5 | 52773 |
| 5942 | 21224 | 64.8 | 57.8 | 17 | 234 | #3 | 52774 |
| 5943 | 21225 | 68.8 | 61.7 (253) | 19 | 240 | #4 | 52775 |
| 5944 | 21226 | 64.8 | 60.0 | 13 | 250 | #3 | 52776 |
| 5945 | 21227 | 60.8 | 50.0 | 14 | 155 | #3 | 52777 |
| 5946 | 21228 | 50.0 | 50.0 | 12 | 150 | #1 | 52778 |
| 5947 | 21229 | 74.4 | 66.5 | 27 | 599 | #5 | 52779 |
| 5948 | 21230 | 64.0 | 56.4 | 14 | 208 | #3 | 52780 |
| 5949 | 21231 | 67.2 | 60.4 | 18 | 242 | #4 | 52781 |
| 5950 | 21232 | 68.0 | 59.3 | 20 | 231 | #4 | 52782 |
| 5951 | 21233 | 64.8 | 57.5 | 15 | 200 | #3 | 52783 |
| 5952 | 21234 | 72.0 | 62.5 | 28 | 676 | #5 | 52784 |
| 5953 | 21235 | 60.0 | 50.0 | 13 | 156 | #2 | 52785 |
| 5954 | 21236 | 72.8 | 63.6 | 23 | 422 | #5 | 52786 |
| 5955 | 21237 | 64.0 | 59.6 | 17 | 198 | #3 | 52787 |
| 5956 | 21238 | 70.4 | 61.8 | 24 | 344 | #5 | 52788 |
| 5957 | 21239 | 66.4 | 59.6 | 17 | 256 | #4 | 52789 |
| 5958 | 21240 | 69.6 | 62.2 | 20 | 303 | #4 | 52790 |
| 5959 | 21241 | 61.6 | 53.5 (155) | 15 | 159 | #3 | 52791 |
| 5960 | 21242 | 70.4 | 63.6 | 21 | 419 | #5 | 52792 |
| 5961 | 21243 | 60.8 | 50.0 | 14 | 195 | #3 | 52793 |
| 5962 | 21244 | 68.0 | 60.0 | 19 | 246 | #4 | 52794 |
| 5963 | 21245 | 70.4 | 61.5 | 19 | 297 | #5 | 52795 |
| 5964 | 21246 | 63.2 | 50.8 (183) | 16 | 155 | #3 | 52796 |
| 5965 | 21247 | 64.8 | 58.5 | 15 | 225 | #3 | 52797 |
| 5966 | 21248 | 68.8 | 61.5 | 21 | 296 | #4 | 52798 |
| 5967 | 21249 | 68.8 | 60.0 | 20 | 251 | #4 | 52799 |
| 5968 | 21250 | 66.4 | 58.5 | 12 | 222 | #4 | 52800 |
| 5969 | 21251 | 60.8 | 50.0 | 13 | 195 | #3 | 52801 |
| 5970 | 21252 | 59.2 | 50.0 | 15 | 179 | #2 | 52802 |
| 5971 | 21253 | 72.8 | 61.5 | 28 | 324 | #5 | 52803 |
| 5972 | 21254 | 50.0 | 50.0 | 12 | 150 | #1 | 52804 |
| 5973 | 21255 | 66.4 | 53.8 | 19 | 218 | #4 | 52805 |
| 5974 | 21256 | 63.2 | 57.1 | 12 | 192 | #3 | 52806 |
| 5975 | 21257 | 66.4 | 50.0 | 16 | 207 | #4 | 52807 |
| 5976 | 21258 | 50.0 | 50.0 (241) | 12 | 150 | #1 | 52808 |
| 5977 | 21259 | 50.0 | 50.0 (239) | 13 | 150 | #1 | 52809 |
| 5978 | 21260 | 64.8 | 50.0 | 13 | 204 | #3 | 52810 |
| 5979 | 21261 | 68.0 | 60.4 | 22 | 249 | #4 | 52811 |
| 5980 | 21262 | 66.4 | 50.2 | 18 | 195 | #4 | 52812 |
| 5981 | 21263 | 70.4 | 60.0 | 18 | 324 | #5 | 52813 |
| 5982 | 21264 | 50.0 | 50.0 | 12 | 150 | #1 | 52814 |
| 5983 | 21265 | 50.0 | 50.0 | 12 | 150 | #1 | 52815 |
| 5984 | 21266 | 68.8 | 61.1 | 19 | 399 | #4 | 52816 |
| 5985 | 21267 | 70.4 | 60.4 | 23 | 248 | #5 | 52817 |
| 5986 | 21268 | 69.6 | 57.8 | 28 | 225 | #4 | 52818 |
| 5987 | 21269 | 65.6 | 50.0 | 14 | 199 | #4 | 52819 |
| 5988 | 21270 | 67.2 | 59.3 | 17 | 221 | #4 | 52820 |
| 5989 | 21271 | 63.2 | 59.2 (272) | 16 | 184 | #3 | 52821 |
| 5990 | 21272 | 64.8 | 58.2 | 17 | 198 | #3 | 52822 |
| 5991 | 21273 | 50.0 | 50.0 | 12 | 150 | #1 | 52823 |
| 5992 | 21274 | 65.6 | 61.1 | 19 | 250 | #4 | 52824 |
| 5993 | 21275 | 65.6 | 58.9 | 21 | 238 | #4 | 52825 |
| 5994 | 21276 | 80.3 (117) | — | 16 | 378 | #7 | 52826 |
| 5995 | 21277 | 50.0 | 50.0 | 12 | 150 | #1 | 52827 |
| 5996 | 21278 | 63.2 | 58.9 | 17 | 219 | #3 | 52828 |
| 5997 | 21279 | 73.6 | 66.5 | 28 | 1019 | #5 | 52829 |
| 5998 | 21280 | 70.4 | 61.8 | 18 | 270 | #5 | 52830 |
| 5999 | 21281 | 68.8 | 61.5 | 19 | 254 | #4 | 52831 |
| 6000 | 21282 | 63.2 | 51.6 | 14 | 196 | #3 | 52832 |
| 6001 | 21283 | 61.6 | 53.1 | 13 | 196 | #3 | 52833 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6002 | 21284 | 72.0 | 62.2 | 24 | 300 | #5 | 52834 |
| 6003 | 21285 | 77.6 | 62.2 | 27 | 345 | #6 | 52835 |
| 6004 | 21286 | 72.0 | 61.8 | 32 | 296 | #5 | 52836 |
| 6005 | 21287 | 70.4 | 63.6 | 30 | 293 | #5 | 52837 |
| 6006 | 21288 | 67.2 | 50.0 | 20 | 202 | #4 | 52838 |
| 6007 | 21289 | 72.0 | 66.9 | 23 | 865 | #5 | 52839 |
| 6008 | 21290 | 50.0 | 50.0 | 12 | 150 | #1 | 52840 |
| 6009 | 21291 | 50.0 | 50.0 | 12 | 150 | #1 | 52841 |
| 6010 | 21292 | 50.0 (72) | — | 12 | 150 | #1 | 52842 |
| 6011 | 21293 | 50.0 | 50.0 | 12 | 150 | #1 | 52843 |
| 6012 | 21294 | 62.4 | 50.0 | 19 | 168 | #3 | 52844 |
| 6013 | 21295 | 50.0 | 50.0 | 12 | 150 | #1 | 52845 |
| 6014 | 21296 | 50.0 | 50.0 | 12 | 150 | #1 | 52846 |
| 6015 | 21297 | 68.0 | 59.6 | 17 | 321 | #4 | 52847 |
| 6016 | 21298 | 50.0 | 50.0 | 12 | 150 | #1 | 52848 |
| 6017 | 21299 | 63.2 | 50.0 (246) | 13 | 181 | #3 | 52849 |
| 6018 | 21300 | 72.0 | 62.5 | 21 | 481 | #5 | 52850 |
| 6019 | 21301 | 64.0 | 59.3 | 13 | 263 | #3 | 52851 |
| 6020 | 21302 | 63.2 | 57.5 | 17 | 193 | #3 | 52852 |
| 6021 | 21303 | 67.2 | 50.0 | 16 | 213 | #4 | 52853 |
| 6022 | 21304 | 62.4 | 50.0 (252) | 15 | 174 | #3 | 52854 |
| 6023 | 21305 | 50.0 | 50.0 | 12 | 150 | #1 | 52855 |
| 6024 | 21306 | 68.0 | 59.3 | 18 | 218 | #4 | 52856 |
| 6025 | 21307 | 71.2 | 60.7 | 28 | 258 | #5 | 52857 |
| 6026 | 21308 | 64.0 | 58.2 | 15 | 225 | #3 | 52858 |
| 6027 | 21309 | 66.4 | 57.8 | 16 | 209 | #4 | 52859 |
| 6028 | 21310 | 68.8 | 59.6 | 36 | 242 | #4 | 52860 |
| 6029 | 21311 | 71.2 | 61.8 | 30 | 323 | #5 | 52861 |
| 6030 | 21312 | 50.0 | 50.0 | 12 | 150 | #1 | 52862 |
| 6031 | 21313 | 50.0 (70) | — | 12 | 150 | #1 | 52863 |
| 6032 | 21314 | 65.6 | 58.2 | 20 | 240 | #4 | 52864 |
| 6033 | 21315 | 73.6 | 63.6 | 26 | 383 | #5 | 52865 |
| 6034 | 21316 | 67.3 (98) | — | 37 | 229 | #4 | 52866 |
| 6035 | 21317 | 61.6 | 58.4 (173) | 18 | 156 | #3 | 52867 |
| 6036 | 21318 | 71.2 | 62.9 | 25 | 374 | #5 | 52868 |
| 6037 | 21319 | 50.0 | 50.0 | 12 | 150 | #1 | 52869 |
| 6038 | 21320 | 65.6 | 57.1 | 15 | 222 | #4 | 52870 |
| 6039 | 21321 | 67.2 | 56.4 | 19 | 235 | #4 | 52871 |
| 6040 | 21322 | 64.8 | 57.8 | 15 | 175 | #3 | 52872 |
| 6041 | 21323 | 70.4 | 61.5 | 22 | 355 | #5 | 52873 |
| 6042 | 21324 | 65.6 | 58.9 | 13 | 199 | #4 | 52874 |
| 6043 | 21325 | 56.0 | 50.0 | 12 | 174 | #2 | 52875 |
| 6044 | 21326 | 68.8 | 59.3 | 35 | 259 | #4 | 52876 |
| 6045 | 21327 | 66.4 | 58.5 | 14 | 227 | #4 | 52877 |
| 6046 | 21328 | 68.0 | 60.4 | 20 | 242 | #4 | 52878 |
| 6047 | 21329 | 66.4 | 50.0 | 17 | 205 | #4 | 52879 |
| 6048 | 21330 | 61.6 | 50.0 | 16 | 186 | #3 | 52880 |
| 6049 | 21331 | 50.0 | 50.0 | 12 | 150 | #1 | 52881 |
| 6050 | 21332 | 64.0 | 52.7 | 12 | 195 | #3 | 52882 |
| 6051 | 21333 | 62.4 | 58.9 | 15 | 217 | #3 | 52883 |
| 6052 | 21334 | 72.8 | 65.5 | 32 | 387 | #5 | 52884 |
| 6053 | 21335 | 55.2 | 50.0 | 13 | 150 | #2 | 52885 |
| 6054 | 21336 | 68.8 | 60.4 | 28 | 222 | #4 | 52886 |
| 6055 | 21337 | 72.0 | 61.5 | 21 | 288 | #5 | 52887 |
| 6056 | 21338 | 62.4 | 55.9 (254) | 17 | 161 | #3 | 52888 |
| 6057 | 21339 | 75.2 | 65.8 | 37 | 552 | #6 | 52889 |
| 6058 | 21340 | 52.0 | 50.0 | 13 | 159 | #1 | 52890 |
| 6059 | 21341 | 71.2 | 64.0 | 31 | 372 | #5 | 52891 |
| 6060 | 21342 | 50.0 | 50.0 | 12 | 150 | #1 | 52892 |
| 6061 | 21343 | 66.4 | 61.1 (203) | 21 | 206 | #4 | 52893 |
| 6062 | 21344 | 50.0 | 50.0 | 12 | 150 | #1 | 52894 |
| 6063 | 21345 | 66.4 | 60.7 | 17 | 301 | #4 | 52895 |
| 6064 | 21346 | 50.0 | 50.0 | 12 | 150 | #1 | 52896 |
| 6065 | 21347 | 70.4 | 61.8 | 19 | 294 | #5 | 52897 |
| 6066 | 21348 | 75.2 | 66.9 | 33 | 475 | #6 | 52898 |
| 6067 | 21349 | 70.6 (102) | — | 24 | 206 | #5 | 52899 |
| 6068 | 21350 | 68.0 | 60.0 | 15 | 271 | #4 | 52900 |
| 6069 | 21351 | 68.8 | 61.5 | 19 | 457 | #4 | 52901 |
| 6070 | 21352 | 66.4 | 58.9 | 19 | 210 | #4 | 52902 |
| 6071 | 21353 | 65.6 | 50.0 | 16 | 206 | #4 | 52903 |
| 6072 | 21354 | 66.4 | 53.5 | 16 | 217 | #4 | 52904 |
| 6073 | 21355 | 50.0 | 50.0 | 12 | 150 | #1 | 52905 |
| 6074 | 21356 | 71.2 | 61.5 | 27 | 286 | #5 | 52906 |
| 6075 | 21357 | 72.0 | 62.5 | 22 | 332 | #5 | 52907 |
| 6076 | 21358 | 67.2 | 58.2 | 18 | 242 | #4 | 52908 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6077 | 21359 | 52.0 | 50.0 | 13 | 150 | #1 | 52909 |
| 6078 | 21360 | 71.2 | 60.4 | 23 | 230 | #5 | 52910 |
| 6079 | 21361 | 68.8 | 61.5 | 21 | 333 | #4 | 52911 |
| 6080 | 21362 | 68.0 | 57.8 | 19 | 242 | #4 | 52912 |
| 6081 | 21363 | 61.6 | 50.0 | 13 | 186 | #3 | 52913 |
| 6082 | 21364 | 71.2 | 64.4 | 28 | 395 | #5 | 52914 |
| 6083 | 21365 | 70.4 | 61.1 | 21 | 432 | #5 | 52915 |
| 6084 | 21366 | 68.8 | 59.3 | 19 | 256 | #4 | 52916 |
| 6085 | 21367 | 50.0 (102) | — | 12 | 150 | #1 | 52917 |
| 6086 | 21368 | 62.4 | 57.1 | 12 | 199 | #3 | 52918 |
| 6087 | 21369 | 68.0 | 61.5 | 23 | 273 | #4 | 52919 |
| 6088 | 21370 | 72.0 | 63.3 | 23 | 336 | #5 | 52920 |
| 6089 | 21371 | 68.0 | 60.0 | 21 | 286 | #4 | 52921 |
| 6090 | 21372 | 62.4 | 50.0 | 13 | 193 | #3 | 52922 |
| 6091 | 21373 | 68.8 | 60.4 | 19 | 274 | #4 | 52923 |
| 6092 | 21374 | 71.2 | 65.1 | 23 | 424 | #5 | 52924 |
| 6093 | 21375 | 65.6 | 50.0 | 22 | 205 | #4 | 52925 |
| 6094 | 21376 | 72.0 | 61.5 | 26 | 308 | #5 | 52926 |
| 6095 | 21377 | 89.6 | 76.4 | 20 | 979 | #8 | 52927 |
| 6096 | 21378 | 69.1 (68) | — | 16 | 150 | #4 | 52928 |
| 6097 | 21379 | 50.0 | 50.0 | 14 | 157 | #1 | 52929 |
| 6098 | 21380 | 64.0 | 58.5 | 13 | 206 | #3 | 52930 |
| 6099 | 21381 | 67.2 | 58.5 | 20 | 189 | #4 | 52931 |
| 6100 | 21382 | 50.0 | 50.0 | 12 | 150 | #1 | 52932 |
| 6101 | 21383 | 68.8 | 60.0 | 23 | 308 | #4 | 52933 |
| 6102 | 21384 | 67.2 | 55.3 | 25 | 219 | #4 | 52934 |
| 6103 | 21385 | 93.0 (71) | — | 24 | 310 | #9 | 52935 |
| 6104 | 21386 | 72.8 | 62.5 | 17 | 254 | #5 | 52936 |
| 6105 | 21387 | 67.2 | 60.7 | 20 | 298 | #4 | 52937 |
| 6106 | 21388 | 63.2 | 53.5 | 13 | 215 | #3 | 52938 |
| 6107 | 21389 | 70.4 | 66.5 | 28 | 498 | #5 | 52939 |
| 6108 | 21390 | 64.0 | 58.2 | 16 | 228 | #3 | 52940 |
| 6109 | 21391 | 66.4 | 60.0 | 23 | 233 | #4 | 52941 |
| 6110 | 21392 | 66.4 | 54.1 (259) | 22 | 200 | #4 | 52942 |
| 6111 | 21393 | 69.6 | 62.5 | 23 | 444 | #4 | 52943 |
| 6112 | 21394 | 67.2 | 50.5 | 20 | 206 | #4 | 52944 |
| 6113 | 21395 | 64.0 | 59.3 | 15 | 257 | #3 | 52945 |
| 6114 | 21396 | 71.2 | 64.4 | 20 | 314 | #5 | 52946 |
| 6115 | 21397 | 81.6 | 75.3 | 22 | 610 | #7 | 52947 |
| 6116 | 21398 | 68.8 | 63.3 | 23 | 428 | #4 | 52948 |
| 6117 | 21399 | 62.4 | 51.6 | 12 | 190 | #3 | 52949 |
| 6118 | 21400 | 65.6 | 60.7 | 15 | 385 | #4 | 52950 |
| 6119 | 21401 | 50.0 | 50.0 | 12 | 150 | #1 | 52951 |
| 6120 | 21402 | 77.6 | 64.4 | 32 | 441 | #6 | 52952 |
| 6121 | 21403 | 66.4 | 59.3 | 30 | 261 | #4 | 52953 |
| 6122 | 21404 | 50.0 | 50.0 | 12 | 150 | #1 | 52954 |
| 6123 | 21405 | 66.4 | 55.6 | 16 | 222 | #4 | 52955 |
| 6124 | 21406 | 65.6 | 59.6 | 21 | 234 | #4 | 52956 |
| 6125 | 21407 | 64.0 | 54.9 | 12 | 201 | #3 | 52957 |
| 6126 | 21408 | 72.0 | 60.7 | 25 | 281 | #5 | 52958 |
| 6127 | 21409 | 64.0 | 57.9 (273) | 16 | 180 | #3 | 52959 |
| 6128 | 21410 | 50.0 | 50.0 (135) | 12 | 150 | #1 | 52960 |
| 6129 | 21411 | 73.6 | 64.7 | 27 | 467 | #5 | 52961 |
| 6130 | 21412 | 64.8 | 50.0 | 14 | 178 | #3 | 52962 |
| 6131 | 21413 | 50.0 | 50.0 | 12 | 150 | #1 | 52963 |
| 6132 | 21414 | 88.0 | 82.2 | 31 | 969 | #8 | 52964 |
| 6133 | 21415 | 64.8 | 50.0 | 18 | 190 | #3 | 52965 |
| 6134 | 21416 | 66.4 | 54.4 (266) | 17 | 191 | #4 | 52966 |
| 6135 | 21417 | 72.0 | 61.8 | 25 | 344 | #5 | 52967 |
| 6136 | 21418 | 64.0 | 57.8 | 14 | 215 | #3 | 52968 |
| 6137 | 21419 | 67.2 | 58.9 | 18 | 247 | #4 | 52969 |
| 6138 | 21420 | 74.4 | 63.3 | 28 | 332 | #5 | 52970 |
| 6139 | 21421 | 67.2 | 62.5 | 21 | 309 | #4 | 52971 |
| 6140 | 21422 | 75.2 | 62.2 | 29 | 328 | #6 | 52972 |
| 6141 | 21423 | 65.6 | 57.8 | 15 | 219 | #4 | 52973 |
| 6142 | 21424 | 67.2 | 50.0 | 17 | 226 | #4 | 52974 |
| 6143 | 21425 | 72.0 | 60.7 | 22 | 281 | #5 | 52975 |
| 6144 | 21426 | 67.2 | 60.4 | 17 | 258 | #4 | 52976 |
| 6145 | 21427 | 64.0 | 55.6 | 15 | 196 | #3 | 52977 |
| 6146 | 21428 | 68.0 | 57.1 | 24 | 247 | #4 | 52978 |
| 6147 | 21429 | 70.4 | 61.5 | 25 | 289 | #5 | 52979 |
| 6148 | 21430 | 50.0 | 50.0 | 12 | 150 | #1 | 52980 |
| 6149 | 21431 | 50.0 | 50.0 | 12 | 150 | #1 | 52981 |
| 6150 | 21432 | 61.6 | 51.6 | 13 | 181 | #3 | 52982 |
| 6151 | 21433 | 50.0 | 50.0 (179) | 13 | 163 | #1 | 52983 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6152 | 21434 | 68.0 | 58.2 | 21 | 210 | #4 | 52984 |
| 6153 | 21435 | 60.8 | 50.0 | 12 | 150 | #3 | 52985 |
| 6154 | 21436 | 64.0 | 58.9 | 20 | 216 | #3 | 52986 |
| 6155 | 21437 | 63.2 | 50.0 | 12 | 165 | #3 | 52987 |
| 6156 | 21438 | 72.0 | 62.2 | 23 | 333 | #5 | 52988 |
| 6157 | 21439 | 68.0 | 61.5 | 20 | 300 | #4 | 52989 |
| 6158 | 21440 | 64.0 | 57.1 | 19 | 218 | #3 | 52990 |
| 6159 | 21441 | 50.0 | 50.0 | 12 | 150 | #1 | 52991 |
| 6160 | 21442 | 73.6 | 65.1 | 28 | 462 | #5 | 52992 |
| 6161 | 21443 | 68.8 | 50.0 | 18 | 191 | #4 | 52993 |
| 6162 | 21444 | 50.0 | 50.0 (186) | 12 | 150 | #1 | 52994 |
| 6163 | 21445 | 65.6 | 57.5 | 15 | 205 | #4 | 52995 |
| 6164 | 21446 | 72.0 | 62.9 | 21 | 395 | #5 | 52996 |
| 6165 | 21447 | 50.0 | 50.0 | 12 | 150 | #1 | 52997 |
| 6166 | 21448 | 61.6 | 50.0 | 12 | 174 | #3 | 52998 |
| 6167 | 21449 | 62.4 | 53.9 (217) | 15 | 178 | #3 | 52999 |
| 6168 | 21450 | 68.0 | 60.7 | 18 | 234 | #4 | 53000 |
| 6169 | 21451 | 68.8 | 61.5 | 18 | 275 | #4 | 53001 |
| 6170 | 21452 | 64.8 | 58.2 | 15 | 201 | #3 | 53002 |
| 6171 | 21453 | 50.0 | 50.0 | 12 | 150 | #1 | 53003 |
| 6172 | 21454 | 71.2 | 62.9 | 23 | 335 | #5 | 53004 |
| 6173 | 21455 | 70.4 | 59.3 | 27 | 256 | #5 | 53005 |
| 6174 | 21456 | 68.8 | 62.2 | 25 | 339 | #4 | 53006 |
| 6175 | 21457 | 64.8 | 50.0 | 13 | 197 | #3 | 53007 |
| 6176 | 21458 | 50.0 (75) | — | 33 | 160 | #1 | 53008 |
| 6177 | 21459 | 64.0 | 50.0 | 15 | 175 | #3 | 53009 |
| 6178 | 21460 | 64.8 | 57.7 (222) | 16 | 179 | #3 | 53010 |
| 6179 | 21461 | 70.4 | 64.4 | 27 | 409 | #5 | 53011 |
| 6180 | 21462 | 57.6 | 50.0 (168) | 14 | 151 | #2 | 53012 |
| 6181 | 21463 | 50.0 | 50.0 | 12 | 150 | #1 | 53013 |
| 6182 | 21464 | 70.4 | 64.7 | 21 | 599 | #5 | 53014 |
| 6183 | 21465 | 50.0 | 50.0 | 12 | 150 | #1 | 53015 |
| 6184 | 21466 | 70.4 | 62.5 | 20 | 332 | #5 | 53016 |
| 6185 | 21467 | 60.0 | 50.0 | 12 | 159 | #2 | 53017 |
| 6186 | 21468 | 64.0 | 57.6 (198) | 18 | 165 | #3 | 53018 |
| 6187 | 21469 | 60.8 | 50.0 | 12 | 205 | #3 | 53019 |
| 6188 | 21470 | 52.8 | 50.0 (273) | 12 | 158 | #1 | 53020 |
| 6189 | 21471 | 65.6 | 58.5 | 17 | 250 | #4 | 53021 |
| 6190 | 21472 | 72.8 | 61.5 | 20 | 314 | #5 | 53022 |
| 6191 | 21473 | 89.4 (66) | — | 38 | 261 | #8 | 53023 |
| 6192 | 21474 | 65.6 | 57.5 | 22 | 220 | #4 | 53024 |
| 6193 | 21475 | 69.6 | 60.7 | 17 | 263 | #4 | 53025 |
| 6194 | 21476 | 50.0 | 50.0 | 12 | 150 | #1 | 53026 |
| 6195 | 21477 | 68.8 | 63.6 | 31 | 390 | #4 | 53027 |
| 6196 | 21478 | 68.8 | 61.4 (267) | 20 | 255 | #4 | 53028 |
| 6197 | 21479 | 65.6 | 50.0 | 15 | 199 | #4 | 53029 |
| 6198 | 21480 | 50.0 | 50.0 | 12 | 150 | #1 | 53030 |
| 6199 | 21481 | 68.8 | 61.5 | 19 | 328 | #4 | 53031 |
| 6200 | 21482 | 66.4 | 58.9 | 16 | 246 | #4 | 53032 |
| 6201 | 21483 | 66.4 | 60.4 | 16 | 238 | #4 | 53033 |
| 6202 | 21484 | 61.6 | 57.8 | 12 | 215 | #3 | 53034 |
| 6203 | 21485 | 66.4 | 61.2 (152) | 23 | 207 | #4 | 53035 |
| 6204 | 21486 | 50.0 (107) | — | 12 | 150 | #1 | 53036 |
| 6205 | 21487 | 50.0 | 50.0 (165) | 12 | 150 | #1 | 53037 |
| 6206 | 21488 | 75.2 | 62.5 | 36 | 371 | #6 | 53038 |
| 6207 | 21489 | 68.8 | 61.5 | 20 | 344 | #4 | 53039 |
| 6208 | 21490 | 65.6 | 58.9 | 17 | 235 | #4 | 53040 |
| 6209 | 21491 | 50.0 | 50.0 | 12 | 150 | #1 | 53041 |
| 6210 | 21492 | 66.4 | 59.3 | 19 | 246 | #4 | 53042 |
| 6211 | 21493 | 68.8 | 58.9 | 18 | 233 | #4 | 53043 |
| 6212 | 21494 | 68.8 | 59.3 | 19 | 266 | #4 | 53044 |
| 6213 | 21495 | 66.4 | 60.0 | 17 | 245 | #4 | 53045 |
| 6214 | 21496 | 68.8 | 58.2 | 25 | 250 | #4 | 53046 |
| 6215 | 21497 | 50.0 | 50.0 | 12 | 150 | #1 | 53047 |
| 6216 | 21498 | 69.6 | 62.5 | 24 | 315 | #4 | 53048 |
| 6217 | 21499 | 67.2 | 59.3 | 17 | 281 | #4 | 53049 |
| 6218 | 21500 | 64.8 | 63.4 (145) | 21 | 182 | #3 | 53050 |
| 6219 | 21501 | 66.4 | 61.1 | 13 | 323 | #4 | 53051 |
| 6220 | 21502 | 69.6 | 60.0 | 20 | 255 | #4 | 53052 |
| 6221 | 21503 | 69.6 | 60.7 | 21 | 268 | #4 | 53053 |
| 6222 | 21504 | 60.0 | 50.0 | 14 | 166 | #2 | 53054 |
| 6223 | 21505 | 67.2 | 57.8 | 19 | 218 | #4 | 53055 |
| 6224 | 21506 | 64.8 | 57.1 | 21 | 206 | #3 | 53056 |
| 6225 | 21507 | 50.0 | 50.0 | 12 | 150 | #1 | 53057 |
| 6226 | 21508 | 67.2 | 58.9 | 18 | 249 | #4 | 53058 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6227 | 21509 | 66.4 | 59.3 | 18 | 271 | #4 | 53059 |
| 6228 | 21510 | 69.6 | 62.9 (272) | 21 | 300 | #4 | 53060 |
| 6229 | 21511 | 70.4 | 60.7 | 22 | 309 | #5 | 53061 |
| 6230 | 21512 | 62.4 | 50.0 | 15 | 214 | #3 | 53062 |
| 6231 | 21513 | 62.4 | 58.2 | 14 | 192 | #3 | 53063 |
| 6232 | 21514 | 64.8 | 50.0 | 13 | 196 | #3 | 53064 |
| 6233 | 21515 | 61.6 | 54.3 (234) | 16 | 155 | #3 | 53065 |
| 6234 | 21516 | 70.4 | 60.0 | 20 | 283 | #5 | 53066 |
| 6235 | 21517 | 68.8 | 62.5 | 22 | 573 | #4 | 53067 |
| 6236 | 21518 | 67.2 | 59.6 | 20 | 268 | #4 | 53068 |
| 6237 | 21519 | 65.6 | 50.0 | 14 | 178 | #4 | 53069 |
| 6238 | 21520 | 50.0 | 50.0 | 12 | 150 | #1 | 53070 |
| 6239 | 21521 | 66.4 | 58.9 | 18 | 228 | #4 | 53071 |
| 6240 | 21522 | 78.4 | 65.2 (270) | 21 | 465 | #6 | 53072 |
| 6241 | 21523 | 66.4 | 50.0 | 13 | 202 | #4 | 53073 |
| 6242 | 21524 | 70.4 | 61.8 | 30 | 330 | #5 | 53074 |
| 6243 | 21525 | 73.6 | 62.2 | 25 | 377 | #5 | 53075 |
| 6244 | 21526 | 67.2 | 61.1 | 24 | 340 | #4 | 53076 |
| 6245 | 21527 | 65.6 | 60.4 | 15 | 261 | #4 | 53077 |
| 6246 | 21528 | 64.8 | 50.9 | 17 | 208 | #3 | 53078 |
| 6247 | 21529 | 65.6 | 50.0 | 14 | 182 | #4 | 53079 |
| 6248 | 21530 | 50.0 | 50.0 | 12 | 150 | #1 | 53080 |
| 6249 | 21531 | 69.6 | 61.5 | 18 | 309 | #4 | 53081 |
| 6250 | 21532 | 50.0 (114) | — | 12 | 150 | #1 | 53082 |
| 6251 | 21533 | 68.0 | 62.5 | 20 | 332 | #4 | 53083 |
| 6252 | 21534 | 63.2 | 54.5 | 20 | 182 | #3 | 53084 |
| 6253 | 21535 | 68.0 | 59.3 | 17 | 221 | #4 | 53085 |
| 6254 | 21536 | 50.0 | 50.0 | 12 | 150 | #1 | 53086 |
| 6255 | 21537 | 50.0 (79) | — | 12 | 150 | #1 | 53087 |
| 6256 | 21538 | 50.0 (107) | — | 12 | 150 | #1 | 53088 |
| 6257 | 21539 | 64.8 | 59.6 | 14 | 216 | #3 | 53089 |
| 6258 | 21540 | 61.6 | 58.5 | 14 | 202 | #3 | 53090 |
| 6259 | 21541 | 70.4 | 63.3 | 23 | 333 | #5 | 53091 |
| 6260 | 21542 | 68.0 | 58.9 | 22 | 236 | #4 | 53092 |
| 6261 | 21543 | 64.0 | 58.9 | 14 | 207 | #3 | 53093 |
| 6262 | 21544 | 68.0 | 61.5 | 20 | 293 | #4 | 53094 |
| 6263 | 21545 | 64.8 | 60.0 | 15 | 256 | #3 | 53095 |
| 6264 | 21546 | 50.0 | 50.0 | 12 | 153 | #1 | 53096 |
| 6265 | 21547 | 75.2 | 61.8 | 19 | 464 | #6 | 53097 |
| 6266 | 21548 | 68.8 | 50.0 | 19 | 208 | #4 | 53098 |
| 6267 | 21549 | 70.4 | 60.0 | 23 | 245 | #5 | 53099 |
| 6268 | 21550 | 68.0 | 57.8 | 17 | 262 | #4 | 53100 |
| 6269 | 21551 | 69.6 | 62.5 | 22 | 349 | #4 | 53101 |
| 6270 | 21552 | 52.8 | 50.0 | 16 | 162 | #1 | 53102 |
| 6271 | 21553 | 50.0 | 50.0 | 12 | 150 | #1 | 53103 |
| 6272 | 21554 | 50.0 | 50.0 | 12 | 150 | #1 | 53104 |
| 6273 | 21555 | 67.2 | 58.5 | 17 | 279 | #4 | 53105 |
| 6274 | 21556 | 50.0 | 50.0 | 12 | 150 | #1 | 53106 |
| 6275 | 21557 | 71.2 | 63.3 | 31 | 353 | #5 | 53107 |
| 6276 | 21558 | 72.8 | 60.7 | 29 | 309 | #5 | 53108 |
| 6277 | 21559 | 68.8 | 61.8 | 20 | 407 | #4 | 53109 |
| 6278 | 21560 | 68.0 | 60.0 | 21 | 259 | #4 | 53110 |
| 6279 | 21561 | 65.6 | 58.2 | 16 | 228 | #4 | 53111 |
| 6280 | 21562 | 50.0 | 50.0 | 12 | 150 | #1 | 53112 |
| 6281 | 21563 | 50.0 | 50.0 | 12 | 150 | #1 | 53113 |
| 6282 | 21564 | 84.6 (78) | — | 32 | 310 | #7 | 53114 |
| 6283 | 21565 | 71.2 | 59.3 | 22 | 261 | #5 | 53115 |
| 6284 | 21566 | 50.0 | 50.0 | 12 | 150 | #1 | 53116 |
| 6285 | 21567 | 66.4 | 56.7 | 24 | 220 | #4 | 53117 |
| 6286 | 21568 | 64.0 | 50.0 | 17 | 184 | #3 | 53118 |
| 6287 | 21569 | 50.0 | 50.0 | 12 | 150 | #1 | 53119 |
| 6288 | 21570 | 69.6 | 59.6 | 24 | 276 | #4 | 53120 |
| 6289 | 21571 | 68.8 | 62.9 | 20 | 329 | #4 | 53121 |
| 6290 | 21572 | 67.2 | 58.5 | 18 | 194 | #4 | 53122 |
| 6291 | 21573 | 65.6 | 51.3 | 18 | 214 | #4 | 53123 |
| 6292 | 21574 | 59.2 | 50.0 | 12 | 166 | #2 | 53124 |
| 6293 | 21575 | 68.0 | 61.1 | 19 | 350 | #4 | 53125 |
| 6294 | 21576 | 64.8 | 50.0 | 18 | 171 | #3 | 53126 |
| 6295 | 21577 | 50.0 | 50.0 | 12 | 150 | #1 | 53127 |
| 6296 | 21578 | 68.8 | 62.2 | 22 | 297 | #4 | 53128 |
| 6297 | 21579 | 50.0 | 50.0 (247) | 12 | 150 | #1 | 53129 |
| 6298 | 21580 | 67.2 | 50.0 | 14 | 203 | #4 | 53130 |
| 6299 | 21581 | 65.6 | 59.9 (274) | 20 | 221 | #4 | 53131 |
| 6300 | 21582 | 67.2 | 58.8 (204) | 28 | 208 | #4 | 53132 |
| 6301 | 21583 | 69.6 | 61.1 | 21 | 258 | #4 | 53133 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6302 | 21584 | 70.4 | 61.5 | 19 | 304 | #5 | 53134 |
| 6303 | 21585 | 77.6 | 50.0 | 25 | 333 | #6 | 53135 |
| 6304 | 21586 | 50.0 | 50.0 | 12 | 176 | #1 | 53136 |
| 6305 | 21587 | 69.6 | 62.2 | 29 | 357 | #4 | 53137 |
| 6306 | 21588 | 50.0 | 50.0 | 12 | 150 | #1 | 53138 |
| 6307 | 21589 | 66.4 | 51.6 | 17 | 199 | #4 | 53139 |
| 6308 | 21590 | 66.4 | 56.4 | 18 | 214 | #4 | 53140 |
| 6309 | 21591 | 67.2 | 60.7 | 17 | 264 | #4 | 53141 |
| 6310 | 21592 | 50.0 | 50.0 | 12 | 150 | #1 | 53142 |
| 6311 | 21593 | 50.0 | 50.0 | 12 | 150 | #1 | 53143 |
| 6312 | 21594 | 60.0 | 50.0 | 12 | 163 | #2 | 53144 |
| 6313 | 21595 | 66.4 | 61.8 (170) | 38 | 196 | #4 | 53145 |
| 6314 | 21596 | 68.0 | 62.9 | 19 | 319 | #4 | 53146 |
| 6315 | 21597 | 64.8 | 60.4 | 18 | 295 | #3 | 53147 |
| 6316 | 21598 | 62.4 | 50.0 | 26 | 160 | #3 | 53148 |
| 6317 | 21599 | 68.8 | 62.5 | 20 | 343 | #4 | 53149 |
| 6318 | 21600 | 80.0 | 77.0 (183) | 16 | 515 | #6 | 53150 |
| 6319 | 21601 | 68.0 | 60.7 (206) | 22 | 208 | #4 | 53151 |
| 6320 | 21602 | 67.2 | 61.8 | 18 | 270 | #4 | 53152 |
| 6321 | 21603 | 50.0 (94) | — | 12 | 150 | #1 | 53153 |
| 6322 | 21604 | 67.2 | 60.4 | 20 | 221 | #4 | 53154 |
| 6323 | 21605 | 68.8 | 61.5 | 20 | 272 | #4 | 53155 |
| 6324 | 21606 | 68.0 | 60.7 | 17 | 353 | #4 | 53156 |
| 6325 | 21607 | 65.6 | 57.1 | 17 | 194 | #4 | 53157 |
| 6326 | 21608 | 68.8 | 57.8 | 24 | 225 | #4 | 53158 |
| 6327 | 21609 | 50.0 | 50.0 | 12 | 150 | #1 | 53159 |
| 6328 | 21610 | 75.2 | 70.2 | 26 | 897 | #6 | 53160 |
| 6329 | 21611 | 64.8 | 52.0 | 13 | 202 | #3 | 53161 |
| 6330 | 21612 | 70.4 | 60.4 | 22 | 300 | #5 | 53162 |
| 6331 | 21613 | 70.4 | 61.5 | 19 | 288 | #5 | 53163 |
| 6332 | 21614 | 50.0 | 50.0 | 12 | 150 | #1 | 53164 |
| 6333 | 21615 | 70.4 | 60.2 (254) | 22 | 257 | #5 | 53165 |
| 6334 | 21616 | 50.0 (72) | — | 12 | 150 | #1 | — |
| 6335 | 21617 | 68.0 | 61.8 | 18 | 280 | #4 | 53166 |
| 6336 | 21618 | 72.0 | 67.1 (155) | 28 | 271 | #5 | 53167 |
| 6337 | 21619 | 69.6 | 56.4 | 18 | 228 | #4 | 53168 |
| 6338 | 21620 | 63.2 | 60.0 | 17 | 275 | #3 | 53169 |
| 6339 | 21621 | 68.8 | 61.1 | 20 | 232 | #4 | 53170 |
| 6340 | 21622 | 60.8 | 50.0 | 12 | 150 | #3 | 53171 |
| 6341 | 21623 | 68.0 | 52.6 (232) | 25 | 215 | #4 | 53172 |
| 6342 | 21624 | 67.0 (112) | — | 31 | 195 | #4 | 53173 |
| 6343 | 21625 | 64.0 | 51.3 (234) | 23 | 176 | #3 | 53174 |
| 6344 | 21626 | 70.4 | 61.8 | 25 | 349 | #5 | 53175 |
| 6345 | 21627 | 50.0 | 50.0 | 12 | 150 | #1 | 53176 |
| 6346 | 21628 | 50.0 | 50.0 | 12 | 150 | #1 | 53177 |
| 6347 | 21629 | 68.0 | 61.1 | 18 | 284 | #4 | 53178 |
| 6348 | 21630 | 64.8 | 53.8 (264) | 16 | 164 | #3 | 53179 |
| 6349 | 21631 | 62.4 | 50.0 (257) | 14 | 177 | #3 | 53180 |
| 6350 | 21632 | 64.0 | 57.8 | 16 | 213 | #3 | 53181 |
| 6351 | 21633 | 60.8 | 50.0 (178) | 17 | 168 | #3 | 53182 |
| 6352 | 21634 | 50.0 | 50.0 | 12 | 150 | #1 | 53183 |
| 6353 | 21635 | 50.0 | 50.0 | 12 | 150 | #1 | 53184 |
| 6354 | 21636 | 76.0 | 63.6 | 36 | 427 | #6 | 53185 |
| 6355 | 21637 | 67.2 | 60.4 | 19 | 223 | #4 | 53186 |
| 6356 | 21638 | 68.0 | 61.8 | 22 | 349 | #4 | 53187 |
| 6357 | 21639 | 69.6 | 62.2 | 19 | 343 | #4 | 53188 |
| 6358 | 21640 | 50.0 | 50.0 | 37 | 180 | #1 | 53189 |
| 6359 | 21641 | 70.4 | 64.0 | 21 | 519 | #5 | 53190 |
| 6360 | 21642 | 50.0 | 50.0 | 12 | 150 | #1 | 53191 |
| 6361 | 21643 | 57.6 | 56.7 (127) | 14 | 174 | #2 | — |
| 6362 | 21644 | 50.0 | 50.0 | 15 | 152 | #1 | 53192 |
| 6363 | 21645 | 64.0 | 51.9 (233) | 16 | 190 | #3 | 53193 |
| 6364 | 21646 | 50.0 | 50.0 | 12 | 150 | #1 | 53194 |
| 6365 | 21647 | 69.6 | 62.9 | 22 | 348 | #4 | 53195 |
| 6366 | 21648 | 72.0 | 65.1 | 24 | 521 | #5 | 53196 |
| 6367 | 21649 | 72.0 | 61.5 | 23 | 305 | #5 | 53197 |
| 6368 | 21650 | 72.0 | 62.2 | 37 | 301 | #5 | 53198 |
| 6369 | 21651 | 50.0 | 50.0 (182) | 14 | 150 | #1 | 53199 |
| 6370 | 21652 | 71.2 | 60.7 | 23 | 264 | #5 | 53200 |
| 6371 | 21653 | 68.8 | 57.8 | 20 | 235 | #4 | 53201 |
| 6372 | 21654 | 50.0 | 50.0 | 12 | 150 | #1 | 53202 |
| 6373 | 21655 | 61.6 | 60.0 | 12 | 199 | #3 | 53203 |
| 6374 | 21656 | 60.8 | 55.4 (195) | 17 | 155 | #3 | 53204 |
| 6375 | 21657 | 61.6 | 57.8 | 13 | 215 | #3 | 53205 |
| 6376 | 21658 | 69.6 | 62.5 | 36 | 321 | #4 | 53206 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6377 | 21659 | 68.8 | 62.2 | 20 | 333 | #4 | 53207 |
| 6378 | 21660 | 70.4 | 62.5 | 27 | 292 | #5 | 53208 |
| 6379 | 21661 | 63.2 | 50.0 (261) | 16 | 160 | #3 | 53209 |
| 6380 | 21662 | 68.0 | 60.0 | 18 | 284 | #4 | 53210 |
| 6381 | 21663 | 50.0 | 50.0 (204) | 12 | 150 | #1 | 53211 |
| 6382 | 21664 | 62.4 | 50.0 | 12 | 165 | #3 | 53212 |
| 6383 | 21665 | 50.0 | 50.0 | 12 | 150 | #1 | 53213 |
| 6384 | 21666 | 50.0 | 50.0 | 12 | 150 | #1 | 53214 |
| 6385 | 21667 | 50.0 | 50.0 | 12 | 150 | #1 | 53215 |
| 6386 | 21668 | 61.6 | 50.0 | 12 | 187 | #3 | 53216 |
| 6387 | 21669 | 71.2 | 62.5 | 22 | 322 | #5 | 53217 |
| 6388 | 21670 | 50.0 | 50.0 | 12 | 150 | #1 | 53218 |
| 6389 | 21671 | 68.0 | 58.9 | 18 | 243 | #4 | 53219 |
| 6390 | 21672 | 67.2 | 58.5 | 15 | 334 | #4 | 53220 |
| 6391 | 21673 | 72.0 | 66.2 | 19 | 376 | #5 | 53221 |
| 6392 | 21674 | 61.6 | 50.0 | 17 | 323 | #3 | 53222 |
| 6393 | 21675 | 59.2 | 56.4 | 12 | 177 | #2 | 53223 |
| 6394 | 21676 | 64.8 | 59.3 | 21 | 238 | #3 | 53224 |
| 6395 | 21677 | 67.2 | 60.4 | 15 | 283 | #4 | 53225 |
| 6396 | 21678 | 64.8 | 58.5 | 13 | 212 | #3 | 53226 |
| 6397 | 21679 | 50.0 | 50.0 | 12 | 150 | #1 | 53227 |
| 6398 | 21680 | 60.0 | 50.0 | 13 | 155 | #2 | 53228 |
| 6399 | 21681 | 69.6 | 62.5 | 21 | 579 | #4 | 53229 |
| 6400 | 21682 | 68.0 | 62.2 | 18 | 260 | #4 | 53230 |
| 6401 | 21683 | 70.4 | 61.1 | 20 | 316 | #5 | 53231 |
| 6402 | 21684 | 50.0 | 50.0 | 12 | 150 | #1 | 53232 |
| 6403 | 21685 | 50.0 | 50.0 | 12 | 150 | #1 | 53233 |
| 6404 | 21686 | 70.4 | 61.5 | 20 | 284 | #5 | 53234 |
| 6405 | 21687 | 50.0 | 50.0 | 12 | 150 | #1 | 53235 |
| 6406 | 21688 | 50.0 | 50.0 | 12 | 150 | #1 | 53236 |
| 6407 | 21689 | 61.6 | 58.2 | 14 | 194 | #3 | 53237 |
| 6408 | 21690 | 67.2 | 61.5 | 22 | 301 | #4 | 53238 |
| 6409 | 21691 | 70.4 | 61.5 | 23 | 418 | #5 | 53239 |
| 6410 | 21692 | 68.8 | 60.4 | 19 | 249 | #4 | 53240 |
| 6411 | 21693 | 67.2 | 58.9 | 17 | 232 | #4 | 53241 |
| 6412 | 21694 | 69.6 | 62.2 | 21 | 280 | #4 | 53242 |
| 6413 | 21695 | 66.4 | 57.6 (257) | 15 | 173 | #4 | 53243 |
| 6414 | 21696 | 63.2 | 51.6 | 17 | 198 | #3 | 53244 |
| 6415 | 21697 | 67.2 | 60.0 | 26 | 304 | #4 | 53245 |
| 6416 | 21698 | 68.8 | 57.8 | 36 | 240 | #4 | 53246 |
| 6417 | 21699 | 65.6 | 58.5 | 15 | 218 | #4 | 53247 |
| 6418 | 21700 | 66.4 | 61.8 | 19 | 270 | #4 | 53248 |
| 6419 | 21701 | 69.6 | 61.8 | 29 | 342 | #4 | 53249 |
| 6420 | 21702 | 62.4 | 59.9 (187) | 29 | 313 | #3 | 53250 |
| 6421 | 21703 | 68.8 | 62.2 | 20 | 268 | #4 | 53251 |
| 6422 | 21704 | 70.4 | 60.4 | 24 | 237 | #5 | 53252 |
| 6423 | 21705 | 77.6 | 65.8 | 32 | 635 | #6 | 53253 |
| 6424 | 21706 | 61.6 | 57.8 | 16 | 183 | #3 | 53254 |
| 6425 | 21707 | 65.6 | 57.8 | 14 | 199 | #4 | 53255 |
| 6426 | 21708 | 69.6 | 61.8 | 18 | 301 | #4 | 53256 |
| 6427 | 21709 | 69.6 | 60.7 | 20 | 274 | #4 | 53257 |
| 6428 | 21710 | 64.8 | 60.0 (160) | 16 | 165 | #3 | 53258 |
| 6429 | 21711 | 65.6 | 50.0 | 14 | 216 | #4 | 53259 |
| 6430 | 21712 | 70.4 | 60.0 | 21 | 319 | #5 | 53260 |
| 6431 | 21713 | 67.2 | 60.1 (223) | 26 | 224 | #4 | 53261 |
| 6432 | 21714 | 64.8 | 57.1 | 21 | 207 | #3 | 53262 |
| 6433 | 21715 | 50.0 | 50.0 | 12 | 150 | #1 | 53263 |
| 6434 | 21716 | 50.0 (67) | — | 12 | 150 | #1 | 53264 |
| 6435 | 21717 | 67.2 | 60.4 | 21 | 269 | #4 | 53265 |
| 6436 | 21718 | 70.4 | 62.5 | 27 | 354 | #5 | 53266 |
| 6437 | 21719 | 64.8 | 50.0 (273) | 16 | 200 | #3 | 53267 |
| 6438 | 21720 | 68.8 | 62.2 | 21 | 451 | #4 | 53268 |
| 6439 | 21721 | 72.0 | 63.6 | 32 | 473 | #5 | 53269 |
| 6440 | 21722 | 68.0 | 58.2 | 17 | 253 | #4 | 53270 |
| 6441 | 21723 | 61.6 | 50.0 | 16 | 162 | #3 | 53271 |
| 6442 | 21724 | 98.4 | 97.1 | 89 | 1342 | #10 | 53272 |
| 6443 | 21725 | 59.2 | 54.0 (137) | 16 | 160 | #2 | 53273 |
| 6444 | 21726 | 61.6 | 52.9 (174) | 19 | 271 | #3 | 53274 |
| 6445 | 21727 | 68.0 | 58.2 | 14 | 229 | #4 | 53275 |
| 6446 | 21728 | 67.2 | 61.1 | 19 | 253 | #4 | 53276 |
| 6447 | 21729 | 67.2 | 61.8 | 20 | 257 | #4 | 53277 |
| 6448 | 21730 | 66.4 | 50.0 | 26 | 243 | #4 | 53278 |
| 6449 | 21731 | 66.4 | 58.5 | 16 | 291 | #4 | 53279 |
| 6450 | 21732 | 64.0 | 50.0 (236) | 16 | 175 | #3 | 53280 |
| 6451 | 21733 | 67.2 | 61.5 | 17 | 287 | #4 | 53281 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6452 | 21734 | 63.2 | 50.0 | 13 | 153 | #3 | 53282 |
| 6453 | 21735 | 71.2 | 64.7 | 26 | 541 | #5 | 53283 |
| 6454 | 21736 | 58.4 | 50.0 | 12 | 151 | #2 | 53284 |
| 6455 | 21737 | 66.4 | 56.7 | 18 | 199 | #4 | 53285 |
| 6456 | 21738 | 67.2 | 57.8 | 16 | 216 | #4 | 53286 |
| 6457 | 21739 | 66.4 | 57.8 | 17 | 208 | #4 | 53287 |
| 6458 | 21740 | 68.0 | 50.0 | 15 | 210 | #4 | 53288 |
| 6459 | 21741 | 75.2 | 64.4 | 21 | 361 | #6 | 53289 |
| 6460 | 21742 | 50.0 | 50.0 | 12 | 150 | #1 | 53290 |
| 6461 | 21743 | 68.0 | 56.7 | 20 | 218 | #4 | 53291 |
| 6462 | 21744 | 63.2 | 53.1 | 17 | 211 | #3 | 53292 |
| 6463 | 21745 | 67.2 | 60.8 (250) | 27 | 213 | #4 | 53293 |
| 6464 | 21746 | 66.4 | 60.9 (220) | 18 | 201 | #4 | 53294 |
| 6465 | 21747 | 69.6 | 63.6 | 19 | 314 | #4 | 53295 |
| 6466 | 21748 | 50.0 | 50.0 (168) | 13 | 150 | #1 | 53296 |
| 6467 | 21749 | 65.6 | 58.5 (236) | 14 | 164 | #4 | 53297 |
| 6468 | 21750 | 66.4 | 60.0 | 16 | 255 | #4 | 53298 |
| 6469 | 21751 | 64.8 | 50.0 | 15 | 190 | #3 | 53299 |
| 6470 | 21752 | 95.7 (69) | — | 23 | 318 | #10 | 53300 |
| 6471 | 21753 | 62.4 | 52.8 (250) | 16 | 163 | #3 | 53301 |
| 6472 | 21754 | 66.4 | 60.9 (253) | 22 | 184 | #4 | 53302 |
| 6473 | 21755 | 68.0 | 59.6 | 22 | 249 | #4 | 53303 |
| 6474 | 21756 | 62.4 | 54.9 | 14 | 193 | #3 | 53304 |
| 6475 | 21757 | 70.4 | 60.7 | 29 | 351 | #5 | 53305 |
| 6476 | 21758 | 72.8 | 63.3 | 26 | 339 | #5 | 53306 |
| 6477 | 21759 | 71.2 | 63.6 | 21 | 438 | #5 | 53307 |
| 6478 | 21760 | 63.2 | 50.0 | 15 | 169 | #3 | 53308 |
| 6479 | 21761 | 50.0 | 50.0 | 12 | 150 | #1 | 53309 |
| 6480 | 21762 | 68.8 | 61.8 | 27 | 293 | #4 | 53310 |
| 6481 | 21763 | 64.8 | 50.5 | 20 | 205 | #3 | 53311 |
| 6482 | 21764 | 59.2 | 50.0 (169) | 16 | 150 | #2 | 53312 |
| 6483 | 21765 | 68.8 | 60.4 | 16 | 278 | #4 | 53313 |
| 6484 | 21766 | 85.6 | 65.8 | 28 | 510 | #8 | 53314 |
| 6485 | 21767 | 50.0 (82) | — | 12 | 150 | #1 | — |
| 6486 | 21768 | 61.6 | 50.0 | 14 | 189 | #3 | 53315 |
| 6487 | 21769 | 50.0 | 50.0 | 12 | 150 | #1 | 53316 |
| 6488 | 21770 | 64.8 | 61.1 | 13 | 210 | #3 | 53317 |
| 6489 | 21771 | 70.4 | 59.6 | 25 | 260 | #5 | 53318 |
| 6490 | 21772 | 68.0 | 59.6 | 17 | 240 | #4 | 53319 |
| 6491 | 21773 | 68.8 | 60.0 | 24 | 238 | #4 | 53320 |
| 6492 | 21774 | 65.6 | 60.0 | 16 | 224 | #4 | 53321 |
| 6493 | 21775 | 50.0 | 50.0 | 17 | 161 | #1 | 53322 |
| 6494 | 21776 | 64.0 | 51.3 | 15 | 190 | #3 | 53323 |
| 6495 | 21777 | 71.2 | 61.8 | 31 | 356 | #5 | 53324 |
| 6496 | 21778 | 61.6 | 50.0 | 17 | 202 | #3 | 53325 |
| 6497 | 21779 | 62.4 | 56.4 | 13 | 185 | #3 | 53326 |
| 6498 | 21780 | 62.4 | 50.0 | 14 | 155 | #3 | 53327 |
| 6499 | 21781 | 71.2 | 62.3 (204) | 20 | 242 | #5 | 53328 |
| 6500 | 21782 | 72.8 | 63.6 | 24 | 498 | #5 | 53329 |
| 6501 | 21783 | 67.2 | 58.9 | 18 | 249 | #4 | 53330 |
| 6502 | 21784 | 50.0 (121) | — | 12 | 150 | #1 | 53331 |
| 6503 | 21785 | 64.8 | 60.0 | 16 | 225 | #3 | 53332 |
| 6504 | 21786 | 68.0 | 62.4 (210) | 18 | 200 | #4 | 53333 |
| 6505 | 21787 | 74.4 | 62.3 (257) | 25 | 338 | #5 | 53334 |
| 6506 | 21788 | 50.0 | 50.0 | 12 | 150 | #1 | 53335 |
| 6507 | 21789 | 70.4 | 65.5 | 31 | 509 | #5 | 53336 |
| 6508 | 21790 | 50.0 | 50.0 | 12 | 150 | #1 | 53337 |
| 6509 | 21791 | 72.0 | 62.9 | 23 | 353 | #5 | 53338 |
| 6510 | 21792 | 57.6 | 50.0 | 13 | 150 | #2 | 53339 |
| 6511 | 21793 | 63.2 | 50.9 | 14 | 192 | #3 | 53340 |
| 6512 | 21794 | 68.8 | 58.9 | 20 | 213 | #4 | 53341 |
| 6513 | 21795 | 66.4 | 57.8 | 21 | 193 | #4 | 53342 |
| 6514 | 21796 | 64.8 | 52.5 (244) | 17 | 214 | #3 | 53343 |
| 6515 | 21797 | 50.0 | 50.0 | 12 | 150 | #1 | 53344 |
| 6516 | 21798 | 71.2 | 60.4 | 23 | 331 | #5 | 53345 |
| 6517 | 21799 | 50.0 | 50.0 (244) | 16 | 155 | #1 | 53346 |
| 6518 | 21800 | 63.2 | 58.2 (273) | 15 | 175 | #3 | 53347 |
| 6519 | 21801 | 72.0 | 64.4 | 28 | 450 | #5 | 53348 |
| 6520 | 21802 | 77.6 | 63.3 | 28 | 327 | #6 | 53349 |
| 6521 | 21803 | 68.8 | 62.2 | 22 | 331 | #4 | 53350 |
| 6522 | 21804 | 64.8 | 50.0 | 12 | 210 | #3 | 53351 |
| 6523 | 21805 | 50.0 | 50.0 | 12 | 150 | #1 | 53352 |
| 6524 | 21806 | 71.2 | 60.7 | 20 | 312 | #5 | 53353 |
| 6525 | 21807 | 61.6 | 51.2 (201) | 15 | 150 | #3 | 53354 |
| 6526 | 21808 | 60.0 | 50.0 (251) | 18 | 173 | #2 | 53355 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6527 | 21809 | 58.3 (120) | — | 13 | 152 | #2 | 53356 |
| 6528 | 21810 | 67.2 | 59.6 | 19 | 272 | #4 | 53357 |
| 6529 | 21811 | 72.0 | 60.7 | 21 | 288 | #5 | 53358 |
| 6530 | 21812 | 69.6 | 62.2 | 22 | 338 | #4 | 53359 |
| 6531 | 21813 | 66.4 | 60.0 | 18 | 286 | #4 | 53360 |
| 6532 | 21814 | 65.6 | 60.9 (202) | 17 | 197 | #4 | 53361 |
| 6533 | 21815 | 68.8 | 60.7 | 20 | 288 | #4 | 53362 |
| 6534 | 21816 | 50.0 | 50.0 | 12 | 150 | #1 | 53363 |
| 6535 | 21817 | 50.0 | 50.0 | 12 | 150 | #1 | 53364 |
| 6536 | 21818 | 50.0 | 50.0 | 12 | 150 | #1 | 53365 |
| 6537 | 21819 | 68.0 | 58.9 | 25 | 255 | #4 | 53366 |
| 6538 | 21820 | 65.6 | 50.0 | 15 | 193 | #4 | 53367 |
| 6539 | 21821 | 62.6 (91) | — | 22 | 265 | #3 | 53368 |
| 6540 | 21822 | 70.4 | 61.8 | 17 | 265 | #5 | 53369 |
| 6541 | 21823 | 70.4 | 64.7 | 19 | 407 | #5 | 53370 |
| 6542 | 21824 | 75.2 | 50.0 | 15 | 341 | #6 | 53371 |
| 6543 | 21825 | 50.0 | 50.0 | 12 | 150 | #1 | 53372 |
| 6544 | 21826 | 64.0 | 58.1 (241) | 19 | 189 | #3 | 53373 |
| 6545 | 21827 | 63.2 | 55.3 | 15 | 190 | #3 | 53374 |
| 6546 | 21828 | 65.6 | 59.6 | 18 | 368 | #4 | 53375 |
| 6547 | 21829 | 69.6 | 63.6 (184) | 19 | 229 | #4 | 53376 |
| 6548 | 21830 | 62.4 | 50.0 | 14 | 193 | #3 | 53377 |
| 6549 | 21831 | 62.4 | 59.6 | 12 | 350 | #3 | 53378 |
| 6550 | 21832 | 64.0 | 51.7 (240) | 17 | 179 | #3 | 53379 |
| 6551 | 21833 | 66.4 | 50.0 | 17 | 209 | #4 | 53380 |
| 6552 | 21834 | 50.0 | 50.0 | 12 | 150 | #1 | 53381 |
| 6553 | 21835 | 68.8 | 60.5 (253) | 19 | 230 | #4 | 53382 |
| 6554 | 21836 | 75.2 | 65.8 | 26 | 518 | #6 | 53383 |
| 6555 | 21837 | 64.0 | 50.0 | 12 | 171 | #3 | 53384 |
| 6556 | 21838 | 66.4 | 58.0 (193) | 16 | 168 | #4 | 53385 |
| 6557 | 21839 | 65.6 | 58.9 | 15 | 230 | #4 | 53386 |
| 6558 | 21840 | 71.2 | 63.3 | 23 | 297 | #5 | 53387 |
| 6559 | 21841 | 67.2 | 61.5 | 21 | 371 | #4 | 53388 |
| 6560 | 21842 | 70.4 | 64.7 | 22 | 363 | #5 | 53389 |
| 6561 | 21843 | 67.2 | 60.4 | 22 | 241 | #4 | 53390 |
| 6562 | 21844 | 63.2 | 50.0 | 12 | 171 | #3 | 53391 |
| 6563 | 21845 | 65.6 | 58.5 | 15 | 254 | #4 | 53392 |
| 6564 | 21846 | 67.2 | 59.6 | 20 | 223 | #4 | 53393 |
| 6565 | 21847 | 61.6 | 50.0 | 13 | 161 | #3 | 53394 |
| 6566 | 21848 | 62.4 | 57.5 | 14 | 204 | #3 | 53395 |
| 6567 | 21849 | 65.6 | 50.0 | 14 | 233 | #4 | 53396 |
| 6568 | 21850 | 60.0 | 58.2 | 12 | 190 | #2 | 53397 |
| 6569 | 21851 | 72.0 | 60.0 | 25 | 272 | #5 | 53398 |
| 6570 | 21852 | 67.2 | 58.9 | 18 | 248 | #4 | 53399 |
| 6571 | 21853 | 66.4 | 59.3 | 29 | 228 | #4 | 53400 |
| 6572 | 21854 | 64.8 | 55.3 (255) | 20 | 186 | #3 | 53401 |
| 6573 | 21855 | 64.8 | 59.3 | 23 | 248 | #3 | 53402 |
| 6574 | 21856 | 66.4 | 57.8 | 15 | 238 | #4 | 53403 |
| 6575 | 21857 | 63.2 | 50.0 (208) | 17 | 156 | #3 | 53404 |
| 6576 | 21858 | 72.0 | 61.1 | 20 | 368 | #5 | 53405 |
| 6577 | 21859 | 71.2 | 61.5 | 19 | 259 | #5 | 53406 |
| 6578 | 21860 | 50.0 | 50.0 | 12 | 150 | #1 | 53407 |
| 6579 | 21861 | 66.4 | 59.3 | 17 | 228 | #4 | 53408 |
| 6580 | 21862 | 59.2 | 50.0 | 12 | 194 | #2 | 53409 |
| 6581 | 21863 | 67.2 | 53.1 | 23 | 243 | #4 | 53410 |
| 6582 | 21864 | 63.2 | 50.0 | 12 | 183 | #3 | 53411 |
| 6583 | 21865 | 50.0 | 50.0 | 12 | 150 | #1 | 53412 |
| 6584 | 21866 | 50.0 (82) | — | 12 | 150 | #1 | 53413 |
| 6585 | 21867 | 69.6 | 61.4 (267) | 18 | 256 | #4 | 53414 |
| 6586 | 21868 | 68.0 | 60.0 | 19 | 268 | #4 | 53415 |
| 6587 | 21869 | 68.8 | 61.8 | 22 | 335 | #4 | 53416 |
| 6588 | 21870 | 61.6 | 57.5 | 16 | 206 | #3 | 53417 |
| 6589 | 21871 | 60.0 | 50.0 | 14 | 176 | #2 | 53418 |
| 6590 | 21872 | 50.0 | 50.0 | 12 | 150 | #1 | 53419 |
| 6591 | 21873 | 98.4 | 93.6 (187) | 93 | 859 | #10 | 53420 |
| 6592 | 21874 | 50.0 (67) | — | 12 | 150 | #1 | 53421 |
| 6593 | 21875 | 64.0 | 50.0 | 12 | 189 | #3 | 53422 |
| 6594 | 21876 | 50.0 | 50.0 | 12 | 150 | #1 | 53423 |
| 6595 | 21877 | 66.4 | 50.0 | 12 | 229 | #4 | 53424 |
| 6596 | 21878 | 65.6 | 58.9 | 15 | 240 | #4 | 53425 |
| 6597 | 21879 | 66.4 | 57.8 | 18 | 216 | #4 | 53426 |
| 6598 | 21880 | 67.2 | 56.0 | 16 | 215 | #4 | 53427 |
| 6599 | 21881 | 72.0 | 62.5 | 22 | 435 | #5 | 53428 |
| 6600 | 21882 | 67.2 | 58.9 | 24 | 244 | #4 | 53429 |
| 6601 | 21883 | 67.2 | 58.5 | 13 | 192 | #4 | 53430 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
| --- | --- | --- | --- | --- | --- | --- | --- |
| 6602 | 21884 | 50.0 | 50.0 | 12 | 150 | #1 | 53431 |
| 6603 | 21885 | 64.8 | 58.9 | 15 | 210 | #3 | 53432 |
| 6604 | 21886 | 65.6 | 50.9 | 12 | 190 | #4 | 53433 |
| 6605 | 21887 | 66.4 | 61.8 | 18 | 272 | #4 | 53434 |
| 6606 | 21888 | 50.0 | 50.0 | 12 | 150 | #1 | 53435 |
| 6607 | 21889 | 63.2 | 50.0 | 15 | 198 | #3 | 53436 |
| 6608 | 21890 | 66.4 | 58.9 | 17 | 210 | #4 | 53437 |
| 6609 | 21891 | 68.0 | 57.5 | 21 | 202 | #4 | 53438 |
| 6610 | 21892 | 50.0 | 50.0 | 12 | 150 | #1 | 53439 |
| 6611 | 21893 | 64.0 | 50.0 | 12 | 192 | #3 | 53440 |
| 6612 | 21894 | 82.4 | 69.1 | 26 | 610 | #7 | 53441 |
| 6613 | 21895 | 75.2 | 71.2 (219) | 20 | 521 | #6 | 53442 |
| 6614 | 21896 | 73.6 | 64.4 | 23 | 402 | #5 | 53443 |
| 6615 | 21897 | 50.0 | 50.0 | 12 | 150 | #1 | 53444 |
| 6616 | 21898 | 64.0 | 50.0 | 16 | 161 | #3 | 53445 |
| 6617 | 21899 | 82.4 | 60.4 (222) | 22 | 473 | #7 | 53446 |
| 6618 | 21900 | 71.2 | 61.5 | 27 | 277 | #5 | 53447 |
| 6619 | 21901 | 72.0 | 62.5 | 28 | 501 | #5 | 53448 |
| 6620 | 21902 | 76.0 | 61.1 | 26 | 411 | #6 | 53449 |
| 6621 | 21903 | 50.0 | 50.0 | 14 | 154 | #1 | 53450 |
| 6622 | 21904 | 74.4 | 67.6 | 33 | 535 | #5 | 53451 |
| 6623 | 21905 | 68.0 | 61.8 | 18 | 309 | #4 | 53452 |
| 6624 | 21906 | 69.6 | 61.8 | 20 | 289 | #4 | 53453 |
| 6625 | 21907 | 53.6 | 50.0 | 17 | 169 | #1 | 53454 |
| 6626 | 21908 | 65.6 | 58.2 | 20 | 224 | #4 | 53455 |
| 6627 | 21909 | 66.4 | 60.0 | 17 | 279 | #4 | 53456 |
| 6628 | 21910 | 66.4 | 60.7 | 17 | 219 | #4 | 53457 |
| 6629 | 21911 | 73.6 | 63.3 | 20 | 319 | #5 | 53458 |
| 6630 | 21912 | 72.0 | 64.4 | 23 | 392 | #5 | 53459 |
| 6631 | 21913 | 50.0 | 50.0 | 12 | 150 | #1 | 53460 |
| 6632 | 21914 | 50.4 | 50.0 | 13 | 157 | #1 | 53461 |
| 6633 | 21915 | 67.2 | 61.2 (224) | 24 | 205 | #4 | 53462 |
| 6634 | 21916 | 66.4 | 61.8 | 15 | 273 | #4 | 53463 |
| 6635 | 21917 | 68.0 | 59.3 | 34 | 286 | #4 | 53464 |
| 6636 | 21918 | 68.8 | 63.3 | 21 | 520 | #4 | 53465 |
| 6637 | 21919 | 66.4 | 60.0 | 24 | 224 | #4 | 53466 |
| 6638 | 21920 | 65.6 | 58.9 | 23 | 232 | #4 | 53467 |
| 6639 | 21921 | 67.2 | 50.0 | 15 | 196 | #4 | 53468 |
| 6640 | 21922 | 50.0 | 50.0 | 16 | 160 | #1 | 53469 |
| 6641 | 21923 | 68.0 | 60.0 | 18 | 293 | #4 | 53470 |
| 6642 | 21924 | 74.4 | 58.9 | 38 | 371 | #5 | 53471 |
| 6643 | 21925 | 61.6 | 50.0 (241) | 15 | 150 | #3 | 53472 |
| 6644 | 21926 | 66.4 | 58.5 | 17 | 276 | #4 | 53473 |
| 6645 | 21927 | 67.2 | 59.6 | 19 | 245 | #4 | 53474 |
| 6646 | 21928 | 64.8 | 53.5 (271) | 18 | 211 | #3 | 53475 |
| 6647 | 21929 | 72.0 | 64.7 | 21 | 434 | #5 | 53476 |
| 6648 | 21930 | 65.6 | 50.0 | 14 | 176 | #4 | 53477 |
| 6649 | 21931 | 69.6 | 60.4 | 16 | 259 | #4 | 53478 |
| 6650 | 21932 | 69.6 | 60.7 | 16 | 274 | #4 | 53479 |
| 6651 | 21933 | 68.0 | 60.7 | 17 | 214 | #4 | 53480 |
| 6652 | 21934 | 72.8 | 62.2 | 20 | 364 | #5 | 53481 |
| 6653 | 21935 | 65.1 (106) | — | 12 | 155 | #4 | 53482 |
| 6654 | 21936 | 50.0 | 50.0 | 12 | 150 | #1 | 53483 |
| 6655 | 21937 | 50.0 | 50.0 | 12 | 150 | #1 | 53484 |
| 6656 | 21938 | 71.2 | 63.6 | 25 | 383 | #5 | 53485 |
| 6657 | 21939 | 50.0 | 50.0 | 12 | 150 | #1 | 53486 |
| 6658 | 21940 | 64.8 | 58.5 | 16 | 211 | #3 | 53487 |
| 6659 | 21941 | 72.0 | 62.5 | 26 | 295 | #5 | 53488 |
| 6660 | 21942 | 61.6 | 53.1 | 13 | 204 | #3 | 53489 |
| 6661 | 21943 | 67.2 | 61.1 | 22 | 236 | #4 | 53490 |
| 6662 | 21944 | 59.5 (79) | — | 39 | 190 | #2 | 53491 |
| 6663 | 21945 | 68.0 | 60.0 | 20 | 272 | #4 | 53492 |
| 6664 | 21946 | 50.0 | 50.0 | 12 | 150 | #1 | 53493 |
| 6665 | 21947 | 67.2 | 59.3 (209) | 21 | 220 | #4 | 53494 |
| 6666 | 21948 | 50.0 | 50.0 | 12 | 150 | #1 | 53495 |
| 6667 | 21949 | 66.4 | 58.9 | 18 | 248 | #4 | 53496 |
| 6668 | 21950 | 90.4 | 90.4 (125) | 20 | 511 | #9 | 53497 |
| 6669 | 21951 | 72.8 | 66.9 | 18 | 482 | #5 | 53498 |
| 6670 | 21952 | 65.6 | 56.0 | 16 | 219 | #4 | 53499 |
| 6671 | 21953 | 65.6 | 61.5 (187) | 19 | 170 | #4 | 53500 |
| 6672 | 21954 | 50.0 | 50.0 | 12 | 150 | #1 | 53501 |
| 6673 | 21955 | 65.6 | 59.3 | 15 | 212 | #4 | 53502 |
| 6674 | 21956 | 66.4 | 56.0 | 19 | 194 | #4 | 53503 |
| 6675 | 21957 | 67.2 | 61.5 | 18 | 269 | #4 | 53504 |
| 6676 | 21958 | 70.4 | 63.3 | 20 | 461 | #5 | 53505 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6677 | 21959 | 50.0 | 50.0 (129) | 17 | 150 | #1 | 53506 |
| 6678 | 21960 | 70.4 | 62.9 | 21 | 377 | #5 | 53507 |
| 6679 | 21961 | 77.6 | 66.5 | 24 | 472 | #6 | 53508 |
| 6680 | 21962 | 72.8 | 62.2 | 27 | 313 | #5 | 53509 |
| 6681 | 21963 | 70.4 | 61.1 | 26 | 239 | #5 | 53510 |
| 6682 | 21964 | 61.6 | 50.0 | 12 | 164 | #3 | 53511 |
| 6683 | 21965 | 74.4 | 61.1 | 19 | 355 | #5 | 53512 |
| 6684 | 21966 | 65.6 | 50.0 | 17 | 189 | #4 | 53513 |
| 6685 | 21967 | 70.4 | 60.0 | 29 | 293 | #5 | 53514 |
| 6686 | 21968 | 68.8 | 58.2 | 20 | 260 | #4 | 53515 |
| 6687 | 21969 | 64.8 | 60.4 | 16 | 265 | #3 | 53516 |
| 6688 | 21970 | 68.0 | 62.9 | 20 | 361 | #4 | 53517 |
| 6689 | 21971 | 68.8 | 61.8 | 20 | 306 | #4 | 53518 |
| 6690 | 21972 | 73.6 | 64.4 | 25 | 349 | #5 | 53519 |
| 6691 | 21973 | 61.6 | 58.5 | 14 | 191 | #3 | 53520 |
| 6692 | 21974 | 50.0 | 50.0 | 12 | 150 | #1 | 53521 |
| 6693 | 21975 | 63.2 | 56.3 (229) | 15 | 161 | #3 | 53522 |
| 6694 | 21976 | 50.0 | 50.0 (273) | 12 | 150 | #1 | 53523 |
| 6695 | 21977 | 68.0 | 60.4 | 17 | 260 | #4 | 53524 |
| 6696 | 21978 | 68.0 | 59.6 | 24 | 216 | #4 | 53525 |
| 6697 | 21979 | 68.0 | 59.6 | 18 | 234 | #4 | 53526 |
| 6698 | 21980 | 59.2 | 56.7 | 12 | 233 | #2 | 53527 |
| 6699 | 21981 | 68.0 | 58.2 | 20 | 257 | #4 | 53528 |
| 6700 | 21982 | 50.0 | 50.0 | 12 | 150 | #1 | 53529 |
| 6701 | 21983 | 50.0 | 50.0 | 12 | 150 | #1 | 53530 |
| 6702 | 21984 | 73.6 | 64.7 | 28 | 989 | #5 | 53531 |
| 6703 | 21985 | 62.4 | 53.2 (222) | 15 | 156 | #3 | 53532 |
| 6704 | 21986 | 65.6 | 59.6 (228) | 21 | 213 | #4 | 53533 |
| 6705 | 21987 | 67.2 | 59.3 | 16 | 236 | #4 | 53534 |
| 6706 | 21988 | 50.0 (67) | — | 12 | 150 | #1 | 53535 |
| 6707 | 21989 | 50.0 | 50.0 (149) | 25 | 150 | #1 | 53536 |
| 6708 | 21990 | 69.6 | 60.7 | 19 | 245 | #4 | 53537 |
| 6709 | 21991 | 73.6 | 63.6 | 25 | 528 | #5 | 53538 |
| 6710 | 21992 | 50.0 | 50.0 | 12 | 150 | #1 | 53539 |
| 6711 | 21993 | 66.4 | 60.0 | 19 | 242 | #4 | 53540 |
| 6712 | 21994 | 50.0 | 50.0 | 12 | 150 | #1 | 53541 |
| 6713 | 21995 | 67.2 | 59.3 | 21 | 205 | #4 | 53542 |
| 6714 | 21996 | 73.6 | 60.7 | 35 | 293 | #5 | 53543 |
| 6715 | 21997 | 68.8 | 60.7 | 17 | 329 | #4 | 53544 |
| 6716 | 21998 | 50.0 | 50.0 | 12 | 150 | #1 | 53545 |
| 6717 | 21999 | 68.0 | 61.1 | 25 | 377 | #4 | 53546 |
| 6718 | 22000 | 83.2 | 67.3 | 39 | 533 | #7 | 53547 |
| 6719 | 22001 | 64.8 | 56.1 (212) | 17 | 180 | #3 | 53548 |
| 6720 | 22002 | 66.4 | 56.2 (256) | 22 | 192 | #4 | 53549 |
| 6721 | 22003 | 68.0 | 60.4 | 23 | 264 | #4 | 53550 |
| 6722 | 22004 | 64.0 | 50.0 | 13 | 180 | #3 | 53551 |
| 6723 | 22005 | 63.2 | 57.8 (173) | 17 | 172 | #3 | 53552 |
| 6724 | 22006 | 50.0 | 50.0 (141) | 12 | 150 | #1 | 53553 |
| 6725 | 22007 | 70.4 | 62.5 | 21 | 427 | #5 | 53554 |
| 6726 | 22008 | 64.8 | 59.3 | 18 | 271 | #3 | 53555 |
| 6727 | 22009 | 76.8 | 66.5 | 28 | 704 | #6 | 53556 |
| 6728 | 22010 | 72.8 | 62.9 | 23 | 354 | #5 | 53557 |
| 6729 | 22011 | 66.4 | 60.0 | 16 | 265 | #4 | 53558 |
| 6730 | 22012 | 79.2 | 59.1 (264) | 31 | 550 | #6 | 53559 |
| 6731 | 22013 | 64.8 | 50.9 | 18 | 216 | #3 | 53560 |
| 6732 | 22014 | 66.4 | 59.5 (232) | 30 | 218 | #4 | 53561 |
| 6733 | 22015 | 70.4 | 59.3 | 26 | 228 | #5 | 53562 |
| 6734 | 22016 | 69.6 | 63.6 | 21 | 383 | #4 | 53563 |
| 6735 | 22017 | 68.8 | 60.0 | 16 | 242 | #4 | 53564 |
| 6736 | 22018 | 64.0 | 57.5 | 13 | 220 | #3 | 53565 |
| 6737 | 22019 | 70.4 | 65.1 | 23 | 376 | #5 | 53566 |
| 6738 | 22020 | 60.0 | 50.0 | 13 | 150 | #2 | 53567 |
| 6739 | 22021 | 68.0 | 61.1 | 22 | 352 | #4 | 53568 |
| 6740 | 22022 | 69.6 | 61.5 | 28 | 345 | #4 | 53569 |
| 6741 | 22023 | 62.4 | 50.0 | 12 | 221 | #3 | 53570 |
| 6742 | 22024 | 68.0 | 60.4 | 19 | 248 | #4 | 53571 |
| 6743 | 22025 | 50.0 | 50.0 | 12 | 150 | #1 | 53572 |
| 6744 | 22026 | 65.6 | 60.4 | 18 | 255 | #4 | 53573 |
| 6745 | 22027 | 65.6 | 58.9 | 17 | 227 | #4 | 53574 |
| 6746 | 22028 | 61.6 | 50.0 (186) | 13 | 164 | #3 | 53575 |
| 6747 | 22029 | 68.8 | 60.4 | 27 | 277 | #4 | 53576 |
| 6748 | 22030 | 66.4 | 60.4 | 21 | 258 | #4 | 53577 |
| 6749 | 22031 | 83.2 | 60.0 | 26 | 468 | #7 | 53578 |
| 6750 | 22032 | 66.4 | 61.1 | 17 | 260 | #4 | 53579 |
| 6751 | 22033 | 67.2 | 60.1 (203) | 19 | 187 | #4 | 53580 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6752 | 22034 | 64.8 | 58.9 | 16 | 240 | #3 | 53581 |
| 6753 | 22035 | 72.0 | 62.9 | 25 | 485 | #5 | 53582 |
| 6754 | 22036 | 68.0 | 59.6 | 17 | 281 | #4 | 53583 |
| 6755 | 22037 | 50.0 | 50.0 | 12 | 150 | #1 | 53584 |
| 6756 | 22038 | 65.6 | 50.6 (239) | 14 | 200 | #4 | 53585 |
| 6757 | 22039 | 67.2 | 61.1 | 19 | 274 | #4 | 53586 |
| 6758 | 22040 | 70.4 | 60.3 (232) | 20 | 248 | #5 | 53587 |
| 6759 | 22041 | 63.2 | 50.0 | 13 | 193 | #3 | 53588 |
| 6760 | 22042 | 60.0 | 50.0 | 13 | 180 | #2 | 53589 |
| 6761 | 22043 | 66.4 | 57.8 | 19 | 225 | #4 | 53590 |
| 6762 | 22044 | 63.2 | 51.4 (253) | 18 | 171 | #3 | 53591 |
| 6763 | 22045 | 50.0 | 50.0 (180) | 12 | 150 | #1 | 53592 |
| 6764 | 22046 | 62.4 | 50.9 | 18 | 188 | #3 | 53593 |
| 6765 | 22047 | 65.6 | 60.0 | 18 | 241 | #4 | 53594 |
| 6766 | 22048 | 66.4 | 56.4 | 20 | 212 | #4 | 53595 |
| 6767 | 22049 | 64.8 | 53.9 (217) | 17 | 161 | #3 | 53596 |
| 6768 | 22050 | 68.8 | 60.4 | 20 | 267 | #4 | 53597 |
| 6769 | 22051 | 70.8 (89) | — | 26 | 174 | #5 | 53598 |
| 6770 | 22052 | 65.6 | 57.8 | 18 | 194 | #4 | 53599 |
| 6771 | 22053 | 50.0 | 50.0 | 12 | 150 | #1 | 53600 |
| 6772 | 22054 | 74.4 | 65.1 | 32 | 459 | #5 | 53601 |
| 6773 | 22055 | 71.2 | 61.1 | 30 | 272 | #5 | 53602 |
| 6774 | 22056 | 68.0 | 60.7 | 18 | 220 | #4 | 53603 |
| 6775 | 22057 | 62.4 | 57.8 | 14 | 202 | #3 | 53604 |
| 6776 | 22058 | 50.0 (87) | — | 12 | 150 | #1 | 53605 |
| 6777 | 22059 | 66.4 | 58.9 | 16 | 334 | #4 | 53606 |
| 6778 | 22060 | 61.6 | 50.0 | 14 | 197 | #3 | 53607 |
| 6779 | 22061 | 50.0 | 50.0 | 12 | 150 | #1 | 53608 |
| 6780 | 22062 | 69.6 | 61.1 | 18 | 267 | #4 | 53609 |
| 6781 | 22063 | 65.6 | 56.0 | 16 | 217 | #4 | 53610 |
| 6782 | 22064 | 67.2 | 57.8 | 21 | 217 | #4 | 53611 |
| 6783 | 22065 | 66.4 | 58.4 (257) | 20 | 209 | #4 | 53612 |
| 6784 | 22066 | 67.2 | 53.8 | 22 | 200 | #4 | 53613 |
| 6785 | 22067 | 68.0 | 60.0 | 23 | 239 | #4 | 53614 |
| 6786 | 22068 | 63.2 | 50.0 (197) | 15 | 164 | #3 | 53615 |
| 6787 | 22069 | 63.2 | 56.1 (212) | 15 | 177 | #3 | 53616 |
| 6788 | 22070 | 65.6 | 56.4 | 12 | 215 | #4 | 53617 |
| 6789 | 22071 | 72.0 | 62.9 | 29 | 309 | #5 | 53618 |
| 6790 | 22072 | 68.0 | 60.0 | 20 | 308 | #4 | 53619 |
| 6791 | 22073 | 71.2 | 60.7 | 19 | 258 | #5 | 53620 |
| 6792 | 22074 | 83.2 | 73.1 | 25 | 621 | #7 | 53621 |
| 6793 | 22075 | 70.4 | 61.8 | 19 | 280 | #5 | 53622 |
| 6794 | 22076 | 62.4 | 57.1 | 17 | 205 | #3 | 53623 |
| 6795 | 22077 | 78.4 | 65.5 | 31 | 428 | #6 | 53624 |
| 6796 | 22078 | 60.8 | 50.2 (203) | 19 | 170 | #3 | 53625 |
| 6797 | 22079 | 74.4 | 64.7 | 26 | 402 | #5 | 53626 |
| 6798 | 22080 | 67.2 | 55.3 | 18 | 206 | #4 | 53627 |
| 6799 | 22081 | 67.2 | 62.7 (166) | 23 | 213 | #4 | 53628 |
| 6800 | 22082 | 74.4 | 64.0 | 29 | 363 | #5 | 53629 |
| 6801 | 22083 | 69.6 | 60.7 | 20 | 304 | #4 | 53630 |
| 6802 | 22084 | 70.4 | 65.5 | 34 | 394 | #5 | 53631 |
| 6803 | 22085 | 68.0 | 57.5 | 16 | 250 | #4 | 53632 |
| 6804 | 22086 | 64.8 | 50.0 | 14 | 182 | #3 | 53633 |
| 6805 | 22087 | 72.0 | 61.1 | 26 | 286 | #5 | 53634 |
| 6806 | 22088 | 64.8 | 58.2 | 18 | 207 | #3 | 53635 |
| 6807 | 22089 | 72.0 | 68.4 (152) | 23 | 255 | #5 | 53636 |
| 6808 | 22090 | 66.4 | 61.1 | 14 | 268 | #4 | 53637 |
| 6809 | 22091 | 50.0 | 50.0 | 12 | 150 | #1 | 53638 |
| 6810 | 22092 | 50.0 | 50.0 | 12 | 150 | #1 | 53639 |
| 6811 | 22093 | 50.0 | 50.0 | 12 | 150 | #1 | 53640 |
| 6812 | 22094 | 71.2 | 60.7 | 21 | 312 | #5 | 53641 |
| 6813 | 22095 | 67.2 | 60.4 | 16 | 241 | #4 | 53642 |
| 6814 | 22096 | 65.6 | 50.0 | 13 | 193 | #4 | 53643 |
| 6815 | 22097 | 62.4 | 50.0 | 12 | 160 | #3 | 53644 |
| 6816 | 22098 | 72.0 | 62.2 | 18 | 371 | #5 | 53645 |
| 6817 | 22099 | 68.0 | 62.2 | 22 | 311 | #4 | 53646 |
| 6818 | 22100 | 70.4 | 64.7 | 21 | 369 | #5 | 53647 |
| 6819 | 22101 | 70.4 | 62.2 | 22 | 383 | #5 | 53648 |
| 6820 | 22102 | 50.0 | 50.0 | 12 | 150 | #1 | 53649 |
| 6821 | 22103 | 68.8 | 60.7 | 27 | 254 | #4 | 53650 |
| 6822 | 22104 | 67.2 | 61.1 | 17 | 250 | #4 | 53651 |
| 6823 | 22105 | 67.2 | 57.5 | 16 | 238 | #4 | 53652 |
| 6824 | 22106 | 65.6 | 58.9 | 15 | 233 | #4 | 53653 |
| 6825 | 22107 | 69.6 | 61.5 | 19 | 309 | #4 | 53654 |
| 6826 | 22108 | 69.6 | 57.8 | 19 | 221 | #4 | 53655 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6827 | 22109 | 64.0 | 57.5 | 13 | 208 | #3 | 53656 |
| 6828 | 22110 | 71.2 | 62.9 | 29 | 469 | #5 | 53657 |
| 6829 | 22111 | 68.0 | 60.4 | 17 | 240 | #4 | 53658 |
| 6830 | 22112 | 67.2 | 58.2 | 14 | 230 | #4 | 53659 |
| 6831 | 22113 | 68.8 | 50.0 | 18 | 263 | #4 | 53660 |
| 6832 | 22114 | 65.6 | 56.4 | 18 | 203 | #4 | 53661 |
| 6833 | 22115 | 70.4 | 62.5 | 22 | 451 | #5 | 53662 |
| 6834 | 22116 | 69.6 | 60.7 | 33 | 283 | #4 | 53663 |
| 6835 | 22117 | 71.2 | 62.5 | 28 | 386 | #5 | 53664 |
| 6836 | 22118 | 50.0 | 50.0 (135) | 12 | 150 | #1 | 53665 |
| 6837 | 22129 | 62.4 | 52.1 (194) | 17 | 151 | #3 | 53666 |
| 6838 | 22120 | 97.6 | 96.7 | 66 | 1359 | #10 | 53667 |
| 6839 | 22121 | 61.6 | 54.4 (182) | 15 | 150 | #3 | 53668 |
| 6840 | 22122 | 62.4 | 58.5 | 17 | 211 | #3 | 53669 |
| 6841 | 22123 | 63.2 | 50.0 (255) | 15 | 171 | #3 | 53670 |
| 6842 | 22124 | 68.0 | 54.2 | 17 | 232 | #4 | 53671 |
| 6843 | 22125 | 68.0 | 59.8 (214) | 22 | 217 | #4 | 53672 |
| 6844 | 22126 | 56.8 (88) | — | 25 | 150 | #2 | 53673 |
| 6845 | 22127 | 64.0 | 58.9 | 18 | 242 | #3 | 53674 |
| 6846 | 22128 | 65.6 | 60.4 | 18 | 215 | #4 | 53675 |
| 6847 | 22129 | 71.2 | 59.6 | 22 | 270 | #5 | 53676 |
| 6848 | 22130 | 50.0 | 50.0 | 12 | 150 | #1 | 53677 |
| 6849 | 22131 | 50.0 | 50.0 | 12 | 150 | #1 | 53678 |
| 6850 | 22132 | 72.8 | 62.2 | 30 | 320 | #5 | 53679 |
| 6851 | 22133 | 68.0 | 57.8 | 15 | 243 | #4 | 53680 |
| 6852 | 22134 | 69.6 | 62.2 | 19 | 412 | #4 | 53681 |
| 6853 | 22135 | 66.4 | 57.5 | 21 | 212 | #4 | 53682 |
| 6854 | 22136 | 50.0 | 50.0 | 12 | 150 | #1 | 53683 |
| 6855 | 22137 | 68.8 | 61.5 | 21 | 296 | #4 | 53684 |
| 6856 | 22138 | 70.4 | 58.9 | 26 | 249 | #5 | 53685 |
| 6857 | 22139 | 65.6 | 60.4 | 21 | 257 | #4 | 53686 |
| 6858 | 22140 | 71.2 | 60.2 (269) | 20 | 285 | #5 | 53687 |
| 6859 | 22141 | 68.8 | 60.4 | 21 | 258 | #4 | 53688 |
| 6860 | 22142 | 80.0 | 59.4 (187) | 29 | 322 | #6 | 53689 |
| 6861 | 22143 | 68.0 | 60.7 | 18 | 285 | #4 | 53690 |
| 6862 | 22144 | 62.4 | 57.8 | 17 | 244 | #3 | 53691 |
| 6863 | 22145 | 65.6 | 50.0 (272) | 12 | 176 | #4 | 53692 |
| 6864 | 22146 | 77.6 | 66.9 | 33 | 740 | #6 | 53693 |
| 6865 | 22147 | 50.0 (89) | — | 12 | 150 | #1 | 53694 |
| 6866 | 22148 | 50.0 | 50.0 | 12 | 150 | #1 | 53695 |
| 6867 | 22149 | 66.4 | 62.4 (173) | 21 | 204 | #4 | 53696 |
| 6868 | 22150 | 68.0 | 61.1 | 16 | 249 | #4 | 53697 |
| 6869 | 22151 | 50.0 | 50.0 | 12 | 150 | #1 | 53698 |
| 6870 | 22152 | 50.0 | 50.0 | 12 | 150 | #1 | 53699 |
| 6871 | 22153 | 73.6 | 66.9 | 32 | 569 | #5 | 53700 |
| 6872 | 22154 | 67.2 | 61.8 | 27 | 299 | #4 | 53701 |
| 6873 | 22155 | 69.6 | 64.4 | 19 | 358 | #4 | 53702 |
| 6874 | 22156 | 68.0 | 60.7 | 21 | 279 | #4 | 53703 |
| 6875 | 22157 | 68.8 | 60.7 | 19 | 261 | #4 | 53704 |
| 6876 | 22158 | 72.0 | 65.5 | 23 | 401 | #5 | 53705 |
| 6877 | 22159 | 70.4 | 61.1 | 20 | 302 | #5 | 53706 |
| 6878 | 22160 | 73.6 | 57.5 | 23 | 265 | #5 | 53707 |
| 6879 | 22161 | 62.4 | 58.2 | 14 | 193 | #3 | 53708 |
| 6880 | 22162 | 68.8 | 59.6 | 22 | 263 | #4 | 53709 |
| 6881 | 22163 | 75.2 | 62.5 | 20 | 338 | #6 | 53710 |
| 6882 | 22164 | 64.0 | 59.6 | 15 | 219 | #3 | 53711 |
| 6883 | 22165 | 70.4 | 61.1 | 22 | 267 | #5 | 53712 |
| 6884 | 22166 | 62.4 | 50.0 | 14 | 202 | #3 | 53713 |
| 6885 | 22167 | 85.9 (78) | — | 27 | 291 | #8 | 53714 |
| 6886 | 22168 | 63.2 | 59.3 (221) | 17 | 157 | #3 | 53715 |
| 6887 | 22169 | 63.2 | 58.2 | 17 | 199 | #3 | 53716 |
| 6888 | 22170 | 66.4 | 59.6 | 19 | 238 | #4 | 53717 |
| 6889 | 22171 | 85.6 | 81.9 (171) | 31 | 543 | #8 | 53718 |
| 6890 | 22172 | 66.4 | 59.0 (249) | 21 | 212 | #4 | 53719 |
| 6891 | 22173 | 50.4 | 50.0 | 12 | 179 | #1 | 53720 |
| 6892 | 22174 | 64.0 | 60.7 | 14 | 219 | #3 | 53721 |
| 6893 | 22175 | 68.8 | 61.8 | 20 | 339 | #4 | 53722 |
| 6894 | 22176 | 64.8 | 57.0 (235) | 16 | 181 | #3 | 53723 |
| 6895 | 22177 | 64.8 | 63.7 (157) | 25 | 185 | #3 | 53724 |
| 6896 | 22178 | 50.0 | 50.0 | 12 | 150 | #1 | 53725 |
| 6897 | 22179 | 70.4 | 63.3 | 21 | 326 | #5 | 53726 |
| 6898 | 22180 | 50.0 | 50.0 | 12 | 150 | #1 | 53727 |
| 6899 | 22181 | 72.0 | 68.4 | 22 | 736 | #5 | 53728 |
| 6900 | 22182 | 62.4 | 50.0 | 14 | 176 | #3 | 53729 |
| 6901 | 22183 | 64.8 | 58.2 | 15 | 201 | #3 | 53730 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6902 | 22184 | 69.6 | 62.2 | 19 | 318 | #4 | 53731 |
| 6903 | 22185 | 68.8 | 58.9 | 17 | 226 | #4 | 53732 |
| 6904 | 22186 | 50.0 | 50.0 | 12 | 150 | #1 | 53733 |
| 6905 | 22187 | 72.0 | 65.8 | 23 | 440 | #5 | 53734 |
| 6906 | 22188 | 61.6 | 57.8 | 15 | 200 | #3 | 53735 |
| 6907 | 22189 | 74.4 | 65.1 | 23 | 512 | #5 | 53736 |
| 6908 | 22190 | 50.0 | 50.0 | 12 | 162 | #1 | 53737 |
| 6909 | 22191 | 70.4 | 62.2 | 25 | 280 | #5 | 53738 |
| 6910 | 22192 | 68.8 | 60.4 | 14 | 368 | #4 | 53739 |
| 6911 | 22193 | 64.0 | 50.0 | 15 | 180 | #3 | 53740 |
| 6912 | 22194 | 66.4 | 60.4 | 16 | 241 | #4 | 53741 |
| 6913 | 22195 | 50.0 | 50.0 | 12 | 150 | #1 | 53742 |
| 6914 | 22196 | 64.0 | 58.9 | 15 | 212 | #3 | 53743 |
| 6915 | 22197 | 70.4 | 62.5 | 26 | 374 | #5 | 53744 |
| 6916 | 22198 | 61.6 | 50.2 | 13 | 174 | #3 | 53745 |
| 6917 | 22199 | 50.0 | 50.0 | 12 | 150 | #1 | 53746 |
| 6918 | 22200 | 73.6 | 63.3 | 40 | 301 | #5 | 53747 |
| 6919 | 22201 | 66.4 | 56.7 | 25 | 206 | #4 | 53748 |
| 6920 | 22202 | 69.6 | 60.7 | 16 | 262 | #4 | 53749 |
| 6921 | 22203 | 50.0 | 50.0 | 12 | 150 | #1 | 53750 |
| 6922 | 22204 | 66.4 | 50.0 (207) | 12 | 150 | #4 | 53751 |
| 6923 | 22205 | 50.0 | 50.0 | 12 | 150 | #1 | 53752 |
| 6924 | 22206 | 66.4 | 56.7 | 18 | 200 | #4 | 53753 |
| 6925 | 22207 | 68.0 | 59.6 | 24 | 250 | #4 | 53754 |
| 6926 | 22208 | 66.4 | 56.7 | 18 | 200 | #4 | 53755 |
| 6927 | 22209 | 71.2 | 62.2 | 20 | 322 | #5 | 53756 |
| 6928 | 22210 | 67.2 | 58.5 | 16 | 265 | #4 | 53757 |
| 6929 | 22211 | 50.0 | 50.0 (171) | 12 | 150 | #1 | 53758 |
| 6930 | 22212 | 72.8 | 58.2 | 14 | 289 | #5 | 53759 |
| 6931 | 22213 | 50.0 | 50.0 | 12 | 150 | #1 | 53760 |
| 6932 | 22214 | 64.8 | 58.9 | 12 | 201 | #3 | 53761 |
| 6933 | 22215 | 56.0 | 50.0 (153) | 18 | 154 | #2 | 53762 |
| 6934 | 22216 | 65.6 | 55.3 | 16 | 220 | #4 | 53763 |
| 6935 | 22217 | 50.0 | 50.0 | 12 | 150 | #1 | 53764 |
| 6936 | 22218 | 69.6 | 65.1 | 20 | 518 | #4 | 53765 |
| 6937 | 22219 | 67.2 | 55.3 | 16 | 228 | #4 | 53766 |
| 6938 | 22220 | 70.4 | 60.0 | 21 | 275 | #5 | 53767 |
| 6939 | 22221 | 69.6 | 59.3 | 24 | 258 | #4 | 53768 |
| 6940 | 22222 | 65.6 | 57.8 | 14 | 198 | #4 | 53769 |
| 6941 | 22223 | 63.2 | 50.0 | 14 | 178 | #3 | 53770 |
| 6942 | 22224 | 66.4 | 60.7 | 21 | 300 | #4 | 53771 |
| 6943 | 22225 | 80.8 | 70.9 | 33 | 614 | #7 | 53772 |
| 6944 | 22226 | 64.0 | 50.0 (224) | 14 | 154 | #3 | 53773 |
| 6945 | 22227 | 63.4 (112) | — | 17 | 163 | #3 | 53774 |
| 6946 | 22228 | 50.4 | 50.0 (152) | 15 | 152 | #1 | 53775 |
| 6947 | 22229 | 66.4 | 61.6 (203) | 18 | 195 | #4 | 53776 |
| 6948 | 22230 | 69.6 | 65.5 | 20 | 357 | #4 | 53777 |
| 6949 | 22231 | 63.2 | 58.5 | 15 | 200 | #3 | 53778 |
| 6950 | 22232 | 50.0 | 50.0 | 12 | 150 | #1 | 53779 |
| 6951 | 22233 | 64.0 | 58.5 | 15 | 250 | #3 | 53780 |
| 6952 | 22234 | 50.0 | 50.0 | 12 | 150 | #1 | 53781 |
| 6953 | 22235 | 50.0 | 50.0 | 12 | 150 | #1 | 53782 |
| 6954 | 22236 | 68.8 | 60.7 | 17 | 282 | #4 | 53783 |
| 6955 | 22237 | 72.0 | 67.9 (162) | 28 | 275 | #5 | 53784 |
| 6956 | 22238 | 50.0 | 50.0 | 12 | 150 | #1 | 53785 |
| 6957 | 22239 | 50.0 | 50.0 | 12 | 150 | #1 | 53786 |
| 6958 | 22240 | 60.8 | 50.0 | 14 | 184 | #3 | 53787 |
| 6959 | 22241 | 68.8 | 61.1 | 21 | 290 | #4 | 53788 |
| 6960 | 22242 | 69.6 | 64.4 | 32 | 434 | #4 | 53789 |
| 6961 | 22243 | 68.8 | 59.3 | 21 | 247 | #4 | 53790 |
| 6962 | 22244 | 67.2 | 61.8 | 17 | 328 | #4 | 53791 |
| 6963 | 22245 | 70.4 | 61.8 | 24 | 278 | #5 | 53792 |
| 6964 | 22246 | 50.0 | 50.0 | 12 | 150 | #1 | 53793 |
| 6965 | 22247 | 61.6 | 50.0 | 13 | 195 | #3 | 53794 |
| 6966 | 22248 | 69.6 | 62.2 | 30 | 295 | #4 | 53795 |
| 6967 | 22249 | 50.0 | 50.0 | 16 | 172 | #1 | 53796 |
| 6968 | 22250 | 68.8 | 61.8 | 18 | 298 | #4 | 53797 |
| 6969 | 22251 | 75.2 | 61.8 | 35 | 360 | #6 | 53798 |
| 6970 | 22252 | 65.6 | 60.0 | 13 | 211 | #4 | 53799 |
| 6971 | 22253 | 73.6 | 69.2 (156) | 33 | 283 | #5 | 53800 |
| 6972 | 22254 | 61.1 (108) | — | 14 | 150 | #3 | 53801 |
| 6973 | 22255 | 58.4 | 50.0 | 15 | 156 | #2 | 53802 |
| 6974 | 22256 | 55.6 (72) | — | 33 | 192 | #2 | 53803 |
| 6975 | 22257 | 65.6 | 50.0 (246) | 16 | 185 | #4 | 53804 |
| 6976 | 22258 | 64.8 | 54.8 (270) | 20 | 179 | #3 | 53805 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 6977 | 22259 | 50.0 | 50.0 | 12 | 150 | #1 | 53806 |
| 6978 | 22260 | 50.0 | 50.0 | 12 | 150 | #1 | 53807 |
| 6979 | 22261 | 65.6 | 50.0 | 20 | 174 | #4 | 53808 |
| 6980 | 22262 | 63.2 | 56.7 | 13 | 196 | #3 | 53809 |
| 6981 | 22263 | 64.8 | 60.4 | 17 | 235 | #3 | 53810 |
| 6982 | 22264 | 61.6 | 50.0 | 13 | 175 | #3 | 53811 |
| 6983 | 22265 | 67.2 | 61.1 | 23 | 317 | #4 | 53812 |
| 6984 | 22266 | 66.4 | 59.6 | 13 | 210 | #4 | 53813 |
| 6985 | 22267 | 50.0 | 50.0 | 12 | 150 | #1 | 53814 |
| 6986 | 22268 | 66.4 | 59.6 | 19 | 262 | #4 | 53815 |
| 6987 | 22269 | 68.8 | 62.2 | 19 | 312 | #4 | 53816 |
| 6988 | 22270 | 71.2 | 60.7 | 24 | 313 | #5 | 53817 |
| 6989 | 22271 | 50.0 | 50.0 | 25 | 227 | #1 | 53818 |
| 6990 | 22272 | 71.2 | 61.1 | 23 | 311 | #5 | 53819 |
| 6991 | 22273 | 94.0 (83) | — | 34 | 370 | #9 | 53820 |
| 6992 | 22274 | 68.0 | 57.8 | 14 | 217 | #4 | 53821 |
| 6993 | 22275 | 71.2 | 62.9 | 22 | 439 | #5 | 53822 |
| 6994 | 22276 | 50.0 (86) | — | 28 | 180 | #1 | 53823 |
| 6995 | 22277 | 67.2 | 55.9 (247) | 20 | 206 | #4 | 53824 |
| 6996 | 22278 | 62.2 (74) | — | 13 | 150 | #3 | 53825 |
| 6997 | 22279 | 50.0 | 50.0 (126) | 12 | 150 | #1 | 53826 |
| 6998 | 22280 | 67.2 | 62.2 | 21 | 350 | #4 | 53827 |
| 6999 | 22281 | 65.6 | 50.0 | 16 | 204 | #4 | 53828 |
| 7000 | 22282 | 69.6 | 61.8 | 21 | 295 | #4 | 53829 |
| 7001 | 22283 | 62.4 | 58.5 | 19 | 187 | #3 | 53830 |
| 7002 | 22284 | 70.4 | 64.6 (192) | 22 | 246 | #5 | 53831 |
| 7003 | 22285 | 69.6 | 61.5 | 18 | 266 | #4 | 53832 |
| 7004 | 22286 | 64.8 | 59.6 | 16 | 226 | #3 | 53833 |
| 7005 | 22287 | 64.8 | 50.0 | 13 | 183 | #3 | 53834 |
| 7006 | 22288 | 66.4 | 57.5 | 18 | 230 | #4 | 53835 |
| 7007 | 22289 | 50.0 | 50.0 | 12 | 150 | #1 | 53836 |
| 7008 | 22290 | 68.8 | 61.8 | 20 | 366 | #4 | 53837 |
| 7009 | 22291 | 68.8 | 62.5 | 18 | 286 | #4 | 53838 |
| 7010 | 22292 | 50.0 | 50.0 | 12 | 150 | #1 | 53839 |
| 7011 | 22293 | 72.8 | 62.2 | 33 | 345 | #5 | 53840 |
| 7012 | 22294 | 64.8 | 50.0 (272) | 14 | 165 | #3 | 53841 |
| 7013 | 22295 | 69.6 | 61.1 | 26 | 322 | #4 | 53842 |
| 7014 | 22296 | 64.0 | 57.5 | 15 | 192 | #3 | 53843 |
| 7015 | 22297 | 62.4 | 50.0 (180) | 16 | 159 | #3 | 53844 |
| 7016 | 22298 | 60.0 | 57.1 | 15 | 204 | #2 | 53845 |
| 7017 | 22299 | 68.0 | 60.7 | 19 | 274 | #4 | 53846 |
| 7018 | 22300 | 63.2 | 50.0 | 12 | 162 | #3 | 53847 |
| 7019 | 22301 | 68.0 | 58.8 (240) | 21 | 207 | #4 | 53848 |
| 7020 | 22302 | 73.6 | 67.1 (246) | 24 | 406 | #5 | 53849 |
| 7021 | 22303 | 67.2 | 58.9 | 16 | 231 | #4 | 53850 |
| 7022 | 22304 | 69.6 | 63.3 | 21 | 348 | #4 | 53851 |
| 7023 | 22305 | 64.8 | 59.3 | 15 | 235 | #3 | 53852 |
| 7024 | 22306 | 67.2 | 60.7 | 20 | 300 | #4 | 53853 |
| 7025 | 22307 | 50.0 | 50.0 | 12 | 150 | #1 | 53854 |
| 7026 | 22308 | 50.0 | 50.0 | 12 | 150 | #1 | 53855 |
| 7027 | 22309 | 67.2 | 61.8 | 17 | 525 | #4 | 53856 |
| 7028 | 22310 | 61.6 | 57.1 | 14 | 204 | #3 | 53857 |
| 7029 | 22311 | 68.0 | 58.9 | 21 | 261 | #4 | 53858 |
| 7030 | 22312 | 50.0 | 50.0 | 12 | 150 | #1 | 53859 |
| 7031 | 22313 | 50.0 | 50.0 | 17 | 162 | #1 | 53860 |
| 7032 | 22314 | 64.0 | 55.4 (240) | 14 | 167 | #3 | 53861 |
| 7033 | 22315 | 50.0 | 50.0 | 12 | 150 | #1 | 53862 |
| 7034 | 22316 | 66.4 | 53.8 | 20 | 210 | #4 | 53863 |
| 7035 | 22317 | 50.0 | 50.0 | 12 | 150 | #1 | 53864 |
| 7036 | 22318 | 65.6 | 58.2 | 17 | 213 | #4 | 53865 |
| 7037 | 22319 | 50.0 | 50.0 | 12 | 150 | #1 | 53866 |
| 7038 | 22320 | 70.4 | 60.4 | 26 | 240 | #5 | 53867 |
| 7039 | 22321 | 69.6 | 62.9 | 23 | 322 | #4 | 53868 |
| 7040 | 22322 | 65.6 | 50.0 | 18 | 191 | #4 | 53869 |
| 7041 | 22323 | 67.2 | 50.0 | 24 | 196 | #4 | 53870 |
| 7042 | 22324 | 65.6 | 60.0 | 20 | 199 | #4 | 53871 |
| 7043 | 22325 | 50.0 | 50.0 | 12 | 150 | #1 | 53872 |
| 7044 | 22326 | 50.0 (103) | — | 18 | 150 | #1 | 53873 |
| 7045 | 22327 | 76.8 | 66.5 | 36 | 499 | #6 | 53874 |
| 7046 | 22328 | 63.2 | 58.9 | 12 | 208 | #3 | 53875 |
| 7047 | 22329 | 50.0 (68) | — | 12 | 150 | #1 | 53876 |
| 7048 | 22330 | 70.4 | 62.2 | 23 | 381 | #5 | 53877 |
| 7049 | 22331 | 69.6 | 61.1 | 20 | 272 | #4 | 53878 |
| 7050 | 22332 | 64.8 | 59.6 | 13 | 206 | #3 | 53879 |
| 7051 | 22333 | 64.8 | 57.5 | 27 | 201 | #3 | 53880 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7052 | 22334 | 68.8 | 61.1 | 22 | 275 | #4 | 53881 |
| 7053 | 22335 | 69.6 | 63.6 | 22 | 464 | #4 | 53882 |
| 7054 | 22336 | 61.6 | 54.2 | 12 | 181 | #3 | 53883 |
| 7055 | 22337 | 62.4 | 58.9 | 13 | 204 | #3 | 53884 |
| 7056 | 22338 | 72.0 | 64.7 | 21 | 403 | #5 | 53885 |
| 7057 | 22339 | 62.4 | 58.5 | 15 | 191 | #3 | 53886 |
| 7058 | 22340 | 80.0 | 65.5 | 37 | 443 | #6 | 53887 |
| 7059 | 22341 | 50.0 | 50.0 | 12 | 150 | #1 | 53888 |
| 7060 | 22342 | 79.2 | 65.8 | 16 | 467 | #6 | 53889 |
| 7061 | 22343 | 72.8 | 63.6 | 30 | 430 | #5 | 53890 |
| 7062 | 22344 | 68.8 | 60.4 | 25 | 263 | #4 | 53891 |
| 7063 | 22345 | 50.0 | 50.0 | 12 | 150 | #1 | 53892 |
| 7064 | 22346 | 64.8 | 60.7 | 17 | 267 | #3 | 53893 |
| 7065 | 22347 | 70.4 | 63.3 | 24 | 344 | #5 | 53894 |
| 7066 | 22348 | 64.8 | 50.0 | 14 | 187 | #3 | 53895 |
| 7067 | 22349 | 65.6 | 60.0 | 20 | 242 | #4 | 53896 |
| 7068 | 22350 | 65.6 | 60.0 | 15 | 220 | #4 | 53897 |
| 7069 | 22351 | 50.0 | 50.0 | 12 | 150 | #1 | 53898 |
| 7070 | 22352 | 50.0 | 50.0 | 12 | 150 | #1 | 53899 |
| 7071 | 22353 | 67.2 | 58.9 | 18 | 246 | #4 | 53900 |
| 7072 | 22354 | 58.3 (108) | — | 12 | 150 | #2 | 53901 |
| 7073 | 22355 | 68.8 | 60.0 | 19 | 282 | #4 | 53902 |
| 7074 | 22356 | 65.6 | 61.1 | 14 | 258 | #4 | 53903 |
| 7075 | 22357 | 72.8 | 62.9 | 21 | 302 | #5 | 53904 |
| 7076 | 22358 | 60.0 | 52.6 (171) | 13 | 153 | #2 | 53905 |
| 7077 | 22359 | 65.6 | 56.7 | 15 | 231 | #4 | 53906 |
| 7078 | 22360 | 68.0 | 60.4 | 20 | 310 | #4 | 53907 |
| 7079 | 22361 | 72.8 | 65.8 | 31 | 477 | #5 | 53908 |
| 7080 | 22362 | 63.2 | 54.4 (215) | 15 | 167 | #3 | 53909 |
| 7081 | 22363 | 64.0 | 58.2 | 13 | 221 | #3 | 53910 |
| 7082 | 22364 | 65.6 | 60.7 | 19 | 242 | #4 | 53911 |
| 7083 | 22365 | 64.0 | 50.0 | 21 | 192 | #3 | 53912 |
| 7084 | 22366 | 68.8 | 61.8 | 22 | 300 | #4 | 53913 |
| 7085 | 22367 | 60.8 | 50.0 | 12 | 184 | #3 | 53914 |
| 7086 | 22368 | 66.4 | 60.7 | 19 | 295 | #4 | 53915 |
| 7087 | 22369 | 68.0 | 62.5 | 18 | 273 | #4 | 53916 |
| 7088 | 22370 | 64.8 | 58.2 | 17 | 229 | #3 | 53917 |
| 7089 | 22371 | 67.2 | 50.0 | 19 | 212 | #4 | 53918 |
| 7090 | 22372 | 64.0 | 56.4 | 15 | 185 | #3 | 53919 |
| 7091 | 22373 | 68.0 | 60.4 | 19 | 249 | #4 | 53920 |
| 7092 | 22374 | 70.4 | 62.2 | 22 | 312 | #5 | 53921 |
| 7093 | 22375 | 72.0 (75) | — | 19 | 194 | #5 | 53922 |
| 7094 | 22376 | 61.6 | 57.5 | 16 | 241 | #3 | 53923 |
| 7095 | 22377 | 65.6 | 54.0 (261) | 15 | 188 | #4 | 53924 |
| 7096 | 22378 | 68.8 | 53.8 | 19 | 226 | #4 | 53925 |
| 7097 | 22379 | 50.0 | 50.0 | 12 | 156 | #1 | 53926 |
| 7098 | 22380 | 68.8 | 63.6 | 21 | 348 | #4 | 53927 |
| 7099 | 22381 | 66.4 | 50.0 | 18 | 217 | #4 | 53928 |
| 7100 | 22382 | 76.8 | 64.4 | 33 | 510 | #6 | 53929 |
| 7101 | 22383 | 99.2 | 97.5 | 87 | 1684 | #10 | 53930 |
| 7102 | 22384 | 50.0 | 50.0 | 12 | 150 | #1 | 53931 |
| 7103 | 22385 | 71.2 | 64.4 | 21 | 601 | #5 | 53932 |
| 7104 | 22386 | 61.6 | 52.0 | 14 | 215 | #3 | 53933 |
| 7105 | 22387 | 64.8 | 58.2 | 16 | 204 | #3 | 53934 |
| 7106 | 22388 | 50.0 | 50.0 | 12 | 150 | #1 | 53935 |
| 7107 | 22389 | 68.0 | 58.9 | 25 | 246 | #4 | 53936 |
| 7108 | 22390 | 70.4 | 63.6 | 20 | 443 | #5 | 53937 |
| 7109 | 22391 | 64.8 | 50.0 | 20 | 174 | #3 | 53938 |
| 7110 | 22392 | 50.0 | 50.0 (135) | 12 | 150 | #1 | 53939 |
| 7111 | 22393 | 68.0 | 61.5 | 25 | 317 | #4 | 53940 |
| 7112 | 22394 | 71.2 | 61.5 | 21 | 304 | #5 | 53941 |
| 7113 | 22395 | 66.4 | 60.4 | 21 | 234 | #4 | 53942 |
| 7114 | 22396 | 67.2 | 60.0 | 17 | 232 | #4 | 53943 |
| 7115 | 22397 | 75.2 | 65.5 | 31 | 673 | #6 | 53944 |
| 7116 | 22398 | 68.0 | 62.5 | 20 | 380 | #4 | 53945 |
| 7117 | 22399 | 61.6 | 50.0 | 12 | 178 | #3 | 53946 |
| 7118 | 22400 | 50.0 | 50.0 | 12 | 150 | #1 | 53947 |
| 7119 | 22401 | 67.2 | 61.5 | 21 | 313 | #4 | 53948 |
| 7120 | 22402 | 64.8 | 50.0 | 16 | 216 | #3 | 53949 |
| 7121 | 22403 | 62.4 | 50.9 | 13 | 202 | #3 | 53950 |
| 7122 | 22404 | 50.0 | 50.0 | 15 | 150 | #1 | 53951 |
| 7123 | 22405 | 64.0 | 60.1 (183) | 21 | 163 | #3 | 53952 |
| 7124 | 22406 | 60.0 | 50.0 (196) | 15 | 150 | #2 | 53953 |
| 7125 | 22407 | 65.6 | 60.4 | 15 | 238 | #4 | 53954 |
| 7126 | 22408 | 70.4 | 62.2 | 23 | 269 | #5 | 53955 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7127 | 22409 | 68.8 | 61.8 | 25 | 371 | #4 | 53956 |
| 7128 | 22410 | 70.4 | 63.3 | 25 | 380 | #5 | 53957 |
| 7129 | 22411 | 60.0 | 50.0 | 14 | 150 | #2 | 53958 |
| 7130 | 22412 | 50.0 | 50.0 | 12 | 150 | #1 | 53959 |
| 7131 | 22413 | 50.0 | 50.0 | 12 | 150 | #1 | 53960 |
| 7132 | 22414 | 50.0 | 50.0 | 12 | 150 | #1 | 53961 |
| 7133 | 22415 | 69.6 | 63.6 | 22 | 568 | #4 | 53962 |
| 7134 | 22416 | 50.0 | 50.0 | 12 | 150 | #1 | 53963 |
| 7135 | 22417 | 60.8 | 57.8 | 12 | 194 | #3 | 53964 |
| 7136 | 22418 | 61.6 | 57.5 | 14 | 206 | #3 | 53965 |
| 7137 | 22419 | 73.6 | 60.7 | 21 | 297 | #5 | 53966 |
| 7138 | 22420 | 66.4 | 62.2 | 16 | 249 | #4 | 53967 |
| 7139 | 22421 | 68.0 | 62.2 | 20 | 278 | #4 | 53968 |
| 7140 | 22422 | 69.6 | 61.1 | 21 | 248 | #4 | 53969 |
| 7141 | 22423 | 67.2 | 60.7 | 22 | 288 | #4 | 53970 |
| 7142 | 22424 | 63.3 (120) | — | 17 | 152 | #3 | 53971 |
| 7143 | 22425 | 68.8 | 62.8 (156) | 20 | 185 | #4 | 53972 |
| 7144 | 22426 | 68.8 | 60.4 | 19 | 261 | #4 | 53973 |
| 7145 | 22427 | 66.4 | 58.9 | 18 | 243 | #4 | 53974 |
| 7146 | 22428 | 69.6 | 60.7 | 19 | 271 | #4 | 53975 |
| 7147 | 22429 | 64.8 | 58.9 | 15 | 222 | #3 | 53976 |
| 7148 | 22430 | 65.6 | 59.3 | 17 | 243 | #4 | 53977 |
| 7149 | 22431 | 64.8 | 50.0 | 15 | 204 | #3 | 53978 |
| 7150 | 22432 | 59.2 | 52.7 | 14 | 155 | #2 | 53979 |
| 7151 | 22433 | 63.2 | 57.8 | 15 | 209 | #3 | 53980 |
| 7152 | 22434 | 66.4 | 65.8 (155) | 24 | 185 | #4 | 53981 |
| 7153 | 22435 | 65.6 | 58.9 | 18 | 266 | #4 | 53982 |
| 7154 | 22436 | 73.6 | 66.2 | 17 | 817 | #5 | 53983 |
| 7155 | 22437 | 50.0 | 50.0 | 12 | 150 | #1 | 53984 |
| 7156 | 22438 | 68.8 | 57.5 | 15 | 243 | #4 | 53985 |
| 7157 | 22439 | 64.0 | 59.6 | 17 | 229 | #3 | 53986 |
| 7158 | 22440 | 69.6 | 59.6 | 27 | 224 | #4 | 53987 |
| 7159 | 22441 | 66.4 | 59.6 | 19 | 219 | #4 | 53988 |
| 7160 | 22442 | 50.0 | 50.0 | 12 | 150 | #1 | 53989 |
| 7161 | 22443 | 57.6 | 54.1 (133) | 16 | 158 | #2 | 53990 |
| 7162 | 22444 | 72.0 | 64.0 | 18 | 589 | #5 | 53991 |
| 7163 | 22445 | 60.0 | 52.0 | 14 | 181 | #2 | 53992 |
| 7164 | 22446 | 70.4 | 63.6 | 21 | 711 | #5 | 53993 |
| 7165 | 22447 | 68.8 | 65.8 (161) | 29 | 254 | #4 | 53994 |
| 7166 | 22448 | 64.0 | 59.6 | 16 | 225 | #3 | 53995 |
| 7167 | 22449 | 60.8 | 54.2 | 13 | 207 | #3 | 53996 |
| 7168 | 22450 | 68.0 | 60.7 | 20 | 264 | #4 | 53997 |
| 7169 | 22451 | 66.4 | 54.2 | 13 | 217 | #4 | 53998 |
| 7170 | 22452 | 66.4 | 60.7 | 22 | 253 | #4 | 53999 |
| 7171 | 22453 | 68.0 | 61.8 | 20 | 279 | #4 | 54000 |
| 7172 | 22454 | 74.4 | 64.4 | 27 | 424 | #5 | 54001 |
| 7173 | 22455 | 71.2 | 59.6 | 25 | 268 | #5 | 54002 |
| 7174 | 22456 | 66.4 | 58.5 | 19 | 215 | #4 | 54003 |
| 7175 | 22457 | 72.0 | 64.7 | 27 | 514 | #5 | 54004 |
| 7176 | 22458 | 68.8 | 61.5 | 22 | 339 | #4 | 54005 |
| 7177 | 22459 | 60.8 | 50.5 | 12 | 191 | #3 | 54006 |
| 7178 | 22460 | 68.0 | 58.2 | 17 | 236 | #4 | 54007 |
| 7179 | 22461 | 69.6 | 61.5 | 21 | 332 | #4 | 54008 |
| 7180 | 22462 | 68.8 | 62.2 | 21 | 471 | #4 | 54009 |
| 7181 | 22463 | 70.4 | 63.6 | 23 | 395 | #5 | 54010 |
| 7182 | 22464 | 65.6 | 59.3 | 18 | 218 | #4 | 54011 |
| 7183 | 22465 | 50.0 | 50.0 | 12 | 150 | #1 | 54012 |
| 7184 | 22466 | 50.0 | 50.0 | 12 | 150 | #1 | 54013 |
| 7185 | 22467 | 50.0 | 50.0 (253) | 12 | 150 | #1 | 54014 |
| 7186 | 22468 | 65.6 | 59.6 | 18 | 239 | #4 | 54015 |
| 7187 | 22469 | 76.0 | 60.7 | 25 | 305 | #6 | 54016 |
| 7188 | 22470 | 77.6 | 62.9 | 16 | 540 | #6 | 54017 |
| 7189 | 22471 | 60.0 | 57.1 | 16 | 181 | #2 | 54018 |
| 7190 | 22472 | 60.0 | 50.0 (226) | 13 | 156 | #2 | 54019 |
| 7191 | 22473 | 69.6 | 61.5 | 24 | 300 | #4 | 54020 |
| 7192 | 22474 | 64.0 | 58.5 | 20 | 224 | #3 | 54021 |
| 7193 | 22475 | 72.0 | 50.0 | 23 | 285 | #5 | 54022 |
| 7194 | 22476 | 70.4 | 59.3 | 15 | 238 | #5 | 54023 |
| 7195 | 22477 | 64.8 | 60.4 | 25 | 288 | #3 | 54024 |
| 7196 | 22478 | 68.8 | 60.4 | 21 | 321 | #4 | 54025 |
| 7197 | 22479 | 66.4 | 61.5 | 21 | 268 | #4 | 54026 |
| 7198 | 22480 | 64.8 | 56.4 | 13 | 203 | #3 | 54027 |
| 7199 | 22481 | 67.2 | 60.6 (236) | 20 | 196 | #4 | 54028 |
| 7200 | 22482 | 70.4 | 64.0 | 20 | 444 | #5 | 54029 |
| 7201 | 22483 | 64.8 | 57.1 | 18 | 219 | #3 | 54030 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7202 | 22484 | 69.3 (88) | — | 12 | 165 | #4 | 54031 |
| 7203 | 22485 | 50.0 | 50.0 | 12 | 150 | #1 | 54032 |
| 7204 | 22486 | 68.0 | 61.5 (213) | 23 | 201 | #4 | 54033 |
| 7205 | 22487 | 69.6 | 62.2 | 20 | 394 | #4 | 54034 |
| 7206 | 22488 | 64.0 | 59.6 | 13 | 258 | #3 | 54035 |
| 7207 | 22489 | 66.4 | 58.5 | 26 | 253 | #4 | 54036 |
| 7208 | 22490 | 90.1 (91) | — | 27 | 378 | #9 | — |
| 7209 | 22491 | 68.8 | 62.5 | 22 | 438 | #4 | 54037 |
| 7210 | 22492 | 68.8 | 61.5 | 19 | 273 | #4 | 54038 |
| 7211 | 22493 | 69.6 | 58.9 | 16 | 239 | #4 | 54039 |
| 7212 | 22494 | 70.4 | 59.6 | 21 | 269 | #5 | 54040 |
| 7213 | 22495 | 70.4 | 60.7 | 20 | 252 | #5 | 54041 |
| 7214 | 22496 | 71.2 | 62.2 | 21 | 334 | #5 | 54042 |
| 7215 | 22497 | 61.6 (112) | — | 24 | 301 | #3 | 54043 |
| 7216 | 22498 | 50.0 | 50.0 | 12 | 150 | #1 | 54044 |
| 7217 | 22499 | 66.4 | 60.4 | 17 | 246 | #4 | 54045 |
| 7218 | 22500 | 50.0 | 50.0 | 12 | 150 | #1 | 54046 |
| 7219 | 22501 | 59.2 | 50.0 | 13 | 179 | #2 | 54047 |
| 7220 | 22502 | 70.4 | 62.9 | 24 | 367 | #5 | 54048 |
| 7221 | 22503 | 50.0 | 50.0 | 12 | 150 | #1 | 54049 |
| 7222 | 22504 | 68.8 | 66.7 (174) | 20 | 244 | #4 | 54050 |
| 7223 | 22505 | 64.0 | 57.5 | 15 | 175 | #3 | 54051 |
| 7224 | 22506 | 79.2 | 67.6 | 30 | 754 | #6 | 54052 |
| 7225 | 22507 | 64.0 | 54.9 | 17 | 255 | #3 | 54053 |
| 7226 | 22508 | 50.0 | 50.0 | 12 | 150 | #1 | 54054 |
| 7227 | 22509 | 64.8 | 60.0 | 15 | 250 | #3 | 54055 |
| 7228 | 22510 | 63.2 | 58.9 | 17 | 198 | #3 | 54056 |
| 7229 | 22511 | 64.0 | 58.5 | 15 | 232 | #3 | 54057 |
| 7230 | 22512 | 58.1 (124) | — | 19 | 156 | #2 | 54058 |
| 7231 | 22513 | 72.0 | 61.8 | 30 | 284 | #5 | 54059 |
| 7232 | 22514 | 61.6 | 50.0 | 12 | 174 | #3 | 54060 |
| 7233 | 22515 | 50.0 | 50.0 | 12 | 150 | #1 | 54061 |
| 7234 | 22516 | 67.2 | 60.4 | 20 | 226 | #4 | 54062 |
| 7235 | 22517 | 75.2 | 60.4 | 20 | 320 | #6 | 54063 |
| 7236 | 22518 | 50.0 | 50.0 | 12 | 150 | #1 | 54064 |
| 7237 | 22519 | 63.2 | 56.4 | 14 | 198 | #3 | 54065 |
| 7238 | 22520 | 50.0 | 50.0 | 12 | 150 | #1 | 54066 |
| 7239 | 22521 | 70.4 | 61.9 (176) | 20 | 214 | #5 | 54067 |
| 7240 | 22522 | 67.2 | 58.5 | 22 | 233 | #4 | 54068 |
| 7241 | 22523 | 66.4 | 59.3 | 18 | 242 | #4 | 54069 |
| 7242 | 22524 | 70.4 | 58.2 | 31 | 252 | #5 | 54070 |
| 7243 | 22525 | 67.2 | 58.8 (165) | 18 | 188 | #4 | 54071 |
| 7244 | 22526 | 67.2 | 58.9 | 18 | 244 | #4 | 54072 |
| 7245 | 22527 | 62.4 | 50.0 | 14 | 198 | #3 | 54073 |
| 7246 | 22528 | 60.0 | 50.0 | 12 | 150 | #2 | 54074 |
| 7247 | 22529 | 69.6 | 61.1 | 21 | 277 | #4 | 54075 |
| 7248 | 22530 | 55.2 | 50.0 (210) | 12 | 150 | #2 | 54076 |
| 7249 | 22531 | 65.6 | 58.5 | 22 | 238 | #4 | 54077 |
| 7250 | 22532 | 60.0 | 54.1 (183) | 16 | 157 | #2 | 54078 |
| 7251 | 22533 | 61.6 | 55.9 (143) | 13 | 155 | #3 | 54079 |
| 7252 | 22534 | 50.0 | 50.0 | 12 | 150 | #1 | 54080 |
| 7253 | 22535 | 50.0 | 50.0 | 12 | 150 | #1 | 54081 |
| 7254 | 22536 | 62.4 | 58.2 | 22 | 232 | #3 | 54082 |
| 7255 | 22537 | 50.0 | 50.0 | 12 | 150 | #1 | 54083 |
| 7256 | 22538 | 86.6 (67) | — | 28 | 258 | #8 | 54084 |
| 7257 | 22539 | 65.6 | 50.0 | 12 | 177 | #4 | 54085 |
| 7258 | 22540 | 50.0 | 50.0 | 12 | 150 | #1 | 54086 |
| 7259 | 22541 | 73.6 | 61.8 | 23 | 327 | #5 | 54087 |
| 7260 | 22542 | 76.8 | 65.8 | 22 | 418 | #6 | 54088 |
| 7261 | 22543 | 68.0 | 59.3 | 19 | 239 | #4 | 54089 |
| 7262 | 22544 | 60.8 | 50.0 | 14 | 155 | #3 | 54090 |
| 7263 | 22545 | 71.2 | 62.2 | 28 | 329 | #5 | 54091 |
| 7264 | 22546 | 62.4 | 50.0 | 12 | 220 | #3 | 54092 |
| 7265 | 22547 | 50.0 | 50.0 | 12 | 150 | #1 | 54093 |
| 7266 | 22548 | 62.4 | 56.4 | 14 | 234 | #3 | 54094 |
| 7267 | 22549 | 71.2 | 65.5 | 22 | 404 | #5 | 54095 |
| 7268 | 22550 | 64.0 | 50.0 | 13 | 195 | #3 | 54096 |
| 7269 | 22551 | 75.2 | 62.2 | 23 | 293 | #6 | 54097 |
| 7270 | 22552 | 50.0 | 50.0 | 12 | 150 | #1 | 54098 |
| 7271 | 22553 | 64.0 | 50.0 | 16 | 164 | #3 | 54099 |
| 7272 | 22554 | 75.2 | 63.3 | 34 | 409 | #6 | 54100 |
| 7273 | 22555 | 59.2 | 50.0 (168) | 17 | 163 | #2 | 54101 |
| 7274 | 22556 | 67.2 | 57.8 | 14 | 217 | #4 | 54102 |
| 7275 | 22557 | 66.4 | 60.4 | 18 | 202 | #4 | 54103 |
| 7276 | 22558 | 50.0 | 50.0 | 12 | 150 | #1 | 54104 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7277 | 22559 | 64.8 | 59.3 | 16 | 233 | #3 | 54105 |
| 7278 | 22560 | 65.6 | 57.8 | 16 | 196 | #4 | 54106 |
| 7279 | 22561 | 64.8 | 58.9 | 17 | 210 | #3 | 54107 |
| 7280 | 22562 | 66.4 | 61.5 | 21 | 277 | #4 | 54108 |
| 7281 | 22563 | 75.2 | 67.3 | 15 | 692 | #6 | 54109 |
| 7282 | 22564 | 65.6 | 61.8 | 17 | 259 | #4 | 54110 |
| 7283 | 22565 | 66.4 | 50.0 | 14 | 198 | #4 | 54111 |
| 7284 | 22566 | 91.5 (94) | — | 25 | 398 | #9 | 54112 |
| 7285 | 22567 | 66.4 | 60.7 | 23 | 307 | #4 | 54113 |
| 7286 | 22568 | 64.0 | 50.6 (237) | 16 | 206 | #3 | 54114 |
| 7287 | 22569 | 50.0 | 50.0 | 12 | 150 | #1 | 54115 |
| 7288 | 22570 | 62.4 | 50.0 | 15 | 183 | #3 | 54116 |
| 7289 | 22571 | 64.0 | 58.5 | 15 | 219 | #3 | 54117 |
| 7290 | 22572 | 63.2 | 50.0 (248) | 14 | 162 | #3 | 54118 |
| 7291 | 22573 | 50.0 | 50.0 | 12 | 150 | #1 | 54119 |
| 7292 | 22574 | 50.0 | 50.0 | 14 | 150 | #1 | 54120 |
| 7293 | 22575 | 68.0 | 61.1 | 19 | 345 | #4 | 54121 |
| 7294 | 22576 | 50.0 | 50.0 | 12 | 150 | #1 | 54122 |
| 7295 | 22577 | 50.0 | 50.0 | 12 | 150 | #1 | 54123 |
| 7296 | 22578 | 68.8 | 58.2 | 19 | 271 | #4 | 54124 |
| 7297 | 22579 | 62.4 | 50.0 | 14 | 173 | #3 | 54125 |
| 7298 | 22580 | 70.4 | 62.9 | 30 | 308 | #5 | 54126 |
| 7299 | 22581 | 62.4 | 58.2 | 15 | 204 | #3 | 54127 |
| 7300 | 22582 | 61.6 | 56.7 | 13 | 202 | #3 | 54128 |
| 7301 | 22583 | 64.0 | 58.2 | 16 | 214 | #3 | 54129 |
| 7302 | 22584 | 64.8 | 58.9 (214) | 17 | 175 | #3 | 54130 |
| 7303 | 22585 | 69.6 | 62.2 | 18 | 300 | #4 | 54131 |
| 7304 | 22586 | 64.8 | 58.9 | 22 | 217 | #3 | 54132 |
| 7305 | 22587 | 84.0 | 80.0 | 26 | 1981 | #7 | 54133 |
| 7306 | 22588 | 89.6 | 70.9 | 26 | 773 | #8 | 54134 |
| 7307 | 22589 | 70.4 | 59.6 | 24 | 282 | #5 | 54135 |
| 7308 | 22590 | 69.6 | 59.6 | 36 | 264 | #4 | 54136 |
| 7309 | 22591 | 64.8 | 60.0 | 22 | 216 | #3 | 54137 |
| 7310 | 22592 | 67.2 | 59.6 | 19 | 261 | #4 | 54138 |
| 7311 | 22593 | 68.0 | 61.1 (257) | 21 | 216 | #4 | 54139 |
| 7312 | 22594 | 72.0 | 59.1 (259) | 24 | 285 | #5 | 54140 |
| 7313 | 22595 | 66.4 | 60.2 (249) | 22 | 228 | #4 | 54141 |
| 7314 | 22596 | 66.4 | 61.1 | 20 | 239 | #4 | 54142 |
| 7315 | 22597 | 65.6 | 59.6 | 17 | 236 | #4 | 54143 |
| 7316 | 22598 | 64.8 | 50.5 | 12 | 182 | #3 | 54144 |
| 7317 | 22599 | 84.8 | 80.0 | 39 | 1007 | #7 | 54145 |
| 7318 | 22600 | 70.4 | 60.4 | 24 | 304 | #5 | 54146 |
| 7319 | 22601 | 64.8 | 61.7 (180) | 16 | 164 | #3 | 54147 |
| 7320 | 22602 | 50.0 | 50.0 | 12 | 150 | #1 | 54148 |
| 7321 | 22603 | 51.2 | 50.0 | 13 | 158 | #1 | 54149 |
| 7322 | 22604 | 68.8 | 59.6 | 18 | 214 | #4 | 54150 |
| 7323 | 22605 | 64.0 | 50.0 | 12 | 167 | #3 | 54151 |
| 7324 | 22606 | 68.0 | 60.4 | 18 | 256 | #4 | 54152 |
| 7325 | 22607 | 62.4 | 50.0 | 15 | 182 | #3 | 54153 |
| 7326 | 22608 | 81.6 | 68.4 | 25 | 473 | #7 | 54154 |
| 7327 | 22609 | 50.0 (74) | — | 12 | 150 | #1 | 54155 |
| 7328 | 22610 | 72.8 | 64.4 | 26 | 400 | #5 | 54156 |
| 7329 | 22611 | 72.8 | 65.5 | 30 | 440 | #5 | 54157 |
| 7330 | 22612 | 68.8 | 62.2 | 32 | 704 | #4 | 54158 |
| 7331 | 22613 | 50.0 | 50.0 | 12 | 150 | #1 | 54159 |
| 7332 | 22614 | 68.0 | 59.6 | 18 | 231 | #4 | 54160 |
| 7333 | 22615 | 66.4 | 50.0 | 14 | 185 | #4 | 54161 |
| 7334 | 22616 | 72.8 | 65.1 | 26 | 542 | #5 | 54162 |
| 7335 | 22617 | 64.0 | 50.0 | 13 | 212 | #3 | 54163 |
| 7336 | 22618 | 52.0 | 50.0 (144) | 12 | 150 | #1 | 54164 |
| 7337 | 22619 | 71.2 | 61.8 | 28 | 279 | #5 | 54165 |
| 7338 | 22620 | 64.0 | 57.5 | 12 | 217 | #3 | 54166 |
| 7339 | 22621 | 68.8 | 61.8 | 19 | 319 | #4 | 54167 |
| 7340 | 22622 | 55.2 | 50.0 (259) | 16 | 157 | #2 | 54168 |
| 7341 | 22623 | 62.4 | 58.2 | 14 | 211 | #3 | 54169 |
| 7342 | 22624 | 64.0 | 51.6 | 12 | 204 | #3 | 54170 |
| 7343 | 22625 | 58.4 | 50.0 | 13 | 157 | #2 | 54171 |
| 7344 | 22626 | 73.9 (88) | — | 27 | 184 | #5 | 54172 |
| 7345 | 22627 | 72.0 | 62.5 | 34 | 307 | #5 | 54173 |
| 7346 | 22628 | 67.2 | 60.7 | 18 | 277 | #4 | 54174 |
| 7347 | 22629 | 50.0 (70) | — | 12 | 150 | #1 | 54175 |
| 7348 | 22630 | 63.2 | 50.0 | 12 | 177 | #3 | 54176 |
| 7349 | 22631 | 68.8 | 63.3 | 19 | 282 | #4 | 54177 |
| 7350 | 22632 | 68.0 | 62.5 | 19 | 354 | #4 | 54178 |
| 7351 | 22633 | 50.0 | 50.0 | 12 | 150 | #1 | 54179 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7352 | 22634 | 67.2 | 60.7 | 17 | 239 | #4 | 54180 |
| 7353 | 22635 | 69.6 | 59.6 | 22 | 293 | #4 | 54181 |
| 7354 | 22636 | 64.0 | 55.8 (215) | 22 | 164 | #3 | 54182 |
| 7355 | 22637 | 67.2 | 57.8 | 24 | 230 | #4 | 54183 |
| 7356 | 22638 | 52.0 | 50.0 (136) | 13 | 151 | #1 | 54184 |
| 7357 | 22639 | 69.6 | 56.4 (264) | 20 | 236 | #4 | 54185 |
| 7358 | 22640 | 72.3 (112) | — | 32 | 238 | #5 | 54186 |
| 7359 | 22641 | 66.4 | 61.5 | 18 | 315 | #4 | 54187 |
| 7360 | 22642 | 67.2 | 57.0 (256) | 19 | 218 | #4 | 54188 |
| 7361 | 22643 | 70.4 | 62.2 | 19 | 297 | #5 | 54189 |
| 7362 | 22644 | 63.2 | 57.6 (139) | 33 | 160 | #3 | 54190 |
| 7363 | 22645 | 62.4 | 54.9 | 16 | 195 | #3 | 54191 |
| 7364 | 22646 | 60.8 | 50.0 | 12 | 160 | #3 | 54192 |
| 7365 | 22647 | 71.2 | 57.8 | 18 | 219 | #5 | 54193 |
| 7366 | 22648 | 70.4 | 65.5 | 21 | 456 | #5 | 54194 |
| 7367 | 22649 | 68.8 | 61.1 | 20 | 292 | #4 | 54195 |
| 7368 | 22650 | 72.8 | 62.5 | 24 | 374 | #5 | 54196 |
| 7369 | 22651 | 67.2 | 57.9 (178) | 15 | 159 | #4 | 54197 |
| 7370 | 22652 | 73.6 | 64.4 | 22 | 413 | #5 | 54198 |
| 7371 | 22653 | 75.2 | 64.4 | 31 | 398 | #6 | 54199 |
| 7372 | 22654 | 67.2 | 59.6 | 15 | 234 | #4 | 54200 |
| 7373 | 22655 | 65.6 | 61.5 | 19 | 331 | #4 | 54201 |
| 7374 | 22656 | 68.8 | 61.5 | 22 | 342 | #4 | 54202 |
| 7375 | 22657 | 61.6 | 56.3 | 15 | 179 | #3 | 54203 |
| 7376 | 22658 | 74.4 | 65.8 (245) | 22 | 424 | #5 | 54204 |
| 7377 | 22659 | 60.0 | 50.0 | 13 | 204 | #2 | 54205 |
| 7378 | 22660 | 69.6 | 51.6 | 21 | 238 | #4 | 54206 |
| 7379 | 22661 | 65.6 | 59.6 | 20 | 229 | #4 | 54207 |
| 7380 | 22662 | 66.4 | 64.2 (162) | 17 | 203 | #4 | 54208 |
| 7381 | 22663 | 67.2 | 59.6 | 24 | 318 | #4 | 54209 |
| 7382 | 22664 | 50.0 | 50.0 | 12 | 150 | #1 | 54210 |
| 7383 | 22665 | 71.2 | 62.5 | 20 | 379 | #5 | 54211 |
| 7384 | 22666 | 50.0 (111) | — | 16 | 150 | #1 | 54212 |
| 7385 | 22667 | 56.8 | 50.0 | 12 | 211 | #2 | 54213 |
| 7386 | 22668 | 68.8 | 60.0 | 24 | 245 | #4 | 54214 |
| 7387 | 22669 | 50.0 (108) | — | 12 | 150 | #1 | 54215 |
| 7388 | 22670 | 66.4 | 60.7 | 21 | 239 | #4 | 54216 |
| 7389 | 22671 | 50.0 | 50.0 | 12 | 150 | #1 | 54217 |
| 7390 | 22672 | 68.0 | 57.8 | 23 | 235 | #4 | 54218 |
| 7391 | 22673 | 68.0 | 53.8 (210) | 21 | 222 | #4 | 54219 |
| 7392 | 22674 | 67.2 | 60.0 | 18 | 224 | #4 | 54220 |
| 7393 | 22675 | 71.2 | 60.0 | 16 | 274 | #5 | 54221 |
| 7394 | 22676 | 62.4 | 50.0 (201) | 14 | 159 | #3 | 54222 |
| 7395 | 22677 | 67.2 | 61.1 | 22 | 242 | #4 | 54223 |
| 7396 | 22678 | 63.2 | 51.6 | 13 | 192 | #3 | 54224 |
| 7397 | 22679 | 69.6 | 62.5 | 20 | 283 | #4 | 54225 |
| 7398 | 22680 | 50.0 | 50.0 | 12 | 150 | #1 | 54226 |
| 7399 | 22681 | 50.0 (118) | — | 12 | 150 | #1 | 54227 |
| 7400 | 22682 | 68.0 | 61.5 | 18 | 296 | #4 | 54228 |
| 7401 | 22683 | 50.0 | 50.0 | 12 | 150 | #1 | 54229 |
| 7402 | 22684 | 61.6 | 55.6 (153) | 22 | 166 | #3 | 54230 |
| 7403 | 22685 | 64.0 | 60.8 (186) | 15 | 188 | #3 | 54231 |
| 7404 | 22686 | 50.0 (71) | — | 12 | 150 | #1 | 54232 |
| 7405 | 22687 | 68.8 | 62.5 | 21 | 437 | #4 | 54233 |
| 7406 | 22688 | 50.0 (81) | — | 12 | 150 | #1 | 54234 |
| 7407 | 22689 | 60.0 | 50.0 (166) | 17 | 151 | #2 | 54235 |
| 7408 | 22690 | 58.4 | 50.0 (232) | 14 | 170 | #2 | 54236 |
| 7409 | 22691 | 64.8 | 50.0 | 16 | 164 | #3 | 54237 |
| 7410 | 22692 | 69.6 | 59.6 | 20 | 241 | #4 | 54238 |
| 7411 | 22693 | 91.2 | 89.4 (170) | 33 | 692 | #9 | 54239 |
| 7412 | 22694 | 65.6 | 58.9 | 13 | 196 | #4 | 54240 |
| 7413 | 22695 | 50.0 | 50.0 | 12 | 150 | #1 | 54241 |
| 7414 | 22696 | 50.0 | 50.0 | 12 | 150 | #1 | 54242 |
| 7415 | 22697 | 64.8 | 58.5 | 12 | 224 | #3 | 54243 |
| 7416 | 22698 | 68.8 | 60.4 | 21 | 276 | #4 | 54244 |
| 7417 | 22699 | 50.0 | 50.0 | 12 | 150 | #1 | 54245 |
| 7418 | 22700 | 68.8 | 60.0 | 22 | 240 | #4 | 54246 |
| 7419 | 22701 | 65.6 | 50.0 | 13 | 205 | #4 | 54247 |
| 7420 | 22702 | 63.2 | 55.6 (198) | 18 | 166 | #3 | 54248 |
| 7421 | 22703 | 68.0 | 60.4 | 18 | 240 | #4 | 54249 |
| 7422 | 22704 | 69.6 | 63.6 | 19 | 356 | #4 | 54250 |
| 7423 | 22705 | 64.0 | 50.0 | 13 | 209 | #3 | 54251 |
| 7424 | 22706 | 50.0 | 50.0 | 12 | 150 | #1 | 54252 |
| 7425 | 22707 | 75.2 | 66.5 | 38 | 1270 | #6 | 54253 |
| 7426 | 22708 | 50.0 | 50.0 | 12 | 150 | #1 | 54254 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7427 | 22709 | 67.2 | 61.5 | 19 | 358 | #4 | 54255 |
| 7428 | 22710 | 60.8 | 58.2 | 12 | 201 | #3 | 54256 |
| 7429 | 22711 | 64.0 | 60.4 | 16 | 233 | #3 | 54257 |
| 7430 | 22712 | 68.0 | 59.6 | 17 | 235 | #4 | 54258 |
| 7431 | 22713 | 61.6 | 50.0 | 35 | 170 | #3 | 54259 |
| 7432 | 22714 | 67.2 | 60.4 | 18 | 290 | #4 | 54260 |
| 7433 | 22715 | 65.6 | 52.0 | 12 | 189 | #4 | 54261 |
| 7434 | 22716 | 64.8 | 50.0 (271) | 13 | 197 | #3 | 54262 |
| 7435 | 22717 | 69.6 | 57.5 (266) | 32 | 261 | #4 | 54263 |
| 7436 | 22718 | 68.8 | 63.3 | 21 | 357 | #4 | 54264 |
| 7437 | 22719 | 68.8 | 61.8 | 23 | 334 | #4 | 54265 |
| 7438 | 22720 | 50.0 | 50.0 | 12 | 150 | #1 | 54266 |
| 7439 | 22721 | 67.2 | 61.5 | 18 | 253 | #4 | 54267 |
| 7440 | 22722 | 50.0 | 50.0 | 12 | 150 | #1 | 54268 |
| 7441 | 22723 | 68.0 | 60.0 | 17 | 236 | #4 | 54269 |
| 7442 | 22724 | 67.2 | 60.0 | 19 | 233 | #4 | 54270 |
| 7443 | 22725 | 68.8 | 58.5 | 26 | 251 | #4 | 54271 |
| 7444 | 22726 | 65.6 | 50.0 (220) | 12 | 164 | #4 | 54272 |
| 7445 | 22727 | 66.4 | 51.6 | 20 | 204 | #4 | 54273 |
| 7446 | 22728 | 72.8 | 63.3 | 23 | 430 | #5 | 54274 |
| 7447 | 22729 | 50.0 (116) | — | 16 | 150 | #1 | 54275 |
| 7448 | 22730 | 50.0 | 50.0 | 12 | 150 | #1 | 54276 |
| 7449 | 22731 | 69.6 | 61.1 | 21 | 285 | #4 | 54277 |
| 7450 | 22732 | 64.0 | 50.0 | 12 | 185 | #3 | 54278 |
| 7451 | 22733 | 50.0 | 50.0 | 12 | 150 | #1 | 54279 |
| 7452 | 22734 | 74.4 | 61.5 | 27 | 300 | #5 | 54280 |
| 7453 | 22735 | 62.4 | 50.0 | 12 | 162 | #3 | 54281 |
| 7454 | 22736 | 69.6 | 61.1 | 20 | 298 | #4 | 54282 |
| 7455 | 22737 | 64.8 | 59.3 | 15 | 225 | #3 | 54283 |
| 7456 | 22738 | 68.0 | 61.5 | 19 | 272 | #4 | 54284 |
| 7457 | 22739 | 72.8 | 62.7 (236) | 24 | 324 | #5 | — |
| 7458 | 22740 | 70.4 | 61.5 | 25 | 295 | #5 | 54285 |
| 7459 | 22741 | 69.6 | 63.3 | 22 | 366 | #4 | 54286 |
| 7460 | 22742 | 64.0 | 50.0 | 16 | 186 | #3 | 54287 |
| 7461 | 22743 | 68.0 | 61.1 | 18 | 300 | #4 | 54288 |
| 7462 | 22744 | 68.0 | 60.0 | 19 | 254 | #4 | 54289 |
| 7463 | 22745 | 67.2 | 61.8 | 19 | 329 | #4 | 54290 |
| 7464 | 22746 | 68.8 | 61.1 | 21 | 311 | #4 | 54291 |
| 7465 | 22747 | 66.4 | 59.3 (194) | 17 | 191 | #4 | 54292 |
| 7466 | 22748 | 77.6 | 53.1 | 19 | 469 | #6 | 54293 |
| 7467 | 22749 | 64.8 | 50.9 | 14 | 193 | #3 | 54294 |
| 7468 | 22750 | 72.0 | 64.0 | 19 | 408 | #5 | 54295 |
| 7469 | 22751 | 69.6 | 64.5 (217) | 19 | 297 | #4 | 54296 |
| 7470 | 22752 | 63.2 | 50.0 | 12 | 201 | #3 | 54297 |
| 7471 | 22753 | 67.2 | 50.5 | 18 | 200 | #4 | 54298 |
| 7472 | 22754 | 72.0 | 63.6 | 24 | 333 | #5 | 54299 |
| 7473 | 22755 | 50.0 | 50.0 | 12 | 150 | #1 | 54300 |
| 7474 | 22756 | 72.0 | 60.0 | 35 | 296 | #5 | 54301 |
| 7475 | 22757 | 72.8 | 64.0 | 24 | 333 | #5 | 54302 |
| 7476 | 22758 | 69.6 | 63.6 | 22 | 393 | #4 | 54303 |
| 7477 | 22759 | 68.0 | 59.3 | 17 | 286 | #4 | 54304 |
| 7478 | 22760 | 50.0 | 50.0 | 12 | 150 | #1 | 54305 |
| 7479 | 22761 | 70.4 | 61.5 | 25 | 282 | #5 | 54306 |
| 7480 | 22762 | 80.8 | 68.4 | 33 | 563 | #7 | 54307 |
| 7481 | 22763 | 64.8 | 59.3 | 14 | 248 | #3 | 54308 |
| 7482 | 22764 | 67.2 | 59.6 | 17 | 271 | #4 | 54309 |
| 7483 | 22765 | 50.0 | 50.0 (271) | 16 | 150 | #1 | 54310 |
| 7484 | 22766 | 50.0 | 50.0 | 12 | 150 | #1 | 54311 |
| 7485 | 22767 | 50.0 | 50.0 | 12 | 150 | #1 | 54312 |
| 7486 | 22768 | 68.8 | 59.3 | 20 | 245 | #4 | 54313 |
| 7487 | 22769 | 68.0 | 62.2 | 20 | 382 | #4 | 54314 |
| 7488 | 22770 | 72.0 | 59.6 | 36 | 241 | #5 | 54315 |
| 7489 | 22771 | 67.2 | 61.5 | 19 | 270 | #4 | 54316 |
| 7490 | 22772 | 50.0 | 50.0 (125) | 12 | 150 | #1 | 54317 |
| 7491 | 22773 | 77.6 | 66.5 | 31 | 527 | #6 | 54318 |
| 7492 | 22774 | 68.0 | 60.4 | 17 | 279 | #4 | 54319 |
| 7493 | 22775 | 78.4 | 66.9 | 37 | 448 | #6 | 54320 |
| 7494 | 22776 | 50.0 | 50.0 | 12 | 150 | #1 | 54321 |
| 7495 | 22777 | 63.2 | 56.7 | 12 | 249 | #3 | 54322 |
| 7496 | 22778 | 80.0 | 65.1 | 18 | 452 | #6 | 54323 |
| 7497 | 22779 | 72.8 | 64.7 | 36 | 455 | #5 | 54324 |
| 7498 | 22780 | 68.8 | 62.5 | 22 | 646 | #4 | 54325 |
| 7499 | 22781 | 61.6 | 52.0 | 15 | 168 | #3 | 54326 |
| 7500 | 22782 | 63.2 | 61.8 (152) | 13 | 167 | #3 | 54327 |
| 7501 | 22783 | 67.2 | 58.9 | 17 | 229 | #4 | 54328 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7502 | 22784 | 62.4 | 54.2 | 14 | 189 | #3 | 54329 |
| 7503 | 22785 | 50.0 | 50.0 | 12 | 150 | #1 | 54330 |
| 7504 | 22786 | 69.6 | 63.6 | 22 | 381 | #4 | 54331 |
| 7505 | 22787 | 57.9 (107) | — | 18 | 172 | #2 | 54332 |
| 7506 | 22788 | 62.4 | 58.9 | 18 | 215 | #3 | 54333 |
| 7507 | 22789 | 50.0 | 50.0 | 12 | 150 | #1 | 54334 |
| 7508 | 22790 | 67.2 | 57.5 | 29 | 237 | #4 | 54335 |
| 7509 | 22791 | 68.8 | 61.1 | 22 | 284 | #4 | 54336 |
| 7510 | 22792 | 50.0 | 50.0 | 12 | 150 | #1 | 54337 |
| 7511 | 22793 | 64.0 | 57.6 (238) | 16 | 185 | #3 | 54338 |
| 7512 | 22794 | 68.8 | 61.1 | 25 | 321 | #4 | 54339 |
| 7513 | 22795 | 67.2 | 60.5 (205) | 22 | 200 | #4 | 54340 |
| 7514 | 22796 | 66.4 | 58.9 | 16 | 240 | #4 | 54341 |
| 7515 | 22797 | 71.2 | 63.3 | 22 | 389 | #5 | 54342 |
| 7516 | 22798 | 66.4 | 59.6 | 16 | 247 | #4 | 54343 |
| 7517 | 22799 | 70.4 | 58.5 (253) | 31 | 238 | #5 | 54344 |
| 7518 | 22800 | 50.0 (75) | — | 12 | 150 | #1 | 54345 |
| 7519 | 22801 | 65.6 | 58.4 (231) | 20 | 183 | #4 | 54346 |
| 7520 | 22802 | 72.0 | 65.1 | 24 | 466 | #5 | 54347 |
| 7521 | 22803 | 73.6 | 62.2 | 24 | 291 | #5 | 54348 |
| 7522 | 22804 | 68.0 | 60.0 | 21 | 285 | #4 | 54349 |
| 7523 | 22805 | 66.4 | 58.5 | 20 | 243 | #4 | 54350 |
| 7524 | 22806 | 63.2 | 50.0 (191) | 16 | 170 | #3 | 54351 |
| 7525 | 22807 | 61.6 | 60.7 (135) | 13 | 150 | #3 | 54352 |
| 7526 | 22808 | 62.4 | 57.8 | 15 | 185 | #3 | 54353 |
| 7527 | 22809 | 50.0 | 50.0 | 12 | 150 | #1 | 54354 |
| 7528 | 22810 | 64.0 | 58.5 | 16 | 214 | #3 | 54355 |
| 7529 | 22811 | 68.8 | 59.3 | 20 | 233 | #4 | 54356 |
| 7530 | 22812 | 87.2 | 70.2 | 23 | 583 | #8 | 54357 |
| 7531 | 22813 | 72.0 | 64.0 (236) | 21 | 310 | #5 | 54358 |
| 7532 | 22814 | 70.4 | 62.5 | 29 | 356 | #5 | 54359 |
| 7533 | 22815 | 50.0 | 50.0 | 12 | 150 | #1 | 54360 |
| 7534 | 22816 | 75.2 | 63.6 | 24 | 317 | #6 | 54361 |
| 7535 | 22817 | 69.6 | 58.5 | 17 | 251 | #4 | 54362 |
| 7536 | 22818 | 50.0 | 50.0 | 12 | 150 | #1 | 54363 |
| 7537 | 22819 | 67.2 | 60.0 | 16 | 247 | #4 | 54364 |
| 7538 | 22820 | 70.4 | 66.2 | 21 | 457 | #5 | 54365 |
| 7539 | 22821 | 68.8 | 60.4 | 17 | 265 | #4 | 54366 |
| 7540 | 22822 | 68.0 | 59.6 | 22 | 291 | #4 | 54367 |
| 7541 | 22823 | 60.8 | 55.1 (196) | 15 | 178 | #3 | 54368 |
| 7542 | 22824 | 66.4 | 60.0 | 19 | 229 | #4 | 54369 |
| 7543 | 22825 | 55.2 | 50.0 (202) | 14 | 150 | #2 | 54370 |
| 7544 | 22826 | 71.2 | 62.9 | 21 | 339 | #5 | 54371 |
| 7545 | 22827 | 64.8 | 50.0 | 20 | 215 | #3 | 54372 |
| 7546 | 22828 | 68.8 | 59.3 | 18 | 276 | #4 | 54373 |
| 7547 | 22829 | 68.8 | 61.8 | 33 | 261 | #4 | 54374 |
| 7548 | 22830 | 68.0 | 60.0 | 20 | 248 | #4 | 54375 |
| 7549 | 22831 | 70.4 | 61.5 | 22 | 338 | #5 | 54376 |
| 7550 | 22832 | 56.8 | 50.0 (189) | 21 | 191 | #2 | 54377 |
| 7551 | 22833 | 67.2 | 61.8 | 17 | 263 | #4 | 54378 |
| 7552 | 22834 | 80.0 | 75.6 (201) | 15 | 533 | #6 | 54379 |
| 7553 | 22835 | 50.0 | 50.0 | 12 | 150 | #1 | 54380 |
| 7554 | 22836 | 69.6 | 59.3 | 47 | 416 | #4 | 54381 |
| 7555 | 22837 | 63.2 | 59.9 (182) | 18 | 183 | #3 | 54382 |
| 7556 | 22838 | 68.8 | 62.2 | 24 | 271 | #4 | 54383 |
| 7557 | 22839 | 64.0 | 57.8 | 17 | 212 | #3 | 54384 |
| 7558 | 22840 | 72.8 | 63.6 | 18 | 358 | #5 | 54385 |
| 7559 | 22841 | 56.8 | 50.0 | 12 | 150 | #2 | 54386 |
| 7560 | 22842 | 72.0 | 63.3 | 22 | 327 | #5 | 54387 |
| 7561 | 22843 | 62.4 | 52.4 | 20 | 200 | #3 | 54388 |
| 7562 | 22844 | 72.4 (76) | — | 16 | 154 | #5 | 54389 |
| 7563 | 22845 | 64.8 | 58.5 | 20 | 201 | #3 | 54390 |
| 7564 | 22846 | 61.6 | 50.0 (252) | 15 | 152 | #3 | 54391 |
| 7565 | 22847 | 75.2 | 64.7 | 21 | 477 | #6 | 54392 |
| 7566 | 22848 | 61.6 | 50.0 | 13 | 165 | #3 | 54393 |
| 7567 | 22849 | 64.0 | 58.2 | 14 | 197 | #3 | 54394 |
| 7568 | 22850 | 67.2 | 58.5 | 20 | 233 | #4 | 54395 |
| 7569 | 22851 | 50.0 | 50.0 | 12 | 150 | #1 | 54396 |
| 7570 | 22852 | 69.6 | 62.9 | 20 | 306 | #4 | 54397 |
| 7571 | 22853 | 64.0 | 58.5 | 16 | 205 | #3 | 54398 |
| 7572 | 22854 | 50.0 | 50.0 | 12 | 150 | #1 | 54399 |
| 7573 | 22855 | 68.8 | 60.0 | 19 | 273 | #4 | 54400 |
| 7574 | 22856 | 67.2 | 61.8 | 22 | 338 | #4 | 54401 |
| 7575 | 22857 | 67.2 | 59.3 | 18 | 214 | #4 | 54402 |
| 7576 | 22858 | 88.2 (76) | — | 21 | 307 | #8 | 54403 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7577 | 22859 | 71.2 | 62.5 | 23 | 318 | #5 | 54404 |
| 7578 | 22860 | 66.4 | 58.2 | 12 | 239 | #4 | 54405 |
| 7579 | 22861 | 50.0 | 50.0 | 12 | 150 | #1 | 54406 |
| 7580 | 22862 | 68.0 | 60.7 | 19 | 305 | #4 | 54407 |
| 7581 | 22863 | 61.6 | 50.0 | 16 | 189 | #3 | 54408 |
| 7582 | 22864 | 60.8 | 53.5 | 12 | 197 | #3 | 54409 |
| 7583 | 22865 | 68.0 | 61.5 | 20 | 297 | #4 | 54410 |
| 7584 | 22866 | 68.8 | 60.0 | 14 | 214 | #4 | 54411 |
| 7585 | 22867 | 73.6 | 61.1 | 20 | 278 | #5 | 54412 |
| 7586 | 22868 | 50.0 | 50.0 | 12 | 150 | #1 | 54413 |
| 7587 | 22869 | 61.6 | 58.6 (181) | 23 | 156 | #3 | 54414 |
| 7588 | 22870 | 63.2 | 50.0 (249) | 15 | 159 | #3 | 54415 |
| 7589 | 22871 | 96.0 | 94.5 | 41 | 1362 | #10 | 54416 |
| 7590 | 22872 | 65.6 | 50.0 | 14 | 232 | #4 | 54417 |
| 7591 | 22873 | 68.8 | 57.5 | 24 | 253 | #4 | 54418 |
| 7592 | 22874 | 70.4 | 63.3 | 20 | 342 | #5 | 54419 |
| 7593 | 22875 | 64.8 | 58.9 | 15 | 210 | #3 | 54420 |
| 7594 | 22876 | 50.0 | 50.0 | 12 | 150 | #1 | 54421 |
| 7595 | 22877 | 65.6 | 59.3 | 14 | 200 | #4 | 54422 |
| 7596 | 22878 | 76.0 | 65.1 | 32 | 428 | #6 | 54423 |
| 7597 | 22879 | 50.0 | 50.0 | 17 | 162 | #1 | 54424 |
| 7598 | 22880 | 50.0 | 50.0 | 12 | 150 | #1 | 54425 |
| 7599 | 22881 | 61.6 | 50.0 (192) | 15 | 150 | #3 | 54426 |
| 7600 | 22882 | 57.6 | 50.0 (162) | 14 | 152 | #2 | 54427 |
| 7601 | 22883 | 63.2 | 56.0 | 12 | 186 | #3 | 54428 |
| 7602 | 22884 | 50.0 | 50.0 | 12 | 150 | #1 | 54429 |
| 7603 | 22885 | 50.0 | 50.0 | 12 | 150 | #1 | 54430 |
| 7604 | 22886 | 67.2 | 50.0 | 16 | 208 | #4 | 54431 |
| 7605 | 22887 | 68.8 | 61.1 | 19 | 272 | #4 | 54432 |
| 7606 | 22888 | 67.2 | 62.2 | 19 | 365 | #4 | 54433 |
| 7607 | 22889 | 64.8 | 60.0 | 20 | 315 | #3 | 54434 |
| 7608 | 22890 | 75.2 | 66.9 | 24 | 477 | #6 | 54435 |
| 7609 | 22891 | 64.8 | 58.4 (209) | 16 | 174 | #3 | 54436 |
| 7610 | 22892 | 75.2 | 50.2 | 28 | 303 | #6 | 54437 |
| 7611 | 22893 | 72.0 | 63.6 | 26 | 491 | #5 | 54438 |
| 7612 | 22894 | 67.2 | 51.6 | 15 | 220 | #4 | 54439 |
| 7613 | 22895 | 65.6 | 58.2 (177) | 15 | 191 | #4 | 54440 |
| 7614 | 22896 | 74.4 | 65.5 | 31 | 478 | #5 | 54441 |
| 7615 | 22897 | 65.6 | 58.5 | 19 | 220 | #4 | 54442 |
| 7616 | 22898 | 67.2 | 60.4 | 21 | 289 | #4 | 54443 |
| 7617 | 22899 | 50.0 (95) | — | 12 | 150 | #1 | 54444 |
| 7618 | 22900 | 63.2 | 50.0 (186) | 17 | 156 | #3 | 54445 |
| 7619 | 22901 | 65.6 | 57.1 | 15 | 189 | #4 | 54446 |
| 7620 | 22902 | 64.8 | 50.0 | 15 | 292 | #3 | 54447 |
| 7621 | 22903 | 67.2 | 60.0 | 22 | 270 | #4 | 54448 |
| 7622 | 22904 | 63.2 | 58.9 | 19 | 210 | #3 | 54449 |
| 7623 | 22905 | 66.4 | 53.8 | 17 | 221 | #4 | 54450 |
| 7624 | 22906 | 71.2 | 63.3 | 20 | 321 | #5 | 54451 |
| 7625 | 22907 | 50.0 (93) | — | 12 | 150 | #1 | 54452 |
| 7626 | 22908 | 76.0 | 64.4 | 43 | 458 | #6 | 54453 |
| 7627 | 22909 | 50.0 (110) | — | 12 | 150 | #1 | 54454 |
| 7628 | 22910 | 67.2 | 58.9 | 21 | 237 | #4 | 54455 |
| 7629 | 22911 | 69.6 | 61.1 | 24 | 319 | #4 | 54456 |
| 7630 | 22912 | 59.2 | 55.1 (158) | 12 | 151 | #2 | 54457 |
| 7631 | 22913 | 68.0 | 58.9 | 18 | 243 | #4 | 54458 |
| 7632 | 22914 | 61.6 | 57.8 | 12 | 189 | #3 | 54459 |
| 7633 | 22915 | 68.0 | 57.8 | 26 | 304 | #4 | 54460 |
| 7634 | 22916 | 66.4 | 56.4 | 16 | 199 | #4 | 54461 |
| 7635 | 22917 | 50.0 (71) | — | 22 | 150 | #1 | 54462 |
| 7636 | 22918 | 63.2 | 58.2 | 16 | 192 | #3 | 54463 |
| 7637 | 22919 | 61.6 | 50.0 | 14 | 157 | #3 | 54464 |
| 7638 | 22920 | 70.4 | 62.9 | 29 | 291 | #5 | 54465 |
| 7639 | 22921 | 71.2 | 60.4 | 27 | 295 | #5 | 54466 |
| 7640 | 22922 | 50.0 | 50.0 | 14 | 150 | #1 | 54467 |
| 7641 | 22923 | 72.0 | 62.2 | 24 | 304 | #5 | 54468 |
| 7642 | 22924 | 50.0 (71) | — | 26 | 150 | #1 | 54469 |
| 7643 | 22925 | 67.2 | 60.0 | 19 | 222 | #4 | 54470 |
| 7644 | 22926 | 64.8 | 57.8 | 16 | 199 | #3 | 54471 |
| 7645 | 22927 | 61.6 | 50.0 | 14 | 182 | #3 | 54472 |
| 7646 | 22928 | 86.4 | 61.1 | 22 | 572 | #8 | 54473 |
| 7647 | 22929 | 70.4 | 62.9 | 26 | 348 | #5 | — |
| 7648 | 22930 | 63.2 | 50.0 (243) | 23 | 167 | #3 | 54474 |
| 7649 | 22931 | 74.4 | 61.8 | 26 | 296 | #5 | 54475 |
| 7650 | 22932 | 67.2 | 59.6 | 17 | 253 | #4 | 54476 |
| 7651 | 22933 | 50.0 (111) | — | 12 | 150 | #1 | 54477 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7652 | 22934 | 71.2 | 62.2 | 19 | 325 | #5 | 54478 |
| 7653 | 22935 | 72.0 | 60.4 | 28 | 269 | #5 | 54479 |
| 7654 | 22936 | 64.8 | 61.1 | 16 | 247 | #3 | 54480 |
| 7655 | 22937 | 72.0 | 62.5 | 24 | 322 | #5 | 54481 |
| 7656 | 22938 | 68.0 | 61.1 | 22 | 271 | #4 | 54482 |
| 7657 | 22939 | 63.2 | 58.2 | 17 | 211 | #3 | 54483 |
| 7658 | 22940 | 67.2 | 61.1 | 19 | 275 | #4 | 54484 |
| 7659 | 22941 | 66.4 | 58.4 (262) | 14 | 191 | #4 | 54485 |
| 7660 | 22942 | 50.0 | 50.0 | 12 | 150 | #1 | 54486 |
| 7661 | 22943 | 50.0 | 50.0 (135) | 12 | 150 | #1 | 54487 |
| 7662 | 22944 | 60.0 | 50.0 | 12 | 177 | #2 | 54488 |
| 7663 | 22945 | 68.8 | 61.8 | 24 | 313 | #4 | 54489 |
| 7664 | 22946 | 69.6 | 60.0 | 21 | 249 | #4 | 54490 |
| 7665 | 22947 | 66.4 | 50.0 | 16 | 200 | #4 | 54491 |
| 7666 | 22948 | 63.2 | 55.6 | 12 | 195 | #3 | 54492 |
| 7667 | 22949 | 71.2 | 64.0 | 25 | 361 | #5 | 54493 |
| 7668 | 22950 | 67.2 | 60.4 | 18 | 339 | #4 | 54494 |
| 7669 | 22951 | 69.6 | 61.1 (226) | 27 | 216 | #4 | 54495 |
| 7670 | 22952 | 63.2 | 58.5 | 12 | 215 | #3 | 54496 |
| 7671 | 22953 | 66.4 | 50.0 | 15 | 200 | #4 | 54497 |
| 7672 | 22954 | 70.4 | 65.8 | 21 | 509 | #5 | 54498 |
| 7673 | 22955 | 50.0 | 50.0 | 12 | 150 | #1 | 54499 |
| 7674 | 22956 | 66.4 | 61.5 | 19 | 305 | #4 | 54500 |
| 7675 | 22957 | 60.0 | 50.0 (202) | 12 | 150 | #2 | 54501 |
| 7676 | 22958 | 50.0 | 50.0 | 12 | 150 | #1 | 54502 |
| 7677 | 22959 | 70.4 | 62.9 | 19 | 314 | #5 | 54503 |
| 7678 | 22960 | 50.0 | 50.0 | 12 | 150 | #1 | 54504 |
| 7679 | 22961 | 68.8 | 61.1 | 19 | 230 | #4 | 54505 |
| 7680 | 22962 | 77.7 (103) | — | 33 | 289 | #6 | 54506 |
| 7681 | 22963 | 50.0 | 50.0 | 12 | 150 | #1 | 54507 |
| 7682 | 22964 | 50.0 | 50.0 | 12 | 150 | #1 | 54508 |
| 7683 | 22965 | 68.8 | 61.1 | 32 | 333 | #4 | 54509 |
| 7684 | 22966 | 62.4 | 50.0 (169) | 16 | 152 | #3 | 54510 |
| 7685 | 22967 | 66.4 | 60.4 | 21 | 277 | #4 | 54511 |
| 7686 | 22968 | 66.4 | 61.8 | 19 | 300 | #4 | 54512 |
| 7687 | 22969 | 63.2 | 50.0 | 12 | 157 | #3 | 54513 |
| 7688 | 22970 | 69.6 | 61.5 | 19 | 276 | #4 | 54514 |
| 7689 | 22971 | 64.8 | 58.9 | 19 | 195 | #3 | 54515 |
| 7690 | 22972 | 64.8 | 53.5 | 16 | 217 | #3 | 54516 |
| 7691 | 22973 | 50.0 | 50.0 | 12 | 150 | #1 | 54517 |
| 7692 | 22974 | 64.8 | 59.3 | 23 | 230 | #3 | 54518 |
| 7693 | 22975 | 50.0 (68) | — | 12 | 150 | #1 | 54519 |
| 7694 | 22976 | 61.6 | 59.3 | 14 | 244 | #3 | 54520 |
| 7695 | 22977 | 64.0 | 59.5 (220) | 18 | 161 | #3 | 54521 |
| 7696 | 22978 | 50.0 | 50.0 | 12 | 150 | #1 | 54522 |
| 7697 | 22979 | 68.8 | 61.8 | 23 | 390 | #4 | 54523 |
| 7698 | 22980 | 69.6 | 63.6 | 20 | 423 | #4 | 54524 |
| 7699 | 22981 | 68.0 | 62.9 | 27 | 373 | #4 | 54525 |
| 7700 | 22982 | 73.6 | 62.5 | 36 | 318 | #5 | 54526 |
| 7701 | 22983 | 63.2 | 50.0 (271) | 14 | 190 | #3 | 54527 |
| 7702 | 22984 | 65.6 | 58.5 | 17 | 217 | #4 | 54528 |
| 7703 | 22985 | 68.8 | 60.0 | 24 | 271 | #4 | 54529 |
| 7704 | 22986 | 61.6 | 53.8 (143) | 15 | 158 | #3 | 54530 |
| 7705 | 22987 | 68.0 | 61.1 | 24 | 310 | #4 | 54531 |
| 7706 | 22988 | 50.0 | 50.0 (241) | 12 | 150 | #1 | 54532 |
| 7707 | 22989 | 68.8 | 61.1 | 22 | 284 | #4 | 54533 |
| 7708 | 22990 | 57.9 (76) | — | 30 | 187 | #2 | 54534 |
| 7709 | 22991 | 64.8 | 61.1 (157) | 21 | 167 | #3 | 54535 |
| 7710 | 22992 | 61.6 | 50.0 | 21 | 193 | #3 | 54536 |
| 7711 | 22993 | 56.0 | 50.0 (263) | 14 | 158 | #2 | 54537 |
| 7712 | 22994 | 50.0 | 50.0 | 12 | 150 | #1 | 54538 |
| 7713 | 22995 | 63.2 | 50.0 (214) | 13 | 152 | #3 | 54539 |
| 7714 | 22996 | 64.0 | 50.0 | 14 | 179 | #3 | 54540 |
| 7715 | 22997 | 50.0 | 50.0 | 12 | 150 | #1 | 54541 |
| 7716 | 22998 | 90.4 | 90.7 (194) | 32 | 801 | #9 | 54542 |
| 7717 | 22999 | 64.0 | 51.2 (254) | 19 | 171 | #3 | 54543 |
| 7718 | 23000 | 67.2 | 59.3 | 16 | 291 | #4 | 54544 |
| 7719 | 23001 | 50.0 | 50.0 | 12 | 150 | #1 | 54545 |
| 7720 | 23002 | 70.4 | 63.6 | 23 | 449 | #5 | 54546 |
| 7721 | 23003 | 60.8 | 50.0 | 14 | 150 | #3 | 54547 |
| 7722 | 23004 | 71.2 | 64.0 | 22 | 415 | #5 | 54548 |
| 7723 | 23005 | 68.8 | 64.9 (171) | 19 | 284 | #4 | 54549 |
| 7724 | 23006 | 50.0 | 50.0 | 12 | 150 | #1 | 54550 |
| 7725 | 23007 | 74.4 | 64.7 | 28 | 448 | #5 | 54551 |
| 7726 | 23008 | 68.0 | 57.8 | 14 | 207 | #4 | 54552 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7727 | 23009 | 64.8 | 57.8 | 19 | 203 | #3 | 54553 |
| 7728 | 23010 | 64.0 | 58.2 | 12 | 179 | #3 | 54554 |
| 7729 | 23011 | 61.6 | 56.4 | 16 | 220 | #3 | 54555 |
| 7730 | 23012 | 64.0 | 50.0 | 23 | 243 | #3 | 54556 |
| 7731 | 23013 | 50.0 | 50.0 | 12 | 150 | #1 | 54557 |
| 7732 | 23014 | 62.4 | 50.2 | 19 | 196 | #3 | 54558 |
| 7733 | 23015 | 50.0 | 50.0 | 12 | 150 | #1 | 54559 |
| 7734 | 23016 | 50.0 | 50.0 | 12 | 150 | #1 | 54560 |
| 7735 | 23017 | 50.0 | 50.0 | 12 | 150 | #1 | 54561 |
| 7736 | 23018 | 69.6 | 51.3 | 17 | 224 | #4 | 54562 |
| 7737 | 23019 | 69.6 | 61.5 | 19 | 275 | #4 | 54563 |
| 7738 | 23020 | 68.8 | 63.1 (225) | 21 | 234 | #4 | 54564 |
| 7739 | 23021 | 74.4 | 64.0 | 28 | 399 | #5 | 54565 |
| 7740 | 23022 | 66.4 | 54.5 (200) | 17 | 197 | #4 | 54566 |
| 7741 | 23023 | 66.4 | 59.3 (214) | 16 | 177 | #4 | 54567 |
| 7742 | 23024 | 72.1 (68) | — | 28 | 163 | #5 | 54568 |
| 7743 | 23025 | 61.6 | 57.8 | 16 | 217 | #3 | 54569 |
| 7744 | 23026 | 68.8 | 61.8 | 25 | 337 | #4 | 54570 |
| 7745 | 23027 | 64.0 | 50.0 | 20 | 183 | #3 | 54571 |
| 7746 | 23028 | 65.6 | 57.4 (244) | 20 | 205 | #4 | 54572 |
| 7747 | 23029 | 68.8 | 63.3 | 20 | 302 | #4 | 54573 |
| 7748 | 23030 | 68.0 | 59.6 | 19 | 270 | #4 | 54574 |
| 7749 | 23031 | 58.7 (75) | — | 17 | 150 | #2 | 54575 |
| 7750 | 23032 | 68.8 | 62.5 | 17 | 407 | #4 | 54576 |
| 7751 | 23033 | 70.4 | 61.5 | 24 | 314 | #5 | 54577 |
| 7752 | 23034 | 65.6 | 59.3 | 20 | 228 | #4 | 54578 |
| 7753 | 23035 | 77.6 | 64.0 | 26 | 502 | #6 | 54579 |
| 7754 | 23036 | 69.6 | 62.1 (161) | 21 | 204 | #4 | 54580 |
| 7755 | 23037 | 64.8 | 57.5 | 16 | 204 | #3 | 54581 |
| 7756 | 23038 | 70.4 | 64.7 | 22 | 642 | #5 | 54582 |
| 7757 | 23039 | 69.6 | 61.1 | 15 | 281 | #4 | 54583 |
| 7758 | 23040 | 50.0 | 50.0 | 12 | 150 | #1 | 54584 |
| 7759 | 23041 | 59.6 (114) | — | 35 | 223 | #2 | 54585 |
| 7760 | 23042 | 77.6 | 65.1 | 19 | 371 | #6 | 54586 |
| 7761 | 23043 | 67.2 | 61.8 | 17 | 279 | #4 | 54587 |
| 7762 | 23044 | 66.4 | 58.7 (242) | 19 | 198 | #4 | 54588 |
| 7763 | 23045 | 68.8 | 64.0 | 20 | 377 | #4 | 54589 |
| 7764 | 23046 | 68.0 | 61.1 | 27 | 241 | #4 | 54590 |
| 7765 | 23047 | 66.4 | 51.3 | 15 | 204 | #4 | 54591 |
| 7766 | 23048 | 88.0 | 60.0 | 29 | 470 | #8 | 54592 |
| 7767 | 23049 | 97.6 | 90.9 | 66 | 1164 | #10 | 54593 |
| 7768 | 23050 | 50.0 | 50.0 | 12 | 150 | #1 | 54594 |
| 7769 | 23051 | 50.0 | 50.0 | 12 | 150 | #1 | 54595 |
| 7770 | 23052 | 68.8 | 61.8 | 25 | 337 | #4 | 54596 |
| 7771 | 23053 | 65.7 (102) | — | 18 | 150 | #4 | 54597 |
| 7772 | 23054 | 67.2 | 59.3 | 14 | 211 | #4 | 54598 |
| 7773 | 23055 | 72.8 | 61.1 | 25 | 342 | #5 | 54599 |
| 7774 | 23056 | 66.4 | 58.9 | 14 | 184 | #4 | 54600 |
| 7775 | 23057 | 62.4 | 50.0 | 12 | 156 | #3 | 54601 |
| 7776 | 23058 | 69.6 | 62.9 | 20 | 421 | #4 | 54602 |
| 7777 | 23059 | 89.6 | 73.1 | 34 | 600 | #8 | 54603 |
| 7778 | 23060 | 66.4 | 60.0 | 20 | 286 | #4 | 54604 |
| 7779 | 23061 | 64.0 | 52.4 | 14 | 214 | #3 | 54605 |
| 7780 | 23062 | 68.8 | 62.5 | 22 | 288 | #4 | 54606 |
| 7781 | 23063 | 63.2 | 56.0 | 15 | 202 | #3 | 54607 |
| 7782 | 23064 | 68.0 | 63.3 | 19 | 349 | #4 | 54608 |
| 7783 | 23065 | 64.8 | 57.8 | 15 | 214 | #3 | 54609 |
| 7784 | 23066 | 71.2 | 63.6 (228) | 23 | 341 | #5 | 54610 |
| 7785 | 23067 | 50.0 | 50.0 (165) | 12 | 150 | #1 | 54611 |
| 7786 | 23068 | 69.6 | 62.2 | 18 | 340 | #4 | 54612 |
| 7787 | 23069 | 81.6 | 61.8 | 30 | 442 | #7 | 54613 |
| 7788 | 23070 | 68.0 | 61.1 (167) | 39 | 204 | #4 | 54614 |
| 7789 | 23071 | 50.0 | 50.0 | 12 | 150 | #1 | 54615 |
| 7790 | 23072 | 50.0 | 50.0 | 18 | 154 | #1 | 54616 |
| 7791 | 23073 | 64.0 | 50.0 | 15 | 185 | #3 | 54617 |
| 7792 | 23074 | 76.8 | 64.7 | 20 | 478 | #6 | 54618 |
| 7793 | 23075 | 50.0 | 50.0 | 12 | 150 | #1 | 54619 |
| 7794 | 23076 | 50.0 | 50.0 | 12 | 150 | #1 | 54620 |
| 7795 | 23077 | 67.2 | 57.8 | 16 | 244 | #4 | 54621 |
| 7796 | 23078 | 50.0 | 50.0 | 12 | 150 | #1 | 54622 |
| 7797 | 23079 | 65.6 | 59.6 | 13 | 193 | #4 | — |
| 7798 | 23080 | 60.0 | 50.0 | 14 | 178 | #2 | 54623 |
| 7799 | 23081 | 68.0 | 59.6 | 16 | 236 | #4 | 54624 |
| 7800 | 23082 | 50.0 | 50.0 | 12 | 150 | #1 | 54625 |
| 7801 | 23083 | 68.0 | 60.0 | 18 | 265 | #4 | 54626 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7802 | 23084 | 66.4 | 57.1 | 18 | 207 | #4 | 54627 |
| 7803 | 23085 | 50.0 (96) | — | 12 | 150 | #1 | 54628 |
| 7804 | 23086 | 64.8 | 59.6 | 17 | 214 | #3 | 54629 |
| 7805 | 23087 | 50.0 (82) | — | 12 | 150 | #1 | 54630 |
| 7806 | 23088 | 70.4 | 61.8 | 27 | 343 | #5 | 54631 |
| 7807 | 23089 | 62.4 | 59.3 | 14 | 242 | #3 | 54632 |
| 7808 | 23090 | 71.2 | 61.1 | 17 | 295 | #5 | 54633 |
| 7809 | 23091 | 50.0 | 50.0 | 12 | 150 | #1 | 54634 |
| 7810 | 23092 | 68.8 | 64.2 (193) | 24 | 252 | #4 | 54635 |
| 7811 | 23093 | 67.2 | 60.0 | 14 | 252 | #4 | 54636 |
| 7812 | 23094 | 63.2 | 57.8 | 15 | 201 | #3 | 54637 |
| 7813 | 23095 | 85.6 | 69.1 | 30 | 608 | #8 | 54638 |
| 7814 | 23096 | 68.0 | 58.5 | 17 | 215 | #4 | 54639 |
| 7815 | 23097 | 70.3 (91) | — | 18 | 176 | #5 | 54640 |
| 7816 | 23098 | 65.6 | 58.5 | 13 | 220 | #4 | 54641 |
| 7817 | 23099 | 50.0 (117) | — | 14 | 150 | #1 | 54642 |
| 7818 | 23100 | 64.8 | 59.3 | 15 | 233 | #3 | 54643 |
| 7819 | 23101 | 69.6 | 59.3 | 16 | 243 | #4 | 54644 |
| 7820 | 23102 | 70.4 | 60.0 | 25 | 256 | #5 | 54645 |
| 7821 | 23103 | 64.8 | 56.7 | 17 | 201 | #3 | 54646 |
| 7822 | 23104 | 50.0 | 50.0 (261) | 12 | 150 | #1 | 54647 |
| 7823 | 23105 | 68.0 | 60.4 | 25 | 235 | #4 | 54648 |
| 7824 | 23106 | 67.2 | 60.4 | 17 | 291 | #4 | 54649 |
| 7825 | 23107 | 68.0 | 55.6 | 25 | 220 | #4 | 54650 |
| 7826 | 23108 | 56.0 | 50.0 | 12 | 150 | #2 | 54651 |
| 7827 | 23109 | 70.4 | 62.2 | 22 | 350 | #5 | 54652 |
| 7828 | 23110 | 66.4 | 56.9 (274) | 14 | 198 | #4 | 54653 |
| 7829 | 23111 | 50.0 | 50.0 | 12 | 150 | #1 | 54654 |
| 7830 | 23112 | 89.6 | 67.3 | 29 | 589 | #8 | 54655 |
| 7831 | 23113 | 70.4 | 62.9 | 24 | 351 | #5 | 54656 |
| 7832 | 23114 | 70.4 | 64.0 | 23 | 365 | #5 | 54657 |
| 7833 | 23115 | 65.6 | 50.0 | 12 | 165 | #4 | 54658 |
| 7834 | 23116 | 66.4 | 63.1 (176) | 26 | 217 | #4 | 54659 |
| 7835 | 23117 | 67.2 | 61.8 | 18 | 270 | #4 | 54660 |
| 7836 | 23118 | 65.6 | 50.0 | 29 | 203 | #4 | 54661 |
| 7837 | 23119 | 64.8 | 50.0 | 16 | 193 | #3 | 54662 |
| 7838 | 23120 | 68.0 | 59.3 | 26 | 253 | #4 | 54663 |
| 7839 | 23121 | 78.4 | 66.2 | 26 | 489 | #6 | 54664 |
| 7840 | 23122 | 70.4 | 60.4 | 21 | 289 | #5 | 54665 |
| 7841 | 23123 | 50.0 | 50.0 (140) | 14 | 150 | #1 | 54666 |
| 7842 | 23124 | 71.2 | 58.2 | 21 | 249 | #5 | 54667 |
| 7843 | 23125 | 67.2 | 62.5 | 21 | 313 | #4 | 54668 |
| 7844 | 23126 | 72.0 | 61.5 | 22 | 301 | #5 | 54669 |
| 7845 | 23127 | 68.0 | 57.8 (223) | 17 | 210 | #4 | 54670 |
| 7846 | 23128 | 67.2 | 57.8 | 16 | 210 | #4 | 54671 |
| 7847 | 23129 | 68.8 | 61.1 | 18 | 346 | #4 | 54672 |
| 7848 | 23130 | 70.4 | 63.3 | 18 | 319 | #5 | 54673 |
| 7849 | 23131 | 72.0 | 69.1 | 25 | 672 | #5 | 54674 |
| 7850 | 23132 | 71.2 | 62.2 | 24 | 347 | #5 | 54675 |
| 7851 | 23133 | 63.2 | 50.0 | 13 | 188 | #3 | 54676 |
| 7852 | 23134 | 64.8 | 50.0 | 12 | 193 | #3 | 54677 |
| 7853 | 23135 | 63.2 | 51.6 | 16 | 204 | #3 | 54678 |
| 7854 | 23136 | 77.6 | 69.5 | 15 | 577 | #6 | 54679 |
| 7855 | 23137 | 65.6 | 54.2 | 15 | 183 | #4 | 54680 |
| 7856 | 23138 | 75.2 | 59.6 | 17 | 342 | #6 | 54681 |
| 7857 | 23139 | 70.4 | 61.8 | 24 | 342 | #5 | 54682 |
| 7858 | 23140 | 65.6 | 60.4 | 17 | 242 | #4 | 54683 |
| 7859 | 23141 | 62.4 | 56.0 | 17 | 177 | #3 | 54684 |
| 7860 | 23142 | 65.6 | 60.4 | 20 | 302 | #4 | 54685 |
| 7861 | 23143 | 68.8 | 61.5 | 29 | 422 | #4 | 54686 |
| 7862 | 23144 | 64.8 | 51.3 | 27 | 208 | #3 | 54687 |
| 7863 | 23145 | 68.0 | 59.3 | 29 | 262 | #4 | 54688 |
| 7864 | 23146 | 68.0 | 60.4 | 20 | 381 | #4 | 54689 |
| 7865 | 23147 | 71.2 | 61.8 | 23 | 314 | #5 | 54690 |
| 7866 | 23148 | 68.0 | 62.2 | 19 | 435 | #4 | 54691 |
| 7867 | 23149 | 67.2 | 59.6 (274) | 21 | 229 | #4 | 54692 |
| 7868 | 23150 | 68.8 | 61.1 | 22 | 287 | #4 | 54693 |
| 7869 | 23151 | 72.8 | 64.0 | 28 | 398 | #5 | 54694 |
| 7870 | 23152 | 64.0 | 60.0 | 13 | 223 | #3 | 54695 |
| 7871 | 23153 | 72.8 | 60.4 | 25 | 288 | #5 | 54696 |
| 7872 | 23154 | 67.2 | 60.0 | 19 | 246 | #4 | 54697 |
| 7873 | 23155 | 64.0 | 55.3 | 14 | 218 | #3 | 54698 |
| 7874 | 23156 | 65.6 | 57.5 | 15 | 200 | #4 | 54699 |
| 7875 | 23157 | 66.4 | 56.7 | 17 | 199 | #4 | 54700 |
| 7876 | 23158 | 70.4 | 61.5 | 20 | 313 | #5 | 54701 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7877 | 23159 | 68.0 | 62.9 | 20 | 409 | #4 | 54702 |
| 7878 | 23160 | 67.2 | 60.7 | 16 | 238 | #4 | 54703 |
| 7879 | 23161 | 64.0 | 50.0 | 35 | 330 | #3 | 54704 |
| 7880 | 23162 | 74.4 | 65.5 | 28 | 423 | #5 | 54705 |
| 7881 | 23163 | 50.0 | 50.0 | 12 | 150 | #1 | 54706 |
| 7882 | 23164 | 70.4 | 61.5 | 30 | 292 | #5 | 54707 |
| 7883 | 23165 | 67.2 | 60.7 | 17 | 247 | #4 | 54708 |
| 7884 | 23166 | 90.4 | 86.2 | 31 | 1663 | #9 | 54709 |
| 7885 | 23167 | 62.4 | 50.0 (190) | 13 | 158 | #3 | 54710 |
| 7886 | 23168 | 68.0 | 61.1 | 16 | 416 | #4 | 54711 |
| 7887 | 23169 | 71.2 | 64.0 | 26 | 999 | #5 | 54712 |
| 7888 | 23170 | 68.0 | 59.3 | 18 | 235 | #4 | 54713 |
| 7889 | 23171 | 60.8 | 50.0 (222) | 12 | 153 | #3 | 54714 |
| 7890 | 23172 | 64.8 | 58.9 | 17 | 228 | #3 | 54715 |
| 7891 | 23173 | 70.4 | 62.9 | 20 | 338 | #5 | 54716 |
| 7892 | 23174 | 70.4 | 62.5 | 21 | 294 | #5 | 54717 |
| 7893 | 23175 | 58.4 | 50.0 | 12 | 163 | #2 | 54718 |
| 7894 | 23176 | 67.2 | 50.0 | 12 | 222 | #4 | 54719 |
| 7895 | 23177 | 67.2 | 56.7 | 16 | 212 | #4 | 54720 |
| 7896 | 23178 | 70.4 | 63.3 | 22 | 451 | #5 | 54721 |
| 7897 | 23179 | 68.8 | 61.1 | 22 | 339 | #4 | 54722 |
| 7898 | 23180 | 62.4 | 50.0 | 12 | 161 | #3 | 54723 |
| 7899 | 23181 | 71.2 | 61.1 | 23 | 278 | #5 | 54724 |
| 7900 | 23182 | 50.0 | 50.0 | 12 | 150 | #1 | 54725 |
| 7901 | 23183 | 65.6 | 55.2 (248) | 18 | 168 | #4 | 54726 |
| 7902 | 23184 | 80.8 | 67.3 | 35 | 608 | #7 | 54727 |
| 7903 | 23185 | 50.0 | 50.0 | 12 | 150 | #1 | 54728 |
| 7904 | 23186 | 66.4 | 61.5 | 21 | 355 | #4 | 54729 |
| 7905 | 23187 | 73.6 | 52.3 (176) | 33 | 430 | #5 | 54730 |
| 7906 | 23188 | 68.8 | 61.8 | 20 | 333 | #4 | 54731 |
| 7907 | 23189 | 98.4 | 96.0 | 81 | 1290 | #10 | 54732 |
| 7908 | 23190 | 64.0 | 53.5 (256) | 18 | 171 | #3 | 54733 |
| 7909 | 23191 | 72.8 | 60.7 | 27 | 325 | #5 | 54734 |
| 7910 | 23192 | 50.0 | 50.0 | 12 | 150 | #1 | 54735 |
| 7911 | 23193 | 84.8 | 84.1 (126) | 22 | 490 | #7 | 54736 |
| 7912 | 23194 | 61.6 | 50.0 | 18 | 169 | #3 | 54737 |
| 7913 | 23195 | 68.8 | 59.3 | 17 | 252 | #4 | 54738 |
| 7914 | 23196 | 71.2 | 62.2 | 25 | 288 | #5 | 54739 |
| 7915 | 23197 | 63.2 | 50.0 | 16 | 174 | #3 | 54740 |
| 7916 | 23198 | 50.0 | 50.0 (204) | 13 | 150 | #1 | 54741 |
| 7917 | 23199 | 50.0 | 50.0 | 12 | 150 | #1 | 54742 |
| 7918 | 23200 | 72.0 | 67.1 (155) | 28 | 271 | #5 | 54743 |
| 7919 | 23201 | 50.0 | 50.0 (135) | 12 | 150 | #1 | 54744 |
| 7920 | 23202 | 50.0 | 50.0 | 12 | 150 | #1 | 54745 |
| 7921 | 23203 | 65.6 | 57.8 | 19 | 250 | #4 | 54746 |
| 7922 | 23204 | 62.4 | 50.0 | 12 | 162 | #3 | 54747 |
| 7923 | 23205 | 50.0 | 50.0 | 12 | 150 | #1 | 54748 |
| 7924 | 23206 | 63.2 | 50.0 | 15 | 205 | #3 | 54749 |
| 7925 | 23207 | 63.2 | 50.0 (227) | 13 | 150 | #3 | 54750 |
| 7926 | 23208 | 70.4 | 59.6 | 22 | 259 | #5 | 54751 |
| 7927 | 23209 | 65.6 | 58.5 | 13 | 228 | #4 | 54752 |
| 7928 | 23210 | 67.2 | 50.0 | 20 | 216 | #4 | 54753 |
| 7929 | 23211 | 65.6 | 60.4 | 20 | 258 | #4 | 54754 |
| 7930 | 23212 | 50.0 | 50.0 | 12 | 150 | #1 | 54755 |
| 7931 | 23213 | 68.8 | 60.7 | 20 | 276 | #4 | 54756 |
| 7932 | 23214 | 72.0 | 64.4 | 27 | 879 | #5 | 54757 |
| 7933 | 23215 | 70.4 | 62.5 | 25 | 343 | #5 | 54758 |
| 7934 | 23216 | 50.0 | 50.0 | 32 | 155 | #1 | 54759 |
| 7935 | 23217 | 68.8 | 62.2 | 21 | 284 | #4 | 54760 |
| 7936 | 23218 | 70.4 | 64.4 | 21 | 414 | #5 | 54761 |
| 7937 | 23219 | 50.0 | 50.0 | 13 | 154 | #1 | 54762 |
| 7938 | 23220 | 70.4 | 60.4 | 23 | 301 | #5 | 54763 |
| 7939 | 23221 | 67.2 | 60.7 | 18 | 455 | #4 | 54764 |
| 7940 | 23222 | 50.0 | 50.0 | 12 | 150 | #1 | 54765 |
| 7941 | 23223 | 73.6 | 62.2 | 28 | 484 | #5 | 54766 |
| 7942 | 23224 | 84.0 | 81.1 (222) | 20 | 726 | #7 | 54767 |
| 7943 | 23225 | 81.6 | 63.3 | 21 | 424 | #7 | 54768 |
| 7944 | 23226 | 67.2 | 59.3 | 14 | 221 | #4 | 54769 |
| 7945 | 23227 | 60.8 | 57.1 | 15 | 221 | #3 | 54770 |
| 7946 | 23228 | 68.0 | 63.3 | 29 | 377 | #4 | 54771 |
| 7947 | 23229 | 74.4 | 62.5 | 25 | 387 | #5 | 54772 |
| 7948 | 23230 | 65.6 | 57.8 | 15 | 194 | #4 | 54773 |
| 7949 | 23231 | 63.2 | 54.2 | 12 | 224 | #3 | 54774 |
| 7950 | 23232 | 62.4 | 58.5 | 13 | 180 | #3 | 54775 |
| 7951 | 23233 | 62.4 | 50.0 (211) | 18 | 163 | #3 | 54776 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 7952 | 23234 | 50.0 | 50.0 | 19 | 151 | #1 | 54777 |
| 7953 | 23235 | 63.2 | 50.0 (204) | 16 | 166 | #3 | 54778 |
| 7954 | 23236 | 59.2 | 50.0 | 12 | 182 | #2 | 54779 |
| 7955 | 23237 | 67.2 | 60.4 | 18 | 271 | #4 | 54780 |
| 7956 | 23238 | 69.6 | 63.6 | 24 | 370 | #4 | 54781 |
| 7957 | 23239 | 64.8 | 50.0 | 16 | 297 | #3 | 54782 |
| 7958 | 23240 | 70.4 | 60.7 | 27 | 346 | #5 | 54783 |
| 7959 | 23241 | 68.0 | 59.6 | 19 | 268 | #4 | 54784 |
| 7960 | 23242 | 68.8 | 61.1 | 22 | 285 | #4 | 54785 |
| 7961 | 23243 | 50.0 | 50.0 | 12 | 150 | #1 | 54786 |
| 7962 | 23244 | 50.0 | 50.0 | 12 | 150 | #1 | 54787 |
| 7963 | 23245 | 64.8 | 54.9 (213) | 15 | 167 | #3 | 54788 |
| 7964 | 23246 | 65.6 | 53.8 | 16 | 178 | #4 | 54789 |
| 7965 | 23247 | 73.0 (74) | — | 21 | 167 | #5 | 54790 |
| 7966 | 23248 | 64.8 | 58.9 | 15 | 217 | #3 | 54791 |
| 7967 | 23249 | 78.4 | 63.6 | 24 | 380 | #6 | 54792 |
| 7968 | 23250 | 68.8 | 58.9 | 20 | 240 | #4 | 54793 |
| 7969 | 23251 | 50.0 | 50.0 (135) | 12 | 150 | #1 | 54794 |
| 7970 | 23252 | 68.0 | 59.6 | 31 | 271 | #4 | 54795 |
| 7971 | 23253 | 64.0 | 60.4 | 17 | 206 | #3 | 54796 |
| 7972 | 23254 | 60.8 | 50.0 | 13 | 162 | #3 | 54797 |
| 7973 | 23255 | 72.0 | 51.0 (208) | 15 | 306 | #5 | 54798 |
| 7974 | 23256 | 69.6 | 63.6 | 22 | 461 | #4 | 54799 |
| 7975 | 23257 | 61.6 | 57.1 | 15 | 207 | #3 | 54800 |
| 7976 | 23258 | 67.2 | 55.6 | 14 | 238 | #4 | 54801 |
| 7977 | 23259 | 69.6 | 60.7 | 19 | 306 | #4 | 54802 |
| 7978 | 23260 | 61.6 | 57.5 | 14 | 195 | #3 | 54803 |
| 7979 | 23261 | 66.4 | 60.7 | 22 | 344 | #4 | 54804 |
| 7980 | 23262 | 66.4 | 58.9 | 14 | 231 | #4 | 54805 |
| 7981 | 23263 | 50.0 | 50.0 | 12 | 150 | #1 | 54806 |
| 7982 | 23264 | 60.0 | 51.1 (180) | 15 | 166 | #2 | 54807 |
| 7983 | 23265 | 64.8 | 58.2 | 17 | 210 | #3 | 54808 |
| 7984 | 23266 | 68.8 | 62.2 | 20 | 306 | #4 | 54809 |
| 7985 | 23267 | 65.6 | 57.5 | 17 | 214 | #4 | 54810 |
| 7986 | 23268 | 64.0 | 50.0 (237) | 14 | 160 | #3 | 54811 |
| 7987 | 23269 | 50.0 | 50.0 | 13 | 165 | #1 | 54812 |
| 7988 | 23270 | 64.0 | 56.0 | 14 | 196 | #3 | 54813 |
| 7989 | 23271 | 70.4 | 62.2 | 18 | 362 | #5 | 54814 |
| 7990 | 23272 | 67.2 | 58.5 | 27 | 211 | #4 | 54815 |
| 7991 | 23273 | 68.8 | 63.3 | 24 | 350 | #4 | 54816 |
| 7992 | 23274 | 54.4 | 50.0 | 12 | 176 | #1 | 54817 |
| 7993 | 23275 | 50.0 | 50.0 | 12 | 150 | #1 | 54818 |
| 7994 | 23276 | 68.8 | 59.6 | 19 | 250 | #4 | 54819 |
| 7995 | 23277 | 72.0 | 60.7 | 22 | 296 | #5 | 54820 |
| 7996 | 23278 | 50.0 | 50.0 (192) | 12 | 150 | #1 | 54821 |
| 7997 | 23279 | 50.0 | 50.0 (207) | 12 | 150 | #1 | 54822 |
| 7998 | 23280 | 68.8 | 63.3 | 24 | 347 | #4 | 54823 |
| 7999 | 23281 | 68.8 | 58.9 | 23 | 250 | #4 | 54824 |
| 8000 | 23282 | 63.2 | 50.0 | 13 | 163 | #3 | 54825 |
| 8001 | 23283 | 68.0 | 62.5 | 22 | 343 | #4 | 54826 |
| 8002 | 23284 | 82.4 | 63.3 | 31 | 448 | #7 | 54827 |
| 8003 | 23285 | 64.0 | 57.3 (248) | 17 | 180 | #3 | 54828 |
| 8004 | 23286 | 50.0 | 50.0 (129) | 12 | 150 | #1 | 54829 |
| 8005 | 23287 | 69.6 | 63.6 | 22 | 441 | #4 | 54830 |
| 8006 | 23288 | 66.4 | 58.5 | 17 | 233 | #4 | 54831 |
| 8007 | 23289 | 66.4 | 60.7 | 21 | 263 | #4 | 54832 |
| 8008 | 23290 | 77.6 | 62.9 | 39 | 351 | #6 | 54833 |
| 8009 | 23291 | 55.2 | 50.0 (144) | 12 | 155 | #2 | 54834 |
| 8010 | 23292 | 68.8 | 62.2 | 22 | 330 | #4 | 54835 |
| 8011 | 23293 | 62.4 | 50.0 | 14 | 164 | #3 | 54836 |
| 8012 | 23294 | 68.8 | 60.0 | 24 | 252 | #4 | 54837 |
| 8013 | 23295 | 50.0 | 50.0 | 12 | 150 | #1 | 54838 |
| 8014 | 23296 | 68.8 | 60.4 | 22 | 260 | #4 | 54839 |
| 8015 | 23297 | 67.2 | 61.5 | 26 | 347 | #4 | 54840 |
| 8016 | 23298 | 80.0 | 71.3 | 30 | 567 | #6 | 54841 |
| 8017 | 23299 | 63.2 | 50.0 (238) | 13 | 163 | #3 | 54842 |
| 8018 | 23300 | 68.0 | 60.7 | 23 | 272 | #4 | 54843 |
| 8019 | 23301 | 65.6 | 62.5 (160) | 22 | 180 | #4 | 54844 |
| 8020 | 23302 | 50.0 | 50.0 | 12 | 150 | #1 | 54845 |
| 8021 | 23303 | 68.0 | 62.5 (200) | 19 | 219 | #4 | 54846 |
| 8022 | 23304 | 72.0 | 66.2 | 27 | 410 | #5 | 54847 |
| 8023 | 23305 | 65.6 | 61.8 | 18 | 296 | #4 | 54848 |
| 8024 | 23306 | 98.4 | 93.0 (157) | 67 | 714 | #10 | 54849 |
| 8025 | 23307 | 69.6 | 65.1 (195) | 26 | 295 | #4 | 54850 |
| 8026 | 23308 | 70.4 | 60.9 (207) | 24 | 259 | #5 | 54851 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8027 | 23309 | 71.2 | 64.4 | 24 | 362 | #5 | 54852 |
| 8028 | 23310 | 68.0 | 59.6 | 17 | 262 | #4 | 54853 |
| 8029 | 23311 | 69.6 | 62.2 | 24 | 378 | #4 | 54854 |
| 8030 | 23312 | 64.8 | 57.5 | 13 | 198 | #3 | 54855 |
| 8031 | 23313 | 61.6 | 56.4 | 14 | 192 | #3 | 54856 |
| 8032 | 23314 | 64.8 | 53.2 (158) | 12 | 158 | #3 | 54857 |
| 8033 | 23315 | 70.4 | 63.3 | 20 | 368 | #5 | 54858 |
| 8034 | 23316 | 68.8 | 61.1 | 21 | 312 | #4 | 54859 |
| 8035 | 23317 | 66.4 | 53.5 | 17 | 306 | #4 | 54860 |
| 8036 | 23318 | 66.4 | 59.6 | 20 | 212 | #4 | 54861 |
| 8037 | 23319 | 66.4 | 58.9 | 17 | 244 | #4 | 54862 |
| 8038 | 23320 | 68.0 | 60.7 | 17 | 234 | #4 | 54863 |
| 8039 | 23321 | 64.0 | 57.5 | 12 | 298 | #3 | 54864 |
| 8040 | 23322 | 64.8 | 50.0 | 13 | 207 | #3 | 54865 |
| 8041 | 23323 | 65.6 | 59.3 | 20 | 206 | #4 | 54866 |
| 8042 | 23324 | 68.8 | 62.2 | 19 | 310 | #4 | 54867 |
| 8043 | 23325 | 68.8 | 61.1 | 17 | 314 | #4 | 54868 |
| 8044 | 23326 | 65.6 | 58.2 | 17 | 201 | #4 | 54869 |
| 8045 | 23327 | 65.6 | 58.5 | 15 | 232 | #4 | 54870 |
| 8046 | 23328 | 68.0 | 50.0 | 16 | 185 | #4 | 54871 |
| 8047 | 23329 | 68.8 | 59.6 | 25 | 248 | #4 | 54872 |
| 8048 | 23330 | 56.7 (120) | — | 12 | 150 | #2 | 54873 |
| 8049 | 23331 | 52.0 | 50.0 | 17 | 189 | #1 | 54874 |
| 8050 | 23332 | 78.4 | 61.1 | 16 | 560 | #6 | 54875 |
| 8051 | 23333 | 50.0 | 50.0 | 12 | 150 | #1 | 54876 |
| 8052 | 23334 | 63.2 | 53.5 | 14 | 203 | #3 | 54877 |
| 8053 | 23335 | 68.0 | 62.2 | 21 | 322 | #4 | 54878 |
| 8054 | 23336 | 74.4 | 67.3 | 25 | 590 | #5 | 54879 |
| 8055 | 23337 | 50.0 | 50.0 | 19 | 151 | #1 | 54880 |
| 8056 | 23338 | 71.2 | 63.6 | 21 | 811 | #5 | 54881 |
| 8057 | 23339 | 71.2 | 62.2 | 22 | 301 | #5 | 54882 |
| 8058 | 23340 | 68.0 | 61.8 | 21 | 384 | #4 | 54883 |
| 8059 | 23341 | 67.2 | 54.5 | 20 | 224 | #4 | 54884 |
| 8060 | 23342 | 66.4 | 59.3 | 23 | 285 | #4 | 54885 |
| 8061 | 23343 | 70.4 | 61.5 | 22 | 324 | #5 | 54886 |
| 8062 | 23344 | 67.2 | 59.3 | 17 | 280 | #4 | 54887 |
| 8063 | 23345 | 50.0 | 50.0 | 12 | 150 | #1 | 54888 |
| 8064 | 23346 | 66.4 | 59.6 | 17 | 273 | #4 | 54889 |
| 8065 | 23347 | 50.0 | 50.0 | 12 | 150 | #1 | 54890 |
| 8066 | 23348 | 63.2 | 50.0 (222) | 15 | 159 | #3 | 54891 |
| 8067 | 23349 | 66.4 | 58.5 | 17 | 231 | #4 | 54892 |
| 8068 | 23350 | 60.8 | 56.7 (224) | 18 | 164 | #3 | 54893 |
| 8069 | 23351 | 50.0 | 50.0 | 12 | 150 | #1 | 54894 |
| 8070 | 23352 | 63.2 | 56.4 (257) | 17 | 157 | #3 | 54895 |
| 8071 | 23353 | 64.8 | 61.1 | 19 | 216 | #3 | 54896 |
| 8072 | 23354 | 68.0 | 62.4 (210) | 18 | 200 | #4 | 54897 |
| 8073 | 23355 | 72.0 | 60.0 | 33 | 268 | #5 | 54898 |
| 8074 | 23356 | 68.0 | 57.5 | 26 | 224 | #4 | 54899 |
| 8075 | 23357 | 69.6 | 60.7 | 20 | 265 | #4 | 54900 |
| 8076 | 23358 | 69.6 | 64.0 | 27 | 279 | #4 | 54901 |
| 8077 | 23359 | 61.6 | 50.0 | 15 | 163 | #3 | 54902 |
| 8078 | 23360 | 71.2 | 68.1 (138) | 23 | 241 | #5 | 54903 |
| 8079 | 23361 | 72.0 | 62.5 | 19 | 323 | #5 | 54904 |
| 8080 | 23362 | 72.8 | 60.0 | 19 | 304 | #5 | 54905 |
| 8081 | 23363 | 75.2 | 66.9 | 20 | 619 | #6 | 54906 |
| 8082 | 23364 | 66.4 | 60.4 | 15 | 242 | #4 | 54907 |
| 8083 | 23365 | 50.0 | 50.0 | 12 | 150 | #1 | 54908 |
| 8084 | 23366 | 63.2 | 50.0 (273) | 19 | 191 | #3 | 54909 |
| 8085 | 23367 | 61.6 | 50.0 | 14 | 153 | #3 | 54910 |
| 8086 | 23368 | 68.8 | 62.2 | 19 | 267 | #4 | 54911 |
| 8087 | 23369 | 72.0 | 62.9 | 28 | 352 | #5 | 54912 |
| 8088 | 23370 | 68.0 | 59.6 | 16 | 250 | #4 | 54913 |
| 8089 | 23371 | 65.6 | 53.2 (205) | 17 | 175 | #4 | 54914 |
| 8090 | 23372 | 69.6 | 63.6 | 27 | 402 | #4 | 54915 |
| 8091 | 23373 | 67.2 | 56.7 | 22 | 205 | #4 | 54916 |
| 8092 | 23374 | 70.4 | 60.4 | 21 | 320 | #5 | 54917 |
| 8093 | 23375 | 74.4 | 69.1 | 15 | 662 | #5 | 54918 |
| 8094 | 23376 | 60.8 | 50.0 (231) | 17 | 162 | #3 | 54919 |
| 8095 | 23377 | 68.0 | 60.7 | 17 | 354 | #4 | 54920 |
| 8096 | 23378 | 66.4 | 55.2 (194) | 18 | 192 | #4 | 54921 |
| 8097 | 23379 | 64.8 | 50.0 | 14 | 172 | #3 | 54922 |
| 8098 | 23380 | 50.0 | 50.0 | 12 | 150 | #1 | 54923 |
| 8099 | 23381 | 50.0 | 50.0 | 12 | 150 | #1 | 54924 |
| 8100 | 23382 | 60.0 | 56.4 | 13 | 192 | #2 | 54925 |
| 8101 | 23383 | 50.0 | 50.0 | 12 | 150 | #1 | 54926 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8102 | 23384 | 50.0 | 50.0 | 12 | 150 | #1 | 54927 |
| 8103 | 23385 | 65.6 | 50.0 | 15 | 182 | #4 | 54928 |
| 8104 | 23386 | 64.0 | 59.3 | 16 | 210 | #3 | 54929 |
| 8105 | 23387 | 67.2 | 60.4 | 19 | 292 | #4 | 54930 |
| 8106 | 23388 | 61.6 | 56.9 (188) | 19 | 153 | #3 | 54931 |
| 8107 | 23389 | 72.0 | 62.5 | 24 | 340 | #5 | 54932 |
| 8108 | 23390 | 68.8 | 62.2 | 21 | 345 | #4 | 54933 |
| 8109 | 23391 | 62.4 | 51.0 (204) | 15 | 175 | #3 | 54934 |
| 8110 | 23392 | 71.2 | 63.3 | 22 | 362 | #5 | 54935 |
| 8111 | 23393 | 98.4 | 96.5 (254) | 81 | 1189 | #10 | 54936 |
| 8112 | 23394 | 64.0 | 53.5 (256) | 18 | 171 | #3 | 54937 |
| 8113 | 23395 | 65.6 | 60.0 | 18 | 277 | #4 | 54938 |
| 8114 | 23396 | 68.8 | 60.7 | 17 | 249 | #4 | 54939 |
| 8115 | 23397 | 64.8 | 59.3 | 19 | 214 | #3 | 54940 |
| 8116 | 23398 | 65.6 | 50.0 | 19 | 220 | #4 | 54941 |
| 8117 | 23399 | 64.0 | 50.0 (242) | 17 | 169 | #3 | 54942 |
| 8118 | 23400 | 68.8 | 61.5 | 19 | 316 | #4 | 54943 |
| 8119 | 23401 | 68.0 | 52.0 | 25 | 221 | #4 | 54944 |
| 8120 | 23402 | 66.4 | 60.0 | 20 | 276 | #4 | 54945 |
| 8121 | 23403 | 69.6 | 61.5 | 20 | 345 | #4 | 54946 |
| 8122 | 23404 | 76.0 | 72.5 (131) | 19 | 389 | #6 | 54947 |
| 8123 | 23405 | 68.0 | 60.7 | 19 | 278 | #4 | 54948 |
| 8124 | 23406 | 66.4 | 52.0 | 19 | 197 | #4 | 54949 |
| 8125 | 23407 | 58.5 (123) | — | 17 | 173 | #2 | 54950 |
| 8126 | 23408 | 67.2 | 60.4 | 19 | 262 | #4 | 54951 |
| 8127 | 23409 | 65.6 | 64.0 | 13 | 431 | #4 | 54952 |
| 8128 | 23410 | 53.0 (115) | — | 16 | 150 | #1 | 54953 |
| 8129 | 23411 | 60.8 | 50.0 | 12 | 158 | #3 | 54954 |
| 8130 | 23412 | 69.6 | 61.8 | 21 | 323 | #4 | 54955 |
| 8131 | 23413 | 68.0 | 61.5 | 18 | 279 | #4 | 54956 |
| 8132 | 23414 | 68.8 | 62.5 | 21 | 294 | #4 | 54957 |
| 8133 | 23415 | 72.0 | 62.2 | 20 | 454 | #5 | 54958 |
| 8134 | 23416 | 65.6 | 60.4 | 18 | 263 | #4 | 54959 |
| 8135 | 23417 | 64.8 | 50.0 | 14 | 164 | #3 | 54960 |
| 8136 | 23418 | 70.4 | 64.0 | 20 | 371 | #5 | 54961 |
| 8137 | 23419 | 68.8 | 60.4 | 20 | 261 | #4 | 54962 |
| 8138 | 23420 | 64.8 | 50.0 | 16 | 187 | #3 | 54963 |
| 8139 | 23421 | 69.6 | 58.9 | 21 | 233 | #4 | 54964 |
| 8140 | 23422 | 68.8 | 61.5 | 22 | 292 | #4 | 54965 |
| 8141 | 23423 | 70.4 | 50.0 | 25 | 267 | #5 | 54966 |
| 8142 | 23424 | 63.2 | 57.8 | 19 | 206 | #3 | 54967 |
| 8143 | 23425 | 50.0 | 50.0 | 13 | 165 | #1 | 54968 |
| 8144 | 23426 | 50.0 | 50.0 | 12 | 150 | #1 | 54969 |
| 8145 | 23427 | 60.8 | 58.4 (178) | 14 | 156 | #3 | 54970 |
| 8146 | 23428 | 64.0 | 59.3 | 16 | 209 | #3 | 54971 |
| 8147 | 23429 | 50.0 | 50.0 | 12 | 150 | #1 | 54972 |
| 8148 | 23430 | 68.8 | 60.4 | 20 | 248 | #4 | 54973 |
| 8149 | 23431 | 61.6 | 50.0 | 14 | 181 | #3 | 54974 |
| 8150 | 23432 | 50.0 | 50.0 | 12 | 150 | #1 | 54975 |
| 8151 | 23433 | 65.6 | 60.8 (255) | 25 | 244 | #4 | 54976 |
| 8152 | 23434 | 66.4 | 56.4 | 18 | 219 | #4 | 54977 |
| 8153 | 23435 | 50.0 (85) | — | 38 | 185 | #1 | 54978 |
| 8154 | 23436 | 67.2 | 58.2 | 18 | 201 | #4 | 54979 |
| 8155 | 23437 | 65.6 | 50.0 | 17 | 179 | #4 | 54980 |
| 8156 | 23438 | 66.4 | 59.5 (262) | 21 | 226 | #4 | 54981 |
| 8157 | 23439 | 65.6 | 50.0 | 20 | 196 | #4 | 54982 |
| 8158 | 23440 | 63.2 | 55.9 (211) | 16 | 188 | #3 | 54983 |
| 8159 | 23441 | 65.6 | 60.0 | 16 | 245 | #4 | 54984 |
| 8160 | 23442 | 61.6 | 50.0 | 13 | 196 | #3 | 54985 |
| 8161 | 23443 | 69.6 | 61.8 | 17 | 263 | #4 | 54986 |
| 8162 | 23444 | 61.6 | 56.8 (155) | 17 | 164 | #3 | 54987 |
| 8163 | 23445 | 50.0 | 50.0 | 12 | 150 | #1 | 54988 |
| 8164 | 23446 | 72.9 (85) | — | 17 | 175 | #5 | 54989 |
| 8165 | 23447 | 74.4 | 66.2 | 24 | 690 | #5 | 54990 |
| 8166 | 23448 | 68.0 | 60.0 | 18 | 231 | #4 | 54991 |
| 8167 | 23449 | 65.6 | 50.0 | 12 | 200 | #4 | 54992 |
| 8168 | 23450 | 68.8 | 61.8 | 21 | 320 | #4 | 54993 |
| 8169 | 23451 | 64.0 | 50.0 | 14 | 211 | #3 | 54994 |
| 8170 | 23452 | 67.2 | 50.0 | 12 | 244 | #4 | 54995 |
| 8171 | 23453 | 66.4 | 60.0 | 17 | 238 | #4 | 54996 |
| 8172 | 23454 | 67.2 | 59.3 | 21 | 272 | #4 | 54997 |
| 8173 | 23455 | 50.0 | 50.0 | 12 | 150 | #1 | 54998 |
| 8174 | 23456 | 68.0 | 61.1 | 20 | 270 | #4 | 54999 |
| 8175 | 23457 | 66.4 | 57.1 | 38 | 211 | #4 | 55000 |
| 8176 | 23458 | 68.0 | 63.3 | 20 | 308 | #4 | 55001 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8177 | 23459 | 70.4 | 64.7 | 21 | 675 | #5 | 55002 |
| 8178 | 23460 | 98.4 | 96.4 | 92 | 1500 | #10 | 55003 |
| 8179 | 23461 | 64.8 | 51.3 (224) | 14 | 167 | #3 | 55004 |
| 8180 | 23462 | 50.0 | 50.0 | 12 | 150 | #1 | 55005 |
| 8181 | 23463 | 72.0 | 62.6 (273) | 27 | 360 | #5 | 55006 |
| 8182 | 23464 | 68.8 | 62.2 | 20 | 311 | #4 | 55007 |
| 8183 | 23465 | 50.0 | 50.0 | 12 | 150 | #1 | 55008 |
| 8184 | 23466 | 63.4 (93) | — | 19 | 235 | #3 | 55009 |
| 8185 | 23467 | 64.0 | 56.9 (218) | 21 | 268 | #3 | 55010 |
| 8186 | 23468 | 68.8 | 62.5 | 20 | 369 | #4 | 55011 |
| 8187 | 23469 | 50.0 | 50.0 | 12 | 150 | #1 | 55012 |
| 8188 | 23470 | 66.4 | 58.9 | 19 | 252 | #4 | 55013 |
| 8189 | 23471 | 72.8 | 65.8 | 24 | 564 | #5 | 55014 |
| 8190 | 23472 | 68.0 | 59.6 | 15 | 220 | #4 | 55015 |
| 8191 | 23473 | 71.2 | 63.6 | 23 | 394 | #5 | 55016 |
| 8192 | 23474 | 73.6 | 65.1 | 38 | 553 | #5 | 55017 |
| 8193 | 23475 | 64.0 | 55.3 | 14 | 183 | #3 | 55018 |
| 8194 | 23476 | 64.0 | 58.2 | 14 | 189 | #3 | 55019 |
| 8195 | 23477 | 50.0 | 50.0 | 12 | 150 | #1 | 55020 |
| 8196 | 23478 | 68.0 | 58.9 | 17 | 227 | #4 | 55021 |
| 8197 | 23479 | 64.8 | 60.0 | 19 | 231 | #3 | 55022 |
| 8198 | 23480 | 68.8 | 60.0 | 31 | 281 | #4 | 55023 |
| 8199 | 23481 | 63.2 | 51.6 (161) | 15 | 164 | #3 | 55024 |
| 8200 | 23482 | 65.6 | 57.3 (171) | 19 | 172 | #4 | 55025 |
| 8201 | 23483 | 66.4 | 58.2 | 16 | 202 | #4 | 55026 |
| 8202 | 23484 | 64.8 | 53.4 (194) | 18 | 172 | #3 | 55027 |
| 8203 | 23485 | 50.0 | 50.0 | 12 | 150 | #1 | 55028 |
| 8204 | 23486 | 72.0 | 61.8 | 21 | 319 | #5 | 55029 |
| 8205 | 23487 | 64.0 | 56.0 | 24 | 190 | #3 | 55030 |
| 8206 | 23488 | 50.0 | 50.0 | 12 | 150 | #1 | 55031 |
| 8207 | 23489 | 64.8 | 59.8 (184) | 23 | 187 | #3 | 55032 |
| 8208 | 23490 | 74.4 | 64.8 (250) | 32 | 308 | #5 | 55033 |
| 8209 | 23491 | 68.0 | 57.8 | 23 | 216 | #4 | 55034 |
| 8210 | 23492 | 62.4 | 51.3 | 14 | 175 | #3 | 55035 |
| 8211 | 23493 | 64.8 | 50.0 | 13 | 152 | #3 | 55036 |
| 8212 | 23494 | 68.0 | 52.0 | 16 | 217 | #4 | 55037 |
| 8213 | 23495 | 68.6 (121) | — | 30 | 219 | #4 | 55038 |
| 8214 | 23496 | 68.0 | 57.5 | 22 | 218 | #4 | 55039 |
| 8215 | 23497 | 50.0 | 50.0 | 12 | 150 | #1 | 55040 |
| 8216 | 23498 | 73.6 | 60.4 | 23 | 336 | #5 | 55041 |
| 8217 | 23499 | 72.0 | 62.5 | 33 | 404 | #5 | 55042 |
| 8218 | 23500 | 64.8 | 58.5 | 14 | 203 | #3 | 55043 |
| 8219 | 23501 | 73.6 | 67.3 | 22 | 600 | #5 | 55044 |
| 8220 | 23502 | 71.2 | 62.2 | 28 | 312 | #5 | 55045 |
| 8221 | 23503 | 65.3 (124) | — | 15 | 162 | #4 | 55046 |
| 8222 | 23504 | 70.4 | 63.3 | 21 | 368 | #5 | 55047 |
| 8223 | 23505 | 51.2 | 50.0 (204) | 14 | 150 | #1 | 55048 |
| 8224 | 23506 | 67.2 | 59.3 | 18 | 238 | #4 | 55049 |
| 8225 | 23507 | 70.4 | 63.3 | 23 | 294 | #5 | 55050 |
| 8226 | 23508 | 66.4 | 60.2 (251) | 20 | 278 | #4 | 55051 |
| 8227 | 23509 | 80.8 | 52.4 | 25 | 457 | #7 | 55052 |
| 8228 | 23510 | 69.6 | 61.8 | 21 | 299 | #4 | 55053 |
| 8229 | 23511 | 63.2 | 54.2 | 21 | 171 | #3 | 55054 |
| 8230 | 23512 | 68.8 | 65.2 (164) | 18 | 228 | #4 | 55055 |
| 8231 | 23513 | 70.4 | 60.7 | 23 | 288 | #5 | 55056 |
| 8232 | 23514 | 72.8 | 67.6 | 23 | 452 | #5 | 55057 |
| 8233 | 23515 | 66.4 | 58.5 | 17 | 222 | #4 | 55058 |
| 8234 | 23516 | 50.0 | 50.0 | 12 | 150 | #1 | 55059 |
| 8235 | 23517 | 69.6 | 60.7 | 20 | 259 | #4 | 55060 |
| 8236 | 23518 | 72.8 | 64.7 | 27 | 440 | #5 | 55061 |
| 8237 | 23519 | 50.0 (107) | — | 12 | 150 | #1 | 55062 |
| 8238 | 23520 | 50.0 | 50.0 | 12 | 150 | #1 | 55063 |
| 8239 | 23521 | 69.6 | 62.5 | 24 | 335 | #4 | 55064 |
| 8240 | 23522 | 65.6 | 59.6 | 15 | 228 | #4 | 55065 |
| 8241 | 23523 | 60.0 | 50.0 | 12 | 167 | #2 | 55066 |
| 8242 | 23524 | 50.0 | 50.0 | 12 | 150 | #1 | 55067 |
| 8243 | 23525 | 70.4 | 58.5 | 24 | 243 | #5 | 55068 |
| 8244 | 23526 | 50.0 | 50.0 | 12 | 150 | #1 | 55069 |
| 8245 | 23527 | 69.6 | 61.1 | 23 | 307 | #4 | 55070 |
| 8246 | 23528 | 50.0 | 50.0 | 12 | 150 | #1 | 55071 |
| 8247 | 23529 | 65.6 | 50.0 | 14 | 202 | #4 | 55072 |
| 8248 | 23530 | 69.6 | 61.1 | 20 | 325 | #4 | 55073 |
| 8249 | 23531 | 61.6 | 56.8 (220) | 16 | 171 | #3 | 55074 |
| 8250 | 23532 | 70.4 | 62.5 | 22 | 353 | #5 | 55075 |
| 8251 | 23533 | 67.2 | 61.8 | 19 | 359 | #4 | 55076 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8252 | 23534 | 63.2 | 58.5 | 17 | 188 | #3 | 55077 |
| 8253 | 23535 | 70.4 | 62.9 | 22 | 333 | #5 | 55078 |
| 8254 | 23536 | 64.0 | 62.6 (147) | 17 | 172 | #3 | 55079 |
| 8255 | 23537 | 50.0 | 50.0 | 12 | 150 | #1 | 55080 |
| 8256 | 23538 | 50.0 | 50.0 | 12 | 150 | #1 | 55081 |
| 8257 | 23539 | 68.8 | 62.6 (222) | 26 | 272 | #4 | 55082 |
| 8258 | 23540 | 68.8 | 61.8 | 20 | 318 | #4 | 55083 |
| 8259 | 23541 | 68.8 | 62.7 (166) | 21 | 209 | #4 | 55084 |
| 8260 | 23542 | 66.4 | 57.1 | 16 | 184 | #4 | 55085 |
| 8261 | 23543 | 78.4 | 64.0 | 25 | 372 | #6 | 55086 |
| 8262 | 23544 | 76.0 | 73.1 | 18 | 736 | #6 | 55087 |
| 8263 | 23545 | 64.8 | 59.3 | 17 | 242 | #3 | 55088 |
| 8264 | 23546 | 50.0 | 50.0 | 12 | 150 | #1 | 55089 |
| 8265 | 23547 | 75.2 | 65.8 | 23 | 515 | #6 | 55090 |
| 8266 | 23548 | 62.4 | 57.3 (157) | 19 | 158 | #3 | 55091 |
| 8267 | 23549 | 65.6 | 59.6 (230) | 16 | 191 | #4 | 55092 |
| 8268 | 23550 | 65.6 | 58.9 | 17 | 228 | #4 | 55093 |
| 8269 | 23551 | 68.0 | 62.5 | 20 | 509 | #4 | 55094 |
| 8270 | 23552 | 50.0 | 50.0 | 12 | 150 | #1 | 55095 |
| 8271 | 23553 | 50.0 (89) | — | 17 | 150 | #1 | 55096 |
| 8272 | 23554 | 64.8 | 50.0 (205) | 15 | 155 | #3 | 55097 |
| 8273 | 23555 | 68.8 | 58.9 | 17 | 210 | #4 | 55098 |
| 8274 | 23556 | 64.0 | 53.7 (229) | 18 | 164 | #3 | 55099 |
| 8275 | 23557 | 57.6 | 53.5 | 18 | 191 | #2 | 55100 |
| 8276 | 23558 | 68.8 | 60.7 | 21 | 328 | #4 | 55101 |
| 8277 | 23559 | 67.7 (93) | — | 12 | 169 | #4 | 55102 |
| 8278 | 23560 | 66.4 | 60.4 | 20 | 291 | #4 | 55103 |
| 8279 | 23561 | 67.2 | 58.2 | 13 | 222 | #4 | 55104 |
| 8280 | 23562 | 67.2 | 60.0 | 16 | 224 | #4 | 55105 |
| 8281 | 23563 | 67.2 | 58.2 | 18 | 233 | #4 | 55106 |
| 8282 | 23564 | 64.8 | 58.2 | 12 | 196 | #3 | 55107 |
| 8283 | 23565 | 62.4 | 50.0 | 18 | 166 | #3 | 55108 |
| 8284 | 23566 | 50.0 | 50.0 | 12 | 150 | #1 | 55109 |
| 8285 | 23567 | 66.4 | 61.8 | 19 | 291 | #4 | 55110 |
| 8286 | 23568 | 83.2 | 79.6 | 23 | 1514 | #7 | 55111 |
| 8287 | 23569 | 50.0 | 50.0 | 12 | 150 | #1 | 55112 |
| 8288 | 23570 | 63.2 | 55.3 | 14 | 217 | #3 | 55113 |
| 8289 | 23571 | 75.2 | 64.0 | 25 | 478 | #6 | 55114 |
| 8290 | 23572 | 66.4 | 56.7 | 21 | 205 | #4 | 55115 |
| 8291 | 23573 | 68.0 | 59.6 | 21 | 251 | #4 | 55116 |
| 8292 | 23574 | 50.0 | 50.0 | 12 | 150 | #1 | 55117 |
| 8293 | 23575 | 50.0 | 50.0 | 12 | 150 | #1 | 55118 |
| 8294 | 23576 | 68.0 | 59.4 (207) | 30 | 210 | #4 | 55119 |
| 8295 | 23577 | 84.1 (82) | — | 18 | 255 | #7 | 55120 |
| 8296 | 23578 | 66.4 | 52.7 | 15 | 198 | #4 | 55121 |
| 8297 | 23579 | 66.4 | 60.0 | 16 | 232 | #4 | 55122 |
| 8298 | 23580 | 50.0 | 50.0 (133) | 15 | 150 | #1 | 55123 |
| 8299 | 23581 | 68.0 | 60.7 | 22 | 263 | #4 | 55124 |
| 8300 | 23582 | 58.4 | 54.5 | 19 | 178 | #2 | 55125 |
| 8301 | 23583 | 72.8 | 62.2 | 32 | 400 | #5 | 55126 |
| 8302 | 23584 | 50.0 | 50.0 | 12 | 150 | #1 | 55127 |
| 8303 | 23585 | 66.4 | 51.3 | 15 | 209 | #4 | 55128 |
| 8304 | 23586 | 62.4 | 50.0 (229) | 14 | 150 | #3 | 55129 |
| 8305 | 23587 | 68.0 | 61.1 | 20 | 252 | #4 | 55130 |
| 8306 | 23588 | 89.6 | 87.9 (157) | 24 | 618 | #8 | 55131 |
| 8307 | 23589 | 68.0 | 61.1 | 20 | 266 | #4 | 55132 |
| 8308 | 23590 | 66.4 | 50.0 | 14 | 222 | #4 | 55133 |
| 8309 | 23591 | 66.4 | 60.4 | 14 | 329 | #4 | 55134 |
| 8310 | 23592 | 66.4 | 59.6 | 24 | 255 | #4 | 55135 |
| 8311 | 23593 | 72.8 | 64.7 | 24 | 369 | #5 | 55136 |
| 8312 | 23594 | 61.6 | 50.0 (196) | 13 | 153 | #3 | 55137 |
| 8313 | 23595 | 69.6 | 59.3 (263) | 19 | 254 | #4 | 55138 |
| 8314 | 23596 | 74.4 | 64.0 | 33 | 410 | #5 | 55139 |
| 8315 | 23597 | 64.8 | 50.0 (253) | 17 | 164 | #3 | 55140 |
| 8316 | 23598 | 66.4 | 51.3 | 18 | 205 | #4 | 55141 |
| 8317 | 23599 | 69.6 | 58.5 | 23 | 215 | #4 | 55142 |
| 8318 | 23600 | 97.6 | 86.4 (220) | 60 | 910 | #10 | 55143 |
| 8319 | 23601 | 80.8 | 74.2 | 24 | 1001 | #7 | 55144 |
| 8320 | 23602 | 50.0 | 50.0 | 12 | 150 | #1 | 55145 |
| 8321 | 23603 | 50.0 | 50.0 | 12 | 150 | #1 | 55146 |
| 8322 | 23604 | 67.2 | 59.6 (178) | 16 | 174 | #4 | 55147 |
| 8323 | 23605 | 66.4 | 59.6 | 15 | 238 | #4 | 55148 |
| 8324 | 23606 | 66.4 | 57.8 | 13 | 237 | #4 | 55149 |
| 8325 | 23607 | 68.0 | 60.7 | 17 | 366 | #4 | 55150 |
| 8326 | 23608 | 85.6 | 78.2 | 27 | 803 | #8 | 55151 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8327 | 23609 | 60.8 | 50.0 (174) | 17 | 159 | #3 | 55152 |
| 8328 | 23610 | 54.7 (75) | — | 36 | 177 | #1 | 55153 |
| 8329 | 23611 | 71.2 | 65.8 | 21 | 415 | #5 | 55154 |
| 8330 | 23612 | 50.0 | 50.0 | 12 | 150 | #1 | 55155 |
| 8331 | 23613 | 70.4 | 60.4 | 31 | 340 | #5 | 55156 |
| 8332 | 23614 | 70.4 | 60.4 | 28 | 260 | #5 | 55157 |
| 8333 | 23615 | 50.0 | 50.0 (208) | 12 | 150 | #1 | 55158 |
| 8334 | 23616 | 65.6 | 50.0 (191) | 18 | 177 | #4 | 55159 |
| 8335 | 23617 | 65.6 | 58.5 | 17 | 208 | #4 | 55160 |
| 8336 | 23618 | 75.2 | 60.0 | 29 | 343 | #6 | 55161 |
| 8337 | 23619 | 50.0 | 50.0 | 12 | 150 | #1 | 55162 |
| 8338 | 23620 | 63.2 | 50.0 | 12 | 169 | #3 | 55163 |
| 8339 | 23621 | 50.0 | 50.0 | 12 | 150 | #1 | 55164 |
| 8340 | 23622 | 92.0 | 90.8 (185) | 25 | 772 | #9 | 55165 |
| 8341 | 23623 | 64.8 | 58.5 | 18 | 190 | #3 | 55166 |
| 8342 | 23624 | 68.8 | 59.6 | 15 | 322 | #4 | 55167 |
| 8343 | 23625 | 53.0 (100) | — | 17 | 150 | #1 | 55168 |
| 8344 | 23626 | 74.4 | 65.8 | 23 | 611 | #5 | 55169 |
| 8345 | 23627 | 50.0 | 50.0 | 12 | 150 | #1 | 55170 |
| 8346 | 23628 | 67.0 (94) | — | 13 | 153 | #4 | 55171 |
| 8347 | 23629 | 50.0 (108) | — | 12 | 150 | #1 | 55172 |
| 8348 | 23630 | 50.0 | 50.0 | 12 | 150 | #1 | 55173 |
| 8349 | 23631 | 68.0 | 61.5 | 21 | 327 | #4 | 55174 |
| 8350 | 23632 | 66.4 | 57.5 | 17 | 213 | #4 | 55175 |
| 8351 | 23633 | 64.0 | 50.0 (258) | 18 | 168 | #3 | 55176 |
| 8352 | 23634 | 65.6 | 50.0 | 14 | 194 | #4 | 55177 |
| 8353 | 23635 | 79.2 | 67.3 | 25 | 534 | #6 | 55178 |
| 8354 | 23636 | 50.0 (76) | — | 12 | 150 | #1 | 55179 |
| 8355 | 23637 | 60.8 | 57.8 | 12 | 226 | #3 | 55180 |
| 8356 | 23638 | 68.0 | 62.2 | 18 | 318 | #4 | 55181 |
| 8357 | 23639 | 50.0 | 50.0 | 12 | 150 | #1 | 55182 |
| 8358 | 23640 | 68.0 | 61.1 | 19 | 305 | #4 | 55183 |
| 8359 | 23641 | 59.2 | 50.0 (164) | 12 | 150 | #2 | 55184 |
| 8360 | 23642 | 70.4 | 62.5 | 23 | 361 | #5 | 55185 |
| 8361 | 23643 | 68.0 | 61.1 | 20 | 273 | #4 | 55186 |
| 8362 | 23644 | 50.0 (114) | — | 12 | 150 | #1 | 55187 |
| 8363 | 23645 | 66.4 | 58.8 (226) | 16 | 213 | #4 | 55188 |
| 8364 | 23646 | 68.0 | 62.9 | 17 | 385 | #4 | 55189 |
| 8365 | 23647 | 59.2 | 50.0 | 16 | 157 | #2 | 55190 |
| 8366 | 23648 | 66.4 | 60.0 | 16 | 262 | #4 | 55191 |
| 8367 | 23649 | 50.0 | 50.0 | 12 | 150 | #1 | 55192 |
| 8368 | 23650 | 50.0 (76) | — | 12 | 150 | #1 | 55193 |
| 8369 | 23651 | 68.8 | 61.1 | 17 | 297 | #4 | 55194 |
| 8370 | 23652 | 68.8 | 61.5 | 18 | 341 | #4 | 55195 |
| 8371 | 23653 | 65.6 | 50.0 (249) | 16 | 161 | #4 | 55196 |
| 8372 | 23654 | 71.2 | 59.6 | 23 | 243 | #5 | 55197 |
| 8373 | 23655 | 50.0 | 50.0 | 12 | 150 | #1 | 55198 |
| 8374 | 23656 | 67.2 | 60.4 | 19 | 250 | #4 | 55199 |
| 8375 | 23657 | 71.2 | 66.5 (227) | 21 | 354 | #5 | 55200 |
| 8376 | 23658 | 50.0 | 50.0 | 12 | 150 | #1 | 55201 |
| 8377 | 23659 | 69.6 | 58.2 | 13 | 308 | #4 | — |
| 8378 | 23660 | 72.0 | 61.8 | 22 | 315 | #5 | 55202 |
| 8379 | 23661 | 80.0 | 69.1 | 28 | 553 | #6 | 55203 |
| 8380 | 23662 | 60.8 | 57.8 | 12 | 196 | #3 | 55204 |
| 8381 | 23663 | 64.8 | 54.6 (273) | 19 | 176 | #3 | 55205 |
| 8382 | 23664 | 70.4 | 62.5 (144) | 19 | 240 | #5 | 55206 |
| 8383 | 23665 | 66.4 | 59.3 | 20 | 245 | #4 | 55207 |
| 8384 | 23666 | 50.0 | 50.0 | 12 | 150 | #1 | 55208 |
| 8385 | 23667 | 64.8 | 50.0 (241) | 12 | 164 | #3 | 55209 |
| 8386 | 23668 | 73.6 | 59.3 | 28 | 364 | #5 | 55210 |
| 8387 | 23669 | 67.2 | 61.5 | 20 | 352 | #4 | 55211 |
| 8388 | 23670 | 50.0 | 50.0 | 12 | 150 | #1 | 55212 |
| 8389 | 23671 | 70.4 | 63.6 | 23 | 527 | #5 | 55213 |
| 8390 | 23672 | 71.2 | 64.4 | 25 | 474 | #5 | 55214 |
| 8391 | 23673 | 67.2 | 58.5 | 16 | 282 | #4 | 55215 |
| 8392 | 23674 | 72.0 | 61.1 | 19 | 344 | #5 | 55216 |
| 8393 | 23675 | 80.0 | 62.9 | 25 | 426 | #6 | 55217 |
| 8394 | 23676 | 73.6 | 60.4 | 27 | 309 | #5 | 55218 |
| 8395 | 23677 | 60.0 | 50.0 | 16 | 159 | #2 | 55219 |
| 8396 | 23678 | 67.2 | 61.1 | 18 | 316 | #4 | 55220 |
| 8397 | 23679 | 66.4 | 60.7 | 27 | 351 | #4 | 55221 |
| 8398 | 23680 | 68.0 | 61.1 | 19 | 363 | #4 | 55222 |
| 8399 | 23681 | 63.2 | 58.9 | 14 | 206 | #3 | 55223 |
| 8400 | 23682 | 64.2 (109) | — | 21 | 157 | #3 | 55224 |
| 8401 | 23683 | 72.8 | 63.6 | 21 | 415 | #5 | 55225 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8402 | 23684 | 64.0 | 58.5 | 16 | 195 | #3 | 55226 |
| 8403 | 23685 | 50.0 | 50.0 | 12 | 150 | #1 | 55227 |
| 8404 | 23686 | 61.6 | 50.0 | 12 | 150 | #3 | 55228 |
| 8405 | 23687 | 64.8 | 59.6 | 19 | 259 | #3 | 55229 |
| 8406 | 23688 | 65.6 | 60.4 | 19 | 245 | #4 | 55230 |
| 8407 | 23689 | 50.0 | 50.0 | 12 | 150 | #1 | 55231 |
| 8408 | 23690 | 64.0 | 58.9 | 16 | 214 | #3 | 55232 |
| 8409 | 23691 | 64.0 | 50.0 | 16 | 202 | #3 | 55233 |
| 8410 | 23692 | 71.2 | 62.9 | 22 | 399 | #5 | 55234 |
| 8411 | 23693 | 62.4 | 56.4 | 13 | 195 | #3 | 55235 |
| 8412 | 23694 | 65.6 | 60.3 (184) | 28 | 195 | #4 | 55236 |
| 8413 | 23695 | 60.8 | 58.7 (179) | 15 | 150 | #3 | 55237 |
| 8414 | 23696 | 50.0 | 50.0 | 12 | 150 | #1 | 55238 |
| 8415 | 23697 | 70.4 | 65.1 | 21 | 361 | #5 | 55239 |
| 8416 | 23698 | 72.0 | 64.0 | 22 | 354 | #5 | 55240 |
| 8417 | 23699 | 65.6 | 50.0 | 20 | 209 | #4 | 55241 |
| 8418 | 23700 | 63.2 | 50.0 (235) | 16 | 157 | #3 | 55242 |
| 8419 | 23701 | 68.0 | 58.5 | 24 | 276 | #4 | 55243 |
| 8420 | 23702 | 70.4 | 64.4 | 21 | 446 | #5 | 55244 |
| 8421 | 23703 | 72.8 | 67.6 (176) | 27 | 284 | #5 | 55245 |
| 8422 | 23704 | 50.0 | 50.0 | 12 | 150 | #1 | 55246 |
| 8423 | 23705 | 65.6 | 58.2 | 16 | 244 | #4 | 55247 |
| 8424 | 23706 | 68.0 | 52.4 | 16 | 224 | #4 | 55248 |
| 8425 | 23707 | 66.4 | 64.5 (155) | 29 | 181 | #4 | 55249 |
| 8426 | 23708 | 50.0 | 50.0 | 12 | 150 | #1 | 55250 |
| 8427 | 23709 | 50.0 | 50.0 | 12 | 150 | #1 | 55251 |
| 8428 | 23710 | 64.8 | 50.0 | 15 | 189 | #3 | 55252 |
| 8429 | 23711 | 66.4 | 52.6 (228) | 22 | 181 | #4 | 55253 |
| 8430 | 23712 | 50.0 | 50.0 | 12 | 150 | #1 | 55254 |
| 8431 | 23713 | 68.0 | 60.7 | 17 | 256 | #4 | 55255 |
| 8432 | 23714 | 75.2 | 65.8 | 28 | 415 | #6 | 55256 |
| 8433 | 23715 | 74.4 | 66.2 | 21 | 481 | #5 | 55257 |
| 8434 | 23716 | 63.2 | 50.0 | 13 | 152 | #3 | 55258 |
| 8435 | 23717 | 64.0 | 52.6 (228) | 14 | 171 | #3 | 55259 |
| 8436 | 23718 | 64.0 | 55.0 (262) | 22 | 181 | #3 | 55260 |
| 8437 | 23719 | 50.0 | 50.0 | 12 | 150 | #1 | 55261 |
| 8438 | 23720 | 73.6 | 65.8 | 40 | 432 | #5 | 55262 |
| 8439 | 23721 | 66.4 | 60.4 | 19 | 230 | #4 | 55263 |
| 8440 | 23722 | 77.6 | 64.7 | 28 | 375 | #6 | 55264 |
| 8441 | 23723 | 89.6 | 67.3 | 39 | 579 | #8 | 55265 |
| 8442 | 23724 | 66.4 | 53.5 | 17 | 231 | #4 | 55266 |
| 8443 | 23725 | 71.2 | 66.2 | 23 | 410 | #5 | 55267 |
| 8444 | 23726 | 69.6 | 65.1 | 20 | 486 | #4 | 55268 |
| 8445 | 23727 | 70.4 | 60.4 | 23 | 371 | #5 | 55269 |
| 8446 | 23728 | 50.0 | 50.0 | 12 | 150 | #1 | 55270 |
| 8447 | 23729 | 64.0 | 57.1 | 14 | 223 | #3 | 55271 |
| 8448 | 23730 | 68.0 | 60.4 | 20 | 234 | #4 | 55272 |
| 8449 | 23731 | 74.4 | 63.3 | 25 | 374 | #5 | 55273 |
| 8450 | 23732 | 69.6 | 65.1 | 21 | 443 | #4 | 55274 |
| 8451 | 23733 | 50.0 | 50.0 | 12 | 150 | #1 | 55275 |
| 8452 | 23734 | 68.8 | 60.8 (186) | 24 | 214 | #4 | 55276 |
| 8453 | 23735 | 68.8 | 50.0 | 23 | 214 | #4 | 55277 |
| 8454 | 23736 | 66.4 | 57.8 | 14 | 249 | #4 | 55278 |
| 8455 | 23737 | 69.6 | 62.9 | 24 | 373 | #4 | 55279 |
| 8456 | 23738 | 67.2 | 60.4 | 18 | 248 | #4 | 55280 |
| 8457 | 23739 | 69.6 | 61.8 | 21 | 294 | #4 | 55281 |
| 8458 | 23740 | 66.4 | 60.0 (265) | 17 | 227 | #4 | 55282 |
| 8459 | 23741 | 65.6 | 58.9 | 18 | 210 | #4 | 55283 |
| 8460 | 23742 | 50.0 | 50.0 | 12 | 150 | #1 | 55284 |
| 8461 | 23743 | 65.6 | 56.7 | 16 | 185 | #4 | 55285 |
| 8462 | 23744 | 73.6 | 56.4 | 29 | 322 | #5 | 55286 |
| 8463 | 23745 | 74.4 | 62.9 | 20 | 394 | #5 | 55287 |
| 8464 | 23746 | 72.8 | 66.2 | 25 | 568 | #5 | 55288 |
| 8465 | 23747 | 67.2 | 61.5 | 21 | 287 | #4 | 55289 |
| 8466 | 23748 | 67.2 | 59.6 | 26 | 274 | #4 | 55290 |
| 8467 | 23749 | 64.8 | 50.0 | 15 | 235 | #3 | 55291 |
| 8468 | 23750 | 68.8 | 58.5 | 25 | 272 | #4 | 55292 |
| 8469 | 23751 | 64.0 | 60.0 | 16 | 223 | #3 | 55293 |
| 8470 | 23752 | 75.2 | 63.9 (263) | 28 | 352 | #6 | 55294 |
| 8471 | 23753 | 64.0 | 64.0 (125) | 17 | 179 | #3 | 55295 |
| 8472 | 23754 | 59.2 | 50.0 | 12 | 150 | #2 | 55296 |
| 8473 | 23755 | 68.0 | 61.1 | 23 | 281 | #4 | 55297 |
| 8474 | 23756 | 64.8 | 58.2 | 17 | 236 | #3 | 55298 |
| 8475 | 23757 | 60.0 | 50.0 | 12 | 150 | #2 | 55299 |
| 8476 | 23758 | 50.0 (95) | — | 12 | 150 | #1 | — |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8477 | 23759 | 64.8 | 50.0 | 15 | 193 | #3 | 55300 |
| 8478 | 23760 | 50.0 | 50.0 | 15 | 150 | #1 | 55301 |
| 8479 | 23761 | 62.4 | 50.9 | 15 | 208 | #3 | 55302 |
| 8480 | 23762 | 64.0 | 56.0 | 20 | 224 | #3 | 55303 |
| 8481 | 23763 | 67.2 | 50.0 | 23 | 233 | #4 | 55304 |
| 8482 | 23764 | 68.0 | 62.4 (181) | 20 | 217 | #4 | 55305 |
| 8483 | 23765 | 71.2 | 62.5 | 19 | 334 | #5 | 55306 |
| 8484 | 23766 | 50.0 | 50.0 | 12 | 150 | #1 | 55307 |
| 8485 | 23767 | 50.0 | 50.0 | 12 | 150 | #1 | 55308 |
| 8486 | 23768 | 67.2 | 60.0 | 19 | 245 | #4 | 55309 |
| 8487 | 23769 | 60.0 | 50.0 | 19 | 165 | #2 | 55310 |
| 8488 | 23770 | 65.6 | 60.1 (233) | 19 | 208 | #4 | 55311 |
| 8489 | 23771 | 67.2 | 62.5 (168) | 18 | 205 | #4 | 55312 |
| 8490 | 23772 | 68.8 | 60.4 | 19 | 307 | #4 | 55313 |
| 8491 | 23773 | 72.8 | 63.6 | 21 | 350 | #5 | 55314 |
| 8492 | 23774 | 61.6 | 50.0 | 12 | 152 | #3 | 55315 |
| 8493 | 23775 | 69.6 | 60.4 | 26 | 241 | #4 | 55316 |
| 8494 | 23776 | 68.8 | 57.8 | 17 | 254 | #4 | 55317 |
| 8495 | 23777 | 69.6 | 61.1 | 23 | 263 | #4 | 55318 |
| 8496 | 23778 | 68.0 | 61.5 | 21 | 416 | #4 | 55319 |
| 8497 | 23779 | 67.2 | 59.3 | 19 | 244 | #4 | 55320 |
| 8498 | 23780 | 60.0 | 50.0 | 16 | 162 | #2 | 55321 |
| 8499 | 23781 | 66.4 | 58.5 | 15 | 187 | #4 | 55322 |
| 8500 | 23782 | 61.3 (119) | — | 13 | 157 | #3 | 55323 |
| 8501 | 23783 | 68.0 | 61.1 | 18 | 268 | #4 | 55324 |
| 8502 | 23784 | 53.6 | 50.0 | 13 | 151 | #1 | 55325 |
| 8503 | 23785 | 63.2 | 50.0 | 30 | 175 | #3 | 55326 |
| 8504 | 23786 | 65.6 | 61.5 | 20 | 353 | #4 | 55327 |
| 8505 | 23787 | 71.2 | 63.3 | 24 | 551 | #5 | 55328 |
| 8506 | 23788 | 63.2 | 51.6 | 18 | 208 | #3 | 55329 |
| 8507 | 23789 | 68.8 | 61.1 | 33 | 305 | #4 | 55330 |
| 8508 | 23790 | 63.2 | 57.5 | 17 | 237 | #3 | 55331 |
| 8509 | 23791 | 83.2 | 55.3 | 25 | 472 | #7 | 55332 |
| 8510 | 23792 | 50.0 | 50.0 | 12 | 150 | #1 | 55333 |
| 8511 | 23793 | 60.0 | 55.6 | 12 | 247 | #2 | 55334 |
| 8512 | 23794 | 67.2 | 60.0 | 17 | 260 | #4 | 55335 |
| 8513 | 23795 | 50.0 | 50.0 | 12 | 150 | #1 | 55336 |
| 8514 | 23796 | 67.2 | 60.0 | 15 | 204 | #4 | 55337 |
| 8515 | 23797 | 50.0 | 50.0 | 12 | 150 | #1 | 55338 |
| 8516 | 23798 | 68.0 | 61.8 | 21 | 422 | #4 | 55339 |
| 8517 | 23799 | 66.4 | 54.5 | 23 | 205 | #4 | 55340 |
| 8518 | 23800 | 66.4 | 58.9 | 16 | 234 | #4 | 55341 |
| 8519 | 23801 | 50.0 | 50.0 | 12 | 150 | #1 | 55342 |
| 8520 | 23802 | 67.2 | 50.0 | 12 | 186 | #4 | 55343 |
| 8521 | 23803 | 66.4 | 57.1 | 16 | 212 | #4 | 55344 |
| 8522 | 23804 | 66.4 | 54.5 | 17 | 203 | #4 | 55345 |
| 8523 | 23805 | 69.6 | 61.8 | 20 | 315 | #4 | 55346 |
| 8524 | 23806 | 67.2 | 50.0 (168) | 14 | 310 | #4 | 55347 |
| 8525 | 23807 | 71.2 | 64.4 | 22 | 451 | #5 | 55348 |
| 8526 | 23808 | 50.0 (82) | — | 30 | 150 | #1 | 55349 |
| 8527 | 23809 | 50.0 | 50.0 | 12 | 150 | #1 | 55350 |
| 8528 | 23810 | 66.4 | 50.0 | 15 | 213 | #4 | 55351 |
| 8529 | 23811 | 71.2 | 61.5 | 24 | 262 | #5 | 55352 |
| 8530 | 23812 | 64.8 | 56.4 | 14 | 191 | #3 | 55353 |
| 8531 | 23813 | 63.2 | 57.5 | 16 | 195 | #3 | 55354 |
| 8532 | 23814 | 68.8 | 61.5 | 19 | 344 | #4 | 55355 |
| 8533 | 23815 | 50.0 | 50.0 | 13 | 161 | #1 | 55356 |
| 8534 | 23816 | 67.2 | 58.9 | 17 | 231 | #4 | 55357 |
| 8535 | 23817 | 72.8 | 62.5 | 24 | 290 | #5 | 55358 |
| 8536 | 23818 | 68.8 | 66.2 (160) | 30 | 251 | #4 | 55359 |
| 8537 | 23819 | 68.8 | 58.5 | 15 | 226 | #4 | 55360 |
| 8538 | 23820 | 74.4 | 64.0 | 24 | 379 | #5 | 55361 |
| 8539 | 23821 | 67.2 | 60.0 | 16 | 277 | #4 | 55362 |
| 8540 | 23822 | 68.8 | 60.4 | 19 | 277 | #4 | 55363 |
| 8541 | 23823 | 70.4 | 61.1 | 18 | 279 | #5 | 55364 |
| 8542 | 23824 | 50.0 | 50.0 | 12 | 150 | #1 | 55365 |
| 8543 | 23825 | 50.0 | 50.0 | 12 | 150 | #1 | 55366 |
| 8544 | 23826 | 50.0 | 50.0 | 12 | 150 | #1 | 55367 |
| 8545 | 23827 | 70.4 | 62.5 | 18 | 313 | #5 | 55368 |
| 8546 | 23828 | 50.0 | 50.0 | 12 | 150 | #1 | 55369 |
| 8547 | 23829 | 72.0 | 61.8 | 36 | 335 | #5 | 55370 |
| 8548 | 23830 | 64.8 | 50.0 | 14 | 189 | #3 | 55371 |
| 8549 | 23831 | 68.8 | 60.4 | 20 | 303 | #4 | 55372 |
| 8550 | 23832 | 63.9 (83) | — | 14 | 153 | #3 | 55373 |
| 8551 | 23833 | 50.0 | 50.0 | 12 | 150 | #1 | 55374 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8552 | 23834 | 50.0 | 50.0 | 12 | 150 | #1 | 55375 |
| 8553 | 23835 | 64.8 | 57.5 | 15 | 245 | #3 | 55376 |
| 8554 | 23836 | 73.6 | 61.5 | 24 | 386 | #5 | 55377 |
| 8555 | 23837 | 65.6 | 59.6 | 20 | 210 | #4 | 55378 |
| 8556 | 23838 | 63.2 | 55.6 | 13 | 185 | #3 | 55379 |
| 8557 | 23839 | 50.0 | 50.0 | 12 | 150 | #1 | 55380 |
| 8558 | 23840 | 66.4 | 58.1 (241) | 18 | 187 | #4 | 55381 |
| 8559 | 23841 | 68.0 | 62.2 | 18 | 350 | #4 | 55382 |
| 8560 | 23842 | 50.0 (88) | — | 12 | 150 | #1 | 55383 |
| 8561 | 23843 | 65.6 | 60.0 | 20 | 245 | #4 | 55384 |
| 8562 | 23844 | 65.6 | 60.0 | 12 | 239 | #4 | 55385 |
| 8563 | 23845 | 66.4 | 59.3 | 25 | 229 | #4 | 55386 |
| 8564 | 23846 | 65.6 | 60.4 | 17 | 249 | #4 | 55387 |
| 8565 | 23847 | 64.8 | 59.3 | 14 | 230 | #3 | 55388 |
| 8566 | 23848 | 66.4 | 63.7 (157) | 20 | 171 | #4 | 55389 |
| 8567 | 23849 | 50.0 | 50.0 | 12 | 150 | #1 | 55390 |
| 8568 | 23850 | 50.0 | 50.0 | 12 | 150 | #1 | 55391 |
| 8569 | 23851 | 68.8 | 61.5 | 21 | 279 | #4 | 55392 |
| 8570 | 23852 | 71.2 | 65.1 | 25 | 424 | #5 | 55393 |
| 8571 | 23853 | 62.4 | 58.9 | 12 | 275 | #3 | 55394 |
| 8572 | 23854 | 68.0 | 60.0 | 18 | 259 | #4 | 55395 |
| 8573 | 23855 | 71.2 | 59.6 | 21 | 266 | #5 | 55396 |
| 8574 | 23856 | 68.8 | 61.1 | 19 | 321 | #4 | 55397 |
| 8575 | 23857 | 68.8 | 61.8 | 19 | 269 | #4 | 55398 |
| 8576 | 23858 | 69.6 | 61.8 | 24 | 312 | #4 | 55399 |
| 8577 | 23859 | 64.8 | 57.5 | 25 | 202 | #3 | 55400 |
| 8578 | 23860 | 66.4 | 60.4 | 17 | 234 | #4 | 55401 |
| 8579 | 23861 | 77.6 | 61.8 | 21 | 506 | #6 | 55402 |
| 8580 | 23862 | 62.4 | 57.1 | 13 | 196 | #3 | 55403 |
| 8581 | 23863 | 71.2 | 65.1 | 21 | 407 | #5 | 55404 |
| 8582 | 23864 | 65.6 | 56.7 | 16 | 201 | #4 | 55405 |
| 8583 | 23865 | 50.0 | 50.0 | 12 | 150 | #1 | 55406 |
| 8584 | 23866 | 63.2 | 53.1 | 15 | 202 | #3 | 55407 |
| 8585 | 23867 | 71.2 | 63.3 | 20 | 315 | #5 | 55408 |
| 8586 | 23868 | 59.2 | 50.0 | 12 | 159 | #2 | 55409 |
| 8587 | 23869 | 69.6 | 60.0 | 20 | 245 | #4 | 55410 |
| 8588 | 23870 | 67.2 | 60.4 | 17 | 248 | #4 | 55411 |
| 8589 | 23871 | 50.0 | 50.0 | 12 | 150 | #1 | 55412 |
| 8590 | 23872 | 66.4 | 52.9 (263) | 21 | 283 | #4 | 55413 |
| 8591 | 23873 | 69.6 | 62.9 | 20 | 315 | #4 | 55414 |
| 8592 | 23874 | 50.0 | 50.0 | 12 | 150 | #1 | 55415 |
| 8593 | 23875 | 68.8 | 60.4 | 24 | 244 | #4 | 55416 |
| 8594 | 23876 | 50.0 (109) | — | 12 | 150 | #1 | 55417 |
| 8595 | 23877 | 65.6 | 60.0 | 16 | 224 | #4 | 55418 |
| 8596 | 23878 | 74.4 | 65.1 | 29 | 863 | #5 | 55419 |
| 8597 | 23879 | 84.0 | 71.3 | 30 | 853 | #7 | 55420 |
| 8598 | 23880 | 66.4 | 58.2 | 22 | 202 | #4 | 55421 |
| 8599 | 23881 | 64.8 | 61.1 (157) | 20 | 177 | #3 | 55422 |
| 8600 | 23882 | 68.8 | 61.5 | 19 | 302 | #4 | 55423 |
| 8601 | 23883 | 62.4 | 59.2 (250) | 15 | 169 | #3 | 55424 |
| 8602 | 23884 | 65.6 | 55.6 | 14 | 205 | #4 | 55425 |
| 8603 | 23885 | 66.4 | 60.7 | 23 | 261 | #4 | 55426 |
| 8604 | 23886 | 50.0 | 50.0 | 12 | 150 | #1 | 55427 |
| 8605 | 23887 | 59.2 | 50.0 | 12 | 164 | #2 | 55428 |
| 8606 | 23888 | 65.6 | 60.2 (259) | 21 | 214 | #4 | 55429 |
| 8607 | 23889 | 93.6 | 90.6 (170) | 28 | 708 | #9 | 55430 |
| 8608 | 23890 | 68.8 | 61.5 | 24 | 313 | #4 | 55431 |
| 8609 | 23891 | 63.2 | 50.0 | 14 | 170 | #3 | 55432 |
| 8610 | 23892 | 68.8 | 56.7 | 17 | 214 | #4 | 55433 |
| 8611 | 23893 | 50.0 (88) | — | 12 | 150 | #1 | 55434 |
| 8612 | 23894 | 64.0 | 57.8 | 15 | 213 | #3 | 55435 |
| 8613 | 23895 | 68.8 | 63.3 | 23 | 448 | #4 | 55436 |
| 8614 | 23896 | 66.4 | 60.0 | 17 | 244 | #4 | 55437 |
| 8615 | 23897 | 61.6 | 56.7 | 17 | 176 | #3 | 55438 |
| 8616 | 23898 | 61.6 | 50.0 | 12 | 193 | #3 | 55439 |
| 8617 | 23899 | 69.6 | 64.0 | 27 | 420 | #4 | 55440 |
| 8618 | 23900 | 73.2 (71) | — | 29 | 162 | #5 | 55441 |
| 8619 | 23901 | 50.0 | 50.0 | 12 | 150 | #1 | 55442 |
| 8620 | 23902 | 68.8 | 60.7 | 25 | 337 | #4 | 55443 |
| 8621 | 23903 | 61.6 | 50.0 | 14 | 180 | #3 | 55444 |
| 8622 | 23904 | 71.2 | 61.1 | 20 | 296 | #5 | 55445 |
| 8623 | 23905 | 65.6 | 55.3 | 15 | 220 | #4 | 55446 |
| 8624 | 23906 | 64.8 | 50.0 | 14 | 167 | #3 | 55447 |
| 8625 | 23907 | 70.4 | 61.1 | 22 | 348 | #5 | 55448 |
| 8626 | 23908 | 89.6 | 66.5 | 32 | 494 | #8 | 55449 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8627 | 23909 | 61.6 | 54.4 (147) | 13 | 150 | #3 | 55450 |
| 8628 | 23910 | 65.6 | 59.5 (227) | 24 | 197 | #4 | 55451 |
| 8629 | 23911 | 60.8 | 50.0 | 15 | 199 | #3 | 55452 |
| 8630 | 23912 | 50.0 | 50.0 | 12 | 150 | #1 | 55453 |
| 8631 | 23913 | 68.0 | 50.0 | 23 | 206 | #4 | 55454 |
| 8632 | 23914 | 69.6 | 63.6 | 22 | 380 | #4 | 55455 |
| 8633 | 23915 | 67.2 | 61.5 | 21 | 410 | #4 | 55456 |
| 8634 | 23916 | 67.2 | 60.7 | 19 | 249 | #4 | 55457 |
| 8635 | 23917 | 50.0 (100) | — | 12 | 150 | #1 | 55458 |
| 8636 | 23918 | 69.6 | 63.3 | 21 | 459 | #4 | 55459 |
| 8637 | 23919 | 62.4 | 50.0 (266) | 13 | 158 | #3 | 55460 |
| 8638 | 23920 | 67.2 | 52.4 | 19 | 233 | #4 | 55461 |
| 8639 | 23921 | 68.8 | 61.1 | 22 | 445 | #4 | 55462 |
| 8640 | 23922 | 64.8 | 59.3 | 15 | 207 | #3 | 55463 |
| 8641 | 23923 | 63.2 | 57.1 | 12 | 195 | #3 | 55464 |
| 8642 | 23924 | 66.4 | 58.9 | 16 | 196 | #4 | 55465 |
| 8643 | 23925 | 50.0 | 50.0 | 12 | 150 | #1 | 55466 |
| 8644 | 23926 | 74.0 (77) | — | 26 | 175 | #5 | 55467 |
| 8645 | 23927 | 75.2 | 66.2 (237) | 32 | 314 | #6 | 55468 |
| 8646 | 23928 | 72.0 | 61.1 | 22 | 252 | #5 | 55469 |
| 8647 | 23929 | 67.2 | 63.6 (184) | 23 | 237 | #4 | 55470 |
| 8648 | 23930 | 70.4 | 58.5 | 18 | 296 | #5 | 55471 |
| 8649 | 23931 | 50.0 | 50.0 | 12 | 170 | #1 | 55472 |
| 8650 | 23932 | 68.0 | 61.5 | 20 | 358 | #4 | 55473 |
| 8651 | 23933 | 72.8 | 62.5 | 33 | 388 | #5 | 55474 |
| 8652 | 23934 | 50.0 | 50.0 | 12 | 150 | #1 | 55475 |
| 8653 | 23935 | 67.2 | 61.5 | 18 | 301 | #4 | 55476 |
| 8654 | 23936 | 81.6 | 65.4 (260) | 23 | 660 | #7 | 55477 |
| 8655 | 23937 | 63.2 | 50.0 | 20 | 191 | #3 | 55478 |
| 8656 | 23938 | 62.4 | 50.0 | 15 | 182 | #3 | 55479 |
| 8657 | 23939 | 73.6 | 65.5 | 21 | 667 | #5 | 55480 |
| 8658 | 23940 | 64.8 | 58.5 | 14 | 210 | #3 | 55481 |
| 8659 | 23941 | 50.0 | 50.0 | 12 | 150 | #1 | 55482 |
| 8660 | 23942 | 62.4 | 50.0 | 13 | 165 | #3 | 55483 |
| 8661 | 23943 | 57.6 | 50.0 (180) | 12 | 168 | #2 | 55484 |
| 8662 | 23944 | 66.4 | 58.5 | 16 | 200 | #4 | 55485 |
| 8663 | 23945 | 67.2 | 61.1 | 17 | 230 | #4 | 55486 |
| 8664 | 23946 | 78.4 | 65.8 | 31 | 460 | #6 | 55487 |
| 8665 | 23947 | 50.0 | 50.0 | 12 | 150 | #1 | 55488 |
| 8666 | 23948 | 71.2 | 64.7 | 22 | 1002 | #5 | 55489 |
| 8667 | 23949 | 68.8 | 62.5 | 16 | 316 | #4 | 55490 |
| 8668 | 23950 | 62.4 | 50.0 | 14 | 162 | #3 | 55491 |
| 8669 | 23951 | 50.0 | 50.0 | 12 | 150 | #1 | 55492 |
| 8670 | 23952 | 50.0 | 50.0 | 12 | 150 | #1 | 55493 |
| 8671 | 23953 | 63.2 | 50.0 | 12 | 175 | #3 | 55494 |
| 8672 | 23954 | 66.4 | 62.2 | 18 | 310 | #4 | 55495 |
| 8673 | 23955 | 70.4 | 62.5 | 25 | 312 | #5 | 55496 |
| 8674 | 23956 | 78.4 | 63.3 | 26 | 395 | #6 | 55497 |
| 8675 | 23957 | 50.0 | 50.0 | 12 | 150 | #1 | 55498 |
| 8676 | 23958 | 68.0 | 56.7 | 14 | 216 | #4 | 55499 |
| 8677 | 23959 | 58.4 | 50.0 | 15 | 159 | #2 | 55500 |
| 8678 | 23960 | 67.2 | 62.2 | 19 | 347 | #4 | 55501 |
| 8679 | 23961 | 66.4 | 57.5 | 20 | 198 | #4 | 55502 |
| 8680 | 23962 | 50.0 | 50.0 | 12 | 150 | #1 | 55503 |
| 8681 | 23963 | 50.0 | 50.0 | 12 | 150 | #1 | 55504 |
| 8682 | 23964 | 63.2 | 50.0 | 12 | 191 | #3 | 55505 |
| 8683 | 23965 | 65.6 | 50.0 | 20 | 199 | #4 | 55506 |
| 8684 | 23966 | 71.2 | 50.0 | 24 | 245 | #5 | 55507 |
| 8685 | 23967 | 50.0 (118) | — | 12 | 150 | #1 | 55508 |
| 8686 | 23968 | 69.6 | 62.9 | 21 | 433 | #4 | 55509 |
| 8687 | 23969 | 50.0 | 50.0 | 12 | 150 | #1 | 55510 |
| 8688 | 23970 | 68.0 | 62.5 | 20 | 456 | #4 | 55511 |
| 8689 | 23971 | 50.0 | 50.0 | 12 | 150 | #1 | 55512 |
| 8690 | 23972 | 50.0 | 50.0 | 12 | 157 | #1 | 55513 |
| 8691 | 23973 | 67.2 | 58.5 | 18 | 239 | #4 | 55514 |
| 8692 | 23974 | 64.8 | 50.0 | 17 | 217 | #3 | 55515 |
| 8693 | 23975 | 73.6 | 64.7 | 32 | 479 | #5 | 55516 |
| 8694 | 23976 | 66.4 | 53.0 (198) | 18 | 178 | #4 | 55517 |
| 8695 | 23977 | 71.2 | 62.9 | 23 | 369 | #5 | 55518 |
| 8696 | 23978 | 69.6 | 62.2 | 28 | 594 | #4 | 55519 |
| 8697 | 23979 | 67.2 | 60.4 | 18 | 238 | #4 | 55520 |
| 8698 | 23980 | 53.6 | 50.0 | 12 | 150 | #1 | 55521 |
| 8699 | 23981 | 60.0 | 50.0 | 12 | 156 | #2 | 55522 |
| 8700 | 23982 | 68.8 | 61.1 | 21 | 286 | #4 | 55523 |
| 8701 | 23983 | 50.0 | 50.0 | 12 | 150 | #1 | 55524 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8702 | 23984 | 68.8 | 60.4 | 18 | 247 | #4 | 55525 |
| 8703 | 23985 | 62.4 | 50.0 (245) | 17 | 161 | #3 | 55526 |
| 8704 | 23986 | 61.6 | 57.2 (222) | 14 | 165 | #3 | 55527 |
| 8705 | 23987 | 61.6 | 50.0 | 13 | 150 | #3 | 55528 |
| 8706 | 23988 | 67.2 | 61.8 | 21 | 293 | #4 | 55529 |
| 8707 | 23989 | 68.8 | 60.4 | 19 | 244 | #4 | 55530 |
| 8708 | 23990 | 65.6 | 63.5 (159) | 20 | 186 | #4 | 55531 |
| 8709 | 23991 | 68.8 | 61.8 | 25 | 387 | #4 | 55532 |
| 8710 | 23992 | 63.2 | 50.0 (242) | 13 | 184 | #3 | 55533 |
| 8711 | 23993 | 70.4 | 62.5 | 20 | 364 | #5 | 55534 |
| 8712 | 23994 | 67.2 | 57.7 (182) | 15 | 272 | #4 | 55535 |
| 8713 | 23995 | 64.0 | 53.2 (205) | 15 | 164 | #3 | 55536 |
| 8714 | 23996 | 72.8 | 72.3 (195) | 20 | 441 | #5 | 55537 |
| 8715 | 23997 | 50.0 | 50.0 | 12 | 150 | #1 | 55538 |
| 8716 | 23998 | 82.4 | 69.0 (216) | 27 | 468 | #7 | 55539 |
| 8717 | 23999 | 63.2 | 50.0 | 14 | 183 | #3 | 55540 |
| 8718 | 24000 | 64.8 | 52.3 (237) | 17 | 163 | #3 | 55541 |
| 8719 | 24001 | 67.2 | 58.9 | 23 | 215 | #4 | 55542 |
| 8720 | 24002 | 50.0 | 50.0 | 12 | 150 | #1 | 55543 |
| 8721 | 24003 | 65.6 | 60.7 | 16 | 217 | #4 | 55544 |
| 8722 | 24004 | 85.6 | 69.8 | 30 | 626 | #8 | 55545 |
| 8723 | 24005 | 63.2 | 50.9 (165) | 18 | 151 | #3 | 55546 |
| 8724 | 24006 | 68.8 | 60.4 | 18 | 271 | #4 | 55547 |
| 8725 | 24007 | 64.8 | 59.3 (199) | 13 | 155 | #3 | 55548 |
| 8726 | 24008 | 64.8 | 50.0 | 14 | 177 | #3 | 55549 |
| 8727 | 24009 | 71.2 | 62.5 | 20 | 339 | #5 | 55550 |
| 8728 | 24010 | 60.0 | 56.7 | 13 | 226 | #2 | 55551 |
| 8729 | 24011 | 68.0 | 62.5 | 27 | 298 | #4 | 55552 |
| 8730 | 24012 | 50.0 | 50.0 | 12 | 150 | #1 | 55553 |
| 8731 | 24013 | 50.0 | 50.0 | 12 | 150 | #1 | 55554 |
| 8732 | 24014 | 56.0 | 50.0 | 15 | 176 | #2 | 55555 |
| 8733 | 24015 | 67.2 | 61.5 | 17 | 278 | #4 | 55556 |
| 8734 | 24016 | 69.6 | 62.9 | 21 | 464 | #4 | 55557 |
| 8735 | 24017 | 50.0 | 50.0 | 12 | 150 | #1 | 55558 |
| 8736 | 24018 | 66.4 | 59.6 | 19 | 223 | #4 | 55559 |
| 8737 | 24019 | 50.0 | 50.0 | 12 | 150 | #1 | 55560 |
| 8738 | 24020 | 65.6 | 57.8 | 19 | 241 | #4 | 55561 |
| 8739 | 24021 | 60.8 | 50.0 | 12 | 151 | #3 | 55562 |
| 8740 | 24022 | 64.8 | 59.6 | 15 | 212 | #3 | 55563 |
| 8741 | 24023 | 50.0 | 50.0 | 12 | 150 | #1 | 55564 |
| 8742 | 24024 | 66.4 | 60.4 | 22 | 305 | #4 | 55565 |
| 8743 | 24025 | 68.0 | 58.2 | 15 | 244 | #4 | 55566 |
| 8744 | 24026 | 64.0 | 50.0 | 13 | 187 | #3 | 55567 |
| 8745 | 24027 | 68.0 | 61.5 | 20 | 346 | #4 | 55568 |
| 8746 | 24028 | 69.6 | 62.2 | 29 | 360 | #4 | 55569 |
| 8747 | 24029 | 62.4 | 55.6 | 12 | 197 | #3 | 55570 |
| 8748 | 24030 | 70.4 | 60.0 | 24 | 277 | #5 | 55571 |
| 8749 | 24031 | 62.4 | 55.0 (262) | 22 | 174 | #3 | 55572 |
| 8750 | 24032 | 63.2 | 58.3 (216) | 16 | 155 | #3 | 55573 |
| 8751 | 24033 | 63.2 | 56.4 | 14 | 197 | #3 | 55574 |
| 8752 | 24034 | 62.4 | 56.7 | 12 | 182 | #3 | 55575 |
| 8753 | 24035 | 71.2 | 62.9 | 31 | 349 | #5 | 55576 |
| 8754 | 24036 | 64.8 | 57.8 | 18 | 214 | #3 | 55577 |
| 8755 | 24037 | 66.4 | 58.5 | 17 | 225 | #4 | 55578 |
| 8756 | 24038 | 64.0 | 60.0 | 24 | 234 | #3 | 55579 |
| 8757 | 24039 | 68.8 | 62.5 | 18 | 479 | #4 | 55580 |
| 8758 | 24040 | 68.0 | 61.8 | 19 | 367 | #4 | 55581 |
| 8759 | 24041 | 68.0 | 61.5 | 25 | 263 | #4 | 55582 |
| 8760 | 24042 | 67.2 | 61.5 | 20 | 298 | #4 | 55583 |
| 8761 | 24043 | 60.8 | 53.1 (160) | 14 | 150 | #3 | 55584 |
| 8762 | 24044 | 63.2 | 60.4 | 23 | 223 | #3 | 55585 |
| 8763 | 24045 | 50.0 | 50.0 | 12 | 150 | #1 | 55586 |
| 8764 | 24046 | 67.2 | 55.3 | 15 | 205 | #4 | 55587 |
| 8765 | 24047 | 50.0 | 50.0 | 12 | 150 | #1 | 55588 |
| 8766 | 24048 | 62.4 | 50.0 | 17 | 191 | #3 | 55589 |
| 8767 | 24049 | 70.4 | 62.2 | 23 | 410 | #5 | 55590 |
| 8768 | 24050 | 50.0 | 50.0 (179) | 12 | 150 | #1 | 55591 |
| 8769 | 24051 | 74.4 | 65.1 | 28 | 360 | #5 | 55592 |
| 8770 | 24052 | 66.4 | 59.6 | 15 | 254 | #4 | 55593 |
| 8771 | 24053 | 78.4 | 60.0 | 39 | 381 | #6 | 55594 |
| 8772 | 24054 | 70.4 | 62.5 | 20 | 336 | #5 | 55595 |
| 8773 | 24055 | 66.4 | 57.8 | 16 | 233 | #4 | 55596 |
| 8774 | 24056 | 50.0 | 50.0 | 12 | 150 | #1 | 55597 |
| 8775 | 24057 | 60.0 | 50.0 | 15 | 184 | #2 | 55598 |
| 8776 | 24058 | 66.4 | 50.0 | 15 | 230 | #4 | 55599 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8777 | 24059 | 67.2 | 60.0 | 17 | 313 | #4 | 55600 |
| 8778 | 24060 | 50.0 | 50.0 | 12 | 150 | #1 | 55601 |
| 8779 | 24061 | 75.2 | 62.9 | 33 | 388 | #6 | 55602 |
| 8780 | 24062 | 70.4 | 64.7 | 26 | 389 | #5 | 55603 |
| 8781 | 24063 | 75.2 | 61.1 | 31 | 371 | #6 | 55604 |
| 8782 | 24064 | 68.0 | 58.2 | 20 | 228 | #4 | 55605 |
| 8783 | 24065 | 50.0 | 50.0 | 12 | 150 | #1 | 55606 |
| 8784 | 24066 | 73.6 | 64.7 | 25 | 410 | #5 | 55607 |
| 8785 | 24067 | 71.2 | 62.9 | 25 | 529 | #5 | 55608 |
| 8786 | 24068 | 61.6 | 57.8 | 13 | 210 | #3 | 55609 |
| 8787 | 24069 | 68.8 | 58.9 | 18 | 232 | #4 | 55610 |
| 8788 | 24070 | 65.6 | 50.0 | 15 | 203 | #4 | 55611 |
| 8789 | 24071 | 70.4 | 62.5 | 18 | 332 | #5 | 55612 |
| 8790 | 24072 | 55.2 | 50.0 (198) | 17 | 155 | #2 | 55613 |
| 8791 | 24073 | 66.4 | 60.7 | 20 | 333 | #4 | 55614 |
| 8792 | 24074 | 70.4 | 62.2 | 21 | 272 | #5 | 55615 |
| 8793 | 24075 | 64.8 | 59.6 | 16 | 252 | #3 | 55616 |
| 8794 | 24076 | 66.4 | 61.1 | 18 | 275 | #4 | 55617 |
| 8795 | 24077 | 71.2 | 63.3 | 20 | 300 | #5 | — |
| 8796 | 24078 | 69.6 | 62.9 | 20 | 326 | #4 | 55618 |
| 8797 | 24079 | 50.0 | 50.0 | 12 | 150 | #1 | 55619 |
| 8798 | 24080 | 67.2 | 60.4 | 19 | 232 | #4 | 55620 |
| 8799 | 24081 | 65.6 | 60.7 (173) | 18 | 188 | #4 | 55621 |
| 8800 | 24082 | 69.6 | 61.8 | 20 | 368 | #4 | 55622 |
| 8801 | 24083 | 64.0 | 50.0 (271) | 12 | 183 | #3 | 55623 |
| 8802 | 24084 | 85.6 | 66.9 | 23 | 520 | #8 | 55624 |
| 8803 | 24085 | 64.0 | 50.0 (274) | 17 | 173 | #3 | 55625 |
| 8804 | 24086 | 61.6 | 50.0 (174) | 19 | 153 | #3 | 55626 |
| 8805 | 24087 | 68.8 | 58.9 | 37 | 257 | #4 | 55627 |
| 8806 | 24088 | 69.6 | 61.1 | 27 | 355 | #4 | 55628 |
| 8807 | 24089 | 64.8 | 50.0 (264) | 28 | 193 | #3 | 55629 |
| 8808 | 24090 | 63.2 | 50.0 | 15 | 199 | #3 | 55630 |
| 8809 | 24091 | 66.4 | 61.1 | 16 | 233 | #4 | 55631 |
| 8810 | 24092 | 50.0 | 50.0 | 12 | 150 | #1 | 55632 |
| 8811 | 24093 | 50.0 | 50.0 | 12 | 150 | #1 | 55633 |
| 8812 | 24094 | 64.0 | 54.5 | 14 | 188 | #3 | 55634 |
| 8813 | 24095 | 72.0 | 65.7 (233) | 27 | 360 | #5 | 55635 |
| 8814 | 24096 | 63.2 | 50.0 | 12 | 173 | #3 | 55636 |
| 8815 | 24097 | 68.8 | 61.1 | 20 | 335 | #4 | 55637 |
| 8816 | 24098 | 63.2 | 56.0 | 15 | 203 | #3 | 55638 |
| 8817 | 24099 | 51.2 | 50.0 | 16 | 210 | #1 | 55639 |
| 8818 | 24100 | 64.0 | 58.4 (197) | 22 | 169 | #3 | 55640 |
| 8819 | 24101 | 62.4 | 50.0 | 14 | 192 | #3 | 55641 |
| 8820 | 24102 | 67.2 | 58.5 | 20 | 247 | #4 | 55642 |
| 8821 | 24103 | 64.0 | 50.0 (272) | 13 | 166 | #3 | 55643 |
| 8822 | 24104 | 72.0 | 61.5 | 24 | 309 | #5 | 55644 |
| 8823 | 24105 | 63.2 | 55.6 (241) | 21 | 170 | #3 | 55645 |
| 8824 | 24106 | 68.8 | 63.3 | 24 | 289 | #4 | 55646 |
| 8825 | 24107 | 68.8 | 56.7 | 18 | 289 | #4 | 55647 |
| 8826 | 24108 | 66.4 | 50.0 | 16 | 326 | #4 | 55648 |
| 8827 | 24109 | 65.6 | 60.4 | 16 | 271 | #4 | 55649 |
| 8828 | 24110 | 70.4 | 62.5 | 21 | 329 | #5 | 55650 |
| 8829 | 24111 | 70.4 | 58.5 | 30 | 252 | #5 | 55651 |
| 8830 | 24112 | 68.8 | 63.3 | 19 | 373 | #4 | 55652 |
| 8831 | 24113 | 70.4 | 67.7 (158) | 24 | 241 | #5 | 55653 |
| 8832 | 24114 | 71.2 | 62.9 | 20 | 290 | #5 | 55654 |
| 8833 | 24115 | 67.2 | 60.0 | 21 | 254 | #4 | 55655 |
| 8834 | 24116 | 64.0 | 61.1 (193) | 15 | 164 | #3 | 55656 |
| 8835 | 24117 | 67.2 | 61.5 | 16 | 284 | #4 | 55657 |
| 8836 | 24118 | 65.6 | 59.4 (229) | 20 | 201 | #4 | 55658 |
| 8837 | 24119 | 99.2 | 98.2 | 125 | 2077 | #10 | 55659 |
| 8838 | 24120 | 68.0 | 58.5 | 13 | 190 | #4 | 55660 |
| 8839 | 24121 | 68.8 | 63.3 | 20 | 383 | #4 | 55661 |
| 8840 | 24122 | 64.0 | 50.0 | 13 | 167 | #3 | 55662 |
| 8841 | 24123 | 68.0 | 57.1 | 17 | 263 | #4 | 55663 |
| 8842 | 24124 | 50.0 | 50.0 | 12 | 150 | #1 | 55664 |
| 8843 | 24125 | 60.8 | 56.7 | 12 | 200 | #3 | 55665 |
| 8844 | 24126 | 60.8 | 50.0 | 12 | 172 | #3 | 55666 |
| 8845 | 24127 | 68.0 | 61.5 | 20 | 543 | #4 | 55667 |
| 8846 | 24128 | 50.0 | 50.0 | 16 | 159 | #1 | 55668 |
| 8847 | 24129 | 73.6 | 65.5 | 25 | 595 | #5 | 55669 |
| 8848 | 24130 | 69.6 | 62.5 | 20 | 405 | #4 | 55670 |
| 8849 | 24131 | 70.2 (114) | — | 20 | 220 | #5 | 55671 |
| 8850 | 24132 | 64.0 | 56.7 | 16 | 204 | #3 | 55672 |
| 8851 | 24133 | 61.6 | 58.9 | 12 | 192 | #3 | 55673 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8852 | 24134 | 50.0 | 50.0 | 12 | 150 | #1 | 55674 |
| 8853 | 24135 | 60.0 | 50.0 | 15 | 150 | #2 | 55675 |
| 8854 | 24136 | 63.2 | 58.2 | 14 | 217 | #3 | 55676 |
| 8855 | 24137 | 64.8 | 59.6 | 16 | 229 | #3 | 55677 |
| 8856 | 24138 | 63.2 | 50.0 | 14 | 156 | #3 | 55678 |
| 8857 | 24139 | 68.8 | 61.8 | 19 | 303 | #4 | 55679 |
| 8858 | 24140 | 50.0 | 50.0 | 12 | 150 | #1 | 55680 |
| 8859 | 24141 | 60.0 | 50.0 | 17 | 155 | #2 | 55681 |
| 8860 | 24142 | 80.9 (68) | — | 13 | 223 | #7 | 55682 |
| 8861 | 24143 | 70.4 | 63.3 | 22 | 418 | #5 | 55683 |
| 8862 | 24144 | 50.0 | 50.0 | 12 | 150 | #1 | 55684 |
| 8863 | 24145 | 75.2 | 63.3 | 31 | 416 | #6 | 55685 |
| 8864 | 24146 | 68.0 | 61.1 | 21 | 323 | #4 | 55686 |
| 8865 | 24147 | 63.2 | 55.3 | 13 | 180 | #3 | 55687 |
| 8866 | 24148 | 50.0 | 50.0 | 12 | 150 | #1 | 55688 |
| 8867 | 24149 | 66.4 | 58.5 | 16 | 230 | #4 | 55689 |
| 8868 | 24150 | 63.2 | 52.8 (180) | 18 | 178 | #3 | 55690 |
| 8869 | 24151 | 78.4 | 68.4 (171) | 17 | 361 | #6 | 55691 |
| 8870 | 24152 | 64.0 | 56.4 | 12 | 220 | #3 | 55692 |
| 8871 | 24153 | 62.4 | 50.0 | 15 | 183 | #3 | 55693 |
| 8872 | 24154 | 82.4 | 83.9 (149) | 22 | 529 | #7 | 55694 |
| 8873 | 24155 | 66.4 | 57.5 | 17 | 222 | #4 | 55695 |
| 8874 | 24156 | 63.2 | 50.0 | 13 | 158 | #3 | 55696 |
| 8875 | 24157 | 50.0 | 50.0 | 12 | 150 | #1 | 55697 |
| 8876 | 24158 | 71.2 | 61.8 | 25 | 362 | #5 | 55698 |
| 8877 | 24159 | 66.4 | 59.5 (262) | 20 | 224 | #4 | 55699 |
| 8878 | 24160 | 64.0 | 50.0 | 13 | 173 | #3 | 55700 |
| 8879 | 24161 | 70.4 | 62.5 | 21 | 344 | #5 | 55701 |
| 8880 | 24162 | 67.2 | 60.4 | 20 | 319 | #4 | 55702 |
| 8881 | 24163 | 72.8 | 62.2 | 27 | 339 | #5 | 55703 |
| 8882 | 24164 | 66.4 | 59.6 | 20 | 279 | #4 | 55704 |
| 8883 | 24165 | 66.4 | 50.0 | 23 | 202 | #4 | 55705 |
| 8884 | 24166 | 64.8 | 50.0 | 20 | 193 | #3 | 55706 |
| 8885 | 24167 | 64.0 | 56.4 (204) | 14 | 167 | #3 | 55707 |
| 8886 | 24168 | 68.0 | 57.5 | 13 | 214 | #4 | 55708 |
| 8887 | 24169 | 65.6 | 63.6 (151) | 21 | 184 | #4 | 55709 |
| 8888 | 24170 | 50.0 | 50.0 (139) | 12 | 150 | #1 | 55710 |
| 8889 | 24171 | 50.0 | 50.0 | 12 | 150 | #1 | 55711 |
| 8890 | 24172 | 50.0 | 50.0 (273) | 12 | 150 | #1 | 55712 |
| 8891 | 24173 | 50.0 | 50.0 | 12 | 150 | #1 | 55713 |
| 8892 | 24174 | 76.8 | 73.5 | 15 | 731 | #6 | 55714 |
| 8893 | 24175 | 63.2 | 58.2 | 13 | 185 | #3 | 55715 |
| 8894 | 24176 | 50.0 | 50.0 | 12 | 150 | #1 | 55716 |
| 8895 | 24177 | 65.6 | 58.9 | 17 | 220 | #4 | 55717 |
| 8896 | 24178 | 63.2 | 59.3 | 15 | 211 | #3 | 55718 |
| 8897 | 24179 | 64.0 | 60.4 | 15 | 295 | #3 | 55719 |
| 8898 | 24180 | 64.0 | 59.6 | 16 | 296 | #3 | 55720 |
| 8899 | 24181 | 71.2 | 64.0 | 22 | 366 | #5 | 55721 |
| 8900 | 24182 | 50.0 | 50.0 | 12 | 150 | #1 | 55722 |
| 8901 | 24183 | 50.0 | 50.0 | 12 | 150 | #1 | 55723 |
| 8902 | 24184 | 65.6 | 59.3 | 22 | 201 | #4 | 55724 |
| 8903 | 24185 | 70.4 | 61.5 | 19 | 316 | #5 | 55725 |
| 8904 | 24186 | 67.2 | 50.0 | 34 | 204 | #4 | 55726 |
| 8905 | 24187 | 67.2 | 61.5 | 19 | 277 | #4 | 55727 |
| 8906 | 24188 | 68.8 | 59.6 | 23 | 262 | #4 | 55728 |
| 8907 | 24189 | 68.0 | 62.5 | 19 | 294 | #4 | 55729 |
| 8908 | 24190 | 65.6 | 50.0 (259) | 19 | 191 | #4 | 55730 |
| 8909 | 24191 | 64.8 | 59.3 | 16 | 250 | #3 | 55731 |
| 8910 | 24192 | 64.8 | 56.7 | 13 | 202 | #3 | 55732 |
| 8911 | 24193 | 68.0 | 62.2 | 21 | 340 | #4 | 55733 |
| 8912 | 24194 | 76.0 | 65.5 | 20 | 350 | #6 | 55734 |
| 8913 | 24195 | 69.6 | 62.5 | 22 | 336 | #4 | 55735 |
| 8914 | 24196 | 60.0 | 57.5 | 16 | 192 | #2 | 55736 |
| 8915 | 24197 | 69.6 | 63.6 | 31 | 337 | #4 | 55737 |
| 8916 | 24198 | 50.0 | 50.0 | 12 | 150 | #1 | 55738 |
| 8917 | 24199 | 72.0 | 63.6 | 27 | 535 | #5 | 55739 |
| 8918 | 24200 | 68.8 | 60.9 (197) | 21 | 195 | #4 | 55740 |
| 8919 | 24201 | 71.2 | 61.8 | 18 | 317 | #5 | 55741 |
| 8920 | 24202 | 50.0 (68) | — | 12 | 150 | #1 | 55742 |
| 8921 | 24203 | 69.6 | 58.2 | 23 | 272 | #4 | 55743 |
| 8922 | 24204 | 65.6 | 56.7 | 14 | 259 | #4 | 55744 |
| 8923 | 24205 | 66.4 | 59.4 (224) | 18 | 189 | #4 | 55745 |
| 8924 | 24206 | 71.2 | 58.3 (216) | 20 | 336 | #5 | — |
| 8925 | 24207 | 50.0 | 50.0 | 12 | 150 | #1 | 55746 |
| 8926 | 24208 | 66.4 | 61.9 (134) | 17 | 163 | #4 | 55747 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 8927 | 24209 | 72.0 | 66.2 (213) | 17 | 377 | #5 | 55748 |
| 8928 | 24210 | 64.8 | 60.4 (225) | 20 | 182 | #3 | 55749 |
| 8929 | 24211 | 64.8 | 57.8 | 15 | 211 | #3 | 55750 |
| 8930 | 24212 | 61.6 | 52.7 | 17 | 193 | #3 | 55751 |
| 8931 | 24213 | 73.5 (117) | — | 21 | 252 | #5 | 55752 |
| 8932 | 24214 | 60.8 | 58.9 | 16 | 187 | #3 | 55753 |
| 8933 | 24215 | 68.8 | 59.6 | 22 | 299 | #4 | 55754 |
| 8934 | 24216 | 67.2 | 59.6 | 20 | 249 | #4 | 55755 |
| 8935 | 24217 | 61.6 | 50.0 | 17 | 202 | #3 | 55756 |
| 8936 | 24218 | 63.2 | 50.0 (223) | 17 | 179 | #3 | 55757 |
| 8937 | 24219 | 68.8 | 60.7 | 18 | 257 | #4 | 55758 |
| 8938 | 24220 | 50.0 (67) | — | 12 | 150 | #1 | 55759 |
| 8939 | 24221 | 64.8 | 60.0 | 23 | 239 | #3 | 55760 |
| 8940 | 24222 | 72.0 | 58.2 | 21 | 321 | #5 | 55761 |
| 8941 | 24223 | 66.4 | 58.9 | 21 | 248 | #4 | 55762 |
| 8942 | 24224 | 67.2 | 61.8 | 21 | 400 | #4 | 55763 |
| 8943 | 24225 | 71.2 | 62.5 | 23 | 427 | #5 | 55764 |
| 8944 | 24226 | 62.0 (71) | — | 13 | 150 | #3 | 55765 |
| 8945 | 24227 | 50.0 | 50.0 | 12 | 150 | #1 | 55766 |
| 8946 | 24228 | 62.4 | 58.9 | 16 | 229 | #3 | 55767 |
| 8947 | 24229 | 68.5 (108) | — | 25 | 195 | #4 | 55768 |
| 8948 | 24230 | 85.6 | 74.2 | 18 | 824 | #8 | 55769 |
| 8949 | 24231 | 82.4 | 68.0 | 39 | 475 | #7 | 55770 |
| 8950 | 24232 | 64.8 | 59.3 (209) | 18 | 191 | #3 | 55771 |
| 8951 | 24233 | 50.0 (95) | — | 12 | 150 | #1 | 55772 |
| 8952 | 24234 | 68.8 | 58.9 | 26 | 215 | #4 | 55773 |
| 8953 | 24235 | 62.4 | 55.6 | 14 | 193 | #3 | 55774 |
| 8954 | 24236 | 80.0 | 67.6 | 26 | 561 | #6 | 55775 |
| 8955 | 24237 | 64.0 | 50.0 | 13 | 221 | #3 | 55776 |
| 8956 | 24238 | 68.0 | 62.5 | 21 | 385 | #4 | 55777 |
| 8957 | 24239 | 65.6 | 66.1 (127) | 23 | 204 | #4 | 55778 |
| 8958 | 24240 | 60.0 | 59.5 (126) | 28 | 155 | #2 | 55779 |
| 8959 | 24241 | 82.4 | 66.5 | 24 | 575 | #7 | 55780 |
| 8960 | 24242 | 72.0 | 62.9 | 22 | 372 | #5 | 55781 |
| 8961 | 24243 | 70.4 | 61.5 | 22 | 426 | #5 | 55782 |
| 8962 | 24244 | 69.6 | 61.5 | 19 | 342 | #4 | 55783 |
| 8963 | 24245 | 66.4 | 59.3 | 21 | 226 | #4 | 55784 |
| 8964 | 24246 | 50.0 | 50.0 | 12 | 150 | #1 | 55785 |
| 8965 | 24247 | 57.6 | 50.0 | 12 | 176 | #2 | 55786 |
| 8966 | 24248 | 63.2 | 50.0 | 16 | 190 | #3 | 55787 |
| 8967 | 24249 | 68.8 | 62.5 | 21 | 366 | #4 | 55788 |
| 8968 | 24250 | 70.4 | 59.6 | 19 | 242 | #5 | 55789 |
| 8969 | 24251 | 72.8 | 63.6 | 21 | 376 | #5 | 55790 |
| 8970 | 24252 | 62.4 | 55.6 (239) | 15 | 163 | #3 | 55791 |
| 8971 | 24253 | 64.0 | 50.0 | 26 | 211 | #3 | 55792 |
| 8972 | 24254 | 58.5 (123) | — | 16 | 155 | #2 | 55793 |
| 8973 | 24255 | 50.0 | 50.0 | 12 | 150 | #1 | 55794 |
| 8974 | 24256 | 76.8 | 65.8 | 30 | 651 | #6 | 55795 |
| 8975 | 24257 | 64.0 | 50.0 (273) | 15 | 199 | #3 | 55796 |
| 8976 | 24258 | 68.8 | 55.3 | 18 | 209 | #4 | 55797 |
| 8977 | 24259 | 66.4 | 60.0 | 19 | 242 | #4 | 55798 |
| 8978 | 24260 | 79.2 | 65.8 | 31 | 433 | #6 | 55799 |
| 8979 | 24261 | 64.0 | 58.5 | 16 | 240 | #3 | 55800 |
| 8980 | 24262 | 52.8 | 50.0 | 15 | 166 | #1 | 55801 |
| 8981 | 24263 | 66.4 | 53.5 | 17 | 199 | #4 | 55802 |
| 8982 | 24264 | 67.7 (96) | — | 19 | 150 | #4 | 55803 |
| 8983 | 24265 | 73.6 | 71.1 (204) | 18 | 459 | #5 | 55804 |
| 8984 | 24266 | 68.8 | 61.5 | 20 | 274 | #4 | 55805 |
| 8985 | 24267 | 84.0 | 71.3 | 18 | 627 | #7 | 55806 |
| 8986 | 24268 | 59.8 (117) | — | 17 | 243 | #2 | 55807 |
| 8987 | 24269 | 68.0 | 50.0 | 17 | 181 | #4 | 55808 |
| 8988 | 24270 | 67.2 | 61.8 | 21 | 351 | #4 | 55809 |
| 8989 | 24271 | 62.4 | 59.9 (162) | 18 | 164 | #3 | 55810 |
| 8990 | 24272 | 67.2 | 60.7 | 20 | 243 | #4 | 55811 |
| 8991 | 24273 | 68.0 | 50.0 (215) | 16 | 191 | #4 | 55812 |
| 8992 | 24274 | 67.2 | 62.2 | 21 | 331 | #4 | 55813 |
| 8993 | 24275 | 68.0 | 58.5 | 18 | 210 | #4 | 55814 |
| 8994 | 24276 | 69.6 | 60.7 | 21 | 284 | #4 | 55815 |
| 8995 | 24277 | 50.0 (80) | — | 12 | 150 | #1 | 55816 |
| 8996 | 24278 | 50.0 (77) | — | 12 | 150 | #1 | 55817 |
| 8997 | 24279 | 67.8 (87) | — | 32 | 158 | #4 | 55818 |
| 8998 | 24280 | 68.8 | 59.3 | 16 | 270 | #4 | 55819 |
| 8999 | 24281 | 50.0 | 50.0 | 12 | 150 | #1 | 55820 |
| 9000 | 24282 | 50.0 | 50.0 (189) | 12 | 150 | #1 | 55821 |
| 9001 | 24283 | 63.2 | 50.0 | 14 | 208 | #3 | 55822 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9002 | 24284 | 50.0 | 50.0 (180) | 12 | 150 | #1 | 55823 |
| 9003 | 24285 | 50.0 | 50.0 | 12 | 150 | #1 | 55824 |
| 9004 | 24286 | 62.4 | 60.0 | 17 | 218 | #3 | 55825 |
| 9005 | 24287 | 56.8 | 50.0 | 12 | 150 | #2 | 55826 |
| 9006 | 24288 | 50.0 | 50.0 | 12 | 150 | #1 | 55827 |
| 9007 | 24289 | 65.6 | 55.3 | 24 | 208 | #4 | 55828 |
| 9008 | 24290 | 70.4 | 61.1 | 26 | 312 | #5 | 55829 |
| 9009 | 24291 | 72.0 | 59.6 | 18 | 264 | #5 | 55830 |
| 9010 | 24292 | 64.8 | 50.0 (266) | 12 | 182 | #3 | 55831 |
| 9011 | 24293 | 66.4 | 58.2 | 19 | 204 | #4 | 55832 |
| 9012 | 24294 | 72.0 | 63.3 | 26 | 570 | #5 | 55833 |
| 9013 | 24295 | 66.4 | 59.6 | 14 | 213 | #4 | 55834 |
| 9014 | 24296 | 63.2 | 50.0 | 12 | 167 | #3 | 55835 |
| 9015 | 24297 | 61.6 | 61.7 (206) | 17 | 182 | #3 | 55836 |
| 9016 | 24298 | 69.6 | 61.5 | 20 | 264 | #4 | 55837 |
| 9017 | 24299 | 65.6 | 58.9 | 17 | 240 | #4 | 55838 |
| 9018 | 24300 | 64.8 | 57.5 | 14 | 218 | #3 | 55839 |
| 9019 | 24301 | 66.4 | 57.5 | 17 | 252 | #4 | 55840 |
| 9020 | 24302 | 50.0 | 50.0 | 12 | 150 | #1 | 55841 |
| 9021 | 24303 | 50.0 (114) | — | 12 | 150 | #1 | 55842 |
| 9022 | 24304 | 63.2 | 54.0 (176) | 27 | 168 | #3 | 55843 |
| 9023 | 24305 | 64.0 | 58.9 (151) | 19 | 181 | #3 | 55844 |
| 9024 | 24306 | 63.2 | 50.0 | 13 | 167 | #3 | 55845 |
| 9025 | 24307 | 72.0 | 62.2 | 34 | 355 | #5 | 55846 |
| 9026 | 24308 | 54.4 | 50.0 (182) | 13 | 151 | #1 | 55847 |
| 9027 | 24309 | 73.6 | 57.1 | 14 | 424 | #5 | 55848 |
| 9028 | 24310 | 74.4 | 62.9 | 37 | 331 | #5 | 55849 |
| 9029 | 24311 | 74.4 | 66.2 | 26 | 487 | #5 | 55850 |
| 9030 | 24312 | 68.4 (114) | — | 23 | 210 | #4 | 55851 |
| 9031 | 24313 | 70.4 | 61.5 | 22 | 311 | #5 | 55852 |
| 9032 | 24314 | 50.0 (79) | — | 12 | 150 | #1 | 55853 |
| 9033 | 24315 | 68.8 | 60.4 | 21 | 242 | #4 | 55854 |
| 9034 | 24316 | 50.0 (75) | — | 12 | 150 | #1 | 55855 |
| 9035 | 24317 | 68.8 | 62.9 | 22 | 343 | #4 | 55856 |
| 9036 | 24318 | 59.2 | 50.0 (169) | 17 | 163 | #2 | 55857 |
| 9037 | 24319 | 55.2 | 50.0 | 12 | 150 | #2 | 55858 |
| 9038 | 24320 | 64.0 | 58.2 | 17 | 206 | #3 | 55859 |
| 9039 | 24321 | 70.4 | 62.2 | 24 | 277 | #5 | 55860 |
| 9040 | 24322 | 73.6 | 65.1 | 22 | 383 | #5 | 55861 |
| 9041 | 24323 | 75.2 | 69.8 | 19 | 569 | #6 | 55862 |
| 9042 | 24324 | 68.0 | 61.8 | 22 | 250 | #1 | 55863 |
| 9043 | 24325 | 71.2 | 61.8 | 22 | 437 | #5 | 55864 |
| 9044 | 24326 | 68.0 | 61.8 | 18 | 274 | #4 | 55865 |
| 9045 | 24327 | 68.0 | 58.2 | 16 | 245 | #4 | 55866 |
| 9046 | 24328 | 77.6 | 64.7 | 21 | 388 | #6 | 55867 |
| 9047 | 24329 | 60.8 | 50.0 | 18 | 164 | #3 | 55868 |
| 9048 | 24330 | 50.0 | 50.0 | 12 | 150 | #1 | 55869 |
| 9049 | 24331 | 50.0 | 50.0 | 12 | 150 | #1 | 55870 |
| 9050 | 24332 | 64.0 | 50.0 | 16 | 225 | #3 | 55871 |
| 9051 | 24333 | 65.6 | 58.5 | 16 | 227 | #4 | 55872 |
| 9052 | 24334 | 66.4 | 58.9 | 20 | 211 | #4 | 55873 |
| 9053 | 24335 | 50.0 | 50.0 | 12 | 150 | #1 | 55874 |
| 9054 | 24336 | 65.6 | 56.0 | 18 | 199 | #4 | 55875 |
| 9055 | 24337 | 68.0 | 61.5 | 18 | 307 | #4 | 55876 |
| 9056 | 24338 | 67.2 | 61.1 | 23 | 321 | #4 | 55877 |
| 9057 | 24339 | 67.2 | 57.8 | 19 | 206 | #4 | 55878 |
| 9058 | 24340 | 67.2 | 61.8 | 18 | 281 | #4 | 55879 |
| 9059 | 24341 | 68.8 | 62.9 | 20 | 334 | #4 | 55880 |
| 9060 | 24342 | 64.0 | 50.0 | 16 | 215 | #3 | 55881 |
| 9061 | 24343 | 59.2 | 50.0 | 19 | 198 | #2 | 55882 |
| 9062 | 24344 | 60.0 | 50.0 | 15 | 163 | #2 | 55883 |
| 9063 | 24345 | 68.8 | 61.5 | 19 | 313 | #4 | 55884 |
| 9064 | 24346 | 69.6 | 63.5 (241) | 25 | 303 | #4 | 55885 |
| 9065 | 24347 | 72.0 | 62.5 | 20 | 333 | #5 | 55886 |
| 9066 | 24348 | 67.2 | 59.3 | 20 | 231 | #4 | 55887 |
| 9067 | 24349 | 67.2 | 59.6 | 16 | 229 | #4 | 55888 |
| 9068 | 24350 | 70.4 | 62.2 | 19 | 314 | #5 | 55889 |
| 9069 | 24351 | 72.0 | 64.4 | 25 | 512 | #5 | 55890 |
| 9070 | 24352 | 68.0 | 61.1 | 18 | 299 | #4 | 55891 |
| 9071 | 24353 | 58.4 | 50.5 | 13 | 191 | #2 | 55892 |
| 9072 | 24354 | 75.2 | 62.9 | 33 | 375 | #6 | 55893 |
| 9073 | 24355 | 63.2 | 57.1 | 14 | 199 | #3 | 55894 |
| 9074 | 24356 | 64.8 | 57.5 (226) | 20 | 192 | #3 | 55895 |
| 9075 | 24357 | 64.8 | 57.5 | 17 | 216 | #3 | 55896 |
| 9076 | 24358 | 70.4 | 62.9 | 21 | 390 | #5 | 55897 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9077 | 24359 | 68.0 | 60.4 | 18 | 252 | #4 | 55898 |
| 9078 | 24360 | 72.8 | 62.5 | 21 | 310 | #5 | 55899 |
| 9079 | 24361 | 50.0 | 50.0 | 12 | 150 | #1 | 55900 |
| 9080 | 24362 | 68.8 | 61.1 | 21 | 271 | #4 | 55901 |
| 9081 | 24363 | 73.6 | 68.4 | 22 | 580 | #5 | 55902 |
| 9082 | 24364 | 66.4 | 61.5 | 24 | 262 | #4 | 55903 |
| 9083 | 24365 | 69.6 | 60.0 | 20 | 265 | #4 | 55904 |
| 9084 | 24366 | 70.4 | 62.2 | 25 | 347 | #5 | 55905 |
| 9085 | 24367 | 68.0 | 59.6 | 17 | 226 | #4 | 55906 |
| 9086 | 24368 | 66.4 | 58.9 | 17 | 219 | #4 | 55907 |
| 9087 | 24369 | 72.8 | 63.3 | 26 | 365 | #5 | 55908 |
| 9088 | 24370 | 64.8 | 55.6 | 14 | 172 | #3 | 55909 |
| 9089 | 24371 | 72.8 | 65.8 | 24 | 492 | #5 | 55910 |
| 9090 | 24372 | 68.8 | 61.1 | 21 | 350 | #4 | 55911 |
| 9091 | 24373 | 50.0 (74) | — | 12 | 150 | #1 | 55912 |
| 9092 | 24374 | 50.0 | 50.0 | 12 | 150 | #1 | 55913 |
| 9093 | 24375 | 63.3 (120) | — | 18 | 177 | #3 | 55914 |
| 9094 | 24376 | 69.6 | 58.2 (273) | 20 | 270 | #4 | 55915 |
| 9095 | 24377 | 66.4 | 59.6 | 17 | 251 | #4 | 55916 |
| 9096 | 24378 | 76.8 | 63.3 | 21 | 282 | #6 | 55917 |
| 9097 | 24379 | 61.6 | 50.0 (191) | 17 | 150 | #3 | 55918 |
| 9098 | 24380 | 67.2 | 59.3 | 25 | 241 | #4 | 55919 |
| 9099 | 24381 | 68.8 | 60.7 | 21 | 327 | #4 | 55920 |
| 9100 | 24382 | 66.4 | 59.3 | 19 | 250 | #4 | 55921 |
| 9101 | 24383 | 68.0 | 60.4 | 19 | 228 | #4 | 55922 |
| 9102 | 24384 | 65.6 | 60.6 (188) | 22 | 198 | #4 | 55923 |
| 9103 | 24385 | 68.0 | 58.9 | 22 | 249 | #4 | 55924 |
| 9104 | 24386 | 68.0 | 60.4 | 22 | 239 | #4 | 55925 |
| 9105 | 24387 | 68.0 | 61.5 | 21 | 293 | #4 | 55926 |
| 9106 | 24388 | 63.2 | 56.7 | 16 | 180 | #3 | 55927 |
| 9107 | 24389 | 75.2 | 62.5 | 28 | 352 | #6 | 55928 |
| 9108 | 24390 | 64.0 | 50.0 | 12 | 186 | #3 | 55929 |
| 9109 | 24391 | 71.2 | 63.3 | 19 | 309 | #5 | 55930 |
| 9110 | 24392 | 84.0 | 81.1 | 22 | 1261 | #7 | 55931 |
| 9111 | 24393 | 61.6 | 58.8 (131) | 24 | 167 | #3 | 55932 |
| 9112 | 24394 | 64.8 | 58.9 | 15 | 212 | #3 | 55933 |
| 9113 | 24395 | 64.0 | 55.3 | 12 | 207 | #3 | 55934 |
| 9114 | 24396 | 67.2 | 60.7 (178) | 17 | 177 | #4 | 55935 |
| 9115 | 24397 | 50.0 | 50.0 | 12 | 150 | #1 | 55936 |
| 9116 | 24398 | 58.4 | 50.0 (169) | 13 | 151 | #2 | 55937 |
| 9117 | 24399 | 66.4 | 59.6 | 22 | 202 | #4 | 55938 |
| 9118 | 24400 | 70.7 (75) | — | 13 | 150 | #5 | 55939 |
| 9119 | 24401 | 64.8 | 50.0 | 12 | 199 | #3 | 55940 |
| 9120 | 24402 | 63.2 | 50.0 | 12 | 161 | #3 | 55941 |
| 9121 | 24403 | 68.0 | 61.8 | 21 | 301 | #4 | 55942 |
| 9122 | 24404 | 68.8 | 58.9 | 25 | 223 | #4 | 55943 |
| 9123 | 24405 | 63.6 (118) | — | 19 | 167 | #3 | 55944 |
| 9124 | 24406 | 50.0 | 50.0 | 12 | 168 | #1 | 55945 |
| 9125 | 24407 | 67.2 | 61.1 | 20 | 336 | #4 | 55946 |
| 9126 | 24408 | 50.0 | 50.0 | 12 | 150 | #1 | 55947 |
| 9127 | 24409 | 68.8 | 58.2 | 18 | 258 | #4 | 55948 |
| 9128 | 24410 | 50.0 (79) | — | 12 | 150 | #1 | — |
| 9129 | 24411 | 69.6 | 61.8 | 21 | 362 | #4 | 55949 |
| 9130 | 24412 | 59.2 | 57.1 | 14 | 185 | #2 | 55950 |
| 9131 | 24413 | 50.0 | 50.0 | 12 | 150 | #1 | 55951 |
| 9132 | 24414 | 65.3 (72) | — | 12 | 211 | #4 | 55952 |
| 9133 | 24415 | 66.4 | 60.7 | 20 | 336 | #4 | 55953 |
| 9134 | 24416 | 66.4 | 63.3 (177) | 18 | 210 | #4 | 55954 |
| 9135 | 24417 | 61.6 | 50.0 (219) | 15 | 150 | #3 | 55955 |
| 9136 | 24418 | 60.0 | 50.0 (228) | 14 | 150 | #2 | 55956 |
| 9137 | 24419 | 66.4 | 50.0 | 17 | 184 | #4 | 55957 |
| 9138 | 24420 | 75.2 | 62.2 | 38 | 327 | #6 | 55958 |
| 9139 | 24421 | 60.8 | 50.0 | 12 | 175 | #3 | 55959 |
| 9140 | 24422 | 67.2 | 58.9 (248) | 24 | 220 | #4 | 55960 |
| 9141 | 24423 | 72.8 | 62.2 | 26 | 311 | #5 | 55961 |
| 9142 | 24424 | 50.0 | 50.0 | 12 | 150 | #1 | 55962 |
| 9143 | 24425 | 65.6 | 58.5 | 15 | 225 | #4 | 55963 |
| 9144 | 24426 | 57.6 | 50.0 | 12 | 150 | #2 | 55964 |
| 9145 | 24427 | 60.8 | 50.0 | 14 | 163 | #3 | 55965 |
| 9146 | 24428 | 65.6 | 60.7 | 19 | 226 | #4 | 55966 |
| 9147 | 24429 | 66.4 | 60.4 | 19 | 315 | #4 | 55967 |
| 9148 | 24430 | 69.6 | 60.7 | 33 | 261 | #4 | 55968 |
| 9149 | 24431 | 68.8 | 59.6 | 21 | 219 | #4 | 55969 |
| 9150 | 24432 | 69.6 | 62.5 | 19 | 355 | #4 | 55970 |
| 9151 | 24433 | 66.4 | 59.6 | 19 | 272 | #4 | 55971 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9152 | 24434 | 50.0 | 50.0 | 12 | 150 | #1 | 55972 |
| 9153 | 24435 | 68.8 | 61.1 | 21 | 274 | #4 | 55973 |
| 9154 | 24436 | 62.4 | 50.0 | 14 | 202 | #3 | 55974 |
| 9155 | 24437 | 68.8 | 61.5 | 25 | 288 | #4 | 55975 |
| 9156 | 24438 | 60.8 | 50.0 | 13 | 188 | #3 | 55976 |
| 9157 | 24439 | 50.0 | 50.0 | 12 | 150 | #1 | 55977 |
| 9158 | 24440 | 68.0 | 61.8 | 34 | 264 | #4 | 55978 |
| 9159 | 24441 | 50.0 | 50.0 | 12 | 150 | #1 | 55979 |
| 9160 | 24442 | 71.2 | 61.5 | 20 | 275 | #5 | 55980 |
| 9161 | 24443 | 64.0 | 54.9 | 13 | 187 | #3 | 55981 |
| 9162 | 24444 | 50.0 | 50.0 | 12 | 150 | #1 | 55982 |
| 9163 | 24445 | 70.4 | 60.2 (196) | 20 | 227 | #5 | 55983 |
| 9164 | 24446 | 71.2 | 61.5 | 23 | 281 | #5 | 55984 |
| 9165 | 24447 | 50.0 | 50.0 | 12 | 150 | #1 | 55985 |
| 9166 | 24448 | 57.6 | 50.0 (158) | 13 | 159 | #2 | 55986 |
| 9167 | 24449 | 68.8 | 59.3 | 24 | 242 | #4 | 55987 |
| 9168 | 24450 | 50.0 (66) | — | 12 | 150 | #1 | 55988 |
| 9169 | 24451 | 63.2 | 51.6 | 13 | 172 | #3 | 55989 |
| 9170 | 24452 | 50.0 | 50.0 | 12 | 150 | #1 | 55990 |
| 9171 | 24453 | 50.0 | 50.0 | 12 | 150 | #1 | 55991 |
| 9172 | 24454 | 66.4 | 60.0 | 16 | 226 | #4 | 55992 |
| 9173 | 24455 | 68.0 | 58.9 | 21 | 212 | #4 | 55993 |
| 9174 | 24456 | 50.0 | 50.0 | 12 | 150 | #1 | 55994 |
| 9175 | 24457 | 69.6 | 63.3 | 25 | 485 | #4 | 55995 |
| 9176 | 24458 | 69.6 | 60.7 | 23 | 280 | #4 | 55996 |
| 9177 | 24459 | 62.4 | 50.0 | 12 | 158 | #3 | 55997 |
| 9178 | 24460 | 71.2 | 61.1 | 22 | 365 | #5 | 55998 |
| 9179 | 24461 | 55.2 | 50.7 (136) | 17 | 159 | #2 | 55999 |
| 9180 | 24462 | 68.0 | 57.8 | 16 | 221 | #4 | 56000 |
| 9181 | 24463 | 64.0 | 55.8 (249) | 16 | 171 | #3 | 56001 |
| 9182 | 24464 | 62.4 | 57.3 (150) | 14 | 150 | #3 | 56002 |
| 9183 | 24465 | 50.0 | 50.0 | 12 | 150 | #1 | 56003 |
| 9184 | 24466 | 50.0 | 50.0 | 12 | 150 | #1 | 56004 |
| 9185 | 24467 | 60.8 | 57.1 | 14 | 172 | #3 | 56005 |
| 9186 | 24468 | 67.2 | 60.4 | 18 | 239 | #4 | 56006 |
| 9187 | 24469 | 62.4 | 50.0 | 14 | 200 | #3 | 56007 |
| 9188 | 24470 | 75.2 | 61.1 | 24 | 387 | #6 | 56008 |
| 9189 | 24471 | 72.8 | 64.0 | 26 | 465 | #5 | 56009 |
| 9190 | 24472 | 68.8 | 62.2 | 21 | 599 | #4 | 56010 |
| 9191 | 24473 | 66.4 | 53.1 | 19 | 201 | #4 | 56011 |
| 9192 | 24474 | 68.0 | 56.4 | 18 | 209 | #4 | 56012 |
| 9193 | 24475 | 68.0 | 60.7 | 18 | 295 | #4 | 56013 |
| 9194 | 24476 | 68.0 | 58.5 | 18 | 228 | #4 | 56014 |
| 9195 | 24477 | 66.4 | 60.3 (204) | 22 | 190 | #4 | 56015 |
| 9196 | 24478 | 62.4 | 58.5 | 12 | 189 | #3 | 56016 |
| 9197 | 24479 | 50.0 (75) | — | 12 | 150 | #1 | 56017 |
| 9198 | 24480 | 72.5 (69) | — | 19 | 150 | #5 | 56018 |
| 9199 | 24481 | 50.0 (82) | — | 12 | 150 | #1 | 56019 |
| 9200 | 24482 | 68.8 | 61.5 | 20 | 339 | #4 | 56020 |
| 9201 | 24483 | 69.6 | 61.8 | 25 | 287 | #4 | 56021 |
| 9202 | 24484 | 62.4 | 50.0 | 17 | 195 | #3 | 56022 |
| 9203 | 24485 | 67.2 | 57.9 (178) | 29 | 175 | #4 | 56023 |
| 9204 | 24486 | 50.0 | 50.0 | 12 | 150 | #1 | 56024 |
| 9205 | 24487 | 69.6 | 62.5 | 32 | 448 | #4 | 56025 |
| 9206 | 24488 | 65.6 | 57.5 | 20 | 231 | #4 | 56026 |
| 9207 | 24489 | 50.0 | 50.0 (147) | 19 | 261 | #1 | 56027 |
| 9208 | 24490 | 50.0 | 50.0 | 12 | 150 | #1 | 56028 |
| 9209 | 24491 | 61.6 | 58.5 (183) | 15 | 150 | #3 | 56029 |
| 9210 | 24492 | 66.4 | 61.1 | 20 | 278 | #4 | 56030 |
| 9211 | 24493 | 66.4 | 58.0 (269) | 28 | 195 | #4 | 56031 |
| 9212 | 24494 | 67.2 | 60.0 | 31 | 263 | #4 | 56032 |
| 9213 | 24495 | 58.4 | 53.5 | 16 | 172 | #2 | 56033 |
| 9214 | 24496 | 67.2 | 50.0 | 21 | 225 | #4 | 56034 |
| 9215 | 24497 | 68.8 | 61.8 | 19 | 341 | #4 | 56035 |
| 9216 | 24498 | 64.0 | 56.0 | 13 | 219 | #3 | 56036 |
| 9217 | 24499 | 70.4 | 61.5 | 21 | 300 | #5 | 56037 |
| 9218 | 24500 | 72.8 | 61.8 | 24 | 330 | #5 | 56038 |
| 9219 | 24501 | 74.4 | 64.0 | 24 | 632 | #5 | 56039 |
| 9220 | 24502 | 69.6 | 62.2 | 22 | 302 | #4 | 56040 |
| 9221 | 24503 | 68.0 | 61.8 | 19 | 324 | #4 | 56041 |
| 9222 | 24504 | 68.8 | 58.8 (257) | 22 | 263 | #4 | 56042 |
| 9223 | 24505 | 50.0 | 50.0 | 12 | 150 | #1 | 56043 |
| 9224 | 24506 | 67.2 | 56.5 (253) | 18 | 204 | #4 | 56044 |
| 9225 | 24507 | 70.4 | 58.5 | 22 | 244 | #5 | 56045 |
| 9226 | 24508 | 76.8 | 71.4 (234) | 14 | 519 | #6 | 56046 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9227 | 24509 | 63.2 | 58.5 | 22 | 178 | #3 | 56047 |
| 9228 | 24510 | 64.0 | 50.0 (216) | 14 | 154 | #3 | 56048 |
| 9229 | 24511 | 68.0 | 60.7 | 18 | 249 | #4 | 56049 |
| 9230 | 24512 | 50.0 | 50.0 | 12 | 150 | #1 | 56050 |
| 9231 | 24513 | 68.0 | 61.5 | 19 | 307 | #4 | 56051 |
| 9232 | 24514 | 61.6 | 55.3 (150) | 14 | 150 | #3 | 56052 |
| 9233 | 24515 | 68.0 | 61.5 | 18 | 304 | #4 | 56053 |
| 9234 | 24516 | 67.2 | 58.9 | 14 | 224 | #4 | 56054 |
| 9235 | 24517 | 67.2 | 61.5 | 21 | 351 | #4 | 56055 |
| 9236 | 24518 | 66.4 | 60.7 | 20 | 256 | #4 | 56056 |
| 9237 | 24519 | 63.2 | 50.0 | 16 | 187 | #3 | 56057 |
| 9238 | 24520 | 68.8 | 60.4 | 20 | 313 | #4 | 56058 |
| 9239 | 24521 | 68.0 | 61.5 | 19 | 313 | #4 | 56059 |
| 9240 | 24522 | 85.6 | 69.8 | 33 | 632 | #8 | 56060 |
| 9241 | 24523 | 50.0 | 50.0 | 12 | 150 | #1 | 56061 |
| 9242 | 24524 | 68.0 | 58.2 | 22 | 231 | #4 | 56062 |
| 9243 | 24525 | 66.4 | 58.9 | 17 | 226 | #4 | 56063 |
| 9244 | 24526 | 72.8 | 62.9 | 33 | 370 | #5 | 56064 |
| 9245 | 24527 | 50.0 | 50.0 | 12 | 150 | #1 | 56065 |
| 9246 | 24528 | 50.0 | 50.0 | 12 | 150 | #1 | 56066 |
| 9247 | 24529 | 70.4 | 61.8 | 19 | 417 | #5 | 56067 |
| 9248 | 24530 | 65.6 | 56.7 | 14 | 219 | #4 | 56068 |
| 9249 | 24531 | 64.8 | 64.0 (172) | 24 | 184 | #3 | 56069 |
| 9250 | 24532 | 69.6 | 61.1 | 20 | 264 | #4 | 56070 |
| 9251 | 24533 | 64.0 | 50.0 | 12 | 171 | #3 | 56071 |
| 9252 | 24534 | 67.2 | 61.5 | 21 | 323 | #4 | 56072 |
| 9253 | 24535 | 66.4 | 63.8 (130) | 17 | 170 | #4 | 56073 |
| 9254 | 24536 | 50.0 | 50.0 | 12 | 150 | #1 | 56074 |
| 9255 | 24537 | 50.0 | 50.0 | 12 | 150 | #1 | 56075 |
| 9256 | 24538 | 60.2 (98) | — | 23 | 150 | #3 | 56076 |
| 9257 | 24539 | 68.8 | 60.0 | 15 | 225 | #4 | 56077 |
| 9258 | 24540 | 67.2 | 60.0 | 21 | 261 | #4 | 56078 |
| 9259 | 24541 | 50.0 (87) | — | 12 | 150 | #1 | 56079 |
| 9260 | 24542 | 70.4 | 62.5 | 20 | 289 | #5 | 56080 |
| 9261 | 24543 | 69.6 | 66.0 (159) | 26 | 253 | #4 | 56081 |
| 9262 | 24544 | 68.0 | 59.6 | 26 | 292 | #4 | 56082 |
| 9263 | 24545 | 88.8 | 89.1 (174) | 29 | 699 | #8 | 56083 |
| 9264 | 24546 | 65.6 | 60.0 | 18 | 251 | #4 | 56084 |
| 9265 | 24547 | 70.4 | 61.8 | 19 | 270 | #5 | 56085 |
| 9266 | 24548 | 52.0 | 50.0 | 13 | 150 | #1 | 56086 |
| 9267 | 24549 | 66.4 | 61.1 | 17 | 310 | #4 | 56087 |
| 9268 | 24550 | 66.4 | 58.5 | 16 | 236 | #4 | 56088 |
| 9269 | 24551 | 68.0 | 61.8 | 19 | 307 | #4 | 56089 |
| 9270 | 24552 | 62.4 | 53.1 | 13 | 184 | #3 | 56090 |
| 9271 | 24553 | 67.2 | 64.7 (170) | 25 | 232 | #4 | 56091 |
| 9272 | 24554 | 66.4 | 59.6 | 21 | 292 | #4 | 56092 |
| 9273 | 24555 | 64.0 | 56.0 | 17 | 194 | #3 | 56093 |
| 9274 | 24556 | 63.2 | 57.1 | 21 | 208 | #3 | 56094 |
| 9275 | 24557 | 89.0 (73) | — | 18 | 287 | #8 | 56095 |
| 9276 | 24558 | 88.0 | 72.7 | 29 | 626 | #8 | 56096 |
| 9277 | 24559 | 64.8 | 55.8 (154) | 25 | 215 | #3 | 56097 |
| 9278 | 24560 | 50.0 | 50.0 | 12 | 150 | #1 | 56098 |
| 9279 | 24561 | 68.0 | 61.8 | 24 | 299 | #4 | 56099 |
| 9280 | 24562 | 64.8 | 56.4 | 21 | 215 | #3 | 56100 |
| 9281 | 24563 | 64.8 | 59.3 | 14 | 231 | #3 | 56101 |
| 9282 | 24564 | 72.0 | 68.4 | 16 | 695 | #5 | 56102 |
| 9283 | 24565 | 84.0 | 66.9 | 25 | 510 | #7 | 56103 |
| 9284 | 24566 | 71.2 | 68.4 (212) | 15 | 386 | #5 | 56104 |
| 9285 | 24567 | 50.0 | 50.0 | 12 | 150 | #1 | 56105 |
| 9286 | 24568 | 50.0 | 50.0 | 12 | 150 | #1 | 56106 |
| 9287 | 24569 | 50.0 (86) | — | 12 | 150 | #1 | 56107 |
| 9288 | 24570 | 50.0 (109) | — | 12 | 150 | #1 | 56108 |
| 9289 | 24571 | 72.8 | 61.8 | 34 | 295 | #5 | 56109 |
| 9290 | 24572 | 50.0 | 50.0 | 12 | 150 | #1 | 56110 |
| 9291 | 24573 | 65.6 | 59.6 | 21 | 231 | #4 | 56111 |
| 9292 | 24574 | 50.0 | 50.0 | 12 | 150 | #1 | 56112 |
| 9293 | 24575 | 68.8 | 60.7 | 21 | 266 | #4 | 56113 |
| 9294 | 24576 | 50.0 | 50.0 | 12 | 150 | #1 | 56114 |
| 9295 | 24577 | 70.4 | 61.5 | 22 | 330 | #5 | 56115 |
| 9296 | 24578 | 64.8 | 57.1 | 20 | 200 | #3 | 56116 |
| 9297 | 24579 | 68.0 | 58.2 | 20 | 225 | #4 | 56117 |
| 9298 | 24580 | 68.0 | 60.5 (266) | 17 | 208 | #4 | 56118 |
| 9299 | 24581 | 50.0 | 50.0 | 12 | 150 | #1 | 56119 |
| 9300 | 24582 | 73.6 | 64.0 | 30 | 366 | #5 | 56120 |
| 9301 | 24583 | 65.6 | 58.2 | 17 | 222 | #4 | 56121 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9302 | 24584 | 50.0 | 50.0 | 12 | 150 | #1 | 56122 |
| 9303 | 24585 | 71.2 | 58.9 | 20 | 264 | #5 | 56123 |
| 9304 | 24586 | 63.2 | 57.9 (164) | 14 | 153 | #3 | 56124 |
| 9305 | 24587 | 62.4 | 57.1 | 15 | 229 | #3 | 56125 |
| 9306 | 24588 | 50.0 (76) | — | 12 | 150 | #1 | 56126 |
| 9307 | 24589 | 64.8 | 58.5 | 17 | 245 | #3 | 56127 |
| 9308 | 24590 | 68.0 | 61.8 | 20 | 366 | #4 | 56128 |
| 9309 | 24591 | 50.0 (81) | — | 12 | 150 | #1 | 56129 |
| 9310 | 24592 | 65.6 | 61.1 | 15 | 213 | #4 | 56130 |
| 9311 | 24593 | 70.4 | 62.2 | 22 | 386 | #5 | 56131 |
| 9312 | 24594 | 63.2 | 59.3 | 15 | 215 | #3 | 56132 |
| 9313 | 24595 | 66.4 | 58.5 | 16 | 231 | #4 | 56133 |
| 9314 | 24596 | 65.6 | 61.4 (207) | 20 | 199 | #4 | 56134 |
| 9315 | 24597 | 70.4 | 66.7 (165) | 25 | 265 | #5 | 56135 |
| 9316 | 24598 | 50.0 | 50.0 | 12 | 150 | #1 | 56136 |
| 9317 | 24599 | 73.6 | 65.5 | 34 | 442 | #5 | 56137 |
| 9318 | 24600 | 71.2 | 62.5 | 29 | 390 | #5 | 56138 |
| 9319 | 24601 | 61.1 (108) | — | 31 | 206 | #3 | 56139 |
| 9320 | 24602 | 50.0 | 50.0 | 12 | 150 | #1 | 56140 |
| 9321 | 24603 | 66.4 | 61.1 | 17 | 262 | #4 | 56141 |
| 9322 | 24604 | 50.4 | 50.0 | 13 | 159 | #1 | 56142 |
| 9323 | 24605 | 68.8 | 64.7 | 22 | 372 | #4 | 56143 |
| 9324 | 24606 | 73.6 | 62.2 | 24 | 300 | #5 | 56144 |
| 9325 | 24607 | 64.8 | 50.0 (270) | 15 | 166 | #3 | 56145 |
| 9326 | 24608 | 66.4 | 61.7 (222) | 23 | 218 | #4 | 56146 |
| 9327 | 24609 | 63.2 | 55.6 | 13 | 184 | #3 | 56147 |
| 9328 | 24610 | 68.0 | 61.1 | 34 | 271 | #4 | 56148 |
| 9329 | 24611 | 68.0 | 60.0 | 37 | 267 | #4 | 56149 |
| 9330 | 24612 | 68.8 | 61.5 | 21 | 296 | #4 | 56150 |
| 9331 | 24613 | 72.8 | 62.2 | 29 | 340 | #5 | 56151 |
| 9332 | 24614 | 61.6 | 50.0 | 13 | 180 | #3 | 56152 |
| 9333 | 24615 | 75.2 | 60.4 | 35 | 319 | #6 | 56153 |
| 9334 | 24616 | 88.0 | 84.0 (131) | 29 | 502 | #8 | 56154 |
| 9335 | 24617 | 66.4 | 59.3 (273) | 22 | 218 | #4 | 56155 |
| 9336 | 24618 | 71.2 | 60.4 | 20 | 278 | #5 | 56156 |
| 9337 | 24619 | 50.0 | 50.0 (156) | 13 | 150 | #1 | 56157 |
| 9338 | 24620 | 64.8 | 57.5 | 16 | 219 | #3 | 56158 |
| 9339 | 24621 | 50.0 | 50.0 | 12 | 150 | #1 | 56159 |
| 9340 | 24622 | 64.0 | 50.0 (183) | 17 | 158 | #3 | 56160 |
| 9341 | 24623 | 69.6 | 64.0 | 23 | 373 | #4 | 56161 |
| 9342 | 24624 | 76.8 | 65.8 | 25 | 417 | #6 | 56162 |
| 9343 | 24625 | 50.0 | 50.0 | 12 | 150 | #1 | 56163 |
| 9344 | 24626 | 68.8 | 61.5 | 21 | 445 | #4 | — |
| 9345 | 24627 | 61.6 | 50.0 | 16 | 191 | #3 | 56164 |
| 9346 | 24628 | 62.4 | 57.1 | 12 | 171 | #3 | 56165 |
| 9347 | 24629 | 76.0 | 65.1 | 27 | 370 | #6 | 56166 |
| 9348 | 24630 | 50.0 | 50.0 | 12 | 150 | #1 | 56167 |
| 9349 | 24631 | 77.6 | 62.2 | 33 | 391 | #6 | 56168 |
| 9350 | 24632 | 70.4 | 60.7 | 18 | 283 | #5 | 56169 |
| 9351 | 24633 | 50.0 | 50.0 | 12 | 150 | #1 | 56170 |
| 9352 | 24634 | 70.4 | 62.9 | 19 | 304 | #5 | 56171 |
| 9353 | 24635 | 64.8 | 50.0 | 12 | 194 | #3 | 56172 |
| 9354 | 24636 | 63.2 | 50.0 | 14 | 181 | #3 | 56173 |
| 9355 | 24637 | 50.0 | 50.0 | 12 | 150 | #1 | 56174 |
| 9356 | 24638 | 64.0 | 59.3 | 18 | 239 | #3 | 56175 |
| 9357 | 24639 | 71.2 | 62.5 | 25 | 320 | #5 | 56176 |
| 9358 | 24640 | 63.2 | 58.5 | 14 | 220 | #3 | 56177 |
| 9359 | 24641 | 65.6 | 59.6 (225) | 16 | 191 | #4 | 56178 |
| 9360 | 24642 | 68.0 | 61.8 | 18 | 286 | #4 | 56179 |
| 9361 | 24643 | 71.2 | 62.2 | 24 | 315 | #5 | 56180 |
| 9362 | 24644 | 63.2 | 58.2 | 18 | 183 | #3 | 56181 |
| 9363 | 24645 | 57.6 | 50.0 (173) | 16 | 156 | #2 | 56182 |
| 9364 | 24646 | 65.6 | 58.2 | 21 | 225 | #4 | 56183 |
| 9365 | 24647 | 68.8 | 62.2 | 26 | 348 | #4 | 56184 |
| 9366 | 24648 | 70.4 | 59.3 | 25 | 284 | #5 | 56185 |
| 9367 | 24649 | 61.6 | 57.5 | 13 | 195 | #3 | 56186 |
| 9368 | 24650 | 64.8 | 52.4 (246) | 14 | 173 | #3 | 56187 |
| 9369 | 24651 | 61.6 | 50.5 | 16 | 197 | #3 | 56188 |
| 9370 | 24652 | 68.0 | 58.2 | 18 | 241 | #4 | 56189 |
| 9371 | 24653 | 74.4 | 63.6 | 30 | 365 | #5 | 56190 |
| 9372 | 24654 | 50.0 | 50.0 | 12 | 150 | #1 | 56191 |
| 9373 | 24655 | 68.8 | 62.2 | 24 | 301 | #4 | 56192 |
| 9374 | 24656 | 69.6 | 61.5 | 25 | 293 | #4 | 56193 |
| 9375 | 24657 | 70.4 (81) | — | 28 | 196 | #5 | 56194 |
| 9376 | 24658 | 67.2 | 60.3 (224) | 21 | 213 | #4 | 56195 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9377 | 24659 | 76.0 | 63.3 | 31 | 438 | #6 | 56196 |
| 9378 | 24660 | 50.0 | 50.0 | 12 | 150 | #1 | 56197 |
| 9379 | 24661 | 68.8 | 63.6 | 22 | 484 | #4 | 56198 |
| 9380 | 24662 | 69.6 | 61.9 (244) | 15 | 267 | #4 | 56199 |
| 9381 | 24663 | 68.8 | 61.8 | 21 | 262 | #4 | 56200 |
| 9382 | 24664 | 72.0 | 62.5 | 21 | 331 | #5 | 56201 |
| 9383 | 24665 | 68.0 | 60.7 | 20 | 239 | #4 | 56202 |
| 9384 | 24666 | 71.2 | 62.2 | 28 | 337 | #5 | 56203 |
| 9385 | 24667 | 67.2 | 61.5 | 20 | 345 | #4 | 56204 |
| 9386 | 24668 | 60.8 | 57.8 | 14 | 214 | #3 | 56205 |
| 9387 | 24669 | 65.6 | 56.4 | 14 | 180 | #4 | 56206 |
| 9388 | 24670 | 64.8 | 58.2 | 14 | 197 | #3 | 56207 |
| 9389 | 24671 | 73.6 | 61.5 | 27 | 289 | #5 | 56208 |
| 9390 | 24672 | 68.8 | 60.4 | 22 | 276 | #4 | 56209 |
| 9391 | 24673 | 76.0 | 64.7 | 35 | 714 | #6 | 56210 |
| 9392 | 24674 | 67.2 | 57.5 | 16 | 222 | #4 | 56211 |
| 9393 | 24675 | 66.4 | 58.9 | 15 | 213 | #4 | 56212 |
| 9394 | 24676 | 50.0 | 50.0 (207) | 12 | 150 | #1 | 56213 |
| 9395 | 24677 | 60.8 | 50.0 | 12 | 160 | #3 | 56214 |
| 9396 | 24678 | 50.0 | 50.0 | 12 | 150 | #1 | 56215 |
| 9397 | 24679 | 50.0 | 50.0 | 12 | 150 | #1 | 56216 |
| 9398 | 24680 | 64.0 | 50.0 | 15 | 172 | #3 | 56217 |
| 9399 | 24681 | 68.0 | 62.5 | 21 | 324 | #4 | 56218 |
| 9400 | 24682 | 73.6 | 65.5 | 28 | 490 | #5 | 56219 |
| 9401 | 24683 | 68.0 | 60.7 | 20 | 284 | #4 | 56220 |
| 9402 | 24684 | 60.0 | 50.0 | 12 | 193 | #2 | 56221 |
| 9403 | 24685 | 66.4 | 57.1 | 20 | 245 | #4 | 56222 |
| 9404 | 24686 | 68.0 | 61.1 | 21 | 338 | #4 | 56223 |
| 9405 | 24687 | 65.6 | 57.8 | 18 | 211 | #4 | 56224 |
| 9406 | 24688 | 62.4 | 57.8 | 13 | 214 | #3 | 56225 |
| 9407 | 24689 | 68.0 | 62.2 | 19 | 295 | #4 | 56226 |
| 9408 | 24690 | 72.8 | 63.3 | 33 | 459 | #5 | 56227 |
| 9409 | 24691 | 65.6 | 58.5 | 18 | 192 | #4 | 56228 |
| 9410 | 24692 | 63.2 | 50.0 | 13 | 194 | #3 | 56229 |
| 9411 | 24693 | 50.0 | 50.0 | 12 | 150 | #1 | 56230 |
| 9412 | 24694 | 50.0 | 50.0 | 14 | 164 | #1 | 56231 |
| 9413 | 24695 | 74.5 (94) | — | 17 | 310 | #5 | 56232 |
| 9414 | 24696 | 67.2 | 62.3 (175) | 22 | 207 | #4 | 56233 |
| 9415 | 24697 | 67.2 | 51.6 | 19 | 226 | #4 | 56234 |
| 9416 | 24698 | 59.2 | 53.8 | 14 | 202 | #2 | 56235 |
| 9417 | 24699 | 62.4 | 54.5 | 12 | 208 | #3 | 56236 |
| 9418 | 24700 | 56.8 | 50.0 | 14 | 150 | #2 | 56237 |
| 9419 | 24701 | 64.8 | 58.5 | 19 | 223 | #3 | 56238 |
| 9420 | 24702 | 63.2 | 58.2 | 16 | 225 | #3 | 56239 |
| 9421 | 24703 | 50.0 | 50.0 | 12 | 150 | #1 | 56240 |
| 9422 | 24704 | 68.8 | 56.7 | 15 | 237 | #4 | 56241 |
| 9423 | 24705 | 67.2 | 50.0 | 19 | 190 | #4 | 56242 |
| 9424 | 24706 | 70.4 | 64.0 | 21 | 399 | #5 | 56243 |
| 9425 | 24707 | 50.0 | 50.0 | 12 | 150 | #1 | 56244 |
| 9426 | 24708 | 59.2 | 50.0 (170) | 12 | 150 | #2 | 56245 |
| 9427 | 24709 | 70.4 | 61.5 | 31 | 261 | #5 | 56246 |
| 9428 | 24710 | 71.2 | 59.3 | 15 | 314 | #5 | 56247 |
| 9429 | 24711 | 68.0 | 60.7 | 21 | 291 | #4 | 56248 |
| 9430 | 24712 | 71.2 | 65.1 | 28 | 449 | #5 | 56249 |
| 9431 | 24713 | 72.0 | 60.7 | 16 | 291 | #5 | 56250 |
| 9432 | 24714 | 72.0 | 59.6 | 19 | 258 | #5 | 56251 |
| 9433 | 24715 | 69.6 | 60.0 | 28 | 237 | #4 | 56252 |
| 9434 | 24716 | 72.0 | 65.1 | 24 | 568 | #5 | 56253 |
| 9435 | 24717 | 70.4 | 61.1 | 19 | 368 | #5 | 56254 |
| 9436 | 24718 | 64.8 | 58.9 | 14 | 181 | #3 | 56255 |
| 9437 | 24719 | 50.0 | 50.0 | 12 | 150 | #1 | 56256 |
| 9438 | 24720 | 68.8 | 58.5 | 17 | 224 | #4 | 56257 |
| 9439 | 24721 | 66.4 | 50.0 | 15 | 197 | #4 | 56258 |
| 9440 | 24722 | 65.3 (124) | — | 25 | 165 | #4 | 56259 |
| 9441 | 24723 | 70.4 | 61.8 | 22 | 510 | #5 | 56260 |
| 9442 | 24724 | 69.6 | 56.1 (264) | 24 | 276 | #4 | 56261 |
| 9443 | 24725 | 68.0 | 60.4 | 17 | 253 | #4 | 56262 |
| 9444 | 24726 | 70.4 | 64.7 | 20 | 411 | #5 | 56263 |
| 9445 | 24727 | 68.8 | 57.8 | 21 | 241 | #4 | 56264 |
| 9446 | 24728 | 67.2 | 54.4 (215) | 19 | 170 | #4 | 56265 |
| 9447 | 24729 | 50.0 (76) | — | 15 | 150 | #1 | — |
| 9448 | 24730 | 70.4 | 62.9 | 26 | 330 | #5 | 56266 |
| 9449 | 24731 | 62.4 | 58.2 | 13 | 227 | #3 | 56267 |
| 9450 | 24732 | 66.4 | 62.5 | 18 | 272 | #4 | 56268 |
| 9451 | 24733 | 68.0 | 54.0 (261) | 16 | 197 | #4 | 56269 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9452 | 24734 | 72.0 | 60.7 | 22 | 287 | #5 | 56270 |
| 9453 | 24735 | 67.2 | 60.8 (273) | 16 | 203 | #4 | 56271 |
| 9454 | 24736 | 66.4 | 56.7 | 17 | 239 | #4 | 56272 |
| 9455 | 24737 | 68.0 | 50.0 | 27 | 231 | #4 | 56273 |
| 9456 | 24738 | 50.0 | 50.0 | 12 | 150 | #1 | 56274 |
| 9457 | 24739 | 68.8 | 62.9 | 19 | 765 | #4 | 56275 |
| 9458 | 24740 | 64.8 | 56.7 | 15 | 216 | #3 | 56276 |
| 9459 | 24741 | 70.4 | 61.1 | 20 | 388 | #5 | 56277 |
| 9460 | 24742 | 66.4 | 61.8 | 19 | 301 | #4 | 56278 |
| 9461 | 24743 | 65.6 | 59.3 | 17 | 269 | #4 | 56279 |
| 9462 | 24744 | 68.8 | 60.7 | 19 | 276 | #4 | 56280 |
| 9463 | 24745 | 50.0 | 50.0 | 12 | 150 | #1 | 56281 |
| 9464 | 24746 | 50.0 | 50.0 | 12 | 150 | #1 | 56282 |
| 9465 | 24747 | 68.0 | 58.2 | 32 | 247 | #4 | 56283 |
| 9466 | 24748 | 50.0 | 50.0 | 12 | 150 | #1 | 56284 |
| 9467 | 24749 | 76.0 | 61.8 | 24 | 332 | #6 | 56285 |
| 9468 | 24750 | 68.0 | 61.1 | 19 | 270 | #4 | 56286 |
| 9469 | 24751 | 68.8 | 60.0 | 23 | 256 | #4 | 56287 |
| 9470 | 24752 | 70.4 | 60.7 | 24 | 273 | #5 | 56288 |
| 9471 | 24753 | 50.0 | 50.0(134) | 12 | 150 | #1 | 56289 |
| 9472 | 24754 | 69.6 | 63.6 | 29 | 500 | #4 | 56290 |
| 9473 | 24755 | 60.8 | 58.9 | 13 | 202 | #3 | 56291 |
| 9474 | 24756 | 75.2 | 62.9 | 27 | 352 | #6 | 56292 |
| 9475 | 24757 | 62.4 | 58.2 | 13 | 223 | #2 | 56293 |
| 9476 | 24758 | 69.6 | 63.6 | 21 | 283 | #4 | 56294 |
| 9477 | 24759 | 89.6(77) | — | 31 | 308 | #8 | 56295 |
| 9478 | 24760 | 68.0 | 58.2 | 19 | 243 | #4 | 56296 |
| 9479 | 24761 | 68.8 | 63.6 | 30 | 534 | #4 | 56297 |
| 9480 | 24762 | 68.0 | 58.9 | 22 | 220 | #4 | 56298 |
| 9481 | 24763 | 60.0 | 57.0(158) | 14 | 150 | #2 | 56299 |
| 9482 | 24764 | 68.8 | 62.2 | 21 | 354 | #4 | 56300 |
| 9483 | 24765 | 64.0 | 56.7 | 12 | 198 | #3 | 56301 |
| 9484 | 24766 | 65.6 | 50.0(240) | 15 | 167 | #4 | 56302 |
| 9485 | 24767 | 54.4 | 50.0(189) | 15 | 150 | #1 | 56303 |
| 9486 | 24768 | 50.0(78) | — | 12 | 150 | #1 | 56304 |
| 9487 | 24769 | 65.5(119) | — | 19 | 186 | #4 | 56305 |
| 9488 | 24770 | 61.6 | 58.8(221) | 14 | 160 | #3 | 56306 |
| 9489 | 24771 | 69.6 | 62.2 | 20 | 340 | #4 | 56307 |
| 9490 | 24772 | 61.6 | 55.3 | 12 | 182 | #3 | 56308 |
| 9491 | 24773 | 64.8 | 54.5 | 15 | 202 | #3 | 56309 |
| 9492 | 24774 | 50.0 | 50.0(126) | 12 | 150 | #1 | 56310 |
| 9493 | 24775 | 68.0 | 61.1 | 20 | 280 | #4 | 56311 |
| 9494 | 24776 | 65.6 | 60.0 | 18 | 301 | #4 | 56312 |
| 9495 | 24777 | 68.0 | 62.2 | 18 | 239 | #4 | 56313 |
| 9496 | 24778 | 65.6 | 60.6(155) | 16 | 164 | #4 | 56314 |
| 9497 | 24779 | 50.0 | 50.0 | 12 | 150 | #1 | 56315 |
| 9498 | 24780 | 50.0 | 50.0 | 12 | 150 | #1 | 56316 |
| 9499 | 24781 | 68.0 | 59.6 | 15 | 217 | #4 | 56317 |
| 9500 | 24782 | 50.0 | 50.0 | 12 | 150 | #1 | 56318 |
| 9501 | 24783 | 64.8 | 58.2 | 14 | 206 | #3 | 56319 |
| 9502 | 24784 | 65.6 | 50.0(220) | 13 | 150 | #4 | 56320 |
| 9503 | 24785 | 50.0 | 50.0 | 12 | 150 | #1 | 56321 |
| 9504 | 24786 | 68.8 | 60.4 | 18 | 253 | #4 | 56322 |
| 9505 | 24787 | 70.4 | 64.7 | 21 | 463 | #5 | 56323 |
| 9506 | 24788 | 72.0 | 60.0 | 19 | 242 | #5 | 56324 |
| 9507 | 24789 | 61.6 | 57.1 | 18 | 204 | #3 | 56325 |
| 9508 | 24790 | 50.0 | 50.0 | 12 | 150 | #1 | 56326 |
| 9509 | 24791 | 50.0 | 50.0 | 12 | 150 | #1 | 56327 |
| 9510 | 24792 | 63.2 | 50.0 | 14 | 195 | #3 | 56328 |
| 9511 | 24793 | 50.0 | 50.0 | 12 | 150 | #1 | 56329 |
| 9512 | 24794 | 62.4 | 56.0 | 15 | 232 | #3 | 56330 |
| 9513 | 24795 | 61.6 | 54.2 | 21 | 221 | #3 | 56331 |
| 9514 | 24796 | 66.4 | 57.5 | 19 | 227 | #4 | 56332 |
| 9515 | 24797 | 50.0 | 50.0 | 12 | 150 | #1 | 56333 |
| 9516 | 24798 | 70.4 | 63.3 | 22 | 361 | #5 | 56334 |
| 9517 | 24799 | 63.2 | 56.2(178) | 16 | 167 | #3 | 56335 |
| 9518 | 24800 | 64.8 | 51.3 | 12 | 333 | #3 | 56336 |
| 9519 | 24801 | 50.0 | 50.0 | 12 | 150 | #1 | 56337 |
| 9520 | 24802 | 73.6 | 61.1 | 26 | 303 | #5 | 56338 |
| 9521 | 24803 | 67.2 | 59.3 | 16 | 250 | #4 | 56339 |
| 9522 | 24804 | 69.6 | 61.5 | 19 | 315 | #4 | 56340 |
| 9523 | 24805 | 68.0 | 60.4 | 20 | 263 | #4 | 56341 |
| 9524 | 24806 | 74.4 | 62.5 | 17 | 431 | #5 | 56342 |
| 9525 | 24807 | 66.4 | 50.0 | 16 | 201 | #4 | 56343 |
| 9526 | 24808 | 67.2 | 60.4 | 18 | 283 | #4 | 56344 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9527 | 24809 | 65.6 | 58.9 | 19 | 272 | #4 | 56345 |
| 9528 | 24810 | 50.0 | 50.0 | 12 | 156 | #1 | 56346 |
| 9529 | 24811 | 50.0 | 50.0(250) | 12 | 150 | #1 | 56347 |
| 9530 | 24812 | 50.0 | 50.0 | 12 | 150 | #1 | 56348 |
| 9531 | 24813 | 50.0 | 50.0 | 12 | 150 | #1 | 56349 |
| 9532 | 24814 | 64.0 | 58.2 | 18 | 226 | #3 | 56350 |
| 9533 | 24815 | 78.4 | 64.4 | 32 | 402 | #6 | 56351 |
| 9534 | 24816 | 69.6 | 58.2 | 17 | 282 | #4 | 56352 |
| 9535 | 24817 | 50.0 | 50.0 | 12 | 150 | #1 | 56353 |
| 9536 | 24818 | 69.6 | 64.4 | 21 | 429 | #4 | 56354 |
| 9537 | 24819 | 60.8 | 57.1 | 14 | 201 | #3 | 56355 |
| 9538 | 24820 | 65.6 | 58.2 | 22 | 210 | #4 | 56356 |
| 9539 | 24821 | 76.0 | 65.5 | 30 | 402 | #6 | 56357 |
| 9540 | 24822 | 65.6(93) | — | 15 | 220 | #4 | 56358 |
| 9541 | 24823 | 62.4 | 50.0 | 13 | 167 | #3 | 56359 |
| 9542 | 24824 | 71.2 | 61.5 | 28 | 299 | #5 | 56360 |
| 9543 | 24825 | 68.8 | 59.3 | 29 | 243 | #4 | 56361 |
| 9544 | 24826 | 68.0 | 60.0 | 18 | 300 | #4 | 56362 |
| 9545 | 24827 | 60.8 | 50.0(241) | 13 | 168 | #3 | 56363 |
| 9546 | 24828 | 71.2 | 63.3 | 28 | 397 | #5 | 56364 |
| 9547 | 24829 | 61.6 | 58.0(150) | 17 | 150 | #3 | 56365 |
| 9548 | 24830 | 50.0 | 50.0 | 12 | 150 | #1 | 56366 |
| 9549 | 24831 | 72.0 | 63.3 | 30 | 668 | #5 | 56367 |
| 9550 | 24832 | 62.4 | 50.0(216) | 15 | 151 | #3 | 56368 |
| 9551 | 24833 | 68.8 | 62.9 | 21 | 358 | #4 | 56369 |
| 9552 | 24834 | 65.6 | 58.9 | 20 | 219 | #4 | 56370 |
| 9553 | 24835 | 70.4 | 62.9 | 21 | 361 | #5 | 56371 |
| 9554 | 24836 | 69.6 | 50.0 | 29 | 228 | #4 | 56372 |
| 9555 | 24837 | 72.0 | 63.3 | 33 | 456 | #5 | 56373 |
| 9556 | 24838 | 76.0 | 65.1 | 40 | 433 | #6 | 56374 |
| 9557 | 24839 | 62.4 | 50.0 | 14 | 150 | #3 | 56375 |
| 9558 | 24840 | 68.0 | 53.0(266) | 17 | 198 | #4 | 56376 |
| 9559 | 24841 | 68.0 | 62.5 | 20 | 317 | #4 | 56377 |
| 9560 | 24842 | 70.4 | 61.8 | 23 | 341 | #5 | 56378 |
| 9561 | 24843 | 69.6 | 63.3 | 19 | 339 | #4 | 56379 |
| 9562 | 24844 | 63.2 | 56.4 | 17 | 204 | #3 | 56380 |
| 9563 | 24845 | 50.0 | 50.0 | 12 | 150 | #1 | 56381 |
| 9564 | 24846 | 70.4 | 63.3 | 22 | 320 | #5 | 56382 |
| 9565 | 24847 | 65.6 | 58.9 | 17 | 240 | #4 | 56383 |
| 9566 | 24848 | 69.3(88) | — | 17 | 154 | #4 | — |
| 9567 | 24849 | 63.1(84) | — | 20 | 150 | #3 | 56384 |
| 9568 | 24850 | 68.0 | 61.8 | 20 | 372 | #4 | 56385 |
| 9569 | 24851 | 72.0 | 62.9 | 21 | 363 | #5 | 56386 |
| 9570 | 24852 | 68.0 | 61.1 | 19 | 258 | #4 | 56387 |
| 9571 | 24853 | 80.0 | 60.7 | 25 | 411 | #6 | 56388 |
| 9572 | 24854 | 50.0(74) | — | 12 | 150 | #1 | 56389 |
| 9573 | 24855 | 69.6 | 63.3 | 25 | 418 | #4 | 56390 |
| 9574 | 24856 | 64.8 | 50.0 | 15 | 189 | #3 | 56391 |
| 9575 | 24857 | 72.8 | 67.7(164) | 35 | 271 | #5 | 56392 |
| 9576 | 24858 | 68.0 | 61.1 | 21 | 391 | #4 | 56393 |
| 9577 | 24859 | 72.0 | 61.8 | 22 | 297 | #5 | 56394 |
| 9578 | 24860 | 70.4 | 61.8 | 25 | 300 | #5 | 56395 |
| 9579 | 24861 | 60.0 | 50.0 | 16 | 170 | #2 | 56396 |
| 9580 | 24862 | 72.0 | 64.4 | 19 | 456 | #5 | 56397 |
| 9581 | 24863 | 64.8 | 61.8 | 12 | 400 | #3 | 56398 |
| 9582 | 24864 | 66.4 | 56.7 | 16 | 275 | #4 | 56399 |
| 9583 | 24865 | 72.0 | 64.0 | 23 | 386 | #5 | 56400 |
| 9584 | 24866 | 67.2 | 59.6 | 18 | 350 | #4 | 56401 |
| 9585 | 24867 | 67.2 | 60.7 | 24 | 260 | #4 | 56402 |
| 9586 | 24868 | 50.0 | 50.0 | 12 | 150 | #1 | 56403 |
| 9587 | 24869 | 50.0 | 50.0 | 12 | 150 | #1 | 56404 |
| 9588 | 24870 | 67.2 | 50.0 | 14 | 213 | #4 | 56405 |
| 9589 | 24871 | 68.0 | 61.1 | 19 | 304 | #4 | 56406 |
| 9590 | 24872 | 72.0 | 63.3 | 29 | 351 | #5 | 56407 |
| 9591 | 24873 | 67.2 | 60.0 | 22 | 259 | #4 | 56408 |
| 9592 | 24874 | 77.9(68) | — | 19 | 186 | #6 | 56409 |
| 9593 | 24875 | 69.6 | 62.2 | 19 | 281 | #4 | 56410 |
| 9594 | 24876 | 68.0 | 60.4 | 19 | 278 | #4 | 56411 |
| 9595 | 24877 | 64.8 | 60.0 | 15 | 237 | #3 | 56412 |
| 9596 | 24878 | 67.2 | 61.1 | 23 | 306 | #4 | 56413 |
| 9597 | 24879 | 64.0 | 56.0 | 16 | 196 | #3 | 56414 |
| 9598 | 24880 | 73.6 | 64.7 | 20 | 507 | #5 | 56415 |
| 9599 | 24881 | 56.0 | 50.0 | 12 | 156 | #2 | 56416 |
| 9600 | 24882 | 67.2 | 58.8(255) | 20 | 217 | #4 | 56417 |
| 9601 | 24883 | 50.0 | 50.0 | 12 | 150 | #1 | 56418 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9602 | 24884 | 50.0 | 50.0 | 12 | 150 | #1 | 56419 |
| 9603 | 24885 | 68.0 | 62.2 | 17 | 306 | #4 | 56420 |
| 9604 | 24886 | 64.0 | 56.3(222) | 15 | 167 | #3 | 56421 |
| 9605 | 24887 | 84.0 | 69.1 | 25 | 722 | #7 | 56422 |
| 9606 | 24888 | 50.0 | 50.0 | 12 | 150 | #1 | 56423 |
| 9607 | 24889 | 65.6 | 58.8(238) | 20 | 217 | #4 | 56424 |
| 9608 | 24890 | 65.6 | 50.0 | 15 | 167 | #4 | 56425 |
| 9609 | 24891 | 78.4 | 73.8 | 24 | 1014 | #6 | 56426 |
| 9610 | 24892 | 65.6 | 59.6 | 18 | 224 | #4 | 56427 |
| 9611 | 24893 | 64.8 | 59.3 | 20 | 258 | #3 | 56428 |
| 9612 | 24894 | 50.0 | 50.0 | 12 | 150 | #1 | 56429 |
| 9613 | 24895 | 68.0 | 63.3 | 22 | 466 | #4 | 56430 |
| 9614 | 24896 | 68.8 | 60.4 | 19 | 291 | #4 | 56431 |
| 9615 | 24897 | 65.6 | 51.4(218) | 18 | 173 | #4 | 56432 |
| 9616 | 24898 | 50.0 | 50.0 | 12 | 150 | #1 | 56433 |
| 9617 | 24899 | 67.2 | 60.7 | 16 | 248 | #4 | 56434 |
| 9618 | 24900 | 61.6 | 55.6 | 15 | 183 | #3 | 56435 |
| 9619 | 24901 | 50.0 | 50.0 | 12 | 150 | #1 | 56436 |
| 9620 | 24902 | 64.0 | 54.8(177) | 22 | 188 | #3 | 56437 |
| 9621 | 24903 | 67.2 | 60.0 | 18 | 259 | #4 | 56438 |
| 9622 | 24904 | 65.6 | 59.6 | 15 | 198 | #4 | 56439 |
| 9623 | 24905 | 67.2 | 59.6 | 20 | 256 | #4 | 56440 |
| 9624 | 24906 | 70.4 | 62.9 | 33 | 352 | #5 | 56441 |
| 9625 | 24907 | 64.8 | 61.8 | 20 | 294 | #3 | 56442 |
| 9626 | 24908 | 61.6 | 57.5 | 14 | 208 | #3 | 56443 |
| 9627 | 24909 | 69.6 | 60.4 | 19 | 253 | #4 | 56444 |
| 9628 | 24910 | 50.0 | 50.0(142) | 12 | 150 | #1 | 56445 |
| 9629 | 24911 | 50.0 | 50.0 | 12 | 150 | #1 | 56446 |
| 9630 | 24912 | 68.0 | 60.7 | 19 | 259 | #4 | 56447 |
| 9631 | 24913 | 66.4 | 59.6 | 17 | 260 | #4 | 56448 |
| 9632 | 24914 | 72.0 | 64.4 | 24 | 815 | #5 | 56449 |
| 9633 | 24915 | 70.4 | 56.4 | 30 | 253 | #5 | 56450 |
| 9634 | 24916 | 60.8 | 56.7 | 16 | 206 | #3 | 56451 |
| 9635 | 24917 | 58.4 | 50.0 | 12 | 165 | #2 | 56452 |
| 9636 | 24918 | 65.6 | 60.0 | 16 | 241 | #4 | 56453 |
| 9637 | 24919 | 63.2 | 50.0 | 12 | 196 | #3 | 56454 |
| 9638 | 24920 | 72.0 | 60.7 | 34 | 289 | #5 | 56455 |
| 9639 | 24921 | 64.8 | 57.8 | 19 | 226 | #3 | 56456 |
| 9640 | 24922 | 50.0 | 50.0 | 12 | 150 | #1 | 56457 |
| 9641 | 24923 | 68.8 | 60.9(243) | 20 | 256 | #4 | 56458 |
| 9642 | 24924 | 68.0 | 61.1 | 19 | 302 | #4 | 56459 |
| 9643 | 24925 | 61.6 | 50.0 | 12 | 171 | #3 | 56460 |
| 9644 | 24926 | 66.4 | 50.5 | 18 | 249 | #4 | 56461 |
| 9645 | 24927 | 69.6 | 59.6 | 18 | 307 | #4 | 56462 |
| 9646 | 24928 | 63.2 | 55.6 | 15 | 192 | #3 | 56463 |
| 9647 | 24929 | 65.6 | 58.2 | 12 | 178 | #4 | 56464 |
| 9648 | 24930 | 62.4 | 52.7 | 12 | 205 | #3 | 56465 |
| 9649 | 24931 | 50.0 | 50.0 | 12 | 150 | #1 | 56466 |
| 9650 | 24932 | 66.2(68) | — | 13 | 150 | #4 | — |
| 9651 | 24933 | 65.6 | 58.2 | 23 | 207 | #4 | 56467 |
| 9652 | 24934 | 70.4 | 63.3 | 24 | 358 | #5 | 56468 |
| 9653 | 24935 | 68.8 | 61.5 | 19 | 271 | #4 | 56469 |
| 9654 | 24936 | 69.6 | 62.5 | 22 | 401 | #4 | 56470 |
| 9655 | 24937 | 65.6 | 59.3 | 15 | 197 | #4 | 56471 |
| 9656 | 24938 | 50.0 | 50.0(156) | 12 | 150 | #1 | 56472 |
| 9657 | 24939 | 63.2 | 50.0(230) | 17 | 165 | #3 | 56473 |
| 9658 | 24940 | 65.6 | 60.4 | 18 | 301 | #4 | 56474 |
| 9659 | 24941 | 66.4 | 59.6 | 21 | 300 | #4 | 56475 |
| 9660 | 24942 | 66.4 | 58.9 | 15 | 231 | #4 | 56476 |
| 9661 | 24943 | 50.0 | 50.0 | 12 | 150 | #1 | 56477 |
| 9662 | 24944 | 62.4 | 50.0 | 12 | 196 | #3 | 56478 |
| 9663 | 24945 | 68.0 | 62.9 | 21 | 296 | #4 | 56479 |
| 9664 | 24946 | 66.4 | 58.9 | 24 | 239 | #4 | 56480 |
| 9665 | 24947 | 50.0 | 50.0 | 12 | 150 | #1 | 56481 |
| 9666 | 24948 | 67.2 | 63.6(187) | 22 | 222 | #4 | 56482 |
| 9667 | 24949 | 65.6 | 50.0 | 14 | 203 | #4 | 56483 |
| 9668 | 24950 | 65.6 | 60.4 | 14 | 259 | #4 | 56484 |
| 9669 | 24951 | 50.0(72) | — | 12 | 150 | #1 | 56485 |
| 9670 | 24952 | 67.2 | 61.5 | 16 | 352 | #4 | 56486 |
| 9671 | 24953 | 50.0 | 50.0 | 12 | 150 | #1 | 56487 |
| 9672 | 24954 | 68.0 | 60.7 | 22 | 244 | #4 | 56488 |
| 9673 | 24955 | 70.4 | 56.7 | 21 | 256 | #5 | 56489 |
| 9674 | 24956 | 50.0 | 50.0 | 12 | 150 | #1 | 56490 |
| 9675 | 24957 | 76.0 | 62.9 | 28 | 337 | #6 | 56491 |
| 9676 | 24958 | 68.0 | 61.1 | 20 | 287 | #4 | 56492 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9677 | 24959 | 65.6 | 60.7 | 20 | 226 | #4 | 56493 |
| 9678 | 24960 | 62.4 | 58.9 | 17 | 245 | #3 | 56494 |
| 9679 | 24961 | 68.0 | 60.4 | 17 | 255 | #4 | 56495 |
| 9680 | 24962 | 68.0 | 57.5 | 20 | 226 | #4 | 56496 |
| 9681 | 24963 | 68.8 | 61.8 | 20 | 462 | #4 | 56497 |
| 9682 | 24964 | 61.6 | 57.9(259) | 17 | 179 | #3 | 56498 |
| 9683 | 24965 | 70.4 | 64.0 | 21 | 419 | #5 | 56499 |
| 9684 | 24966 | 63.2 | 50.0 | 13 | 185 | #3 | 56500 |
| 9685 | 24967 | 66.4 | 57.8 | 17 | 205 | #4 | 56501 |
| 9686 | 24968 | 70.4 | 58.2 | 17 | 209 | #5 | 56502 |
| 9687 | 24969 | 71.2 | 61.1 | 22 | 344 | #5 | 56503 |
| 9688 | 24970 | 65.6 | 59.2(240) | 22 | 218 | #4 | 56504 |
| 9689 | 24971 | 67.2 | 57.8 | 17 | 207 | #4 | 56505 |
| 9690 | 24972 | 68.0 | 56.4 | 20 | 374 | #4 | 56506 |
| 9691 | 24973 | 71.2 | 61.5 | 23 | 412 | #5 | 56507 |
| 9692 | 24974 | 72.0 | 67.5(169) | 36 | 286 | #5 | 56508 |
| 9693 | 24975 | 50.0 | 50.0 | 12 | 150 | #1 | 56509 |
| 9694 | 24976 | 69.6 | 60.0 | 17 | 262 | #4 | 56510 |
| 9695 | 24977 | 61.6 | 50.0(170) | 13 | 150 | #3 | 56511 |
| 9696 | 24978 | 60.0 | 56.0 | 12 | 192 | #2 | 56512 |
| 9697 | 24979 | 67.2 | 50.0 | 15 | 237 | #4 | 56513 |
| 9698 | 24980 | 68.0 | 61.1 | 20 | 319 | #4 | 56514 |
| 9699 | 24981 | 67.2 | 60.7 | 20 | 323 | #4 | 56515 |
| 9700 | 24982 | 67.2 | 60.0 | 16 | 257 | #4 | 56516 |
| 9701 | 24983 | 71.2 | 61.1 | 21 | 262 | #5 | 56517 |
| 9702 | 24984 | 68.8 | 62.6(243) | 26 | 264 | #4 | 56518 |
| 9703 | 24985 | 70.4 | 60.4 | 27 | 281 | #5 | 56519 |
| 9704 | 24986 | 67.2 | 61.8 | 19 | 230 | #4 | 56520 |
| 9705 | 24987 | 60.0 | 54.9 | 12 | 203 | #2 | 56521 |
| 9706 | 24988 | 70.4 | 60.0 | 23 | 267 | #5 | 56522 |
| 9707 | 24989 | 69.6 | 63.3(240) | 21 | 265 | #4 | 56523 |
| 9708 | 24990 | 66.4 | 58.9 | 22 | 256 | #4 | 56524 |
| 9709 | 24991 | 65.6 | 57.8 | 16 | 216 | #4 | 56525 |
| 9710 | 24992 | 68.0 | 62.5 | 21 | 303 | #4 | 56526 |
| 9711 | 24993 | 68.0 | 60.0 | 20 | 354 | #4 | 56527 |
| 9712 | 24994 | 70.4 | 61.1 | 23 | 257 | #5 | 56528 |
| 9713 | 24995 | 67.2 | 58.2 | 15 | 217 | #4 | 56529 |
| 9714 | 24996 | 59.2 | 50.0(236) | 14 | 150 | #2 | 56530 |
| 9715 | 24997 | 67.2 | 58.8(272) | 19 | 224 | #4 | 56531 |
| 9716 | 24998 | 74.4 | 64.4 | 20 | 370 | #5 | 56532 |
| 9717 | 24999 | 56.8(111) | — | 13 | 155 | #2 | 56533 |
| 9718 | 25000 | 70.4 | 62.9 | 23 | 309 | #5 | 56534 |
| 9719 | 25001 | 81.0(79) | — | 12 | 260 | #7 | 56535 |
| 9720 | 25002 | 65.6 | 50.0(273) | 16 | 192 | #4 | 56536 |
| 9721 | 25003 | 64.0 | 58.5 | 15 | 267 | #3 | 56537 |
| 9722 | 25004 | 76.0 | 61.5 | 31 | 330 | #6 | 56538 |
| 9723 | 25005 | 63.4(82) | — | 13 | 150 | #3 | — |
| 9724 | 25006 | 74.6(67) | — | 19 | 162 | #5 | 56539 |
| 9725 | 25007 | 69.6 | 62.5 | 24 | 404 | #4 | 56540 |
| 9726 | 25008 | 64.8 | 57.5 | 18 | 204 | #3 | 56541 |
| 9727 | 25009 | 50.0(105) | — | 12 | 150 | #1 | 56542 |
| 9728 | 25010 | 50.0(82) | — | 35 | 170 | #1 | — |
| 9729 | 25011 | 73.8(84) | — | 19 | 191 | #5 | 56543 |
| 9730 | 25012 | 51.2 | 50.0(155) | 12 | 150 | #1 | 56544 |
| 9731 | 25013 | 50.0 | 50.0 | 12 | 150 | #1 | 56545 |
| 9732 | 25014 | 65.6 | 59.3 | 16 | 236 | #4 | 56546 |
| 9733 | 25015 | 50.0 | 50.0(139) | 12 | 150 | #1 | 56547 |
| 9734 | 25016 | 65.6 | 56.4 | 23 | 206 | #4 | 56548 |
| 9735 | 25017 | 68.8 | 61.8 | 19 | 331 | #4 | 56549 |
| 9736 | 25018 | 50.0 | 50.0 | 12 | 150 | #1 | 56550 |
| 9737 | 25019 | 65.6 | 63.4(164) | 21 | 197 | #4 | 56551 |
| 9738 | 25020 | 64.0 | 54.2(273) | 16 | 190 | #3 | 56552 |
| 9739 | 25021 | 72.0 | 64.4 | 18 | 300 | #5 | 56553 |
| 9740 | 25022 | 69.6 | 62.5 | 21 | 347 | #4 | 56554 |
| 9741 | 25023 | 61.6 | 50.0(217) | 17 | 150 | #3 | 56555 |
| 9742 | 25024 | 69.6 | 59.6 | 23 | 244 | #4 | 56556 |
| 9743 | 25025 | 63.2 | 55.5(209) | 16 | 164 | #3 | 56557 |
| 9744 | 25026 | 69.7(66) | — | 15 | 150 | #4 | 56558 |
| 9745 | 25027 | 50.0 | 50.0 | 12 | 150 | #1 | 56559 |
| 9746 | 25028 | 68.8 | 60.7 | 18 | 295 | #4 | 56560 |
| 9747 | 25029 | 50.0(79) | — | 12 | 150 | #1 | 56561 |
| 9748 | 25030 | 69.6 | 58.5 | 16 | 249 | #4 | 56562 |
| 9749 | 25031 | 70.4 | 61.1 | 21 | 283 | #5 | 56563 |
| 9750 | 25032 | 65.6 | 51.3 | 13 | 245 | #4 | 56564 |
| 9751 | 25033 | 50.0 | 50.0 | 29 | 281 | #1 | 56565 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9752 | 25034 | 59.2 | 56.0 | 14 | 189 | #2 | 56566 |
| 9753 | 25035 | 67.2 | 57.8(251) | 18 | 210 | #4 | 56567 |
| 9754 | 25036 | 65.6 | 50.0 | 12 | 190 | #4 | 56568 |
| 9755 | 25037 | 60.0 | 50.0 | 13 | 161 | #2 | 56569 |
| 9756 | 25038 | 68.0 | 61.1 | 21 | 247 | #4 | 56570 |
| 9757 | 25039 | 56.0 | 50.0(206) | 14 | 150 | #2 | 56571 |
| 9758 | 25040 | 72.0 | 64.4 | 22 | 661 | #5 | 56572 |
| 9759 | 25041 | 57.6 | 53.1(256) | 12 | 150 | #2 | 56573 |
| 9760 | 25042 | 81.6 | 60.7 | 25 | 468 | #7 | 56574 |
| 9761 | 25043 | 64.0 | 50.0 | 12 | 160 | #3 | 56575 |
| 9762 | 25044 | 64.8 | 59.6 | 16 | 232 | #3 | 56576 |
| 9763 | 25045 | 64.0 | 50.0 | 16 | 180 | #3 | 56577 |
| 9764 | 25046 | 67.2 | 50.0 | 14 | 191 | #4 | 56578 |
| 9765 | 25047 | 68.0 | 60.7 | 17 | 318 | #4 | 56579 |
| 9766 | 25048 | 69.6 | 62.5 | 20 | 278 | #4 | 56580 |
| 9767 | 25049 | 63.2 | 58.8(204) | 18 | 161 | #3 | 56581 |
| 9768 | 25050 | 71.2 | 65.8 | 20 | 556 | #5 | 56582 |
| 9769 | 25051 | 63.2 | 60.7(178) | 19 | 180 | #3 | 56583 |
| 9770 | 25052 | 50.0 | 50.0 | 12 | 150 | #1 | 56584 |
| 9771 | 25053 | 64.8 | 55.3 | 12 | 196 | #3 | 56585 |
| 9772 | 25054 | 66.4 | 59.5(200) | 24 | 197 | #4 | 56586 |
| 9773 | 25055 | 55.2 | 50.0(273) | 12 | 167 | #2 | 56587 |
| 9774 | 25056 | 64.8 | 58.5 | 14 | 206 | #3 | 56588 |
| 9775 | 25057 | 50.0 | 50.0 | 12 | 150 | #1 | 56589 |
| 9776 | 25058 | 72.8 | 63.6 | 22 | 356 | #5 | 56590 |
| 9777 | 25059 | 64.8 | 59.6 | 16 | 243 | #3 | 56591 |
| 9778 | 25070 | 69.6 | 61.5 | 23 | 276 | #4 | 56592 |
| 9779 | 25061 | 63.2 | 56.0 | 14 | 191 | #3 | 56593 |
| 9780 | 25062 | 68.0 | 62.5 | 21 | 374 | #4 | 56594 |
| 9781 | 25063 | 50.0 | 50.0 | 12 | 150 | #1 | 56595 |
| 9782 | 25064 | 62.4 | 50.0 | 12 | 166 | #3 | 56596 |
| 9783 | 25065 | 70.4 | 62.2 | 20 | 296 | #5 | 56597 |
| 9784 | 25066 | 64.8 | 50.0 | 16 | 204 | #3 | 56598 |
| 9785 | 25067 | 70.4 | 60.0 | 18 | 263 | #5 | 56599 |
| 9786 | 25068 | 70.4 | 64.0 | 22 | 580 | #5 | 56600 |
| 9787 | 25069 | 71.2 | 58.5 | 29 | 249 | #5 | 56601 |
| 9788 | 25070 | 71.2 | 64.4 | 28 | 464 | #5 | 56602 |
| 9689 | 25071 | 68.5(92) | — | 12 | 157 | #4 | 56603 |
| 9790 | 25072 | 67.2 | 57.8 | 20 | 211 | #4 | 56604 |
| 9791 | 25073 | 66.4 | 60.0 | 17 | 261 | #4 | 56605 |
| 9792 | 25074 | 50.0 | 50.0 | 12 | 150 | #1 | 56606 |
| 9793 | 25075 | 70.4 | 61.6(229) | 27 | 223 | #5 | 56607 |
| 9794 | 25076 | 50.0(75) | — | 36 | 177 | #1 | 56608 |
| 9795 | 25077 | 50.0 | 50.0 | 12 | 150 | #1 | 56609 |
| 9796 | 25078 | 65.6 | 50.0 | 13 | 234 | #4 | 56610 |
| 9797 | 25079 | 64.8 | 50.0(235) | 17 | 165 | #3 | 56611 |
| 9798 | 25080 | 64.0 | 58.2 | 16 | 184 | #3 | 56612 |
| 9799 | 25081 | 73.6 | 64.7 | 25 | 466 | #5 | 56613 |
| 9800 | 25082 | 50.0 | 50.0 | 12 | 150 | #1 | 56614 |
| 9801 | 25083 | 64.0 | 50.0(256) | 24 | 222 | #3 | 56615 |
| 9802 | 25084 | 50.0 | 50.0 | 12 | 150 | #1 | 56616 |
| 9803 | 25085 | 66.4 | 55.3 | 18 | 222 | #4 | 56617 |
| 9804 | 25086 | 86.6(82) | — | 30 | 333 | #8 | 56618 |
| 9805 | 25087 | 68.8 | 52.1(165) | 17 | 262 | #4 | 56619 |
| 9806 | 25088 | 71.2 | 62.2 | 22 | 377 | #5 | 56620 |
| 9807 | 25089 | 68.8 | 60.0 | 17 | 264 | #4 | 56621 |
| 9808 | 25090 | 50.0 | 50.0(132) | 12 | 150 | #1 | 56622 |
| 9809 | 25091 | 68.0 | 61.1 | 22 | 309 | #4 | 56623 |
| 9810 | 25092 | 68.0 | 60.4 | 18 | 287 | #4 | 56624 |
| 9811 | 25093 | 62.4 | 60.5(195) | 21 | 163 | #3 | 56625 |
| 9812 | 25094 | 68.0 | 63.6 | 17 | 425 | #4 | 56626 |
| 9813 | 25095 | 64.8 | 58.5 | 15 | 213 | #3 | 56627 |
| 9814 | 25096 | 69.6 | 61.1 | 20 | 284 | #4 | 56628 |
| 9815 | 25097 | 86.4 | 85.2(135) | 23 | 497 | #8 | 56629 |
| 9816 | 25098 | 72.4(76) | — | 17 | 163 | #5 | 56630 |
|  | 25099 | 50.0 | 50.0 | 12 | 150 | #1 | 56631 |
| 9817 | 25100 | 68.8 | 60.0 | 28 | 343 | #4 | 56632 |
| 9818 | 25101 | 76.0 | 75.8(132) | 29 | 347 | #6 | 56633 |
| 9819 | 25102 | 50.0 | 50.0 | 12 | 150 | #1 | 56634 |
| 9820 | 25103 | 63.2 | 60.7(145) | 15 | 154 | #3 | 56635 |
| 9821 | 25104 | 50.0 | 50.0 | 13 | 154 | #1 | 56636 |
| 9822 | 25105 | 80.0 | 64.7 | 22 | 521 | #6 | 56637 |
| 9823 | 25106 | 69.6 | 58.9 | 21 | 231 | #4 | 56638 |
|  | 25107 | 69.1(68) | — | 12 | 163 | #4 | 56639 |
| 9824 | 25108 | 62.4 | 50.0 | 16 | 150 | #3 | 56640 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9825 | 25109 | 67.2 | 61.1(175) | 20 | 269 | #4 | — |
| 9826 | 25110 | 62.4 | 51.1(176) | 15 | 150 | #3 | 56641 |
|  | 25111 | 64.8 | 57.8 | 13 | 216 | #3 | 56642 |
| 9827 | 25112 | 50.0(52) | — | 12 | 150 | #1 | — |
|  | 25113 | 64.8 | 50.0 | 15 | 180 | #3 | 56643 |
|  | 25114 | 66.4 | 59.4(192) | 20 | 181 | #4 | 56644 |
|  | 25115 | 50.0(89) | — | 17 | 150 | #1 | 56645 |
|  | 25116 | 70.3(111) | — | 22 | 208 | #5 | 56646 |
| 9828 | 25117 | 50.0(51) | — | 12 | 150 | #1 | — |
|  | 25118 | 70.4 | 60.7 | 24 | 374 | #5 | 56647 |
| 9829 | 25119 | 66.4 | 59.3(258) | 18 | 307 | #4 | 56648 |
| 9830 | 25120 | 64.8 | 56.2(169) | 18 | 173 | #3 | 56649 |
| 9831 | 25121 | 50.0(59) | — | 12 | 150 | #1 | — |
|  | 25122 | 64.8 | 50.0(256) | 19 | 160 | #3 | 56650 |
| 9832 | 25123 | 50.0(57) | — | 12 | 150 | #1 | — |
| 9833 | 25124 | 68.0 | 59.6 | 20 | 235 | #4 | 56651 |
| 9834 | 25125 | 71.2 | 64.6(212) | 23 | 296 | #5 | 56652 |
|  | 25126 | 68.0 | 60.4 | 22 | 263 | #4 | 56653 |
| 9835 | 25127 | 66.4 | 60.7 | 20 | 237 | #4 | 56654 |
| 9836 | 25128 | 86.4 | 59.9(242) | 30 | 477 | #8 | 56655 |
| 9837 | 25129 | 58.0(112) | — | 17 | 150 | #2 | 56656 |
|  | 25130 | 69.6 | 58.5 | 18 | 234 | #4 | 56657 |
| 9838 | 25131 | 70.9(86) | — | 23 | 195 | #5 | 56658 |
| 9839 | 25132 | 70.4 | 60.0 | 24 | 275 | #5 | 56659 |
| 9840 | 25133 | 67.2 | 52.1(194) | 26 | 232 | #4 | 56660 |
| 9841 | 25134 | 50.0 | 50.0(250) | 12 | 150 | #1 | 56661 |
| 9842 | 25135 | 65.6 | 59.6 | 16 | 232 | #4 | 56662 |
| 9843 | 25136 | 64.8 | 54.8(272) | 19 | 190 | #3 | 56663 |
| 9844 | 25137 | 50.0(119) | — | 15 | 150 | #1 | 56664 |
|  | 25138 | 57.6 | 50.0(214) | 16 | 150 | #2 | 56665 |
| 9845 | 25139 | 62.5(96) | — | 13 | 154 | #3 | 56666 |
| 9846 | 25140 | 66.4 | 65.2(138) | 21 | 205 | #4 | 56667 |
| 9847 | 25141 | 67.2 | 60.0 | 21 | 357 | #4 | 56668 |
| 9848 | 25142 | 68.1(113) | — | 31 | 207 | #4 | 56669 |
| 9849 | 25143 | 50.0(64) | — | 12 | 150 | #1 | 56670 |
|  | 25144 | 66.4 | 58.5 | 15 | 247 | #4 | 56671 |
| 9850 | 25145 | 76.8 | 70.5 | 21 | 792 | #6 | 56672 |
| 9851 | 25146 | 67.2 | 60.3(214) | 22 | 221 | #4 | 56673 |
| 9852 | 25147 | 64.0 | 50.0 | 21 | 212 | #3 | 56674 |
| 9853 | 25148 | 50.0 | 50.0(137) | 12 | 150 | #1 | 56675 |
| 9854 | 25149 | 72.0 | 60.4 | 26 | 285 | #5 | 56676 |
| 9855 | 25150 | 72.8 | 64.8(213) | 20 | 309 | #5 | 56677 |
| 9856 | 25151 | 64.8 | 56.4 | 12 | 239 | #3 | 56678 |
| 9857 | 25152 | 62.4 | 50.0 | 28 | 350 | #3 | 56679 |
| 9858 | 25153 | 66.4 | 57.1(191) | 17 | 193 | #4 | — |
| 9859 | 25154 | 63.2 | 50.0 | 14 | 179 | #3 | 56680 |
| 9860 | 25155 | 60.8 | 51.5(233) | 13 | 157 | #3 | 56681 |
| 9861 | 25156 | 57.6 | 50.0 | 12 | 156 | #2 | 56682 |
| 9862 | 25157 | 63.6(121) | — | 13 | 150 | #3 | 56683 |
| 9863 | 25158 | 50.0(78) | — | 12 | 150 | #1 | 56684 |
| 9864 | 25159 | 54.6(97) | — | 16 | 150 | #1 | 56685 |
| 9865 | 25160 | 69.6 | 62.2 | 32 | 478 | #4 | 56686 |
| 9866 | 25161 | 63.2 | 60.1(218) | 14 | 168 | #3 | 56687 |
| 9867 | 25162 | 62.4 | 58.9(158) | 13 | 150 | #3 | 56688 |
| 9868 | 25163 | 84.0 | 59.3 | 25 | 451 | #7 | 56689 |
| 9869 | 25164 | 64.8 | 56.3(215) | 19 | 172 | #3 | 56690 |
| 9870 | 25165 | 63.2 | 57.8 | 12 | 240 | #3 | — |
| 9871 | 25166 | 68.8 | 69.2(133) | 19 | 197 | #4 | — |
| 9872 | 25167 | 57.1(112) | — | 15 | 150 | #2 | — |
| 9873 | 25168 | 70.4 | 64.3(199) | 27 | 241 | #5 | 56691 |
| 9874 | 25169 | 64.8 | 60.4 | 16 | 231 | #3 | 56692 |
|  | 25170 | 67.2 | 58.6(261) | 16 | 190 | #4 | 56693 |
| 9875 | 25171 | 65.6 | 57.1 | 17 | 208 | #4 | 56694 |
| 9876 | 25172 | 64.0 | 50.0 | 14 | 182 | #3 | 56695 |
| 9877 | 25173 | 64.8 | 56.4 | 20 | 184 | #3 | 56696 |
| 9878 | 25174 | 67.2 | 61.1 | 19 | 251 | #4 | 56697 |
| 9879 | 25175 | 73.6 | 68.0 | 24 | 532 | #5 | 56698 |
| 9880 | 25176 | 63.2 | 61.1(157) | 17 | 220 | #3 | 56699 |
| 9881 | 25177 | 64.0 | 57.8 | 17 | 193 | #3 | 56700 |
| 9882 | 25178 | 70.4 | 62.5 | 20 | 348 | #5 | 56701 |
| 9883 | 25179 | 70.4 | 59.6 | 21 | 269 | #5 | 56702 |
| 9884 | 25180 | 50.0(101) | — | 12 | 150 | #1 | 56703 |
| 9885 | 25181 | 50.0(66) | — | 12 | 150 | #1 | 56704 |
|  | 25182 | 69.6 | 61.8 | 16 | 360 | #4 | 56705 |
| 9886 | 25183 | 65.6 | 50.0 | 13 | 183 | #4 | 56706 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9887 | 25184 | 74.4 | 72.6(135) | 24 | 354 | #5 | 56707 |
| 9888 | 25185 | 68.0 | 61.1 | 14 | 370 | #4 | 56708 |
| 9889 | 25186 | 56.0(116) | — | 17 | 150 | #2 | — |
| 9890 | 25187 | 64.8 | 59.7(159) | 23 | 157 | #3 | — |
| 9891 | 25188 | 69.6 | 60.4 | 21 | 277 | #4 | 56709 |
| 9892 | 25189 | 50.0 | 50.0 | 12 | 150 | #1 | 56710 |
| 9893 | 25190 | 64.8 | 59.6 | 17 | 210 | #3 | 56711 |
| 9894 | 25191 | 73.2(71) | — | 16 | 176 | #5 | 56712 |
|  | 25192 | 70.4 | 62.9 | 32 | 504 | #5 | 56713 |
| 9895 | 25193 | 77.6 | 66.2 | 33 | 550 | #6 | 56714 |
| 9896 | 25194 | 50.0(115) | — | 14 | 150 | #1 | 56715 |
| 9897 | 25195 | 62.4 | 53.7(175) | 29 | 227 | #3 | 56716 |
| 9898 | 25196 | 72.0 | 63.3 | 24 | 600 | #5 | 56717 |
|  | 25197 | 73.6 | 64.0 | 26 | 449 | #5 | 56718 |
| 9899 | 25198 | 61.6 | 53.9(232) | 12 | 221 | #3 | 56719 |
| 9900 | 25199 | 63.2 | 61.1(157) | 17 | 220 | #3 | 56720 |
| 9901 | 25200 | 58.4 | 50.0(189) | 17 | 150 | #2 | 56721 |
| 9902 | 25201 | 69.6 | 61.5 | 21 | 347 | #4 | 56722 |
| 9903 | 25202 | 74.6(122) | — | 24 | 315 | #5 | 56723 |
| 9904 | 25203 | 50.0(67) | — | 12 | 150 | #1 | 56724 |
| 9905 | 25204 | 60.0 | 55.9(161) | 15 | 150 | #2 | 56725 |
| 9906 | 25205 | 67.2 | 58.5 | 18 | 291 | #4 | 56726 |
|  | 25206 | 68.8 | 63.6 | 19 | 664 | #4 | 56727 |
|  | 25207 | 70.5(88) | — | 15 | 219 | #5 | 56728 |
| 9907 | 25208 | 70.0(80) | — | 35 | 170 | #4 | 56729 |
| 9908 | 25209 | 62.4 | 50.0 | 15 | 150 | #3 | 56730 |
| 9909 | 25210 | 65.6 | 55.7(228) | 16 | 161 | #4 | 56731 |
| 9910 | 25211 | 70.4 | 68.8(240) | 15 | 476 | #5 | 56732 |
| 9911 | 25212 | 61.5(109) | — | 14 | 151 | #3 | 56733 |
| 9912 | 25213 | 68.8 | 67.4(138) | 20 | 219 | #4 | 56734 |
| 9913 | 25214 | 72.0 | 62.2 | 21 | 308 | #5 | 56735 |
| 9914 | 25215 | 69.6 | 62.4(181) | 21 | 258 | #4 | 56736 |
|  | 25216 | 50.0(114) | — | 12 | 150 | #1 | 56737 |
| 9915 | 25217 | 65.6 | 56.7 | 17 | 197 | #4 | 56738 |
| 9916 | 25218 | 50.0(94) | — | 12 | 150 | #1 | 56739 |
| 9917 | 25219 | 70.4 | 58.6(222) | 28 | 312 | #5 | 56740 |
| 9918 | 25220 | 50.0(53) | — | 12 | 150 | #1 | — |
|  | 25221 | 70.4 | 58.9 | 15 | 312 | #5 | 56741 |
| 9919 | 25222 | 50.0(50) | — | 12 | 150 | #1 | — |
| 9920 | 25223 | 60.8 | 50.0(220) | 15 | 166 | #3 | 56742 |
| 9921 | 25224 | 79.2 | 74.5 | 15 | 816 | #6 | 56743 |
| 9922 | 25225 | 66.4 | 60.8(143) | 17 | 174 | #4 | 56744 |
| 9923 | 25226 | 72.8 | 70.2 | 12 | 1204 | #5 | 56745 |
| 9924 | 25227 | 61.6 | 50.0(253) | 14 | 174 | #3 | 56746 |
| 9925 | 25228 | 82.4 | 80.0 | 24 | 1456 | #7 | 56747 |
| 9926 | 25229 | 68.8 | 63.5(208) | 20 | 277 | #4 | 56748 |
| 9927 | 25230 | 55.8(95) | — | 12 | 150 | #2 | 56749 |
| 9928 | 25231 | 58.4 | 50.0(226) | 37 | 187 | #2 | 56750 |
| 9929 | 25232 | 70.4 | 66.2 | 15 | 626 | #5 | 56751 |
| 9930 | 25233 | 50.0(52) | — | 12 | 150 | #1 | — |
|  | 25234 | 68.0 | 60.3(242) | 24 | 220 | #4 | 56752 |
| 9931 | 25235 | 68.8 | 61.5 | 23 | 300 | #4 | 56753 |
| 9932 | 25236 | 89.6 | 61.5 | 23 | 735 | #8 | 56754 |
|  | 25237 | 50.0 | 50.0 | 12 | 150 | #1 | 56755 |
| 9933 | 25238 | 66.3(92) | — | 18 | 152 | #4 | 56756 |
| 9934 | 25239 | 50.0(65) | — | 12 | 150 | #1 | 56757 |
| 9935 | 25240 | 64.0 | 50.0 | 12 | 193 | #3 | 56758 |
| 9936 | 25241 | 50.0(75) | — | 12 | 150 | #1 | 56759 |
| 9937 | 25242 | 50.0 | 50.0 | 12 | 150 | #1 | 56760 |
| 9938 | 25243 | 68.8 | 65.9(164) | 20 | 231 | #4 | 56761 |
| 9939 | 25244 | 50.0(58) | — | 12 | 150 | #1 | — |
| 9940 | 25245 | 65.6 | 50.0(248) | 13 | 150 | #4 | 56762 |
| 9941 | 25246 | 50.0(75) | — | 12 | 150 | #1 | 56763 |
| 9942 | 25247 | 72.8 | 64.7 | 23 | 433 | #5 | 56764 |
| 9943 | 25248 | 71.2 | 61.8 | 20 | 570 | #5 | 56765 |
| 9944 | 25249 | 69.6 | 61.8 | 23 | 345 | #4 | 56766 |
| 9945 | 25250 | 50.0(82) | — | 12 | 150 | #1 | 56767 |
|  | 25251 | 50.4 | 50.0(255) | 16 | 155 | #1 | 56768 |
| 9946 | 25252 | 67.2 | 60.0 | 28 | 285 | #4 | 56769 |
| 9947 | 25253 | 76.0 | 53.1 | 15 | 432 | #6 | 56770 |
| 9948 | 25254 | 65.6 | 61.1 | 18 | 248 | #4 | 56771 |
| 9949 | 25255 | 50.0(87) | — | 12 | 150 | #1 | 56772 |
| 9950 | 25256 | 78.4 | 72.5(211) | 20 | 537 | #6 | 56773 |
| 9951 | 25257 | 64.0 | 50.0 | 13 | 182 | #3 | 56774 |
|  | 25258 | 64.0 | 54.3(254) | 16 | 167 | #3 | 56775 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 9952 | 25259 | 68.0 | 50.0 | 18 | 241 | #4 | 56776 |
| 9953 | 25260 | 70.4 | 62.2 | 20 | 423 | #5 | 56777 |
| 9954 | 25261 | 66.4 | 57.7(265) | 18 | 184 | #4 | 56778 |
| 9955 | 25262 | 70.4 | 63.4(175) | 24 | 259 | #5 | 56779 |
|  | 25263 | 50.0(53) | — | 12 | 150 | #1 | — |
| 9956 | 25264 | 63.2 | 59.3(177) | 25 | 166 | #3 | 56780 |
|  | 25265 | 64.0 | 55.6(266) | 14 | 184 | #3 | 56781 |
| 9957 | 25266 | 64.0 | 58.7(235) | 20 | 174 | #3 | 56782 |
|  | 25267 | 68.0 | 61.5 | 21 | 367 | #4 | 56783 |
| 9958 | 25268 | 75.2 | 71.8(131) | 38 | 287 | #6 | 56784 |
| 9959 | 25269 | 60.8 | 53.5(142) | 13 | 152 | #3 | 56785 |
| 9960 | 25270 | 61.6 | 55.3(197) | 14 | 151 | #3 | 56786 |
|  | 25271 | 50.0(110) | — | 12 | 150 | #1 | 56787 |
| 9961 | 25272 | 63.2(87) | — | 14 | 150 | #3 | 56788 |
| 9962 | 25273 | 63.2 | 50.0 | 15 | 218 | #3 | 56789 |
| 9963 | 25274 | 70.4(98) | — | 22 | 193 | #5 | 56790 |
|  | 25275 | 64.8 | 60.0(265) | 22 | 233 | #3 | 56791 |
| 9964 | 25276 | 66.4 | 57.5 | 19 | 228 | #4 | 56792 |
| 9965 | 25277 | 64.8 | 50.0(243) | 14 | 154 | #3 | 56793 |
| 9966 | 25278 | 65.6 | 55.6 | 15 | 236 | #4 | 56794 |
| 9967 | 25279 | 50.0(113) | — | 14 | 159 | #1 | 56795 |
| 9968 | 25280 | 64.8 | 58.1(160) | 13 | 167 | #3 | 56796 |
| 9969 | 25281 | 65.6(96) | — | 14 | 157 | #4 | 56797 |
| 9970 | 25282 | 62.4 | 55.2(268) | 15 | 180 | #3 | 56798 |
|  | 25283 | 67.2 | 61.1 | 25 | 242 | #4 | 56799 |
| 9971 | 25284 | 67.2 | 57.5(266) | 24 | 203 | #4 | 56800 |
| 9972 | 25285 | 65.6 | 50.0 | 12 | 197 | #4 | 56801 |
| 9973 | 25286 | 60.0 | 50.0(171) | 12 | 153 | #2 | 56802 |
| 9974 | 25287 | 50.0(60) | — | 12 | 150 | #1 | — |
| 9975 | 25288 | 68.0 | 61.1 | 21 | 277 | #4 | 56803 |
| 9976 | 25289 | 71.2 | 63.4(235) | 20 | 291 | #5 | — |
| 9977 | 25290 | 72.0 | 50.0 | 15 | 332 | #5 | 56804 |
|  | 25291 | 61.6 | 56.7 | 14 | 203 | #3 | 56805 |
| 9978 | 25292 | 87.0(77) | — | 25 | 293 | #8 | 56806 |
| 9979 | 25293 | 64.8 | 57.7(208) | 18 | 174 | #3 | 56807 |
| 9980 | 25294 | 50.0(76) | — | 12 | 150 | #1 | 56808 |
| 9981 | 25295 | 50.0 | 50.0 | 12 | 150 | #1 | 56809 |
| 9982 | 25296 | 80.0 | 78.9(209) | 15 | 632 | #6 | 56810 |
| 9983 | 25297 | 67.2 | 59.6(213) | 20 | 243 | #4 | 56811 |
|  | 25298 | 50.0(55) | — | 12 | 150 | #1 | — |
|  | 25299 | 50.0(53) | — | 12 | 150 | #1 | — |
| 9984 | 25300 | 69.2(78) | — | 16 | 160 | #4 | 56812 |
| 9985 | 25301 | 63.2 | 58.0(150) | 22 | 174 | #3 | 56813 |
|  | 25302 | 66.4 | 63.9(155) | 18 | 190 | #4 | — |
| 9986 | 25303 | 50.0(73) | — | 36 | 175 | #1 | 56814 |
| 9987 | 25304 | 64.8 | 52.6(249) | 16 | 180 | #3 | 56815 |
| 9988 | 25305 | 50.0(101) | — | 12 | 150 | #1 | 56816 |
| 9989 | 25306 | 50.0 | 50.0 | 12 | 150 | #1 | 56817 |
| 9990 | 25307 | 66.4 | 58.2(220) | 19 | 174 | #4 | 56818 |
|  | 25308 | 50.0(118) | — | 15 | 150 | #1 | 56819 |
| 9991 | 25309 | 68.0 | 57.1 | 30 | 241 | #4 | 56820 |
|  | 25310 | 68.8 | 62.3(175) | 19 | 209 | #4 | 56821 |
| 9992 | 25311 | 65.6 | 51.3 | 12 | 213 | #4 | 56822 |
|  | 25312 | 69.3(88) | — | 19 | 161 | #4 | 56823 |
| 9993 | 25313 | 83.2 | 79.4(170) | 22 | 508 | #7 | — |
| 9994 | 25314 | 84.8 | 73.1 | 27 | 650 | #7 | 56824 |
|  | 25315 | 65.6 | 62.4(157) | 24 | 222 | #4 | 56825 |
| 9995 | 25316 | 50.0(81) | — | 12 | 150 | #1 | 56826 |
| 9996 | 25317 | 61.6 | 58.2 | 14 | 187 | #3 | 56827 |
|  | 25318 | 72.0 | 64.4 | 23 | 446 | #5 | 56828 |
| 9997 | 25319 | 79.2 | 73.1 | 16 | 928 | #6 | 56829 |
| 9998 | 25320 | 73.6 | 72.8(151) | 21 | 334 | #5 | 56830 |
| 9999 | 25321 | 50.0(52) | — | 12 | 150 | #1 | — |
|  | 25322 | 68.8 | 66.5(170) | 18 | 330 | #4 | 56831 |
| 10000 | 25323 | 74.4 | 65.1 | 29 | 431 | #5 | 56832 |
| 10001 | 25324 | 68.0 | 62.2 | 18 | 324 | #4 | 56833 |
| 10002 | 25325 | 74.4 | 71.3 | 19 | 949 | #5 | 56834 |
| 10003 | 25326 | 62.0(92) | — | 14 | 150 | #3 | 56835 |
| 10004 | 25327 | 50.0(73) | — | 12 | 150 | #1 | — |
| 10005 | 25328 | 68.8 | 60.0 | 18 | 268 | #4 | 56836 |
|  | 25329 | 68.0 | 64.9(191) | 19 | 245 | #4 | 56837 |
| 10006 | 25330 | 62.4 | 60.7(201) | 15 | 190 | #3 | 56838 |
| 10007 | 25331 | 76.8 | 74.9 | 22 | 896 | #6 | 56839 |
|  | 25332 | 73.6 | 65.8 | 31 | 475 | #5 | 56840 |
| 10008 | 25333 | 50.0 | 50.0 | 12 | 150 | #1 | 56841 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10009 | 25334 | 50.0 | 50.0(186) | 12 | 150 | #1 | 56842 |
| 10010 | 25335 | 50.0(55) | — | 12 | 150 | #1 | — |
| 10011 | 25336 | 70.8(65) | — | 14 | 160 | #5 | 56843 |
| 10012 | 25337 | 64.8 | 58.5 | 14 | 231 | #3 | 56844 |
| 10013 | 25338 | 63.2 | 56.4 | 13 | 193 | #3 | 56845 |
| 10014 | 25339 | 50.0 | 50.0 | 12 | 150 | #1 | 56846 |
| 10015 | 25340 | 64.8 | 57.5 | 12 | 216 | #3 | 56847 |
| 10016 | 25341 | 50.0 | 50.0 | 12 | 150 | #1 | 56848 |
| 10017 | 25342 | 70.4 | 61.1 | 21 | 263 | #5 | — |
| 10018 | 25343 | 63.2 | 59.7(201) | 19 | 169 | #3 | 56849 |
| 10019 | 25344 | 85.5(55) | — | 33 | 196 | #8 | — |
| 10020 | 25345 | 68.0 | 64.4 | 15 | 463 | #4 | 56850 |
| 10021 | 25346 | 64.8 | 55.3 | 20 | 181 | #3 | 56851 |
| 10022 | 25347 | 62.4 | 57.8 | 16 | 187 | #3 | 56852 |
| 10023 | 25348 | 63.2 | 50.0(219) | 15 | 150 | #3 | 56853 |
| 10024 | 25349 | 78.4 | 68.7 | 19 | 575 | #6 | 56854 |
| 10025 | 25350 | 64.8 | 61.1(167) | 16 | 166 | #3 | 56855 |
| 10026 | 25351 | 65.6 | 60.0 | 20 | 243 | #4 | 56856 |
|  | 25352 | 56.8 | 55.9(127) | 14 | 150 | #2 | 56857 |
| 10027 | 25353 | 50.0 | 50.0 | 12 | 150 | #1 | 56858 |
| 10028 | 25354 | 71.2 | 63.3 | 27 | 426 | #5 | 56859 |
|  | 25355 | 50.0 | 50.0 | 12 | 150 | #1 | 56860 |
| 10029 | 25356 | 66.4 | 61.5 | 16 | 244 | #4 | 56861 |
|  | 25357 | 70.4 | 63.3 | 20 | 373 | #5 | 56862 |
| 10030 | 25358 | 78.4 | 68.4 | 27 | 519 | #6 | 56863 |
| 10031 | 25359 | 60.8(79) | — | 16 | 150 | #3 | 56864 |
| 10032 | 25360 | 55.2 | 50.0(160) | 20 | 150 | #2 | 56865 |
| 10033 | 25361 | 50.0 | 50.0 | 28 | 173 | #1 | 56866 |
|  | 25362 | 68.0 | 59.3 | 25 | 232 | #4 | 56867 |
| 10034 | 25363 | 64.8 | 53.4(247) | 15 | 180 | #3 | 56868 |
| 10035 | 25364 | 75.2 | 64.7 | 31 | 447 | #6 | 56869 |
| 10036 | 25365 | 70.4 | 60.7 | 20 | 276 | #5 | 56870 |
| 10037 | 25366 | 56.4(94) | — | 20 | 150 | #2 | 56871 |
| 10038 | 25367 | 72.0 | 64.7 | 13 | 527 | #5 | 56872 |
| 10039 | 25368 | 72.0 | 61.8 | 19 | 302 | #5 | 56873 |
| 10040 | 25369 | 90.6(64) | — | 19 | 249 | #9 | — |
|  | 25370 | 62.4 | 56.7(261) | 12 | 156 | #3 | 56874 |
| 10041 | 25371 | 50.0 | 50.0 | 36 | 182 | #1 | 56875 |
| 10042 | 25372 | 50.0(105) | — | 14 | 150 | #1 | 56876 |
| 10043 | 25373 | 64.0 | 50.0 | 16 | 197 | #3 | 56877 |
| 10044 | 25374 | 67.2 | 56.4(149) | 16 | 268 | #4 | — |
| 10045 | 25375 | 67.2 | 56.7 | 16 | 332 | #4 | 56878 |
| 10046 | 25376 | 73.4(79) | — | 28 | 189 | #5 | 56879 |
|  | 25377 | 64.8 | 50.0 | 13 | 194 | #3 | 56880 |
| 10047 | 25378 | 50.0 | 50.0 | 14 | 163 | #1 | 56881 |
| 10048 | 25379 | 67.2 | 66.2(136) | 22 | 210 | #4 | 56882 |
|  | 25380 | 50.0 | 50.0(274) | 12 | 150 | #1 | 56883 |
| 10049 | 25381 | 74.4 | 72.4 | 12 | 1578 | #5 | 56884 |
| 10050 | 25382 | 68.0 | 59.9(177) | 20 | 193 | #4 | 56885 |
| 10051 | 25383 | 60.0 | 60.0(140) | 15 | 150 | #2 | 56886 |
|  | 25384 | 60.8 | 50.0(195) | 15 | 158 | #3 | 56887 |
|  | 25385 | 50.0(89) | — | 12 | 150 | #1 | 56888 |
| 10052 | 25386 | 68.0 | 58.5 | 16 | 215 | #4 | 56889 |
| 10053 | 25387 | 65.6 | 58.9 | 17 | 213 | #4 | 56890 |
|  | 25388 | 65.6 | 56.4 | 14 | 209 | #4 | — |
| 10054 | 25389 | 50.0(61) | — | 12 | 150 | #1 | 56891 |
|  | 25390 | 68.8 | 61.2(188) | 24 | 219 | #4 | 56892 |
| 10055 | 25391 | 69.6 | 62.9 | 18 | 349 | #4 | 56893 |
| 10056 | 25392 | 61.2(121) | — | 15 | 164 | #3 | 56894 |
| 10057 | 25393 | 68.8 | 50.0 | 26 | 249 | #4 | 56895 |
| 10058 | 25394 | 64.0 | 55.2(261) | 18 | 170 | #3 | 56896 |
| 10059 | 25395 | 50.0 | 50.0 | 12 | 150 | #1 | 56897 |
| 10060 | 25396 | 69.6 | 58.5 | 20 | 258 | #4 | 56898 |
|  | 25397 | 60.8 | 55.6 | 13 | 204 | #3 | 56899 |
| 10061 | 25398 | 67.2 | 61.5 | 18 | 323 | #4 | 56900 |
| 10062 | 25399 | 66.4 | 56.4 | 17 | 205 | #4 | 56901 |
|  | 25400 | 68.8 | 62.7(201) | 22 | 242 | #4 | 56902 |
| 10063 | 25401 | 68.8 | 60.7 | 20 | 342 | #4 | 56903 |
| 10064 | 25402 | 71.2 | 50.0 | 25 | 311 | #5 | 56904 |
| 10065 | 25403 | 50.0(90) | — | 12 | 150 | #1 | 56905 |
| 10066 | 25404 | 55.6(72) | — | 34 | 168 | #2 | 56906 |
| 10067 | 25405 | 50.0(78) | — | 12 | 150 | #1 | 56907 |
| 10068 | 25406 | 66.4 | 61.6(219) | 20 | 250 | #4 | 56908 |
| 10069 | 25407 | 66.4 | 50.0 | 13 | 233 | #4 | 56909 |
| 10070 | 25408 | 70.4 | 58.5 | 19 | 240 | #5 | 56910 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10071 | 25409 | 66.7(111) | — | 21 | 156 | #4 | 56911 |
| | 25410 | 71.2 | 65.1 | 19 | 484 | #5 | 56912 |
| 10072 | 25411 | 50.0(71) | — | 12 | 150 | #1 | 56913 |
| | 25412 | 64.0 | 64.0(139) | 21 | 179 | #3 | 56914 |
| 10073 | 25413 | 74.4 | 58.9 | 19 | 329 | #5 | 56915 |
| 10074 | 25414 | 64.0 | 51.1(233) | 18 | 179 | #3 | 56916 |
| 10075 | 25415 | 64.8 | 56.6(272) | 16 | 181 | #3 | 56917 |
| 10076 | 25416 | 64.8 | 50.0(186) | 16 | 151 | #3 | 56918 |
| 10077 | 25417 | 66.1(59) | — | 14 | 150 | #4 | — |
| 10078 | 25418 | 65.6 | 58.2(220) | 18 | 191 | #4 | 56919 |
| 10079 | 25419 | 60.0 | 50.0 | 14 | 181 | #2 | 56920 |
| 10080 | 25420 | 50.0(64) | — | 12 | 150 | #1 | 56921 |
| | 25421 | 66.4 | 60.0 | 19 | 255 | #4 | 56922 |
| 10081 | 25422 | 50.0(68) | — | 12 | 150 | #1 | 56923 |
| 10082 | 25423 | 61.6 | 58.2 | 15 | 214 | #3 | — |
| | 25424 | 70.4 | 60.7 | 22 | 271 | #5 | — |
| 10083 | 25425 | 68.0 | 50.0 | 16 | 193 | #4 | 56924 |
| 10084 | 25426 | 68.0 | 60.7(214) | 21 | 239 | #4 | 56925 |
| 10085 | 25427 | 67.2 | 61.1 | 20 | 245 | #4 | 56926 |
| 10086 | 25428 | 70.4 | 61.1 | 17 | 432 | #5 | 56927 |
| 10087 | 25429 | 67.2 | 59.2(233) | 21 | 208 | #4 | 56928 |
| 10088 | 25430 | 60.8 | 60.0(160) | 17 | 160 | #3 | 56929 |
| 10089 | 25431 | 64.8 | 59.3 | 14 | 191 | #3 | 56930 |
| 10090 | 25432 | 50.0 | 50.0 | 12 | 150 | #1 | 56931 |
| 10091 | 25433 | 65.6 | 58.9 | 15 | 277 | #4 | 56932 |
| 10092 | 25434 | 65.5(113) | — | 14 | 150 | #4 | 56933 |
| 10093 | 25435 | 50.0(57) | — | 12 | 150 | #1 | — |
| 10094 | 25436 | 61.4(101) | — | 39 | 191 | #3 | 56934 |
| 10095 | 25437 | 50.0 | 50.0(130) | 12 | 150 | #1 | 56935 |
| 10096 | 25438 | 62.4 | 50.0 | 13 | 178 | #3 | 56936 |
| | 25439 | 78.4 | 75.9(191) | 14 | 522 | #6 | 56937 |
| 10097 | 25440 | 50.0(51) | — | 12 | 150 | #1 | — |
| 10098 | 25441 | 67.1(85) | — | 20 | 152 | #4 | 56938 |
| 10099 | 25442 | 60.0 | 56.7(164) | 12 | 155 | #2 | 56939 |
| 10100 | 25443 | 68.8 | 62.2 | 22 | 474 | #4 | 56940 |
| 10101 | 25444 | 66.4 | 62.0(200) | 18 | 196 | #4 | 56941 |
| 10102 | 25445 | 65.6 | 61.8 | 18 | 260 | #4 | 56942 |
| 10103 | 25446 | 62.4 | 58.4(137) | 13 | 150 | #3 | 56943 |
| 10104 | 25447 | 68.0 | 62.2 | 18 | 298 | #4 | 56944 |
| 10105 | 25448 | 64.0 | 62.0(184) | 19 | 158 | #3 | 56945 |
| 10106 | 25449 | 69.6 | 62.5 | 18 | 325 | #4 | — |
| 10107 | 25450 | 78.4 | 70.2 | 19 | 752 | #6 | 56946 |
| 10108 | 25451 | 50.0(67) | — | 12 | 150 | #1 | 56947 |
| 10109 | 25452 | 61.6 | 54.6(183) | 12 | 150 | #3 | 56948 |
| 10110 | 25453 | 68.4(79) | — | 15 | 163 | #4 | 56949 |
| | 25454 | 50.0 | 50.0 | 12 | 150 | #1 | 56950 |
| 10111 | 25455 | 50.0 | 50.0 | 12 | 150 | #1 | 56951 |
| 10112 | 25456 | 66.4 | 61.8 | 15 | 286 | #4 | 56952 |
| 10113 | 25457 | 68.8 | 50.0 | 38 | 257 | #4 | 56953 |
| 10114 | 25458 | 64.8 | 59.9(202) | 17 | 178 | #3 | 56954 |
| 10115 | 25459 | 76.8 | 60.7 | 13 | 391 | #6 | 56955 |
| 10116 | 25460 | 76.8 | 62.9 | 28 | 388 | #6 | 56956 |
| 10117 | 25461 | 69.6 | 65.5(165) | 14 | 280 | #4 | 56957 |
| 10118 | 25462 | 50.0 | 50.0 | 12 | 150 | #1 | 56958 |
| 10119 | 25463 | 64.0 | 50.0(218) | 16 | 166 | #3 | 56959 |
| 10120 | 25464 | 58.9(90) | — | 17 | 150 | #2 | 56960 |
| | 25465 | 68.8 | 65.5 | 21 | 373 | #4 | — |
| | 25466 | 75.2 | 64.0 | 20 | 703 | #6 | 56961 |
| 10121 | 25467 | 50.0 | 50.0 | 12 | 150 | #1 | 56962 |
| | 25468 | 50.0(65) | — | 12 | 150 | #1 | 56963 |
| 10122 | 25469 | 77.0(61) | — | 35 | 178 | #6 | — |
| 10123 | 25470 | 50.0 | 50.0 | 12 | 150 | #1 | 56964 |
| 10124 | 25471 | 68.8 | 63.3 | 18 | 523 | #4 | 56965 |
| 10125 | 25472 | 74.4 | 71.4(140) | 16 | 364 | #5 | 56966 |
| 10126 | 25473 | 50.0(79) | — | 12 | 150 | #1 | 56967 |
| 10127 | 25474 | 67.2 | 61.5(213) | 21 | 208 | #4 | 56968 |
| 10128 | 25475 | 61.6 | 58.8(131) | 15 | 233 | #3 | 56969 |
| 10129 | 25476 | 67.2 | 57.5 | 18 | 209 | #4 | 56970 |
| 10130 | 25477 | 64.8 | 57.1 | 16 | 216 | #3 | 56971 |
| 10131 | 25478 | 64.0 | 50.0(195) | 17 | 158 | #3 | 56972 |
| 10132 | 25479 | 60.8 | 56.7(141) | 15 | 166 | #3 | 56973 |
| 10133 | 25480 | 50.0 | 50.0 | 12 | 150 | #1 | 56974 |
| 10134 | 25481 | 68.0 | 60.7 | 12 | 706 | #4 | 56975 |
| 10135 | 25482 | 82.4 | 73.1 | 18 | 875 | #7 | 56976 |
| 10136 | 25483 | 59.2 | 50.0(200) | 14 | 271 | #2 | 56977 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10137 | 25484 | 63.2 | 57.5 | 14 | 194 | #3 | 56978 |
|  | 25485 | 50.0(82) | — | 12 | 150 | #1 | 56979 |
| 10138 | 25486 | 68.2(85) | — | 22 | 172 | #4 | 56980 |
| 10139 | 25487 | 69.6 | 60.7 | 19 | 249 | #4 | 56981 |
| 10140 | 25488 | 73.6 | 60.8(260) | 23 | 303 | #5 | 56982 |
|  | 25489 | 66.4 | 61.2(178) | 20 | 198 | #4 | 56983 |
| 10141 | 25490 | 62.4 | 50.0(256) | 14 | 165 | #3 | 56984 |
| 10142 | 25491 | 50.0 | 50.0 | 12 | 150 | #1 | 56985 |
| 10143 | 25492 | 50.0(59) | — | 12 | 150 | #1 | — |
| 10144 | 25493 | 61.6 | 50.0 | 13 | 171 | #3 | 56986 |
| 10145 | 25494 | 64.8 | 56.1(223) | 18 | 266 | #3 | 56987 |
| 10146 | 25495 | 55.2(96) | — | 17 | 150 | #2 | 56988 |
|  | 25496 | 72.0 | 62.2 | 26 | 320 | #5 | 56989 |
| 10147 | 25497 | 61.6 | 50.7(221) | 15 | 156 | #3 | 56990 |
| 10148 | 25498 | 50.0(69) | — | 12 | 150 | #1 | — |
| 10149 | 25499 | 72.0 | 71.1(135) | 14 | 312 | #5 | 56991 |
| 10150 | 25500 | 67.6(105) | — | 22 | 182 | #4 | — |
|  | 25501 | 50.0(78) | — | 33 | 160 | #1 | — |
| 10151 | 25502 | 63.2 | 50.0 | 16 | 156 | #3 | 56992 |
| 10152 | 25503 | 67.8(87) | — | 13 | 150 | #4 | 56993 |
| 10153 | 25504 | 60.0 | 56.7 | 12 | 220 | #2 | 56994 |
| 10154 | 25505 | 64.8 | 60.4 | 13 | 241 | #3 | 56995 |
|  | 25506 | 66.4 | 58.5 | 19 | 214 | #4 | 56996 |
| 10155 | 25507 | 58.7(92) | — | 12 | 196 | #2 | 56997 |
| 10156 | 25508 | 50.0 | 50.0 | 12 | 150 | #1 | 56998 |
| 10157 | 25509 | 66.4 | 62.9 | 14 | 453 | #4 | 56999 |
| 10158 | 25510 | 68.8 | 61.5 | 37 | 342 | #4 | 57000 |
| 10159 | 25511 | 68.0 | 59.6 | 16 | 276 | #4 | 57001 |
| 10160 | 25512 | 50.0 | 50.0(190) | 12 | 150 | #1 | 57002 |
| 10161 | 25513 | 59.2 | 50.0(273) | 16 | 154 | #2 | 57003 |
| 10162 | 25514 | 50.0(50) | — | 12 | 150 | #1 | — |
| 10163 | 25515 | 60.8 | 50.0(188) | 12 | 150 | #3 | 57004 |
| 10164 | 25516 | 64.8 | 57.1 | 14 | 197 | #3 | 57005 |
| 10165 | 25517 | 76.8 | 50.0 | 20 | 314 | #6 | 57006 |
| 10166 | 25518 | 65.6 | 59.3 | 16 | 231 | #4 | 57007 |
| 10167 | 25519 | 64.8 | 50.0 | 14 | 186 | #3 | 57008 |
|  | 25520 | 64.0 | 59.3 | 16 | 229 | #3 | 57009 |
| 10168 | 25521 | 64.8 | 55.2(252) | 19 | 175 | #3 | — |
| 10169 | 25522 | 68.0 | 65.4(136) | 20 | 197 | #4 | 57010 |
| 10170 | 25523 | 75.6(86) | — | 22 | 208 | #6 | 57011 |
| 10171 | 25524 | 60.0 | 53.0(166) | 13 | 150 | #2 | 57012 |
| 10172 | 25525 | 75.2 | 74.1(224) | 15 | 536 | #6 | 57013 |
| 10173 | 25526 | 67.2 | 60.0 | 21 | 253 | #4 | 57014 |
| 10174 | 25527 | 50.0(73) | — | 12 | 150 | #1 | 57015 |
| 10175 | 25528 | 67.0(88) | — | 18 | 164 | #4 | — |
| 10176 | 25529 | 69.9(83) | — | 15 | 185 | #4 | 57016 |
| 10177 | 25530 | 76.8 | 64.4 | 13 | 585 | #6 | 57017 |
| 10178 | 25531 | 50.0(84) | — | 12 | 150 | #1 | 57018 |
| 10179 | 25532 | 64.0 | 60.4 | 15 | 255 | #3 | 57019 |
| 10180 | 25533 | 51.2 | 50.0(271) | 12 | 154 | #1 | 57020 |
| 10181 | 25534 | 60.8 | 59.3(194) | 13 | 150 | #3 | — |
| 10182 | 25535 | 68.0 | 60.5(220) | 20 | 197 | #4 | 57021 |
|  | 25536 | 64.0 | 61.2(152) | 20 | 159 | #3 | 57022 |
| 10183 | 25537 | 70.4 | 61.1 | 19 | 346 | #5 | — |
| 10184 | 25538 | 64.4(59) | — | 23 | 170 | #3 | — |
| 10185 | 25539 | 87.2 | 83.2(137) | 23 | 475 | #8 | 57023 |
| 10186 | 25540 | 50.0(65) | — | 12 | 150 | #1 | 57024 |
| 10187 | 25541 | 66.4(113) | — | 15 | 172 | #4 | 57025 |
| 10188 | 25542 | 70.4 | 63.6 | 22 | 526 | #5 | 57026 |
| 10189 | 25543 | 65.6 | 50.0 | 15 | 186 | #4 | 57027 |
| 10190 | 25544 | 67.2 | 61.5(218) | 19 | 232 | #4 | 57028 |
| 10191 | 25545 | 50.0(70) | — | 12 | 150 | #1 | 57029 |
| 10192 | 25546 | 68.0 | 63.7(160) | 19 | 199 | #4 | 57030 |
| 10193 | 25547 | 50.0 | 50.0 | 12 | 150 | #1 | — |
|  | 25548 | 50.0(118) | — | 12 | 150 | #1 | 57031 |
| 10194 | 25549 | 64.0 | 55.0(171) | 15 | 162 | #3 | 57032 |
|  | 25550 | 50.0 | 50.0(141) | 13 | 150 | #1 | 57033 |
| 10195 | 25551 | 50.0 | 50.0 | 12 | 150 | #1 | 57034 |
| 10196 | 25552 | 69.6 | 61.5 | 15 | 389 | #4 | 57035 |
| 10197 | 25553 | 62.6(107) | — | 16 | 150 | #3 | 57036 |
| 10198 | 25554 | 72.0 | 62.5 | 22 | 391 | #5 | 57037 |
| 10199 | 25555 | 60.8 | 55.3(150) | 15 | 165 | #3 | 57038 |
| 10200 | 25556 | 50.0 | 50.0 | 12 | 150 | #1 | 57039 |
| 10201 | 25557 | 50.0(83) | — | 12 | 150 | #1 | — |
| 10202 | 25558 | 63.2 | 53.1 | 17 | 196 | #3 | 57040 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10203 | 25559 | 50.0 | 50.0 | 12 | 150 | #1 | 57041 |
|  | 25560 | 72.8 | 63.6 | 25 | 492 | #5 | 57042 |
| 10204 | 25561 | 58.5(82) | — | 13 | 150 | #2 | 57043 |
|  | 25562 | 67.2 | 64.1(181) | 20 | 225 | #4 | 57044 |
| 10205 | 25563 | 64.8 | 56.9(195) | 16 | 157 | #3 | 57045 |
| 10206 | 25564 | 64.0 | 58.9 | 16 | 212 | #3 | 57046 |
| 10207 | 25565 | 68.0 | 63.3 | 15 | 506 | #4 | 57047 |
| 10208 | 25566 | 57.6 | 56.7(127) | 35 | 213 | #2 | 57048 |
| 10209 | 25567 | 69.6 | 62.2 | 18 | 404 | #4 | 57049 |
| 10210 | 25568 | 65.6 | 50.2 | 13 | 193 | #4 | — |
| 10211 | 25569 | 65.6 | 58.5 | 19 | 235 | #4 | 57050 |
|  | 25570 | 64.0 | 50.0(192) | 15 | 178 | #3 | 57051 |
|  | 25571 | 68.0 | 63.6 | 15 | 781 | #4 | 57052 |
| 10212 | 25572 | 64.8 | 50.0 | 13 | 177 | #3 | 57053 |
| 10213 | 25573 | 76.0 | 68.7 | 24 | 1176 | #6 | 57054 |
| 10214 | 25574 | 63.2 | 59.2(179) | 15 | 159 | #3 | 57055 |
| 10215 | 25575 | 68.0 | 61.1 | 30 | 255 | #4 | 57056 |
| 10216 | 25576 | 64.0 | 50.8(264) | 16 | 163 | #3 | 57057 |
|  | 25577 | 64.8 | 60.4 | 13 | 232 | #3 | 57058 |
| 10217 | 25578 | 67.2 | 50.5 | 17 | 195 | #4 | 57059 |
| 10218 | 25579 | 67.2 | 59.6 | 29 | 315 | #4 | 57060 |
| 10219 | 25580 | 61.6 | 50.0(171) | 12 | 153 | #3 | 57061 |
| 10220 | 25581 | 87.2 | 57.8 | 28 | 657 | #8 | 57062 |
| 10221 | 25582 | 50.0(51) | — | 12 | 150 | #1 | — |
| 10222 | 25583 | 69.3(75) | — | 14 | 150 | #4 | 57063 |
| 10223 | 25584 | 64.8 | 50.0 | 14 | 196 | #3 | 57064 |
| 10224 | 25585 | 67.2 | 59.3 | 21 | 235 | #4 | 57065 |
| 10225 | 25586 | 68.0 | 60.7 | 16 | 304 | #4 | 57066 |
| 10226 | 25587 | 50.0 | 50.0(182) | 12 | 150 | #1 | 57067 |
| 10227 | 25588 | 64.0 | 54.5 | 17 | 253 | #3 | 57068 |
| 10228 | 25589 | 65.6 | 57.1 | 15 | 194 | #4 | 57069 |
| 10229 | 25590 | 64.8 | 50.0 | 15 | 180 | #3 | 57070 |
| 10230 | 25591 | 68.8 | 60.9(151) | 18 | 257 | #4 | 57071 |
|  | 25592 | 68.0 | 61.1 | 19 | 337 | #4 | 57072 |
| 10231 | 25593 | 50.0 | 50.0(186) | 13 | 150 | #1 | 57073 |
| 10232 | 25594 | 64.8 | 57.6(271) | 17 | 202 | #3 | — |
| 10233 | 25595 | 76.0 | 65.1 | 36 | 442 | #6 | 57074 |
| 10234 | 25596 | 50.0(63) | — | 12 | 150 | #1 | — |
| 10235 | 25597 | 63.2 | 60.0 | 17 | 216 | #3 | 57075 |
| 10236 | 25598 | 76.8 | 74.2 | 15 | 995 | #6 | 57076 |
| 10237 | 25599 | 62.4 | 50.0(270) | 14 | 163 | #3 | 57077 |
| 10238 | 25600 | 57.6 | 50.0(167) | 12 | 154 | #2 | 57078 |
| 10239 | 25601 | 68.0 | 67.9(140) | 19 | 223 | #4 | 57079 |
| 10240 | 25602 | 67.2 | 58.5 | 19 | 245 | #4 | — |
| 10241 | 25603 | 61.6 | 50.0(216) | 12 | 150 | #3 | 57080 |
|  | 25604 | 59.2 | 58.3(127) | 34 | 184 | #2 | — |
| 10242 | 25605 | 65.6 | 58.6(249) | 18 | 184 | #4 | 57081 |
| 10243 | 25606 | 50.0 | 50.0 | 12 | 150 | #1 | 57082 |
| 10244 | 25607 | 50.0(83) | — | 12 | 150 | #1 | — |
| 10245 | 25608 | 57.6 | 50.0(171) | 17 | 150 | #2 | 57083 |
| 10246 | 25609 | 68.8 | 60.0 | 23 | 274 | #4 | 57084 |
| 10247 | 25610 | 64.8 | 59.1(257) | 15 | 209 | #3 | 57085 |
| 10248 | 25611 | 81.6 | 73.5 | 21 | 892 | #7 | 57086 |
| 10249 | 25612 | 50.0 | 50.0(186) | 12 | 150 | #1 | 57087 |
| 10250 | 25613 | 67.2 | 64.1(192) | 15 | 347 | #4 | 57088 |
| 10251 | 25614 | 66.4 | 58.9 | 19 | 209 | #4 | 57089 |
| 10252 | 25615 | 71.2 | 64.7 | 13 | 535 | #5 | 57090 |
| 10253 | 25616 | 64.8 | 50.0 | 12 | 205 | #3 | 57091 |
|  | 25617 | 76.8 | 68.7 | 28 | 944 | #6 | 57092 |
| 10254 | 25618 | 66.7(78) | — | 17 | 161 | #4 | 57093 |
|  | 25619 | 69.6 | 61.8(254) | 23 | 291 | #4 | 57094 |
| 10255 | 25620 | 88.8 | 73.8 | 25 | 853 | #8 | 57095 |
| 10256 | 25621 | 72.8 | 62.5 | 27 | 408 | #5 | 57096 |
| 10257 | 25622 | 51.9(106) | — | 16 | 154 | #1 | 57097 |
| 10258 | 25623 | 67.2 | 61.6(159) | 25 | 203 | #4 | 57098 |
| 10259 | 25624 | 66.4 | 65.2(138) | 13 | 244 | #4 | 57099 |
| 10260 | 25625 | 78.2(124) | — | 22 | 367 | #6 | 57000 |
| 10261 | 25626 | 54.4 | 50.0(156) | 15 | 162 | #1 | 57101 |
| 10262 | 25627 | 50.0(116) | — | 12 | 150 | #1 | 57102 |
| 10263 | 25628 | 61.6 | 59.1(149) | 15 | 153 | #3 | 57103 |
| 10264 | 25629 | 50.0 | 50.0 | 12 | 150 | #1 | 57104 |
| 10265 | 25630 | 63.2 | 59.3 | 13 | 271 | #3 | 57105 |
|  | 25631 | 64.0 | 61.0(154) | 16 | 164 | #3 | — |
| 10266 | 25632 | 50.0(94) | — | 12 | 150 | #1 | 57106 |
| 10267 | 25633 | 64.0 | 58.2 | 15 | 204 | #3 | 57107 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10268 | 25634 | 50.0 | 50.0 | 12 | 150 | #1 | 57108 |
| 10269 | 25635 | 68.0 | 60.7 | 27 | 255 | #4 | 57109 |
| 10270 | 25636 | 78.4 | 77.4(133) | 25 | 358 | #6 | 57110 |
| 10271 | 25637 | 85.6 | 77.7(269) | 33 | 792 | #8 | 57111 |
| 10272 | 25638 | 64.0 | 50.0(272) | 12 | 175 | #3 | 57112 |
| 10273 | 25639 | 65.1(109) | — | 17 | 163 | #4 | 57113 |
| 10274 | 25640 | 70.4 | 62.5 | 20 | 383 | #5 | 57114 |
|  | 25641 | 66.4 | 60.9(233) | 24 | 197 | #4 | — |
| 10275 | 25642 | 68.8 | 60.0 | 19 | 288 | #4 | 57115 |
| 10276 | 25643 | 61.6 | 50.0 | 13 | 190 | #3 | 57116 |
| 10277 | 25644 | 72.8 | 71.5(137) | 21 | 318 | #5 | 57117 |
| 10278 | 25645 | 78.4 | 57.5 | 22 | 408 | #6 | 57118 |
| 10279 | 25646 | 61.6 | 51.9(162) | 15 | 150 | #3 | 57119 |
| 10280 | 25647 | 72.0 | 62.2 | 25 | 433 | #5 | 57120 |
|  | 25648 | 71.2 | 63.6 | 25 | 557 | #5 | 57121 |
| 10281 | 25649 | 50.0(69) | — | 12 | 150 | #1 | 57122 |
| 10282 | 25650 | 68.8 | 50.0(234) | 21 | 182 | #4 | 57123 |
|  | 25651 | 69.6 | 59.3 | 22 | 304 | #4 | — |
| 10283 | 25652 | 69.6 | 62.5 | 21 | 409 | #4 | 57124 |
| 10284 | 25653 | 50.0(76) | — | 12 | 150 | #1 | 57125 |
| 10285 | 25654 | 50.0(95) | — | 16 | 153 | #1 | 57126 |
| 10286 | 25655 | 64.8 | 50.0(201) | 18 | 173 | #3 | 57127 |
| 10287 | 25656 | 65.6 | 65.2(141) | 19 | 189 | #4 | 57128 |
| 10288 | 25657 | 68.0 | 61.1 | 18 | 414 | #4 | 57129 |
|  | 25658 | 64.8 | 60.4 | 16 | 471 | #3 | 57130 |
| 10289 | 25659 | 68.8 | 59.3 | 17 | 254 | #4 | 57131 |
| 10290 | 25660 | 50.0 | 50.0(238) | 12 | 150 | #1 | 57132 |
|  | 25661 | 50.0(106) | — | 12 | 150 | #1 | 57133 |
| 10291 | 25662 | 68.8 | 61.5 | 19 | 266 | #4 | 57134 |
| 10292 | 25663 | 50.0 | 50.0 | 12 | 150 | #1 | 57135 |
| 10293 | 25664 | 50.0(69) | — | 12 | 150 | #1 | 57136 |
| 10294 | 25665 | 66.4 | 61.2(165) | 17 | 174 | #4 | 57137 |
| 10295 | 25666 | 68.0 | 54.7(203) | 14 | 221 | #4 | 57138 |
| 10296 | 25667 | 68.0 | 56.4 | 17 | 244 | #4 | 57139 |
| 10297 | 25668 | 63.2 | 62.2(127) | 17 | 153 | #3 | 57140 |
| 10298 | 25669 | 65.6 | 55.3(273) | 16 | 185 | #4 | 57141 |
|  | 25670 | 50.0(52) | — | 12 | 150 | #1 | — |
| 10299 | 25671 | 68.8 | 57.3(255) | 26 | 215 | #4 | 57142 |
| 10300 | 25672 | 50.0(66) | — | 12 | 150 | #1 | 57143 |
|  | 25673 | 63.2 | 50.0 | 14 | 195 | #3 | 57144 |
| 10301 | 25674 | 72.0 | 61.5 | 23 | 264 | #5 | 57145 |
| 10302 | 25675 | 73.6 | 64.7 | 21 | 400 | #5 | 57146 |
| 10303 | 25676 | 71.1(76) | — | 12 | 152 | #5 | 57147 |
|  | 25677 | 69.6 | 64.1(198) | 26 | 290 | #4 | 57148 |
| 10304 | 25678 | 65.8(79) | — | 13 | 150 | #4 | 57149 |
| 10305 | 25679 | 68.0 | 53.8 | 22 | 233 | #4 | 57150 |
| 10306 | 25680 | 71.2 | 61.1 | 29 | 289 | #5 | 57151 |
| 10307 | 25681 | 60.8 | 51.0(149) | 17 | 157 | #3 | 57152 |
| 10308 | 25682 | 69.6 | 65.1 | 16 | 567 | #4 | 57153 |
|  | 25683 | 63.2 | 50.0 | 13 | 192 | #3 | 57154 |
| 10309 | 25684 | 50.0(61) | — | 12 | 150 | #1 | — |
| 10310 | 25685 | 79.4(63) | — | 19 | 172 | #6 | — |
| 10311 | 25686 | 64.8 | 58.6(191) | 15 | 183 | #3 | 57155 |
| 10312 | 25687 | 69.6 | 63.6 | 21 | 405 | #4 | 57156 |
| 10313 | 25688 | 64.0 | 58.5 | 16 | 229 | #3 | 57157 |
| 10314 | 25689 | 70.4 | 66.4(152) | 23 | 242 | #5 | 57158 |
| 10315 | 25690 | 61.3(93) | — | 19 | 157 | #3 | 57159 |
| 10316 | 25691 | 50.0(119) | — | 15 | 158 | #1 | 57160 |
| 10317 | 25692 | 50.0 | 50.0(147) | 12 | 150 | #1 | 57161 |
| 10318 | 25693 | 63.2 | 59.0(200) | 20 | 177 | #3 | 57162 |
|  | 25694 | 64.0 | 56.0(207) | 20 | 159 | #3 | 57163 |
| 10319 | 25695 | 65.6 | 58.2 | 18 | 200 | #4 | 57164 |
| 10320 | 25696 | 50.0(88) | — | 13 | 150 | #1 | 57165 |
|  | 25697 | 50.0 | 50.0 | 12 | 150 | #1 | 57166 |
| 10321 | 25698 | 69.6 | 61.5 | 19 | 291 | #4 | 57167 |
| 10322 | 25699 | 63.2 | 50.0 | 12 | 185 | #3 | 57168 |
| 10323 | 25700 | 72.0 | 60.0 | 18 | 247 | #5 | — |
| 10324 | 25701 | 63.2 | 57.0(244) | 16 | 169 | #3 | 57169 |
| 10325 | 25702 | 68.2(107) | — | 18 | 193 | #4 | 57170 |
| 10326 | 25703 | 50.0 | 50.0 | 12 | 150 | #1 | 57171 |
|  | 25704 | 68.0 | 61.5 | 20 | 308 | #4 | 57172 |
| 10327 | 25705 | 50.0 | 50.0 | 12 | 150 | #1 | 57173 |
| 10328 | 25706 | 76.7(73) | — | 13 | 200 | #6 | 57174 |
| 10329 | 25707 | 66.4 | 60.4(222) | 18 | 207 | #4 | 57175 |
| 10330 | 25708 | 64.8 | 50.0(237) | 16 | 158 | #3 | 57176 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10331 | 25709 | 87.2 | 70.9 | 34 | 624 | #8 | 57177 |
| 10332 | 25710 | 50.0(107) | — | 12 | 150 | #1 | 57178 |
| 10333 | 25711 | 85.2(61) | — | 35 | 206 | #8 | — |
| 10334 | 25712 | 88.8 | 83.6 | 21 | 1052 | #8 | 57179 |
| 10335 | 25713 | 55.1(107) | — | 25 | 155 | #2 | 57180 |
|  | 25714 | 50.0(54) | — | 12 | 150 | #1 | — |
| 10336 | 25715 | 68.8 | 60.7 | 23 | 281 | #4 | 57181 |
| 10337 | 25716 | 50.0(62) | — | 12 | 150 | #1 | — |
|  | 25717 | 60.8 | 50.0(235) | 13 | 170 | #3 | — |
|  | 25718 | 77.6 | 66.5 | 30 | 571 | #6 | 57182 |
| 10338 | 25719 | 61.6 | 50.0(179) | 14 | 150 | #3 | 57183 |
|  | 25720 | 50.0 | 50.0(129) | 40 | 195 | #1 | 57184 |
| 10339 | 25721 | 72.8 | 63.3 | 21 | 438 | #5 | 57185 |
|  | 25722 | 62.4 | 61.6(159) | 21 | 155 | #3 | 57186 |
| 10340 | 25723 | 50.0 | 50.0 | 12 | 150 | #1 | 57187 |
| 10341 | 25724 | 69.6 | 61.1 | 19 | 290 | #4 | 57188 |
| 10342 | 25725 | 69.0(84) | — | 13 | 186 | #4 | 57189 |
| 10343 | 25726 | 50.0(55) | — | 12 | 150 | #1 | — |
| 10344 | 25727 | 65.6 | 58.9(263) | 19 | 208 | #4 | 57190 |
| 10345 | 25728 | 70.7(92) | — | 17 | 182 | #5 | 57191 |
|  | 25729 | 68.7(99) | — | 19 | 172 | #4 | 57192 |
| 10346 | 25730 | 70.4 | 61.1 | 24 | 290 | #5 | 57193 |
| 10347 | 25731 | 71.2 | 62.2 | 26 | 368 | #5 | 57194 |
|  | 25732 | 67.2 | 61.5 | 16 | 254 | #4 | 57195 |
| 10348 | 25733 | 76.8 | 67.3 | 25 | 873 | #6 | 57196 |
| 10349 | 25734 | 62.4 | 50.0(243) | 14 | 162 | #3 | 57197 |
| 10350 | 25735 | 69.6 | 64.9(188) | 17 | 328 | #4 | 57198 |
| 10351 | 25736 | 50.0(99) | — | 12 | 150 | #1 | 57199 |
| 10352 | 25737 | 61.6 | 50.0 | 12 | 180 | #3 | 57200 |
| 10353 | 25738 | 67.2 | 56.2(249) | 19 | 206 | #4 | 57201 |
|  | 25739 | 50.0(72) | — | 12 | 150 | #1 | 57202 |
| 10354 | 25740 | 53.6(112) | — | 13 | 150 | #1 | 57203 |
| 10355 | 25741 | 67.2 | 58.9 | 15 | 230 | #4 | 57204 |
| 10356 | 25742 | 61.6 | 50.0(161) | 16 | 150 | #3 | 57205 |
| 10357 | 25743 | 50.0 | 50.0 | 12 | 150 | #1 | 57206 |
| 10358 | 25744 | 72.0 | 62.5 | 22 | 357 | #5 | 57207 |
| 10359 | 25745 | 65.6 | 58.0(181) | 12 | 165 | #4 | 57208 |
| 10360 | 25746 | 72.0 | 61.1 | 22 | 334 | #5 | 57209 |
| 10361 | 25747 | 52.0 | 50.0(170) | 13 | 152 | #1 | 57210 |
|  | 25748 | 50.0(105) | — | 12 | 150 | #1 | 57211 |
| 10362 | 25749 | 50.0(57) | — | 12 | 150 | #1 | — |
| 10363 | 25750 | 50.0(73) | — | 12 | 150 | #1 | 57212 |
| 10364 | 25751 | 56.4(101) | — | 40 | 195 | #2 | 57213 |
| 10365 | 25752 | 50.0(88) | — | 12 | 150 | #1 | 57214 |
| 10366 | 25753 | 77.6 | 68.4 | 15 | 909 | #6 | 57215 |
| 10367 | 25754 | 88.8 | 68.4 | 22 | 680 | #8 | 57216 |
|  | 25755 | 50.0 | 50.0(210) | 12 | 150 | #1 | 57217 |
| 10368 | 25756 | 68.8 | 58.9 | 16 | 213 | #4 | 57218 |
| 10369 | 25757 | 50.4 | 50.0 | 12 | 153 | #1 | 57219 |
|  | 25758 | 50.0(68) | — | 12 | 150 | #1 | 57220 |
| 10370 | 25759 | 73.6 | 68.0 | 18 | 607 | #5 | 57221 |
| 10371 | 25760 | 50.0 | 50.0 | 12 | 150 | #1 | 57222 |
| 10372 | 25761 | 50.0 | 50.0(168) | 12 | 150 | #1 | 57223 |
| 10373 | 25762 | 72.0 | 60.4(225) | 22 | 314 | #5 | 57224 |
| 10374 | 25763 | 50.0 | 50.0 | 12 | 150 | #1 | 57225 |
| 10375 | 25764 | 67.2 | 60.0 | 25 | 253 | #4 | 57226 |
| 10376 | 25765 | 50.0 | 50.0 | 12 | 150 | #1 | 57227 |
| 10377 | 25766 | 72.0 | 65.5(174) | 23 | 295 | #5 | 57228 |
| 10378 | 25767 | 64.8 | 63.8(138) | 27 | 211 | #3 | 57229 |
|  | 25768 | 64.8 | 56.9(255) | 20 | 195 | #3 | 57230 |
| 10379 | 25769 | 69.6 | 65.2(181) | 25 | 261 | #4 | — |
| 10380 | 25770 | 71.2 | 64.7(170) | 21 | 241 | #5 | 57231 |
| 10381 | 25771 | 50.0(85) | — | 12 | 150 | #1 | 57232 |
| 10382 | 25772 | 65.6 | 57.1(233) | 19 | 174 | #4 | 57233 |
| 10383 | 25773 | 50.0(119) | — | 14 | 150 | #1 | — |
| 10384 | 25774 | 62.4 | 51.7(172) | 12 | 167 | #3 | 57234 |
| 10385 | 25775 | 61.6 | 54.2 | 13 | 203 | #3 | 57235 |
| 10386 | 25776 | 67.2 | 62.9 | 14 | 623 | #4 | 57236 |
| 10387 | 25777 | 68.0 | 62.5 | 20 | 427 | #4 | 57237 |
| 10388 | 25778 | 67.2 | 58.9 | 15 | 361 | #4 | 57238 |
|  | 25779 | 50.0 | 50.0 | 13 | 175 | #1 | 57239 |
| 10389 | 25780 | 68.8 | 60.4 | 20 | 242 | #4 | — |
| 10390 | 25781 | 50.0(64) | — | 12 | 150 | #1 | 57240 |
|  | 25782 | 50.0(57) | — | 12 | 150 | #1 | — |
| 10391 | 25783 | 73.5(83) | — | 15 | 166 | #5 | 57241 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10392 | 25784 | 68.0 | 61.8 | 20 | 434 | #4 | 57242 |
| 10393 | 25785 | 70.4 | 62.2 | 20 | 286 | #5 | 57243 |
| 10394 | 25786 | 60.0 | 56.7 | 15 | 228 | #2 | 57244 |
| 10395 | 25787 | 77.6 | 66.5(254) | 14 | 569 | #6 | 57245 |
| 10396 | 25788 | 64.0 | 58.4(149) | 15 | 161 | #3 | 57246 |
| 10397 | 25789 | 75.2 | 62.9 | 17 | 379 | #6 | 57247 |
|  | 25790 | 64.0 | 60.1(208) | 20 | 198 | #3 | 57248 |
| 10398 | 25791 | 62.4 | 50.0 | 13 | 176 | #3 | 57249 |
| 10399 | 25792 | 50.0 | 50.0(128) | 12 | 150 | #1 | 57250 |
| 10400 | 25793 | 64.0 | 58.9 | 18 | 231 | #3 | 57251 |
| 10401 | 25794 | 93.3(60) | — | 29 | 264 | #9 | — |
| 10402 | 25795 | 66.4 | 59.7(221) | 25 | 207 | #4 | 57252 |
| 10403 | 25796 | 64.8 | 56.7 | 15 | 186 | #3 | 57253 |
| 10404 | 25797 | 76.0 | 67.6 | 18 | 613 | #6 | 57254 |
| 10405 | 25798 | 83.2 | 79.6 | 25 | 1031 | #7 | 57255 |
| 10406 | 25799 | 65.2(122) | — | 21 | 179 | #4 | 57256 |
|  | 25800 | 64.8 | 63.8(130) | 18 | 177 | #3 | 57257 |
| 10407 | 25801 | 72.7(88) | — | 33 | 199 | #5 | 57258 |
| 10408 | 25802 | 50.0 (56) | — | 12 | 150 | #1 | — |
|  | 25803 | 82.4 | 66.5 | 27 | 453 | #7 | 57259 |
| 10409 | 25804 | 66.3 (101) | — | 15 | 203 | #4 | 57260 |
| 10410 | 25805 | 64.0 | 50.0 | 17 | 184 | #3 | 57261 |
| 10411 | 25806 | 66.4 | 59.6 | 17 | 230 | #4 | 57262 |
| 10412 | 25807 | 60.8 | 50.0 (209) | 15 | 159 | #3 | 57263 |
| 10413 | 25808 | 68.8 (96) | — | 21 | 179 | #4 | — |
| 10414 | 25809 | 71.2 | 58.5 | 15 | 287 | #5 | 57264 |
| 10415 | 25810 | 62.1 (87) | — | 17 | 152 | #3 | 57265 |
| 10416 | 25811 | 61.6 | 53.5 | 18 | 187 | #3 | 57266 |
| 10417 | 25812 | 62.4 | 50.0 (236) | 12 | 166 | #3 | 57267 |
| 10418 | 25813 | 91.2 | 89.6 (134) | 26 | 507 | #9 | 57268 |
| 10419 | 25814 | 62.4 | 57.5 | 18 | 220 | #3 | 57269 |
| 10420 | 25815 | 63.2 | 52.7 (150) | 16 | 177 | #3 | 57270 |
| 10421 | 25816 | 50.0 (109) | — | 19 | 195 | #1 | 57271 |
|  | 25817 | 64.0 | 50.0 (208) | 13 | 177 | #3 | — |
| 10422 | 25818 | 63.2 | 50.9 (169) | 19 | 169 | #3 | 57272 |
| 10423 | 25819 | 50.0 | 50.0 | 12 | 150 | #1 | 57273 |
| 10424 | 25820 | 63.2 | 50.0 | 15 | 173 | #3 | 57274 |
|  | 25821 | 68.0 | 56.7 | 16 | 209 | #4 | 57275 |
| 10425 | 25822 | 62.4 | 50.8 (238) | 14 | 167 | #3 | 57276 |
| 10426 | 25823 | 64.0 | 59.5 (168) | 16 | 164 | #3 | 57277 |
| 10427 | 25824 | 69.6 | 61.1 | 20 | 320 | #4 | 57278 |
|  | 25825 | 74.4 | 58.2 (184) | 20 | 356 | #5 | 57279 |
| 10428 | 25826 | 50.0 | 50.0 | 12 | 150 | #1 | 57280 |
| 10429 | 25827 | 63.2 | 61.1 (157) | 14 | 165 | #3 | 57281 |
| 10430 | 25828 | 50.0 | 50.0 | 12 | 150 | #1 | 57282 |
| 10431 | 25829 | 66.7 (84) | — | 16 | 162 | #4 | 57283 |
| 10432 | 25830 | 71.8 (85) | — | 18 | 165 | #5 | 57284 |
| 10433 | 25831 | 50.0 (58) | — | 12 | 150 | #1 | — |
|  | 25832 | 77.9 (77) | — | 16 | 248 | #6 | 57285 |
| 10434 | 25833 | 50.0 | 50.0 | 12 | 150 | #1 | 57286 |
| 10435 | 25834 | 50.0 | 50.0 (167) | 12 | 150 | #1 | 57287 |
| 10436 | 25835 | 68.0 | 59.6 | 17 | 299 | #4 | 57288 |
| 10437 | 25836 | 70.4 | 62.2 | 28 | 349 | #5 | 57289 |
| 10438 | 25837 | 60.0 | 51.5 (235) | 13 | 151 | #2 | 57290 |
| 10439 | 25838 | 89.6 | 86.5 | 38 | 1103 | #8 | 57291 |
| 10440 | 25839 | 67.2 | 58.2 | 24 | 244 | #4 | 57292 |
| 10441 | 25840 | 64.8 | 50.5 | 14 | 199 | #3 | 57293 |
| 10442 | 25841 | 73.6 | 64.4 | 15 | 434 | #5 | 57294 |
| 10443 | 25842 | 72.8 | 67.7 (164) | 23 | 302 | #5 | 57295 |
| 10444 | 25843 | 68.5 (92) | — | 15 | 156 | #4 | — |
| 10445 | 25844 | 50.0 (115) | — | 12 | 150 | #1 | 57296 |
|  | 25845 | 68.8 | 62.9 | 23 | 439 | #4 | 57297 |
|  | 25846 | 64.8 | 50.0 | 17 | 178 | #3 | 57298 |
| 10446 | 25847 | 64.8 | 59.7 (191) | 18 | 183 | #3 | 57299 |
| 10447 | 25848 | 71.2 | 63.6 | 24 | 321 | #5 | 57300 |
| 10448 | 25849 | 50.0 | 50.0 | 38 | 282 | #1 | 57301 |
| 10449 | 25850 | 75.3 (77) | — | 26 | 192 | #6 | 57302 |
| 10450 | 25851 | 70.4 | 68.4 | 16 | 904 | #5 | 57303 |
| 10451 | 25852 | 50.0 (52) | — | 12 | 150 | #1 | — |
| 10452 | 25853 | 73.6 | 70.2 | 25 | 809 | #5 | 57304 |
| 10453 | 25854 | 50.0 | 50.0 | 12 | 150 | #1 | 57305 |
| 10454 | 25855 | 65.9 (85) | — | 12 | 150 | #4 | 57306 |
| 10455 | 25856 | 67.2 | 61.8 (170) | 20 | 220 | #4 | — |
|  | 25857 | 62.4 | 50.0 (263) | 20 | 168 | #3 | 57307 |
| 10456 | 25858 | 50.0 | 50.0 | 12 | 150 | #1 | 57308 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10457 | 25859 | 50.0 (57) | — | 12 | 150 | #1 | — |
| 10458 | 25860 | 64.8 | 51.0 (239) | 21 | 179 | #3 | 57309 |
| 10459 | 25861 | 61.6 | 50.0 (236) | 14 | 163 | #3 | 57310 |
|  | 25862 | 78.4 | 50.0 | 12 | 418 | #6 | 57311 |
| 10460 | 25863 | 72.0 | 64.4 | 28 | 460 | #5 | 57312 |
| 10461 | 25864 | 50.0 (52) | — | 12 | 150 | #1 | — |
| 10462 | 25865 | 63.2 | 54.1 (194) | 15 | 201 | #3 | 57313 |
| 10463 | 25866 | 70.4 | 66.5 | 24 | 438 | #5 | 57314 |
| 10464 | 25867 | 61.6 | 58.5 | 14 | 198 | #3 | 57315 |
| 10465 | 25868 | 70.4 | 66.9 | 19 | 707 | #5 | 57316 |
| 10466 | 25869 | 94.6 (74) | — | 49 | 334 | #9 | 57317 |
| 10467 | 25870 | 68.8 | 60.0 | 12 | 508 | #4 | 57318 |
| 10468 | 25871 | 72.8 | 70.9 | 13 | 781 | #5 | 57319 |
|  | 25872 | 68.8 | 59.3 | 19 | 255 | #4 | 57320 |
| 10469 | 25873 | 64.8 | 58.2 | 15 | 205 | #3 | 57321 |
|  | 25874 | 65.6 | 59.6 | 17 | 257 | #4 | 57322 |
| 10470 | 25875 | 62.4 | 59.6 | 13 | 717 | #3 | 57323 |
| 10471 | 25876 | 65.6 | 52.0 | 15 | 257 | #4 | 57324 |
| 10472 | 25877 | 68.8 | 58.5 | 16 | 222 | #4 | 57325 |
| 10473 | 25878 | 64.5 (107) | — | 15 | 200 | #3 | 57326 |
| 10474 | 25879 | 64.7 (119) | — | 13 | 195 | #3 | 57327 |
| 10475 | 25880 | 61.7 (107) | — | 16 | 150 | #3 | 57328 |
|  | 25881 | 50.0 (113) | — | 12 | 150 | #1 | 57329 |
| 10476 | 25882 | 59.2 | 54.8 (135) | 12 | 150 | #2 | 57330 |
|  | 25883 | 68.8 | 63.5 (148) | 21 | 256 | #4 | 57331 |
| 10477 | 25884 | 62.4 | 61.5 (208) | 17 | 188 | #3 | 57332 |
| 10478 | 25885 | 59.2 | 55.2 (134) | 15 | 180 | #2 | 57333 |
| 10479 | 25886 | 50.0 | 50.0 | 12 | 150 | #1 | 57334 |
| 10480 | 25887 | 50.0 | 50.0 (139) | 16 | 150 | #1 | 57335 |
| 10481 | 25888 | 64.0 | 56.7 (164) | 18 | 159 | #3 | 57336 |
| 10482 | 25889 | 50.0 (109) | — | 14 | 150 | #1 | 57337 |
| 10483 | 25890 | 65.6 | 60.4 | 19 | 248 | #4 | 57338 |
| 10484 | 25891 | 65.6 | 50.0 | 13 | 245 | #4 | 57339 |
| 10485 | 25892 | 65.6 | 62.3 (183) | 18 | 275 | #4 | 57340 |
| 10486 | 25893 | 64.8 | 50.0 | 13 | 212 | #3 | 57341 |
|  | 25894 | 64.7 (68) | — | 16 | 150 | #3 | 57342 |
| 10487 | 25895 | 75.2 | 71.6 | 29 | 1222 | #6 | 57343 |
| 10488 | 25896 | 64.0 | 57.8 | 20 | 214 | #3 | 57344 |
|  | 25897 | 64.0 | 64.7 (139) | 16 | 175 | #3 | 57345 |
| 10489 | 25898 | 65.6 | 58.2 | 18 | 234 | #4 | 57346 |
|  | 25899 | 65.6 | 59.7 (149) | 17 | 178 | #4 | 57347 |
| 10490 | 25900 | 68.0 | 59.2 (265) | 20 | 215 | #4 | 57348 |
| 10491 | 25901 | 71.2 | 61.8 | 19 | 310 | #5 | 57349 |
| 10492 | 25902 | 66.4 | 57.1 | 22 | 202 | #4 | 57350 |
| 10493 | 25903 | 50.0 | 50.0 | 12 | 150 | #1 | 57351 |
| 10494 | 25904 | 70.4 | 65.1 (212) | 22 | 310 | #5 | 57352 |
| 10495 | 25905 | 65.6 | 65.2 (135) | 19 | 190 | #4 | 57353 |
| 10496 | 25906 | 68.0 | 56.4 | 17 | 216 | #4 | 57354 |
| 10497 | 25907 | 72.8 | 61.5 | 20 | 448 | #5 | 57355 |
|  | 25908 | 80.0 | 72.4 | 38 | 1003 | #6 | 57356 |
| 10498 | 25909 | 68.0 | 66.7 (150) | 23 | 208 | #4 | 57357 |
| 10499 | 25910 | 50.0 (54) | — | 12 | 150 | #1 | — |
| 10500 | 25911 | 63.2 | 58.5 | 15 | 192 | #3 | 57358 |
| 10501 | 25912 | 71.2 | 65.5 | 29 | 575 | #5 | 57359 |
| 10502 | 25913 | 66.4 | 59.3 | 20 | 269 | #4 | 57360 |
| 10503 | 25914 | 50.0 | 50.0 | 12 | 150 | #1 | 57361 |
| 10504 | 25915 | 69.9 (103) | — | 37 | 200 | #4 | 57362 |
|  | 25916 | 71.2 | 64.7 | 21 | 990 | #5 | 57363 |
|  | 25917 | 80.8 | 67.6 | 29 | 472 | #7 | 57364 |
| 10505 | 25918 | 64.0 | 63.6 (129) | 21 | 175 | #3 | 57365 |
| 10506 | 25919 | 61.6 | 50.0 (174) | 12 | 168 | #3 | 57366 |
| 10507 | 25920 | 50.0 (82) | — | 12 | 150 | #1 | 57367 |
| 10508 | 25921 | 70.4 | 64.0 | 21 | 587 | #5 | 57368 |
| 10509 | 25922 | 68.8 | 62.2 | 20 | 504 | #4 | 57369 |
| 10510 | 25923 | 64.0 | 56.1 (230) | 18 | 177 | #3 | 57370 |
| 10511 | 25924 | 50.0 (101) | — | 12 | 150 | #1 | 57371 |
| 10512 | 25925 | 50.0 (99) | — | 12 | 150 | #1 | 57372 |
| 10513 | 25926 | 76.8 | 71.1 (232) | 16 | 517 | #6 | 57373 |
| 10514 | 25927 | 50.0 | 50.0 | 12 | 150 | #1 | 57374 |
|  | 25928 | 64.0 | 50.0 | 13 | 198 | #3 | 57375 |
| 10515 | 25929 | 50.0 | 50.0 (178) | 15 | 150 | #1 | 57376 |
| 10516 | 25930 | 69.6 | 60.4 | 23 | 294 | #4 | 57377 |
| 10517 | 25931 | 64.8 | 50.0 (215) | 20 | 162 | #3 | 57378 |
|  | 25932 | 50.0 (61) | — | 12 | 150 | #1 | — |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10518 | 25933 | 64.8 | 60.7 (140) | 16 | 157 | #3 | — |
|  | 25934 | 66.4 | 65.9 (179) | 21 | 194 | #4 | — |
| 10519 | 25935 | 62.4 | 52.7 | 18 | 163 | #3 | 57379 |
|  | 25936 | 69.6 | 64.3 (182) | 27 | 265 | #4 | 57380 |
| 10520 | 25937 | 68.8 | 60.4 | 21 | 266 | #4 | 57381 |
|  | 25938 | 68.0 | 59.3 | 30 | 241 | #4 | 57382 |
| 10521 | 25939 | 64.0 | 51.4 (179) | 14 | 154 | #3 | 57383 |
| 10522 | 25940 | 70.4 | 60.7 | 24 | 410 | #5 | 57384 |
| 10523 | 25941 | 64.8 | 58.2 | 16 | 245 | #3 | 57385 |
| 10524 | 25942 | 71.2 | 70.6 (136) | 24 | 270 | #5 | 57386 |
| 10525 | 25943 | 60.8 | 50.0 (184) | 13 | 150 | #3 | 57387 |
| 10526 | 25944 | 62.4 | 58.2 | 12 | 168 | #3 | 57388 |
| 10527 | 25945 | 66.4 | 54.9 (235) | 21 | 208 | #4 | 57389 |
| 10528 | 25946 | 72.6 (62) | — | 17 | 150 | #5 | — |
|  | 25947 | 65.6 | 53.0 (268) | 18 | 204 | #4 | 57390 |
| 10529 | 25948 | 72.0 | 64.0 | 17 | 581 | #5 | 57391 |
| 10530 | 25949 | 50.0 (115) | — | 19 | 153 | #1 | 57392 |
| 10531 | 25950 | 68.0 | 53.6 (211) | 23 | 252 | #4 | 57393 |
| 10532 | 25951 | 50.0 | 50.0 | 12 | 150 | #1 | 57394 |
| 10533 | 25952 | 62.4 | 50.0 (219) | 14 | 167 | #3 | — |
| 10534 | 25953 | 62.4 | 54.9 (175) | 15 | 158 | #3 | 57395 |
| 10535 | 25954 | 71.2 | 62.2 | 20 | 291 | #5 | 57396 |
| 10536 | 25955 | 66.4 | 56.4 (163) | 16 | 178 | #4 | 57397 |
| 10537 | 25956 | 67.2 | 52.6 (211) | 22 | 195 | #4 | 57398 |
| 10538 | 25957 | 67.2 (67) | — | 14 | 151 | #4 | 57399 |
| 10539 | 25958 | 68.0 | 59.4 (217) | 20 | 212 | #4 | 57400 |
| 10540 | 25959 | 65.6 | 58.5 | 19 | 235 | #4 | 57401 |
|  | 25960 | 64.0 | 50.0 (192) | 15 | 178 | #3 | 57402 |
|  | 25961 | 68.0 | 63.6 | 15 | 781 | #4 | 57403 |
| 10541 | 25962 | 50.0 | 50.0 | 12 | 150 | #1 | 57404 |
| 10542 | 25963 | 63.2 | 53.4 (223) | 19 | 188 | #3 | 57405 |
| 10543 | 25964 | 64.0 | 50.0 (174) | 16 | 170 | #3 | 57406 |
| 10544 | 25965 | 50.0 (56) | — | 12 | 150 | #1 | — |
| 10545 | 25966 | 72.0 | 62.9 | 28 | 573 | #5 | — |
| 10546 | 25967 | 50.0 | 50.0 | 12 | 150 | #1 | 57407 |
|  | 25968 | 64.8 | 54.5 (176) | 15 | 169 | #3 | 57408 |
| 10547 | 25969 | 50.0 | 50.0 (212) | 12 | 150 | #1 | 57409 |
| 10548 | 25970 | 63.2 | 58.1 (258) | 13 | 204 | #3 | 57410 |
| 10549 | 25971 | 50.0 (72) | — | 12 | 150 | #1 | 57411 |
| 10550 | 25972 | 66.4 | 61.5 | 18 | 578 | #4 | 57412 |
|  | 25973 | 65.1 (109) | — | 34 | 233 | #4 | 57413 |
| 10551 | 25974 | 71.2 | 65.1 | 16 | 554 | #5 | 57414 |
| 10552 | 25975 | 67.2 | 55.6 | 16 | 199 | #4 | — |
| 10553 | 25976 | 68.0 | 65.4 (133) | 19 | 195 | #4 | 57415 |
| 10554 | 25977 | 68.8 | 58.9 | 17 | 229 | #4 | 57416 |
| 10555 | 25978 | 50.0 | 50.0 | 12 | 150 | #1 | 57417 |
| 10556 | 25979 | 65.6 | 58.9 | 16 | 166 | #4 | 57418 |
| 10557 | 25980 | 50.0 | 50.0 (157) | 12 | 150 | #1 | 57419 |
| 10558 | 25981 | 63.2 | 50.0 (175) | 17 | 150 | #3 | 57420 |
| 10559 | 25982 | 71.2 | 64.8 (253) | 20 | 434 | #5 | 57421 |
|  | 25983 | 79.2 | 66.5 | 30 | 757 | #6 | 57422 |
| 10560 | 25984 | 68.0 | 54.5 | 20 | 256 | #4 | 57423 |
| 10561 | 25985 | 74.4 | 64.0 | 24 | 586 | #5 | 57424 |
|  | 25986 | 63.2 | 59.3 | 23 | 256 | #3 | 57425 |
| 10562 | 25987 | 64.0 | 59.9 (207) | 17 | 168 | #3 | 57426 |
| 10563 | 25988 | 65.6 | 62.1 (132) | 19 | 195 | #4 | 57427 |
| 10564 | 25989 | 50.0 (62) | — | 12 | 150 | #1 | — |
| 10565 | 25990 | 58.5 (123) | — | 16 | 173 | #2 | 57428 |
|  | 25991 | 66.4 | 55.3 | 15 | 222 | #4 | 57429 |
| 10566 | 25992 | 67.2 | 55.3 | 14 | 199 | #4 | 57430 |
| 10567 | 25993 | 68.8 | 61.5 | 21 | 300 | #4 | 57431 |
| 10568 | 25994 | 50.0 (62) | — | 12 | 150 | #1 | — |
| 10569 | 25995 | 68.8 | 60.0 | 19 | 248 | #4 | 57432 |
| 10570 | 25996 | 57.8 (116) | — | 14 | 151 | #2 | — |
| 10571 | 25997 | 66.4 | 66.0 (141) | 20 | 214 | #4 | 57433 |
|  | 25998 | 76.0 | 70.7 (205) | 14 | 485 | #6 | 57434 |
| 10572 | 25999 | 83.2 | 64.7 | 35 | 560 | #7 | 57435 |
|  | 26000 | 78.4 | 73.5 | 23 | 1021 | #6 | 57436 |
| 10573 | 26001 | 50.0 | 50.0 | 12 | 150 | #1 | — |
| 10574 | 26002 | 68.0 | 58.2 | 16 | 279 | #4 | 57437 |
| 10575 | 26003 | 66.4 | 58.5 | 14 | 228 | #4 | 57438 |
| 10576 | 26004 | 66.4 | 60.7 | 17 | 221 | #4 | 57439 |
| 10577 | 26005 | 64.8 | 59.3 | 16 | 255 | #3 | 57440 |
| 10578 | 26006 | 64.8 | 58.2 | 22 | 219 | #3 | 57441 |
| 10579 | 26007 | 61.6 | 50.0 | 12 | 150 | #3 | 57442 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10580 | 26008 | 50.0 (70) | — | 12 | 150 | #1 | 57443 |
|  | 26009 | 73.6 | 67.3 | 21 | 497 | #5 | 57444 |
| 10581 | 26010 | 66.4 | 54.9 (264) | 17 | 195 | #4 | 57445 |
| 10582 | 26011 | 62.3 (114) | — | 14 | 150 | #3 | 57446 |
| 10583 | 26012 | 50.0 (70) | — | 12 | 150 | #1 | 57447 |
| 10584 | 26013 | 64.0 | 50.0 (232) | 14 | 178 | #3 | 57448 |
| 10585 | 26014 | 69.6 | 60.0 | 19 | 274 | #4 | 57449 |
| 10586 | 26015 | 61.6 | 54.7 (172) | 15 | 162 | #3 | 57450 |
| 10587 | 26016 | 89.2 (65) | — | 33 | 282 | #8 | 57451 |
| 10588 | 26017 | 73.6 | 68.4 | 17 | 506 | #5 | 57452 |
|  | 26018 | 60.0 | 50.0 | 13 | 201 | #2 | 57453 |
| 10589 | 26019 | 50.0 (82) | — | 12 | 150 | #1 | 57454 |
| 10590 | 26020 | 67.2 | 61.1 | 24 | 326 | #4 | 57455 |
| 10591 | 26021 | 59.2 | 50.0 | 14 | 184 | #2 | 57456 |
| 10592 | 26022 | 72.8 | 62.2 | 24 | 402 | #5 | — |
| 10593 | 26023 | 64.0 | 60.0 | 13 | 213 | #3 | 57457 |
| 10594 | 26024 | 72.8 | 65.7 (216) | 35 | 371 | #5 | 57458 |
|  | 26025 | 67.2 | 59.9 (172) | 28 | 215 | #4 | 57459 |
|  | 26026 | 57.4 (94) | — | 17 | 157 | #2 | 57460 |
| 10595 | 26027 | 63.2 | 54.0 (174) | 15 | 153 | #3 | 57461 |
| 10596 | 26028 | 50.0 (50) | — | 12 | 150 | #1 | — |
|  | 26029 | 52.0 | 50.0 (182) | 15 | 150 | #1 | 57462 |
| 10597 | 26030 | 65.6 | 56.4 | 15 | 187 | #4 | 57463 |
| 10598 | 26031 | 63.2 | 60.5 (223) | 16 | 273 | #3 | 57464 |
| 10599 | 26032 | 67.2 | 59.6 | 15 | 251 | #4 | 57465 |
|  | 26033 | 63.2 | 50.0 | 17 | 170 | #3 | 57466 |
| 10600 | 26034 | 65.0 (120) | — | 32 | 252 | #3 | 57467 |
| 10601 | 26035 | 50.0 (97) | — | 12 | 150 | #1 | 57468 |
|  | 26036 | 50.0 (75) | — | 12 | 150 | #1 | 57469 |
| 10602 | 26037 | 71.2 | 61.1 | 22 | 287 | #5 | 57470 |
|  | 26038 | 66.0 (103) | — | 15 | 186 | #4 | 57471 |
| 10603 | 26039 | 70.4 | 63.3 | 19 | 355 | #5 | 57472 |
| 10604 | 26040 | 66.4 | 50.2 | 12 | 246 | #4 | 57473 |
| 10605 | 26041 | 50.0 | 50.0 | 12 | 150 | #1 | 57474 |
| 10606 | 26042 | 62.4 | 55.2 (165) | 14 | 150 | #3 | 57475 |
| 10607 | 26043 | 68.8 | 60.4 | 27 | 292 | #4 | 57476 |
| 10608 | 26044 | 66.4 | 58.2 | 16 | 218 | #4 | 57477 |
| 10609 | 26045 | 72.0 | 65.1 | 12 | 439 | #5 | 57478 |
| 10610 | 26046 | 50.0 (55) | — | 12 | 150 | #1 | — |
| 10611 | 26047 | 74.4 | 67.3 | 24 | 554 | #5 | 57479 |
| 10612 | 26048 | 67.2 | 60.4 | 18 | 252 | #4 | 57480 |
| 10613 | 26049 | 70.4 | 64.7 | 18 | 444 | #5 | 57481 |
| 10614 | 26050 | 70.4 | 64.4 (205) | 22 | 286 | #5 | 57482 |
|  | 26051 | 63.2 | 55.6 | 16 | 169 | #3 | 57483 |
| 10615 | 26052 | 66.4 | 55.6 (187) | 20 | 226 | #4 | — |
| 10616 | 26053 | 71.2 | 63.3 | 25 | 315 | #5 | 57484 |
|  | 26054 | 73.6 | 65.1 | 31 | 497 | #5 | 57485 |
| 10617 | 26055 | 66.4 | 60.0 | 14 | 238 | #4 | 57486 |
|  | 26056 | 78.4 | 66.5 | 30 | 655 | #6 | 57487 |
| 10618 | 26057 | 50.0 (71) | — | 28 | 150 | #1 | 57488 |
| 10619 | 26058 | 71.2 | 62.5 | 23 | 368 | #5 | 57489 |
|  | 26059 | 50.0 (53) | — | 12 | 150 | #1 | — |
| 10620 | 26060 | 69.6 | 62.2 | 24 | 387 | #4 | 57490 |
| 10621 | 26061 | 65.6 | 59.2 (228) | 18 | 225 | #4 | — |
| 10622 | 26062 | 69.6 | 61.8 | 18 | 492 | #4 | 57491 |
| 10623 | 26063 | 65.0 (103) | — | 40 | 195 | #4 | 57492 |
|  | 26064 | 50.0 (84) | — | 12 | 150 | #1 | 57493 |
| 10624 | 26065 | 64.2 (120) | — | 15 | 170 | #3 | 57494 |
| 10625 | 26066 | 75.2 | 65.8 | 35 | 451 | #6 | 57495 |
|  | 26067 | 72.0 | 62.5 | 25 | 364 | #5 | 57496 |
| 10626 | 26068 | 52.0 | 50.0 (133) | 13 | 150 | #1 | 57497 |
| 10627 | 26069 | 64.8 | 56.0 | 17 | 192 | #3 | 57498 |
| 10628 | 26070 | 50.0 | 50.0 (154) | 12 | 150 | #1 | 57499 |
| 10629 | 26071 | 61.6 | 50.0 (175) | 16 | 173 | #3 | 57500 |
| 10630 | 26072 | 72.0 | 61.1 | 22 | 413 | #5 | 57501 |
| 10631 | 26073 | 66.4 (122) | — | 17 | 189 | #4 | 57502 |
| 10632 | 26074 | 64.0 | 50.0 | 14 | 224 | #3 | 57503 |
| 10633 | 26075 | 71.2 | 60.7 | 16 | 321 | #5 | 57504 |
| 10634 | 26076 | 63.2 | 50.0 (245) | 20 | 151 | #3 | 57505 |
| 10635 | 26077 | 85.6 | 78.2 | 23 | 1167 | #8 | 57506 |
| 10636 | 26078 | 50.0 | 50.0 | 12 | 150 | #1 | 57507 |
| 10637 | 26079 | 50.0 | 50.0 | 12 | 150 | #1 | 57508 |
| 10638 | 26080 | 63.2 | 59.2 (179) | 14 | 163 | #3 | 57509 |
| 10639 | 26081 | 69.6 | 60.7 | 24 | 268 | #4 | 57510 |
| 10640 | 26082 | 71.2 | 63.1 (203) | 24 | 252 | #5 | 57511 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10641 | 26083 | 67.2 | 60.0 | 19 | 258 | #4 | 57512 |
| 10642 | 26084 | 64.8 | 62.2 (143) | 16 | 166 | #3 | 57513 |
| 10643 | 26085 | 66.4 | 58.9 | 16 | 236 | #4 | 57514 |
| 10644 | 26086 | 67.2 | 56.5 (262) | 16 | 174 | #4 | 57515 |
|  | 26087 | 73.6 | 62.2 | 25 | 327 | #5 | 57516 |
| 10645 | 26088 | 50.0 (82) | — | 13 | 150 | #1 | 57517 |
|  | 26089 | 50.0 (109) | — | 12 | 150 | #1 | 57518 |
| 10646 | 26090 | 64.8 | 53.9 (204) | 16 | 164 | #3 | 57519 |
| 10647 | 26091 | 62.4 | 59.8 (164) | 16 | 158 | #3 | 57520 |
| 10648 | 26092 | 64.8 | 56.7 | 17 | 190 | #3 | 57521 |
| 10649 | 26093 | 50.0 | 50.0 | 12 | 150 | #1 | 57522 |
| 10650 | 26094 | 64.0 | 59.4 (187) | 16 | 171 | #3 | 57523 |
| 10651 | 26095 | 65.6 | 56.0 | 22 | 185 | #4 | 57524 |
| 10652 | 26096 | 65.6 | 59.6 | 18 | 271 | #4 | 57525 |
| 10653 | 26097 | 71.2 | 66.2 | 17 | 560 | #5 | 57526 |
| 10654 | 26098 | 75.2 | 66.5 | 21 | 561 | #6 | 57527 |
| 10655 | 26099 | 50.0 | 50.0 (143) | 12 | 150 | #1 | 57528 |
| 10656 | 26100 | 84.8 | 76.4 | 21 | 1183 | #7 | 57529 |
| 10657 | 26101 | 50.0 (87) | — | 12 | 150 | #1 | 57530 |
| 10658 | 26102 | 69.6 | 59.6 | 22 | 259 | #4 | 57531 |
| 10659 | 26103 | 50.0 (53) | — | 12 | 150 | #1 | — |
| 10660 | 26104 | 66.4 | 61.9 (147) | 15 | 182 | #4 | 57532 |
| 10661 | 26105 | 75.4 (69) | — | 17 | 244 | #6 | 57533 |
|  | 26106 | 50.0 | 50.0 | 12 | 150 | #1 | 57534 |
| 10662 | 26107 | 80.0 | 73.8 | 24 | 1152 | #6 | 57535 |
| 10663 | 26108 | 50.0 (118) | — | 12 | 150 | #1 | 57536 |
| 10664 | 26109 | 68.0 | 59.3 | 20 | 240 | #4 | 57537 |
| 10665 | 26110 | 65.6 | 58.7 (213) | 19 | 185 | #4 | — |
|  | 26111 | 62.4 | 50.0 (190) | 14 | 150 | #3 | 57538 |
| 10666 | 26112 | 50.0 (59) | — | 12 | 150 | #1 | — |
|  | 26113 | 62.4 | 56.3 (197) | 31 | 172 | #3 | 57539 |
| 10667 | 26114 | 70.4 | 62.6 (203) | 21 | 246 | #5 | 57540 |
| 10668 | 26115 | 65.6 | 58.4 (178) | 15 | 232 | #4 | 57541 |
| 10669 | 26116 | 71.2 | 61.1 | 18 | 252 | #5 | 57542 |
|  | 26117 | 60.8 | 54.7 (139) | 13 | 150 | #3 | 57543 |
| 10670 | 26118 | 60.0 | 58.6 (128) | 15 | 279 | #2 | 57544 |
| 10671 | 26119 | 72.0 | 63.3 | 22 | 369 | #5 | 57545 |
| 10672 | 26120 | 69.6 | 58.2 | 23 | 250 | #4 | 57546 |
| 10673 | 26121 | 67.2 | 59.6 | 15 | 270 | #4 | 57547 |
| 10674 | 26122 | 60.4 (101) | — | 13 | 150 | #3 | 57548 |
|  | 26123 | 50.0 (90) | — | 14 | 150 | #1 | 57549 |
| 10675 | 26124 | 64.8 | 63.3 (150) | 32 | 177 | #3 | — |
|  | 26125 | 50.0 (65) | — | 12 | 150 | #1 | 57550 |
| 10676 | 26126 | 70.4 | 60.4 (245) | 17 | 408 | #5 | 57551 |
| 10677 | 26127 | 62.4 | 53.8 (156) | 14 | 150 | #3 | 57552 |
| 10678 | 26128 | 51.0 (102) | — | 13 | 150 | #1 | 57553 |
| 10679 | 26129 | 50.0 | 50.0 | 12 | 150 | #1 | 57554 |
| 10680 | 26130 | 64.8 | 58.2 | 12 | 207 | #3 | 57555 |
| 10681 | 26131 | 75.2 | 71.6 (261) | 20 | 585 | #6 | 57556 |
| 10682 | 26132 | 68.9 (119) | — | 21 | 172 | #4 | 57557 |
| 10683 | 26133 | 61.6 | 57.1 (205) | 14 | 160 | #3 | 57558 |
| 10684 | 26134 | 50.0 (50) | — | 12 | 150 | #1 | — |
| 10685 | 26135 | 64.0 | 50.4 (224) | 17 | 152 | #3 | — |
|  | 26136 | 71.2 | 64.4 | 23 | 452 | #5 | 57559 |
| 10686 | 26137 | 66.4 | 54.5 | 20 | 208 | #4 | 57560 |
|  | 26138 | 88.0 | 85.8 | 33 | 1501 | #8 | 57561 |
| 10687 | 26139 | 63.2 | 50.0 | 14 | 178 | #3 | 57562 |
| 10688 | 26140 | 62.4 | 59.3 | 15 | 277 | #3 | 57563 |
| 10689 | 26141 | 50.0 (56) | — | 12 | 150 | #1 | — |
| 10690 | 26142 | 63.4 (123) | — | 15 | 167 | #3 | 57564 |
| 10691 | 26143 | 61.1 (108) | — | 15 | 150 | #3 | 57565 |
| 10692 | 26144 | 61.6 | 50.7 (229) | 12 | 150 | #3 | 57566 |
| 10693 | 26145 | 65.6 | 57.8 (211) | 15 | 183 | #4 | 57567 |
| 10694 | 26146 | 58.4 | 50.0 | 18 | 157 | #2 | 57568 |
| 10695 | 26147 | 64.0 | 50.0 (192) | 17 | 165 | #3 | 57569 |
| 10696 | 26148 | 76.0 | 68.9 (270) | 15 | 554 | #6 | 57570 |
| 10697 | 26149 | 71.2 | 62.9 | 27 | 341 | #5 | 57571 |
| 10698 | 26150 | 50.0 | 50.0 | 12 | 150 | #1 | 57572 |
|  | 26151 | 65.6 | 59.8 (239) | 19 | 296 | #4 | 57573 |
| 10699 | 26152 | 64.0 | 50.8 (246) | 16 | 159 | #3 | 57574 |
| 10700 | 26153 | 82.4 | 68.4 | 26 | 541 | #7 | 57575 |
| 10701 | 26154 | 63.2 | 56.7 | 12 | 250 | #3 | 57576 |
| 10702 | 26155 | 62.3 (122) | — | 14 | 150 | #3 | 57577 |
|  | 26156 | 50.0 | 50.0 | 12 | 150 | #1 | 57578 |
| 10703 | 26157 | 67.2 | 61.5 | 22 | 426 | #4 | 57579 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10704 | 26158 | 66.4 | 60.9 (215) | 23 | 204 | #4 | 57580 |
| 10705 | 26159 | 50.0 (57) | — | 29 | 150 | #1 | — |
| 10706 | 26160 | 50.0 (98) | — | 12 | 150 | #1 | 57581 |
| 10707 | 26161 | 67.2 | 60.0 | 17 | 293 | #4 | 57582 |
| 10708 | 26162 | 67.2 | 58.8 (260) | 21 | 265 | #4 | 57583 |
| 10709 | 26163 | 64.8 | 58.5 | 16 | 219 | #3 | 57584 |
| 10710 | 26164 | 58.4 | 50.0 (174) | 14 | 150 | #2 | 57585 |
| 10711 | 26165 | 72.0 (93) | — | 16 | 208 | #5 | 57586 |
| 10712 | 26166 | 70.8 (65) | — | 12 | 150 | #5 | 57587 |
|  | 26167 | 82.4 | 76.0 | 27 | 739 | #7 | 57588 |
| 10713 | 26168 | 69.6 | 65.9 (164) | 29 | 249 | #4 | 57589 |
| 10714 | 26169 | 67.2 | 60.4 | 38 | 334 | #4 | 57590 |
| 10715 | 26170 | 50.0 (75) | — | 12 | 150 | #1 | 57591 |
|  | 26171 | 64.0 | 59.3 | 18 | 200 | #3 | 57592 |
| 10716 | 26172 | 50.0 (100) | — | 12 | 150 | #1 | 57593 |
| 10717 | 26173 | 68.0 | 58.2 | 33 | 203 | #4 | 57594 |
|  | 26174 | 50.0 | 50.0 | 12 | 150 | #1 | 57595 |
| 10718 | 26175 | 60.8 | 51.2 (213) | 15 | 162 | #3 | 57596 |
| 10719 | 26176 | 68.8 | 65.9 (208) | 20 | 263 | #4 | 57597 |
| 10720 | 26177 | 73.6 | 72.0 | 12 | 1037 | #5 | 57598 |
| 10721 | 26178 | 50.0 | 50.0 | 12 | 150 | #1 | 57599 |
|  | 26179 | 69.6 | 60.7 | 27 | 262 | #4 | 57600 |
| 10722 | 26180 | 70.4 | 60.7 | 23 | 319 | #5 | 57601 |
| 10723 | 26181 | 64.0 | 55.3 | 23 | 204 | #3 | 57602 |
| 10724 | 26182 | 64.0 | 63.7 (146) | 17 | 180 | #3 | 57603 |
| 10725 | 26183 | 50.0 (110) | — | 12 | 150 | #1 | 57604 |
| 10726 | 26184 | 68.0 | 60.8 (265) | 19 | 351 | #4 | 57605 |
| 10727 | 26185 | 71.2 | 62.9 | 25 | 366 | #5 | 57606 |
| 10728 | 26186 | 60.8 | 57.1 | 13 | 186 | #3 | 57607 |
| 10729 | 26187 | 61.5 (104) | — | 14 | 155 | #3 | 57608 |
|  | 26188 | 50.0 | 50.0 | 12 | 150 | #1 | 57609 |
| 10730 | 26189 | 69.6 | 62.5 | 23 | 640 | #4 | 57610 |
| 10731 | 26190 | 73.6 | 60.4 | 21 | 273 | #5 | 57611 |
|  | 26191 | 65.6 | 58.5 | 14 | 197 | #4 | 57612 |
| 10732 | 26192 | 69.6 | 63.6 | 20 | 482 | #4 | 57613 |
| 10733 | 26193 | 77.6 | 66.2 | 26 | 548 | #6 | 57614 |
| 10734 | 26194 | 67.2 | 61.5 (226) | 22 | 238 | #4 | 57615 |
| 10735 | 26195 | 69.6 | 70.0 (130) | 21 | 231 | #4 | 57616 |
| 10736 | 26196 | 68.8 (96) | — | 15 | 234 | #4 | 57617 |
| 10737 | 26197 | 50.0 | 50.0 | 12 | 150 | #1 | 57618 |
| 10738 | 26198 | 64.0 | 59.6 | 15 | 263 | #3 | 57619 |
| 10739 | 26199 | 50.0 (66) | — | 12 | 150 | #1 | 57620 |
| 10740 | 26200 | 64.8 | 50.0 | 13 | 198 | #3 | 57621 |
| 10741 | 26201 | 65.6 | 58.5 | 20 | 239 | #4 | 57622 |
| 10742 | 26202 | 64.8 | 50.0 | 19 | 187 | #3 | 57623 |
| 10743 | 26203 | 63.2 | 60.2 (161) | 14 | 165 | #3 | 57624 |
| 10744 | 26204 | 74.4 | 64.4 | 25 | 431 | #5 | 57625 |
| 10745 | 26205 | 68.8 | 61.1 | 25 | 275 | #4 | 57626 |
| 10746 | 26206 | 61.6 | 56.7 (231) | 13 | 153 | #3 | 57627 |
| 10747 | 26207 | 68.8 | 60.7 | 19 | 318 | #4 | 57628 |
| 10748 | 26208 | 61.6 | 50.0 (188) | 14 | 150 | #3 | 57629 |
| 10749 | 26209 | 85.9 (64) | — | 31 | 215 | #8 | — |
| 10750 | 26210 | 75.2 | 58.9 (219) | 13 | 383 | #6 | 57630 |
| 10751 | 26211 | 67.2 | 59.6 | 22 | 243 | #4 | 57631 |
| 10752 | 26212 | 52.8 | 50.0 | 14 | 150 | #1 | 57632 |
| 10753 | 26213 | 50.0 (61) | — | 12 | 150 | #1 | — |
| 10754 | 26214 | 72.0 | 60.0 | 13 | 325 | #5 | 57633 |
| 10755 | 26215 | 63.2 | 50.0 (202) | 15 | 167 | #3 | 57634 |
| 10756 | 26216 | 50.0 | 50.0 (129) | 12 | 150 | #1 | 57635 |
| 10757 | 26217 | 64.0 | 50.0 (180) | 30 | 181 | #3 | 57636 |
| 10758 | 26218 | 62.4 | 50.0 | 12 | 162 | #3 | 57637 |
| 10759 | 26219 | 50.0 (51) | — | 12 | 150 | #1 | — |
| 10760 | 26220 | 64.0 | 61.1 (167) | 19 | 210 | #3 | 57638 |
| 10761 | 26221 | 69.6 | 61.8 | 20 | 350 | #4 | 57639 |
| 10762 | 26222 | 66.4 | 53.6 (274) | 19 | 223 | #4 | 57640 |
| 10763 | 26223 | 75.2 | 60.7 | 21 | 384 | #6 | 57641 |
|  | 26224 | 60.0 | 60.6 (137) | 12 | 164 | #2 | 57642 |
| 10764 | 26225 | 65.6 | 59.9 (207) | 19 | 214 | #4 | 57643 |
| 10765 | 26226 | 50.0 (74) | — | 12 | 150 | #1 | 57644 |
| 10766 | 26227 | 70.4 | 62.5 | 22 | 478 | #5 | 57645 |
| 10767 | 26228 | 72.8 | 68.6 (156) | 31 | 252 | #5 | 57646 |
| 10768 | 26229 | 50.0 (56) | — | 12 | 150 | #1 | — |
| 10769 | 26230 | 64.0 | 50.0 | 12 | 176 | #3 | 57647 |
| 10770 | 26231 | 60.0 | 56.5 (193) | 12 | 153 | #2 | 57648 |
| 10771 | 26232 | 68.8 | 62.2 (259) | 23 | 283 | #4 | 57649 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10772 | 26233 | 64.8 | 58.5 | 15 | 213 | #3 | 57650 |
|  | 26234 | 71.2 | 59.0 (239) | 24 | 261 | #5 | 57651 |
| 10773 | 26235 | 78.4 | 59.3 | 16 | 533 | #6 | 57652 |
| 10774 | 26236 | 50.0 (98) | — | 12 | 150 | #1 | 57653 |
| 10775 | 26237 | 50.0 | 50.0 | 12 | 150 | #1 | 57654 |
| 10776 | 26238 | 59.2 | 50.0 (167) | 15 | 150 | #2 | 57655 |
| 10777 | 26239 | 52.8 | 50.0 (152) | 13 | 150 | #1 | 57656 |
|  | 26240 | 69.6 | 62.2 | 22 | 407 | #4 | 57657 |
| 10778 | 26241 | 50.0 (51) | — | 12 | 150 | #1 | — |
| 10779 | 26242 | 65.6 | 56.7 | 17 | 201 | #4 | 57658 |
| 10780 | 26243 | 67.2 | 60.0 | 19 | 264 | #4 | — |
| 10781 | 26244 | 66.4 | 50.0 | 14 | 209 | #4 | 57659 |
| 10782 | 26245 | 50.0 | 50.0 (161) | 18 | 150 | #1 | 57660 |
| 10783 | 26246 | 64.8 | 57.3 (185) | 16 | 169 | #3 | 57661 |
| 10784 | 26247 | 76.8 | 62.5 | 20 | 320 | #6 | 57662 |
| 10785 | 26248 | 50.0 (72) | — | 12 | 150 | #1 | 57663 |
|  | 26249 | 67.2 | 60.7 | 18 | 314 | #4 | 57664 |
| 10786 | 26250 | 50.0 (53) | — | 12 | 150 | #1 | — |
| 10787 | 26251 | 63.5 (63) | — | 13 | 150 | #3 | — |
|  | 26252 | 50.0 (78) | — | 12 | 150 | #1 | 57665 |
| 10788 | 26253 | 78.4 | 65.9 (170) | 17 | 409 | #6 | 57666 |
| 10789 | 26254 | 63.2 | 58.2 | 24 | 240 | #3 | 57667 |
| 10790 | 26255 | 71.2 | 62.9 | 22 | 486 | #5 | — |
| 10791 | 26256 | 50.0 (81) | — | 12 | 150 | #1 | 57668 |
| 10792 | 26257 | 63.2 | 50.0 (179) | 15 | 168 | #3 | 57669 |
| 10793 | 26258 | 68.0 | 59.3 | 18 | 250 | #4 | 57670 |
| 10794 | 26259 | 50.0 | 50.0 (178) | 12 | 150 | #1 | 57671 |
| 10795 | 26260 | 64.8 | 57.5 | 15 | 202 | #3 | 57672 |
| 10796 | 26261 | 66.4 | 50.0 | 14 | 188 | #4 | 57673 |
| 10797 | 26262 | 64.8 | 58.1 (227) | 21 | 177 | #3 | 57674 |
| 10798 | 26263 | 50.0 (111) | — | 12 | 150 | #1 | 57675 |
| 10799 | 26264 | 62.4 | 51.9 (185) | 17 | 163 | #3 | 57676 |
|  | 26265 | 69.6 | 62.2 | 25 | 419 | #4 | 57677 |
| 10800 | 26266 | 68.0 | 60.4 | 19 | 300 | #4 | 57678 |
|  | 26267 | 68.0 | 61.5 | 17 | 287 | #4 | 57679 |
| 10801 | 26268 | 64.8 | 62.0 (142) | 18 | 171 | #3 | 57680 |
| 10802 | 26269 | 81.7 (115) | — | 21 | 386 | #7 | 57681 |
| 10803 | 26270 | 69.6 | 62.2 | 20 | 381 | #4 | 57682 |
| 10804 | 26271 | 50.0 | 50.0 | 12 | 150 | #1 | 57683 |
|  | 26272 | 50.0 | 50.0 | 12 | 150 | #1 | 57684 |
|  | 26273 | 50.0 | 50.0 | 12 | 150 | #1 | 57685 |
| 10805 | 26274 | 50.0 (87) | — | 15 | 155 | #1 | 57686 |
| 10806 | 26275 | 67.2 | 60.9 (248) | 17 | 271 | #4 | 57687 |
| 10807 | 26276 | 50.0 | 50.0 | 12 | 150 | #1 | 57688 |
| 10808 | 26277 | 68.0 | 58.9 | 22 | 212 | #4 | 57689 |
| 10809 | 26278 | 50.0 | 50.0 (140) | 12 | 158 | #1 | 57690 |
| 10810 | 26279 | 69.6 | 58.2 | 20 | 227 | #4 | 57691 |
|  | 26280 | 50.0 (104) | — | 12 | 150 | #1 | 57692 |
| 10811 | 26281 | 50.0 | 50.0 | 12 | 150 | #1 | 57693 |
| 10812 | 26282 | 61.6 | 50.0 (243) | 16 | 182 | #3 | 57694 |
| 10813 | 26283 | 50.0 | 50.0 | 12 | 150 | #1 | 57695 |
| 10814 | 26284 | 88.0 | 69.7 (274) | 27 | 622 | #8 | 57696 |
| 10815 | 26285 | 70.4 | 60.4 | 28 | 280 | #5 | 57697 |
| 10816 | 26286 | 63.2 | 55.1 (243) | 16 | 166 | #3 | 57698 |
| 10817 | 26287 | 50.0 (114) | — | 13 | 150 | #1 | 57699 |
| 10818 | 26288 | 64.0 | 60.2 (196) | 16 | 186 | #3 | 57700 |
| 10819 | 26289 | 68.0 | 61.5 | 21 | 300 | #4 | 57701 |
| 10820 | 26290 | 68.0 | 62.5 | 22 | 315 | #4 | 57702 |
| 10821 | 26291 | 72.8 | 61.5 | 24 | 365 | #5 | 57703 |
| 10822 | 26292 | 55.2 (87) | — | 15 | 150 | #2 | 57704 |
| 10823 | 26293 | 64.8 | 56.7 | 12 | 174 | #3 | 57705 |
| 10824 | 26294 | 68.8 | 60.5 (238) | 19 | 213 | #4 | 57706 |
|  | 26295 | 76.0 | 68.0 | 23 | 559 | #6 | 57707 |
| 10825 | 26296 | 66.7 (105) | — | 20 | 169 | #4 | 57708 |
| 10826 | 26297 | 73.6 | 61.1 | 23 | 345 | #5 | 57709 |
| 10827 | 26298 | 63.2 | 61.8 (173) | 15 | 158 | #3 | 57710 |
|  | 26299 | 67.2 | 55.6 | 16 | 211 | #4 | 57711 |
| 10828 | 26300 | 50.0 (77) | — | 12 | 150 | #1 | 57712 |
| 10829 | 26301 | 67.2 | 61.5 | 21 | 288 | #4 | 57713 |
| 10830 | 26302 | 67.2 | 58.5 | 16 | 212 | #4 | 57714 |
| 10831 | 26303 | 52.8 | 50.0 (138) | 38 | 320 | #1 | 57715 |
|  | 26304 | 50.0 (56) | — | 12 | 150 | #1 | — |
| 10832 | 26305 | 61.6 | 50.0 (197) | 15 | 150 | #3 | 57716 |
| 10833 | 26306 | 67.2 | 64.3 (140) | 27 | 188 | #4 | 57717 |
| 10834 | 26307 | 69.6 | 62.2 | 23 | 327 | #4 | 57718 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10835 | 26308 | 61.6 | 50.0 (269) | 13 | 155 | #3 | 57719 |
| 10836 | 26309 | 71.2 | 60.7 | 35 | 276 | #5 | 57720 |
|  | 26310 | 69.6 | 63.5 (200) | 22 | 254 | #4 | 57721 |
| 10837 | 26311 | 66.4 | 61.8 (186) | 20 | 212 | #4 | 57722 |
| 10838 | 26312 | 50.0 | 50.0 (128) | 13 | 150 | #1 | 57723 |
| 10839 | 26313 | 50.0 (106) | — | 12 | 150 | #1 | 57724 |
| 10840 | 26314 | 69.5 (59) | — | 34 | 179 | #4 | — |
|  | 26315 | 69.6 | 66.2 (225) | 14 | 433 | #4 | 57725 |
| 10841 | 26316 | 66.4 | 61.5 | 18 | 344 | #4 | 57726 |
| 10842 | 26317 | 64.8 | 58.2 | 13 | 210 | #3 | 57727 |
| 10843 | 26318 | 75.2 | 68.7 | 21 | 859 | #6 | 57728 |
| 10844 | 26319 | 61.6 | 56.4 (266) | 14 | 177 | #3 | 57729 |
| 10845 | 26320 | 68.0 | 61.1 | 13 | 363 | #4 | 57730 |
| 10846 | 26321 | 64.8 (71) | — | 15 | 150 | #3 | 57731 |
| 10847 | 26322 | 50.0 (83) | — | 12 | 150 | #1 | 57732 |
| 10848 | 26323 | 67.6 (71) | — | 17 | 150 | #4 | 57733 |
|  | 26324 | 78.6 (56) | — | 12 | 172 | #6 | — |
| 10849 | 26325 | 50.0 (94) | — | 12 | 150 | #1 | 57734 |
| 10850 | 26326 | 60.0 | 56.0 | 12 | 188 | #2 | 57735 |
|  | 26327 | 63.3 (109) | — | 12 | 155 | #3 | 57736 |
| 10851 | 26328 | 50.0 | 50.0 (236) | 12 | 150 | #1 | 57737 |
| 10852 | 26329 | 50.0 | 50.0 | 13 | 165 | #1 | 57738 |
| 10853 | 26330 | 67.2 | 60.4 | 22 | 280 | #4 | 57739 |
| 10854 | 26331 | 50.0 (101) | — | 12 | 150 | #1 | 57740 |
| 10855 | 26332 | 72.0 | 62.2 | 21 | 401 | #5 | 57741 |
| 10856 | 26333 | 69.6 | 60.7 | 12 | 318 | #4 | 57742 |
| 10857 | 26334 | 71.4 (77) | — | 21 | 179 | #5 | 57743 |
|  | 26335 | 65.6 | 50.0 | 12 | 211 | #4 | 57744 |
| 10858 | 26336 | 75.2 | 68.4 | 24 | 1218 | #6 | 57745 |
| 10859 | 26337 | 50.0 (67) | — | 12 | 150 | #1 | 57746 |
| 10860 | 26338 | 68.0 | 62.1 (269) | 25 | 301 | #4 | 57747 |
| 10861 | 26339 | 63.2 | 50.0 (273) | 29 | 163 | #3 | 57748 |
| 10862 | 26340 | 69.6 | 59.3 | 25 | 284 | #4 | 57749 |
| 10863 | 26341 | 50.0 | 50.0 | 12 | 150 | #1 | 57750 |
| 10864 | 26342 | 64.8 | 54.3 (151) | 16 | 182 | #3 | 57751 |
| 10865 | 26343 | 80.8 | 76.7 | 24 | 1532 | #7 | 57752 |
| 10866 | 26344 | 92.0 | 65.4 (217) | 36 | 630 | #9 | 57753 |
| 10867 | 26345 | 64.8 | 63.9 (144) | 32 | 305 | #3 | 57754 |
| 10868 | 26346 | 72.7 (99) | — | 27 | 209 | #5 | 57755 |
| 10869 | 26347 | 68.8 | 59.6 | 30 | 241 | #4 | 57756 |
| 10870 | 26348 | 57.1 (84) | — | 33 | 222 | #2 | 57757 |
| 10871 | 26349 | 50.0 (69) | — | 12 | 150 | #1 | 57758 |
|  | 26350 | 60.0 | 50.0 (169) | 15 | 167 | #2 | 57759 |
| 10872 | 26351 | 50.0 | 50.0 (176) | 12 | 150 | #1 | 57760 |
| 10873 | 26352 | 90.4 | 85.5 | 40 | 1128 | #9 | 57761 |
| 10874 | 26353 | 70.4 | 63.3 | 20 | 444 | #5 | 57762 |
| 10875 | 26354 | 50.0 | 50.0 | 12 | 150 | #1 | — |
| 10876 | 26355 | 69.6 | 62.9 | 23 | 781 | #4 | 57763 |
|  | 26356 | 50.0 (80) | — | 12 | 150 | #1 | — |
| 10877 | 26357 | 50.0 (89) | — | 39 | 190 | #1 | 57764 |
| 10878 | 26358 | 70.4 | 58.9 | 20 | 237 | #5 | 57765 |
| 10879 | 26359 | 66.4 | 59.3 | 19 | 239 | #4 | 57766 |
| 10880 | 26360 | 64.0 | 63.8 (127) | 19 | 199 | #3 | 57767 |
| 10881 | 26361 | 74.4 | 53.8 | 18 | 408 | #5 | — |
| 10882 | 26362 | 66.4 | 58.2 (201) | 20 | 182 | #4 | — |
| 10883 | 26363 | 68.8 | 63.9 (183) | 24 | 240 | #4 | 57768 |
| 10884 | 26364 | 68.8 (93) | — | 16 | 167 | #4 | 57769 |
| 10885 | 26365 | 67.2 | 54.7 (245) | 18 | 197 | #4 | 57770 |
| 10886 | 26366 | 60.0 | 51.7 (178) | 13 | 150 | #2 | 57771 |
| 10887 | 26367 | 50.0 | 50.0 | 12 | 150 | #1 | 57772 |
|  | 26368 | 70.4 | 58.2 | 28 | 261 | #5 | 57773 |
| 10888 | 26369 | 73.7 (76) | — | 18 | 175 | #5 | 57774 |
|  | 26370 | 68.0 | 60.7 | 24 | 266 | #4 | 57775 |
| 10889 | 26371 | 64.0 | 58.7 (172) | 15 | 168 | #3 | 57776 |
| 10890 | 26372 | 71.2 | 63.5 (178) | 23 | 252 | #5 | 57777 |
| 10891 | 26373 | 69.6 | 64.1 (217) | 26 | 271 | #4 | 57778 |
| 10892 | 26374 | 50.0 | 50.0 | 12 | 150 | #1 | 57779 |
| 10893 | 26375 | 67.2 | 63.6 | 13 | 492 | #4 | 57780 |
| 10894 | 26376 | 77.6 | 67.6 | 32 | 603 | #6 | 57781 |
| 10895 | 26377 | 69.6 | 60.9 (235) | 21 | 231 | #4 | 57782 |
|  | 26378 | 68.8 | 62.9 | 21 | 520 | #4 | 57783 |
| 10896 | 26379 | 64.0 | 53.7 (175) | 14 | 156 | #3 | 57784 |
| 10897 | 26380 | 70.4 | 60.7 | 17 | 280 | #5 | 57785 |
| 10898 | 26381 | 69.6 | 60.4 | 23 | 312 | #4 | 57786 |
|  | 26382 | 71.2 | 62.9 | 28 | 347 | #5 | 57787 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10899 | 26383 | 50.0 | 50.0 (135) | 12 | 150 | #1 | 57788 |
| 10900 | 26384 | 63.2 | 50.0 | 12 | 156 | #3 | 57789 |
| 10901 | 26385 | 68.0 | 62.2 | 16 | 326 | #4 | 57790 |
| 10902 | 26386 | 64.0 | 54.1 (159) | 23 | 204 | #3 | 57791 |
| 10903 | 26387 | 65.6 | 59.9 (137) | 19 | 161 | #4 | 57792 |
| 10904 | 26388 | 66.4 | 51.6 | 15 | 285 | #4 | 57793 |
| 10905 | 26389 | 50.0 | 50.0 (274) | 12 | 150 | #1 | 57794 |
| 10906 | 26390 | 72.8 | 68.3 (180) | 17 | 309 | #5 | 57795 |
| 10907 | 26391 | 50.0 | 50.0 | 12 | 150 | #1 | 57796 |
| 10908 | 26392 | 68.8 | 59.6 | 31 | 232 | #4 | 57797 |
|  | 26393 | 68.0 | 61.5 | 22 | 312 | #4 | 57798 |
| 10909 | 26394 | 64.0 | 51.5 (268) | 15 | 174 | #3 | 57799 |
| 10910 | 26395 | 50.0 (93) | — | 12 | 150 | #1 | 57800 |
| 10911 | 26396 | 68.8 | 62.2 | 19 | 273 | #4 | 57801 |
| 10912 | 26397 | 63.2 | 50.0 | 14 | 193 | #3 | 57802 |
| 10913 | 26398 | 55.6 (108) | — | 16 | 155 | #2 | 57803 |
| 10914 | 26399 | 70.4 | 60.7 | 33 | 284 | #5 | 57804 |
|  | 26400 | 75.4 (61) | — | 20 | 168 | #6 | — |
| 10915 | 26401 | 83.2 | 71.6 | 29 | 666 | #7 | — |
| 10916 | 26402 | 50.0 (112) | — | 12 | 150 | #1 | 57805 |
| 10917 | 26403 | 69.6 | 61.5 | 21 | 317 | #4 | 57806 |
| 10918 | 26404 | 58.3 (120) | — | 15 | 161 | #2 | 57807 |
| 10919 | 26405 | 50.0 | 50.0 (126) | 12 | 150 | #1 | 57808 |
| 10920 | 26406 | 61.3 (93) | — | 19 | 157 | #3 | 57809 |
| 10921 | 26407 | 72.8 | 61.5 | 22 | 306 | #5 | 57810 |
| 10922 | 26408 | 68.0 | 60.9 (253) | 20 | 228 | #4 | 57811 |
| 10923 | 26409 | 50.0 | 50.0 | 12 | 150 | #1 | 57812 |
| 10924 | 26410 | 68.8 | 63.6 | 25 | 289 | #4 | 57813 |
|  | 26411 | 66.4 | 65.2 (135) | 19 | 177 | #4 | 57814 |
| 10925 | 26412 | 68.8 | 66.0 (156) | 21 | 234 | #4 | 57815 |
| 10926 | 26413 | 50.0 (118) | — | 17 | 150 | #1 | 57816 |
| 10927 | 26414 | 64.0 | 51.8 (197) | 14 | 179 | #3 | 57817 |
| 10928 | 26415 | 73.6 | 68.0 | 32 | 632 | #5 | 57818 |
| 10929 | 26416 | 67.0 (103) | — | 18 | 172 | #4 | 57819 |
|  | 26417 | 67.9 (78) | — | 12 | 153 | #4 | 57820 |
| 10930 | 26418 | 65.6 | 60.0 | 22 | 276 | #4 | 57821 |
| 10931 | 26419 | 66.4 | 60.6 (246) | 21 | 211 | #4 | 57822 |
| 10932 | 26420 | 50.0 (50) | — | 12 | 150 | #1 | — |
|  | 26421 | 68.0 | 60.4 | 17 | 239 | #4 | 57823 |
| 10933 | 26422 | 65.6 | 50.0 | 12 | 186 | #4 | 57824 |
| 10934 | 26423 | 72.6 (95) | — | 23 | 194 | #5 | 57825 |
|  | 26424 | 68.0 | 60.4 | 21 | 322 | #4 | 57826 |
| 10935 | 26425 | 50.0 (63) | — | 12 | 150 | #1 | — |
|  | 26426 | 50.0 (114) | — | 12 | 150 | #1 | 57827 |
| 10936 | 26427 | 68.8 | 61.5 | 22 | 282 | #4 | 57828 |
|  | 26428 | 50.0 (67) | — | 12 | 150 | #1 | 57829 |
| 10937 | 26429 | 65.6 | 54.0 (224) | 16 | 184 | #4 | 57830 |
| 10938 | 26430 | 63.2 | 50.0 | 15 | 184 | #3 | 57831 |
| 10939 | 26431 | 50.0 (89) | — | 27 | 150 | #1 | 57832 |
| 10940 | 26432 | 73.6 | 54.9 | 16 | 435 | #5 | 57833 |
| 10941 | 26433 | 80.8 | 65.8 | 23 | 457 | #7 | 57834 |
| 10942 | 26434 | 67.9 (81) | — | 18 | 166 | #4 | 57835 |
| 10943 | 26435 | 82.4 | 72.7 | 30 | 944 | #7 | 57836 |
|  | 26436 | 78.4 | 63.6 | 22 | 471 | #6 | 57837 |
| 10944 | 26437 | 62.4 | 58.8 (240) | 15 | 198 | #3 | 57838 |
| 10945 | 26438 | 50.0 | 50.0 | 12 | 150 | #1 | 57839 |
| 10946 | 26439 | 62.4 | 50.0 | 12 | 185 | #3 | 57840 |
| 10947 | 26440 | 53.6 | 50.0 (134) | 12 | 150 | #1 | 57841 |
| 10948 | 26441 | 68.8 | 61.8 | 23 | 337 | #4 | 57842 |
| 10949 | 26442 | 68.0 | 61.1 | 18 | 276 | #4 | — |
| 10950 | 26443 | 65.6 | 50.0 (263) | 14 | 166 | #4 | 57843 |
| 10951 | 26444 | 68.8 | 64.6 (161) | 22 | 216 | #4 | 57844 |
| 10952 | 26445 | 50.0 (50) | — | 12 | 150 | #1 | — |
| 10953 | 26446 | 70.4 | 61.0 (218) | 26 | 244 | #5 | 57845 |
| 10954 | 26447 | 68.0 | 60.4 | 19 | 235 | #4 | 57846 |
|  | 26448 | 67.2 | 65.2 (161) | 24 | 222 | #4 | 57847 |
| 10955 | 26449 | 63.2 | 50.0 | 17 | 213 | #3 | 57848 |
|  | 26450 | 68.8 | 60.4 | 17 | 295 | #4 | 57849 |
|  | 26451 | 50.0 | 50.0 (140) | 12 | 150 | #1 | 57850 |
| 10956 | 26452 | 76.8 | 60.0 | 19 | 426 | #6 | 57851 |
| 10957 | 26453 | 68.8 | 62.9 | 20 | 362 | #4 | 57852 |
| 10958 | 26454 | 69.6 | 66.4 (134) | 27 | 221 | #4 | 57853 |
| 10959 | 26455 | 66.4 | 50.0 | 14 | 183 | #4 | 57854 |
| 10960 | 26456 | 64.8 | 50.0 (219) | 18 | 157 | #3 | 57855 |
| 10961 | 26457 | 62.4 | 61.6 (138) | 16 | 161 | #3 | 57856 |

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 10962 | 26458 | 70.4 | 70.4 (152) | 15 | 348 | #5 | 57857 |
| 10963 | 26459 | 67.2 | 59.3 | 17 | 201 | #4 | 57858 |
| | 26460 | 50.0 | 50.0 (214) | 14 | 150 | #1 | 57859 |
| 10964 | 26461 | 67.3 (110) | — | 17 | 179 | #4 | 57860 |
| | 26462 | 68.8 | 61.8 | 21 | 282 | #4 | 57861 |
| 10965 | 26463 | 50.0 (78) | — | 12 | 150 | #1 | 57862 |
| 10966 | 26464 | 67.0 (103) | — | 14 | 150 | #4 | 57863 |
| | 26465 | 68.0 | 60.4 | 20 | 296 | #4 | 57864 |
| 10967 | 26466 | 65.6 | 58.5 | 18 | 235 | #4 | 57865 |
| 10968 | 26467 | 72.0 | 72.0 (125) | 12 | 302 | #5 | 57866 |
| | 26468 | 63.2 | 56.0 | 16 | 184 | #3 | 57867 |
| 10969 | 26469 | 62.4 | 57.1 | 13 | 204 | #3 | 57868 |
| 10970 | 26470 | 64.0 | 58.8 (228) | 17 | 252 | #3 | 57869 |
| 10971 | 26471 | 68.0 | 60.7 | 18 | 310 | #4 | 57870 |
| 10972 | 26472 | 64.0 | 57.0 (235) | 17 | 182 | #3 | 57871 |
| 10973 | 26473 | 66.4 | 52.2 (255) | 21 | 202 | #4 | 57872 |
| 10974 | 26474 | 64.0 | 50.0 | 15 | 177 | #3 | 57873 |
| 10975 | 26475 | 64.8 | 59.6 | 15 | 275 | #3 | 57874 |
| 10976 | 26476 | 64.0 | 59.2 (233) | 14 | 193 | #3 | 57875 |
| 10977 | 26477 | 91.2 | 82.2 | 35 | 900 | #9 | 57876 |
| 10978 | 26478 | 50.0 | 50.0 | 12 | 150 | #1 | 57877 |
| 10979 | 26479 | 60.3 (116) | — | 20 | 167 | #3 | 57878 |
| 10980 | 26480 | 64.0 | 59.1 (164) | 19 | 165 | #3 | 57879 |
| 10981 | 26481 | 58.4 | 50.0 | 15 | 166 | #2 | 57880 |
| | 26482 | 63.2 | 50.0 | 17 | 183 | #3 | 57881 |
| 10982 | 26483 | 69.6 | 59.3 | 32 | 239 | #4 | 57882 |
| 10983 | 26484 | 64.0 | 53.8 | 16 | 176 | #3 | 57883 |
| 10984 | 26485 | 50.0 (63) | — | 12 | 150 | #1 | 57884 |
| 10985 | 26486 | 69.6 | 60.7 | 28 | 254 | #4 | 57885 |
| 10986 | 26487 | 67.2 | 60.4 | 17 | 234 | #4 | 57886 |
| 10987 | 26488 | 50.0 (94) | — | 12 | 150 | #1 | 57887 |
| | 26489 | 50.0 | 50.0 (165) | 12 | 150 | #1 | 57888 |
| 10988 | 26490 | 65.6 | 59.0 (227) | 17 | 210 | #4 | 57889 |
| 10989 | 26491 | 50.0 | 50.0 | 12 | 150 | #1 | 57890 |
| | 26492 | 72.8 | 61.5 | 24 | 304 | #5 | 57891 |
| | 26493 | 72.0 | 61.8 | 23 | 393 | #5 | 57892 |
| 10990 | 26494 | 50.0 (52) | — | 12 | 150 | #1 | — |
| 10991 | 26495 | 85.6 (104) | — | 30 | 365 | #8 | 57893 |
| 10992 | 26496 | 64.8 | 50.0 | 15 | 203 | #3 | 57894 |
| 10993 | 26497 | 68.0 (97) | — | 21 | 177 | #4 | 57895 |
| 10994 | 26498 | 50.0 (50) | — | 12 | 150 | #1 | — |
| 10995 | 26499 | 68.8 | 61.8 | 22 | 272 | #4 | 57896 |
| | 26500 | 70.4 | 64.7 (187) | 22 | 248 | #5 | 57897 |
| 10996 | 26501 | 54.9 (91) | — | 14 | 150 | #1 | 57898 |
| 10997 | 26502 | 53.2 (77) | — | 16 | 150 | #1 | 57899 |
| 10998 | 26503 | 50.0 | 50.0 | 12 | 150 | #1 | 57900 |
| 10999 | 26504 | 64.8 | 62.8 (164) | 18 | 198 | #3 | 57901 |
| 11000 | 26505 | 66.4 | 58.9 | 16 | 208 | #4 | — |
| 11001 | 26506 | 70.4 | 61.5 | 29 | 358 | #5 | 57902 |
| 11002 | 26507 | 71.2 | 61.8 | 20 | 311 | #5 | 57903 |
| 11003 | 26508 | 79.8 (89) | — | 21 | 258 | #6 | 57904 |
| 11004 | 26509 | 64.0 | 50.0 | 28 | 182 | #3 | 57905 |
| 11005 | 26510 | 70.4 | 61.1 | 19 | 333 | #5 | 57906 |
| 11006 | 26511 | 64.8 | 59.3 | 14 | 276 | #3 | 57907 |
| 11007 | 26512 | 70.4 | 62.5 | 21 | 372 | #5 | 57908 |
| 11008 | 26513 | 60.0 | 54.0 (139) | 18 | 155 | #2 | 57909 |
| | 26514 | 66.2 (68) | — | 13 | 161 | #4 | 57910 |
| 11009 | 26515 | 62.4 | 50.0 (231) | 18 | 183 | #3 | 57911 |
| | 26516 | 50.0 (83) | — | 12 | 150 | #1 | 57912 |
| 11010 | 26517 | 70.4 | 59.6 | 22 | 276 | #5 | 57913 |
| 11011 | 26518 | 67.2 | 62.2 | 20 | 322 | #4 | 57914 |
| 11012 | 26519 | 67.2 | 59.3 | 25 | 248 | #4 | 57915 |
| 11013 | 26520 | 70.4 | 63.3 | 21 | 718 | #5 | 57916 |
| 11014 | 26521 | 69.8 (106) | — | 28 | 188 | #4 | 57917 |
| 11015 | 26522 | 50.0 (68) | — | 12 | 150 | #1 | 57918 |
| | 26523 | 50.0 (74) | — | 12 | 150 | #1 | 57919 |
| 11016 | 26524 | 64.0 | 51.2 (160) | 13 | 152 | #3 | 57920 |
| 11017 | 26525 | 64.0 | 50.0 | 13 | 170 | #3 | 57921 |
| 11018 | 26526 | 64.4 (87) | — | 14 | 173 | #3 | 57922 |
| 11019 | 26527 | 64.8 (71) | — | 20 | 150 | #3 | 57923 |
| 11020 | 26528 | 62.4 | 50.0 (219) | 14 | 163 | #3 | 57924 |
| | 26529 | 63.2 | 55.3 | 14 | 200 | #3 | 57925 |
| 11021 | 26530 | 50.0 (69) | — | 12 | 150 | #1 | 57926 |
| 11022 | 26531 | 69.6 | 62.9 | 12 | 782 | #4 | 57927 |
| 11023 | 26532 | 50.0 (71) | — | 12 | 150 | #1 | 57928 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11024 | 26533 | 50.0 (88) | — | 12 | 150 | #1 | 57929 |
| | 26534 | 50.0 | 50.0 | 12 | 150 | #1 | 57930 |
| 11025 | 26535 | 83.2 | 72.7 | 22 | 730 | #7 | 57931 |
| 11026 | 26536 | 67.2 | 61.5 | 12 | 252 | #4 | 57932 |
| 11027 | 26537 | 67.2 | 58.9 | 19 | 234 | #4 | 57933 |
| | 26538 | 72.8 | 63.3 | 27 | 581 | #5 | 57934 |
| 11028 | 26539 | 70.4 | 50.0 | 15 | 303 | #5 | 57935 |
| 11029 | 26540 | 50.0 | 50.0 | 12 | 150 | #1 | 57936 |
| 11030 | 26541 | 63.2 | 50.0 (248) | 15 | 172 | #3 | 57937 |
| 11031 | 26542 | 50.0 (66) | — | 12 | 150 | #1 | 57938 |
| 11032 | 26543 | 68.6 (121) | — | 18 | 195 | #4 | 57939 |
| 11033 | 26544 | 66.4 | 50.0 (266) | 16 | 184 | #4 | — |
| 11034 | 26545 | 72.8 | 64.4 | 21 | 361 | #5 | 57940 |
| 11035 | 26546 | 62.1 (124) | — | 19 | 233 | #3 | 57941 |
| 11036 | 26547 | 68.8 | 60.7 | 20 | 261 | #4 | 57942 |
| 11037 | 26548 | 64.0 | 60.5 (152) | 16 | 180 | #3 | — |
| 11038 | 26549 | 50.0 | 50.0 | 12 | 150 | #1 | 57943 |
| 11039 | 26550 | 87.2 | 64.7 | 28 | 482 | #8 | 57944 |
| 11040 | 26551 | 71.2 | 60.7 | 22 | 268 | #5 | 57945 |
| 11041 | 26552 | 68.0 | 62.9 | 20 | 399 | #4 | 57946 |
| 11042 | 26553 | 55.2 (105) | — | 14 | 176 | #2 | 57947 |
| | 26554 | 71.2 | 67.6 | 21 | 447 | #5 | 57948 |
| 11043 | 26555 | 67.2 | 62.6 (179) | 19 | 201 | #4 | 57949 |
| 11044 | 26556 | 62.4 | 50.0 (225) | 13 | 164 | #3 | 57950 |
| 11045 | 26557 | 66.4 | 50.0 | 22 | 208 | #4 | 57951 |
| 11046 | 26558 | 50.0 (50) | — | 12 | 150 | #1 | — |
| | 26559 | 50.5 (103) | — | 12 | 160 | #1 | 57952 |
| 11047 | 26560 | 64.8 | 61.2 (178) | 18 | 178 | #3 | 57953 |
| | 26561 | 67.2 | 61.1 | 18 | 275 | #4 | 57954 |
| | 26562 | 76.0 | 66.5 | 31 | 455 | #6 | 57955 |
| 11048 | 26563 | 69.6 (56) | — | 24 | 187 | #4 | — |
| 11049 | 26564 | 64.0 | 50.2 | 16 | 198 | #3 | 57956 |
| 11050 | 26565 | 60.0 | 52.7 | 12 | 201 | #2 | 57957 |
| 11051 | 26566 | 67.2 | 59.5 (269) | 19 | 223 | #4 | 57958 |
| | 26567 | 65.6 | 58.9 | 15 | 273 | #4 | 57959 |
| 11052 | 26568 | 64.2 (106) | — | 15 | 169 | #3 | 57960 |
| 11053 | 26569 | 72.8 | 70.0 (130) | 17 | 327 | #5 | 57961 |
| 11054 | 26570 | 64.0 | 50.0 | 15 | 176 | #3 | 57962 |
| 11055 | 26571 | 56.8 | 56.3 (126) | 24 | 170 | #2 | 57963 |
| 11056 | 26572 | 50.0 (117) | — | 12 | 150 | #1 | 57964 |
| 11057 | 26573 | 67.2 | 60.4 | 17 | 263 | #4 | 57965 |
| 11058 | 26574 | 50.0 (50) | — | 12 | 150 | #1 | — |
| 11059 | 26575 | 50.0 | 50.0 | 12 | 150 | #1 | 57966 |
| 11060 | 26576 | 50.0 (56) | — | 12 | 150 | #1 | — |
| 11061 | 26577 | 64.8 | 58.8 (182) | 16 | 205 | #3 | 57967 |
| 11062 | 26578 | 66.4 | 57.1 | 13 | 189 | #4 | 57968 |
| 11063 | 26579 | 64.8 | 57.9 (195) | 18 | 224 | #3 | 57969 |
| 11064 | 26580 | 70.4 | 62.9 | 22 | 358 | #5 | 57970 |
| 11065 | 26581 | 53.6 | 50.0 | 15 | 151 | #1 | 57971 |
| 11066 | 26582 | 80.8 | 77.1 (179) | 19 | 524 | #7 | 57972 |
| 11067 | 26583 | 70.4 (71) | — | 12 | 150 | #5 | 57973 |
| 11068 | 26584 | 68.0 | 60.3 (257) | 21 | 203 | #4 | 57974 |
| 11069 | 26585 | 50.0 (53) | — | 12 | 150 | #1 | — |
| 11070 | 26586 | 66.4 | 50.0 | 17 | 197 | #4 | 57975 |
| 11071 | 26587 | 78.4 | 64.4 | 25 | 639 | #6 | 57976 |
| 11072 | 26588 | 50.0 (115) | — | 12 | 150 | #1 | 57977 |
| | 26589 | 50.0 (118) | — | 12 | 150 | #1 | 57978 |
| | 26590 | 68.0 | 58.9 | 13 | 370 | #4 | 57979 |
| 11073 | 26591 | 62.4 | 50.0 (249) | 15 | 171 | #3 | 57980 |
| | 26592 | 50.0 (96) | — | 12 | 150 | #1 | 57981 |
| 11074 | 26593 | 64.0 | 51.8 (170) | 15 | 150 | #3 | 57982 |
| 11075 | 26594 | 50.0 | 50.0 (269) | 12 | 150 | #1 | 57983 |
| 11076 | 26595 | 50.0 (99) | — | 12 | 150 | #1 | 57984 |
| 11077 | 26596 | 50.0 (70) | — | 12 | 150 | #1 | 57985 |
| 11078 | 26597 | 65.6 | 57.9 (240) | 20 | 196 | #4 | 57986 |
| 11079 | 26598 | 62.4 | 56.4 | 16 | 267 | #3 | 57987 |
| 11080 | 26599 | 66.4 | 65.2 (132) | 16 | 174 | #4 | 57988 |
| | 26600 | 66.4 | 58.9 | 22 | 222 | #4 | 57989 |
| 11081 | 26601 | 50.0 | 50.0 | 12 | 150 | #1 | 57990 |
| 11082 | 26602 | 69.6 | 60.0 | 21 | 228 | #4 | — |
| | 26603 | 72.8 | 57.2 (271) | 23 | 404 | #5 | 57991 |
| 11083 | 26604 | 50.0 | 50.0 | 12 | 150 | #1 | 57992 |
| 11084 | 26605 | 50.0 | 50.0 | 12 | 150 | #1 | 57993 |
| 11085 | 26606 | 70.4 | 62.5 | 20 | 358 | #5 | 57994 |
| 11086 | 26607 | 79.2 | 60.0 | 21 | 449 | #6 | 57995 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11087 | 26608 | 79.7 (59) | — | 12 | 157 | #6 | — |
| 11088 | 26609 | 63.2 | 60.3 (141) | 20 | 183 | #3 | 57996 |
|  | 26610 | 52.8 | 50.0 (179) | 19 | 150 | #1 | 57997 |
| 11089 | 26611 | 66.4 | 59.3 (243) | 16 | 194 | #4 | 57998 |
|  | 26612 | 69.6 | 60.4 | 20 | 312 | #4 | 57999 |
| 11090 | 26613 | 52.9 (121) | — | 12 | 154 | #1 | 58000 |
|  | 26614 | 65.6 | 62.1 (140) | 21 | 183 | #4 | 58001 |
| 11091 | 26615 | 67.2 | 64.4 (146) | 19 | 202 | #4 | 58002 |
|  | 26616 | 74.4 | 62.9 | 30 | 471 | #5 | 58003 |
| 11092 | 26617 | 64.0 | 63.8 (138) | 17 | 185 | #3 | 58004 |
| 11093 | 26618 | 87.2 | 83.6 | 33 | 4594 | #8 | 58005 |
| 11094 | 26619 | 62.4 | 50.7 (223) | 17 | 162 | #3 | 58006 |
| 11095 | 26620 | 50.0 (55) | — | 12 | 150 | #1 | — |
| 11096 | 26621 | 50.0 (59) | — | 12 | 150 | #1 | — |
|  | 26622 | 72.8 | 64.2 (226) | 24 | 288 | #5 | 58007 |
| 11097 | 26623 | 50.0 (92) | — | 12 | 150 | #1 | 58008 |
|  | 26624 | 56.4 (101) | — | 16 | 183 | #2 | 58009 |
| 11098 | 26625 | 72.8 | 62.5 | 22 | 294 | #5 | 58010 |
| 11099 | 26626 | 50.0 (58) | — | 12 | 150 | #1 | — |
| 11100 | 26627 | 73.6 | 68.7 | 12 | 575 | #5 | 58011 |
| 11101 | 26628 | 72.0 | 57.1 | 14 | 340 | #5 | 58012 |
| 11102 | 26629 | 50.0 | 50.0 | 12 | 150 | #1 | 58013 |
| 11103 | 26630 | 50.0 | 50.0 | 12 | 150 | #1 | 58014 |
| 11104 | 26631 | 64.8 | 52.5 (236) | 13 | 182 | #3 | 58015 |
| 11105 | 26632 | 61.6 | 58.5 | 12 | 204 | #3 | 58016 |
| 11106 | 26633 | 50.0 (52) | — | 12 | 150 | #1 | — |
| 11107 | 26634 | 72.8 | 64.7 | 16 | 458 | #5 | 58017 |
| 11108 | 26635 | 64.8 | 59.3 | 17 | 209 | #3 | 58018 |
| 11109 | 26636 | 79.2 | 75.6 | 18 | 886 | #6 | 58019 |
| 11110 | 26637 | 64.0 | 60.0 (155) | 16 | 171 | #3 | 58020 |
| 11111 | 26638 | 50.0 | 50.0 (149) | 15 | 150 | #1 | 58021 |
| 11112 | 26639 | 68.0 | 61.8 | 20 | 303 | #4 | 58022 |
| 11113 | 26640 | 64.8 | 60.4 | 18 | 244 | #3 | 58023 |
| 11114 | 26641 | 68.0 | 62.9 | 20 | 435 | #4 | 58024 |
| 11115 | 26642 | 76.1 (67) | — | 13 | 161 | #6 | 58025 |
| 11116 | 26643 | 58.4 | 52.7 (165) | 14 | 150 | #2 | 58026 |
| 11117 | 26644 | 67.2 | 60.7 | 23 | 273 | #4 | 58027 |
| 11118 | 26645 | 50.0 (85) | — | 12 | 150 | #1 | — |
| 11119 | 26646 | 68.0 | 59.6 | 21 | 233 | #4 | 58028 |
|  | 26647 | 71.2 | 63.3 | 26 | 451 | #5 | 58029 |
| 11120 | 26648 | 50.0 (70) | — | 12 | 150 | #1 | 58030 |
|  | 26649 | 50.0 (59) | — | 12 | 150 | #1 | — |
| 11121 | 26650 | 65.6 | 50.0 | 20 | 170 | #4 | 58031 |
| 11122 | 26651 | 67.2 | 60.7 | 20 | 368 | #4 | 58032 |
| 11123 | 26652 | 64.8 | 60.8 (227) | 18 | 207 | #3 | 58033 |
| 11124 | 26653 | 66.4 | 60.9 (235) | 19 | 205 | #4 | — |
| 11125 | 26654 | 67.2 | 59.6 | 15 | 234 | #4 | 58034 |
| 11126 | 26655 | 67.8 (121) | — | 20 | 197 | #4 | 58035 |
| 11127 | 26656 | 67.2 | 59.6 | 20 | 267 | #4 | — |
| 11128 | 26657 | 63.2 | 57.1 (177) | 18 | 185 | #3 | 58036 |
| 11129 | 26658 | 50.0 (119) | — | 14 | 150 | #1 | 58037 |
| 11130 | 26659 | 68.5 (92) | — | 19 | 172 | #4 | 58038 |
| 11131 | 26660 | 50.0 | 50.0 | 12 | 150 | #1 | 58039 |
| 11132 | 26661 | 64.8 | 57.1 | 19 | 209 | #3 | 58040 |
| 11133 | 26662 | 50.0 (124) | — | 12 | 150 | #1 | 58041 |
| 11134 | 26663 | 50.0 (94) | — | 12 | 150 | #1 | 58042 |
| 11135 | 26664 | 63.1 (65) | — | 12 | 150 | #3 | 58043 |
| 11136 | 26665 | 50.0 | 50.0 | 12 | 150 | #1 | 58044 |
| 11137 | 26666 | 68.8 | 65.6 (154) | 19 | 244 | #4 | 58045 |
| 11138 | 26667 | 71.2 | 62.2 | 22 | 427 | #5 | 58046 |
| 11139 | 26668 | 50.0 (69) | — | 12 | 150 | #1 | 58047 |
| 11140 | 26669 | 69.6 | 65.1 | 19 | 637 | #4 | 58048 |
| 11141 | 26670 | 66.4 | 64.8 (182) | 22 | 208 | #4 | 58049 |
| 11142 | 26671 | 68.0 | 60.7 | 18 | 270 | #4 | — |
| 11143 | 26672 | 67.2 | 57.1 | 18 | 226 | #4 | 58050 |
| 11144 | 26673 | 68.8 | 64.6 (161) | 25 | 224 | #4 | 58051 |
| 11145 | 26674 | 92.3 (91) | — | 26 | 400 | #9 | 58052 |
| 11146 | 26675 | 64.8 | 50.0 | 13 | 182 | #3 | 58053 |
| 11147 | 26676 | 50.0 | 50.0 | 12 | 150 | #1 | 58054 |
| 11148 | 26677 | 70.4 | 61.7 (261) | 21 | 272 | #5 | 58055 |
| 11149 | 26678 | 72.0 | 63.6 | 22 | 332 | #5 | 58056 |
| 11150 | 26679 | 61.6 | 50.0 | 12 | 174 | #3 | 58057 |
| 11151 | 26680 | 50.0 (66) | — | 12 | 150 | #1 | — |
|  | 26681 | 70.4 | 60.0 | 18 | 258 | #5 | 58058 |
| 11152 | 26682 | 64.0 | 50.0 (188) | 14 | 165 | #3 | 58059 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11153 | 26683 | 50.0 | 50.0 | 12 | 150 | #1 | 58060 |
| 11154 | 26684 | 70.4 | 61.1 | 24 | 299 | #5 | 58061 |
| 11155 | 26685 | 64.8 | 59.5 (185) | 17 | 188 | #3 | 58062 |
| 11156 | 26686 | 85.6 | 81.2 (181) | 18 | 599 | #8 | 58063 |
|  | 26687 | 70.4 | 65.5 | 15 | 500 | #5 | 58064 |
| 11157 | 26688 | 64.8 | 56.4 | 15 | 207 | #3 | 58065 |
| 11158 | 26689 | 64.8 | 53.6 (252) | 17 | 171 | #3 | 58066 |
| 11159 | 26690 | 68.8 | 52.4 | 29 | 234 | #4 | 58067 |
| 11160 | 26691 | 50.0 (54) | — | 12 | 150 | #1 | — |
| 11161 | 26692 | 50.0 (107) | — | 12 | 150 | #1 | 58068 |
| 11162 | 26693 | 65.6 | 60.0 | 17 | 227 | #4 | 58069 |
| 11163 | 26694 | 67.2 | 56.8 (266) | 20 | 207 | #4 | 58070 |
| 11164 | 26695 | 59.2 | 52.4 (191) | 13 | 150 | #2 | 58071 |
| 11165 | 26696 | 73.9 (69) | — | 18 | 193 | #5 | 58072 |
|  | 26697 | 72.8 | 62.9 | 28 | 298 | #5 | 58073 |
| 11166 | 26698 | 50.0 (53) | — | 12 | 150 | #1 | — |
| 11167 | 26699 | 61.6 | 50.0 | 12 | 150 | #3 | 58074 |
| 11168 | 26700 | 68.0 | 59.2 (250) | 23 | 219 | #4 | 58075 |
| 11169 | 26701 | 57.8 (116) | — | 12 | 183 | #2 | 58076 |
| 11170 | 26702 | 60.8 | 60.8 (125) | 13 | 202 | #3 | 58077 |
| 11171 | 26703 | 73.6 | 62.2 | 38 | 324 | #5 | 58078 |
| 11172 | 26704 | 64.0 | 56.2 (176) | 14 | 167 | #3 | — |
| 11173 | 26705 | 67.2 | 59.6 | 21 | 216 | #4 | 58079 |
| 11174 | 26706 | 72.0 | 67.4 (218) | 31 | 419 | #5 | 58080 |
| 11175 | 26707 | 67.2 | 61.5 | 20 | 348 | #4 | 58081 |
| 11176 | 26708 | 56.0 | 50.0 | 12 | 207 | #2 | 58082 |
| 11177 | 26709 | 60.2 (88) | — | 15 | 155 | #3 | 58083 |
| 11178 | 26710 | 50.0 (50) | — | 12 | 150 | #1 | — |
| 11179 | 26711 | 60.0 | 51.0 (204) | 14 | 158 | #2 | 58084 |
| 11180 | 26712 | 72.0 | 62.5 | 25 | 545 | #5 | 58085 |
| 11181 | 26713 | 72.2 (90) | — | 18 | 188 | #5 | 58086 |
| 11182 | 26714 | 67.2 | 65.0 (143) | 18 | 191 | #4 | 58087 |
| 11183 | 26715 | 67.2 | 61.1 | 19 | 317 | #4 | 58088 |
| 11184 | 26716 | 50.0 | 50.0 | 12 | 150 | #1 | 58089 |
| 11185 | 26717 | 78.6 (56) | — | 17 | 172 | #6 | — |
| 11186 | 26718 | 50.0 (51) | — | 12 | 150 | #1 | — |
| 11187 | 26719 | 68.0 | 60.2 (249) | 20 | 264 | #4 | 58090 |
| 11188 | 26720 | 70.4 | 64.7 | 14 | 389 | #5 | 58091 |
| 11189 | 26721 | 64.0 | 50.0 (270) | 13 | 188 | #3 | 58092 |
| 11190 | 26722 | 50.0 (53) | — | 12 | 150 | #1 | — |
| 11191 | 26723 | 77.6 | 60.1 (188) | 19 | 369 | #6 | 58093 |
| 11192 | 26724 | 50.0 | 50.0 | 12 | 150 | #1 | — |
| 11193 | 26725 | 76.0 | 69.5 | 18 | 781 | #6 | 58094 |
|  | 26726 | 50.0 (106) | — | 12 | 150 | #1 | 58095 |
| 11194 | 26727 | 65.6 | 55.1 (214) | 16 | 170 | #4 | 58096 |
|  | 26728 | 61.6 | 50.0 | 12 | 170 | #3 | 58097 |
| 11195 | 26729 | 64.0 | 55.6 | 14 | 222 | #3 | 58098 |
| 11196 | 26730 | 70.4 | 65.9 (173) | 27 | 292 | #5 | 58099 |
| 11197 | 26731 | 63.2 | 50.0 | 12 | 199 | #3 | 58100 |
| 11198 | 26732 | 67.2 | 61.5 | 20 | 299 | #4 | 58101 |
| 11199 | 26733 | 62.4 | 57.8 | 13 | 202 | #3 | 58102 |
| 11200 | 26734 | 74.4 | 50.0 | 17 | 321 | #5 | 58103 |
| 11201 | 26735 | 72.8 | 68.7 | 15 | 596 | #5 | 58104 |
| 11202 | 26736 | 68.8 | 60.7 | 20 | 355 | #4 | 58105 |
| 11203 | 26737 | 78.4 | 77.0 (135) | 19 | 383 | #6 | 58106 |
|  | 26738 | 72.8 | 64.7 | 29 | 398 | #5 | 58107 |
| 11204 | 26739 | 60.4 (106) | — | 15 | 226 | #3 | 58108 |
| 11205 | 26740 | 68.8 | 60.7 | 20 | 244 | #4 | 58109 |
| 11206 | 26741 | 66.4 | 59.6 | 17 | 220 | #4 | 58110 |
| 11207 | 26742 | 50.0 (75) | — | 12 | 150 | #1 | 58111 |
| 11208 | 26743 | 76.8 | 69.1 | 31 | 568 | #6 | 58112 |
| 11209 | 26744 | 66.2 (74) | — | 15 | 151 | #4 | 58113 |
| 11210 | 26745 | 50.0 (50) | — | 12 | 150 | #1 | — |
| 11211 | 26746 | 60.8 | 55.1 (138) | 17 | 159 | #3 | 58114 |
| 11212 | 26747 | 63.2 | 58.9 | 24 | 242 | #3 | 58115 |
| 11213 | 26748 | 65.6 | 50.0 | 18 | 226 | #4 | 58116 |
| 11214 | 26749 | 50.0 (115) | — | 12 | 150 | #1 | 58117 |
|  | 26750 | 76.0 | 63.9 (194) | 16 | 356 | #6 | 58118 |
| 11215 | 26751 | 66.7 (99) | — | 16 | 165 | #4 | 58119 |
| 11216 | 26752 | 64.8 | 57.1 | 15 | 196 | #3 | 58120 |
| 11217 | 26753 | 50.0 | 50.0 (203) | 12 | 150 | #1 | 58121 |
| 11218 | 26754 | 64.0 | 62.7 (150) | 20 | 194 | #3 | 58122 |
| 11219 | 26755 | 72.0 | 59.3 | 12 | 400 | #5 | 58123 |
| 11220 | 26756 | 68.8 | 60.0 | 32 | 261 | #4 | 58124 |
| 11221 | 26757 | 61.6 | 61.6 (125) | 12 | 151 | #3 | 58125 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11222 | 26758 | 50.0 | 50.0 | 12 | 150 | #1 | 58126 |
| 11223 | 26759 | 67.2 | 60.4 | 21 | 362 | #4 | 58127 |
| 11224 | 26760 | 50.0 (63) | — | 12 | 150 | #1 | 58128 |
| 11225 | 26761 | 50.0 (84) | — | 18 | 153 | #1 | 58129 |
|  | 26762 | 62.4 | 57.5 | 12 | 240 | #3 | 58130 |
| 11226 | 26763 | 68.8 | 56.0 | 24 | 284 | #4 | 58131 |
|  | 26764 | 68.0 | 59.6 | 16 | 223 | #4 | 58132 |
| 11227 | 26765 | 62.4 | 58.2 (146) | 18 | 162 | #3 | 58133 |
|  | 26766 | 63.2 | 54.6 (185) | 15 | 163 | #3 | 58134 |
| 11228 | 26767 | 73.6 | 68.0 (169) | 21 | 309 | #5 | 58135 |
| 11229 | 26768 | 69.6 | 60.7 | 21 | 288 | #4 | 58136 |
| 11230 | 26769 | 59.2 | 50.0 | 13 | 150 | #2 | 58137 |
|  | 26770 | 50.0 | 50.0 | 12 | 150 | #1 | 58138 |
| 11231 | 26771 | 84.0 | 81.5 | 25 | 1122 | #7 | 58139 |
| 11232 | 26772 | 57.6 | 50.0 (261) | 15 | 181 | #2 | 58140 |
| 11233 | 26773 | 68.8 | 61.8 (170) | 22 | 220 | #4 | 58141 |
| 11234 | 26774 | 68.0 | 61.1 | 15 | 533 | #4 | 58142 |
| 11235 | 26775 | 68.0 | 58.5 | 31 | 248 | #4 | 58143 |
| 11236 | 26776 | 50.0 (94) | — | 12 | 150 | #1 | 58144 |
|  | 26777 | 70.3 (74) | — | 16 | 152 | #5 | 58145 |
| 11237 | 26778 | 68.8 | 61.5 | 22 | 347 | #4 | 58146 |
|  | 26779 | 50.0 (72) | — | 12 | 150 | #1 | 58147 |
| 11238 | 26780 | 65.6 | 60.4 (207) | 20 | 200 | #4 | 58148 |
| 11239 | 26781 | 71.2 | 56.8 (185) | 14 | 317 | #5 | 58149 |
| 11240 | 26782 | 55.2 | 50.0 | 12 | 159 | #2 | 58150 |
| 11241 | 26783 | 74.1 (58) | — | 38 | 207 | #5 | — |
| 11242 | 26784 | 50.0 (60) | — | 12 | 150 | #1 | — |
|  | 26785 | 50.0 | 50.0 (149) | 12 | 150 | #1 | 58151 |
| 11243 | 26786 | 61.4 (83) | — | 40 | 211 | #3 | 58152 |
| 11244 | 26787 | 64.0 | 56.8 (162) | 16 | 172 | #3 | 58153 |
| 11245 | 26788 | 63.2 | 56.4 | 25 | 201 | #3 | — |
| 11246 | 26789 | 68.0 | 62.2 | 20 | 340 | #4 | — |
| 11247 | 26790 | 50.0 (51) | — | 12 | 150 | #1 | — |
|  | 26791 | 75.2 | 71.4 (133) | 18 | 321 | #6 | — |
| 11248 | 26792 | 77.6 | 50.0 | 28 | 447 | #6 | 58154 |
| 11249 | 26793 | 76.0 | 61.8 | 19 | 537 | #6 | 58155 |
| 11250 | 26794 | 81.6 | 73.8 | 24 | 695 | #7 | 58156 |
|  | 26795 | 67.4 (92) | — | 14 | 162 | #4 | 58157 |
| 11251 | 26796 | 50.0 (64) | — | 12 | 150 | #1 | 58158 |
| 11252 | 26797 | 64.0 | 50.0 | 14 | 261 | #3 | 58159 |
| 11253 | 26798 | 68.2 (88) | — | 15 | 174 | #4 | 58160 |
| 11254 | 26799 | 67.2 | 58.9 (258) | 19 | 205 | #4 | 58161 |
| 11255 | 26800 | 63.2 | 54.0 (174) | 17 | 172 | #3 | 58162 |
| 11256 | 26801 | 69.6 | 61.8 | 22 | 435 | #4 | 58163 |
| 11257 | 26802 | 64.0 | 58.5 | 15 | 218 | #3 | 58164 |
| 11258 | 26803 | 50.0 (59) | — | 12 | 150 | #1 | — |
| 11259 | 26804 | 56.8 | 53.4 (133) | 14 | 163 | #2 | 58165 |
|  | 26805 | 65.6 | 57.4 (197) | 35 | 186 | #4 | 58166 |
| 11260 | 26806 | 70.4 | 65.3 (167) | 13 | 317 | #5 | 58167 |
| 11261 | 26807 | 67.2 | 65.0 (180) | 22 | 235 | #4 | 58168 |
|  | 26808 | 50.9 (108) | — | 15 | 153 | #1 | — |
| 11262 | 26809 | 68.0 | 63.1 (179) | 21 | 206 | #4 | 58169 |
| 11263 | 26810 | 65.6 | 64.2 (265) | 15 | 411 | #4 | 58170 |
| 11264 | 26811 | 56.6 (113) | — | 15 | 160 | #2 | 58171 |
| 11265 | 26812 | 83.2 | 78.5 | 23 | 854 | #7 | 58172 |
| 11266 | 26813 | 74.4 | 60.0 | 21 | 310 | #5 | 58173 |
| 11267 | 26814 | 62.4 | 50.5 | 14 | 161 | #3 | 58174 |
| 11268 | 26815 | 50.0 | 50.0 (227) | 15 | 162 | #1 | 58175 |
| 11269 | 26816 | 64.0 | 64.0 (136) | 16 | 201 | #3 | 58176 |
| 11270 | 26817 | 52.8 | 50.0 (195) | 12 | 176 | #1 | 58177 |
| 11271 | 26818 | 50.0 | 50.0 (134) | 12 | 150 | #1 | 58178 |
| 11272 | 26819 | 50.0 (85) | — | 12 | 150 | #1 | 58179 |
| 11273 | 26820 | 63.2 | 50.0 (218) | 16 | 155 | #3 | 58180 |
|  | 26821 | 50.0 (67) | — | 12 | 150 | #1 | 58181 |
| 11274 | 26822 | 75.8 (62) | — | 16 | 155 | #6 | — |
| 11275 | 26823 | 50.0 (75) | — | 12 | 150 | #1 | 58182 |
| 11276 | 26824 | 60.8 | 50.0 (250) | 16 | 158 | #3 | 58183 |
|  | 26825 | 68.8 | 62.5 | 21 | 385 | #4 | 58184 |
| 11277 | 26826 | 50.0 (73) | — | 12 | 150 | #1 | 58185 |
|  | 26827 | 50.0 (124) | — | 12 | 150 | #1 | 58186 |
| 11278 | 26828 | 65.6 | 58.5 | 14 | 228 | #4 | 58187 |
| 11279 | 26829 | 66.4 | 60.0 | 17 | 280 | #4 | 58188 |
|  | 26830 | 50.0 (54) | — | 12 | 150 | #1 | — |
| 11280 | 26831 | 63.2 | 50.2 (245) | 17 | 170 | #3 | 58189 |
| 11281 | 26832 | 62.4 | 50.0 (258) | 15 | 182 | #3 | 58190 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11282 | 26833 | 62.4 | 50.0 | 12 | 188 | #3 | 58191 |
|  | 26834 | 68.8 | 62.9 | 20 | 302 | #4 | 58192 |
| 11283 | 26835 | 84.1 (63) | — | 26 | 204 | #7 | — |
|  | 26836 | 69.6 | 67.6 | 18 | 660 | #4 | 58193 |
|  | 26837 | 50.0 (79) | — | 12 | 150 | #1 | 58194 |
| 11284 | 26838 | 65.6 | 50.0 | 16 | 193 | #4 | 58195 |
| 11285 | 26839 | 50.0 | 50.0 (139) | 12 | 150 | #1 | 58196 |
|  | 26840 | 60.8 | 55.6 | 13 | 185 | #3 | 58197 |
| 11286 | 26841 | 68.8 | 61.1 | 20 | 365 | #4 | 58198 |
| 11287 | 26842 | 73.6 | 63.6 | 35 | 471 | #5 | 58199 |
| 11288 | 26843 | 60.8 | 53.7 (227) | 16 | 182 | #3 | 58200 |
| 11289 | 26844 | 69.6 | 65.1 | 14 | 417 | #4 | 58201 |
| 11290 | 26845 | 70.9 (117) | — | 26 | 217 | #5 | 58202 |
| 11291 | 26846 | 63.2 | 58.5 (260) | 16 | 160 | #3 | 58203 |
| 11292 | 26847 | 61.8 (89) | — | 14 | 150 | #3 | 58204 |
| 11293 | 26848 | 59.0 (105) | — | 15 | 168 | #2 | 58205 |
| 11294 | 26849 | 64.0 | 50.0 | 14 | 244 | #3 | 58206 |
| 11295 | 26850 | 64.0 | 59.8 (194) | 14 | 279 | #3 | 58207 |
| 11296 | 26851 | 64.0 | 61.0 (249) | 12 | 347 | #3 | 58208 |
|  | 26852 | 69.6 | 60.7 | 22 | 260 | #4 | 58209 |
| 11297 | 26853 | 70.4 | 60.7 | 18 | 315 | #5 | 58210 |
| 11298 | 26854 | 67.2 | 60.7 | 23 | 261 | #4 | 58211 |
|  | 26855 | 68.8 | 63.3 (226) | 16 | 391 | #4 | 58212 |
| 11299 | 26856 | 65.3 (118) | — | 21 | 179 | #4 | 58213 |
| 11300 | 26857 | 69.3 (101) | — | 15 | 207 | #4 | 58214 |
| 11301 | 26858 | 52.3 (109) | — | 12 | 150 | #1 | 58215 |
| 11302 | 26859 | 71.2 | 63.6 | 23 | 444 | #5 | 58216 |
| 11303 | 26860 | 64.0 | 53.3 (214) | 14 | 167 | #3 | 58217 |
| 11304 | 26861 | 67.6 (74) | — | 19 | 150 | #4 | 58218 |
| 11305 | 26862 | 65.6 | 61.1 | 15 | 254 | #4 | 58219 |
| 11306 | 26863 | 66.4 | 50.0 (184) | 17 | 158 | #4 | 58220 |
| 11307 | 26864 | 60.8 | 51.5 (196) | 37 | 182 | #3 | 58221 |
| 11308 | 26865 | 50.0 (60) | — | 12 | 150 | #1 | — |
|  | 26866 | 50.4 | 50.0 (189) | 37 | 299 | #1 | 58222 |
| 11309 | 26867 | 68.8 | 50.0 | 24 | 205 | #4 | 58223 |
| 11310 | 26868 | 76.0 | 66.9 | 21 | 522 | #6 | 58224 |
| 11311 | 26869 | 69.6 | 62.2 | 27 | 363 | #4 | 58225 |
| 11312 | 26870 | 75.0 (64) | — | 18 | 162 | #5 | 58226 |
| 11313 | 26871 | 61.6 | 58.2 | 14 | 217 | #3 | — |
| 11314 | 26872 | 68.0 | 62.9 | 18 | 323 | #4 | 58227 |
| 11315 | 26873 | 51.2 | 50.0 (135) | 14 | 150 | #1 | 58228 |
|  | 26874 | 60.0 | 57.1 (177) | 13 | 167 | #2 | 58229 |
| 11316 | 26875 | 55.2 | 50.0 (170) | 13 | 157 | #2 | 58230 |
| 11317 | 26876 | 50.0 | 50.0 | 12 | 150 | #1 | 58231 |
| 11318 | 26877 | 71.4 (56) | — | 12 | 150 | #5 | — |
| 11319 | 26878 | 68.8 | 65.4 (179) | 21 | 251 | #4 | 58232 |
| 11320 | 26879 | 73.6 | 61.8 | 23 | 313 | #4 | 58233 |
| 11321 | 26880 | 67.2 | 60.3 (267) | 20 | 218 | #4 | 58234 |
| 11322 | 26881 | 50.0 (63) | — | 12 | 150 | #1 | — |
| 11323 | 26882 | 75.4 (122) | — | 28 | 300 | #6 | — |
| 11324 | 26883 | 62.4 | 59.2 (223) | 21 | 177 | #3 | 58235 |
| 11325 | 26884 | 67.2 | 57.5 | 19 | 234 | #4 | 58236 |
| 11326 | 26885 | 67.2 | 59.4 (251) | 20 | 222 | #4 | 58237 |
| 11327 | 26886 | 72.5 (80) | — | 26 | 179 | #5 | 58238 |
|  | 26887 | 69.7 (89) | — | 13 | 190 | #4 | 58239 |
| 11328 | 26888 | 76.8 | 66.2 | 26 | 459 | #6 | 58240 |
| 11329 | 26889 | 64.8 (88) | — | 13 | 150 | #3 | 58241 |
| 11330 | 26890 | 65.4 (81) | — | 21 | 162 | #4 | — |
| 11331 | 26891 | 67.2 | 60.7 | 31 | 327 | #4 | 58242 |
| 11332 | 26892 | 62.4 | 58.6 (140) | 16 | 157 | #3 | 58243 |
| 11333 | 26893 | 66.4 | 58.2 | 21 | 207 | #4 | 58244 |
| 11334 | 26894 | 65.6 | 60.4 | 15 | 269 | #4 | 58245 |
| 11335 | 26895 | 69.6 | 63.3 | 16 | 400 | #4 | 58246 |
| 11336 | 26896 | 68.0 | 58.2 | 18 | 383 | #4 | 58247 |
| 11337 | 26897 | 50.0 | 50.0 (130) | 12 | 150 | #1 | 58248 |
| 11338 | 26898 | 67.2 | 61.1 | 21 | 261 | #4 | 58249 |
| 11339 | 26899 | 64.0 | 50.0 | 12 | 169 | #3 | 58250 |
| 11340 | 26900 | 58.4 | 52.3 (172) | 13 | 156 | #2 | 58251 |
| 11341 | 26901 | 50.0 (98) | — | 12 | 150 | #1 | 58252 |
| 11342 | 26902 | 72.0 | 58.7 (242) | 26 | 275 | #5 | 58253 |
| 11343 | 26903 | 63.2 | 50.0 (272) | 13 | 174 | #3 | 58254 |
| 11344 | 26904 | 50.0 (79) | — | 12 | 150 | #1 | 58255 |
| 11345 | 26905 | 67.2 | 60.8 (171) | 17 | 164 | #4 | 58256 |
| 11346 | 26906 | 69.6 | 60.5 (238) | 39 | 257 | #4 | 58257 |
| 11347 | 26907 | 50.0 | 50.0 (141) | 12 | 150 | #1 | 58258 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11348 | 26908 | 64.8 | 58.2 | 16 | 213 | #3 | 58259 |
| 11349 | 26909 | 63.1 (103) | — | 18 | 150 | #3 | 58260 |
| | 26910 | 67.2 | 54.9 (153) | 18 | 262 | #4 | 58261 |
| 11350 | 26911 | 50.0 (60) | — | 12 | 150 | #1 | — |
| 11351 | 26912 | 75.0 (88) | — | 19 | 227 | #5 | 58262 |
| 11352 | 26913 | 72.0 | 65.1 | 31 | 362 | #5 | 58263 |
| 11353 | 26914 | 68.0 | 60.7 | 20 | 280 | #4 | 58264 |
| 11354 | 26915 | 50.0 | 50.0 | 12 | 150 | #1 | 58265 |
| 11355 | 26916 | 68.0 | 62.9 | 22 | 496 | #4 | 58266 |
| 11356 | 26917 | 64.8 | 59.6 | 16 | 245 | #3 | 58267 |
| 11357 | 26918 | 65.6 | 54.8 (219) | 20 | 162 | #4 | 58268 |
| 11358 | 26919 | 63.2 | 56.3 (167) | 17 | 161 | #3 | 58269 |
| 11359 | 26920 | 66.4 | 59.3 | 19 | 278 | #4 | 58270 |
| 11360 | 26921 | 50.0 | 50.0 | 12 | 150 | #1 | 58271 |
| 11361 | 26922 | 60.0 (120) | — | 19 | 161 | #2 | 58272 |
| 11362 | 26923 | 81.8 (55) | — | 40 | 195 | #7 | — |
| | 26924 | 50.0 (81) | — | 12 | 150 | #1 | 58273 |
| 11363 | 26925 | 76.8 | 67.2 (192) | 31 | 399 | #6 | 58274 |
| 11364 | 26926 | 64.0 | 50.0 (215) | 15 | 171 | #3 | 58275 |
| 11365 | 26927 | 50.0 | 50.0 (266) | 28 | 242 | #1 | — |
| 11366 | 26928 | 50.0 | 50.0 (202) | 16 | 197 | #1 | 58276 |
| 11367 | 26929 | 69.4 (72) | — | 15 | 150 | #4 | 58277 |
| 11368 | 26930 | 65.4 (104) | — | 14 | 240 | #4 | 58278 |
| 11369 | 26931 | 50.0 (87) | — | 12 | 150 | #1 | 58279 |
| | 26932 | 65.6 | 58.2 | 14 | 189 | #4 | 58280 |
| 11370 | 26933 | 66.4 | 55.3 | 20 | 201 | #4 | 58281 |
| | 26934 | 50.0 (54) | — | 12 | 150 | #1 | — |
| 11371 | 26935 | 64.9 (114) | — | 16 | 163 | #3 | 58282 |
| 11372 | 26936 | 79.2 | 75.3 | 16 | 1367 | #6 | 58283 |
| 11373 | 26937 | 65.6 | 58.2 | 17 | 249 | #4 | 58284 |
| | 26938 | 50.0 | 50.0 | 12 | 150 | #1 | 58285 |
| 11374 | 26939 | 67.0 (103) | — | 27 | 171 | #4 | 58286 |
| | 26940 | 84.0 | 66.5 | 19 | 629 | #7 | 58287 |
| 11375 | 26941 | 67.9 (78) | — | 16 | 150 | #4 | 58288 |
| 11376 | 26942 | 66.4 | 50.0 | 15 | 195 | #4 | 58289 |
| 11377 | 26943 | 53.6 | 50.0 | 14 | 173 | #1 | 58290 |
| 11378 | 26944 | 59.6 (109) | — | 14 | 150 | #2 | 58291 |
| 11379 | 26945 | 78.4 | 75.5 (212) | 24 | 584 | #6 | 58292 |
| 11380 | 26946 | 60.0 | 50.0 | 12 | 184 | #2 | — |
| | 26947 | 67.2 | 60.7 | 17 | 279 | #4 | 58293 |
| 11381 | 26948 | 60.8 | 50.0 | 13 | 163 | #3 | 58294 |
| 11382 | 26949 | 79.3 (58) | — | 13 | 173 | #6 | — |
| 11383 | 26950 | 71.2 | 63.3 | 28 | 554 | #5 | 58295 |
| 11384 | 26951 | 65.6 | 55.9 (227) | 18 | 180 | #4 | 58296 |
| 11385 | 26952 | 72.8 | 70.1 (134) | 16 | 309 | #5 | 58297 |
| 11386 | 26953 | 68.0 | 62.2 | 23 | 308 | #4 | 58298 |
| 11387 | 26954 | 50.0 (76) | — | 12 | 150 | #1 | 58299 |
| | 26955 | 50.0 (54) | — | 12 | 150 | #1 | — |
| 11388 | 26956 | 71.2 | 50.0 | 15 | 303 | #5 | 58300 |
| | 26957 | 68.0 | 64.7 | 16 | 509 | #4 | 58301 |
| | 26958 | 68.8 | 61.5 | 17 | 346 | #4 | 58302 |
| 11389 | 26959 | 63.2 | 60.0 | 15 | 201 | #3 | 58303 |
| | 26960 | 68.0 | 60.7 | 22 | 245 | #4 | 58304 |
| 11390 | 26961 | 50.0 | 50.0 | 12 | 150 | #1 | 58305 |
| 11391 | 26962 | 50.0 (123) | — | 12 | 150 | #1 | 58306 |
| 11392 | 26963 | 50.0 | 50.0 | 12 | 150 | #1 | 58307 |
| | 26964 | 55.5 (110) | — | 14 | 160 | #2 | 58308 |
| 11393 | 26965 | 66.4 | 64.8 (128) | 12 | 263 | #4 | 58309 |
| 11394 | 26966 | 61.7 (115) | — | 13 | 160 | #3 | 58310 |
| 11395 | 26967 | 62.4 | 50.0 (202) | 12 | 154 | #3 | 58311 |
| | 26968 | 65.6 | 57.9 (240) | 16 | 190 | #4 | 58312 |
| 11396 | 26969 | 66.4 | 57.8 | 23 | 264 | #4 | — |
| 11397 | 26970 | 61.6 | 50.0 | 14 | 194 | #3 | 58313 |
| 11398 | 26971 | 77.6 | 57.2 (243) | 21 | 477 | #6 | 58314 |
| 11399 | 26972 | 68.0 | 61.1 | 20 | 598 | #4 | 58315 |
| | 26973 | 92.0 | 85.5 | 44 | 1002 | #9 | 58316 |
| 11400 | 26974 | 72.0 | 70.8 (137) | 18 | 301 | #5 | 58317 |
| 11401 | 26975 | 67.2 (58) | — | 13 | 150 | #4 | — |
| | 26976 | 50.0 (66) | — | 12 | 150 | #1 | 58318 |
| 11402 | 26977 | 64.8 | 57.5 (174) | 16 | 196 | #3 | 58319 |
| 11403 | 26978 | 71.2 | 62.9 | 25 | 358 | #5 | 58320 |
| 11404 | 26979 | 68.8 | 57.1 | 16 | 208 | #4 | 58321 |
| 11405 | 26980 | 82.4 | 71.6 | 30 | 636 | #7 | 58322 |
| 11406 | 26981 | 50.0 (102) | — | 12 | 150 | #1 | 58323 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11407 | 26982 | 80.7 (109) | — | 18 | 332 | #7 | 58324 |
|  | 26983 | 77.6 | 68.4 | 32 | 570 | #6 | 58325 |
| 11408 | 26984 | 73.6 | 69.8 | 17 | 874 | #5 | 58326 |
| 11409 | 26985 | 67.5 (114) | — | 24 | 187 | #4 | 58327 |
| 11410 | 26986 | 50.0 | 50.0 | 12 | 160 | #1 | 58328 |
| 11411 | 26987 | 57.1 (70) | — | 13 | 150 | #2 | 58329 |
| 11412 | 26988 | 74.4 | 65.5 | 20 | 527 | #5 | 58330 |
| 11413 | 26989 | 60.3 (63) | — | 38 | 185 | #3 | — |
| 11414 | 26990 | 67.2 | 50.0 | 16 | 204 | #4 | 58331 |
| 11415 | 26991 | 50.0 (52) | — | 12 | 150 | #1 | — |
| 11416 | 26992 | 50.0 (81) | — | 12 | 150 | #1 | 58332 |
|  | 26993 | 65.6 | 59.3 | 21 | 257 | #4 | 58333 |
| 11417 | 26994 | 80.0 | 80.4 (143) | 24 | 461 | #6 | 58334 |
| 11418 | 26995 | 69.6 | 60.7 | 21 | 259 | #4 | 58335 |
| 11419 | 26996 | 67.2 | 61.1 | 20 | 286 | #4 | 58336 |
| 11420 | 26997 | 71.9 (57) | — | 23 | 155 | #5 | — |
| 11421 | 26998 | 72.8 | 69.8 | 18 | 509 | #5 | 58337 |
| 11422 | 26999 | 77.6 | 66.5 | 30 | 667 | #6 | 58338 |
| 11423 | 27000 | 64.0 | 55.6 | 17 | 235 | #3 | — |
| 11424 | 27001 | 66.2 (80) | — | 12 | 150 | #4 | — |
| 11425 | 27002 | 50.0 | 50.0 (154) | 14 | 150 | #1 | 58339 |
| 11426 | 27003 | 64.0 | 50.0 (176) | 15 | 150 | #3 | 58340 |
| 11427 | 27004 | 69.6 | 61.8 | 20 | 394 | #4 | 58341 |
| 11428 | 27005 | 50.0 | 50.0 (149) | 14 | 150 | #1 | 58342 |
| 11429 | 27006 | 65.6 | 56.6 (228) | 18 | 181 | #4 | 58343 |
| 11430 | 27007 | 84.8 | 74.5 | 20 | 815 | #7 | 58344 |
| 11431 | 27008 | 67.2 | 64.6 (130) | 17 | 260 | #4 | 58345 |
|  | 27009 | 67.2 | 56.7 | 17 | 217 | #4 | 58346 |
| 11432 | 27010 | 83.5 (109) | — | 40 | 351 | #7 | 58347 |
| 11433 | 27011 | 72.8 | 68.7 | 19 | 1084 | #5 | 58348 |
| 11434 | 27012 | 68.8 | 59.3 (270) | 22 | 261 | #4 | 58349 |
| 11435 | 27013 | 64.0 | 60.9 (151) | 17 | 275 | #3 | — |
| 11436 | 27014 | 50.0 (90) | — | 12 | 150 | #1 | 58350 |
| 11437 | 27015 | 65.0 (100) | — | 12 | 155 | #3 | 58351 |
|  | 27016 | 67.2 | 62.8 (188) | 27 | 222 | #4 | 58352 |
| 11438 | 27017 | 70.4 | 59.6 | 15 | 419 | #5 | 58353 |
| 11439 | 27018 | 69.6 | 64.4 | 21 | 457 | #4 | 58354 |
| 11440 | 27019 | 74.4 | 65.1 (235) | 23 | 330 | #5 | 58355 |
| 11441 | 27020 | 50.0 | 50.0 | 29 | 150 | #1 | 58356 |
|  | 27021 | 50.0 | 50.0 | 12 | 150 | #1 | 58357 |
| 11442 | 27022 | 50.0 (60) | — | 12 | 150 | #1 | — |
|  | 27023 | 64.0 | 50.0 (229) | 15 | 170 | #3 | 58358 |
|  | 27024 | 65.6 | 62.8 (156) | 22 | 175 | #4 | 58359 |
| 11443 | 27025 | 50.0 | 50.0 (184) | 14 | 150 | #1 | 58360 |
| 11444 | 27026 | 66.7 (78) | — | 12 | 158 | #4 | 58361 |
| 11445 | 27027 | 72.0 | 63.6 | 28 | 336 | #5 | 58362 |
| 11446 | 27028 | 51.6 (62) | — | 12 | 150 | #1 | — |
| 11447 | 27029 | 66.4 | 50.0 | 16 | 183 | #4 | 58363 |
|  | 27030 | 50.0 (54) | — | 12 | 150 | #1 | — |
| 11448 | 27031 | 68.0 | 62.0 (213) | 23 | 247 | #4 | 58364 |
| 11449 | 27032 | 64.8 | 60.3 (194) | 22 | 178 | #3 | 58365 |
| 11450 | 27033 | 50.0 (52) | — | 12 | 150 | #1 | — |
| 11451 | 27034 | 80.8 | 59.9 (267) | 26 | 473 | #7 | 58366 |
| 11452 | 27035 | 68.0 | 61.5 | 19 | 278 | #4 | 58367 |
| 11453 | 27036 | 50.0 (65) | — | 12 | 150 | #1 | 58368 |
| 11454 | 27037 | 50.0 (122) | — | 13 | 150 | #1 | 58369 |
|  | 27038 | 75.2 (117) | — | 25 | 384 | #6 | 58370 |
| 11455 | 27039 | 63.2 | 50.0 | 15 | 179 | #3 | 58371 |
| 11456 | 27040 | 72.0 | 66.3 (196) | 24 | 325 | #5 | — |
| 11457 | 27041 | 70.4 | 67.1 (143) | 20 | 229 | #5 | 58372 |
| 11458 | 27042 | 70.4 | 63.3 | 19 | 320 | #5 | 58373 |
| 11459 | 27043 | 67.2 | 58.2 | 20 | 206 | #4 | 58374 |
| 11460 | 27044 | 68.0 | 50.0 | 14 | 200 | #4 | 58375 |
| 11461 | 27045 | 72.6 (73) | — | 19 | 195 | #5 | 58376 |
| 11462 | 27046 | 50.0 | 50.0 | 12 | 150 | #1 | 58377 |
| 11463 | 27047 | 66.4 | 58.0 (269) | 18 | 253 | #4 | 58378 |
| 11464 | 27048 | 63.2 | 50.0 | 13 | 164 | #3 | 58379 |
|  | 27049 | 50.0 (99) | — | 12 | 150 | #1 | 58380 |
| 11465 | 27050 | 73.6 | 65.7 (245) | 14 | 448 | #5 | 58381 |
|  | 27051 | 50.0 (81) | — | 12 | 150 | #1 | 58382 |
| 11466 | 27052 | 84.0 | 82.5 | 25 | 1232 | #7 | 58383 |
|  | 27053 | 87.2 | 83.6 | 33 | 5111 | #8 | 58384 |
|  | 27054 | 77.3 (75) | — | 18 | 234 | #6 | 58385 |
| 11467 | 27055 | 64.8 | 59.3 (199) | 17 | 166 | #3 | 58386 |
| 11468 | 27056 | 72.8 | 62.9 | 29 | 429 | #5 | 58387 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11469 | 27057 | 66.4 | 61.1 | 15 | 359 | #4 | 58388 |
|  | 27058 | 71.2 | 60.7 | 19 | 304 | #5 | 58389 |
| 11470 | 27059 | 66.4 | 50.0 | 19 | 192 | #4 | 58390 |
| 11471 | 27060 | 68.8 | 59.6 | 18 | 293 | #4 | 58391 |
| 11472 | 27061 | 72.0 | 65.8 | 18 | 523 | #5 | 58392 |
| 11473 | 27062 | 64.8 | 60.9 (174) | 19 | 202 | #3 | — |
|  | 27063 | 64.8 | 62.1 (153) | 16 | 194 | #3 | 58393 |
| 11474 | 27064 | 58.4 | 52.1 (140) | 15 | 173 | #2 | 58394 |
| 11475 | 27065 | 70.4 | 63.6 | 26 | 559 | #5 | 58395 |
| 11476 | 27066 | 50.0 (87) | — | 12 | 150 | #1 | 58396 |
| 11477 | 27067 | 61.6 | 60.2 (161) | 17 | 190 | #3 | 58397 |
| 11478 | 27068 | 69.6 | 62.9 | 26 | 353 | #4 | 58398 |
| 11479 | 27069 | 84.3 (51) | — | 22 | 199 | #7 | — |
| 11480 | 27070 | 66.4 | 59.6 | 17 | 223 | #4 | 58399 |
| 11481 | 27071 | 76.0 | 66.9 | 25 | 658 | #6 | — |
| 11482 | 27072 | 63.2 | 60.0 (185) | 16 | 240 | #3 | 58400 |
| 11483 | 27073 | 82.4 | 71.9 (196) | 14 | 565 | #7 | 58401 |
| 11484 | 27074 | 75.6 (86) | — | 16 | 255 | #6 | 58402 |
| 11485 | 27075 | 63.2 | 50.0 (176) | 16 | 151 | #3 | 58403 |
| 11486 | 27076 | 66.4 | 54.4 (228) | 19 | 218 | #4 | 58404 |
| 11487 | 27077 | 50.0 | 50.0 (204) | 13 | 160 | #1 | 58405 |
| 11488 | 27078 | 50.0 (124) | — | 12 | 150 | #1 | 58406 |
| 11489 | 27079 | 71.2 | 62.9 | 14 | 443 | #5 | 58407 |
| 11490 | 27080 | 50.0 | 50.0 | 12 | 150 | #1 | 58408 |
| 11491 | 27081 | 50.0 (60) | — | 12 | 150 | #1 | — |
|  | 27082 | 50.0 (84) | — | 12 | 150 | #1 | 58409 |
| 11492 | 27083 | 70.4 | 54.4 (241) | 24 | 239 | #5 | 58410 |
| 11493 | 27084 | 50.0 (70) | — | 12 | 150 | #1 | 58411 |
| 11494 | 27085 | 57.5 (120) | — | 30 | 299 | #2 | 58412 |
|  | 27086 | 62.1 (87) | — | 18 | 228 | #3 | 58413 |
| 11495 | 27087 | 66.4 | 58.9 | 19 | 253 | #4 | 58414 |
| 11496 | 27088 | 66.4 | 59.3 | 17 | 219 | #4 | 58415 |
| 11497 | 27089 | 63.3 (109) | — | 12 | 150 | #3 | 58416 |
| 11498 | 27090 | 50.0 (62) | — | 12 | 150 | #1 | — |
|  | 27091 | 50.0 (68) | — | 12 | 150 | #1 | 58417 |
| 11499 | 27092 | 68.0 | 62.2 | 21 | 285 | #4 | 58418 |
| 11500 | 27093 | 50.0 | 50.0 | 12 | 150 | #1 | 58419 |
| 11501 | 27094 | 58.4 | 50.0 (150) | 12 | 151 | #2 | 58420 |
| 11502 | 27095 | 50.0 (64) | — | 12 | 150 | #1 | 58421 |
| 11503 | 27096 | 78.7 (61) | — | 40 | 236 | #6 | — |
| 11504 | 27097 | 71.2 | 67.3 (211) | 16 | 406 | #5 | 58422 |
|  | 27098 | 50.0 | 50.0 | 12 | 150 | #1 | 58423 |
| 11505 | 27099 | 50.0 (74) | — | 12 | 150 | #1 | 58424 |
| 11506 | 27100 | 50.0 (98) | — | 20 | 150 | #1 | 58425 |
| 11507 | 27101 | 57.6 | 50.0 (144) | 15 | 152 | #2 | 58426 |
| 11508 | 27102 | 65.6 | 51.9 (216) | 12 | 188 | #4 | 58427 |
| 11509 | 27103 | 88.8 | 78.5 | 33 | 791 | #8 | 58428 |
| 11510 | 27104 | 50.0 | 50.0 | 12 | 150 | #1 | 58429 |
| 11511 | 27105 | 67.2 | 61.8 | 18 | 380 | #4 | 58430 |
| 11512 | 27106 | 84.0 | 65.3 (271) | 21 | 469 | #7 | 58431 |
|  | 27107 | 75.2 | 71.3 (143) | 18 | 300 | #6 | 58432 |
| 11513 | 27108 | 66.4 | 62.9 (159) | 19 | 207 | #4 | 58433 |
| 11514 | 27109 | 73.6 | 65.1 | 32 | 504 | #5 | 58434 |
| 11515 | 27110 | 64.8 | 58.8 (228) | 16 | 196 | #3 | 58435 |
| 11516 | 27111 | 50.0 | 50.0 | 12 | 150 | #1 | 58436 |
| 11517 | 27112 | 58.4 | 50.0 | 21 | 169 | #2 | 58437 |
| 11518 | 27113 | 50.0 (112) | — | 12 | 150 | #1 | 58438 |
| 11519 | 27114 | 50.0 | 50.0 (145) | 12 | 150 | #1 | 58439 |
| 11520 | 27115 | 68.6 (121) | — | 20 | 225 | #4 | 58440 |
| 11521 | 27116 | 50.0 | 50.0 | 12 | 150 | #1 | 58441 |
| 11522 | 27117 | 50.0 (61) | — | 12 | 150 | #1 | — |
| 11523 | 27118 | 50.0 (82) | — | 12 | 150 | #1 | 58442 |
| 11524 | 27119 | 62.4 | 50.0 (175) | 12 | 161 | #3 | 58443 |
| 11525 | 27120 | 50.0 (99) | — | 12 | 150 | #1 | 58444 |
| 11526 | 27121 | 66.4 | 59.6 | 19 | 215 | #4 | 58445 |
|  | 27122 | 50.0 (75) | — | 12 | 150 | #1 | 58446 |
| 11527 | 27123 | 50.0 | 50.0 (140) | 12 | 150 | #1 | 58447 |
| 11528 | 27124 | 73.6 | 69.1 | 16 | 782 | #5 | 58448 |
| 11529 | 27125 | 72.0 | 65.8 | 18 | 432 | #5 | 58449 |
| 11530 | 27126 | 65.6 | 58.2 (268) | 18 | 201 | #4 | 58450 |
| 11531 | 27127 | 64.0 | 63.6 (129) | 18 | 170 | #3 | 58451 |
|  | 27128 | 50.0 (69) | — | 12 | 150 | #1 | 58452 |
| 11532 | 27129 | 67.2 | 59.3 | 15 | 252 | #4 | 58453 |
| 11533 | 27130 | 50.0 (79) | — | 13 | 150 | #1 | — |
| 11534 | 27131 | 76.8 | 68.4 | 36 | 716 | #6 | 58454 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11535 | 27132 | 50.0 | 50.0 (134) | 12 | 150 | #1 | 58455 |
| 11536 | 27133 | 59.0 (78) | — | 14 | 150 | #2 | 58456 |
| 11537 | 27134 | 52.4 (103) | — | 13 | 150 | #1 | 58457 |
| 11538 | 27135 | 67.2 | 59.6 | 16 | 325 | #4 | 58458 |
| 11539 | 27136 | 74.4 | 69.8 | 15 | 591 | #5 | 58459 |
| 11540 | 27137 | 61.6 | 50.0 | 20 | 175 | #3 | 58460 |
| 11541 | 27138 | 65.6 | 60.4 (169) | 15 | 177 | #4 | 58461 |
| 11542 | 27139 | 50.0 | 50.0 (166) | 12 | 150 | #1 | 58462 |
| 11543 | 27140 | 66.4 | 61.5 | 18 | 398 | #4 | 58463 |
| 11544 | 27141 | 83.2 | 66.9 | 23 | 465 | #7 | 58464 |
|  | 27142 | 66.9 (121) | — | 23 | 204 | #4 | 58465 |
| 11545 | 27143 | 68.8 | 61.4 (171) | 21 | 249 | #4 | 58466 |
| 11546 | 27144 | 61.6 | 50.0 | 15 | 166 | #3 | 58467 |
| 11547 | 27145 | 70.4 | 63.2 (193) | 37 | 311 | #5 | 58468 |
| 11548 | 27146 | 72.8 | 65.1 | 28 | 617 | #5 | 58469 |
|  | 27147 | 69.6 | 64.4 (194) | 21 | 257 | #4 | 58470 |
| 11549 | 27148 | 50.0 (76) | — | 12 | 150 | #1 | 58471 |
| 11550 | 27149 | 93.7 (79) | — | 24 | 350 | #9 | 58472 |
| 11551 | 27150 | 60.0 | 57.7 (196) | 17 | 171 | #2 | 58473 |
| 11552 | 27151 | 50.0 (51) | — | 12 | 150 | #1 | — |
| 11553 | 27152 | 80.8 (73) | — | 30 | 219 | #7 | 58474 |
| 11554 | 27153 | 50.0 (84) | — | 12 | 150 | #1 | 58475 |
| 11555 | 27154 | 65.6 | 52.8 (265) | 17 | 204 | #4 | 58476 |
| 11556 | 27155 | 63.2 | 50.0 (221) | 17 | 171 | #3 | 58477 |
| 11557 | 27156 | 50.0 (58) | — | 12 | 150 | #1 | — |
|  | 27157 | 64.0 | 50.0 | 21 | 174 | #3 | 58478 |
| 11558 | 27158 | 67.2 | 60.7 | 21 | 280 | #4 | 58479 |
| 11559 | 27159 | 60.8 | 58.6 (157) | 12 | 170 | #3 | 58480 |
| 11560 | 27160 | 63.2 | 58.6 (220) | 17 | 221 | #3 | 58481 |
| 11561 | 27161 | 69.6 | 63.3 | 19 | 345 | #4 | 58482 |
| 11562 | 27162 | 66.4 | 59.3 | 16 | 224 | #4 | 58483 |
| 11563 | 27163 | 50.0 (55) | — | 12 | 150 | #1 | — |
| 11564 | 27164 | 67.6 (111) | — | 18 | 167 | #4 | 58484 |
| 11565 | 27165 | 60.0 (105) | — | 13 | 150 | #2 | 58485 |
| 11566 | 27166 | 67.0 (100) | — | 31 | 165 | #4 | 58486 |
| 11567 | 27167 | 50.0 (54) | — | 12 | 150 | #1 | — |
| 11568 | 27168 | 63.2 | 50.0 | 13 | 193 | #3 | 58487 |
| 11569 | 27169 | 50.0 (123) | — | 12 | 150 | #1 | 58488 |
|  | 27170 | 50.0 | 50.0 | 12 | 150 | #1 | 58489 |
| 11570 | 27171 | 63.0 (100) | — | 13 | 155 | #3 | 58490 |
| 11571 | 27172 | 72.2 (72) | — | 18 | 158 | #5 | 58491 |
| 11572 | 27173 | 50.0 (109) | — | 12 | 150 | #1 | 58492 |
|  | 27174 | 68.0 (75) | — | 15 | 151 | #4 | 58493 |
| 11573 | 27175 | 50.0 (99) | — | 12 | 150 | #1 | 58494 |
| 11574 | 27176 | 58.4 | 50.0 (268) | 15 | 150 | #2 | 58495 |
| 11575 | 27177 | 68.8 | 64.0 | 13 | 426 | #4 | 58496 |
| 11576 | 27178 | 68.0 | 56.7 | 20 | 227 | #4 | 58497 |
| 11577 | 27179 | 64.0 | 50.0 | 16 | 167 | #3 | 58498 |
|  | 27180 | 66.4 | 51.3 | 14 | 305 | #4 | 58499 |
| 11578 | 27181 | 67.2 | 62.2 | 15 | 417 | #4 | 58500 |
| 11579 | 27182 | 69.6 | 59.6 (235) | 24 | 272 | #4 | 58501 |
| 11580 | 27183 | 50.0 | 50.0 | 12 | 150 | #1 | 58502 |
|  | 27184 | 50.0 | 50.0 (220) | 12 | 150 | #1 | 58503 |
| 11581 | 27185 | 69.6 | 60.0 | 23 | 270 | #4 | 58504 |
| 11582 | 27186 | 71.4 (105) | — | 20 | 193 | #5 | 58505 |
| 11583 | 27187 | 72.8 | 67.4 (144) | 13 | 319 | #5 | 58506 |
| 11584 | 27188 | 63.2 | 50.9 | 14 | 182 | #3 | 58507 |
| 11585 | 27189 | 63.2 | 55.8 (240) | 20 | 178 | #3 | 58508 |
| 11586 | 27190 | 66.4 | 54.2 | 16 | 217 | #4 | 58509 |
| 11587 | 27191 | 82.4 | 76.7 | 24 | 991 | #7 | 58510 |
| 11588 | 27192 | 70.4 | 61.1 | 20 | 319 | #5 | 58511 |
| 11589 | 27193 | 66.4 | 50.0 | 15 | 210 | #4 | 58512 |
| 11590 | 27194 | 62.4 | 50.0 (241) | 15 | 163 | #3 | 58513 |
|  | 27195 | 68.0 | 61.1 | 23 | 249 | #4 | 58514 |
| 11591 | 27196 | 64.8 | 50.0 (233) | 19 | 160 | #3 | 58515 |
| 11592 | 27197 | 80.8 | 78.2 | 30 | 1860 | #7 | 58516 |
| 11593 | 27198 | 69.6 | 56.0 | 17 | 251 | #4 | 58517 |
| 11594 | 27199 | 50.0 | 50.0 | 12 | 150 | #1 | 58518 |
| 11595 | 27200 | 68.8 | 63.0 (138) | 18 | 186 | #4 | 58519 |
| 11596 | 27201 | 71.1 (76) | — | 12 | 152 | #5 | 58520 |
| 11597 | 27202 | 66.4 | 63.6 (165) | 15 | 179 | #4 | 58521 |
| 11598 | 27203 | 50.0 | 50.0 (177) | 12 | 150 | #1 | 58522 |
| 11599 | 27204 | 65.6 | 64.4 (146) | 25 | 302 | #4 | 58523 |
| 11600 | 27205 | 76.5 (51) | — | 17 | 155 | #6 | — |
| 11601 | 27206 | 68.8 | 50.0 | 18 | 350 | #4 | 58524 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
| --- | --- | --- | --- | --- | --- | --- | --- |
| 11602 | 27207 | 61.6 | 54.5 (233) | 15 | 155 | #3 | — |
| 11603 | 27208 | 50.0 (53) | — | 12 | 150 | #1 | — |
| 11604 | 27209 | 50.0 | 50.0 | 12 | 150 | #1 | 58525 |
|  | 27210 | 69.6 | 62.9 | 19 | 286 | #4 | 58526 |
|  | 27111 | 64.4 (73) | — | 21 | 157 | #3 | 58527 |
| 11605 | 27112 | 50.0 (75) | — | 12 | 150 | #1 | 58528 |
| 11606 | 27113 | 50.0 (93) | — | 12 | 151 | #1 | 58529 |
| 11607 | 27114 | 50.0 (94) | — | 12 | 150 | #1 | 58530 |
| 11608 | 27115 | 69.6 | 63.2 (242) | 22 | 269 | #4 | — |
| 11609 | 27116 | 62.1 (103) | — | 22 | 292 | #3 | 58531 |
|  | 27117 | 87.2 | 81.5 | 22 | 838 | #8 | 58532 |
| 11610 | 27118 | 53.9 (89) | — | 14 | 150 | #1 | 58533 |
| 11611 | 27119 | 68.8 | 61.8 | 18 | 354 | #4 | 58534 |
| 11612 | 27220 | 63.2 | 50.0 (203) | 15 | 161 | #3 | 58535 |
| 11613 | 27221 | 73.6 | 57.1 | 14 | 461 | #5 | 58536 |
| 11614 | 27222 | 66.4 | 55.6 | 14 | 203 | #4 | 58537 |
| 11615 | 27223 | 50.0 (57) | — | 12 | 150 | #1 | — |
| 11616 | 27224 | 62.4 | 56.7 (254) | 21 | 185 | #3 | 58538 |
|  | 27225 | 64.8 | 57.1 | 13 | 216 | #3 | 58539 |
| 11617 | 27226 | 50.0 (87) | — | 12 | 150 | #1 | 58540 |
|  | 27227 | 50.0 (106) | — | 12 | 150 | #1 | 58541 |
|  | 27228 | 63.2 | 50.0 | 14 | 178 | #3 | 58542 |
| 11618 | 27229 | 66.4 | 61.1 | 17 | 265 | #4 | 58543 |
| 11619 | 27230 | 65.6 | 58.2 (232) | 19 | 186 | #4 | 58544 |
|  | 27231 | 63.2 | 63.4 (131) | 15 | 153 | #3 | 58545 |
|  | 27232 | 72.0 | 63.2 (190) | 24 | 317 | #5 | 58546 |
| 11620 | 27233 | 73.6 | 63.1 (268) | 33 | 369 | #5 | 58547 |
| 11621 | 27234 | 60.0 | 50.0 | 12 | 166 | #2 | 58548 |
| 11622 | 27235 | 50.0 | 50.0 (160) | 12 | 150 | #1 | 58549 |
| 11623 | 27236 | 73.6 | 61.5 (213) | 18 | 354 | #5 | 58550 |
| 11624 | 27237 | 50.0 (106) | — | 12 | 150 | #1 | 58551 |
| 11625 | 27238 | 63.2 | 50.0 | 18 | 216 | #3 | 58552 |
| 11626 | 27239 | 67.2 | 50.0 (212) | 15 | 260 | #4 | 58553 |
| 11627 | 27240 | 54.8 (84) | — | 24 | 218 | #1 | 58554 |
| 11628 | 27241 | 66.4 | 59.6 | 14 | 222 | #4 | 58555 |
| 11629 | 27242 | 66.3 (92) | — | 17 | 163 | #4 | 58556 |
| 11630 | 27243 | 50.0 (68) | — | 12 | 150 | #1 | — |
| 11631 | 27244 | 76.8 | 66.5 | 23 | 442 | #6 | 58557 |
| 11632 | 27245 | 62.4 | 50.0 | 13 | 171 | #3 | 58558 |
| 11633 | 27246 | 50.0 | 50.0 (129) | 12 | 150 | #1 | 58559 |
| 11634 | 27247 | 71.2 | 61.8 | 28 | 385 | #5 | 58560 |
| 11635 | 27248 | 65.6 | 64.1 (131) | 20 | 188 | #4 | 58561 |
|  | 27249 | 65.6 | 62.2 (147) | 20 | 193 | #4 | 58562 |
| 11636 | 27250 | 73.5 (98) | — | 15 | 256 | #5 | 58563 |
| 11637 | 27251 | 69.6 | 62.6 (222) | 22 | 257 | #4 | 58564 |
| 11638 | 27252 | 67.2 | 63.0 (162) | 25 | 198 | #4 | 58565 |
| 11639 | 27253 | 73.6 | 68.7 (227) | 15 | 477 | #5 | 58566 |
| 11640 | 27254 | 55.0 (120) | — | 14 | 162 | #2 | 58567 |
| 11641 | 27255 | 64.0 | 54.0 (248) | 15 | 159 | #3 | 58568 |
| 11642 | 27256 | 70.4 | 68.0 | 18 | 695 | #5 | 58569 |
| 11643 | 27257 | 70.0 (90) | — | 17 | 199 | #4 | 58570 |
| 11644 | 27258 | 64.0 | 50.0 | 13 | 192 | #3 | 58571 |
| 11645 | 27259 | 50.0 (104) | — | 12 | 150 | #1 | 58572 |
| 11646 | 27260 | 70.4 | 62.2 (196) | 23 | 265 | #5 | 58573 |
| 11647 | 27261 | 50.0 | 50.0 | 12 | 150 | #1 | 58574 |
| 11648 | 27262 | 80.0 | 77.8 | 16 | 1165 | #6 | 58575 |
| 11649 | 27263 | 50.0 | 50.0 | 12 | 150 | #1 | 58576 |
| 11650 | 27264 | 67.2 | 61.8 | 25 | 264 | #4 | 58577 |
| 11651 | 27265 | 61.6 | 55.0 (171) | 17 | 161 | #3 | 58578 |
|  | 27266 | 50.0 (71) | — | 12 | 150 | #1 | 58579 |
| 11652 | 27267 | 67.2 | 58.9 (263) | 19 | 219 | #4 | 58580 |
| 11653 | 27268 | 71.2 | 66.9 (178) | 19 | 371 | #5 | 58581 |
| 11654 | 27269 | 73.6 | 62.5 | 22 | 359 | #5 | 58582 |
| 11655 | 27270 | 61.6 | 52.0 | 15 | 189 | #3 | — |
| 11656 | 27271 | 67.2 | 58.2 | 14 | 205 | #4 | 58583 |
| 11657 | 27272 | 50.0 (97) | — | 12 | 150 | #1 | 58584 |
| 11658 | 27273 | 50.0 | 50.0 (144) | 16 | 150 | #1 | 58585 |
| 11659 | 27274 | 67.2 | 63.3 | 14 | 513 | #4 | 58586 |
|  | 27275 | 66.4 | 61.1 | 20 | 258 | #4 | 58587 |
| 11660 | 27276 | 50.0 (88) | — | 12 | 150 | #1 | 58588 |
| 11661 | 27277 | 60.8 | 50.0 (164) | 18 | 151 | #3 | 58589 |
| 11662 | 27278 | 65.6 | 50.0 | 12 | 160 | #4 | 58590 |
| 11663 | 27279 | 96.2 (78) | — | 34 | 363 | #10 | 58591 |
| 11664 | 27280 | 60.8 | 54.8 (166) | 15 | 151 | #3 | 58592 |
| 11665 | 27281 | 64.8 | 64.4 (146) | 17 | 177 | #3 | 58593 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11666 | 27282 | 68.8 | 62.2 | 18 | 307 | #4 | — |
| 11667 | 27283 | 72.0 | 65.5 | 16 | 542 | #5 | 58594 |
| 11668 | 27284 | 72.0 | 68.3 (189) | 20 | 332 | #5 | 58595 |
| 11669 | 27285 | 76.8 | 72.0 | 16 | 821 | #6 | 58596 |
| 11670 | 27286 | 68.8 | 62.2 | 14 | 383 | #4 | 58597 |
| 11671 | 27287 | 64.0 | 57.5 | 17 | 196 | #3 | 58598 |
| 11672 | 27288 | 50.0 (51) | — | 12 | 150 | #1 | — |
|  | 27289 | 64.0 | 58.0 (176) | 17 | 180 | #3 | 58599 |
| 11673 | 27290 | 57.6 | 50.0 (154) | 15 | 152 | #2 | — |
| 11674 | 27291 | 64.8 | 57.7 (220) | 19 | 197 | #3 | 58600 |
| 11675 | 27292 | 50.0 | 50.0 | 12 | 150 | #1 | 58601 |
| 11676 | 27293 | 67.2 | 56.5 (207) | 19 | 198 | #4 | 58602 |
| 11677 | 27294 | 80.0 | 61.5 | 23 | 421 | #6 | 58603 |
|  | 27295 | 63.2 | 51.1 (190) | 16 | 163 | #3 | 58604 |
| 11678 | 27296 | 68.8 | 60.7 | 20 | 243 | #4 | 58605 |
| 11679 | 27297 | 64.0 | 50.0 | 12 | 224 | #3 | 58606 |
| 11680 | 27298 | 82.0 (61) | — | 30 | 193 | #7 | — |
|  | 27299 | 72.0 | 65.8 | 27 | 804 | #5 | 58607 |
| 11681 | 27300 | 71.2 | 61.8 | 29 | 302 | #5 | 58608 |
| 11682 | 27301 | 71.2 | 50.9 | 15 | 355 | #5 | 58609 |
| 11683 | 27302 | 67.2 | 58.9 | 20 | 233 | #4 | 58610 |
| 11684 | 27303 | 70.4 | 60.7 | 23 | 299 | #5 | 58611 |
| 11685 | 27304 | 64.0 | 59.3 | 15 | 207 | #3 | 58612 |
| 11686 | 27305 | 64.0 | 59.6 (208) | 15 | 178 | #3 | 58613 |
| 11687 | 27306 | 83.2 | 71.9 (146) | 25 | 429 | #7 | — |
| 11688 | 27307 | 65.6 | 58.7 (201) | 18 | 195 | #4 | 58614 |
| 11689 | 27308 | 50.0 (108) | — | 12 | 150 | #1 | 58615 |
| 11690 | 27309 | 67.2 | 50.0 | 12 | 247 | #4 | 58616 |
| 11691 | 27310 | 68.8 | 61.8 | 21 | 334 | #4 | — |
| 11692 | 27311 | 50.0 | 50.0 | 12 | 150 | #1 | 58617 |
| 11693 | 27312 | 50.0 (69) | — | 12 | 150 | #1 | 58618 |
| 11694 | 27313 | 50.0 (67) | — | 12 | 150 | #1 | 58619 |
| 11695 | 27314 | 70.4 | 50.0 | 18 | 296 | #5 | 58620 |
| 11696 | 27315 | 68.8 | 50.0 | 15 | 205 | #4 | 58621 |
| 11697 | 27316 | 50.0 (67) | — | 12 | 150 | #1 | 58622 |
| 11698 | 27317 | 65.6 | 59.1 (274) | 20 | 190 | #4 | 58623 |
| 11699 | 27318 | 71.4 (77) | — | 20 | 158 | #5 | 58624 |
| 11700 | 27319 | 50.0 | 50.0 (223) | 33 | 263 | #1 | 58625 |
| 11701 | 27320 | 80.0 | 68.4 | 25 | 666 | #6 | 58626 |
| 11702 | 27321 | 64.0 | 62.2 (156) | 17 | 182 | #3 | 58627 |
| 11703 | 27322 | 63.2 | 55.6 (180) | 15 | 152 | #3 | 58628 |
|  | 27323 | 60.8 | 50.0 (183) | 14 | 150 | #3 | 58629 |
| 11704 | 27324 | 67.2 | 62.5 | 19 | 304 | #4 | 58630 |
| 11705 | 27325 | 63.9 (108) | — | 16 | 169 | #3 | 58631 |
|  | 27326 | 68.8 | 60.4 | 20 | 280 | #4 | 58632 |
| 11706 | 27327 | 73.7 (76) | — | 19 | 159 | #5 | 58633 |
| 11707 | 27328 | 67.4 (92) | — | 15 | 150 | #4 | 58634 |
| 11708 | 27329 | 50.0 (67) | — | 12 | 150 | #1 | 58635 |
| 11709 | 27330 | 74.4 | 66.5 | 15 | 514 | #5 | 58636 |
|  | 27331 | 68.8 | 61.8 | 19 | 295 | #4 | 58637 |
| 11710 | 27332 | 65.6 | 53.8 | 15 | 204 | #4 | 58638 |
| 11711 | 27333 | 72.9 (70) | — | 13 | 153 | #5 | 58639 |
| 11712 | 27334 | 63.2 | 50.0 (216) | 17 | 175 | #3 | 58640 |
| 11713 | 27335 | 65.6 | 57.1 | 15 | 225 | #4 | 58641 |
| 11714 | 27336 | 71.2 | 62.5 | 30 | 415 | #5 | 58642 |
| 11715 | 27337 | 71.2 | 61.8 | 19 | 316 | #5 | 58643 |
|  | 27338 | 72.0 | 65.1 (249) | 28 | 317 | #5 | 58644 |
| 11716 | 27339 | 68.6 (102) | — | 16 | 167 | #4 | 58645 |
|  | 27340 | 69.6 | 61.5 | 25 | 410 | #4 | 58646 |
| 11717 | 27341 | 66.4 | 56.8 (222) | 20 | 222 | #4 | 58647 |
| 11718 | 27342 | 60.8 | 50.0 (166) | 15 | 162 | #3 | 58648 |
| 11719 | 27343 | 69.4 (124) | — | 17 | 282 | #4 | 58649 |
| 11720 | 27344 | 68.8 | 60.7 | 19 | 278 | #4 | 58650 |
| 11721 | 27345 | 71.2 | 63.4 (235) | 33 | 289 | #5 | 58651 |
|  | 27346 | 50.0 (53) | — | 12 | 150 | #1 | — |
| 11722 | 27347 | 76.8 | 65.0 (203) | 24 | 347 | #6 | 58652 |
| 11723 | 27348 | 66.1 (109) | — | 22 | 259 | #4 | 58653 |
| 11724 | 27349 | 50.0 (83) | — | 12 | 150 | #1 | 58654 |
| 11725 | 27350 | 65.6 | 61.2 (178) | 19 | 197 | #4 | 58655 |
| 11726 | 27351 | 68.0 | 58.5 | 28 | 215 | #4 | 58656 |
| 11727 | 27352 | 65.6 | 61.4 (158) | 19 | 179 | #4 | 58657 |
| 11728 | 27353 | 70.4 | 63.6 | 22 | 342 | #5 | — |
| 11729 | 27354 | 62.4 | 61.5 (130) | 15 | 166 | #3 | 58658 |
| 11730 | 27355 | 50.0 (54) | — | 12 | 150 | #1 | — |
| 11731 | 27356 | 70.3 (91) | — | 23 | 175 | #5 | 58659 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11732 | 27357 | 50.0 (63) | — | 12 | 150 | #1 | — |
| 11733 | 27358 | 71.2 | 61.5 | 25 | 279 | #5 | — |
| 11734 | 27359 | 64.8 | 50.0 | 12 | 166 | #3 | 58660 |
| 11735 | 27360 | 65.6 | 59.3 | 17 | 240 | #4 | 58661 |
| 11736 | 27361 | 64.0 | 50.0 (237) | 14 | 185 | #3 | 58662 |
| 11737 | 27362 | 60.0 | 50.0 | 13 | 180 | #2 | 58663 |
| 11738 | 27363 | 62.4 | 50.0 | 15 | 165 | #3 | 58664 |
| 11739 | 27364 | 61.6 | 50.0 | 14 | 161 | #3 | 58665 |
| 11740 | 27365 | 50.0 | 50.0 | 12 | 150 | #1 | 58666 |
| 11741 | 27366 | 50.0 | 50.0 | 12 | 150 | #1 | 58667 |
| 11742 | 27367 | 50.0 | 50.0 | 12 | 150 | #1 | 58668 |
|  | 27368 | 64.8 | 52.5 (236) | 13 | 182 | #3 | 58669 |
| 11743 | 27369 | 68.8 | 59.3 | 23 | 290 | #4 | 58670 |
| 11744 | 27370 | 67.2 | 63.0 (192) | 20 | 195 | #4 | 58671 |
|  | 27371 | 64.8 | 62.5 (176) | 18 | 180 | #3 | 58672 |
| 11745 | 27372 | 50.0 (69) | — | 12 | 150 | #1 | 58673 |
| 11746 | 27373 | 66.4 | 50.0 | 16 | 193 | #4 | 58674 |
| 11747 | 27374 | 65.6 | 57.1 | 14 | 181 | #4 | 58675 |
| 11748 | 27375 | 68.8 | 59.3 | 22 | 278 | #4 | 58676 |
| 11749 | 27376 | 64.0 | 57.3 (211) | 15 | 182 | #3 | 58677 |
| 11750 | 27377 | 67.2 | 58.7 (271) | 21 | 228 | #4 | 58678 |
|  | 27378 | 67.3 (113) | — | 17 | 169 | #4 | 58679 |
| 11751 | 27379 | 61.2 (121) | — | 20 | 178 | #3 | 58680 |
| 11752 | 27380 | 72.0 | 60.4 | 24 | 295 | #5 | 58681 |
| 11753 | 27381 | 67.2 | 61.5 | 15 | 399 | #4 | 58682 |
| 11754 | 27382 | 69.6 | 61.8 | 33 | 453 | #4 | 58683 |
| 11755 | 27383 | 68.8 | 62.9 | 21 | 326 | #4 | 58684 |
| 11756 | 27384 | 50.0 (56) | — | 12 | 150 | #1 | 58685 |
| 11757 | 27385 | 69.6 | 63.4 (216) | 23 | 255 | #4 | 58686 |
|  | 27386 | 68.8 | 60.7 | 21 | 295 | #4 | 58687 |
| 11758 | 27387 | 64.8 | 56.6 (152) | 15 | 160 | #3 | — |
| 11759 | 27388 | 60.7 (117) | — | 15 | 152 | #3 | 58688 |
| 11760 | 27389 | 63.2 | 60.6 (175) | 13 | 181 | #3 | 58689 |
|  | 27390 | 50.0 (78) | — | 12 | 150 | #1 | 58690 |
| 11761 | 27391 | 50.0 (96) | — | 12 | 150 | #1 | 58691 |
|  | 27392 | 50.0 (87) | — | 12 | 150 | #1 | 58692 |
| 11762 | 27393 | 64.8 | 50.0 | 18 | 194 | #3 | 58693 |
| 11763 | 27394 | 61.1 (95) | — | 13 | 150 | #3 | 58694 |
|  | 27395 | 76.0 | 66.2 | 18 | 479 | #6 | 58695 |
| 11764 | 27396 | 50.0 (112) | — | 15 | 155 | #1 | 58696 |
| 11765 | 27397 | 67.2 | 60.4 | 18 | 282 | #4 | 58697 |
|  | 27398 | 50.0 (55) | — | 12 | 150 | #1 | — |
| 11766 | 27399 | 64.0 | 56.7 | 16 | 235 | #3 | 58698 |
| 11767 | 27400 | 50.0 (58) | — | 12 | 150 | #1 | 58699 |
|  | 27401 | 53.1 (96) | — | 14 | 150 | #1 | — |
| 11768 | 27402 | 65.6 | 57.9 (266) | 25 | 187 | #4 | 58700 |
|  | 27403 | 50.0 | 50.0 | 12 | 150 | #1 | 58701 |
| 11769 | 27404 | 72.8 | 65.8 | 21 | 563 | #5 | 58702 |
| 11770 | 27405 | 50.0 | 50.0 | 12 | 150 | #1 | 58703 |
|  | 27406 | 50.0 | 50.0 (132) | 12 | 150 | #1 | 58704 |
| 11771 | 27407 | 50.0 (53) | — | 12 | 150 | #1 | — |
| 11772 | 27408 | 82.4 | 78.5 | 20 | 1182 | #7 | 58705 |
| 11773 | 27409 | 50.0 | 50.0 | 12 | 150 | #1 | 58706 |
| 11774 | 27410 | 64.0 | 59.9 (192) | 14 | 182 | #3 | 58707 |
| 11775 | 27411 | 68.0 | 57.8 | 15 | 219 | #4 | — |
| 11776 | 27412 | 74.4 | 62.5 | 26 | 369 | #5 | 58708 |
| 11777 | 27413 | 62.4 | 53.2 (156) | 14 | 172 | #3 | 58709 |
| 11778 | 27414 | 61.6 | 50.0 (259) | 25 | 269 | #3 | 58710 |
| 11779 | 27415 | 68.0 | 59.6 | 21 | 219 | #4 | 58711 |
| 11780 | 27416 | 72.8 | 69.3 (166) | 16 | 354 | #5 | 58712 |
| 11781 | 27417 | 73.6 | 68.0 (169) | 21 | 309 | #5 | 58713 |
| 11782 | 27418 | 78.9 (71) | — | 26 | 184 | #6 | 58714 |
| 11783 | 27419 | 63.2 | 59.3 (135) | 14 | 179 | #3 | 58715 |
| 11784 | 27420 | 67.2 | 66.7 (156) | 26 | 252 | #4 | 58716 |
| 11785 | 27421 | 70.4 | 61.5 | 21 | 310 | #5 | 58717 |
| 11786 | 27422 | 64.0 | 59.6 | 22 | 215 | #3 | 58718 |
| 11787 | 27423 | 73.6 | 58.9 | 18 | 378 | #5 | 58719 |
|  | 27424 | 66.4 | 63.5 (170) | 21 | 185 | #4 | 58720 |
| 11788 | 27425 | 66.7 (99) | — | 16 | 151 | #4 | 58721 |
| 11789 | 27426 | 68.8 | 60.4 | 23 | 251 | #4 | 58722 |
| 11790 | 27427 | 60.8 | 55.3 | 12 | 203 | #3 | 58723 |
|  | 27428 | 62.4 | 54.5 | 12 | 208 | #3 | 58724 |
| 11791 | 27429 | 50.0 (108) | — | 12 | 150 | #1 | 58725 |
| 11792 | 27430 | 83.8 (74) | — | 19 | 290 | #7 | 58726 |
| 11793 | 27431 | 68.0 | 58.8 (216) | 18 | 189 | #4 | 58727 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11794 | 27432 | 70.4 | 61.1 | 21 | 400 | #5 | 58728 |
| 11795 | 27433 | 50.0 (52) | — | 12 | 150 | #1 | — |
|  | 27434 | 72.0 | 66.2 | 22 | 464 | #5 | 58729 |
| 11796 | 27435 | 63.6 (107) | — | 16 | 152 | #3 | 58730 |
| 11797 | 27436 | 68.8 | 60.0 | 23 | 252 | #4 | 58731 |
| 11798 | 27437 | 69.6 | 66.5 (164) | 28 | 229 | #4 | — |
| 11799 | 27438 | 86.4 | 60.7 (206) | 28 | 493 | #8 | 58732 |
| 11800 | 27439 | 50.0 (83) | — | 12 | 150 | #1 | 58733 |
| 11801 | 27440 | 69.6 | 60.7 | 24 | 306 | #4 | 58734 |
| 11802 | 27441 | 71.8 (78) | — | 12 | 150 | #5 | 58735 |
| 11803 | 27442 | 52.5 (118) | — | 12 | 150 | #1 | 58736 |
| 11804 | 27443 | 67.2 | 61.8 | 17 | 268 | #4 | 58737 |
|  | 27444 | 72.8 | 62.2 | 18 | 353 | #5 | 58738 |
| 11805 | 27445 | 50.0 (97) | — | 12 | 150 | #1 | 58739 |
| 11806 | 27446 | 71.2 | 61.1 | 23 | 315 | #5 | 58740 |
| 11807 | 27447 | 68.8 | 52.7 | 22 | 257 | #4 | — |
| 11808 | 27448 | 77.4 (53) | — | 34 | 165 | #6 | — |
|  | 27449 | 59.2 | 50.0 (205) | 14 | 271 | #2 | 58741 |
| 11809 | 27450 | 68.8 (93) | — | 21 | 164 | #4 | 58742 |
|  | 27451 | 76.0 | 65.1 | 26 | 424 | #6 | 58743 |
| 11810 | 27452 | 72.8 | 63.5 | 26 | 357 | #5 | 58744 |
| 11811 | 27453 | 68.8 | 61.5 | 22 | 398 | #4 | — |
| 11812 | 27454 | 60.8 | 56.0 | 13 | 185 | #3 | 58745 |
| 11813 | 27455 | 76.2 (63) | — | 19 | 161 | #6 | — |
| 11814 | 27456 | 66.4 | 60.3 (234) | 24 | 217 | #4 | 58746 |
| 11815 | 27457 | 66.4 | 56.2 (256) | 18 | 193 | #4 | 58747 |
| 11816 | 27458 | 89.6 | 82.6 (195) | 32 | 697 | #8 | 58748 |
| 11817 | 27459 | 64.8 | 60.0 | 20 | 235 | #3 | 58749 |
| 11818 | 27460 | 50.0 (60) | — | 12 | 150 | #1 | — |
| 11819 | 27461 | 67.2 | 54.4 (193) | 16 | 191 | #4 | 58750 |
| 11820 | 27462 | 64.0 | 59.3 | 18 | 367 | #3 | 58751 |
| 11821 | 27463 | 63.2 | 57.8 | 13 | 219 | #3 | 58752 |
| 11822 | 27464 | 61.9 (105) | — | 18 | 159 | #3 | 58753 |
|  | 27465 | 67.2 | 61.0 (195) | 26 | 198 | #4 | 58754 |
| 11823 | 27466 | 78.4 | 62.5 | 15 | 366 | #6 | 58755 |
| 11824 | 27467 | 50.0 | 50.0 | 12 | 150 | #1 | 58756 |
| 11825 | 27468 | 63.2 | 60.7 (163) | 12 | 150 | #3 | 58757 |
|  | 27469 | 68.8 | 56.7 | 17 | 202 | #4 | 58758 |
| 11826 | 27470 | 73.6 | 50.0 | 20 | 322 | #5 | 58759 |
| 11827 | 27471 | 65.4 (104) | — | 18 | 169 | #4 | 58760 |
|  | 27472 | 67.2 | 60.0 | 18 | 233 | #4 | 58761 |
| 11828 | 27473 | 65.6 | 60.7 | 13 | 417 | #4 | 58762 |
| 11829 | 27474 | 50.0 (79) | — | 12 | 150 | #1 | 58763 |
| 11830 | 27475 | 62.4 | 50.9 (226) | 15 | 155 | #3 | 58764 |
| 11831 | 27476 | 63.2 | 53.1 (213) | 15 | 179 | #3 | 58765 |
| 11832 | 27477 | 63.6 (107) | — | 16 | 175 | #3 | 58766 |
| 11833 | 27478 | 74.4 | 62.5 | 36 | 492 | #5 | 58767 |
| 11834 | 27479 | 50.0 | 50.0 (200) | 12 | 150 | #1 | 58768 |
| 11835 | 27480 | 74.4 | 64.7 | 38 | 358 | #5 | 58769 |
|  | 27481 | 63.2 | 56.5 (232) | 17 | 175 | #3 | 58770 |
| 11836 | 27482 | 61.6 | 50.0 (183) | 15 | 156 | #3 | — |
| 11837 | 27483 | 50.0 (66) | — | 12 | 150 | #1 | 58771 |
| 11838 | 27484 | 66.4 | 59.6 | 17 | 211 | #4 | 58772 |
| 11839 | 27485 | 69.6 | 64.3 (213) | 21 | 266 | #4 | 58773 |
| 11840 | 27486 | 62.4 | 55.4 (168) | 14 | 155 | #3 | 58774 |
| 11841 | 27487 | 68.0 | 61.1 | 21 | 287 | #4 | 58775 |
| 11842 | 27488 | 77.6 | 76.4 (144) | 28 | 422 | #6 | 58776 |
| 11843 | 27489 | 64.0 | 57.8 | 13 | 181 | #3 | 58777 |
| 11844 | 27490 | 80.0 | 761.1 (255) | 24 | 700 | #6 | 58778 |
|  | 27491 | 50.0 | 50.0 | 15 | 174 | #1 | 58779 |
|  | 27492 | 63.2 | 50.0 | 18 | 192 | #3 | 58780 |
| 11845 | 27493 | 67.2 | 55.6 | 18 | 289 | #4 | 58781 |
| 11846 | 27494 | 50.0 (53) | — | 12 | 150 | #1 | — |
| 11847 | 27495 | 64.0 | 50.0 (219) | 14 | 160 | #3 | 58782 |
| 11848 | 27496 | 60.8 | 50.0 (212) | 13 | 151 | #3 | 58783 |
| 11849 | 27497 | 50.4 | 50.0 | 19 | 177 | #1 | 58784 |
| 11850 | 27498 | 50.0 (72) | — | 12 | 150 | #1 | 58785 |
| 11851 | 27499 | 50.0 | 50.0 | 12 | 150 | #1 | 58786 |
| 11852 | 27500 | 76.0 | 62.5 | 21 | 459 | #6 | 58787 |
| 11853 | 27501 | 64.0 | 59.3 | 15 | 243 | #3 | 58788 |
|  | 27502 | 50.0 (72) | — | 12 | 150 | #1 | 58789 |
| 11854 | 27503 | 50.0 | 50.0 | 12 | 150 | #1 | 58790 |
| 11855 | 27504 | 64.8 | 58.9 | 16 | 255 | #3 | 58791 |
| 11856 | 27505 | 50.0 (112) | — | 12 | 150 | #1 | 58792 |
|  | 27506 | 64.8 | 61.7 (188) | 15 | 285 | #3 | 58793 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11857 | 27507 | 50.0 (101) | — | 12 | 150 | #1 | 58794 |
| | 27508 | 61.6 | 55.4 (139) | 13 | 150 | #3 | 58795 |
| 11858 | 27509 | 63.2 | 50.0 (185) | 17 | 157 | #3 | 58796 |
| 11859 | 27510 | 64.8 | 52.4 (227) | 16 | 180 | #3 | 58797 |
| 11860 | 27511 | 71.2 | 61.5 | 20 | 301 | #5 | 58798 |
| 11861 | 27512 | 50.0 (56) | — | 12 | 150 | #1 | — |
| 11862 | 27513 | 50.0 (67) | — | 12 | 150 | #1 | 58799 |
| 11863 | 27514 | 51.5 (68) | — | 14 | 150 | #1 | 58800 |
| | 27515 | 50.0 (56) | — | 12 | 150 | #1 | — |
| 11864 | 27516 | 60.8 | 51.6 (161) | 19 | 157 | #3 | 58801 |
| 11865 | 27517 | 68.8 | 61.5 | 22 | 328 | #4 | 58802 |
| 11866 | 27518 | 57.6 | 50.0 | 12 | 158 | #2 | 58803 |
| 11867 | 27519 | 62.4 | 62.2 (156) | 14 | 155 | #3 | 58804 |
| | 27520 | 62.4 | 50.0 | 15 | 163 | #3 | 58805 |
| 11868 | 27521 | 71.2 | 68.4 | 14 | 1099 | #5 | 58806 |
| 11869 | 27522 | 68.8 | 57.1 | 18 | 245 | #4 | 58807 |
| 11870 | 27523 | 70.4 | 64.4 | 27 | 572 | #5 | 58808 |
| 11871 | 27524 | 70.4 | 62.1 (219) | 20 | 252 | #5 | 58809 |
| | 27525 | 82.4 | 50.0 | 27 | 450 | #7 | 58810 |
| | 27526 | 61.6 | 53.1 (260) | 17 | 154 | #3 | 58811 |
| 11872 | 27527 | 59.2 | 50.0 (203) | 15 | 159 | #2 | 58812 |
| 11873 | 27528 | 76.0 | 70.2 | 17 | 767 | #6 | 58813 |
| 11874 | 27529 | 67.2 | 61.1 | 16 | 306 | #4 | 58814 |
| 11875 | 27530 | 73.6 | 65.5 | 19 | 518 | #5 | 58815 |
| 11876 | 27531 | 58.0 (88) | — | 16 | 151 | #2 | 58816 |
| | 27532 | 50.0 (78) | — | 12 | 150 | #1 | 58817 |
| 11877 | 27533 | 63.2 | 58.2 (189) | 18 | 176 | #3 | 58818 |
| 11878 | 27534 | 52.5 (118) | — | 15 | 186 | #1 | 58819 |
| 11879 | 27535 | 64.8 | 50.0 | 13 | 186 | #3 | 58820 |
| 11880 | 27536 | 56.8 | 50.0 (207) | 13 | 152 | #2 | 58821 |
| | 27537 | 66.4 | 59.3 | 21 | 244 | #4 | 58822 |
| 11881 | 27538 | 84.0 | 81.5 | 21 | 1372 | #7 | 58823 |
| 11882 | 27539 | 65.6 | 57.0 (242) | 19 | 223 | #4 | 58824 |
| | 27540 | 62.4 | 53.8 | 12 | 248 | #3 | 58825 |
| 11883 | 27541 | 61.6 | 53.1 (239) | 13 | 160 | #3 | 58826 |
| 11884 | 27542 | 69.6 | 60.7 | 18 | 202 | #4 | 58827 |
| 11885 | 27543 | 50.0 (55) | — | 12 | 150 | #1 | — |
| 11886 | 27544 | 50.0 (51) | — | 12 | 150 | #1 | — |
| 11887 | 27545 | 74.4 | 66.9 | 18 | 873 | #5 | 58828 |
| 11888 | 27546 | 50.0 | 50.0 (134) | 12 | 151 | #1 | 58829 |
| 11889 | 27547 | 60.0 | 50.0 | 12 | 239 | #2 | 58830 |
| 11890 | 27548 | 50.0 | 50.0 | 12 | 150 | #1 | 58831 |
| 11891 | 27549 | 72.8 | 67.6 | 18 | 871 | #5 | 58832 |
| 11892 | 27550 | 69.9 (83) | — | 18 | 184 | #4 | 58833 |
| 11893 | 27551 | 68.0 | 62.2 | 21 | 355 | #4 | 58834 |
| | 27552 | 68.0 | 63.6 | 14 | 787 | #4 | 58835 |
| 11894 | 27553 | 64.0 | 60.8 (153) | 18 | 174 | #3 | 58836 |
| | 27554 | 65.6 | 59.3 | 19 | 209 | #4 | 58837 |
| 11895 | 27555 | 62.4 | 57.5 | 14 | 189 | #3 | 58838 |
| | 27556 | 75.7 (74) | — | 26 | 178 | #6 | 58839 |
| 11896 | 27557 | 64.8 | 60.2 (201) | 18 | 199 | #3 | 58840 |
| 11897 | 27558 | 70.4 | 60.7 | 20 | 279 | #5 | 58841 |
| | 27559 | 50.0 | 50.0 | 12 | 150 | #1 | 58842 |
| 11898 | 27560 | 71.2 | 61.5 (234) | 21 | 282 | #5 | 58843 |
| 11899 | 27561 | 65.6 | 56.0 | 15 | 214 | #4 | 58844 |
| 11900 | 27562 | 67.2 | 57.8 | 14 | 254 | #4 | 58845 |
| 11901 | 27563 | 50.0 (67) | — | 12 | 150 | #1 | — |
| | 27564 | 64.0 | 55.3 | 12 | 203 | #3 | 58846 |
| 11902 | 27565 | 82.0 (61) | — | 16 | 205 | #7 | — |
| 11903 | 27566 | 60.8 | 50.0 | 12 | 194 | #3 | 58847 |
| 11904 | 27567 | 50.0 (77) | — | 12 | 150 | #1 | 58848 |
| 11905 | 27568 | 67.2 | 60.7 | 21 | 234 | #4 | 58849 |
| 11906 | 27569 | 69.6 | 67.5 (154) | 21 | 237 | #4 | 58850 |
| 11907 | 27570 | 65.6 | 50.0 (264) | 14 | 162 | #4 | 58851 |
| 11908 | 27571 | 65.3 (95) | — | 15 | 150 | #4 | 58852 |
| | 27572 | 50.0 (104) | — | 12 | 150 | #1 | 58853 |
| 11909 | 27573 | 66.4 (113) | — | 19 | 173 | #4 | 58854 |
| | 27574 | 71.2 | 62.9 | 22 | 479 | #5 | 58855 |
| 11910 | 27575 | 65.6 | 61.7 (214) | 15 | 235 | #4 | 58856 |
| 11911 | 27576 | 72.0 | 61.1 | 24 | 333 | #5 | 58857 |
| 11912 | 27577 | 50.0 (86) | — | 12 | 150 | #1 | 58858 |
| 11913 | 27578 | 50.0 (71) | — | 12 | 150 | #1 | 58859 |
| 11914 | 27579 | 50.0 (55) | — | 12 | 150 | #1 | — |
| 11915 | 27580 | 67.2 | 60.0 | 19 | 242 | #4 | 58860 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11916 | 27581 | 68.0 | 60.0 | 28 | 261 | #4 | 58861 |
|  | 27582 | 69.6 | 61.1 | 20 | 274 | #4 | — |
| 11917 | 27583 | 70.8 (72) | — | 21 | 170 | #5 | 58862 |
| 11918 | 27584 | 50.0 (99) | — | 12 | 150 | #1 | 58863 |
|  | 27585 | 50.0 (56) | — | 12 | 150 | #1 | — |
| 11919 | 27586 | 64.0 | 58.2 | 14 | 196 | #3 | 58864 |
| 11920 | 27587 | 64.8 | 57.8 (256) | 19 | 190 | #3 | — |
| 11921 | 27588 | 68.0 | 57.1 | 14 | 191 | #4 | 58865 |
|  | 27589 | 50.0 | 50.0 (125) | 12 | 150 | #1 | 58866 |
| 11922 | 27590 | 50.0 (81) | — | 12 | 150 | #1 | 58867 |
|  | 27591 | 64.0 | 50.0 (182) | 14 | 166 | #3 | 58868 |
| 11923 | 27592 | 67.2 | 60.0 | 18 | 243 | #4 | 58869 |
| 11924 | 27593 | 50.0 | 50.0 (149) | 12 | 150 | #1 | 58870 |
|  | 27594 | 58.4 | 50.0 (212) | 13 | 191 | #2 | — |
| 11925 | 27595 | 64.8 | 58.5 | 18 | 194 | #3 | 58871 |
| 11926 | 27596 | 60.0 | 50.0 | 13 | 159 | #2 | 58872 |
| 11927 | 27597 | 50.0 (103) | — | 12 | 150 | #1 | — |
| 11928 | 27598 | 50.0 (114) | — | 12 | 150 | #1 | 58873 |
|  | 27599 | 67.2 | 57.8 | 15 | 273 | #4 | 58874 |
| 11929 | 27600 | 63.3 (79) | — | 13 | 150 | #3 | 58875 |
|  | 27601 | 72.0 | 64.0 | 33 | 538 | #5 | 58876 |
| 11930 | 27602 | 61.6 | 59.3 | 23 | 334 | #3 | 58877 |
| 11931 | 27603 | 50.0 | 50.0 | 12 | 150 | #1 | 58878 |
| 11932 | 27604 | 66.4 | 66.4 (125) | 19 | 168 | #4 | 58879 |
|  | 27605 | 60.8 | 50.0 (199) | 17 | 158 | #3 | 58880 |
| 11933 | 27606 | 50.0 (56) | — | 12 | 150 | #1 | — |
| 11934 | 27607 | 86.4 | 60.7 | 19 | 422 | #8 | 58881 |
| 11935 | 27608 | 70.4 | 62.5 | 20 | 290 | #5 | 58882 |
| 11936 | 27609 | 52.8 | 50.0 (158) | 14 | 150 | #1 | 58883 |
| 11937 | 27610 | 50.0 | 50.0 | 12 | 150 | #1 | 58884 |
| 11938 | 27611 | 76.0 | 50.0 | 27 | 269 | #6 | 58885 |
| 11939 | 27612 | 65.6 | 57.8 | 14 | 220 | #4 | 58886 |
| 11940 | 27613 | 65.6 | 62.9 (140) | 16 | 156 | #4 | 58887 |
| 11941 | 27614 | 61.6 | 57.1 | 19 | 196 | #3 | 58888 |
|  | 27615 | 64.8 (122) | — | 18 | 171 | #3 | 58889 |
| 11942 | 27616 | 50.0 (77) | — | 12 | 150 | #1 | 58890 |
| 11943 | 27617 | 69.6 | 60.0 | 19 | 238 | #4 | 58891 |
| 11944 | 27618 | 73.4 (79) | — | 14 | 194 | #5 | 58892 |
|  | 27619 | 63.2 | 56.2 (203) | 18 | 216 | #3 | 58893 |
| 11945 | 27620 | 50.0 (105) | — | 12 | 150 | #1 | 58894 |
| 11946 | 27621 | 77.8 (81) | — | 37 | 254 | #6 | 58895 |
| 11947 | 27622 | 60.8 | 58.8 (211) | 15 | 168 | #3 | 58896 |
| 11948 | 27623 | 64.0 | 50.0 (221) | 17 | 169 | #3 | 58897 |
| 11949 | 27624 | 71.4 (77) | — | 18 | 155 | #5 | 58898 |
|  | 27625 | 50.0 (117) | — | 12 | 150 | #1 | 58899 |
| 11950 | 27626 | 78.4 | 65.4 (234) | 34 | 367 | #6 | 58900 |
| 11951 | 27627 | 64.0 | 50.0 | 15 | 184 | #3 | 58901 |
| 11952 | 27628 | 66.4 | 61.3 (163) | 18 | 243 | #4 | 58902 |
| 11953 | 27629 | 65.6 | 52.4 (212) | 15 | 175 | #4 | 58903 |
| 11954 | 27630 | 50.0 | 50.0 | 12 | 150 | #1 | 58904 |
|  | 27631 | 50.0 | 50.0 | 12 | 150 | #1 | 58905 |
| 11955 | 27632 | 60.8 | 57.1 (133) | 17 | 162 | #3 | 58906 |
| 11956 | 27633 | 76.0 | 63.3 | 34 | 401 | #6 | 58907 |
| 11957 | 27634 | 63.2 | 57.8 | 13 | 187 | #3 | 58908 |
| 11958 | 27635 | 64.0 | 50.0 (216) | 13 | 150 | #3 | 58909 |
| 11959 | 27636 | 75.2 | 66.9 | 24 | 1109 | #6 | 58910 |
| 11960 | 27637 | 67.2 | 59.3 | 26 | 222 | #4 | 58911 |
| 11961 | 27638 | 65.6 | 58.9 | 17 | 223 | #4 | 58912 |
| 11962 | 27639 | 64.8 | 60.0 | 19 | 305 | #3 | 58913 |
| 11963 | 27640 | 50.0 | 50.0 | 12 | 150 | #1 | 58914 |
| 11964 | 27641 | 68.8 | 62.4 (263) | 15 | 354 | #4 | 58915 |
| 11965 | 27642 | 64.0 | 51.3 | 16 | 206 | #3 | 58916 |
|  | 27643 | 63.2 | 60.4 | 18 | 324 | #3 | 58917 |
| 11966 | 27644 | 62.4 | 50.0 (244) | 16 | 165 | #3 | 58918 |
|  | 27645 | 65.6 | 54.9 | 17 | 187 | #4 | 58919 |
| 11967 | 27646 | 68.0 | 62.2 | 21 | 332 | #4 | 58920 |
| 11968 | 27647 | 50.0 (63) | — | 12 | 150 | #1 | — |
| 11969 | 27648 | 66.4 | 50.0 (273) | 15 | 174 | #4 | 58921 |
|  | 27649 | 50.0 | 50.0 | 12 | 150 | #1 | 58922 |
| 11970 | 27650 | 56.8 | 50.0 (184) | 12 | 150 | #2 | 58923 |
| 11971 | 27651 | 88.8 | 76.7 | 37 | 1376 | #8 | 58924 |
|  | 27652 | 82.7 (104) | — | 21 | 358 | #7 | 58925 |
| 11972 | 27653 | 50.0 (93) | — | 12 | 150 | #1 | 58926 |
|  | 27654 | 68.0 | 60.0 | 22 | 300 | #4 | 58927 |
|  | 27655 | 65.6 | 58.7 (254) | 21 | 211 | #4 | 58928 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 11973 | 27656 | 73.6 | 65.5 | 23 | 562 | #5 | 58929 |
| 11974 | 27657 | 71.2 | 65.8 | 18 | 563 | #5 | 58930 |
| 11975 | 27658 | 63.2 | 57.9 (140) | 13 | 171 | #3 | 58931 |
| 11976 | 27659 | 65.6 | 60.4 | 17 | 248 | #4 | 58932 |
| 11977 | 27660 | 73.6 | 67.6 | 33 | 845 | #5 | 58933 |
| 11978 | 27661 | 50.0 (103) | — | 12 | 150 | #1 | 58934 |
| 11979 | 27662 | 67.2 | 59.3 | 21 | 248 | #4 | 58935 |
| 11980 | 27663 | 50.0 (55) | — | 12 | 150 | #1 | — |
| 11981 | 27664 | 63.2 | 59.3 | 13 | 210 | #3 | 58936 |
| 11982 | 27665 | 75.2 | 72.4 | 19 | 805 | #6 | 58937 |
| 11983 | 27666 | 63.0 (92) | — | 16 | 150 | #3 | 58938 |
| 11984 | 27667 | 61.6 | 53.5 | 13 | 197 | #3 | — |
| 11985 | 27668 | 65.5 (55) | — | 13 | 150 | #4 | — |
| 11986 | 27669 | 70.4 | 56.7 | 25 | 235 | #5 | 58939 |
| 11987 | 27670 | 50.0 (102) | — | 12 | 150 | #1 | 58940 |
| 11988 | 27671 | 62.4 | 56.8 (234) | 17 | 294 | #3 | 58941 |
|  | 27672 | 69.6 | 61.1 | 28 | 327 | #4 | 58942 |
| 11989 | 27673 | 66.4 | 59.6 | 18 | 230 | #4 | 58943 |
| 11990 | 27674 | 68.8 | 66.2 | 13 | 689 | #4 | 58944 |
| 11991 | 27675 | 50.0 (79) | — | 12 | 150 | #1 | 58945 |
| 11992 | 27676 | 50.0 | 50.0 | 12 | 150 | #1 | 58946 |
| 11993 | 27677 | 50.0 (62) | — | 12 | 150 | #1 | — |
| 11994 | 27678 | 70.4 | 63.6 | 21 | 340 | #5 | 58947 |
|  | 27679 | 50.0 (60) | — | 12 | 150 | #1 | — |
| 11995 | 27680 | 50.0 | 50.0 | 12 | 150 | #1 | 58948 |
|  | 27681 | 72.8 | 61.5 | 24 | 304 | #5 | 58949 |
|  | 27682 | 72.0 | 61.8 | 23 | 393 | #5 | 58950 |
| 11996 | 27683 | 64.0 | 50.0 (218) | 13 | 183 | #3 | 58951 |
| 11997 | 27684 | 68.0 | 61.8 | 17 | 266 | #4 | 58952 |
| 11998 | 27685 | 50.0 (97) | — | 12 | 150 | #1 | 58953 |
| 11999 | 27686 | 60.8 | 50.0 (168) | 12 | 150 | #3 | 58954 |
| 12000 | 27687 | 80.0 (55) | — | 15 | 169 | #6 | — |
| 12001 | 27688 | 68.7 (115) | — | 19 | 214 | #4 | 58955 |
| 12002 | 27689 | 50.0 (75) | — | 12 | 150 | #1 | 58956 |
|  | 27690 | 66.4 | 58.2 | 15 | 211 | #4 | 58957 |
| 12003 | 27691 | 59.2 | 50.0 (191) | 21 | 170 | #2 | 58958 |
|  | 27692 | 50.0 (65) | — | 12 | 150 | #1 | 58959 |
| 12004 | 27693 | 63.2 | 50.0 | 14 | 189 | #3 | 58960 |
| 12005 | 27694 | 50.0 | 50.0 | 12 | 150 | #1 | 58961 |
| 12006 | 27695 | 68.0 | 60.7 | 22 | 329 | #4 | 58962 |
| 12007 | 27696 | 50.0 | 50.0 (173) | 12 | 150 | #1 | 58963 |
| 12008 | 27697 | 50.0 | 50.0 (151) | 12 | 150 | #1 | 58964 |
|  | 27698 | 64.0 | 64.1 (128) | 20 | 190 | #3 | 58965 |
| 12009 | 27699 | 69.6 | 62.2 | 24 | 329 | #4 | 58966 |
| 12010 | 27700 | 69.6 | 64.7 | 18 | 467 | #4 | 58967 |
| 12011 | 27701 | 64.0 | 56.6 (244) | 21 | 173 | #3 | 58968 |
| 12012 | 27702 | 83.3 (78) | — | 27 | 289 | #7 | 58969 |
|  | 27703 | 84.9 (73) | — | 26 | 266 | #7 | 58970 |
| 12013 | 27704 | 67.2 | 66.2 (139) | 26 | 194 | #4 | 58971 |
| 12014 | 27705 | 70.4 | 61.5 | 25 | 388 | #5 | 58972 |
| 12015 | 27706 | 66.1 (109) | — | 15 | 184 | #4 | 58973 |
| 12016 | 27707 | 63.2 | 60.0 (160) | 18 | 165 | #3 | 58974 |
| 12017 | 27708 | 64.8 | 60.0 (155) | 17 | 174 | #3 | 58975 |
|  | 27709 | 50.0 (89) | — | 12 | 150 | #1 | 58976 |
| 12018 | 27710 | 70.4 | 52.0 (196) | 20 | 287 | #5 | 58977 |
|  | 27711 | 66.4 | 60.4 | 16 | 263 | #4 | 58978 |
| 12019 | 27712 | 65.6 | 50.0 | 18 | 216 | #4 | 58979 |
| 12020 | 27713 | 66.4 | 57.5 | 17 | 216 | #4 | 58980 |
| 12021 | 27714 | 72.0 | 68.4 (152) | 23 | 290 | #5 | 58981 |
| 12022 | 27715 | 84.6 (52) | — | 38 | 186 | #7 | — |
| 12023 | 27716 | 80.8 | 65.8 | 33 | 532 | #7 | 58982 |
|  | 27717 | 66.4 | 58.9 | 14 | 352 | #4 | 58983 |
| 12024 | 27718 | 64.0 | 56.1 (244) | 13 | 163 | #3 | 58984 |
| 12025 | 27719 | 50.0 (102) | — | 12 | 150 | #1 | 58985 |
| 12026 | 27720 | 71.2 | 63.3 | 22 | 362 | #5 | 58986 |
| 12027 | 27721 | 50.0 | 50.0 | 12 | 150 | #1 | 58987 |
| 12028 | 27722 | 50.0 (105) | — | 12 | 150 | #1 | 58988 |
|  | 27723 | 64.0 | 58.0 (226) | 16 | 175 | #3 | 58989 |
| 12029 | 27724 | 50.0 | 50.0 (267) | 12 | 150 | #1 | 58990 |
| 12030 | 27725 | 68.8 | 58.5 | 28 | 226 | #4 | 58991 |
| 12031 | 27726 | 64.9 (114) | — | 17 | 182 | #3 | 58992 |
| 12032 | 27727 | 50.0 (112) | — | 12 | 150 | #1 | 58993 |
| 12033 | 27728 | 50.0 (59) | — | 12 | 150 | #1 | — |
| 12034 | 27729 | 77.6 | 67.3 | 38 | 495 | #6 | 58994 |
| 12035 | 27730 | 50.0 (68) | — | 12 | 150 | #1 | 58995 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 12036 | 27731 | 70.4 | 61.6 (185) | 21 | 239 | #5 | 58996 |
| 12037 | 27732 | 64.0 | 56.7 | 13 | 174 | #3 | 58997 |
|  | 27733 | 55.2 | 53.5 (129) | 16 | 150 | #2 | 58998 |
| 12038 | 27734 | 71.2 | 61.5 | 25 | 419 | #5 | 58999 |
| 12039 | 27735 | 65.6 | 59.3 | 12 | 274 | #4 | 59000 |
| 12040 | 27736 | 64.0 | 59.3 | 17 | 311 | #3 | 59001 |
| 12041 | 27737 | 66.4 | 60.0 (230) | 18 | 188 | #4 | 59002 |
| 12042 | 27738 | 74.4 | 72.0 | 15 | 744 | #5 | 59003 |
| 12043 | 27739 | 50.0 (86) | — | 12 | 150 | #1 | 59004 |
|  | 27740 | 53.7 (121) | — | 13 | 150 | #1 | — |
| 12044 | 27741 | 67.2 | 51.6 (213) | 19 | 199 | #4 | 59005 |
| 12045 | 27742 | 64.0 | 50.0 | 15 | 182 | #3 | — |
| 12046 | 27743 | 64.8 | 58.9 | 16 | 250 | #3 | 59006 |
| 12047 | 27744 | 68.0 | 63.9 (194) | 16 | 343 | #4 | 59007 |
| 12048 | 27745 | 68.0 | 58.9 | 22 | 269 | #4 | 59008 |
| 12049 | 27746 | 68.0 | 61.1 | 23 | 271 | #4 | 59009 |
|  | 27747 | 70.4 | 61.5 | 18 | 283 | #5 | 59010 |
| 12050 | 27748 | 62.4 | 58.5 | 19 | 250 | #3 | 59011 |
| 12051 | 27749 | 59.2 | 50.0 | 13 | 214 | #2 | 59012 |
| 12052 | 27750 | 77.6 | 58.9 | 24 | 381 | #6 | 59013 |
| 12053 | 27751 | 60.8 | 50.0 (177) | 13 | 150 | #3 | 59014 |
| 12054 | 27752 | 66.4 | 65.4 (211) | 18 | 346 | #4 | 59015 |
| 12055 | 27753 | 59.2 | 56.5 (207) | 15 | 150 | #2 | — |
|  | 27754 | 76.0 | 74.1 (197) | 22 | 507 | #6 | 59016 |
|  | 27755 | 77.6 | 68.4 | 20 | 638 | #6 | 59017 |
| 12056 | 27756 | 69.6 | 58.5 | 23 | 241 | #4 | 59018 |
| 12057 | 27757 | 63.6 (121) | — | 20 | 167 | #3 | 59019 |
| 12058 | 27758 | 50.0 (114) | — | 12 | 150 | #1 | 59020 |
| 12059 | 27759 | 66.4 | 60.0 | 18 | 253 | #4 | 59021 |
| 12060 | 27760 | 59.2 | 50.0 (244) | 14 | 164 | #2 | 59022 |
|  | 27761 | 69.6 | 62.2 | 21 | 491 | #4 | 59023 |
| 12061 | 27762 | 50.0 | 50.0 (126) | 12 | 150 | #1 | 59024 |
| 12062 | 27763 | 66.4 | 60.0 | 21 | 371 | #4 | 59025 |
|  | 27764 | 61.6 | 58.2 | 14 | 195 | #3 | 59026 |
| 12063 | 27765 | 66.4 | 61.1 | 26 | 245 | #4 | 59027 |
|  | 27766 | 67.2 | 56.7 | 16 | 223 | #4 | 59028 |
| 12064 | 27767 | 61.6 | 50.0 (229) | 15 | 165 | #3 | 59029 |
| 12065 | 27768 | 80.0 | 71.6 | 15 | 685 | #6 | 59030 |
| 12066 | 27769 | 68.8 | 53.1 (273) | 21 | 200 | #4 | 59031 |
| 12067 | 27770 | 50.0 | 50.0 (135) | 12 | 150 | #1 | 59032 |
| 12068 | 27771 | 70.4 | 63.3 | 21 | 402 | #5 | 59033 |
| 12069 | 27772 | 74.4 | 63.6 | 23 | 468 | #5 | 59034 |
| 12070 | 27773 | 72.0 | 64.7 | 21 | 444 | #5 | 59035 |
| 12071 | 27774 | 65.6 | 50.0 (266) | 17 | 189 | #4 | 59036 |
| 12072 | 27775 | 88.0 | 60.2 (186) | 32 | 494 | #8 | 59037 |
| 12073 | 27776 | 64.8 | 54.2 | 14 | 171 | #3 | 59038 |
|  | 27777 | 69.6 | 63.3 | 19 | 374 | #4 | 59039 |
| 12074 | 27778 | 72.8 | 67.3 | 30 | 580 | #5 | 59040 |
| 12075 | 27779 | 79.2 | 50.7 (274) | 17 | 389 | #6 | 59041 |
|  | 27780 | 67.2 | 60.7 | 25 | 198 | #4 | — |
| 12076 | 27781 | 64.8 | 56.8 (220) | 20 | 187 | #3 | 59042 |
| 12077 | 27782 | 62.4 | 61.3 (137) | 18 | 159 | #3 | 59043 |
| 12078 | 27783 | 50.0 (91) | — | 12 | 150 | #1 | 59044 |
| 12079 | 27784 | 64.0 | 50.0 | 17 | 169 | #3 | 59045 |
|  | 27785 | 68.8 | 61.5 | 22 | 263 | #4 | 59046 |
| 12080 | 27786 | 72.0 | 62.9 | 29 | 381 | #5 | 59047 |
| 12081 | 27787 | 76.8 | 66.9 | 26 | 457 | #6 | 59048 |
| 12082 | 27788 | 66.4 | 59.7 (191) | 20 | 193 | #4 | 59049 |
| 12083 | 27789 | 63.2 | 50.0 | 12 | 166 | #3 | 59050 |
|  | 27790 | 68.0 | 61.1 | 19 | 387 | #4 | 59051 |
| 12084 | 27791 | 64.0 | 58.5 | 19 | 220 | #3 | 59052 |
|  | 27792 | 50.0 (56) | — | 12 | 150 | #1 | — |
| 12085 | 27793 | 61.6 | 57.1 | 20 | 176 | #3 | 59053 |
| 12086 | 27794 | 83.2 | 78.2 | 22 | 1032 | #7 | 59054 |
| 12087 | 27795 | 68.8 | 61.8 | 16 | 366 | #4 | 59055 |
| 12088 | 27796 | 65.6 | 57.5 | 16 | 200 | #4 | 59056 |
| 12089 | 27797 | 66.4 | 53.4 (208) | 17 | 199 | #4 | 59057 |
| 12090 | 27798 | 71.2 | 64.1 (237) | 18 | 464 | #5 | 59058 |
| 12091 | 27799 | 66.4 | 54.9 | 21 | 223 | #4 | 59059 |
| 12092 | 27800 | 50.0 (72) | — | 12 | 150 | #1 | 59060 |
| 12093 | 27801 | 72.0 | 50.0 | 23 | 329 | #5 | 59061 |
| 12094 | 27802 | 62.4 | 59.2 (152) | 18 | 188 | #3 | 59062 |
|  | 27803 | 61.6 | 50.0 | 12 | 160 | #3 | 59063 |
| 12095 | 27804 | 75.2 | 61.1 | 19 | 470 | #6 | 59064 |
| 12096 | 27805 | 69.5 (82) | — | 15 | 155 | #4 | 59065 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 12097 | 27806 | 64.0 | 61.9 (147) | 29 | 181 | #3 | 59066 |
| 12098 | 27807 | 66.4 | 56.0 | 15 | 188 | #4 | 59067 |
| 12099 | 27808 | 77.3 (88) | — | 32 | 242 | #6 | 59068 |
| 12100 | 27809 | 63.2 | 55.8 (206) | 14 | 179 | #3 | 59069 |
| 12101 | 27810 | 65.9 (85) | — | 20 | 150 | #4 | 59070 |
| 12102 | 27811 | 67.2 | 58.9 | 17 | 236 | #4 | 59071 |
| 12103 | 27812 | 68.0 | 62.8 (274) | 21 | 304 | #4 | 59072 |
| 12104 | 27813 | 50.0 (99) | — | 12 | 150 | #1 | 59073 |
| 12105 | 27814 | 69.6 | 62.3 (257) | 20 | 294 | #4 | 59074 |
| 12106 | 27815 | 50.0 (105) | — | 17 | 150 | #1 | 59075 |
| 12107 | 27816 | 66.4 | 50.0 | 15 | 194 | #4 | 59076 |
| 12108 | 27817 | 67.2 | 58.2 | 17 | 199 | #4 | 59077 |
| 12109 | 27818 | 50.0 | 50.0 (241) | 12 | 150 | #1 | 59078 |
| 12110 | 27819 | 64.0 | 60.9 (230) | 15 | 221 | #3 | 59079 |
| 12111 | 27820 | 76.8 | 70.5 | 19 | 929 | #6 | 59080 |
| 12112 | 27821 | 68.8 | 62.5 | 25 | 323 | #4 | 59081 |
| 12113 | 27822 | 62.4 | 53.8 (145) | 16 | 163 | #3 | 59082 |
| 12114 | 27823 | 50.0 | 50.0 | 12 | 150 | #1 | 59083 |
| 12115 | 27824 | 64.0 | 53.6 (192) | 19 | 166 | #3 | 59084 |
| 12116 | 27825 | 64.8 | 60.4 | 19 | 250 | #3 | 59085 |
| 12117 | 27826 | 62.4 | 51.6 | 14 | 185 | #3 | 59086 |
| 12118 | 27827 | 63.9 (122) | — | 19 | 242 | #3 | 59087 |
| 12119 | 27828 | 50.0 (79) | — | 12 | 150 | #1 | 59088 |
| 12120 | 27829 | 50.0 (70) | — | 12 | 150 | #1 | 59089 |
|  | 27830 | 63.3 (109) | — | 13 | 207 | #3 | 59090 |
| 12121 | 27831 | 63.2 | 52.8 (231) | 20 | 168 | #3 | — |
| 12122 | 27832 | 50.0 | 50.0 (129) | 14 | 150 | #1 | 59091 |
|  | 27833 | 64.8 | 59.0 (161) | 16 | 175 | #3 | 59092 |
| 12123 | 27834 | 76.8 | 72.0 | 23 | 883 | #6 | 59093 |
|  | 27835 | 67.2 | 63.3 | 12 | 513 | #4 | 59094 |
| 12124 | 27836 | 62.4 | 60.1 (168) | 18 | 161 | #3 | 59095 |
| 12125 | 27837 | 69.6 | 61.8 | 22 | 273 | #4 | 59096 |
|  | 27838 | 60.8 | 58.5 (130) | 18 | 184 | #3 | 59097 |
| 12126 | 27839 | 59.3 (113) | — | 13 | 150 | #2 | 59098 |
| 12127 | 27840 | 50.0 (117) | — | 12 | 150 | #1 | 59099 |
| 12128 | 27841 | 50.0 (51) | — | 12 | 150 | #1 | — |
| 12129 | 27842 | 67.2 | 56.7 | 19 | 213 | #4 | 59100 |
| 12130 | 27843 | 50.0 | 50.0 (153) | 12 | 150 | #1 | 59101 |
| 12131 | 27844 | 63.2 | 56.7 | 12 | 299 | #3 | 59102 |
| 12132 | 27845 | 66.4 | 50.0 | 12 | 258 | #4 | 59103 |
|  | 27846 | 64.0 | 58.7 (196) | 17 | 168 | #3 | 59104 |
| 12133 | 27847 | 73.6 | 66.2 | 25 | 571 | #5 | 59105 |
| 12134 | 27848 | 53.6 | 50.0 (201) | 15 | 151 | #1 | 59106 |
| 12135 | 27849 | 62.4 | 50.0 (221) | 15 | 161 | #3 | 59107 |
| 12136 | 27850 | 68.8 | 58.1 (260) | 20 | 213 | #4 | 59108 |
|  | 27851 | 77.6 (98) | — | 26 | 258 | #6 | 59109 |
| 12137 | 27852 | 72.0 | 60.0 | 33 | 306 | #5 | 59110 |
| 12138 | 27853 | 63.2 | 50.0 (209) | 16 | 172 | #3 | 59111 |
| 12139 | 27854 | 64.0 | 57.6 (170) | 17 | 158 | #3 | 59112 |
|  | 27855 | 69.6 | 61.5 | 23 | 404 | #4 | 59113 |
| 12140 | 27856 | 79.2 | 68.7 | 39 | 668 | #6 | 59114 |
| 12141 | 27857 | 50.0 | 50.0 (265) | 12 | 150 | #1 | 59115 |
| 12142 | 27858 | 68.0 | 58.0 (262) | 20 | 211 | #4 | 59116 |
| 12143 | 27859 | 74.4 | 60.7 | 29 | 306 | #5 | 59117 |
|  | 27860 | 50.0 (60) | — | 12 | 150 | #1 | — |
| 12144 | 27861 | 66.4 | 64.2 (159) | 30 | 309 | #4 | 59118 |
|  | 27862 | 71.0 (100) | — | 23 | 311 | #5 | 59119 |
| 12145 | 27863 | 50.0 (61) | — | 12 | 150 | #1 | — |
| 12146 | 27864 | 85.6 | 74.2 | 31 | 632 | #8 | 59120 |
| 12147 | 27865 | 64.8 | 50.0 (267) | 16 | 165 | #3 | 59121 |
| 12148 | 27866 | 50.0 (92) | — | 12 | 150 | #1 | 59122 |
| 12149 | 27867 | 50.0 (51) | — | 12 | 150 | #1 | — |
|  | 27868 | 60.8 | 50.0 | 12 | 157 | #3 | 59123 |
| 12150 | 27869 | 63.2 | 58.9 | 12 | 206 | #3 | 59124 |
| 12151 | 27870 | 70.4 | 64.0 | 20 | 394 | #5 | 59125 |
| 12152 | 27871 | 69.6 | 62.5 | 21 | 349 | #4 | 59126 |
| 12153 | 27872 | 67.2 | 55.6 | 17 | 333 | #4 | 59127 |
| 12154 | 27873 | 50.0 | 50.0 | 12 | 150 | #1 | 59128 |
| 12155 | 27874 | 67.7 (65) | — | 33 | 196 | #4 | 59129 |
| 12156 | 27875 | 67.2 | 63.3 | 16 | 463 | #4 | 59130 |
| 12157 | 27876 | 50.0 | 50.0 | 12 | 150 | #1 | 59131 |
| 12158 | 27877 | 69.2 (91) | — | 28 | 185 | #4 | 59132 |
|  | 27878 | 68.8 | 62.6 (230) | 21 | 237 | #4 | 59133 |
| 12159 | 27879 | 70.4 | 61.5 | 19 | 441 | #5 | 59134 |

-continued

| Contig SEQ ID NO | novel DNA SEQ ID NOs | 125 bp % identity | 275 bp % identity | 100% identity length | Blast score | hybridiz. conditions | Polypep. subsequence SEQ ID NO |
|---|---|---|---|---|---|---|---|
| 12160 | 27880 | 62.4 | 50.0 | 14 | 186 | #3 | 59135 |
|  | 27881 | 50.0 (58) | — | 21 | 150 | #1 | — |
| 12161 | 27882 | 82.4 | 62.5 | 24 | 595 | #7 | 59136 |
|  | 27883 | 66.4 | 61.9 (189) | 18 | 214 | #4 | 59137 |
| 12162 | 27884 | 73.6 | 66.2 | 17 | 516 | #5 | 59138 |
|  | 27885 | 69.6 | 61.5 | 20 | 360 | #4 | 59139 |
| 12163 | 27886 | 60.8 | 54.7 (172) | 15 | 166 | #3 | 59140 |
| 12164 | 27887 | 66.4 | 60.7 (244) | 24 | 207 | #4 | 59141 |
| 12165 | 27888 | 50.0 (89) | — | 12 | 150 | #1 | 59142 |
| 12166 | 27889 | 62.3 (77) | — | 12 | 150 | #3 | 59143 |
|  | 27890 | 74.4 | 65.1 | 25 | 422 | #5 | 59144 |
|  | 27891 | 68.0 (122) | — | 25 | 185 | #4 | 59145 |
| 12167 | 27892 | 50.0 (79) | — | 12 | 150 | #1 | — |
| 12168 | 27893 | 50.0 (64) | — | 12 | 150 | #1 | 59146 |
| 12169 | 27894 | 50.0 | 50.0 | 12 | 150 | #1 | 59147 |
| 12170 | 27895 | 50.0 | 50.0 | 12 | 150 | #1 | 59148 |
| 12171 | 27896 | 63.2 | 58.1 (136) | 15 | 231 | #3 | 59149 |
| 12172 | 27897 | 68.8 | 59.6 | 20 | 269 | #4 | 59150 |
|  | 27898 | 68.0 | 61.5 (252) | 25 | 239 | #4 | 59151 |
| 12173 | 27899 | 71.2 | 65.1 | 17 | 1357 | #5 | 59152 |
|  | 27900 | 67.2 | 60.7 | 16 | 626 | #4 | 59153 |
| 12174 | 27901 | 76.0 | 63.3 | 30 | 503 | #6 | 59154 |
|  | 27902 | 70.4 | 66.5 | 23 | 721 | #5 | 59155 |
| 12175 | 27903 | 64.0 | 54.9 (204) | 16 | 158 | #3 | 59156 |
| 12176 | 27904 | 50.0 (112) | — | 12 | 150 | #1 | 59157 |
| 12177 | 27905 | 60.0 | 52.4 (143) | 14 | 159 | #2 | 59158 |
| 12178 | 27906 | 50.0 | 50.0 (183) | 13 | 150 | #1 | 59159 |
| 12179 | 27907 | 56.7 (104) | — | 13 | 150 | #2 | 59160 |
|  | 27908 | 50.0 | 50.0 | 12 | 150 | #1 | 59161 |
| 12180 | 27909 | 72.0 | 63.3 | 25 | 332 | #5 | 59162 |
| 12181 | 27910 | 50.0 (60) | — | 12 | 150 | #1 | — |
| 12182 | 27911 | 50.0 | 50.0 | 12 | 150 | #1 | 59163 |
| 12183 | 27912 | 50.0 (57) | — | 12 | 150 | #1 | — |
| 12184 | 27913 | 72.0 | 62.5 | 31 | 315 | #5 | 59164 |
| 12185 | 27914 | 72.8 | 62.2 | 26 | 298 | #5 | 59165 |
| 12186 | 27915 | 68.8 | 64.7 | 18 | 457 | #4 | 59166 |
| 12187 | 27916 | 63.2 | 54.2 | 12 | 255 | #3 | 59167 |
| 12188 | 27917 | 69.6 | 61.1 | 21 | 342 | #4 | — |
| 12189 | 27918 | 63.2 | 50.0 | 13 | 169 | #3 | 59168 |
| 12190 | 27919 | 79.2 (53) | — | 33 | 190 | #6 | — |
| 12191 | 27920 | 71.2 | 50.0 | 16 | 320 | #5 | 59169 |
| 12192 | 27921 | 50.0 | 50.0 | 12 | 150 | #1 | 59170 |
| 12193 | 27922 | 64.8 | 58.2 (184) | 17 | 177 | #3 | 59171 |
|  | 27923 | 73.6 | 62.5 | 15 | 442 | #5 | 59172 |
| 12194 | 27924 | 65.6 | 58.2 | 12 | 196 | #4 | 59173 |
| 12195 | 27925 | 92.0 | 62.1 (195) | 31 | 543 | #9 | 59174 |
|  | 27926 | 63.9 (97) | — | 15 | 150 | #3 | 59175 |
| 12196 | 27927 | 53.0 (117) | — | 12 | 158 | #1 | 59176 |
| 12197 | 27928 | 50.0 | 50.0 | 12 | 150 | #1 | 59177 |
| 12198 | 27929 | 72.0 | 64.7 | 19 | 373 | #5 | 59178 |
| 12199 | 27930 | 63.2 | 61.2 (147) | 17 | 164 | #3 | 59179 |
| 12200 | 27931 | 50.0 (55) | — | 12 | 150 | #1 | — |

SEQUENCE LISTING

The patent contains a lengthy "Sequence Listing" section. A copy of the "Sequence Listing" is available in electronic form from the USPTO web site (http://seqdata.uspto.gov/sequence.html?DocID=6703491B1). An electronic copy of the "Sequence Listing" will also be available from the USPTO upon request and payment of the fee set forth in 37 CFR 1.19(b)(3).

What is claimed is:

1. An isolated nucleic acid of not more than 15 kilobases comprising the nucleotide sequence set forth in SEQ ID NO:10340 or a reverse complement thereof.

2. The nucleic acid of claim 1 which is DNA.

3. A recombinant vector comprising the nucleic acid of claim 1.

4. A recombinant host cell containing the vector of claim 3.

5. A method for producing Drosophila melanogaster chitin synthase protein comprising growing a recombinant cell containing the recombinant vector of claim 3 such that the chitin synthase protein encoded by said nucleic acid is expressed by the cell, and recovering the expressed chitin synthase protein.

6. A recombinant host cell containing the nucleic acid of claim 1, said nucleic acid being recombinant.

7. An isolated RNA comprising the sequence of SEQ ID NO:10,504 wherein T (thymidine) residues are substituted by U (uracil) residues.

8. An isolated nucleic acid consisting of the nucleotide sequence set forth in SEQ ID NO:10540 or a reverse complement thereof.

9. An isolated first nucleic acid that hybridizes under high stringency conditions to a second nucleic acid consisting of the nucleotide sequence set forth in SEQ ID NO:10540 or a reverse complement thereof, wherein said first nucleic acid encodes a chitin synthase and consists of a nucleotide sequence of not more than 15 kilobases.

10. An isolated nucleic acid of not more than 15 kilobases comprising the nucleotide sequence set forth in SEQ ID NO:3 or a reverse complement thereof.

11. The nucleic acid of claim 10 which is DNA.

12. A recombinant vector comprising the nucleic acid of claim 10.

13. A recombinant host cell containing the vector of claim 12.

14. A method for producing a G-protein coupled receptor (GPCR) protein comprising growing a recombinant cell containing the recombinant vector of claim 12 such that the GPCR protein encoded by said nucleic acid is expressed by the cell, and recovering the expressed GPCR protein.

15. A recombinant host cell containing the nucleic acid of claim 10, said nucleic acid being recombinant.

16. An isolated first nucleic acid that hybridizes under high stringency conditions to a second nucleic acid consisting of the nucleotide sequence set forth in SEQ ID NO:3 or a reverse complement thereof, wherein said first nucleic acid encodes a G-protein coupled receptor and consists of a nucleotide sequence of not more than 15 kilobases.

17. An isolated nucleic acid consisting of the nucleotide sequence set forth in SEQ ID NO:3 or a reverse complement thereof.

18. An isolated RNA comprising the sequence of SEQ ID NO:3 wherein T (thymidine) residues are substituted by U (uracil) residues.

* * * * *